US010835585B2

(12) United States Patent
Fritsch et al.

(10) Patent No.: US 10,835,585 B2
(45) Date of Patent: Nov. 17, 2020

(54) SHARED NEOANTIGENS

(71) Applicants: THE BROAD INSTITUTE INC., Cambridge, MA (US); DANA-FARBER CANCER INSTITUTE, INC., Boston, MA (US); THE GENERAL HOSPITAL CORPORATION, Boston, MA (US)

(72) Inventors: Edward F. Fritsch, Cambridge, MA (US); Nir Hacohen, Brookline, MA (US); Michael S. Rooney, Boston, MA (US); Sachet Ashok Shukla, Natick, MA (US); Catherine J. Wu, Brookline, MA (US); Pavan Bachireddy, Boston, MA (US); Jing Sun, Brookline, MA (US)

(73) Assignees: The Broad Institute, Inc., Cambridge, MA (US); Dana Farber Cancer Institute, Inc., Boston, MA (US); The General Hospital Corporation, Boston, MA (US)

( * ) Notice: Subject to any disclaimer, the term of this patent is extended or adjusted under 35 U.S.C. 154(b) by 41 days.

(21) Appl. No.: 15/575,328

(22) PCT Filed: May 20, 2016

(86) PCT No.: PCT/US2016/033452
§ 371 (c)(1),
(2) Date: Nov. 17, 2017

(87) PCT Pub. No.: WO2016/187508
PCT Pub. Date: Nov. 24, 2016

(65) Prior Publication Data
US 2018/0153975 A1 Jun. 7, 2018

Related U.S. Application Data

(60) Provisional application No. 62/179,877, filed on May 20, 2015, provisional application No. 62/389,377, filed on Feb. 23, 2016.

(51) Int. Cl.
| | | |
|---|---|---|
| A61K 39/00 | (2006.01) | |
| A61P 35/00 | (2006.01) | |
| C07K 14/47 | (2006.01) | |
| C12Q 1/6886 | (2018.01) | |

(52) U.S. Cl.
CPC .. *A61K 39/0011* (2013.01); *A61K 39/001104* (2018.08); *A61K 39/001151* (2018.08); *A61K 39/001152* (2018.08); *A61K 39/001162* (2018.08); *A61K 39/001164* (2018.08); *A61P 35/00* (2018.01); *C07K 14/4748* (2013.01); *C12Q 1/6886* (2013.01); *A61K 2039/515* (2013.01); *A61K 2039/70* (2013.01); *C12N 2320/31* (2013.01); *C12N 2320/34* (2013.01); *C12Q 2600/158* (2013.01); *G01N 2800/56* (2013.01); *G01N 2800/60* (2013.01); *G01N 2800/7028* (2013.01)

(58) Field of Classification Search
None
See application file for complete search history.

(56) References Cited

U.S. PATENT DOCUMENTS

| | | |
|---|---|---|
| 3,854,480 A | 12/1974 | Zaffaroni |
| 3,870,790 A | 3/1975 | Lowey et al. |
| 4,210,644 A | 7/1980 | Ewing et al. |
| 4,226,859 A | 10/1980 | Stach |
| 4,369,172 A | 1/1983 | Schor et al. |
| 4,379,454 A | 4/1983 | Campbell et al. |
| 4,452,775 A | 6/1984 | Kent |
| 4,588,585 A | 5/1986 | Mark et al. |
| 4,603,112 A | 7/1986 | Paoletti et al. |
| 4,656,127 A | 4/1987 | Mundy |
| 4,675,189 A | 6/1987 | Kent et al. |

(Continued)

FOREIGN PATENT DOCUMENTS

| | | |
|---|---|---|
| EP | 2390363 A1 | 11/2011 |
| EP | 2569633 A2 | 3/2013 |

(Continued)

OTHER PUBLICATIONS

Pietras et al (2006, 11:704-717).*

(Continued)

*Primary Examiner* — Laura B Goddard
(74) *Attorney, Agent, or Firm* — Foley Hoag LLP

(57) ABSTRACT

Disclosed herein in one aspect is a pharmaceutical composition comprising a plurality of neoantigenic peptides and a pharmaceutically acceptable carrier, each neoantigenic peptide comprising a tumor-specific neoepitope capable of binding to an HLA protein in a subject, each tumor-specific neoepitope comprising a tumor-specific mutation present in a tumor, wherein (a) the composition comprises neoantigenic peptides comprising tumor-specific mutations present in at least 1% of subjects in a population of subjects suffering from cancer; (b) the composition comprises neoantigenic peptides comprising tumor-specific neoepitopes which bind to HLA proteins present in at least 5% of subjects in the population; and (c) the composition comprises at least one neoantigenic peptide capable of eliciting an immune response against a tumor present in at least 5% of the subjects in the population of subjects suffering from cancer.

35 Claims, No Drawings
Specification includes a Sequence Listing.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,690,915 A | 9/1987 | Rosenberg |
| 4,722,848 A | 2/1988 | Paoletti et al. |
| 4,743,249 A | 5/1988 | Loveland |
| 4,751,180 A | 6/1988 | Cousens et al. |
| 4,769,330 A | 9/1988 | Paoletti et al. |
| 4,816,540 A | 3/1989 | Onishi |
| 4,842,866 A | 6/1989 | Horder et al. |
| 4,844,893 A | 7/1989 | Honsik et al. |
| 4,906,169 A | 3/1990 | Chien et al. |
| 4,935,233 A | 6/1990 | Bell et al. |
| 4,973,468 A | 11/1990 | Chiang et al. |
| 5,023,084 A | 6/1991 | Chien et al. |
| 5,035,891 A | 7/1991 | Runkel et al. |
| 5,110,587 A | 5/1992 | Paoletti et al. |
| 5,133,974 A | 7/1992 | Paradissis et al. |
| 5,174,993 A | 12/1992 | Paoletti |
| 5,185,146 A | 2/1993 | Altenburger |
| 5,198,223 A | 3/1993 | Gale et al. |
| 5,204,253 A | 4/1993 | Sanford et al. |
| 5,217,720 A | 6/1993 | Sekigawa et al. |
| 5,279,833 A | 1/1994 | Rose |
| 5,364,773 A | 11/1994 | Paoletti et al. |
| 5,407,686 A | 4/1995 | Patel et al. |
| 5,422,119 A | 6/1995 | Casper |
| 5,494,807 A | 2/1996 | Paoletti et al. |
| 5,541,171 A | 7/1996 | Rhodes et al. |
| 5,580,859 A | 12/1996 | Felgner et al. |
| 5,589,466 A | 12/1996 | Felgner et al. |
| 5,658,785 A | 8/1997 | Johnson |
| 5,686,281 A | 11/1997 | Roberts |
| 5,705,190 A | 1/1998 | Broad et al. |
| 5,736,152 A | 4/1998 | Dunn |
| 5,756,101 A | 5/1998 | Paoletti et al. |
| 5,762,938 A | 6/1998 | Paoletti et al. |
| 5,766,597 A | 6/1998 | Paoletti et al. |
| 5,766,882 A | 6/1998 | Falkner et al. |
| 5,770,212 A | 6/1998 | Falkner et al. |
| 5,811,104 A | 9/1998 | Dale et al. |
| 5,833,975 A | 11/1998 | Paoletti et al. |
| 5,843,728 A | 12/1998 | Seed et al. |
| 5,849,303 A | 12/1998 | Wasmoen et al. |
| 5,849,589 A | 12/1998 | Tedder et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 5,942,235 A | 8/1999 | Paoletti |
| 5,989,562 A | 11/1999 | Wasmoen et al. |
| 5,990,091 A | 11/1999 | Tartaglia et al. |
| 5,994,136 A | 11/1999 | Naldini et al. |
| 6,004,777 A | 12/1999 | Tartaglia et al. |
| 6,004,811 A | 12/1999 | Seed et al. |
| 6,013,516 A | 1/2000 | Verma et al. |
| 6,090,393 A | 7/2000 | Fischer |
| 6,130,066 A | 10/2000 | Tartaglia et al. |
| 6,156,567 A | 12/2000 | Fischer |
| 6,159,477 A | 12/2000 | Audonnet et al. |
| 6,165,782 A | 12/2000 | Naldini et al. |
| 6,214,353 B1 | 4/2001 | Paoletti et al. |
| 6,228,846 B1 | 5/2001 | Audonnet et al. |
| 6,258,595 B1 | 7/2001 | Gao et al. |
| 6,265,189 B1 | 7/2001 | Paoletti et al. |
| 6,277,558 B1 | 8/2001 | Hudson |
| 6,284,240 B1 | 9/2001 | Seed et al. |
| 6,309,647 B1 | 10/2001 | Paoletti et al. |
| 6,312,682 B1 | 11/2001 | Kingsman et al. |
| 6,352,694 B1 | 3/2002 | June et al. |
| 6,392,013 B1 | 5/2002 | Seed et al. |
| 6,406,705 B1 | 6/2002 | Davis et al. |
| 6,410,014 B1 | 6/2002 | Seed et al. |
| 6,428,953 B1 | 8/2002 | Naldini et al. |
| 6,475,769 B1 | 11/2002 | Wilson et al. |
| 6,489,458 B2 | 12/2002 | Hackett et al. |
| 6,534,055 B1 | 3/2003 | June et al. |
| 6,537,540 B1 | 3/2003 | Burstein et al. |
| 6,537,594 B1 | 3/2003 | Paoletti et al. |
| 6,569,457 B2 | 5/2003 | Ullah et al. |
| 6,638,534 B1 | 10/2003 | Ishibashi et al. |
| 6,682,743 B2 | 1/2004 | Mayr |
| 6,713,068 B1 | 3/2004 | Audonnet et al. |
| 6,753,162 B1 | 6/2004 | Seed et al. |
| 6,761,893 B2 | 7/2004 | Chaplin et al. |
| 6,780,407 B1 | 8/2004 | Paoletti et al. |
| 6,780,417 B2 | 8/2004 | Kaslow et al. |
| 6,793,926 B1 | 9/2004 | Rasty et al. |
| 6,797,514 B2 | 9/2004 | Berenson et al. |
| 6,821,515 B1 | 11/2004 | Cleland et al. |
| 6,867,041 B2 | 3/2005 | Berenson et al. |
| 6,869,794 B2 | 3/2005 | Vogels et al. |
| 6,887,466 B2 | 5/2005 | June et al. |
| 6,893,865 B1 | 5/2005 | Lockert et al. |
| 6,905,680 B2 | 6/2005 | June et al. |
| 6,905,681 B1 | 6/2005 | June et al. |
| 6,905,874 B2 | 6/2005 | Berenson et al. |
| 6,913,752 B2 | 7/2005 | Chaplin et al. |
| 6,913,922 B1 | 7/2005 | Bout et al. |
| 6,923,973 B1 | 8/2005 | Cox et al. |
| 6,924,128 B2 | 8/2005 | Allen |
| 6,936,466 B2 | 8/2005 | Feldhaus |
| 6,943,019 B2 | 9/2005 | Wilson et al. |
| 6,953,690 B1 | 10/2005 | Gao et al. |
| 6,955,808 B2 | 10/2005 | Curiel |
| 6,974,695 B2 | 12/2005 | Vogels et al. |
| 6,991,797 B2 | 1/2006 | Andersen et al. |
| 7,029,848 B2 | 4/2006 | Vogels et al. |
| 7,045,313 B1 | 5/2006 | Moss et al. |
| 7,097,842 B2 | 8/2006 | Suter et al. |
| 7,115,391 B1 | 10/2006 | Chen et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,172,893 B2 | 2/2007 | Rabinowitz et al. |
| 7,175,843 B2 | 2/2007 | June et al. |
| 7,189,536 B2 | 3/2007 | Chaplin et al. |
| 7,198,784 B2 | 4/2007 | Kingsman et al. |
| 7,232,566 B2 | 6/2007 | June et al. |
| 7,255,862 B1 | 8/2007 | Tartaglia et al. |
| 7,259,015 B2 | 8/2007 | Kingsman et al. |
| 7,283,337 B2 | 10/2007 | Sakai et al. |
| 7,303,910 B2 | 12/2007 | Bebbington et al. |
| 7,335,364 B2 | 2/2008 | Chaplin et al. |
| 7,351,585 B2 | 4/2008 | Mitrophanous et al. |
| 7,384,644 B2 | 6/2008 | Chaplin et al. |
| 7,445,924 B2 | 11/2008 | Chaplin et al. |
| 7,459,270 B2 | 12/2008 | Chaplin et al. |
| 7,572,631 B2 | 8/2009 | Berenson et al. |
| 7,608,279 B2 | 10/2009 | Parisot et al. |
| 7,628,980 B2 | 12/2009 | Suter et al. |
| 7,705,120 B2 * | 4/2010 | Lillie .................. C12Q 1/6886 530/350 |
| 7,708,949 B2 | 5/2010 | Stone et al. |
| 7,741,465 B1 | 6/2010 | Eshhar et al. |
| 7,767,449 B1 | 8/2010 | Paoletti |
| 7,892,533 B2 | 2/2011 | Suter et al. |
| 7,897,156 B2 | 3/2011 | Ackermann et al. |
| 7,923,017 B2 | 4/2011 | Chaplin et al. |
| 7,939,086 B2 | 5/2011 | Chaplin et al. |
| 7,964,395 B2 | 6/2011 | Chaplin et al. |
| 7,964,396 B2 | 6/2011 | Chaplin et al. |
| 7,964,398 B2 | 6/2011 | Chaplin et al. |
| 7,985,739 B2 | 7/2011 | Kay et al. |
| 8,034,334 B2 | 10/2011 | Dudley et al. |
| 8,088,379 B2 | 1/2012 | Robbins et al. |
| 8,163,293 B2 | 4/2012 | Chaplin |
| 8,211,422 B2 | 7/2012 | Eshhar et al. |
| 8,227,432 B2 | 7/2012 | Hackett et al. |
| 8,236,560 B2 | 8/2012 | Chaplin et al. |
| 8,268,325 B2 | 9/2012 | Chaplin et al. |
| 8,268,329 B2 | 9/2012 | Chaplin et al. |
| 8,278,036 B2 | 10/2012 | Kariko et al. |

(56) References Cited

U.S. PATENT DOCUMENTS

| | | |
|---|---|---|
| 8,309,098 B2 | 11/2012 | Howley et al. |
| 8,372,622 B2 | 2/2013 | Suter et al. |
| 8,399,645 B2 | 3/2013 | Campana et al. |
| 8,404,658 B2 | 3/2013 | Hajjar et al. |
| 8,454,972 B2 | 6/2013 | Nabel et al. |
| 8,470,598 B2 | 6/2013 | Chaplin et al. |
| 8,697,854 B2 | 4/2014 | Schendel et al. |
| 8,796,414 B2 | 8/2014 | Johnston |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,115,402 B2 | 8/2015 | Hacohen et al. |
| 9,909,159 B2 | 3/2018 | Marras et al. |
| 10,426,824 B1 | 10/2019 | Hacohen et al. |
| 2003/0104008 A1 | 6/2003 | Loosmore et al. |
| 2004/0013648 A1 | 1/2004 | Kingsman et al. |
| 2004/0053304 A1 | 3/2004 | Markowitz |
| 2006/0008468 A1 | 1/2006 | Chiang et al. |
| 2006/0163385 A1 | 7/2006 | Link et al. |
| 2006/0252077 A1 | 11/2006 | Buzby |
| 2006/0258607 A1 | 11/2006 | Jarosch et al. |
| 2007/0003442 A1 | 1/2007 | Link et al. |
| 2007/0025970 A1 | 2/2007 | Kingsman et al. |
| 2007/0055049 A1 | 3/2007 | Grey et al. |
| 2007/0083334 A1* | 4/2007 | Mintz .................... G16B 40/00 702/19 |
| 2007/0134197 A1 | 6/2007 | Eichner et al. |
| 2007/0184489 A1 | 8/2007 | Griffiths et al. |
| 2007/0195127 A1 | 8/2007 | Ahn et al. |
| 2008/0003142 A1 | 1/2008 | Link et al. |
| 2008/0014222 A1 | 1/2008 | Simmons et al. |
| 2008/0014589 A1 | 1/2008 | Link et al. |
| 2008/0254008 A1 | 10/2008 | Dropulic et al. |
| 2009/0005254 A1 | 1/2009 | Griffiths et al. |
| 2009/0026082 A1 | 1/2009 | Rothberg et al. |
| 2009/0111106 A1 | 4/2009 | Mitrophanous et al. |
| 2009/0131543 A1 | 5/2009 | Weitz et al. |
| 2009/0136494 A1 | 5/2009 | Ponath et al. |
| 2009/0186042 A1 | 7/2009 | Johnston et al. |
| 2009/0220980 A1 | 9/2009 | Hoon et al. |
| 2010/0137143 A1 | 6/2010 | Rothberg et al. |
| 2010/0137163 A1 | 6/2010 | Link et al. |
| 2010/0158951 A1 | 6/2010 | Randolph et al. |
| 2010/0210529 A1 | 8/2010 | van der Burg et al. |
| 2010/0282617 A1 | 11/2010 | Rothberg et al. |
| 2010/0297071 A1 | 11/2010 | Ishibashi et al. |
| 2010/0304989 A1 | 12/2010 | Von Hoff et al. |
| 2011/0097312 A1 | 4/2011 | Molldrem |
| 2011/0257890 A1 | 10/2011 | Weinschenk et al. |
| 2011/0293571 A1 | 12/2011 | Widdowson et al. |
| 2011/0293637 A1* | 12/2011 | Hacohen ................. A61P 35/00 424/173.1 |
| 2012/0082691 A1 | 4/2012 | Rammensee et al. |
| 2012/0219947 A1 | 8/2012 | Yurkovetsky et al. |
| 2012/0244133 A1 | 9/2012 | Rosenberg et al. |
| 2012/0288539 A1 | 11/2012 | Eber |
| 2012/0295960 A1 | 11/2012 | Palfi et al. |
| 2013/0071414 A1 | 3/2013 | Dotti et al. |
| 2013/0210014 A1 | 8/2013 | Sharman |
| 2013/0295110 A1 | 11/2013 | Binder et al. |
| 2014/0056986 A1 | 2/2014 | Desai et al. |
| 2014/0178438 A1 | 6/2014 | Sahin et al. |
| 2014/0256595 A1 | 9/2014 | Link et al. |
| 2014/0322716 A1 | 10/2014 | Robins |
| 2015/0140041 A1 | 5/2015 | Vitiello |
| 2015/0224182 A1 | 8/2015 | Hunt et al. |
| 2016/0008447 A1 | 1/2016 | Hacohen et al. |
| 2016/0101170 A1 | 4/2016 | Hacohen et al. |
| 2016/0310584 A1 | 10/2016 | Fritsch et al. |
| 2016/0326593 A1 | 11/2016 | Clement et al. |
| 2016/0331822 A1 | 11/2016 | Hacohen et al. |
| 2016/0339090 A1 | 11/2016 | Hacohen et al. |
| 2017/0160269 A1 | 6/2017 | Linnemann et al. |
| 2017/0233821 A1 | 8/2017 | Lianidou et al. |
| 2017/0298441 A1 | 10/2017 | Wu et al. |
| 2018/0000913 A1 | 1/2018 | Hacohen et al. |
| 2018/0055922 A1 | 3/2018 | Hacohen et al. |
| 2018/0127803 A1 | 5/2018 | Lei et al. |
| 2018/0153975 A1 | 6/2018 | Fritsch et al. |
| 2019/0060428 A1 | 2/2019 | Fritsch |
| 2019/0060432 A1 | 2/2019 | Hacohen et al. |
| 2019/0099475 A1* | 4/2019 | Benz .................... C07K 16/30 |

FOREIGN PATENT DOCUMENTS

| | | |
|---|---|---|
| EP | 2574346 A1 | 4/2013 |
| FR | 2650840 A1 | 2/1991 |
| JP | 2003/517274 A | 5/2003 |
| JP | 2003/523365 A | 8/2003 |
| JP | 2003/535024 A | 11/2003 |
| JP | 2005/505271 A | 2/2005 |
| JP | 2005/529187 A | 9/2005 |
| JP | 2006/526628 A | 11/2006 |
| JP | 2009/532664 A | 9/2009 |
| JP | 2012/522500 A | 9/2012 |
| JP | 2013/530943 A | 8/2013 |
| WO | WO-2014/184744 A1 | 0/0000 |
| WO | WO-9102087 A1 | 2/1991 |
| WO | WO-9106309 A1 | 5/1991 |
| WO | WO-92/15672 A1 | 9/1992 |
| WO | WO-9215322 A1 | 9/1992 |
| WO | WO-9215712 A1 | 9/1992 |
| WO | WO-9324640 A2 | 12/1993 |
| WO | WO-95/27780 A1 | 10/1995 |
| WO | WO-95/30018 A2 | 11/1995 |
| WO | WO-96/18372 A2 | 6/1996 |
| WO | WO-00/20587 A2 | 4/2000 |
| WO | WO-00/66153 A1 | 11/2000 |
| WO | WO-2001/89788 A2 | 11/2001 |
| WO | WO-2003020763 A2 | 3/2003 |
| WO | WO-2003/057171 A2 | 7/2003 |
| WO | WO-03/086459 A1 | 10/2003 |
| WO | WO-03/106692 A2 | 12/2003 |
| WO | WO-2004/002627 A2 | 1/2004 |
| WO | WO-2004026897 A1 | 4/2004 |
| WO | WO2004030615 * | 4/2004 |
| WO | WO-2004033685 A1 | 4/2004 |
| WO | WO-2004044004 A2 | 5/2004 |
| WO | WO-2004/058801 A2 | 7/2004 |
| WO | WO-2004074322 A1 | 9/2004 |
| WO | WO-2004/091763 A2 | 10/2004 |
| WO | WO-2005/021151 A2 | 3/2005 |
| WO | WO-2005087261 A2 | 9/2005 |
| WO | WO-2005/113595 A2 | 12/2005 |
| WO | WO-2005114215 A2 | 12/2005 |
| WO | WO-2006000830 A2 | 1/2006 |
| WO | WO-2006/040551 A2 | 4/2006 |
| WO | WO-2006/040554 A1 | 4/2006 |
| WO | WO-2006/096571 A2 | 9/2006 |
| WO | WO-2006/121168 A1 | 11/2006 |
| WO | WO-2006125962 A2 | 11/2006 |
| WO | WO-2007015540 A1 | 2/2007 |
| WO | WO-2007/059033 A1 | 5/2007 |
| WO | WO-2007/089541 A2 | 8/2007 |
| WO | WO-2007/095033 A2 | 8/2007 |
| WO | WO-2007/101227 A2 | 9/2007 |
| WO | WO-2007/124090 A2 | 11/2007 |
| WO | WO-2007/133710 A2 | 11/2007 |
| WO | WO-2008/011344 A2 | 1/2008 |
| WO | WO-2008038002 A2 | 4/2008 |
| WO | WO-2008039818 A2 | 4/2008 |
| WO | WO-2008/063227 A2 | 5/2008 |
| WO | WO-2008/096831 A1 | 8/2008 |
| WO | WO-2008/109075 A2 | 9/2008 |
| WO | WO-2009/014708 A1 | 1/2009 |
| WO | WO-2009032477 A2 | 3/2009 |
| WO | WO-2009043520 A1 | 4/2009 |
| WO | WO-2009/126306 A2 | 10/2009 |
| WO | WO-2010033949 A1 | 3/2010 |
| WO | WO-2010/045345 A2 | 4/2010 |

(56) References Cited

FOREIGN PATENT DOCUMENTS

| | | |
|---|---|---|
| WO | WO-2011/051489 A2 | 5/2011 |
| WO | WO-2011/079176 A2 | 6/2011 |
| WO | WO-2011/143656 A2 | 11/2011 |
| WO | WO-2011134944 A2 | 11/2011 |
| WO | WO-2011146862 A1 | 11/2011 |
| WO | WO-2012027379 A2 | 3/2012 |
| WO | WO-2012/079000 A1 | 6/2012 |
| WO | WO-2012/095639 A2 | 7/2012 |
| WO | WO-2012/101112 A1 | 8/2012 |
| WO | WO-2012/159643 A1 | 11/2012 |
| WO | WO-2012/159754 A2 | 11/2012 |
| WO | WO-2013/026027 A1 | 2/2013 |
| WO | WO-2013/036201 A1 | 3/2013 |
| WO | WO-2013039889 A1 | 3/2013 |
| WO | WO-2013040371 A2 | 3/2013 |
| WO | WO-2013/086464 A1 | 6/2013 |
| WO | WO-2013/123031 A2 | 8/2013 |
| WO | WO-2013133405 A1 | 9/2013 |
| WO | WO-2013/173223 A1 | 11/2013 |
| WO | WO-2013166321 A1 | 11/2013 |
| WO | WO-2013176915 A1 | 11/2013 |
| WO | WO-2014/009535 A2 | 1/2014 |
| WO | WO-2014/012051 A1 | 1/2014 |
| WO | WO-2014011987 A1 | 1/2014 |
| WO | WO-2014018863 A1 | 1/2014 |
| WO | WO-2014047561 A1 | 3/2014 |
| WO | WO-2014/056986 A1 | 4/2014 |
| WO | WO-2014/059173 A2 | 4/2014 |
| WO | WO-2014/083173 A1 | 6/2014 |
| WO | WO-2014085802 A1 | 6/2014 |
| WO | WO-2014/133567 A1 | 9/2014 |
| WO | WO-2014/133568 A1 | 9/2014 |
| WO | WO-2014/150924 A2 | 9/2014 |
| WO | WO-2014134165 A1 | 9/2014 |
| WO | WO-2014/168874 A2 | 10/2014 |
| WO | WO-2014172606 A1 | 10/2014 |
| WO | 2014/197369 A1 | 12/2014 |
| WO | WO-2014191128 A1 | 12/2014 |
| WO | WO-2015/085233 A1 | 6/2015 |
| WO | WO-2015/095811 A2 | 6/2015 |
| WO | WO-2016/020710 A1 | 2/2016 |
| WO | WO-2016/100975 A1 | 6/2016 |
| WO | WO-2016/201049 A2 | 12/2016 |
| WO | WO-2017/173321 A1 | 10/2017 |
| WO | WO-2017/184590 A1 | 10/2017 |
| WO | WO-2018/140391 A1 | 8/2018 |

OTHER PUBLICATIONS

Song et al (2013, Cellular & Molecular Immunology, 10:490-496).*
IEDB Analysis Resource for MHC-I binding predictions (printed Oct. 2019).*
IEDB Analysis Resource for MHC-II binding predictions (printed Oct. 2019).*
McCleskey et al (American J Clinical Pathology, 2015, 144:756-763; published Jan. 11, 2015).*
Jiang et al (Cancer, 2014, 120:1329-1337).*
Alvarez, "Present and future evolution of advanced breast cancer therapy," Breast Cancer Research, 12(Suppl 2):S1 (2010).
Backert et al., "Immunoinformatics and epitope prediction in the age of genomic medicine," Genome Medicine, 7:119 (2015).
Behrends et al., "Network organization of the human autophagy system," Nature, 466(7302):68-76 (2010).
Berg et al., "Detection of artifacts and peptide modifications in liquid chromatography/mass spectrometry data using two-dimensional signal intensity map data visualization," Rapid Commun Mass Spectrom, 20(10):1558-1562 (2006).
Boen et al., "Identification of T Cell Ligands in a Library of Peptides Covalently Attached to HLA-DR4," J Immunol, 165:2040-2047 (2000).
Boon et al., "Human T Cell Responses Against Melanoma," Annu Rev Immunol, 24: 175-208 (2006).

Carreno et al., "A dendritic cell vaccine increases the breadth and diversity of melanoma neoantigen-specific T cells," Science, 348(6239):803-808 (2015).
Chen et al., Molecular Pharmaceutics, 3:109-111 (2010).
Declaration by Professor John Haanen, M.D., Ph.D.
Di Stasi et al., "Inducible apoptosis as a safety switch for adoptive cell therapy," New England Journal of Medicine, 365(18):1673-1683 (2011).
Dössinger et al., "MHC multimer-guided and cell culture-independent isolation of functional T cell receptors from single cells facilitates TCR identification for immunotherapy," PloS one, 8(4):e61384 (2013).
Extracts from the USPTO patent register.
Final Rejection for U.S. Appl. No. 13/108,610, "Compositions and Methods of Identifying Tumor Specific Neoantigens," dated May 12, 2014.
Final Rejection for U.S. Appl. No. 14/794,449, "Compositions and Methods of Identifying Tumor Specific Neoantigens," dated Sep. 13, 2017.
Final Rejection for U.S. Appl. No. 14/877,125, "Compositions and Methods for Personalized Neoplasia Vaccines," dated Oct. 25, 2017.
Final Rejection for U.S. Appl. No. 15/038,504, "Compositions and Methods for Diagnosing, Evaluating and Treating Cancer by Means of the DNA Methyl," dated Apr. 30, 2018.
Final Rejection for U.S. Appl. No. 15/038,504, "Compositions and Methods for Diagnosing, Evaluating and Treating Cancer by Means of the DNA Methyl," dated Dec. 21, 2018.
Final Rejection for U.S. Appl. No. 15/102,129, "Formulations for Neoplasia Vaccines," dated Sep. 14, 2018.
Final Rejection for U.S. Appl. No. 15/105,961, "Combination Therapy With Neoantigen Vaccine," dated Jul. 5, 2018.
Final Rejection for U.S. Appl. No. 15/187,174, "Compositions and Methods of Identifying Tumor Specific Neoantigens," dated May 25, 2017.
Final Rejection for U.S. Appl. No. 15/187,174, "Compositions and Methods of Identifying Tumor Specific Neoantigens," dated Oct. 12, 2018.
Friedberg et al., "Inhibition of Syk with fostamatinib disodium has significant clinical activity in non-Hodgkin lymphoma and chronic lymphocytic leukemia," Blood, 115:2578-2585 (2011).
Gazdar, "Activating and resistance mutations of EGFR in non-small-cell lung cancer: role in clinical response to EGFR tyrosine kinase inhibitors," Oncogene, 28:S24-S31 (2009).
Han et al., "Linking T-Cell Receptor Sequence to Fucntional Phenotype at the Single-Cell Level," Nat Biotechnol, 32:684-692 (2014).
Hombrink et al., "Identification of Biological Relevant Minor Histocompatibility Antigens within the B-lymphocyte-Derived HLA-Ligandome Using a Reverse Immunology Approach," Clin Cancer Res, 21(9):2177-2186 (2015).
Illumina, "Immunotherapy, the Next Generation of Cancer Treatment, NGS-guided assessment of interactions between tumors and the immune system leads to new discoveries in immuno-oncology," (2016).
Jarmalavicius et al., "High Immunogenicity of the Human Leukocyte Antigen Peptidomes of Melanoma Tumor Cells," J Biol Chem, 287(40):33401-33411 (2012).
Johnson et al., "Discovery of Naturally Processed and HLA-Presented Class I Peptides from Vaccinia Virus Infection using Mass Spectrometry for Vaccine Development," Vaccine, 28(1):38-47 (2009).
Kalaora et al., "Use of HLA peptidomics and whole exome sequencing to identify human immunogenic neo-antigens," Oncotarget, 7(5):5110-5117 (2016).
Kandoth et al., "Mutational landscape and significance across 12 major cancer types," Nature, 502:333-339 (2013).
Keskin et al., "Neoantigen vaccine generates intratumoral T cell responses in phase lb glioblastoma trial," Nature, 565(7738):234-239 (2019).
Kim et al., "mTOR inhibitors radiosensitize PTEN-deficient non-small-cell lung cancer cells harboring an EGFR activating mutation by inducing autophagy," J Cell Biochem, 114(6):1248-1256 (2013).

(56) References Cited

OTHER PUBLICATIONS

Kim et al., "Positional Bias of MHC Class I Restricted T-Cell Epitopes in Viral Antigens Is Likely due to a Bias in Conservation," PLoS Comput Biol, 9:el002884 (2013).
Klug et al., "Characterization of MHC Ligands for Peptide Based Tumor Vaccination," Current Pharmaceutical Design, 15(28): 3221-3236 (2009).
Lata et al., "MHCBN 4.0: A database of MHC/TAP binding peptides and T-cell epitopes," BMC Research Notes, 2(1): 61 (2009).
Linardou et al., "Assessment of somatic k-RAS mutations as a mechanism associated with resistance to EGFR-targeted agents: a systematic review and meta-analysis of studies in advanced non-small-cell lung cancer and metastatic colorectal cancer," Lancet Oncol, 9(10):962-972 (2008).
Linardou et al., "Somatic EGFR mutations and efficacy of tyrosine kinase inhibitors in NSCLC," Nat Rev Clin Oncol, 6(6):352-366 (2009).
Lucas et al., "About human tumor antigens to be used in immunotherapy," Semin Immunol, 20(5):301-307 (2008).
Luo et al. "Machine learning methods for Predicting hla—Peptide Binding activity," Bioinformatics and Biology Insights, 9(s3):21-29 (2015).
Mosmann et al., "TH1 and TH2 Cells: Different Patterns of Lymphokine Secretion Lead to Different Functional Properties," Ann Rev Immunol, 7:145-173 (1989).
Nielsen et al., "NetMHCpan-3.0; improved prediction of binding to MHC class I molecules integrating information from multiple receptor and peptide length datasets," Genome Medicine, 8:33 (2016).
Non-Final Office Action for U.S. Appl. No. 13/108,610, "Compositions and Methods of Identifying Tumor Specific Neoantigens," dated Aug. 15, 2013.
Non-Final Office Action for U.S. Appl. No. 13/108,610, "Compositions and Methods of Identifying Tumor Specific Neoantigens," dated Dec. 3, 2014.
Non-Final Office Action for U.S. Appl. No. 14/794,449, "Compositions and Methods of Identifying Tumor Specific Neoantigens," dated Dec. 29, 2016.
Non-Final Office Action for U.S. Appl. No. 14/794,449, "Compositions and Methods of Identifying Tumor Specific Neoantigens," dated Jul., 24, 2018.
Non-Final Office Action for U.S. Appl. No. 14/877,125, "Compositions and Methods for Personalized Neoplasia Vaccines," dated Mar. 27, 2017.
Non-Final Office Action for U.S. Appl. No. 14/877,125, "Compositions and Methods for Personalized Neoplasia Vaccines," dated Nov. 2, 2018.
Non-Final Office Action for U.S. Appl. No. 15/038,504, "Compositions and Methods for Diagnosing, Evaluating and Treating Cancer by Means of the DNA Methyl," dated Sep. 6, 2017.
Non-Final Office Action for U.S. Appl. No. 15/102,129, "Formulations for Neoplasia Vaccines," dated Dec. 17, 2018.
Non-Final Office Action for U.S. Appl. No. 15/102,129, "Formulations for Neoplasia Vaccines," dated Jul. 28, 2017.
Non-Final Office Action for U.S. Appl. No. 15/102,129, "Formulations for Neoplasia Vaccines," dated Mar. 7, 2018.
Non-Final Office Action for U.S. Appl. No. 15/105,961, "Combination Therapy With Neoantigen Vaccine," dated Jan. 8, 2019.
Non-Final Office Action for U.S. Appl. No. 15/105,961, "Combination Therapy With Neoantigen Vaccine," dated Nov. 20, 2017.
Non-Final Office Action for U.S. Appl. No. 15/187,174, "Compositions and Methods of Identifying Tumor Specific Neoantigens," dated Dec. 5, 2016.
Non-Final Office Action for U.S. Appl. No. 15/187,174, "Compositions and Methods of Identifying Tumor Specific Neoantigens," dated Jan. 22, 2018.
Non-Final Office Action for U.S. Appl. No. 15/513,127, "Use of Clonal Evolution Analysis for Ibrutinib Resistance in Chronic Lymphocytic Leukemia Patients," dated Nov. 26, 2018.
Non-Final Office Action for U.S. Appl. No. 15/537,785, "Methods for Profiling the T Cell Repertoire," dated Dec. 21, 2018.
Non-Final Office Action for U.S. Appl. No. 16/181,098, "Compositions and Methods of Identifying Tumor Specific Neoantigens," dated Jan. 31, 2019.
Notice of Allowance for U.S. Appl. No. 13/108,610, "Compositions and Methods of Identifying Tumor Specific Neoantigens," dated Jun. 11, 2015.
Notice of Allowance for U.S. Appl. No. 13/108,610, "Compositions and Methods of Identifying Tumor Specific Neoantigens," dated May 12, 2015.
Notice of Allowance for U.S. Appl. No. 15/102,129, "Formulations for Neoplasia Vaccines," dated Oct. 12, 2018.
Assignment Register extract (accessed Oct. 20, 2016).
Prints-outs from the UniProtKB database concerning the CEP170, PARVA and FLT3 genes.
Restriction Requirement for U.S. Appl. No. 13/108,610, "Compositions and Methods of Identifying Tumor Specific Neoantigens," dated Mar. 7, 2013.
Restriction Requirement for U.S. Appl. No. 14/794,449, "Compositions and Methods of Identifying Tumor Specific Neoantigens," dated Oct. 26, 2016.
Restriction Requirement for U.S. Appl. No. 14/877,125, "Compositions and Methods for Personalized Neoplasia Vaccines," dated Nov. 18, 2016.
Restriction Requirement for U.S. Appl. No. 15/038,504, "Compositions and Methods for Diagnosing, Evaluating and Treating Cancer by Means of the DNA Methyl," dated Jun. 22, 2017.
Restriction Requirement for U.S. Appl. No. 15/102,129, "Formulations for Neoplasia Vaccines," dated May 8, 2017.
Restriction Requirement for U.S. Appl. No. 15/105,961, "Combination Therapy With Neoantigen Vaccine," dated Jul. 13, 2017.
Restriction Requirement for U.S. Appl. No. 15/187,174, "Compositions and Methods of Identifying Tumor Specific Neoantigens," dated Sep. 9, 2016.
Restriction Requirement for U.S. Appl. No. 15/513,127, "Use of Clonal Evolution Analysis for Ibrutinib Resistance in Chronic Lymphocytic Leukemia Patients," dated Aug. 13, 2018.
Restriction Requirement for U.S. Appl. No. 15/537,785, "Methods for Profiling the T Cell Repertoire," dated Mar. 22, 2018.
Restriction Requirement for U.S. Appl. No. 15/575,328, "Shared Neoantigens," dated Feb. 7, 2019.
Robinson et al., "DNA vaccines for viral infections: Basic studies and applications," Adv Virus Res, 55:1-74 (2000).
Rubin et al., "Mutation patterns in cancer genomes," PNAS, 106(51):21766-21770 (2009).
Sahin et al., "Personalized RNA mutanome vaccines mobilize poly-specific therapeutic immunity against cancer," Nature, 547(7662):222-226 (2017).
Srivastava et al., "Modeling the Repertoire of True Tumor-Specific MHC I Epitopes in a Human Tumor," PLoS One, 4(7):e6094 (2009).
Srivastava, "Therapeutic Cancer Vaccines," Curr Opin Immunol, 18: 201-205 (2006).
Stranzl et al., "NetCTLpan: pan-specific MHC class I pathway epitope predictions," Immunogenetics, 62(6):357-368 (2010).
Sun et al., Material bionics and Thinking Innovation, 176-177 (2012).
Tang et al., "NeoantigenR: An annotation based pipeline for tumor neoantigen identification from sequencing data," bioRxiv preprint first posted online Aug. 8, 2017.
Trolle et al., "Automated benchmarking of peptide-MHC class I binding predictions," Bioinformatics, 31(13):2174-2181 (2015).
Turchaninova et al., "Pairing of T-cell receptor chains via emulsion PCR," Eur J Immunol, 43:2507-2515 (2013).
Van Buuren et al., "High sensitivity of cancer exome-based CD8 T cell neo-antigen identification," Oncolmmunology, 3(5):e28836 (2014).
Vogel et al., "Mass Spectrometry Reveals Changes in MHC I Antigen Presentation After Lentivector Expression of a Gene Regulation System," Molecular Therapy—Nucleic Acids, 2:e75 (2013).
Wang et al., Functional Polymeric Material, 1-44 (2010).
Wraith, "The Future of Immunotherapy: A 20-Year Perspective," Front Immunol, 8:1668 (2017).

(56) References Cited

OTHER PUBLICATIONS

Zhang et al., "The impact of next-generation sequencing on genomics," J Genet Genomics, 38(3):95-109 (2011).
Zhang et al., Oncology, 1-44 (2005).
U.S. Appl. No. 16/188,737, filed Nov. 13, 2018, Pending.
U.S. Appl. No. 15/102,129, filed Jun. 6, 2016, 2016-0310584, Pending.
U.S. Appl. No. 15/537,839, filed Jun. 19, 2017, Pending.
U.S. Appl. No. 15/735,566, filed Dec. 11, 2017, Pending.
11781409.5 (opposition therin), May 16, 2011, 2569633, 2569633, Granted-opposition pending.
"CT-011 and p53 Genetic Vaccine for Advance Solid Tumor," National Library of Medicine, updated:Jun. 30, 2011, XP002738554, https://clinicaltrials.gov/archive/NCT01386502/2011_06_30, Clinical Trials Identifier NCT01386502.
"Monoclonal Antibody Therapy and Vaccine Therapy in Treating Patients with Stage IV Melanoma That Has Been Removed by Surgery," National Library of Medicine, 2010, XP002738553, https:clinicaltrials.gov/archive/NCT01176474/2010_08_05.
Acknowledgment of Receipt dated Jun. 28, 2017 for Response to Notices of Opposition of EP2569633.
Albert et al., "Direct Selection of Human Genomic Loci by Microarray Hybridization," Nat Methods, 4(11): 903-905 (2007).
Allison, "The Mode of Action of Immunological Adjuvants," Dev Biol Stand, 92: 3-11 (1998).
Alyea et al., "Toxicity and Efficacy of Defined Doses of CD4+ Donor Lymphocytes for Treatment of Relapse After Allogeneic Bone Marrow Transplant," Blood, 91(10):3671-3680 (1998).
Amara et al., "Control of a mucosal challenge and prevention of AIDS by a multiprotein DNA/MVA vaccine," Science, 292(5514):69-74 (2001).
Amato et al., "Vaccination of metastatic renal cancer patients with MVA-5T4: a randomized, double-blind, placebo-controlled phase III study," Clin Can Res, 16(22):5539-47 (2010).
Amato et al., "Vaccination of renal cell cancer patients with modified vaccinia ankara delivering tumor antigen 5T4 (TroVax) administered with interleukin 2: a phase II trial," Clin Cancer Res, 14(22):7504-10 (2008).
Anderson et al., "Next Generation DNA Sequencing and the Future of Genomic Medicine," Genes, 1:38-69 (2010).
Annunziata et al., "Frequent Engagement of the Classical and Alternative NF-KB Pathways by Diverse Genetic Abnormalities in Multiple Myeloma," Cancer Cell, 12(2):115-130 (2007).
Antoine et al., "The complete genomic sequence of the modified vaccinia Ankara strain: comparison with other orthopoxviruses," Virology, 244(2):365-96 (1998).
Antonis et al., "Vaccination with recombinant modified vaccinia virus Ankara expressing bovine respiratory syncytial virus (bRSV) proteins protects calves against RSV challenge," Vaccine, 25(25):4818-4827 (2007).
Applicant's Authorization and Release Form of the Massachusetts General Hospital, Aug. 12, 2008; and Supplemental Release to Applicant of the Partners Healthcare System, Aug. 13, 2008.
Attia et al., "Autoimmunity Correlates With Tumor Regression in Patients With Metastatic Melanoma Treated with Anti-Cytotoxic T-Lymphocyte Antigen-4," J Clin Oncol, 23.(25): 6043-6053 (2005).
Aucouturier et al., "Adjuvants designed for veterinary and human vaccines," Vaccine, 19(17-19):2666-2672 (2001).
Austen et al., "Mutations in the ATM Gene Lead to Impaired Overall and Treatment-Free Survival that is Independent of IGVH Mutation Status in Patients with B-CLL," Blood, 106(9):3175-3182 (2005).
Avogadri et al. "Modulation of CTLA-4 and GITR for Cancer Immunotherapy," Curr Top Microbiol Immunol, 344:211 (2011).
Azvolinsky et al., "PD-1 Inhibitor MK-3475 Again Shows Promise in Advanced Melanoma," Cancer Network, 2013. [Retrieved online] http://www.cancernetwork.com/melanoma/pd-1-inhibitor-mk-3475-again-shows-promise-advanced-melanoma.

Bachem et al., "Superior antigen cross-presentation and XCR1 expression define human CD11c+ CD141+ cells as homologues of mouse CD8+ dendritic cells," Journal of Experimental Medicine, 207(6):1273-1281 (2010).
Bachireddy et al., "Reversal of in situ T cell exhaustion during effective human anti-leukemia responses to donor lymphocyte infusion," Blood, 123(9):1412-1421 (2013).
Baden et al., "First-in-human evaluation of the safety and immunogenicity of a recombinant adenovirus serotype 26 FflV-1 Env vaccine (IPCAVD 001)," J Infect Dis, 207(2):240-247 (2012).
Balagaan et al., "Stable and efficient intraocular gene transfer using pseudotyped EIAV lentiviral vectors," J Gene Med, 8:275-285 (2005).
Balakrishnan et al, "Novel Somatic and Germline Mutations in Cancer Candidate Genes in Glioblastoma, Melanoma, and Pancreatic Carcinoma," Cancer Res, 67: 3545-3550 (2007).
Baskar et al., "Autologous Lymphoma Vaccines Induce Human T Cell Responses Against Multiple, Unique Epitopes," J Clin Invest, 113:1498-1510 (2004).
Baurain et al., "High Frequency of Autologous Anti-Melanoma CTL Directed Against an Antigen Generated by a Point Mutation in a New Helicase Gene," J Immunol, 164: 6057-6066 (2000).
Beck et al., "Enterocolitis in Patients With Cancer After Antibody Blockade of Cytotoxicity TLymphocyte-Associated Antigen 4," J Clin Oncol, 24(15): 2283-2289 (2006).
Bellucci et al., "Complete Response to Donor Lymphocyte Infusion in Multiple Myeloma is Associated with Antibody Responses to Highly Expressed Antigens," Blood, 103: 656-663 (2004).
Bentley et al., "Accurate Whole Human Genome Sequencing using Reversible Terminator Chemistry," Nature, 456(7218): 53-59 (2008).
Bettelli et al., "TH-17 cells in the circle of immunity and autoimmunity," Nat Immunol, 8:345-350 (2007).
Bhardwaj et al., "TLR AGONISTS: Are They Good Adjuvants?," Cancer J, 16:382-391 (2010).
Bisht et al., "Severe acute respiratory syndrome coronavirus spike protein expressed by attenuated vaccinia virus protectively immunizes mice," Proc Natl Acad Sci, 101:6641-46 (2004).
Blanchard et al., "Modified vaccinia virus Ankara undergoes limited replication in human cells and lacks several immunomodulatory proteins: implications for use as a human vaccine," Journal of General Virology, 79(5):1159-1167 (1998).
Boisguerin et al., "Translation of genomis-guided RNA-based personalised cancer vaccaines: towards the bedside," British J Cancer, 111:1469-1475 (2014).
Boni et al. "Adoptive transfer of allogeneic tumor-specific T cells mediates effective regression of large tumors across major histocompatibility barriers," Blood, 112(12):4746-4754 (2008).
Boon, "Toward a Genetic Analysis of Tumor Rejection Antigens," Adv Cancer Res, 58:177-210 (1992).
Bowerman et al., "Engineering the binding properties of the T cell receptor:peptide:MHC ternary complex that governs T cell activity," Mol Immunol, 46(15):3000-3008 (2009).
Brandle et al., "A Mutated HLA-A2 Molecule Recognized by Autologous Cytotoxic T Lymphocytes on a Human Renal Cell Carcinoma," J Exp Med, 183: 2501-2508 (1996).
Brinckerhoff et al., "Melanoma Vaccines," Curr Opin Oncol, 12:163-173 (2000).
Broad Institute Article, Jan. 29, 2009, "Turning Cancer's Strength Into Weakness," (2009).
Brochier et al., "Large-scale eradication of rabies using recombinant vaccinia-rabies vaccine," Nature, 354:520-552 (1991).
Brown et al., "Neo-antigens predicted by tumor genome meta-analysis correlate with increased patient survival," Genome Res, 24(5):743-750 (2014).
Brunsvig et al., "Telomerase Peptide Vaccination: A Phase I/II Study in Patients with Non-Small Cell Lung Cancer," Cancer Immunol Immunother, 55(12): 1553-1564 (2006).
Buchschacher et al., "Human immunodeficiency virus vectors for inducible expression of foreign genes." Journal of virology, 66(5):2731-2739 (1992).
Buckwalter et al., "'It is the antigen(s), stupid' and other lessons from over a decade of vaccitherapy of human cancer," Seminar in Immunology, 20(5):296-300 (2008).

(56) References Cited

OTHER PUBLICATIONS

Buller et al., "Decreased virulence of recombinant vaccinia virus expression vectors is associated with a thymidine kinase-negative phenotype," Nature, 317:813-815 (1985).
Buller et al., "Deletion of the vaccinia virus growth factor gene reduces virus virulence," Journal of virology, 62(3):866-874 (1988).
Burger et al., "Safety and activity of ibrutinib plus rituximab for patients with high-risk chronic lymphocytic leukaemia: a single-arm, phase 2 study," Lancet Oncology, 15(10):1090-1099 (2014).
Böhm et al., DNA vector constructs that prime hepatitis B surface antigen-specific cytotoxic T lymphocyte and antibody responses in mice after intramuscular injection. Journal of immunological methods 193(1): 29-40 (1996).
Cai et al., "Peptides Derived From Mutated BCR-ABL Elicit T Cell Immunity in CML Patients," Blood, 116(21): 388-388 (2010).
Carpten et al., "A transforming mutation in the pleckstrin homology domain of AKT1 in cancer," Nature, 448(26):439-444 (2004).
Carreno et al., "IL-12p70-producing patient DC vaccine elicits Tc1-polarized immunity," Journal of Clinical Investigation, 123(8):3383-94 (2013).
Carter et al., "Identification and validation of cell surface antigens for antibody targeting in oncology," Endocrine-Related Cancer, 11:659-687 (2004).
Caskey et al., "Synthetic double-stranded RNA induces innate immune responses similar to a live viral vaccine in humans," The Journal of experimental medicine, 208(12):2357-2366 (2011).
Certified Priority Document for U.S. Appl.n No. 61/334,866, filed May 14, 2010.
Chang et al., "Peptide length-based prediction of peptide-MHC class II binding," Bioinformatics, 22(22): 2761-2767 (2006).
Chatila, "The Regulatory T Cell Transcriptosome: E Pluribus Unum," Immunity, 27(5):693-695 (2007).
Chen et al., "Recombinant modified vaccinia virus Ankara expressing the spike glycoprotein of severe acute respiratory syndrome coronavirus induces protective neutralizing antibodies primarily targeting the receptor binding region," Journal of virology, 79.5:2678-2688 (2005).
Chen et al.,"Induction of CD8+ T cell responses to dominant and subdominant epitopes and protective immunity to Sendai virus infection by DNA vaccination," The Journal of Immunology, 160(5):2425-2432 (1998).
Chianese-Bullock et al., "Multi-peptide vaccines vialed as peptide mixtures can be stable reagents for use in peptide-based immune therapies," Vaccine, 27(11):1764-1770 (2009).
Chiari et al., "Two Antigens Recognized by Autologous Cytolytic T Lymphocytes on a Melanoma Result from a Single Point Mutation in an Essential Housekeeping Gene," Cancer Res, 59: 5785-5792 (1999).
Child et al., "Insertional inactivation of the large subunit of ribonucleotide reductase encoded by vaccinia virus is associated with reduced virulence in vivo," Virology, 174(2):625-629 (1990).
Chinese Office Action dated Jun. 12, 2017 in corresponding CN Application No. 2014800322910.
Chroboczek et al., "The Sequence of the Genome of Adenovirus Type 5 and Its Comparison with the Genome of Adenovirus Type 2," Virology, 186:280-285 (1992).
Ciofani et al., "A Validated Regulatory Network for Th17 Cell Specification," Cell, 151(2):289-303 (2012).
Clinical trial NCT 01970358, Patrick Ott, A Phase I Study With a Personalized NeoAntigen Cancer Vaccine in Melanoma, p. 1-6, Retrieved from https://clinicaltrials.gov/ct2/show/NCT01970358 downloaded Jun. 20, 2017.
Coffman et al., "Vaccine Adjuvants: Putting Innate Immunity to Work," Immunity 33:492-503 (2010).
Conlon et al., "Mouse, but not Human STING, Binds and Signals in Response to the Vascular Disrupting Agent 5,6-Dimethylxanthenone-4-Acetic Acid," Journal of Immunology, 190:5216-25 (2013).
Consolidated Table of Documents filed in Opposition to date in Response to Notices of Opposition of EP2569633 dated Jun. 28, 2017.

Corbett et al., "Aerosol immunization with NYVAC and MVA vectored vaccines is safe, simple, and immunogenic," Proc Natl Acad Sci, 105(6):2046-51 (2008).
Cox et al., "Induction of cytotoxic T lymphocytes by recombinant canarypox (ALVAC) and attenuated vaccinia (NYVAC) viruses expressing the HIV-1 envelope glycoprotein," Virology, 195(2):845-850 (1993).
Crozat et al., "The XC chemokine receptor 1 is a conserved selective marker of mammalian cells homologous to mouse CD8α+ dendritic cells," Journal of Experimental Medicine, 207(6):1283-1292 (2010).
Daheshia et al., "Suppression of ongoing ocular inflammatory disease by topical administration of plasmid DNA encoding IL-10," The Journal of Immunology 159(4):1945-1952 (1997).
De Plaen et al., "Immunogenic (tum-) Variants of Mouse Tumor P815: Cloning of the Gene of Tum-Antigen P91A and Identification of the Tum-Mutation," PNAS, 85: 2274-2278 (1988).
Declaration by Stephen Johnston filed during the prosecution of granted U.S. Pat. No. 8,796,414 Nov. 20, 2013.
Declaration of Dr Nir Hacohen on Feb. 16, 2014.
Declaration of Dr. John C. Castle executed on Nov. 9, 2016.
Dengjel et al., "Glycan side chains on naturally presented MHC class II ligands," J. Mass Spectrom, 40:100-104 (2005).
Dermer et al., "Another Anniversary for the War on Cancer," Biotech, 12:320 (1994).
Didierlaurent et al., "Attenuated poxviruses expressing a synthetic HIV protein stimulate HLA-A2-restricted cytotoxic T-cell responses," Vaccine, 22(25-26):3395-3403 (2004).
Ding et al., "Genome remodelling in a basal-like breast cancer metastasis and xenograft," Nature, 464:999-1005 (2010).
Dreicer et al., "Mva-MUC1-IL2 vaccine immunotherapy (TG4010) improves PSA doubling time in patients with prostate cancer with biochemical failure," Investigational new drugs, 27(4):379-386 (2009).
Dudley et al., "Cancer Regression and Autoimmunity in Patients After Clonal Repopulation with Antitumor Lymphocytes," Science, 298: 850-854 (2002).
DuPage et al., "Expression of tumour-specific antigens underlies cancer immunoediting," Nature, 482(7385):405-409 (2012).
Dupuis et al., "Dendritic Cells Internalize Vaccine Adjuvant after Intramuscular Injection," Cell Immunol, 186(1): 18-27 (1998).
Earl et al., "Immunogenicity of a highly attenuated MVA smallpox vaccine and protection against monkeypox," Nature, 428:182 (2004).
Engelhard, "Structure of peptides associated with MHC class I molecules," Curr Opin Immunol, 6(1):13-23 (1994).
Erlich et al., "Next-generation sequencing for HLA typing of class I loci," BMC Genomics, 12:42 (2011).
Esteban, "Attenuated poxvirus vectors MVA and NYVAC as promising vaccine cadidates against HIV/AIDS," Human vaccines, 5(12):867-871 (2009).
Estep et al., "Mutation Analysis of BRAF, MEK1 and MEK2 in 15 Ovarian Cancer Cell Lines: Implications for Therapy," PLoS One, 12:e1279 (2007).
Extended European Search Report dated Apr. 11, 2016, which issued during prosecution of EP Application No. 15198284.0.
Extended European Search Report received for EP patent application No. EP11781409, dated Apr. 10, 2014.
Extended Search Report in Corresponding European Application No. 11781409.5, dated Apr. 14, 2014.
Ezzell, "Cancer 'Vaccines': An idea whose time has come?," J NIH Res, 7:46 (1995).
Farsaci et al., "Consequence of dose scheduling of sunitinib on host immune response elements and vaccine combination therapy," Int J Cancer, 130:1948-1959 (2012).
Felgner et al., "Lipofection: A Highly Efficient, Lipid-Mediated DNA-Transfection Procedure," PNAS, 84(21): 7413-7417 (1987).
Ferrier-Rembert et al., "Short-and long-term immunogenicity and protection induced by non-replicating smallpox vaccine candidates in mice and comparison with the traditional 1st generation vaccine," Vaccine, 26(14):1794-1804 (2008).
Finke et al., "Sunitinib Reverses Type-1 Immune Suppression and Decreases T-Regulatory Cells in Renal Cell Carcinoma Patients," Clin Cancer Res, 14(20):6674-6682 (2008).

(56) References Cited

OTHER PUBLICATIONS

Flexner et al., "Prevention of vaccinia virus infection in imiminodeficient mice by vector-directed IL-2 expression," Nature, 330(6145):259-262 (1987).
Frederick et al., "BRAF inhibition is associated with enhanced melanoma antigen expression and a more favorable tumor microenvironment in patients with metastatic melanoma," Clin Cancer Res, 19:1225-1231 (2013).
Fritsch et al., "Personal neoantigen cancer vaccines: The momentum builds," Oncoimmunology, 3(6):e29311 (2014).
Fynan et al., "DNA vaccines: protective immunizations by parenteral, mucosal, and gene-gun inoculations," PNAS, 90 (24): 11478-82 (1993).
Gabrilovich et al., "IL-12 and Mutant P53 Peptide-Pulsed Dendritic Cells for the Specific Immunotherapy of Cancer," J Immunother Emphasis Tumor Immunol, 19(6): 414-418 (1996).
Gallego-Gomez et al., "Differences in virus-induced cell morphology and in virus maturation between MVA and other strains (WR, Ankara, and NYCBH) of vaccinia virus in infected human cells," Journal of virology, 77(19):10606-10622 (2003).
Gallois et al., "A needle in the 'cancer vaccine' haystack," Nature medicine, 16(8):854-856 (2010).
Garcia-Marco et al., "Frequent Somatic Deletion of the 13q12.3 locus Encompassing BRCA2 in Chronic Lymphocytic Leukemia," Blood, 88: 1568-1575 (1996).
Gherardi et al., "Prime-boost immunization schedules based on influenza virus and vaccinia virus vectors potentiate cellular immune responses against human immunodeficiency virus Env protein systemically and in the genitorectal draining lymph nodes," Journal of virology, 77(12):7048-7057 (2003).
Ghiringhelli et al., "Metronomic cyclophosphamide regimen selectively depletes CD4+CD25+ regulatory T cells and restores T and NK effector functions in end stage cancer patients," Cancer Immunol Immunother, 56:641-648 (2007).
Gibney et al., "Safety and efficacy of adjuvant anti-PD1 therapy (nivolumab) in combination with vaccine in resected high-risk metastatic melanoma.," J Clin Oncol, Abstract 9056 (2013).
Gilboa, "The Makings of a Tumor Rejection Antigen," Immunity, 11: 263-270 (1999).
Gluzman, "SV40-transformed simian cells support the replication of early SV40 mutants," Cell, 23:175-182 (1981).
Gnirke et al., "Solution Hybrid Selection with Ultra-Long Oligonucleotides for Massively Parallel Targeted Sequencing," Nat Biotechnol, 27(2): 182-189 (2009).
Goebel et al., "The complete DNA sequence of vaccinia virus," Virology, 179(1):247-266 (1990).
Gomez et al., "Efficient CD8+ T cell response to the HIV-env V3 loop epitope from multiple virus isolates by a DNA prime/vaccinia virus boost (rWR and rMVA strains) immunization regime and enhancement by the cytokine IFN-γ," Virus research, 105:11-22 (2004).
Gomez et al., "Head-to-head comparison on the immunogenicity of two HIV/AIDS vaccine candidates based on the attenuated poxvirus strains MVA and NYVAC co-expressing in a single locus the HIV-1 BX08 gp120 and HIV-1IIIB Gag-Pol-Nef proteins of Glade B," Vaccine, 25(15):2863-2885 (2007).
Gomez et al., "MVA and NYVAC as vaccines against emergent infectious diseases and cancer," Current gene therapy, 11(:3):189-217 (2011).
Gomez et al., "The poxvirus vectors MVA and NYVAC as gene delivery systems for vaccination against infectious diseases and cancer," Current gene therapy, 8(2):97-120 (2008).
Gomez et al., "Virus distribution of the attenuated MVA and NYVAC poxvirus strains in mice," Journal of General Virology, 88(9):2473-2478 (2007).
Gotter et al., "Medullary Epithelial Cells of the Human Thymus Express a Highly Diverse Selection of Tissue-specific Genes Colocalized in Chromosomal Clusters," J Exp Med, 199(2):155-166 (2004).
Goya et al., "SNVMix:predicting single nucleotide variants from next-generation sequencing of tumors," Bioinformatics, Original Paper, 26(6): 730-736 (2010).
Greco et al., "Improving the safety of cell therapy with the TK-suicide gene," Front Pharmacol, 6:95 (2015).
Greenman et al., "Patterns of somatic mutation in human cancer genomes," Nature, 446:153-158 (2007).
Gregoriadis et al., "Improving the therapeutic efficacy of peptides and proteins: A role for polysialic acids," Int J Pharmaceutics, 300(1-2):125-30 (2005).
Gubin et al., "Checkpoint blockade cancer immunotherapy targets tumor-specific mutant antigens," Nature, 515:577-581 (2014).
Gueguen et al., "An Antigen Recognized by Autologous CTLs on a Human Bladder Carcinoma," J Immunol, 160(12): 6188-6194 (1998).
Guo et al., "Different length peptides bind to HLA-Aw68 similarity at their ends but bulge on in the middle," Nature, 360:364-366 (1992).
Hacohen et al., "Getting Personal with Neoantigen-Based Therapeutic Cancer Vaccines," Cancer Immunol. Res, 1(1):11-15 (2013).
Halabi et al., "Prognostic model for predicting survival in men with hormone-refractory metastatic prostate cancer," Journal of Clinical Oncology, 21(7):1232-1237 (2003).
Hel et al., "Potentiation of simian immunodeficiency virus (SIV)-specific CD4+ and CD8+ T cell responses by a DNA-SIV and NYVAC-SIV prime/boost regimen," The Journal of Immunology, 167(12):7180-7191 (2001).
Herbst et al., "Predictive Correlates of Response to the Anti-PD-L1 Antibody MPDL3280A in Cancer Patients," Nature, 515(7528):563-567 (2014).
Herman et al., "Differences in the Recognition by CTL of Peptides Presented by the HLAB* 4402 and the HLA-B*4403 Molecules Which Differ by a Single Amino Acid," Tissue Antigens, 53: 111-121 (1999).
Hersey et al., "Phase I/II study of treatment with dendritic cell vaccines in patient with disseminated melanoma," Cancer Immunol Immunoother, 53:125-134 (2004).
Hocker et al., "Ultraviolet Radiation and Melanoma: A Systematic Review and Analysis of Reported Sequence Variants," Hum Mutat, 28(6): 578-588 (2007).
Hodi et al., "Biologic Activity of Cytotoxic T Lymphocyte-Associated Antigen 4 Antibody Blockade in Previously Vaccinated Metastatic Melanoma and Ovarian Carcinoma Patients," PNAS, 100: 4712-4717 (2003).
Hodi et al., "Immunologic and Clinical Effects of Antibody Blockade of Cytotoxic T Lymphocyte-Associated Antigen 4 in Previously Vaccinated Cancer Patients," PNAS, 105: 3005-3010 (2008).
Hodi et al., "Improved Survival with Ipilimumab in Patients with Metastatic Melanoma," New Engl J Med, 363:711-723 (2010).
Honig et al., "Phase 1 clinical trial of a recombinant canarypoxvirus (ALVAC) vaccine expressing human carcinoembryonic antigen and the B7.1 co-stimulatory molecule," Cancer Immunol Immunother, 49:504-514 (2000).
Huang et al., "Mucosal priming with replicative Tiantan vaccinia and systemic boosting with DNA vaccine raised strong mucosal and systemic HIV-specific immune responses," Vaccine, 25(52):8874-8884 (2007).
Huang et al., "T Cells Associated With Tumor Regression Recognize Frameshifted Products of the CDKN2A Tumor Suppressor Gene Locus and a Mutated HLA Class I Gene Product," J Immunol, 172(10):6057-6064 (2004).
Humphries et al., "Lineage tracing reveals multipotent stem cells maintain human adenomas and the pattern of clonal expansion in tumor evolution," PNAS, 110(27):e2490-e2499 (2013).
Hutchings et al., "Combination of protein and viral vaccines induces potent cellular and humoral immune responses and enhanced protection from murine malaria challenge," Infect Immun, 75(12):5819-26 (2007).
Intellectual Property Policy for Partners-Affiliated Hospitals and Institutions, Aug. 15, 2002.
International Preliminary Report on Patentability for International Application No. PCT/US2011/036665 dated Nov. 20, 2012.
International Preliminary Report on Patentability for International Application No. PCT/US2014/033185 dated Oct. 22, 2015.

(56) References Cited

OTHER PUBLICATIONS

International Preliminary Report on Patentability for International Application No. PCT/US2014/067146 dated May 31, 2016.
International Preliminary Report on Patentability for International Application No. PCT/US2014/068746 dated Jun. 7, 2016.
International Preliminary Report on Patentability for International Application No. PCT/US2014/068893 dated Jun. 7, 2016.
International Preliminary Report on Patentability for International Application No. PCT/US2014/071707 dated Jun. 21, 2016.
International Preliminary Report on Patentability for International Application No. PCT/US2015/067143 dated Jun. 20, 2017.
International Search Report and Written Opinion for International Application No. PCT/US/2015/051340 dated Dec. 21, 2015.
International Search Report and Written Opinion for International Application No. PCT/US/2016/033452 dated May 20, 2016.
International Search Report and Written Opinion for International Application No. PCT/US/2016/036605 dated Jan. 16, 2017.
International Search Report and Written Opinion for International Application No. PCT/US2011/036665 dated Jul. 2, 2012.
International Search Report and Written Opinion for International Application No. PCT/US2014/033185 dated Nov. 5, 2014.
International Search Report and Written Opinion for International Application No. PCT/US2014/067146 dated Mar. 31, 2015.
International Search Report and Written Opinion for International Application No. PCT/US2015/067143 dated Apr. 12, 2016.
International Search Report for International Application No. PCT/US2014/068746 dated Mar. 23, 2015.
International Search Report for International Application No. PCT/US2014/068893 dated Apr. 9, 2015.
International Search Report for International Application No. PCT/US2014/071707 dated Sep. 10, 2015.
Invention Agreement of the Dana-Farber Cancer Institute, 1 Jul. 1997.
Itoh et al., "Personalized peptide vaccines: A new therapeutic modality for cancer," Cancer Sci, 97:970-976 (2006).
Japanese Office Action dated Jan. 22, 2018, which issured during prosecution of JP 2016-507587.
Japanese Office Action from Application No. 2013-510360 dated Apr. 28, 2015.
Jensen et al., "Design and implementation of adoptive therapy with chimeric antigen receptor-modified T cells," Immunol Rev, 257(1):127-144 (2014).
Ji et al., "An immune-active tumor microenvironment favors clinical response to ipilimumab," Cancer Immunol Immunother, 61(7):1019-1031 (2011).
Jocham et al., "Adjuvant Autologous Renal Tumour Cell Vaccine and Risk of Tumour Progression in Patients with Renal-Cell Carcinoma After Radical Nephrectomy: Phase III, Randomised Controlled Trial," Lancet, 363: 594-599 (2004).
Johann et al., "GLVR1, a receptor for gibbon ape leukemia virus, is homologous to a phosphate permease of Neurospora crassa and is expressed at high levels in the brain and thymus," Journal of Virology, 66(3):1635-1640 (1992).
Jun et al., "Progress in T cell adoptive Immunotherapy for Malignant Solid Tumors," Chin Med Biotechnol, 3(1):1-7 (2008).
Kanduri et al., "Differential genome-wide array-based methylation profiles in prognostic subsets of chronic lymphocytic leukemia," Blood, 115(2):296-305 (2010).
Kantoff et al. "Overall survival analysis of a phase II randomized controlled trial of a Poxviral-based PSA-targeted immunotherapy in metastatic castration-resistant prostate cancer," Journal of Clinical Oncology, 28(7):1099-1105 (2010).
Kanzler et al., "Therapeutic Targeting of Innate Immunity with Toll-like Receptor Agonists and Antagonists," Nat Med, 13: 552-559 (2007).
Karanikas et al., "High frequency of cytolytic T lymphocytes directed against a tumor-specific mutated antigen detectable with HLA tetramers in the blood of a lung carcinoma patient with long survival," Cancer Res, 61:3718-3724 (2001).

Kaufman et al., "Phase II randomized study of vaccine treatment of advanced prostate cancer (E7897): a trial of the Eastern Cooperative Oncology Group," Journal of Clinical Oncology, 22(11):2122-2132 (2004).
Kawakami et al., "Identification of human tumor antigens and its implications for diagnosis and treatment of cancer," Cancer Sci, 95(10): 784-791 (2004).
Keats et al., "Promiscuous Mutations Activate the Noncanonical NF-KB Pathway in Multiple Myeloma," Cancer Cell, 12: 131-144 (2007).
Kenter et al., "Phase I Immunotherapeutic Trial with Long Peptides Spanning the E6 and E7 Sequences of High-Risk Human Papillomavirus 16 in End-Stage Cervical Cancer Patients Show Low Toxicity and Robust Immunogenicity," Clin. Cancer Research, 14(1):169-177 (2008).
Keogh et al., "Identification of New Epitopes from Four Different Tumor-Associated Antigens: Recognition of Naturally Processed Epitopes Correlates with HLA-A□201-Binding Affinity," J Immunol, 167:787-796 (2001).
Kessler et al., "Identification of T-cell epitopes for cancer immunotherapy," Leukemia, 21:1859-1874 (2007).
Khalili et al., "In silico prediction of tumor antigens derived from functional missense mutations of the cancer gene census," Oncoimmunology, 1(8):1281-1289 (2012).
Kim et al., "Anticancer flavonoids are mouse-selective STING agonists," ACS chemical biology, 8(7):1396-1401 (2013).
Kim et al., "TroVax, a recombinant modified vaccinia Ankara virus encoding 5T4: lessons learned and future development," Human vaccines, 6(10):784-791 (2010).
Kobayashi et al., "Peptide epitope identification for tumor-reactive CD4 T cells," Current opinion in immunology, 20(2):221-227 (2008).
Koh et al., "Immunological consequences of using three different clinical/laboratory techniques of emulsifying peptide-based vaccines in incomplete Freund's adjuvant," J Translational Med, 4:42 (2006).
Komarova et al., "Evolution of Ibrutinib Resistance in Chronic Lymphcytic Leukemia (CLL)," Proceedings of the National Academy of Sciences, 111(38):13906-13911 (2014).
Kornher et al., "Mutation Detection Using Nucleotide Analogs That Alter Electrophoretic Mobility," Nucleic Acids Res, 17(19): 7779-7784 (1989).
Kotwal et al., "Vaccinia virus encodes two proteins that are structurally related to members of the plasma serine protease inhibitor superfamily," Journal of virology, 63(2):600-606 (1989).
Kreiter et al., "Mutant MHC Class II epitopes drive therapeutic immune responses to cancer," Nature, 520:692 (2015).
Krieg, "Therapeutic potential of Toll-like receptor 9 activation," Nature reviews Drug discovery, 5(6):471-484 (2006).
Kronenberger et al., "A Polyvalent Cellular Vaccine Induces T-cell Responses Against Specific Self-antigens Overexpressed in Chronic Lymphocytic B-cell Leukemia," J Immunother, 31(8):723-730 (2008).
Kuppuswamy et al., "Single Nucleotide Primer Extension to Detect Genetic Diseases: Experimental Application to Hemophilia B (Factor IX) and Cystic Fibrosis Genes," PNAS, 88(4): 1143-1147 (1991).
Kyte et al., "Telomerase Peptide Vaccination Combined with Temozolomide: A Clinical Trial in Stage IV Melanoma Patients," Clin Cancer Res, 17(13):4568-4580 (2011).
Ladetto et al., "Real-Time Polymerase Chain Reaction in Multiple Myeloma: Quantitative Analysis of Tumor Contamination of Stem Cell Harvests," Exp Hematol, 30: 529-536 (2002).
Landau et al., "Chronic lymphocytic leukemia: molecular heterogeneity revealed by high-throughput genomics," Genome Med, 5:47 (2013).
Landau et al., "Evolution and Impact of Subclonal Mutations in Chronic Lymphocytic Leukemia," Cell, 152:714-726 (2013).
Landau et al., "Increased Local Disorder of DNA Methylation Forms the Basis of High Intra-Leukemic Epigenetic Heterogeneity and Enhances CLL Evolution," Blood, 122:596 (2013).

(56) References Cited

OTHER PUBLICATIONS

Le et al., "Next-Generation Cancer Vaccine Approaches: Integrating Lessons Learned From Current Successes With Promising Biotechnologic Advances," J Natl Compr Cancer Network, 11:766-772 (2013).
Le Mercier et al., "Beyond CTLA-4 and PD-1, the generation Z of negative checkpoint regulators," Front Immunol, 6:418 (2015).
Leitner et al., "Immune responses induced by intramuscular or gene gun injection of protective deoxyribonucleic acid vaccines that express the circumsporozoite protein from Plasmodium berghei malaria parasites," J Immunol, 159(12):6112-6119 (1997).
Lemmel et al., "Differential quantitative analysis of MHC ligands by mass spectrometry using stable isotope labeling," Nature Biotechnology, 22(4):450-454 (2004).
Lennerz et al., "The Response of Autologous T Cells to a Human Melanoma is Dominated by Mutated Neoantigens," PNAS, 102(44):16013-10618 (2005).
Letter from Mathys & Squire dated Jun. 28, 2017 accompanying Response to Notices of Opposition of EP2569633.
Letter from Mathys & Squire dated Jun. 29, 2017+B245:B256.
Lewin et al., "DNA is the Genetic Material: Mutations Change the Sequence of DNA," Genes IV, 4:68-69 (1990).
Lewis et al., "DNA Vaccines: A Review," Advances in Virus Research, 54:129-88 (1999).
Ley et al., "DNA sequencing of a cytogenetically normal acute myeloid leukaemia genome," Nature, 456: 66-72 (2008).
Ley et al., "DNMT3A Mutations in Acute Myeloid Leukemia, The New England Journal of Medicine," 363: 2423-2433 (2010).
Li et al., "Cancer Genome Sequencing and Its Implications for Personalized Cancer Vaccines," Cancers 3(4):4191-4211 (2011).
Lin et al., "Evaluation of Mhc-II Peptide Binding Prediction Servers: Applications for Vaccine Research," BMC Bioinformatics, 9: S22 (2008).
Linard et al., "A ras-Mutated Peptide Targeted by CTL Infiltrating a Human Melanoma Lesion," J Immunol, 168:4802-4808 (2002).
Lindhout et al., "Site-specific enzymatic polysialylation of therapeutic proteins using bacterial enzymes," PNAS, 108(18):7397-7402 (2011).
Linnemann et al., "High-throughput identification of antigen-specific TCRs by TCR gene capture," Nat Med, 19(11):1534-1541 (2013).
Liu et al., "Athlates:accurate typing of human leukocyte antigen through exome sequencing," Nucleic Acids Res, 41(14):e142 (2013).
Luckow al.,"Trends in the Development of Baculovirus Expression Vectors," Nat Biotechnol, 6:47-55 (1988).
Lundegaard et al., "NetMHC-3.0: accurate web accessible predictions of human, mouse and monkey MHC class I affinities for peptides of length 8-11," Nucleic Acids Research, 36: W509.W512 (2008).
Lundegaard et al., "Prediction of epitopes using neural network based methods," J Immunol Methods, 374(1-2):26-34 (2011).
Lundegaard et al., "State of the art and challenges in sequence based T-cell epitope prediction," Immunome Research, 6(Suppl 2): S3 (2010).
Macconaill et al., Profiling Critical Cancer Gene Mutations in Clinical Tumor Samples, PLoS One, 4(11):e7887 (2009).
Machiels et al., "Peptide-Based Cancer Vaccines," Seminars in Oncology, 29(5):494-502 (2002).
Mackett et al., "Vaccinia virus: a selectable eukaryotic cloning and expression vector," PNAS, 79:7415-7419 (1982).
Maeurer et al., "New treatment options for patients with melanoma: review of melanoma-derived T-cell epitopebased peptide vaccines," Melanom Research, 6:11-24 (1996).
Maker et al., "Intrapatient Dose Escalation of Anti-CTLA-4 Antibody in Patients With Metastatic Melanoma," J Immunother, 29: 455-463 (1997).
Malavota et al., "Interpretation of the dissolution of insoluble peptide sequences based on the acid☐base properties of the solvent," Protein Sci, 15(6):1476-1488 (2006).

Malcikova et al., "Identification of somatic hypermutations in the TP53 gene in B-cell chronic lymphocytic leukemia," Molecular Immunol, 45(5):1525-1529 (2008).
Mandelboim et al., "Regression of Established Murine Carcinoma Metastases Following Vaccination with Tumor-Associated Antigen Peptides," Nature Medicine, 1(11):1179-1183 (1995).
Mandl et al., "Immunotherapy with MVA-BN®-HER2 induces HER-2-specific Th1 immunity and alters the intratumoral balance of effector and regulatory T cells," Cancer Immunol Immunother, 61(1):19-29 (2012).
Mandruzzato et al., "A CASP-8 Mutation Recognized by Cytolytic T Lymphocytes on a Human Head and Neck Carcinoma," J Exp Med, 186: 785-793 (1997).
Mannino et al., "Liposome Mediated Gene Transfer," Biotechniques, 6(7): 682-690 (1988).
Maratea et al. "Deletion and fusion analysis of the phage φX174 lysis gene E," Gene 40(1):39-46 (1985).
Mardis et al., "Cancer genome sequencing: a review," Human Molecular Genetics, 18(2):R163-R168 (2009).
Mardis et al., "Recurring Mutations Found by Sequencing an Acute Myeloid Leukemia Genome," New Engl J Med, 361:1058-1066 (2009).
Margulies et al., "Genome Sequencing in Open Microfabricated High Density Picoliter Reactors," Nature, 15:437(7057): 376-380 (2005).
Marijt et al., "Hematopoiesis-Restricted Minor Histocompatibility Antigens HA-1-or HA-2-specific T Cells can Induce Complete Remissions of Relapsed Leukemia," PNAS, 100: 2742-2747 (2003).
Marina et al., "Serologic Markers of Effective Tumor Immunity Against Chronic Lymphocytic Leukemia Include Nonmutated B-Cell Antigens," Cancer Res, 70(4): 1344-1355 (2010).
Mark et al., "Site-specific mutagenesis of the human fibroblast interferon gene," PNAS, 81(18):5662-5666 (1984).
Marshall et al., "Phase I Study in Cancer Patients of a Replication-Defective Avipox Recombinant Vaccine That Expresses Human Carcinoembryonic Antigen," J Clin Oncol, 17:332-337 (1999).
Matsushita et al., "Cancer Exome Analysis Reveals a T Cell Dependent Mechanism of Cancer Immunoediting," Nature, 482(7385):400-404 (2012).
Maus et al., "Adoptive Immunotherapy for Cancer or Viruses," Annual Review of Immunology, 32:189-225 (2014).
Mayr et al., "Abstammung, Eigenschaften and Verwendung des attenuierten Vaccinia-Stammes MVA (Translated Summary)," Infection, 3(1):6-14 (1975).
Mayr, "The smallpox vaccination strain MVA: marker, genetic structure, experience gained with the parenteral vaccination and behavior in organisms with a debilitated defence mechanism (author's transl)," Zentralbl Bakteriol 167(5-6):375-9 (1978).
McCurdy et al., "Modified Vaccinia Ankara: Potential as an Alternative Smallpox Vaccine," Clin Infect Dis, 38:1749-1753 (2004).
Melief et al., "Immunotherapy of established (pre)malignant disease by synthetic long peptide vaccines," Nature Rev Cancer, 8:351-360 (2008).
Men et al., "Assessment of Immunogenicity of Human Melan-A Peptide Analogues in HLA-A*0201/Kb Transgenic Mice," J Immunol, 162:3566-3573 (1999).
Merrifield, "Solid Phase Peptide Synthesis. I. The Synthesis of a Tetrapeptide," J Am Chem Soc, 85(14):2149-2154 (1963).
Meyer et al., "Mapping of deletions in the genome of the highly attenuated vaccinia virus MVA and their influence on virulence," J Gen Virol, 72:1031-1038 (1991).
Meyerson et al., "Advances in understanding cancer genomes through second-generation sequencing," Nat Rev Genetics, 11:685-696 (2010).
Midgley, "Vaccinia virus strain NYVAC induces substantially lower and qualitatively different human antibody responses compared with strains Lister and Dryvax," J Gen Virol, 89:2992-2997 (2008).
Miller et al., "Construction and properties of retrovirus packaging cells based on gibbon ape leukemia virus," Virol, 65:2220-2224 (1991).

(56) References Cited

OTHER PUBLICATIONS

Mooij, "Differential CD4+ versus CD8+ T-Cell Responses Elicited by Different Poxvirus-Based Human Immunodeficiency Virus Type 1 Vaccine Candidates Provide Comparable Efficacies in Primates," J Virol, 82(6):2975-2988 (2008).
Mor et al., "Complexity of the cytokine and antibody response elicited by immunizing mice with Plasmodium yoelii circumsporozoite protein plasmid DNA," J Immunol, 155(4):2039-2046 (1995).
Moss, "Reflections on the early development of poxvirus vectors," Vaccine, 31(39): 4220-4222 (2013).
Mullally et al., "Beyond HLA: The Significance of Genomic Variation for Allogeneic Hematopoietic Stem Cell Transplantation," Blood, 109: 1355-1362 (2007).
Murphy et al., "Antigen Presentation to T Lymphocytes," Janeway's Immunobiology, 7th Edition, 5:182-83 & 197 (2008).
Murphy et al., "Genetic construction, expression, and melanoma-selective cytotoxicity of a diphtheria toxin-related alpha-melanocyte-stimulating hormone fusion protein," PNAS, 83:8258-8262 (1986).
Murphy et al., "Phase I Clinical Trial: T-Cell Therapy for Prostate Cancer Using Autologous Dendritic Cells Pulsed with HLA-A0201-Specific Peptides from Prostate-Specific Membrane Antigen," Prostate, 29(6): 371-380 (1996).
Musey et al., "HIV-1 Vaccination Administered Intramuscularly Can Induce Both Systemic and Mucosal T Cell Immunity in HIV-1-Uninfected Individuals," J Immunol, 171(2):1094-1101 (2003).
Najera et al., "Cellular and Biochemical Differences between Two Attenuated Poxvirus Vaccine Candidates (MVA and NYVAC) and Role of the C7L Gene," J Virol, 80(12):6033-6047 (2006).
Nam et al., "Different contribution of co-stimulatory molecules B7.1 and B7.2 to the immune response to recombinant modified vaccinia virus ankara vaccine expressing prM/E proteins of Japanese encephalitis virus and two hepatitis B virus vaccines," Acta Virol, 51:125-30 (2007).
Nishimura et al, "Distinct Role of Antigen-Specific T Helper Type 1 (Th1) and Th2 Cells in Tumor Eradication in Vivo," J Ex Med, 190(5):617-27 (1999).
Nocentini et al., "A new member of the tumor necrosis factor/nerve growth factor receptor family inhibits T cell receptor-induced apoptosis," PNAS, 94(12):6216-6221 (1997).
Notice of Opposition to European Patent No. EP2569633—Agenus Inc. (Opponent) dated Nov. 9, 2016.
Notice of Opposition to European Patent No. EP2569633—Dr. Christian Muller (Opponent) dated Nov. 9, 2016.
Notice of Opposition to European Patent No. EP2569633—Gritstone Oncology, Inc. (Opponent) dated Nov. 7, 2016.
Notice of Opposition to European Patent No. EP2569633—James Poole Limited (Opponent) dated Nov. 9, 2016.
Notice of Opposition to European Patent No. EP2569633—Strawman Limited (Opponent) dated Nov. 10, 2016.
Novellino et al., "A listing of human tumor antigens recognized by T cells: Mar. 2004 update," Cancer Immunol Immunother, 54(3):187-207 (2005).
Nyren et al., "Solid Phase DNA Minisequencing by an Enzymatic Luminometric Inorganic Pyrophosphate Detection Assay," Anal Biochem, 208(1): 171-175 (1993).
O'Shea et al., "Signal transduction and Th17 cell differentiation," Microbes Infect, 11(5):599-611 (2009).
Oakes et al., "Evolution of DNA Methylation Is Linked to Genetic Aberrations in Chronic Lymphocytic Leukemia," Cancer Discov, 4(3):348-361 (2014).
Oakes et al., "Heterogeneity and Evolution of DNA Methylation in Chronic Lymphocyctic Leukemia," Blood, 122(21):1626 (2013).
Ofran et al., "Identification of Human Minor Histocompatibility Antigens (MHA) by Combining Bioinformatic Prediction of Peptide Epitopes with Validation of T Cell Reactivity in Patient Blood Samples after Allogeneic Hematopoietic Stem Cell Transplantation," Biol Bone Marrow Transplant, 14:1 (Abstract #2) (2008).
Opaysky et al., CpG Island Methylation in a Mouse Model of Lymphoma Is Driven by the Genetic Configuration of Tumor Cells, PLoS Genetics, 3(9):e167 (2007).
Opposition Letter—Agenus Inc. (Opponent) in European Patent 2569633, dated Nov. 9, 2016.
Opposition Letter—Dr. Christian Muller (Opponent) in European Patent No. 2569633, dated Nov. 9, 2016.
Opposition Letter—Gritstone Oncology Inc. (Opponent) in European Application No. 11781409.5 dated Nov. 7, 2016.
Opposition Letter—James Poole Limited (Opponent) in European Patent No. 2569633, dated Nov. 9, 2016.
Opposition Letter—Strawman Limited (Opponent) in European Patent No. 2569633 dated Nov. 10, 2016.
Ott et al., "An Immunogenic personal neoantigen vaccine for patients with melanoma," Nature, 547:217-221 (2017).
Ott et al., "Vaccines and Melanoma," Hematol Oncol Clin N Am, 28(3):559-569 (2014).
Oudard et al., "A phase II study of the cancer vaccine TG4010 alone and in combination with cytokines in patients with metastatic renal clear-cell carcinoma: clinical and immunological findings," Cancer Immunol Immunother, 60(2): 261-271 (2011).
Page et al., "Immune Modulation in Cancer with Antibodies," Annu Rev Med, 65:185-202 (2014).
U.S. Appl. No. 13/108,610, filed May 16, 2011.
Pan et al., "Epigenomic Evaluation in diffuse Large B-Cell Lymphomas," Blood, Nov. 15, 2013, 122(21) XP55174946.
Panicali et al., "Construction of live vaccines by using genetically engineered poxviruses: biological activity of recombinant vaccinia virus expressing influenza virus hemagglutinin," PNAS, 80(17):5364-5368 (1983).
Panicali et al., "Construction of poxviruses as cloning vectors: insertion of the thymidine kinase gene from herpes simplex virus into the DNA of infectious vaccinia virus," 79(16):4927-4931 (1982).
Pantaleo et al., "Poxvirus vector-based HIV vaccines," Curr Opin HIV-AIDS, 5:391-396 (2010).
Paoletti, "Applications of pox virus vectors to vaccination: an update," PNAS, 93(21):11349-53 (1996).
Parker et al., "Scheme for Ranking Potential HLA-A2 Binding Peptides Based on Independent Binding of Individual Peptide Side-Chains," J Immunol, 152(1): 163-175 (1994).
Parkhurst et al., "Improved induction of melanoma-reactive CTL with peptides from the melanoma antigen gp100 modified at HLA-A*0201-binding residues", The Journal of Immunology, 157: 2539-2548 (1996).
Parmiani et al., "Unique Human Tumor Antigens: Immunobiology and Use in Clinical Trials," J Immunol, 178: 1975-1979 (2007).
Pasmant et al., "Characterization of a Germ-Line Deletion, Including the Entire INK4/ARF Locus, in a Melanoma-Neural System Tumor Family: Identification of ANRIL, an Antisense Noncoding RNA Whose Expression Coclusters with ARF," Cancer Res, 67(8):3963-3969 (2007).
Perez et al., "A new era in anticancer peptide vaccines," Cancer, 116(9):2071-2080 (2010).
Perkvs et al., "Poxvirus□based vaccine candidates for cancer, AIDS, and other infectious diseases," J Leukocyte Biol, 58(1):1-13 (1995).
Perreau et al., "DNA/NYVAC Vaccine Regimen Induces HIV-Specific CD4 and CD8 T-Cell Responses in Intestinal Mucosa," J Virol, 85(19):9854-9862 (2011).
Peters et al., "The Immune Epitope Database and Analysis Resource: From Vision to Blueprint," PLoS Biol, 3(3): e91 (2005).
Peters et al., "The many faces of TH-17 Cells," Curr Opin Immunol, 23(6):702-706 (2011).
Petsch et al., "Protective efficacy of in vitro synthesized, specific mRNA vaccines against influenza A virus infection," Nat Biotechnol, 30(12):1210-1216 (2012).
Phan et al., "Cancer regression and autoimmunity induced by cytotoxic T lymphocyte-associated antigen 4 blockade in patients with metastatic melanoma," PNAS, 100(14):8372-8377 (2003).
Pilla et al., "Multipeptide vaccination in cancer patient," Expert Opin Biol Ther, 9(8):1043-1055 (2009).
Piros et al., "Market Opportunity for Molecular Diagnostics in Personalized Cancer Therapy," Handbook of Clinical Nanomedicine: Law, Business, Regulation, Safety and Risk, Chapter 14:1-29 (2016).

(56) References Cited

OTHER PUBLICATIONS

Pleasance et al., "A comprehensive catalogue of somatic mutations from a human cancer genome," Nature, 463:191-196 (2010).
Pleasance et al., "A small-cell lung cancer genome with complex signatures of tobacco exposure," Nature, 463: 184-190 (2010).
Poirot et al., "Multiplex genome edited T-cell manufacturing platform for "off-the-shelf" adoptive T-cell immunotherapies," Cancer Res, 75(18):3853 (2015).
Policy Reallocating Ownership of Intellectual Property Covered by the Intellectual Property Policy, Sep. 18, 2002.
Poulet, "Development and registration of recombinant veterinary vaccines: The example of the canarypox vector platform," Vaccine, 25(30):5606-5612 (2007).
Prezant et al., "Trapped-Oligonucleotide Nucleotide Incorporation (TONI) Assay, a Simple Method for Screening Point Mutations," Hum Mutat, 1(2): 159-164 (1992).
Provan et al., "Eradication of Polymerase Chain Reaction-Detectable Chronic Lymphocytic Leukemia Cells is Associated with Improved Outcome After Bone Marrow Transplantation," Blood, 88: 2228-2235 (1996).
U.S. Appl. No. 61/334,866, filed May 14, 2010.
Rajasagi et al., "Systematic Identification of Personal Mutated Tumor-Specific Neoantigens in CLL," Blood, 120(21):954 (2012).
Rajasagi et al., "Systematic identification of personal tumor-specific neoantigens in chronic lymphocytic leukemia," Blood, 124(3): 453 (2014).
Rammensee et al., "Cancer Vaccines: Some Basic Considerations," Genomic and Personalized Medicine, 5:573-589 (2009).
Rammensee et al., "MHC ligands and peptide motifs: first listing," Immunogenetics, 41:178 (1995).
Rammensee et al., "SYFPEITHI: Database for MHC Ligands and Peptide Motifs," Immunogenetics, 50(3-4): 213-219 (1999).
Rammensee et al., "Towards Patient-Specific Tumor Antigen Selection for Vaccination," Immunological Reviews, Blackwell Publishing Munksgaard, 188:164-176 (2002).
Ramos et al., "An Inducible Caspase 9 Suicide Gene to Improve the Safety of Mesenchymal Stromal Cell Therapies," Stem Cells, 28(6):1107-1115 (2010).
Reifenberger et al., "Frequent Alterations of Ras Signaling Pathway Genes in Sporadic Malignant Melanomas," Int J Cancer, 109: 377-384 (2004).
Response to Notices of Opposition of EP2569633, dated Jun. 28, 2017.
Ressing et al., "Human CTL epitopes encoded by human papillomavirus type 16 E6 and E7 identified through in vivo and in vitro immunogenicity studies of HLA-A*0201-binding peptides.," J Immunol, 154(11):5934-5943 (1995).
Restifo et al., "Adoptive immunotherapy for cancer: harnessing the T cell response," Nat Rev Immunol, 12(4):269-281 (2015).
Ribas et al., "Antitumor Activity in Melanoma and Anti-Self Responses in a Phase I Trial with the Anti-Cytotoxic T Lymphocyte-Associated Antigen 4 Monoclonal Antibody CP-675,206," J Clin Oncol, 23(35): 8968-8977 (2005).
Rifenberger et al., "Frequent Alterations of Ras Signaling Pathway Genes in Sporadic Malignant Melanomas," Int J Cancer, 109:377-384 (2004).
Rizvi et al., "Mutational landscape determines sensitivity to PD-1 blockade in non-small cell lung cancer," Science, 348(6230):124-128 (2015).
Robbins et al., "A mutated beta-catenin gene encodes a melanoma-specific antigen recognized by tumor infiltrating lymphocytes," J Exp Med, 183(3):1185-1192 (1996).
Rolph et al., "Recombinant viruses as vaccines and immunological tools," Curr Opin Immunol, 9(4):517-524 (1997).
Ronchetti et al., "Frontline:GITR, a member of the TNF receptor superfamily,is costimulatory to mouse T lymphocytesubpopulations," Eur J Immunol, 34(3):613-622 (2004).
Rondon et al., "Graft-versus-Leukemia Effect After Allogeneic Bone Marrow Transplantation for Chronic Lymphocytic Leukemia," Bone Marrow Transplant, 18: 669-672 (1996).
Rooney et al., "Molecular and Genetic Properties of Tumors Associated with Local Immune Cytolytic Activity," Cell, 160(1-2):48-61 (2015).
Rosenberg et al., "Adoptive cell transfer as personalized immunotherapy for human cancer," Science, 348(6230):62-68 (2015).
Rosenberg et al., "Cancer Immunotherapy: Moving Beyond Current Vaccines," Nat Med, 10:909-915 (2004).
Rubinfeld et al., "Stabilization of Beta-Catenin by Genetic Defects in Melanoma Cell Lines," Science, 275(5307):1790-1792 (1997).
Rupprecht et al., "Oral immunization and protection of raccoons (*Procyon lotor*) with a vaccinia-rabies glycoprotein recombinant virus vaccine," PNAS, 83:7947-7950 (1986).
Sabado et al., "Preparation of Tumor Antigen-loaded Mature Dendritic Cells for Immunotherapy," J Vis Exp, 78:50085 (2013).
Sabbatini et al., "Phase I trial of overlapping long peptides from a tumor self-antigen and Poly-ICLC shows rapid induction of integrated immune response in ovarian cancer patients," Clin Cancer Res, 18:6497-6508 (2012).
Sadelain, "Eliminating Cells Gone Astray," New Engl J Med, 365:1735-1737 (2011).
Sampson et al., "An epidermal growth receptor variant III-targeted vaccine is safe and immunogenic in patients with glioblastomas multiforme," Mol Cancer Ther, 8(10):2773-2779 (2009).
Sampson et al., "Greater chemotherapy-induced lymphopenia enhances tumor-specific immune responses that eliminate EGFRvIII-expressing tumor cells in patients with glioblastoma," Neuro-Oncology, 13(3):324-333 (2011).
Sampson et al., "Immunologic Escape After Prolonged Progression-Free Survival With Epidermal Growth Factor Receptor Variant III Peptide Vaccination in Patients With Newly Diagnosed Glioblastoma," J Clin Oncol, 28(31):4722-4729 (2010).
Sancho, "The Block in Assembly of Modified Vaccinia Virus Ankara in HeLa Cells Reveals New Insights into Vaccinia Virus Morphogenesis," J Virol, 76(16):8313-8334 (2002).
Sanderson et al., "Autoimmunity in a Phase I Trial of a Fully Human Anti-Cytotoxic T-Lymphocyte Antigen-4 Monoclonal Antibody With Multiple Melanoma Peptides and Montanide ISA 51 for Patients With Resected Stages III and IV Melanoma," J Clin Oncol, 23(4):741-750 (2005).
Saterdal et al., "Frameshift-mutation-derived peptides as tumor-specific antigens in inherited and spontaneous colorectal cancer," Proceedings of the National Academy of Sciences 98(23): 13255-13260 (2001).
Sato et al., "Intraepithelial CD8+ tumor-infiltrating lymphocytes and a high CD8+/regulatory T cell ratio are associated with favorable prognosis in ovarian cancer," PNAS, 102(51):1838-18543 (2005).
Schaffner et al., "Somatic ATM Mutations Indicate a Pathogenic Role of ATM in B-Cell Chronic Lymphocytic Leukemia," Blood, 94: 748-753 (1999).
Scheibenbogen et al., "Analysis of the T Cell Response to Tumor and Viral Peptide Antigens by an IFNγ-Elispot Assay," Int. J. Cancer, 71:932-936 (1997).
Schietinger et al., "Specificity in cancer immunotherapy," Semin. Immunol, 20(5)276-285 (2008).
Schneider et al, "Induction of CD8+ T cells using heterologous prime-boost immunisation strategies," Immunol Rev, 170(1):29-38 (1999).
Schuh et al., "Monitoring chronic lymphocytic leukemia progression by whole genome sequencing reveals heterogeneous clonal evolution patterns," Blood, 120(20):4191-4196 (2012).
Schwitalle et al., "Immunogenic peptides generated by frameshift mutations in DNA mismatch repair-deficient cancer cells," Cancer Immunity, 4(1):14 (2004).
Scriba et al., "Modified vaccinia Ankara☐expressing Ag85A, a novel tuberculosis vaccine, is safe in adolescents and children, and induces polyfunctional CD4+ T cells," Eur J Immunol, 40(1):279-290 (2010).
Sedegah et al., "Protection against malaria by immunization with plasmid DNA encoding circumsporozoite protein," PNAS, 91(21):9866-9870 (1994).
Segal et al., "Epitope Landscape in Breast and Colorectal Cancer," Cancer Res, 68: 889-892 (2008).

(56) References Cited

OTHER PUBLICATIONS

Sensi et al., "Unique Tumor Antigenesis: Evidence for Immune Control of Genome Integrity and Immunogenic for T Cell-Mediated Patient-Specific Immunotherapy," Clin Cancer Res, 12(7): :5023-5032 (2006).
Sette et al., "Peptide binding to the most frequent HLA-A class I alleles measured by quantitative molecular binding assays," Molecular Immunology, 31(11): 813-822 (1994).
Sette et al., "The relationship between class I binding affinity and immunogenicity of potential cytotoxic T cell epitopes," J Immunol, 153:5586-5592 (1994).
Shames et al., "A Genome-Wide Screen for Promoter Methylation in Lung Cancer Identifies Novel Methylation Markers for Multiple Malignancies," PLoS Med, 3(12):e486 (2006).
Sharei et al., "Ex Vivo Cytosolic Delivery of Functional Macromolecules to Immune Cells," PLoS One, 10(4):e0118803 (2015).
Sharma et al., "Novel cancer immunotherapy agents with survival benefit: recent successes and next steps," Nat Rev Cancer, 11(11):805-812 (2011).
Shastri et al., "Presentation of endogenous peptide/MHC class I complexes is profoundly influenced by specific C-terminal flanking residues," J Immunol, 155:4339 (1995).
Shida, "Effects and virulences of recombinant vaccinia viruses derived from attenuated strains that express the human T-cell leukemia virus type I envelope gene," J Virol, 62(12):4474-4480 (1988).
Shukla et al., "Topics in Cancer Genomics," Graduate Theses and Dissertations, Paper 13796 (2014). [accessed online] https://search.proquest.com/docview/1558874754.
Sidney et al., "Measurement of MHC/Peptide Interactions by Gel Filtration or Monoclonal Antibody Capture," Curr Protoc Immunol: 18.3.1-18.3.36 (2013).
Siegmund et al., "Inferring clonal expansion and cancer stem cell dynamics from DNA methylation patterns in colorectal cancers," PNAS, 106(12):4828-4833 (2009).
Singh-Jasuga et al., "Correlation of T-cell response, clinical activity and regulatory T-cell levels in renal cell carcinoma patients treated with IMA901, a novel multi-peptide vaccine," J Clin Conology, 25:18S, Abstract #3017 (2007).
Sizemore, "Attenuated Shigella as a DNA Delivery Vehicle for DNA-Mediated Immunization," Science, 270(5234):299-303 (1995).
Sjoblom et al., "The Consensus Coding Sequences of Human Breast and Colorectal Cancers," Science, 314(5797):268-274 (2006).
Slingluff et al., "Immunologic and Clinical Outcomes of a Randomized Phase II Trial of Two Multipeptide Vaccines for Melanoma in the Adjuvant Setting," Clin Cancer Res, 13(21):6386-6395 (2007).
Smith et al., "Construction and characterization of an infectious vaccinia virus recombinant that expresses the influenza hemagglutinin gene and induces resistance to influenza virus infection in hamsters," PNAS, 80(23):7155-7159 (1983).
Smith et al., "Infectious vaccinia virus recombinants that express hepatitis B virus surface antigen," Nature, 302:490-495 (1983).
Snyder et al., "Genetic Basis for Clinical Response to CTLA-4 Blockade in Melanoma," New Engl J Med, 371(23):2189-2199 (2014).
Snyder et al., "Immunogenic peptide discovery in cancer genomes," Cuff Opin Genet Dev, 30:7-16 (2015).
Soiffer et al., "Vaccination with irradiated autologous melanoma cells engineered to secrete human granulocyte-macrophage colony-stimulating factor generates potent antitumor immunity in patients with metastatic melanoma," PNAS, 95(22):13141-13146 (1998).
Soiffer et al., "Vaccination With Irradiated, Autologous Melanoma Cells Engineered to Secrete Granulocyte-Macrophage Colony-Stimulating Factor by Adenoviral-Mediated Gene Transfer Augments Antitumor Immunity in Patients With Metastatic Melanoma," J Clin Oncol, 21(17):3343-3350 (2003).
Sokolov., "Primer Extension Technique for the Detection of Single Nucleotide in Genomic DNA," Nucleic Acids Res. 18(12): 3671 (1990).

Sommnerfeit et al., "Receptor interference groups of 20 retroviruses plating on human cells," Virol, 176:58-59 (1990).
Speiser et al., "Molecularly defined vaccines for cancer immunotherapy, and protective T cell immunity," Semin Immunol, 22(3):144-154 (2010).
Spitler, "Cancer Vaccines: The Interferon Analogy," Cancer Biother, 10:1-3 (1995).
Staehler et al., "An open label study to evaluate the safety and immunogenicity of the peptide based cancer vaccine IMA901," ASCO meeting 2007; Abstract No. 3017.
Stahl-Hennig et al., "Synthetic double-stranded RNAs are adjuvants for the induction of T helper 1 and humoral immune responses to human papillomavirus in rhesus macaques," PLoS pathogens, 5(4):e1000373 (2009).
Stankovic et al., "Microarray Analysis Reveals that TP53- and ATM-Mutant B-CLLs Share a Defect in Activating Proapoptotic Responses after DNA Damage but are Distinguished byMajor Differences in Activating Prosurvival Responses," Blood, 103:291-300 (2004).
Stover et al., "New Use of BCG for Recombinant Vaccines," Nature, 351(6326): 456-460 (1991).
Stratton et al., "The Cancer Genome," Nature, 458(7239):719-724 (2009).
Su et al., "Immunological and Clinical Responses in Metastatic Renal Cancer Patients Vaccinated with Tumor RNA-Transfected Dendritic Cells," Cancer Res, 63: 2127-2133 (2003).
Submission in opposition proceedings of EP 2569633, dated Jun. 28, 2017.
Sullivan et al., "Expression and Characterization of Herpes Simplex Virus Type 1 (HSV-1) Glycoprotein G (gG) by Recombinant Vaccinia Virus: Neutralization of HSV-1 Infectivity with Anti-gG Antibody," Gen Vir, 68:2587-2598 (1987).
Syvanen et al., "A Primer-Guided Nucleotide Incorporatiopn Assay in the Genotyping of Apoliprotein E," Genomics, 8(4): 684-692 (1990).
Syvanen et al., "Identification of Individuals by Analysis of Biallelic DNA Markers, Using PCR and Solid-Phase Minisequencing," Am J Hum Genet, 52(1): 46-59 (1993).
Table S4 Somatic mutations Identified in Breast or Colorectal Cancers filed on Nov. 7, 2016 in Notice of Opposition by Gritstone Oncology Inc. to EP 2569633.
Table S5 Breast CAN-genes, filed on Nov. 7, 2016, in Notice of Opposition by Gritstone Oncology Inc., to EP Patent No. 2569633.
Table S6 Colorectal CAN-genes, filed on Nov. 7, 2016 in Notice of Opposition by Gritstone Oncology Inc. to EP Patent No. 2569633.
Tartaglia et al., "NYVAC: A highly attenuated strain of vaccinia virus," Virology, 188(1):217-232 (1992).
Thomas et al., "High-Throughput Oncogene Mutation Profiling in Human Cancer," Nat Genet, 39: 347-351 (2007).
Thompson et al., "Aberrations of the B-Cell Receptor B29 (CD79b) Gene in Chronic Lymphocytic Leukemia," Blood, 90(4):1387-1394 (1997).
Thornton et al., "Characterisation of TP53 Abnormalities in Chronic Lymphocytic Leukaemia," Hematol J, 5: 47-54 (2004).
Timmerman et al., "Idiotype-Pulsed Dendritic Cell Vaccination for B-Cell Lymphoma: Clinical and Immune Responses in 35 Patients," Blood, 99: 1517-1526 (2002).
Tjoa et al., "Follow-Up Evaluation of Prostate Cancer Patients Infused with Autologous Dendritic Cells Pulsed with PSMA Peptides," Prostate, 32(4): 272-278 (1997).
Tjoa et al., "Follow☐up evaluation of prostate cancer patients infused with autologous dendritic cells pulsed with PSMA peptides," The Prostate, 32(4):272-278 (1997).
Tong et al., "Methods and protocols for prediction of immunogenic epitopes, Briefings in Bioinformatics," 8(2): 96-108 (2008).
Tourdot et al., "A general strategy to enhance immunogenicity of low-affinity HLA-A2.1-associated peptides: implication in the identificatiioonn of cryptic tumor epitopes," Eur. J. Immunol, 30:3411-3421 (2000).
Toze et al., "Myeloablative Allografting for Chronic Lymphocytic Leukemia: Evidence for Potent Graft-versus-Leukemia Effect Associated with Graft-versus-Host Disease," Bone Marrow Transplant, 36: 825-830 (2005).

(56) References Cited

OTHER PUBLICATIONS

Tumeh et al., "PD-1 blockade induces responses by inhibiting adaptive immune resistance," Nature, 515(7528):568-571 (2014).
U.S. Final Office Action dated May 25, 2017 and issued in U.S. Appl. No. 15/187,174.
U.S. Final Rejection dated Sep. 13, 2017 and issued in U.S. Appl. No. 14/794,449.
U.S. Non-Final Office Action dated Jan. 22, 2018 and issued in U.S. Appl. No. 15/187,174.
U.S. Non-Final Office Action dated Dec. 5, 2016 and issued in U.S. Appl. No. 15/187,174.
U.S. Non-Final Office Action dated Dec. 29, 2016 and issued in U.S. Appl. No. 14/794,449.
Ueda et al., "Germ Line and Somatic Mutations of BRAF V599E in Ovarian Carcinoma," Int J Gynecol Cancer, 17: 794-797 (2007).
Ugozzoli et al., "Detection of Specific Alleles by Using Allele-Specific Primer Extension Followed by Capture on Solid Support," Genet Anal Tech AppL, 9(4): 107-112 (1992).
UniProtKB Printouts—Q5SVV79 filed on Nov. 2016 in Muller Opposition to EP 2569633.
Van de Roemer et al., "P1737:IVAC: Individualized vaccines for cancer," Immunology 137(Suppl. 1):715, Sep. 2012.
Van der Bruggen et al., "A Gene Encoding an Antigen Recognized by Cytolytic T Lymphocytes on a Human Melanoma," Science, 254: 1643-1647 (1991).
Van Pel et al., "Tumor Cell Variants Obtained by a Mutageneis of a Lewis Lung Carcinoma Cell Line: Immune Rejection by Syngeneic Mice," PNAS, 76(10): 5282-5285 (1979).
Van Rooij et al., "Tumor Exome Analysis Reveals Neoantigen-Specific T-Cell Reactivity in an 1pilimumab-Responsive Melanoma," Journal of Clinical Oncology, 31(32):e439-e442 (2013).
Van Trappen et al., "Somatic Mitochondrial DNA Mutations in Primary and Metastatic Ovarian Cancer," Gynecol Oncol, 104: 129-133 (2007).
Verardi et al., "A vaccinia virus renaissance: new vaccine and immunotherapeutic uses after smallpox eradication," Human vaccines & immunotherapeutics, 8(7):961-970 (2012).
Verhoef et al., "Des-enkephalin-γ-endorphin (DEγE): Biotransformation in rat, dog and human plasma," Eur J Drug Metab Ph, 11(4):291-302 (1986).
Vogelstein et al., "Cancer Genome Landscapes," Science, 339(6127): 1546-1558 (2013).
Volpe et al., "Alternative BCR/ABL Splice Variants in Philadelphia Chromosome-Positive Leukemias Result in Novel Tumor-Specific Fusion Proteins that May Represent Potential Targets for Immunotherapy Approaches," Cancer Res, 67(11):5300-5307 (2007).
Von Krempelhuber et al., "A randomized, double-blind, dose-finding Phase II study to evaluate immunogenicity and safety of the third generation smallpox vaccine candidate IMVAMUNE®," Vaccine, 28(5):1209-1216 (2010).
Von Mehren et al., "Pilot study of a dual gene recombinant avipox vaccine containing both carcinoembryonic antige (CEA.) and B7.1 transgenes in patients with, recurrent CEA-expressing adenocarcinomas," Clin Cancer Res, 6:2219-28 (2000).
Walter et al., "DNA Methylation Profiling Defines Clinically Relevant Biological Subsets of Non-small Cell Lung Cancer," Clin Cancer Res, 18(8):2360-2373 (2012).
Walter et al., "Multipeptide immune response to cancer vaccine IMA901 after single-dose cyclophosphamide associates with longer patient survival," Nature medicine, 18(8):1254 (2012).
Wang, "Tumor Antigens Discovery: Perspectives for Cancer Therapy", Molecular Medicine, 3(11): 716-731 (1997).
Watson et al., "SHP-1: the next checkpoint target for cancer immunotherapy?," Biochem Soc Trans, 44(2):356-362 (2016).
Weber et al., "Safety, Efficacy, and Biomarkers of Nivolumab With Vaccine in Ipilimumab-Refractory or—Naive Melanoma," J Clin Oncol, 31:4311-4318 (2013).
Webster et al., "Enhanced T cell-mediated protection against malaria in human challenges by using the recombinant poxviruses FP9 and modified vaccinia virus Ankara," Proceedings of the National Academy of Sciences, 102(13):4836-4841 (2005).
Weiner et al., "Genetic vaccines," Scientific American, 281(1):50-57 (1999).
Weinschenk et al., "Integrated Functional Genomics Approach for the Design of Patientindividual Antitumor Vaccines," Cancer Res, 62: 5818-5827 (2002).
Weyer et al., "Generation and evaluation of a recombinant modified vaccinia virus Ankara vaccine for rabies," Vaccine, 25(21):4213-4222 (2007).
Weyer et al., "Poxvirus-vectored vaccines for rabies—a review," Vaccine, 27(51):7198-7201 (2009).
Whelan et al., "Safety and immunogenicity of boosting BCG vaccinated subjects with BCG: comparison with boosting with a new TB vaccine, MVA85A," PLoS One, 4(6):e5934 (2009).
Wiktor et al., "Protection from rabies by a vaccinia virus recombinant containing the rabies virus glycoprotein gene," Proceedings of the National Academy of Sciences, 81(22):7194-7198 (1984).
Willmore-Payne et al., "Human Malignant Melanoma: Detectection of BRAF- and c-kit-Activating Mutations by High-Resolution Amplicon Melting Analysis," Hum Pathol, 36: 486-493 (2005).
Wilson et al., "Formation of infectious hybrid virions with gibbon ape leukemia virus and human T-cell leukemia virus retroviral envelope glycoproteins and the gag and pol proteins of Moloney murine leukemia virus," Journal of virology, 63(5):2374-2378 (1989).
Wolfel et al., "A p16INK4a-insensitive CDK4 mutant targeted by cytolytic T lymphocytes in a human melanoma," Science, 269(5228):1281-1284 (1995).
Wolff et al., "Direct Gene Transfer into Mouse Muslce in Vivo," Science, 247(4949):1465-1468 (1990).
Wood et al., "The Genomic Landscapes of Human Breast and Colorectal Cancers," Science, 318: 1108-1113 (2007).
Woodbury et al., "Introduction to Macromolecular Binding Equilibria," CRC Press, 13:978 (2007).
Wu et al., "Detection of a potent humoral response asscoiated with immune-induced remission of chronic myelogenous leukemia," J Clin Invest, 106(5):705-714 (2000).
Wu et al., "Graft-versus-Leukemia Target Antigens in Chronic Myelogenous Leukemia Are Expressed on Myeloid Progenitor Cells," Clin Cancer Res, 11(12):4504-4511 (2005).
Wu et al., "Induction of Tumor Immunity Following Allogeneic Stem Cell Transplantation," Adv Immunol, 90: 133-173 (2006).
Wu et al., "Mouse Model of Human Ovarian Endometrioid Adenocarcinoma Based on Somatic Defects in the Wnt/6-Catenin and PI3K/Pten Signaling Pathways," Cancer Cell, 11: 321-333 (2007).
Wu et al., "Reconstitution of T-Cell Receptor Repertoire Diversity Following T-Cell Depleted Allogeneic Bone Marrow Transplantation is Related to Hematopoietic Chimerism," Blood, 95: 352-359 (2000).
Wyatt et al., "Marker rescue of the host range restriction defects of modified vaccinia virus Ankara," Virology, 251(2):334-342 (1998).
Wyatt et al., "Multiprotein HIV type 1 Glade B DNA and MVA vaccines: construction, expression, and immunogenicity in rodents of the MVA component," AIDS research and human retroviruses, 20(6):645-653 (2004).
Yang et al. "CML66, a broadly immunogenic tumor antigen, elicits a humoral immune response associated with remission of chronic myelogenous leukemia," PNAS, 98(13):7492-7497 (2001).
Yao et al., "Advances in targeting cell surface signalling molecules for immune modulation," Nature Rev Drug Discov, 12:130-146 (2013).
Yilma, "Prospects for the total eradication of rinderpest," Vaccine, 7(6):484-485 (1989).
Yokoyama et al., "Matrilysin (MMP-7) Is a Novel Broadly Expressed Tumor Antigen Recognized by Antigen-Specific T Cells," Clin Cancer Res, 14(17): 5503-5511 (2008).
Yosef et al., "Dynamic regulatory network controlling TH17 cell differentiation," Nature, 496(7446):461-468 (2013).
You et al., "Understanding Prediction Systems for HLA-Binding Peptides and T-Cell Epitope Identification," Pattern Recognition in Bioinformatics, Lecture Notes in Computer Science, 4474: 337-348 (2007).

(56) References Cited

OTHER PUBLICATIONS

Zhang et al., "Graft-versus-Leukemia Antigen CML66 Elicits Coordinated B-Cell and T-Cell Immunity after Donor Lymphocyte Infusion," Clin Cancer Res, 16: 2729-2739 (2010).
Zhang et al., "Intratumoral T Cells, recurrence, and survival in epithelial ovarian cancer," New Engl J Med, 348(3):203-213 (2003).
Zhang et al., "Machine learning competition in immunology-prediction of HLA class I molecules," J Immunol Methods 374:1-4 (2009).
Zhou et al., "Diverse CD8+ T-Cell Responses to Renal Cell Carcinoma Antigens in Patients Treated with an Autologous Granulocyte-Macrophage Colony-Stimulating Factor Gene-Transduced Renal Tumor Cell Vaccine," Cancer Res, 65: 1079-1088 (2005).
Zhou et al., "Long-term outcome after haploidentical stem cell transplant and infusion of T cells expressing the inducible caspase 9 safety transgene," Blood, 123(25):3895-3905 (2014).
Zhou et al., "Transcriptional regulatory networks in Th17 cell differentiation," Curr Opin Immunol, 21(2):146-152 (2009).
Zhou et al., Persistance of Multiple Tumor-Specific T-Cell Clones is Associated with Complete Tumor Regression in a Melanoma Patient Receiving Adoptive Cell transfer Therapy, J Immunother, 28(1):53-62 (2005).
Zitvogel et al., "Immunological aspects of cancer chemotherapy," Nature reviews immunology, 8:59 (2008).
A. Cai, et al., Mutated BCR-ABL Generates Immunogenic T-Cell Epitopes in CML Patients, Clinical Cancer Research) Aug. 21, 2012) vol. 18, No. 20, p. 5761-5772.
L. Van Den Broeke, et al., Identification and Epitope Enhancement of a PAX-FKHR Fusion Protein Breakpoint Epitope in Alveolar Rhabdomyosarcoma Cells Created by a Tumorigenic Chromosomal Translocation Inducing CTL Capable of Lysing Human Tumors, Cancer Research, American Association for Cancer Research, US (Feb. 1, 2006) vol. 66, No. 3, p. 1818-1823.
E. Fritsch, et al., HLA-Binding Properties of Tumor Neoepitopes in Humans, Cancer Immunology Research (Jun. 2014) vol. 2, No. 6, p. 522-529.
Acevedo et al., "Analysis of the mechanisms mediating tumor-specific changes in gene expression in human liver tumors," Cancer Res, 68(8):2641-2651 (2008).
Adams, "Toll-like receptor agonists in cancer therapy," Immunotherapy, 1(6):949-964 (2009).
Akiyama et al., "GATA-4 and GATA-5 transcription factor genes and potential downstream antitumor target genes are epigenetically silenced in colorectal and gastric cancer," Mol Cell Biol, 23:8429-8439 (2003).
Alarcon et al., "DNA vaccines: technology and application as anti-parasite and anti-microbial agents," Advances in Parasitology, 42:343-410 (1999).
Ali et al., "In situ regulation of DC subsets and T cells mediates tumor regression in mice," Cancer Immunotherapy, 1(8):1-10 (2009).
Ali et al., "Infection-mimicking materials to program dendritic cells in situ," Nat Mater, 8:151-8 (2009).
Almeida et al., "CTdatabase: a knowledge-base of high- throughput and curated data on cancer-testis antigens," Nucleic acids research, 37:D816-819 (2008).
Altman et al., "Phenotypic analysis of antigen-specific T lymphocytes," Science, 274(5284):94-6 (1996).
Anders et al., "HTSeq-A Python framework to work with high-throughput sequencing data," Bioinformatics, 31(2):166-169 (2015).
Andersen et al., "Parallel detection of antigen-specific T cell responses by combinatorial encoding of MHC multimers," Nature protocols, 7(5):891-902 (2012).
Ausubel, "A botanical macroscope," Proceedings of the National Academy of Sciences, 106(31):12569-12570 (2009).
Balazsi et al., "Cellular decision making and biological noise: from microbes to mammals," Cell, 144(6):910-925 (2011).
Balch et al., "Final version of 2009 AJCC melanoma staging and classification," Journal of clinical oncology, 27(36):6199-6206 (2009).
Barbie et al., "Systematic RNA interference reveals that oncogenic KRAS-driven cancers require TBK1," Nature, 462:108-112 (2009).

Barretina et al., "The Cancer Cell Line Encyclopedia enables predictive modelling of anticancer drug sensitivity," Nature, 483:603-607 (2012).
Baylin, "A decade of exploring the cancer epigenome-biological and translational implications," Nat Rev Cancer, 11:726-734 (2005).
Baylin, "DNA methylation and gene silencing in cancer," Nat Clin Pract Oncol 2, Suppl 1, S4-11 (2005).
Benson, "Tandem repeats finder: a program to analyze DNA sequences," Nucleic acids research, 27(2):573-580 (1999).
Benton et al., "Screening lambdagt recombinant clones by hybridization to single plaques in situ," Science, 196(4286):180-182 (1977).
Berger et al., "The genomic complexity of primary human prostate cancer," Nature, 470:214-220 (2011).
Berger et al.,"Melanoma genome sequencing reveals frequent PREX2 mutations," Nature, 485(7399):502 (2012).
Berman et al., "Regions of focal DNA hypermethylation and long-range hypomethylation in colorectal cancer coincide with nuclear lamina-associated domains," Nat Genet, 44:40-46 (2012).
Bindea et al., "Spatiotemporal dynamics of intratumoral immune cells reveal the immune landscape in human cancer," Immunity, 39:782-795 (2013).
Bird, "DNA methylation patterns and epigenetic memory," Genes Dev, 16:6-21 (2002).
Birrell et al., "A genome-wide screen in *Saccharomyces cerevisiae* for genes affecting UV radiation sensitivity," Proceedings of the National Academy of Sciences 98(22):12608-12613 (2001).
Bishop et al., "APOBEC-mediated editing of viral RNA," Science, 305:645 (2004).
Bock et al., "BiQ Analyzer: visualization and quality control for DNA methylation data from bisulfite sequencing," Bioinformatics, 21:4067-4068 (2005).
Bock et al., "Reference Maps of human ES and iPS cell variation enable high-throughput characterization of pluripotent cell lines," Cell, 144:439-452 (2011).
Bogunovic et al., "TLR4 engagement during TLR3-induced proinflammatory signaling in dendritic cells promotes IL-10-mediated suppression of antitumor immunity," Cancer Res, 71(16):5467-5476 (2011).
Boller et al. "Characterization of the antibody response specific for the human endogenous retrovirus HTDV/HERV-K," Journal of virology, 7I(6):4581-4588 (1997).
Boquest et al., "Isolation and transcription profiling of purified uncultured human stromal stem cells: alteration of gene expression after in vitro cell culture," Molecular biology of the cell, 16(3):1131-1141 (2005).
Boscardin et al., "Antigen targeting to dendritic cells elicits long-lived T cell help for antibody responses," Journal of Experimental Medicine, 203(3):599-606 (2006).
Boyle et al., "Gel-free multiplexed reduced representation bisulfite sequencing for large-scale DNA methylation profiling," Genome Biol, 13:R92 (2012).
Boyle et al., "Tapasin-related protein TAPBPR is an additional component of the MHC class I presentation pathway," Proceedings of the National Academy of Sciences, 110: 3465-3470 (2013).
Bozic et al., "Dynamics of targeted cancer therapy," Trends Mol Med, 18:311-316 (2012).
Bozic et al., "Evolutionary dynamics of cancer in response to targeted combination therapy," Elife, 2:e00747 (2013).
Brahmer et al., "Safety and activity of anti-PD-L1 antibody in patients with advanced cancer," N Engl J Med, 366(26):2455-2465 (2012).
Brown et al., "Integrative genomic analysis implicates gain of PIK3CA at 3g26 and MYC at 8q24 in chronic lymphocytic leukemia," Clin Cancer Res, 8:3791-802 (2012).
Burger et al., "B cell receptor signaling in chronic lymphocytic leukemia," Trends Immunol, 34:592-601 (2013).
Burkhardt et al., "Autologous CLL cell vaccination early after transplant induces leukemia-specific T cells," The Journal of clinical investigation, 123(9):3756-3765 (2013).
Buser et al., "Unique composite hematolymphoid tumor consisting of a pro-T lymphoblastic lymphoma and an indeterminate dendritic

(56) References Cited

OTHER PUBLICATIONS cell tumor: evidence for divergent common progenitor cell differentiation," Pathobiology, 81:199-205 (2014).
Byrd et al., "Targeting BTK with ibrutinib in relapsed chronic lymphocytic leukemia," The New England journal of medicine, 369:32-42 (2013).
Bystryn et al., "Double-blind trial of a polyvalent, shed-antigen, melanoma vaccine," Clin Cancer Res, 7(7):1882-1887 (2001).
Cahill et al., "450K-array analysis of chronic lymphocytic leukemia cells reveals global DNA methylation to be relatively stable over time and similar in resting and proliferative compartments," Leukemia, 27:150-158 (2013).
Cancer Genome Atlas Network, "Comprehensive molecular characterization of human colon and rectal cancer," Nature, 487:330-337 (2012).
Cancer Genome Atlas Network, "Comprehensive molecular portraits of human breast tumours," Nature, 490:61-70 (2012).
Cancer Genome Atlas Research Network, "Comprehensive genomic characterization defines human glioblastoma genes and core pathways," Nature, 455(7216):1061-1068 (2008).
Cancer Genome Atlas Research Network, "Comprehensive genomic characterization of squamous cell lung cancers," Nature, 489, 519-525 (2012).
Cancer Genome Atlas Research Network, "Comprehensive molecular characterization of clear cell renal cell carcinoma," Nature, 499:43-49 (2013).
Cancer Genome Atlas Research Network, "Comprehensive molecular characterization of gastric adenocarcinoma," Nature, 513:202-209 (2014).
Cancer Genome Atlas Research Network, "Genomic and epigenomic landscapes of adult de novo acute myeloid leukemia," New England Journal of Medicine, 368(22):2059-2074 (2013).
Cancer Genome Atlas Research Network, "Integrated genomic analyses of ovarian carcinoma," Nature, 474: 609-615 (2011).
Carter et al., "Absolute quantification of somatic DNA alterations in human cancer," Nat Biotechnol, 30:413-21 (2012).
Carter et al., "Accurate estimation of homologue-specific DNA concentration-ratios in cancer samples allows long-range haplotyping," Nature Precedings, 59-87 (2011).
Castle et al., "Exploiting the mutanome for tumor vaccination," Cancer research, 72(5):1081-1091 (2012).
CBOL Plant Working Group, "A DNA barcode for land plants," PNAS, 106(31):12794-12797 (2009).
Chang et al., "Immune selection of hot-spot beta 2-microglobulin gene mutations, HLA-A2 allospecificity loss, and antigen-processing machinery component down-regulation in melanoma cells derived from recurrent metastases following immunotherapy," Journal of immunology, 174:1462-1471 (2005).
Chapman et al., "Initial genome sequencing and analysis of multiple myeloma," Nature, 471:467-472 (2011).
Cheever, "Twelve immunotherapy drugs that could cure cancers," Immunological reviews, 222:357-368 (2008).
Chen et al., "Impact of replication timing on non-CpG and CpG substitution rates in mammalian genomes," Genome Res, 20:447-457 (2010).
Chen et al., "Langerhans Cell Sarcoma Arising from Chronic Lymphocytic Lymphoma/Small Lymphocytic Leukemia: Lineage Analysis and BRAF V600E Mutation Study," N Am J Sci, 5:386-91 (2013).
Chen et al., "Molecular mechanisms of T cell co-stimulation and co-inhibition," Nature reviews Immunology, 13:227-242 (2013).
Chim et al., "Epigenetic dysregulation of the Wnt signalling pathway in chronic lymphocytic leukaemia," J Clin Pathol, 61:1214-1219 (2008).
Chiron et al., "Cell-cycle reprogramming for PI3K inhibition overrides a relapse-specific C481S BTK mutation revealed by longitudinal functional genomics in mantle cell lymphoma," Cancer Discov, 4:1022-35 (2014).
Christian et al., "Targeting DNA double-strand breaks with TAL effector nucleases," Genetics, 186(2):757-761 (2010).

Church, "Genomes for all," Sci Am, 294(1):46-54 (2006).
Cibulskis et al., "ContEst: estimating cross-contamination of human samples in next-generation sequencing data," Bioinformatics, 27:2601-2602 (2011).
Cibulskis et al., "Sensitive detection of somatic point mutations in impure and heterogeneous cancer samples," Nat Biotechnol, 31:213-9 (2013).
Cleveland, "LOWESS: A program for smoothing scatterplots by robust locally weighted regression," The American Statistician, 35:54 (1981).
Coulie et al., "A mutated intron sequence codes for an antigenic peptide recognized by cytolytic T lymphocytes on a human melanoma," Proc Natl Acad Sci USA, 92(17):7976-7980 (1995).
De et al., "Aberration in DNA methylation in B-cell lymphomas has a complex origin and increases with disease severity," PLoS Genet. 9:e1003137 (2013).
De Magalhaes et al., "Next-generation sequencing in aging research: emerging applications, problems, pitfalls and possible solutions," Ageing Research Reviews, 9(3):315-323 (2010).
DeLuca et al., "Rna-SeQC: RNA-seq metrics for quality control and process optimization," Bioinformatics, 28:1530-2 (2012).
DePristo et al., "A framework for variation discovery and genotyping using next-generation DNA sequencing data," Nature Genetics, 43:491-498 (2011).
Ding et al., "Somatic mutations affect key pathways in lung adenocarcinoma," Nature, 455:1069-1075 (2008).
Dohner et al., "Genomic aberrations and survival in chronic lymphocytic leukemia," The New England journal of medicine, 343:1910-1916 (2000).
Doody et al., "PRDMI/BLIMP-1 Modulates IFN—Dependent Control of the MHC Class I Antigen-Processing and Peptide-Loading Pathway," The Journal of Immunology, 179:7614-7623 (2007).
Dubey et al., "The immunodominant antigen of an ultraviolet-induced regressor tumor is generated by a somatic point mutation in the DEAD (SEQ ID No: 62) box helicase p68," The Journal of experimental medicine, 185(4):695-705 (1997).
Eckhardt et al., "DNA methylation profiling of human chromosomes 6, 20 and 22," Nat Genet, 38:1378-1385 (2006).
Eden et al., "Discovering motifs in ranked lists of DNA sequences," PLoS computational biology, 3, e39 (2007).
Eden et al., "GOrilla: a tool for discovery and visualization of enriched GO terms in ranked gene lists," BMC bioinformatics, 10:48 (2009).
Eggermont et al., "Ulceration and stage are predictive of interferon efficacy in melanoma: results of the phase III adjuvant trials EORTC 18952 and EORTC 18991," Eur J Cancer, 48(2):218-225 (2012).
Ehrlich, "DNA hypomethylation in cancer cells," Epigenomics, 1:239-259 (2009).
Engler et al., "A one pot, one step, precision cloning method with high throughput capability," PloS one 3(11):e3647 (2008).
Engler et al., "Golden gate shuffling: a one-pot DNA shuffling method based on type IIs restriction enzymes," PloS one, 4(5):e5553 (2009).
Escobar et al., "Bayesian density estimation and inference using mixtures," Journal of the American Statistical Association, 90:577-588 (1995).
Fais et al., "Chronic lymphocytic leukemia B cells express restricted sets of mutated and unmutated antigen receptors," The Journal of clinical investigation, 102:1515-25 (1998).
Fan et al., "The multi substrate adapter Gabl regulates hepatocyte growth factor (scatter factor)-c-Met signaling for cell survival and DNA repair," Molecular and cellular biology, 21:4968-4984 (2001).
Fantom Consortium et al., "A promoter-level mammalian expression atlas," Nature, 507:462-470 (2014).
Feigner et al., "Lipofection: a highly efficient, lipid-mediated DNA-transfection procedure," PNAS, 84(21):7413-7414 (1987).
Fisher et al., "A scalable, fully automated process for construction of sequence-ready human exome targeted capture libraries," Genome Biol, 12:R1 (2011).
Flaherty et al., "From genes to drugs: targeted strategies for melanoma," Nat Rev Cancer, 12(5):349-361 (2012).

(56) References Cited

OTHER PUBLICATIONS

Flynn et al., "Immunization with HIV Gag targeted to dendritic cells followed by recombinant New York vaccinia virus induces robust T-cell immunity in nonhuman primates," Proc Natl Acad Sci, 108(17):7131-7136 (2011).
Forconi et al., "Genome-wide DNA analysis identifies recurrent imbalances predicting outcome in chronic lymphocytic leukaemia with 17p deletion," British journal of haematology, 143:532-6 (2008).
Fransen et al., "Controlled local delivery of CTLA-4 blocking antibody induces CD8+ T-cell-dependent tumor eradication and decreases risk of toxic side effects," Clin Cancer Res, 19(19):5381-5389 (2013).
Fritsch et al., "Translational repression of MCL-1 couples stress-induced eIF2 alpha phosphorylation to mitochondrial apoptosis initiation," The Journal of biological chemistry, 282:22551-62 (2007).
Furman et al., "Ibrutinib resistance in chronic lymphocytic leukemia," The New England journal of medicine, 370(24):2352 (2014).
Furman et al., "Idelalisib and rituximab in relapsed chronic lymphocytic leukemia," The New England journal of medicine, 370:997-1007 (2014).
Gao et al., "Integrative analysis of complex cancer genomics and clinical profiles using the cBioPortal," Science signaling, 6(269):pi1 (2013).
Garimella et al., "Identification of novel molecular regulators of tumor necrosis factor-related apoptosis-inducing ligand (TRAIL)-induced apoptosis in breast cancer cells by RNAi screening," Breast cancer research, 16(2):R41 (2014).
Garofalo et al., "miR-221&222 regulate TRAIL resistance and enhance tumorigenicity through PTEN and TIMP3 downregulation," Cancer Cell, 16(6):498-509 (2009).
Garraway et al., "Lessons from the cancer genome," Cell, 153:17-37 (2013).
Gaucher et al., "Yellow fever vaccine induces integrated multilineage and polyfunctional immune responses," The Journal of experimental medicine, 205(13):3119-3131 (2008).
Gevaert et al., "Protein identification methods in proteomics," Electrophoresis: An International Journal, 21(6):1145-1154 (2000).
Giaever et al., "Functional profiling of the Saccharomyces cerevisiae genome," Nature, 418(6896):387-391 (2002).
Giannopoulos et al., "Peptide vaccination elicits leukemia-associated antigen-specific cytotoxic CD8+ T-cell responses in patients with chronic lymphocytic leukemia," Leukemia, 24(4):798-805 (2010).
Gibbs et al., "Abundant quantitative trait loci exist for DNA methylation and gene expression in human brain," PLoS genetics, 6:e1000952 (2010).
Gros et al., "PD-1 identifies the patient-specific CD8+ tumor-reactive repertoire infiltrating human tumors," The Journal of clinical investigation, 124(5):2246-2259 (2014).
Grunstein et al., "Colony hybridization: a method for the isolation of cloned DNAs that contain a specific gene," PNAS, 72(10):3961-3965 (1975).
GTEx Consortium, The Genotype-Tissue Expression (GTEx) project, Nature genetics, 45:580-585 (2013).
Guo et al., "Droplet microfluidics for high-throughput biological assays," Lab Chip, 12:2146-55 (2012).
Guthals et al., "Shotgun Protein Sequencing with Meta-contig Assembly," Molecular and Cellular Proteomics, 1(10):1084-96 (2012).
Hadrup et al., "Parallel detection of antigen-specific T-eeil responses by multidimensional encoding of MHC multimers," Nature Methods, 6(7):520-26 (2009).
Hall, "Advanced sequencing technologies and their wider impact in microbiology," Journal of experimental biology, 210(9):1518-1525 (2007).
Hanahan et al., "Hallmarks of cancer: the next generation," Cell, 144:646-674 (2011).
Hansen et al., "Increased methylation variation in epigenetic domains across cancer types," Nat Genet, 43:768-775 (2011).
Hanzelmann et al., "GSVA: gene set variation analysis for microarray and RNA-Seq data," BMC bioinformatics, 14:7 (2013).
Harris et al., "Comparison of sequencing-based methods to profile DNA methylation and identification of monoallelic epigenetic modifications," Nat Biotechnol, 28:1097-1105 (2010).
Harris et al., "RNA editing enzyme APOBECI and some of its homologs can act as DNA mutators," Molecular cell, 1095):1247-1253 (2002).
Heemskerk et al., "The cancer antigenome," EMBO Journal, 32(2):194-203 (2013).
Herbeuval et al., "HAART reduces death ligand but not death receptors in lymphoid tissue of HIV-infected patients and simian immunodeficiency virus-infected macaques," AIDS, 23:35-40 (2009).
Herman et al., "ibrutinib-induced lymphocytosis in patients with chronic lymphocytic leukemia: correlative analyses from a phase II study," Leukemia, 28:2188 (2014).
Hinrichs et al., "Exploiting the curative potential of adoptive T-cell therapy for cancer," Immunological reviews, 257:56-71 (2014).
Hombrink et al., "High-Throughput Identification of Potential Minor Histocompatibility Antigens by MHC Tetramer-Based Screening: Feasibility and Limitations," Plos One, 6(8):1-11 (2011).
Honigberg et al., "The Bruton tyrosine kinase inhibitor PCI-32765 blocks B-cell activation and is efficacious in models of autoimmune disease and B-cell malignancy," PNAS, 107:13075-13080 (2010).
Illingworth et al., "Orphan CpG islands identify numerous conserved promoters in the mammalian genome," PLoS Genet, 6(9):e1001134 (2010).
Inokuchi et al., "DCC protein expression in hematopoietic cell populations and its relation to leukemogenesis," J Clin Invest, 97:852-857 (1996).
Izeradjene et al., "Casein kinase II (CK2) enhances death-inducing signaling complex (DISC) activity in TRAIL-induced apoptosis in human colon carcinoma cell lines," Oncogene, 24:2050-2058 (2005).
Jaatinen et al., "Global gene expression profile of human cord blood-derived CD133+ cells," Stem Cells, 24:631-641 (2006).
Jemal et al., "Cancer statistics, 2007," CA: a cancer journal for clinicians, 57:43-66 (2007).
Jennewein et al., "Sumoylation of peroxisome proliferator-activated receptor gamma by apoptotic cells prevents lipopolysaccharide-induced NCoR removal from kappaB binding sites mediating transrepression of proinflammatory cytokines," Journal of immunology, 181:5646-5652 (2008).
Johnson et al., "Single-cell perforin and granzyme expression reveals the anatomical localization of effector CD8+ T cells in influenza virus-infected mice," PNAS, 100:2657-2662 (2003).
Jones et al., "Functions of DNA methylation: islands, start sites, gene bodies and beyond," Nat Rev Genet, 13:484-492 (2012).
Jones et al., "InterProScan 5: genome-scale protein function classification," Bioinformatics, 30:1236-1240 (2014).
Jones et al., "The epigenomics of cancer," Cell, 128:683-692 (2007).
Kannan et al., "Vaccination strategies in follicular lymphoma," Current hematologic malignancy reports, 4(4):189-195 (2009).
Karnani et al., "Pan-S replication patterns and chromosomal domains defined by genome-tiling arrays of ENCODE genomic areas," Genome research, 17:865-876 (2007).
Karolchik et al., "The UCSC Table Browser data retrieval tool," Nucleic acids research, 32:D493-496 (2004).
Kawai et al., "TLR signaling," Seminars in immunology, 19(1):24-32 (2007).
Kenter et al., "Vaccination against HPV-16 oncoproteins for vulvar intraepithelial neoplasia," New England Journal of Medicine, 361(19):1838-1847 (2009).
Khong et al., "Natural selection of tumor variants in the generation of "tumor escape" phenotypes," Nature immunology, 3:999-1005 (2002).
Kim et al., "A Myc network accounts for similarities between embryonic stem and cancer cell transcription programs," Cell, 143:313-324 (2010).
Kim et al., "TopHat2: accurate alignment of transcriptomes in the presence of insertions, deletions and gene fusions," Genome biology, 14:R36 (2013).

(56) References Cited

OTHER PUBLICATIONS

Kimmel et al., "[54] Identification and characterization of specific clones: Strategy for confirming the validity of presumptive clones," Methods in enzymology, 152:507-511 (1987).
Kirkwood et al., "High- and Low-dose Interferon Alpha-2b in High-isk Melanoma: First Analysis of Intergroup Trial E1690/S9111/C9190," J Clin Oncol, 18:2444-2458 (2000).
Kirkwood et al., "Interferon alfa-2b Adjuvant Therapy of High-Risk Resected Cutaneous Melanoma: The Eastern Cooperative Oncology Group Trial EST 1684," J Clin Oncol, 14:7-17 (1996).
Klebanoff et al., "Therapeutic cancer vaccines:are we there yet?," Immunol Rev, 239(1):27-44 (2011).
Klein et al., "Droplet Barcoding for Single-Cell Transcriptomics Applied to Embryonic Stem Cells," Cell, 161:1187-1201 (2015).
Kloor et al., "Immune evasion of microsatellite unstable colorectal cancers," International journal of cancer, 127:1001-1010 (2010).
Koch, "Combining morphology and DNA barcoding resolves the taxonomy of Western Malagasy Liotrigona Moure, 1961," African Invertebrates, 51(2):413-421 (2010).
Kreso et al., "Variable clonal repopulation dynamics influence chemotherapy response in colorectal cancer," Science, 339:543-548 (2013).
Kress et al., "DNA barcodes: Genes, genomics, and bioinformatics," PNAS, 105(8):2761-2762 (2008).
Kress et al., "Use of DNA barcodes to identify flowering plants," PNAS, 102(23):8369-8374 (2005).
Kulis et al., "Epigenomic analysis detects widespread gene-body DNA hypomethylation in chronic lymphocytic leukemia," Nat Genet, 44:1236-1242 (2012).
Lahaye et al., "DNA barcoding the floras of biodiversity hotspots," PNAS, 105(8):2923-2928 (2008).
Landan et al., "Epigenetic polymorphism and the stochastic formation of differentially methylated regions in normal and cancerous tissues," Nat Genet, 44:1207-1214 (2012).
Landau et al., "Clonal evolution in hematological malignancies and therapeutic implications," Leukemia, 28:34-43 (2014).
Landau et al., "Evolution and impact of subclonal mutations in chronic lymphocytic leukemia," Cell, 152(4):714-726 (2013).
Langmead et al., "Fast gapped-read alignment with Bowtie 2," Nature methods, 9:357-359 (2012).
Langmead et al., "Ultrafast and memory-efficient alignment of short DNA sequences to the human genome," Genome Biology, 10:R25 (2009).
Lawrence et al., "Discovery and saturation analysis of cancer genes across 21 tumour types," Nature, 505:495-501 (2014).
Lawrence et al., "Mutational heterogeneity in cancer and the search for new cancer-associated genes," Nature, 499:214-218 (2013).
Le et al., "Evaluation of Ipilimumab in combination with allogeneic pancreatic tumor cells transfected with a GM-CSF gene in previously treated pancreatic cancer," J Immunother, 36(7):382-389 (2013).
Lee et al., "Sequential amplification of cloned DNA as tandem multimers using class-IIS restriction enzymes," Genetic Analysis: Biomolecular Engineering, 13(6):139-145 (1996).
Leffers et al., "Immunization with a P53 synthetic long peptide vaccine induces P53☐specific immune responses in ovarian cancer patients, a phase II trial," Int J Cancer, 125(9):2104-2113 (2009).
Leffers et al., "Long☐term clinical and immunological effects of p53☐SLP☐ vaccine in patients with ovarian cancer," Int J Cancer, 130(1):105-112 (2012).
Lemay et al., "Dok-3, a Novel Adapter Molecule Involved in the Negative Regulation of Immunoreceptor Signaling," Mol Cell Biol, 20:2743-2754 (2000).
Lewintre et al., "Analysis of chronic lymphotic leukemia transcriptomic profile: differences between molecular subgroups," Leuk Lymphoma, 50:68-79 (2009).
Li et al., "Fast and accurate short read alignment with Burrows-Wheeler Transform," Bioinformatics, 25(14):1754-1760 (2009).
Li et al., "Inactivating mutations of the chromatin remodeling gene ARID2 in hepatocellular carcinoma," Nature Genetics, 43:828-829 (2011).
Li et al., "Mapping short DNA sequencing reads and calling variants using mapping quality scores," Genome Res, 18:1851-1858 (2008).
Li et al., "RSEM: accurate transcript quantification from RNA-Seq data with or without a reference genome," BMC Bioinformatics,12:323 (2011).
Li et al., "The Sequence Alignment/Map format and SAMtools," Bioinformatics, 25(16):2078-2079 (2009).
Li et al.,"Fast and accurate long-read alignment with Burrows-Wheeler transform," Bioinformatics, 26(5):589-595 (2010).
Liggins et al., "MORC4, a novel member of the MORC family, is highly expressed in a subset of diffuse large B-cell lymphomas," Brit J Haematol, 138:479-486 (2007).
Lim et al., "Transcriptome analyses of mouse and human mammary cell subpopulations reveal multiple conserved genes and pathways," Breast Cancer Res, 12:R21 (2010).
Lin et al., "Relevance of the immunoglobulin VH somatic mutation status in patients with chronic lymphocytic leukemia treated with fludarabine, cyclophosphamide, and rituximab (FCR) or related chemoimmunotherapy regimens," Blood, 113:3168-71 (2009).
Link et al., "Electric control of droplets in microfluidic devices," Angew Chem Int Ed Engl, 45(16):2556-2560 (2006).
Liu et al., "Systematic identification of type I and type II interferon-induced antiviral factors," PNAS, 109(11):4239-4244 (2012).
Livak et al. "Methods for qPCR gene expression profiling applied to 1440 lymphoblastoid single cells," Methods, 59(1):71-79 (2013).
Llobet et al., "CK2 controls TRAIL and Fas sensitivity by regulating FLIP levels in endometrial carcinoma cells," Oncogene, 27:2513-2524 (2008).
Lohr et al., "Discovery and prioritization of somatic mutations in diffuse large B-cell lymphoma (DLBCL) by whole-exome sequencing," PNAS, 109(10):3879-3884 (2012).
Lu et al., "Mutated regions of nucleophosmin 1PPP1R3B Is Recognized by T Cells Used to Treat a Melanoma Patient Who Experienced a Durable Complete Tumor Regression," J Immunol, 190(12):6034-6042 (2013).
Lund et al., "Coordination of early protective immunity to viral infection by regulatory T cells," Science, 320(5880):1220-1224 (2008).
Macosko et al., "Highly Parallel Genome-wide Expression Profiling of Individual Cells Using Nanoliter Droplets," Cell, 161(5):1202-1214 (2015).
Maegawa et al., "Age-related epigenetic drift in the pathogenesis of MDS and AML," Genome Res, 24:580-591 (2014).
Manghera et al, "Endogenous retrovirus-K promoter: a landing strip for inflammatory transcription factors?," Retrovirol, 10:16 (2013).
Marabelle et al., "Depleting tumor-specific Tregs at a single site eradicates disseminated tumors," J Clin Invest, 1123(6):2447-2463(2013).
Marcais et al., "A fast, lock-free approach for efficient parallel counting of occurrences of k-mers," Bioinformatics, 27(6):764-770 (2011).
Mayer et al., "A revised nomenclature for transcribed human endogenous retroviral loci," Mobile DNA, 2:7 (2011).
Mazutis et al., "Single-cell analysis and sorting using droplet-based microfluidics," Nat Protoc, 8:870-891 (2013).
McCormack et al., "HLA-A*3101 and Carbamazepine-Induced Hypersensitivity Reactions in Europeans," New Engl J Med, 364:1134-1143 (2011).
McDermott et al., "Immune Therapy for Kidney Cancer: A Second Dawn?," Semin Oncol, 40(4):492-498 (2013).
McFadden et al., "Genetic and clonal dissection of murine small cell lung carcinoma progression by genome sequencing," Cell, 156(6):1298-1311 (2014).
McKenna et al., "The Genome Analysis Toolkit: a MapReduce framework for analyzing next-generation DNA sequencing data," Genome Res, 20(9):1297-1303 (2010).
Medema et al., "Immune Escape of Tumors in Vivo by Expression of Cellular Flice-Inhibitory Protein," J Exp Med, 190:1033-1038 (1999).

(56) References Cited

OTHER PUBLICATIONS

Meissner et al., "Genome-scale DNA methylation maps of pluripotent and differentiated cells," Nature, 454:766-770 (2008).
Menke et al., "Genetic interactions between the Wilms' tumor 1 gene and the p53 gene," Cancer Res, 62(22):6615-6620 (2002).
Mermel et al., "GISTIC2.0 facilitates sensitive and confident localization of the targets of focal somatic copy-number alteration in human cancers," Genome Biol, 12:R41 (2011).
Messmer et al., "In vivo measurements document the dynamic cellular kinetics of chronic lymphocytic leukemia B cells," J Clin Invest, 115(3):755-764 (2005).
Missale et al., "HLA-A31- and HLA-Aw68-restricted cytotoxic T cell responses to a single hepatitis B virus nucleocapsid epitope during acute viral hepatitis," J Exp Med, 177(3):751-762 (1993).
Mocellin et al., "Interferon Alpha Adjuvant Therapy in Patients With High-Risk Melanoma: A Systematic Review and Meta-analysis," JNCI, 102(7):493-501 (2010).
Morison et al., "A census of mammalian imprinting," Trends Genet, 21(8):457-465 (2005).
Morozov et al., "The Transmembrane Protein of the Human Endogenous Retrovirus—K (HERV-K) Modulates Cytokine Release and Gene Expression," PloS one 8(8):e70399 (2013).
Morton et al., "Prolonged Survival of Patients Receiving Active Immunotherapy With Canvaxin Therapeutic Polyvalent Vaccine After Complete Resection of Melanoma Metastatic to Regional Lymph Nodes," Ann Surg, 236(4):438-448 (2002).
Nielsen et al., "NetMHCpan, a Method for Quantitative Predictions of Peptide Binding to Any HLA-A and -B Locus Protein of Known Sequence," PloS one, 2:e796 (2007).
Novershtern et al., "Densely Interconnected Transcriptional Circuits Control Cell States in Human Hematopoiesis," Cell, 144(2):296-309 (2011).
Oh et al., "Neutrophil isolation protocol," J Vis Exp (2008).
Ohnishi et al., "Premature Termination of Reprogramming In Vivo Leads to Cancer Development through Altered Epigenetic Regulation," Cell, 156(4):663-677 (2014).
Okada et al., "Induction of CD8+ T-Cell Responses Against Novel Glioma-Associated Antigen Peptides and Clinical Activity by Vaccinations With α-Type 1 Polarized Dendritic Cells and Polyinosinic-Polycytidylic Acid Stabilized by Lysine and Carboxymethylcellulose in Patients With Recurrent Malignant Glioma," J Clin Oncol, 29(3):330-336 (2011).
Oshiumi et al., "DEAD/H BOX 3 (DDX3) helicase binds the RIG-I adaptor IPS-1 to up-regulate IFN-beta-inducing potential," Eur J Immunol, 40:940-948 (2010).
Ott et al., "CTLA-4 and PD-1/PD-L1 Blockade: New Immunotherapeutic Modalities with Durable Clinical Benefit in Melanoma Patients," Clin Cancer Res, 19(19):5300-5309 (2013).
Padgett et al., "Creating seamless junctions independent of restriction sites in PCR cloning," Gene, 168:31-35 (1996).
Pages, et al., "Effector Memory T Cells, Early Metastasis, and Survival in Colorectal Cancer," New Engl J Med, 353:2654-2666 (2005).
Pei et al., "Genome-wide DNA methylation analysis reveals novel epigenetic changes in chronic lymphocytic leukemia," Epigenetics, 7:567-578 (2012).
Peng et al., "DOK3 Negatively Regulates LPS Responses and Endotoxin Tolerance," PloS one 7:e39967 (2012).
Perez et al., "p63 consensus DNA-binding site: identification, analysis and application into a p63MH algorithm," Oncogene, 26:7363-7370 (2007).
Pieters et al., "On guard: coronin proteins in innate and adaptive immunity," Nat Rev Immunol, 13:510-518 (2013).
Pirard et al., "Interferon Alpha as Adjuvant Postsurgical Treatment of Melanoma: A Meta-Analysis," Dermatology, 208(1):43-48 (2004).
Powell et al., "NCoR1 Mediates Papillomavirus E8ΛE2C Transcriptional Repression," J Virol, 84:4451-4460 (2010).
Pujadas et al., "Regulated noise in the epigenetic landscape of development and disease," Cell, 148(6):1123-1131 (2012).
Qin et al., "Soft lithography for micro- and nanoscale patterning," Nat Protoc, 5:491-502 (2010).
Quesada et al., "Exome sequencing identifies recurrent mutations of the splicing factor SF3B1 gene in chronic lymphocytic leukemia," Nat Genet, 44:47-52 (2012).
Quezada et al.,"CTLA4 blockade and Gm-Csf combination immunotherapy alters the intratumor balance of effector and regulatory T cells," J Clin Invest, 116(7):1935-1945 (2006).
Ramskold et al., "Full-length mRNA-Seq from single-cell levels of RNA and individual circulating tumor cells," Nat Biotechnol, 30:777-782 (2012).
Rassenti et al., "Relative value of ZAP-70, CD38, and immunoglobulin mutation status in predicting aggressive disease in chronic lymphocytic leukemia," Blood, 112:1923-1930 (2008).
Raval et al., "Downregulation of Death-Associated Protein Kinase 1 (DAPK1) in Chronic Lymphocytic Leukemia," Cell, 129(5):879-890 (2007).
Ravi et al., "Sensitization of Tumor Cells to Apo2 Ligand/TRAIL-induced Apoptosis by Inhibition of Casein Kinase II," Cancer Res, 62(15):4180-4185 (2002).
Richter et al., "Mechanistic Determinants of Biotherapeutics Absorption Following SC Administration," The AAPS Journal, 14(3):559-568 (2012).
Rini et al., "Biology and Treatment of Advanced Renal Cell Carcinoma: A Global Perspective," Semin Oncol, 40(4):419-420 (2013).
Robbins et al., "Mining exomic sequencing data to identify mutated antigens recognized by adoptively transferred tumor-reactive T cells," Nat Med, 19(6):747-752 (2013).
Robinson et al., "A phase I-II trial of multiple-dose polyriboinosic-polyribocytidylic acid in patieonts with leukemia or solid tumors," J Natl Cancer Inst, 57(3):599-602 (1976).
Robinson et al., "edgeR: a Bioconductor package for differential expression analysis of digital gene expression data," Bioinformatics, 26(1):139-140 (2010).
Robinson et al., "Integrative genomics viewer," Nat Biotechnol, 29:24-26 (2011).
Rosenberg, "Raising the Bar: The Curative Potential of Human Cancer Immunotherapy," Sci Transl Med, 4(127):127ps128 (2012).
Rossi et al., "Integrated mutational and cytogenetic analysis identifies new prognostic subgroups in chronic lymphocytic leukemia," Blood, 121:1403-1412 (2013).
Rubio-Moscardo et al., "Characterization of 8p21.3 chromosomal deletions in B-cell lymphoma: TRAIL-R1 and TRAIL-R2 as candidate dosage-dependent tumor suppressor genes," Blood, 106:3214-3222 (2005).
Rutledge et al., "Tumor-Infiltrating Lymphocytes in Glioblastoma Are Associated with Specific Genomic Alterations and Related to Transcriptional Class," Clin Cancer Res, 19:4951-4960 (2013).
Salem et al., "Defining the Antigen-Specific T-Cell Response to Vaccination and Poly(I:C)/TLR3 Signaling: Evidence of Enhanced Primary and Memory CD8 T-Cell Responses and Antitumor Immunity," J Immunother, 28(3):220-228 (2005).
Samuels et al., "Oncogenic P13K and its role in cancer," Curr Opin Oncol, 18:77-82n (2006).
Sato et al., "Discovery of Novel Targets for Aberrant Methylation in Pancreatic Carcinoma Using High-Throughput Microarrays," Cancer Res, 63(13):3735-3742 (2003).
Saturno et al., "Combining TRAIL with PI3 Kinase or HSP90 inhibitors enhances apoptosis in colorectal cancer cells via suppression of survival signaling," Oncotarget, 4(8):1185-1198 (2013).
Saunders et al., "Strelka: accurate somatic small-variant calling from sequenced tumor-normal sample pairs," Bioinformatics, 28(14):1811-1817 (2012).
Schmitt et al., "Transcriptional Profiling of Human Endogenous Retrovirus Group HERV-K(HML-2) Loci in Melanoma," Genome Biol Evol, 5(2):307-328 (2013).
Schreiber et al., "Cancer Immunoediting: Integrating Immunity's Roles in Cancer Suppression and Promotion," Science, 331(6024):1565-1570 (2011).
Schumacher et al., "Prognostic Significance of Activated CD8+ T Cell Infiltrations within Esophageal Carcinomas," Cancer Res, 61(10):3932-3936 (2001).

(56) References Cited

OTHER PUBLICATIONS

Schuster et al., "Vaccination With Patient-Specific Tumor-Derived Antigen in First Remission Improves Disease-Free Survival in Follicular Lymphoma," J Clin Oncol, 29(20):2787-2794 (2011).
Seberg et al., "How Many Loci Does it Take to DNA Barcode a Crocus?," PLoS One 4(2):e4598 (2009).
Secchiero et al., "Aberrant expression of TRAIL in B chronic lymphocytic leukemia (B-CLL) cells," J Cell Physiol, 205(2):246-252 (2005).
Sensi et al., "Unique tumor antigens: evidence for immune control of genome integrity and immunogenic targets for T cell-mediated patient-specific immunotherapy," Clin Cancer, Res 12:5023-5032 (2006).
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, 2(2):117-125 (2002).
Shalek et al., "Single-cell RNA-seq reveals dynamic paracrine control of cellular variation," Nature, 510(7505):363-369 (2014).
Shannon, "A Mathematical Theory of Communication," Bell System Technical Journal, 27(3):379-423 (1948).
Shao et al., "Clonally related histiocytic/dendritic cell sarcoma and chronic lymphocytic leukemia/small lymphocytic lymphoma: a study of seven cases," Mod Pathol, 24:1421-1432 (2011).
Shendure et al., "Next-generation DNA sequencing," Nat Biotechnol, 26(10):1135-1145 (2008).
Shipony et al., "Dynamic and static maintenance of epigenetic memory in pluripotent and somatic cells," Nature, 513:115-119 (2014).
Sidney et al., "HLA class I supertypes: a revised and updated classification," BMC Immunol, 9:1 (2008).
Siegel et al., "Cancer statistics, 2013," CA, 63(1):11-30 (2013).
Simmons et al., "Local secretion of anti-CTLA-4 enhances the therapeutic efficacy of a cancer immunotherapy with reduced evidence of systemic autoimmunity," Cancer Immunol Immunother, 57(8):1263-1270 (2008).
Simpson et al., "Cancer/testis antigens, gametogenesis and cancer," Nat Rev Cancer, 5:615-625 (2005).
Simpson et al., "Fc-dependent depletion of tumor-infiltrating regulatory T cells co-defines the efficacy of anti-CTLA-4 therapy against melanoma," J Exp Med, 210(9):1695-1710 (2013).
Slingluff et al., "Randomized Multicenter Trial of the Effects of Melanoma-Associated Helper Peptides and Cyclophosphamide on the Immunogenicity of a Multipeptide Melanoma Vaccine," J Clin Oncol, 29(21):2924-2932 (2011).
Smith et al., "Comparison of biosequences," Adv Appl Math, 2(4):482-489 (1981).
Smoley et al., "Standardization of fluorescence in situ hybridization studies on chronic lymphocytic leukemia (CLL) blood and marrow cells by the CLL Research Consortium," Cancer Genet Cytogenet, 203(2):141-148 (2010).
Soares et al. "A subset of dendritic cells induces CD4+ T cells to produce IFN-gamma by an IL-12-independent but CD70-dependent mechanism in vivo," J Exp Med, 2215(11):1095-1106 (2007).
Soininen et al., "Analysing diet of small herbivores: the efficiency of DNA barcoding coupled with high-throughput pyrosequencing for deciphering the composition of complex plant mixtures," Front Zool, 6:16 (2009).
Song et al., "c-Cbl acts as a mediator of Src-induced activation of the PI3K-Akt signal transduction pathway during TRAIL treatment," Cellular Signalling, 22(3):377-385 (2010).
Sosman et al., "A phase 2 trial of complete resection for stage IV melanoma: results of Southwest Oncology Group Clinical Trial S9430," Cancer, 117(20):4740-4706 (2011).
Speetjens et al., "Induction of p53-Specific Immunity by a p53 Synthetic Long Peptide Vaccine in Patients Treated for Metastatic Colorectal Cancer," Clin Cancer Res, 15(3):1086-1095 (2009).
Spencer et al., "Non-genetic origins of cell-to-cell variability in TRAIL-induced apoptosis," Nature, 459:428-432 (2009).

Spranger et al., "Up-regulation of PD-LI, IDO, and Tregs in the melanoma tumor microenvironment is driven by CD8+ T cells," Sci Transl Med, 5(200):200ra116 (2013).
Stransky et al., "The Mutational Landscape of Head and Neck Squamous Cell Carcinoma," Science, 333:1157-1160 (2011).
Su et al., "Next-generation sequencing and its applications in molecular diagnostics" Exp Rev Mol Diagn, 11(3):333-343 (2011).
Subramanian et al., "Gene set enrichment analysis: a knowledge-based approach for interpreting genome-wide expression profiles," PNAS, 102:15545-15550 (2005).
Suzuki et al., "A Novel Glycosylphosphatidyl Inositol-Anchored Protein on Human Leukocytes: A Possible Role for Regulation of Neutrophil Adherence and Migration," J Immunol, 162(7):4277-4284 (1999).
Sykulev et al., "Evidence that a Single Peptide-MHC Complex on a Target Cell Can Elicit a Cytolytic T Cell Response," Immunity, 4:565-571 (1996).
Tang et al., "The landscape of viral expression and host gene fusion and adaptation in human cancer," Nat Commun, 4:2513 (2013).
Ten Bosch et al., "Keeping Up With the Next Generation: Massively Parallel Sequencing in Clinical Diagnostics," J Mol Diagn, 10(6):484-492 (2008).
Teng et al., "A human TAPBP (TAPASIN)-related gene, TAPBP-R," Eur J Immunol, 32:1059-1068 (2002).
Testori et al., "Phase III comparison of vitespen, an autologous tumor-derived heat shock protein gp96 peptide complex vaccine, with physician's choice of treatment for stage IV melanoma: the C-100-21 Study Group," J Clin Oncol, 26(6):955-962 (2008).
Textor et al., "Human NK cells are alerted to induction of p53 in cancer cells by upregulation of the NKG2D ligands ULBPI and ULBP2," Cancer Res, 71:5998-6009 (2011).
Timp et al., "Cancer as a dysregulated epigenome allowing cellular growth advantage at the expense of the host," Nat Rev Cancer, 13:497-510 (2013).
Topalian et al., "Safety, Activity, and Immune Correlates of Anti-PD-1 Antibody in Cancer," N Engl J Med, 366(26):2443-2454 (2012).
Topalian et al., "Survival, Durable Tumor Remission, and Long-Term Safety in Patients With Advanced Melanoma Receiving Nivolumab," J Clin Oncol, 32(10):1020-1030 (2014).
Tough et al., "Induction of bystander T cell proliferation by viruses and type I interferon in vivo," Science, 272(5270):1947-1950 (1996).
Tran et al., "Cancer Immunotherapy Based on Mutation-Specific CD4+ T Cells in a Patient with Epithelial Cancer," Science, 344(6184):641-645 (2014).
Trumpfheller et al., "Intensified and protective CD4+ T cell immunity in mice with anti-dendritic cell HIV gag fusion antibody vaccine," J Exp Med, 203(3):607-617 (2006).
Trumpfheller et al., "The microbial mimic poly IC induces durable and protective CD4+ cell immunity together with a dendritic cell targeted vaccine," PNAS, 105(7):2574-2579 (2008).
Tucker et al., "Massively Parallel Sequencing:The Next Big Thing in Genetic Medicine," Am J Hum Genet, 85(2):142-154 (2009).
Uderhardt et al., "12/15-lipoxygenase orchestrates the clearance of apoptotic cells and maintains immunologic tolerance," Immunity, 36(5):834-846 (2012).
Ushijima et al., "Fidelity of the methylation pattern and its variation in the genome," Genome research, 13:868-874 (2005).
Uyttenhove et al., "Evidence for a tumoral immune resistance mechanism based on tryptophan degradation by indoleamine 2,3-di oxygenase," Nature medicine, 9:1269-1274 (2003).
Vaishampayan et al., "Active immunotherapy of metastatic melanoma with allogeneic melanoma lysates and interferon alpha," Clin Cancer Res, 8(12):3696-3701 (2002).
Van Elsas et al., "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," Journal of Experimental Medicine, 190(3):355-366 (1999).

(56) References Cited

OTHER PUBLICATIONS

Van Poelgeest et al., "HPV16 synthetic long peptide (HPV16-SLP) vaccination therapy of patients with advanced or recurrent HPV16-induced gynecological carcinoma, a phase II trial," J Transl Med, 11:88 (2013).
Van Rooij et al., "Tumor exome analysis reveals neoantigen-specific T-cell reactivity in an ipilimumab-responsive melanoma," Journal of clinical oncology: official journal of the American Society of Clinical Oncology, 31:32 (2013).
Vermeij et al., "Potentiation of a p53-SLP vaccine by cyclophosphamide in ovarian cancer: a single-arm phase II study," Int J Cancer, 131(5):E670-680 (2012).
Wahl et al., "[43] Molecular hybridization of immobilized nucleic acids: Theoretical concepts and practical considerations," Methods in enzymology, Academic Press, 152:399-407 (1987).
Wang et al., "Role of protein kinase CK2 in the regulation of tumor necrosis factor-related apoptosis inducing ligand-induced apoptosis in prostate cancer cells," Cancer research, 66:2242-2249 (2006).
Wang et al., "SF3B1 and other novel cancer genes in chronic lymphocytic leukemia," N Engl J Med, 365:2497-2506 (2011).
Wang et al., "Widespread plasticity in CTCF occupancy linked to DNA methylation," Genome Res, 22:1680-1688 (2012).
Weber et al., "Assembly of Designer TAL Effectors by Golden Gate Cloning," PLoS One, 6:e19722 (2001).
Welters et al., "Induction of tumor-specific CD4+ and CD8+ T-cell immunity in cervical cancer patients by a human papillomavirus type 16 E6 and E7 long peptides vaccine," Clinical cancer research, 14(1):178-187 (2008).
Welters et al., "Success or failure of vaccination for HPV16-positive vulvar lesions correlates with kinetics and phenotype of induced T-cell responses," PNAS, 107(26):11895-11899 (2010).
Wheatley et al., "Does adjuvant interferon-alpha for high-risk melanoma provide a worthwhile benefit?A meta-analysis of the randomised trials," Cancer treatment reviews, 29(4):241-252 (2003).
Widschwendter et al., "Epigenetic stem cell signature in cancer," Nat Genet, 39:157-158 (2007).
Wierda et al., "Multivariable model for time to first treatment in patients with chronic lymphocytic leukemia," J Clin Oncol, 29:4088-4095 (2011).
Winzeler et al., "Functional characterization of the S. cerevisiae genome by gene deletion and parallel analysis," science, 285(5429):901-906 (1999).
Wolchok et al., "Nivolumab plus ipilimumab in advanced melanoma," N Engl J Med, 369(2):122-133 (2013).
Wong et al., "Module map of stem cell genes guides creation of epithelial cancer stem cells," Cell Stem Cell, 2:333-344 (2008).
Woodfine et al., "Quantitative analysis of DNA methylation at all human imprinted regions reveals preservation of epigenetic stability in adult somatic tissue," Epigenetics & chromatin, 4:1 (2011).
Woyach et al., "Resistance mechanisms for the Bruton's tyrosine kinase inhibitor ibrutinib," The New England journal of medicine, 370:2286-94 (2014).
Xi et al., "BSMAP: whole genome bisulfite sequence MAPping program," BMC bioinformatics, 10:232 (2009).
Xie et al., "Stepwise reprogramming of B cells into macrophages," Cell, 117(5):663-676 (2004).
Xu et al., "Design of 240,000 orthogonal 25mer DNA barcode probes," Proceedings of the National Academy of Sciences, pnas-0812506106 (2009).
Yan et al., "Pbaf chromatin-remodeling complex requires a novel specificity subunit, BAF200, to regulate expression of selective interferon-responsive genes," Genes & development, 19(14):1662-1667 (2005).
Yang et al., "Meta-analysis followed by replication identifies loci in or near CDKN1B, TET3, CD80, DRAM1, and ARID5B as associated with systemic lupus erythematosus in Asians," American journal of human genetics, 92:41-51 (2013).
Yoshihara et al., Inferring tumour purity and stromal and immune cell admixture from expression data,: Nature communications 4:2612 (2013).
Yoshitake et al., "Cross□linking of GPI□080, a possible regulatory molecule of cell adhesion, induces up□regulation of CD11b/CD18 expression on neutrophil surfaces and shedding of L□ selectin," Journal of leukocyte biology, 71(2):205-211 (2002).
Young et al., "Resurrection of endogenous retroviruses in antibody-deficient mice," Nature, 491(7426):774 (2012).
Yu et al., "Nucleic acid-sensing Toll-like receptors are essential for the control of endogenous retrovirus viremia and ERV-induced tumors," Immunity, 37(5):867-879 (2012).
Yuille et al., "TCL1 is activated by chromosomal rearrangement or by hypomethylation," Genes, Chromosomes and Cancer, 30(4):336-341 (2001).
Zeestraten et al., "Addition of interferon-alpha to the p53-SLP(R) vaccine results in increased production of interferon-gamma in vaccinated colorectal cancer patients: a phase I/11 clinical trial," Int J Cancer, 132(7):1581-1591 (2013).
Zhang et al., "Machine learning competition in immunology-prediction of HLA class I binding peptides," J Immunol Methods 374:1-4 (2009).
Zhou et al., "A hypermorphic missense mutation in PLCG2, encoding phospholipase Cgamma2, causes a dominantly inherited autoinflammatory disease with immunodeficiency," Am J Hum Genet, 91:713-20 (2012).
Zhu et al., "Toll like receptor-3 ligand poly-ICLC promotes the efficacy of peripheral vaccinations with tumor antigen-derived peptide epitopes in murine CNS tumor models," Journal of translational medicine, 5:10 (2007).
Ziller et al., "Charting a dynamic DNA methylation landscape of the human genome," Nature, 500:477-481 (2013).
Zorn et al., "A natural cytotoxic T cell response in a spontaneously regressing human melanoma targets a neoantigen resulting from a somatic point mutation," Eur J Immunol, 29(2):592-601 (1999).
Zwaveling et al., "Established human papillomavirus type 16-expressing tumors are effectively eradicated following vaccination with long peptides," J Immunol, 169(1):350-358 (2002).
U.S. Appl. No. 15/187,174, filed Jun. 20, 2016, 2016-0331822, Abandoned.
U.S. Appl. No. 16/181,098, filed Nov. 5, 2018, 2019-0060432, Published.
Andreatta et al., "Gapped sequence alignment using artificial neural networks: application to the MHC class I system," Bioinformatics 32(4):511-517 (2016).
Bassani-Sternberg et al., "Mass Spectrometry of Human Leukocyte Antigen Class I Peptidomes Reveals Strong Effects of Protein Abundance and Turnover on Antigen Presentation," Mol Cell Proteomics, 14:658-673 (2015).
Boisgerault et al., "Definition of the HLA-A29 peptide ligand motif allows prediction of potential T-cell epitopes from the retinal soluble antigen, a candidate autoantigen in birdshot retinopathy," PNAS, 93:3466-3470 (1996).
Bourdetsky et al., The nature and extent of contributions by defective ribosome products to the HLA peptidome, PNAS, III, E1591-E1599 (2014).
Bremel et al., "An integrated approach to epitope analysis I: Dimensional reduction, visualization and prediction of MHC binding using amino acid principal components and regression approaches," Immunome Res, 6:7 (2010).
Caron et al., "Analysis of MHC immunopeptidomes using mass spectrometry," Mol Cell Proteomics (2015), doi: 10.1074/mcp.OI 15.052431.
Chowell et al., "TCR contact residue hydrophobicity is a hallmark of immunogenic CD8($_+$) T cell epitopes," PNAS, 112:E1754-E1762 (2015).
Christianson et al., "Defining human ERAD networks through an integrative mapping strategy," Nat Cell Biol, 14:93-105 (2012).
Eichmann et al., "Identification and characterisation of peptide binding motifs of six autoimmune disease-associated human leukocyte antigen-class I molecules including HLA-B*39:06," Tissue Antigens 84(4):378-388 (2014).
Elias et al., Target-decoy search strategy for increased confidence in large-scale protein identifications by mass spectrometry, Nat Meth, 4:207-214 (2007).

(56) References Cited

OTHER PUBLICATIONS

Eyers et al., "CONSeQuence: prediction of reference peptides for absolute quantitative proteomics using consensus machine learning approaches," Mol Cell Proteomics (2011); 10(11):M110.003384. doi: 10.1074/mcp.MI 10.003384. Epub Aug. 3, 2011.
Fruci et al., "Altered expression of endoplasmic reticulum aminopeptidases ERAPI and ERAP2 in transformed non-lymphoid human tissues," J Cell Physiol, 2I6(3):742-749 (2008).
Fusaro et al., "Prediction of high-responding peptides for targeted protein assays by mass spectrometry" Nat Biotechnol, 27(2):190-198 (2009).
Guasp et al., "The Peptidome of Behcet's Disease-Associated HLA-B*51 :01 Includes Two Subpeptidomes Differentially Shaped by Endoplasmic Reticulum Aminopeptidase 1," Arthritis Rheumatol, 68:505-515 (2016).
Guruprasad et al., "Correlation between stability of a protein and its dipeptide composition: a novel approach for predicting in vivo stability of a protein from its primary sequence," Protein Eng, 4(2):155-161 (1990).
Harndahl et al., "Peptide-MHC class I stability is a better predictor than peptide affinity of CTL immunogenicity," Eur J Immunol, 42:1405-1416 (2012).
Harndahl et al., "Real-time, High-Throughput Measurements of Peptide-MHC-I Dissociation Using a Scintillation Proximity Assay," J Immunol Methods, 374:5-12 (2011).
Hickman et al., "Toward a Definition of Self: Proteomic Evaluation of the Class I Peptide Repertoire," J Immunol, 172:2944-2952 (2004).
Hoof et al., "NetMHCpan, a method for MHC class I binding prediction beyond humans," Immunogenetics, 61:1-13 (2009).
Hunt et al., "Characterization of peptides bound to the class I MHC molecule HLA-A2.1 by mass spectrometry," Science, 255:1261-1263 (1992).
Ishihama et al., "Exponentially Modified Protein Abundance Index (emPAI) for Estimation of Absolute Protein Amount in Proteomics by the Number of Sequenced Peptides per Protein," Mol Cell Proteomics, 4:1265-1272 (2005).
Jeffery et al., "The Influence of HLA Class I Alleles and Heterozygosity on the Outcome of Human T Cell Lymphotropic Virus Type I Infection," J Immunol, 165:7278-7284 (2000).
Jorgensen et al., "NetMHC stab—predicting stability of peptide-MHC-I complexes; impacts for cytotoxic T lymphocyte epitope discovery," Immunology 141:18-26 (2014).
Keskin et al., "Direct identification of an HPV-16 tumor antigen from cervical cancer biopsy specimens," Front Immunol, 2:75 (2011).
Keskin et al., "Physical detection of influenza A epitopes identifies a stealth subset on human lung epithelium evading natural CD8 immunity," PNAS, 112(7):2151-2156 (2015).
Kesmir et al., "Prediction of proteasome cleavage motifs by neural networks," Protein Eng, 15(4):287-296 (2002).
Kim et al., "Derivation of an amino acid similarity matrix for peptide:MHC binding and its application as a Bayesian prior," BMC Bioinformatics, 10:1-11 (2009).
Kronke et al. "Lenalidomide causes selective degradation of IKZFI and IKZF3 in multiple myeloma cells," Science, 343(6168): 301-305 (2014).
Kronke et al. "Lenalidomide induces ubiquitination and degradation of CKIa in del(5q) MDS," Nature, 523(7559):183-188 (2015).
Larsen et al., "Large-scale validation of methods for cytotoxic T-lymphocyte epitope prediction," BMC Bioinformatics, 8:424-424 (2007).
Linnemann et al., "High-throughput epitope discovery reveals frequent recognition of neo-antigens by CD4+ T cells in human melanoma," Nat Med, 21:81-85 (2015).
Llano et al., "Best-Characterized HIV-1 CTL Epitopes: The 2013 Update," HIV Mol Immunol , 3-25 (2013).
Lorente et al., "Diversity of Natural Self-Derived Ligands Presented by Different HLA Class I Molecules in Transporter Antigen Processing-Deficient Cells," PLoS One 8:e59118 (2013).

Ma, "Novor: Real-Time Peptide de Novo Sequencing Software," J Am Soc Mass Spectrom, 26:1885-1894 (2015).
McMurtrey et al., "Toxoplasma gondii peptide ligands open the gate of the HLA class I binding groove," eLife 5:e12556 (2016).
Milner et al., "The Effect of Proteasome Inhibition on the Generation of the Human Leukocyte Antigen (HLA) Peptidome," Mol Cell Proteomics, 12:1853-1864 (2013).
Milner et al., "The Turnover Kinetics of Major Histocompatibility Complex Peptides of Human Cancer Cells*," Mol Cell Proteomics, 5:357-365 (2006).
Mommen et al., "Expanding the detectable HLA peptide repertoire using electron-transfer/higher-energy collision dissociation (EThcD)," PNAS III, 4507-4512 (2014).
Mommen et al., "Sampling From the Proteome to the Human Leukocyte Antigen-DR (HLA-DR) Ligandome Proceeds Via High Specificity," Mol Cell Proteomics MCP, 15:1412-1423 (2016).
Muntel et al., "Abundance-based Classifier for the Prediction of Mass Spectrometric Peptide Detectability Upon Enrichment (PPA)," Mol Cell Proteomics, 14:430-440 (2015).
Ng et al., "Dereplication and de novo sequencing of nonribosomal peptides," Nat Meth, 6:596-599 (2009).
Nielsen et al., "The role of the proteasome in generating cytotoxic T-cell epitopes: insights obtained from improved predictions of proteasomal cleavage," Immunogenetics, 57:33-41 (2005).
Oates et al., "D(2)P(2): database of disordered protein predictions," Nucleic Acids Res, 41:D508-D516 (2013).
Osorio et al., "Stability Analysis of Antimicrobial Peptides in Solvation Conditions by Molecular Dynamics," Adv Comp Bio, 232:127-131 (2014).
Pritchard et al., "Exome Sequencing to Predict Neoantigens in Melanoma," Cancer Immunol Res, 3:992-998 (2015).
Rappsilber et al., "Protocol for micro-purification, enrichment, pre-fractionation and storage of peptides for proteomics using StageTips," Nat Protoc, 2(8):1896-1906 (2007).
Reche et al., "Elicitation from virus-naive individuals of cytotoxic T lymphocytes directed against conserved HIV-1 epitopes," Med Immunol, 5:1 (2006).
Robinson et al., "The IPD and FMGT/HLA database: allele variant databases," Nucleic Acids Res, 43:D423-D431 (2015).
Rock et al., "Re-examining class-I presentation and the DRiP hypothesis," Trends Immunol, 35(4):144-152 (2014).
Ruggles et al., "An analysis of the sensitivity of proteogenomic mapping of somatic mutations and novel splicing events in cancer," Cell Proteomics, 15(3):1060-1071 (2015).
Saveanu et al., "Concerted peptide trimming by human ERAPI and ERAP2 aminopeptidase complexes in the endoplasmic reticulum," Nat Immunol, 6:689-697 (2005).
Saxova et al., "Predicting proteasomal cleavage sites: a comparison of available methods," Int Immunol, 15:781-787 (2003).
Schumacher et al., "Neoantigens in cancer immunotherapy," Science, 348:69-74 (2015).
Searle et al., "Using Data Independent Acquisition (DIA) to Model High-responding Peptides for Targeted Proteomics Experiments," Mol Cell Proteomics, 14:2331-2340 (2015).
Shimizu et al., "Production of human cells expressing individual transferred HLA-A,-B,-C genes using an HLA-A,-B,-C null human cell line," J Immunol, 142(9):3320-3328 (1989).
Shimizu et al., "Transfer of cloned human class I major histocompatibility complex genes into HLA mutant human lymphoblastoid cells," Mol Cell Biol, 6(4):1074-1087 (1986).
Sidney et al., "Measurement of MHC/Peptide Interactions by Gel Filtration" Curr Prot Immunol, 31(1):18.3.1-18.3.19 (1999).
Sowa et al., "Defining the Human Deubiquitinating Enzyme Interaction Landscape," Cell, 138(2):389-403 (2009).
Trolle et al., "The Length Distribution of Class 1-Restricted T Cell Epitopes Is Determined by Both Peptide Supply and MHC Allele-Specific Binding Preference," J Immunol (2016), doi: 10.4049/jimmunol.1501721.
Tynan et al., "T cell receptor recognition of a "super-bulged" major histocompatibility complex class I-bound peptide," Nat Immunol, 6:1114-1122 (2005).

(56) References Cited

OTHER PUBLICATIONS

Udeshi et al., "Methods for quantification of in vivo changes in protein ubiquitination following proteasome and deubiquitinase inhibition," Mol Cell Proteomics, 11:148-159 (2012).
Vita et al., "The immune epitope database (IEDB) 3.0," Nucleic Acids Res, 43:D405-D412 (2015).
Walz et al., "The antigenic landscape of multiple myeloma: mass spectrometry (re)defines targets for T-cell-based immunotherapy," Blood 126:1203-1213 (2015).
Yewdell, "DRiPs solidify: progress in understanding endogenous MHC class I antigen processing," Trends Immunol, 32(11):548-558 (2011).
Zhang et al., "Dana-Farber repository for machine learning in immunology," J Immunol Methods, 374(1-2):18-25 (2011).
Dressman et al., "Gene expression profiles of multiple breast cancer phenotypes and response to neoadjuvant chemotherapy," Clin Cancer Res, 12(3):819-826 (2006).
Final Rejection for U.S. Appl. No. 15/102,129, "Formulations for Neoplasia Vaccines," dated Aug. 15, 2019.
Final Rejection for U.S. Appl. No. 15/105,961, "Combination Therapy With Neoantigen Vaccine," dated Aug. 23, 2019.
Final Rejection for U.S. Appl. No. 15/537,785, "Methods for Profiling the T Cell Repertoire," dated Jul. 18, 2019.
Haanen et al., "Immunotherapy of melanoma," Euro J Canc Supp 11:97-105 (2013).
Kim et al., "Inactivating mutations of caspase-8 in colorectal carcinomas," Gastroenterology, 125:708-715 (2003).
Loveridge et al., "The genetic contribution to human T-cell receptor repertoire," Immunology, 74:246-250 (1991).
Non-Final Rejection for U.S. Appl. No. 15/537,839, "Molecular Biomarkers for Cancer Immunotherapy," dated Oct. 8, 2019.
Notice of Allowance for U.S. Appl. No. 16/188,737, "Compositions and Methods of Identifying Tumor Specific Neoantigens," dated Jul. 25, 2019.
Soung et al., "Capase-8 gene is frequently inactivated by the frameshift somatic mutation 1225_1226delTG in hepatocellular carcinomas," Oncogene, 24:141-147 (2005).
Supplementary Materials from Third Party Observation in EP Application No. 15198284.0, 2009.
Chang et al., "Use of tumor genomic profiling to reveal mechanisms of resistance to the BTK inhibitor ibrutinib in chronic lymphocytic leukemia (CLL)," J Clin Oncol, 31(15S):Abstract 7014 (2013).
DeKosky et al., "High-throughput sequencing of the paired human immunoglobulin heavy and light chain repertoire," Nature Biotech 166-170 (2013).
Du et al., "The Significance and Therapeutic Potential of GATA3 Expression and Mutation in Breast Cancer: A Systematic Review," Med Res Rev, 35(6):1300-1315 (2015).
Final Rejection for U.S. Appl. No. 14/794,449, "Compositions and Methods of Identifying Tumor Specific Neoantigens," dated Apr. 5, 2019.
Final Rejection for U.S. Appl. No. 14/877,125, "Compositions and Methods for Personalized Neoplasia Vaccines," dated May 24, 2019.
Final Rejection for U.S. Appl. No. 15/513,127, "Use of Clonal Evolution Analysis for Ibrutinib Resistance in Chronic Lymphocytic Leukemia Patients," dated May 17, 2019.
Final Rejection for U.S. Appl. No. 16/181,098, "Compositions and Methods of Identifying Tumor Specific Neoantigens," dated Jun. 17, 2019.
Mackall et al., "Targeting tumor specific translocations in sarcomas in pediatric patients for immunotherapy," Clinical Orthopaedics and Related Research, 373:25-31 (2000).
Mardis, "The impact of next-generation sequencing technology on genetics," Trends in Genetics, 24(3):133-141 (2007).
Non-Final Office Action for U.S. Appl. No. 15/102,129, "Formulations for Neoplasia Vaccines," dated Apr. 26, 2019.
Non-Final Office Action for U.S. Appl. No. 15/575,328, "Shared Neoantigens," dated Jun. 27, 2019.
O'Mahony et al., "A Pilot Study of CTLA-4 Blockade after Cancer Vaccine Failure in Patients with Advanced Malignancy" Clin Canc Res 13(3):958-964 (2007).
Peters et al., "Accurate whole-genome sequencing and haplotyping from 10 to 20 human cells," Nature 487:190-195 (2012).
Restriction Requirement for U.S. Appl. No. 15/537,839, "Molecular Biomarkers for Cancer Immunotherapy," dated Jun. 20, 2019.
Vita et al., "The Immune Epitope Database 2.0," Nucleic Acids Res, 38:D854-D862 (2010).
U.S. Appl. No. 16/094,786, filed Oct. 18, 2018, Pending.
U.S. Appl. No. 13/108,610, filed May 16, 2011, 2011-0293637, U.S. Pat. No. 9,115,402, Granted.
U.S. Appl. No. 14/794,449, filed Jul. 8, 2015, 2016-00008447, Published.
U.S. Appl. No. 15/187,174, filed Jun. 20, 2016, 2016-0331822, Published.
U.S. Appl. No. 15/800,732, filed Nov. 1, 2017, 2018-0055922, Published.
U.S. Appl. No. 16/181,098, filed Nov. 5, 2018, Pending.
U.S. Appl. No. 16/188,737, filed Nov. 13, 2018, U.S. Pat. No. 10,426,824, Granted.
U.S. Appl. No. 16/381,791, filed Apr. 11, 2019, Pending.
U.S. Appl. No. 16/528,195, filed Jul. 31, 2019, Pending.
U.S. Appl. No. 14/877,125, filed Oct. 7, 2015, 2016-0101170, Published.
U.S. Appl. No. 15/102,129, filed Jun. 6, 2016, 2016-0310584, Published.
U.S. Appl. No. 15/038,504, filed May 23, 2016, 2016-0326593, Published.
U.S. Appl. No. 15/105,961, filed Jun. 17, 2016, 2016-0339090, Published.
U.S. Appl. No. 15/537,785, filed Jun. 19, 2017, 2018-0000913, Published.
U.S. Appl. No. 15/537,839, filed Jun. 19, 2017, 2019-0127803, Published.
U.S. Appl. No. 15/575,328, filed Nov. 17, 2017, 2018-0153975, Published.
U.S. Appl. No. 15/513,127, filed Mar. 21, 2017, 2017-0298441, Published.
U.S. Appl. No. 15/735,566, filed Dec. 11, 2017, 2019-0060428, Published.
U.S. Appl. No. 16/480,535, filed Jul. 24, 2019, Pending.
PCT/US18/14831, Jan. 23, 2018, WO2018/140391, Published.
11781409.5 (opposition therein), May 16, 2011, 2569633, 2569633, Granted-opposition pending.

* cited by examiner

SHARED NEOANTIGENS

RELATED APPLICATIONS AND INCORPORATION BY REFERENCE

This application is a § 371 of international patent application Serial No. PCT/US2016/033452 filed May 20, 2016, which published as PCT Publication No. WO 2016/187508 on Nov. 24, 2016, which claims priority and benefit of U.S. Provisional application Ser. No. 62/179,877 filed May 20, 2015 and U.S. Provisional application Ser. No. 62/389,377 filed Feb. 23, 2016.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a "lengthy" Sequence Listing which has been submitted electronically in ASCII format and is hereby incorporated by reference in its entirety. Said ASCII format, created on Aug. 11, 2016, is named 47608_99_2007_SL.txt and is 10,252,288 bytes in size.

FIELD OF THE INVENTION

The present invention relates to methods and compositions for treating neoplasias, e.g. tumors, particularly using at least one neoantigenic peptide which is suitable for treating a significant proportion of subjects in a population suffering from cancer.

BACKGROUND OF THE INVENTION

Approximately 1.6 million Americans are diagnosed with neoplasia every year, and approximately 580,000 people in the United States are expected to die of the disease in 2013. Over the past few decades there been significant improvements in the detection, diagnosis, and treatment of neoplasia, which have significantly increased the survival rate for many types of neoplasia. However, only about 60% of people diagnosed with neoplasia are still alive 5 years after the onset of treatment, which makes neoplasia the second leading cause of death in the United States.

Currently, there are a number of different existing cancer therapies, including ablation techniques (e.g., surgical procedures, cryogenic/heat treatment, ultrasound, radiofrequency, and radiation) and chemical techniques (e.g., pharmaceutical agents, cytotoxic/chemotherapeutic agents, monoclonal antibodies, and various combinations thereof). Unfortunately, such therapies are frequently associated with serious risk, toxic side effects, and extremely high costs, as well as uncertain efficacy.

There is a growing interest in cancer therapies that seek to target cancerous cells with a patient's own immune system (e.g., cancer vaccines) because such therapies may mitigate/eliminate some of the herein-described disadvantages. Cancer vaccines are typically composed of tumor antigens and immunostimulatory molecules (e.g., cytokines or TLR ligands) that work together to induce antigen-specific cytotoxic T cells that target and destroy tumor cells. Current cancer vaccines may contain shared tumor antigens, which are native proteins (i.e.—proteins encoded by the DNA of all the normal cells in the individual) that are selectively expressed or over-expressed in tumors found in many individuals. While such shared tumor antigens are useful in identifying particular types of tumors, they are not ideal as immunogens for targeting a T-cell response to a particular tumor type because they are subject to the immune dampening effects of self-tolerance. Vaccines containing tumor-specific and patient-specific neoantigens can overcome some of the disadvantages of vaccines containing shared tumor antigens. However, the use of patient-specific neoantigens requires sequencing of individual subject's genomes, as well as the production of personalized compositions comprising a combination of neoantigens present in that individual subject. Accordingly, there is still a need for improved methods and compositions for delivering cancer vaccines.

Citation or identification of any document in this application is not an admission that such document is available as prior art to the present invention.

SUMMARY OF THE INVENTION

Preferred statements (features) and embodiments of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous. Hereto, the present invention is in particular captured by any one or any combination of one or more of the below statements and embodiments, with any other statement and/or embodiments.

It is an objective of the invention to provide methods and compositions for the treatment of a population of cancer patients by eliciting an immune response targeting the cancer. In one aspect, the present invention relates to a pharmaceutical composition comprising at least one neoantigenic peptide and a pharmaceutically acceptable carrier, each at least one neoantigenic peptide comprising a tumor-specific neoepitope capable of binding to an HLA protein in a subject, each tumor-specific neoepitope comprising a tumor-specific mutation present in a tumor. The composition may include one neoantigenic peptide. In other embodiments, the composition may include more than 100 neoantigenic peptides. Preferably, the composition includes about 20 neoantigenic peptides. The at least one neoantigenic peptide may include a tumor-specific mutation. The mutation may be recurrent. Preferably, the mutation is present in a large proportion of a population. A recurrent mutation may be based on the mutation being present in a tumor in at least 1% of subjects in a population of subjects suffering from cancer. The composition may include at least one neoantigenic peptide containing a tumor-specific neoepitope which binds to an HLA protein present in at least 5% of subjects in the population of subjects suffering from cancer. Additionally, the composition may contain at least one neoantigenic peptide capable of eliciting an immune response against a tumor present in at least 5% of the subjects in the population of subjects suffering from cancer. The ability to elicit an immune response refers to the ability of the immune system to present an antigen to a lymphocyte. In order for the immune system to present an antigen, the antigen needs to be presented by a subjects HLA proteins. In order to elicit an immune response against a tumor, the tumor needs to contain the mutations leading to expression of the antigen. In order for the composition to provide a benefit to a population in need thereof, the population has to include subjects that express an HLA allele capable of binding the at least one neoantigenic peptide present in the composition and the population has to include subjects containing tumors with mutations that lead to neoantigenic epitopes present in the neoantigenic peptides.

The composition may be specific to a population of subjects suffering from cancer that share a characteristic. The population may have cancer or may have a specific cancer. The population may share a common set of HLA subtypes. They may share HLA subtypes based on ethnicity. Not being bound by a theory the percentage of HLA types in a population can be predicted based on ethnicity without testing. Not being bound by a theory, different populations express different HLA types capable of binding different neoantigenic peptides. Therefore a composition can be formulated to provide a benefit to a large proportion of that population, whereas the composition would not provide a benefit to another population. Not being bound by a theory, different cancers contain different mutations and thus compositions tailored to specific cancers can be used to provide a greater benefit to a population with one type of cancer as compared to a population that includes more than one type. In one embodiment, the population is suffering from adrenocortical carcinoma (ACC), bladder urothelial carcinoma (BLCA), breast invasive carcinoma (BRCA), cervical squamous cell carcinoma and endocervical adenocarcinoma (CESC), colon adenocarcinoma (COAD), Chronic lymphocytic Leukaemia (CLL), colorectal cancer (CRC), Diffuse large B-cell lymphoma (DLBCL), glioblastoma multiforme (GBM), head and neck squamous cell carcinoma (HNSC), kidney chromophobe (KICH), kidney renal clear cell carcinoma (KIRC), kidney renal papillary cell carcinoma (KIRP), acute myeloid leukemia (LAML), liver hepatocellular carcinoma (LIHC), lung adenocarcinoma (LUAD), lung squamous cell carcinoma (LUSC), multiple myeloma (MM), ovarian serous cystadenocarcinoma (OV), pancreatic adenocarcinoma (PAAD), prostate adenocarcinoma (PRAD), rectum adenocarcinoma (READ), skin cutaneous melanoma (SKCM), stomach adenocarcinoma (STAD), testicular germ cell tumors (TGCT), thyroid adenocarcinoma (THCA), uterine corpus endometrioid carcinoma (UCEC), or uterine carcinosarcoma (UCS).

In one embodiment, the population of subjects is suffering from CLL; the at least one tumor-specific mutation comprises any combination of mutations in Table 8 with an exemplary disease of "CLL"; and at least one of a set of six of the at least one tumor-specific mutation will be found in 17.49?% of subjects in the CLL population. The population of subjects may be suffering from BLCA, the at least one tumor-specific mutation comprises any combination of mutations in Table 8 with an exemplary disease of "BLCA"; and at least one of a set of six of the at least one tumor-specific mutation will be found in 26.92% of subjects in the population. The population of subjects may be suffering from BRCA; the at least one tumor-specific mutation comprises any combination of mutations in Table 8 with an exemplary disease of "BRCA"; and at least one of a set of 18 of the at least one tumor-specific mutation will be found in 36.04% of subjects in the population. The population of subjects may be suffering from COAD; the at least one tumor-specific mutation comprises any combination of mutations in Table 8 with an exemplary disease of "COAD"; and at least one of a set of three of the at least one tumor-specific mutation will be found in 27.14% of subjects in the population. The population of subjects may be suffering from GBM; the at least one tumor-specific mutation comprises any combination of mutations in Table 8 with an exemplary disease of "GBM"; and at least one of a set of 14 of the at least one tumor-specific mutation will be found in 34.36% of subjects in the population. The population of subjects may be suffering from HNSC; the at least one tumor-specific mutation comprises any combination of mutations in Table 8 with an exemplary disease of "HNSC"; and at least one of a set of 10 of the at least one tumor-specific mutation will be found in 21.61% of subjects in the population. The population of subjects may be suffering from KIRC; the at least one tumor-specific mutation comprises any combination of mutations in Table 8 with an exemplary disease of "KIRC"; and at least one of a set of four of the at least one tumor-specific mutation will be found in 6% of subjects in the population. The population of subjects may be suffering from LAML; the at least one tumor-specific mutation comprises any combination of mutations in Table 8 with an exemplary disease of "LAML"; and at least one of a set of 11 of the at least one tumor-specific mutation will be found in 47.45% of subjects in the population. The population of subjects may be suffering from LUAD; the at least one tumor-specific mutation comprises any combination of mutations in Table 8 with an exemplary disease of "LUAD"; and at least one of a set of 11 of the at least one tumor-specific mutation will be found in 33.42% of subjects in the population. The population of subjects may be suffering from LUSC; the at least one tumor-specific mutation comprises any combination of mutations in Table 8 with an exemplary disease of "LUSC"; and at least one of a set of two of the at least one tumor-specific mutation will be found in 7.87% of subjects in the population. The population of subjects may be suffering from OV; the at least one tumor-specific mutation comprises any combination of mutations in Table 8 with an exemplary disease of "OV"; and at least one of a set of ten of the at least one tumor-specific mutation will be found in 22.78% of subjects in the population. The population of subjects may be suffering from READ; the at least one tumor-specific mutation comprises any combination of mutations in Table 8 with an exemplary disease of "READ"; and at least one of a set of two of the at least one tumor-specific mutation will be found in 20.51% of subjects in the population. The population of subjects may be suffering from SKCM; the at least one tumor-specific mutation comprises any combination of mutations in Table 8 with an exemplary disease of "SKCM"; and at least one of a set 64 of the at least one tumor-specific mutation will be found in 90.91% of subjects in the population. The population of subjects may be suffering from UCEC; the at least one tumor-specific mutation comprises any combination of mutations in Table 8 with an exemplary disease of "UCEC"; and at least one of a set of 30 of the at least one tumor-specific mutation will be found in 67.74% of subjects in the population. The population of subjects may be suffering from ACC; the at least one tumor-specific mutation comprises any combination of mutations in Table 8 with an exemplary disease of "ACC"; and at least one of a set of 161 of the at least one tumor-specific mutation will be found in 50% of subjects in the population. The population of subjects may be suffering from CESC; the at least one tumor-specific mutation comprises any combination of mutations in Table 8 with an exemplary disease of "CESC"; and at least one of a set of four of the at least one tumor-specific mutation will be found in 23.71% of subjects in the population. The population of subjects may be suffering from CRC; the at least one tumor-specific mutation comprises any combination of mutations in Table 8 with an exemplary disease of "CRC"; and at least one of a set of 15 of the at least one tumor-specific mutation will be found in 56.65% of subjects in the population. The population of subjects may be suffering from DLBCL; the at least one tumor-specific mutation comprises any combination of mutations in Table 8 with an exemplary disease of "DLBCL"; and at least one of a set of 2 of the at least one tumor-specific mutation will be found in 13.79% of subjects in the population. The population of subjects may be suffering from KICH; the at least one tumor-specific mutation comprises any combination of mutations in Table 8 with an exemplary disease of "KICH"; and at least one of a set of 24 of the at least one tumor-specific mutation will be found in 50% of subjects in the population. The population of subjects may be suffering from KIRP; the at least one tumor-specific mutation comprises any combination of mutations in Table 8 with an exemplary disease of "KIRP"; and at least one of a set of nine of the at least one tumor-specific mutation will be found in 42.24% of subjects in the population. The population of subjects may be suffering from LIHC; the at least one tumor-specific mutation comprises any combination of mutations in Table 8 with an exemplary disease of "LIHC"; and at least one of a set of 2 of the at least one tumor-specific mutation will be found in 6.57% of subjects in the population. The population of subjects may be suffering from MM; the at least one tumor-specific mutation comprises any combination of mutations in Table 8 with an exemplary disease of "MM"; and at least one of a set of 6 of the at least one tumor-specific mutation will be found in 23.9% of subjects in the population. The population of subjects may be suffering from PRAD; the at least one tumor-specific mutation comprises any combination of mutations in Table 8 with an exemplary disease of "PRAD"; and at least one of a set of 24 of the at least one tumor-specific mutation will be found in 39.85% of subjects in the population. The population of subjects may be suffering from STAD; the at least one tumor-specific mutation comprises any combination of mutations in Table 8 with an exemplary disease of "STAD"; and at least one of a set of 150 of the at least one tumor-specific mutation will be found in 48.79% of subjects in the population. The population of subjects may be suffering from TGCT; the at least one tumor-specific mutation comprises any combination of mutations in Table 8 with an exemplary disease of "TGCT"; and at least one of a set of 14 of the at least one tumor-specific mutation will be found in 51.61% of subjects in the population. The population of subjects may be suffering from THCA; the at least one tumor-specific mutation comprises any combination of mutations in Table 8 with an exemplary disease of "THCA"; and at least one of a set of five of the at least one tumor-specific mutation will be found in 69.88% of subjects in the population. The population of subjects may be suffering from UCS; the at least one tumor-specific mutation comprises any combination of mutations in Table 8 with an exemplary disease of "UCS"; and at least one of a set of two of the at least one tumor-specific mutation will be found in 16.07% of subjects in the population. The population of subjects may be suffering from PAAD; the at least one tumor-specific mutation comprises any combination of mutations in Table 8 with an exemplary disease of "PAAD"; and at least one of a set of 53 of the at least one tumor-specific mutation will be found in 50% of subjects in the population. The population of subjects may also be suffering from a solid tumor. The solid tumor may be clear cell Renal Cell Carcinoma (ccRCC), melanoma, sarcoma, or a cancer of the bladder, colon, brain, breast, head and neck, endometrium, lung, ovary, pancreas or prostate. The population of subjects may be suffering from a liquid tumor. The liquid tumor may be Non-Hodgkin's lymphoma or leukemia.

In another embodiment, the at least one tumor-specific mutation has an incidence of at least 500 patients a year in the population of subjects suffering from cancer, and wherein the at least one mutation may be a mutation listed for the population in Table 9. The at least one neoantigenic peptide may be at least one peptide listed in Table 9.

In another embodiment, the population suffering from cancer is being treated with a drug or therapy. The population suffering from cancer may have been previously treated with, is currently being treated with, or is selected to treated with ibrutinib, erlotinib, imatinib, gefitinib, crizotinib, trastuzumab, vemurafenib, RAF/MEK or antiestrogen therapy.

In another embodiment, the composition comprises at least one neoantigenic peptide capable of eliciting an immune response against a tumor present in at least 5%, 10%, 20%, 30%, 40%, 50%, 60%, 70%, 80%, 90%, 95% or 99% of subjects in a population of subjects suffering from cancer.

In another embodiment, at least 5%, 10%, 20%, 30%, 40%, 50%, 60%, 70%, 80%, 90%, 95% or 99% of subjects in the population has at least one tumor-specific mutation present in the composition; and at least 5%, 10%, 20%, 30%, 40%, 50%, 60%, 70%, 80%, 90%, 95% or 99% of subjects in the population has at least one HLA protein which binds to a tumor-specific neoepitope present in the composition.

In one embodiment, the tumor-specific mutations comprise splice-variant mutations, point mutations, and/or frameshift mutations. In another embodiment, the tumor-specific mutations comprise drug resistance mutations. In one embodiment, the neoantigenic peptides include not only the resulting mutated neoantigen protein sequence, but a long peptide region surrounding and including the mutation and includes all contiguous segments within it (see Tables 1-4). In one embodiment, the tumor-specific mutations are present in one or more genes encoding a protein selected from the group consisting of Programmed Death-Ligand 1 (PD-L1), androgen receptor (AR), Bruton's Tyrosine Kinase (BTK), Epidermal Growth Factor Receptor (EGFR), BCR-Abl, c-kit, PIK3CA, HER2, EML4-ALK, KRAS, ALK, ROS1, AKT1, BRAF, MEKJ, MEK2, NRAS, RAC1, and ESR1. In one embodiment, the tumor-specific mutations are present in one or more genes listed in any of the Tables presented herein. In one embodiment, the at least one tumor-specific mutation is derived from alternative splicing of PD-L1 or AR. In one embodiment, the at least one tumor-specific mutation is derived from splice variant sPD-L1, AR-V1 or AR-V7. In one embodiment, the least one tumor-specific mutation is a drug resistance mutation selected from the group consisting of BTK/C481S, EGFR/T790M, BCR-Abl/T315I, BCR-Abl/Y253H, BCR-Abl/E255K, BCR-Abl/E255V, c-kit/T670L PIK3CA/E545K, PIK3CA/E542K, HER2/G776(YVMA), HER2/E545K, EML4-ALK/G1269A, KRAS/G12V/D, ALK/L196M, ALK/G1202R, ALK/S1206Y, ALK/1151T(ins), ALK/F1174C, ROS1/G2032R, AKT1/E17K, BRAF/V600E, MEK1/Q56P, MEK1/E203K, MEK1/C121S, MEK1/V60E, MEK1/G128V, MEK1/V54I, MEK1/P124S, MEK1/P124L, NRAS/Q61K/L/R, NRAS/T58I, MEK2/C125S, RAC1/P29S, ESR1/S463P, AR/V534E, AR/P535H, AR/L536Q, AR/L536R, AR/Y537C, AR/Y537S, AR/Y537N, AR/D538G and AR/F876L. In one embodiment, the drug resistance mutation is induced by treatment with ibrutinib, erlotinib, imatinib, gefitinib, crizotinib, trastuzumab, vemurafenib, RAF/MEK or antiestrogen therapy. In another embodiment, a subject has a drug resistance mutation before treatment.

In another embodiment, the composition comprises at least 2, 3, 4, 5, 6, 7, 8, 9, 10, 11, 12, 13, 14, 15, 16, 17, 18, 19 or 20 neoantigenic peptides. The composition may include 15 to 20 neoantigenic peptides. The composition may include greater than 100, 200, or 300 neoantigenic peptides. Each neoantigenic peptide may be from about 5 to about 50 amino acids in length.

In another embodiment, the pharmaceutical composition is an immunogenic or vaccine composition. The pharmaceutical composition may further comprise an immunomodulator or adjuvant. The immunodulator or adjuvant may be selected from the group consisting of poly-ICLC, 1018 ISS, aluminum salts, Amplivax, ASIS, BCG, CP-870,893, CpG7909, CyaA, cyclic di-nucleotides such as STING, dSLIM, GM-CSF, IC30, IC31, Imiquimod, ImuFact IMP321, IS Patch, ISS, ISCOMATRIX, Juvlmmune, LipoVac, MF59, monophosphoryllipid A, Montanide IMS 1312, Montanide ISA 206, Montanide ISA 50V, Montanide ISA-51, OK-432, OM-174, OM-197-MP-EC, ONTAK, PepTel®, vector system, PLGA microparticles, resiquimod, SRL172, Virosomes and other Virus-like particles, YF-17D, VEGF trap, R848, beta-glucan, Pam3Cys, and Aquila's QS21 stimulon.

In another embodiment, the pharmaceutical composition comprises one or more neoantigenic peptides as defined in Table 1, 2, 3 or 4.

In one embodiment, each tumor-specific neoepitope binds to HLA-A, -B or -C or to HLADRB, HLADBM XXXXX with a $K_D$ of less than 500 nM.

In another aspect, the present invention relates to a method of treating or preventing a tumor in a subject in need thereof by administering to the subject any pharmaceutical composition as described herein.

In one embodiment, a method of treating or preventing a tumor in a patient in need thereof is provided, comprising administering to a patient a composition comprising at least one neoantigenic peptide and a pharmaceutically acceptable carrier, each at least one neoantigenic peptide comprising a tumor-specific neoepitope capable of binding to an HLA protein in a subject, each tumor-specific neoepitope comprising a tumor-specific mutation present in a tumor, wherein the composition comprises at least one neoantigenic peptide comprising a tumor-specific mutation present in a tumor in at least 1% of subjects in a population of subjects suffering from cancer; the composition comprises at least one neoantigenic peptide comprising a tumor-specific neoepitope which binds to an HLA protein present in at least 5% of subjects in the population of subjects suffering from cancer; and the composition comprises at least one neoantigenic peptide capable of eliciting an immune response against a tumor present in at least 5% of the subjects in the population of subjects suffering from cancer.

In one embodiment, the population of subjects is suffering from adrenocortical carcinoma (ACC), bladder urothelial carcinoma (BLCA), breast invasive carcinoma (BRCA), cervical squamous cell carcinoma and endocervical adenocarcinoma (CESC), colon adenocarcinoma (COAD), Chronic lymphocytic Leukaemia (CLL), colorectal cancer (CRC), Diffuse large B-cell lymphoma (DLBCL), glioblastoma multiforme (GBM), head and neck squamous cell carcinoma (HNSC), kidney chromophobe (KICH), kidney renal clear cell carcinoma (KIRC), kidney renal papillary cell carcinoma (KIRP), acute myeloid leukemia (LAML), liver hepatocellular carcinoma (LIHC), lung adenocarcinoma (LUAD), lung squamous cell carcinoma (LUSC), multiple myeloma (MM), ovarian serous cystadenocarcinoma (OV), pancreatic adenocarcinoma (PAAD), prostate adenocarcinoma (PRAD), rectum adenocarcinoma (READ), skin cutaneous melanoma (SKCM), stomach adenocarcinoma (STAD), testicular germ cell tumors (TGCT), thyroid adenocarcinoma (THCA), uterine corpus endometrioid carcinoma (UCEC), or uterine carcinosarcoma (UCS). In one embodiment, the population of subjects is suffering from a solid tumor. The solid tumor may be clear cell Renal Cell Carcinoma (ccRCC), melanoma, sarcoma, or a cancer of the bladder, colon, brain, breast, head and neck, endometrium, lung, ovary, pancreas or prostate. In one embodiment, the population of subjects is suffering from a liquid tumor. The liquid tumor may be Non-Hodgkin's lymphoma or leukemia.

In one embodiment, the population suffering from cancer was treated with, is being treated with, or is selected to treated with ibrutinib, erlotinib, imatinib, gefitinib, crizotinib, trastuzumab, vemurafenib, RAF/MEK or antiestrogen therapy.

In one embodiment, the at least one neoantigenic peptide is capable of eliciting an immune response against a tumor present in at least 5%, 10%, 20%, 30%, 40%, 50%, 60%, 70%, 80%, 90%, 95% or 99% of subjects in the population of subjects suffering from cancer. In one embodiment, at least 5%, 10%, 20%, 30%, 40%, 50%, 60%, 70%, 80%, 90%, 95% or 99% of subjects in the population has at least one tumor-specific mutation present in the composition and, at least 5%, 10%, 20%, 30%, 40%, 50%, 60%, 70%, 80%, 90%, 95% or 99% of subjects in the population has at least one HLA protein which binds to a tumor-specific neoepitope present in the composition.

In another embodiment, the tumor-specific mutations comprise splice-variant mutations, point mutations, and/or frameshift mutations. The tumor-specific mutations may be drug resistance mutations. The tumor-specific mutations may be present in one or more genes encoding a protein selected from the group consisting of Programmed Death-Ligand 1 (PD-L1), androgen receptor (AR), Bruton's Tyrosine Kinase (BTK), Epidermal Growth Factor Receptor (EGFR), BCR-Abl, c-kit, PIK3CA, HER2, EML4-ALK, KRAS, ALK, ROS1, AKT1, BRAF, MEK1, MEK2, NRAS, RAC1, and ESR1. The tumor-specific mutations may be present in one or more genes listed in any of the Tables. The at least one tumor-specific mutation may be derived from alternative splicing of PD-L1 or AR. The at least one tumor-specific mutation may be derived from splice variant sPD-L1, AR-V1 or AR-V7.

In one embodiment, the at least one tumor-specific mutation is a drug resistance mutation selected from the group consisting of BTK/C481S, EGFR/T790M, BCR-Abl/T315I, BCR-Abl/Y253H, BCR-Abl/E255K, BCR-Abl/E255V, c-kit/T670I, PIK3CA/E545K, PIK3CA/E542K, HER2/G776(YVMA), HER2/E545K, EML4-ALK/G1269A, KRAS/G12V/D, ALK/L196M, ALK/G1202R, ALK/S1206Y, ALK/I151T(ins), ALK/F174C, ROS1/G2032R, AKT1/E17K, BRAF/V600E, MEK1/Q56P, MEK1/E203K, MEK1/C121S, MEK1/V60E, MEK1/G128V, MEK1/V54I, MEK1/P124S, MEK1/P124L, NRAS/Q61K/L/R, NRAS/ T58I, MEK2/C125S, RAC1/P29S, ESR1/S463P, AR/V534E, AR/P535H, AR/L536Q, AR/L536R, AR/Y537C, AR/Y537S, AR/Y537N, AR/D538G and AR/F876L. The drug resistance mutation may be induced by treatment with ibrutinib, erlotinib, imatinib, gefitinib, crizotinib, trastuzumab, vemurafenib, RAF/MEK or antiestrogen therapy.

In another embodiment, the composition comprises at least 2, 3, 4, 5, 6, 7, 8, 9, 10, 11, 12, 13, 14, 15, 16, 17, 18, 19 or 20 neoantigenic peptides. In a preferred embodiment, the composition comprises 15 to 20 neoantigenic peptides.

In another embodiment, each neoantigenic peptide is from about 5 to about 50 amino acids in length.

In another embodiment, the composition is an immunogenic or vaccine composition. For instance, the immunogenic or vaccine composition may comprise an immunomodulator or adjuvant. The immunodulator or adjuvant may be selected from the group consisting of poly-ICLC, 1018 ISS, aluminum salts, Amplivax, AS15, BCG, CP-870,893, CpG7909, CyaA, cyclic di-nucleotides such as STING, dSLIM, GM-CSF, IC30, IC31, Imiquimod, ImuFact IMP321, IS Patch, ISS, ISCOMATRIX, JuvImmune, Lipo-Vac, MF59, monophosphoryllipid A, Montanide IMS 1312, Montanide ISA 206, Montanide ISA 50V, Montanide ISA-51, OK-432, OM-174, OM-197-MP-EC, ONTAK, PepTel®, vector system, PLGA microparticles, resiquimod, SRL172, Virosomes and other Virus-like particles, YF-17D, VEGF trap, R848, beta-glucan, Pam3Cys, and Aquila's QS21 stimulon.

In one embodiment, the composition comprises one or more neoantigenic peptides as defined in Table 1, 2, 3 or 4.

In one embodiment, each tumor-specific neoepitope binds to HLA-A, -B or -C or to HLADRB, HLADBM XXXXX with a $K_D$ of less than 500 nM.

In another aspect, the present invention provides a method of prophylactic cancer treatment comprising selecting a cancer drug for a patient in need thereof, the drug selected from the group consisting of ibrutinib, erlotinib, imatinib, gefitinib, crizotinib, trastuzumab, vemurafenib, RAF/MEK and antiestrogen therapy; and administering prophylactically to the subject, before drug resistant mutations can be detected, a pharmaceutical composition comprising neoantigenic peptides derived from drug resistant mutations associated with the selected cancer drug.

The shared neoantigen immunogenic composition can be administered via subcompositions, each containing a portion of the neoantigens, and sub-compositions can be administered to different places on the subject or patient; for instance, a composition comprising 20 different neoantigens, can be administered in four (4) subcompositions, each containing 5 of the 20 different neoantigens, and the four (4) subcompositions can be administered so as to endeavor to deliver each subcomposition to a separate set of draining lymph nodes of the patient, e.g., to each of the arms and legs (e.g., thigh or upper thigh or near buttocks or lower back on each side of the patient) so as to endeavor to deliver fewer neoantigens to each set of draining lymph nodes of the patient or subject and thereby limit competition between neoantigens. Of course, the number of locations and hence number of subcompositions can vary, e.g., the skilled practitioner could consider administration at or near the spleen to have a fifth point of administration, and the skilled practitioner can vary the locations such that only one, two or three are used (e.g., each arm and a leg, each of legs and one arm, each of the legs and no arms, or only both arms). The shared neoantigen immunogenic composition administered at the aforementioned various intervals can be different formulations, and the subcompositions administered at different places on the subject or patient during a single administration can be different compositions. For instance, a first administration can be of a whole shared neoantigen immunogenic composition and a next or later administration can be of a vector (e.g., viral vector or plasmid) that has expression of antigen(s) in vivo. Likewise, in the administration of different subcompositions to different locations on the patient or subject, some of the subcompositions can comprise a whole antigen and some of the subcompositions can comprise a vector (e.g., viral vector or plasmid) that has expression of antigen(s) in vivo. And some compositions and subcompositions can comprise both vector(s) (e.g., viral vector or plasmid) that has/have expression of antigen(s) in vivo and whole antigens. Some vectors (e.g., poxvirus) that have expression of antigen(s) in vivo can have an immunostimulatory or adjuvanting effect, and hence compositions or subcompositions that contain such vectors can be self-adjuvanting. Also, by changing up the nature of how the antigens are presented to the immune system, the administrations can "prime" and then "boost" the immune system. And in this text, when there is mention of a "vaccine" it is intended that the invention comprehends immunogenic compositions, and when there is mention of a patient or subject it is intended that such an individual is a patient or subject in need of the herein disclosed treatments, administrations, compositions, and generally the subject invention.

Moreover, the invention applies to the use of any type of expression vector, such as a viral expression vector, e.g., poxvirus (e.g., orthopoxvirus or avipoxvirus such as vaccinia virus, including Modified Vaccinia Ankara or MVA, MVA-BN, NYVAC according to WO-A-92/15672, fowlpox, e.g., TROVAX, canarypox, e.g., ALVAC (WO-A-95/27780 and WO-A-92/15672) pigeonpox, swinepox and the like), adenovirus, AAV, herpesvirus, and lentivirus; or a plasmid or DNA or nucleic acid molecule vector. Some vectors that are cytoplasmic, such as poxvirus vectors, may be advantageous. However adenovirus, AAV and lentivirus can also be advantageous to use in the practice of the invention.

In a ready-for-use, especially reconstituted, shared neoantigen immunogenic composition, the vector, e.g., viral vector, is present in the quantities within the ambit of the skilled person from this disclosure and the knowledge in the art (such as in patent and scientific literature cited herein).

Whole antigen or vector, e.g., recombinant live vaccines may exist in a freeze-dried form allowing their storage and are reconstituted immediately before use in a solvent or excipient, which can include an adjuvant as herein discussed.

The subject of the invention is therefore also a vaccination or immunization set or kit comprising, packaged separately, freeze-dried vaccine and a solution, advantageously including an adjuvant compound as herein discussed for the reconstitution of the freeze-dried vaccine.

The subject of the invention is also a method of vaccination or immunization comprising or consisting essentially of or consisting of administering, e.g., by the parenteral, preferably subcutaneous, intramuscular or intradermal, route or by the mucosal route a vaccine or immunogenic composition in accordance with the invention at the rate of one or more administrations. Optionally this method includes a preliminary step of reconstituting the freeze-dried shared neoantigen immunogenic composition (e.g., if lyophilized whole antigen or vector) in a solution, advantageously also including an adjuvant.

In one embodiment, the shared neoantigen immunogenic composition is administered at a dose of about 10 μg to 1 mg per 70 kg individual as to each neoantigenic peptide. In another embodiment, the shared neoantigen immunogenic composition is administered at an average weekly dose level of about 10 μg to 2000 μg per 70 kg individual as to each neoantigenic peptide. In another related embodiment, the administration is intravenous. In one embodiment, the shared neoantigen immunogenic composition is administered intravenously or subcutaneously.

In another embodiment, the method further comprises (a) obtaining a sample of tumor tissue from each subject; (b) detecting one or more of the tumor-specific mutations in the sample; and (c) selecting a subject from the population of subjects for treatment with the at least one neoantigenic peptides if at least one of the tumor-specific mutations are detected in the sample from the subject.

In another embodiment, the method further comprises (a) determining HLA allotypes present in each subject; and (b) selecting a subject from the population of subjects for treatment with the at least one neoantigenic peptides if one or more HLA allotypes present in the subject binds to one or more of the tumor-specific neoepitopes present in the at least one neoantigenic peptides.

Embodiments of the present invention relate to compositions and methods using shared neoantigens, which (unlike shared native (non-mutated) antigens derived from genes differentially expressed in tumors) have desirable properties such as not being subject to the immune-dampening effects of central tolerance and high tumor specificity. This is because the neoantigens are expressed only in tumor tissue, e.g. are generated by tumor-specific mutations or splicing defects. Such splice variants or mutations may generate immunogenic epitopes across a variety of HLA alleles, thus covering a significant proportion of the population. Moreover, because these mutations may be present in a significant proportion of subjects suffering from cancer, the compositions described herein do not require sequencing of whole genomes of subjects and may be used as an "off-the-shelf" product to treat multiple subjects. For instance, the method may simply involve detecting in a tumor sample from the subject one or more of the specific mutations present in the composition, and administering the composition to subjects in which at least one mutation is present. This is in contrast to methods using patient-specific neoantigen mixtures, which require whole genome or whole exome sequencing of each subject and the production of personalized treatment compositions.

Other embodiments relate to a combination therapy wherein the methods of treatment using a shared neoantigen composition of the present invention are used in concert with a current drug regimen. The shared neoantigen composition may be administered prophylactically. In one embodiment, a patient in need thereof is treated with chemotherapy and/or a targeted therapy in combination with a shared neoantigen immunogenic composition before a drug resistance mutation can be detected. The shared neoantigen immunogenic composition can be tailored to include neoantigen peptides specific to the resistance mutations associated with a chosen therapy. In another embodiment, the shared neoantigen composition is administered before the subject is treated with a chemotherapy and/or a targeted therapy, to generate an immune response to cells harboring a drug resistance mutation before such cells develop. The administering can be serially or sequentially or at substantially the same time or substantially simultaneously. For example, the administering of the shared neoantigen immunogenic composition and the administering of a cancer therapy can be at about the same time or substantially simultaneously. Alternatively, the administering of the shared neoantigen immunogenic composition can be on one time schedule, e.g., weekly, biweekly, every three weeks, monthly, bimonthly, every quarter year (every three months), every third of a year (every four months), every five months, twice yearly (every six months), every seven months, every eight months, every nine months, every ten months, every eleven months, annually or the like, and the administering of the cancer therapy can be on a different schedule that is typical for the therapy such that the subject or patient has two different treatment schedules running concomitantly and the administering of the shared neoantigen immunogenic composition and the administering of the cancer therapy can be sequentially or serially. In preferred embodiments the subject may be treated with ibrutinib, erlotinib, imatinib, gefitinib, crizotinib, trastuzumab, vemurafenib, RAF/MEK or antiestrogen therapy.

In another aspect the present invention provides a diagnostic method for early detection and tracking of cancer progression by determining the presence of at least one neoantigenic peptide of the present invention in a patient sample. The patient sample may be derived from blood, sputum, saliva, urine, tumor tissue, lymphatic fluid, semen or feces.

In one embodiment, the diagnostic method is used before administering the shared neoantigen composition as described herein. The diagnostic method may include comparing the amount of shared neoantigen mutations in a series of at least two samples taken during treatment with a cancer therapy and/or shared neoantigen composition. Not being bound by a theory, an increase or decrease in shared neoantigen mutations can be used to determine treatment efficacy.

In one embodiment, the mutated genes can be detected using PCR based methods or sequencing. Reverse transcription PCR (RT-PCR) can be used to detect mutations in transcribed neoantigen genes. Additionally, any sequencing technique can be used to determine the presence of a mutation. In a preferred embodiment, pyrosequencing is used. The present invention also provides for a kit that includes primers that are specific to sequences encompassing the neoantigen mutations.

In another embodiment the mutated genes are detected by immunological detection methods. Antibodies specific to the shared neoantigen mutations can be used to detect the mutations. The antibodies may be bound to an array. The array may include antibodies to detect more than one of the shared neoantigen mutations of the present invention. The antibodies can be configured for use in an ELISA assay. Therefore, a composition or kit may be provided that includes antibodies specifically recognizing the shared neoantigens of the present invention.

In another aspect the present invention provides a method of treating or preventing a tumor in a population of subjects in need thereof, comprising administering to a subject an agent comprising an extracellular ligand-binding domain recognizing a tumor-specific neoepitope comprising a tumor-specific mutation having an incidence of at least 1% of subjects in the population. The agent may be an antibody, antibody fragment, antibody drug conjugate, aptamer, CAR, or T cell receptor. The antibody or antibody fragment may be humanized, fully humanized, or chimeric. The antibody fragment may be a nanobody, Fab, Fab', (Fab')2, Fv, ScFv, diabody, triabody, tetrabody, Bis-scFv, minibody, Fab2, or Fab3 fragment. The tumor-specific mutation may be a mutation listed for any population in Table 9. The tumor-specific mutation may be within a gene containing an extracellular domain. The tumor-specific mutation may be FGFR3 S249C, ERBB3 V104M, EGFR L858R, MUC4 H4205Q, PDGFRA R483fs, TMEM52 23_26LLPL>L, or PODXL 28_30PSP>P. The tumor-specific mutation may be within the extracellular domain. The tumor-specific mutation comprises FGFR3 S249C or ERBB3 V104M. Not being bound by a theory, the presence of a neoepitope in a protein with an extracellular domain allows the neoepitope to be presented on the surface of a cell. Not being bound by a theory, the presence of a neoepitope in the extracellular domain allows the neoepitope to be presented on the surface of a cell.

The invention is further described by the following numbered paragraphs:

1. An isolated neoantigenic peptide comprising a tumor-specific neoepitope defined in Tables 1-9, wherein the isolated neoantigenic peptide is not a native polypeptide.
2. An isolated neoantigenic peptide 100 amino acids or less in length which comprises a tumor-specific neoepitope defined in Tables 1-9.
3. The isolated neoantigenic peptide of paragraph 1 or 2, which is between about 5 to about 50 amino acids in length.
4. The isolated neoantigenic peptide of any of paragraphs 1-3, which is between about 15 to about 35 amino acids in length.
5. The isolated neoantigenic peptide of paragraph 4, which is about 15 amino acids or less in length.
6. The isolated neoantigenic peptide of paragraph 5, which is between about 8 and about 11 amino acids in length.
7. The isolated neoantigenic peptide of paragraph 6, which is 9 or 10 amino acids in length.
8. The isolated neoantigenic peptide of any of paragraphs 1-7, which binds major histocompatibility complex (MHC) class I.
9. The isolated neoantigenic peptide of paragraph 8, which binds MHC class I with a binding affinity of less than about 500 nM.
10. The isolated neoantigenic peptide of any of paragraphs 1-3, which is about 30 amino acids or less in length.
11. The isolated neoantigenic peptide of paragraph 10, which is between about 6 and about 25 amino acids in length.
12. The isolated neoantigenic peptide of paragraph 11, which is between about 15 and about 24 amino acids in length.
13. The isolated neoantigenic peptide of paragraph 11, which is between about 9 and about 15 amino acids in length.
14. The isolated neoantigenic peptide of any of paragraphs 1-3 and 10-13, which binds MHC class II.
15. The isolated neoantigenic peptide of paragraph 14, which binds MHC class II with a binding affinity of less than about 1000 nM.
16. The isolated neoantigenic peptide of any of paragraphs 1-15, further comprising flanking amino acids.
17. The isolated neoantigenic peptide of paragraph 16, wherein the flanking amino acids are not native flanking amino acids.
18. The isolated neoantigenic peptide of any of paragraphs 1-17, which is linked to at least a second neoantigenic peptide.
19. The isolated neoantigenic peptide of paragraph 18, wherein peptides are linked using a poly-glycine or poly-serine linker.
20. The isolated neoantigenic peptide of paragraph 18 or 19, wherein the second neoantigenic peptide binds MHC class I or class II with a binding affinity of less than about 1000 nM.
21. The isolated neoantigenic peptide of paragraph 20, wherein the second neoantigenic peptide binds MHC class I or class II with a binding affinity of less than about 500 nM.
22. The isolated neoantigenic peptide of paragraph 20 or 21, wherein both of the neoepitopes bind to human leukocyte antigen (HLA)-A, -B, -C, -DP, -DQ, or -DR.
23. The isolated neoantigenic peptide of any of paragraphs 20-22, wherein the isolated neoantigenic peptide and the second neoantigenic peptide binds a class I HLA or the isolated neoantigenic peptide and the second neoantigenic peptide binds a class II HLA.
24. The isolated neoantigenic peptide of any of paragraphs 20-22, wherein the isolated neoantigenic peptide binds a class II HLA and the second neoantigenic peptide binds a class I HLA or the isolated neoantigenic peptide binds a class I HLA and the second neoantigenic peptide binds a class II HLA.
25. The isolated neoantigenic peptide of any of paragraphs 1-24, further comprising modifications which increase in vivo half-life, cellular targeting, antigen uptake, antigen processing, MHC affinity, MHC stability, or antigen presentation.
26. The isolated neoantigenic peptide of paragraph 25, wherein the modification is conjugation to a carrier protein, conjugation to a ligand, conjugation to an antibody, PEGylation, polysialylation HESylation, recombinant PEG mimetics, Fc fusion, albumin fusion, nanoparticle attachment, nanoparticulate encapsulation, cholesterol fusion, iron fusion, acylation, amidation, glycosylation, side chain oxidation, phosphorylation, biotinylation, the addition of a surface active material, the addition of amino acid mimetics, or the addition of unnatural amino acids.
27. The isolated neoantigenic peptide of paragraph 25, wherein the cells that are targeted are antigen presenting cells.
28. The isolated neoantigenic peptide of paragraph 27, wherein the antigen presenting cells are dendritic cells.
29. The isolated neoantigenic peptide of paragraph 29, wherein the dendritic cells are targeted using the CD141, DEC205, or XCR1 marker.
30. A pharmaceutical composition comprising at least one neoantigenic peptide and a pharmaceutically acceptable carrier, each at least one neoantigenic peptide comprising a tumor-specific neoepitope capable of binding to an HLA protein in a subject, each tumor-specific neoepitope comprising a tumor-specific mutation present in a tumor, wherein:
    (a) the composition comprises at least one neoantigenic peptide comprising a tumor-specific mutation present in a tumor in at least 1% of subjects in a population of subjects suffering from cancer;
    (b) the composition comprises at least one neoantigenic peptide comprising a tumor-specific neoepitope which binds to an HLA protein present in at least 5% of subjects in the population of subjects suffering from cancer; or
    (c) the composition comprises at least one neoantigenic peptide capable of eliciting an immune response against a tumor present in at least 5% of the subjects in the population of subjects suffering from cancer.
31. The pharmaceutical composition of paragraph 30, wherein the population of subjects is suffering from adrenocortical carcinoma (ACC), bladder urothelial carcinoma (BLCA), breast invasive carcinoma (BRCA), cervical squamous cell carcinoma and endocervical adenocarcinoma (CESC), colon adenocarcinoma (COAD), Chronic lymphocytic Leukaemia (CLL), colorectal cancer (CRC), Diffuse large B-cell lymphoma (DLBCL), glioblastoma multiforme (GBM), head and neck squamous cell carcinoma (HNSC), kidney chromophobe (KICH), kidney renal clear cell carcinoma (KIRC), kidney renal papillary cell carcinoma (KIRP), acute myeloid leukemia (LAML), liver hepatocellular carcinoma (LIHC), lung adenocarcinoma (LUAD), lung squamous cell carcinoma (LUSC), multiple myeloma (MM), ovarian serous cystadenocarcinoma (OV), pancreatic adenocarcinoma (PAAD), prostate adenocarcinoma (PRAD), rectum adenocarcinoma (READ), skin cutaneous melanoma (SKCM), stomach adenocarcinoma (STAD), testicular germ cell tumors (TGCT), thyroid adenocarcinoma (THCA), uterine corpus endometrioid carcinoma (UCEC), or uterine carcinosarcoma (UCS).

32. The pharmaceutical composition of paragraph 30 or 31, wherein the population suffering from cancer was treated with, is being treated with, or is selected to be treated with a cancer therapeutic, optionally ibrutinib, erlotinib, imatinib, gefitinib, crizotinib, trastuzumab, vemurafenib, RAF/MEK inhibitor or antiestrogen therapy.

33. The pharmaceutical composition of any of paragraphs 30-33, wherein the tumor-specific mutations comprise splice-variant mutations, point mutations, and/or frameshift mutations.

34. The pharmaceutical composition of any of paragraphs 30-33, wherein the at least one neoantigenic peptide comprises at least one neoantigenic peptide derived from a long peptide region flanking and including the tumor specific mutation, and wherein all contiguous segments within the long peptide are included.

35. The pharmaceutical composition of any of paragraphs 30-34, wherein the tumor-specific mutations are present in one or more genes listed in Tables 1-9.

36. The pharmaceutical composition of any of paragraphs 30-35, wherein the composition comprises at least one neoantigenic peptide as defined in any of Tables 1-9.

37. The pharmaceutical composition of any of paragraphs 30-36, wherein the tumor-specific mutations are present in one or more genes encoding a protein selected from the group consisting of Programmed Death-Ligand 1 (PD-L1), androgen receptor (AR), Bruton's Tyrosine Kinase (BTK), Epidermal Growth Factor Receptor (EGFR), BCR-Abl, c-kit, PIK3CA, HER2, EML4A-ALK, KRAS, ALK, ROS1, AKT1, BRAF, MEK1, MEK2, NRAS, RAC1, and ESR1.

38. The pharmaceutical composition of paragraph 37, wherein at least one tumor-specific mutation is derived from alternative splicing of PD-L1 or AR.

39. The pharmaceutical composition of paragraph 38, wherein at least one tumor-specific mutation is derived from splice variant sPD-L1, AR-V1 or AR-V7.

40. The pharmaceutical composition of any of paragraphs 30-39, wherein the tumor-specific mutations comprise drug resistance mutations.

41. The pharmaceutical composition of paragraph 40, wherein at least one tumor-specific mutation is a drug resistance mutation selected from the group consisting of BTK/C481S, EGFR/T790M, BCR-Abl/T315I, BCR-Abl/Y253H, BCR-Abl/E255K, BCR-Abl/E255V, c-kit/T670I, PIK3CA/E545K, PIK3CA/E542K, HER2/G776(YVMA), HER2/E545K, EML4-ALK/G1269A, KRAS/G12V/D, ALK/L1196M, ALK/G1202R, ALK/S1206Y, ALK/I1151T (ins), ALK/F1174C, ROS1/G2032R, AKT1/E17K, BRAF/V600E, MEK1/Q56P, MEK1/E203K, MEK1/C121S, MEK1/V60E, MEK1/G128V, MEK1/V154I, MEK1/P124S, MEK1/P124L, NRAS/Q61K/L/R, NRAS/T58I, MEK2/C125S, RAC1/P29S, ESR1/S463P, AR/V534E, AR/P535H, AR/L536Q, AR/L536R, AR/Y537C, AR/Y537S, AR/Y537N, AR/D538G and AR/F876L.

42. The pharmaceutical composition of any of paragraphs 30-41, wherein the at least one tumor-specific mutation has an incidence of at least 500 patients a year in the population of subjects suffering from cancer, and wherein the at least one mutation comprises a mutation listed for the population in Table 9.

43. The pharmaceutical composition of paragraph 42, wherein the at least one neoantigenic peptide comprises at least one peptide listed in Table 9.

44. The pharmaceutical composition of any of paragraphs 30-36, wherein:
(a) the population of subjects is suffering from CLL; and
(b) the at least one tumor-specific mutation comprises any combination of mutations selected from the group consisting of SF3B1:p.K700E, MYD88:p.L273P, NOTCH1:p.P2514fs, ABCA11P:p.E901D, AHNAK:p.D3823E, ZNF814:p.E348D, AHNAK:p.V1220I, AHNAK:p.H1203N, ANKRD30A:p.A232V, APOOL:p.138L, EGR2:p.H397N, MKI67:p.H2213D, NRAS:p.Q61R, PLIN4:p.M691V, XPO1:p.E571K, ZCRB1:p.L76F, ZNF700:p.N652H, ZNF700:p.Q654R, ZNF844:p.D458H, AHNAK:p.A4046V, ANKRD36:p.P337R, C1orf170:p.T203I, CAST:p.D639E, EGR2:p.E369K, GPR123:p.L630P, IKZF3:p.L162R, MUC4:p.P4224R, OR9Q1:p.M34L, PKD2:p.Y486F, PRAMEF11:p.R104Q, SYNJ1:p.I681F, TP53:p.R248Q, TP53:p.R248W, TRPV2:p.L627del, ZNF254:p.S498A, ZNF732:p.A459T, ZNF749:p.E530Q, ZNF845:p.M423I, ABCA11P:p.G900E, ACRC:p.E243D, ACRC:p.A244V, ACSL3:p.T188S, ADAMTS2:p.D948N, AGAP6:p.S127L AHNAK:p.A2114G, ANKRD36:p.D1014Y, ARID3A:p.G550fs, ARID4A:p.D1154E, ATP2B4:p.R183H, ATRNL1:p.L1244F, BNC1:p.Y937N, BRAF:p.K601N, BTLA:p.Q86K, C14orf177:p.G90V, C2orf44:p.N456K, C3orf15:p.R552Q, CACNA2D1:p.Y376N, CALD1:p.E340K, CCDC15:p.P488H, CCDC79:p.N440T, CCNB3:p.A932T, CD109:p.L470Q, CD209:p.Q189L, CKAP2:p.*684K, CMA1:p.I81K, CMIP:p.A230T, CNTNAP4:p.112F, CRYM:p.*315K, DICER1:p.E1705K, DPCR1:p.L716P, EIF3A:p.M1093L, EIF4G3:p.R8H, ETFDH:p.I281F, EWSR1:p.Y656C, F5:p.L1332P, F5:p.L1253F, FAM50A:p.H317R, FBXL13:p.S102R, FBXW7:p.R465H, FHL:p.D184E, FILIP1:p.1522K, FRG1B:p.Q39K, GNB1:p.I80T, GPR110:p.R443G, GPR98:p.Y6152F, HDGFL1:p.188_189insA, IGF2BP2:p.T186S, IL1R2:p.L364fs, KIAA1109:p.L4680P, KRAS:p.G13D, KRTAP19-1:p.G61 S, MAF:p.G53fs, MAGEC1:p.L609H, MAP2K1:p.K57N, MED12:p.L36R, MED12:p.G44S, METAP2:p.Y137N, METTL9:p.Y57F, MGP:p.V15L, MKI67:p.R2222K, MUC16:p.T11005I, MUC4:p.S3941N, MUC4:p.S3941G, MUC4:p.V3091L, MUC4:p.S2951Y, MUC4:p.A2841S, MUC4:p.S2760A, MUC4:p.T2335M, MUC4:p.T1627K, MUC4:p.T1547S, MUC4:p.H1133Q, MYD88:p.M240T, NEDD4L:p.P194del, NEFH:p.S704T, NRG4:p.G21fs, OR2A25:p.S105C, OR4C16:p.Y63F, OR4N4:p.L150fs, PABPC1:p.K254fs, PIWIL1:p.372fs, PLCD3:p.E499fs, PLEKHB1:p.S146P, PPIL4:p.S382R, PRDM4:p.*802K, PRG4:p.N675H, PRKAB1:p.P104H, R3HDM2:p.S592G, R3HDM2:

p.S588N, R3HDM2:p.R206W, RPS2:p.R200G, RPTN: p.G364S, SF3B1:p.K666E, SF3B1:p.N626Y, SF3B1: p.Y623C, SIX3:p.I27L, SLC39A7:p.L456fs, SLC6A9: p.R94K, TFG:p.A382V, TGOLN2:p.K83R, TGOLN2: p.T80S, TLR2:p.D327V, TNKS2:p.T619fs, TP53: p.R273H, TP53:p.C242F, TP53:p.R175H, TWISTNB: p.H306Q, UBXN7:p.A276V, WDR78:p.N110K, XIRP2:p.V3008E, ZNF382:p.H186Q, ZNF578: p.R306H, ZNF578:p.G311S, ZNF578:p.H334R, ZNF700:p.S649C, ZNF705A:p.D298N, ZNF836: p.K608Q, and ZNF836:p.I571N; and 45. The pharmaceutical composition of any of paragraphs 30-36, wherein:
(a) the population of subjects is suffering from BLCA; and
(b) the at least one tumor-specific mutation comprises any combination of mutations selected from the group consisting of PIK3CA:p.E545K, FGFR3:p.S249C, TP53:p.R248Q, PIK3CA:p.E542K, RXRA:p.S427F, ZNF814:p.D404E, FBXW7:p.R505G, NOTCH2: p.P6fs, TP53:p.E285K, ANKRD30A:p.A353P, C3orf70:p.S6L, EFCAB6:p.R379K, ERCC2:p.N238S, FAM47C:p.Q225E, FOXQ1:p.S135L, HLA-A: p.Q78R, MUC4:p.H4205Q, OTUD4:p.T909I, SLAMF1:p.S277fs, SPRED3:p.S128del, TMCO2: p.S15fs, TP53:p.R280T, TP53:p.E271K, TP53: p.A159V, ZNF706:p.I8N, ZNF706:p.R3P, ACACB: p.E2318Q, ACPP:p.E321K, ACRC:p.A264V, ADAMTS2:p.23_24insL, AFF3:p.E919K, AHNAK: p.S4150F, AHNAK:p.D2889H, AHNAK:p.V1940A, ALX4:p.R126Q, ANKRD12:p.E627K, ANKRD32: p.T999N, ARID1A:p.S614L, ASXL2:p.117_118SS>S, ATP12A:p.R858C, ATP9A:p.R519Q, BCAS3: p.T214M, BPI:p.M255I, CACNG8:p.V146G, CAMSAP1:p.T466fs, CDC27:p.I91fs, CDKN1A:p.E44fs, CEP192:p.S2058L, CGB8:p.T18A, CHRNA3: p.L23del, CHST4:p.D352N, CLIP 1:p.S018fs, COX6A1:p.S8L, CREBBP:p.D1435H, CRIPAK: p.M48fs, CSPG5:p.D119N, CUL1:p.E485K, DLC1: p.S741T, DLL3:p.D318H, DOPEY2:p.E1196K, ECM1:p.E266K, EEF1A2:p.Y418S, EEF2K:p.E673K, EMILIN1:p.R27G, ERBB2:p.S310F, ERBB3:p.M91I, ERBB3:p.V104L, ERBB3:p.D297Y, ERCC2:p.Y14C, FAM155A:p.Q86del, FAM43B:p.E272del, FASTKD3: p.Q625E, FBXW7:p.S546L, FGFR3:p.R248C, FGFR3:p.G380R, FGFRL1:p.H479fs, GBE1:p.M587I, GIMAP1-GIMAP5:p.S311C, GNA13:p.R200G, HiFOO:p.A214fs, HEATR7B2:p.E1109K, HISTIHID: p.I81M, HRAS:p.G12D, HRCT1:p.H92P, ILF3: p.E484K, KCNK2:p.S6W, KIAA0907:p.Q446P, KIF23:p.E350K, KLF5:p.S118L, KLHL15:p.D185G, LAMA4:p.E639K, LILRA1:p.H410Y, LILRB1: p.L479del, LLGL2:p.P955fs, LPIN1:p.S974L, LRRC16A:p.D227N, LRTM2:p.S139L, LURAP1L: p.55_56insGGG, MAGEC1:p.P553del, MCL1: p.E171del, MN1:p.S472L, MUC7:p.A191V, MVP: p.E412K, NBPF10:p.E3455K, NFE2L2:p.E79K, NFE2L2:p.R34G, NOS1AP:p.Q306del, OR2T35: p.V319fs, OR4N2:p.L150fs, PABPC3:p.K333fs, PAX3:p.S197L, PBX2:p.E70K, PBXIP1:p.H729del, PCDP1:p.E537K, PEX1:p.I370fs, PHLDA3:p.E82K, PLEKHM2:p.S459L, PLVAP:p.A321V, POLR3B: p.L372F, POTEC:p.R477Q, PPL:p.H326Y, PPP1R15A:p.E196K, PRDM16:p.E271Q, PRIC285: p.E1289Q, PRMT8:p.S31P, PUF60:p.S396L, RAB11FIP4:p.S596L, RAD51C:p.D167N, RAD51C: p.Y224H, RALGPS1:p.R381Q, RARS2:p.R6C, RBM26:p.P644A, RERE:p.K176N, RXRA:p.S427Y, SERPINA12:p.R211G, SF3B1:p.E902K, SLC6A9: p.R243W, SLC9A5:p.L447F, SPESP1:p.F121L, SRPRB:p.G14S, SYN2:p.A34del, SYTL2:p.I440M, TAB3:p.R211T, TAF1B:p.R292C, TAOK2:p.L981del, TAS1R3:p.E525K, TAS2R9:p.E163Q, TBC1D1: p.S71F, TBC1D2B:p.R920Q, TFPI2:p.R222C, TM6SF1:p.S15W, TMEM131:p.K640fs, TMEM19: p.G331fs, TP53:p.R273C, TP53:p.R248W, TP53: p.R175H, TP53:p.K132N, TRAM1:p.E41Q, TSKS: p.E513K, TTN:p.C20935G, UBOX5:p.S417L, UGP2: p.D262H, VGF:p.E433K, XAB2:p.E782K, XYLB: p.S87F, ZC3H4:p.E798K, ZNF208:p.K852E, ZNF208: p.I647S, ZNF626:p.G198E, ZNF749:p.Q457E, ZNF761:p.H373R, ZNF799:p.T43A, ZNF799: p.W41G, ZNF799:p.E589G, ZNF844:p.P503R, ZNF845:p.M423T, ZNF845:p.T479M, ZNF860: p.H464R, ZNF878:p.S181R, ZNF91:p.R333H, and ZNF91:p.H305R.

46. The pharmaceutical composition of any of paragraphs 30-43, wherein:
(a) the population of subjects is suffering from BRCA; and
(b) the at least one tumor-specific mutation comprises any combination of frameshift mutations selected from the group consisting of GATA3:p.L328fs, GATA3: p.N334fs, GATA3:p.L344fs, GATA3:p.H400fs, GATA3:p.S408fs, GATA3:p.S430fs, GATA3:p.H434fs, GATA3:p.H435fs, and GATA3:p.S408fs.

47. The pharmaceutical composition of any of paragraphs 30-36, wherein:
(a) the population of subjects is suffering from BRCA; and
(b) the at least one tumor-specific mutation comprises any combination of mutations selected from the group consisting of PIK3CA:p.H1047R, PIK3CA:p.E545K, PIK3CA:p.E542K, AKT1:p.E17K, TP53:p.R175H, PIK3CA:p.N345K, PIK3CA:p.H1047L, SF3B1: p.K700E, GATA3:p.S408fs, PIK3CA:p.E726K, TP53: p.Y220C, TP53:p.H193R, PIK3CA:p.Q546R, TP53: p.R273C, TP53:p.R248W, TP53:p.R273H, TP53: p.I195T, TP53:p.H179R, FGFR2:p.N549K, NUP93: p.E14K, PIK3CA:p.C420R, PIK3CA:p.E453K, PIK3CA:p.Q546K, TP53:p.V216M, TP53:p.C176F, CDH1:p.E243K, ERBB2:p.L755S, KRAS:p.G12V, PIK3CA:p.E545A, TBL1XR1:p.I141fs, TP53: p.G266E, TP53:p.R248Q, TP53:p.Y163C, TP53: p.C141Y, TP53:p.G108fs, ACPP:p.R43W, AKT2: p.I289M, ARHGAP9:p.R137C, C9orf174:p.R136W, CDC42BPA:p.P675T, COL12A1:p.S395L, CRISPLD1:p.R222W, CT47B1: p.234_243EKLTEEATEE>E, CYP1A2:p.V483M, DAB2IP:p.E161K, DGKB:p.S13L, DMD:p.K1772N, DPEP1:p.V11L, ERBB2:p.S310F, ERBB2:p.D769Y, ERBB3:p.E928G, ESYT1:p.R816W, FAM179A: p.A831T, FAM58BP:p.A70T, FMN2:p.S751F, GALNTL6:p.K567del, GATA3:p.L328fs, GATA3: p.N334fs, GATA3:p.L344fs, GATA3:p.H400fs, GATA3:p.S408fs, GATA3:p.S430fs, GATA3:p.H434fs, GATA3:p.H435fs, GDAP1:p.T307A, GRB14: p.A300T, GUCY2C:p.G549C, IL17B:p.R34W, KCNB2:p.R231H, KIF1B:p.R1320W, KIF26B: p.V1113M, KLF4:p.K434Q, LY9:p.I69L, MAP2K4: p.S184L, MAP2K4:p.S251L MAP2K4:p.T261fs, MAP3K1:p.L318fs, MAP3K1:p.I761fs, MAP3K1: p.V1346del, MAP3K1:p.L1384fs, MAPK13:p.E315K, MAPK4:p.V100M, MARCH5:p.R170C, MBP: p.E120K, MEFV:p.R377H, METTL15:p.Q53E, MS4A4A:p.V99M, MUC17:p.R4415H, MYH6:p.T847M, MYO5B:p.A405V, NARS2:p.P240R, NLGN4X:p.D382N, NLRC4:p.R288W, OR13G1:p.R258H, OR2AK2:p.V451, OTOF:p.T388M, PACSIN2:p.Q331H, PALM2-AKAP2:p.A299T, PCDH19:p.R286C, PCDHGC5:p.D664N, PIK3CA:p.R88Q, PIK3CA:p.E110del, PIK3CA:p.K111del, PIK3CA:p.PVPHGLEDL447del, PIK3CA:p.L455fs, PIK3CA:p.M1004I, PIK3CA:p.M1043I, PIK3CA:p.N1044Y, PIK3R1:p.KPDL567del, PREX2:p.R363Q, PRRX1:p.A196V, PTEN:p.V317fs, RGSL1:p.V222I, RUNX1:p.R142fs, RUNX1:p.D96fs, SCN2A:p.R36K, SLC25A32:p.Q83E, SLC25A45:p.G106C, STRA6:p.Q68R, STX6:p.H153D, TBX3:p.H187Y, TFPT:p.S252C, TINAG:p.R332W, TMEM71:p.R63Q, TP53:p.E286K, TP53:p.R282W, TP53:p.V272M, TP53:p.S241fs, TP53:p.C238fs, TP53:p.C238F, TP53:p.C238Y, TP53:p.Y234C, TP53:p.Y220S, TP53:p.R209fs, TP53:p.G199V, TP53:p.L194R, TP53:p.H193L, TP53:p.H193Y, TP53:p.V173L, TP53:p.V173M, TP53:p.K132N, TP53:p.R110fs, TUBD1:p.A200V, VLDLR:p.R231H, VWA3A:p.V955I, VWF:p.K1720N, XPO1:p.E571K, and ZNF268:p.F901 del.

48. The pharmaceutical composition of any of paragraphs 30-36, wherein:
(a) the population of subjects is suffering from COAD; and
(b) the at least one tumor-specific mutation comprises any combination of mutations selected from the group consisting of KRAS:p.G12D, BRAF:p.V600E, KRAS:p.G12V, ACVR2A:p.K435fs, GRB14:p.KKK295del, SEC63:p.L532fs, TGFBR2:p.E125fs, ATR:p.K771fs, ICA1:p.N204fs, KRAS:p.G12C, TP53:p.R175H, ABCA8:p.R842Q, ACTL7B:p.R354H, ACVR2A:p.K435fs, AIM2:p.K340fs, ALG2:p.S302Y, ANKIB1:p.K144fs, ARSG:p.V131I, ATP10D:p.R311H, AXIN2:p.W663fs, C5orf30:p.D4N, CACNG3:p.V134I, CASP5:p.K78fs, CC2D2A:p.R1284C, CDH10:p.E349K, DNMT1:p.E432K, DOCK2:p.G170R, DOCK5:p.E177K, EGR2:p.R390H, ERBB3:p.V104M, FAM135B:p.R884H, FBXW7:p.R505C, FBXW7:p.R465H, FHDC1:p.R254W, FOXL1:p.N89K, HCN4:p.R525H, HLA-DMA:p.E84K, HTR3B:p.R236C, ITGA4:p.T673M, KIF18A:p.R17C, KIF20B:p.E991K, KLHL5:p.R326C, KRAS:p.A146T, KRAS:p.G13D, LPHN3:p.R1183Q, MAP2K4:p.R287H, MAPK8IP1:p.L217fs, MFSD5:p.R280Q, MUC16:p.R8606H, MYO6:p.D1180N, NAA25:p.S807Y, NBPF14:p.V44L, NRAS:p.Q61K, NRAS:p.G13R, PAX3:p.T424M, PGAM1:p.R240H, PHF3:p.R1410I, PIK3CA:p.R88Q, PIK3CA:p.E545K, PIK3CA:p.H1047R, PLXNA3:p.V14fs, POSTN:p.R508C, PTPRU:p.D1434N, PYGO2:p.Q150fs, RBBP7:p.E274K, SFPQ:p.R611Q, SGSM1:p.F117L, SLC25A40:p.R96Q, SLC8A1:p.R431H, SLITRK3:p.S298L, SPATA22:p.S150L, SUN3:p.E128K, TGFBR1:p.S241L, TP53:p.R273H, TP53:p.R273C, TP53:p.R248W, TRPV5:p.R492H, USP40:p.S851L, VPS13C:p.D1359Y, ZBTB24:p.L607I, ZNF434:p.R306C, ZNF443:p.R301I, ZNF484:p.R138C, and ZNF770:p.S441P.

49. The pharmaceutical composition of any of paragraphs 30-36, wherein:
(a) the population of subjects is suffering from GBM; and
(b) the at least one tumor-specific mutation comprises any combination of mutations selected from the group consisting of HSD17B7P2:p.N175S, IDH1:p.R132H, EGFR:p.A289V, EGFR:p.G598V, WASH3P:p.G175S, ZNF814:p.D404E, RPSA:p.Q111E, NBPF10:p.E3455K, TP53:p.R248Q, BRAF:p.V600E, EGFR:p.A289T, PRB2:p.N230del, RGPD5:p.P1760A, TP53:p.R175H, CHEK2:p.K373E, EGFR:p.R108K, EGFR:p.R222C, PIK3CA:p.E545K, PIK3R1:p.G376R, POTEC:p.K507E, SDHAP2:p.V195E, SLC6A10P:p.K88N, TP53:p.R282W, TP53:p.R273H, CD3EAP:p.K219del, DST:p.R146C, EGFR:p.A289D, EGFR:p.H304Y, FRG1B:p.S71N, GOLGA8DP:p.A116E, KRTAP4-11:p.R121K, KRTAP4-11:p.S48R, MAP3K1:p.P324L, OGDH:p.I78fs, PODXL:p.S162fs, PSPH:p.V145I, SPINT1:p.A316V, TP53:p.R248W, TP53:p.G245S, TP53:p.Y220C, TP53:p.R158H, TSHZ2:p.A222T, UBC:p.L149R, ZDHHC4:p.R300H, ZNF844:p.R447P, AASS:p.T878fs, ABCC10:p.R570W, ADAM29:p.V205I, ADAMTS8:p.V524M, AGAP3:p.R766W, AICDA:p.Y144F, AK7:p.A159V, AK8:p.D243A, ANO2:p.R334C, AOX1:p.A507V, ARHGAP5:p.M691L, CALN1:p.V2311I, CARM1:p.A202V, CD163L1:p.V721M, CD1D:p.L25fs, CD209:p.A283T, CDH18:p.A195T, CILP2:p.V553M, CIZ1:p.L89P, CLOCK:p.L123fs, COL6A5:p.T2224M, CSF2RB:p.G298S, CSMD3:p.E171K, CYP2D6:p.H352R, DCAF12L1:p.R335H, DCAF12L2:p.R246H, DPP10:p.V183I, DPY19L2P1:p.R378Q, DQX1:p.R505H, DRD5:p.S275R, DVL2:p.V66G, EFCAB6:p.R379K, EGFR:p.L62R, EGFR:p.R252C, EGFR:p.P596S, EGFR:p.P596L, EGFR:p.G598A, EGFR:p.E709K, EPHA1:p.A184T, ERC2:p.R20H, ESPNP:p.R627Q, FAM126B:p.R382H, FBN3:p.V886I, FGF14:p.T229M, FLG2:p.H1901fs, FLG:p.R2886H, FLNA:p.V1240M, FOXG1:p.H57del, FPR2:p.R54Q, FRG1B:p.K13N, FRG1B:p.A53T, GABRA6:p.V314L, GJB3:p.R160H, GLT8D2:p.A178V, GRM3:p.R183C, HERC1:p.R2330H, HNF1B:p.T417M, HTRA3:p.Q403R, IDH1:p.R132G, IFNA10:p.L80F, IFNA10:p.V79A, JHDM1D:p.R313H, JPH1:p.A395T, KEL:p.V411M, KIAA0907:p.R516fs, KIAA1704:p.D88del, KLK6:p.R120H, KRAS:p.G12D, KRTAP4-7:p.L121V, KRTAP4-7:p.L148V, KRTAP5-4:p.S131C, LAT2:p.L18W, LIMK2:p.R203H, LUM:p.R330C, MCOLN3:p.V141I, MGAT4B:p.T444P, MUC17:p.V77M, MUC17:p.3204_3205insP, MYO1D:p.T109M, MYO6:p.Q914fs, NAP1L5:p.140_141EE>E, NF1:p.F1658fs, NHP2L1:p.R84C, NLRP5:p.R737W, NPTX1:p.A263T, NUFIP2:p.Q29del, ODF4:p.R61C, OR11H12:p.H154P, OR2A7:p.V18I, OR2H1:p.V287I, OR2T12:p.R184H, OR5D13:p.R236C, OR5P2:p.A100V, OR6N2:p.R293C, PASD1:p.A236del, PCDH11X:p.T486M, PCDHB13:p.P221L, PDGFRA:p.E229K, PDGFRB:p.S650L, PHC3:p.T35del, PIK3C2B:p.R287fs, PIK3CA:p.M V, PIK3CA:p.R88Q, PIK3CA:p.M1043V, PIK3CA:p.H1047R, PIK3R1:p.K379N, PODNL1:p.A150V, POTEE:p.V166M, POTEG:p.R136H, PRKCD:p.G432fs, PROKR2:p.V297I, PTEN:p.C136Y, PTEN:p.S170N, PTEN:p.R173H, PTEN:p.T277I, PTEN:p.V317fs, PTPN14:p.E716del, R3HDM2:p.412_413QQ>Q, RAB11FIP5:p.R170H, RASAL3:p.R82H, RB1:p.N316fs, RDH8:p.A198V, REN:p.15_16LL>L, RIMBP2:p.R830H, SCAF11:p.E926fs, SCN7A:p.R1358H, SCNN1G:p.R564H, SDHAP2:p.R31C, SDHAP3:p.A66T, SEMG2:p.R292C, SH3RF2:p.R318C, SHB:p.A460T, SIGLEC10:p.T250M, SLC13A5:p.Q273P, SLC17A9:p.V324I, SLC22A9:

p.R407Q, SLC26A3:p.V881, SLC5A3:p.A302fs, SLC9A4:p.R631H, SPAM1:p.R346Q, SPEN:p.E803fs, SPTA1:p.A2011V, SUSD5:p.T513M, SYNE1: p.R8468H, TARSL2:p.G366D, TAS2R41:p.A255T, TAT:p.R367H, TFPI2:p.R206C, THSD7B:p.R90C, TMEM147:p.A92V, TMEM156:p.R81C, TMPRSS6: p.V302L, TNFSF9:p.A232T, TP53:p.C238F, TP53: p.C238Y, TP53:p.Y234C, TP53:p.V216M, TP53: p.H179R, TP53:p.T155N, TRAPPC10:p.K133fs, TTN: p.R21402W, TTN:p.V16403M, TUBBP5:p.V102M, TYRP1:p.T352fs, UBC:p.R73L, UGT2B28:p.P289H, USH2A:p.R3719H, WASH6P:p.L211V, ZFP42: p.V227I, ZFP42:p.T264M, ZNF181:p.V305G, ZNF280B:p.E400K, ZNF534:p.N583K, ZNF563: p.W208fs, ZNF844:p.F487L, and ZPBP:p.R154C.

50. The pharmaceutical composition of any of paragraphs 30-36, wherein:
(a) the population of subjects is suffering from HNSC; and
(b) the at least one tumor-specific mutation comprises any combination of mutations selected from the group consisting of PIK3CA:p.E545K, PIK3CA:p.E542K, TP53:p.R175H, PIK3CA:p.H1047R, TP53:p.R282W, TP53:p.R248Q, TP53:p.R273H, TP53:p.R248W, TP53:p.G245S, RHOA:p.E40Q, EP300:p.D1399N, HRAS:p.G13V, MB21D2:p.Q311E, NFE2L2:p.E79Q, TP53:p.H179Y, FBXW7:p.R505G, HIST1H2BF: p.E77K, HRAS:p.G12D, MAPK1:p.E322K, NFE2L2: p.D29H, TP53:p.P278S, TP53:p.C242F, TP53: p.Y220C, TP53:p.H193L, TP53:p.H179R, TP53: p.V157F, TP53:p.R110L, AKNAD1:p.K620R, ANXA6:p.R231Q, AP1G2:p.D243N, ATAD5: p.D441N, ATP6AP2:p.E119Q, B2M:p.M1I, BCL11A: p.E579K, C1orf172:p.Y30fs, C7orf57:p.E30K, CCDC135:p.E313K, CDH12:p.P706T, CDH7: p.Q225K, CDK11B:p.E79del, CDKN2A:p.H83Y, CHCHD4:p.T79M, CIRH1A:p.S250I, CLSTN2: p.P759L, CRB1:p.L628fs, DENND5B:p.G1023E, DNAH5:p.Q1797E, DSP:p.R160G, EDA:p.L58F, EFCAB6:p.E1002K, ELF4:p.S415L, EP300: p.C1164Y, EPHA3:p.T802R, EPHA6:p.D952H, ERBB2:p.M916I, ESRRA:p.D219N, FAM101A: p.I89del, FBXO24:p.M553V, FCAR:p.V233M, GPANK1:p.Y351fs, GPR20:p.V300I, GPRASP1: p.S706L, GPRIN3:p.R633fs, GRID2:p.T649fs, GRM3:p.P682L, GUCY2F:p.S404L, HCRTR2: p.D100Y, HIST1H3C:p.K37M, HIST1H4C:p.R68P, HLX:p.S12T, HOXD10:p.Y151C, HPS3:p.K812N, HRAS:p.G12A, HRAS:p.G12S, IFT140:p.E664K, INPPL1:p.T493M, ITGA10:p.R669Q, ITGB1: p.D158N, KIAA1429:p.D1526N, KIAA1429:p.S138F, KPRP:p.E553fs, KSR2:p.T555M, LINGO2:p.P410T, LPCAT1:p.V187del, MAGEB3:p.V75A, MAP3K7: p.E524Q, MAP4K3:p.P657fs, MAP9:p.K485N, MARS2:p.R481Q, MBOAT7:p.R424W, MUC16: p.R12774H, MUC5B:p.T4388M, MYH11:p.E993K, MYOCD:p.T493M, MYOM1:p.R63Q, NANOS3: p.S183L, NCOR1:p.R1561Q, NCOR1:p.Q169E, NCR1:p.D213N, NFE2L2:p.E79K, ODZ1:p.R366M, OPN1MW:p.A285T, OR2M2:p.A95fs, OR2M3: p.M273I, OR2T33:p.R120S, OR6V1:p.1248fs, PABPC5:p.P58L, PACSIN1:p.E359K, PIK3CA: p.M1043V, PIK3CA:p.H1047L, PIWIL1:p.V699M, PLIN5:p.430_431insNG, PLXNA3:p.P58S, PRB1: p.R274fs, PRSS1:p.D107N, RAC1:p.A159V, RGS7: p.L21fs, RPA1:p.R31H, RPL18:p.R178fs, SF11: p.R821Q, SLC35D3:p.*417S, SLC5A7:p.G336C, SMARCA4:p.P913L, STAT3:p.D661V, SYCP2: p.K474N, SYT6:p.R249H, TBX21:p.E494K, THSD7A:p.R1046C, THSD7A:p.C728F, TMC3: p.R934S, TMTC2:p.T409R, TP53:p.E285K, TP53: p.C275F, TP53:p.R273C, TP53:p.G266E, TP53: p.G262V, TP53:p.R249S, TP53:p.G245V, TP53: p.C238F, TP53:p.M237I, TP53:p.Y236C, TP53: p.Y236D, TP53:p.R196P, TP53:p.PHHERC177del, TP53:p.V173L, TP53:p.V173M, TP53:p.Y163C, TP53:p.P151T, TP53:p.V143M, TP53:p.P58fs, URI1: p.S13fs, ZNF177:p.K384N, ZNF750:p.S96fs, and ZZZ3:p.R5Q.

51. The pharmaceutical composition of any of paragraphs 30-36, wherein:
(a) the population of subjects is suffering from KIRC; and
(b) the at least one tumor-specific mutation comprises any combination of mutations selected from the group consisting of WASH3P:p.G175S, VHL:p.L89H, VHL: p.S111N, WDR52:p.V1227G, KRT1: p.552_559YGSGGSSY>Y, KRTAP1-1:p.S34C, PALM2-AKAP2:p.1075_1076insEA, ZNF814: p.D404E, DOPEY2:p.Y2048S, KAT2B:p.W111fs, PABPC1:p.E156fs, PCDHGC5:p.G599V, PIK3CA: p.E545K, RRAD:p.A278E, SIRPA:p.D131del, UQCRFS1:p.I83V, VHL:p.P45L, VHL:p.V74D, VHL: p.R82P, VHL:p.L116fs, VHL:p.L158V, VHL:p.L169P, WDR73:p.DGTRSQ315del, ABCA3:p.E95D, ABCC5:p.L1090fs, ACADS:p.R330H, ACAN: p.G952E, ACSM2A:p.L402fs, ADAM23:p.K380M, ADH1A:p.D154V, AFF3:p.SA620del, AGAP6: p.D69fs, AGAP7:p.E71fs, AHNAK:p.5_6insE, AIDA: p.K247M, ALAS1:p.G302R, ANAPC16:p.R95fs, ANK2:p.N453S, ANKRD36:p.K378R, ARHGEF5: p.E487G, ARSD:p.AGV234del, ARSD:p.A234G, ATP2A1:p.G704C, ATP7A:p.Q990fs, AVIL:p.G299fs, AXDND1:p.EQ991del, BAP1:p.N78S, BAP1:p.M1I, BLM:p.H660Q, BMPER:p.RIAL444del, BRK1: p.K70Q, BTRC:p.I416M, C16orf55:p.D118A, C19orf33:p.K102E, C20orf132:p.E382D, C2orf71:p.1225_1226insS, C6orf132: p.173_182PPPLLLEPPP>P, CASP5:p.R23fs, CATSPER4:p.T425M, CCDC120:p.I8V, CCR5: p.S185I, CCZ1:p.E214D, CD7:p.P174fs, CDAN1: p.L646fs, CDH23:p.F1132Y, CDK5RAP2:p.H1592Q, CENPB:p.E410V, CERCAM:p.A85fs, CHEK2: p.K373E, CHIT1:p.P284fs, CLCN2:p.645_645R>RR, CLUL1:p.G463R, CNTNAP4:p.Y436S, CUL9: p.D1726E, CWC25:p.K364E, CXorf51B:p.V431, DDX39B:p.F149fs, DIRAS1:p.G79C, DISP2: p.F1021S, DNMBP:p.T78P, DOCK8:p.A177fs, DPCR1:p.H383N, DPCR1:p.L768del, EGFR: p.L838M, ENPEP:p.F289C, ESPNP: p.W122fs, FAM105A:p.H126N, FAM186A: p.IPPQAQELEIPL1556del, FAM194B: p.EEEEYL135del, FAM22F:p.S691 del, FAM22F: p.P690fs, FAM47A:p.LRPEPPETGVSH235del, FAM47C:p.P388S, FAM78A:p.W192L, FBXO34: p.Q294fs, FGFR3:p.R571fs, FGFR3:p.P716H, FMN2: p.AIPPPPPLPGA956del, FOXD4L4:p.C405fs, FUT6: p.S140fs, GJA1:p.A31 fs, GOLGA5: p.L492I, GPM6A:p.A50V, GPRIN1: p.231_239RKEDPGSLR>R, GRAMD1B:p.P356H, GREB1:p.S344Y, GRM6:p.A718fs, GUSB:p.L501V, GUSB:p.C500R, HBB:p.F86C, HDAC6:p.G977D, HEXDC:p.T482P, HNFJB:p.N302K, HNRPLL: p.M327V, HRC:p.P439fs, HSFX2:p.D92E, IL1RAP: p.F50C, IVL:p.EQQEGQLKHP167del, KANK4: p.S253P, KCNJ18:p.E378K, KIAA1751:p.K97N, KRT1:p.SSYGSGG557del, KRT2:p.L299W, KRT4: p.F154fs, KRTAP10-6:p.49_49P>PSCCAP, KRTAP5-7:p.C120Y, KRTAP9-2:p.CCQP140del, LARS: p.P185fs, LCP1:p.P445fs, LOC338651: p.PHRSHSPPWS102del, LRCH2:p.D717G, LTA4H: p.F107L, LYST:p.Q710H, MAFA:p.207_208HH>H, MAGEC1:p.P239del, MAP2K5:p.Q445R, MAPKAPK2:p.T214fs, MARCKS:p.K152fs, MED12L: p.P2071 S, MEGF6:p.A582fs, MGST3:p.G143fs, MLXIPL:p.S790R, MOCOS:p.S849P, MST1R: p.M464V, MTOR:p.C1483F, MTOR:p.L1460P, MUC16:p.P11260A, MUC17:p.R1227fs, MUC17: p.H1228fs, MUC2:p.1480_1481insI, MUC6: p.P1569fs, MYO3A:p.N525S, NBPF3:p.D491V, NCOR1P1:p.L52P, NDUFA4L2:p.G3fs, NEFH: p.651_651K>KAKSPEK, NES:p.V611L, NFAT5: p.Q906E, NOXO1:p.G3fs, NR2C1:p.S270I, NSMCE2: p.Q31fs, NUDT21:p.W13fs, ODZ2:p.W628fs, ONECUT1:p.L424M, OR10A3:p.F73V, OR4F4: p.E15G, OR4N2:p.L150fs, OR51B5:p.A66fs, OR7C1: p.F104fs, PABPC1:p.Y408F, PABPC1:p.K333fs, PABPC1:p.A181T, PABPC3:p.P191T, PALLD: p.A996T, PALM2-AKAP2:p.G1118fs, PARD6A: p.G84fs, PASK:p.T62I, PCDH15:p.C1713F, PCNT: p.G136S, PGM5:p.G426fs, PGPEP1L:p.R164fs, PIK3C2B:p.F1473L, PIK3CA:p.N1044K, PIK3R5: p.L371R, PITRM1:p.P816T, PLIN4:p.T347I, PODXL: p.28_30PSP>P, POLR1C:p.K332Q, POTED:p.I214V, PPM1E:p.R311W, PRKCE:p.Q157fs, PROX1: p.V225D, PRRC2C:p.P1883T, PRX:p.P549L, PSD3: p.T563P, PTCH1:p.P689H, RANBP3:p.L386W, RASGEF1C:p.A188T, RGPD6:p.F946L, RHEB: p.Y35N, RIMBP3:p.A396del, RIN3:p.L449V, RLIM: p.S501R, RNF17:p.S351C, RUNX2:p.P466H, SCAF1: p.P208fs, SDK1:p.K508fs, SECISBP2:p.D608E, SERPIN B3:p.S209C, SESTD1:p.I306M, SFRP4: p.P325fs, SH3KBP1:p.P563fs, SIPA1L3:p.G777A, SLC13A2:p.L493fs, SLC16A9:p.CVLLGG470del, SLC25A5:p.A118T, SLC44A5:p.V70F, SLC4A8: p.N229K, SLC52A1:p.G370del, SLC52A2:p.G399fs, SLC6A10P:p.K88N, SLC6A4:p.A85fs, SLC9B1: p.V446fs, SON:p.VLESSAVT1359del, SP8: p.G165del, SPAG1:p.353_354insD, SPATA9:p.C189F, SPEG:p.A992fs, SPTB:p.T1864I, SRA1:p.V110L, STAT6:p.P354fs, STK11IP:p.A155E, STXBP3: p.E279G, SVIL:p.M93T, SYNE1:p.R8468S, SYNJ2: p.K832T, SYNPO:p.G619fs, TAOK2:p.Q899fs, TAS2R38:p.I311T, TBC1D12:p.F608Y, TBC1D1: p.H277R, TBC1D3:p.A556fs, TBC1D3C:p.A495fs, TBC1D3F:p.A556fs, TCF7:p.H140P, TDRD10: p.W276C, THRAP3:p.K551R, TMEM102:p.A110P, TMEM161B:p.L142P, TMEM230:p.D140G, TMEM47:p.G87S, TRDN:p.*730Y, TTBK1: p.T1065S, UBE2O:p.R1118fs, UBR5:p.T1306fs, UPK3A:p.G272fs, VHL:p.G39S, VHL:p.S65L, VHL: p.N78D, VHL:p.R79P, VHL:p.W88L, VHL:p.L89P, VHL:p.R107P, VHL:p.S111R, VHL:p.H115N, VHL: p.D121Y, VHL:p.G123fs, VHL:p.D126fs, VHL: p.L128H, VHL:p.L135F, VHL:p.I151T, VHL:p.L153P, VHL:p.L158P, VHL:p.Q164fs, VHL:p.L184P, VHL: p.L188P, WASH6P:p.315_316insAPP, WASH6P: p.T201M, WWP2:p.G458A, ZCCHC6:p.K937N, ZFAND2B:p.I49T, ZFR2:p.Y107N, ZNF273: p.N319K, ZNF462:p.S650T, ZNF516:p.A256D, ZNF519:p.H431Y, ZNF687:p.F858C, ZNF732: p.E227Q, ZNF880:p.Q406R, ZP3:p.V362fs, and ZRANB1:p.*735fs.

52. The pharmaceutical composition of any of paragraphs 30-36, wherein:
  (a) the population of subjects is suffering from LAML; and
  (b) the at least one tumor-specific mutation comprises any combination of mutations selected from the group consisting of NPM1:p.W288fs, DNMT3A:p.R882H, NPM1:p.L287fs, IDH2:p.R140Q, IDH1:p.R132C, FLT3:p.D835Y, DNMT3A:p.R882C, FLT3: p.600_601insFREYEYD, IDH1:p.R132H, NRAS: p.G13D, U2AF1:p.S34F, KIT:p.D816V, FLT3: p.D835E, IDH2:p.R72K, NRAS:p.G12D, WT1: p.S381fs, ABTB1:p.L249fs, DNMT3A:p.R736H, FLT3:p.D835H, KRAS:p.G12D, NPM:p.L287fs, NRAS:p.Q61H, NRAS:p.Q61K, PHACTR1:p.V251fs, RBBP4:p.E330K, RUNX1:p.R135G, and U2AF1: p.S34Y.

53. The pharmaceutical composition of any of paragraphs 30-36, wherein:
  (a) the population of subjects is suffering from LUAD; and
  (b) the at least one tumor-specific mutation comprises any combination of mutations selected from the group consisting of KRAS:p.G12C, KRAS:p.G12V, EGFR: p.L858R, U2AF1:p.S34F, KRAS:p.G12A, TP53: p.R158L, KRAS:p.G12D, PIK3CA:p.E545K, TP53: p.R273L, EGFR:p.ELREA746del, KRAS:p.G13D, A2ML1:p.S654fs, BRAF:p.G469V, CTNNB1:p.S37F, EGFR:p.G719A, KRAS:p.G13C, MYOF:p.G165fs, EGFR:p.S768I, FAM47C:p.G948W, KRAS:p.Q61L, MYH10:p.L1091fs, NRAS:p.Q61L, OR4C3:p.H130fs, PI15:p.V22F, RAD50:p.D69Y, RIT1:p.M90I, TP53: p.C275F, TP53:p.R249M, TP53:p.R249G, TP53: p.R248P, TP53:p.R175H, TP53:p.Y163C, TP53: p.A159P, TP53:p.V157F, TP53:p.G154V, ABCB1: p.R467L, ACBD3:p.R224L, ACTA1:p.G275C, ACTN2:p.D893Y, ADAM30:p.Q741H, ADAMTS14: p.G238C, ADAMTS20:p.R1251S, ADAMTS20: p.R541L, ADAMTS5:p.L549M, ADAMTS9: p.G659W, ADCY2:p.P1016T, ADCY5:p.G623C, AFP: p.A182G, AHDC1:p.P155Q, AKAP1: p.LDRNEEG317del, ALKBH1:p.K137E, ANK2: p.Q3076L, ANKRD44:p.G339C, ANO3:p.A41S, AP1G1:p.R723L, APBB2:p.T243fs, APOB:p.L973M, APOBR:p.R840L, AQP10:p.Q261L, ARAP3: p.R1226L, ARFIP2:p.R86L, ARHGAP36:p.P16H, ARL13B:p.R358L, ASCC2:p.R365L, ASPM:p.S240F, ASXL3:p.P1470Q, ATRN:p.P197Q, AVIL:p.G64W, AXDND1:p.W101R, B3GAT1:p.R125L, BARX2: p.R68P, BCL9L:p.G980C, BCOR:p.N1459S, BEND2: p.P536Q, BMS1:p.G455V, BRAF:p.V600E, BRAF: p.G466V, BRD9:p.G330W, BRF1:p.V469L, BRWD3: p.H160N, BTRC:p.G260W, C11orf68:p.V135L, C15orf2:p.V753F, C15orf2:p.G906W, C18orf8: p.M61I, C1GALT1:p.G299V, C1orf173:p.G1454S, C1orf173:p.S688Y, C1orf87:p.R541L, C2orf53: p.P272H, C3orf20:p.R740L, C7:p.R687S, C7orf58: p.G140W, C7orf58:p.R238L, CACNA1A:p.S772Y, CACNA1D:p.R1073L, CACNA1E:p.R2089Q, CACNA2D1:p.A352E, CACNG3:p.R232W, CADPS: p.R959S, CALB2:p.R258C, CAMK2B:p.G131V, CARD11:p.I1065M, CCDC111:p.R417L, CCDC141: p.E1204V, CCDC19:p.R279L, CCDC19:p.R207L, CCKAR:p.L271M, CD1B:p.W41L, CDH10:p.S577R, CDH10:p.R472C, CDH10:p.R128S, CDH18:p.A721S, CDH20:p.P433H, CDH6:p.Q237K, CDK13:p.R880S, CDK4:p.R24L, CELF4:p.A309P, CFDP1:p.P129fs, CHN1:p.K264N, CHRNA4:p.S396R, CHRNA9: p.P361Q, CLCNKA:p.P124Q, CLEC12B:p.W217L, CLK4:p.R68L, CNTFR:p.D252Y, CNTN6:p.R807M, CNTNAP2:p.F395L, COL19A1:p.P538Q, COL5A2: p.G612W, COL5A2:p.G516W, COL9A1:p.R211Q, CPE:p.P290Q, CPNE8:p.Q127H, CPSF4:p.P219Q, CRIPAK:p.S180fs, CROT:p.Q580H, CRTC3:p.S363L, CSMD2:p.P1855Q, CSMD3:p.T2810N, CSMD3: p.P2727T, CSMD3:p.Q174H, CUBN:p.G596C, CUL4B:p.R91S, CUL7:p.L371F, CXCL9:p.K122N, CXCR4:p.E345Q, CXorf59:p.R198M, CYP11B1: p.R498G, CYP27A1:p.P112Q, CYP2B6:p.A444E, DACH2:p.R539L, DCC:p.R446H, DDX56:p.R329L, DEFA1:p.W90C, DENND2A:p.R688Q, DENND2A: p.R499L, DMBT1:p.R1521L, DNAH5:p.R3822L, DNAH9:p.S2993R, DNAI2:p.V231L, DPP6:p.L757F, DSG4:p.R128L, DST:p.A4410S, DZIP3:p.M322L, EBF3:p.R231 S, EFCAB4B:p.E265Q, EHHADH: p.Q704H, ELAVL2:p.L263F, EMR1:p.R493H, ENAH: p.R514L, ENPP1:p.G738E, EPB41L3:p.A896S, EPG5:p.R2289L, EPHA1:p.G111V, EPHB6:p.R337H, EPRS:p.V1151L, ERBB2:p.S310Y, ERBB2: p.774_775insAYVM, ERBB2:p.776_776G>VC, ERN2:p.T295K, FAM120B:p.P467H, FAM127C: p.F52L, FAM135B:p.W240C, FAM210B:p.L112F, FAM47A:p.R690L, FAM47B:p.W163C, FAM47B: p.L567F, FAM5C:p.R457G, FAM70B:p.P277T, FAM71B:p.L583M, FAM75A6:p.R304S, FAM75A6: p.P54L, FAM75D1:p.R1265S, FARP1:p.R299L, FAT1:p.R4359L, FAT3:p.R1266H, FAT3:p.G1899V, FAT3:p.H3574N, FBXO18:p.M144I, FBXO31: p.G443fs, FCGBP:p.A1022S, FCRL2:p.V505L, FERD3L:p.P92H, FGB:p.E339Q, FGFR2:p.E116K, FGFRL1:p.R243L, FGFRL1:p.V274L, FKBPL: p.R320L, FLG2:p.G1545V, FLG2:p.L572F, FLG: p.P3254H, FLG:p.P2466Q, FMN2:p.P992T, FOLH1: p.A643S, FOXRED1:p.R136L, FRAS1:p.C382F, FRG2B:p.D142Y, FRMPD1:p.E1093Q, FSHB: p.T43N, GABRA5:p.Q224K, GADL1:p.L352I, GAL3ST3:p.A271S, GALNT14:p.D234E, GAS8: p.R313S, GATA3:p.M443I, GCDH:p.R82C, GEM: p.R268L, GFRAL:p.Q308K, GIT2:p.R123L, GJB4: p.R22S, GLB1L2:p.I407M, GLOD4:p.Q223fs, GNAO1:p.P283Q, GPNMB:p.I74M, GPR137B: p.G240C, GPR158:p.P762L, GPR98:p.G4307W, GRB7:p.R239L, GRHL1:p.G608W, GRID1:p.R683L, GRIK1:p.R368Q, GRM5:p.P895fs, GTF2E1:p.R192L, H3F3C:p.R131L, HAO2:p.H12N, HCN1:p.R231Q, HECW1:p.A183S, HGF:p.M686T, HIP1:p.R940L, HIST1H1E:p.R25P, HLA-DMA:p.A236fs, HOXA5: p.G11C, HS3ST3A1:p.G399W, HSD17B6:p.F209L, HSPA13:p.V85L, HSPBAP1:p.R282L, HTR5A: p.W298C, IGHMBP2:p.R615S, IL2:p.R103M, IL2RA: p.G61W, IL32:p.P215T, ING1:p.A220S, INMT: p.G56V, ITGA8:p.G616C, ITGAD:p.L528fs, ITGAX: p.R283H, ITIH1:p.G254W, ITIH2:p.L842V, ITK: p.R29L, ITPR2:p.P358Q, JMJD1C:p.R1198S, KCNA1:p.G376C, KCNH8:p.M455I, KCNJ3: p.L430F, KCNK18:p.G23V, KCNK2:p.R166L, KEAP1:p.G603W, KEAP1:p.R260L, KEAP1:p.S144F, KHDRBS2:p.S203L, KIAA1211:p.P1203Q, KIAA1549:p.L1272F, KIAA1755:p.Q108H, KIF15: p.E252Q, KIF9:p.G480R, KIRREL:p.G604C, KLF5: p.E419Q, KRAS:p.Q61H, KRTAP10-12:p.R64P, KRTAP27-1:p.M124I, KRTAP4-5:p.C91F, KRTAP5-1:p.S193Y, L1CAM:p.R632S, L3MBTL4:p.W162L, LAMA1:p.D1030Y, LAMB1:p.T1610fs, LAMB4: p.G1239W, LAMB4:p.G588W, LEF1:p.I53V, LEKR1: p.Q450K, LIM2:p.S150T, LIPJ:p.P236Q, LPHN3: p.E740D, LPPR4:p.R527S, LRFN5:p.N132K, LRP1B: p.G3563C, LRP2:p.M4039I, LRRC4C:p.Q1L, LRRIQ1:p.W792L, LRRTM4:p.S243Y, MAGEA10: p.R7H, MAGEC2:p.W109C, MAGI1:p.G1156V, MAGI2:p.P1044T, MAK:p.P373Q, MAP2K1:p.K57N, MARCH11:p.R193L, MEPE:p.G142C, MKI67: p.R1081 S, MKRN3:p.P448H, MLL3:p.N393K, MLL3:p.Q356K, MMRN1:p.A1013S, MOGAT2: p.Q66fs, MXRA5:p.D324Y, MYH4:p.T790M, MYH8: p.R1117C, MYH8:p.H1006N, MYO5B:p.R708L, MYO7B:p.P2040H, MYO9B:p.R94L, MYT1L: p.P351Q, NAA11:p.T184K, NAB1:p.L72F, NAV1: p.R938L, NBPF15:p.G665E, NCAM2:p.G698C, NCAPD2:p.R220L, NDST3:p.V427I, NEK2:p.R239S, NFIA:p.L294F, NLRP3:p.R157C, NOTCH2: p.R2105L, NR4A2:p.R314L, NRG1:p.V481L, NRXN1:p.R813S, NRXN1:p.A660S, NRXN3: p.P23H, NRXN3:p.R103C, NTM:p.G333C, NUAK1: p.G173C, NYAP2:p.R437L, ODZ3:p.P218Q, OIT3: p.R508S, OOEP:p.R101C, OPN1LW:p.P283H, OR10H4:p.M199I, OR10J1:p.L157Q, OR10X1: p.L298I, OR10Z1:p.L205F, OR14A16:p.G160C, OR2A25:p.M80L, OR2AG2:p.G249W, OR2AK2: p.W37C, OR2H2:p.L205F, OR2J2:p.G234W, OR2L13:p.M106I, OR2L13:p.T242A, OR2L3:p.M1I, OR2L3:p.L67I, OR2L8:p.R121C, OR2L8:p.R171S, OR2M2:p.F177L, OR2M2:p.F323L, OR2M5: p.V205L, OR2T12:p.M258L, OR2T27:p.D1 Y, OR2T33:p.P165Q, OR2T34:p.C246F, OR2T6: p.V213L, OR4C12:p.D309Y, OR4C12:p.M279I, OR4C16:p.L162M, OR4M2:p.A119S, OR4M2: p.A161 S, OR51V1:p.P298T, OR5AS1:p.M391, OR5B12:p.S289C, OR5B17:p.M266I, OR5D14: p.H246N, OR5D16:p.P264T, OR5D18:p.R123H, OR5F1:p.G44V, OR5J2:p.A36S, OR5L1:p.T275N, OR6C65:p.I154fs, OR6C75:p.G94W, OR6K2:p.P79Q, OR8D2:p.R306M, OR9A2:p.R289W, OR9G9: p.R169L, P2RX7:p.P142Q, P2RY10:p.T10K, P2RY10:p.V196L, PABPC5:p.R99S, PAPPA2: p.P917T, PAPPA2:p.P1706H, PBLD:p.P55Q, PCDH10:p.R587S, PCDH10:p.V986L, PCDH11X: p.R1010I, PCDHAC2:p.A742V, PCDHB5:p.P649S, PCDHGC5:p.K12N, PCDHGC5:p.P684H, PCLO: p.P3946T, PCMTD1:p.R271M, PDPR:p.G793W, PDYN:p.G191W, PDZD2:p.R565S, PDZD8:p.S980G, PFKM:p.R118S, PIGM:p.R225L, PIK3CA:p.E542K, PIK3CG:p.V165L, PLLRA:p.S291fs, PLCE1: p.G564C, PLCL1:p.M564I, PLEKHA6:p.R110L, PNKP:p.G174W, POGZ:p.G75W, POLE:p.R573L, POM121L12:p.P231T, POM121L12:p.P242H, POTEE:p.V288M, POTEM:p.S78R, POU3F3: p.D321Y, PPT2:p.R265L, PRDM16:p.P1036L, PRELP:p.D201Y, PRPF40B:p.R160S, PRPF6: p.R763L, PTEN:p.R234L, PTPN11:p.G503V, PTPN13:p.E2067K, PTPRJ:p.G334W, PTPRT: p.R928L, PTPRU:p.P559S, PXDNL:p.P1456T, QSOX1:p.R401L, QSOX2:p.R683L, RAB13: p.R167L, RAB8A:p.G20W, RAPGEFL1:p.R356L, RBM19:p.G390W, RCL1:p.P112Q, REG1B:p.W57L, REG3A:p.S150L, REG4:p.G110V, RIMS2:p.R55L, RIT2:p.R85L, RLN2:p.S138C, RNF20:p.P529Q, RORB:p.G94W, RPL10L:p.K187T, RPRD2:p.R97S, RTN1:p.S103R, RUNX2:p.R337M, RYR2:p.K2413N, RYR2:p.M4334I, RYR2:p.P1670T, RYR3:p.P1670T, S100PBP:p.R5L, S1PR1:p.L104F, SAGE1:p.H298Q, SALL1:p.E965K, SALL1:p.R898W, SALL4:p.R187L, SBSPON: p.G133W, SCAF8:p.G740C, SCG2:p.P252Q, SCML4: p.L261F, SCN2A:p.T155K, SEC24D:p.A50fs, SEC61A2:p.G126V, SERPINA12:p.D253Y, SERPINA9:p.M414I, SERPINC1:p.R45L, SGIP1: p.R502L, SH3GL3:p.R174L, SH3PXD2A:p.S759L, SI:p.V1217F, SKOR1:p.Y883C, SLC1A2:p.F348fs, SLC24A5:p.R35S, SLC25A48:p.R101S, SLC35E2: p.R201L, SLC39A12:p.C628S, SLC39A6:p.R53L, SLC4A5:p.I533V, SLC5A1:p.G53W, SLC5A7: p.G442V, SLC6A11:p.W299L, SLC6A2:p.5354C, SLC8A1:p.G433C, SLIT1:p.R1460L, SLITRK5: p.R68L, SLITRK5:p.R468M, SLITRK6:p.N741K, SORL1:p.R205L, SOS1:p.N233Y, SOX9:p.E75K, SPAG16:p.V439L, SPIN4:p.Y171C, SPRR2D: p.P30fs, SPTA1:p.G2367C, SPTA1:p.D2243Y, SSX3: p.P127T, ST18:p.H778Q, STAC3:p.G117W, STOML3:p.D86Y, STX2:p.R107L, SUMF2:p.G110E, SUN3:p.P339Q, SV2C:p.P60Q, SYNDIG1:p.D135Y, SYNE1:p.K8632E, TARS2:p.E199K, TAS2R16: p.Q177H, TCOF1:p.K264R, TCTE1:p.S127I, TDO2: p.Q197H, THSD7A:p.G810W, THSD7A:p.R801L, TIFAB:p.D43E, TIGD4:p.S312F, TLL1:p.P53Q, TMPRSS11E:p.G259C, TMTC1:p.A864D, TMTC1: p.G212V, TMX3:p.R51C, TNNI1:p.R67L, TNR: p.L692I, TOP2A:p.R736L, TP53:p.R337L, TP53: p.E285K, TP53:p.R283P, TP53:p.D281N, TP53: p.C277F, TP53:p.V274F, TP53:p.R273H, TP53: p.I255F, TP53:p.R249S, TP53:p.M237I, TP53: p.S215I, TP53:p.C176F, TP53:p.R10L, TP53: p.G105C, TP53:p.P72fs, TPO:p.E558K, TRAF6: p.R502S, TRIM42:p.Q127K, TRIM48:p.A93D, TRIM4:p.R398L, TRIM51:p.W131C, TRIM9: p.R337S, TRIML:p.H399Q, TRPM3:p.G298W, TSC1: p.G378C, TSG101:p.R276S, TSHZ1:p.K501N, TSHZ3:p.G677V, TTF2:p.R761S, TUBA3C:p.Q176fs, UBAC1:p.K330N, UBE2J2:p.G193W, UBR1: p.G1647W, UGT2B7:p.M214I, VMP1:p.E369Q, VPS13B:p.G2575W, VSTM2A:p.G75V, VWA3B: p.R557L, WBP11:p.P227fs, WDR52:p.G612C, WDR59:p.R837S, WDR75:p.P287Q, WDR88: p.G100W, ZCCHC5:p.G335W, ZFHX4:p.L811F, ZFHX4:p.T1663N, ZFHX4:p.H2511Q, ZFP14: p.Q17L, ZIC1:p.A112E, ZNF154:p.T408N, ZNF223: p.G23W, ZNF295:p.S732C, ZNF322:p.K106N, ZNF385D:p.T226S, ZNF454:p.S190I, ZNF492: p.P392H, ZNF521:p.G640C, ZNF521:p.P270H, ZNF536:p.G186C, ZNF536:p.G663W, ZNF644: p.G21W, ZNF716:p.H263L, ZNF71:p.V411L, ZNF782:p.G484W, ZNF831:p.Q617K, ZNF98: p.C492F, and ZSWIM2:p.S214Y.

54. The pharmaceutical composition of any of paragraphs 30-36, wherein:
    (a) the population of subjects is suffering from LUSC; and
    (b) the at least one tumor-specific mutation comprises any combination of mutations selected from the group consisting of PIK3CA:p.E545K, TP53:p.R158L, KRTAP5-5:p.GCG47del, NFE2L2:p.E79Q, CDKN2A: p.D108Y, DHX9:p.V40G, MAFA:p.207_208HH>H, NFE2L2:p.R34Q, PBX2:p.Y262F, PIK3CA:p.E542K, TP53:p.R273L, TP53:p.C242F, TP53:p.R175G, TP53: p.Y163C, TP53:p.V157F, AICDA:p.R131G, ALPK2: p.D53N, ANKFN1:p.M280I, ARPC1A:p.F212L, ASXL2:p.S1081L, C1orf74:p.D254N, C3orf30: p.D227E, CCDC121:p.W397L, CHN2:p.143M, CLEC4C:p.R179L, CLN3:p.G206S, CNTN5: p.T178N, COL2A1:p.G2753C, CPS1:p.T855K, CSMD3:p.T1094K, CSMD3:p.Q691K, DDX11: p.R167T, EGFR:p.L861Q, EME1:p.D570H, EP300: p.D1399N, ESYT3:p.S574F, FAM135B:p.L648M, FAM135B:p.Q285H, FAM47A:p.G372W, FBXW7: p.R505G, FGFR3:p.S249C, GALNT13:p.G358C, GNL3L:p.K20N, GPC5:p.R347L, HCN1:p.A714S, HCN1:p.R659L, HCN1:p.G499V, HCN1:p.P326T, HERC2P3:p.A803V, HEXDC:p.T482P, HIST1H3B: p.E74K, HIST2H2BE:p.G54D, IFNA10:p.V79A, IL7R:p.S54L, INADL:p.P1340A, ISX:p.C2F, ITGAX: p.R685H, ITPR1:p.E1883Q, KCNN3:p.80_81insQQ, KEAP1:p.G480W, KEAP1:p.R470C, KEAP1: p.V155F, KIAA1751:p.L63F, KIAA2022:p.C345F, KIR3DL2:p.K229E, KLF5:p.E419Q, LAMA4: p.M1293I, LMLN:p.G199C, LRP2:p.A516V, LRRC66:p.F458L, LSG1:p.R517L, LUM:p.R310L, MB21D2:p.Q311E, MCHR1:p.S306F, MKRN3: p.G270V, MUC16:p.N11594K, NFE2L2:p.G81S, NFE2L2:p.G31A, NFE2L2:p.L30F, NFE2L2:p.D29H, OR2B11:p.G10V, OR2T2:p.F13V, OR4K2:p.C254F, OR51F2:p.R67P, OR51S1:p.R159Q, OR5D18: p.T271K, OR8H2:p.L166F, OR8J3:p.S160L, OR8K3: p.K235N, PCDHB1:p.N568K, PHIP:p.I1681M, PIK3CA:p.E726K, PIK3CA:p.H1047R, PLCE1: p.G439C, PRSS57:p.E39Q, PYHIN1:p.G148A, RANBP6:p.I984L, RBMXL1:p.G305C, REG1B: p.M67I, RGS6:p.W366L, RNF5:p.T136I, RP1: p.S1771L, RRP15:p.L214F, RYR2:p.E711K, SAMD3: p.Q206H, SLITRK3:p.R214L, SON:p.S908L, SP4: p.E1 del, STK11:p.G279fs, TARBP1:p.L782V, TBCD: p.R476C, TMPRSS11F:p.R274Q, TP53:p.R337L, TP53:p.E271K, TP53:p.R267P, TP53:p.G245V, TP53: p.Y234C, TP53:p.Y220C, TP53:p.H214R, TP53: p.H193L, TP53:p.H179L, TPTE:p.M541I, TRIM7: p.L332I, TTN:p.T32425M, ZFP36L2:p.D240N, ZNF208:p.H883Q, ZNF48:p.R235H, ZNF626: p.K473R, ZNF676:p.P43T, ZZZ3:p.R162Q.

55. The pharmaceutical composition of any of paragraphs 30-36, wherein:
    (a) the population of subjects is suffering from OV; and
    (b) the at least one tumor-specific mutation comprises any combination of mutations selected from the group consisting of TP53:p.R273H, TP53:p.Y220C, TP53: p.R248Q, TP53:p.R175H, TP53:p.R273C, TP53: p.I195T, TP53:p.R248W, TP53:p.R282W, TP53: p.C176Y, TP53:p.V157F, TP53:p.S241F, TP53: p.H179R, TP53:p.G245S, TP53:p.H193R, ADCY2: p.V888I, B2M:p.M1V, BAP1:p.R227C, CYP4A11: p.V185F, DNAH5:p.R3197Q, GART:p.K807fs, GRIN2B:p.R519Q, HRNR:p.M1fs, KLHL29: p.L716fs, KRAS:p.G12V, MGA:p.R2435Q, MYO3A: p.N525S, NPAS2:p.Q201R, NRAS:p.Q61R, PDAP1: p.K55fs, PGAP1:p.F565C, TP53:p.S315fs, TP53: p.C275Y, TP53:p.R273L, TP53:p.V272M, TP53: p.G266V, TP53:p.G266R, TP53:p.D259Y, TP53: p.P250L, TP53:p.G245D, TP53:p.G245V, TP53: p.G244C, TP53:p.C238fs, TP53:p.Y236C, TP53: p.Y234C, TP53:p.V216M, TP53:p.S215R, TP53: p.Y205C, TP53:p.L194R, TP53:p.P191del, TP53: p.Y163C, TP53:p.A159V, TP53:p.K132N, TRPC7: p.D210V, UXS1:p.V100L, WNT11:p.C344Y, and ZNF295:p.E885A.

56. The pharmaceutical composition of any of paragraphs 30-36, wherein:
    (a) the population of subjects is suffering from READ; and (b) the at least one tumor-specific mutation comprises any combination of mutations selected from the group consisting of KRAS:p.G12V, TP53:p.R273H, KRAS:p.A146T, KRAS:p.G12D, TP53:p.R175H, AKAP9:p.L3482I, APBA1:p.E624K, BAG5:p.D439N, C17orf97:p.E230D, CDH23:p.F177L, CERS3:p.E95D, DNAH5:p.R982H, ERBB2:p.V842I, GABRB3:p.D500N, KRAS:p.G13D, KRAS:p.G12C, KRAS:p.G12S, LRP6:p.R675Q, MACF1:p.F722L, MBOAT2:p.R43Q, MYO1D:p.E246K, NLRC4:p.E409K, NRAP:p.E327K, NRAS:p.Q61K, PCDH15:p.R1552I, PIK3CA:p.N345K, PIK3CA:p.E545K, POLE:p.S459F, PPP2R2B:p.P326L, SMAD4:p.R361H, TP53:p.R248W, ZFP2:p.R150I, and ZNF563:p.K26N.

57. The pharmaceutical composition of any of paragraphs 30-36, wherein:
(a) the population of subjects is suffering from SKCM; and
(b) the at least one tumor-specific mutation comprises any combination of mutations selected from the group consisting of BRAF:p.V600E, NRAS:p.Q61R, NRAS:p.Q61K, HSD17B7P2:p.N175S, BRAF:p.V600K, DISP1:p.G732L, IDH1:p.R132C, NRAS:p.Q61L, MUC16:p.P5119S, RAC1:p.P29S, WASH3P:p.G175S, AGAP9:p.M248V, C15orf23:p.S24F, DNAH5:p.D3236N, SPTLC3:p.R97K, TMC5:p.R276C, CFB:p.R314M, FRG1B:p.A50P, INMT:p.S212F, LOC649330:p.G93E, MAP2K1:p.P124S, RGS7:p.R44C, STK19:p.D89N, ADAM30:p.G97L, ARL16:p.G6R, ARMC4:p.E22K, BRAF:p.K601E, CAPN13:p.P405S, CD1C:p.R89C, CLCC1:p.P406Q, CNTN5:p.S379F, DNAH5:p.R742Q, EEF1B2:p.S43G, FRG1B:p.I59V, GABRG1:p.E205K, IARS2:p.R832C, IL32:p.D218fs, ISX:p.R86C, KLHDC7A:p.E635K, NAP1L4:p.P285Q, NBPF10:p.Q908E, OR2A5:p.S71L, OR4E2:p.R226Q, OR4M1:p.G41E, OR4M2:p.S268F, OR4N2:p.G41E, OR51B2:p.S163L, PCDHGC5:p.R293C, PCLO:p.R4133C, PHGDH:p.G173L, POTEG:p.D51N, PPP6C:p.R301C, PRAMEF11:p.C84S, PSG9:p.E404K, PTPRB:p.D1560N, RNF152:p.P95S, SPAG16:p.P488S, SPATA8:p.E18K, TAF1A:p.R172M, TCEB3C:p.E308K, THSD7B:p.E126K, TTN:p.E12129K, XIRP2:p.D2439N, and ZNF831:p.R1393Q.

58. The pharmaceutical composition of any of paragraphs 30-36, wherein:
(a) the population of subjects is suffering from UCEC; and
(b) the at least one tumor-specific mutation comprises any combination of mutations selected from the group consisting of RPL22:p.K15fs, PTEN:p.R130G, PTEN:p.R130Q, KRAS:p.G12D, KRAS:p.G12V, PIK3CA:p.H1047R, PIK3CA:p.R88Q, PIK3CA:p.E545K, PTEN:p.V317fs, FGFR2:p.S252W, PIK3CA:p.E542K, CTNNB1:p.S37F, POLE:p.P286R, PPP2R1A:p.P179R, CTNNB1:p.S37C, KRAS:p.G13D, CTNNB1:p.D32N, CTNNB1:p.S33F, CTNNB1:p.G34R, KIAA2026:p.R574C, LIMCH1:p.R806fs, PIK3CA:p.H1047L, ALPK2:p.K523fs, CTNNB1:p.S33C, FBXW7:p.R505C, HPD:p.R284fs, KRAS:p.G12A, PIK3CA:p.R93Q, POLE:p.V411L, TP53:p.R248W, ABCA11P:p.R385I, ABI1:p.K445N, ACSM2B:p.K195N, APOB:p.F3102L, ASCC3:p.R136Q, C12orf4:p.R335Q, CCDC132:p.R838C, CHD4:p.R975H, CSDE1:p.R220C, CTNNB1:p.D32Y, CTNNB1:p.S33Y, CTNNB1:p.T41I, EXOC1:p.R588C, FBXW7:p.R465H, FGFR2:p.N549K, FUBP1:p.R430C, GEN1:p.S509L, IK:p.E90fs, KIF20B:p.E54K, MAX:p.H28R, MBOAT2:p.R43Q, METTL14:p.R298P, MFGE8:p.D170N, MS4A8B:p.S3L, NSMCE1:p.D244N, OXR1:p.E122K, PCDH19:p.E530K, PIK3CA:p.R108H, PIK3CA:p.N345K, PIK3CA:p.C420R, PIK3CA:p.Q546P, PIK3CA:p.Q546R, PTEN:p.R130L, RBL2:p.E127K, RXFP1:p.S223Y, SF3B1:p.R957Q, SLC20A1:p.P328fs, SOX17:p.S403I, TNS1:p.Q659del, TP53:p.R273H, TP53:p.R273C, TP53:p.R248Q, TTN:p.D16823N, TXNL1:p.R234C, ZFHX3:p.R1893fs, ZNF180:p.R625I, ZNF257:p.R392I, ZNF354B:p.D609N, ZNF43:p.R280C, ZNF709:p.R468L ZNF765:p.S254L, ABCA5:p.R1476Q, ACVR1:p.R206H, ADAD1:p.S11L, ADAM9:p.R256Q, ADD3:p.E570K, ADGB:p.S1124L, AGXT2:p.R502C, AMBN:p.S225Y, ANKDD1A:p.R24H, ARHGEF33:p.R46I, ATP10B:p.L1304I, ATP2C1:p.E724K, ATP9A:p.R290Q, ATR:p.R1814fs, AVL9:p.F34L, BMPER:p.R241Q, BTN3A2:p.E153K, C14orf118:p.R279I, C14orf166B:p.F230L, C3orf23:p.R217C, C3orf62:p.R185Q, CACNA1C:p.S710L, CAGE1:p.E539K, CARD10:p.KE272del, CCDC144A:p.S1264L, CCDC168:p.D5020Y, CCDC36:p.R209I, CD55:p.E156K, CEP44:p.S253L, CIITA:p.E728K, CREBBP:p.P2094L, CTNNB1:p.S37A, CTTNBP2:p.S420L, DCT:p.R532Q, DIAPH2:p.E121K, DLG2:p.S624L, DNAH10:p.R1888Q, DNAH14:p.R1367C, DNAH7:p.R2961Q, DNAH8:p.R1347H, DNAJC13:p.E1248K, DNMT1:p.E51K, DST:p.S767Y, DYNC2H1:p.E883D, EMR1:p.R631Q, EPHX4:p.R282Q, ERCC6L2:p.L445I, F10:p.E117K, FAM155B:p.E158K, FAM83B:p.R206Q, FARP1:p.S383L, FAT3:p.A4159T, FBXW7:p.R689W, FBXW7:p.R465C, FBXW7:p.G423V, FN1:p.R290C, FZD6:p.R416Q, GABRA3:p.R73H, GABRA4:p.R460Q, GALNTL2:p.E395K, GFAP:p.A233T, GGA2:p.A63V, GIGYF2:p.R227H, GNPTAB:p.R1189Q, GPR112:p.S1283Y, GPR98:p.R4142W, GRIA3:p.S646Y, GRM6:p.E363D, HMCN1:p.S133Y, HSPA4L:p.R483C, HTR2A:p.S219L, INTS7:p.R940C, INTS7:p.R106I, ITM2C:p.E167K, JAKMIP2:p.R283I, KCND3:p.S438L, KCNS2:p.D211N, KDM1B:p.F361L, KIAA0556:p.L330I, KIAA1147:p.A149V, KIF23:p.R150Q, KIF27:p.K925N, KIF9:p.R594Q, KLHL13:p.E213K, KLHL28:p.E33K, LIN9:p.R183W, LRBA:p.E2103K, LRP2:p.R2432I, MAGI2:p.L450M, MC5R:p.A109T, MEGF10:p.S1053L, MKI67:p.T1664fs, MKLN1:p.F485L, MMRN1:p.F917L, MSH4:p.E730K, MTOR:p.S2215Y, MUC7:p.S336L, MYBPC2:p.R646H, N4BP2L2:p.R506C, NAPSA:p.R121Q, NCOA7:p.E369D, NCR1:p.R258W, NEK11:p.R374Q, NHEJ1:p.R109Q, NNMT:p.E233K, NOTCH4:p.15_16LL>L, NPY1R:p.A371T, NRAS:p.Q61R, OGDHL:p.R57C, OMA1:p.R445Q, OPRM1:p.R462C, OR4C12:p.F248L, OR5AK2:p.K89N, OSBPL6:p.R577Q, PCDHAC2:p.K138N, PCDHB12:p.R289C, PCDHGC5:p.A70T, PIK3CA:p.R38H, PIK3CA:p.E39K, PIK3CA:p.E110del, PIK3CA:p.K111E, PIK3CA:p.Q546K, PIK3CA:p.M1043V, PIK3CA:p.M1043I, PLA2G3:p.R201Q, PLXNA1:p.E1295K, PON1:p.R306Q, POTEE:p.R303I, POTEF:p.K674N, PPP2R1A:p.S256F, PPP2R3B:p.F310L, PRAM1:p.A268T, PREX1:p.E1246K, PRKCQ:p.A324V, PTEN:p.R130P, PVRL4:p.A358T, RAI2:p.S385Y, RBM39:p.T353I, RELN:p.F2722L, RFPL1:p.R148Q, ROBO2:

p.D1018N, ROS1:p.R245I, RPS6KA6:p.S394Y, RSBN1:p.E572K, RYR1:p.A2576T, SACS:p.R2906Q, SCAPER:p.R366Q, SELP:p.R429W, SENP7:p.S673Y, SEPHS1:p.E13K, SFRP4:p.R232Q, SGK1:p.K367del, SIX1:p.E191K, SLC10A7:p.S261L, SLC12A2: p.R828Q, SLC6A4:p.R495Q, SLC7A2:p.R322W, SMCR8:p.E175K, SOS1:p.N233Y, SPOP:p.E50K, STRN3:p.K218N, STXBP6:p.D92N, SULT1E1: p.R77Q, SUN3:p.L124I, SUSD1:p.R343C, SYNM: p.R516Q, TAF1:p.R843W, TDRD3:p.R322Q, THADA:p.S1941L, TLN2:p.S208L, TMEM161B: p.R315Q, TMPRSS3:p.R16Q, TP53:p.Y220C, TPTE: p.S423L, TRANK1:p.E846K, TRPC5:p.S490L, TRPM3:p.R429W, TSSK1B:p.E301K, TTLL7: p.R751H, TTN:p.S20317L, TTN:p.E6404K, TTN: p.R4434Q, TTN:p.R2506Q, UGT8:p.E102K, USF1: p.R52Q, USP16:p.R455Q, USP25:p.R873H, USP33: p.R36Q, VPRBP:p.R802Q, VPS3B:p.R692Q, WDR65:p.F110C, YTHDC2:p.E185K, ZFYVE1: p.R266Q, ZKSCAN1:p.R541fs, ZNF117:p.R157I, ZNF180:p.R569I, ZNF195:p.R59Q, ZNF254: p.K179N, ZNF263:p.R510I, ZNF333:p.R554Q, ZNF354B:p.R402I, ZNF442:p.R309Q, ZNF454: p.R376I, ZNF485:p.R374I, ZNF488:p.R206Q, ZNF559:p.E284K, ZNF594:p.R287I, ZNF611: p.R390I, ZNF645:p.R154C, ZNF649:p.R338Q, ZNF649:p.R198I, ZNF674:p.R405I, ZNF675:p.R220I, ZNF678:p.R564I, ZNF732:p.R354I, ZNF780A: p.R466Q, ZNF823:p.R547I, ZNF836:p.R854I, ZNF836:p.R630I, ZNF841:p.R757I, and ZNF98: p.R370I.

59. The pharmaceutical composition of any of paragraphs 30-36, wherein:
    (a) the population of subjects is suffering from ACC; and
    (b) the at least one tumor-specific mutation comprises any combination of mutations selected from the group consisting of ZFPM1:p.EPL444del, GARS:p.P42A, ZNF517:p.V349A, LRIG1:p.L24V, CCDC102A: p.R96W, OPRD1:p.C27F, SOWAHA:p.R124P, LACTB:p.M5L, TOR3A:p.F13L, ZFPM1:p.E444fs, ZNF787:p.D367del, LRIG1:p.L26V, IRX3:p.L422P, TRIOBP:p.H1300R, TUBA1C:p.L146F, ZFPM1: p.P445fs, ZFPM1:p.446_447LA>P, TPO:p.S398T, USP42:p.R779P, ERCC2:p.D312N, GLTPD2: p.D209E, OTOP1:p.LLW 104del, RINL:p.P402L, AMDHD1:p.S3G, ASPDH:p.Q266R, KCNK17: p.S21G, TMEM247:p.Q128E, MUC5B:p.D682G, OBSCN:p.R4516W, FAM184B:p.R784W, SEMA5B: p.V840D, ZNF598:p.E25G, ADAD2:p.G44E, C1orf106:p.R538C, ZAR1:p.Q42H, PANK2:p.G126A, PODXL:p.28_30PSP>P, SALL3:p.L593V, THEM4: p.L17R, C2orf81:p.T315P, CLDN23:p.V210M, FAM109A:p.GGG156del, FPGS:p.122V, HHIPL1: p.V692A, MUC5B:p.M2869T, PLEC:p.R1386Q, SYT8:p.R373W, TAF5:p.S130A, TMEM189-UBE2V1:p.N6D, UQCRFS1:p.S6A, B3GNT6: p.L316fs, CCDC105:p.P499T, CLIC6:p.Q298E, IDUA:p.T374P, NOTCH2:p.C19W, RGS9BP:p.A96S, RREB1:p.G783V, SP8:p.G165del, WDR34:p.W60G, C19orf10:p.G12R, CELSR2:p.16_17insP, FAM75C1: p.71_71H>HLVSQRH, GPRIN2:p.R446H, KBTBD13:p.A81V, OGFR:p.S557T, PODXL: p.30_30P>PSP, BHLHE22:p.L62Q, C4orf32:p.G32E, C5orf65:p.Q245R, KNDC1:p.V806D, KRTAP10-6: p.49_49P>PSCCAP, LRP11:p.P92R, MAP1S: p.S411C, NOL9:p.S58A, RASIP1:p.R601C, RGMB: p.S63R, SARM1:p.R23P, TSC22D2:p.A419T, ZNF628:p.T230A, ZNF814:p.A337V, AATK: p.A541T, BTBD11:p.G265A, CRIPAK:p.C143R, KCTD3:p.F9V, KRT8:p.S59A, MUC5B:p.S681G, NCOR2:p.1846_1847insSSG, OGFR:p.E556K, APOE:p.C130R, C10orf95:p.A85S, C13orf33: p.R59G, CRIPAK:p.C174R, FAM18B2:p.C51Y, GLI3: p.P998L, GLTSCR2:p.Q389R, HECTD2:p.P19A, IRF2BPL:p.123_125QQQ>Q, MEX3C: p.179_182AAAA>A, NEFH:p.EE658del, RNF49: p.S9G, RNF222:p.A133T, SEZ6L2:p.R74P, TNIP2: p.R73G, ARRDC4:p.T79A, B3GNT6:p.P330fs, BAG1:p.G45R, C22orf26:p.P28L, CHDH:p.E40A, COQ2:p.V66L, CTGF:p.H83D, DLEU7:p.A83V, EPPK1:p.D2378H, FAM86C1:p.R30P, FZD1: p.93_94insP, GPRIN2:p.V241M, GPX1: p.11_13AAA>A, HES3:p.P96T, JMJD4:p.A11V, KANK3:p.R359H, LPPR2:p.A186S, NEFH: p.665_666insEE, NOM 1:p.R24G, RNF39:p.G263C, SCRT1:p.S133A, SNED1:p.L1228P, TTLL11: p.122_123insKA, ZCCHC3:p.A159del, ZNF219: p.QP233del, ASB16:p.T249A, ASB2:p.H515P, ATP9B:p.S39G, AVL9:p.G7fs, C17orf96:p.L63V, C19orf29:p.A499V, CRB2:p.T1110M, CRIPAK: p.P173R, CRIPAK:p.I190L, CSGALNACT2:p.L362F, CTBS:p.LAL31del, CTNNB1:p.S45P, DMRT1: p.S45T, DOK7:p.G461D, FBRSL1:p.A836V, FEZ2: p.P50L, FRG1:p.S169N, HSD17B1:p.G313S, IBA57: p.S130R, KIF1A:p.E917D, KRTAP9-1: p.160_160Q>QPSCGSSCCQ, LURAP1L: p.55_56insGGG, NMU:p.A19E, NMU:p.A18E, NOXA1:p.D6E, NPTX1:p.G100D, PLIN5:p.R306W, TBP:p.95_96insQ, TMEM200C:p.S498G, TNXB: p.V706fs, VARS:p.P51S, ZC3H12D:p.P405S, and ZZEF1:p.V30A.

60. The pharmaceutical composition of any of paragraphs 30-36, wherein:
    (a) the population of subjects is suffering from CESC; and
    (b) the at least one tumor-specific mutation comprises any combination of mutations selected from the group consisting of PIK3CA:p.E545K, PIK3CA:p.E542K, MAPK1:p.E322K, EP300:p.D1399N, ERBB2: p.S310F, ERBB3:p.V104M, KRAS:p.G12D, ANKRD12:p.E721Q, ANKRD36:p.M1144T, MICA: p.G318fs, PIK3CA:p.E726K, PTEN:p.R130Q, ABCD1:p.S606P, ACTL7B:p.E211K, ADAM21: p.F129C, ADAMTS12:p.P1053A, AKT1:p.E17K, ANKLE1:p.V643L, ANO3:p.M956I, AOAH:p.R326T, APOD:p.S115L, ASCC1:p.H207Y, ATM:p.S800F, AURKA:p.S387L, BAG5:p.M286I, C12orf43:p.E28Q, C16orf3:p.G65S, C3orf70:p.S6L, C4orf21:p.E800Q, CALB2:p.K60N, CALCB:p.R81T, CCDC152: p.E153Q, CCDC53:p.R58C, CDC27:p.P242S, CFHR5:p.R441H, CLOCK:p.L123fs, CMYA5: p.E2733K, CNTRL:p.P185S, CSHL1:p.R117Q, CSMD3:p.H952Y, CTNNB1:p.D32G, CTSH: p.E254Q, DHPS:p.F49L, DMPK:p.R44H, DNAH14: p.F622fs, DNAH3:p.E3367Q, DNAH8:p.E587D, DNASE1L1:p.D212N, ECE2:p.D254N, FAM71B: p.H445D, FAM73A:p.G23V, FAS:p.E261K, FBXW7: p.R505G, FBXW7:p.R465C, FEZF2:p.E82K, FKBPL: p.E161Q, FMNL1:p.E927Q, GPATCH3:p.E275Q, GPR142:p.P304T, GPRIN2:p.T100P, GRAMD2: p.II23M, HERC2:p.S329F, HGF:p.G229A, HIF3A: p.A72T, HIST1H1B:p.K188N, HIST1H2AL:p.R30P, HIST2H2AC:p.R30P, HLA-C:p.N104K, HLA-DPB1: p.G114fs, HRNR:p.G2539S, INVS:p.R799K, JPH3: p.Q433H, JUP:p.S627L, KIAA1211:p.R308fs, KIAA1211:p.E309fs, KLK2:p.E161K, KRAS: p.G13D, KRAS:p.G12V, LIN9:p.E231K, LOC151174: p.P90S, LRRC37A3:p.A406D, LRTM2:p.L176V, MEPE:p.S30T, MUC12:p.R2634C, MUC4:p.S2936L, MYOM2:p.D988N, NFE2L2:p.D29H, NOTCH2: p.R2298W, NPIPL1:p.P250L, NR5A2:p.E80K, NYAP2:p.R197Q, OBSL1:p.E1642K, OR13C2:p.L9V, OSBP:p.Q721H, PAOX:p.H107Y, PDILT:p.E500K, PIAS3:p.D460N, PLEKHO2:p.E351Q, PNRC1: p.R73C, PPP4R1:p.L597F, PREP:p.F469L, PRKDC: p.Q3568E, PSME3:p.R231W, RANBP6:p.R915W, RCAN2:p.D440N, RNPC3:p.E116fs, SDHAP1: p.H66Y, SDHAP2:p.S37fs, SERPINA3:p.K158N, SERPINA4:p.R98C, SF1:p.R255W, SGSM1:p.E818K, SIM1:p.V213M, SLC10A4:p.F281L, SLC25A5: p.I79F, SLC35G2:p.K62fs, SLC4A9:p.R617C, SLCO2A1:p.M479I, SND1:p.Q38E, SPATA17: p.R72K, SRSF12:p.S150C, TADA2B:p.E67K, TCTEX1D2:p.S74L, TEDDM1:p.M166I, TEX15: p.E1652Q, TMC2:p.E92D, TMEM131:p.E1319Q, TNKS2:p.T619fs, TNS1:p.Q659del, TP53:p.E285K, TRAF3:p.S9F, TRIM61:p.K98N, TRPM1:p.M996I, TUFT1:p.L101F, U2AF1:p.S34F, UNC93B1: p.V498M, USP4:p.L259V, VCAN:p.S1308C, WDR17: p.P278S, ZBED4:p.S385L, ZEB2:p.E1094K, ZFYVE9:p.M1147I, ZNF16:p.R452W, ZNF677: p.R131T, and ZSWIM4:p.E407K.

61. The pharmaceutical composition of any of paragraphs 30-36, wherein:
   (a) the population of subjects is suffering from CRC; and
   (b) the at least one tumor-specific mutation comprises any combination of mutations selected from the group consisting of KRAS:p.G12D, KRAS:p.G12V, BRAF: p.V600E, KRAS:p.G13D, TP53:p.R175H, PIK3CA: p.E545K, FBXW7:p.R465H, KRAS:p.A146T, PIK3CA:p.H1047R, TP53:p.R248W, CDC27: p.D555E, SMAD4:p.R361H, TP53:p.R273H, KRAS: p.G12C, NRAS:p.Q61K, ERBB2:p.V842I, ERBB3: p.V104M, FBXW7:p.R465C, PIK3CA:p.R88Q, PIK3CA:p.E542K, TP53:p.R273C, TP53:p.G245S, AXIN2:p.G665fs, C16orf45:p.T106N, C20orf26: p.R1088Q, DNMT1:p.E432K, FBXW7:p.R505C, HLCS:p.E362K, HPSE2:p.K58N, KIF14:p.R598Q, KIF18A:p.R17C, KIF20B:p.E991K, KLHL5: p.R326K, KLK2:p.P57L, KRAS:p.G12A, KRAS: p.G12S, LPHN3:p.R1183Q, LRP6:p.R675Q, MYH8: p.R1048Q, NRAP:p.E327K, NRAS:p.G12C, PIK3CA: p.N345K, POSTN:p.R508C, PPP2R1A:p.R183W, PTEN:p.R130Q, RAF1:p.S257L, SDK1:p.T1181M, SGSM1:p.F1117L, TCF7L2:p.R482fs, TP53: p.R282W, TRIM23:p.R289Q, UGT8:p.E102K, ZNF491:p.R343Q, A2M:p.R732Q, AADACL4: p.A266T, ABCA8:p.E1158K, ABCA8:p.R842Q, ABCA8:p.A696T, ABCB8:p.R345H, ACACA: p.R1731C, ACADM:p.F48C, ACOT9:p.R50Q, ACPP: p.R105Q, ACTL7B:p.R354H, ACTL9:p.R331H, ACVR1:p.S290L, ADAM30:p.S314Y, ADAM32: p.R559Q, ADAMTS16:p.D817N, ADAMTS4: p.R156W, ADCY5:p.R661H, AGMAT:p.V313M, AGPAT4:p.A212T, AKAP12:p.E1282K, AKAP9: p.L3482I, ALB:p.S294L, ALDH1L1:p.A870T, ALG2: p.S302Y, AMOTL1:p.R676Q, AMPD1:p.K502N, AMPH:p.R292W, ANKRD6:p.R479C, APBA1: p.K730N, APBA1:p.E624K, APC:p.E847fs, APC: p.F1354fs, APC:p.M1413fs, APOB:p.R3136C, APOB: p.A43V, APPL1:p.R668W, AQPEP:p.A309T, ARF4: p.R149H, ARFGEF1:p.D1632N, ARHGAP32: p.E1253K, ARHGAP36:p.R128C, ARHGAP36: p.A147V, ARHGAP5:p.D890fs, ARNTL:p.T395M, ARPP21:p.R338H, ARSG:p.V131I, ASCC3: p.R1197Q, ATP10D:p.R311H, ATP6V0A4:p.R191Q, ATP9B:p.R265Q, AXDND1:p.E930D, AXIN2: p.W663fs, B2M:p.L13fs, B3GALNT1:p.R145Q, BACH 1:p.R538Q, BAG5:p.D439N, BBOX1: p.F176V, BCL2L11:p.R91Q, BCL7A:p.T52M, BCLAF1:p.R37fs, BEND5:p.R198C, BICD2: p.R162H, BLVRA:p.S44L, BMP3:p.R344W, BNC2: p.R512W, BRPF1:p.R66C, BRWD3:p.R787C, BTBD7:p.S436L, BUB1B:p.F996L, BZRAP1: p.V1627I, C11orf330:p.R111C, C14orf101:p.E295K, C14orf102:p.D115N, C14orf105:p.R100I, C15orf2: p.V488I, C15orf33:p.D340N, C16orf87:p.R151I, C1RL:p.L351fs, C22orf40:p.P32fs, C3orf39:p.R333W, C5orf30:p.D4N, C5orf4:p.R114Q, C6orf170:p.K724T, C7orf63:p.A10T, CACHD1:p.S720Y, CACNA1A: p.T665M, CACNA2D3:p.A332T, CACNB2:p.R608H, CACNG3:p.V134I, CACNG3:p.A138V, CACNG5: p.G121R, CADM1:p.S190L, CADPS:p.A1073T, CAPRIN2:p.E13K, CARD11:p.R423Q, CASC1:p.R54Q, CASP14:p.RSW, CBFB:p.E152K, CC2D2A: p.R1284C, CCDC18:p.K615N, CCDC60:p.R230H, CCDC81:p.R259I, CCDC88C:p.P1851fs, CCKBR: p.V236M, CD101:p.D283Y, CD101:p.R594Q, CD180: p.N228T, CDC14B:p.R375C, CDCA7L:p.P405fs, CDH10:p.E349K, CDH12:p.D674N, CDH20: p.A134V, CDH23:p.F177L, CDH2:p.D547Y, CDH9: p.F523L, CDK16:p.R108C, CEACAM5:p.L640I, CEP152:p.E21K, CERS3:p.E95D, CHD4:p.R975H, CHD5:p.A801V, CIZ1:p.V668A, CLEC18A:p.R423H, CLTCL1:p.R481W, CMAS:p.R110Q, CNRIP1: p.R102W, COBLL1:p.K732N, COL4A1:p.R1082I, COL17A1:p.P1004L, COL4A6:p.L550I, COL6A3: p.D2792N, COPB1:p.R425C, CORO2A:p.*526R, COX15:p.L86I, CSMD1:p.S781Y, CTCFL:p.E423K, CTDNEP1:p.E126K, CTTNBP2:p.R164C, CYP4B1: p.E434D, DACH2:p.R539C, DBC1:p.V216I, DBF4B: p.S254Y, DCHS2:p.F2149L, DCLK2:p.S549Y, DDI1: p.R275Q, DENND4A:p.P357H, DENND4C: p.R1081Q, DHTKD1:p.R410Q, DISP1:p.R763C, DKK2:p.R230H, DKK4:p.R203Q, DLC1:p.A350V, DLC1:p.E222D, DMD:p.R3195H, DNAH5:p.R982H, DNAH5:p.R224Q, DNAH9:p.D1547N, DNAJC24: p.E61K, DNM1:p.A251T, DNMT1:p.E1531Q, DNMT3B:p.R92W, DOCK10:p.A1830V, DOCK1: p.E864K, DOCK2:p.G170R, DOCK3:p.R1183C, DOCK5:p.E177K, DOK5:p.R274W, DPP8:p.G165R, DPY19L1:p.F378L, DUOX2:p.F880L, DVL2: p.A601fs, EBAG9:p.E187K, EBF3:p.G255fs, EDNRB:p.L450R, EGR2:p.R390H, EHD3:p.E44K, EIF2C1:p.R139Q, ELF3:p.F305fs, ELMOD2: p.T141M, EMR2:p.S75L, ENAM:p.R373H, ENOX2: p.R356W, ENTPD7:p.E327K, EPG5:p.D369N, EPHB2:p.R392H, ERCC6:p.V780I, ERCC6L: p.R505Q, ERRFI1:p.A421T, ESCO1:p.R300Q, ETV6: p.R369W, F8:p.S2269Y, FAM123B:p.F173fs, FAM135B:p.R884H, FAM169B:p.K165N, FAM170A: p.E56K, FAM171B:p.D459N, FAM181A:p.R109H, FAM5B:p.R402C, FBXO11:p.A432V, FBXW7: p.R689W, FBXW7:p.S582L, FBXW7:p.R14Q, FGF14:p.A236V, FHDC1:p.R254W, FHOD3: p.A225T, FHOD3:p.E813K, FMO3:p.F510L, FNDC1: p.R652H, FOXK1:p.R354W, FOXN3:p.P96fs, FPGT-TNNI3K:p.R455H, FZD3:p.D367N, GABRA4: p.R460Q, GABRA5:p.S126N, GABRB3:p.D500N, GALNTL5:p.R262I, GJA1:p.R362Q, GLRA3: p.L454I, GLRA3:p.F132L, GOLGA4:p.Q1536H, GP2: p.S41L, GPC6:p.A214T, GPLD1:p.R717Q, GPR125: p.R113Q, GPR156:p.F754L, GPR158:p.D566N, GPR21:p.R216H, GPR61:p.A62T, GPR98:p.R4142W, GPRC5A:p.V30I, GRAP2:p.E69D, GRIA1:p.R218C, GRIA2:p.R845Q, GRM7:p.R679Q, GTF3A:p.K306N, HAO1:p.R172C, HARS2:p.R168H, HBB:p.F42L, HCN4:p.R525H, HDAC5:p.A1044T, HGF:p.S467Y, HIPK4:p.R280H, HLA-DMA:p.E84K, HMG20A: p.E248D, HPS3:p.S468L, HRSP12:p.R120Q, HS3ST1:p.E287K, HTR3B:p.R236C, HTR5A: p.R152C, HTT:p.D1548N, HYDIN:p.R1187C, HYDIN:p.R939Q, HYDIN:p.R451Q, HYOU1: p.R158C, IFT172:p.A944V, IGJ:p.R77Q, IL17RA: p.Q803fs, IL1RAPL2:p.T647M, IL3:p.A90T, IL5RA: p.L47I, INPP5D:p.R523Q, INPP5K:p.R263C, IRAK3: p.R267Q, IREB2:p.R419Q, ITGA4:p.T673M, ITGA4: p.F900L, ITIH5:p.A912T, ITK:p.E196K, JAG1: p.A462T, JAK1:p.V310I, KAL1:p.V303L KBTBD8: p.V549I, KCNA3:p.A415V, KCND3:p.S438L, KCNMB4:p.F209L, KCTD20:p.L314fs, KDELC1: p.L447I, KIAA0528:p.R181Q, KIAA0556:p.R1082W, KIAA1109:p.S4937Y, KIAA1804:p.V474M, KIAA1804:p.R477W, KLF16B:p.R145Q, KIF26B: p.A1114V, KPNA4:p.R29Q, KRAS:p.K117N, KRAS: p.Q61L, KRAS:p.Q61K, KRT6B:p.L197P, L1CAM: p.T186M, LALBA:p.A41 T, LAMA4:p.A558V, LBX1: p.R176W, LPAR4:p.R145Q, LRP1B:p.K2623N, LRP2:p.R3043C, LRP2:p.S737L, LRRC18:p.R218W, LRRC3J:p.K23T, LRRC7:p.R1389H, LZTS2: p.P100fs, MACF1:p.S292L, MACF1:p.F722L, MAEL:p.R345C, MAGEE1:p.V380M, MAGI1: p.R1198C, MAP1B:p.E2046D, MAP2:p.K530N, M4AP2K4:p.R287H, MAP3K4:p.R275Q, M4AP7D2: p.R487C, MALPK8IP1:p.L217fs, MBOAT2:p.R43Q, MCF2L2:p.R926Q, MECOM:p.R969C, METTL16: p.R200Q, METTL21A:p.R174Q, METTL6:p.F56L, MFF:p.R162C, MFSD5:p.R280Q, MIA3:p.Q356H, MMAA:p.R326C, MORC1:p.D113Y, MORC2: p.R740H, MPDZ:p.L804I, MR1:p.S46L, MRPL47: p.L234I, MS4A8B:p.S3L, MSH4:p.K464N, MSH6: p.T1085fs, MSH6:p.R1095H, MUC16:p.R8606H, MYH13:p.D311N, MYH7:p.R1689C, MYO1D: p.E246K, MYO3A:p.N525H, MYO6:p.D1180N, MYO9A:p.R2179Q, MYO9A:p.R167Q, MYOZ2: p.E251K, MYT1:p.E226K, NAA25:p.S807Y, NCAM1:p.R474W, NCOA4:p.R562Q, NEB: p.D5434N, NEB:p.L1591I, NEB:p.E1214K, NEDD9: p.A798T, NEDD9:p.A316T, NEK1:p.R608C, NFASC: p.V256I, NINL:p.R1366C, NLRC4:p.D593N, NLRC4: p.E409K, NLRP4:p.V229I, NLRP5:p.R392H, NME9: p.E75K, NOLC1:p.T428M, NPC1:p.E451K, NPSR1: p.R235Q, NRAS:p.Q61L, NRAS:p.G13R, NRAS: p.G12D, NRG2:p.T246M, NTN4:p.E59K, NUB1: p.R373Q, NUDT15:p.S83 Y, NUF2:p.S340L, NUP88: p.A302V, ODZ1:p.R2556W, OGDHL:p.A427T, OGFRL1:p.E427K, OLFM4:p.K132N, OPRM1: p.R353H, OR10A3:p.S93Y, OR2M3:p.R235H, OR52W1:p.R133C, OR5AU1:p.R312H, OR5B17: p.R163H, OR8S1:p.A99V, OSTN:p.R115Q, OTOL1: p.V431I, OTUD3:p.R277I, PAN3:p.S580N, PANK3: p.R260I, PAX3:p.T424M, PCBP1:p.L102Q, PCDH10: p.V477M, PCDH15:p.R1552I, PCDHAC2:p.A519I, PCDHAC2:p.E190K, PCDHAC2:p.A266T, PCDHAC2:p.A156V, PCDHAC2:p.E271K, PCDHAC2: p.A736V, PCDHB5:p.D51Y, PCDHB8:p.D235N, PCDHGC5:p.S289L, PCDHGC5:p.V662M, PCNXL2: p.R135Q, PCOLCE2:p.A348V, PCOLCE2:p.R87H, PDE4B:p.S417L, PGAM1:p.R240H, PHF3:p.R1410I, PIAS2:p.S519L, PIGR:p.A580T, PIK3CA:p.D350G, PIK3CA:p.E545A, PIK3CA:p.E545G, PIK3CA: p.Q546K, PIP4K2C:p.R204H, PKHD1L:p.F1856L, PLA2G4A:p.E443K, PLCG2:p.E544K, PLCG2: p.D973N, PLEKHA6:p.V328fs, PLEKHG4B: p.E384K, PLK1:p.D233G, PLOD3:p.R297fs, PLSCR3:p.E77K, PLXNC1:p.S462L, PLXNC1: p.R819C, POLA1:p.E603D, POLE:p.S459F, POLE: p.V411L, POLQ:p.R860Q, PPP2R2B:p.P326L, PPP2R5C:p.S259Y, PRAMEF4:p.R248H, PREX1: p.V731I, PRKAA2:p.R407Q, PRKAR2B:p.S309L, PRKCI:p.R480C, PRKRA:p.K122N, PSG8:p.R397C, PSG8:p.R320C, PSMD12:p.R201Q, PTPDC1: p.R430W, PTPN12:p.R765Q, PTPN13:p.S887L, PTPRD:p.L053I, PTPRU:p.D1434N, PXDN:p.P856fs, PXDNL:p.T1312M, QRSL1:p.S226L, RAB7L1: p.R79W, RALGAPA1:p.R398C, RANBP2:p.R1231C, RBBP7:p.E313K, RBBP7:p.E274K, RBFOX2: p.A340T, RBMXL1:p.R331Q, RHOBTB1:p.T464M, RIMS2:p.R599Q, RIN3:p.S708L, RLBP1:p.D281N, RLBP1:p.A72V, RNASET2:p.A127V, RNF113B: p.A172V, RNF150:p.R236Q, RNF150:p.S208L, RNF43:p.S216L, ROR2:p.D672N, RPL6:p.F193C, RPS6KA5:p.E166K, RSPO2:p.R28C, RUVBL1: p.E431K, RUVBL1:p.R117C, RWDD2B:p.R254H, RXFP3:p.R13C, RYR3:p.R2705Q, SAGE1:p.R229C, SCFD2:p.R545W, SCML4:p.R194Q, SCN10A: p.T1570M, SCN11A:p.A1688T, SCN11A:p.V1289I, SCN11A:p.V566I, SCUBE2:p.V342M, SEMA3A: p.D81N, SEMA4D:p.R252Q, SEPHS1:p.R371Q, SEZ6L:p.S207L, SFPQ:p.R611Q, SFSWAP:p.S617Y, SGCG:p.A220V, SGCZ:p.I41M, SH3TC2:p.R89C, SIGLEC11:p.S363F, SIPA1L1:p.R1063Q, SIPA1L1: p.S1227Y, SLC12A1:p.S292L, SLC22A15:p.S201L, SLC24A2:p.A134V, SLC25A40:p.R96Q, SLC2A7: p.A65T, SLC30A9:p.R194H, SLC33A1:p.S542L, SLC35F3:p.A280T, SLC39A7:p.R382C, SLC43A1: p.P133L, SLC43A3:p.R216H, SLC44A5:p.R185H, SLC6A2:p.A562T, SLC8A1:p.R431H, SLFN12L: p.F232fs, SLITRK1:p.R52H, SLITRK3:p.S298L, SMAD2:p.R321Q, SMARCA4:p.R38 Q, SOCS5: p.S464L, SORBS1:p.V1156M, SORBS1:p.F570L, SORCS2:p.R320W, SOX6:p.R719W, SPATA22: p.S150L, SPEG:p.A944V, SPTB:p.R86C, SPTBN4: p.A1993V, STIM2:p.R572Q, STT3B:p.D583Y, SULT1C4:p.R85Q, SUN3:p.E128K, SUPT6H: p.A957T, SYNE1:p.I1249L, SYNE1:p.R170W, SYNE2:p.K3103N, SYNGR4:p.R169Q, SYT7: p.T349M, TANK:p.S380L, TAS1R2:p.R270C, TAS2R:p.F183L, TCF7L2:p.R488C, TDRD10: p.S322L, TECTB:p.L29I, TEKT5:p.R401H, TGFBR1: p.S241L, THAP5:p.S287Y, THSD7B:p.R90H, TLL1: p.T153M, TLL2:p.S872L, TM9SF2:p.R91H, TMCC3: p.R110H, TMEM132A:p.R481C, TMEM132D: p.R578W, TMEM55A:p.R189Q, TMEM74:p.R125Q, TMPRSS11A:p.S288L, TNIP2:p.A139T, TOP2B: p.R656H, TOX:p.S354L, TP53:p.G244D, TP53: p.R175C, TPO:p.A826T, TPR:p.S2155L, TPTE2: p.R258Q, TPTE:p.S423L, TRAK1:p.D627N, TRAPPC11:p.R568Q, TRIM23:p.R396Q, TRIM44: p.D331N, TRIO:p.R661W, TRPA1:p.K54N, TRPC5: p.S490L, TRPM6:p.R995H, TRPM7:p.R1862C, TRPM7:p.R843Q, TRPS1:p.R1125W, TRPV5: p.R492H, TRRAP:p.R3515W, TSHZ1:p.R881M, TTC21A:p.S270Y, TTN:p.R22795C, TTN:p.R3193Q, TTN:p.R328H, TUBA3D:p.R243Q, TUFT1:p.A340T, TXNDC15:p.R343Q, UBE2NL:p.R86I, UBIAD1: p.A97T, UGT2A1:p.N97fs, USH2A:p.F2369L, USP11:p.A286T, USP25:p.R119Q, USP26:p.R861Q, USP29:p.F81L, USP31:p.D391N, USP40:p.S851L, UTP14A:p.V148I, VAV3:p.E685K, VCAN:p.R1125H, VPS13C:p.D1359Y, WBSCR17:p.R228C, WDR3: p.E841K, WDR52:p.A157T, XKR6:p.R268Q, XPOT: p.R541W, YTHDC1:p.R267Q, YTHDC2:p.E634K, ZBBX:p.R596I, ZBTB24:p.L607I, ZC3H13:p.R103Q, ZCWPW2:p.D144N, ZEB2:p.R156H, ZFHX4: p.E237D, ZFP14:p.R386C, ZFP28:p.R525I, ZFP2: p.R150I, ZFP3:p.R273I, ZFP90:p.R330Q, ZHX2: p.V790I, ZIC4:p.S305L, ZIM3:p.D352N, ZKSCAN4: p.R319Q, ZMYM4:p.R1446Q, ZNF117:p.R185I, ZNF167:p.R683I, ZNF180:p.R401I, ZNF19:p.R349I, ZNF205:p.R384C, ZNF236:p.S1480L, ZNF248: p.R568I, ZNF259:p.R174I, ZNF266:p.R512Q, ZNF266:p.R344Q, ZNF280B:p.E363K, ZNF283: p.R392Q, ZNF32:p.S62L, ZNF345:p.R82Q, ZNF345: p.R334I, ZNF350:p.R310Q, ZNF434:p.R306C, ZNF439:p.E239D, ZNF439:p.R262I, ZNF443: p.R301I, ZNF445:p.L682M, ZNF470:p.R641I, ZNF471:p.R282I, ZNF484:p.R138C, ZNF528: p.R279Q, ZNF563:p.K26N, ZNF573:p.R350I, ZNF583:p.R344I, ZNF585A:p.E638K, ZNF585A: p.E491D, ZNF625:p.R235Q, ZNF652:p.K327N, ZNF677:p.R451I, ZNF678:p.R368I, ZNF699:p.R41I, ZNF70:p.R244L ZNF770:p.S441P, ZNF774:p.R423Q, ZNF782:p.K247T, ZNF7:p.R337I, and ZNF831: p.E949D.

62. The pharmaceutical composition of any of paragraphs 30-36, wherein:
    (a) the population of subjects is suffering from DLBCL, and
    (b) the at least one tumor-specific mutation comprises any combination of mutations selected from the group consisting of EZH2:p.Y641F, MYD88:p.L273P, BCL2: p.G33R, CARD11:p.E626K, ADCY2:p.A87V, BCL2: p.N172S, BCL2:p.H20Q, BRAF:p.K601E, BTG1: p.L31F, CACNA1E:p.R1458C, CARD11:p.E93D, CD79B:p.Y197D, CD79B:p.Y197H, CREBBP: p.R1446H, GRID1:p.E622K, HIST1H1C:p.A65V, HIST1H1E:p.G133A, HIST1H3B:p.A48S, KRAS: p.G13D, MYD88:p.S251N, PABPC1:p.R94C, PIM1: p.L164F, PIM1:p.L184F, POU2F2:p.T239A, POU2F2: p.T239S, RELN:p.R2971Q, SLC25A48:p.A67T, STAT6:p.D468H, TNF:p.L47F, and TRAF7:p.R11H.

63. The pharmaceutical composition of any of paragraphs 30-36, wherein:
    (a) the population of subjects is suffering from KICH; and
    (b) the at least one tumor-specific mutation comprises any combination of mutations selected from the group consisting of ACR:p.W279C, AGRN: p.1284_1285VT>A, C7orf25:p.R384fs, CAMSAP1: p.T466fs, CBWD6:p.E102fs, DOCK8:p.L1111fs, EBPL:p.Q196P, EBPL:p.L89V, GFM1:p.A17fs, GOLGA6L6:p.D570E, ITGA5:p.A48D, LUZP2: p.S154fs, MTMR9:p.K193fs, MUC16:p.P10452fs, MUC4:p.S2832P, ODF2L:p.K407fs, RHBDD3: p.G34fs, RILPL1:p.S358R, TAS2R30:p.L236fs, TRRAP:p.A973S, UBR5:p.K2120fs, URGCP: p.G639fs, ZNF98:p.A222T, and ZSWIM6:p.Q610fs.

64. The pharmaceutical composition of any of paragraphs 30-36, wherein:
    (a) the population of subjects is suffering from KIRP; and
    (b) the at least one tumor-specific mutation comprises any combination of mutations selected from the group consisting of FAM18B2:p.C51Y, ZNF598:p.E25G, NEFH:p.E645K, EEF1B2:p.S43G, NEFH: p.AKSPEKEE652del, OBP2B:p.K61N, SKI:p.A62G, C14orf126:p.R6W, KRT8:p.S59A, ACSBG2:p.I250M, ASIC2:p.R46L, CSGALNACT2:p.L362F, FRG1B: p.A50P, IDUA:p.H33Q, KRTAP4-5:p.S74C, SCAF11: p.E926fs, SYN2:p.A34del, ZNF814:p.R322K, BMS1: p.E878D, JMY:p.P822T, KIF1A:p.E917D, KRTAP4-7: p.S57P, LAMA5:p.L2223R, LRP1:p.P1058T, MED16: p.H449Q, MUC2:p.T1488P, MUC5B:p.D682G, NACA2:p.R75K, NEFH:p.665_666insEE, OR2L8: p.S201fs, RGPD5:p.P1760A, RRN3:p.P1 S, RRN3: p.R9C, STAG3L2:p.L81fs, ZNF814:p.G320E, ACP6: p.V29G, AHNAK2:p.S2166F, AHNAK2:p.P1215S, AP1G1:p.1782fs, AQP2:p.N68T, BAIAP2L2: p.V396M, BMP6:p.Q118L, BST1:p.G36A, CDR1: p.V31A, CLDN7:p.S172A, CLIP 1:p.S1018fs, COL18A1:p.G884fs, CROCC:p.A355P, CTAGE15P: p.A364V, CUBN:p.I2816M, DMRT2:p.T106S, DPY19L1:p.V249L, DSPP:p.D1047N, EBPL: p.L189V, EIF4G1:p.E465del, EXOSC2:p.R11P, FAM216A:p.P36S, FCGR2A:p.V222G, FMOD: p.S331R, FOLR2:p.Q112R, FRG1B:p.L20P, GAGE2B:p.9_10insY, GDPD5:p.G593fs, GIMAP8: p.A544S, GLUD2:p.R300G, GLUD2:p.S496R, GPR135:p.Q5P, HOXD8:p.Q67H, IER5:p.R194G, IL25:p.C168fs, JSRP1:p.V92A, KRAS:p.G12D, KRTAP1-1:p.Y86C, KRTAP4-11:p.L161V, LTBP1: p.L163P, MAML2:p.Q591K, MAPK7:p.A501D, MEF2A:p.P99S, MET:p.H1094Y, MET:p.M1250T, MST1:p.N435fs, MUC2:p.T1582R, MUC2:p.T1722I, MUC4:p.A4222T, MUC4:p.T2335M, MUC4: p.P1138L, MUC5B:p.S1098A, MUC5B:p.S3431N, MYH7:p.A1487T, NBPF10:p.R39fs, NBPF10: p.Y638S, NEFH:p.654_654S>SPEKAKS, PARG: p.A584T, PBX2:p.Y262F, PIP4K2A:p.R219K, RLIM: p.S471P, RUNX2:p.Q71E, SGK223:p.R63S, SMARCB1:p.L365fs, SRCAP:p.Q1875fs, TBC1D2B: p.R920Q, TCF7L2:p.R482fs, TMEM131:p.K640fs, TMEM60:p.K77fs, TPPP:p.R30K, TRPV3:p.A218E, TTBK2:p.C83W, UBXN11:p.S510G, UGT1 A1:p.T4A, UTS2R:p.A289E, YBX1:p.P250L, ZNF514:p.V81G, ZNF516:p.A256D, ZNF681: p.K405Q, ZNF814:p.D404E, ZNF814:p.P323H, ZXDB:p.G206R.

65. The pharmaceutical composition of any of paragraphs 30-36, wherein:
    (a) the population of subjects is suffering from LIHC and
    (b) the at least one tumor-specific mutation comprises any combination of mutations selected from the group consisting of TP53:p.R249S, CTNNB1:p.D32V, CTNNB1:p.D32G, CTNNB1:p.S33P, CTNNB1: p.K335I, CTNNB1:p.H36P, EEF1A1:p.T432L, GNAS: p.R844C, OR2T4:p.V137L, TP53:p.H193R, ATXN1: p.Q217H, CSMD3:p.F2383fs, CTNNB1:p.D32N, CTNNB1:p.S33C, CTNNB1:p.G34V, CTNNB1: p.S45P, CTNNB1:p.N387K, DHRS4:p.I218T, DNM2: p.E378D, F5:p.Q426L, GALNTL5:p.A45T, GPX1: p.P77R, GRM8:p.R852C, IDH1:p.R132C, KIF26B: p.A2033T, KRT8:p.S59A, LOC100132247:p.T532P, NEB:p.D3854H, PIK3CA:p.H1047R, SOLH: p.R714H, TP53:p.R158H, TP53:p.V157F, and ZNF638:p.D400N.

66. The pharmaceutical composition of any of paragraphs 30-36, wherein:

(a) the population of subjects is suffering from MM: and
(b) the at least one tumor-specific mutation comprises any combination of mutations selected from the group consisting of NRAS:p.Q61R, KRAS:p.Q61H, KRAS:p.G13D, NRAS:p.Q61K, BRAF:p.V600E, NRAS:p.Q61H, NRAS:p.G13R, ZNF717:p.W315C, ATP13A4:p.V431G, DNAJC12:p.R135K, IRF4:p.K123R, KRAS:p.A146T, KRAS:p.Q61R, KRAS:p.G12A, KRAS:p.G12D, ZNF717:p.N594I, ACTG1:p.A22P, ARL6IP1:p.M75L, BEND2:p.E630K, BRAF:p.G469A, CDHR1:p.R218G, DIS3:p.R780K, DMXL2:p.D2412E, DNAJC10:p.I80K, EGR1:p.Q9H, FGFR3:p.*807S, IDH1:p.R132C, IL6ST:p.P216H, INTS12:p.M1V, KRAS:p.K117N, KRAS:p.A59G, KRAS:p.G12R, MAX:p.R36W, MLL5:p.G492E, NBPF1:p.E810K, NRAS:p.Q61L, NRAS:p.G12D, ODF2L:p.E294K, PADI2:p.T114P, PNLIP:p.T37M, PRDM1:p.S588C, PTPN11:p.E76K, PTPN14:p.E286K, RBM6:p.V675G, SCN10A:p.R142H, SRGAP1:p.T61M, SUSD1:p.T168P, TAS2R16:p.V231I, TINAG:p.E403K, TRIP12:p.L1775P, and ZNF717:p.C844S.

67. The pharmaceutical composition of any of paragraphs 30-36, wherein:
(a) the population of subjects is suffering from PRAD; and
(b) the at least one tumor-specific mutation comprises any combination of mutations selected from the group consisting of HSD17B7P2:p.N175S, RGPD5:p.P1760A, FRG1B:p.L52S, EEF1B2:p.S43G, FRG1B:p.I10T, FRG1B:p.A53T, LRRC37A2:p.T102S, NBPF10:p.E3455K, PTH2:p.L22V, CYP2D7P1:p.S32A, FAM47C:p.N648D, MAP3K9:p.E38del, MUC4:p.H4205Q, CHEK2:p.K373E, FRG1B:p.A11T, FRG1B:p.A50P, HLA-J:p.R124W, KRTAP1-5:p.I88T, KRTAP4-9:p.D18V, NPIP:p.A271V, PDGFRA:p.R483fs, ZNF780A:p.Q600H, ZNF845:p.R925H, ZNF91:p.R333H, ARFGAP3:p.N299fs, BTN2A3P:p.P3S, FNBP4:p.TT58del, HLA-A:p.Q78R, LOC554223:p.RAPWMEQ147del, PODXL:p.28_30PSP>P, POLI:p.D17del, SPOP:p.F133L, SYN2:p.A34del, TMEM52:p.23_26LLPL>L, UBC:p.L149R, ZNF208:p.I647S, ZNF799:p.E589G, ZNF814:p.D404E, ASTN2:p.L221del, B4GALNT1:p.G88fs, C16orf74:p.S21del, CCDC15:p.H458P, CD209:p.R129W, CNTNAP1:p.S1029I, DBR1:p.541_542DD>D, FAM22F:p.S691del, FRG1B:p.D32V, FRG1B:p.I34T, FRG1B:p.N55D, FRG1B:p.I59V, FRG1B:p.S71N, KIF25:p.W3R, KRTAP4-11:p.L161V, KRTAP4-11:p.M93V, KRTAP4-11:p.R51K, KRTAP4-6:p.S153Y, LILRB5:p.S598P, LMOD2:p.E24del, LOC645752:p.L40P, LRP1:p.P1058T, LRRIQ3:p.K244fs, LURAP1L:p.55_56insGGG, MLLT10:p.V463E, MYOCD:p.Q310del, NBPF10:p.N1369D, OTUD4:p.T909I, PARG:p.A584T, PEX1:p.I370fs, POTEC:p.K507E, POTEC:p.R477Q, POU4F2:p.68_69insG, PRG4:p.T417P, SDHAP2:p.R31C, SPOP:p.F133C, SPOP:p.W131G, TIMD4:p.T152del, TMEM121:p.P299del, TP53:p.G245S, UBC:p.R73L, UBC:p.I191T, WASH3P:p.G175S, ZMIZ1:p.D1048fs, ZNF709:p.T413I, ACADS:p.R330H, ADAMTS7:p.K1357fs, AFF2:p.R597H, AGAP6:p.S127I, AK302238:p.A44T, AK302879:p.Q191R, ALDH1A2:p.R85C, ANAPC1:p.T537A, ANKRD36C:p.H438R, AP4B1:p.R276W, ARFGAP2:p.S38N, BBS9:p.F268fs, BC139719:p.L133R, BRAF:p.G469A, C22orf43:p.D171del, CANT1:p.K131R, CHD3:p.E35del, CLEC4A:p.R209H, CNOT3:p.E20K, CNPY3:p.17_18LL>L, CNTNAP3B:p.S317T, CNTNAP3B:p.M1247I, CTNNB1:p.T41A, DDX10:p.D788del, DLC1:p.S741T, DPY19L2:p.M210V, EDC4:p.S617del, EFCAB6:p.R379K, ERC2:p.927_928HH>H, FAM111B:p.S269fs, FEM1A:p.L620M, FHOD3:p.A632fs, FLJ43860:p.L850fs, FMN2:p.G59del, FNBP4:p.914_915PP>P, FRG1:p.E86del, FRG1B:p.K13N, FRG1B:p.P42Q, GABRB1:p.R416C, GABRR2:p.A368V, GAGE2B:p.9_10insY, GOLGA8DP:p.N84H, GOT2:p.R355W, GPATCH4:p.K210fs, HDGFL1:p.188_189insA, HLA-DQB2:p.G250S, HLA-DQB2:p.R247H, IDH1:p.R132H, 1L27:p.E176del, IRF2BPL:p.123_125QQQ>Q, KANK3:p.DGDS489del, KIAA1462:p.858_859SS>S, KRTAP4-11:p.S48R, KRTAP4-7:p.S57P, KRTAP4-8:p.C95S, LPHN3:p.R826H, LRP10:p.L11del, LRP5:p.S1609P, LRRC16B:p.R787W, MAS1L:p.R324G, MECOM:p.R915Q, MED12:p.L1224F, MED12L:p.Q2115del, MESP2:p.GQGQGQGQ195del, MGAT4C:p.T345M, MLEC:p.E238del, MSLNL:p.T68P, MUC7:p.S173P, MYC:p.Q37del, NBPF10:p.N440D, NLRP6:p.E611del, NOX3:p.C404fs, OR1M1:p.V69I, OR7E24:p.L7fs, OTUD4:p.A153del, PANK2:p.T417fs, PCLO:p.S496P, PCNT:p.S162G, PCSK9:p.23_24insL, PHOSPHO1:p.S32del, POU4F1:p.H108del, PRAMEF8:p.R319H, PRDM7:p.M387L, PRG4:p.T597P, PTPRD:p.R1323C, PTPRF:p.R1174Q, ROBO3:p.RS1367del, ROCK 1:p.T518S, RPTN:p.G296S, RTL1:p.152_152E>EE, SIRPA:p.V233I, SLC2A6:p.A230D, SLC8A2:p.E710del, SMG7:p.E846fs, SNAPC4:p.S542del, SP8:p.G165del, SPOP:p.F133I, SPOP:p.F33V, SPOP:p.F102C, SPOP:p.F102V, SRSF11:p.G17fs, SRSF4:p.K396del, SSPO:p.S4198fs, STAG3L2:p.L81fs, STK19:p.R18fs, TBC1D2B:p.R920Q, TBC1D9:p.P1233T, TCHH:p.P1158R, TCOF1:p.K1366del, TNRC18:p.2664_2665SS>S, TP53:p.R248Q, TP53:p.R175H, TP53:p.C141G, TSPAN4:p.L92V, UBXN11:p.GPGPGPSP504del, UTP3:p.E81del, WASH3P:p.L187V, ZAN:p.P717L, ZAN:p.L878P, ZFP90:p.R591fs, ZNF761:p.H373R, and ZNF91:p.H305R.

68. The pharmaceutical composition of any of paragraphs 30-36, wherein:
(a) the population of subjects is suffering from STAD; and
(b) the at least one tumor-specific mutation comprises any combination of mutations selected from the group consisting of RNF43:p.G659fs, BZRAP1:p.P1416fs, XYLT2:p.Y526fs, LARP4B:p.T163fs, PGM5:p.I98V, ZBTB20:p.P692fs, ARID1A:p.G1848fs, FHOD3:p.P334fs, KIAA0182:p.T120fs, ATP6V1B1:p.Y383fs, PIK3CA:p.H1047R, FRMD4A:p.P1005fs, PIK3CA:p.E545K, CDC14A:p.N123fs, KRAS:p.G13D, MLL2:p.T172fs, BCORL1:p.S1679fs, PLEKHA6:p.V328fs, C9orf131:p.P342fs, CD4:p.Q164fs, FBXW7:p.R465C, GNG12:p.T68fs, IRS4:p.G591fs, JARID2:p.V422fs, KIAA0195:p.I902fs, MBD6:p.P732fs, MVK:p.P138fs, PAMR1:p.G101fs, WNT16:p.W165fs, ZNF43:p.N251fs, ABCA6:p.L306fs, ADAM28:p.K73fs, AOC3:p.L79fs, ATP2A:p.R819fs, B2M:p.L13fs, C6orf89:p.P58fs, CNTLN:p.K1305fs, CR2:p.V206fs, DYRK4:p.K468fs, ERBB3:p.V104M, GLI1:p.W272fs, KRAS:p.G12D, MLL2:p.T72fs, MSH6:p.T1085fs, NLK:p.C190fs, OR5M3:p.T89fs, PAX6:p.P375fs, PTEN:p.L265fs, RABGAP1:p.K928fs, RAD51 AP2:p.T316fs, SVIL:p.G1862fs, TP53:p.R273H, WNK4:p.G606fs, ARID1A:p.P2139fs, AXIN2:p.G665fs, C13orf33:p.R67fs, C1QTNF5:

p.P308fs, CELSR1:p.G614fs, CRYGD:p.G159fs, DCHS1:p.R235fs, DDC:p.I433fs, EDNRB:p.Y383fs, EPHA2:p.P460fs, FOXN3:p.P96fs, HDAC4:p.P901fs, INF2:p.S527fs, KIRREL2:p.V649fs, KLF3:p.I104fs, KLHL14:p.P231fs, MAP7D3:p.Q308fs, OTX2: p.R44fs, PAFAH1B1:p.K302fs, PLAGL2:p.P10fs, POLM:p.P97fs, PRPF40B:p.I31fs, RALGAPB: p.T379fs, SBNO1:p.N1139fs, SERPINI1:p.L81 fs, SH3KBP1:p.L574fs, SLC2A7:p.H686fs, SLC27A3: p.P643fs, TBX4:p.S370fs, TP53:p.R273C, TP53: p.R175H, TRAM1L1:p.R345fs, WBP1:p.P138fs, ABCC4:p.L883fs, AKAP13:p.K2785fs, ALDH3A1: p.P562fs, ALPK2:p.L356fs, ARFGEF1:p.P1552fs, ARID1A:p.G1848fs, AVPR1A:p.F351fs, BAX: p.M38fs, C14orf43:p.P33fs, C1QTNF5:p.G194fs, C7orf50:p.L179fs, CDC25C:p.K322fs, CETN3: p.K63fs, CHD3:p.P597fs, CTCF:p.K202fs, CTSC: p.F05fs, DDX17:p.G163fs, DLGAP3:p.G377fs, EBF3: p.G255fs, FHDC1:p.F100fs, FILIP1L:p.K749fs, FLNB:p.W529fs, GBP7:p.G431fs, GCC2:p.E700fs, GPR161:p.G517fs, IWS1:p.S802fs, KIAA0240: p.K895fs, KIAA1967:p.P415fs, LRRC43:p.D558fs, MACF1:p.R707fs, MBD6:p.G780fs, MLL3: p.F4496fs, MPRIP:p.A35 fs, MUC6: p.2129_2130SS>S, NOX5:p.P467fs, OPTN:p.P24fs, OR4K5:p.F177fs, PIK3CA:p.N345K, PIK3CA: p.E542K, PLXNA1:p.P1016fs, PNPLA7:p.P1199fs, PODN:p.I301fs, PPP2R3B:p.T389fs, PRSS36: p.L680fs, RGL2:p.G203fs, RHOQ:p.V190fs, RNF111: p.R771fs, RTN2:p.P313fs, SALL4:p.V995fs, SBF1: p.P1076fs, SETDB2:p.R715fs, SNAPC2:p.T292fs, SPG20:p.F232fs, SRCAP:p.P1876fs, STAT2:p.P489fs, TCHP:p.E172fs, TP53:p.R282W, TP53:p.R248Q, USP21:p.K474fs, WDR7:p.G262fs, ZBTB7C: p.E157fs, ZFC3H1:p.K385fs, ZNF124:p.T339fs, ZNF626:p.K115fs, ADNP2:p.S322fs, AGAP1: p.G127fs, ALDH2:p.L286fs, ARHGAP5:p.D890fs, ARHGEF17:p.A615fs, ARID1A:p.Y1324fs, ART 1:p.I243fs, ASCL4:p.D35fs, ATXN2L:p.G998fs, B3GNT5:p.F30fs, BCKDHA:p.H37fs, BCL9L: p.P1127fs, BEND3:p.D265fs, BNC2:p.S575R, BRD3: p.P24fs, C12orf51:p.P4235fs, C1R:p.P216fs, C7orf49: p.G130fs, CA2:p.I145fs, CABP5:p.R145fs, CASD1: p.F781fs, CASP8:p.R471fs, CCDC153:p.P200fs, CD93:p.D280fs, CROT:p.L32fs, CSF3R:p.P468fs, CTCF:p.K202fs, ERBB2:p.S310F, FAM46D:p.S69R, FBN3:p.G601fs, FBXO21:p.F144fs, GAS6:p.G150fs, GLYR1:p.G380fs, GXYLT1:p.L223fs, HAUS6: p.S530fs, IGF2R:p.T1314fs, ITGB1:p.L378I, KDM3B:p.P1316fs, KIF13A:p.K1115fs, KLF3: p.S224fs, LARP1:p.A223fs, LRP1:p.G1488fs, LRP1: p.G1488fs, MAGEE2:p.Q45fs, MAMSTR:p.P162fs, MAPK15:p.Q511fs, MLL2:p.P647fs, MOCS2: p.P22fs, MTG1:p.L105fs, MTG1:p.H327fs, MTIF2: p.N109fs, NID2:p.R1035fs, PAX2:p.P395fs, PCCA: p.R230H, PDZD2:p.R01fs, PFKP:p.M593fs, PIK3CA: p.R88Q, PLA2G1B:p.L53fs, PLAU:p.R201fs, PMEPA1:p.P208fs, POP1:p.K750fs, PTCH1: p.P1307fs, PTPRT:p.P1075fs, RDBP:p.P6fs, RNMT: p.K392fs, ROBO2:p.P1080fs, RUNDC3B:p.L6fs, SDAD1:p.K275fs, SLC10A6:p.G109fs, SNAPC1: p.D21 fs, SPATA5L1:p.C685fs, SPTA1:p.K1732T, STAT5B:p.P367fs, SYT4:p.M1fs, TAF1L:p.K851fs, TAP2:p.L75fs, TBL1XR1:p.N126fs, THEMIS: p.K406fs, TMEM79:p.P161fs, TP53:p.C176F, TP53BP2:p.K69fs, TP53RK:p.L174fs, UBQLN2: p.A523fs, UHRF1BP1:p.I1330fs, VPRBP:p.K939fs, VPS13B:p.T56fs, WASF3:p.P305fs, YLPM1: p.E1178fs, ZC3H13:p.K1006fs, ZC3H18:p.P825fs, ZC3H4:p.E779Q, ZNF48:p.P247fs, ZNF608: p.A465fs, ZNF878:p.S238fs, ZSCAN18:p.P225fs, ABCB1:p.R527fs, ABCB6:p.G318fs, ACACB: p.G255fs, ACP1:p.Q123fs, ACTL6A:p.L88fs, ADAMTSL4:p.G778fs, AGBL5:p.I420fs, AHI1: p.K303fs, AKAP9:p.M3743fs, AKD1:p.R1209fs, ANKRD40:p.D99E, ARHGEF5:p.S1512fs, ARID1A: p.K1071fs, ARID3A:p.S557G, ARPP21:p.I130fs, ASPN:p.F67fs, ASXL3:p.E873fs, ATP6V1C2: p.R312fs, BEST3:p.P444fs, BRAF:p.P403fs, BRMS1: p.G107fs, BTBD11:p.T451fs, BTBD11:p.A561V, C11orf9:p.S261fs, C14orf102:p.R90fs, C14orf43: p.Q36fs, C15orf52:p.G98fs, C19orf21:p.R262C, C19orf70:p.P50fs, C20orf160:p.P46fs, C3:p.P890fs, CADPS2:p.N468fs, CASC3:p.S232F, CASC3: p.P603L, CASC3:p.P645L, CASC3:p.S658L, CASKIN2:p.P727fs, CBLL1:p.E138fs, CBLN3: p.P69fs, CCDC108:p.P164fs, CCDC148:p.K420fs, CCDC153:p.P200fs, CCDC169-SOHLH2:p.K162R, CCDC88A:p.K677fs, CD1E:p.F85V, CD3EAP: p.K218fs, CDH11:p.K357T, CDH1:p.D254Y, CDH23: p.V403I, CFI:p.K37fs, CHPF2:p.D645fs, CIC: p.R507fs, CIC:p.A1114fs, CIC:p.A1114fs, CLSTN1: p.T615M, CNBD1:p.L396P, CNGA4:p.K510T, CNOT6:p.S248fs, CNTROB:p.R920fs, COL9A1: p.P283fs, CPAMD8:p.P784fs, CR1L:p.L79fs, CRB1: p.F630V, CSMD1:p.L3410V, CTNNA3:p.K856fs, CTNND1:p.I447fs, CTSD:p.P89fs, CUX1:p.A439fs, CYP7B1:p.K332T, DAB21P:p.D994fs, DNAH11: p.T871fs, DNAH8:p.K1688fs, DNAJC1:p.K193fs, DNM2:p.P791fs, DSTN:p.F101fs, DYRK1B: p.Q545fs, EAF2:p.V109fs, EDNRB:p.A104V, EEA1: p.N570fs, EFHA1:p.F290fs, EGR1:p.P332fs, EIF4G3: p.K563fs, ELK3:p.S173fs, ENTPD2:p.G204fs, EOMES:p.G332fs, EPHA10:p.P868fs, EPHB6: p.G54fs, EPHX1:p.P132fs, EPPK1:p.G2015fs, ERBB4:p.M1fs, ESF1:p.T99fs, EXOSC8:p.L160fs, FAM113B:p.R5 fs, FAM116A:p.L44 fs, FAM135B: p.S645R, FAM151A:p.P117fs, FAM193A:p.D428fs, FAM193A:p.D428fs, FAM214B:p.A42fs, FAM40B: p.R740C, FAM70B:p.S19L, FASTKD1:p.K3fs, FBXW7:p.R479Q, FBXW9:p.G298fs, FER:p.L474fs, FERMT2:p.K152fs, FGGY:p.G138fs, FIGNL1: p.K309fs, FLG:p.K159fs, FLNB:p.W529fs, FOLH1: p.S501fs, FYB:p.G324fs, GABRD:p.Q412fs, GALNTL1:p.W317fs, GANAB:p.L23fs, GCDH: p.L389fs, GIMAP7:p.V276fs, GIPC3:p.G227fs, GLI3: p.P033fs, GLIPR1L2:p.G92fs, GNPNAT1:p.F54fs, GON4L:p.M134fs, GPATCH4:p.K210fs, GRK4: p.K22fs, GTF3C1:p.S767fs, GTF3C4:p.E562fs, H2AFY2:p.K144fs, HCFC1R1:p.P83fs, HCRTR2: p.S9fs, HCRTR2:p.S9fs, HDLBP:p.G747fs, HECA: p.R333fs, HIVEP3:p.H554fs, HIVEP3:p.P534fs, HLA-C:p.P209fs, HOOK1:p.L361fs, HOXD8: p.P122fs, HTT:p.G697fs, IBTK:p.K1213fs, IDE: p.K37fs, IFT172:p.A837T, INPPL1:p.A974fs, INPPL1:p.P1154fs, INSM2:p.T533fs, INTS12: p.L14fs, INVS:p.R815fs, IPO11:p.S844fs, IRX6: p.A425V, ISG20L2:p.P288fs, ITGB8:p.A7fs, JARID2: p.G394fs, JHDM1D:p.R97fs, KBTBD6:p.G442fs, KCNC1:p.K455fs, KCNH2:p.G149A, KCNJ10: p.P102fs, KCNMB2:p.N151K, KCTD21:p.T6M, KIAA0586:p.A1592fs, KIAA1009:p.F406fs, KIAA1109:p.E1588fs, KIAA2026:p.K690fs, KIF26B: p.S1065fs, KIF6:p.L204fs, KIRREL:p.P335fs, KLC2:

p.T568fs, KRAS:p.Q61H, KRAS:p.G12S, MAN1C1: p.G431fs, MAP A:p.P2063fs, MAP2:p.K1472fs, MAP3K12:p.R449del, MAP7D1:p.A80fs, MGST2: p.K102fs, MKI67:p.T1664fs, MKL1:p.P307fs, MLL2: p.P2354fs, MLL2:p.L656fs, MLL2:p.P647fs, MLL2: p.L1877fs, MMP3:p.I64fs, MPDZ:p.K1582fs, MTUS2:p.R1005W, MUC16:p.A6156T, MYB: p.R481fs, MYEOV:p.L269fs, MYH11:p.K1263del, MYO18A:p.P209fs, MYO7A:p.I539fs, MYOCD: p.G226fs, NAA16:p.H514fs, NBEA:p.V2247fs, NCAPD3:p.Q909fs, NCAPH:p.T466fs, NCOR2: p.P1308fs, NEFM:p.A213V, NEK8:p.V690fs, NF1: p.T676fs, NHLRC1:p.F204fs, NKD1:p.P286fs, NPR3: p.Y138H, NT5M:p.P206fs, NUFIP2:p.R224fs, NUP210:p.L135fs, NYNRIN:p.G113fs, OBSCN: p.G997fs, OGDH:p.Y948fs, OR4C16:p.S135R, OR51A7:p.L124R, OR7C1:p.C179fs, OSBP2: p.H627fs, OTOF:p.E1304K, P2RX1:p.R20fs, PALB2: p.M296fs, PALB2:p.N280fs, PANK1:p.K400fs, PAPD4:p.C225fs, PAPPA2:p.I1683fs, PARP15: p.K461fs, PARP4:p.K847fs, PCDH10:p.N118fs, PCDH10:p.P225fs, PCGF3:p.H63fs, PELI2:p.G197fs, PHACTR1:p.V251 fs, PHACTR2:p.S237fs, PHACTR4:p.S354fs, PHKB:p.K642fs, PIAS3: p.H116fs, PIGO:p.P787fs, PIGT:p.A346fs, PIK3R3: p.M341fs, PITPNM1:p.P295fs, PKN2:p.K76fs, PLA2G15:p.W230fs, PLAG1:p.K184fs, PLEKHO1: p.T254fs, PLOD3:p.R297fs, PLOD3:p.P296fs, PLXNA2:p.P464fs, POLQ:p.L1430fs, PPARGC1B: p.P135fs, PPL:p.P454fs, PPM1H:p.P226fs, PPP1R12C:p.P372fs, PREX2:p.R562fs, PRICKLE4: p.Q109fs, PRKAR1B:p.P87fs, PRKCG:p.R345C, PRMT8:p.S28fs, PROX1:p.F592fs, PRRG3:p.R163fs, PSD2:p.G256fs, PTCHD3:p.F588fs, PTPN4:p.N319fs, PTPRC:p.Q895H, PWWP2B:p.S84fs, PYGO2: p.Q150fs, RABGAP1:p.K928fs, RB1CC1:p.N1711fs, RBM6:p.R96fs, RHOA:p.Y42C, RIMS1:p.R71G, RIMS2:p.V401fs, RING1:p.G171fs, RINT1:p.L107fs, RNF43:p.P116fs, ROBO2:p.K1293fs, RPS6KA6: p.K109fs, RRS1:p.N45fs, RSF1:p.K386fs, RUSC2: p.P486fs, RXFP3:p.A60V, SAFB:p.W798fs, SCARF1: p.R614Q, SCLT1:p.K109fs, SERPINB12:p.Q168fs, SGK3:p.L61fs, SGOL2:p.E407fs, SIGLEC1:p.P318fs, SIK1:p.Q678fs, SLC6A6:p.G98fs, SLC25A17: p.F28fs, SLC26A7:p.1629fs, SLC32A1:p.V494I, SLC4A3:p.L061fs, SLC7A10:p.P157fs, SLC9A2: p.T746fs, SLITRK1:p.K45fs, SND1:p.H721fs, SOAT1:p.F64fs, SORBS2:p.E1158fs, SOX7:p.L309fs, SPAG17:p.Q264fs, SPTY2D1:p.P485fs, SRCIN1: p.P865fs, SREBF2:p.H763fs, SRRT:p.G102fs, STAB1:p.P1120fs, STRADA:p.R333fs, STX2: p.K252fs, SV2A:p.E138fs, SYCP2:p.M176fs, SYNJ2: p.P1111fs, TAS2R10:p.L196fs, TBC1D22B:p.A75fs, TEAD2:p.P298fs, TFE3:p.G482fs, TGM6:p.T358fs, TIMM44:p.K83fs, TIMP3:p.A199fs, TLR4:p.L498V, TMEM132D:p.P206fs, TMEM41A:p.F156fs, TMEM41B:p.F230fs, TMTC4:p.R611C, TNK2: p.P632fs, TOPBP1:p.I1381fs, TP53:p.E286K, TP53: p.P152fs, TRIP11:p.K541fs, TRPA1:p.T673fs, TRPM8:p.H765fs, TTF1:p.K336fs, TTI1:p.R707H, TTN:p.E15192D, U2AF2:p.L175fs, UBC:p.G684fs, UBR4:p.P2802fs, UPF2:p.E1033D, UPK2:p.P49fs, USP13:p.I1116fs, USP15:p.K782fs, VASH1:p.G3fs, VEZF1:p.355_356insN, VPS13A:p.F2883fs, WAPAL: p.R522fs, WDFY3:p.L842fs, WDR59:p.N160fs, WDR5:p.N214fs, WDR60:p.Q412fs, WDTC1: p.M287fs, WHSC1L1:p.K418fs, WNT1:p.W167fs, XIRP2:p.E1007D, YBX2:p.P226fs, YIF1A:p.R131fs, ZBBX:p.E151del, ZBTB40:p.L262fs, ZBTB7C: p.G342fs, ZBTB7C:p.D154fs, ZC3H18:p.T701fs, ZDHHC5:p.E651 del, ZDHHC7:p.P316fs, ZFHX3: p.R1893fs, ZFHX3:p.E763fs, ZFHX4:p.L408fs, ZHX3:p.N249K, ZIM3:p.I384fs, ZKSCAN5:p.D13fs, ZMYM4:p.K345fs, ZNF236:p.T1410M, ZNF23: p.F122fs, ZNF334:p.K426fs, ZNF358:p.T130fs, ZNF701:p.L296fs, ZNF711:p.L737fs, and ZNF831: p.A49fs.

69. The pharmaceutical composition of any of paragraphs 30-36, wherein:
(a) the population of subjects is suffering from TGCT; and
(b) the at least one tumor-specific mutation comprises any combination of mutations selected from the group consisting of FAM18B2:p.C51Y, BTN2A3P:p.P3S, MUC2:p.G1715S, NBPF10:p.L44V, SP8:p.G156S, DCP1B:p.Q252H, DEK:p.E41D, ERC1:p.K692R, FAM104B:p.D75H, FRG1B:p.M49V, KRTAP10-10: p.V234M, LRRCC1:p.A6V, NRAS:p.Q61R, PNPLA4: p.L223P, ANKLE1:p.C644fs, ANKLE1:p.C644fs, KIT:p.D816H, KIT:p.D816Y, MUC2:p.T1597I, PSMD11:p.A5V, RHPN2:p.V73M, RUNX2:p.Q71E, SP4:p.E7K, TUBA1C:p.L146F, ZNF814:p.Y324H, ADAMTS17:p.N572T, ATRX:p.K1936R, BCL11B: p.E535D, BMP2K:p.Q460H, BMP2K:p.H487Q, C12orf32:p.D60V, C22orf43:p.K19E, CDC27: p.N571I, CDC27:p.P242S, DDX11:p.K208fs, EBPL: p.L189V, EZH2:p.K510R, FAM86A:p.A141T, GAS2L2:p.D189A, GRID2IP:p.LS754del, HGC6.3: p.E171G, KIT:p.D816V, KIT:p.N822Y, KIT:p.N822K, KRAS:p.Q61R, KRAS:p.G12V, KRTAP1-1:p.I116V, LRRC37BP1:p.Y166D, MEF2A:p.R127Q, MFF: p.S7F, MST1:p.R347W, MUC4:p.S3048L, MUC6: p.H2000Q, MUC6:p.P1977H, NAT10:p.I393T, OPLAH:p.A900D, PIEZO1:p.Q749E, PRAMEF4: p.F300V, RBM10:p.E184D, SERINC2:p.T121P, SPIN2A:p.M150V, SRRM2:p.A2257S, SSBP3:p.K6R, ZNF680:p.R501W, ABCC8:p.Y512C, ABCC9: p.L466P, ABCD1:p.H169Q, ABL2:p.P19T, ACVR2B: p.R48C, AHDC1:p.P33fs, AHNAK2:p.L1640M, ALPPL2:p.W31 S, AMMECR1:p.G77C, ANK3: p.D1322E, ANKHD1-EIF4EBP3:p.G60S, ANKRD11: p.Y2015S, ANKRD11:p.K369R, ANKRD50: p.V637M, APBB3:p.L450P, ARHGAP24:p.T35A, ARID4B:p.G1076A, ARMC3:p.A514T, ARRB2: p.T99P, ATAD5:p.I305V, ATXN3: p.305_306insQQQQQQQ, AVPR1B:p.G39R, AXDND1:p.E994Q, BAI2:p.A231G, BEST3:p.P383L, BIRC6:p.V414L, BIRC8:p.A225M, BRWD1: p.K1319R, BTN2A2:p.L15F, C12orf51:p.A2644T, C12orf65:p.K143T, C16orf62:p.L244I, C1QBP: p.T225I, C1orf167:p.S123G, C5orf25:p.Y4F, CACNA1E:p.G2080S, CAPNS1:p.LV303del, CCDC159:p.A332S, CDKAL1:p.P409L, CDYL: p.V48A, CDYL:p.A60G, CELSR2:p.L17P, CHD4: p.E138D, CKAP5:p.G576A, CLCC1:p.K52R, CMTM8:p.S26T, CNKSR2:p.P249L, CNTN5:p.I501T, COG5:p.H617R, COL15A1:p.K708R, COL6A3: p.A2378D, CRYGB:p.R143G, CSGALNACT2: p.L362F, CUL4A:p.I438F, CXXC1:p.Q156H, CYP19A1:p.F406L, DCLRE1B:p.F28I, DDX11: p.A376T, DDX11:p.E680D, DEPDC5:p.R1525Q, DLC1:p.S741T, DNMT1:p.R995Q, DOCK11: p.Q169E, DSPP:p.D1047N, E2F7:p.I91S, EBF1: p.D353G, ECI2:p.K55R, EEF1A2:p.Y418S, EIF3J: p.A8G, EML6:p.K805R, EPAS1:p.S474T, EPRS:

p.L1335I, ERICH1:p.E327K, FAM101B:p.L5P, FAM104A:p.M1R, FAM110D:p.R71H, FAM155A: p.Q95R, FAM186A:p.G1492E, FAM194B:p.Y139H, FAM21B:p.P1231S, FAM32A:p.K9R, FAM46B: p.H416R, FAM48B1:p.I499V, FAM48B1:p.A516P, FAM5C:p.S425W, FAM86C2P:p.C120Y, FBXL14: p.V48G, FRMPD3:p.Q832del, FRS2:p.L47S, GDF5: p.E105fs, GPNMB:p.C3fs, GPT2:p.R10P, H2AFV: p.Q125R, HDLBP:p.R503C, HERC2:p.R2129C, HIST1H2BJ:p.K13R, HLX:p.N231K, HMGB3: p.E198D, HSF4:p.R169W, HSF4:p.S491P, HYAL4: p.D222N, INO80E:p.P206fs, INTS4:p.S460A, IQCF6: p.R3H, ITPR1:p.M1569I, ITPR3:p.R1698G, KANSL3:p.G376E, KCNA4:p.E627del, KDM5A: p.P423S, KDM6A:p.Y362fs, KIAA0020:p.K63R, KIDINS220:p.N851 S, KIT:p.W557G, KLHDC2: p.W321S, KRAS:p.A146T, KRAS:p.Q61H, KRAS: p.Q61L, KRAS:p.G12A, KRAS:p.G12R, KRBA1: p.R839G, KRTAP4-8:p.T63S, L2HGDH:p.P441del, LAMC3:p.P174Q, LHCGR:p.L16Q, LOC401296: p.L144M, LPHN2:p.F906I, LRP12:p.G310C, LTB4R: p.F73L, LTBP3:p.L35del, LUC7L3:p.S148T, LYPD4: p.T64K, MAMLD1:p.Q572L, MAP4K2:p.R341G, MAPK7:p.A501D, MAT2A:p.E166G, MED12L: p.C1292Y, MESP2:p.Q182E, MEX3C:p.R534S, MIER2:p.L131F, MLL5:p.Y66C, MLLT3: p.177_178SS>S, MMS19:p.D1005N, MRPS25: p.E119del, MSH6:p.D576A, MTIF3:p.G65E, MUC17: p.M1807T, MUC17:p.T2279N, MUC17:p.G2474S, MUC2:p.TTPSPP1475del, MUC2:p.T1568M, MUC2: p.T1580N, MUC2:p.T1704I, MUC2:p.T1706M, MUC4:p.H1117D, MUC5B:p.R1097H, MYEF2: p.K323E, MYEOV:p.L302H, MYH8:p.A785V, MYO1A:p.N584K, NAP1L3:p.P353R, NAV1: p.I1433M, NCAM1:p.E131G, NEB:p.D3107N, NEFH:p.V670E, NELL2:p.G170D, NHS:p.D1561N, NKD2:p.H447del, NSD1:p.T461R, NT5C3:p.A3P, NYAP1:p.P480S, OBSCN:p.A908T, OR10J1: p.R244Q, OR1S2:p.M298I, OR2L3:p.K294R, OR6K6: p.F311L, PABPC3:p.V325fs, PBX2:p.Y262F, PCDHB4:p.P255F, PCMTD1:p.V281A, PCP4L1: p.K64R, PDE3A:p.A98E, PDIA6:p.N56K, PDS5A: p.L1309F, PHLDA2:p.R28S, PIGR:p.V183G, PIK3CA:p.E545K, PIK3CD:p.C381R, PKD1: p.T938M, PLEKHM1:p.A895V, PLEKHN1:p.A600D, PLXND1:p.R367L, PMS2:p.K651R, PNMA3: p.E200G, POTEF:p.S112G, PRAMEF8:p.I448V, PRDM2:p.E278D, PRODH:p.L527V, PRPF31: p.R289W, PSME4:p.N495D, PTGR1:p.E40A, PTPRB: p.Q726H, RABGEF1:p.N207D, RAC1:p.P34R, RANBP17:p.M900I, REV3L:p.A30S, RFC3:p.I82N, RFC3:p.K296N, RIMBP3:p.Q1154R, RPL19: p.R151C, RPL5:p.R58fs, RPTN:p.M538I, RRAD: p.A278E, RYR1:p.D668Y, RYR2:p.L2023F, SAFB: p.G799V, SCRIB:p.G332V, SDK1:p.Y2146C, SEC16A:p.T443K, SEC31B:p.P905S, SELO: p.R565Q, SELP:p.A297T, SI:p.I1681K, SLC2A7: p.H268Q, SLC37A1:p.V528I, SLC38A1:p.G100R, SMARCA2:p.D1158A, SMARCA5:p.T156fs, SMC3: p.E970Q, SMG1:p.P2696H, SNRNP200:p.A2129G, SPIN2B:p.M150V, ST6GALNAC1:p.S354N, STAMBPL1:p.Y143H, STARD8:p.G662A, STON1-GTF2A1L:p.N451S, SYMPK:p.A336G, TAS2R8: p.W98C, TCHH:p.W1016R, TET1:p.T1472S, TIAM1: p.G247M, TNS1:p.P183S, TOR1AIP2:p.G146R, TPRX1:p.S216P, TPRX1:p.S200P, TRMT61A: p.S244I, TSPAN4:p.L92V, TTF1:p.Q530R, UBE2M: p.G131D, UBR5:p.R2517S, UGT2B11:p.R447I, UMODL1:p.M559I, UNC93A:p.V445A, USP46: p.Q137R, VWA2:p.G317D, VWA7:p.V792G, WASH3P:p.L187V, WNT5B:p.K327E, WRN: p.E510D, XDH:p.P410S, ZAN:p.S755P, ZC3H11A: p.I777T, ZC3H7A:p.C575S, ZDHHC11:p.H250Q, ZFHX4:p.D3239N, ZKSCAN3:p.K200A, ZMYM4: p.T367I, ZNF174:p.P353T, ZNF322:p.Y353C, ZNF592:p.K324Q, ZNF592:p.P500T, ZNF782: p.C145F, ZNF799:p.C453R, ZNF804B:p.P644S, and ZNRF3:p.R889W.

70. The pharmaceutical composition of any of paragraphs 30-36, wherein:
(a) the population of subjects is suffering from THCA; and
(b) the at least one tumor-specific mutation comprises any combination of mutations selected from the group consisting of BRAF:p.V600E, NRAS:p.Q61R, HRAS: p.Q61R, NRAS:p.Q61K, OTUD4:p.T909I, HRAS: p.Q61K, NLRP6:p.E611G, AKT1:p.E17K, ANKMY1: p.N302I, ATP6V1A:p.L237P, CYP19A1:p.S113I, DCUN1D4:p.L275P, DGCR8:p.E518K, DLC1: p.S741T, DNAH10:p.C1853F, EIF1AX:p.G9D, FAM75D5:p.L222P, FCGRT:p.P40A, KRAS:p.Q61K, LMX1B:p.Q285del, MAS1L:p.R324G, MED15: p.S35I, MEGF6:p.Y393C, ODZ2:p.A1529V, OR5L1: p.R122H, OR6K6:p.F311L, OTX1:p.D315N, POTEE: p.S75G, SCN5A:p.D1978H, TOP2A:p.K1199E, and TSG101:p.K265R.

71. The pharmaceutical composition of any of paragraphs 30-36, wherein:
(a) the population of subjects is suffering from UCS; and
(b) the at least one tumor-specific mutation comprises any combination of mutations selected from the group consisting of TP53:p.R248Q, ZNF814:p.D404E, BTN2A3P:p.P3S, FBXW7:p.R465C, FRG1B:p.G65E, MUC4:p.H4205Q, NBPF10:p.V99F, PIK3CA: p.E545K, PIK3CA:p.H1047R, PPP2R1A:p.P179R, DDX11L2:p.*128Q, FBXW7:p.R479Q, FRG1B: p.K13N, FRG1B:p.L52S, HSD17B7P2:p.N175S, KRAS:p.G12V, LOC283788:p.S37G, TP53:p.R273H, TP53:p.S241Y, ADAMTS12:p.E359K, BCL2L11: p.L187fs, CDC27:p.L460fs, CHEK2:p.K373E, ESPNP:p.W122fs, FBXW7:p.R689W, FBXW7: p.R505G, FBXW7:p.R465H, FCGBP:p.V4019M, FRG1B:p.I10T, FRG1B:p.D32V, FRG1B:p.R37K, KRAS:p.G12D, LOC100233156:p.R21C, LOC283788:p.I46M, LRP1B:p.L1392F, MAMLD1: p.Q572L, MST1P9:p.L319P, MUC4:p.A2390T, MUC4:p.G2172S, NBPF10:p.E3455K, PIK3CA: p.G106V, PODXL:p.28_30PSP>P, POTEC:p.R477Q, PPP2R1A:p.R183W, PPP2R1A:p.S219L, PTPN18: p.TG378del, RGPD3:p.N756D, RPL13AP20: p.G107R, SAMD4B:p.R477W, SMAP1:p.E169fs, TP53:p.H193R, TP53:p.H179R, TP53:p.R175H, TUBBP5:p.R119H, and U2AF1:p.S34F.

72. The pharmaceutical composition of any of paragraphs 30-36, wherein:
(a) the population of subjects is suffering from PAAD; and
(b) the at least one tumor-specific mutation comprises any combination of mutations selected from the group consisting of RBM14:p.AAAAAAA286del, KRAS: p.G12D, JMY:p.PPPPPPPPPPPP811 del, RIOK1: p.D69del, LCE2A:p.SSGGCCGSSSGGCC47del, KRAS:p.G12V, C1QB:p.GPKGPMGPKGGPGAP GAP90del, ZFHX3:p.V777del, DBR1: p.541_542DD>D, AEBP1:p.K1133del, KRAS:

p.G12R, RBM47:p.495_502AAAAAAAA>A, AP3S1: p.K41fs, MLL2:p.AEGPHLSPQPEELHLSPQ792del, RFX1:p.386_401GGGGGGGGGGGGGSG>G, AXDND1:p.EQ991del, HERC2P3:p.A803V, RGPD3: p.N756D, FNDC1:p.D180del, ANAPC1:p.T537A, IRS4:p.21_22AA>A, GIGYF2:p.Q1005del, NCOA3: p.Q1253fs, SIK3:p.950_951QQ>Q, GPR6: p.AAAAATAAGGPDTGEWGPPA36del, NBPF12: p.D1323fs, SHROOM4:p.1156_1157EE>E, ZMIZ2: p.VAAAAATATATATAT153del, DGKK:p.PAPP41del, LZTS1:p.RTQDLEGALRTKGLEL432del, CASQ2: p.395_396DD>D, DCP1B:p.251_252insH, ESPNP: p.296_317PPPPSFPPPPPPPGTQLPPPPP>P, KBTBD6:p.T403K, NBPF16:p.D449fs, ANKRD36C: p.H438R, ESPN: p.PPPPPPSFPPPPPPPGTQLPP430del, FCGBP: p.A2493V, KRAS:p.Q61H, NCOA3:p.Q276del, OR2T2:p.C203fs, TMCC1:p.Q565L, BCKDHA: p.G129fs, ESPNP:p.H64fs, GNAS:p.R844H, NBPF14: p.R25C, OGFOD1:p.G477fs, RBM12:p.P693S, SLC38A10:p.1071_107211>I, SORBS2:p.P866S, TP53:p.R248W, TP53:p.R175H, and UBAC1: p.E269del.

73. The pharmaceutical composition of any of paragraphs 30-72, wherein the composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 neoantigenic peptides.

74. The pharmaceutical composition of paragraph 73, wherein the composition comprises 15 to 20 neoantigenic peptides.

75. The pharmaceutical composition of paragraphs 73 or 74, further comprising at least one additional neoantigenic peptide which is specific for an individual patient's tumor.

76. The pharmaceutical composition of paragraph 75, wherein the patient specific neoantigenic peptide is selected by identifying sequence differences between the genome, exome, and/or transcriptome of the patient's tumor sample and the genome, exome, and/or transcriptome of a non-tumor sample.

77. The pharmaceutical composition of paragraph 75, wherein the samples are fresh or formalin-fixed paraffin embedded tumor tissues, freshly isolated cells, or circulating tumor cells.

78. The pharmaceutical composition of paragraph 75, wherein the sequence differences are determined by Next Generation Sequencing.

79. The pharmaceutical composition of any of paragraphs 30-78, wherein each neoantigenic peptide is from about 5 to about 50 amino acids in length.

80. The pharmaceutical composition of paragraph 79, wherein each neoantigenic peptide is between about 15 to about 35 amino acids in length; is about 15 amino acids or less in length; is about 8 and about 11 amino acids in length; or is 9 or 10 amino acids in length.

81. The pharmaceutical composition of paragraph 79 or 80, wherein each neoantigenic peptide binds major histocompatibility complex (MHC) class I.

82. The pharmaceutical composition of any one of paragraphs 30-81, wherein each neoantigenic peptide binds to MHC class I with a binding affinity of less than about 500 nM, or optionally each neoantigenic peptide binds to HLA-A, -B or -C with a $K_D$ of less than 500 nM.

83. The pharmaceutical composition of paragraph 79, wherein each neoantigenic peptide is about 30 amino acids or less in length; is between about 6 and about 25 amino acids in length; is between about 15 and about 24 amino acids in length; or is between about 9 and about 15 amino acids in length.

84. The pharmaceutical composition of paragraph 79, 82 or 83, wherein each neoantigenic peptide binds major histocompatibility complex (MHC) class II.

85. The pharmaceutical composition of paragraph 84, wherein each neoantigenic peptide binds to MHC class I with a binding affinity of less than about 500 nM, or optionally each neoantigenic peptide binds to HLA-A, -B or -C with a $K_D$ of less than 500 nM.

86. The pharmaceutical composition of any of paragraphs 30-85, wherein at least one neoantigenic peptide further comprises flanking amino acids.

87. The pharmaceutical composition of paragraph 86, wherein the flanking amino acids are not native flanking amino acids.

88. The pharmaceutical composition of any of paragraphs 30-87, which at least one neoantigenic peptide is linked to at least a second neoantigenic peptide.

89. The pharmaceutical composition of paragraph 88, wherein peptides are linked using a poly-glycine or poly-serine linker.

90. The pharmaceutical composition of paragraph 88 or 89, wherein the second neoantigenic peptide binds MHC class I or class II with a binding affinity of less than about 1000 nM.

91. The pharmaceutical composition of any of paragraphs 88-90, wherein the second neoantigenic peptide binds MHC class I or class II with a binding affinity of less than about 500 nM.

92. The pharmaceutical composition of any of paragraphs 88-91, wherein both of the neoepitopes bind to human leukocyte antigen (HLA)-A, -B, -C, -DP, -DQ, or -DR.

93. The pharmaceutical composition of any of paragraphs 88-92, wherein the isolated neoantigenic peptide and the second neoantigenic peptide binds a class I HLA or the isolated neoantigenic peptide and the second neoantigenic peptide binds a class II HLA.

94. The pharmaceutical composition of any of paragraphs 88-92, wherein the isolated neoantigenic peptide binds a class II HLA and the second neoantigenic peptide binds a class I HLA or the isolated neoantigenic peptide binds a class I HLA and the second neoantigenic peptide binds a class II HLA.

95. The pharmaceutical composition of any of paragraphs 30-94, wherein at least one neoantigenic peptide further comprises modifications which increase in vivo half-life, cellular targeting, antigen uptake, antigen processing, MHC affinity, MHC stability, or antigen presentation.

96. The pharmaceutical composition of paragraph 95, wherein the modification is conjugation to a carrier protein, conjugation to a ligand, conjugation to an antibody, PEGylation, polysialylation HESylation, recombinant PEG mimetics, Fc fusion, albumin fusion, nanoparticle attachment, nanoparticulate encapsulation, cholesterol fusion, iron fusion, acylation, amidation, glycosylation, side chain oxidation, phosphorylation, biotinylation, the addition of a surface active material, the addition of amino acid mimetics, or the addition of unnatural amino acids.

97. The pharmaceutical composition of paragraph 95, wherein the cells that are targeted are antigen presenting cells.

98. The pharmaceutical composition of paragraph 97, wherein the antigen presenting cells are dendritic cells.

99. The pharmaceutical composition of paragraph 98, wherein the dendritic cells are targeted using DEC205, XCR1, CD197, CD80, CD86, CD123, CD209, CD273, CD283, CD289, CD184, CD85h, CD85j, CD85k, CD85d, CD85g, CD85a, CD141, CD11c, CD83, TSLP receptor, or CD1a marker.

100. The pharmaceutical composition of paragraph 99, wherein the dendritic cells are targeted using the CD141, DEC205, or XCR1 marker.

101. The pharmaceutical composition of any of paragraphs 30-100, which is an immunogenic or vaccine composition.

102. The pharmaceutical composition of paragraph 101, further comprising an immunomodulator or adjuvant.

103. The pharmaceutical composition of paragraph 102, wherein the immunodulator or adjuvant is selected from the group consisting of Poly(I:C), Poly-ICLC, STING agonist, 1018 ISS, aluminium salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312 VG, Montanide ISA 206 VG, Montanide ISA 50 V2, Montanide ISA 51 VG, OK-432, OM-174, OM-197-MP-EC, ISA-TLR2 agonist, ONTAK, PepTel®. vector system, PLG microparticles, resiquimod, SRL172, virosomes and other virus-like particles, YF-17D, VEGF trap, R848, beta-glucan, Pam3Cys, Pam3CSK4, acrylic or methacrylic polymers, copolymers of maleic anhydride, and QS21 stimulon.

104. An isolated polynucleotide encoding the isolated neoantigenic peptide of any of paragraphs 1-24.

105. The isolated polynucleotide of paragraph 104, which is RNA.

106. The isolated polynucleotide of paragraph 105, wherein the RNA is modified to increase stability, increase cellular targeting, increase translation efficiency, adjuvanticity, cytosol accessibility, and/or decrease cytotoxicity.

107. The isolated polynucleotide of paragraph 106, wherein the modification is conjugation to a carrier protein, conjugation to a ligand, conjugation to an antibody, codon optimization, increased GC-content, incorporation of modified nucleosides, incorporation of 5'-cap or cap analog, and/or incorporation of an unmasked poly-A sequence.

108. A cell comprising the polynucleotide of any of paragraphs 104-107.

109. A vector comprising the polynucleotide of any one of paragraphs 104-107.

110. The vector of paragraph 110, in which the polynucleotide is operably linked to a promoter.

111. The vector of paragraphs 109 or 110, which is a plasmid, phage, transposon, cosmid, virus, or virion.

112. The vector of paragraph 111, which is an adeno-associated virus, herpesvirus, lentivirus, or pseudotypes thereof.

113. An in vivo delivery system comprising the isolated polynucleotide of any of paragraphs 104-107.

114. The delivery system of paragraph 113, wherein the delivery system includes spherical nucleic acids, viruses, virus-like particles, plasmids, bacterial plasmids, or nanoparticles.

115. A cell comprising the vector or delivery system of any of paragraphs 109-114.

116. The cell of paragraph 115, which is an antigen presenting cell.

117. The cell of paragraph 116, which is a dendritic cell.

118. The cell of paragraph 117, which is an immature dendritic cell.

119. A composition comprising at least one polynucleotide of any of paragraphs 104-107.

120. The composition of paragraph 119, wherein the composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the isolated polynucleotides.

121. The composition of paragraph 120, wherein the composition comprises between about 2 and about 20 polynucleotides.

122. The composition of any one of paragraphs 119-121, wherein the composition further comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 additional neoantigenic polynucleotides encoding for additional neoantigenic peptides.

123. The composition of paragraph 122, wherein the composition comprises between about 4 and about 20 additional neoantigenic polynucleotides.

124. The composition of paragraph 122, wherein the isolated polynucleotides and the additional neoantigenic polynucleotides are linked.

125. The composition of paragraph 124, wherein the polynucleotides are linked using nucleic acids that encode a poly-glycine or poly-serine linker.

126. The composition of any of paragraphs 122-125, wherein at least one of the additional neoantigenic peptide is specific for an individual patient's tumor.

127. The composition of paragraph 126, wherein the patient specific neoantigenic peptide is selected by identifying sequence differences between the genome, exome, and/or transcriptome of the patient's tumor sample and the genome, exome, and/or transcriptome of a non-tumor sample.

128. The composition of paragraph 127, wherein the samples are fresh or formalin-fixed paraffin embedded tumor tissues, freshly isolated cells, or circulating tumor cells.

129. The composition of paragraphs 127 or 128, wherein the sequence differences are determined by Next Generation Sequencing.

130. A T cell receptor (TCR) capable of binding at least one neoantigenic peptide listed in any of paragraphs 1-27, optionally a neoantigenic peptide comprising FGFR3 S249C, ERBB3 V104M, EGFR L858R, MUC4 H4205Q, PDGFRA R483fs, TMEM52 23_26LLPL>L, or PODXL 28_30PSP>P.

131. The TCR of paragraph 130, which is capable of binding the isolated neoantigenic peptide in the context of MHC class I or class II.

132. A chimeric antigen receptor comprising: (i) a T cell activation molecule; (ii) a transmembrane region; and (iii) an antigen recognition moiety capable of binding an isolated neoantigenic peptide of any one of paragraphs 1-27.

133. The chimeric antigen receptor of paragraph 132, wherein CD3-zeta is the T cell activation molecule.

134. The chimeric antigen receptor of paragraph 132 or 133, further comprising at least one costimulatory signaling domain.

135. The chimeric antigen receptor of any of paragraphs 132-134, wherein the signaling domain is CD28, 4-1BB, ICOS, OX40, ITAM, or Fc epsilon RI-gamma.

136. The chimeric antigen receptor of any of paragraphs 132-135, wherein the antigen recognition moiety is capable of binding the isolated neoantigenic peptide in the context of MHC class I or class II.

137. The chimeric antigen receptor of any of paragraphs 132-136, comprising the CD3-zeta, CD28, CTLA-4, ICOS, BTLA, KIR, LAG3, CD137, OX40, CD27, CD40L, Tim-3, A2aR, or PD-1 transmembrane region.

138. The chimeric antigen receptor of any of paragraphs 132-137, wherein the tumor-specific epitope is located in the extracellular domain of a tumor associated polypeptide, optionally the tumor-specific epitope comprises FGFR3 S249C, ERBB3 V104M, EGFR L858R, MUC4 H4205Q, PDGFRA R483fs, TMEM52 23_26LLPL>L, or PODXL 28_30PSP>P.

139. A T cell comprising the T cell receptor or chimeric antigen receptor of any of paragraphs 130-138.

140. The T cell of paragraph 139, which is a helper or cytotoxic T cell.

141. A nucleic acid comprising a promoter operably linked to a polynucleotide encoding the T cell receptor of paragraph 130 or 131.

142. The nucleic acid of paragraph 141, wherein the TCR is capable of binding the at least one neoantigenic peptide in the context of major histocompatibility complex (MHC) class I or class II.

143. A nucleic acid comprising a promoter operably linked to a polynucleotide encoding the chimeric antigen receptor of any of paragraphs 132-138.

144. The nucleic acid of paragraph 143, wherein the antigen recognition moiety is capable of binding the at least one neoantigenic peptide in the context of major histocompatibility complex (MHC) class I or class II.

145. The nucleic acid of paragraphs 143 or 144, wherein the tumor-specific epitope is located in the extracellular domain of a tumor associated polypeptide.

146. The nucleic acid of any of paragraphs 143-145, comprising the CD3-zeta, CD28, CTLA-4, ICOS, BTLA, KIR, LAG3, CD137, OX40, CD27, CD40L, Tim-3, A2aR, or PD-1 transmembrane region.

147. An antibody capable of binding at least one neoantigenic peptide listed in Tables 1-9.

148. A modified cell transfected or transduced with the nucleic acid of any one of paragraphs 141-146.

149. The modified cell of paragraph 148, wherein the modified cell is a T cell, tumor infiltrating lymphocyte, NK-T cell, TCR-expressing cell, CD4+ T cell, CD8+ T cell, or NK cell.

150. A composition comprising the T cell receptor or chimeric antigen receptor of any of paragraphs 130-138.

151. A composition comprising autologous patient T cells containing the T cell receptor or chimeric antigen receptor of any of paragraphs 130-138.

152. The composition of paragraph 150 or 151, further comprising an immune checkpoint inhibitor.

153. The composition of paragraph 150 of 151, further comprising at least two immune checkpoint inhibitors.

154. The composition of paragraph 152 or 153, wherein the immune checkpoint inhibitor inhibits a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof.

155. The composition of paragraph 154, wherein the immune checkpoint inhibitor interacts with a ligand of a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof.

156. The composition of any of paragraphs 119-129 or 150-156, further comprising an immune modulator or adjuvant.

157. The composition of paragraph 156, wherein the immune modulator is a co-stimulatory ligand, a TNF ligand, an Ig superfamily ligand, CD28, CD80, CD86, ICOS, CD40L, OX40, CD27, GITR, CD30, DR3, CD69, or 4-1BB.

158. The composition of paragraph 156, wherein the immune modulator is at least one cancer cell or cancer cell extract.

159. The composition of paragraph 158, wherein the cancer cell is autologous to the subject in need of the composition.

160. The composition of paragraph 159, wherein the cancer cell has undergone lysis or been exposed to UV radiation.

161. The composition of paragraph 156, wherein the composition further comprises an adjuvant.

162. The composition of paragraph 161, wherein the adjuvant is selected from the group consisting of: Poly(I:C), Poly-ICLC, STING agonist, 1018 ISS, aluminium salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312 VG, Montanide ISA 206 VG, Montanide ISA 50 V2, Montanide ISA 51 VG, OK-432, OM-174, OM-197-MP-EC, ISA-TLR2 agonist, ONTAK, PepTel®. vector system, PLG microparticles, resiquimod, SRL172, virosomes and other virus-like particles, YF-17D, VEGF trap, R848, beta-glucan, Pam3Cys, Pam3CSK4, acrylic or methacrylic polymers, copolymers of maleic anhydride, and QS21 stimulon.

163. The composition of paragraph 161 or 162, wherein the adjuvant induces a humoral immune response when administered to a subject.

164. The composition of paragraph 162, wherein the adjuvant induces a T helper cell type I response when administered to a subject.

165. An in vivo delivery system comprising the pharmaceutical composition of any of paragraphs 30-103.

166. The delivery system of paragraph 165, wherein the delivery system includes cell-penetrating peptides, nanoparticulate encapsulation, virus like particles, or liposomes.

167. The delivery system of paragraph 166, wherein the cell-penetrating peptide is TAT peptide, herpes simplex virus VP22, transportan, or Antp.

168. A cell comprising the isolated neoantigenic peptide of any of paragraphs 1-29.

169. The cell of paragraph 168, which is an antigen presenting cell.

170. The cell of paragraph 169, which is a dendritic cell.

171. A method of treating cancer or initiating, enhancing, or prolonging an anti-tumor responses in a subject in need thereof comprising administering to the subject the peptide, polynucleotide, vector, composition, antibody, or cells of any of paragraphs 1-164.

172. A method of prophylactic cancer treatment comprising:
(a) selecting a cancer drug for a patient in need thereof, the drug selected from the group consisting of ibrutinib, erlotinib, imatinib, gefitinib, crizotinib, trastuzumab, vemurafenib, RAF/MEK inhibitors, and antiestrogen therapy, and (b) administering prophylactically to the subject, a pharmaceutical composition according to any of paragraphs 30-103 wherein the at least one neoantigenic peptide is derived from drug resistant mutations associated with the selected cancer drug.

173. A method of treating or preventing a tumor in a population of subjects in need thereof, comprising administering to a subject an agent comprising an extracellular ligand-binding domain recognizing a tumor-specific neoepitope comprising a tumor-specific mutation having an incidence of at least 1% of subjects in the population.

174. The method according to any of paragraphs 171-173, wherein the tumor-specific mutation comprises a mutation listed for any population in Table 9.

175. The method according to any of paragraphs 171-173, wherein the tumor-specific mutation is within a gene containing an extracellular domain.

176. The method according to paragraph 175, wherein the tumor-specific mutation comprises FGFR3 S249C, ERBB3 V104M, EGFR L858R, MUC4 H4205Q, PDGFRA R483fs, TMEM52 23_26LLPL>L, or PODXL 28_30PSP>P.

177. The method according to paragraph 176, wherein the tumor-specific mutation is within the extracellular domain.

178. The method according to paragraph 177, wherein the tumor-specific mutation comprises FGFR3 S249C or ERBB3 V104M.

179. The method of any of paragraph 171-178, wherein the subject is a human.

180. The method of paragraph 179, wherein the subject has cancer.

181. The method of paragraph 180, wherein the cancer is selected from the group consisting of urogenital, gynecological, lung, gastrointestinal, head and neck cancer, malignant glioblastoma, malignant mesothelioma, non-metastatic or metastatic breast cancer, malignant melanoma, Merkel Cell Carcinoma or bone and soft tissue sarcomas, haematologic neoplasias, multiple myeloma, acute myelogenous leukemia, chronic myelogenous leukemia, myelodysplastic syndrome and acute lymphoblastic leukemia, non-small cell lung cancer (NSCLC), breast cancer, metastatic colorectal cancers, hormone sensitive or hormone refractory prostate cancer, colorectal cancer, ovarian cancer, hepatocellular cancer, renal cell cancer, pancreatic cancer, gastric cancer, oesophageal cancers, hepatocellular cancers, cholangiocellular cancers, head and neck squamous cell cancer soft tissue sarcoma, and small cell lung cancer.

182. The method of any of paragraphs 171-181, wherein the subject has undergone surgical removal of the tumor.

183. The method of any of paragraphs 171-182, wherein the peptide, polynucleotide, vector, composition, or cells is administered via intravenous, intraperitoneal, intratumoral, intradermal, or subcutaneous administration.

184. The method of paragraph 183, wherein the peptide, polynucleotide, vector, composition, or cells is administered into an anatomic site that drains into a lymph node basin.

185. The method of paragraph 184, wherein administration is into multiple lymph node basins.

186. The method of any one of paragraphs 183-185, wherein administration is by a subcutaneous or intradermal route.

187. The method of paragraph 183, wherein peptide is administered.

188. The method of paragraph 187, wherein administration is intratumorally.

189. The method of paragraph 183, wherein polynucleotide, optionally RNA, is administered.

190. The method of paragraph 189, wherein the polynucleotide is administered intravenously.

191. The method of paragraph 183, wherein the cell is a T cell or dendritic cell.

192. The method of paragraph 191, wherein the peptide or polynucleotide comprises an antigen presenting cell targeting moiety.

193. The method of any of paragraphs 171-192, further comprising administering at least one immune checkpoint inhibitor to the subject.

194. The method of paragraph 193, wherein the checkpoint inhibitor is a biologic therapeutic or a small molecule.

195. The method of paragraph 193 or 194, wherein the checkpoint inhibitor is selected from the group consisting of a monoclonal antibody, a humanized antibody, a fully human antibody and a fusion protein or a combination thereof.

196. The method of any of paragraphs 193-195, wherein the checkpoint inhibitor inhibits a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof.

197. The method of any of paragraphs 193-196, wherein the checkpoint inhibitor interacts with a ligand of a checkpoint protein selected from the group consisting of CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, and B-7 family ligands or a combination thereof.

198. The method of any of paragraphs 193-197, wherein two or more checkpoint inhibitors are administered.

199. The method of paragraph 198, wherein the checkpoint inhibitors are: (i) ipilimumab or tremelimumab, and (ii) nivolumab.

200. The method of any of paragraphs 193-199, wherein the checkpoint inhibitor and the composition are administered simultaneously or sequentially in any order.

201. The method of paragraph 200, wherein the peptide, polynucleotide, vector, composition, or cells is administered prior to the checkpoint inhibitor.

202. The method of paragraph 200, wherein the peptide, polynucleotide, vector, composition, or cells is administered after the checkpoint inhibitor.

203. The method of paragraph 200, wherein administration of the checkpoint inhibitor is continued throughout neoantigen peptide, polynucleotide, vector, composition, or cell therapy.

204. The method of any of paragraphs 193-203, wherein the neoantigen peptide, polynucleotide, vector, composition, or cell therapy is administered to subjects that only partially respond or do not respond to checkpoint inhibitor therapy.

205. The method of any one of paragraphs 193-204, wherein the checkpoint inhibitor is administered intravenously or subcutaneously.

206. The method of paragraph 205, wherein the checkpoint inhibitor is administered subcutaneously within about 2 cm of the site of administration of the composition.

207. The method of paragraph 206, wherein the composition is administered into the same draining lymph node as the checkpoint inhibitor.

208. The method of any of paragraphs 171-207, further comprising administering an additional therapeutic agent to the subject either prior to, simultaneously with, or after treatment with the peptide, polynucleotide, vector, composition, or cells.

209. The method of paragraph 208, wherein the additional agent is a chemotherapeutic agent, an immunomodulatory drug, an immune metabolism modifying drug, a targeted therapy, radiation an anti-angiogenesis agent, or an agent that reduces immune-suppression.

210. The method of paragraph 209, wherein the chemotherapeutic agent is an alkylating agent, a topoisomerase inhibitor, an anti-metabolite, or an anti-mitotic agent.

211. The method of paragraph 208, wherein the additional agent is an anti-glucocorticoid induced tumor necrosis factor family receptor (GITR) agonistic antibody or antibody fragment, ibrutinib, docetaxeol, cisplatin, or cyclophosphamide.

212. The method of any of paragraphs 171-211, which elicits a CD4+ T cell immune response.

213. The method of any of paragraphs 171-212, which elicits a CD4+ T cell immune response and a CD8+ T cell immune response.

214. A method for stimulating an immune response in a subject, comprising administering an effective amount of modified cells or composition of any of paragraphs 30-103, 108, 115-129, 139, 140, 148-164, and 168-170.

215. The method of paragraph 214, wherein the immune response is cytotoxic and/or humoral immune response.

216. The method of paragraph 214, wherein the method stimulates a T cell-mediated immune response in a subject.

217. The method of paragraph 216, wherein the T cell-mediated immune response is directed against a target cell.

218. The method of paragraph 217, wherein the target cell is a tumor cell.

219. The method of any of paragraphs 214-218, wherein the modified cells are transfected or transduced in vivo.

220. The method of any of paragraphs 214-219, wherein the modified cells are transfected or transduced ex vivo.

221. The method of any of paragraphs 214-220, wherein the modified cells are autologous patient T cells.

222. The method of paragraph 221, wherein the autologous patient T cells are obtained from a patient that has received a neoantigen peptide or nucleic acid vaccine.

223. The method of paragraph 222, wherein the neoantigen peptide or nucleic acid vaccine comprises at least one personalized neoantigen.

224. The method of paragraph 223, wherein the neoantigen peptide or nucleic acid vaccine comprises at least one additional neoantigenic peptide listed in Tables 1-9.

225. The method of paragraph 224, wherein the patient received a chemotherapeutic agent, an immunomodulatory drug, an immune metabolism modifying drug, targeted therapy or radiation prior to and/or during receipt of the neoantigen peptide or nucleic acid vaccine.

226. The method of any of paragraphs 222-225, wherein the patient receives treatment with at least one checkpoint inhibitor.

227. The method of any of paragraphs 222-226, wherein the autologous T cells are obtained from a patient that has already received at least one round of T cell therapy containing a neoantigen.

228. The method of any of paragraphs 222-227, wherein the method further comprises adoptive T cell therapy.

229. The method of paragraph 228, wherein the adoptive T cell therapy comprises autologous T-cells.

230. The method of paragraph 229, wherein the autologous T-cells are targeted against tumor antigens.

231. The method of paragraph 228 or 229 wherein the adoptive T cell therapy further comprises allogenic T-cells.

232. The method of paragraph 231, wherein the allogenic T-cells are targeted against tumor antigens.

233. The method of any of paragraphs 227-231, wherein the adoptive T cell therapy is administered before the checkpoint inhibitor.

234. A method for evaluating the efficacy of any of paragraphs 171-213, comprising: (i) measuring the number or concentration of target cells in a first sample obtained from the subject before administering the modified cell, (ii) measuring the number concentration of target cells in a second sample obtained from the subject after administration of the modified cell, and (iii) determining an increase or decrease of the number or concentration of target cells in the second sample compared to the number or concentration of target cells in the first sample.

235. The method of paragraph 234, wherein treatment efficacy is determined by monitoring a clinical outcome; an increase, enhancement or prolongation of anti-tumor activity by T cells; an increase in the number of anti-tumor T cells or activated T cells as compared with the number prior to treatment; B cell activity; CD4 T cell activity; or a combination thereof.

236. The method of paragraph 235, wherein treatment efficacy is determined by monitoring a biomarker.

237. The method of paragraph 236, wherein the biomarker is selected from the group consisting of CEA, Her-2/neu, bladder tumor antigen, thyroglobulin, alpha-fetoprotein, PSA, CA 125, CA19.9, CA 15.3, leptin, prolactin, osteopontin, IGF-II, CD98, fascin, sPIgR, 14-3-3 eta, troponin I, and b-type natriuretic peptide.

238. The method of paragraph 235, wherein clinical outcome is selected from the group consisting of tumor regression; tumor shrinkage; tumor necrosis; anti-tumor response by the immune system; tumor expansion, recurrence or spread; or a combination thereof.

239. The method of paragraph 235, wherein the treatment effect is predicted by presence of T cells or by presence of a gene signature indicating T cell inflammation or a combination thereof.

240. A kit comprising a neoantigen therapeutic of any of paragraphs 1-164.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Nothing herein is intended as a promise.

These and other embodiments are disclosed or are obvious from and encompassed by, the following Detailed Description.

DETAILED DESCRIPTION OF THE INVENTION

To facilitate an understanding of the present invention, a number of terms and phrases are defined herein:

Unless specifically stated or obvious from context, as used herein, the term "about" is understood as within a range of normal tolerance in the art, for example within 2 standard deviations of the mean. About can be understood as within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Unless specifically stated or obvious from context, as used herein, the term "or" is understood to be inclusive. Unless specifically stated or obvious from context, as used herein, the terms "a," "an," and "the" are understood to be singular or plural.

All gene name symbols refer to the gene as commonly known in the art. Gene symbols may be those referred to by the HUGO Gene Nomenclature Committee (HGNC). Any reference to the gene symbol is a reference made to the entire gene or variants of the gene. The HUGO Gene Nomenclature Committee is responsible for providing human gene naming guidelines and approving new, unique human gene names and symbols. All human gene names and symbols can be searched at www.genenames.org, the HGNC website, and the guidelines for their formation are available there (www.genenames.org/guidelines).

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease (e.g., a neoplasia, tumor, etc.).

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "analog" is meant a molecule that is not identical, but has analogous functional or structural features. For example, a tumor specific neo-antigen polypeptide analog retains the biological activity of a corresponding naturally-occurring tumor specific neo-antigen polypeptide, while having certain biochemical modifications that enhance the analog's function relative to a naturally-occurring polypeptide. Such biochemical modifications could increase the analog's protease resistance, membrane permeability, or half-life, without altering, for example, ligand binding. An analog may include an unnatural amino acid.

"Combination therapy" is intended to embrace administration of therapeutic agents (e.g. neoantigenic peptides described herein) in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. For example, one combination of the present invention may comprise a pooled sample of neoantigenic peptides administered at the same or different times, or they can be formulated as a single, co-formulated pharmaceutical composition comprising the peptides. As another example, a combination of the present invention (e.g., a pooled sample of tumor specific neoantigens) may be formulated as separate pharmaceutical compositions that can be administered at the same or different time. As used herein, the term "simultaneously" is meant to refer to administration of one or more agents at the same time. For example, in certain embodiments, the neoantigenic peptides are administered simultaneously. Simultaneously includes administration contemporaneously, that is during the same period of time. In certain embodiments, the one or more agents are administered simultaneously in the same hour, or simultaneously in the same day. Sequential or substantially simultaneous administration of each therapeutic agent can be effected by any appropriate route including, but not limited to, oral routes, intravenous routes, sub-cutaneous routes, intramuscular routes, direct absorption through mucous membrane tissues (e.g., nasal, mouth, vaginal, and rectal), and ocular routes (e.g., intravitreal, intraocular, etc.). The therapeutic agents can be administered by the same route or by different routes. For example, one component of a particular combination may be administered by intravenous injection while the other component(s) of the combination may be administered orally. The components may be administered in any therapeutically effective sequence. The phrase "combination" embraces groups of compounds or non-drug therapies useful as part of a combination therapy.

The term "neoantigen" or "neoantigenic" means a class of tumor antigens that arises from a tumor-specific mutation(s) which alters the amino acid sequence of genome encoded proteins.

By "neoplasia" is meant any disease that is caused by or results in inappropriately high levels of cell division, inappropriately low levels of apoptosis, or both. For example, cancer is an example of a neoplasia. Examples of cancers include, without limitation, leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). Lymphoproliferative disorders are also considered to be proliferative diseases.

The term "vaccine" is meant to refer in the present context to a pooled sample of tumor-specific neoantigenic peptides, for example at least two, at least three, at least four, at least five, or more neoantigenic peptides. A "vaccine" is to be understood as meaning a composition for generating immunity for the prophylaxis and/or treatment of diseases (e.g., neoplasia/tumor). Accordingly, vaccines are medicaments which comprise antigens and are intended to be used in humans or animals for generating specific defense and protective substance by vaccination. A "vaccine composition" can include a pharmaceutically acceptable excipient, carrier or diluent.

The term "pharmaceutically acceptable" refers to approved or approvable by a regulatory agency of the Federal or a state government or listed in the U.S. Pharmacopeia or other generally recognized pharmacopeia for use in animals, including humans.

A "pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" of pooled tumor specific neoantigens as recited herein may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH2)n-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts for the pooled tumor specific neoantigens provided herein, including those listed by Remington's Pharmaceutical Sciences, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

By a "polypeptide" or "peptide" is meant a polypeptide that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide. An isolated polypeptide may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein, the terms "prevent," "preventing," "prevention," "prophylactic treatment," and the like, refer to reducing the probability of developing a disease or condition in a subject, who does not have, but is at risk of or susceptible to developing a disease or condition.

The term "prime/boost" or "prime/boost dosing regimen" is meant to refer to the successive administrations of a vaccine or immunogenic or immunological compositions. The priming administration (priming) is the administration of a first vaccine or immunogenic or immunological composition type and may comprise one, two or more administrations. The boost administration is the second administration of a vaccine or immunogenic or immunological composition type and may comprise one, two or more administrations, and, for instance, may comprise or consist essentially of annual administrations. In certain embodiments, administration of the neoplasia vaccine or immunogenic composition is in a prime/boost dosing regimen.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

A "receptor" is to be understood as meaning a biological molecule or a molecule grouping capable of binding a ligand. A receptor may serve, to transmit information in a cell, a cell formation or an organism. The receptor comprises at least one receptor unit and frequently contains two or more receptor units, where each receptor unit may consist of a protein molecule, in particular a glycoprotein molecule. The receptor has a structure that complements the structure of a ligand and may complex the ligand as a binding partner. Signaling information may be transmitted by conformational changes of the receptor following binding with the ligand on the surface of a cell. According to the invention, a receptor may refer to particular proteins of MHC classes I and II capable of forming a receptor/ligand complex with a ligand, in particular a peptide or peptide fragment of suitable length.

The term "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

The terms "treat," "treated," "treating," "treatment," and the like are meant to refer to reducing or ameliorating a disorder and/or symptoms associated therewith (e.g., a neoplasia or tumor). "Treating" may refer to administration of the therapy to a subject after the onset, or suspected onset, of a cancer. "Treating" includes the concepts of "alleviating", which refers to lessening the frequency of occurrence or recurrence, or the severity, of any symptoms or other ill effects related to a cancer and/or the side effects associated with cancer therapy. The term "treating" also encompasses the concept of "managing" which refers to reducing the severity of a particular disease or disorder in a patient or delaying its recurrence, e.g., lengthening the period of remission in a patient who had suffered from the disease. It is appreciated that, although not precluded, treating a disorder or condition does not require that the disorder, condition, or symptoms associated therewith be completely eliminated.

The term "therapeutic effect" refers to some extent of relief of one or more of the symptoms of a disorder (e.g., a neoplasia or tumor) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved.

The terms "spacer" or "linker" as used in reference to a fusion protein refers to a peptide that joins the proteins comprising a fusion protein. Generally, a spacer has no specific biological activity other than to join or to preserve some minimum distance or other spatial relationship between the proteins or RNA sequences. However, in certain embodiments, the constituent amino acids of a spacer may be selected to influence some property of the molecule such as the folding, net charge, or hydrophobicity of the molecule.

Suitable linkers for use in an embodiment of the present invention are well known to those of skill in the art and include, but are not limited to, straight or branched-chain carbon linkers, heterocyclic carbon linkers, or peptide linkers. The linker is used to separate two neoantigenic peptides by a distance sufficient to ensure that, in a preferred embodiment, each neoantigenic peptide properly folds. Preferred peptide linker sequences adopt a flexible extended conformation and do not exhibit a propensity for developing an ordered secondary structure. Typical amino acids in flexible protein regions include Gly, Asn and Ser. Virtually any permutation of amino acid sequences containing Gly, Asn and Ser would be expected to satisfy the above criteria for a linker sequence. Other near neutral amino acids, such as Thr and Ala, also may be used in the linker sequence. Still other amino acid sequences that may be used as linkers are disclosed in Maratea et al. (1985), Gene 40: 39-46; Murphy et al. (1986) Proc. Nat'l. Acad. Sci. USA 83: 8258-62; U.S. Pat. Nos. 4,935,233; and 4,751,180.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The therapy disclosed herein constitutes a new method for treating various types of cancer. The therapy described herein also provides a method of therapy for achieving clinical benefit without an unacceptable level of side effects.

In one aspect the present invention relates to methods for the treatment of neoplasia, and more particularly tumors, by administering to a subject a vaccine or immunogenic composition comprising a plurality of tumor specific neoantigenic peptides. As described in more detail herein, in some embodiments the composition provides a specific, optimized subset of tumor-specific neoantigens suitable for the treatment of tumors in a high proportion of subjects suffering from cancer. In some embodiments, the tumor specific neoantigens may together bind to a high overall proportion of HLA allotypes present in the subject population.

The immune system can be classified into two functional subsystems: the innate and the acquired immune system. The innate immune system is the first line of defense against infections, and most potential pathogens are rapidly neutralized by this system before they can cause, for example, a noticeable infection. The acquired immune system reacts to molecular structures, referred to as antigens, of the intruding organism. There are two types of acquired immune reactions, which include the humoral immune reaction and the cell-mediated immune reaction. In the humoral immune reaction, antibodies secreted by B cells into bodily fluids bind to pathogen-derived antigens, leading to the elimination of the pathogen through a variety of mechanisms, e.g. complement-mediated lysis. In the cell-mediated immune reaction, T-cells capable of destroying other cells are activated. For example, if proteins associated with a disease are present in a cell, they are fragmented proteolytically to peptides within the cell. Specific cell proteins then attach themselves to the antigen or peptide formed in this manner and transport them to the surface of the cell, where they are presented to the molecular defense mechanisms, in particular T-cells, of the body. Cytotoxic T cells recognize these antigens and kill the cells that harbor the antigens.

The molecules that transport and present peptides on the cell surface are referred to as proteins of the major histocompatibility complex (MHC). MHC proteins are classified into two types, referred to as MHC class I and MHC class II. The structures of the proteins of the two MHC classes are very similar; however, they have very different functions. Proteins of MHC class I are present on the surface of almost all cells of the body, including most tumor cells. MHC class I proteins are loaded with antigens that usually originate from endogenous proteins or from pathogens present inside cells, and are then presented to naïve or cytotoxic T-lymphocytes (CTLs). MHC class II proteins are present on dendritic cells, B-lymphocytes, macrophages and other antigen-presenting cells. They mainly present peptides, which are processed from external antigen sources, i.e. outside of the cells, to T-helper (Th) cells. Most of the peptides bound by the MHC class I proteins originate from cytoplasmic proteins produced in the healthy host cells of an organism itself, and do not normally stimulate an immune reaction. Accordingly, cytotoxic T-lymphocytes that recognize such self-peptide-presenting MHC molecules of class I are deleted in the thymus (central tolerance) or, after their release from the thymus, are deleted or inactivated, i.e. tolerized (peripheral tolerance). MHC molecules are capable of stimulating an immune reaction when they present peptides to non-tolerized T-lymphocytes. Cytotoxic T-lymphocytes have both T-cell receptors (TCR) and CD8 molecules on their surface. T-Cell receptors are capable of recognizing and binding peptides complexed with the molecules of MHC class I. Each cytotoxic T-lymphocyte expresses a unique T-cell receptor which is capable of binding specific MHC/peptide complexes.

The peptide antigens attach themselves to the molecules of MHC class I by competitive affinity binding within the endoplasmic reticulum, before they are presented on the cell surface. Here, the affinity of an individual peptide antigen is directly linked to its amino acid sequence and the presence of specific binding motifs in defined positions within the amino acid sequence. If the sequence of such a peptide is known, it is possible to manipulate the immune system against diseased cells using, for example, peptide vaccines.

One of the critical barriers to developing curative and tumor-specific immunotherapy is the identification and selection of highly specific and restricted tumor antigens to avoid autoimmunity. Tumor neoantigens, which arise as a result of genetic change (e.g., inversions, translocations, deletions, missense mutations, splice site mutations, etc.) within malignant cells, represent the most tumor-specific class of antigens. Neoantigens have rarely been used in cancer vaccine or immunogenic compositions due to technical difficulties in identifying them, selecting optimized neoantigens, and producing neoantigens for use in a vaccine or immunogenic composition. These problems may be addressed by:

identifying mutations in neoplasias/tumors which are present at the DNA level in tumor but not in matched germline samples from a high proportion of subjects having cancer;

analyzing the identified mutations with one or more peptide-MHC binding prediction algorithms to generate a plurality of neoantigen T cell epitopes that are expressed within the neoplasia/tumor and that bind to a high proportion of patient HLA alleles; and synthesizing the plurality of neoantigenic peptides selected from the sets of all neoantigen peptides and predicted binding peptides for use in a cancer vaccine or immunogenic composition suitable for treating a high proportion of subjects having cancer.

For example, translating sequencing information into a therapeutic vaccine may include:

(1) Prediction of mutated peptides that can bind to HLA molecules of a high proportion of individuals. Efficiently choosing which particular mutations to utilize as immunogen requires the ability to predict which mutated peptides would efficiently bind to a high proportion of patient's HLA alleles. Recently, neural network based learning approaches with validated binding and non-binding peptides have advanced the accuracy of prediction algorithms for the major HLA-A and -B alleles.

(2) Formulating the drug as a multi-epitope vaccine of long peptides. Targeting as many mutated epitopes as practically possible takes advantage of the enormous capacity of the immune system, prevents the opportunity for immunological escape by down-modulation of a particular immune targeted gene product, and compensates for the known inaccuracy of epitope prediction approaches. Synthetic peptides provide a particularly useful means to prepare multiple immunogens efficiently and to rapidly translate identification of mutant epitopes to an effective vaccine. Peptides can be readily synthesized chemically and easily purified utilizing reagents free of contaminating bacteria or animal substances. The small size allows a clear focus on the mutated region of the protein and also reduces irrelevant antigenic competition from other components (unmutated protein or viral vector antigens).

(3) Combination with a strong vaccine adjuvant. Effective vaccines require a strong adjuvant to initiate an immune response. As described below, poly-ICLC, an agonist of TLR3 and the RNA helicase-domains of MDA5 and RIG3, has shown several desirable properties for a vaccine adjuvant. These properties include the induction of local and systemic activation of immune cells in vivo, production of stimulatory chemokines and cytokines, and stimulation of antigen-presentation by DCs. Furthermore, poly-ICLC can induce durable CD4+ and CD8+ responses in humans. Importantly, striking similarities in the upregulation of transcriptional and signal transduction pathways were seen in subjects vaccinated with poly-ICLC and in volunteers who had received the highly effective, replication-competent yellow fever vaccine. Furthermore, >90% of ovarian carcinoma patients immunized with poly-ICLC in combination with a NYES0-1 peptide vaccine (in addition to Montanide) showed induction of CD4+ and CD8+ T cell, as well as antibody responses to the peptide in a recent phase 1 study. At the same time, polyICLC has been extensively tested in more than 25 clinical trials to date and exhibited a relatively benign toxicity profile.

The above-described advantages of the invention are described further herein.

As described herein, there is a large body of evidence in both animals and humans that mutated epitopes are effective in inducing an immune response and that cases of spontaneous tumor regression or long term survival correlate with CD8+ T-cell responses to mutated epitopes (Buckwalter and Srivastava P K. "It is the antigen(s), stupid" and other lessons from over a decade of vaccitherapy of human cancer. Seminars in immunology 20:296-300 (2008); Karanikas et al, High frequency of cytolytic T lymphocytes directed against a tumor-specific mutated antigen detectable with HLA tetramers in the blood of a lung carcinoma patient with long survival. Cancer Res. 61:3718-3724 (2001); Lennerz et al, The response of autologous T cells to a human melanoma is dominated by mutated neoantigens. Proc Natl Acad Sci USA. 102:16013 (2005)) and that "immunoediting" can be tracked to alterations in expression of dominant mutated antigens in mice and man (Matsushita et al, Cancer exome analysis reveals a T-cell-dependent mechanism of cancer immunoediting Nature 482:400 (2012); DuPage et al, Expression of tumor-specific antigens underlies cancer immunoediting Nature 482:405 (2012); and Sampson et al, Immunologic escape after prolonged progression-free survival with epidermal growth factor receptor variant III peptide vaccination in patients with newly diagnosed glioblastoma J Clin Oncol. 28:4722-4729 (2010)).

Sequencing technology has revealed that each tumor contains multiple, patient-specific mutations that alter the protein coding content of a gene. Such mutations create altered proteins, ranging from single amino acid changes (caused by missense mutations) to addition of long regions of novel amino acid sequence due to frame shifts, read-through of termination codons or translation of intron regions (novel open reading frame mutations; neoORFs). These mutated proteins are valuable targets for the host's immune response to the tumor as, unlike native proteins, they are not subject to the immune-dampening effects of self-tolerance. Therefore, mutated proteins are more likely to be immunogenic and are also more specific for the tumor cells compared to normal cells of the patient.

In one embodiment, the neoantigenic peptides in the composition together have affinity to a plurality of MHC molecules, e.g. which together cover a large proportion of the target population. Efficiently choosing which particular mutations to utilize as immunogen requires the ability to predict which mutated peptides would efficiently bind to the HLA alleles present in the patient population. Recently, neural network based learning approaches with validated binding and non-binding peptides have advanced the accuracy of prediction algorithms for the major HLA-A and -B alleles. Utilizing the recently improved algorithms for predicting which missense mutations create strong binding peptides to cognate MHC molecules, a set of peptides representative of optimal mutated epitopes (both neoORF and missense) for the patient population may be identified and prioritized (Zhang et al, Machine learning competition in immunology—Prediction of HLA class I binding peptides J Immunol Methods 374:1 (2011); Lundegaard et al Prediction of epitopes using neural network based methods J Immunol Methods 374:26 (2011)).

Targeting as many mutated epitopes as practically possible takes advantage of the enormous capacity of the immune system, prevents the opportunity for immunological escape by down-modulation of a particular immune targeted gene product, and compensates for the known inaccuracy of epitope prediction approaches. Synthetic peptides provide a particularly useful means to prepare multiple immunogens efficiently and to rapidly translate identification of mutant epitopes to an effective vaccine or immunogenic composition. Peptides can be readily synthesized chemically and easily purified utilizing reagents free of contaminating bacteria or animal substances. The small size allows a clear focus on the mutated region of the protein and also reduces irrelevant antigenic competition from other components (unmutated protein or viral vector antigens).

In one embodiment the drug formulation is a multi-epitope vaccine or immunogenic composition of long peptides. Such "long" peptides undergo efficient internalization, processing and cross-presentation in professional antigen-presenting cells such as dendritic cells, and have been shown to induce CTLs in humans (Melief and van der Burg, Immunotherapy of established (pre) malignant disease by synthetic long peptide vaccines Nature Rev Cancer 8:351 (2008)). In one embodiment at least 2 peptides are prepared for immunization. In some embodiments 20 or more peptides are prepared for immunization. In one embodiment the neoantigenic peptide ranges from about 5 to about 50 amino acids in length. In another embodiment peptides from about 15 to about 35 amino acids in length is synthesized. In preferred embodiment the neoantigenic peptide ranges from about 20 to about 35 amino acids in length.

Production of Tumor Specific Neoantigens

The present invention is based, at least in part, on the ability to present the immune system of the patient with a pool of tumor specific neoantigens. One of skill in the art from this disclosure and the knowledge in the art will appreciate that there are a variety of ways in which to produce such tumor specific neoantigens. In general, such tumor specific neoantigens may be produced either in vitro or in vivo. Tumor specific neoantigens may be produced in vitro as peptides or polypeptides, which may then be formulated into a neoplasia vaccine or immunogenic composition and administered to a subject. As described in further detail herein, such in vitro production may occur by a variety of methods known to one of skill in the art such as, for example, peptide synthesis or expression of a peptide/polypeptide from a DNA or RNA molecule in any of a variety of bacterial, eukaryotic, or viral recombinant expression systems, followed by purification of the expressed peptide/polypeptide. Alternatively, tumor specific neoantigens may be produced in vivo by introducing molecules (e.g., DNA, RNA, viral expression systems, and the like) that encode tumor specific neoantigens into a subject, whereupon the encoded tumor specific neoantigens are expressed. The methods of in vitro and in vivo production of neoantigens is also further described herein as it relates to pharmaceutical compositions and methods of delivery of the therapy.

In certain embodiments the present invention includes modified neoantigenic peptides. As used herein in reference to neoantigenic peptides, the terms "modified", "modification" and the like refer to one or more changes that enhance a desired property of the neoantigenic peptide, where the change does not alter the primary amino acid sequence of the neoantigenic peptide. "Modification" includes a covalent chemical modification that does not alter the primary amino acid sequence of the neoantigenic peptide itself. Such desired properties include, for example, prolonging the in vivo half-life, increasing the stability, reducing the clearance, altering the immunogenicity or allergenicity, enabling the raising of particular antibodies, cellular targeting, antigen uptake, antigen processing, MHC affinity, MHC stability, or antigen presentation. Changes to a neoantigenic peptide that may be carried out include, but are not limited to, conjugation to a carrier protein, conjugation to a ligand, conjugation to an antibody, PEGylation, polysialylation HESylation, recombinant PEG mimetics, Fc fusion, albumin fusion, nanoparticle attachment, nanoparticulate encapsulation, cholesterol fusion, iron fusion, acylation, amidation, glycosylation, side chain oxidation, phosphorylation, biotinylation, the addition of a surface active material, the addition of amino acid mimetics, or the addition of unnatural amino acids.

The clinical effectiveness of protein therapeutics is often limited by short plasma half-life and susceptibility to protease degradation. Studies of various therapeutic proteins (e.g., filgrastim) have shown that such difficulties may be overcome by various modifications, including conjugating or linking the polypeptide sequence to any of a variety of non-proteinaceous polymers, e.g., polyethylene glycol (PEG), polypropylene glycol, or polyoxyalkylenes (see, for example, typically via a linking moiety covalently bound to both the protein and the nonproteinaceous polymer, e.g., a PEG). Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

PEGs suitable for conjugation to a polypeptide sequence are generally soluble in water at room temperature, and have the general formula $R(0\text{-}CH_2\text{—}CH_2)_nO\text{—}R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, but certain embodiments have a molecular weight between 500 and 20,000 while other embodiments have a molecular weight between 4,000 and 10,000.

The present disclosure also contemplates compositions of conjugates wherein the PEGs have different n values and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. For example, cation exchange chromatography may be used to separate conjugates, and a fraction is then identified which contains the conjugate having, for example, the desired number of PEGs attached, purified free from unmodified protein sequences and from conjugates having other numbers of PEGs attached.

PEG may be bound to a polypeptide of the present disclosure via a terminal reactive group (a "spacer"). The spacer is, for example, a terminal reactive group which mediates a bond between the free amino or carboxyl groups of one or more of the polypeptide sequences and polyethylene glycol. The PEG having the spacer which may be bound to the free amino group includes N-hydroxysuccinylimide polyethylene glycol which may be prepared by activating succinic acid ester of polyethylene glycol with N-hydroxy succinylimide. Another activated polyethylene glycol which may be bound to a free amino group is 2,4-bis(O-methoxypolyethyleneglycol)-6-chloro-s-triazine which may be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH>7), and longer reaction time tend to increase the number of PEGs attached. Various means known in the art may be used to terminate the reaction. In some embodiments the reaction is terminated by acidifying the reaction mixture and freezing at, e.g., −20° C.

The present disclosure also contemplates the use of PEG Mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present. Glycosylation can dramatically affect the physical properties of proteins and can also be important in protein stability, secretion, and subcellular localization. Proper glycosylation can be essential for biological activity. In fact, some genes from eucaryotic organisms, when expressed in bacteria (e.g., *E. coli*) which lack cellular processes for glycosylating proteins, yield proteins that are recovered with little or no activity by virtue of their lack of glycosylation.

Addition of glycosylation sites can be accomplished by altering the amino acid sequence. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment of the present disclosure comprises the generation and use of N-glycosylation variants.

The polypeptide sequences of the present disclosure may optionally be altered through changes at the DNA level, particularly by mutating the DNA encoding the polypeptide at preselected bases such that codons are generated that will translate into the desired amino acids. Another means of increasing the number of carbohydrate moieties on the polypeptide is by chemical or enzymatic coupling of glycosides to the polypeptide.

Removal of carbohydrates may be accomplished chemically or enzymatically, or by substitution of codons encoding amino acid residues that are glycosylated. Chemical deglycosylation techniques are known, and enzymatic cleavage of carbohydrate moieties on polypeptides can be achieved by the use of a variety of endo- and exo-glycosidases.

Dihydrofolate reductase (DHFR)—deficient Chinese Hamster Ovary (CHO) cells are a commonly used host cell for the production of recombinant glycoproteins. These cells do not express the enzyme beta-galactoside alpha-2,6-sialyltransferase and therefore do not add sialic acid in the alpha-2,6 linkage to N-linked oligosaccharides of glycoproteins produced in these cells.

The present disclosure also contemplates the use of polysialylation, the conjugation of peptides and proteins to the naturally occurring, biodegradable a-(2-8) linked polysialic acid ("PSA") in order to improve their stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of activity in vivo activity, and reduction in immunogenicity and antigenicity (see, e.g., G. Gregoriadis et al., Int. J. Pharmaceutics 300(1-2): 125-30). As with modifications with other conjugates (e.g., PEG), various techniques for site-specific polysialylation are available (see, e.g., T. Lindhout et al., PNAS 108(18)7397-7402 (2011)).

Additional suitable components and molecules for conjugation include, for example, thyroglobulin; albumins such as human serum albumin (HAS); tetanus toxoid; Diphtheria toxoid; polyamino acids such as poly(D-lysine:D-glutamic acid): VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

Fusion of albumin to one or more polypeptides of the present disclosure can, for example, be achieved by genetic manipulation, such that the DNA coding for HSA, or a fragment thereof, is joined to the DNA coding for the one or more polypeptide sequences. Thereafter, a suitable host can be transformed or transfected with the fused nucleotide sequences in the form of, for example, a suitable plasmid, so as to express a fusion polypeptide. The expression may be effected in vitro from, for example, prokaryotic or eukaryotic cells, or in vivo from, for example, a transgenic organism. In some embodiments of the present disclosure, the expression of the fusion protein is performed in mammalian cell lines, for example, CHO cell lines. Transformation is used broadly herein to refer to the genetic alteration of a cell resulting from the direct uptake, incorporation and expression of exogenous genetic material (exogenous DNA) from its surroundings and taken up through the cell membrane(s). Transformation occurs naturally in some species of bacteria, but it can also be effected by artificial means in other cells.

Furthermore, albumin itself may be modified to extend its circulating half-life. Fusion of the modified albumin to one or more Polypeptides can be attained by the genetic manipulation techniques described above or by chemical conjugation; the resulting fusion molecule has a half-life that exceeds that of fusions with non-modified albumin. (See WO2011/051489).

Several albumin-binding strategies have been developed as alternatives for direct fusion, including albumin binding through a conjugated fatty acid chain (acylation). Because serum albumin is a transport protein for fatty acids, these natural ligands with albumin-binding activity have been used for half-life extension of small protein therapeutics. For example, insulin determir (LEVEMIR), an approved product for diabetes, comprises a myristyl chain conjugated to a genetically-modified insulin, resulting in a long-acting insulin analog.

Another type of modification is to conjugate (e.g., link) one or more additional components or molecules at the N- and/or C-terminus of a polypeptide sequence, such as another protein (e.g., a protein having an amino acid sequence heterologous to the subject protein), or a carrier molecule. Thus, an exemplary polypeptide sequence can be provided as a conjugate with another component or molecule.

A conjugate modification may result in a polypeptide sequence that retains activity with an additional or complementary function or activity of the second molecule. For example, a polypeptide sequence may be conjugated to a molecule, e.g., to facilitate solubility, storage, in vivo or shelf half-life or stability, reduction in immunogenicity, delayed or controlled release in vivo, etc. Other functions or activities include a conjugate that reduces toxicity relative to an unconjugated polypeptide sequence, a conjugate that targets a type of cell or organ more efficiently than an unconjugated polypeptide sequence, or a drug to further counter the causes or effects associated with a disorder or disease as set forth herein (e.g., diabetes).

A Polypeptide may also be conjugated to large, slowly metabolized macromolecules such as proteins; polysaccharides, such as sepharose, agarose, cellulose, cellulose beads; polymeric amino acids such as polyglutamic acid, polylysine; amino acid copolymers; inactivated virus particles; inactivated bacterial toxins such as toxoid from diphtheria, tetanus, cholera, leukotoxin molecules; inactivated bacteria; and dendritic cells.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Purification methods such as cation exchange chromatography may be used to separate conjugates by charge difference, which effectively separates conjugates into their various molecular weights. For example, the cation exchange column can be loaded and then washed with ~20 mM sodium acetate, pH ~4, and then eluted with a linear (0 M to 0.5 M) NaCl gradient buffered at a pH from about 3 to 5.5, e.g., at pH ~4.5. The content of the fractions obtained by cation exchange chromatography may be identified by molecular weight using conventional methods, for example, mass spectroscopy, SDS-PAGE, or other known methods for separating molecular entities by molecular weight.

In certain embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product may require less frequent administration.

Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

The present disclosure contemplates the use of other modifications, currently known or developed in the future, of the Polypeptides to improve one or more properties. One such method for prolonging the circulation half-life, increasing the stability, reducing the clearance, or altering the immunogenicity or allergenicity of a polypeptide of the present disclosure involves modification of the polypeptide sequences by hesylation, which utilizes hydroxyethyl starch derivatives linked to other molecules in order to modify the molecule's characteristics. Various aspects of hesylation are described in, for example, U.S. Patent Appln. Nos. 2007/0134197 and 2006/0258607.

In Vitro Peptide/Polypeptide Synthesis

Proteins or peptides may be made by any technique known to those of skill in the art, including the expression of proteins, polypeptides or peptides through standard molecular biological techniques, the isolation of proteins or peptides from natural sources, in vitro translation, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and Gen-Pept databases located at the National Institutes of Health website. The coding regions for known genes may be amplified and/or expressed using the techniques disclosed herein or as would be known to those of ordinary skill in the art. Alternatively, various commercial preparations of proteins, polypeptides and peptides are known to those of skill in the art.

Peptides can be readily synthesized chemically utilizing reagents that are free of contaminating bacterial or animal substances (Merrifield RB: Solid phase peptide synthesis. I. The synthesis of a tetrapeptide. J. Am. Chem. Soc. 85:2149-54, 1963). In certain embodiments, neoantigenic peptides are prepared by (1) parallel solid-phase synthesis on multichannel instruments using uniform synthesis and cleavage conditions; (2) purification over a RP-HPLC column with column stripping; and re-washing, but not replacement, between peptides; followed by (3) analysis with a limited set of the most informative assays. The Good Manufacturing Practices (GMP) footprint can be defined around the set of peptides for an individual patient, thus requiring suite changeover procedures only between syntheses of peptides for different patients.

Alternatively, a nucleic acid (e.g., a polynucleotide) encoding a neoantigenic peptide of the invention may be used to produce the neoantigenic peptide in vitro. The polynucleotide may be, e.g., DNA, cDNA, PNA, CNA, RNA, either single- and/or double-stranded, or native or stabilized forms of polynucleotides, such as e.g. polynucleotides with a phosphorothiate backbone, or combinations thereof and it may or may not contain introns so long as it codes for the peptide. In one embodiment in vitro translation is used to produce the peptide. Many exemplary systems exist that one skilled in the art could utilize (e.g., Retic Lysate IVT Kit, Life Technologies, Waltham, Mass.).

An expression vector capable of expressing a polypeptide can also be prepared. Expression vectors for different cell types are well known in the art and can be selected without undue experimentation. Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host (e.g., bacteria), although such controls are generally available in the expression vector. The vector is then introduced into the host bacteria for cloning using standard techniques (see, e.g., Sambrook et al. (1989) Molecular Cloning, A Laboratory Manual, Cold Spring Harbor Laboratory, Cold Spring Harbor, N.Y.).

Expression vectors comprising the isolated polynucleotides, as well as host cells containing the expression vectors, are also contemplated. The neoantigenic peptides may be provided in the form of RNA or cDNA molecules encoding the desired neoantigenic peptides. One or more neoantigenic peptides of the invention may be encoded by a single expression vector.

The term "polynucleotide encoding a polypeptide" encompasses a polynucleotide which includes only coding sequences for the polypeptide as well as a polynucleotide which includes additional coding and/or non-coding sequences. Polynucleotides can be in the form of RNA or in the form of DNA. DNA includes cDNA, genomic DNA, and synthetic DNA; and can be double-stranded or single-stranded, and if single stranded can be the coding strand or non-coding (anti-sense) strand.

In embodiments, the polynucleotides may comprise the coding sequence for the tumor specific neoantigenic peptide fused in the same reading frame to a polynucleotide which aids, for example, in expression and/or secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide.

In embodiments, the polynucleotides can comprise the coding sequence for the tumor specific neoantigenic peptide fused in the same reading frame to a marker sequence that allows, for example, for purification of the encoded polypeptide, which may then be incorporated into the personalized neoplasia vaccine or immunogenic composition. For example, the marker sequence can be a hexa-histidine tag (SEQ ID NO: 33733) supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like.

In embodiments, the polynucleotides may comprise the coding sequence for one or more of the tumor specific neoantigenic peptides fused in the same reading frame to create a single concatamerized neoantigenic peptide construct capable of producing multiple neoantigenic peptides.

In certain embodiments, isolated nucleic acid molecules having a nucleotide sequence at least 60% identical, at least 65% identical, at least 70% identical, at least 75% identical, at least 80% identical, at least 85% identical, at least 90% identical, at least 95% identical, or at least 96%, 97%, 98% or 99% identical to a polynucleotide encoding a tumor specific neoantigenic peptide of the present invention, can be provided.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 970%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The isolated tumor specific neoantigenic peptides described herein can be produced in vitro (e.g., in the laboratory) by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest is produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (e.g., by synthesis, site-directed mutagenesis, or another method), the polynucleotide sequences encoding a particular isolated polypeptide of interest is inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host.

Recombinant expression vectors may be used to amplify and express DNA encoding the tumor specific neoantigenic peptides. Recombinant expression vectors are replicable DNA constructs which have synthetic or cDNA-derived DNA fragments encoding a tumor specific neoantigenic peptide or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail herein. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous, and in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

Useful expression vectors for eukaryotic hosts, especially mammals or humans include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are well known in the art (see Pouwels et al., Cloning Vectors: A Laboratory Manual, Elsevier, N.Y., 1985).

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), 293, HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography, and the like), centrifugation, differential solubility, or by any other standard technique for protein purification. Affinity tags such as hexahistidine (SEQ ID NO: 33733), maltose binding domain, influenza coat sequence, glutathione-S-transferase, and the like can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

In Vivo Peptide/Polypeptide Synthesis

The present invention also contemplates the use of nucleic acid molecules as vehicles for delivering neoantigenic peptides/polypeptides to the subject in need thereof, in vivo, in the form of, e.g., DNA/RNA vaccines (see, e.g., WO2012/159643, and WO2012/159754, hereby incorporated by reference in their entirety).

In one embodiment neoantigens may be administered to a patient in need thereof by use of a plasmid. These are plasmids which usually consist of a strong viral promoter to drive the in vivo transcription and translation of the gene (or complementary DNA) of interest (Mor, et al., (1995). The Journal of Immunology 155 (4): 2039-2046). Intron A may sometimes be included to improve mRNA stability and hence increase protein expression (Leitner et al. (1997).The Journal of Immunology 159 (12): 6112-6119). Plasmids also include a strong polyadenylation/transcriptional termination signal, such as bovine growth hormone or rabbit beta-globulin polyadenylation sequences (Alarcon et al., (1999). Adv. Parasitol. Advances in Parasitology 42: 343-410; Robinson et al., (2000). Adv. Virus Res. Advances in Virus Research 55: 1-74; Böhm et al., (1996). Journal of Immunological Methods 193 (1): 29-40.). Multicistronic vectors are sometimes constructed to express more than one immunogen, or to express an immunogen and an immunostimulatory protein (Lewis et al., (1999). Advances in Virus Research (Academic Press) 54: 129-88).

Because the plasmid is the "vehicle" from which the immunogen is expressed, optimising vector design for maximal protein expression is essential (Lewis et al., (1999). Advances in Virus Research (Academic Press) 54: 129-88). One way of enhancing protein expression is by optimising the codon usage of pathogenic mRNAs for eukaryotic cells. Another consideration is the choice of promoter. Such promoters may be the SV40 promoter or Rous Sarcoma Virus (RSV).

Plasmids may be introduced into animal tissues by a number of different methods. The two most popular approaches are injection of DNA in saline, using a standard hypodermic needle, and gene gun delivery. A schematic outline of the construction of a DNA vaccine plasmid and its subsequent delivery by these two methods into a host is illustrated at Scientific American (Weiner et al., (1999) Scientific American 281 (1): 34-41). Injection in saline is normally conducted intramuscularly (IM) in skeletal muscle, or intradermally (ID), with DNA being delivered to the extracellular spaces. This can be assisted by electroporation by temporarily damaging muscle fibres with myotoxins such as bupivacaine; or by using hypertonic solutions of saline or sucrose (Alarcon et al., (1999). Adv. Parasitol. Advances in Parasitology 42: 343-410). Immune responses to this method of delivery can be affected by many factors, including needle type, needle alignment, speed of injection, volume of injection, muscle type, and age, sex and physiological condition of the animal being injected (Alarcon et al., (1999). Adv. Parasitol. Advances in Parasitology 42: 343-410).

Gene gun delivery, the other commonly used method of delivery, ballistically accelerates plasmid DNA (pDNA) that has been adsorbed onto gold or tungsten microparticles into the target cells, using compressed helium as an accelerant (Alarcon et al., (1999). Adv. Parasitol. Advances in Parasitology 42: 343-410: Lewis et al., (1999). Advances in Virus Research (Academic Press) 54: 129-88).

Alternative delivery methods may include aerosol instillation of naked DNA on mucosal surfaces, such as the nasal and lung mucosa, (Lewis et al., (1999). Advances in Virus Research (Academic Press) 54: 129-88) and topical administration of pDNA to the eye and vaginal mucosa (Lewis et al., (1999) Advances in Virus Research (Academic Press) 54: 129-88). Mucosal surface delivery has also been achieved using cationic liposome-DNA preparations, biodegradable microspheres, attenuated Shigella or Listeria vectors for oral administration to the intestinal mucosa, and recombinant adenovirus vectors. DNA or RNA may also be delivered to cells following mild mechanical disruption of the cell membrane, temporarily permeabilizing the cells. Such a mild mechanical disruption of the membrane can be accomplished by gently forcing cells through a small aperture (Ex Vivo Cytosolic Delivery of Functional Macromolecules to Immune Cells, Sharei et al, PLOS ONE|DOI: 10.1371/journal.pone.0118803 Apr. 13, 2015).

The method of delivery determines the dose of DNA required to raise an effective immune response. Saline injections require variable amounts of DNA, from 10 μg-1 mg, whereas gene gun deliveries require 100 to 1000 times less DNA than intramuscular saline injection to raise an effective immune response. Generally, 0.2 µg-20 µg are required, although quantities as low as 16 ng have been reported. These quantities vary from species to species, with mice, for example, requiring approximately 10 times less DNA than primates. Saline injections require more DNA because the DNA is delivered to the extracellular spaces of the target tissue (normally muscle), where it has to overcome physical barriers (such as the basal lamina and large amounts of connective tissue, to mention a few) before it is taken up by the cells, while gene gun deliveries bombard DNA directly into the cells, resulting in less "wastage" (See e.g., Sedegah et al., (1994). Proceedings of the National Academy of Sciences of the United States of America 91 (21): 9866-9870; Daheshia et al., (1997). The Journal of Immunology 159 (4): 1945-1952; Chen et al., (1998). The Journal of Immunology 160 (5): 2425-2432; Sizemore (1995) Science 270 (5234): 299-302; Fynan et al., (1993) Proc. Natl. Acad. Sci. U.S.A. 90 (24): 11478-82).

In one embodiment, a neoplasia vaccine or immunogenic composition may include separate DNA plasmids encoding, for example, one or more neoantigenic peptides/polypeptides as identified in according to the invention. As discussed herein, the exact choice of expression vectors can depend upon the peptide/polypeptides to be expressed, and is well within the skill of the ordinary artisan. The expected persistence of the DNA constructs (e.g., in an episomal, non-replicating, non-integrated form in the muscle cells) is expected to provide an increased duration of protection.

One or more neoantigenic peptides of the invention may be encoded and expressed in vivo using a viral based system (e.g., an adenovirus system, an adeno associated virus (AAV) vector, a poxvirus, or a lentivirus). In one embodiment, the neoplasia vaccine or immunogenic composition may include a viral based vector for use in a human patient in need thereof, such as, for example, an adenovirus (see, e.g., Baden et al. First-in-human evaluation of the safety and immunogenicity of a recombinant adenovirus serotype 26 HIV-1 Env vaccine (IPCAVD 001). J Infect Dis. 2013 Jan. 15; 207(2):240-7, hereby incorporated by reference in its entirety). Plasmids that can be used for adeno associated virus, adenovirus, and lentivirus delivery have been described previously (see e.g., U.S. Pat. Nos. 6,955,808 and 6,943,019, and U.S. Patent application No. 20080254008, hereby incorporated by reference).

The peptides and polypeptides of the invention can also be expressed by a vector, e.g., a nucleic acid molecule as herein-discussed, e.g., RNA or a DNA plasmid, a viral vector such as a poxvirus, e.g., orthopox virus, avipox virus, or adenovirus, AAV or lentivirus. This approach involves the use of a vector to express nucleotide sequences that encode the peptide of the invention. Upon introduction into an acutely or chronically infected host or into a noninfected host, the vector expresses the immunogenic peptide, and thereby elicits a host CTL response.

Among vectors that may be used in the practice of the invention, integration in the host genome of a cell is possible with retrovirus gene transfer methods, often resulting in long term expression of the inserted transgene. In a preferred embodiment the retrovirus is a lentivirus. Additionally, high transduction efficiencies have been observed in many different cell types and target tissues. The tropism of a retrovirus can be altered by incorporating foreign envelope proteins, expanding the potential target population of target cells. A retrovirus can also be engineered to allow for conditional expression of the inserted transgene, such that only certain cell types are infected by the lentivirus. Cell type specific promoters can be used to target expression in specific cell types. Lentiviral vectors are retroviral vectors (and hence both lentiviral and retroviral vectors may be used in the practice of the invention). Moreover, lentiviral vectors are preferred as they are able to transduce or infect non-dividing cells and typically produce high viral titers. Selection of a retroviral gene transfer system may therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the desired nucleic acid into the target cell to provide permanent expression. Widely used retroviral vectors that may be used in the practice of the invention include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., (1992) J. Virol. 66:2731-2739; Johann et al., (1992) J. Virol. 66:1635-1640; Sommnerfelt et al., (1990) Virol. 176:58-59; Wilson et al., (1998) J. Virol. 63:2374-2378; Miller et al., (1991) J. Virol. 65:2220-2224; PCT/US94/05700).

Also useful in the practice of the invention is a minimal non-primate lentiviral vector, such as a lentiviral vector based on the equine infectious anemia virus (EIAV) (see, e.g., Balagaan, (2006) J Gene Med; 8: 275-285, Published online 21 Nov. 2005 in Wiley InterScience (www.interscience.wiley.com). DOI: 10.1002/jgm.845). The vectors may have cytomegalovirus (CMV) promoter driving expression of the target gene. Accordingly, the invention contemplates amongst vector(s) useful in the practice of the invention: viral vectors, including retroviral vectors and lentiviral vectors.

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for delivery to the Brain, see, e.g., US Patent Publication Nos. US20110293571; US20040013648, US20070025970, US20090111106 and U.S. Pat. No. 7,259,015. In another embodiment lentiviral vectors are used to deliver vectors to the brain of those being treated for a disease.

As to lentivirus vector systems useful in the practice of the invention, mention is made of U.S. Pat. Nos. 6,428,953, 6,165,782, 6,013,516, 5,994,136, 6,312,682, and 7,198,784, and documents cited therein.

In an embodiment herein the delivery is via an lentivirus. Zou et al. administered about 10 µl of a recombinant lentivirus having a titer of $1 \times 10^9$ transducing units (TU)/ml by an intrathecal catheter. These sort of dosages can be adapted or extrapolated to use of a retroviral or lentiviral vector in the present invention. For transduction in tissues such as the brain, it is necessary to use very small volumes, so the viral preparation is concentrated by ultracentrifugation. The resulting preparation should have at least $10^8$ TU/ml, preferably from $10^8$ to $10^9$ TU/ml, more preferably at least $10^9$ TU/ml. Other methods of concentration such as ultrafiltration or binding to and elution from a matrix may be used.

In other embodiments the amount of lentivirus administered may be $1.\text{x}.10^5$ or about $1.\text{x}.10^5$ plaque forming units (PFU), $5.\text{x}.10^5$ or about $5.\text{x}.10^5$ PFU, $1.\text{x}.10^6$ or about $1.\text{x}10^6$ PFU, $5.\text{x}.10^6$ or about $5.\text{x}.10^6$ PFU, $1.\text{x}.10^7$ or about $1.\text{x}.10^7$ PFU, $5.\text{x}.10^7$ or about $5.\text{x}.10^7$ PFU, $1.\text{x}.10^8$ or about $1.\text{x}.10^8$ PFU, $5.\text{x}.10^8$ or about $5.\text{x}.10^8$ PFU, $1.\text{x}.10^9$ or about $1.\text{x}.10^9$ PFU, $5.\text{x}.10^9$ or about $5.\text{x}.10^9$ PFU, $1.\text{x}.10^{10}$ or about 1.x.$10^{10}$ PFU or 5.x.$10^{10}$ or about 5.x.$10^{10}$ PFU as total single dosage for an average human of 75 kg or adjusted for the weight and size and species of the subject. One of skill in the art can determine suitable dosage. Suitable dosages for a virus can be determined empirically.

Also useful in the practice of the invention is an adenovirus vector. One advantage is the ability of recombinant adenoviruses to efficiently transfer and express recombinant genes in a variety of mammalian cells and tissues in vitro and in vivo, resulting in the high expression of the transferred nucleic acids. Further, the ability to productively infect quiescent cells, expands the utility of recombinant adenoviral vectors. In addition, high expression levels ensure that the products of the nucleic acids will be expressed to sufficient levels to generate an immune response (see e.g., U.S. Pat. No. 7,029,848, hereby incorporated by reference).

As to adenovirus vectors useful in the practice of the invention, mention is made of U.S. Pat. No. 6,955,808. The adenovirus vector used can be selected from the group consisting of the Ad5, Ad35, Ad11, C6, and C7 vectors. The sequence of the Adenovirus 5 ("Ad5") genome has been published. (Chroboczek, J., Bieber, F., and Jacrot, B. (1992) The Sequence of the Genome of Adenovirus Type 5 and Its Comparison with the Genome of Adenovirus Type 2, Virology 186, 280-285; the contents if which is hereby incorporated by reference). Ad35 vectors are described in U.S. Pat. Nos. 6,974,695, 6,913,922, and 6,869,794. Ad11 vectors are described in U.S. Pat. No. 6,913,922. C6 adenovirus vectors are described in U.S. Pat. Nos. 6,780,407; 6,537,594; 6,309,647; 6,265,189; 6,156,567; 6,090,393; 5,942,235 and 5,833,975. C7 vectors are described in U.S. Pat. No. 6,277,558. Adenovirus vectors that are E1-defective or deleted, E3-defective or deleted, and/or E4-defective or deleted may also be used. Certain adenoviruses having mutations in the E1 region have improved safety margin because E1-defective adenovirus mutants are replication-defective in non-permissive cells, or, at the very least, are highly attenuated. Adenoviruses having mutations in the E3 region may have enhanced the immunogenicity by disrupting the mechanism whereby adenovirus down-regulates MHC class I molecules. Adenoviruses having E4 mutations may have reduced immunogenicity of the adenovirus vector because of suppression of late gene expression. Such vectors may be particularly useful when repeated re-vaccination utilizing the same vector is desired. Adenovirus vectors that are deleted or mutated in E1, E3, E4, E1 and E3, and E1 and E4 can be used in accordance with the present invention. Furthermore, "gutless" adenovirus vectors, in which all viral genes are deleted, can also be used in accordance with the present invention. Such vectors require a helper virus for their replication and require a special human 293 cell line expressing both E1a and Cre, a condition that does not exist in natural environment. Such "gutless" vectors are non-immunogenic and thus the vectors may be inoculated multiple times for re-vaccination. The "gutless" adenovirus vectors can be used for insertion of heterologous inserts/genes such as the transgenes of the present invention, and can even be used for co-delivery of a large number of heterologous inserts/genes.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^8$ particles (e.g., about $1 \times 10^8$-$1 \times 10^{11}$ particles or about $1 \times 10^8$-$1 \times 10^{12}$ particles), and most preferably at least about $1 \times 10^9$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In terms of in vivo delivery, AAV is advantageous over other viral vectors due to low toxicity and low probability of causing insertional mutagenesis because it doesn't integrate into the host genome. AAV has a packaging limit of 4.5 or 4.75 Kb. Constructs larger than 4.5 or 4.75 Kb result in significantly reduced virus production. There are many promoters that can be used to drive nucleic acid molecule expression. AAV ITR can serve as a promoter and is advantageous for eliminating the need for an additional promoter element. For ubiquitous expression, the following promoters can be used: CMV, CAG, CBh, PGK, SV40, Ferritin heavy or light chains, etc. For brain expression, the following promoters can be used: SynapsinI for all neurons, CaMKIIalpha for excitatory neurons, GAD67 or GAD65 or VGAT for GABAergic neurons, etc. Promoters used to drive RNA synthesis can include: Pol III promoters such as U6 or H1. The use of a Pol II promoter and intronic cassettes can be used to express guide RNA (gRNA).

With regard to AAV vectors useful in the practice of the invention, mention is made of U.S. Pat. Nos. 5,658,785, 7,115,391, 7,172,893, 6,953,690, 6,936,466, 6,924,128, 6,893,865, 6,793,926, 6,537,540, 6,475,769 and 6,258,595, and documents cited therein.

As to AAV, the AAV can be AAV1, AAV2, AAV5 or any combination thereof. One can select the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The above promoters and vectors are preferred individually.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{50}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. In a preferred embodiment, AAV is used with a titer of about 2×10$^{13}$ viral genomes/milliliter, and each of the striatal hemispheres of a mouse receives one 500 nanoliter injection. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In another embodiment effectively activating a cellular immune response for a neoplasia vaccine or immunogenic composition can be achieved by expressing the relevant neoantigens in a vaccine or immunogenic composition in a non-pathogenic microorganism. Well-known examples of such microorganisms are *Mycobacterium bovis* BCG, *Salmonella* and *Pseudomona* (See, U.S. Pat. No. 6,991,797, hereby incorporated by reference in its entirety).

In another embodiment a Poxvirus is used in the neoplasia vaccine or immunogenic composition. These include orthopoxvirus, avipox, vaccinia, MVA, NYVAC, canarypox, ALVAC, fowlpox, TROVAC, etc. (see e.g., Verardi et al., Hum Vaccin Immunother. 2012 July; 8(7):961-70; and Moss, Vaccine. 2013; 31(39): 4220-4222). Poxvirus expression vectors were described in 1982 and quickly became widely used for vaccine development as well as research in numerous fields. Advantages of the vectors include simple construction, ability to accommodate large amounts of foreign DNA and high expression levels.

Information concerning poxviruses that may be used in the practice of the invention, such as Chordopoxvirinae subfamily poxviruses (poxviruses of vertebrates), for instance, orthopoxviruses and avipoxviruses, e.g., vaccinia virus (e.g., Wyeth Strain, WR Strain (e.g., ATCC® VR-1354), Copenhagen Strain, NYVAC, NYVAC.1, NYVAC.2, MVA, MVA-BN), canarypox virus (e.g., Wheatley C93 Strain, ALVAC), fowlpox virus (e.g., FP9 Strain, Webster Strain, TROVAC), dovepox, pigeonpox, quailpox, and raccoon pox, inter alia, synthetic or non-naturally occurring recombinants thereof, uses thereof, and methods for making and using such recombinants may be found in scientific and patent literature, such as:

U.S. Pat. Nos. 4,603,112, 4,769,330, 5,110,587, 5,174, 993, 5,364,773, 5,572,938, 5,494,807, 5,766,597, 7,767,449, 6,780,407, 6,537,594, 6,265,189, 6,214, 353, 6,130,066, 6,004,777, 5,990,091, 5,942,235, 5,833,975, 5,766,597, 5,756,101, 7,045,313, 6,780, 417, 8,470,598, 8,372,622, 8,268,329, 8,268,325, 8,236,560, 8,163,293, 7,964,398, 7,964,396, 7,964, 395, 7,939,086, 7,923,017, 7,897,156, 7,892,533, 7,628,980, 7,459,270, 7,445,924, 7,384,644, 7,335, 364, 7,189,536, 7,097,842, 6,913,752, 6,761,893, 6,682,743, 5,770,212, 5,766,882, and 5,989,562, and Panicali, D. Proc. Natl. Acad. Sci. 1982; 79; 4927-493, Panicali D. Proc. Natl. Acad. Sci. 1983; 80(17): 5364-8, Mackett, M. Proc. Natl. Acad. Sci. 1982; 79: 7415-7419, Smith G L. Proc. Natl. Acad. Sci. 1983; 80(23): 7155-9, Smith G L. Nature 1983; 302: 490-5, Sullivan V J. Gen. Vir. 1987; 68: 2587-98, Perkus M Journal of Leukocyte Biology 1995; 58:1-13, Yilma T D. Vaccine 1989; 7: 484-485, Brochier B. Nature 1991; 354: 520-22, Wiktor, T J. Proc. Natl Acd. Sci. 1984; 81: 7194-8, Rupprecht, C E. Proc. Natl Acd. Sci. 1986; 83: 7947-50, Poulet, H Vaccine 2007; 25(July): 5606-12, Weyer J. Vaccine 2009; 27(November): 7198-201, Buller, R M Nature 1985; 317(6040): 813-5, Buller R M. J. Virol. 1988; 62(3):866-74, Flexner, C. Nature 1987; 330(6145): 259-62, Shida, H. J. Virol. 1988; 62(12): 4474-80, Kotwal, G J. J. Virol. 1989; 63(2): 600-6, Child, S J. Virology 1990; 174(2): 625-9, Mayr A. Zentralbl Bakteriol 1978; 167(5,6): 375-9, Antoine G. Virology. 1998; 244(2): 365-96, Wyatt, L S. Virology 1998; 251(2): 334-42, Sancho, M C. J. Virol. 2002; 76(16); 8313-34, Gallego-Gomez, J C. J. Virol. 2003; 77(19); 10606-22), Goebel S J. Virology 1990; (a,b) 179: 247-66, Tartaglia, J. Virol. 1992; 188(1): 217-32, Najera J L. J. Virol. 2006; 80(12): 6033-47, Najera, J L. J. Virol. 2006; 80: 6033-6047, Gomez, C E. J. Gen. Virol. 2007; 88: 2473-78, Mooij, P. Jour. Of Virol. 2008; 82: 2975-2988, Gomez, C E. Curr. Gene Ther. 2011; 11: 189-217, Cox, W. Virology 1993; 195: 845-50, Perkus, M. Jour. Of Leukocyte Biology 1995; 58: 1-13, Blanchard T J. J Gen Virology 1998; 79(5): 1159-67, Amara R. Science 2001; 292: 69-74, Hel, Z., J. Immunol. 2001; 167: 7180-9, Gherardi M M. J. Virol. 2003; 77: 7048-57, Didierlaurent, A. Vaccine 2004; 22: 3395-3403, Bissht H. Proc. Nat. Aca. Sci. 2004; 101: 6641-46, McCurdy L H. Clin. Inf. Dis 2004; 38: 1749-53, Earl P L. Nature 2004; 428: 182-85, Chen Z. J. Virol. 2005; 79: 2678-2688, Najera J L. J. Virol. 2006; 80(12); 6033-47, Nam J H. Acta. Virol. 2007; 51: 125-30, Antonis A F. Vaccine 2007; 25: 4818-4827, B Weyer J. Vaccine 2007; 25: 4213-22, Ferrier-Rembert A. Vaccine 2008; 26(14): 1794-804, Corbett M. Proc. Natl. Acad. Sci. 2008; 105(6): 2046-51, Kaufman H L., J. Clin. Oncol. 2004; 22: 2122-32, Amato, R J. Clin. Cancer Res. 2008; 14(22): 7504-10, Dreicer R. Invest New Drugs 2009; 27(4): 379-86, Kantoff P W. J. Clin. Oncol. 2010, 28, 1099-1105, Amato R J. J. Clin. Can. Res. 2010; 16(22): 5539-47, Kim, D W. Hum. Vaccine. 2010; 6: 784-791, Oudard, S. Cancer Immunol. Immunother. 2011; 60: 261-71, Wyatt, L S. Aids Res. Hum. Retroviruses. 2004; 20: 645-53, Gomez, C E. Virus Research 2004; 105: 11-22, Webster, D P. Proc. Natl. Acad. Sci. 2005; 102: 4836-4, Huang, X. Vaccine 2007; 25: 8874-84, Gomez, C E. Vaccine 2007a; 25: 2863-85, Esteban M. Hum. Vaccine 2009; 5: 867-871, Gomez, C E. Curr. Gene therapy 2008; 8(2): 97-120, Whelan, K T. Plos one 2009; 4(6): 5934, Scriba, T J. Eur. Jour. Immuno. 2010; 40(1): 279-90, Corbett, M. Proc. Natl. Acad. Sci. 2008; 105: 2046-2051, Midgley, C M. J. Gen. Virol. 2008; 89: 2992-97, Von Krempelhuber, A. Vaccine 2010; 28: 1209-16, Perreau, M. J. Of Virol. 2011; October: 9854-62, Pantaleo, G. Curr Opin HIV-AIDS. 2010: 5: 391-396, each of which is incorporated herein by reference.

In another embodiment the vaccinia virus is used in the neoplasia vaccine or immunogenic composition to express a neoantigen. (Rolph et al., Recombinant viruses as vaccines and immunological tools. Curr Opin Immunol 9:517-524, 1997). The recombinant vaccinia virus is able to replicate within the cytoplasm of the infected host cell and the polypeptide of interest can therefore induce an immune response. Moreover, Poxviruses have been widely used as vaccine or immunogenic composition vectors because of their ability to target encoded antigens for processing by the major histocompatibility complex class I pathway by directly infecting immune cells, in particular antigen-presenting cells, but also due to their ability to self-adjuvant.

In another embodiment ALVAC is used as a vector in a neoplasia vaccine or immunogenic composition. ALVAC is a canarypox virus that can be modified to express foreign transgenes and has been used as a method for vaccination against both prokaryotic and eukaryotic antigens (Horig H, Lee D S, Conkright W, et al. Phase I clinical trial of a recombinant canarypoxvirus (ALVAC) vaccine expressing human carcinoembryonic antigen and the B7.1 co-stimulatory molecule. Cancer Immunol Immunother 2000; 49:504-14; von Mehren M, Arlen P, Tsang K Y, et al. Pilot study of a dual gene recombinant avipox vaccine containing both carcinoembryonic antigen (CEA) and B7.1 transgenes in patients with recurrent CEA-expressing adenocarcinomas. Clin Cancer Res 2000; 6:2219-28; Musey L, Ding Y, Elizaga M, et al. HIV-1 vaccination administered intramuscularly can induce both systemic and mucosal T cell immunity in HIV-1-uninfected individuals. J Immunol 2003; 171:1094-101; Paoletti E. Applications of pox virus vectors to vaccination: an update. Proc Natl Acad Sci USA 1996; 93:11349-53; U.S. Pat. No. 7,255,862). In a phase I clinical trial, an ALVAC virus expressing the tumor antigen CEA showed an excellent safety profile and resulted in increased CEA-specific T-cell responses in selected patients; objective clinical responses, however, were not observed (Marshall J L, Hawkins M J, Tsang K Y, et al. Phase I study in cancer patients of a replication-defective avipox recombinant vaccine that expresses human carcinoembryonic antigen. J Clin Oncol 1999; 17:332-7).

In another embodiment a Modified Vaccinia Ankara (MVA) virus may be used as a viral vector for a neoantigen vaccine or immunogenic composition. MVA is a member of the Orthopoxvirus family and has been generated by about 570 serial passages on chicken embryo fibroblasts of the Ankara strain of Vaccinia virus (CVA) (for review see Mayr, A., et al., Infection 3, 6-14, 1975). As a consequence of these passages, the resulting MVA virus contains 31 kilobases less genomic information compared to CVA, and is highly host-cell restricted (Meyer, H. et al., J. Gen. Virol. 72, 1031-1038, 1991). MVA is characterized by its extreme attenuation, namely, by a diminished virulence or infectious ability, but still holds an excellent immunogenicity. When tested in a variety of animal models, MVA was proven to be avirulent, even in immuno-suppressed individuals. Moreover, MVA-BN®-HER2 is a candidate immunotherapy designed for the treatment of HER-2-positive breast cancer and is currently in clinical trials. (Mandl et al., Cancer Immunol Immunother. January 2012; 61(1): 19-29). Methods to make and use recombinant MVA has been described (e.g., see U.S. Pat. Nos. 8,309,098 and 5,185,146 hereby incorporated in its entirety).

In another embodiment the modified Copenhagen strain of vaccinia virus, NYVAC and NYVAC variations are used as a vector (see U.S. Pat. No. 7,255,862; PCT WO 95/30018; U.S. Pat. Nos. 5,364,773 and 5,494,807, hereby incorporated by reference in its entirety).

In one embodiment recombinant viral particles of the vaccine or immunogenic composition are administered to patients in need thereof. Dosages of expressed neoantigen can range from a few to a few hundred micrograms, e.g., 5 to 500 .mu.g. The vaccine or immunogenic composition can be administered in any suitable amount to achieve expression at these dosage levels. The viral particles can be administered to a patient in need thereof or transfected into cells in an amount of about at least $10^{3.5}$ pfu; thus, the viral particles are preferably administered to a patient in need thereof or infected or transfected into cells in at least about $10^4$ pfu to about $10^6$ pfu; however, a patient in need thereof can be administered at least about $10^8$ pfu such that a more preferred amount for administration can be at least about $10^7$ pfu to about $10^9$ pfu. Doses as to NYVAC are applicable as to ALVAC, MVA, MVA-BN, and avipoxes, such as canarypox and fowlpox.

Vaccine or Immunogenic Composition Adjuvant

Effective vaccine or immunogenic compositions advantageously include a strong adjuvant to initiate an immune response. As described herein, poly-ICLC, an agonist of TLR3 and the RNA helicase-domains of MDA5 and RIG3, has shown several desirable properties for a vaccine or immunogenic composition adjuvant. These properties include the induction of local and systemic activation of immune cells in vivo, production of stimulatory chemokines and cytokines, and stimulation of antigen-presentation by DCs. Furthermore, poly-ICLC can induce durable CD4+ and CD8+ responses in humans. Importantly, striking similarities in the upregulation of transcriptional and signal transduction pathways were seen in subjects vaccinated with poly-ICLC and in volunteers who had received the highly effective, replication-competent yellow fever vaccine. Furthermore, >90% of ovarian carcinoma patients immunized with poly-ICLC in combination with a NY-ESO-1 peptide vaccine (in addition to Montanide) showed induction of CD4+ and CD8+ T cell, as well as antibody responses to the peptide in a recent phase 1 study. At the same time, poly-ICLC has been extensively tested in more than 25 clinical trials to date and exhibited a relatively benign toxicity profile. In addition to a powerful and specific immunogen the neoantigen peptides may be combined with an adjuvant (e.g., poly-ICLC) or another anti-neoplastic agent. Without being bound by theory, these neoantigens are expected to bypass central thymic tolerance (thus allowing stronger anti-tumor T cell response), while reducing the potential for autoimmunity (e.g., by avoiding targeting of normal self-antigens). An effective immune response advantageously includes a strong adjuvant to activate the immune system (Speiser and Romero, Molecularly defined vaccines for cancer immunotherapy, and protective T cell immunity Seminars in Immunol 22:144 (2010)). For example, Toll-like receptors (TLRs) have emerged as powerful sensors of microbial and viral pathogen "danger signals", effectively inducing the innate immune system, and in turn, the adaptive immune system (Bhardwaj and Gnjatic, TLR AGONISTS: Are They Good Adjuvants? Cancer J. 16:382-391 (2010)). Among the TLR agonists, poly-ICLC (a synthetic double-stranded RNA mimic) is one of the most potent activators of myeloid-derived dendritic cells. In a human volunteer study, poly-ICLC has been shown to be safe and to induce a gene expression profile in peripheral blood cells comparable to that induced by one of the most potent live attenuated viral vaccines, the yellow fever vaccine YF-17D (Caskey et al, Synthetic double-stranded RNA induces innate immune responses similar to a live viral vaccine in humans J Exp Med 208:2357 (2011)). In a preferred embodiment Hiltonol®, a GMP preparation of poly-ICLC prepared by Oncovir, Inc, is utilized as the adjuvant. In other embodiments, other adjuvants described herein are envisioned. For instance oil-in-water, water-in-oil or multiphasic W/O/W; see, e.g., U.S. Pat. No. 7,608,279 and Aucouturier et al, Vaccine 19 (2001), 2666-2672, and documents cited therein.

Indications

Examples of cancers and cancer conditions that can be treated with the therapy of this document include, but are not limited to a patient in need thereof that has been diagnosed as having cancer, or at risk of developing cancer. The subject may have a solid tumor such as breast, ovarian, prostate, lung, kidney, gastric, colon, testicular, head and neck, pancreas, brain, melanoma, and other tumors of tissue organs and hematological tumors, such as lymphomas and leukemias, including acute myelogenous leukemia, chronic myelogenous leukemia, chronic lymphocytic leukemia, T cell lymphocytic leukemia, and B cell lymphomas, tumors of the brain and central nervous system (e.g., tumors of the meninges, brain, spinal cord, cranial nerves and other parts of the CNS, such as glioblastomas or medulla blastomas); head and/or neck cancer, breast tumors, tumors of the circulatory system (e.g., heart, mediastinum and pleura, and other intrathoracic organs, vascular tumors, and tumor-associated vascular tissue); tumors of the blood and lymphatic system (e.g., Hodgkin's disease, Non-Hodgkin's disease lymphoma, Burkitt's lymphoma, AIDS-related lymphomas, malignant immunoproliferative diseases, multiple myeloma, and malignant plasma cell neoplasms, lymphoid leukemia, myeloid leukemia, acute or chronic lymphocytic leukemia, monocytic leukemia, other leukemias of specific cell type, leukemia of unspecified cell type, unspecified malignant neoplasms of lymphoid, hematopoietic and related tissues, such as diffuse large cell lymphoma, T-cell lymphoma or cutaneous T-cell lymphoma); tumors of the excretory system (e.g., kidney, renal pelvis, ureter, bladder, and other urinary organs); tumors of the gastrointestinal tract (e.g., esophagus, stomach, small intestine, colon, colorectal, rectosigmoid junction, rectum, anus, and anal canal); tumors involving the liver and intrahepatic bile ducts, gall bladder, and other parts of the biliary tract, pancreas, and other digestive organs; tumors of the oral cavity (e.g., lip, tongue, gum, floor of mouth, palate, parotid gland, salivary glands, tonsil, oropharynx, nasopharynx, puriform sinus, hypopharynx, and other sites of the oral cavity); tumors of the reproductive system (e.g., vulva, vagina, Cervix uteri, uterus, ovary, and other sites associated with female genital organs, placenta, penis, prostate, testis, and other sites associated with male genital organs); tumors of the respiratory tract (e.g., nasal cavity, middle ear, accessory sinuses, larynx, trachea, bronchus and lung, such as small cell lung cancer and non-small cell lung cancer); tumors of the skeletal system (e.g., bone and articular cartilage of limbs, bone articular cartilage and other sites); tumors of the skin (e.g., malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneoum and peritoneum, eye, thyroid, adrenal gland, and other endocrine glands and related structures, secondary and unspecified malignant neoplasms of lymph nodes, secondary malignant neoplasm of respiratory and digestive systems and secondary malignant neoplasm of other sites. Thus the population of subjects described herein may be suffering from one of the above cancer types. In other embodiments, the population of subjects may be all subjects suffering from solid tumors, or all subjects suffering from liquid tumors.

Of special interest is the treatment of Non-Hodgkin's Lymphoma (NHL), clear cell Renal Cell Carcinoma (ccRCC), metastatic melanoma, sarcoma, leukemia or a cancer of the bladder, colon, brain, breast, head and neck, endometrium, lung, ovary, pancreas or prostate. In certain embodiments, the melanoma is high risk melanoma.

Cancers that can be treated using the therapy described herein may include among others cases which are refractory to treatment with other chemotherapeutics. The term "refractory, as used herein refers to a cancer (and/or metastases thereof), which shows no or only weak antiproliferative response (e.g., no or only weak inhibition of tumor growth) after treatment with another chemotherapeutic agent. These are cancers that cannot be treated satisfactorily with other chemotherapeutics. Refractory cancers encompass not only (i) cancers where one or more chemotherapeutics have already failed during treatment of a patient, but also (ii) cancers that can be shown to be refractory by other means, e.g., biopsy and culture in the presence of chemotherapeutics.

The therapy described herein is also applicable to the treatment of patients in need thereof who have not been previously treated.

The therapy described herein is also applicable where the subject has no detectable neoplasia but is at high risk for disease recurrence.

Also of special interest is the treatment of patients in need thereof who have undergone Autologous Hematopoietic Stem Cell Transplant (AHSCT), and in particular patients who demonstrate residual disease after undergoing AHSCT. The post-AHSCT setting is characterized by a low volume of residual disease, the infusion of immune cells to a situation of homeostatic expansion, and the absence of any standard relapse-delaying therapy. These features provide a unique opportunity to use the claimed neoplastic vaccine or immunogenic composition compositions to delay disease relapse.

Pharmaceutical Compositions/Methods of Delivery

The present invention is also directed to pharmaceutical compositions comprising an effective amount of one or more neoantigenic peptides as described herein (including a pharmaceutically acceptable salt, thereof), optionally in combination with a pharmaceutically acceptable carrier, excipient or additive.

When administered as a combination, the therapeutic agents (i.e. the neoantigenic peptides) can be formulated as separate compositions that are given at the same time or different times, or the therapeutic agents can be given as a single composition.

The compositions may be administered once daily, twice daily, once every two days, once every three days, once every four days, once every five days, once every six days, once every seven days, once every two weeks, once every three weeks, once every four weeks, once every two months, once every six months, or once per year. The dosing interval can be adjusted according to the needs of individual patients. For longer intervals of administration, extended release or depot formulations can be used.

The compositions of the invention can be used to treat diseases and disease conditions that are acute, and may also be used for treatment of chronic conditions. In particular, the compositions of the invention are used in methods to treat or prevent a neoplasia. In certain embodiments, the compounds of the invention are administered for time periods exceeding two weeks, three weeks, one month, two months, three months, four months, five months, six months, one year, two years, three years, four years, or five years, ten years, or fifteen years; or for example, any time period range in days, months or years in which the low end of the range is any time period between 14 days and 15 years and the upper end of the range is between 15 days and 20 years (e.g., 4 weeks and 15 years, 6 months and 20 years). In some cases, it may be advantageous for the compounds of the invention to be administered for the remainder of the patient's life. In preferred embodiments, the patient is monitored to check the progression of the disease or disorder, and the dose is adjusted accordingly. In preferred embodiments, treatment according to the invention is effective for at least two weeks, three weeks, one month, two months, three months, four months, five months, six months, one year, two years, three years, four years, or five years, ten years, fifteen years, twenty years, or for the remainder of the subject's life.

Surgical resection uses surgery to remove abnormal tissue in cancer, such as mediastinal, neurogenic, or germ cell tumors, or thymoma. In certain embodiments, administration of the composition is initiated following tumor resection. In other embodiments, administration of the neoplasia vaccine or immunogenic composition is initiated 1, 2, 3, 4, 5, 6, 7, 8, 9, 10, 11, 12, 13, 14, 15 or more weeks after tumor resection. Preferably, administration of the neoplasia vaccine or immunogenic composition is initiated 4, 5, 6, 7, 8, 9, 10, 11 or 12 weeks after tumor resection.

Prime/boost regimens refer to the successive administrations of a vaccine or immunogenic or immunological compositions. In certain embodiments, administration of the neoplasia vaccine or immunogenic composition is in a prime/boost dosing regimen, for example administration of the neoplasia vaccine or immunogenic composition at weeks 1, 2, 3 or 4 as a prime and administration of the neoplasia vaccine or immunogenic composition is at months 2, 3 or 4 as a boost. In another embodiment heterologous prime-boost strategies are used to ellicit a greater cytotoxic T-cell response (see Schneider et al., Induction of CD8+ T cells using heterologous prime-boost immunisation strategies, Immunological Reviews Volume 170, Issue 1, pages 29-38, August 1999). In another embodiment DNA encoding neoantigens is used to prime followed by a protein boost. In another embodiment protein is used to prime followed by boosting with a virus encoding the neoantigen. In another embodiment a virus encoding the neoantigen is used to prime and another virus is used to boost. In another embodiment protein is used to prime and DNA is used to boost. In a preferred embodiment a DNA vaccine or immunogenic composition is used to prime a T-cell response and a recombinant viral vaccine or immunogenic composition is used to boost the response. In another preferred embodiment a viral vaccine or immunogenic composition is coadministered with a protein or DNA vaccine or immunogenic composition to act as an adjuvant for the protein or DNA vaccine or immunogenic composition. The patient can then be boosted with either the viral vaccine or immunogenic composition, protein, or DNA vaccine or immunogenic composition (see Hutchings et al., Combination of protein and viral vaccines induces potent cellular and humoral immune responses and enhanced protection from murine malaria challenge. Infect Immun. 2007 December; 75(12):5819-26. Epub 2007 Oct. 1).

The pharmaceutical compositions can be processed in accordance with conventional methods of pharmacy to produce medicinal agents for administration to patients in need thereof, including humans and other mammals.

Modifications of the neoantigenic peptides can affect the solubility, bioavailability and rate of metabolism of the peptides, thus providing control over the delivery of the active species. Solubility can be assessed by preparing the neoantigenic peptide and testing according to known methods well within the routine practitioner's skill in the art.

In certain embodiments of the pharmaceutical composition the pharmaceutically acceptable carrier comprises water. In certain embodiments, the pharmaceutically acceptable carrier further comprises dextrose. In certain embodiments, the pharmaceutically acceptable carrier further comprises dimethylsulfoxide. In certain embodiments, the pharmaceutical composition further comprises an immunomodulator or adjuvant. In certain embodiments, the immunodulator or adjuvant is selected from the group consisting of poly-ICLC, STING agonist, 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, SRL172, Virosomes and other Virus-like particles, YF-17D, VEGF trap, R848, beta-glucan, Pam3Cys, and Aquila's QS21 stimulon. In certain embodiments, the immunomodulator or adjuvant comprises poly-ICLC.

Xanthenone derivatives such as, for example, Vadimezan or AsA404 (also known as 5,6-dimethylxanthenone-4-acetic acid (DMXAA)), may also be used as adjuvants according to embodiments of the invention. Alternatively, such derivatives may also be administered in parallel to the vaccine or immunogenic composition of the invention, for example via systemic or intratumoral delivery, to stimulate immunity at the tumor site. Without being bound by theory, it is believed that such xanthenone derivatives act by stimulating interferon (IFN) production via the stimulator of IFN gene ISTING) receptor (see e.g., Conlon et al. (2013) Mouse, but not Human STING, Binds and Signals in Response to the Vascular Disrupting Agent 5,6-Dimethylxanthenone-4-Acetic Acid, Journal of Immunology, 190: 5216-25 and Kim et al. (2013) Anticancer Flavonoids are Mouse-Selective STING Agonists, 8:1396-1401).

The vaccine or immunological composition may also include an adjuvant compound chosen from the acrylic or methacrylic polymers and the copolymers of maleic anhydride and an alkenyl derivative. It is in particular a polymer of acrylic or methacrylic acid cross-linked with a polyalkenyl ether of a sugar or polyalcohol (carbomer), in particular cross-linked with an allyl sucrose or with allylpentaerythritol. It may also be a copolymer of maleic anhydride and ethylene cross-linked, for example, with divinyl ether (see U.S. Pat. No. 6,713,068 hereby incorporated by reference in its entirety).

In certain embodiments, the pH modifier can stabilize the adjuvant or immunomodulator as described herein.

In certain embodiments, a pharmaceutical composition comprises: one to five peptides, dimethylsulfoxide (DMSO), dextrose, water, succinate, poly I: poly C, poly-L-lysine, carboxymethylcellulose, and chloride. In certain embodiments, each of the one to five peptides is present at a concentration of 300 µg/ml. In certain embodiments, the pharmaceutical composition comprises ≤3% DMSO by volume. In certain embodiments, the pharmaceutical composition comprises 3.6-3.7% dextrose in water. In certain embodiments, the pharmaceutical composition comprises 3.6-3.7 mM succinate (e.g., as sodium succinate) or a salt thereof. In certain embodiments, the pharmaceutical composition comprises 0.5 mg/ml poly I: poly C. In certain embodiments, the pharmaceutical composition comprises 0.375 mg/ml poly-L-Lysine. In certain embodiments, the pharmaceutical composition comprises 1.25 mg/ml sodium carboxymethylcellulose. In certain embodiments, the pharmaceutical composition comprises 0.225% sodium chloride.

Pharmaceutical compositions comprise the herein-described tumor specific neoantigenic peptides in a therapeutically effective amount for treating diseases and conditions (e.g., a neoplasia/tumor), which have been described herein, optionally in combination with a pharmaceutically acceptable additive, carrier and/or excipient. One of ordinary skill in the art from this disclosure and the knowledge in the art will recognize that a therapeutically effective amount of one of more compounds according to the present invention may vary with the condition to be treated, its severity, the treatment regimen to be employed, the pharmacokinetics of the agent used, as well as the patient (animal or human) treated.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., ocular, oral, topical or parenteral, including gels, creams ointments, lotions and time released implantable preparations, among numerous others. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

The active compound is included in the pharmaceutically acceptable carrier or diluent in an amount sufficient to deliver to a patient a therapeutically effective amount for the desired indication, without causing serious toxic effects in the patient treated.

Oral compositions generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material herein discussed, a liquid carrier such as a fatty oil. In addition, dosage unit forms can contain various other materials which modify the physical form of the dosage unit, for example, coatings of sugar, shellac, or enteric agents.

Formulations of the present invention suitable for oral administration may be presented as discrete units such as capsules, cachets or tablets each containing a predetermined amount of the active ingredient as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein.

Methods of formulating such slow or controlled release compositions of pharmaceutically active ingredients, are known in the art and described in several issued US patents, some of which include, but are not limited to, U.S. Pat. Nos. 3,870,790; 4,226,859; 4,369,172; 4,842,866 and 5,705,190, the disclosures of which are incorporated herein by reference in their entireties. Coatings can be used for delivery of compounds to the intestine (see, e.g., U.S. Pat. Nos. 6,638,534, 5,541,171, 5,217,720, and 6,569,457, and references cited therein).

The active compound or pharmaceutically acceptable salt thereof may also be administered as a component of an elixir, suspension, syrup, wafer, chewing gum or the like. A syrup may contain, in addition to the active compounds, sucrose or fructose as a sweetening agent and certain preservatives, dyes and colorings and flavors.

Solutions or suspensions used for ocular, parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose.

In certain embodiments, the pharmaceutically acceptable carrier is an aqueous solvent, i.e., a solvent comprising water, optionally with additional co-solvents. Exemplary pharmaceutically acceptable carriers include water, buffer solutions in water (such as phosphate-buffered saline (PBS), and 5% dextrose in water (D5W). In certain embodiments, the aqueous solvent further comprises dimethyl sulfoxide (DMSO), e.g., in an amount of about 1-4%, or 1-3%. In certain embodiments, the pharmaceutically acceptable carrier is isotonic (i.e., has substantially the same osmotic pressure as a body fluid such as plasma).

In one embodiment, the active compounds are prepared with carriers that protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid, and polylactic-co-glycolic acid (PLGA). Methods for preparation of such formulations are within the ambit of the skilled artisan in view of this disclosure and the knowledge in the art.

A skilled artisan from this disclosure and the knowledge in the art recognizes that in addition to tablets, other dosage forms can be formulated to provide slow or controlled release of the active ingredient. Such dosage forms include, but are not limited to, capsules, granulations and gel-caps.

Liposomal suspensions may also be pharmaceutically acceptable carriers. These may be prepared according to methods known to those skilled in the art. For example, liposomal formulations may be prepared by dissolving appropriate lipid(s) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension. Other methods of preparation well known by those of ordinary skill may also be used in this aspect of the present invention.

The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations and compositions suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

The parenteral preparation can be enclosed in ampoules, disposable syringes or multiple dose vials made of glass or plastic. If administered intravenously, preferred carriers include, for example, physiological saline or phosphate buffered saline (PBS).

For parenteral formulations, the carrier usually comprises sterile water or aqueous sodium chloride solution, though other ingredients including those which aid dispersion may be included. Of course, where sterile water is to be used and maintained as sterile, the compositions and carriers are also sterilized. Injectable suspensions may also be prepared, in which case appropriate liquid carriers, suspending agents and the like may be employed.

Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Administration of the active compound may range from continuous (intravenous drip) to several oral administrations per day (for example, Q.I.D.) and may include oral, topical, eye or ocular, parenteral, intramuscular, intravenous, subcutaneous, transdermal (which may include a penetration enhancement agent), buccal and suppository administration, among other routes of administration, including through an eye or ocular route.

The neoplasia vaccine or immunogenic composition, and any additional agents, may be administered by injection, orally, parenterally, by inhalation spray, rectally, vaginally, or topically in dosage unit formulations containing conventional pharmaceutically acceptable carriers, adjuvants, and vehicles. The term parenteral as used herein includes, into a lymph node or nodes, subcutaneous, intravenous, intramuscular, intrasternal, infusion techniques, intraperitoneally, eye or ocular, intravitreal, intrabuccal, transdermal, intranasal, into the brain, including intracranial and intradural, into the joints, including ankles, knees, hips, shoulders, elbows, wrists, directly into tumors, and the like, and in suppository form.

In certain embodiments, the vaccine or immunogenic composition is administered intravenously or subcutaneously. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way.

The tumor specific neoantigenic peptides may be administered through a device suitable for the controlled and sustained release of a composition effective in obtaining a desired local or systemic physiological or pharmacological effect. The method includes positioning the sustained released drug delivery system at an area wherein release of the agent is desired and allowing the agent to pass through the device to the desired area of treatment.

The tumor specific neoantigenic peptides may be utilized in combination with at least one known other therapeutic agent, or a pharmaceutically acceptable salt of said agent. Examples of known therapeutic agents which can be used for combination therapy include, but are not limited to, corticosteroids (e.g., cortisone, prednisone, dexamethasone), non-steroidal anti-inflammatory drugs (NSAIDS) (e.g., ibuprofen, celecoxib, aspirin, indomethicin, naproxen), alkylating agents such as busulfan, cis-platin, mitomycin C, and carboplatin; antimitotic agents such as colchicine, vinblastine, paclitaxel, and docetaxel; topo I inhibitors such as camptothecin and topotecan; topo II inhibitors such as doxorubicin and etoposide; and/or RNA/DNA antimetabolites such as 5-azacytidine, 5-fluorouracil and methotrexate; DNA antimetabolites such as 5-fluoro-2'-deoxy-uridine, ara-C, hydroxyurea and thioguanine; antibodies such as HERCEPTIN and RITUXAN.

It should be understood that in addition to the ingredients particularly mentioned herein, the formulations of the present invention may include other agents conventional in the art having regard to the type of formulation in question, for example, those suitable for oral administration may include flavoring agents.

Pharmaceutically acceptable salt forms may be the preferred chemical form of compounds according to the present invention for inclusion in pharmaceutical compositions according to the present invention.

The present compounds or their derivatives, including prodrug forms of these agents, can be provided in the form of pharmaceutically acceptable salts. As used herein, the term pharmaceutically acceptable salts or complexes refers to appropriate salts or complexes of the active compounds according to the present invention which retain the desired biological activity of the parent compound and exhibit limited toxicological effects to normal cells. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, and polyglutamic acid, among others; (b) base addition salts formed with metal cations such as zinc, calcium, sodium, potassium, and the like, among numerous others.

The compounds herein are commercially available or can be synthesized. As can be appreciated by the skilled artisan, further methods of synthesizing the compounds of the formulae herein is evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, 2nd. Ed., Wiley-VCH Publishers (1999); T. W. Greene and P. G. M. Wuts, Protective Groups in Organic Synthesis, 3rd. Ed., John Wiley and Sons (1999); L. Fieser and M. Fieser, Fieser and Fieser's Reagents for Organic Synthesis, John Wiley and Sons (1999); and L. Paquette, ed., Encyclopedia of Reagents for Organic Synthesis, John Wiley and Sons (1995), and subsequent editions thereof.

The additional agents that may be included with the tumor specific neo-antigenic peptides of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Dosage

When the agents described herein are administered as pharmaceuticals to humans or animals, they can be given per se or as a pharmaceutical composition containing active ingredient in combination with a pharmaceutically acceptable carrier, excipient, or diluent.

Actual dosage levels and time course of administration of the active ingredients in the pharmaceutical compositions of the invention can be varied so as to obtain an amount of the active ingredient which is effective to achieve the desired therapeutic response for a particular patient, composition, and mode of administration, without being toxic to the patient. Generally, agents or pharmaceutical compositions of the invention are administered in an amount sufficient to reduce or eliminate symptoms associated with neoplasia, e.g. cancer or tumors.

A preferred dose of an agent is the maximum that a patient can tolerate and not develop serious or unacceptable side effects. Exemplary dose ranges include 0.01 mg to 250 mg per day, 0.01 mg to 100 mg per day, 1 mg to 100 mg per day, 10 mg to 100 mg per day, 1 mg to 10 mg per day, and 0.01 mg to 10 mg per day. A preferred dose of an agent is the maximum that a patient can tolerate and not develop serious or unacceptable side effects. In embodiments, the agent is administered at a concentration of about 10 micrograms to about 100 mg per kilogram of body weight per day, about 0.1 to about 10 mg/kg per day, or about 1.0 mg to about 10 mg/kg of body weight per day.

In embodiments, the pharmaceutical composition comprises an agent in an amount ranging between 1 and 10 mg, such as 1, 2, 3, 4, 5, 6, 7, 8, 9, or 10 mg.

In embodiments, the therapeutically effective dosage produces a serum concentration of an agent of from about 0.1 ng/ml to about 50-100 mg/ml. The pharmaceutical compositions 5 typically should provide a dosage of from about 0.001 mg to about 2000 mg of compound per kilogram of body weight per day. For example, dosages for systemic administration to a human patient can range from 1-10 mg/kg, 20-80 mg/kg, 5-50 mg/kg, 75-150 mg/kg, 100-500 mg/kg, 250-750 mg/kg, 500-1000 mg/kg, 1-10 mg/kg, 5-50 mg/kg, 25-75 mg/kg, 50-100 mg/kg, 100-250 mg/kg, 50-100 mg/kg, 250-500 mg/kg, 500-750 mg/kg, 750-1000 mg/kg, 1000-1500 mg/kg, 10 1500-2000 mg/kg, 5 mg/kg, 20 mg/kg, 50 mg/kg, 100 mg/kg, 500 mg/kg, 1000 mg/kg, 1500 mg/kg, or 2000 mg/kg. Pharmaceutical dosage unit forms are prepared to provide from about 1 mg to about 5000 mg, for example from about 100 to about 2500 mg of the compound or a combination of essential ingredients per dosage unit form.

In embodiments, about 50 nM to about 1 µM of an agent is administered to a subject. In related embodiments, about 50-100 nM, 50-250 nM, 100-500 nM, 250-500 nM, 250-750 nM, 500-750 nM, 500 nM to 1 µM, or 750 nM to 1 µM of an agent is administered to a subject.

Determination of an effective amount is well within the capability of those skilled in the art, especially in light of the detailed disclosure provided herein. Generally, an efficacious or effective amount of an agent is determined by first administering a low dose of the agent(s) and then incrementally increasing the administered dose or dosages until a desired effect (e.g., reduce or eliminate symptoms associated with viral infection or autoimmune disease) is observed in the treated subject, with minimal or acceptable toxic side effects. Applicable methods for determining an appropriate dose and dosing schedule for administration of a pharmaceutical composition of the present invention are described, for example, in Goodman and Gilman's The Pharmacological Basis of Therapeutics, Goodman et al., eds., 11th Edition, McGraw-Hill 2005, and Remington: The Science and Practice of Pharmacy, 20th and 21st Editions, Gennaro and University of the Sciences in Philadelphia, Eds., Lippencott Williams & Wilkins (2003 and 2005), each of which is hereby incorporated by reference.

Preferred unit dosage formulations are those containing a daily dose or unit, daily sub-dose, as herein discussed, or an appropriate fraction thereof, of the administered ingredient.

The dosage regimen for treating a disorder or a disease with the tumor specific neoantigenic peptides of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods.

The amounts and dosage regimens administered to a subject can depend on a number of factors, such as the mode of administration, the nature of the condition being treated, the body weight of the subject being treated and the judgment of the prescribing physician; all such factors being within the ambit of the skilled artisan from this disclosure and the knowledge in the art.

The amount of compound included within therapeutically active formulations according to the present invention is an effective amount for treating the disease or condition. In general, a therapeutically effective amount of the present preferred compound in dosage form usually ranges from slightly less than about 0.025 mg/kg/day to about 2.5 g/kg/day, preferably about 0.1 mg/kg/day to about 100 mg/kg/day of the patient or considerably more, depending upon the compound used, the condition or infection treated and the route of administration, although exceptions to this dosage range may be contemplated by the present invention. In its most preferred form, compounds according to the present invention are administered in amounts ranging from about 1 mg/kg/day to about 100 mg/kg/day. The dosage of the compound can depend on the condition being treated, the particular compound, and other clinical factors such as weight and condition of the patient and the route of administration of the compound. It is to be understood that the present invention has application for both human and veterinary use.

For oral administration to humans, a dosage of between approximately 0.1 to 100 mg/kg/day, preferably between approximately 1 and 100 mg/kg/day, is generally sufficient.

Where drug delivery is systemic rather than topical, this dosage range generally produces effective blood level concentrations of active compound ranging from less than about 0.04 to about 400 micrograms/cc or more of blood in the patient. The compound is conveniently administered in any suitable unit dosage form, including but not limited to one containing 0.001 to 3000 mg, preferably 0.05 to 500 mg of active ingredient per unit dosage form. An oral dosage of 10-250 mg is usually convenient.

According to certain exemplary embodiments, the vaccine or immunogenic composition is administered at a dose of about 10 µg to 1 mg per neoantigenic peptide. According to certain exemplary embodiments, the vaccine or immunogenic composition is administered at an average weekly dose level of about 10 µg to 2000 µg per neoantigenic peptide.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The invention provides for pharmaceutical compositions containing at least one tumor specific neoantigen described herein. In embodiments, the pharmaceutical compositions contain a pharmaceutically acceptable carrier, excipient, or diluent, which includes any pharmaceutical agent that does not itself induce the production of an immune response harmful to a subject receiving the composition, and which may be administered without undue toxicity. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful for treating and/or preventing viral infection and/or autoimmune disease.

A thorough discussion of pharmaceutically acceptable carriers, diluents, and other excipients is presented in Remington's Pharmaceutical Sciences (17th ed., Mack Publishing Company) and Remington: The Science and Practice of Pharmacy (21st ed., Lippincott Williams & Wilkins), which are hereby incorporated by reference. The formulation of the pharmaceutical composition should suit the mode of administration. In embodiments, the pharmaceutical composition is suitable for administration to humans, and can be sterile, non-particulate and/or non-pyrogenic.

Pharmaceutically acceptable carriers, excipients, or diluents include, but are not limited to, saline, buffered saline, dextrose, water, glycerol, ethanol, sterile isotonic aqueous buffer, and combinations thereof.

Wetting agents, emulsifiers and lubricants, such as sodium lauryl sulfate and magnesium stearate, as well as coloring agents, release agents, coating agents, sweetening, flavoring and perfuming agents, preservatives, and antioxidants can also be present in the compositions.

Examples of pharmaceutically-acceptable antioxidants include, but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In embodiments, the pharmaceutical composition is provided in a solid form, such as a lyophilized powder suitable for reconstitution, a liquid solution, suspension, emulsion, tablet, pill, capsule, sustained release formulation, or powder.

In embodiments, the pharmaceutical composition is supplied in liquid form, for example, in a sealed container indicating the quantity and concentration of the active ingredient in the pharmaceutical composition. In related embodiments, the liquid form of the pharmaceutical composition is supplied in a hermetically sealed container.

Methods for formulating the pharmaceutical compositions of the present invention are conventional and well known in the art (see Remington and Remington's). One of skill in the art can readily formulate a pharmaceutical composition having the desired characteristics (e.g., route of administration, biosafety, and release profile).

Methods for preparing the pharmaceutical compositions include the step of bringing into association the active ingredient with a pharmaceutically acceptable carrier and, optionally, one or more accessory ingredients. The pharmaceutical compositions can be prepared by uniformly and intimately bringing into association the active ingredient with liquid carriers, or finely divided solid carriers, or both, and then, if necessary, shaping the product. Additional methodology for preparing the pharmaceutical compositions, including the preparation of multilayer dosage forms, are described in Ansel's Pharmaceutical Dosage Forms and Drug Delivery Systems (9th ed., Lippincott Williams & Wilkins), which is hereby incorporated by reference.

Pharmaceutical compositions suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) described herein, a derivative thereof, or a pharmaceutically acceptable salt or prodrug thereof as the active ingredient(s). The active ingredient can also be administered as a bolus, electuary, or paste.

In solid dosage forms for oral administration (e.g., capsules, tablets, pills, dragees, powders, granules and the like), the active ingredient is mixed with one or more pharmaceutically acceptable carriers, excipients, or diluents, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions can also comprise buffering agents. Solid compositions of a similar type can also be prepared using fillers in soft and hard-filled gelatin capsules, and excipients such as lactose or milk sugars, as well as high molecular weight polyethylene glycols and the like.

A tablet can be made by compression or molding, optionally with one or more accessory ingredients. Compressed tablets can be prepared using binders (for example, gelatin or hydroxypropylmethyl cellulose), lubricants, inert diluents, preservatives, disintegrants (for example, sodium starch glycolate or cross-linked sodium carboxymethyl cellulose), surface-actives, and/or dispersing agents. Molded tablets can be made by molding in a suitable machine a mixture of the powdered active ingredient moistened with an inert liquid diluent.

The tablets and other solid dosage forms, such as dragees, capsules, pills, and granules, can optionally be scored or prepared with coatings and shells, such as enteric coatings and other coatings well known in the art.

In some embodiments, in order to prolong the effect of an active ingredient, it is desirable to slow the absorption of the compound from subcutaneous or intramuscular injection. This can be accomplished by the use of a liquid suspension of crystalline or amorphous material having poor water solubility. The rate of absorption of the active ingredient then depends upon its rate of dissolution which, in turn, can depend upon crystal size and crystalline form. Alternatively, delayed absorption of a parenterally-administered active ingredient is accomplished by dissolving or suspending the compound in an oil vehicle. In addition, prolonged absorption of the injectable pharmaceutical form can be brought about by the inclusion of agents that delay absorption such as aluminum monostearate and gelatin.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants or infusion devices.

Materials for use in the preparation of microspheres and/or microcapsules include biodegradable/bioerodible polymers such as polyglactin, poly-(isobutyl cyanoacrylate), poly(2-hydroxyethyl-L-glutamine) and poly(lactic acid).

Biocompatible carriers which can be used when formulating a controlled release parenteral formulation include carbohydrates such as dextrans, proteins such as albumin, lipoproteins or antibodies.

Materials for use in implants can be non-biodegradable, e.g., polydimethylsiloxane, or biodegradable such as, e.g., poly(caprolactone), poly(lactic acid), poly(glycolic acid) or poly(ortho esters).

In embodiments, the active ingredient(s) are administered by aerosol. This is accomplished by preparing an aqueous aerosol, liposomal preparation, or solid particles containing the compound. A nonaqueous (e.g., fluorocarbon propellant) suspension can be used. The pharmaceutical composition can also be administered using a sonic nebulizer, which would minimize exposing the agent to shear, which can result in degradation of the compound.

Ordinarily, an aqueous aerosol is made by formulating an aqueous solution or suspension of the active ingredient(s) together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Dosage forms for topical or transdermal administration of an active ingredient(s) includes powders, sprays, ointments, pastes, creams, lotions, gels, solutions, patches and inhalants. The active ingredient(s) can be mixed under sterile conditions with a pharmaceutically acceptable carrier, and with any preservatives, buffers, or propellants as appropriate.

Transdermal patches suitable for use in the present invention are disclosed in Transdermal Drug Delivery: Developmental Issues and Research Initiatives (Marcel Dekker Inc., 1989) and U.S. Pat. Nos. 4,743,249, 4,906,169, 5,198,223, 4,816,540, 5,422,119, 5,023,084, which are hereby incorporated by reference. The transdermal patch can also be any transdermal patch well known in the art, including transscrotal patches. Pharmaceutical compositions in such transdermal patches can contain one or more absorption enhancers or skin permeation enhancers well known in the art (see, e.g., U.S. Pat. Nos. 4,379,454 and 4,973,468, which are hereby incorporated by reference). Transdermal therapeutic systems for use in the present invention can be based on iontophoresis, diffusion, or a combination of these two effects.

Transdermal patches have the added advantage of providing controlled delivery of active ingredient(s) to the body. Such dosage forms can be made by dissolving or dispersing the active ingredient(s) in a proper medium. Absorption enhancers can also be used to increase the flux of the active ingredient across the skin. The rate of such flux can be controlled by either providing a rate controlling membrane or dispersing the active ingredient(s) in a polymer matrix or gel.

Such pharmaceutical compositions can be in the form of creams, ointments, lotions, liniments, gels, hydrogels, solutions, suspensions, sticks, sprays, pastes, plasters and other kinds of transdermal drug delivery systems. The compositions can also include pharmaceutically acceptable carriers or excipients such as emulsifying agents, antioxidants, buffering agents, preservatives, humectants, penetration enhancers, chelating agents, gel-forming agents, ointment bases, perfumes, and skin protective agents.

Examples of emulsifying agents include, but are not limited to, naturally occurring gums, e.g. gum acacia or gum tragacanth, naturally occurring phosphatides, e.g. soybean lecithin and sorbitan monooleate derivatives.

Examples of antioxidants include, but are not limited to, butylated hydroxy anisole (BHA), ascorbic acid and derivatives thereof, tocopherol and derivatives thereof, and cysteine.

Examples of preservatives include, but are not limited to, parabens, such as methyl or propyl p-hydroxybenzoate and benzalkonium chloride.

Examples of humectants include, but are not limited to, glycerin, propylene glycol, sorbitol and urea.

Examples of penetration enhancers include, but are not limited to, propylene glycol, DMSO, triethanolamine, N,N-dimethylacetamide, N,N-dimethylformamide, 2-pyrrolidone and derivatives thereof, tetrahydrofurfuryl alcohol, propylene glycol, diethylene glycol monoethyl or monomethyl ether with propylene glycol monolaurate or methyl laurate, eucalyptol, lecithin, TRANSCUTOL, and AZONE.

Examples of chelating agents include, but are not limited to, sodium EDTA, citric acid and phosphoric acid.

Examples of gel forming agents include, but are not limited to, Carbopol, cellulose derivatives, bentonite, alginates, gelatin and polyvinylpyrrolidone.

In addition to the active ingredient(s), the ointments, pastes, creams, and gels of the present invention can contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons, and volatile unsubstituted hydrocarbons, such as butane and propane.

Injectable depot forms are made by forming microencapsule matrices of compound(s) of the invention in biodegradable polymers such as polylactide-polyglycolide. Depending on the ratio of compound to polymer, and the nature of the particular polymer employed, the rate of compound release can be controlled. Examples of other biodegradable polymers include poly(orthoesters) and poly(anhydrides). Depot injectable formulations are also prepared by entrapping the drug in liposomes or microemulsions which are compatible with body tissue.

Subcutaneous implants are well known in the art and are suitable for use in the present invention. Subcutaneous implantation methods are preferably non-irritating and mechanically resilient. The implants can be of matrix type, of reservoir type, or hybrids thereof. In matrix type devices, the carrier material can be porous or non-porous, solid or semi-solid, and permeable or impermeable to the active compound or compounds. The carrier material can be biodegradable or may slowly erode after administration. In some instances, the matrix is non-degradable but instead relies on the diffusion of the active compound through the matrix for the carrier material to degrade. Alternative subcutaneous implant methods utilize reservoir devices where the active compound or compounds are surrounded by a rate controlling membrane, e.g., a membrane independent of component concentration (possessing zero-order kinetics). Devices consisting of a matrix surrounded by a rate controlling membrane also suitable for use.

Both reservoir and matrix type devices can contain materials such as polydimethylsiloxane, such as SILASTIC, or other silicone rubbers. Matrix materials can be insoluble polypropylene, polyethylene, polyvinyl chloride, ethylvinyl acetate, polystyrene and polymethacrylate, as well as glycerol esters of the glycerol palmitostearate, glycerol stearate, and glycerol behenate type. Materials can be hydrophobic or hydrophilic polymers and optionally contain solubilizing agents.

Subcutaneous implant devices can be slow-release capsules made with any suitable polymer, e.g., as described in U.S. Pat. Nos. 5,035,891 and 4,210,644, which are hereby incorporated by reference.

In general, at least four different approaches are applicable in order to provide rate control over the release and transdermal permeation of a drug compound. These approaches are: membrane-moderated systems, adhesive diffusion-controlled systems, matrix dispersion-type systems and microreservoir systems. It is appreciated that a controlled release percutaneous and/or topical composition can be obtained by using a suitable mixture of these approaches.

In a membrane-moderated system, the active ingredient is present in a reservoir which is totally encapsulated in a shallow compartment molded from a drug-impermeable laminate, such as a metallic plastic laminate, and a rate-controlling polymeric membrane such as a microporous or a non-porous polymeric membrane, e.g., ethylene-vinyl acetate copolymer. The active ingredient is released through the rate controlling polymeric membrane. In the drug reservoir, the active ingredient can either be dispersed in a solid polymer matrix or suspended in an unleachable, viscous liquid medium such as silicone fluid. On the external surface of the polymeric membrane, a thin layer of an adhesive polymer is applied to achieve an intimate contact of the transdermal system with the skin surface. The adhesive polymer is preferably a polymer which is hypoallergenic and compatible with the active drug substance.

In an adhesive diffusion-controlled system, a reservoir of the active ingredient is formed by directly dispersing the active ingredient in an adhesive polymer and then by, e.g., solvent casting, spreading the adhesive containing the active ingredient onto a flat sheet of substantially drug-impermeable metallic plastic backing to form a thin drug reservoir layer.

A matrix dispersion-type system is characterized in that a reservoir of the active ingredient is formed by substantially homogeneously dispersing the active ingredient in a hydrophilic or lipophilic polymer matrix. The drug-containing polymer is then molded into disc with a substantially well-defined surface area and controlled thickness. The adhesive polymer is spread along the circumference to form a strip of adhesive around the disc.

A microreservoir system can be considered as a combination of the reservoir and matrix dispersion type systems. In this case, the reservoir of the active substance is formed by first suspending the drug solids in an aqueous solution of water-soluble polymer and then dispersing the drug suspension in a lipophilic polymer to form a multiplicity of unleachable, microscopic spheres of drug reservoirs.

Any of the herein-described controlled release, extended release, and sustained release compositions can be formulated to release the active ingredient in about 30 minutes to about 1 week, in about 30 minutes to about 72 hours, in about 30 minutes to 24 hours, in about 30 minutes to 12 hours, in about 30 minutes to 6 hours, in about 30 minutes to 4 hours, and in about 3 hours to 10 hours. In embodiments, an effective concentration of the active ingredient(s) is sustained in a subject for 4 hours, 6 hours, 8 hours, 10 hours, 12 hours, 16 hours, 24 hours, 48 hours, 72 hours, or more after administration of the pharmaceutical compositions to the subject.

Vaccine or Immunogenic Compositions

The present invention is directed in some aspects to pharmaceutical compositions suitable for the prevention or treatment of cancer. In one embodiment, the composition comprises at least an immunogenic composition, e.g., a neoplasia vaccine or immunogenic composition capable of raising a specific T-cell response. The neoplasia vaccine or immunogenic composition comprises neoantigenic peptides and/or neoantigenic polypeptides corresponding to tumor specific neoantigens as described herein.

A suitable neoplasia vaccine or immunogenic composition can preferably contain a plurality of tumor specific neoantigenic peptides. In an embodiment, the vaccine or immunogenic composition can include between 1 and 100 sets of peptides, more preferably between 1 and 50 such peptides, even more preferably between 10 and 30 sets peptides, even more preferably between 15 and 25 peptides. According to another preferred embodiment, the vaccine or immunogenic composition can include at least one peptides, more preferably 2, 3, 4, or 5 peptides, In certain embodiments, the vaccine or immunogenic composition can comprise 5, 6, 7, 8, 9, 10, 11, 12, 13, 14, 15, 16, 17, 18, 19, 20, 21, 22, 23, 24, 25, 26, 27, 28, 29, or 30 different peptides.

The optimum amount of each peptide to be included in the vaccine or immunogenic composition and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c, i.d., i.p., i.m., and i.v. Preferred methods of DNA injection include i.d., i.m., s.c, i.p. and i.v. For example, doses of between 1 and 500 mg 50 µg and 1.5 mg, preferably 10 µg to 500 µg, of peptide or DNA may be given and can depend from the respective peptide or DNA. Doses of this range were successfully used in previous trials (Brunsvig P F, et al., Cancer Immunol Immunother. 2006; 55(12): 1553-1564; M. Staehler, et al., ASCO meeting 2007; Abstract No 3017). Other methods of administration of the vaccine or immunogenic composition are known to those skilled in the art.

In one embodiment of the present invention the different tumor specific neoantigenic peptides and/or polypeptides are selected for use in the neoplasia vaccine or immunogenic composition so as to maximize the likelihood of generating an immune attack against the neoplasias/tumors in a high proportion of subjects in the population. Without being bound by theory, it is believed that the inclusion of a diversity of tumor specific neoantigenic peptides can generate a broad scale immune attack against a neoplasia/tumor. In one embodiment, the selected tumor specific neoantigenic peptides/polypeptides are encoded by missense mutations. In a second embodiment, the selected tumor specific neoantigenic peptides/polypeptides are encoded by a combination of missense mutations and neoORF mutations. In a third embodiment, the selected tumor specific neoantigenic peptides/polypeptides are encoded by neoORF mutations.

In one embodiment in which the selected tumor specific neoantigenic peptides/polypeptides are encoded by missense mutations, the peptides and/or polypeptides are chosen based on their capability to associate with the MHC molecules of a high proportion of subjects in the population. Peptides/polypeptides derived from neoORF mutations can also be selected on the basis of their capability to associate with the MHC molecules of the patient population.

The vaccine or immunogenic composition is capable of raising a specific cytotoxic T-cells response and/or a specific helper T-cell response.

The vaccine or immunogenic composition can further comprise an adjuvant and/or a carrier. Examples of useful adjuvants and carriers are given herein. The peptides and/or polypeptides in the composition can be associated with a carrier such as, e.g., a protein or an antigen-presenting cell such as e.g. a dendritic cell (DC) capable of presenting the peptide to a T-cell.

Adjuvants are any substance whose admixture into the vaccine or immunogenic composition increases or otherwise modifies the immune response to the mutant peptide. Carriers are scaffold structures, for example a polypeptide or a polysaccharide, to which the neoantigenic peptides, is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response.

Suitable adjuvants include, but are not limited to 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PEPTEL. vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox. Quil or Superfos. Several immunological adjuvants (e.g., MF59) specific for dendritic cells and their preparation have been described previously (Dupuis M, et al., Cell Immunol. 1998; 186(1): 18-27; Allison A C; Dev Biol Stand. 1998; 92:3-11). Also cytokines may be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

Toll like receptors (TLRs) may also be used as adjuvants, and are important members of the family of pattern recognition receptors (PRRs) which recognize conserved motifs shared by many micro-organisms, termed "pathogen-associated molecular patterns" (PAMPS). Recognition of these "danger signals" activates multiple elements of the innate and adaptive immune system. TLRs are expressed by cells of the innate and adaptive immune systems such as dendritic cells (DCs), macrophages, T and B cells, mast cells, and granulocytes and are localized in different cellular compartments, such as the plasma membrane, lysosomes, endosomes, and endolysosomes. Different TLRs recognize distinct PAMPS. For example, TLR4 is activated by LPS contained in bacterial cell walls, TLR9 is activated by unmethylated bacterial or viral CpG DNA, and TLR3 is activated by double stranded RNA. TLR ligand binding leads to the activation of one or more intracellular signaling pathways, ultimately resulting in the production of many key molecules associated with inflammation and immunity (particularly the transcription factor NF-κB and the Type-I interferons). TLR mediated DC activation leads to enhanced DC activation, phagocytosis, upregulation of activation and co-stimulation markers such as CD80, CD83, and CD86, expression of CCR7 allowing migration of DC to draining lymph nodes and facilitating antigen presentation to T cells, as well as increased secretion of cytokines such as type I interferons, IL-12, and IL-6. All of these downstream events are critical for the induction of an adaptive immune response.

Among the most promising cancer vaccine or immunogenic composition adjuvants currently in clinical development are the TLR9 agonist CpG and the synthetic double-stranded RNA (dsRNA) TLR3 ligand poly-ICLC. In preclinical studies poly-ICLC appears to be the most potent TLR adjuvant when compared to LPS and CpG due to its induction of pro-inflammatory cytokines and lack of stimulation of IL-10, as well as maintenance of high levels of co-stimulatory molecules in DCs1. Furthermore, poly-ICLC was recently directly compared to CpG in non-human primates (rhesus macaques) as adjuvant for a protein vaccine or immunogenic composition consisting of human papillomavirus (HPV)16 capsomers (Stahl-Hennig C, Eisenblatter M, Jasny E, et al. Synthetic double-stranded RNAs are adjuvants for the induction of T helper 1 and humoral immune responses to human papillomavirus in rhesus macaques. PLoS pathogens. April 2009; 5(4)).

CpG immuno stimulatory oligonucleotides have also been reported to enhance the effects of adjuvants in a vaccine or immunogenic composition setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly, it enhances dendritic cell maturation and differentiation, resulting in enhanced activation of Th1 cells and strong cytotoxic T-lymphocyte (CTL) generation, even in the absence of CD4 T-cell help. The Th1 bias induced by TLR9 stimulation is maintained even in the presence of vaccine adjuvants such as alum or incomplete Freund's adjuvant (IFA) that normally promote a Th2 bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg, Nature Reviews, Drug Discovery, 5, June 2006, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, GERMANY), which is a preferred component of the pharmaceutical composition of the present invention. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C)(e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafinib, XL-999, CP-547632, pazopanib, ZD2171, AZD2171, ipilimumab, tremelimumab, and SC58175, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

Poly-ICLC is a synthetically prepared double-stranded RNA consisting of polyI and polyC strands of average length of about 5000 nucleotides, which has been stabilized to thermal denaturation and hydrolysis by serum nucleases by the addition of polylysine and carboxymethylcellulose. The compound activates TLR3 and the RNA helicase-domain of MDA5, both members of the PAMP family, leading to DC and natural killer (NK) cell activation and production of a "natural mix" of type I interferons, cytokines, and chemokines. Furthermore, poly-ICLC exerts a more direct, broad host-targeted anti-infectious and possibly antitumor effect mediated by the two IFN-inducible nuclear enzyme systems, the 2'5'-OAS and the P1/eIF2a kinase, also known as the PKR (4-6), as well as RIG-I helicase and MDA5.

In rodents and non-human primates, poly-ICLC was shown to enhance T cell responses to viral antigens, cross-priming, and the induction of tumor-, virus-, and autoantigen-specific CD8+ T-cells. In a recent study in non-human primates, poly-ICLC was found to be essential for the generation of antibody responses and T-cell immunity to DC targeted or non-targeted HIV Gag p24 protein, emphasizing its effectiveness as a vaccine adjuvant.

In human subjects, transcriptional analysis of serial whole blood samples revealed similar gene expression profiles among the 8 healthy human volunteers receiving one single s.c. administration of poly-ICLC and differential expression of up to 212 genes between these 8 subjects versus 4 subjects receiving placebo. Remarkably, comparison of the poly-ICLC gene expression data to previous data from volunteers immunized with the highly effective yellow fever vaccine YF 17D showed that a large number of transcriptional and signal transduction canonical pathways, including those of the innate immune system, were similarly upregulated at peak time points.

More recently, an immunologic analysis was reported on patients with ovarian, fallopian tube, and primary peritoneal cancer in second or third complete clinical remission who were treated on a phase 1 study of subcutaneous vaccination with synthetic overlapping long peptides (OLP) from the cancer testis antigen NY-ESO-1 alone or with Montanide-ISA-51, or with 1.4 mg poly-ICLC and Montanide. The generation of NY-ESO-1-specific CD4+ and CD8+ T-cell and antibody responses were markedly enhanced with the addition of poly-ICLC and Montanide compared to OLP alone or OLP and Montanide.

A vaccine or immunogenic composition according to the present invention may comprise more than one different adjuvant. Furthermore, the invention encompasses a therapeutic composition comprising any adjuvant substance including any of those herein discussed. It is also contemplated that the peptide or polypeptide, and the adjuvant can be administered separately in any appropriate sequence.

A carrier may be present independently of an adjuvant. The carrier may be covalently linked to the antigen. A carrier can also be added to the antigen by inserting DNA encoding the carrier in frame with DNA encoding the antigen. The function of a carrier can for example be to confer stability, to increase the biological activity, or to increase serum half-life. Extension of the half-life can help to reduce the number of applications and to lower doses, thus are beneficial for therapeutic but also economic reasons. Furthermore, a carrier may aid presenting peptides to T-cells. The carrier may be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier may be a physiologically acceptable carrier acceptable to humans and safe. However, tetanus toxoid and/or diptheria toxoid are suitable carriers in one embodiment of the invention. Alternatively, the carrier may be dextrans for example sepharose.

Cytotoxic T-cells (CTLs) recognize an antigen in the form of a peptide bound to an MHC molecule rather than the intact foreign antigen itself. The MHC molecule itself is located at the cell surface of an antigen presenting cell. Thus, an activation of CTLs is only possible if a trimeric complex of peptide antigen, MHC molecule, and APC is present. Correspondingly, it may enhance the immune response if not only the peptide is used for activation of CTLs, but if additionally APCs with the respective MHC molecule are added. Therefore, in some embodiments the vaccine or immunogenic composition according to the present invention additionally contains at least one antigen presenting cell.

The antigen-presenting cell (or stimulator cell) typically has an MHC class I or II molecule on its surface, and in one embodiment is substantially incapable of itself loading the MHC class I or II molecule with the selected antigen. As is described in more detail herein, the MHC class I or II molecule may readily be loaded with the selected antigen in vitro.

CD8+ cell activity may be augmented through the use of CD4+ cells. The identification of CD4 T+ cell epitopes for tumor antigens has attracted interest because many immune based therapies against cancer may be more effective if both CD8+ and CD4+T lymphocytes are used to target a patient's tumor. CD4+ cells are capable of enhancing CD8 T cell responses. Many studies in animal models have clearly demonstrated better results when both CD4+ and CD8+ T cells participate in anti-tumor responses (see e.g., Nishimura et al. (1999) Distinct role of antigen-specific T helper type 1 (TH1) and Th2 cells in tumor eradication in vivo. J Ex Med 190:617-27). Universal CD4+ T cell epitopes have been identified that are applicable to developing therapies against different types of cancer (see e.g., Kobayashi et al. (2008) Current Opinion in Immunology 20:221-27). For example, an HLA-DR restricted helper peptide from tetanus toxoid was used in melanoma vaccines to activate CD4+ T cells non-specifically (see e.g., Slingluff et al. (2007) Immunologic and Clinical Outcomes of a Randomized Phase II Trial of Two Multipeptide Vaccines for Melanoma in the Adjuvant Setting, Clinical Cancer Research 13(21):6386-95). It is contemplated within the scope of the invention that such CD4+ cells may be applicable at three levels that vary in their tumor specificity: 1) a broad level in which universal CD4+ epitopes (e.g., tetanus toxoid) may be used to augment CD8+ cells; 2) an intermediate level in which native, tumor-associated CD4+ epitopes may be used to augment CD8+ cells; and 3) a patient specific level in which neoantigen CD4+ epitopes may be used to augment CD8+ cells in a patient specific manner. Although current algorithms for predicting CD4 epitopes are limited in accuracy, it is a reasonable expectation that many long peptides containing predicted CD8 neoepitopes will also include CD4 epitopes. CD4 epitopes are longer than CD8 epitopes and typically are 10-12 amino acids in length although some can be longer (Kreiter et al, Mutant MHC Class II epitopes drive therapeutic immune responses to cancer, Nature (2015). Thus the neoantigenic epitopes described herein, either in the form of long peptides (>25 amino acids) or nucleic acids encoding such long peptides, may also boost CD4 responses in a tumor and patient-specific manner (level (3) above).

CD8+ cell immunity may also be generated with neoantigen loaded dendritic cell (DC) vaccine. DCs are potent antigen-presenting cells that initiate T cell immunity and can be used as cancer vaccines when loaded with one or more peptides of interest, for example, by direct peptide injection. For example, patients that were newly diagnosed with metastatic melanoma were shown to be immunized against 3 HLA-A*0201-restricted gp100 melanoma antigen-derived peptides with autologous peptide pulsed CD40L/IFN-g-activated mature DCs via an IL-12p70-producing patient DC vaccine (see e.g., Carreno et al (2013) L-12p70-producing patient DC vaccine elicits Tc1-polarized immunity, Journal of Clinical Investigation, 123(8):3383-94 and Ali et al. (2009) In situ regulation of DC subsets and T cells mediates tumor regression in mice, Cancer Immunotherapy, 1(8):1-10). It is contemplated within the scope of the invention that neoantigen loaded DCs may be prepared using the synthetic TLR 3 agonist Polyinosinic-Polycytidylic Acid-poly-L-lysine Carboxymethylcellulose (Poly-ICLC) to stimulate the DCs. Poly-ICLC is a potent individual maturation stimulus for human DCs as assessed by an upregulation of CD83 and CD86, induction of interleukin-12 (IL-12), tumor necrosis factor (TNF), interferon gamma-induced protein 10 (IP-10), interleukin 1 (IL-1), and type I interferons (IFN), and minimal interleukin 10 (IL-10) production. DCs may be differentiated from frozen peripheral blood mononuclear cells (PBMCs) obtained by leukapheresis, while PBMCs may be isolated by Ficoll gradient centrifugation and frozen in aliquots.

Illustratively, the following 7 day activation protocol may be used. Day 1—PBMCs are thawed and plated onto tissue culture flasks to select for monocytes which adhere to the plastic surface after 1-2 hr incubation at 37° C. in the tissue culture incubator. After incubation, the lymphocytes are washed off and the adherent monocytes are cultured for 5 days in the presence of interleukin-4 (IL-4) and granulocyte macrophage-colony stimulating factor (GM-CSF) to differentiate to immature DCs. On Day 6, immature DCs are pulsed with the keyhole limpet hemocyanin (KLH) protein which serves as a control for the quality of the vaccine and may boost the immunogenicity of the vaccine. The DCs are stimulated to mature, loaded with peptide antigens, and incubated overnight. On Day 7, the cells are washed, and frozen in 1 ml aliquots containing 4-20×10(6) cells using a controlled-rate freezer. Lot release testing for the batches of DCs may be performed to meet minimum specifications before the DCs are injected into patients (see e.g., Sabado et al. (2013) Preparation of tumor antigen-loaded mature dendritic cells for immunotherapy, J. Vis Exp. August 1; (78). doi: 10.3791/50085).

A DC vaccine may be incorporated into a scaffold system to facilitate delivery to a patient. Therapeutic treatment of a patients neoplasia with a DC vaccine may utilize a biomaterial system that releases factors that recruit host dendritic cells into the device, differentiates the resident, immature DCs by locally presenting adjuvants (e.g., danger signals) while releasing antigen, and promotes the release of activated, antigen loaded DCs to the lymph nodes (or desired site of action) where the DCs may interact with T cells to generate a potent cytotoxic T lymphocyte response to the cancer neoantigens. Implantable biomaterials may be used to generate a potent cytotoxic T lymphocyte response against a neoplasia in a patient specific manner. The biomaterial-resident dendritic cells may then be activated by exposing them to danger signals mimicking infection, in concert with release of antigen from the biomaterial. The activated dendritic cells then migrate from the biomaterials to lymph nodes to induce a cytotoxic T effector response. This approach has previously been demonstrated to lead to regression of established melanoma in preclinical studies using a lysate prepared from tumor biopsies (see e.g., Ali et al. (2209) In situ regulation of DC subsets and T cells mediates tumor regression in mice, Cancer Immunotherapy 1(8):1-10; Ali et al. (2009) Infection-mimicking materials to program dendritic cells in situ. Nat Mater 8:151-8), and such a vaccine is currently being tested in a Phase I clinical trial recently initiated at the Dana-Farber Cancer Institute. This approach has also been shown to lead to regression of glioblastoma, as well as the induction of a potent memory response to prevent relapse, using the C6 rat glioma model.24 in the current proposal. The ability of such an implantable, biomatrix vaccine delivery scaffold to amplify and sustain tumor specific dendritic cell activation may lead to more robust anti-tumor immunosensitization than can be achieved by traditional subcutaneous or intra-nodal vaccine administrations.

The present invention may include any method for loading a neoantigenic peptide onto a dendritic cell. One such method applicable to the present invention is a microfluidic intracellular delivery system. Such systems cause temporary membrane disruption by rapid mechanical deformation of human and mouse immune cells, thus allowing the intracellular delivery of biomolecules (Sharei et al., 2015, PLOS ONE).

Preferably, the antigen presenting cells are dendritic cells. Suitably, the dendritic cells are autologous dendritic cells that are pulsed with the neoantigenic peptide. The peptide may be any suitable peptide that gives rise to an appropriate T-cell response. T-cell therapy using autologous dendritic cells pulsed with peptides from a tumor associated antigen is disclosed in Murphy et al. (1996) The Prostate 29, 371-380 and Tjua et al. (1997) The Prostate 32, 272-278. In certain embodiments the dendritic cells are targeted using CD141, DEC205, or XCR1 markers. CD141+XCR1+DC's were identified as a subset that may be better suited to the induction of anti-tumor responses (Bachem et al., J. Exp. Med. 207, 1273-1281 (2010); Crozat et al., J. Exp. Med. 207, 1283-1292 (2010); and Gallois & Bhardwaj, Nature Med. 16, 854-856 (2010)).

Thus, in one embodiment of the present invention the vaccine or immunogenic composition containing at least one antigen presenting cell is pulsed or loaded with one or more peptides of the present invention. Alternatively, peripheral blood mononuclear cells (PBMCs) isolated from a patient may be loaded with peptides ex vivo and injected back into the patient. As an alternative the antigen presenting cell comprises an expression construct encoding a peptide of the present invention. The polynucleotide may be any suitable polynucleotide and it is preferred that it is capable of transducing the dendritic cell, thus resulting in the presentation of a peptide and induction of immunity.

The inventive pharmaceutical composition may be compiled so that the selection, number and/or amount of peptides present in the composition covers a high proportion of subjects in the population. The selection may be dependent on the specific type of cancer, the status of the disease, earlier treatment regimens, and, of course, the HLA-haplotypes present in the patient population.

Pharmaceutical compositions comprising the peptide of the invention may be administered to an individual already suffering from cancer. In therapeutic applications, compositions are administered to a patient in an amount sufficient to elicit an effective CTL response to the tumor antigen and to cure or at least partially arrest symptoms and/or complications. An amount adequate to accomplish this is defined as "therapeutically effective dose." Amounts effective for this use can depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 μg to about 50,000 μg of peptide for a 70 kg patient, followed by boosting dosages or from about 1.0 μg to about 10,000 μg of peptide pursuant to a boosting regimen over weeks to months depending upon the patient's response and condition and possibly by measuring specific CTL activity in the patient's blood. It should be kept in mind that the peptide and compositions of the present invention may generally be employed in serious disease states, that is, life-threatening or potentially life threatening situations, especially when the cancer has metastasized. For therapeutic use, administration should begin as soon as possible after the detection or surgical removal of tumors. This is followed by boosting doses until at least symptoms are substantially abated and for a period thereafter.

The pharmaceutical compositions (e.g., vaccine compositions) for therapeutic treatment are intended for parenteral, topical, nasal, oral or local administration. Preferably, the pharmaceutical compositions are administered parenterally, e.g., intravenously, subcutaneously, intradermally, or intramuscularly. The compositions may be administered at the site of surgical excision to induce a local immune response to the tumor. The invention provides compositions for parenteral administration which comprise a solution of the peptides and vaccine or immunogenic compositions are dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

A liposome suspension containing a peptide may be administered intravenously, locally, topically, etc. in a dose which varies according to, inter alia, the manner of administration, the peptide being delivered, and the stage of the disease being treated. For targeting to the immune cells, a ligand, such as, e.g., antibodies or fragments thereof specific for cell surface determinants of the desired immune system cells, can be incorporated into the liposome.

For solid compositions, conventional or nanoparticle nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant can, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%-20%, by weight of the composition, preferably 0.25-5%. The balance of the composition is ordinarily propellant. A carrier can also be included as desired, as with, e.g., lecithin for intranasal delivery.

The peptides and polypeptides of the invention can be readily synthesized chemically utilizing reagents that are free of contaminating bacterial or animal substances (Merrifield RB: Solid phase peptide synthesis. I. The synthesis of a tetrapeptide. J. Am. Chem. Soc. 85:2149-54, 1963).

The peptides and polypeptides of the invention can also be expressed by a vector, e.g., a nucleic acid molecule as herein-discussed, e.g., RNA or a DNA plasmid, a viral vector such as a poxvirus, e.g., orthopox virus, avipox virus, or adenovirus, AAV or lentivirus. This approach involves the use of a vector to express nucleotide sequences that encode the peptide of the invention. Upon introduction into an acutely or chronically infected host or into a noninfected host, the vector expresses the immunogenic peptide, and thereby elicits a host CTL response.

For therapeutic or immunization purposes, nucleic acids encoding the peptide of the invention and optionally one or more of the peptides described herein can also be administered to the patient. A number of methods are conveniently used to deliver the nucleic acids to the patient. For instance, the nucleic acid can be delivered directly, as "naked DNA". This approach is described, for instance, in Wolff et al., Science 247: 1465-1468 (1990) as well as U.S. Pat. Nos. 5,580,859 and 5,589,466. The nucleic acids can also be administered using ballistic delivery as described, for instance, in U.S. Pat. No. 5,204,253. Particles comprised solely of DNA can be administered. Alternatively, DNA can be adhered to particles, such as gold particles. Generally, a plasmid for a vaccine or immunological composition can comprise DNA encoding an antigen (e.g., one or more neoantigens) operatively linked to regulatory sequences which control expression or expression and secretion of the antigen from a host cell, e.g., a mammalian cell; for instance, from upstream to downstream, DNA for a promoter, such as a mammalian virus promoter (e.g., a CMV promoter such as an hCMV or mCMV promoter, e.g., an early-intermediate promoter, or an SV40 promoter—see documents cited or incorporated herein for useful promoters), DNA for a eukaryotic leader peptide for secretion (e.g., tissue plasminogen activator), DNA for the neoantigen(s), and DNA encoding a terminator (e.g., the 3' UTR transcriptional terminator from the gene encoding Bovine Growth Hormone or bGH polyA). A composition can contain more than one plasmid or vector, whereby each vector contains and expresses a different neoantigen. Mention is also made of Wasmoen U.S. Pat. No. 5,849,303, and Dale U.S. Pat. No. 5,811,104, whose text may be useful. DNA or DNA plasmid formulations can be formulated with or inside cationic lipids; and, as to cationic lipids, as well as adjuvants, mention is also made of Loosmore U.S. Patent Application 2003/0104008. Also, teachings in Audonnet U.S. Pat. Nos. 6,228,846 and 6,159,477 may be relied upon for DNA plasmid teachings that can be employed in constructing and using DNA plasmids that contain and express in vivo.

The nucleic acids can also be delivered complexed to cationic compounds, such as cationic lipids. Lipid-mediated gene delivery methods are described, for instance, in WO1996/18372; WO 1993/24640; Mannino & Gould-Fogerite, BioTechniques 6(7): 682-691 (1988); U.S. Pat. No. 5,279,833; WO 1991/06309; and Feigner et al., Proc. Natl. Acad. Sci. USA 84: 7413-7414 (1987).

RNA encoding the peptide of interest (e.g., mRNA) can also be used for delivery (see, e.g., Kiken et al, 2011; Su et al, 2011; see also U.S. Pat. No. 8,278,036; Halabi et al. J Clin Oncol (2003) 21:1232-1237; Petsch et al, Nature Biotechnology 2012 Dec. 7; 30(12):1210-6).

Viral vectors as described herein can also be used to deliver the neoantigenic peptides of the invention. Vectors can be administered so as to have in vivo expression and response akin to doses and/or responses elicited by antigen administration.

A preferred means of administering nucleic acids encoding the peptide of the invention uses minigene constructs encoding multiple epitopes. To create a DNA sequence encoding the selected CTL epitopes (minigene) for expression in human cells, the amino acid sequences of the epitopes are reverse translated. A human codon usage table is used to guide the codon choice for each amino acid. These epitope-encoding DNA sequences are directly adjoined, creating a continuous polypeptide sequence. To optimize expression and/or immunogenicity, additional elements can be incorporated into the minigene design. Examples of amino acid sequence that could be reverse translated and included in the minigene sequence include: helper T lymphocyte, epitopes, a leader (signal) sequence, and an endoplasmic reticulum retention signal. In addition, MHC presentation of CTL epitopes may be improved by including synthetic (e.g. poly-alanine) or naturally-occurring flanking sequences adjacent to the CTL epitopes.

The minigene sequence is converted to DNA by assembling oligonucleotides that encode the plus and minus strands of the minigene. Overlapping oligonucleotides (30-100 bases long) are synthesized, phosphorylated, purified and annealed under appropriate conditions using well known techniques. The ends of the oligonucleotides are joined using T4 DNA ligase. This synthetic minigene, encoding the CTL epitope polypeptide, can then cloned into a desired expression vector.

Standard regulatory sequences well known to those of skill in the art are included in the vector to ensure expression in the target cells. Several vector elements are required: a promoter with a down-stream cloning site for minigene insertion; a polyadenylation signal for efficient transcription termination; an *E. coli* origin of replication; and an *E. coli* selectable marker (e.g. ampicillin or kanamycin resistance). Numerous promoters can be used for this purpose, e.g., the human cytomegalovirus (hCMV) promoter. See, U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences can also be considered for increasing minigene expression. It has recently been proposed that immuno stimulatory sequences (ISSs or CpGs) play a role in the immunogenicity of DNA' vaccines. These sequences could be included in the vector, outside the minigene coding sequence, if found to enhance immunogenicity.

In some embodiments, a bicistronic expression vector, to allow production of the minigene-encoded epitopes and a second protein included to enhance or decrease immunogenicity can be used. Examples of proteins or polypeptides that could beneficially enhance the immune response if co-expressed include cytokines (e.g., IL2, IL12, GM-CSF), cytokine-inducing molecules (e.g. LeIF) or costimulatory molecules. Helper (HTL) epitopes could be joined to intracellular targeting signals and expressed separately from the CTL epitopes. This would allow direction of the HTL epitopes to a cell compartment different than the CTL epitopes. If required, this could facilitate more efficient entry of HTL epitopes into the MHC class II pathway, thereby improving CTL induction. In contrast to CTL induction, specifically decreasing the immune response by co-expression of immunosuppressive molecules (e.g. TGF-$\beta$) may be beneficial in certain diseases.

Once an expression vector is selected, the minigene is cloned into the polylinker region downstream of the promoter. This plasmid is transformed into an appropriate *E. coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

Purified plasmid DNA can be prepared for injection using a variety of formulations. The simplest of these is reconstitution of lyophilized DNA in sterile phosphate-buffer saline (PBS). A variety of methods have been described, and new techniques may become available. As noted herein, nucleic acids are conveniently formulated with cationic lipids. In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Target cell sensitization can be used as a functional assay for expression and MHC class I presentation of minigene-encoded CTL epitopes. The plasmid DNA is introduced into a mammalian cell line that is suitable as a target for standard CTL chromium release assays. The transfection method used is dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 labeled and used as target cells for epitope-specific CTL lines. Cytolysis, detected by 51 Cr release, indicates production of MHC presentation of mini gene-encoded CTL epitopes.

In vivo immunogenicity is a second approach for functional testing of minigene DNA formulations. Transgenic mice expressing appropriate human MHC molecules are immunized with the DNA product. The dose and route of administration are formulation dependent (e.g. IM for DNA in PBS, IP for lipid-complexed DNA). Twenty-one days after immunization, splenocytes are harvested and restimulated for 1 week in the presence of peptides encoding each epitope being tested. These effector cells (CTLs) are assayed for cytolysis of peptide-loaded, chromium-51 labeled target cells using standard techniques. Lysis of target cells sensitized by MHC loading of peptides corresponding to minigene-encoded epitopes demonstrates DNA vaccine function for in vivo induction of CTLs.

Peptides may be used to elicit CTL ex vivo, as well. The resulting CTL, can be used to treat chronic tumors in patients in need thereof that do not respond to other conventional forms of therapy, or does not respond to a peptide vaccine approach of therapy. Ex vivo CTL responses to a particular tumor antigen are induced by incubating in tissue culture the patient's CTL precursor cells (CTLp) together with a source of antigen-presenting cells (APC) and the appropriate peptide. After an appropriate incubation time (typically 1-4 weeks), in which the CTLp are activated and mature and expand into effector CTL, the cells are infused back into the patient, where they destroy their specific target cell (i.e., a tumor cell). In order to optimize the in vitro conditions for the generation of specific cytotoxic T cells, the culture of stimulator cells are maintained in an appropriate serum-free medium.

Prior to incubation of the stimulator cells with the cells to be activated, e.g., precursor CD8+ cells, an amount of antigenic peptide is added to the stimulator cell culture, of sufficient quantity to become loaded onto the human Class I molecules to be expressed on the surface of the stimulator cells. In the present invention, a sufficient amount of peptide is an amount that allows about 200, and preferably 200 or more, human Class I MHC molecules loaded with peptide to be expressed on the surface of each stimulator cell. Preferably, the stimulator cells are incubated with >2 µg/ml peptide. For example, the stimulator cells are incubates with >3, 4, 5, 10, 15, or more µg/ml peptide.

Resting or precursor CD8+ cells are then incubated in culture with the appropriate stimulator cells for a time period sufficient to activate the CD8+ cells. Preferably, the CD8+ cells are activated in an antigen-specific manner. The ratio of resting or precursor CD8+(effector) cells to stimulator cells may vary from individual to individual and may further depend upon variables such as the amenability of an individual's lymphocytes to culturing conditions and the nature and severity of the disease condition or other condition for which the within-described treatment modality is used. Preferably, however, the lymphocyte: stimulator cell ratio is in the range of about 30:1 to 300:1. The effector/stimulator culture may be maintained for as long a time as is necessary to stimulate a therapeutically useable or effective number of CD8+ cells.

The induction of CTL in vitro requires the specific recognition of peptides that are bound to allele specific MHC class I molecules on APC. The number of specific MHC/peptide complexes per APC is crucial for the stimulation of CTL, particularly in primary immune responses. While small amounts of peptide/MHC complexes per cell are sufficient to render a cell susceptible to lysis by CTL, or to stimulate a secondary CTL response, the successful activation of a CTL precursor (pCTL) during primary response requires a significantly higher number of MHC/peptide complexes. Peptide loading of empty major histocompatability complex molecules on cells allows the induction of primary cytotoxic T lymphocyte responses.

Since mutant cell lines do not exist for every human MHC allele, it is advantageous to use a technique to remove endogenous MHC-associated peptides from the surface of APC, followed by loading the resulting empty MHC molecules with the immunogenic peptides of interest. The use of non-transformed (non-tumorigenic), noninfected cells, and preferably, autologous cells of patients as APC is desirable for the design of CTL induction protocols directed towards development of ex vivo CTL therapies. This application discloses methods for stripping the endogenous MHC-associated peptides from the surface of APC followed by the loading of desired peptides.

A stable MHC class I molecule is a trimeric complex formed of the following elements: 1) a peptide usually of 8-10 residues, 2) a transmembrane heavy polymorphic protein chain which bears the peptide-binding site in its a1 and a2 domains, and 3) a non-covalently associated non-polymorphic light chain, p2microglobuiin. Removing the bound peptides and/or dissociating the p2microglobulin from the complex renders the MHC class I molecules nonfunctional and unstable, resulting in rapid degradation. All MHC class I molecules isolated from PBMCs have endogenous peptides bound to them. Therefore, the first step is to remove all endogenous peptides bound to MHC class I molecules on the APC without causing their degradation before exogenous peptides can be added to them.

Two possible ways to free up MHC class I molecules of bound peptides include lowering the culture temperature from 37° C. to 26° C. overnight to destabilize p2microglobulin and stripping the endogenous peptides from the cell using a mild acid treatment. The methods release previously bound peptides into the extracellular environment allowing new exogenous peptides to bind to the empty class I molecules. The cold-temperature incubation method enables exogenous peptides to bind efficiently to the MHC complex, but requires an overnight incubation at 26° C. which may slow the cell's metabolic rate. It is also likely that cells not actively synthesizing MHC molecules (e.g., resting PBMC) would not produce high amounts of empty surface MHC molecules by the cold temperature procedure.

Harsh acid stripping involves extraction of the peptides with trifluoroacetic acid, pH 2, or acid denaturation of the immunoaffinity purified class I-peptide complexes. These methods are not feasible for CTL induction, since it is important to remove the endogenous peptides while preserving APC viability and an optimal metabolic state which is critical for antigen presentation. Mild acid solutions of pH 3 such as glycine or citrate-phosphate buffers have been used to identify endogenous peptides and to identify tumor associated T cell epitopes. The treatment is especially effective, in that only the MHC class I molecules are destabilized (and associated peptides released), while other surface antigens remain intact, including MHC class II molecules. Most importantly, treatment of cells with the mild acid solutions do not affect the cell's viability or metabolic state. The mild acid treatment is rapid since the stripping of the endogenous peptides occurs in two minutes at 4° C. and the APC is ready to perform its function after the appropriate peptides are loaded. The technique is utilized herein to make peptide-specific APCs for the generation of primary antigen-specific CTL. The resulting APC are efficient in inducing peptide-specific CD8+CTL.

Activated CD8+ cells may be effectively separated from the stimulator cells using one of a variety of known methods. For example, monoclonal antibodies specific for the stimulator cells, for the peptides loaded onto the stimulator cells, or for the CD8+ cells (or a segment thereof) may be utilized to bind their appropriate complementary ligand. Antibody-tagged molecules may then be extracted from the stimulator-effector cell admixture via appropriate means, e.g., via well-known immunoprecipitation or immunoassay methods.

Effective, cytotoxic amounts of the activated CD8+ cells can vary between in vitro and in vivo uses, as well as with the amount and type of cells that are the ultimate target of these killer cells. The amount can also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, and even more preferably, about $1 \times 10^9$ to about $1 \times 10^{10}$ activated CD8+ cells are utilized for adult humans, compared to about $5 \times 10^6$-$5 \times 10^7$ cells used in mice.

Preferably, as discussed herein, the activated CD8+ cells are harvested from the cell culture prior to administration of the CD8+ cells to the individual being treated. It is important to note, however, that unlike other present and proposed treatment modalities, the present method uses a cell culture system that is not tumorigenic. Therefore, if complete separation of stimulator cells and activated CD8+ cells are not achieved, there is no inherent danger known to be associated with the administration of a small number of stimulator cells, whereas administration of mammalian tumor-promoting cells may be extremely hazardous.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8+ cells via intravenous infusion is appropriate.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Wei, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments are discussed in the sections that follow.

Therapeutic Methods

The present invention provides methods of inducing a neoplasia/tumor specific immune response in a subject, vaccinating against a neoplasia/tumor, treating and or alleviating a symptom of cancer in a subject by administering the subject a plurality of neoantigenic peptides or composition of the invention.

According to the invention, the herein-described neoplasia vaccine or immunogenic composition may be used for a patient that has been diagnosed as having cancer, or at risk of developing cancer.

The claimed combination of the invention is administered in an amount sufficient to induce a CTL response.

Additional Therapies

The tumor specific neoantigen peptides and pharmaceutical compositions described herein can also be administered in a combination therapy with another agent, for example a therapeutic agent. In certain embodiments, the additional agents can be, but are not limited to, chemotherapeutic agents, anti-angiogenesis agents and agents that reduce immune-suppression.

The neoplasia vaccine or immunogenic composition can be administered before, during, or after administration of the additional agent. In embodiments, the neoplasia vaccine or immunogenic composition is administered before the first administration of the additional agent. In other embodiments, the neoplasia vaccine or immunogenic composition is administered after the first administration of the additional therapeutic agent (e.g., 1, 2, 3, 4, 5, 6, 7, 8, 9, 10, 11, 12, 13, 14 days or more). In embodiments, the neoplasia vaccine or immunogenic composition is administered simultaneously with the first administration of the additional therapeutic agent.

The therapeutic agent is for example, a chemotherapeutic or biotherapeutic agent, radiation, or immunotherapy. Any suitable therapeutic treatment for a particular cancer may be administered. Examples of chemotherapeutic and biotherapeutic agents include, but are not limited to, an angiogenesis inhibitor, such as hydroxy angiostatin K1-3, DL-α-Difluoromethyl-ornithine, endostatin, fumagillin, genistein, minocycline, staurosporine, and thalidomide; a DNA intercaltor/cross-linker, such as Bleomycin, Carboplatin, Carmustine, Chlorambucil, Cyclophosphamide, cis-Diammineplatinum (II) dichloride (Cisplatin), Melphalan, Mitoxantrone, and Oxaliplatin; a DNA synthesis inhibitor, such as (±)-Amethopterin (Methotrexate), 3-Amino-1,2,4-benzotriazine 1,4-dioxide, Aminopterin, Cytosine β-D-arabinofuranoside, 5-Fluoro-5'-deoxyuridine, 5-Fluorouracil, Ganciclovir, Hydroxyurea, and Mitomycin C; a DNA-RNA transcription regulator, such as Actinomycin D, Daunorubicin, Doxorubicin, Homoharringtonine, and Idarubicin; an enzyme inhibitor, such as S(+)-Camptothecin, Curcumin, (−)-Deguelin, 5,6-Dichlorobenzimidazole 1-β-D-ribofuranoside, Etoposide, Formestane, Fostriecin, Hispidin, 2-Imino-1-imidazoli-dineacetic acid (Cyclocreatine), Mevinolin, Trichostatin A, Tyrphostin AG 34, and Tyrphostin AG 879; a gene regulator, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid all trans (Vitamin A acid), 9-cis-Retinoic Acid, 13-cis-Retinoic acid, Retinol (Vitamin A), Tamoxifen, and Troglitazone; a microtubule inhibitor, such as Colchicine, docetaxel, Dolastatin 15, Nocodazole, Paclitaxel, Podophyllotoxin, Rhizoxin, Vinblastine, Vincristine, Vindesine, and Vinorelbine (Navelbine); and an unclassified therapeutic agent, such as 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-α, Rapamycin, Sex hormone-binding globulin, Thapsigargin, and Urinary trypsin inhibitor fragment (Bikunin). The therapeutic agent may be altretamine, amifostine, asparaginase, capecitabine, cladribine, cisapride, cytarabine, dacarbazine (DTIC), dactinomycin, dronabinol, epoetin alpha, filgrastim, fludarabine, gemcitabine, granisetron, ifosfamide, irinotecan, lansoprazole, levamisole, leucovorin, megestrol, mesna, metoclopramide, mitotane, omeprazole, ondansetron, pilocarpine, prochloroperazine, or topotecan hydrochloride. The therapeutic agent may be a monoclonal antibody or small molecule such as rituximab (Rituxan®), alemtuzumab (Campath®), Bevacizumab (Avastin®), Cetuximab (Erbitux®), panitumumab (Vectibix®), and trastuzumab (Herceptin®), Vemurafenib (Zelboraf@) imatinib mesylate (Gleevec®), erlotinib (Tarceva®), gefitinib (Iressa®), Vismodegib (Erivedge™), 90Y-ibritumomab tiuxetan, 131I-tositumomab, ado-trastuzumab emtansine, lapatinib (Tykerb®), pertuzumab (Perjeta™), ado-trastuzumab emtansine (Kadcyla™), regorafenib (Stivarga®), sunitinib (Sutent®), Denosumab (Xgeva®), sorafenib (Nexavar®), pazopanib (Votrient®), axitinib (Inlyta®), dasatinib (Sprycel®), nilotinib (Tasigna®), bosutinib (Bosulif®), ofatumumab (Arzerra®), obinutuzumab (Gazyva™), ibrutinib (Imbruvica™), idelalisib (Zydelig®), crizotinib (Xalkori®), erlotinib (Tarceva®), afatinib dimaleate (Gilotrif®), ceritinib (LDK378/Zykadia), Tositumomab and 131I-tositumomab (Bexxar®), ibritumomab tiuxetan (Zevalin®), brentuximab vedotin (Adcetris®), bortezomib (Velcade®), siltuximab (Sylvant™), trametinib (Mekinist®), dabrafenib (Tafinlar®), pembrolizumab (Keytruda®), carfilzomib (Kyprolis®), Ramucirumab (Cyramza™), Cabozantinib (Cometriq™), vandetanib (Caprelsa®), Optionally, the therapeutic agent is a neoantigen. The therapeutic agent may be a cytokine such as interferons (INFs), interleukins (ILs), or hematopoietic growth factors. The therapeutic agent may be INF-α, IL-2, Aldesleukin, IL-2, Erythropoietin, Granulocyte-macrophage colony-stimulating factor (GM-CSF) or granulocyte colony-stimulating factor. The therapeutic agent may be a targeted therapy such as toremifene (Fareston®), fulvestrant (Faslodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zolinza®), romidepsin (Istodax®), bexarotene (Targretin®), pralatrexate (Folotyn®), lenaliomide (Revlimid®), belinostat (Beleodaq™), lenaliomide (Revlimid®), pomalidomide (Pomalyst®), Cabazitaxel (Jevtana®), enzalutamide (Xtandi®), abiraterone acetate (Zytiga®), radium 223 chloride (Xofigo®), or everolimus (Afinitor®). Additionally, the therapeutic agent may be an epigenetic targeted drug such as HDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi). For prostate cancer treatment, a preferred chemotherapeutic agent with which anti-CTLA-4 can be combined is paclitaxel (TAXOL).

In certain embodiments, the one or more additional agents are one or more anti-glucocorticoid-induced tumor necrosis factor family receptor (GITR) agonistic antibodies. GITR is a costimulatory molecule for T lymphocytes, modulates innate and adaptive immune system and has been found to participate in a variety of immune responses and inflammatory processes. GITR was originally described by Nocentini et al. after being cloned from dexamethasone-treated murine T cell hybridomas (Nocentini et al. Proc Natl Acad Sci USA 94:6216-6221.1997). Unlike CD28 and CTLA-4, GITR has a very low basal expression on naive CD4+ and CD8+ T cells (Ronchetti et al. Eur J Immunol 34:613-622. 2004). The observation that GITR stimulation has immunostimulatory effects in vitro and induced autoimmunity in vivo prompted the investigation of the antitumor potency of triggering this pathway. A review of Modulation Of Ctla 4 And Gitr For Cancer Immunotherapy can be found in Cancer Immunology and Immunotherapy (Avogadri et al. Current Topics in Microbiology and Immunology 344. 2011). Other agents that can contribute to relief of immune suppression include checkpoint inhibitors targeted at another member of the CD28/CTLA4 Ig superfamily such as BTLA, LAG3, ICOS, PDL1 or KIR (Page et a, Annual Review of Medicine 65:27 (2014)). In further additional embodiments, the checkpoint inhibitor is targeted at a member of the TNFR superfamily such as CD40, OX40, CD137, GITR, CD27 or TIM-3. In some cases targeting a checkpoint inhibitor is accomplished with an inhibitory antibody or similar molecule. In other cases, it is accomplished with an agonist for the target; examples of this class include the stimulatory targets OX40 and GITR.

In certain embodiments, the one or more additional agents are synergistic in that they increase immunogenicity after treatment. In one embodiment the additional agent allows for lower toxicity and/or lower discomfort due to lower doses of the additional therapeutic agents or any components of the combination therapy described herein. In another embodiment the additional agent results in longer lifespan due to increased effectiveness of the combination therapy described herein. Chemotherapeutic treatments that enhance the immunological response in a patient have been reviewed (Zitvogel et al., Immunological aspects of cancer chemotherapy. Nat Rev Immunol. 2008 January; 8(1):59-73). Additionally, chemotherapeutic agents can be administered safely with immunotherapy without inhibiting vaccine specific T-cell responses (Perez et al., A new era in anticancer peptide vaccines. Cancer May 2010). In one embodiment the additional agent is administered to increase the efficacy of the therapy described herein. In one embodiment the additional agent is a chemotherapy treatment. In one embodiment low doses of chemotherapy potentiate delayed-type hypersensitivity (DTH) responses. In one embodiment the chemotherapy agent targets regulatory T-cells. In one embodiment cyclophosphamide is the therapeutic agent. In one embodiment cyclophosphamide is administered prior to vaccination. In one embodiment cyclophosphamide is administered as a single dose before vaccination (Walter et al., Multipeptide immune response to cancer vaccine IMA901 after single-dose cyclophosphamide associates with longer patient survival. Nature Medicine; 18:8 2012). In another embodiment, cyclophosphamide is administered according to a metronomic program, where a daily dose is administered for one month (Ghiringhelli et al., Metronomic cyclophosphamide regimen selectively depletes CD4+ CD25+ regulatory T cells and restores T and NK effector functions in end stage cancer patients. Cancer Immunol Immunother 2007 56:641-648). In another embodiment taxanes are administered before vaccination to enhance T-cell and NK-cell functions (Zitvogel et al., 2008). In another embodiment a low dose of a chemotherapeutic agent is administered with the therapy described herein. In one embodiment the chemotherapeutic agent is estramustine. In one embodiment the cancer is hormone resistant prostate cancer. A ≥50% decrease in serum prostate specific antigen (PSA) was seen in 8.7% of advanced hormone refractory prostate cancer patients by personalized vaccination alone, whereas such a decrease was seen in 54% of patients when the personalized vaccination was combined with a low dose of estramustine (Itoh et al., Personalized peptide vaccines: A new therapeutic modality for cancer. Cancer Sci 2006; 97: 970-976). In another embodiment glucocorticoids are administered with or before the therapy described herein (Zitvogel et al., 2008). In another embodiment glucocorticoids are administered after the therapy described herein. In another embodiment Gemcitabine is administered before, simultaneously, or after the therapy described herein to enhance the frequency of tumor specific CTL precursors (Zitvogel et al., 2008). In another embodiment 5-fluorouracil is administered with the therapy described herein as synergistic effects were seen with a peptide based vaccine (Zitvogel et al., 2008). In another embodiment an inhibitor of Braf, such as Vemurafenib, is used as an additional agent. Braf inhibition has been shown to be associated with an increase in melanoma antigen expression and T-cell infiltrate and a decrease in immunosuppressive cytokines in tumors of treated patients (Frederick et al., BRAF inhibition is associated with enhanced melanoma antigen expression and a more favorable tumor microenvironment in patients with metastatic melanoma. Clin Cancer Res. 2013; 19:1225-1231). In another embodiment an inhibitor of tyrosine kinases is used as an additional agent. In one embodiment the tyrosine kinase inhibitor is used before vaccination with the therapy described herein. In one embodiment the tyrosine kinase inhibitor is used simultaneously with the therapy described herein. In another embodiment the tyrosine kinase inhibitor is used to create a more immune permissive environment. In another embodiment the tyrosine kinase inhibitor is sunitinib or imatinib mesylate. It has previously been shown that favorable outcomes could be achieved with sequential administration of continuous daily dosing of sunitinib and recombinant vaccine (Farsaci et al., Consequence of dose scheduling of sunitinib on host immune response elements and vaccine combination therapy. Int J Cancer; 130: 1948-1959). Sunitinib has also been shown to reverse type-1 immune suppression using a daily dose of 50 mg/day (Finke et al., Sunitinib Reverses Type-1 Immune Suppression and Decreases T-Regulatory Cells in Renal Cell Carcinoma Patients. Clin Cancer Res 2008; 14(20)). In another embodiment targeted therapies are administered in combination with the therapy described herein. Doses of targeted therapies has been described previously (Alvarez, Present and future evolution of advanced breast cancer therapy. Breast Cancer Research 2010, 12(Suppl 2):S1). In another embodiment temozolomide is administered with the therapy described herein. In one embodiment temozolomide is administered at 200 mg/day for 5 days every fourth week of a combination therapy with the therapy described herein. Results of a similar strategy have been shown to have low toxicity (Kyte et al., Telomerase Peptide Vaccination Combined with Temozolomide: A Clinical Trial in Stage IV Melanoma Patients. Clin Cancer Res; 17(13) 2011). In another embodiment the therapy is administered with an additional therapeutic agent that results in lymphopenia. In one embodiment the additional agent is temozolomide. An immune response can still be induced under these conditions (Sampson et al., Greater chemotherapy-induced lymphopenia enhances tumor-specific immune responses that eliminate EGFRvIII-expressing tumor cells in patients with glioblastoma. Neuro-Oncology 13(3):324-333, 2011).

Patients in need thereof may receive a series of priming vaccinations with a mixture of tumor-specific peptides. Additionally, over a 4 week period the priming may be followed by two boosts during a maintenance phase. All vaccinations are subcutaneously delivered. The vaccine or immunogenic composition is evaluated for safety, tolerability, immune response and clinical effect in patients and for feasibility of producing vaccine or immunogenic composition and successfully initiating vaccination within an appropriate time frame. The first cohort can consist of 5 patients, and after safety is adequately demonstrated, an additional cohort of 10 patients may be enrolled. Peripheral blood is extensively monitored for peptide-specific T-cell responses and patients are followed for up to two years to assess disease recurrence.

Administering a Combination Therapy Consistent with Standard of Care

In another aspect, the therapy described herein provides selecting the appropriate point to administer a combination therapy in relation to and within the standard of care for the cancer being treated for a patient in need thereof. The studies described herein show that the combination therapy can be effectively administered even within the standard of care that includes surgery, radiation, or chemotherapy. The standards of care for the most common cancers can be found on the website of National Cancer Institute (www.cancer.gov/cancertopics). The standard of care is the current treatment that is accepted by medical experts as a proper treatment for a certain type of disease and that is widely used by healthcare professionals. Standard or care is also called best practice, standard medical care, and standard therapy. Standards of Care for cancer generally include surgery, lymph node removal, radiation, chemotherapy, targeted therapies, antibodies targeting the tumor, and immunotherapy. Immunotherapy can include checkpoint blockers (CBP), chimeric antigen receptors (CARs), and adoptive T-cell therapy. The combination therapy described herein can be incorporated within the standard of care. The combination therapy described herein may also be administered where the standard of care has changed due to advances in medicine.

Incorporation of the combination therapy described herein may depend on a treatment step in the standard of care that can lead to activation of the immune system. Treatment steps that can activate and function synergistically with the combination therapy have been described herein. The therapy can be advantageously administered simultaneously or after a treatment that activates the immune system.

Incorporation of the combination therapy described herein may depend on a treatment step in the standard of care that causes the immune system to be suppressed. Such treatment steps may include irradiation, high doses of alkylating agents and/or methotrexate, steroids such as glucosteroids, surgery, such as to remove the lymph nodes, imatinib mesylate, high doses of TNF, and taxanes (Zitvogel et al., 2008). The combination therapy may be administered before such steps or may be administered after.

In one embodiment the combination therapy may be administered after bone marrow transplants and peripheral blood stem cell transplantation. Bone marrow transplantation and peripheral blood stem cell transplantation are procedures that restore stem cells that were destroyed by high doses of chemotherapy and/or radiation therapy. After being treated with high-dose anticancer drugs and/or radiation, the patient receives harvested stem cells, which travel to the bone marrow and begin to produce new blood cells. A "mini-transplant" uses lower, less toxic doses of chemotherapy and/or radiation to prepare the patient for transplant. A "tandem transplant" involves two sequential courses of high-dose chemotherapy and stem cell transplant. In autologous transplants, patients receive their own stem cells. In syngeneic transplants, patients receive stem cells from their identical twin. In allogeneic transplants, patients receive stem cells from their brother, sister, or parent. A person who is not related to the patient (an unrelated donor) also may be used. In some types of leukemia, the graft-versus-tumor (GVT) effect that occurs after allogeneic BMT and PBSCT is crucial to the effectiveness of the treatment. GVT occurs when white blood cells from the donor (the graft) identify the cancer cells that remain in the patient's body after the chemotherapy and/or radiation therapy (the tumor) as foreign and attack them. Immunotherapy with the combination therapy described herein can take advantage of this by vaccinating after a transplant. Additionally, the transferred cells may be presented with neoantigens of the combination therapy described herein before transplantation.

In one embodiment the combination therapy is administered to a patient in need thereof with a cancer that requires surgery. In one embodiment the combination therapy described herein is administered to a patient in need thereof in a cancer where the standard of care is primarily surgery followed by treatment to remove possible micro-metastases, such as breast cancer. Breast cancer is commonly treated by various combinations of surgery, radiation therapy, chemotherapy, and hormone therapy based on the stage and grade of the cancer. Adjuvant therapy for breast cancer is any treatment given after primary therapy to increase the chance of long-term survival. Neoadjuvant therapy is treatment given before primary therapy. Adjuvant therapy for breast cancer is any treatment given after primary therapy to increase the chance of long-term disease-free survival. Primary therapy is the main treatment used to reduce or eliminate the cancer. Primary therapy for breast cancer usually includes surgery, a mastectomy (removal of the breast) or a lumpectomy (surgery to remove the tumor and a small amount of normal tissue around it; a type of breast-conserving surgery). During either type of surgery, one or more nearby lymph nodes are also removed to see if cancer cells have spread to the lymphatic system. When a woman has breast-conserving surgery, primary therapy almost always includes radiation therapy. Even in early-stage breast cancer, cells may break away from the primary tumor and spread to other parts of the body (metastasize). Therefore, doctors give adjuvant therapy to kill any cancer cells that may have spread, even if they cannot be detected by imaging or laboratory tests.

In one embodiment the combination therapy is administered consistent with the standard of care for Ductal carcinoma in situ (DCIS). The standard of care for this breast cancer type is:
1. Breast-conserving surgery and radiation therapy with or without tamoxifen.
2. Total mastectomy with or without tamoxifen.
3. Breast-conserving surgery without radiation therapy.

The combination therapy may be administered before breast conserving surgery or total mastectomy to shrink the tumor before surgery. In another embodiment the combination therapy can be administered as an adjuvant therapy to remove any remaining cancer cells. In another embodiment patients diagnosed with stage I, II, IIIA, and Operable IIIC breast cancer are treated with the combination therapy as described herein. The standard of care for this breast cancer type is:
1. Local-regional treatment:
   Breast-conserving therapy (lumpectomy, breast radiation, and surgical staging of the axilla).
   Modified radical mastectomy (removal of the entire breast with level I-II axillary dissection) with or without breast reconstruction.
   Sentinel node biopsy.
2. Adjuvant radiation therapy postmastectomy in axillary node-positive tumors:
   For one to three nodes: unclear role for regional radiation (infra/supraclavicular nodes, internal mammary nodes, axillary nodes, and chest wall).
   For more than four nodes or extranodal involvement: regional radiation is advised.
3. Adjuvant systemic therapy In one embodiment the combination therapy is administered as a neoadjuvant therapy to shrink the tumor. In another embodiment the combination is administered as an adjuvant systemic therapy.

In another embodiment patients diagnosed with inoperable stage IIIB or IIIC or inflammatory breast cancer are treated with the combination therapy as described herein. The standard of care for this breast cancer type is:
1. Multimodality therapy delivered with curative intent is the standard of care for patients with clinical stage IIIB disease.
2. Initial surgery is generally limited to biopsy to permit the determination of histology, estrogen-receptor (ER) and progesterone-receptor (PR) levels, and human epidermal growth factor receptor 2 (HER2/neu) overexpression. Initial treatment with anthracycline-based chemotherapy and/or taxane-based therapy is standard. For patients who respond to neoadjuvant chemotherapy, local therapy may consist of total mastectomy with axillary lymph node dissection followed by postoperative radiation therapy to the chest wall and regional lymphatics. Breast-conserving therapy can be considered in patients with a good partial or complete response to neoadjuvant chemotherapy. Subsequent systemic therapy may consist of further chemotherapy. Hormone therapy should be administered to patients whose tumors are ER-positive or unknown. All patients should be considered candidates for clinical trials to evaluate the most appropriate fashion in which to administer the various components of multimodality regimens.

In one embodiment the combination therapy is administered as part of the various components of multimodality regimens. In another embodiment the combination therapy is administered before, simultaneously with, or after the multimodality regimens. In another embodiment the combination therapy is administered based on synergism between the modalities. In another embodiment the combination therapy is administered after treatment with anthracycline-based chemotherapy and/or taxane-based therapy (Zitvogel et al., 2008). Treatment after administering the combination therapy may negatively affect dividing effector T-cells. The combination therapy may also be administered after radiation.

In another embodiment the combination therapy described herein is used in the treatment in a cancer where the standard of care is primarily not surgery and is primarily based on systemic treatments, such as Chronic Lymphocytic Leukemia (CLL).

In another embodiment patients diagnosed with stage I, II, III, and IV Chronic Lymphocytic Leukemia are treated with the combination therapy as described herein. The standard of care for this cancer type is:
1. Observation in asymptomatic or minimally affected patients
2. Rituximab
3. Ofatumomab
4. Oral alkylating agents with or without corticosteroids
5. Fludarabine, 2-chlorodeoxyadenosine, or pentostatin
6. Bendamustine
7. Lenalidomide
8. Combination chemotherapy.
   combination chemotherapy regimens include the following:
   Fludarabine plus cyclophosphamide plus rituximab.
   Fludarabine plus rituximab as seen in the CLB-9712 and CLB-9011 trials.
   Fludarabine plus cyclophosphamide versus fludarabine plus cyclophosphamide plus rituximab.
   Pentostatin plus cyclophosphamide plus rituximab as seen in the MAYO-MC0183 trial, for example.
   Ofatumumab plus fludarabine plus cyclophosphamide.
   CVP: cyclophosphamide plus vincristine plus prednisone.
   CHOP: cyclophosphamide plus doxorubicin plus vincristine plus prednisone.
   Fludarabine plus cyclophosphamide versus fludarabine as seen in the E2997 trial [NCT00003764] and the LRF-CLL4 trial, for example.
   Fludarabine plus chlorambucil as seen in the CLB-9011 trial, for example.
9. Involved-field radiation therapy.
10. Alemtuzumab
11. Bone marrow and peripheral stem cell transplantations are under clinical evaluation.
12. Ibrutinib In one embodiment the combination therapy is administered before, simultaneously with or after treatment with Rituximab or Ofatumomab. As these are monoclonal antibodies that target B-cells, treatment with the combination therapy may be synergistic. In another embodiment the combination therapy is administered after treatment with oral alkylating agents with or without corticosteroids, and Fludarabine, 2-chlorodeoxyadenosine, or pentostatin, as these treatments may negatively affect the immune system if administered before. In one embodiment bendamustine is administered with the combination therapy in low doses based on the results for prostate cancer described herein. In one embodiment the combination therapy is administered after treatment with bendamustine.

In another embodiment, therapies targeted to specific recurrent mutations in genes that include extracellular domains are used in the treatment of a patient in need thereof suffering from cancer. The genes may advantageously be well-expressed genes. Well expressed may be expressed in "transcripts per million" (TPM). A TPM greater than 100 is considered well expressed. Well expressed genes may be FGFR3, ERBB3, EGFR, MUC4, PDGFRA, MMP12, TMEM52, and PODXL. The therapies may be a ligand capable of binding to an extracellular neoantigen epitope. Such ligands are well known in the art and may include therapeutic antibodies or fragments thereof, antibody-drug conjugates, engineered T cells, or aptamers. Engineered T cells may be chimeric antigen receptors (CARs). Antibodies may be fully humanized, humanized, or chimeric. The antibody fragments may be a nanobody, Fab, Fab', (Fab')2, Fv, ScFv, diabody, triabody, tetrabody, Bis-scFv, minibody, Fab2, or Fab3 fragment. Antibodies may be developed against tumor-specific neoepitopes using known methods in the art.

Adoptive Cell Transfer (ACT)

Aspects of the invention involve the adoptive transfer of immune system cells, such as T cells, specific for selected antigens, such as tumor associated antigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144). Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322). Alternative CAR constructs may be characterized as belonging to successive generations. First-generation CARs typically consist of a single-chain variable fragment of an antibody specific for an antigen, for example comprising a $V_L$ linked to a $V_H$ of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3 ζ-chain, CD97, GDI 1a-CD18, CD2, ICOS, CD27, CD154, CDS, OX40, 4-1BB, or CD28 signaling domains (for example scFv-CD28-4-1BB-CD3ζ or scFv-CD28-OX40-CD3 see U.S. Pat. Nos. 8,906,682; 8,399,645; 5,686,281; PCT Publication No. WO2014134165; PCT Publication No. WO2012079000). Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3 and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoreponsive cell, thereby treating or preventing the disease (such as a neoplasia, a pathogen infection, an autoimmune disorder, or an allogeneic transplant reaction).

In one embodiment, the treatment can be administrated into patients undergoing an immunosuppressive treatment. The cells or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6): 1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853). Cells may be edited using any DNA targeting protein, including, but not limited to a CRISPR system, Zinc Finger binding protein, TALE or TALEN as known in the art. DNA targeting proteins may be delivered to an immune cell by any method known in the art. In preferred embodiments, cells are edited ex vivo and transferred to a subject in need thereof. Immunoresponsive cells, CAR T cells or any cells used for adoptive cell transfer may be edited. Editing may be performed to eliminate potential alloreactive T-cell receptors (TCR), disrupt the target of a chemotherapeutic agent, block an immune checkpoint, activate a T cell, and/or increase the differentiation and/or proliferation of functionally exhausted or dysfunctional CD8+ T-cells (see PCT Patent Publications: WO2013176915, WO2014059173, WO2014172606, WO2014184744, and WO2014191128). Editing may result in inactivation of a gene.

By inactivating a gene it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1;

112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDICDI). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT1 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1 or TIM-3. In preferred embodiments, the gene locus involved in the expression of PD-1 or CTLA-4 genes is targeted. In other preferred embodiments, combinations of genes are targeted, such as but not limited to PD-1 and TIGIT.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ3, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ3.

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Selecting the Patient Population Most Likely to Benefit from the Therapy

In another aspect, the invention provides selecting for the patients in need thereof most likely to benefit from the therapy of the present invention. Although the compositions and methods of the present invention are typically applicable in a high proportion of subjects suffering from cancer, the method may still comprise one or more steps of selecting patients from the patient population who are likely to benefit. For instance, the method may comprise selecting subjects whose tumors contain one or more of the mutations represented in the neoantigenic peptides in the composition. In another embodiment, the method may comprise selecting subjects having at least one HLA allele which binds to one or more neoepitopes represented in the neoantigenic peptides in the composition.

Vaccine or Immunogenic Composition Kits and Co-Packaging

In an aspect, the invention provides kits containing any one or more of the elements discussed herein to allow administration of the therapy. Elements may be provided individually or in combinations, and may be provided in any suitable container, such as a vial, a bottle, or a tube. In some embodiments, the kit includes instructions in one or more languages, for example in more than one language. In some embodiments, a kit comprises one or more reagents for use in a process utilizing one or more of the elements described herein. Reagents may be provided in any suitable container. For example, a kit may provide one or more delivery or storage buffers. Reagents may be provided in a form that is usable in a particular process, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more of the vectors, proteins and/or one or more of the polynucleotides described herein. The kit may advantageously allow the provision of all elements of the systems of the invention. Kits can involve vector(s) and/or particle(s) and/or nanoparticle(s) containing or encoding RNA(s) for 1-50 or more neoantigen mutations to be administered to an animal, mammal, primate, rodent, etc., with such a kit including instructions for administering to such a eukaryote; and such a kit can optionally include any of the anti-cancer agents described herein. The kit may include any of the components above (e.g. vector(s) and/or particle(s) and/or nanoparticle(s) containing or encoding RNA(s) for 1-50 or more neoantigen mutations, neoantigen proteins or peptides) as well as instructions for use with any of the methods of the present invention.

In one embodiment the kit contains at least one vial with an immunogenic composition or vaccine. In one embodiment the kit contains at least one vial with an immunogenic composition or vaccine and at least one vial with an anti-cancer agent. In one embodiment kits may comprise ready to use components that are mixed and ready to administer. In one aspect a kit contains a ready to use immunogenic or vaccine composition and a ready to use anti-cancer agent. The ready to use immunogenic or vaccine composition may comprise separate vials containing different pools of immunogenic compositions. The immunogenic compositions may comprise one vial containing a viral vector or DNA plasmid and the other vial may comprise immunogenic protein. The ready to use anticancer agent may comprise a cocktail of anticancer agents or a single anticancer agent. Separate vials may contain different anti-cancer agents. In another embodiment a kit may contain a ready to use anti-cancer agent and an immunogenic composition or vaccine in a ready to be reconstituted form. The immunogenic or vaccine composition may be freeze dried or lyophilized. The kit may comprise a separate vial with a reconstitution buffer that can be added to the lyophilized composition so that it is ready to administer. The buffer may advantageously comprise an adjuvant or emulsion according to the present invention. In another embodiment the kit may comprise a ready to reconstitute anti-cancer agent and a ready to reconstitute immunogenic composition or vaccine. In this aspect both may be lyophilized. In this aspect separate reconstitution buffers for each may be included in the kit. The buffer may advantageously comprise an adjuvant or emulsion according to the present invention. In another embodiment the kit may comprise single vials containing a dose of immunogenic composition and anti-cancer agent that are administered together. In another aspect multiple vials are included so that one vial is administered according to a treatment timeline. One vial may only contain the anti-cancer agent for one dose of treatment, another may contain both the anti-cancer agent and immunogenic composition for another dose of treatment, and one vial may only contain the immunogenic composition for yet another dose. In a further aspect the vials are labeled for their proper administration to a patient in need thereof. The immunogen or anti-cancer agents of any embodiment may be in a lyophilized form, a dried form or in aqueous solution as described herein. The immunogen may be a live attenuated virus, protein, or nucleic acid as described herein.

In one embodiment the anticancer agent is one that enhances the immune system to enhance the effectiveness of the immunogenic composition or vaccine. In a preferred embodiment the anti-cancer agent is a checkpoint inhibitor.

In another embodiment the kit contains multiple vials of immunogenic compositions and anti-cancer agents to be administered at different time intervals along a treatment plan. In another embodiment the kit may comprise separate vials for an immunogenic composition for use in priming an immune response and another immunogenic composition to be used for boosting. In one aspect the priming immunogenic composition could be DNA or a viral vector and the boosting immunogenic composition may be protein. Either composition may be lyophilized or ready for administering. In another embodiment different cocktails of anti-cancer agents containing at least one anti-cancer agent are included in different vials for administration in a treatment plan.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1 sPDL1 Generates Immunogenic Epitopes Across a Variety of HLA Alleles.

PDL1 (CD274) is a trans-membrane protein which interacts with PD1 (CD279; PDCD1) on T cells and may be involved in multiple forms of natural immune suppression (such as during gestation). Expression of PDL1 is also utilized by tumor cells as a way to evade host immune response. sPDL1 is an alternate spliced form of the PDL1 gene. This alternate spliced form is caused by a lack of splicing at the end of Exon 4, reading into the $4^{th}$ intron. The transcript terminates within intron 4. The translation product is in frame for 18 amino acids before a stop codon is encountered.

The translated product lacks the transmembrane domain typically found in PDL1 and thus is secreted. It also contains a cysteine within the neoORF translated from the intron and appears to dimerize in the media. The secreted form appears to block binding between PDL1 and PD1.

Applicants analyzed the predicted binding possibilities for 9 and 10mer peptides containing the neoORF region encoded by the intron. The analysis is shown for predicted 9mer peptides Table 1. The values in bolded font are alleles that are present at a frequency >5% in the indicated population. Notably, the common HLA allele A0210 in the Caucasian population is predicted to have a reasonably tight binding peptide. A similar analysis shows that 10mer peptides are also predicted to be potentially immunogenic, including for the A0201 allele (85 nM). Tumor cells expressing the alternate form of the PDL1 message would be thus rendered as targets of the immune system.

These peptides could be utilized across multiple patients (either HLA-restricted or more broadly if the patient is expected to have some probability to contain a relevant HLA allele) as a "Shared Neoantigen". Note that given the relatively short size of the neoORF region of sPDL1, two or three long overlapping peptides could be used as a mixture, allowing targeting of any HLA allele, even rare alleles, and reducing the need to prepare a different product for each patient based on their HLA type.

This neoORF may also contain a CD4 epitope although prediction algorithms for CD4 epitopes are not highly accurate. The presence of a CD4 epitope could be assessed in vitro with naive T cells or in patient samples.

TABLE 1

(SEQ ID NOS 1-23, respectively, in order of appearance)

ENHTAELVIP
GNILNVSIKICLTLSPST

| HLA | peptide 9mers | affinity (nM) | Caucasian | Black | Asian | Hispanic |
|---|---|---|---|---|---|---|
| A0201 | VIPGNILNV | 182 | 28.3% | 11.4% | 9.7% | 19.7% |
| B4001 | AELVIPGNI | 144 | 4.0% | 1.0% | 12.0% | 1.3% |
| A3201 | NILNVSIKI | 491 | 3.2% | 1.6% | 0.3% | 2.6% |
| A3201 | VSIKICLTL | 224 | 3.2% | 1.6% | 0.3% | 2.6% |
| A2301 | VSIKICLTL | 468 | 2.3% | 11.6% | 0.2% | 3.5% |
| B4002 | AELVIPGNI | 53 | 1.6% | 0.3% | 7.6% | 5.0% |
| B4901 | AELVIPGNI | 108 | 1.4% | 3.1% | 0.0% | 2.3% |
| B4102 | AELVIPGNI | 192 | 1.0% | 0.6% | 0.0% | 0.5% |
| A0205 | VIPGNILNV | 170 | 0.8% | 2.3% | 0.1% | 1.4% |
| B5801 | VSIKICLTL | 373 | 0.8% | 4.3% | 4.5% | 1.3% |
| A6802 | HTAEVIPG | 170 | 0.7% | 6.4% | 0.0% | 2.4% |
| B4405 | AELVIPGNI | 219 | 0.6% | 0.0% | 0.0% | 0.2% |
| B4101 | AELVIPGNI | 92 | 0.5% | 0.6% | 0.0% | 1.1% |
| B4501 | AELVIPGNI | 302 | 0.4% | 5.3% | 0.0% | 1.5% |
| B1517 | VSIKICLTL | 23 | 0.3% | 0.5% | 0.1% | 0.6% |
| A0206 | VIPGNILNV | 85 | 0.2% | 0.0% | 4.7% | 4.1% |
| A0202 | VIPGNILNV | 90 | 0.1% | 4.4% | 0.0% | 0.7% |
| A6901 | HTAEVIPG | 283 | 0.1% | 0.1% | 0.0% | 0.5% |
| A6901 | NILNVSIKI | 162 | 0.1% | 0.1% | 0.0% | 0.5% |
| B1503 | IKICLTLSP | 408 | 0.1% | 6.5% | 0.1% | 1.5% |
| B1503 | VSIKICLTL | 138 | 0.1% | 6.5% | 0.1% | 1.5% |
| A0203 | VIPGNILNV | 98 | 0.0% | 0.0% | 5.2% | 0.0% |

Example 2

Androgen Receptor Generates Immunogenic Epitopes Across a Variety of HLA Alleles.

The androgen receptor was identified as another alternate spliced form of a message that results in a neoORF which may be specifically expressed in tumor cells. Alternate splicing results in at least two isoforms that bring in cryptic exons that are .neoORFs.

Of these alternate transcripts, AR-V1 and AR-V7 were consistently seen in hormone resistant prostate cancer samples.

The immunogenic potential of these neoORFs was unknown and thus Applicants conducted predicted binding analysis across a number of common HLA alleles. These are shown for HLA A alleles (Table 2).

TABLE 2

(SEQ ID NOS 24, 27, 28, 30, 25, 29, 31, 26, 32, 33, 41, 43, 45, 34, 42, 44, 46, 35, 47, 36, 48, 37, 49 and 38-40, respectively, in order of appearance)

| | A0201 | | | A0301 | | | A1101 | | | A3001 | | |
|---|---|---|---|---|---|---|---|---|---|---|---|---|
| Caucasian | 28.30% | | | 13.70% | | | 6.00% | | | 1.60% | | |
| Asian | 9.70% | | | 0.90% | | | 22.40% | | | 1.40% | | |
| Hispanic | 19.65% | | | 7.59% | | | 4.88% | | | 2.20% | | |
| Black | 11.40% | | | 7.10% | | | 1.00% | | | 6.50% | | |
| | RVFGVSEWL | SEQ2 | 233 | RVGNCKHLK | SEQ1 | 122 | RVGNCKHLK | SEQ1 | 33 | RVGNCKHLK | SEQ1 | 30 |
| | GMTLGAVVV | SEQ2 | 282 | | | | VVVSERILR | SEQ2 | 359 | KFRVGNCKH | SEQ1 | 103 |
| | MTLGEKFRV | SEQ1 | 400 | | | | | | | KFRVGNCKHL | SEQ1 | 190 |

| | A3101 | | | A3201 | | | A3301 | | | A6801 | | | A | B | |
|---|---|---|---|---|---|---|---|---|---|---|---|---|---|---|---|
| | 2.40% | | | 3.20% | | | 0.70% | | | 3.40% | | | 30.30% | 6.80% | Caucasian |
| | 3.40% | | | 0.30% | | | 0.60% | | | 0.30% | | | 28.70% | 19.70% | Asian |
| | 4.72% | | | 2.62% | | | 1.97% | | | 4.46% | | | 26.46% | 7.86% | Hispanic |
| | 1.00% | | | 1.60% | | | 1.70% | | | 3.20% | | | 20.40% | 2.10% | Black |
| | RVGNCKHLK | SEQ1 | 70 | RVFGVSEWL | SEQ2 | 41 | NCKHLKMTR | SEQ1 | 385 | VVVSERILR | SEQ2 | 47 | | | |
| | TLGAVVVSER | SEQ2 | 121 | ILRVFGVSEW | SEQ2 | 255 | TLGAVVVSER | SEQ2 | 417 | TLGAVVVSER | SEQ2 | 84 | | | |
| | VVVSERILR | SEQ2 | 127 | | | | | | | EAGMTLGEK | SEQ 1 | 230 | | | |
| | GMTLGEKFR | SEQ1 | 199 | | | | | | | LGAVVVSER | SEQ2 | 268 | | | |

TABLE 2-continued (SEQ ID NOS 24, 27, 28, 30, 25. 29, 31, 26, 32, 33, 41, 43, 45, 34, 42. 44,
46, 35, 47,36, 48.37, 49 and 38-40, respectively, in order of appearance)

| AVVVSERILR | SEQ2 | 230 | AVVVSERILR | SEQ2 | 339 |
|---|---|---|---|---|---|
| AGMTLGEKFR | SEQ1 | 284 | | | |
| GNCKHLKMTR | SEQ1 | 466 | | | |
| LGAVVVSER | SEQ2 | 488 | | | |

Again, as for sPDL1, a number of peptides are predicted to be immunogenic binders and these can be applied across a large subset of patients. These immunogenic peptides can be used across multiple patients.

Example 3

Drug Resistant Mutations.

Treatment with various chemotherapeutic agents, particularly with targeted therapies such as tyrosine kinase inhibitors, frequently leads to new mutations in the target molecules that resist the activity of the therapeutic. Multiple strategies to overcome this resistance are being evaluated, including development of second generation therapies that are not affected by these mutations and treatment with multiple agents including those that act downstream of the resistance mutation.

Applicants have evaluated the immunogenic potential of the mutated peptides created by these resistance mutations and have found that for some, predicted immunogenic peptides are created that can bind to a range of HLA alleles. Two specific examples are provided below as well as data for a range of resistance variants.

BTK/C481S

A very common mutation to ibrutinib, a molecule targeting Bruton's Tyrosine Kinase (BTK) and used for CLL and certain lymphomas, is a Cysteine to Serine change at position 481. This change produces a number of binding peptides which bind to a range of HLA molecules.

Shown are results of binding predictions for 9mer peptides. Similar binding peptides can be found for 10mer peptides (Table 3). Only peptides with mutant predicted affinity below 150 nM are included. Expanding the range of peptides up to 500 nM would also significantly increase the number of HLA range.

TABLE 3

(SEQ ID NOS 50-72, respectively, in order of appearance)

| HLA | peptide 9mers | Affinity (nM) MUT | Affinity (nM) NAT | Caucasian | Black | Asian | Hispanic |
|---|---|---|---|---|---|---|---|
| A0201 | SLLNYLREM | 97 | 278 | 28.3% | 11.4% | 9.7% | 19.7% |
| A2402 | EYMANGSLL | 95 | 120 | 9.3% | 2.0% | 23.1% | 12.4% |
| B1801 | TEYMANGSL | 80 | 252 | 6.1% | 3.5% | 0.4% | 4.1% |
| B1501 | MANGSLLNY | 91 | 158 | 5.8% | 0.8% | 12.1% | 2.6% |
| B3501 | MANGSLLNY | 17 | 17 | 5.6% | 6.1% | 2.4% | 6.0% |
| B4001 | TEYMANGSL | 10 | 24 | 4.0% | 1.0% | 12.0% | 1.3% |
| A3101 | LLNYLREMR | 43 | 206 | 2.4% | 1.0% | 3.4% | 4.7% |
| A2301 | EYMANGSLL | 122 | 133 | 2.3% | 11.6% | 0.2% | 3.5% |
| A2902 | MANGSLLNY | 17 | 10 | 2.0% | 4.4% | 0.0% | 4.1% |
| B4002 | TEYMANGSL | 45 | 110 | 1.6% | 0.3% | 7.6% | 5.0% |
| B4102 | TEYMANGSL | 133 | 341 | 1.0% | 0.6% | 0.0% | 0.5% |
| B5801 | MANGSLLNY | 40 | 35 | 0.8% | 4.3% | 4.5% | 1.3% |
| A3301 | LLNYLREMR | 91 | 188 | 0.7% | 1.7% | 0.6% | 2.0% |
| A3002 | MANGSLLNY | 16 | 15 | 0.5% | 6.6% | 0.0% | 2.8% |
| A6804 | EYMANGSLL | 47 | 448 | 0.0% | 0.0% | 0.0% | 0.0% |
| B1801 | TEYMANGSL | 44 | 252 | 6.1% | 3.5% | 0.4% | 4.1% |
| B1501 | MANGSLLNY | 42 | 158 | 5.8% | 0.8% | 12.1% | 2.6% |
| B3501 | MANGSLLNY | 40 | 17 | 5.6% | 6.1% | 2.4% | 6.0% |
| B4001 | TEYMANGSL | 38 | 24 | 4.0% | 1.0% | 12.0% | 1.3% |
| A3101 | LLNYLREMR | 36 | 206 | 2.4% | 1.0% | 3.4% | 4.7% |
| A2301 | EYMANGSLL | 34 | 133 | 2.3% | 11.6% | 0.2% | 3.5% |
| A2902 | MANGSLLNY | 32 | 10 | 2.0% | 4.4% | 0.0% | 4.1% |
| B4002 | TEYMANGSL | 30 | 110 | 1.6% | 0.3% | 7.6% | 5.0% |

Such peptide immunogens are preferably utilized prophylactically (prior to detection of resistant disease) to induce an immunogenic response capable of killing any pre-existing or newly mutated cells or could also be used at the time of detection of disease recurrence following or during therapy. These peptides could be utilized across multiple patients (either HLA-restricted or more broadly if the patient is expected with some probability to contain a relevant HLA allele).

EGFR/T790M

Erlotinib, which targets the tyrosine kinase domain of the Epidermal Growth Factor Receptor (EGFR), is commonly used in the treatment of lung cancer and resistant tumors invariably develop following therapy. A common mutation found in resistant clones is a Threonine to methionine mutation at position 790. This change produces a number of binding peptides which bind to a range of HLA molecules (Table 4).

TABLE 4

|  |  |  |  |  |  |  | SUM |
|---|---|---|---|---|---|---|---|
| Caucasian | 2.3% | 3.9% | 4.0% | 3.2% | 3.2% |  | 17% |
| Black | 11.6% | 0.3% | 1.5% | 1.6% | 1.6% |  | 17% |
| Asian | 0.2% | 0.0% | 3.9% | 0.3% | 0.3% |  | 5% |
| Hispanic | 3.5% | 0.9% | 2.8% | 2.6% | 2.6% |  | 12% |
|  | A23C1 | A2501 | A2601 | A3201 | A3201 |  |  |
|  | VQLIMQLMPF 366 | STVQLIMQLM 125 | STVQLIMQLM 67 | QLIMQLMPF 155 VQLIMQLMPF 426 | QLIMQLMPF 155 VQLIMQLMPF 426 |  |  |
| Caucasian | 4.2% | 5.8% | 2.9% | 1.4% | 0.4% | 1.6% | 16% |
| Black | 1.2% | 0.8% | 0.1% | 0.3% | 0.1% | 0.3% | 3% |
| Asian | 1.2% | 12.1% | 0.2% | 2.4% | 0.0% | 7.6% | 24% |
| Hispanic | 1.2% | 2.6% | 1.8% | 1.0% | 2.2% | 5.0% | 14% |
|  | B1302 | B1501 | B3801 | B3901 | B3906 | B4002 |  |
|  | MQLMPFGCLL 125 | MQLMPFGCLL 488 QLIMQLMPF 23 VQLIMQLMPF 73 | MQLMPFGCLL 400 | MQLMPFGCLL 213 | MQLMPFGCLL 400 | MQLMPFGCL 221 MQLMPFGCLL 103 VQLIMQLMPF 365 |  |

(SEQ ID NOS 73,74,74-76,73,73,78,78,78,78,78,79,80,78,77 and 77, respectively, in order of apperance)

As stated herein, such peptide immunogens are ideally utilized prophylactically (prior to detection of resistant disease) to induce an immunogenic response capable of killing any pre-existing or newly mutated cells or are also used at the time of detection of disease recurrence following or during therapy. These peptides could be utilized across multiple patients (either HLA-restricted or more broadly if the patient is expected with some probability to contain a relevant HLA allele).

Note that as an immunogen, only a single long peptide containing the mutated amino acid and at least 10 amino acids on either side of the mutated amino acid would be sufficient to contain all the epitopes listed. Thus, all the HLA alleles shown, as well as any additional alleles that have not been shown in this analysis would be covered. For the Caucasian population, the HLA A alleles shown represent 17% of the population distribution of alleles and the HLA B alleles represent 16% of the population distribution of alleles. As each individual has two HLA A alleles and two HLA B alleles, approximately 50% of Caucasian patients will be expected to have at least one of the alleles shown and thus benefit from immune therapy with a vaccine targeting this molecule. This rationale also applies to any other single amino acid mutation discussed herein.

Other Resistance Variants

In addition to the specific resistance cases discussed herein, there are many other observed resistance mutations to targeted therapy. Each of these are also used to define immunogenic epitopes that could be utilized as vaccine for immunotherapy targeting those cells containing the resistance mutations (Table 5).

TABLE 5

| Drug | Gene | Resistance mutation | Sensitive | Refs |
|---|---|---|---|---|
| Imatinib | BCR-Abl | T315I |  | http://www.mycancergenome.org/content/disease/chronic-myeloid-leukemia/ |
| Imatinib | BCR-Abl | Y253H |  | http://www.mycancergenome.org/content/disease/chronic-myeloid-leukemia/ |
| Imatinib | BCR-Abl | E255K |  | http://www.mycancergenome.org/content/disease/chronic-myeloid-leukemia/ |
| Imatinib | BCR-Abl | E255V |  | http://www.mycancergenome.org/content/disease/chronic-myeloid-leukemia/ |
| Imatinib | c-kit | T670I |  | http://www.mycancergenome.org/content/disease/gist/kit/50/ |
| Erlotinib/gefitinib | PIK3CA | E545K |  | PMC1570180; PMC3132801 |
| Erlotinib/gefitinib | HER2 | G776(YVMA) |  | PMID 16843263; 15753357 |
| Erlotinib/gefitinib | EML4-ALK | G1269A |  | http://www.ncbi.nlm.nih.gov/pubmed/22235099?dopt=Abstract |
| Crizotinib | KRAS | G12V/D |  | http://www.ncbi.nlm.nih.gov/pubmed/22235099?dopt=Abstract |
| Crizotinib | ALK | L1196M |  | http://stm.sciencemag.org/content/4/120/120ra17 |
| Crizotinib | ALK | G1202R |  | http://stm.sciencemag.org/content/4/120/120ra17 |
| Crizotinib | ALK | S1206Y |  | http://stm.sciencemag.org/content/4/120/120ra17 |
| Crizotinib | ALK | 1151T(ins) |  | http://stm.sciencemag.org/content/4/120/120ra17 |
| Crizotinib | ALK | F1174C |  | http://cancerdiscovery.aacrjournals.org/content/4/6/662 |
| Crizotinib | ROS1 | G2032R |  | http://www.nejm.org/doi/full/10.1056/NEJMoa1215530 |
| Crizotinib | PIK3CA | E542K |  | http://www.mycancergenome.org/content/disease/breast-cancer/ |
| Trastuzumab | Her2 | E545K |  | http://www.mycancergenome.org/content/disease/breast-cancer/ |
| Trastuzumab | Hwe2 | H1047R |  | http://www.mycancergenome.org/content/disease/breast-cancer/ |
| Trastuzumab | AKT1 | E17K |  | http://www.ncbi.nlm.nih.gov/pmc/articles/PMC2834432/ |
| Trastuzumab | BRAF |  | V600E |  |
| Vemurafenib | MEK1 | Q56P |  | http://www.ncbi.nlm.nih.gov/pubmed/23569304 |
| Vemurafenib | MEK1 | E203K |  | http://www.ncbi.nlm.nih.gov/pubmed/23569304 |
| Vemurafenib | MEK1 | C121S |  | http://cancerdiscovery.aacrjournals.org/content/4/1/94.long |
| Vemurafenib | NRAS | Q61K/L |  | http://www/ncbi.nlm.nih.gov/pubmed/23569304 |
| Vemurafenib | NRAS | Q61R |  | http://cancerdiscovery.aacrjournals.org/content/4/1/94.long |
| Vemurafenib | NRAS | T58I |  | http://cancerdiscovery.aacrjournals.org/content/4/1/94.long |
| Vemurafenib | MEK2 | C125S |  | http://cancerdiscovery.aacrjournals.org/content/4/1/94.long |
| Vemurafenib | MEK1 | V60E |  | http://cancerdiscovery.aacrjournals.org/content/4/1/94.long |

TABLE 5-continued

| Drug | Gene | Resistance mutation | Sensitive | Refs |
|---|---|---|---|---|
| RAF/MEK | MEK1 | G128V | | http://cancerdiscovery.aacrjournals.org/content/4/1/94.long |
| RAF/MEK | MEK1 | V154I | | http://cancerdiscovery.aacrjournals.org/content/4/1/94.long |
| RAF/MEK | MEK1 | P124S | | http://cancerdiscovery.aacrjournals.org/content/4/1/94.long |
| RAF/MEK | MEK1 | P124L | | http://cancerdiscovery.aacrjournals.org/content/4/1/94.long |
| RAF/MEK | RAC1 | P29S | | http://cancerdiscovery.aacrjournals.org/content/4/1/94.long |
| RAF/MEK | ESR1 | S463P | | http://cancerdiscovery.aacrjournals.org/content/4/1/94.long |
| Antiestrogen therapy | AR | V534E | | http://www.mycancergenome.org/content/disease/breast-cancer/er/314/ |
| Antiestrogen therapy | AR | P535H | | http://www.mycancergenome.org/content/disease/breast-cancer/er/314/ |
| Antiestrogen therapy | AR | L536Q | | http://www.mycancergenome.org/content/disease/breast-cancer/er/314/ |
| Antiestrogen therapy | AR | L536R | | http://www.mycancergenome.org/content/disease/breast-cancer/er/314/ |
| Antiestrogen therapy | AR | Y537C | | http://www.mycancergenome.org/content/disease/breast-cancer/er/314/ |
| Antiestrogen therapy | AR | Y537S | | http://www.mycancergenome.org/content/disease/breast-cancer/er/314/ |
| Antiestrogen therapy | AR | Y537N | | http://www.mycancergenome.org/content/disease/breast-cancer/er/314/ |
| Antiestrogen therapy | AR | D538G | | http://www.mycancergenome.org/content/disease/breast-cancer/er/314/ |
| Antiestrogen therapy | AR | F876L | | http://cancerdiscovery.aacrjournals.org/content/early/2013/06/18/2159-8290.CD-13-0226 |

A number of these examples have been used to predict immunogenic epitopes. These results are summarized in Table 6, in which for each resistance mutation, the number of potential binding peptides (with predicted affinity <500 nM) for each mutation are shown for multiple Human HLA alleles.

TABLE 6

| RES 500 | Caucasian | Black | Asian | ABL1:p.T315I 80 | ALK:p.F1174C 80 | ALK:p.F1174L 80 | ALK:p.G1202R 80 | ALK:p.G1269A 80 | ALK:p.L1196M 80 | ALK:p.S1206Y 80 | AR:p.F876L 80 |
|---|---|---|---|---|---|---|---|---|---|---|---|
| hla_a_01_01 | 0.143 | 0.047 | 0.012 | | | | | | | | |
| hla_a_02_01 | 0.283 | 0.114 | 0.097 | | | | | | | 1 | |
| hla_a_02_03 | 0 | 0 | 0.052 | | | | | | | | |
| hla_a_02_07 | 0 | 0 | 0.08 | | 1 | | | | | | |
| hla_a_03_01 | 0.137 | 0.071 | 0.009 | | | 1 | | | | | |
| hla_a_11_01 | 0.06 | 0.01 | 0.224 | | | | | 1 | 2 | | |
| hla_a_23_01 | 0.023 | 0.116 | 0.002 | 2 | | 2 | | 1 | 2 | | 2 |
| hla_a_24_02 | 0.093 | 0.02 | 0.231 | 1 | | | | | 1 | | |
| hla_a_30_01 | 0.016 | 0.065 | 0.014 | | 1 | 1 | 2 | | | 1 | 1 |
| hla_a_30_02 | 0.005 | 0.066 | 0 | 2 | | | | | | 2 | |
| hla_a_33_03 | 0.004 | 0.041 | 0.072 | | | | 3 | 1 | | 3 | |
| hla_a_68_02 | 0.007 | 0.064 | 0 | | | | 1 | | | | |
| hla_a_74_01 | 0 | 0.051 | 0.001 | | | | | | | | |
| hla_b_07_02 | 0.118 | 0.062 | 0.015 | | | | 1 | | 2 | 3 | 1 |
| hla_b_08_01 | 0.098 | 0.039 | 0.002 | | | | 2 | | 1 | 3 | |
| hla_b_15_01 | 0.058 | 0.008 | 0.121 | 1 | | | 3 | | | | 1 |
| hla_b_15_02 | 0 | 0 | 0.066 | 1 | | | 1 | | | | 1 |
| hla_b_15_03 | 0.001 | 0.065 | 0.001 | 5 | | 3 | 1 | 2 | 4 | 4 | 4 |
| hla_b_18_01 | 0.061 | 0.035 | 0.004 | 2 | | 1 | 1 | | 1 | | |
| hla_b_35_01 | 0.056 | 0.061 | 0.024 | 3 | | | 1 | | 1 | 2 | 2 |
| hla_b_40_01 | 0.04 | 0.01 | 0.12 | 3 | 1 | 1 | 1 | 1 | 1 | | 1 |
| hla_b_40_02 | 0.016 | 0.003 | 0.076 | 3 | | 1 | | | 2 | | 2 |
| hla_b_42_01 | 0 | 0.057 | 0 | | | | | | | | |
| hla_b_44_02 | 0.071 | 0.014 | 0.002 | | | 1 | | | | | 1 |
| hla_b_45_01 | 0.004 | 0.053 | 0 | | | 1 | | | | | 1 |
| hla_b_46_01 | 0 | 0 | 0.082 | | | | | | | | |
| hla_b_51_01 | 0.051 | 0.021 | 0.04 | | | | | | 2 | | |
| hla_b_53_01 | 0.003 | 0.11 | 0 | 1 | | | | | | 1 | |

| RES 500 | Caucasian | Black | Asian | BTK:p.C481S 80 | EGFR:p.T790M 80 | KRAS:p.G12D 80 | MAP2K1:p.C121S 80 | MAP2K1:p.E203K 80 | MAP2K1:p.G128V 80 | MAP2K1:p.P124L 80 | MAP2K1:p.P124S 80 |
|---|---|---|---|---|---|---|---|---|---|---|---|
| hla_a_01_01 | 0.143 | 0.047 | 0.012 | 2 | 1 | 1 | 1 | 3 | | 1 | 2 |
| hla_a_02_01 | 0.283 | 0.114 | 0.097 | 1 | 2 | 2 | 1 | 3 | | 2 | 1 |
| hla_a_02_03 | 0 | 0 | 0.052 | 2 | 1 | | | | | 2 | 1 |
| hla_a_02_07 | 0 | 0 | 0.08 | | | | | | | | |
| hla_a_03_01 | 0.137 | 0.071 | 0.009 | 1 | | | | | | 1 | |
| hla_a_11_01 | 0.06 | 0.01 | 0.224 | 2 | | 2 | | | 1 | | |

TABLE 6-continued

| | | | | MAP2K1:p.Q56P 80 | MAP2K1:p.V154I 80 | MAP2K1:p.V60E 80 | MAP2K2:p.C125S 80 | MAP2K2:p.L46F 80 | MAP2K2:p.N126D 80 | MAP2K2:p.V35M 80 | NRAS:p.Q61R 80 |
|---|---|---|---|---|---|---|---|---|---|---|---|
| hla_a_23_01 | 0.023 | 0.116 | 0.002 | 1 | | | | | 1 | | 2 |
| hla_a_24_02 | 0.093 | 0.02 | 0.231 | 1 | | | | | 1 | 1 | 1 |
| hla_a_30_01 | 0.016 | 0.065 | 0.014 | | 2 | | | | | | 1 |
| hla_a_30_02 | 0.005 | 0.066 | 0 | 2 | | | | | | 4 | 5 |
| hla_a_33_03 | 0.004 | 0.041 | 0.072 | 2 | | | 3 | | 3 | | |
| hla_a_68_02 | 0.007 | 0.064 | 0 | 1 | 2 | | | 1 | | | 1 |
| hla_a_74_01 | 0 | 0.051 | 0.001 | 1 | | 1 | | 2 | | | |
| hla_b_07_02 | 0.118 | 0.062 | 0.015 | | | | | 2 | | | |
| hla_b_08_01 | 0.098 | 0.039 | 0.002 | | | | | | | | |
| hla_b_15_01 | 0.058 | 0.008 | 0.121 | 3 | 2 | | 2 | 1 | 3 | 1 | 2 |
| hla_b_15_02 | 0 | 0 | 0.066 | 3 | 2 | | 2 | 1 | 3 | 3 | 3 |
| hla_b_15_03 | 0.001 | 0.065 | 0.001 | 8 | 7 | | 7 | 2 | 6 | 8 | 8 |
| hla_b_18_01 | 0.061 | 0.035 | 0.004 | 2 | | | | | 1 | 1 | 1 |
| hla_b_35_01 | 0.056 | 0.061 | 0.024 | 3 | 1 | | 2 | 1 | 3 | | 3 |
| hla_b_40_01 | 0.04 | 0.01 | 0.12 | 2 | 1 | | 2 | | 3 | 1 | 1 |
| hla_b_40_02 | 0.016 | 0.003 | 0.076 | 2 | 3 | | 3 | | 1 | 1 | 1 |
| hla_b_42_01 | 0 | 0.057 | 0 | | | | | | | | |
| hla_b_44_02 | 0.071 | 0.014 | 0.002 | | | 1 | | | | | |
| hla_b_45_01 | 0.004 | 0.053 | 0 | 3 | 1 | | 2 | | 1 | 1 | 1 |
| hla_b_46_01 | 0 | 0 | 0.082 | | | | 1 | 1 | | | |
| hla_b_51_01 | 0.051 | 0.021 | 0.04 | | | | | 1 | | | |
| hla_b_53_01 | 0.003 | 0.11 | 0 | 2 | | | | 2 | | | |

| RES 500 | Caucasian | Black | Asian | MAP2K1:p.Q56P 80 | MAP2K1:p.V154I 80 | MAP2K1:p.V60E 80 | MAP2K2:p.C125S 80 | MAP2K2:p.L46F 80 | MAP2K2:p.N126D 80 | MAP2K2:p.V35M 80 | NRAS:p.Q61R 80 |
|---|---|---|---|---|---|---|---|---|---|---|---|
| hla_a_01_01 | 0.143 | 0.047 | 0.012 | | 1 | | 1 | | 1 | 1 | 1 |
| hla_a_02_01 | 0.283 | 0.114 | 0.097 | | 1 | | 1 | | 1 | 1 | |
| hla_a_02_03 | 0 | 0 | 0.052 | | | | | | | | |
| hla_a_02_07 | 0 | 0 | 0.08 | | | | | | | | |
| hla_a_03_01 | 0.137 | 0.071 | 0.009 | 1 | 1 | | | | | | |
| hla_a_11_01 | 0.06 | 0.01 | 0.224 | 1 | | | | | | | |
| hla_a_23_01 | 0.023 | 0.116 | 0.002 | | | | | | | | |
| hla_a_24_02 | 0.093 | 0.02 | 0.231 | | | | | | | | |
| hla_a_30_01 | 0.016 | 0.065 | 0.014 | 2 | | 1 | | | | | 1 |
| hla_a_30_02 | 0.005 | 0.066 | 0 | | 1 | | 3 | | 4 | | 1 |
| hla_a_33_03 | 0.004 | 0.041 | 0.072 | 1 | | | | | | | |
| hla_a_68_02 | 0.007 | 0.064 | 0 | | | | | | | | |
| hla_a_74_01 | 0 | 0.051 | 0.001 | 1 | | | | 1 | | | |
| hla_b_07_02 | 0.118 | 0.062 | 0.015 | 1 | | | | | | | |
| hla_b_08_01 | 0.098 | 0.039 | 0.002 | | | | 2 | | 1 | | |
| hla_b_15_01 | 0.058 | 0.008 | 0.121 | | | | | | | | |

TABLE 6-continued

| RES 500 | Caucasian | Black | Asian | NRAS:p.T58I 80 | PIK3CA:p.E545K 80 | PLCG2:p.R665W 80 | ROS1:p.G2032A 80 |
|---|---|---|---|---|---|---|---|
| hla_b_15_02 | 0 | 0 | 0.066 | | | | |
| hla_b_15_03 | 0.001 | 0.065 | 0.001 | | | | |
| hla_b_18_01 | 0.061 | 0.035 | 0.004 | | | | |
| hla_b_35_01 | 0.056 | 0.061 | 0.024 | 1 | | | |
| hla_b_40_01 | 0.04 | 0.01 | 0.12 | 2 | | 2 | 1 |
| hla_b_40_02 | 0.016 | 0.003 | 0.076 | 7 | | | |
| hla_b_42_01 | 0 | 0.057 | 0 | 2 | | | |
| hla_b_44_01 | 0.071 | 0.014 | 0.002 | 2 | | | 1 |
| hla_b_44_02 | 0.004 | 0.053 | 0 | 3 | | | 1 |
| hla_b_45_01 | 0 | 0 | 0.082 | 2 | | | |
| hla_b_46_01 | 0 | 0 | 0.04 | 1 | | | |
| hla_b_51_01 | 0.051 | 0.021 | 0.04 | | | | |
| hla_b_53_01 | 0.003 | 0.11 | 0 | | | | 3 |

| RES 500 | Caucasian | Black | Asian | NRAS:p.T58I 80 | PIK3CA:p.E545K 80 | PLCG2:p.R665W 80 | ROS1:p.G2032A 80 |
|---|---|---|---|---|---|---|---|
| hla_a_01_01 | 0.143 | 0.047 | 0.012 | 1 | | | 1 |
| hla_a_02_01 | 0.283 | 0.114 | 0.097 | 1 | | | 3 |
| hla_a_02_03 | 0 | 0 | 0.052 | 1 | | | 3 |
| hla_a_02_07 | 0 | 0 | 0.08 | | | | |
| hla_a_03_01 | 0.137 | 0.071 | 0.009 | | | | |
| hla_a_11_01 | 0.06 | 0.01 | 0.224 | | | | 2 |
| hla_a_23_01 | 0.023 | 0.116 | 0.002 | | | | |
| hla_a_24_02 | 0.093 | 0.02 | 0.231 | | | | |
| hla_a_30_01 | 0.016 | 0.065 | 0.014 | 1 | | 1 | 2 |
| hla_a_30_02 | 0.005 | 0.066 | 0 | | | 1 | 1 |
| hla_a_33_03 | 0.004 | 0.041 | 0.072 | | | | 2 |
| hla_a_68_02 | 0.007 | 0.064 | 0 | | | 1 | |
| hla_a_74_01 | 0 | 0.051 | 0.001 | | | | 2 |
| hla_b_07_02 | 0.118 | 0.062 | 0.015 | | | 1 | 2 |
| hla_b_08_01 | 0.098 | 0.039 | 0.002 | 3 | | 4 | 5 |
| hla_b_15_01 | 0.058 | 0.008 | 0.121 | | | 1 | 2 |
| hla_b_15_02 | 0 | 0 | 0.066 | | | 1 | 1 |
| hla_b_15_03 | 0.001 | 0.065 | 0.001 | | 2 | | 3 |
| hla_b_18_01 | 0.061 | 0.035 | 0.004 | | | | 3 |
| hla_b_35_01 | 0.056 | 0.061 | 0.024 | | | 1 | |
| hla_b_40_01 | 0.04 | 0.01 | 0.12 | | | | |
| hla_b_40_02 | 0.016 | 0.003 | 0.076 | | 1 | 2 | 2 |
| hla_b_42_01 | 0 | 0.057 | 0 | | | | |
| hla_b_44_01 | 0.071 | 0.014 | 0.002 | | | 1 | |
| hla_b_44_02 | 0.004 | 0.053 | 0 | | | 1 | |
| hla_b_45_01 | 0 | 0 | 0.082 | | | | |
| hla_b_46_01 | 0 | 0 | 0.04 | | | | |
| hla_b_51_01 | 0.051 | 0.021 | 0.04 | | | | |
| hla_b_53_01 | 0.003 | 0.11 | 0 | | | | |

In all of the above examples, predictions are only shown for a subset of HLA alleles. These are often but not exclusively the most abundant alleles in each ethnic population. Additional alleles are readily predicted.

Moreover, for a given immunization designed to attack resistant variants for a given resistance mutation, multiple peptides, each targeting a separate possible resistance variant that may arise, are utilized to benefit the broadest set of patients.

Example 4

Cancer Subtype Specific Immunogenic Compositions.

Table 7 shows a data summary for the number of mutations found within a population of samples specific to a cancer subtype. Each mutation found within the data set for each disease leads to at least one predicted binder to any one of 33 HLA alleles selected based on being found in at least 5% of any one of the three ethnic populations (Caucasian, Black, Asian). A combination of neoantigenic peptides derived from polypeptides resulting from these mutations can be used in an immunogenic composition. Based on the number of peptides from the mutations selected, a larger percentage of patients may receive a benefit from the vaccine. Table 7 shows the number of mutations that are recurrent in each cancer specific data set. Also shown are the percentage of subjects in each data set that will have at least a single mutation when selecting recurrent mutations. For example, an immunogenic composition for SKCM that includes neoantigenic peptides derived from 64 recurrent mutations described herein covers 90.91% of patients in this population, whereby each subject will contain at least one of the neoantigenic mutations.

| Exemplary disease | recurrence (muts that occur in >= given # samples) | # unique muts in the set | # samples that have at least one mutation in the set | total # samples | percentage |
|---|---|---|---|---|---|
| SKCM | 5 | 64 | 230 | 253 | 90.91 |
| SKCM | 4 | 200 | 241 | 253 | 95.26 |
| SKCM | 3 | 707 | 247 | 253 | 97.63 |
| SKCM | 2 | 4437 | 250 | 253 | 98.81 |
| SKCM | 1 | 103732 | 253 | 253 | 100 |
| ACC | 5 | 161 | 90 | 90 | 100 |
| ACC | 4 | 219 | 90 | 90 | 100 |
| ACC | 3 | 299 | 90 | 90 | 100 |
| ACC | 2 | 546 | 90 | 90 | 100 |
| ACC | 1 | 10310 | 90 | 90 | 100 |
| BLCA | 5 | 6 | 35 | 130 | 26.92 |
| BLCA | 4 | 9 | 47 | 130 | 36.15 |
| BLCA | 3 | 26 | 77 | 130 | 59.23 |
| BLCA | 2 | 181 | 121 | 130 | 93.08 |
| BLCA | 1 | 25605 | 130 | 130 | 100 |
| BRCA | 5 | 18 | 320 | 888 | 36.04 |
| BRCA | 4 | 25 | 337 | 888 | 37.95 |
| BRCA | 3 | 35 | 357 | 888 | 40.2 |
| BRCA | 2 | 148 | 475 | 888 | 53.49 |
| BRCA | 1 | 31457 | 886 | 888 | 99.77 |
| CESC | 5 | 4 | 46 | 194 | 23.71 |
| CESC | 4 | 7 | 55 | 194 | 28.35 |
| CESC | 3 | 12 | 65 | 194 | 33.51 |
| CESC | 2 | 145 | 133 | 194 | 68.56 |
| CESC | 1 | 25585 | 194 | 194 | 100 |
| CRC | 5 | 15 | 132 | 233 | 56.65 |
| CRC | 4 | 22 | 142 | 233 | 60.94 |
| CRC | 3 | 53 | 160 | 233 | 68.67 |
| CRC | 2 | 711 | 209 | 233 | 89.7 |
| CRC | 1 | 55287 | 233 | 233 | 100 |
| DLBCL | 5 | 0 | 0 | 58 | 0 |
| DLBCL | 4 | 2 | 8 | 58 | 13.79 |
| DLBCL | 3 | 4 | 13 | 58 | 22.41 |
| DLBCL | 2 | 30 | 38 | 58 | 65.52 |
| DLBCL | 1 | 7435 | 57 | 58 | 98.28 |
| HNSC | 5 | 10 | 83 | 384 | 21.61 |
| HNSC | 4 | 15 | 97 | 384 | 25.26 |
| HNSC | 3 | 27 | 123 | 384 | 32.03 |
| HNSC | 2 | 154 | 227 | 384 | 59.11 |
| HNSC | 1 | 43143 | 384 | 384 | 100 |
| KICH | 5 | 0 | 0 | 66 | 0 |
| KICH | 4 | 0 | 0 | 66 | 0 |
| KICH | 3 | 0 | 0 | 66 | 0 |
| KICH | 2 | 24 | 33 | 66 | 50 |
| KICH | 1 | 2576 | 66 | 66 | 100 |
| KIRP | 5 | 9 | 68 | 161 | 42.24 |
| KIRP | 4 | 18 | 86 | 161 | 53.42 |
| KIRP | 3 | 35 | 104 | 161 | 64.6 |
| KIRP | 2 | 117 | 139 | 161 | 86.34 |
| KIRP | 1 | 10482 | 161 | 161 | 100 |
| LIHC | 5 | 2 | 13 | 198 | 6.57 |
| LIHC | 4 | 5 | 25 | 198 | 12.63 |
| LIHC | 3 | 10 | 38 | 198 | 19.19 |
| LIHC | 2 | 33 | 73 | 198 | 36.87 |
| LIHC | 1 | 18574 | 198 | 198 | 100 |
| LUAD | 5 | 11 | 134 | 401 | 33.42 |
| LUAD | 4 | 17 | 152 | 401 | 37.91 |
| LUAD | 3 | 35 | 185 | 401 | 46.13 |
| LUAD | 2 | 611 | 330 | 401 | 82.29 |
| LUAD | 1 | 101222 | 399 | 401 | 99.5 |
| MM | 5 | 6 | 49 | 205 | 23.9 |
| MM | 4 | 8 | 55 | 205 | 26.83 |
| MM | 3 | 16 | 71 | 205 | 34.63 |
| MM | 2 | 51 | 101 | 205 | 49.27 |
| MM | 1 | 7116 | 204 | 205 | 99.51 |
| PRAD | 5 | 24 | 104 | 261 | 39.85 |
| PRAD | 4 | 38 | 133 | 261 | 50.96 |
| PRAD | 3 | 83 | 174 | 261 | 66.67 |
| PRAD | 2 | 205 | 213 | 261 | 81.61 |
| PRAD | 1 | 10174 | 261 | 261 | 100 |
| STAD | 5 | 150 | 141 | 289 | 48.79 |
| STAD | 4 | 245 | 156 | 289 | 53.98 |
| STAD | 3 | 613 | 201 | 289 | 69.55 |
| STAD | 2 | 2729 | 269 | 289 | 93.08 |
| STAD | 1 | 97578 | 289 | 289 | 100 |
| TGCT | 5 | 14 | 80 | 155 | 51.61 |
| TGCT | 4 | 25 | 99 | 155 | 63.87 |
| TGCT | 3 | 64 | 124 | 155 | 80 |
| TGCT | 2 | 338 | 149 | 155 | 96.13 |
| TGCT | 1 | 7632 | 155 | 155 | 100 |
| THCA | 5 | 5 | 283 | 405 | 69.88 |
| THCA | 4 | 5 | 283 | 405 | 69.88 |
| THCA | 3 | 7 | 287 | 405 | 70.86 |
| THCA | 2 | 31 | 300 | 405 | 74.07 |
| THCA | 1 | 4439 | 405 | 405 | 100 |
| UCS | 5 | 2 | 9 | 56 | 16.07 |
| UCS | 4 | 10 | 31 | 56 | 55.36 |
| UCS | 3 | 19 | 41 | 56 | 73.21 |
| UCS | 2 | 55 | 53 | 56 | 94.64 |
| UCS | 1 | 3805 | 56 | 56 | 100 |
| CLL | 5 | 6 | 46 | 263 | 17.49 |
| CLL | 4 | 19 | 74 | 263 | 28.14 |
| CLL | 3 | 38 | 100 | 263 | 38.02 |
| CLL | 2 | 157 | 167 | 263 | 63.5 |
| CLL | 1 | 7870 | 263 | 263 | 100 |
| GBM | 5 | 14 | 100 | 291 | 34.36 |
| GBM | 4 | 24 | 125 | 291 | 42.96 |
| GBM | 3 | 45 | 153 | 291 | 52.58 |
| GBM | 2 | 221 | 252 | 291 | 86.6 |
| GBM | 1 | 14142 | 291 | 291 | 100 |
| KIRC | 5 | 4 | 25 | 417 | 6 |
| KIRC | 4 | 8 | 41 | 417 | 9.83 |
| KIRC | 3 | 23 | 78 | 417 | 18.71 |
| KIRC | 2 | 291 | 292 | 417 | 70.02 |
| KIRC | 1 | 17725 | 417 | 417 | 100 |

| Exemplary disease | recurrence (muts that occur in >= given # samples) | # unique muts in the set | # samples that have at least one mutation in the set | total # samples | percentage |
|---|---|---|---|---|---|
| LAML | 5 | 11 | 93 | 196 | 47.45 |
| LAML | 4 | 12 | 95 | 196 | 48.47 |
| LAML | 3 | 16 | 101 | 196 | 51.53 |
| LAML | 2 | 27 | 114 | 196 | 58.16 |
| LAML | 1 | 1458 | 195 | 196 | 99.49 |
| LUSC | 5 | 2 | 14 | 178 | 7.87 |
| LUSC | 4 | 4 | 22 | 178 | 12.36 |
| LUSC | 3 | 15 | 50 | 178 | 28.09 |
| LUSC | 2 | 130 | 138 | 178 | 77.53 |
| LUSC | 1 | 42062 | 178 | 178 | 100 |
| OV | 5 | 10 | 72 | 316 | 22.78 |
| OV | 4 | 12 | 80 | 316 | 25.32 |
| OV | 3 | 14 | 86 | 316 | 27.22 |
| OV | 2 | 56 | 151 | 316 | 47.78 |
| OV | 1 | 12840 | 316 | 316 | 100 |
| PAAD | 5 | 53 | 146 | 146 | 100 |
| PAAD | 4 | 69 | 146 | 146 | 100 |
| PAAD | 3 | 123 | 146 | 146 | 100 |
| PAAD | 2 | 398 | 146 | 146 | 100 |
| PAAD | 1 | 23715 | 146 | 146 | 100 |
| UCEC | 5 | 30 | 168 | 248 | 67.74 |
| UCEC | 4 | 81 | 196 | 248 | 79.03 |
| UCEC | 3 | 302 | 217 | 248 | 87.5 |
| UCEC | 2 | 2797 | 237 | 248 | 95.56 |
| UCEC | 1 | 112636 | 248 | 248 | 100 |
| COAD | 5 | 3 | 19 | 70 | 27.14% |
| COAD | 4 | 7 | 20 | 70 | 28.57% |
| COAD | 3 | 11 | 25 | 70 | 35.71% |
| COAD | 2 | 84 | 44 | 70 | 62.86% |
| COAD | 1 | 16670 | 70 | 70 | 100.00% |
| READ | 5 | 0 | 0 | 39 | 0.00% |
| READ | 4 | 2 | 8 | 39 | 20.51% |
| READ | 3 | 5 | 16 | 39 | 41.03% |
| READ | 2 | 33 | 29 | 39 | 74.36% |
| READ | 1 | 12132 | 39 | 39 | 100.00% |

Table 8 shows the specific recurrent mutations for each cancer subtype, as well as the peptides that each mutation generates and the flanking peptide that includes the peptides ("ACC", "BLCA", "BRCA", "CESC", "COAD", "CLL", "CRC", "DLBCL", "GBM", "HNSC", "KICH", "KIRC", "KIRP", "LAML", "LIHC", "LUAD", "LUSC", "MM", "OV", "PAAD", "PRAD", "READ", "SKCM", "STAD", "TGCT", "THCA", "UCEC", and "UCS"). Frameshift mutations are denoted with a "fs". "Del" and "Ins" indicate deletions and inserts. The number of peptides that are generated from each mutation that binds to a specific HLA allele are shown. The recurrent mutations include frameshift mutations and create HLA binders across many alleles.

TABLE 8

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| A2M | c.2195G>A | p.R732Q | FYESDVMGRGHARLVHVEEPHTETV[p.R732Q]QKYFPETWIWDLVVVNSAGVAEVGVT | VQKYFPETW, QKYFPETWI, ETVQKYPFET, VQKYFPETWI.Q KYFPETWIW, EPHTETVQKY | CRC |
| A2ML1 | c.1960_1961 insC | p.S654fs | YDQCPVSGPWDFPQPLIDPMPQGHS [p.S654fs]EPAPHYLEALVL* | HSEPAFHYL, MPQGHSEPA, PQGHSEPAF, GHSEPAPHY, FH VLEALVL, EPAPHYLEA, QGHSEPAPHY, EPAPHYLEAL, MPQ GHSEPAF, SEPAPHYLEA | LUAD |
| AADAC L4 | c.796G>A | p.A266T | VPLLSRKFMVTSLCNVLAIDLSWRD[p.A266T]TILNGTCVPPDVNRKYEKWLSPDNIP | IDLSWRDTI, SWRDTILNG, DTILNGTCV, IDLSWRDTIL | CRC |
| AASS | c.2634_2635 insC | p.T878fs | KTIDLVAYGDINGFSAMAKTVGLPT[p.T878fs]RHGSQNVA* | MAKTVGLPTR, LPTRHGSQNV | GBM |
| ABCA 11P | c.1154G>T | p.R385I | TGEKPYTCGECGKTFRQSANLVHR[p.R385I]IIHTGEKP YKCEDCGKAFGRYTALNQ | VHRIIHTGEK, QSANLVHRI | UCEC |
| ABCA3 | c.285G>C | p.E95D | TFPPPGDTWELAYIPSHSDAAKTVT[p.E95D]DTVRRALVINMRVRGFPSEKDFEDYI | KTVTDTVRR, VTDTVRRALV, AAKTVTDTVR, DAAKTVT DTV, TVTDTVRRAL | KIRC |
| ABCA5 | c.4427G>A | p.R1476Q | PQITLLDEPSTGMDPKAKQHMWRAI[p.R1476Q]QTAFKNRKRAAILTTHYME EAEAVCD | HMWRAIQTA, IQTAFKNRK, MWRAIQTAFK, AIQTAFKNR, Q TAFKNRKR, MWRAIQTAFK, AIQTAFKNRK, HMWRAIQTAF, KQHMWRAIQ, RAIQTQFKNR, QHMWRAIQTA | UCEC |
| ABCA6 | c.917delT | p.L306fs | FVTIIITFTQIIVMTGFMVIFILFF[p.L306fs]YMAYLW* | MVIFILFFY, VIFILFFYM, ILFFYMAYL, LFFYMAYLW, FILF FYMAY, MVIFILFFYM, VIFILFFYMA, FILFFYMAYL, ILFFY MAYLW, FMVIFILFFY, IFILFFYMAY | STAD |
| ABCA8 | c.2086G>A | p.A696T | STQFMDEADILADRKVFLSQGKLKC[p.A696T]TGSSLFLKKKWGIGYHLSLQLN EICV | KLKCTGSSL, CTGSSLFLK, TGSSLFLKK, LKCTGSSLF, FLSQGKL KCT, CTGSSLFLKK, KCTGSSLFLK, KLKCTGSSLF, GKLKCTG SSL, LKCTGSSLFL | CRC |
| ABCA8 | c.2525G>A | p.R842Q | RLVEMEQVLSLNKMRKTIGGVALW[p.R842Q]QQQICAIARVRLLKLKHERKAL LALL | ALWQQQICA, WQQQICAIA, ALWQQQICAI | CRC |
| ABCA8 | c.3472G>A | p.E1158K | NSGIWSFCFYVVTVFSVAGFAPSIF[p.E1158K]KSDIPFIFTFLIPPATMIGCLFLSSH | AGPQFSIFK, IFKSDIPPI, SIFKSDIPF, FKSDIPFIF, SIFKSDIPF I, VAGFAPSIFK, IFKSDIPFIF, KSDIPFIFTF, FAFSIFKSDI, FSIFKSDIPF | CRC |
| ABCB1 | c.1400G>T | p.R467L | RLYDPTEGMVSVDGQDIRTINVRFL[p.R467L]LEIIGVVSQEPVLFATTIAENIRYGR | RTINVRFLL, FLLEIIGVV, RFLLEIIGV, INVRFLLEI, FLLEIIGVVS, TINVRFLLEI, RFLLEIIGVV, RTINVRFLLE | LUAD |
| ABCB1 | c.1581_1582 delAG | p.R527fs | VKEANAYDFIMKLPHKFDTLVGERG[p.R527fs]PVEWWAEAEDRHCTCPGSQP QDPPAG* | TLVGERGPV, GERGPVEWW, AEAEDRHCT, DTLVGERGPV, GERGPVEWWA | STAD |
| ABCB6 | c.953delG | p.G318fs | LTEKAPWNSLAWTVTSYVFLKFLQG[p.G318fs]VALAVQAS* | FLQGVALAV, FLKFLQGVA, LKFLQGVAL, YVFLKFLQGV, FLK FLQGVAL, KFLQGVALAV, LKFLQGVALA | STAD |
| ABCB8 | c.1034G>A | p.R345H | SRQCQEQIARAMGVADEALGNVRTV[p.R345H]HAFAMEQREEERY GAELEACRCRAEE | NVRTVHAFA, GNVRTVHAF, VRTVHAFAM, ALGNVRTVHA, TVHAFAMEQR, NVRTVHAFAM, LGNVRTVHAF | CRC |
| ABCC10 | c.1708C>T | p.R570W | RMLILPLNNFPVVINGLLEAKVSLD[p.R570W]MIQLFLDLLPNHNPQ AYYSPDPPAEPS | SLDWIQLFL, VSLDWIQLF, DWIQLFLDL, LEAKVSLDW, KVSL DWIQLF, AKVSLDWIQL, LEAKVSLDWI, LDWIQLFLDL | GBM |
| ABCC4 | c.2648delT | p.L883fs | VAVIPWIAIPLVPLGIIFILRRYF[p.L883fs]WKRQEM* | IFLRRYFWK, FIFLRRYFW, RYFWKRQEM, FLRRYFWKR, FIFL RRYFWK, IFIFLRRYFW, IFLRRYFWK, RRYFWKRQEM | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ABCC5 | c.3269de\|T | p.L1090fs | HAYNKKQEFLHRYQELLDDNQAPFF[p.L1090fs]CLRVRCGGWLCGWTSSASPSSPPRG* | WLCGWTSSA,SASPSSPPR,RVRCGGWLC,NQAPFFCLR,QA PFFCLRV,NQAPFFCLRV,SSASPSSPPR,RVRCGGWLCG,DN QAPFFCLR,CLRVRCGGWL | KIRC |
| ABCC8 | c.1535A>G | p.Y512C | STLEYSNERLKQTNEMLRGIKLLKL[p.Y512C]CAWENIFRTRVETTRRKEMTS LRAFA | IKLLKLCAW,LKLCAWENI,KLCAWENIF,LLKLCAWENI,KLC AWENIFR,CAWENIFRTR,LKLCAWENIF | TGCT |
| ABCC9 | c.1397T>C | p.L466P | IIMGVILLYNLLGSSALVGAAVIVL[p.L466P]PAPIQYFIATKLAEAQKSTLDYSTER | AVIVLPAPI,IVLPAPIQY,VLPAPIQYF,LPAPIQYFI,VLPAPIQY FI,IVLPAPIQYF,AAVIVLPAPI,VIVLPAPIQY,LPAPIQYFIA | TGCT |
| ABCD1 | c.1816T>C | p.S606P | DVVHLHHILQREGGWEAMCDWKDVL[p.S606P]PGGEKQRIGMARMFYHRPKYALLDEC | LPGGEKQRI,DVLPGGEKQR | CESC |
| ABCD1 | c.507C>A | p.H169Q | ATFVNSAIRYLEGQLALSFRSRLVA[p.H169Q]QAYRLYFSQQTYYRVSNMDCRLRNPD | RLVAQAYRL,VAQAYRLYF,RSRLVAQAY,LVAQAYRLY,RLV AQAYRLY,RSRLVAQAYF,LVAQAYRLYF,SFRSRLVAQA,FRSRL VAQAY,SRLVAQAYRL | TGCT |
| ABI1 | c.1335G>T | p.K445N | DYEDEEAAVQYNDPYADGDPAWAP[p.K445N]NNY IEKVVAIYDYTKDKDDELSFMEG | DPAWAPNNY,AWAPNNYIEK,WAPNNYIEKV,DPAWAPNNYI | UCEC |
| ABL2 | c.55C>A | p.P19T | MGQQVGRVGEAPGLQQPQ[p.P19T]TRGIRGSSAARP SGRRRDPAGRITET | LQQPQTRGI,QTRGIRGSSA | TGCT |
| ABTB1 | c.747_748 insC | p.L249fs | TIEPPPADPRLREDMALLADCALPP[p.L249fs]RAPR* | CALPPRAPR,LLADCALPPR,DCALPPRAPR | LAML |
| ACACA | c.5191C>T | p.R1731C | ARAEGIPRIYVSANSGARIGLAEEI[p.R1731C]CHMFH VAVVVDPEDPYKGYRYLYLTPQ | GLAEEICHM,EICHMFHVA,LAEEICHMF,ICHMFHVAW,EEI CHMFHV,GLAEEICHMF,IGLAEEICHM,EEICHMFHVA,AEE ICHMFHV | CRC |
| ACACB | c.6952G>C | p.E2318Q | VAVQFADFHDTPGRMLEKGVISDIL[p.E2318Q]WK TARTFLYWRLRRLLLEDQVKQEI | ILQWKTART,VISDILQWK,QWKTARTFL,DILQWKTAR,LQ WKTARTF,GVISDILQWK,ILQWKTARTF,QWKTARTFLY,LQ WKTARTFL | BLCA |
| ACACB | c.763de\|G | p.G255fs | EHKKLDLHRDFTVASPAEFVTRFGG[p.G255fs]IGSS RRCLLPTTGLPP* | SSRRCLLPT,RFGGIGSSR,RCLLPTTGL,SSRRCLLPTT,AEFVTR FGGI,RRCLLPTTGL | STAD |
| ACACB | c.143T>G | p.F48C | QHTKANRQREPGLGFSFEFTEQQKE[p.F48C]CQAT ARKFAREEIIPVAAEYDKTGEY | QQKECQATA,QQKECQATAR,CQATARKFAR, KECQATARKF,TEQQKECQAT | CRC |
| ACADS | c.989G>A | p.R330H | TKLQVIQFKLADMALALESARLLTW[p.R330H]HA AMLKDNKKPFIKEAAMAKLAASEA | RLLTWHAAM,LLTWHAAML,LLTWHAAMLK,HAAMLKDNK, SARLLTWHA,ARLLTWHAA,RLLTWHAAML,LLTWHAAMLK, SARLLTWHAA,HAAMLKDNKK,ESARLLTWHA,LESARLL TWH,ARLLTWHAAM | KIRC,PRAD |
| ACBD3 | c.671G>T | p.R224L | REEEEERLQKEEEKRRREEEERLR[p.R224L]LEE EERRRLEEERLRLEQQKQQIMAA | REEEEERLRL | LUAD |
| ACOT9 | c.149G>A | p.R50Q | GPQNPKKQGIFHIHEACSSIVHNHV[p.R50Q]QDKLR EIVGASTNWRDHVKAMEERKL | VQDKLREIV,SIHVNHVQDK,HVNHVQDKLR | CRC |
| ACP1 | c.368de\|A | p.Q123fs | DLNRKSNQVKTCKAKIELLGSYDPQ[p.Q123fs]NNLL LKIPIMGMTLTLRRCTSSVSGAAERSWRRPTEAGSCP AAASLTRPHPEVLHFSVGV* | SLTRPHPEV,LLKIPIMGM,TLRRCTSSV,IMGMTLTLR,MGM TLTLRR,SSVSGAAER,RSWRRPTEA,LTRPHPEVL,GAAERS WRR,CTSSVSGAA,EVLHFSVGV,RPHPEVLHF,HPEVLHFSV, NLLLKIPIM,GSYDPQNNL,TEAGSCPAA,GSCPAAASL,AAAS LTRPH,AERSWRRPT,LLLKIPIMGM,LTLRRCTSSV,SLTRPHP EVL,IMGMTLTLRR,SYDPQNNLLL,ASLTRPHPEV,LTRPHPE VLH,PIMGMTLTLR,SGAAERSWRR,IPIMGMTLTL,RPTEAG SCPA,GSYDPQNNLL,LKIPIMGMTL,TEAGSCPAAA,PEVLH FSVGV,DPQNNLLKI | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ACP6 | c.86T>G | p.V29G | GVFSMRLWTPVGVLTSLAYCLHQRR[p.V29G]GALAELQRADGQCPVDRSLLKLKMVQ | CLHQRRGAL, HQRRGALAE, QRRGALAEL, CLHQRRGALA, H QRRGALAEL, YCLHQRRGAL | KIRP |
| ACPP | c.127C>T | p.R43W | FLFLLFFWLDRSVLAEKLKFVTLVF[p.R43W]HGDRSPIDTFTDPIKESSWPQGFG | TLVFWHGDR, LKFVTLVFW, FWHGDRSPI, VTLVFWHGDR, VFWHGDRSPI | BRCA |
| ACPP | c.314G>A | p.R105Q | ELGEYIRKRYRKFLNESYKHEQVYI[p.R105Q]STDVDRTLMSAMTNLAALFPPEGVS | HEQVYIQST, IQSTDVDRTL | CRC |
| ACPP | c.961G>A | p.E321K | LQMALDVYNGLLPPYASCHLTELYF[p.E321K]KKGEYFVEMYYRNETQHEPYPLMLPG | HLTELYFKK, LYFKKGEYF, ELYFKKGEY, KKGEYFVEM, LYFKK GEYFV, SCHLTELYFK, ELYFKKGEYF, TELYFKKGEY, FKKGEYF VEM, KKGEYFVEMY | BLCA |
| ACR | c.837G>T | p.W279C | YVVVGITSWGVGCARAKRPGIYTAT[p.W279C]CPYLNWIASKIGSNALRMIQSATPPP | GIYTATCPY, IYTATCPYL, CPYLNWIAS, TATCPYLNW, GIYTA TCPYL, YTATCPYLNW, TATCPYLNWI | KICH |
| ACSBG2 | c.750T>G | p.I250M | AVLIYTSGTTGIPKGVMLSHDNITW[p.I250M]MAGAVTKDFKLTDKHETWSYLPLSH | NITWMAGAV, TWMAGAVTK, MAGAVTKDF, LSHDNITWM, MLSH DNITWM, ITWMAGAVTK, MAGAVTKDFK, DNIT WMAGAV, WMAGAVTKDF | KIRP |
| ACSL3 | c.562A>T | p.T188S | AIFCETRAEWMIAAQACFMYNFQLV[p.T188S]LYATLGGPAIVHALNETEVTNIITS | FMYNFQLVS, FQLVSLYAT, QLVSLYATL, MYNFQLVSL, YNF QLVSLY, FMYNFQLVSL, FQLVSLYATL, SLYATLGGPA, MYNF QLVSLY, YNFQLVSLYA | CLL |
| ACSM2A | c.1206_1207 insC | p.L402fs | PGYMGTAASCYDVQIIDDKGNVLPP[p.L402fs]RHRRRHWHQGQTHQAYRHLLWLCGQSRQDSSQHSRRLLAPWRPGNQR* | HQAYRHLLW, AYRHLLWLC, SSQHSRRLL, SQHSRRLLA, HSR RLLAPW, RLLAPWRPG, HQGQTHQAY, NVLPPRHRR, VLPP RHRRR, QSQTHQAYR, RHWHQGQTH, QAYRHLLWL, HQA YRHLLWL, THQAYRHLLW, QTHQAYRHLL, SSQHSRRLLA, H SRRLLAPWR, WHQGQTHQAY, NVLPPRHRRR, HQGQTHQ AYR, HLLWLCGQSR, LAPWRPGNQR, GQTHQAYRHL, GQSR QDSSQH, SQHSRRLLAP, QHSRRLLAPW | KIRC |
| ACSM2B | c.585G>T | p.K195N | VASECPSLRIKLLVSEKSCDGWLNF[p.K195N]KLLNEASTTHHCVETGSQEASAIYF | GWLNFNKLL | UCEC |
| ACTA1 | c.823G>T | p.G275C | ITIGNERFRCPETLFQPSFIGMESA[p.G275C]IHETTYNSIMKCDIDIRKDIYANNV | FIGMESACI, SACIHETTY, ESACIHET, MESACIHET, ESACIH ETTY, CIHETTYNSI, SFIGMESACI, MESACIHETT | LUAD |
| ACTG1 | c.64G>C | p.A22P | MEEEIAALVIDNGSGMCKAGF[p.A22P]PGDDAPRAVFPPSIVGRPRHQGVMGM | FPGDDAPRA, FPGDDAPRAV | MM |
| ACTL6A | c.264delA | p.L88fs | GPTYYIDTNALRVPRENMEAISPLK[p.L88fs]MGWLKTGIVSKLFWIIPTKCMSNQKPVSILFSCQRHRGILEQRERN* | KMGWLKTGI, GIVSKLFWI, WLKTGIVSK, KLFWIIPTK, ILFSC QRHR, VSILFSCQR, IVSKLFWII, NQKPVSILF, PTKCMSNQK, MEAISPLKM, LKTGIVSKL, SKLFWIIPT, MSNQKPVSI, KMG WLKTGIV, CMSNQKPVSI, ISPLKMGWLK, GWLKTGIVSK, SILFS CQRHR, NMEAISPLKM, LKMGWLKTGI, LKTGIVSKLF, MSN QKPVSIL, SNQKPVSILF, FSCQRHRGIL, EAISPLKMGW | STAD |
| ACTL7B | c.1061G>A | p.R354H | TGFKEEMAANVLLCGGCTMLDGFPE[p.R354H]HFQRELSLLCPGDSPAVAAAPERKTS | HFQRELSLL, DGFPEHFQR, FPEHFQREL, TMLDGFPEH, MLD GFPEHF, EHFQRELSL, MLDGFPEHF | CRC |
| ACTL7B | c.631G>A | p.E211K | IYSYGKTSGLVVESGHGVSHWPIS[p.E211K]GDVLPGLTSRADYAGGDLTNYLMQL | VSHVVPISK, VPISKGDVL, GVSHVVPISK, HVVPISKGDV | CESC |
| ACTL9 | c.992G>A | p.R331H | EVPGLSPVGLSTMAKQSLRKLSLEM[p.R331H]HADLAQNVLLCGGSSLFTGFEGRFRA | LEMHADLAQ, HADLAQNVL, KLSLEMHADL, EMHADLAQN V, MHADLAQNVL | CRC |
| ACTN2 | c.2677G>T | p.D893Y | AYSGPGSVPGALDYAAFSSALYGES[p.D893Y]YL* | SSALYGESY, SALYGESYL, FSSALYGESY, SSALYGESYL | LUAD |
| ACVR1 | c.617G>A | p.R206H | ADLLDHSCTSGSGSGLPFLVQRTVA[p.R206H]HQITLLECVGKGRYGEVWRGSWQGEN | HQITLLECV, TVAHQITLL, RTVAHQITL, FLVQRTVAH, VQRT VAHQI, RTVAHQITLL, VQRTVAHQIT, QRTVAHQITL, HQITLLECVG | UCEC |
| ACVR1 | c.869C>T | p.S290L | FIASDMTSRHSSTQLMLITHYHEMG[p.S290L]LLYDYLQLTTLDTVSCLRIVLSIASG | GLLYDYLQL, GLLYDYLQLT, LLYDYLQLT, ITHYHEMGL, HEM GLLY, YHEMGLLYDY, HEMGLLYDYL, MGLLYDYLQL, GLLYDYL, LLYDYLQLT, ITHYHEMGLL, THYHE MGLLY, YHEMGLLYDYL, HEMGLLYDYL, MGLLYDYLQL | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ADAD1 | c.32C>T | p.S1IL | MASNNHWFQS[p.S1IL]LQVPSFAQMLKKNLPVQPATKTITTP | SNNHWFQSL, FQSLQVPSF, LQVPSFAQM, FQSLQVPSFA, S LQVPSFAQM, LQVPSFAQML, WFQSLQVPSF, ASNNHWFQSL | UCEC |
| ADAD2 | c.131G>A | p.G44E | LAASLQISPQPRPWRPLPAQAQSAW[p.G44E]EPAPAPATYRAEGGWPQVSVLRDSGP | QSAWEPAPA, EPAPAPATY, AQAQSAWEP, AQSAWEPAP, WEPAPAPAT, AQAQSAWEPA, AQAQSAWEPA, SAWEPAP APA, WEPAPATY | ACC |
| ADAM23 | c.1139A>T | p.K380M | EKDQIDITTNPVQMLHEFSKYRQRI[p.K380M]MQHADAVHLISRVTFHYKRSSLSYFG | RIMQHADAV, MQHADAVHL, KYRQRIMQH, FSKYRQRIM, I MQHADAVH, IMQHADAVHL, MQHADAVHLI, KYRQRIMQ HA, RQRIMQHADA, SKYRQRIMQH, RIMQHADAVH | KIRC |
| ADAM28 | c.217_218 insA | p.K73fs | QEQFETELKYKMTINGKIAVLYLKK[p.K73fs]KQEPPCTRLHGNIL* | CTRLHGNIL, KQEPPCTRL, KIAVLYLKKK, YLKKKQEPPC, KKQ EPPCTRL, KQEPPCTRLH | STAD |
| ADAM29 | c.613G>A | p.V205I | IDNSTQKQSSTVGWHIHFRIVEIVV[p.V205I]IIDNYLYIRYERNDSKLLEDLYIVYN | RIVEIVVI, VIIDNYLYI, VVIIDNLYI, IVVIIDNYL, FRIVEIVVI, IIDNYLYIRY, VVIIDNYLYI, VIIDNYLYIR, HFRIVEIVVI, IVV IIDNYLY, EIVVIIDNYL, VEIVVIIDNY | GBM |
| ADAM30 | c.2223G>T | p.Q741H | LKPKQEKMPLSKAKTQEESKTKTV[p.Q741H]HEESKTKTGQEESEAKTGQEESKAKT | KTKTVHEES, KTKTVHEESK, KTVHEESKTK | LUAD |
| ADAM30 | c.289_290 GG>TT | p.G97L | KHVLHLWPKRLLLPRHLRVFSFTEH[p.G97L]LELLEDHPYIPKDCNYMGSVKESLDSK | RVFSFTEHL, SFTEHLELL, FSFTEHLEL, LELLEDHPY, HLELLED HPY, VFSFTEHLEL, LRVFSFTEHL, FSFTEHLELL, LELLEDHPYI | SKCM |
| ADAM30 | c.941C>A | p.S314Y | SSDWAHLYLQRKYNDALAWSFGKVC[p.S314Y]YLEYAGSVSTLLDTNILAPATWSAHE | WSFGKVCYL, CYLEYAGSV, AWSFGKVCY, FGKVCYLEY, SFG KVCYLEY, LAWSFGKVCY | CRC |
| ADAM32 | c.1676G>A | p.R559Q | DRNNKVFCGWRNLICGRLVCTYPT[p.R559Q]QKPFHQENGDVIYAFVRDSVCITVDY | LVCTYPTQK, CTYPTQKPF, RLVCTYPTQK, CTYPTQKPFH, VC TYPTQKPF | CRC |
| ADAM9 | c.767G>A | p.R256Q | NQTAVREEMILLANYLDSMYIMLNI[p.R256Q]QIVLVGLEIWTNGNLINIVGGAGDVL | YIMLNIQIV, IMLNIQIVL, MLNIQIVLV, MYIMLNIQI, SMYIM LNIQI, IMLNIQIVLV, IMLNIQIVL, MYIMLNIQIV, IQIVLVGLEI | UCEC |
| ADAMTS12 | c.1075G>A | p.E359K | LNPVHHDVAVLLTRKDICAGFNRPC[p.E359K]KTLGLSHLSGMCQPHRSCNINEDSGL | CAGFNRPCK, CKTLGLSHL, KTLGLSHLSG, FNRPCKTLGL, AGFNRPCKTL | UCS |
| ADAMTS12 | c.3157C>G | p.P1053A | RPRMLTPTGPESMSTSTPAISSPS[p.P1053A]ATTASKEDLGGKQWQDSSTQPELSS | TPAISSPSA, ISSPSATTA, AISSPSATTA, SSPSATTASK, STPAIS SPSA, TPAISSPSAT | CESC |
| ADAMTS14 | c.712G>T | p.G238C | QQEWAEPDGDLHNEAFGLGDLPNLL[p.G238C]CLVGDQLGDTERKRRHAKPGSYSIEV | DLPNLLCLV, NLLCLVGDQL | LUAD |
| ADAMTS16 | c.2449G>A | p.D817N | LRRYYLNGHWTVDWPGRYKFSGTTF[p.D817N]NYRRSYNPENLIATGPTNETLIVEL | FSGTTFNYR, KFSGTTFNY, TTFNYRRSY, SGTTFNYRR, FSGTT FNYRR, KFSGTTFNYR, YKFSGTTFNY, GTTFNYRRSY | CRC |
| ADAMTS17 | c.1715A>C | p.N572T | SPWGAWSMCSRTCGTGARFRQRKCD[p.N572T]TPPPGPGGTHCPGASVEHAVCENLPC | RQRKCDTPP, RQRKCDTPPP | TGCT |
| ADAMTS2 | c.2842G>A | p.D948N | WEPCSQTCGRTGMQVRSVRCIQPLH[p.D948N]NNTTRSVHAKHCNDARPESRRACSRE | LHNNTTRSV, SVRCIQPLHN, LHNNTTRSVH | CLL |
| ADAMTS20 | c.1622G>T | p.R541L | KLHKGCFTQHVPPADGTDCGPGMHC[p.R541L]LHGLCVNKETETRPVNGEWGPWEPYS | CLHGLCVNK, GMHCLHGLCV, GPGMHCLHGL | LUAD |
| ADAMTS20 | c.3751C>A | p.R1251S | GKTTRQVLCMNYHQPIDENYCDPEV[p.R1251S]SPLMEQECSLAACPPAHSHFPSSPVQ | SPLMEQECSL | LUAD |
| ADAMTS4 | c.466C>T | p.R156W | TINGDPESVASLHWDGGALLGVLQY[p.R156W]WGAELHLQPLEGGTPNSAGGPGAHIL | VLQYWGAEL, ALLGVLQYW, QYWGAELHL, LQYWGAELH, L LGVLQYWGA, LQYWGAELHL, GALLGVLQYW, WGAELHLQPL | CRC |
| ADAMTS5 | c.1645C>A | p.L549M | QGQMVCLTKKLPAVEGTPCGKGRIC[p.L549M]MQGKCVDKTKKKYSTSSHGNWGSWG | KGRICMQGK, TPCGKGRICM | LUAD |
| ADAMTS8 | c.1570G>A | p.V524M | TPCGPGHLCSEGSCLPEEEVERPKP[p.V524M]MADGGWAPWGECSRTCGGGVQFS | KPMADGGWA, EEVERPKPM, MADGGWAPW, PMADGG WAPW, EEEVERPKPM | GBM |
| ADAMTS9 | c.1975G>T | p.G659W | FKSCNTEPCLKQKRDFRDEQCAHFD[p.G659W]WKHFNINGLLPNVRWVPKYSGILMKD | HFDWKHFNI, CAHFDWKHF, WKHFNINGL, DEQCAHFDW, AHFDWKHFNI, WKHFNINGLL | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ADAMTSL4 | c.2332_2333 insG | p.G778fs | TSCSRSCGPGTQHRQLQCRQEFGGG[p.G778fs]WL LGAPGALWTSPPAQHHPVLPAAPLWPLGSWLSLEPV LRAVRPGPEKPAGSLCWEQW* | WLLGAPGAL,GSWLSLEPV,SLEPVLRAV,RAVRPGPEK,SWLSLEPVL, HPVLPAAPL,LPAAPLWPL,SPPAQHHPV,PPAQHH PVL,WPLGSWLSL,GPEKPAGSL,RQEFGGGWL,QEFGGGW LL,LLGAPGALW,AQHHPVLPA,QHHPVLPAA,APLWPLGS W,VLPAAPLWPL,AQHHPVLPAA,WLSLEPVLRA,LWPLGS WLSL,AVRPGPEKPA,SWLSLEPVLR,SLEPVLRAVR,TSPPAQHH PV,SPPAQHHPVL,APLWPLGSWL,RQEFGGGWLL,WLL GAPGALW,GSWLSLEPVL,QEFGGGWLLG,HPVLPAAPLW | STAD |
| ADCY2 | c.260C>T | p.A87V | LAVFFALGLEVEDHVAFLITVPTAL[p.A87V]VI FFAIFILVCIESVFKKLLRLFSLV | LVIFFAIPI,VIFFAIFIL,LITVPTALV,TVPTALVIF,TALVIFFAI, PTALVIFFA,ALVIFFAIF,ITVPTALVI,VPTALVIFF,FLITVPTALV, ALVIFFAIFI,VIFFAIFILV,TTVPTALVIF,TVPTALVIFF, TALVIFFAIF,PTALVIFFAI,LVIFFAIFIL,VPTALVIFFA | DLBCL |
| ADCY2 | c.2662G>A | p.V888I | HVAEHFLARSLKNEELYHQSYDCVC[p.V888I]IM FASIPDFKEFYTESDVNKEGLECL | SYDCVCIMF,IMFASIPDF,QSYDCVCIM,HQSYDCVCI,IMFA SIPDFK,CIMFASIPDF,HQSYDCVCIM,QSYDCVCIMF | OV |
| ADCY2 | c.3046C>A | p.P1016T | SFNDFKLRVGINHGPVIAGVIGAQK[p.1016] TQYDIWGNTVNVASRMDSTGVLDKIQ | AQKTQYDIW,TQYDIWGNTV,GVIGAQKTQY | LUAD |
| ADCY5 | c.1982G>A | p.R661H | SIETFLILRCTQKRKEEKAMIAKMN[p.R661H] HQRTNSIGHNPPHWGAERPFYN HLGG | MIAKMNHQR,KAMIAKMNH,KMNHQRTNS,HQRTNSIGH, MNHQRTNSI,KMNHQRTNSI,AMIAKMNHQR | CRC |
| ADD3 | c.1708G>A | p.E570K | HGPPAPNPFSHLTEGELEEYKRTI[p.E570K]K RKQQGLEDAEQELLSDDASSVSQIQ | TIKRKQQGL,RTIKRKQQGL | UCEC |
| ADGB | c.3371C>T | p.S1124L | PCNSFAIKEIRDYYIPNDKKILFRYI[p.S1124L]L VKVLTPQPATIQVRTSKPDAFIKLQ | ILFRYLVKV,KILFRYLVK,LFRYLVLKVL,KKILFRYLV,KILFRYLVK V,ILFRYLVKVL,KKILFRYLVK,LVKVLTPQPA | UCEC |
| ADH1A | c.461A>T | p.D154V | SRFTCRKPIHHFLGISTFSQYTVV[p.D154V]V ENAVAKIDAASPLEKVCLIGCGFST | YTVVVENAV,VVVENAVAK,TFSQYTVVV,SQYTVVVEN,STFSQYTV VV,SQYTVVENA,VVVENAVAKI,TVVVENAVAK,YTVVVENAV A,VENAVAKIDA | KIRC |
| ADNP2 | c.965del|C | p.S322fs | NSPSPAAGQPVTVAQGAPGSLTHSP[p.S322fs] LLLANPT* | SLTHSPLL,GSLTHSPLL,LTHSPLLLA,SLTHSPLLLA,APGSLTHSPL | STAD |
| AFF2 | c.1790G>A | p.R597H | VKTNASQVPAEPKERPLLSLIREKA[p.R597H]HP RPTQKIPETKLAKHKLSTTSETVS | KAHPRPTQK,LIREKAHPR,REKAHPRPT,KAHPRPTQKI,SLIREKAHPR | PRAD |
| AFF3 | c.2755G>A | p.E919K | INKNEKMLRSPISPLSDASKHKYTS[p.E919K]KD LTSSSRPNGNSLFTSASSSKKPKA | ASKHKYTSK,TSKDLTSSSR,SKHKYTSKDL | BLCA |
| AFP | c.545C>G | p.A182G | TFMNKFIYEIARRHPFLYAPTILLW[p.A182G]GAR YDKIIPSCCKAENAVECFQTKAA | LLWGARYDK,LWGARYDKI,TILLLWGARY,PTILLWGAR,PTIL LWGARY,YAPTILLWGA,LLWGARYDKI,ILLWGARYDK,LYAPTILLWG | LUAD |
| AGAP1 | c.381del|C | p.G127fs | GGRFKKEIVDGQSYLLLIRDEGGP[p.G127fs]R RRSLPCGWTLLYLSSAWRMK* | LPCGWTLL,SLPCGWTLL,LLYLSSAWR,YLLSSAWRMK,RSL PCGWTL,LYLSSAWRM,WTLLYLSSA,GPRRRSLPC,TLLYLSS AW,LLYLSSAWRM,RSLPCGWTLLY,RSLPCGWTLL,LIRDEGGPRR,LYLSSAW RMK,SLPCGWTLLY,TLLYLSSAWR,RRSLPCGWTL,WTLLYL SSAW,LPCGWTLLYL | STAD |
| AGAP3 | c.2296C>T | p.R766W | VWEGALGGYSKPGPDACREEKERWI[p.R766W] WAKYEQKLFLAPLPSSDVPLGQQLLR | WIWAKYEQK,IWAKYEQKL,KERWIWAKY,WAKYEQKLF,E EKERWIWA,WIWAKYEQKL,IWAKYEQKLF,RWIWAKYEQK, REEKERWIWA | GBM |
| AGAP6 | c.207del|C | p.D69fs | MAAAVQPAEVTVEVGEDLHMHVRD [p.D69fs]GRCLKLWSLTFLPIQSQAQYS RGTLKQKLWSLTFLLPIQRQA QYSRGTLKQML* | TLKQKLWSL,HVRDGRCLK,CLKLWSLTF,LWSLTFLPI,YSRG TLKQK,KQKLWSLTL,HMHHVRDGR,LPIQSQAQY,LKLWSL TFL,SQAQYSRGT,QKLWSLTLL,KLWSLTLLPI,KLWSLTLLPI, CLKLWSLTFL,KQKLWSLTL,RCLKLWSLTF,HVRDGRCLKL, FLPIQSQAQY,LTFLPIQSQA,DGRCLKLWSL,SQAQYSRGTL, LKQKLWSLTL,YSRGTLKQML | KIRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| AGAP6 | c.380G>T | p.S127I | NPSANPEASTIFQRNSQTDVVEIRR[p.S127I]INCTNHVSAVRPSQQYSLCSTIFLDD | RRINCTNHV,RINCTNHVSA | CLL, PRAD |
| AGAP7 | c.211de|G | p.E71fs | AAAVQPAEVTVEVGEDLHMHVRDR[p.E71fs]RCLKLWSLTLLPIQRQAQYSRGTLKQML* | HMHHVRDRR,HVRDRRCLK,CLKLWSLTL,RRCLKLWSL,LKLWSLTLL,KLWSLTLLPI,CLKLWSLTLLL,HVRDRRCLKL,DRRCLKLWSL,RCLKLWSLTL,YSRGTLKQML | KIRC |
| AGAP9 | c.742A>G | p.M248V | STSQEDPQFSVPPTANTPTPVCKLS[p.M248V]VRWSNLFTSEKGSDPDERKAPENHA | KLSVRWSNL,LSVRWSNLF,SVRWSNLFT,KLSVRWSNLF,SVRWSNLFTS,TPTPVCKLSV,CKLSVRWSNL,TPVCKLSVRW | SKCM |
| AGBL5 | c.1260_1261 insC | p.1420fs | KLNSVWIMPQQSAGLEESAPDTIPP[p.I420fs]QREWRCLLCGPAWTCFQKGLLHVRKQL* | CFQKGLLHV,TIPPQREWR,FQKGLLHVR,RCLLCGPAW,LCGPAWTCF,REWRCLLCG,CGPAWTCFQK,DTIPPQREWR,CFQKGLLHVR,LLCGPAWTCF,WRCLLCGPAW,REWRCLLCGP | STAD |
| AGMAT | c.937G>A | p.V313M | TGTPEIAGLTPSQALEIIRGCQGLN[p.V313M]MMGCDLVEVSPPYDLSGNTALLAANL | MMGCDLVEV,IIRGCQGLNM,RGCQGLNMM,GLNMMGCDLV,NMMGCDLVEV,IIRGCQGLNMM,IRGCQGLNMM | CRC |
| AGPAT4 | c.634G>A | p.A212T | ISMQVARAKGLPRLKHHLLPRTKGF[p.A212T]ITVRSLRNVSAVTDCTLNFRNNEN | RTKGFTITV,FTITVRSLR,LPRTKGFTI,LLPRTKGFTI,RTKGFTITVR,KGFTITVRSL,GFTITVRSLR,LPRTKGFTIT | CRC |
| AGRN | c.3851_3853 de|TGA | p.1284_1285 VT>A | GATSGAIAAGATARATATASRLPSSA[p.1284_1285 VT>A]APRAPHPSHTSQPVAKTTAAPTTRRPPTFSQTFRIAPSMCITKPEVDFAVEVF[p.R502C]CSALTQHMERRAK* | ASRLPSSAA,RLPSSAAPR,SSAAPRAPH,APRAPHPSH,LPSSAAPRA,RLPSSAAPRA,APRAPHPSHT | KICH |
| AGXT2 | c.1504C>T | p.R502C | FSQTFRIAPSMCITKPEVDFAVEVF[p.R502C]CSALTQHMERRAK* | FAVEVFCSA,FCSALTQHM,VEVFCSALT,FAVEVFCSAL,CSALTQHMER,VFCSALTQHM | UCEC |
| AHI1 | c.909_910 insA | p.K303fs | DDEISSMEQSTEDSMQDDTKPKPK[p.K303fs]NKKED* | KPKPKKNKK | STAD |
| AHNAK | c.12449C>T | p.S4150F | KAPKISMPEVDLNLKGPKMKGDVDV[p.S4150F]FLPKVEGDLKGPEVDIKGPKVDIDVP | KMKGDVDVF,KMKGDVDVFL,KGDVDVFLPK,PKMKGDVDVF | BLCA |
| AHNAK | c.15_16 insGAG | p.5_6insE | MEKEE[p.5_6insE]ETTRELLLPNWQGSGSHGLITAQRDDGV | KEEETTREL,EEETTRELL,KEEETTRELL,EEETTRELLL | KIRC |
| AHNAK | c.3658G>A | p.V1220I | ISMPDVDLHLKGPKVKGDVDVSVPK[p.V1220I]IEGEMKVPDVEIKGPKMDIDAPDVEV | IEGEMKVPDV,VPKIEGEMKV | CLL |
| AHNAK | c.6341C>G | p.A2114G | PDVSLREGPEGKLKGPKLKMPEMHFK[p.A2114G]GPKISMPDVDLHLKGPKVKGDVDVSL | HFKGKPISM,MHFKGPKISM,PEMHFKGPKI | CLL |
| AHNAK | c.8665C>G | p.D2889H | LKGPEVDLKGPKVDIDVPDVNVQGP[p.D2889H]HWHLKMPKMKMPKFSMPGFKAEGPEV | VQGPHWHLK,NVQGPHWHL,NVQGPHWHLK,HWHLKMPKMK,VQGPHWHLKM | BLCA |
| AHNAK2 | c.3643C>T | p.P1215S | APKVEADVSLPSMQGDLKTTDLSIQ[p.P1215S]SPSADLEVHAGQVDVKLLEGHVPEGA | SPSADLEVH | KIRP |
| AHNAK2 | c.4918C>A | p.L1640M | PDVKMSLSSMEVDVQAPRAKLDGAQ[p.L1640M]MEGDLSLADKAVTAKDSKFKMPKFKM | AQMEGDLSL,QMEGDLSLA,RAKLDGAQM,AQMEGDLSLA | TGCT |
| AHNAK2 | c.6497C>T | p.S2166F | LANKDLTTKDSKFKMPKFKMPSFGV[p.S2166F]FAPGKSIEASVDVSPPKAPHPKMSLPS | KMPSFGVFA,SFGVFAPGK,FKMPSFGVF,GVFAPGKSI,MPSFGVFAP,PSFGVFAPGK,KFKMPSFGVF,MPSFGVFAPG,FKMPSFGVFA | KIRP |
| AICDA | c.391C>G | p.R131G | LRIFTARLYFCEDRKAEPEGLRRLH[p.R131G]GAGVQIAIMTFKDYFYCWNTFVENHE | RLHGAGVQI,GLRRLHGAGV,RLHGAGVQIA,RRLHGAGVQI,LHGAGVQIAI,HGAGVQIAIM | LUSC |
| AICDA | c.431A>T | p.Y144F | RKAEPEGLRRLHRAGVQIAIMTFKD[p.Y144F]FFYCWNTFVENHERTFKAWEGLHENS | IMTFKDFFY,MTFKDFFYC,FFYCWNTFV,TFKDFFYCW,DFFYCWNTF,IAIMTFKDF,AIMTFKDFF,KDFFYCWNT,AIMTFKDFFY,IAIMTFKDFF,MTFKDFFYCW,KDFFYCWNTF,DFFYCWNTFV | GBM |
| AIDA | c.740A>T | p.K247M | VDIELQKHVEKLTKGAAIFFEFKHY[p.K247M]MPKKRFTSTKCFAFMEMDEIKPGPIV | IFFEFKHYM,EFKHYMPKK,MPKKRFTST,FEFKHYMPK,KHYMPKKRF,YMPKKRFTST,MPKKRFTSTK,FFEFKHYMPK,EFKHYMPKKR,AIFFEFKHYM,FKHYMPKKRF | KIRC |
| AK302879 | c.572A>G | p.Q191R | AVSTQQQEEDRSSSCREAVLQWRLQ[p.Q191R]RTIKEQALLNAHTQVTESLKQVQLE | AVLQWRLQR,QWRLQRTIK,RTIKEQALL,LQWRLQRTI,VLQWRLQRTI,EAVLQWRLQR,LQRTIKEQAL | PRAD |
| AK7 | c.476C>T | p.A159V | SALSEEVSHFEKRKLFILLSTVMTW[p.A159V]VRSKALDPEDSEVPFTEEDYRRRKSH | LLSTVMTWV,VMTWVRSKA,ILLSTVMTWV,TVMTWVRSK,MTWVRSKAL,LSTVMTWVR,ILLSTVMTWVR,TVMTWVRSKA,VMTWVRSKAL,STVMTWVRSK,LLSTVMTWVR,KAL,STVMTWVRSK,LLSTVMTWVR | GBM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| AK8 | c.728A>C | p.D243A | KLLEYHRNIVRVIPSYPKILKVISA[p.D243A]AQ PCVDVFYQALIYVQSNHRTNAPFT | KILKVISAA,VISAAQPCV,AAQPCVDVFY,AAQPCVDVF,KVIS AAQPCV,AAQPCVDVFY,SAAQPCVDVF | GBM |
| AKAP12 | c.3844G>A | p.E1282K | ILSKTEGTQEADQYADEKTKDVPFF[p.E1282K]KG LEGSIDTGITVSREKVTEVALKGE | KTDVPFFK,KDVPFFKGL,KTKDVPFFKG | CRC |
| AKAP13 | c.8353del A | p.K2785fs | QAPASTSASTRLFGLTKPKEKKEKK[p.K2785fs]RR TKPAALSPVMVPRQKYQQRVKRSSADPLPLC* | ALSPVMVPR,KRRTKPAAL,RTKPAALSP,RQKYQQRVK,QQRVKRSSA, RVKRSSADP,RSSADPLPL,KPAALSPVM,EKKRRT KPA,YQQRVKRS,VKRSSADPL,RTKPAALSPV,AALSPVM PVMV,VPRQKYQQRV,KRRTKPAAL,TKPAALSPVM,YQQRVKRSSA, KRSSADPLPL,SPVMVPRQKY PR,RQKYQQRVKR,RVKRSSADPL,MVPRQKYQQR,KPAALS | STAD |
| AKAP9 | c.10444C>A | p.L3482I | RRILYQNLNEPTTWSLTSDRTRNWV[p.L3482I]IQ QKIEGETKESNYAKLIEMNGGGTG | RTRNWVIQQ,SDRTRNWVI,RNWVIQQKI,RTRNWVIQQK | CRC |
| AKAP9 | c.11229del G | p.M3743fs | YLLLLGGFQECEDATLALLARMGG[p. M3743fs]SQLSRI* | RMGGSQLSR,LARMGGSQL,RMGGSQLSRI,LLARMGGSQL | STAD |
| AKD1 | c.3625del A | p.R1209fs | DMKAKIRVDTIAKRRAELILERDKK[p.R1209fs] GGRMLLEMMKRLVRKNLKKT MMILKTSLKMSFQKMRKR* | MLLEMMKRL,TMMILKTSL,NLKKTMMIL,RMLLEMMKR,E MMKRLVRK,RLVRKNLKK,MMILKTSLK,TSLKMSFQK,KMS FQKMRK,MSFQKMRKR,KRLVRKNLK,KNLKKTMMI,LKKT MMILK,KTMMILKTS,KTSLKMSFQ,SLKMSFQKM,MKRLV RKNL,MILKTSLKM,KGGRMLLEM,RNLKKTMM,LKTSLK MSF,MLLEMMKRLV,MMILKTSLKM,NLKKTMMILK,TMM ILKTSLK,KTSLKMSFQK,KMSFQKMRKR,GGRMLLEMMK, MMKRLVRKNL,MKRLVRKNLK,KRLVRKNLKK,KTMMILKTS L,SLKMSFQKMR,ILKTSLKMSF,LERDKKGGRM,KKGGRML LEM,RMLLEMMKRL,RKNLKKTMMI,TSLKMSFQKM | STAD |
| AKNAD1 | c.1859A>G | p.K620R | AEMTAPSPSCAFCRRLLEWKQNVEK[p.K620R]RGHG RINCGRFSIVLHEKAPHSDSTP | NVEKRGHGR,RGHGRINCGR | HNSC |
| AKT1 | c.49G>A | p.E17K | MSDVAIVKEGWLHKRG[p.E17K]KYIKTWRPR YFLLKNDGTFIGYKERP | WLHKRGKYI,LHKRGKYIK,RGKYIKTWR,KYIKTWRPR,GWL HKRGKY,WLHKRGKYIK,KYIKTWRPRY,HKRGKYIKTW | BRCA, CESC, THCA |
| AKT2 | c.867C>G | p.I289M | EYLHSRDVVYRDIKLENLMLDKDGH[p.I289M]MKI TDFGLCKEGISDGATMKTFCGTP | LMLDKDGHM,HMKITDFGL,MLDKDGHMK,MLDKDGHM KI,LMLDKDGHMK | BRCA |
| ALAS1 | c.904G>C | p.G302R | PRVCGAVMDTLKQHGAGAGGTRNIS[p.G302R]RTS KFHVDLERELADLHGKDAALLFS | GTRNISRTS,ISRTSKFHV,RTSKFHVDL,RNISRTSKF,NISRTS KFHV,GTRNISRTSK,TRNISRTSKF | KIRC |
| ALB | c.881C>T | p.S294L | CCHGDLLECADDRADLAKYICENQD[p.S294L] LISSKLKECCEKPLLEKSHCIAEVEN | YICENQDLI,KYICENQDL,NQDLISSKL,CENQDLISS,KYICEN QDLI,AKYICENQDL | CRC |
| ALDH1A2 | c.253C>T | p.R85C | PATGEQVCEVQEADKADIDKAVQAA[p.R85C]CLAFS LGSVWRRMDASERGRLLDKLA | CLAFSLGSV,QAACLAFSL,AVQAACLAF,VQAACLAFSL,KAV QAACLAF,CLAFSLGSVW | PRAD |
| ALDH1L1 | c.2608G>A | p.A870T | KALYVSDKLQAGTVFVNTYNKTDVA[p.A870T]TPFGG FKQSGFGKDLGEAALNEYLRV | VATPFGGFK,DVATPFGGF,NKTDVATPF,DVATPFGGFK,YN KTDVATPF,TDVATPFGGF | CRC |
| ALDH2 | c.858del G | p.L286fs | TEIGRVIQVAAGSSNLKRVTLELGG[p.L286fs]RAPTS SCQMPIWIGPWNRPTSPCSSTRASAAVPAPGPSCRRTS MMSLWSGALPGPSLGWSGTPLIARPSRGRRWMKLSLR RSSATSTRGSKRGRSCCCVVGALLLTVVTSSS PLCLEMCRMA* | SMMSLWSGA,MMSLWSGAL,SLGWSGTPL,VVGALLLTV,K LSLRRSSA,ATSTRGSKR,QMPIWIGPW,STRASAAVP,RTSM MSLWS,IARPSRGRR,PSRGRRWMK,RGRRWMKLS,RWM KLSLRR,SLRRSSATS,SATSTRGSK,STRGSKRGR,RGRSCCVV G,SSSPLCLEM,PIWIGPWNR,SSTRASAAV,TVVTSSSPL,RP TSPCSST,GPSCRRTSM,RPSRGRRWM,LELGGRAPT,RAPTS SCQM,CRRTSMMSL,RRTSMMSLW,SLWSGALPG,SGALP GPSL,LGWSGTPLI,GRRWMKLSL,RSCCVVGAL,MPIWIGP WN,SMMSLWSGAL,SLGWSGTPLI,CVVGALLLTV,VVGALL LTVV,SATSTRGSK,CQMPIWIGPW,STRASAAVPA,RASAA VPAPG,SCRRTSMMSL,RTSMMSLWSG,TSMMSLWSGA,R | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ALDH3A1 | c.1685de lC | p.P562fs | ETFSHRRSCLVRPLMNDEGLKVRYP[p.P562fs]R ARPR* | PSRGRRWMK,RGRRWMKLSL,GSKRGRSCCVV,RGRSCCVV GA,RSCCVGALL,MPIWIGPWNR,LIARPSRGRR,SATSTRG SKR,CSSTRASAAV,LTVVTSSSPL,APTSSCQMPI,GPWNRPT SPC,SPCSSTRASA,GPSCRRTSMM,GRAPTSSCQM,CRRTS MMSLW,MSLWSGALPG,WSGALPGPSL,GALPGPSLGW,I ARPSRGRRW,MKLSLRRSSA,GRSCCVVGAL,TSSSPLCLEM, LELGGRAPTS,SPLCLEMCRM | STAD |
| ALG2 | c.905C>A | p.S302Y | NVEHYQELKKMVQQSDLGQYVTFLR[p.S302Y]YFSD KQKISLLHSCTCVLYTPSNEHF | GLKVRYPRA,KVRYPRARP,EGLKVRYPR,GLKVRYPRAR,KV RYPRARPR | CRC |
| ALKBH1 | c.409A>G | p.K137E | WHWVKQCLKLYSQKPNVCNLDKHMS[p.K137E]EEE TQDLWEQSKEFLRYKEATKRRPR | TFLRYFSDK,QYVTFLRYF,RYFSDKQKI,GQYTFLRY,YVTFL RYFS,LGQYVTFLRY,VTFLRYFSDK,FLRYFSDKQK,GQYVTFLRYF | LUAD |
| ALPK2 | c.1067de lT | p.L356fs | ECSDVMTDYSNAVWQRNLLGTEHVF[p.L356fs]Y* | SEEETQDLW,HMSEEETQDL,MSEEETQDLW | STAD |
| ALPK2 | c.1568de lA | p.K523fs | LLSGESENSGMSQCWETAADKRVGG[p.K523fs]RT YGARGVQGNLPG* | LLGTEHVFY,NLLGTEHVFY | UCEC |
| ALPK2 |  |  |  | RVGGRTYGA,RTYGARGVQ,RVGGRTYGAR,RTYGARGVQ G,TAADKRVGGR,ADKRVGGRTY |  |
| ALPPL2 | c.157G>A | p.D53N | DAVLRCIISGQPKPEVTWYKNGQAI[p.D53N]NGS GIISNYEFFENQYIHVLHLSCCT | NGSGIISNY,GQAINGSGI,INGSGIISNY,GQAINGSGII | LUSC |
| ALX4 | c.92G>C | p.W31S | VLLLGLRLQLSLGIIPVEEENPDF[p.W31S]SN RQAAEALGAAKKLQPAQTAAKNLI | SNRQAAEAL,FSNRQAAEAL | TGCT |
| AMBN | c.377G>A | p.R126Q | PPPQPQPQQQQPQPQPPAQPHLYLQ[p.R126Q]QG ACKTPPDGSLKLQEGSSGHSAALQ | YLQQGACKT,HLYLQQGACK,LQQGACKTPP | BLCA |
| AMDHD1 | c.674C>A | p.S225Y | QGPSLPGLDFADPQGSTIFQIARLI[p.S225Y]YH GPMPQNKQSPLYPGMLYVPFGANQ | IFQIARLIY,FQIARLIYH,ARLIYHGPM,TIFQIARLIY,IARLIYH GPM,IYHGPMPQNK,FQIARLIYHG | UCEC |
| AMPH | c.7A>G | p.S3G | MA[p.S3G]GGHSLLLENAQQVVLVCARGERFLAR | MAGGHSLLL | ACC |
| ANAPC1 | c.874C>T | p.R292W | PSPLPSPTASPNHTLAPASPAPARP[p.R292W]WS PSQTRKGPPVPLPKVTPTKELQQ | APARPWSPS,RPWSPSQTRK | CRC |
| ANAPC1 | c.1609A>G | p.T537A | PGLPAPSLTMSNTMRPRSTPLDGVS[p.T537A]APK PLSKLLGSLDEVVLLSPVPELRD | VSAPKPLSK,APKPLSKLL,GVSAPKPLSK | PAAD,PRAD |
| ANK2 | c.1358A>G | p.N453S | TESGLTPIHVAAFMGHLNIVLLLLQ[p.N453S]SG ASPDVTNIRGETALHMAARAGQVE | VLLLLQSGA,LQSGASPDV,LLQSGASPDV,LQSGASPDVT | KIRC |
| ANK2 | c.9227A>T | p.Q3076L | DDEAFEARVKEEEQKIFGLMVDRQS[p.Q3076L]LG TTPDTTPARTPTEEGTPTSEQNPF | GLMVDRQSL,RQSLGTTPD,LMVDRQSLGT,FGLMVDRQSL, RQSLGTTPDT | LUAD |
| ANK3 | c.3966T>A | p.D1322E | LATQLYRELICVPYMAKFVVFAKMN[p.D1322E]E PVESSLRCFCMTDDKVDKTLEQQEN | KMNEPVESS,VVFAKMNEPV,KMNEPVESSL,EPVESSLRCF | TGCT |
| ANKDD1A | c.71G>A | p.R24H | MQEELAWETDGLLPLERQLHEAA[p.R24H]HQNN VGRMQELIGRRVNTRARNHVGR | HEAAHQNNV,AHQNNVGRM,EAAHQNNVGR,LERQLHEA AH,RQLHEAAHQN,AAHQNNVGRM | UCEC |
| ANKFN1 | c.840G>T | p.M280I | YRLYRRMKTGPEHARAPEMPTNVCL[p.M280I]IVT SSTSLTVSFQEPLSVNAAVVTRY | EMPTNVCLI,LIVTSSTSL,MPTNVCLIV,CLIVTSSTSL,EMPTN VCLIV,IVTSSTSLTV,MPTNVCLIVT,PEMPTNVCLI | LUSC |
| ANKLE1 | c.1930_1933 de lTGTT | p.C644fs | TAAPISGFRRGVCVCVCVCVCVCVC[p.C644fs]VCV CVCREHPGRSPPG* | CVCREHPGR,REHPGRSPP,CVCVCVCVCR,REHPGRSPPG | TGCT |
| ANKLE1 | c.1932_1933 de lTT | p.C644fs | TAAPISGFRRGVCVCVCVCVCVCVC[p.C644fs]VCV CVCVGSTQADLPQAERGLCYRWYCWRGSK* | RWYCWRGSK,CYRWYCWRG,QAERGLCYR,LCYRWYCWR, PQAERGLCY,AERGLCYRW,RGLCYRWYCW,GLCYRWYCW R,LPQAERGLCY,AERGLCYRWY | TGCT |
| ANKMY1 | c.905A>T | p.N302I | KELDARIFLNEIPPFVEDGEPWFII[p.N302I]IE TPLLVKIQKQTYKFRNKPAHTSWN | FIIIETPLL,IIIETPLLV,IETPLLVK,IETPLLVKI,FIIIETPLLV, IIIETPLLVK,WFIIIETPLL,GEPWFIIIET | THCA |
| ANKRD11 | c.1106A>G | p.K369R | KDEYEFDEDDEQDRVPPVDDKHLLK[p.K369R]RD YRKETKSNSFISIPKMEVKSYTKN | HLLKRDYRK,KHLLKRDYR,KHLLKRDYRK | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ANKRD11 | c.6044A>C | p.Y2015S | SPKRFCPADPLHSAAPGPFSASEAP[p.Y2015S]S PAPPASPAPYALPVAEPGLEDVKDG | SASEAPSPA, EAPSPAPPA, SPAPPASPA, FSASEAPSPA, SPAP PASPAP, SEAPSPAPPA | TGCT |
| ANKRD12 | c.1879G>A | p.E627K | HKEKSKHQKDFHLEFGEKSNAKIKD[p.E627K]KD HSPTFENSDCTLKKMDKEGKTLKK | KSNAKIKDK, KDKDHSPTF, IKDKDHSPTF | BLCA |
| ANKRD12 | c.2161G>C | p.E721Q | WKENFFKSDETEDLFLNMEHESLTL[p.E721Q]QK KSKLEKNIKDDKSTKEKHVSKERN | LQKKSKLEK, TLQKKSKLEK | CESC |
| ANKRD32 | c.2996C>A | p.T999N | SEFILASKGLTHLNELLMACKSHKE[p.T999N]N TSVHTDWLLDLYAGNIKTLQKLPHI | KSHKENTSV, NTSVHTDWLL, NTSVHTDWL, KSHKENTSVH, KENTSVHTDW | BLCA |
| ANKRD36 | c.1010C>G | p.P337R | TSDKDDSVSNTATEIKDEQKSGTVL[p.P337R]RA VEQCLNRSLYRPDAVAQPVTENEF | KSGTVLRAV, EQKSGTVLR, QKSGTVLRAV | CLL |
| ANKRD36 | c.1133A>G | p.K378R | VAQPVTENEFSLESEIISKLYIPKR[p.K378R]R IISPRSIKDVLPPVEEAVDRCLYLL | RIISPRSIK, LYIPKRRI, KLYIPKRRI, KRRIISPRS, IPKRRIISP, RRIISPRSI, ISKLYIPKRR, KLYIPKRRII, KRRIISPRSI, IPKRRIISPR | KIRC |
| ANKRD36 | c.3040G>T | p.D1014Y | SEKPPGLKATSDEKDSVLNIARGKK[p.D1014Y]Y GEKTRTVSSQKPPTLKATSDEDDSV | RGKKYGEKTR, KKYGEKTRTV | CLL |
| ANKRD36 | c.3431T>C | p.M1144T | KSRTVSSPKQPALKAICDKEDSVPN[p.M1144T]TATE KKDEQLSGTVSCQKQPALKATS | SVPNTATEK, KEDSVPNTA, SVPNTATEKK, KEDSVPNTAT | CESC |
| ANKRD36C | c.1313A>G | p.H438R | LEKDTIKNQNLEKKYLKDFEIVKRK[p.H438R] REDLQKA | IVKRKREDL | PAAD, PRAD |
| ANKRD50 | c.1909G>A | p.V637M | WTALRSAAWGGHTEVVSALLYAGVK[p.V637M]MD CADADSRTALRAAAWGGHEDIVLN | ALLYAGVKM, SALLYAGVKM | TGCT |
| ANKRD6 | c.1435C>T | p.R479C | TQHQMRVLDKLMVERLSAERTECLN[p.R479C]CL QQHSDTEKHEGEKRQISLVDELKT | CLQQHSDTEK, AERTECLNCL | CRC |
| ANO2 | c.1000C>T | p.R334C | PLHDGEYDSPEDDMNDRKLLYQEWA[p.R334C]CY GVFYKFQPIDLIRKYFGEKIGLYF | YQEWACYGV, WACYGVFYK, ACYGVFYKF, LLYQEWACY, E WACYGVFY, QEWACYGVF, LYQEWACYGV, YQEWACYGVF, WACYGVFYKF, KLLYQEWACY, EWACYGVFYK, QEWACYGVFY | GBM |
| ANO3 | c.121G>T | p.A41S | GMNISKSEITKETSLKPSRRSLPCL[p.A41S]SQ SYAYSKLSQSTSLFQSTESESQA | LSQSYAYSK, SLPCLSQSY, SLPCLSQSYA, CLSQSYAYSK, RSLP CLSQSY, SQSYAYSKSL, LPCLSQSYAY | LUAD |
| ANO3 | c.2868G>T | p.M956I | IAYLIPDVPKGLHDRIRREKYIVQE[p.M956I]IM YEAELEHLQQQRRKSGQPVHHEWP | LVQEIMYEA, KYLVQEIMY, IMYEAELEH, REKYLVQEI, EKYLV QEI, QEIMYEAEL, YLVQEIMYEA, IMYEAELEHL, RREKYLV QEI, REKYLVQEIM, EKYLVQEIMY, VQEIMYEAEL | CESC |
| ANXA6 | c.692G>A | p.R231Q | RSKQHLRLVFDEYLKTTGKPIEASI[p.R231Q]Q GELSGDFPEKLMLAVVKCIRSTPEYF | IQGELSGDF, IEASIQGEL | HNSC |
| AOC3 | c.237_238 insG | p.L79fs | QSQLFADLSREELTAVMRFLTQRLG[p.L79fs]A RAGGCSPGPALGQLCLLSGVAAASQGCSPGSLG QGEPPTCPGGTGHRLLWQATPAQRE* | GQLCLLSGV, CLLSGVAAA, RLLWQATPA, RFLTQRLGA, FLT QRLGAR, LWQATPAQR, SPGPALGQL, GPALGQLCL, CPGGT GHRL, TQRLGARAG, SQGCSPGSL, FLTQRLGARA, RFLTQRL GAR, LLWQATPAQR, GPALGQLCLL, CPGGTGHRLL, MRFLT QRLGA, GQLCLLSGVA, HRLLWQATPA | STAD |
| AOX1 | c.1520C>T | p.A507V | GRHWNEQMLDIACRLLINEVSLLGS[p.A507V]V PGGKVEFKRTLIISFLFKFYLEVSA | LLGSVPGGK, NEVSLLGSV, LLGSVPGGKV, SLLGSVPGGK, SV PGGKVEFK, GSVPGGKVEF | GBM |
| AP1G1 | c.2168G>T | p.R723L | NDIAAGIPSITAYSKNGLKIEFTFE[p.R723L]L SNTNPSVTVITIQASNSTELDMTDF | ELSNTNPSV, LKIEFTFEL, FELSNTNPS, IEFTFELSN, GLKIEFTF EL, IEFTFELSNT, FELSNTNPSV | LUAD |
| AP1G2 | c.727G>A | p.D243N | PQLVHLIRTLVTMGYSTEHSISGVS[p.D243N]N PFLQVQILRLLRILGRNHEESSETM | GVSNPFLQV, NPFLQVQIL, SISGVSNPF, SISGVSNPFL, HSISGVS NPF, NPFLQVQILR, VSNPFLQVQI | HNSC |
| AP3S1 | c.121_124 del AAGA | p.K41fs | LSKFYQPYSEDTQQQIIRETFHLVS[p.K41fs]E MKMFVIS* | LVSEMKMF, TFHLVSEMK, ETFHLVSEM, FHLVSEMKM, HL VSEMKMF, SEMKMFVIS, RETFHLVSE, HLVSEMKMFV, LVS EMKMFVI, ETFHLVSEMK, RETFHLVSEM, FHLVSEMKMF | PAAD |
| AP4B1 | c.826C>T | p.R276W | VVMGATKLFLILAKMPHVQTDVLVL[p.R276W]W VKGPLLAACSSSSRELCFVALCHVR | VQTDVLVWV, VLVWVKGPL, QTDVLVWVK, HVQTDVLVW, VLVWVKGPLL, HVQTDVLVWV, VQTDVLVWVK, DVLVWVKGPL | PRAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| APBA1 | c.1870G>A | p.E624K | LIAQSIGQAFSVAYQEFLRANGINPK[p.E624K]K DLSQKEYSDLLNTQDMYNDDLIHFS | FLRANGINPK, GINPKDLSQK, NPKDLSQKEY | CRC |
| APBA1 | c.2190G>T | p.K730N | QIMSINGTLSVLQPLSTCQSIIKGL[p.K730N]NN QSRVKLNIVRCPPVTVLIRRPDL | GLNNQSRVK, KGLNNQSRVK, IIKGLNNQSR | CRC |
| APBB2 | c.729_730 insC | p.T243fs | EDGQVATVSSSPETKKDHPKTGAKT[p.T243fs]R LCTAPDPEPGTER* | GAKTRLCTA, KTRLCTAPD, KTRLCTAPDP, HPKTGAKTRL | LUAD |
| APC | c.2540de1A | p.E847fs | PYLNTTVLPSSSSRGLDSSRSEK[p.E847fs] IEVWRENAELV* | SSRSEKIEV, EWRENAEL, EWRENAELV, SSRSEKIEVW, IE VWRENAEL | CRC |
| APC | c.4060de1T | p.F1354fs | PRTKSRLQGSSLSSESARHKAVEF[p.F1354fs]L QERNLPPKVLRHPKVHLNTMFRRPHSCLADVLLSVHLI VLRVRLPAPFRVNHAVEW* | CLADVLLSV, VLLSVHLIV, LLSVHLIVL, TMFRRPHSC, SVHLIV LRV, KVHLNTMFR, LSVHLIVLR, VVRLPAPFR, RVVRLPAPF, K VVLRHPKV, VLRHPKVHL, MFRRPHSCL, VLRVVRLPA, KAVE FLQER, NLPPKVVLR, HLIVLRVVR, DVLLSVHLI, HPKVHLNT M, RPHSCLADV, APFRVNHAV, ARHKAVEFL, RNLPPKVVL, F RVNHAVEW, LPAPFRVNH, VEFLQERNL, QERNLPPKV, ADV LLSVHL, TMFRRPHSCL, VLLSVHLIVL, SVHLIVLRVV, HLIVLR VVRL, FLQERNLPPK, KVHLNTMFRR, RVVRLPAPFR, SARHK AVEFL, RNLPPKVVLR, MFRRPHSCLA, VVRLPAPFRV, LLSVHLIVLR, DVLLSVHLIV, LSVHLIVLR, HPKVHLNTMF, RPHSCL ADVL, LPAPFRVNHA, NTMFRRPHSC, LQERNLPPKV, RHPK VHLNTM, HLNTMFRRPH, CLADVLLSVH, LRWRLPAPF, ADVLLSVHLI | CRC |
| APOB | c.128C>T | p.A43V | LLLLLAGARAEEEMLENVSLVCPKD[p.A43V]VTRFKH LRKYTYNYEAEESSGVPGTA | VTRFKHLRK, LVCPKDVTR, DVTRFKHLR, VTRFKHLRKY, SLV CPKDVTR, DVTRFKHLRK, LVCPKDVTRF | CRC |
| APOB | c.2917C>A | p.L973M | TKTEVIPPLIENRQSWSVCKQVFPG[p.L973M]MN YCTSGAYSNASTDSASYYPLTGD | GMNYCTSGA, KQVFPGMNY, MNYCTSGAY, GMNYCTSGA Y, SVCKQVFPGM, CKQVFPGMNY, KQVFPGMNYC | LUAD |
| APOB | c.9306C>A | p.F3102L | FLSPSAQQASWQVSARFNQYKYNQN[p.F3102L]L SAGNNENIMEAHVGINGEANLDFLN | NQYKYNQNL, YKYNQNLSA, NLSAGNNENI, QYKYNQNLSA, FNQYKYNQNL, NQYKYNQNLS, YKYNQNLSAG, LSAGNNENIM | UCEC |
| APOB | c.9406C>T | p.R3136C | MEAHVGINGEANLDFLNIPLTIPEM[p.R3136C]C LPYTIITTPPLKDFSLWEKTGLKEP | TIPEMCLPY, PEMCLPYTI, LTIPEMCLPY, PEMCLPYTII, IPLTI PEMCL, IPEMCLPYTI | CRC |
| APOBR | c.2519G>T | p.R840L | SQVEAFESREGGPWGGRVEAEESAG[p.R840L]V EDSCGLDPAGSQTARAEGMGAMVEA | VEAEESAGV, VEDSCGLDPA | LUAD |
| APOD | c.344C>T | p.S115L | IEGEATPVNLTEPAKLLEVKFSWFMP[p.S115L]LA PYWILATDYENYALVYSCTCIIQL | FMPLAPYWI, WFMPLAPYW, KFSWFMPLA, SWFMPLAPY, MPLAPYWIL, VKFSWFMPL, FSWFMPLAPY, FMPLAPYWIL, SWFMPLAPYW, WFMPLAPYWI, EVKFSWFMPL, VKFSWF MPLA, MPLAPYWILA | CESC |
| APOE | c.388T>C | p.C130R | EETRARLSKELQAAQARLGADMEDV[p.C130R]R GRLVQYRGEVQAMLGQSTEELRVRL | RGRLVQYRG, MEDVRGRLV, DVRGRLVQYR | ACC |
| APOOL | c.412A>C | p.I138L | PKMGVITVSGLAGLVSARKGSKFKK[p.I138L]L TYPLGLATLGATVCYPVQSVIIAKV | KLTYPLGLA, KFKKLTYPL, GSKFKKLTY, KKLTYPLGL, LTYPLGL ATL, KFKKLTYPLG, KGSKFKKLTY, SKFKKLTYPL, FKKLTYPLGL | CLL |
| APPL1 | c.2002C>T | p.R668W | ERVKEKQQKELNKQKQIEKDLEEQS[p.R668W]W LIAASSRPNQASSEGQFVVLSSSQS | SWLIAASSR, LEEQSWLIA, EEQSWLIAA, QSWLIAASSR, IEK DLEEQSW, LEEQSWLIAA, EEQSWLIAAS, KDLEEQSWLI | CRC |
| AQP10 | c.782A>T | p.Q261L | SAGNGWWWVPVVAPLVGATVGTATY[p.Q261L]L LLVALHHPEGPEPAQDLIVSAQHKAS | GTATYLLIV, ATYLLVAL, ATVGTATYL, TVGTATYLL, GTATYL LLVA, ATYLLVALH, ATVGTATYLL | LUAD |
| AQP2 | c.203A>C | p.N68T | QIAMAFGLGIGTLVQALGHISGAHI[p.N68T]TPAV TVACLVGCHVSVLRAAFYVAAQ | HITPAVTVA, SGAHITPAV, TPAVTVACL, AHITPAVTV, HISG AHITPA, ITPAVTVACL, TPAVTVACLV, AHITPAVTVA | KIRP |
| AQPEP | c.925G>A | p.A309T | KEDVNGSKWTVTFSTTPHMPTYLV[p.A309T]TFVI CDYDHVNRTERGKEIRIWARKD | HMPTYLVTF, PTYLVTFVI, TYLVTFVIC, LVTFVICDY, MPTYLVTFV, HMPTYLVTFV, PHMPTYLVTF, YLVTFVICDY, MPTYLVTFVI | CRC |
| ARAP3 | c.3677G>T | p.R1226L | ASLLLKKVPLAQAGCLFTGIRRESP[p.R1226L]L VGLLRCREEPPRLLGSRFQERFFLL | GIRRESPLV, TGIRRESPL, RRESPLVGL, RESPLVGLL, FTGIRRE SPL, IRRESPLVGL | LUAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ARF4 | c.446G>A | p.R149H | FANKQDLPNAMAISEMTDKLGLQSLp.R149H]H NRTWYVQATCATQGTGLYEGLDWLS | SLHNRTWYV,HNRTWYYQA,QSLHNRTWY,LQSLHNRTW,QS LHNRTWYV,LQSLHNRTWY,KLGLQSLHNR,GLQSLHNRTW | CRC |
| ARFGAP2 | c.113G>A | p.S38N | LFKRLRAVPTNKACFDCGAKNPSWA[p.S38N]N ITYGVFLCIDCSGVHRSLGVHLSFI | SWANITYGV,NPSWANITY,WANITYGVF,AKNPSWANI,ANITYGVF L,SWANITYGVF,GAKNPSWAN,KNPSWANIT,NI TYGVFLCI,WANITYGVFL | PRAD |
| ARFGAP3 | c.896de|A | p.N299fs | SLRLAYKDLEIQMKKDEKMNISGKK[p.N299fs] MLTQTDSAWDLEIAEVLFHIQ* | KMLTQTDSA,EIAEVLFHI,KMNISGKKM,DSAWDLEIA,MLT QTDSAW,TQTDSAWDL,LEIAEVLFH,WDLEIAEVL,QTDSA WDLEI,SAWDLEIAEV,KMNISGKKML,EKMNISGKKM,KK MLTQTDSA,KMLTQTDSAW,LEIAEVLFHI,WDLEIAEVLF | PRAD |
| ARFGEF1 | c.4654_4655 insC | p.P1552fs | LDIFKTIPHALLTWRPNSGETAPP[p.P1552fs]T SISCK* | ETAPPTSIS,GETAPPTSI,ETAPPTSISC | STAD |
| ARFGEF1 | c.4894G>A | p.D1632N | KPPEQKLFAALLIKCVQLELIQTI[p.D1632N] NNIVFFPATSKKEDAENLAAAQRDAV | ELIQTINNI,LIQTINNIV,QTINNIVFF,IQTINNIVF,TINNIVFFP A,ELIQTINNIV,IQTINNIVF,LIQTINNIVF,LELIQTINNI | CRC |
| ARFIP2 | c.257G>T | p.R86L | GLIPTGSGRHPSHSTTPSGPGDEVA[p.R86L]L GIAGEKPDIVKKWGINTYKCTKQLL | VALGIAGEK,ALGIAGEKF,DEVALGIAG,VALGIAGEKF,DEVAL GIAGE | LUAD |
| ARHGAP24 | c.103A>G | p.T35A | NPQQGQGRQNAIKCGWLRKQGGFVK[p.T35A]A WHTRWFVLKGDQLYYFKDEDETKPL | KAWHTRWFV,AWHTRWFVL,GFVKAWHTR,RKQGGFVKA, KQGGFVKAW,FVKAWHTRW,VKAWHTRWF,AWHTRWF VLK,GFVKAWHTRW,KAWHTRWFVL,FVKAWHTRWF,RKQGGFVKAW | TGCT |
| ARHGAP32 | c.3757G>A | p.E1253K | LEFADKSPTPNLPSDKIYPSGSPI[p.E1253K] KENTSTATMTYMTTTPATAQMSTKEA | SPKENTSTA,KENTSTATM,KIYPPSGSPK,SPKENTSTAT,KENT STATMT | CRC |
| ARHGAP36 | c.382C>T | p.R128C | GQQRAVSHKTFGISLEEVLVNEFTR[p.R128C] CKHLELTATMQVEEATGQAAGRRRGN | LVNEFTRCK,FTRCKHLEL,CKHLELTAT,NEFTRCKHL,VLVNE FTRCK,CKHLELTATM | CRC |
| ARHGAP36 | c.440C>T | p.A147V | VNEFTRRKHLELTATMQVEEATGQA[p.A147V] VGRRRGNVVRRVFGR.IRRFFSRRNE | VGRRRGNVV,VEEQTGQAV,VGRRRGNVR | CRC |
| ARHGAP36 | c.47C>A | p.P16H | MGGCIPPLKAARALC[p.P16H]HRIMPPL LLLSAFIFLVSVLGGAPGH | KAARALCHR,AARALCHRI,RALCHRIMP,LKAARALCH,ARA LCHRIM,HRIMPPLLL,ALCHRIMPPL,KAARALCHRI,AARAL CHRIM,RALCHRIMPP,HRIMPPLLL | LUAD |
| ARHGAP5 | c.2071A>T | p.M691L | ESLSFIGEFIGKIRTEASQIRKDKY[p.M691L] LANLPFTLILANQRDSISKNLPILRH | YLANLPFTL,KYLANLPFT,QIRKDKYLA,LANLPFTLI,DKYLAN LPF,SQIRKDKYL,RKDKYLANL,YLANLPFTLI,KYLANLPFTL,K DKYLANLPF,LANLPFTLIL | GBM |
| ARHGAP5 | c.2670de|T | p.D890fs | RAFLSEVQDTIPVQLVAVTDSQADF[p.D890fs] LKMRLSKS* | VTDSQADFL,FLKMRLSKS,DFLKMRLSK,VTDSQADFLK,SQ ADFLKMRL,DSQADFLKMR | CRC,STAD |
| ARHGAP9 | c.409C>T | p.R137C | QQVSLAEGDRFLLLRKTNSDWWLAR[p.R137C]C LEAPSTSRPIFVPAAYMIEESIPSQ | SDWWLARCL,WLARCLEAPS | BRCA |
| ARHGEF17 | c.1844de|C | p.A615fs | VQEARQVFEKIQRMGAQQDDGSDAP[p.A615fs] LEALTQGGM* | LEQLTGQGM,QQDDGSDAPL | STAD |
| ARHGEF5 | c.1460A>G | p.E487G | PISLLGSFLITEESPDKEIDQNSQQE[p.E487G]GSRL RKGTVSSQGTEVVFASASVTPP | GSRLRKGTV,SQQEGSRLRK | KIRC |
| ARHGEF5 | c.4535de|C | p.S1512fs | EKLRWISALAMPREELDLLECYNSP[p.S1512fs] RYSAFEPTSPERMMWHWRKPTW* | RMMNWHWRK,NWHWRKPTW,CYNSPRYSA,LLECYNSP R,YNSPRYSAF,LECYNSPRY,LLECYNSPRY,MMNWHWRKP T,SAFEPTSPER,CYNSPRYSAF,RMMNWHWRKP,DLLECYN SPR,SPRYSAFEPT,MNWHWRKPTW,FEPTSPERMM,SPERMMNWHW | STAD |
| ARID1A | c.1841C>T | p.S614L | QTAYSQORFPPPQELSQDSFGSQAS[p.S614L]LA PSMTSSKGGQEDMNLSLQSRPSSL | SLAPSMTSS,LAPSMTSSK,DSFGSQASL,SQASLAPSM,SLAP SMTSSK,DSFGSQASLA,GSQASLAPSM,SQASLAPSMT | BLCA |
| ARID1A | c.3211de|A | p.K1071fs | KPLDLYRLYVSVKEIGLTQVNKNK[p.K1071fs]N GGNLQPTSMWAHQAVLPAP* | SMWAHQAVL,NLQPTSMWA,TSMWAHQAV,WAHQAVL PA,LQPTSMWAH,TSMWAHQAVL,SMWAHQAVLP,MWAHQAVLPA | STAD |
| ARID1A | c.3972de|C | p.Y1324fs | STGPQPNLMPSNPDSGMYSPSRYP[p.Y1324fs]RSS SSSSNDMIPWAISSPPKAPLLAAPSPASRLQCINSN SRITSGQWMAHMALLPSGTKGRCTACHTALGRGSLSSS | GQWMAHNAL,KMYTTSNAM,YYTSMAMPI,SNAMPILP L,HMALLPSGT,LLSADQQAA,MALLPSGTK,KLPSLPLSK,PM AISSPPK,QWMAHMALL,MYSPSRYPR,KGRCTACHT,LSKM | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| | | | SCPQPSPSLPASNKLPSLPLSKMYTTSMAMPILPLPQLL SADQQAAPRTNFHSSLAETVSLHPLAPMPSKTCHHK* | YTTSM, RTNFHSSLA, HPLAPMPSK, LAAPSPASR, TACHTAL GR, HTALGRGSL, TTSMAMPIL, ETVSLHPLA, YPRSSSSSS, IP MAISSPP, SPASRLQCI, LPASNKLPS, LPSLPLSKM, MPILPLP QL, APRTNFHSS, QQAAPRTNF, SSSNDMIPM, VSLHPLAPM, SSSSSSNDM, ISSPPKAPL, SRITSGQWM, MAHMALLPS, AH MALLPSG, RCTACHTAL, SNKLPSLPL, SKMYTTSMA, FHSSLA ETV, SSLAETVSL, AETVSLHPL, LPLPQLLLS, GQWMAHMAL L, AMPILPLPQL, LLLSADQQAA, WMAHMALLPS, KLPSLPLSK M, GMYSPSRYPR, HMALLPSGTK, CTACHTALGR, MYTTSM AMPI, IPMAISSPPK, RLQCINSNSR, KGRCTACHTA, ASNKLP SLPL, LSKMYTTSMA, TSMAMPILPL, RTNFHSSLAE, ITSGQ WMAHM, LLAAPSPASR, LSADQQAAPR, SSNDMIPMAI, YT TSMAMPIL, TVSLHPLAPM, YPRSSSSSSS, SPPKAPLLAA, APL LAAPSPA, CPQPSPSLPA, SPSLPASNKL, LPASNKLPSL, MPIL PLPQLL, APRTNFHSSL, SKMYTTSMAM, LPSLPLSKMY, SSSS SSSNDM, SSSSNDMIPM, ISSPPKAPLL, LAAPSPASRL, LQCI NSNSRI, SGQWMAHMAL, GRCTACHTAL, SSCPQPSPSL, K MYTTSMAMP, DQQAAPRTNF, QQAAPRTNFH, HSSLAETVSL, LAETVSLHPL, LPLPQLLLSA, AETVSLHPLA | |
| ARID1A | c.5542de|G | p.G1848fs | VDCSDKLGRVQEFDSGLLHWRIGGG[p.G1848s] TPLSISRPTSRARQSCCLPGLT HPAHQPIGSM* | RQSCCLPGL, CLPGLTHPA, LSISRPTSR, ISRPTSRAR, RARQSCCLP, LTHPAHQPL, RPTSRARQS, WRIGGGTPL, LPGLTHPA H, GLTHPAHQPL, LLHWRIGGGT, SISRPTSRAR, HWRIGGGT PL, TSRARQSCCL, RARQSCCLPG, RPTSRARQSC, HPAHQPL GSM, RIGGGTPLSI, ARQSCCLPGL, RQSCCLPGLT | STAD |
| ARID1A | c.6415de|C | p.P2139fs | RLVLETLSKLLSIQDNNVDLILATPP[p.P2139fs] AAWRSCIALWCASSVTERTRCAGRWLWYCWPTWLRGTA WQLVPLQCRRAVSATSWAS* | IALWCASSV, ALWCASSVT, WLRGTAWQL, GTAWQLVPL, IL ATPPSAA, AWRSCIALW, RWLWYCWPT, WLWYCWPTW, LWYCWPTWL, RTRCAGRWL, RAVSATSWA, RCAGRWLWY, WYCWPTWLR, QLVPLQCR, WPTWLRGTA, VPLQCRRAV, SAAW RSCIA, LATPPSAAW, AAWRSCIAL, LQCRRAVSA, RR AVSATSW, CIALWCASSV, WLWYCWPTWL, WLRGTAWQL V, CAGRWLWYCW, RWLWYCWPTW, TWLRGTAWQL, RTR CAGRWLW, LATPPSAAWR, LWCASSVTER, VTERTRCAGR, LWYCWPTWLR, SAAWRSCIAL, WPTWLRGTAW, ILATPPSA AW, AAWRSCIALW, TERTRCAGRW, RGTAWQLVPL, LQCR RAVSAT, CRRAVSATSW, RAVSATSWAS | STAD |
| ARID3A | c.1649_1650 de|GA | p.G550fs | NGIMYTGVLFAQPPAPTPTSAPNKG[p.G550fs]R RRRRQQQQRRRPGRKHRNQRRPGWASGAVHTLHIYLK* | QQRRRPGRK, AVHTLHIYL, GAVHTLHIY, WASGAVHTL, RPG WASGAV, NQRRPGWAS, AVHTLHIYLK, GWASGQVHTL, Q QQRRRPGRK, SGAVHTLHIY, RQQQQRRRPG | CLL |
| ARID4A | c.3462T>A | p.D1154E | LNVSKPQKLARSPARISPHIKDGEK[p.D1154E]EK HREKHPNSSPRTYKWSFQLNELDN | HIKDGEKEK | CLL |
| ARL13B | c.1073G>T | p.R358L | ETDRPSLESANGKKKTKKLRMKRNH[p.R358L]L VEPLNIDDCAPESPTPPPPPPVGW | KLRMKRNHL, RMKRNHLVE, LRMKRNHLV, KRNHLVEPL, KL RMKRNHLV, RMKRNHLVEP, MKRNHLVEPL, KKLRMKRNHL | LUAD |
| ARL16 | c.16G>A | p.G6R | MRVAG[p.G6R]RRALSRGAELRVPGGAKHGMCLLLGA | RVAGRRALS, MRVAGRRAL, RVAGRRALSR, AGRRALSRGA, RRALSRGAEL | SKCM |
| ARL6IP1 | c.223A>T | p.M75L | GVVSLVFLIIYYLDPSVLSGVSCFV[p.M75L]L FLCLADYLVPILAPRIFGSNKWTTE | GVSCFVLFL, SGVSCFVLF, VLFLCLADY, LSGVSCFVL, VLSGVS CFVL, VLFLCLADYL, LSGVSCFVLF, FVLFLCLADY | MM |
| ARMC3 | c.1540G>A | p.A514T | LRSKNDEVRKHASWAVMVCAGDELT[p.A514T]TNEL CRLGALDILEEVNVSGTRKNKF | TTNELCRLGA | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ARMC4 | c.64G>A | p.E22K | MGVALRKLTQWTAAGHTGIL[p.E22K]KITPL NEAILKEIIVFVESFIYKHPQ | KITPLNEAI,AGHGTGILK,TGILKITPL,LKITPLNEA,ILKITPLNE A,AAGHGTGILK,LKITPLNEAI | SKCM |
| ARNTL | c.1184C>T | p.T395M | GTSCYEYFHQDDIGHLAECHRQVLQ[p.T395M] MREKITTNCYKFKIKDGSFITLRSRW | RQVLQMREK,LQMREKTT,AECHRQVLQM,RQVLQMREKI, LQMREKITTN,MREKITTNCY | CRC |
| ARPC1A | c.636C>A | p.F212L | SKMPFGQLMSEFGGSGTGGVVHGVS[p.F212L]L SASGSRLAVVVSHDSTVSVADASKSV | WVHGVSLSA,VSLSASGSRL,GGWVHGVSL,SLSASGSRLA,GV SLSASGSR,VSLSASGSRL,LSASGSRLAW | LUSC |
| ARPP21 | c.1013G>A | p.R338H | SSSENELKWSDHQRAWSTDSDSSN[p.R338H]HNLK PAMTKTASFGGITVLTRGDSTS | HNLKPAMTK,SNHNLKPAM,SSNHNLKPAM | CRC |
| ARPP21 | c.388del|A | p.I130fs | HNVEKDIATYYCALWEVHSKLGKK[p.I130fs]S RYLVPEQSLSLQINNLMQMFPPSPLFFFLQLLKQS SRRLEHTFVFLRNFSLMLLRYIGKKRRA TRFWDPRRGTP* | SLSLQINNL,MQMFPPSPL,RLEHTFVFL,FVFLRNFSL,FLRNF SLML,LQINNLMQM,LFFFLQLLK,LMLLRYIGK,MLLRYIGKK, RNFSLMLLR,RATRFWDPR,RYLVPEQSL,QMFPPSPLF,MF PPSPLFF,RRLEHTFVF,VFLRNFSLM,HSKLGKKSR,KLGKKSR YL,LGKKSRYLV,KSRYLVPEQ,KQSSRRLEH,SRRLEHTF,RYI GKKRRA,IGKKRRATR,ATRFWDPRR,NFSLMLLRY,LLRYIGKKR, SPLFFFLQL,LLKQSSRRL,YIGKKRAT,QINNLMQMF,HT FVFLRNF,SKLGKKSRY,LSLQINNLM,LRNFSLMLL,GKKRRA TRF,KKRRATRFW,FPPSPLFFF,PPSPLFFFL,KLGKKSRYLV,Y LVPEQSLSL,LMQMFPPSPL,FVFLRNFSLM,FLRNFSLMLL,S LSLQINNLM,PLFFFLQLLK,RLEHTFVFLR,SLMLLRYIGK,LML LRYIGKK,LQINNLMQMF,MQMFPPSPLF,QMFPPSPLFF,M FPPSPLFFF,RRLEHTFVFL,TFVFLRNFSL,VFLRNFSLML,KSR YLVPEQS,SSRRLEHTFV,HTFVFLRNFS,RATRFWDPRR,ATR FWDPRRG,HSKLGKKSRY,RNFSLMLLRY,FLQLLKQSSR,ML LRYIGKKR,LLRYIGKKRR,YIGKKRRQTR,FPPSPLFFFL,SPLFF FLQLL,SRYLVPEQSL,SLQINNLMQM,LKQSSRRLEH,KQSSR RLEHT,QSSRRLEHTF,SRRLEHTFVF,VPEQSLSLQI | STAD |
| ARRB2 | c.295A>C | p.T99P | LSFRKDLFIATYQAFPPVPNPRPP[p.T99P]PR LQDRLLRKLGQHAHPFFTVRMPL | RPPPRLQDRL | TGCT |
| ARRDC4 | c.235A>G | p.T79A | ALRLEAQGRATAAWGPSTCPRASAS[p.T79A]A AALAVFSEVEYLNVRLSLREPPAGE | RASASAAAL,ASASASAAA,SASAAALA,SASAAALAV,CPRASASAA,ASA AALAVF,AAALAVFSEV,STCPRASASA,RASASAAALA,ASAS AALAV,CPRASASAAA,SASAAALAVF | ACC |
| ARSD | c.701C>G | p.A234G | LGILTLAAGQTCGFFSVSARAVTGM[p.A234G]GGVG CLFFISWYSSFGFVRRWNCILM | MGGVGCLFF,SARAVTGMG,GMGGVGCLF,GMGGVGCLF F,SARAVTGMGG,TGMGGVGCLF | KIRC |
| ARSD | c.701_709 del|CCGGC GTGG | p.AGV234 del | LGILTLAAGQTCGFFSVSARAVTGM[p.AGV234de|] GCLFFISWYSSFGFVRRW NCILMRNHDVTEQPMV | TGMGCLFFI,VTGMGCLFF,SARAVTGMG,AVTGMGCLF, GMGCLFFISW,MGCLFFISWY,RAVTGMGCLF,AVTGMGCLFF | KIRC |
| ARSG | c.391G>A | p.V131I | FAVTSVGGLPLNETTLAEVLQQAGY[p.V131I]ITG IIGKWHLGHHGSYHPNFRGFDYY | QQAGYITGI,EVLQQAGYI,LQQAGYITG,LQQAGYITGI,QQAGYI TGII,AGYITGIIGK,GYITGIIGKW,AEVLQQAGYI | CRC |
| ART1 | c.729del|C | p.I243fs | IWTCLGAPIKGYSFFPGEEEVLIPP[p.I243fs] LRPSK* | LIPPLRPSK,EEEVLIPPL,VLIPPLRPSK,GEEEVLIPPL | STAD |
| ASB16 | c.745A>G | p.T249A | QHVALYLEHGADVGLRTSQGETALN[p.T249A]AA CAGAEGPGSCRRHQAAARRLLEAG | ALNAACAGA,ETALNAACA,SQGETALNA,GETALNAAC,SQ GETALNAA,GETALNAACA | ACC |
| ASCC1 | c.619C>T | p.H207Y | QEEVLAKCSMDHGVDSSIFQNPKKL[p.H207Y]YL TIGMLVLLSEEEIQQTCEMLQQCK | YLTIGMLVL,FQNPKKLYL,KLYLTIGM,KLYLTIGMLV,YLTIGMLVLL, KKLY,NPKKLYLTI,KKLYLTIGM,KLYLTIGMLV,YLTIGMVLL, IFQNPKKLYL,LYLTIGMLVL,SIFQNPKKLY,KKLYLTIGML | CESC |
| ASCC2 | c.1094G>T | p.R365L | CDNIQGFIEEFLQIFSSLLQEKRFL[p.R365L]L DYDALFPVAEDISLLQQASSVLDET | LLQEKRFLL,FLLDYDAL,RFLLDYDAL,QEKRFLLDY,LDYDAL FPV,SLLQEKRFLL,FLLDYDALFP,LLDYDALFPV,RFLLDYDAL F,LQEKRFLLDY,KRFLLDYDAL,LDYDALFPVA | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ASCC3 | c.3590G>A | p.R1197Q | VKQCVHQIPSVMMEASIQPITRTVL[p.R1197Q]QVTLSIYADFTWNDQVHGTVGEPWWI | TVLQVTLSI,VLQVTLSIY,LQVTLSIYA,VLQVTLSIYA,ITRTV LQVTL,RTVLQVTLSI,TVLQVTLSIY,QPITRTVLQV | CRC |
| ASCC3 | c.407G>A | p.R136Q | ETKAIKQMFGPFPSSSATAACNATN[p.R136Q]QIISHFSQDDLTALVQMTEKEHGDRV | ATNQIISHF,TAACNATNQI,NATNQIISHF | UCEC |
| ASCL4 | c.105de|C | p.D35fs | ALPYSLRTAPLGVPGTLPGLPRRDP[p.D35fs]SGSPCVWTPRAGSGRAAAAHGDSTCPCRWTAPSSPPSSASATSASGSGCAA* | RAGSGRAA,STCPCRWTA,WTAPSSPPS,TPRAGSGRA,AP SSPPSSA,DPSGSPCVW,RAGSGRAAAA,RWTAPSSPPS,SG SPCVWTPR,TPRAGSGRAA | STAD |
| ASIC2 | c.137G>T | p.R46L | RMAREEPAPAALAAAGQPGGGRGGE[p.R46L]LALQGPGVARRGRPSLSRAKLHGLRH | ELALQGPGV,GELALQGPG,QPGGGRGGEL,GELQLQGPGV | KIRP |
| ASPDH | c.797A>G | p.Q266R | AVHTRRENPAEPGAVTGSATVTAFW[p.Q266R]RSLLACCQLPSRPGIHLC* | SATVTAFWR,TAFWRSLLA,RSLLACCQL,TVTAFWRSL, VTAFWRSLL,GSATVTAFWR,ATVTAFWRSL, TVTAFWRSLL,VTAFWRSLLA,WRSLLACCQL | ACC |
| ASPM | c.719C>T | p.S240F | EENKIPISPISPAFNECHGATCLPL[p.S240F]FVRRSTTYSSLHASENRELLNVHSAN | ATCLPLFVR,HGATCLPLF,FVRRSTTYS,LFVRRSTTY, TCLPLFVRR,LPLFVRRST,ATCLPLFVRR,LPLFVRRSTT, PLFVRRSTTY,CHGATCLPLF | LUAD |
| ASPN | c.201de|T | p.F67fs | DDDDDDDDEDNSLFPTREPRSHFF[p.F67fs]HLICFQCVHLDVSAIHELYIAQI* | DVSAIHELY,SHFFHLICF,CFQCVHLDV,RSHFFHLIC, EPRSHFFHL,HLICFQCVH,LDVSAIHEL,HLICFQCVHL, HLDVSAIHEL,AIHELYIAQI,RSHFFHLICF,DVSAIHELYI, EPRSHFFHLI,REPRSHFFHL,FQCVHLDVSA,LDVSAIHELY | STAD |
| ASTN2 | c.661_663 de|CTG | p.L221de| | EIVEEQMHILHISVMGGLIALLLLL[p.L221de|]VFTVALYAQRRWQKRRRIPQKSASTEAT | LIALLLLIV,ALLLLLVFT,IALLLLIVF,GLIALLLLIV, ALLLLLVFTV,LIALLLLVF | PRAD |
| ASXL2 | c.3242C>T | p.S1081L | EGLSKATQDQILQTLIQRVRRQNLL[p.S1081L]LVVPPSQFNFAHSGFQLEDISTSQRF | RVRRQNLLL,LLLVVPPSQF,RRQNLLLVV,RQNLLLVVP,RVRR QNLLV,LLLVVPPSQF,LVVPPSQFNF,RQNLLLVPP | LUSC |
| ASXL3 | c.2618de|A | p.E873fs | SIPELASTEMIKVKNHSVLQRTEKK[p.E873fs]CYLHHWNYLSFLKGQIIREMSFHLLNYRTSNISHQWIRLHFQKALEIKHISKGVHRVG* | EMSFHLLNY,YLHHWNYLS,IIREMSFHL,YLSFLKGQI,LLNYR TSNI,HISKGVHRV,MSFHLLNYR,ALEIKHISK,HWNYLSFLK, QWIRLHFQK,CYLHHWNYL,LHHWNYLSF,SHQWIRLHF,W IRLHFQKA,KCYLHHWNY,RTSNISHQW,SFLKGQIIR,SNISH QWIR,EIKHISKGV,GQIIREMSF,LQRTEKKCY,HWWNYLSFL, LSFLKGQII,LKGQIIREM,REMSFHLLN,IRLHFQKAL,LHFQK ALEI,FQKALEIKH,YLHHWNYLSF,HLLNYRTSNI,YLSFLKGQI I,FLKGQIIREM,QIIREMSFHL,IIREMSFFLL,RLFIFQKALEI,H QWIRLHFQK,KALEIKHISK,HHWNYLSFLK,LSFLKGQIIR,CY LHHWNYLS,NYLSFLKGQI,ISHQWIRLHF,KCYLHHWNYL,R TSNISHQWI,KKCYLHHWNY,REMSFHLLNY,EMSFHLLNYR, SNISHQWIR,MSFHLLNYRT,WIRLHFQKAL,LQRTEKKCYL, LHFIWNYLSFL,KGQIIREMSF,LNYRTSNISH,YRTSNISHQW, FQKALEIKHI,LEIKHISKGV,KHISKGVHRV,TEKKCYLHHW | STAD |
| ASXL3 | c.4409C>A | p.P1470Q | NRADNSGKPQQPPGGPAPAAINRSI[p.P1470Q]CKVIVDHSTTLTSSLSLTVSVSESSE | AINRSIQCK,RSIQCKVIV,AINRSIQCKV,AINRSIQCKV | LUAD |
| ATAD5 | c.913A>G | p.I305V | EIPDSTMSICVPSETVDEIVKSGYI[p.I305V]GESENSEISQQVRFKTVTVLAQVHPI | YIGESENSEI | TGCT |
| ATM | c.2399C>T | p.S800F | SLRNMMQLCTRCLSNCTKKSPNKIA[p.S800F]FGFFLRLLTSKLMNDIADICKSLASF | KIAFGFFLR,APGFFLRLL,SPNKIAGFF,KKSPNKIAF,NKIAFGF FL,IAFGFFLRL,KIAFGFFLRL,KSPNKIAFGF,NKIAFGFFLR,SP NKIAGFF,TKKSPNKIAF,IAFGFFLRLL | CESC |
| ATP10B | c.3910C>A | p.L1304I | CNSPTNPYWVMEGQLSNPTFYLVCF[p.L1304I]ITPVVALLPRYFFLSLQGTCGKSLIS | YLVCFITPV,LVCFITPVV,FITPVVAL,CFITPVVAL,YLVCFI TPVV,FVLVCFITPV,CFITPVALL,ITPVVALLPR,NPTFYLVCFI | UCEC |
| ATP10D | c.932G>A | p.R311H | AVVGIVVYAGHETKAMLNNSGPRYK[p.R311H]HSKLERRANTDVLMCVMLLVIMCLTG | SGPRYKHSK,RYKHSKLER,GPRYKHSKL,NSGPRYKHSK | CRC |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ATP12A | c.2572C>T | p.R858C | LGTDIIPSIALAYEKAESDIMNRKP[p.R858C]C HKNKDRLVNQPLAVYSLHIGLMQA | IMNRKPCHK, MNRKPCHKNK, DIMNRKPCHK | BLCA |
| ATP2A1 | c.2110G>T | p.G704C | VEPSHKSKIVEYLQSYDEITAMTGD[p.G704C]CV NDAPALKKAEIGIAMGSGTAVAKT | CVNDAPALK, ITAMTGDCV, AMTGDCVNDA, CVNDAPALK K, EITAMTGDCV | KIRC |
| ATP2A1 | c.2457_2458 insC | p.R819 fs | LVTDGLPATALGFNPPDLDIMDRPP[p.R819fs]PE PQGAPHQWLALLPLHGNRGLCGCSHRGSSCLVVPVR* | HQWLALLPL, GSSCLVVPV, RGLCGCSHR, ALLPLHGNR, SSCL VVPVR, APHQWLALL, LPLHGNRGL, LPLHGNRGL, CSHRGSSCL, EPQGAP HQW, LLPLHGNRGL, GSSCLVVPVR, CSHRGSSCLV, LALLPL HGNR, HQWLALLPLH, SHRGSSCLW, RGSSCLVVPV | STAD |
| ATP2B4 | c.548G>A | p.R183H | SVIIVIVLVTAFNDWSKEKQFRGLQC[p.R183H]HIE QEQKFSIIRNGGLIQLPVAEIVV | KQFRGLQCH, CHIEQEQKF, KQFRGLQCHI | CLL |
| ATP2C1 | c.2170G>A | p.E724K | GTDVCKEAADMILVDDDFQTIMSAI[p.E724K]KE GKGIYNNIKNFVRFQLSTSIAALT | IMSAIKEGK, AIKEGKGIY, TIMSAIKEGK, SAIKEGKGIY, DFQTI MSAIK, KEGKGIYNNI | UCEC |
| ATP6 AP2 | c.355G>C | p.E119Q | ISYPLENAVPFSLDSVANSIHSLFS[p.E119Q] QETPVVLQLAPSEERVYMVGKANSV | SLFSQETPV, FSQETPVVL, QETPVVLQL, SLFSQETPVV, HSLFSQETPV, LFSQETPVVL, SQETPVVLQL, QETPVVLQLA | HNSC |
| ATP6 V0A4 | c.572G>A | p.R191Q | MTGKLGFIAGVINRERMASFERLLW[p. R191Q]QICRGNVYLKFSEMDAPLEDPV TKEE | SFERLLWQI, WQICRGNVY, FERLLWQIC, LL WQICRGNV, WQICRGNVYL, QICRGNV YLK, LWQICRGNVY, ASFERLLWQI | CRC |
| ATP6 V1A | c.710T>C | p.L237P | RQVRPVTEKLPANHPLLTGQRVLDA[p.L237P]PF PCVQGGTTAIPGAFGCGKTVISQS | VLDAPFPCV, GQRVLDAPF, RVLDAPFPCV, TGQRVLDAPF | THCA |
| ATP6 V1B1 | c.1149de|C | p.Y383 fs | DLTGFITEGQIYDVDRQLHNRQIYPP[p.Y383fs]STCS LPCRG* | IYPPSTCSL, RQIYPPSTC, QIYPPSTCSL, RQIYPPSTCS | STAD |
| ATP6 V1C2 | c.934_935 insAG | p.R312fs | STFPDHKVKVTPLGNPDRPAAGQTD[p.R312fs]KE RERVRARVRAPCCAGSR* | KERERVRAR, RERVRARVR, RVRARVRAP, RARVRAPCC, RV RAPCCAG, RAPCCAGSR, RVRARVRAPC, RARVRAPCCA, RV RAPCCAGS, KERERVRARV, RERVRARVRA | STAD |
| ATP7A | c.2968_2969 insA | p.Q990 fs | IVETYFPGYNRSISRTETIIRFAFQ[p.Q990fs]SL YHSSVVCMSLFTGTGHSNCCDGGYRSRCSKWHTNKRWR AIGDGS* | HSNCCDGGY, FQSLYHSSV, SLYHSSVVC, LYHSSVVCM, IIRFA FQSL, RFAFQSLYH, GGYRSRCSK, RSRCSKWHT, RCSKWHT NK, CSKWHTNKR, KWHTNKRWR, HTNKRWRAI, RWRAIGD GS, IRFAFQSLY, QSLYHSSVV, SSVVCMSLF, FAFQSLYHS, HSS VYCMSL, MSLFTGTGFI, SKWHTNKRW, SLYFISSVYCM, TIIR FAFQSL, HSNCCDGGYR, IIRFAFQSLY, RSRCSKWHTN, KWH TNKRWRA, HTNKRWRAIG, FQSLYHSSVY, HSVYCMSLF, G HSNCCDGGY, ETIIRFAFQS, FAFQSLYHSS, YHSSVVCMSL, G GYRSRCSKW | KIRC |
| ATP9A | c.1556G>A | p.R519Q | VYQASSPDEVALIVQWTESVGLTLVG[p.R519Q]Q DQSSMQLRTPGDQILNFTILQIFPF | LVGQDQSSM, GQDQSSMQL, TLVGQDQSSM | BLCA |
| ATP9A | c.869G>A | p.R290Q | ASGTVVGVLYTGRELRSVMNTSNP[p.R290Q]QS KIGLFDLEVNCLTKLLFGALVVVS | NTSNPQSKI, NPQSKIGLF, VMNTSNPQSK | UCEC |
| ATP9B | c.115A>G | p.S39G | AAAANRKRAAYYSAAGPRPGADRH[p.S39G]GR YQLEDESAHLDEMPLMMSEEGFEN | RPGADRHGRY | ACC |
| ATR | c.5440de|A | p.R1814 fs | NYLAADGKSTTWSVRLGQLLLSAKK[p.R1814fs]E ISQLFMTH* | AKKEISQLF, KKEISQLFM, KEISQLFMT, SAKKEISQLF, AKKEI SQLFM, KEISQLFMTH | UCEC |
| ATRN | c.590C>A | p.P197Q | LRFNHFATECSWDHLYVYDGDSIYA[p.P197Q]QL VAAFSGLIVPERDGNETVPEWAT | SIYAQLVAA, QLVAAFSGL, IYAQLVAAF, AQLVAAFSG, AQLIV AAFSGL, QLVAAFSGLI, SIYAQLVAAF, DSIYAQLVAA | LUAD |
| ATRNL1 | c.3732A>T | p.L1244F | IAFSQHNTIMDLVQFFVTFFSCFLS[p.L1244F] FLLVAAVWKIKQTCWASRREQLLR | FSCFLSFLL, FLSFLLVAA, FFSCFLSFL, LSFLLVAAV, TFFSCFLSF, FLLVAAVVW, FSCFLSFLLV, FFSCFLSFLL, FLSFLLVAAV, VTF FSCFLSF, TFFSCFLSFL, SFLLVAAVVW, LSFLLVAAVV | CLL |
| ATRX | c.5807A>G | p.K1936R | IASDSDETSMSLSSDDYTKKKKKGK[p.K1936R]RG KKDSSSGSGSDNDVEVIKVNNSR | YTKKKKKGKR | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ATXN1 | c.651G>T | p.Q217H | GHKAEQQQQQQQQQQQQHQHQQQQQ[p.Q217H]H QQQQQQQHLSRAPGLITPGSPPPA | HQHQQQQQH, HQQQQQQQH | LIHC |
| AURKA | c.1160C>T | p.S387L | RLLKHNPSQRPMLREVLEHPWITAN[p.S387L]L SKPSNCQNKESASKQS* | HPWITANLS, LSKPSNCQNK, LEHPWITQNL | CESC |
| AVIL | c.190G>T | p.G64W | EGDCYVILSTRRVASLLSQDIHFWI[p.G64W] WKDSSQDEQSCAAIYTTQLDDYLGGS | SQDIHFWIW, SQDIHFWIWK, LSQDIHFWIW | LUAD |
| AVIL | c.896_897 insG | p.G299 fs | DLLNHDDCYILDQSGTKIYVWKGKG[p.G299fs] SHKG* | VWKGKGSHK, YVWKGKGSHK | KIRC |
| AVL9 | c.102C>A | p.F34L | DGVPRGPVLHIVVGHHHKKGCQVE[p.F34L]LSY PPLIPGDHDSHTLPEEWKYLPF | KGCQVELSY, HKKGCQVEL, CQVELSYPP, VELSYPPLI, CQVEL SYPPL, KKGCQVELSY | UCEC |
| AVL9 | c.21_22insG | p.G7fs | MEKARRGG[p.G7fs]GWRPPGARTAHRGGRISPQE GLPG* | KARRGGWR, RTAHRGGRI, RPPGARTAH, GRISPQEGL, KA RRGGGWRP, GWRPPGARTA, GARTAHRGGR, MEKARRGGGW | ACC |
| AVPR1A | c.1053del|T | p.F351fs | ENPTITITALLGSLNSCCNPWIYMF[p.F351fs]LV AISFKTVFKASHAAKT* | WIYMFLVAI, YMFLVAISF, FLVAISFKT, LVAISFKTV, TVFKAS HAA, MFLVAISFK, AISFKTVFK, IYMFLVAIS, KTVFKASHA, VF KASHAAK, VAISFKTVF, ISFKTVFKA, FKTVFKASH, NPWIYM FLV, FLVAISFKTV, AISFKTVFKA, YMFLVAISFK, VAISFKTVFK, TVFKASHAAK, PWIYMFLVAI, IYMFLVAISF, SFKTVFKASH, KTVFKASHAA, LVAISFKTVF, NPWIYMFLVA | STAD |
| AVPR1B | c.115G>A | p.G39R | RGTLSAPNATTPWLGRDEELAKVEI[p.G39R]R VLATVLVLATGGNLAVLLTLGQLGR | RVLATVLVL, ELAKVEIRV, EIRVLATVL, VEIRVLATV, RVLATVLVLA, KVEIRVLATV, EIRVLATVLV, AKVEIRVLAT, VEIRVLAT VL, IRVLATVLVL, EELAKVEIRV | TGCT |
| AXDND1 | c.2790G>T | p.E930D | WRESAKQGTLAQKYLEAMAVIEHMQ[p.E930D]K LLEVENRARQAEKFEDAYEKLHH | HMQDKLLEV, AVIEHMQDK, IEHMQDKLL, AVIEHMQDKL | CRC |
| AXDND1 | c.301T>C | p.W101R | CPENLLPPKKIKTPKGTLPRLVDHV[p.W101R]RH HPVRRNKFKYLIDHPVSLTGAGRD | HVRHHPVRR, RHHPVRRNK, RLVDHVRHH, LVDHVRHHPV, HVRHHPVRRN, RHHPVRRNKF | LUAD |
| AXIN2 | c.1988_199 4de|GGGGGG | p.W663fs | QSTKKAYPLESARSSPGERASRHHL[p.W663fs]ST AGTPAPPVPTCSPRTLRCLP* | HLSTAGTPA, RASRHHLST, ASRHHLSTA, PTCSPRTLR, TPAPPVPT, VPTCSPRTL, RASRHHLSTA, ASRHHLSTAG, HHLSTAGTPA | CRC |
| AXIN2 | c.1993_1994 insG | p.G665fs | KKAYPLESARSSPGERASRHHLWGG[p.G665fs]QQ RAPPHHPPCPPVHPGPCDASPDPTQHAGSAGGGLSQAS* | HLWGGQQRA, GQQRAPPHH | CRC |
| AXIN2 | c.1994de|G | p.G665fs | TKKAYPLESARSSPGERASRHHLWG[p.G665fs]AT AGTPAPPVPTCSPRTLRCLP* | HLWGATAGT, ASRHHLWGA, PTCSPRTLR, TPAPPVPT, VP TCSPRTL, RASRHHLWGA, WGATAGTPA, RASRHHLWGA, ASRHHLWG AT, RHHLWGATAG | STAD |
| B2M | c.1A>G | p.M1V | [p.M1V]VSRSVALAVLALLSLSGLEAIQRTPK | VSRSVALAV, VRSVALAVL | OV |
| B2M | c.37_38de|CT | p.L13fs | MSRSVALAVLALLS[p.L13fs]FWPGGYPAYSK DSGLLTSSSREWKVKFPELLCVWVSSIRH* | LLSFWPGGY, LLCVWVSSI, LITSSSREWK, SSSREWKVK, KFPE LLCVW, KVKFPELLC, FWPGGYPAY, TSSSREWKV, EWKVKF PEL, LAVLALLSF, SFWPGGYPA, LLITSSSREW, SSSREWKVKF, WKVKFPELL, VKFPELLCV, REWKVKFPE, FPELLCVWV, ELLC VWVSSI, ALLSFWPGGY, LLTSSSREWK, TSSSREWKVK, SFW PGGYPAY, KFPELLCVWV, KVKFPELLCV, DSGLLTSSSR, LLCV WVSSIR, LSFWPGGYPA, LTSSSREWKV, YPAYSKDSGL, ALA VLALLSF, LAVLALLSFW, GLLTSSSREW, SSSREWKVKF, REW KVKFPEL, VKFPELLCVW | CRC, STAD |
| B2M | c.3G>A | p.M1I | [p.M1I]ISRSVALAVLALLSLSGLEAIQRTPK | ISRSVALAV, IRSVALAVL | HNSC |
| B3GALNT1 | c.434G>A | p.R145Q | QEAEKEDKMLALSLEDEHLLYGDII[p.R145Q]Q QDFLDTYNNLTLKTIMAFRWVTEFC | IQQFLDTY, LYGDIIQQDF, IIQQDFLDTY | CRC |
| B3GAT1 | c.374G>T | p.R125L | AELTRMANTLLHVPNLHWLVVEDAP[p.R125L]LRTP LTARLLRDTGLNYTHLHVETPR | WLVVEDAPL, VEDAPLRTPL | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| B3GNT5 | c.88del T | p.F30fs | GRRVKKWQLIIQLFATCFLASLMFF[p.F30fs]GNQSIITL* | FLASLMFFG, LMFFGNQSI, MFFGNQSII, FGNQSIITL, FLASL MFFGN, SLMFFGNQSI, LMFFGNQSII, FFGNQSIITL | STAD |
| B4GALNT1 | c.263_264insG | p.G88fs | PVRIKEQVVGLLAWNNCSCESSGGG[p.G88fs]PPPPLPETSPSY* | PLPETSPSY, PPLPETSPSY | PRAD |
| BACH1 | c.1613G>A | p.R538Q | ESCSAREQECEVKLPFNAQRIISLS[p.R538Q]QNDQSLLKMHKLTPEQLDCIHDIRR | SQNDFQSLL, AQRIISLSQ, IISLSQNDF, LSQNDFQSL, SLSQN DFQSL, SQNDFQSLLK, RIISLSQNDF, LSQNDFQSLL | CRC |
| BAG1 | c.133G>C | p.G45R | RLRALRPGREPRQSEPPAQRGPPPS[p.G45R]RRPPARSTASGHDRPTRGAAAGARRP | AQRGPPPSR, AQRGPPPSRR, GPPPSRRPPA | ACC |
| BAI2 | c.692C>G | p.A231G | EECGRAAGRACGFAQPGCSCPGEAG[p.A231G]GSTTTTSPGPPAAHTLSNALVPGGP | GEAGGGSTT, GEAGGGSTTT | TGCT |
| BAIAP2L2 | c.1186G>A | p.V396M | SSASGWFPEATVKALEEGPVNPMTP[p.V396M]MTPMTSMTSMSPMTPMNPGNELPSRS | NPMTPMTPM, GPVNPMTPM, TPMTPMTSM, MTPMTPM TSM, MTPMTSMTSM, TPMTPMTSMT | KIRP |
| BAP1 | c.233A>G | p.N78S | IEERRSRRKVSTLVDDTSVIDDDIV[p.N78S]SNMFFAHQLIPNSCATHALLSVLLNC | IVSNMFFAH, DIVSNMFFA, SNMFFAHQL, SNMFFAHQLI, V SNMFFAHQL | KIRC |
| BAP1 | c.679C>T | p.R227C | WTDKARRVIMERIGLATAGEPYHDI[p.R227C]CFNLMAVPDRRIKYEARLHVLKVNR | PYHDICFNL, DICFNLMAV, YHDICFNLM, GEPYHDICF, HDIC FNLMA, PYHDICFNLM, DICFNLMAW, EPYHDICFNL, HDICFNLMAV | OV |
| BARX2 | c.203G>C | p.R68P | SLYSVCPSLVVRPKPLHSCTGSPSL[p.R68P]PAYPLLSVITRQPTVISHLVPATPGI | TGSPSLPAY, LPAYPLLSV, SPSLPAYPL, CTGSPSLPAY, SLPAY PLLSV, SPSLPAYPLL, LPAYPLLSVI | LUAD |
| BAX | c.114_115insG | p.M38fs | SEQIMKTGALLLQGFIQDRAGRMGG[p.M38fs]GTRAGPGPGASGCVHQEAERVSQAHRGRTGQ* | RMGGGGTRA, GTRAGPGPG, RVSQAHRGR, QEAERVSQA, AGRMGGGGTR, GTRAGPGPGA, RMGGGGTRAG, HQEAER VSQA, QEAERVSQAH | STAD |
| BBOX1 | c.526T>G | p.F176V | RLTGASDKPGEVSKLGKRMGFLYLT[p.F176V]VYGHTWQVQKIDANNVAYTTGKLSF | RMGFLYLTV, TVVGHTWQV, YLTVYGHTW, MGFLYLTVV, FLYLT VYGHT, FLYLTVVYG, RMGFLYLTVV, LYLTVYGHTW, KRMGFLYLTV | CRC |
| BBS9 | c.802del T | p.F268fs | ALDICIVSFNQSASSVFVLGERNFF[p.F268fs]ALRIMDKFDS* | VLGERNFFA, FALRIMDK, RNFFALRIM, FVLGERNFFA, VLGERN FFAL, NFFALRIMDK, FFALRIMDKF, GERNFFALRI, ERNFFALRIM | PRAD |
| BC139719 | c.398T>G | p.L133R | SSKSRNAPRSSCGNCGARAPEHPPV[p.L133R]RVESLNLPLLNGLREEGPGVFSRSV | PPVRRVESL, HPPVRRVESL, RVESLNLPL | PRAD |
| BCAS3 | c.641C>T | p.T214M | DLHCNKRILVVVLQEKIAAFDSCTF[p.T214M]MKKFFVTSCYPCPGPNMNPIALGSRW | CTFMKKFFV, AFDSCTFMK, TFMKKFFVT, AAFDSCTFM, FM KKFFVTS, MKKFFVTSC, FMKKFFVTSC, AAFDSCTFMK, AFD SCTFMKK, MKKFFVTSCY, IAAFDSCTFM, FDSCTFMKKF | BLCA |
| BCKDHA | c.111del C | p.H37fs | RGLSQAALLLRQPGARGLARSHPP[p.H37fs]GSSSSFHLWMTSPSSQGPRRSL* | SSSSFHLWM, RSHPPGSSS, HPPGSSSSF, SSQGPRRSL, GSSS SFHLW, FHLWMTSPS, WMTSPSSQG, MTSPSSQGPR, RGLARSH PPG, RSHPPGSSSS, SHPPGSSSSF, GSSSSFHLWM, FHLWMTSPSS | STAD |
| BCKDHA | c.385_395del GGGGACTGGGC | p.G129fs | LCCFWPVGIAAPCLAQKVSLCVGLG[p.G129fs]IKEKNAPQKQRAIYLRREGGR* | SLCVGLGIK, CVGLGIKEK, KQRAIYLRR, IYLRREGGR, APQKQ RAIY, KVSLCVGLGI, VSLCVGLGIK, GIKEKNAPQK, KQRAIYLR RE, AIYLRREGGR, APQKQRAIYL | PAAD |
| BCL11A | c.1735G>A | p.E579K | SMQHFSEAFHQVLGEKHKRGHLAEA[p.E579K]KGHRDTCDEDSVAGESDRIDDGTVNG | HLAEAKGHR, AEAKGHRDT | HNSC |
| BCL2 | c.515A>G | p.N172S | IVAFFEPFGGVMCVESVNREMSPLVD[p.N172S]SIALWMTEYLNRLHLTWIQDNGGWDA | LVDSIALWM, SIALWMTEY, EMSPLVDSI, MSPLVDSIA, SPL VDSIAL, REMSPLVDS, DSIALWMTEY, SIALWMTEYL, MSPL VDSIAL, REMSPLVDSI, SPLVDSIALW | DLBCL |
| BCL2 | c.6C>T>G | p.H20Q | MAHAGRTGYDNREIVMKYI[p.H20Q]QYKLSQRGYEWDAGDVGAAPPGAAPA | VMKYIQYKL, IVMKYIQYK, YIQYKLSQR, IQYKLSQRG, REIVM KYIQ, IVMKYIQYKL, EIVMKYIQYK, IQYKLSQRGY, KYIQYKLS QR, REIVMKIYQY | DLBCL |
| BCL2 | c.97G>A | p.G33R | GYDNREIVMKYIHYKLSQRGYEWDA[p.G33R]DVGAAPPGAAPAPGIFSSQPGHTPH | YEWDARDVG, SQRGYEWDAR, YEWDARDVGA | DLBCL |
| BCL2L11 | c.272G>A | p.R91Q | PPASPGPFATRSPLFIFMRRSSLLS[p.R91Q]QSSSGYFSFDTDRSPAPMSCDKSTQT | QSSSGYFSF, LLSQSSSGY, LSQSSSGYF, SQSSSGYFS, SQSSSG YFSF, SLLSQSSSGY, LLSQSSSGYF, FMRRSSLLSQ | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| BCL2L11 | c.560_561 insA | p.L187fs | YARRVFLNNYQAAEDHPRMVILRLL[p.L187fs]T LHCPPGVENALTGSLRSRDTMQTFCLFK TRPSTAVSWCHYAASGSLVEGAGDVSEDT ELDGTTFLFITTQQNF* | STAVSWCHY,TAVSWCHYY,ELDGTTFLF,LTLHCPPGV,AVS WCHYYA,SLVEGAGDV,MVILRLLTL,TMQTFCLFK,DTMQTFCLF,H YYAASGSL,YYAASGSLV,LFITTQQNF,RSRDTMQTF, LFKPTRPST,VSWCHYYAA,TFCLFKPTR,CPPGVENAL,KPTR PSTAV,RMVILRLLT,VENALTGSL,GSLRSRDTM,TELDGTTF L,STAVSWCHYY,ELDGTTFLFI,RMVILRLLTL,LLTLHCPPGV, AVSWCHYYAA,FLFITTQQNF,DTMQTFCLFK,QTFCLFKPTR, HYYAASGSLV,TELDGTTFLF,RSRDTMQTFC,LFKPTRPSTA, PSTAVSWCHY,NALTGSLRSR,TAVSWCHYYQ,LRSRDTMQ TF,RDTMQTFCLF,MQTFCLFKPT,CHYYAASGSL | UCS |
| BCL7A | c.155C>T | p.T52M | KVRKWEKKWTVGDTSLRIYKVVVPV[p.T52M]ME PKVDDKNKNKKKGKDEKCGSEVTT | RIYKWPVM,KWVPVMEPK,LRIYKWVPVM | CRC |
| BCL9L | c.2938G>T | p.G980C | PQTPSQMVPLPSANPPGPLKSPQVL[p.G980C]CSSL SVRSPTGSPSRLKSPSMAVPSP | QVLCSSLSV,SPQVLCSSSL,QVLCSSLSVR | LUAD |
| BCL9L | c.3379_3380 insC | p.P1127fs | YHNAIKTIATSDDELLPDRPLLPPP[p.P1127fs]T TTAGLRARDQQQPAQPDAPELSRCPEPYGH EPARPAAPV* | LLPPPTTTA,RARDQQQPA,LSRCPEPYG,ELSRCPEPY,TTTA GLRAR,EPARPAAPV,RPLLPPPTT,LPPPTTTAGL,QPAQPD APEL,YGHEPARPAA,HEPARPAAPV | STAD |
| BCLAF1 | c.109_110 insCA | p.R37fs | RSKSRSQSSSRSRSRSHSRKKRYSS[p.R37fs]T GLVPEHIQGLVVEIVCILEIIVAITEIEE* | LVVEIVCIL,CILEIIVAI,IVAITEII,LVPEHIQGL,HIQGLV VEI,GLVVEIVCI,EIVCILEII,EIIVAITEI,SRKKRYSST,KKRY SSTGL,KRYSSTGLV,VEIVCILEI,VPEHIQGLV,GLVPEHIQGL,LVP EHIQGLV,HIQGLVVEIV,GLVVEIVCIL,HSRKKRYSST,KKRYSSTGL V,EIVCILEIIV,EIIVAITEII,VPEHIQGLVV,RKKRYSSTGL,LEIIV AITEI,VEIVCILEII | CRC |
| BCOR | c.4376A>G | p.N1459S | LPCSSSPQETTQSRPMPPEARRLIV[p.N1459S]S KNAGETLLQRAARLGYEEVVLYCLE | EARRLIVSK,VSKNAGETL,SKNAGETLL | LUAD |
| BEND2 | c.1607C>A | p.P536Q | RILFSKEILISSSVDIHLKDSQSLD[p.P536Q]QN KMAALREYLATTFPTCDLHEHGKD | DQNKMAALR,SQSLDQNKM,SLDQNKMAAL | LUAD |
| BEND2 | c.1888G>A | p.E630K | NDQRGRDGEGCSWMFQPMNNSKMR[p.E630K]K KRNLQPNSNAIPEGMREPSTDNPEE | PMNNSKMRK,MNNSKMRKK,KMRKKRNLQ,SKMRKKRNL, KMRKKRNLQP,MNNSKMRKKR,NSKMRKKRNL | MM |
| BEND3 | c.793del|G | p.D265fs | FQPPPEYQLTAAELKQIVDQSLSGG[p.D265fs]T WPAACWCSSSPSSSATWTSPGAAVPVALRPSASWSR CTCSSSATMWRSTTPR* | SLSGGTWPA,TWWRSTTPR,GAAVPVALR,CSSSATMWR,T SPGAAVPV,VPVALRPSA,RPSASWSRC,CTCSSSATM,DQSL SGGTW,VALRPSASW,WPAACWCSS,SLSGGTWPAA,ATW TSPGAAV,WTSPGAAVPV,ALRPSASWSR,ATMWRSTTPR, WSRCTCSSSA,SSATWTSPGA,SPGAAVPVAL,RPSASWSRC T,SSSPSSSATW,RCTCSSSATM,WPAACWCSSS | STAD |
| BEND5 | c.592C>T | p.R198C | LEDAVVPRALYEELLRNYQQQQEEM[p.R198C]CH LQQELERTRRQLVQQAKKLKEYGA | QQQEEMCHL,YQQQQEEMCH,QQQQEEMCHL,EEMCHLQQEL | CRC |
| BEST3 | c.1148C>T | p.P383L | SFLGSTVQMGKQMPKNEWKMEDIKI[p.P383L]LLP QPQFQCAKSDPGG* | KMEDIKILL,WKMEDIKIL,KILLPQPQF,LLPQPQFQCA,WK MEDIKILL,IKILLPQPQF | TGCT |
| BEST3 | c.1331_1332 insC | p.P444fs | SSMFLPRDDLSPARDLLDVPSRNPP[p.P444fs]QG LTHLEEILLPRKPHAALQHGRAVHHQGDQPDKH FTEPDPTVQCENFPHQNATGT* | HLEEILLPR,LPRRKPHAA,AALQHGRAV,FPHQNATGT,LQH GRAVHH,CENFPPIQNA,LLPRRKPHAA,HLEEILLPRR,HAAL QHGRAV,VPSRNPPGQL,LPRRKPHAAL,AALQHGRAVH,LQ HGRAVHHQ,HQGDQPDKHF,KHFTEPDPTV,CENFPHQNAT | STAD |
| BHLHE22 | c.185T>A | p.L62Q | STPPGMDLSLAPPPRERPASSSSSP[p.L62Q]QG CFEPADDPEGAGLLLLPPGGGGGGS | SPQGCFEPA,SSSSPQGCF,RPASSSSSPQ,SSSSPQGCF | ACC |
| BICD2 | c.485G>A | p.R162H | SENERLASVAQELKEINQNVEIQRG[p.R162H]HL RDDIKEYKFRERARLLQDYSELEEE | RGHLRDDIK,HLRDDIKEY,HLRDDIKEYK,NVEIQRGHLR,IQR GHLRDDI,GHLRDDIKEY | CRC |
| BIRC6 | c.1240G>C | p.V414L | SCFGSGSCPHFLAAATKRGKICIWD[p.V414L]LSK LMKVHLKFEINAYDPAIVQQLIL | KICIWDLSK,CIWDLSKLMK,LSKLMKVHLK,ICIWDLSKLM | TGCT |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| BIRC8 | c.673_674 GC>AT | p.A225M | VFIPCGHLVTCKQCAEAVDRCPMCS[p.A225M]M VIDFKQRVFMS* | MVIDFKQRV, MCSMVIDFK, VDRCPMCSM, PMCSMVIDF, S MVIDFKQRV, PMCSMVIDFK, CSMVIDFKQR, CPMCSMVID F, MVIDFKQRVF | TGCT |
| BLM | c.1980T>A | p.H660Q | ASRNLKHERFQSLSFPHTKEMMKIF[p.H660Q]Q KKFGLHNFRTNQLEAINAALLGEDC | KIFQKKFGL, EMMKIFQKK, KEMMKIFQK, MMKIFQKKF, FQ KKFGLHN, QKKFGLHNF, KIFQKKFGLH, EMMKIFQKKF, FQK KFGLHNF, KEMMKIFQKK, MMKIFQKKFG, MKIFQKKFGL | KIRC |
| BLVRA | c.131C>T | p.S44L | AGSVRMDLRNPHPSSAFLNLIGFV[p.S44L]LR RELGSIDGVQQISLEDALSSQEVE | FLNLIGFVL, VLRRELGSI, NLIGFVLRR, IGFVLRREL, FVLRREL GSI, AFLNLIGFVL, FLNLIGFVLR | CRC |
| BMP2K | c.1461C>G | p.H487Q | QQQQQQQQQQQQQQQQQQQQ[p.H487Q]QH HHHHHHLLQDAYMQQYQHATQQQQ | QQHHHHHHHL, QHHHHHHHL | TGCT |
| BMP3 | c.1030C>T | p.R344W | KPYKTLQAQAPEKSKNKKQRKGPH[p.R344W]WK SQTLQFDEQTLKKARRKQWIEPRN | HWKSQTLQF, KQRKGPHWK, GPHWKSQTL, KKQRKGPHW, KKQRKGPHWK, KORKGPHWKS, KKKQRKGPHW, PHWKSQTLQF | CRC |
| BMP6 | c.353A>T | p.Q118L | PRPLHGLQQPOPPALRQQEEQQQQ[p.Q118L]L LPRGEPPPGRLKSAPLFMLDLYNAL | QEEQQQQQL, QQEEQQQQQL, QEEQQQQQLL | KIRP |
| BMPER | c.1329_1340 del|GCGCA TCGCGCT | p.RIAL4 44del | KSVELVLGESRVSLQQHLTVRWNGS[p.RIAL444del|] PCRAPHFHIDLDGYLLKVTTKAGLEISWDGDSFVEVM | RWNGSPCRA, TVRWNGSPCR, NGSPCRAPHF, SPCRAPHFHI | KIRC |
| BMPER | c.722G>A | p.R241 Q | PPGQCCPKCLQRKVFDLPFGSCLF[p.R 241Q]QSDVYDNGSSFLYDNCTACTCR DSTV | SCLFQSDVY, GSCLFQSDVY, LPFGSCLFQS | UCEC |
| BMS1 | c.1364G>T | p.G455V | KAIFGDEDESGSDDEEDDEMSEDD[p.G455V]VLE NGSSDEEAEEENAEMTDQYMAV | DEMSEDDVL | LUAD |
| BMS1 | c.2634G>T | p.E878D | GEMQKQAQLNRAEFEDQDDEARVQY[p.E878D]DG FRPGMYVRIEINVPCEFVQNFDP | YDGFRPGMY, DGFRPGMYV, VQYDGFRPG, QYDGFRPGM Y, EARVQYDGFR, DGFRPGMYVR, VQYDGFRPGM, DEARVQYDGF | KIRP |
| BNC1 | c.2809T>A | p.Y937 N | MEKADQSLASLPSGLPITCHLCQKT[p.Y 937N]NSNKGTFRAHYKTVHLRQLHKC KVPG | KTNSNKGTF, TNSNKGTFR, HLCQKTNSNK, KTNSNKGTFR, QKTNSNKGTF | CLL |
| BNC2 | c.1534C>T | p.R512 W | NRHSANPNPRLHMPMLRNNRDKDLI [p.R512W]WATSGAATPVIASTKSNLAL TSPGRP | LIWATSGAA, DLIWATSGA, DLIWATSGAA, WATSGAATPV | CRC |
| BNC2 | c.1723A>C | p.S575 R | LQNPLPSQLVFSGLKTVQPVPPFYR[p.S 575R]RLLTPGEMVSPPTSLPTSPIIPTSG T | RLLTPGEMV, QPVPPFYRR, VPPFYRRLL, RRLLTPGEM, QPV PPFYRRL, YRRLLTPGEM | STAD |
| BPI | c.765G>T | p.M25 5I | IDSVAGINYGLVAPPATTAETLDVQ[p. M255I]IKGEFYSENHHNPPPFAPPVME FPAA | LDVQIKGEF, TTAETLDVQI, LDVQIKGEFY | BLCA |
| BRAF | c.1208de|C | p.P403f s | NIDDLIRDQGFRGDGGSTTGLSATP[p.P 403fs]LPHYLAH* | LSATPLPHY, SATPLPHYL, GLSATPLPH, TPLPHYLAH, GLSAT PLPHY, STTGLSATPL, LSATPLPHYL | STAD |
| BRAF | c.1397G>T | p.G466 V | LGRRDSSDDWEIPDGQITVGQRIGS[p. G466V]VSFGTVYKGKWHGDVAVKML NVTAPT | SVSFGTVYK, GSVSFGTVY, GQRIGSVSF, RIGSVSFGTV, GSVS FGTVYK, VSFGTVYKGK, IGSVSFGTVY, ITVGQRIGSV, VQQRI GSVSF | LUAD |
| BRAF | c.1406G>C | p.G469 A | RDSSDDWEIPDGQITVGQRIGSGSF[p. G469A]ATVYKGKWHGDVAVKMLNVT APTPQQ | GSGSFATVY, SGSFATVYK, SFATVYKGK, FATVYKGKW, RIGS GSFATV, GSGSFATVYK, GSFATVYKGK, SFATVYKGKW, GQR IGSGSFA, GSGSFATVY | MM, PRAD |
| BRAF | c.1406G>T | p.G469 V | RDSSDDWEIPDGQITVGQRIGSGSF[p. G469V|VTVYKGKWHGDVAVKMLNVT APTPQQ | SGSFVTVYK, SFVTVYKGK, GSGSFVTVY, RIGSGSFVTV, GSG SFVTVYK, GSFVTVYKGK, SFVTVYKGKW, GQRIGSGSFV, IGS GSFVTVY | LUAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| BRAF | c.1798_1799GT>AA | p.V600K | RDLKSNNIFLHEDLTVKIGDFGLAT[p.V600K]KKSRWSGSGHQFEQLSGSILWMAPEVIR | ATKKSRWSG,KKSRWSGSH,ATKKSRWSGS,DFGLATKKSR, FGLATKKSRW | SKCM |
| BRAF | c.1799T>A | p.V600E | RDLKSNNIFLHEDLTVKIGDFGLAT[p.V600E]KKSRWSGSHQFEQLSGSILWMAPEVI | DFGLATEKSR, FGLATEKSRW | CRC, GBM, LUAD, MM, SKCM, THCA |
| BRAF | c.1801A>G | p.K601E | DLKSNNIFLHEDLTVKIGDFGLATV[p.K601E]ESRWSGSHQFEQLSGSILWMAPEVIR | VESRWSGSH,DFGLATVESR,ESRWSGSHQF,FGLATVESRW | DLBCL, SKCM |
| BRAF | c.1803A>T | p.K601N | DLKSNNIFLHEDLTVKIGDFGLATV[p.K601N]NSRWSGSHQFEQLSGSILWMAPEVIR | GLATVNSRW,DFGLATVNSR,NSRWSGSHQF,FGLATVNSRW | CLL |
| BRD3 | c.70_71insC | p.P24fs | MSTATTVAPAGIPATPGPVNPPPP[p.P24fs]GGLQPQQARPQDQPAAVHAECGGEDAL,LETPVRLAL,GEDALETPV,LLPARGRNQI,PVRLAL GEDALETPVRLALLPARGRNQIEPAGLS* | RGRNQIEPA,ETPVRLALL,RPQDQPAAV,LPARGRNQI,AEC LPAR,RLALLPARGR,TPVRLALLPA,QQARPQDQPA,ALETP VRLAL,LETPVRLALL | STAD |
| BRD9 | c.988G>T | p.G330W | HAADEARDRINRFLPGGKMGYLKRN[p.G330W]WDGSLLYSVVNTAEPDADEEETHPVD | RNWDGSLLY,KMGYLKRNW,LKRNWDGSL,KRNWDGSLL, WDGSLLYSV,YLKRNWDGSL,KRNWDGSLLY,GKMGYLKRN W,LKRNWDGSLL,WDGSLLYSVV | LUAD |
| BRF1 | c.1405G>T | p.V469L | DGELDLSGIDDLEIDRYILNESEAR[p.V469L]LKAELWMRENAEYLREQREKEARIAK | ILNESEARL,RLKAELWMR,SEARLKAEL,ARLKAELWM,NES EARLKA,YILNESEARL,ILNESEARLK,SEARLKAELW | LUAD |
| BRK1 | c.208A>C | p.K70Q | SRLATLNEKLTALERRIEYIEARVT[p.K70Q]QGETLT* | ARVTQGETL,EARVTQGET | KIRC |
| BRMS1 | c.321del|G | p.G107fs | LSQLRLREEVGAERAPEYTEPLGG[p.G107fs]CSGASRFAFRWQGSTRASVWM* | WQGSTRASV,SGASRFAFR,ASRFAFRWQ,AFRWQGSTR,G GCSGASRF,CSGASRFAF,FAFRWQGST,FRWQGSTRA,GAS RFAFRW,CSGASRFAFR,FAFRWQGSTR,ASRFAFRWQG,RF AFRWQGST,AFRWQGSTRA,RWQGSTRASV,LGGCSGASR F,GCSGASRFAF,SGASRFAFRW,FRWQGSTRAS,WQGSTR ASVW | STAD |
| BRPF1 | c.196C>T | p.R66C | HLYHYDHDNPPPQQTPLRKHKKKG[p.R66C]CQSRPANKQSPSPSEVSQSPGREVMS | GCQSRPANK,KHKKKGCQSR,KGCQSRPANK | CRC |
| BRWD1 | c.3956A>G | p.K1319R | TSSGRRRVHDGKKSIRATNYVESNW[p.K1319R]RKQCKELVNLIFQCEDSEPFRQPVDL | NYVESNWRK,ATNYVESNWR,RKQCKELVNL | TGCT |
| BRWD3 | c.2359C>T | p.R787C | TVEKKKPSYTTQRNDYEPSCCGRSL[p.R787C]CRTQRKRQHTYQTRSNIEHNSQASCQ | RSLCRTQRK,CGRSLCRTQR,RSLCRTQRKR | CRC |
| BRWD3 | c.478C>A | p.H160N | VNYVKPPNVVNITSARQLTGCSRFG[p.H160N]NIFPSSAYQHIKMHKRILGHLSSVYC | CSRFGNIFP,RFGNIFPSS,GNIFPSSAY,GCSRFGNIF,SRFGNI FPS,CSRFGNIFPS,RFGNIFPSSA,FGNIFPSSAY,TGCSRFGNI F | LUAD |
| BST1 | c.107G>C | p.G36A | LLQLLIQLLLLLLLLAAGGARARWR[p.G36A]AEGTSAHLRDIFLGRCAEYRALLSPE | RARWRAEGT,RWRAEGTSA,WRAEGTSAH,RAEGTSAHL,G ARARWRAEG,RARWRAEGTS,RWRAEGTSAH,ARWRAEG TSA,WRAEGTSAHL | KIRP |
| BTBD11 | c.1352del|C | p.T451fs | LSDLVSRAMHHLQPLNAKHHCNGTP[p.T451fs]CTTSRGHCTGSPRPCTPFAISCTAHKWNGKTPTWSLPKSTSRWKGPSSCCRR* | CTAHKWNGK,KIPTWSLPK,FAISCTAHK,KWNGKTPTW,R GHCTGSPR,TSRWKGPSS,WSLPKSTSR,SPRPCTPFA,NGKT PTWSL,KHHGNGTPC,GSPRPCTPF,HKWNGKTPT,TPFAISC TA,SLPKSTSRWK,RWKGPSSCCR,TWSLPKSTSR,CTPFAISC | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| BTBD11 | c.1682C>T | p.A561V | LLPGVDCEPRQLRADDCFCASRKLD[p.A561V]VVAIEAKFKQDLGFRMLNCGRTDLVK | TA,SPRPCTPFAI,AKHHGNGTPC,TGSPRPCTPF,FAISCTAH KW,HKWNGKTPTW,WSLPKSTSRW,TPFAISCTAH KLDVVAIEA,VVAIEAKFK,ASRKLDVVA,KLDVVAIEAK,ASRK LDVVAI,DVVAIEAKFK,RKLDVVAIEA,LDVVAIEAKF | STAD |
| BTBD11 | c.794G>C | p.G265A | CMESLFRDIYSRVVASGVPRSCSGP[p.G265A]ASGSGSGPGPSSGPGAAPAADK EREA | VPRSCSGPA,VPRSCSGPAS | ACC |
| BTBD7 | c.1307C>T | p.S436L | HPYGSKWVHRQALHFLCEEFSQVMTL[p.S436L]LDVFYELSKDHLLTAIQSDYLQA SEQ | MTLDVFYEL,QVMTLDVFY,SQVMTLDVF,EEFSQVMTL,V MTLDVFYEL,TLDVFYELSK,FSQVMTLDVF,SQVMTLDVFY, MTLDVFYELS,CEEFSQVMTL | CRC |
| BTG1 | c.91C>T | p.L31F | TRAATMIGEIAAAVSFISKFLRTKG[p.L31F]FTSERQLQTFSQSLQELLAEHYKHH W | RTKGFTSER,FLRTKGFTS,SKFLRTKGF,KGFTSERQL,FLRTK GFTSE,FTSERQLQTF,ISKFLRTKGF | DLBCL |
| BTLA | c.256C>A | p.Q86K | KYCANRPHVTWCKLNGTTCVKLEDR[p.Q86K]KTSWKEEKNISFFILHFEPVLPND NG | KLEDRKTSW,KLEDRKTSWK,TTCVKLEDRK,VKLEDRKTSW | CLL |
| BTN2A2 | c.43C>T | p.L15F | MEPAAALHFSLLPAS[p.L15F]FLLLLLLLLLSLCALVSAQFTVVGPA | FSLPASFLL,SLPASFLLL,SFLLLLLLL,LPASFLLLL, LHFSLPASF,ASFLLLLLL,FSLPASFLLL,SLPASFLLLL, HFSLPASFLL,SFLLLLLLLL,ALHFSLPASF,LPASFLLLLL, LHFSLPASFL,ASFLLLLLLL | TGCT |
| BTN3A2 | c.457G>A | p.E153K | FQDGDFYEKALVELKVAALGSNLHV[p.E153K]KVKGYEDGGIHLECRSTGWYPQ PQIQ | ALGSNLHVK,GSNLHVVK,NLHVKVKGY,ALGSNLHVKV,A ALGSNLHVK | UCEC |
| BTRC | c.1248T>G | p.I416M | FNNGMMVTCSKDRSIAVWDMASPTD[p.I416M]MTLRRVLVGHRAAVNVVDF DDKYIVS | MASPTDMTL,WDMASPTDM,MASPTDMTLR,MTLRRVLV GH,DMASPTDMTL,SPTDMTLRRV | KIRC |
| BTRC | c.778G>T | p.G260W | TDSLWRGLAERRGWGQYLFKNKPPD[p.G260W]WNAPPNSFYRALYPKIIQDIE TIESN | KNKPPDWNA,WNAPPNSFY,YLFKNKPPDW,DWNAPPNS FY,WNAPPNSFYR | LUAD |
| BUB1B | c.2988C>A | p.F996L | VFWDGSFWKLSQNISELKDGELWNK[p.F996L]LFVRILNANDEATVSVLGELAAE MNG | KLFVRILNA,LWNKLFVRI,ELWNKLFVR,GELWNKLFV | CRC |
| BZRAP1 | c.4248_4249 insA | p.P1416fs | CLEDMPGLVGGSSRRRGGGSPEKPP[p.P1416fs]KPQAASRSPRTLQPTSQQQW APGLWTTGPHTGEGWPPRN* | SQQQWAPGL,HTGEGWPPR,QQQWAPGLW,QWAPGLW TT,ASRSPRTLQ,AASRSPRTL,LQPTSQQQW,QQWAPGLW T,SQQQWAPGLW,ASRSPRTLQP,TLQPTSQQQW,QQWA PGLWTT | STAD |
| BZRAP1 | c.4879G>A | p.V1627I | VLRPSTAELVPARSPSETLAYQHLP[p.V1627I]IRIFVALFDYDPVSMSPNPDAGE EEL | TLAYQHLPI,HLPIRIFVA,AYQHLPIR,LAYQHLPIR,LPIRIFVA L,YQHLPIRIF,YQHLPIRIFV,HLPIRIFVAL,AYQHLPIRIF, IRIFVALFDY,TLAYQHLPIR,ETLAYQHLPI,LPIRIFVALF, LAVQHLPIRI | CRC |
| C10orf95 | c.253G>T | p.A85S | GRRRRSCSPAPTWPPLCCYPQSRPT[p.A85S]SSAAGPGACMRASGRPHGNTTA STAP | QSRPTSSAA,YPQSRPTSS,YPQSRPTSSA,SSAAGPGACM | ACC |
| C11orf30 | c.3331C>T | p.R1111C | KQTASQVEQPIITQGSSVTKITFEG[p.R1111C]CQPPTVTKITGGSSVPKLTSPVTSIS | FEGCQPPTV | CRC |
| C11orf68 | c.403G>T | p.V135L | PGSPNSEPVGWIAVYQGGYSPNSGD[p.V135L]LQGLQAAWEALQTSGRPITPG TLRQL | GDLQGLQAA,SPNSGDLQGL,GDLQGLQAAW | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| C11orf9 | c.782_783 insC | p.S261fs | QLLQQHGAELPTHPSKKRKHSESPP[p.S261fs]QHPQCPDAEWNDQTGAWDRD SPASAPHSSPIATLASPGSALPGWFLA SQHCPCPDTALAPARCPLPRPPAGQ* | SALPGPWFL,ALPGPWFLA,FLASQHCPC,ALAPARCPL,TLA SPGSAL,ASAPHSSPI,ATLASPGSA,HSSPIATLA,APHSSPIAT, AEWNDQTGA,RDSPASAPH,GSALPGPWF,HPQCPDAEW, LPGPWFLAS,CPDTALAPA,ASAPHSSPIA,ATLASPGSAL,SA LPGPWFLA,LAPARCPLPR,APHSSPIATL,TALAPARCPL,RK HSESPPQH,AEWNDQTGAW,SQHCPCPDTA,SPIATLASPG, SPGSALPGPW | STAD |
| C12orf32 | c.179A>T | p.D60V | LPITHTRQVPSKPIDHSTITSWVSP[p.D6 0V]VFDTAAGSLFPAYQKHQNRAHSS RK | TITSWVSPV,WVSPVFDTA,ITSWVSPVF,SPVFDTAAG,STIT SWVSPV,WVSPVFDTAA,VFDTAAGSLF,TITSWVSPVF | TGCT |
| C12orf4 | c.1004G>A | p.R335Q | KLHRLQTALSLYSTSLCGLVLLVDN[p.R 35Q]QINSYSGIKRDFATVCQECTDFHF PR | LVDNQINSY,NQINSYSGI,QINSYSGIK,GLVLLVDNQI,LLVD NQINSY,QINSYSGIKR | UCEC |
| C12orf43 | c.82G>C | p.E28Q | APSGTVSDSESSNSSDAEELERCR[p.E 28Q]QAAMPAWGLEQRPHVAGKPRA GAANS | RCRQAAMPA,QAAMPAWGL,LERCRQAAM,CRQAAMPA W,RQAAMPAWG,EELERCRQA,RQAAMPAWGL,ELERCR QAAM,RCRQAAMPAW,EELERCRQA,AEELERCRQA | CESC |
| C12orf65 | c.428A>C | p.K143T | VFYNGENSPVHKEKREAAKKKQERK[p.- K143T]TRAKETLEKKKLLKELWESSKKVH* | KQERKTRAK,KITRAKETL,RKTRAKETL,KITRAKETLEK,ERKT RAKETL | TGCT |
| C13orf33 | c.200de|G | p.R67fs | QPGAFQLSGDQLVVARPGEPAAARG[p.R67fs]ASTSSVTASCASTGSSTASAATS RGMWN* | STASAATSR,STGSSTASA,ASAATSRGM,SAATSRGMW,GE PAAARGA,SSTASAATSR,AARGASTSSV,STSSVTASCA,EPA AARGAST,RGASTSSVTA,TASAATSRGM,ASAATSRGMW | STAD |
| C14orf101 | c.883G>A | p.E295K | FSLAKSEIGSSMSEILLSQVTNMRT[p.E2 95K]KLSFNIQALAVCANICLATKDRQNPS | KLSFNIQAL,RTKLSFNIQ,TNMRTKLSF,KLSFNIQALA,NMR TKLSFNI,LSQVTNMRTK,RTKLSFNIQA,SQVTNMRTKL,VT NMRTKLSF,KLSFNIQAL | CRC |
| C14orf102 | c.268de|A | p.R90fs | SSDESDTNKKLKQTSRKKKKKKK[p.R 90fs]GSISIIRKQRGSMGRRVAAGLRQT PILKRTNLPEALEAVKRNLRNRIKEIMLQ LILDIALFGLRTFRL* | NL,PEALEAV,IMLQLILDI,MLQLILDIA,ILDIALFGL,RIKEIML QL,GLRQTPILK,ALFGLRTFR,KGSISIIRK,IALFGLRTF,LFGLR TPRL,IIRKQRGSM,KQRGSMGRR,RGSMGRRVA,GSMGRR VAA,MGRRVAAGL,AVKRNLRNR,KRNLRNRIK,RNRIKEIML, SISIIRKQR,TPILKRTNL,SMGRRVAAG,NLRNRIKEI,QLILDI ALF,KKKKGSISI,KKKKGSISII,KRTNLPEAL,LRNRIKEIM,KEIM LQLIL,LQLILDIAL,SMGRRVAAGL,IMLQLILDIA,MLQLILDIA L,LILDIALFGL,ALFGLRTFRL,ILKRTNLPEA,RIKEIMLQLI,AG LRQTPILK,IALFGLRTFR,KQRGSMGRRV,RGSMGRRVAA, MGRRVAAGLR,GLRQTPILKR,RTNLPEALEA,AVKRNLRNRI, EAVKRNLRNR,EIMLQLILDI,SIIRKQRGSM,NLRNRIKEIM,L QLILDIALF,DIALFGLRTF,KKKKGSISII,RRVAAGLRQT,VAAG LRQTPI,LKRTNLPEAL,IKEIMLQLIL | STAD |
| C14orf102 | c.343G>A | p.D115N | RKHQHHKKTKRKHGPSSSSRSETDT[p.- D115N]NSEKDKPSRGVGGSKKESEEPN QGNN | RSETDTNSEK | CRC |
| C14orf105 | c.299G>T | p.R100I | ASRDMYFDIPLEHRETSIIKRHPPQ[p.R1 00I]ILQKLEPIDLPRVITSGRLLSQREAR GECVPGFTVPNLLPKWAPDHCSEVE[p.- | IIKRHPPQI,IKRHPPQIL,SIIKRHPPQI,IIKRHPPQIL,KRHPPQ ILQK | CRC |
| C14orf118 | c.836G>T | p.R279I | R279I]IMDSGLDKFSDSTFLLPSRPAQR GYH | EIMDSGLDK,IMDSGLDKF,EIMDSGLDKF,SEVEIMDSGL | UCEC |
| C14orf126 | c.16C>T | p.R6W | MAEGS[p.R6W]WIPQARALLQQCLHA RLQIRPADGDV | EGSWIPQAR,SWIPQARAL,QEGSWIPQA,SWIPQARALL,G SWIPARAL | KIRP |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| C14orf166B | c.690C>A | p.F230L | DSAALLCQALSTNYQIKKLDLSHNQ[p.F230L]LSDVGGEHLGQMLAINVGLTSLDLSW | KLDLSHNQL,QLSDVGGEHL,KKLDLSHNQL | UCEC |
| C14orf177 | c.269G>T | p.G90V | CCGECSTCFCTEEKSECQRHEETSP[p.G90V]VSCNHQIMSASTISAFCATPRFKQLF | SPVSCNHQI,CQRHEETSPV,SPVSCNHQIM | CLL |
| C14orf43 | c.939del C | p.P313fs | GLQPAGPLGQSHLAHHSMAPYPFPP[p.P313fs]TQI* | PYPFPPTQI,MAPYPFPPT,SMAPYPFPT,APYPFPPTQI | STAD |
| C15orf2 | c.1462G>A | p.V488I | LALPADIVPILGDQSNEKGGSYNSV[p.V488I]IGAAPLTSDPPTPPSSTPSFKPPVTR | NSVIGAAPL,KGGSYNSVI,GSYNSVIGAA,YNSVIGAAPL | CRC |
| C15orf2 | c.2257G>T | p.V753F | PGSGNTQPSGNTASVQGSTSLPAQS[p.V753F]FRAPATASNHPLNPGATPQKFGAPD | SLPAQSFRA,TSLPAQSFR,QSFRAPATA,LPAQSFRAP,STSLPAQSF,AQSFRAPAT,STSLPAQSFR,SFRAPATASN,LPAQSFRAPA,GSTSLPAQSF,AQSFRAPATA | LUAD |
| C15orf2 | c.2716G>T | p.G906W | RPPTTTSSHPLNTGSISHSTLGATD[p.G906W]WQQKSDSSFILGNPATPAPVIGLTSP | WQQKSDSSF,LGATDWQQK,WQQKSDSSFI | LUAD |
| C15orf23 | c.71C>T | p.S24F | MAAPEAPPLDRVFRITWLSTECD[p.S24F]FHPLPPSYRKFLFETQAADLAGGTTV | TWLSTECDF,DFHPLPPSY,STECDFHPL,DFHPLPPSYR,LSTECDFHPL,CDFHPLPPSY | SKCM |
| C15orf33 | c.1018G>A | p.D340N | GSKKAPAKSVKERIADSQEHLSTSI[p.D340N]NFNIIKILNNPRAYTLPISKEESRLS | SINFNIIKI,TSINFNIIK,ISTSINFNI,STSINFNII,EHIST SINF,INFNIIKIL,HISTSINFNI,STSINFNIIK,TSINFNIIKI,QEHISTSINF,ISTSINFNII | CRC |
| C15orf52 | c.294del G | p.G98fs | RKKNQALLRRYQEIQEDRRQAEQGG[p.G98fs]WL* | RQAEQGGWL | STAD |
| C16orf3 | c.193G>A | p.G65S | RACPVACPVGCPIACPVSCPVACPV[p.G65S]SCPVGSMATAPQGLSPQEWEADRETG | VACPVSCPV,PVACPVSCPV,CPVSCPVGSM | CESC |
| C16orf55 | c.353A>C | p.D118A | RASNETLVSCSSSGSDQQRTIREPE[p.D118A]AWGPYRRHRNPSTADAYNSHLKE* | REPEAWGPY,RTIREPEAW,EAWGPYRHR,IREPEAWGPY | KIRC |
| C16orf62 | c.730C>A | p.L244I | SDTSVIQFYPSKFVLITDILDTFGK[p.L244I]IVYERIFSMCVDSRSVLPDHFSPENA | IVYERIFSM,TFGKIVYER,DILDTFGKI,LDTFGKIVY,GKIVYERIF,ILDTFGKIVY,TFGKIVYERI,KIVYERIFSM,DTFGKIVYER,FGKIVYERIF | TGCT |
| C16orf74 | c.61_63delAGC | p.S21del | MGLKMSCLKGFQMCVSSSSS[p.S21del]HDEAPVLNDKHLDVPDIIITPPTTGMM | MCVSSSSSH,QMCVSSSSSH | PRAD |
| C16orf87 | c.452G>T | p.R151I | ANLSDEKAFVFSVALAEINRKIINQ[p.R151I]LLIL* | KIINQILIL,NRKIINQIL,RKIINQILI,EINRKIINQI,RKIINQILIL | CRC |
| C17orf96 | c.187C>G | p.L63V | LCLRALAFCALAKPRASSLGPGPGE[p.L63V]VAARSPVLRGPQAPLRPGGWAPDGLK | SLGPGPGEV,VAARSPVLR,EVAARSPVL,GEVAARSPV,EVAARSPVL,GEVAARSPVL | ACC |
| C19orf10 | c.34G>C | p.G12R | MAAPSGGWNGV[p.G12R]RASLWAALLLGAVALRPAEAVSEPTT | GVRASLWAA,RASLWAALL,VRASLWAAL,GVRASLWAAL,GWNGVRASLW,RASLWAALLL,GGWNGVRASL,VRASLWAALL | ACC |
| C19orf21 | c.784C>T | p.R262C | PHLANGHVVPIKPQVKGVVREENKV[p.R262C]CAVPTWASVQVVDDPGSLASVESPGTYDQELLGPSDKSQAALQKAGEVVPP[p. | CAVPTWASV,RENKVCAV,NKVCAVPTW,EENKVCAVPT | STAD |
| C19orf70 | c.150del C | p.P50fs | P50fs]PCTSSASTCVSRQACRYPSSQPLQRFTFPSVTPGMQAS* | CVSRQACRY,LQRFTFPSV,SSASTCVS,SQPLQRFTF,TFPPSVTPGM,RQACRYPSS,CTSSASTCV,FTFPSVTPG,VPPCTSSA,CRYPSSQPL,GEVVPPCT,PLQRFTFPSV,FTFPSVTPGM,TSSASTCVSR,STCVSRQACR,SSQPLQRFTF,YPSSQPLQRF,FPSVTPGMQA,RQACRYPSSQ,LQRFTFPSVT | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| C1QBP | c.674C>T | p.T225I | ESDIFSIREVSFQSTGESEWKDTNV[p.T225I]ILNTDSLDWALYDHLMDFLADRGVDN | NYILNTDSL, SEWKDTNYI, ILNTDSLDW, ILNTDSLDWA, SEWKDTNYI, YILNTDSLDW | TGCT |
| C1QTNF5 | c.582_583 insG | p.G194fs | CVWHIQVATDHAIQLKIEALSIESV[p.G194fs]GLLPF* | ALSIESVGL, IESVGLLPF, LSIESVGLL, ALSIESVGLL, EALSIESVGL, SIESVGLLPF | STAD |
| C1QTNF5 | c.924de|C | p.P308fs | NCADGSETNCSAKFSGSVEQSHPP[p.P308fs]PRLLAP* | QSHPPRLLA, VEQSHPPRL | STAD |
| C1R | c.647de|C | p.P216fs | AECSSELYTEASGYISSLEYPRSYP[p.P216fs]LTCAATTASGWSGASPCTSSSWSLLILMTTSKYTAPMTSYRSMPTGRTLASSVGSKGPPTSTPAAMLWICCSSOMSRGTAGAGSCATPPRSSSAPSPRP* | TSSSWSLLI, ILMTTSKYT, SMPTGRTLA, QMSRGTAGA, LLILMTTSK, TLASSVGSK, YTAPMTSYR, RSSSAPSPR, RSYPLTCAA, TTSKYTAPM, MTSYRSMPT, SYRSMPTGR, RSMPTGRTL, RTLASSVGS, SSQMSRGTA, AGSCATPPR, ATPPRSSSA, LILMTTSKY, KYTAPMTSY, TTASGWSGA, CTSSSWSLL, STPAAMLWI, YPRSYPLTC, APMTSYRSM, MPTGRTLAS, LEYPRSYPL, CAATTASGW, SSSWSLLIL, SSWSLLILM, LMTTSKYTA, SKYTAPMTS, LWICCSSQM, SQMSRGTAG, YPLTCAATT, PPTSTPAAM, TSTPAAMLW, TPAAMLWIC, CTSSSWSLLI, SLEYPRSYP, L, ILMTTSKYTA, MLWICCSSOM, SQMSRGTAGA, SLLILMTT SK, RTLASSVGSK, TSYRSMPTGR, RSYPLTCAAT, MTTSKYTAPM, KYTAPMTSYR, RSMPTGRTLA, LLILMTTSKY, SKYTAPM TSY, WICCSSQMSR, TTASGWSGAS, YTAPMTSYRS, YPRSYPLTCA, YPLTCAATTA, SPCTSSSWSL, MPTGRTLASS, GPPTST PAAM, LEYPRSYPLT, GASPCTSSSW, TSSSWSLLIL, SSSWSLLILM, YRSMPTGRTL, SKGPPTSTPA | STAD |
| C1RL | c.1051de|C | p.L351fs | PDYRQNESHNFSGDIALLELQHSIP[p.L351fs]WAPTSSRSVCPIMRPSTAAACWATSVGLAWRWAG* | AAACWATSV, ELQHSIPWA, IMRPSTAAA, ATSVGLAWR, SS RSVCPIM, IPWAPTSSR, STAAACWAT, APTSSRSVC, CPIMR PSTA, LELQHSIPW, LQHSIPWAP, WATSVGLAW, RPSTAAA CW, TSVGLAWRW, TAAACWATSV, CWATSVGLAW, SSRSV CPIMR, IMRPSTAAAC, SIPWAPTSSR, WATSVGLAWR, STA AACWATS, CPIMRPSTAA, RPSTAAACWA, LLELQHSIPW, LE LQHSIPWA, LQHSIPWAPT, TSSRSVCPIM, AACWATSVGL, GEWELCRAA, CRAAPGPAY, WELCRAAPG, LCRAAPGPAY, WELCRAAPGP, GEWELCRAAP | CRC |
| C1orf106 | c.1612C>T | p.R538C | PPGYFPAGRYVVAESPLPGEWEL[p.R538C]CRAAPGPAYEEEGTPLRYQRLVPSRS | LEPLGSSTL, ALEPLGSSTL | ACC |
| C1orf167 | c.367A>G | p.S123G | WWHLRALGPDATSSCTKTPSALEPL[p.S123G]GSSTLQDSLEKVPRAPTLPDTLQGSL | LEPLGSSTL, ALEPLGSSTL | TGCT |
| C1orf173 | c.2063C>A | p.S688Y | ESFENVLKEGTEKGTQEIAEGLSEK[p.S688Y]YGKHVSAEEKEKDKSKLWEESTAQVK | IAEGLSEKY, GLSEKYGKHV, YGKHVSAEEK, EIAEGLSEKY, SEKYGKHVSA | LUAD |
| C1orf173 | c.4360G>A | p.G1454S | AGVGTPGALERKTSGLGQEQEGSE[p.G1454S]SQEFAATGSGDGRQETGAAEKFRLGLS | EERGSESQEA, QEEGSESQEA, EEGSESQEAA | LUAD |
| C1orf74 | c.760G>A | p.D254N | PGLRDILNTWEKDLRTRFRTQNDFA[p.D254N]NLSISSEIVTLPAVAL* | NLSISSEIV, RTQNDFANL, FANLSISSEI, RFRTQNDFAN, FRT QNDFANL, TQNDFANLSI | LUSC |
| C1orf87 | c.1622G>T | p.R541L | LSPQKIDQALRFRSGENMLLEPAL[p.R541L]LYLKEL* | MLLEPALLY, NMLLEPALL, LLEPALLYL, MLLEPALLYL, LLEPA LLYLK, NMLLEPALLY, EPALLYLKEL | LUAD |
| C20orf132 | c.1146A>C | p.E382D | LKLPLRFQRLGHLVALMALLCGDPQ[p.E382D]DKVAEEAAEGIHSLLHITLRLKYITH | LLCGDPQDKV | KIRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| C20orf160 | c.136delC | p.P46fs | KAGRRAACRSSVSRRPLHSMPLYPP[p.P46fs]TTSTPRFCCVTTWRKRSSSWATLPG* | HSMPLYPPT,SSTPRFCCV,RFCCVTTWR,RKRSSSWAT,KRSSSWATL,MPLYPPTTS,RFCCVTTWRK,TWRKRSSSWA,RKRSSSWATL,RSSSWATLPG,TSSTPRFCCV,MPLYPPTSS,HSMPLYPPTT,TTWRKRSSSW,TPRFCCVTTW | STAD |
| C20orf26 | c.3263G>A | p.R1088Q | LEVQMAQPNYGLELVTGSAKNGTYF[p.R1088Q]QIHINKYKMVETITCLSREPFPASNY | TYFQIHINK,FQIHINKYK,YFQIHINKY,AKNGTYFQI,GTYFQIHINK,TYFQIHINKY,SAKNGTYFQI,YFQIHINKYK,FQIHINKYKM,AKNGTYFQIH | CRC |
| C22orf26 | c.83C>T | p.P28L | ASATAAWHCPPLCLPLPASAPTSP[p.P28L]LNPATRPAPGPRRARCPQSAHPAPT | APTSPLNPA,LPASAPTSPL,SPLNPATRPA | ACC |
| C22orf40 | c.96_97insC | p.P32fs | RPLGVFECELCTLTAPYSYVGQKPP[p.P32fs]QHPVDGPPGGKLCHEGSLHLRQGQIPGPRLVLQFVQQAGVCGPGMQFILLQEILPLCPGEHQCFSSGNSARLGEKESSIKEDPQPARFSDVSATGARSSGGTLHRAPGPACARDAAELGAAMPGLVSGPLGAALQPRGAGVQLGAATGPGSCSKRVVQRMPDKTQPGTRPGPPTCPSGPRPE* | LQFVQQAGV,MQPILLQEI,LLQEILPPL,RLGEKESSI,ALQPRGAGV,GQIPGPRLV,TLHRAPGPA,GLVSGPLGA,LVSGPLGAA,ATGPSCSK,RSSGGTLHR,VVQRQMPDK,GQKPPQHPV,HLRQGQIPG,GNSARLGEK,KTQPGTRPG,GTRPGPPTC,CFSSGNSAR,FSSGNSARL,DAAELGAAM,GPRLVLQFV,GARSSGGTL,GPACARDAA,MPGLVSGPL,QPRGAGVQL,SLHLRQGQI,GKLCHEGSL,LCHEGSLHL,GVCGPGMQF,GEHQCFSSG,KEDPQPARF,ARFSDVSAT,LHRAPGPAC,VSGPLGAAL,SKRVVQRQM,RQMPDKTQP,AELGAAMPG,KLCHEGSLHL,VLQFVQQAGV,GMQFILLQEI,MQFILLQEIL,ILLQEILPPL,LLQEILPPLC,AMPGLVSGPL,RLVLQFVQQA,ELGAAMPGLV,GLVSGPLGAA,LVSGPLGAAL,RLGEKESSIK,RVVQRQMPDK,AATGPGSCSK,SGNSARLGEK,SIKEDPQPAR,RSSGGTLHRA,GTLHRAPGPA,IPGPRLVLQF,QQAGVCGPGM,RQGQIPGPRL,GQIPGPRLVL,LQFVQQAGVC,AGVCGPGMQF,HQCFSSGNSA,IKEDPQPARF,RDAAELGAAM,AELGAAMPGL,LQPRGAGVQL,VQLGAATGPG,CSKRVVQRQM,RQMPDKTQPG,GEHQCFSSGN | CRC |
| C22orf43 | c.55A>G | p.K19E | MGNILTCCINSHCGWPRG[p.K19E]EDAPCYESDTDIYETVAATSESTTV | WPRGEDAPC,GEDAPCYES,WPRGEDAPCY | TGCT |
| C22orf44 | c.1368T>A | p.N456K | IMLEEEPSITSGESQTTYSTFSAPL[p.N456K]KANRKKLIESLSPDFCHQNKGLLLT | YSTFSAPLK,STFSAPLKK,PLKKANRKK,SAPLKKANR,TYSTFSAPLK,YSTFSAPLKK,STFSAPLKKA,SAPLKKANRK,FSAPLKKANR | CLL |
| C2orf53 | c.815C>A | p.P272H | VEYPICLVCLRPRSPSCPLPRYRTG[p.P272H]RLLAPPQLLPCVQQESGPLRIGIGGRPQPPTLDPTSTSYESQLGQNSSSS | RYRTGHRLL,RTGHRLLAF,HRLLAPPQL,RYRTGHRLLA,LPRYRTGHRL,YRTGHRLLAP,GHRLLAPPQL,HRLLAPPQLL | LUAD |
| C2orf71 | c.3675_3676insAGC | p.1225_1226insS | 225_1226inss]SEESPKKDTEPCSSPCSPELQGGTRRAS | SSSEESPK,SSSSEESPKK,SQLGQNSSSS | KIRC |
| C2orf81 | c.943A>C | p.T315P | LELRSEGVPCIASGVLVSYPSVGGA[p.T315P]PRPSASCQQQRAGHSDVRLSAHHHRM | YPSVGGAPR,SYPSVGGAPR | ACC |
| C3 | c.2670delC | p.P890fs | LLHNPAFCSLATTKRRHQQTVTIPP[p.P890fs]SPRCPFHMSSCR* | TVTIPPSPR,IPPSPRCPF,QTVTIPPSPR,SPRCPFHMSS,HQQTVTIPPS | STAD |
| C3orf15 | c.1655G>A | p.R552Q | RTCHALQEDEKLVKKAEKQVTLALQ[p.R552Q]QQRNLHEHKVSLVENHLAGLEGRALA | VTLALQQQR,QQRNLHEHK,KQVTLALQQ,QQQRNLHEH,QVTLALQQQR,KQVTLALQQQ,LQQQRNLHEH,QQRNLHEHKV | CLL |
| C3orf20 | c.2219G>T | p.R740L | IISSQNYTSTGQLQWLLNTLYNHQQ[p.R740L]LGRGSPCIQCRYDSYRLLQYDLDSPL | LYNHQQLGR,QQLGRGSPC,TLYNHQQLGR,HQQLGRGSPC,QQLGRGSPCI | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| C3orf23 | c.649C>T | p.R217C | SWLDNNGKSAVKKLKNSLPLRKELD[p.R217C]CLKDELSHQLQLSDIRWQRSWGIAHR | CLKDELSHQL, KELDCLKDEL, LPLRKELDCL | UCEC |
| C3orf30 | c.681C>A | p.D227E | AERRTSEQITHRLSKLSERRPSVQI[p.D227E]ESGSSVPSDQSPSVQIDSGSSVPSDQ | VQIESGSSV, IESGSSVPS, SVQIESGSSV, VQIESGSSVP | LUSC |
| C3orf39 | c.997C>T | p.R333W | LALAQFPQMKTVTVSLEDHTFADVV[p.R333W]WLVSNASMLVSMHGAQLVTTLFLPRG | TFADVVWLV, WLVSNASML, HTFADVVWL, DVVWLVSNA, VWLVSNASM, HTFADVVWLV, WLVSNASMLV, VWLVSNASML, VVWLVSNASM | CRC |
| C3orf62 | c.554G>A | p.R185Q | SNMPLNNSSQEVTKDLLDMIDHTSI[p.R185Q]QTIEELAGKIEFENELNHMCGHCQDS | QTIEELQGK, IDHTSIQTI, TSIQTIEEL, MIDHTSIQTI, HTSIQTIEEL, QTIEELQGKI | UCEC |
| C3orf70 | c.17C>T | p.S6L | MSAAA[p.S6L]LPASERGWKSEKLDEAQALARSCAAAR | AAALPASER, SAAALPASER, AALPASERGW | BLCA, CESC |
| C4orf21 | c.2398G>C | p.E800Q | SKDTEAHISEPEDLGKIRSPPPDHV[p.E800Q]QVETAREGKQYWNPRNSSELSGLVNT | VQVETAREG | CESC |
| C5orf30 | c.10G>A | p.D4N | MEV[p.D4N]NINGESRSTLTLPFPGAEANSPGKA | EVNINGESR | CRC |
| C5orf4 | c.341G>A | p.R114Q | LFFWSFNGLLLVVDTTGKPNFISRY[p.R114Q]QIQVGKNEPVDPVKLRQSIRTVLFNQ | FISRYQIQV, ISRYQIQVGK, KPNFISRYQI, YQIQVGKNEP | CRC |
| C5orf65 | c.734A>G | p.Q245R | PRAAGAPRPRLLLRTGSLDESLGPL[p.Q245R]RAAAGFVQTALARKLSPEAPAPSSAT | SLGPLRAAA, GPLRAAAGF, RAAAGFVQTA, ESLGPLRAAA, D ESLGPLRAA | ACC |
| C6orf170 | c.2171A>C | p.K724T | RTGAINECVTFIFNRYAKKLQVSRH[p.K724T]TKFGYGVLVTRVASTAAGGIALKKSG | KLQVSRHTK, VSRHTKFGY, HTKFGYGVL, LQVSRHTKF, RHTKFGYGV, TKFGYGVLV, KLQVSRHTKF, KKLQVSRHTK, VSRHTKFGYG, HTKFGYGVLV, QVSRHTKFGY, RHTKFGYGVL, TKFGYGVLVT | CRC |
| C6orf89 | c.172_173insC | p.P58fs | GMSEKAIEKEIRQLLEKNEPQRPPP[p.P58fs]AVSSPYSCV* | AVSSPYSCV, EPQRPPPAV, PPPAVSSPY, RPPPAVSSPY | STAD |
| C7 | c.2059C>A | p.R687S | GMSLEGPSAFLCGSSLKWSPEMKNA[p.R687S]SCVQKENPLTQAVPKCQRWEKLQNSR | EMKNASCVQK, SPEMKNASCV | LUAD |
| C7orf49 | c.389delG | p.G130fs | GSSEEEDSGHKQALAPGLSPSQRPG[p.G130fs]VPALPVAGALRRRRKRMC* | SORPGVPAL, AGALRRRRK, GALRRRRKR, ALRRRRKRM, RP GVPALPV, GLSPSQRPGV, VAGALRRRRK, SPSQRPGVPA, RP GVPALPVA, VPALPVAGAL, ALRRRRKRMC, SQRPGVPALP | STAD |
| C7orf50 | c.535delC | p.L179fs | RARELITVQKAEALMRELEDEGSDPP[p.L179fs]CRGGPSASDRCCSCSPSGFSAGRGRCPVQGCLRPHRVQLLRRWGPGSPAGQRLSKGFQLLRWWGPGSPAPEPRKGPFPPDPDPWPVTAVTVMAGSVPSAQSVDALESPGPLALEGPSSPRNLLWREMSIFLPGIF* | RLSKGFQLL, VWAGSVPSA, NLLWREMSI, CLRPHRVQL, EM SIFLPGI, LSKGFQLLR, MSIFLPGIF, RPFHVQLLR, RVQLLRR WG, RWWGPGSPA, LWREMSIFL, TVMAGSVPS, APEPRKG PF, WPVTAVTVM, GPSSPRNLL, LLWREMSIF, RRWGPGSPA, QRLSKGFQL, SKGFQLLRW, KGFQLLRWW, LESPGPLAL, RE MSIFLPG, DPPWPVTAV, TVMAGSVPSA, LLWREMSIFL, FSA GRGRCPV, CLRPHRVQLL, RLSKGFQLLR, REMSIFLPGI, RGR CPVQGCL, RPHRVQLLR, GSPAGQRLSK, CSPSGFSAGR, LA LEGPSSPR, FPPPDPPWPV, TAVTVMAGSV, GPGSPAGQRL, VPSAQSVDAL, SPRNLLWREM, EMSIFLPGIF, RCCSCSPSGF, LRRWGPGSPA, RRWGPGSPAG, GQRLSKGFQL, QRLSKGFQ LL, LSKGFQLLRW, FQLLRWWGPG, LRWWGPGSPA, ALESP GPLAL, LEGPSSPRNL, RNLLWREMSI, NLLWREMSIF, CPVQ | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| C7orf57 | c.88G>A | p.E30K | SKELQGATHRYAPCDWYHVPVKRS[p.E30K]KKAVDAPPASQIPGLSNLGDSHSENL | GCLRPH,WPVTAVTVMA,PPWPVTAVTV,GFPPPDDPW,GPSSPRNLLW HVPVKRSKK,KKAVDAPPA,YYHVPVKRSK,RSKKAVDAPP,V PVKRSKKAV | HNSC |
| C7orf58 | c.418G>T | p.G140W | HQHILTQHGYTVVIAEERLNAGLGP[p.G140W]WLLEQGDLGSWDLLICLSSKK AEGTP | RLNAGLGPW,RLNAGLGPWL | LUAD |
| C7orf58 | c.713G>T | p.R238L | PSVCLDQGMQLKPSTSSHLLKTVKP[p.R238L]LVWKPGDWSREQLNETTVLAP HETIF | LLKTVKPLV,KTVKPLVWK,HLLKTVKPL,LKTVKPLVW,HLLK TVKPLV,LVWKPGDWSR,SHLLKTVKPL,LLKTVKPLVW | LUAD |
| C7orf63 | c.28G>A | p.A10T | MWTEEAGAT[p.A10T]TEAQESGIRNKSSSSQIPVVGVVTE | EEAGATTEA,TEEAGATTEA | CRC |
| C9orf131 | c.1024del|C | p.P342fs | GYETHLETTGHKKMPQAFEPPMPPP[p.P342fs]ANPQLLCQNPEKLALKEDLLYL RTSGEPWDTERNLRPLSLQCQSLALP* | LALKEDLLY,ALKEDLLYL,SLQCQSLAL,KLALKEDLL,QLLCQN PEK,MPPPANPQL,ERNLRPLSL,YLRTSGEPW,CQNPEKLAL, FEPPMPPPA,QLLCQNPEKL,KLALKEDLLY,CQNPEKLALK,L YLRTSGEPW,ALKEDLLYLR,MPPPANPQLL,RPLSLQCQSL,L ALKEDLLYL,TERNLRPLSL,LSLQCQSLAL,GEPWDTERNL | STAD |
| C9orf174 | c.406C>T | p.R136W | ITNHREKKLQQSTKVWCLNQSAESL[p.R136W]ICAMRGGENRPPARVQSSS EELELR | ESLWICAMR,NQSAESLWI,AESLWICAM,QSAESLWICA,CL NQSAESLWM,SAESLWICAM | BRCA |
| CABP5 | c.433del|C | p.R145fs | NGDGEITLVELQQAMQRLLGERLTP[p.R145fs]GRSLRLSGRLMLMETAQLTLKS L* | RLSGRLMLM,LMLMETAQL,MLMETAQLT,RLTPGRSLR,RS LRLSGRL,SLRLSGRLM,ERLTPGRSL,LRLSGRLML,LMETAQ LTL,RLMLMETAQL,MLMETAQLTL,RLTPGRSLRL,LMETAQ LTLK,RSLRLSGRLM,SLRLSGRLML,SGRLMLMETA,ETAQLT LKSL,GERLTPGRSL,LRLSGRLMLM | STAD |
| CACHD1 | c.2159C>A | p.S720Y | SLMDKAFDPTRRQWYLHAVANPGLI[p.S720Y]YLTGPYLDVGGAGVVTI SHTIHSSS | AVANPGLIY,LIYLTGPYL,YLTGPYLDV,GLIYLTGPY,VANPGL IYL,AVANPGLIYL,GLIYLTGPYL,YLTGPYLDV,HAVANPGLIY | CRC |
| CACNA1A | c.1994C>T | p.T665M | NFDEGTPPTNFDTFPAAIMTVFQIL[p.T665M]MGEDWNEVMYDGIKSQGGVQ GGMVFS | LMGEDWNEV,IMWFQIIM,FQIIMGEDW,MGEDWNEV M,MGEDWNEVMY,ILMGEDWNEV,LMGEDWNEVM,VF QIIMGEDW,AIMTVFQIIM | CRC |
| CACNA1A | c.2315C>A | p.S772Y | EVSPLSAANMSIAVKEQQKNQKPAK[p.S772Y]YVWEQRTSEMRKQNLLASREA LYNEM | PAKYVWEQR,NQKPAKYVW,YVWEQRTSEM,QQKNQKPA KY | LUAD |
| CACNA1C | c.2129C>T | p.S710L | RRSTFDNFPQSLLTVFQILTGEDWN[p.S710L]LVMYDGIMAYGGPSFPGMLVCIY FII | ILLTGEDWNL,LTGEDWNLV,GEDWNLVMY,NLVMYDGIM, TGEDWNLVMY,ILLTGEDWNLV,LVMYDGIMAY,LTGEDWN LVM | UCEC |
| CACNA1D | c.3218G>T | p.R1073L | AKSNPEECRGLFLIYKDGDVDSPVV[p.R1073L]LERIWQNSDFNFDNVLSAMMA LFTVS | SPVVLERIW,DVDSPVVLER,LERIWQNSDF | LUAD |
| CACNA2D1 | c.1055C>A | p.A352E | AKGITDYKKGFSFAFEQLLNYNVSR[p.A352E]ENCNKIIMLFTDGGEERAQEIFNK YN | RENCNKIIM,RENCNKIIML | LUAD |
| CACNA2D3 | c.994G>A | p.A332T | CLNGTLVQADRTNKEHFREHLDKLF[p.A332T]TKGIGMLDIALNEAFNILSDFNH TGQ | KLFTKGIGM,REHLDKLFT,KLFTKGIGML | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CACNB2 | c.1823G>A | p.R608H | ASHRDHNRDETHGSDHRHRESRH[p.R608H]HSRDVDREQDHNECNKQRSRHKSKDR | RHRESRHHSR,RESRHHSRDV | CRC |
| CACNG3 | c.400G>A | p.V134I | ILSVTLLFFGGLCVAASEFHRSRHN[p.V134I]ILSAGIFFVSAGLSNIIGIIVYISA | RSRHNILS,FHRSRHNII,HRSRHNIIL,SRHNIILSA,RSRHNIILSA,EFHRSRHNII,FHRSRHNIL,SEFHRSRHNI | CRC |
| CACNG3 | c.413C>T | p.A138V | TLLFFGGLCVAASEFHRSRHNVILS[p.A138V]GIFFVSAGLSNIIGIIVYISANAGD | ILSVGIFFV,VILSVGIFF,NVILSVGIF,SRHNVILSV,VILSVGIFFV,RSRHNVILSV,LSVGIFFVSA,NVILSVGIFF,RHNVILSVGI,HNVILSVGIF | CRC |
| CACNG3 | c.694C>T | p.R232W | LRAKSHSEFLKKSTFARLPPYRYRF[p.R232W]WRRSSSRSTEPRSRDLSPISKGFHTI | RYRFWRRSS,RFWRRSSSR,PPYRYRFWR,PYYRFWRR,YRFWRRSSS,LPPYRYRFW,RLPPYRYRFW,RYRFWRRSSS,RFWRRSSSR,LPPYRYRFWR,PPYRYRFWR,YRYRFWRRSS | LUAD |
| CACNG5 | c.361G>A | p.G121R | MIRSATPFPLVSLFFMFIGFILNNI[p.G121R]RHIRPHRTILAFVSGIFFILSGLSLV | FILNNIRHI,NIRHIRPHR,ILNNIRHIR,RHIRPHRTI,GFILNNIRHI,FIGFILNNIR,FILNNIRHIR,NNIRHIRPHR,RHIRPHRTIL | CRC |
| CACNG8 | c.437T>G | p.V146G | LRVRASSIFPLSAILLLLGGVCV[p.V146G]GASRVYKSKRNIILGAGILFVAAGLS | LLGGVCVGA,CVGASRVYK,GASRVYKSK,VCVGASRVY,LLLGGVCVGA,VGASRVYKSK,GVCVGASRVY | BLCA |
| CADM1 | c.569C>T | p.S190L | NCTAMASKPATTIRWFKGNTELKGK[p.S190L]LEVEEWSDMYTVTSQLMLKVHKEDDG | LEVEEWSDM,TELKGKLEV,LEVEEWSDMY | CRC |
| CADPS | c.2875C>A | p.R959S | DAALEVQPPDTWDSPLFQLLNDFL[p.R959S]STDYNLCNGKFHKHLQDLFAPLWRY | LNDFLSTDY,FLSTDYNLC,DFLSTDYNL,LLNDFLSTDY,STDYNLCNGK,FQLLNDFLST,NDFLSTDYNL | LUAD |
| CADPS | c.3217G>A | p.A1073T | PSWMAAIYDADNGSGTSEDLFWKLD[p.A1073T]TLQTFIRDLHWPEEFGKHLEQRLKL | KLDTLQTFI,WKLDTLQTF,KLDTLQTFIR,FWKLDTLQTF,WKLDTLQTFI | CRC |
| CALB2 | c.180G>C | p.K60N | YIEGKELENFFQELEKARKGSGMMS[p.K60N]NSDNFGEKMKEFMQKYDKNSDGKIEM | NSDNFGEKM,GMMSNSDNF,SNSDNFGEK,MSNSDNFGEK,SGMMSNSDNF | CESC |
| CALB2 | c.772C>T | p.R258C | KEMNIQQLTNYRKSVMSLAEAGKLY[p.R258C]CKDLEIVLCSEPPM* | KLYCKDLEI,KLYCKDLEIVL,LYCKDLEIVL | LUAD |
| CALCB | c.242G>C | p.R81T | DYVQMKASELKQEQETQGSSSAAQK[p.R81T]TACNTATCVTHRLAGLLSRSGGMVKS | AQKTACNTA,KTACNTATCV,AQKTACNTAT | CESC |
| CALD1 | c.1018G>A | p.E340K | ERMREEKRAAEERQRIKEEEKRAA[p.E340K]KERQRIKEEEKRAAEERQRIKEEEKR | AAKERQRIK,RAAKERQRI,RAAKERQRIK | CLL |
| CALN1 | c.691G>A | p.V231I | LNETSGNCQTEFEGVHSQKQNRQTC[p.V231I]IRKSLICAFAMAFIISVMLIAANQIL | KQNRQTCIR,QNRQTCIRK,CIRKSLICA,RQTCIRKSL,IRKSLICAF,KQNRQTCIRK,SQKQNRQTCI,CIRKSLICAF,RQTCIRKSLI | GBM |
| CAMK2B | c.392G>T | p.G131V | EYYSEADASHCIQQILEAVLHCHQM[p.G131V]VVHRDLKPENLLLASKCKGAAVKLA | AVLHCHQMV,VLHCHQMVV,MVVHRDLK,AVLHCHQMVV,VLHCHQMVVV,QMVVHRDLK,EAVLHCHQMV,HQMVVVHRDL | LUAD |
| CAMSAP1 | c.1396_1397insA | p.T466fs | RHRSNSLTRVDGQPRGAAIAWPEKK[p.T466fs]NQACVPANTFCSTSRCEL* | VPANTFCST,QACVPANTF,KKNQACVPA,WPEKKNQACV,NQACVPANTF | BLCA |
| CAMSAP1 | c.1396del|A | p.T466fs | RHRSNSLTRVDGQPRGAAIAWPEKK[p.T466fs]PGLRPSQHLLYITLRVVKWIPALATASAWPAPSAKTVWHPTLLI* | LLLYITLRV,LLYITLRVV,RVVKWIPAL,GLRPSQHLL,VVKWIPALA,SAWPAPSAK,HLLLYITLR,KWIPALATA,LYITLRVVK,ASAWPAPSA,SAKTVWHPT,KTVWHPTLL,IPALATASA,WPAPSAKTV,SQHLLYIT,AMPA,TVWHPTLLI,IPALATASA,WPAPSAKTV,SQHLLYIT,VKWIPALAT,AKTVWHPTL,LLLYITLRV,ALA | KICH |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CANT1 | c.392A>G | p.K131R | RIAVIADLDTESRAQEENTWFSYLK[p.K131R]RGYLTLSDSGDKVAVEWDKDHGVLES | TASAWPA, GLRPSQHLLL, YITLRVVKWI, RVVKWIPALA, WI PALATASA, LLYITLRVVK, ASAWPAPSAK, LYITLRVVKM, TLR VVKWIPA, SAKTVWHPTL, KTVWHPTLLI, LRPSQHLLLY, TAS AWPAPSA, KPGLRPSQHL, RPSQHLLLYI, IPALATASAW, WP APSAKTVW, SAHLLLYITL, LRVVKWIPAL, VKWIPALATA, AK TVWHPTLL | PRAD |
| CAPN S1 | c.906_911 de\|GCTGGT | p.LV303 de\| | LHTSSELQSPSSYFASRPWVRAKGL[p.LV303de\|]LGFPVLTLHPLPLPSGCS* | YLKRGYLTL, NTWFSYLKR, SYLKRGYLT, WFSYLKRGY, FSYLK RGYL, YLKRGYLTLS, SYLKRGYLTL, TWFSYLKRGY, ENTWFSY LKR | TGCT |
| CAPRIN2 | c.37G>A | p.E13K | MEVQVSQASLGF[p.E13K]KLTSVEKSLREWSRLSREVIAWLCPS | GLLGFPVLT, WVRAKGLLG, VRAKGLLGF, AKGLLGPV, KGLL GFPVL, GLLGFPVLTL, RAKGLLGFPV, WVRAKGLLGF, RPWV RAKGLL, AKGLLGFPVL | CRC |
| CARD11 | c.1268G>A | p.R423Q | IEKDKYRKQIRELEEKNDEMRIEMV[p.R423Q]QREACIVNLESKLRRLSKDSNNLDQS | SLGFKLTSV, VSQASLGFK, GFKLTSVEK, SQASLGFKL, QVSQ ASLGFK, LGFKLTSVEK, KLTSVEKSLR, SQASLGFKLT, FKLTSV EKSL | CRC |
| CARD11 | c.1876G>A | p.E626K | LDDDSHERYSFGPSSIHSSSSHQS[p.E626K]KGLDAYDLEQVNLMFRKFSLER PFRP | EMRIEMVQR, DEMRIEMVQ, IEMVQREAC, MRIEMVQREA, IEMVQREACI, VQREACIVNL | DLBCL |
| CARD11 | c.279G>C | p.E93D | SKINRAGRLLDILHTKGQRGVVFL[p.E93D]DSLEFYYPELYKLVTGKEPTRRFSTI | SSSSSHQSK, HQSKGLDAY, HSSSSSHQSK, SHQSKGLDAY | DLBCL |
| CARD11 | c.3195C>G | p.I1065M | ANIEAVAAKNHCLLEAGIGCTRDL[p.I1065M]MKSNIYPIVLFIRVCEKNIKRFR KLL | FLDSLEFYY, GYVVFLDSL, VVFLDSLEF, VFLDSLEFY, FLDSLEF YYP, VVFLDSLEFY, YVVFLDSLEF, RGYVVFLDSL, VFLDSLEFY Y, DSLEFYYPEL | LUAD |
| CARM1 | c.605C>T | p.A202V | LQNHTDFKDKIVLDVGCGSGILSFF[p.A202V]VAQAGARKIYAVEASTMAQHAE VLVK | LMKSNIYPI, RDLMKSNIY, MKSNIYPIV, DLMKSNIYPI, LMKS NIYPIV, GIGCTRDLMK, CTRDLMKSNI, MKSNIYPIVL | GBM |
| CASC1 | c.161G>A | p.R54Q | ERRLKEEEARLKYEKEEMERLEIQ[p.R54Q]QIEKEKWHRLEAKDLERRNEEL EELY | ILSFFVAQA, FVAQAGARK, SFFVAQAGA, FFVAQAGAR, LSF FVAQAG, GILSFFVAQA, FVAQAGARKI, SFFVAQAGAR, VA QAGARKIY, CGSGILSFFV, LSFFVAQAGA RLEIQQIEK, MERLEIQQI | CRC |
| CASC3 | c.1808C>T | p.P603L | MNLPHPGLHPHQTPAPLPNPGLYPP[p.P603L]LVSMSPGQPPPQQLLAPTYFSA PGVM | GLYPPLVSM, NPGLYPPLIV, GLYPPLVSMS, LPNPGLYPPL | STAD |
| CASC3 | c.1934C>T | p.P645L | TYFSAPCVMNFGNPSYPYAPGALPP[p.P645L]LPPPHLYPNTQAPSQVYGGVTY YNPA | YAPGALPPL, LPPLPPPHL, ALPPLPPHL, PYAPGALPPL, LPPL PPPHLY | STAD |
| CASC3 | c.1973>T | p.S658L | PSYPYAPGALPPPPPHLYPNTQAP[p.S658L]LQVYGGVTYNPAQQQVQPKPS PPRR | NTQAPLQVY, LYPNTQAPL, LQVYGGVTY, APLQVYGGV, HL YPNTQAPL, LQVYGGVTYY, QAPLQVYGGV, YPNTQAPLQV | STAD |
| CASC3 | c.695C>T | p.S232F | RQRKLWKDEGRWEHDKFREDEQAPK[p.S232F]FRQELIALYGYDIRSAHNPDDI KPRR | KFRQELIAL, APKFRQELI, REDEQAPKF, FRQELIALY, KPRQEL IALY, EQAPKFRQEL | STAD |
| CASD1 | c.2341de\|T | p.F781fs | DLAQIIIPKDNSSLLKRLACIAAFF[p.F781fs]VDSSSYHPFKINQNIRFQKF* | DSSSYHPFK, INQNIRFQK, AFFVDSSSY, LACIAAFFV, HPFKIN QNI, VDSSSYHPF, FKINQNIRF, NQNIRFQKF, FVDSSSYHPF, RLACIAAFFV, KINQNIRFQK, INQNIRFQKF, AAFFVDSSSY, H PFKINQNIR, DSSSYHPFKI | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CASP14 | c.13C>T | p.R5W | MSNP[p.R5W]WSLEEEKYDMSGARLALILCVTKARE | NPWSLEEEKY | CRC |
| CASP5 | c.67del|A | p.R23fs | MAAVPRVEGVFIFLIEDSGKKK[p.R23fs]GVRILKLCSKVSFRVDWITS* | RILKLCSKV, KVSFRVDWI, KLCSKVSPR, KKKGVRILK, GKKKG VRIL, KKGVRILKL, LKLCSKVSF, SKVSFRVDW, KLCSKVSFRV, GVRILKLCSK, SGKKKGVRIL, ILKLCSKVSF, KKKGVRILKL, SKV SPRVDWI | KIRC |
| CASP8 | c.1413del|A | p.R471fs | YEVSNKDDKKNMGKQMPQPTFTLRK[p.R471fs]NLSSLLIDGAILFVLFCFV FLRQNLALSPRLECSGVISAHRKLRLPG SGHSPASASRVAGTTGARHHTWLIF* | LLIDGAILF, LIDGAILFV, IDGAILFVL, DGAILFVLF, FVLFCFVFL, TLRKNLSSL, FVFLRQNLA, VLPCFVFLR, AILFVLFCF, LFVLFCVFV, CSGVISAHR, SGVISAHRK, RVAG TTGAR, DGAILFVLF, AILFVLFCF, LFVLFCVFV, CFVFLRQNL, V FLRQNLAI, RQNLALSPR, VISAHRKLR, KLRLPGSGH, GARHH TWLI, LPGSGHSPA, LRKNLSSLI, RKNLSSLLI, ARHHTWLIF, I DGAILFVL, FTLRKNLSSL, NLSSLLIDGA, LLIDGAILFV, LIDGAI LFVL, AILFVLFCFV, FVFLRQNLAL, TLRKNLSSLI, RLECSGVIS A, RLPGSGHSPA, FVLFCFVFLR, CSGVISAFIRK, IDGAILFVLF, GAILFVLFCF, ILFVLFCVFV, RQNLALSPRL, KLRLPGSGHS, SG HSPASASR, ASRVAGTTGA, GARHHTWLIF, RVAGTTGARH, ECSGVISAHR, GVISAHRKLR, QPTFTLRKNL, SLLIDGAILF | STAD |
| CAST | c.1917T>A | p.D639E | DDALDKLSDSLGQRQPDPDENKPME[p.D639E]EKVKEKAKAEHRDKLGERDDTI PPEY | MEEKVKEKA | CLL |
| CATSPER4 | c.1274C>T | p.T425M | MIVEEVRAIRFNQEQESEVLNRRSS[p.T425M]MSGSLETTSSKDIRQMSQQQDL LSAL | SMSGSLETT, EVLNRRSSM, RRSSMSGSL, NRRSSMSGSL, SE VLNRRSSM | KIRC |
| CBFB | c.454G>A | p.E152K | FDEERAQQEDALAQQAFEEARRRTR[p.E152K]KFEDRDRSHREEMEVRVSQLLA VTGK | EARRRTRKF, RTRKFEDRDR, RKFEDRDRSH, EEARRRTRKF | CRC |
| CBLL1 | c.413del|A | p.E138fs | PIKIYGRMIPCKHVFCYDCAILHEK[p.E138fs]REIRCVQAVVILCSELSSVHEVL SSCVALFKGAREHICLRETYRLISTIAI* | ILCSELSSV, VLSSCVALF, CLRETYRLI, LSSCVALFK, CVALFKG AR, HICLRETYR, GAREHICLR, TYRLISTIA, ILHEKREIR, EIRCV QAVV, ELSSVHEVL, EVLSSCVAL, ETYRLISTI, REIRCVQAV, R CVQAVVIL, SELSSVFIEV, HEVLSSCVA, ALFKGAREH, EHICLR ETY, RETYRLIST, YRLISTIAI, REHICLRET, HEKREIRCV, VILCSELSSV, SVHEVLSSCV, ALFKGAREHI, VLSSCVALFK, TYRLISTIAI, EHICLRETYR, ETYRLISTIA, EVLSSCVAL, REIRCVQAVV, SELSSVHEVL, HEVLSSCVAL, REHICLRETY, RETYRLISTI | STAD |
| CBLN3 | c.206del|C | p.P69fs | ECLVVCEPGRAAAGPGGAALGEAP[p.P69fs]LGEWHLLRSEATTMSQQGKPA MAPVGPSTSTRSW* | AMAPVGPST, ATTMSQQGK, QGKPAMAPV, APLGEWHLL, MSQQGKPAM, APVGPSTST, LLRSEATTM, GAALGEAPL, GE WHLLRSE, GPSTSTRSW, EAPLGEWHLL, TTMSQQGKPA, KP AMAPVGPS, TMSQQGKPAM, HLLRSEATTM, GEAPLGEW HL, GEWHLLRSEA, QQGKPAMAPV, AMAPVGPSTS | STAD |
| CBWD6 | c.304_305 insG | p.E102fs | ESGEGSALEKSLAVSQGGELYEEWL[p.E102fs]GT* | GELYEEWLGT | KICH |
| CC2D2A | c.3850C>T | p.R1284C | ESQEDEKLLQATEKFQAECALKFPN[p.R1284C]CQCLTTVIDISGKTVFITRY LKPLNP | LKFPNCQCL, FPNCQCLTT, ALKFPNCQCL, CQCLTTVIDI, FPN CQCLTTV, AECALKFPNC | CRC |
| CCDC108 | c.3492del|C | p.P1164fs | LERDPTPCELTYKVPTRHSMSQIPP[p.P1164fs]SSPL* | SQIPPSSPL, MSQIPPSSPL | STAD |
| CCDC111 | c.1250G>T | p.R417L | GIKGGIRRWNYFPEELLVDICKY[p.R417L]LWCENIGRAFIKSNNIMILVDL | LVYDICKYL, VYDICKYLW, YLWCENIGR, CKYLWCENI, LLVYD ICKYL, YLWCENIGRA, LVYDICKYLW | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CCDC120 | c.22A>G | p.I8V | KNEVW MEVKGQL[p.I8V]VSSPTFNAPAALFGE AAPQVKSERLR | LVSSPTFNA,GQLVSSPTF,MEVKGQLVS,QLVSSPTFNA,ME VKGQLVSS,KGQLVSSPTF | KIRC |
| CCDC121 | c.1190G>T | p.W397L | IEQAQKLTATQSHLENRKQQLQQEQL[p. W397L]LYLESLIQARQRLQGSHNQCLN RQDV | QQLQQEQLY,KQQLQQEQL,QEQLYLESL,QLYLESLIQA,KQ QLQQEQLY,LYLESLIQAR,RKQQLQQEQL,QQLQQEQLYL, QQEQLYLESL,QEQLYLESLI | LUSC |
| CCDC132 | c.2512C>T | p.R838C | NIYVDALLKEFQFNRRLNEVSKRV[p.R 838C]CIPLPVSNILWEHCIRLANRTIV EGY | CIPLPVSNI,VSKRVCIPL,KRVCIPLPV,NEVSKRVCI,EVSKRVC IPL,SKRVCIPLPV | UCEC |
| CCDC135 | c.937G>A | p.E313K | AEKAKPDALHGLRVHSWVLVLSGKR[p. E313K]KVPENFFIDPFTGHSYSTQDEHF LGI | GKRKVPENF,RKVPENFFI,WVLVLSGKR,KRKVPENFFI,GK RKVPENFF | HNSC |
| CCDC144A | c.3791C>T | p.S1264L | NTTSIKTQMELTIKDLESEISRIKT[p. S1264L]LQADFNKTELERYKELYLEEV KVRES | KTLQADFNK,ISRIKTLQA,RIKTLQADF,SEISRIKTL,LQADFN KTEL,RIKTLQADFN,EISRIKTLQA,SRIKTLQADF | UCEC |
| CCDC148 | c.1260del A | p.K420fs | KEEEKEKLWKKELLQRAEKKKKIK[p. K420fs]NTGPRKNRSGKKWK* | KIKNTGPRK,KNRSGKKWK,RKNRSGKKW | STAD |
| CCDC15 | c.1463C>A | p.P488H | ILPKYQDQNFLPKDQNFLSRDQHVL[p. P488H]HKDQDILPKYQDQNFLPKDQN FLSRD | LSRDQHVLH,LSRDQHVLHK | CLL |
| CCDC152 | c.457G>C | p.E153Q | GYKKEISKLYQDMQRKVELNEEKHK[p. E153Q]QLIEKKEMEISELNAKLRSQEKE KQN | KHKQLIEKK,KQLIEKKEMEI,QLIEKKEMEI,HKQLIEKKEM | CESC |
| CCDC153 | c.598_599insC | p.P200fs | QWDGAALRLHARHKEQQRQFGLTPP[p. P200fs]WIFEATSP* | LTPPWIFEA,RQFGLTPPWI,QFGLTPPWI,FGLTPPWIF,RQF GLTPPWI,GLTPPWIFEA,QFGLTPPWIF,QROFGLTPPW | STAD |
| CCDC153 | c.599del C | p.P200fs | QQWDGAALRLHARHKEQQRQFGLTP[p. P200fs]LDL* | QRQFGLTPL,RQFGLTPLD,RQFGLTPLDL,QQRQFGLTPL | STAD |
| CCDC159 | c.994G>T | p.A332S | KELSDIWSAVHVLQNSIDSLTLCSG[p.A 332S]SCPKASSLRGHKGHQCLSPPLPS WDS | TLCSGSCPK,TLCSGSCPKA,LTLCSGSCPK,GSCPKASSLR | TGCT |
| CCDC168 | c.15058G>T | p.D5020Y | GYTLSNSKGPVQPTAQGEEKGGLRI[p. D5020Y]YMEDKMLPKCTDLKAKQLLLS DILNT | YMEDKMLPK,GLRIYMEDK,EEKGGLRIY,LRIYMEDKM,RIY MEDKML,IYMEDKMLPK,GEEKGGLRIY,EEKGGLRIYM | UCEC |
| CCDC169-SOHLH2 | c.485A>G | p.K162R | LDDCIFNMVLLKVPSSLSAEELEAI[p.K1 62R]RLIRFGKKKNTHSLFVFIIPENFKGC | AIRLIRFGK,RLIRFGKKK,ELEAIRLIR,LEAIRLIRF,EELE AIRLI,AEELEAIRL,AIRLIRFGKK,EAIRLIRFGK,EELEAI RLIR,AEELEAIRLI | STAD |
| CCDC19 | c.620G>T | p.R207L | KLRMEQEEELKDMSKIILNAKCHAI[p.R 207L]LDAQILEKQAIQKELDTEEKRLDQ MM | ILDAQILEK,LNAKCHAIL,HAILDAQIL,ILNAKCHAIL, AIILDAQILEK | LUAD |
| CCDC19 | c.836G>T | p.R279L | RIRGRRQIVEQMEKNQEERSLLAEQ[p. R279L]LEQEKEQMLEYMEQLQEEDLK DMERR | LEQEKEQML,EERSLLAEQL | LUAD |
| CCDC36 | c.626G>T | p.R209I | AQNDLVFEAVQDKGNMEQAILEMKK[p. R209I]IFEARQGEFIEMKSNLKHLEVL VAQQ | IFEARQGEF,EMKKIFEAR,AILEMKKIF,LEMKKIFEA, KIFEARQGEF,QAILEMKKIF | UCEC |
| CCDC53 | c.172C>T | p.R58C | FVVHTVQFLNRFSTVCEEKLADLSL[p.R 58C]CIQQIETTLNILDAKLSSIPGLDDVT | KLADLSLCI,ADLSLCIQQI | CESC |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CCDC60 | c.689G>A | p.R230H | GQKWEHFITAPKTKKFKIPTMRVTN[p.R230H]HKPSRRGSTLSLSRASGGSSPQSSMI | PTMRVTNHK, RVTNHKPSR, VTNHKPSRR, RVTNHKPSRR | CRC |
| CCDC79 | c.1319A>C | p.N440T | IEQLEREGNEEEIQRENYQDNISSM[p.N440T]TISIQNTWKHLHADRIGRGSKAEDED | NISSMTISI, TISIQNTWK, MTISIQNTW, YQDNISSMT, YQDNISSMTI, MTISIQNTWK, SMTISIQNTW | CLL |
| CCDC81 | c.776G>T | p.R259I | NRERKCKLKDQSDKEEGTRDISSPK[p.R259I]LLRDRQALFPAKVTNVSLLEKFERSEITCEKIEALEQENSELERENRKLKK[p.K6 77fs]NIG* | ILRDRQALF, DISSPKILR, RDISSPKIL, KILRDRQAL, GTRDISSPKI, KILRDRQALF, RENRKLKKNI | CRC |
| CCDC88A | c.2031_2032 insA | p.K677fs | | | STAD |
| CCDC88C | c.5553_5554 insC | p.P1851fs | QKLGAPEALGGRETGSHTLQSPAPP[p.P1851fs]QLP* | LQSPAPPQL, TLQSPAPPQL | CRC |
| CCKAR | c.811C>A | p.L271M | QKKSAKERKPSTTSSGKYEDSDGCY[p.L271M]MQKTRPPRKLELRQLSTGSSSRANRI | YMQKTRPPR, MQKTRPPRK, YEDSDGCYM, YMQKTRPPRK, MQKTRPPRKL, CYMQKTRPPR | LUAD |
| CCKBR | c.706G>A | p.V236M | SARVRQTWSVLLLLLLFFIPGVVMA[p.V236M]MAYGLISRELYLGLRFDGDSDSDSQS | FIPGVVMAM, VVMAMAYGL, VMAMAYGLI, AMAYGLISR, MAMAYGLIS, FIPGVVMAMA, VVMAMAYGLI, MAMAYGLISR, FFIPGVVMAM, MAYGLISREL, IPGVVMAMAY | CRC |
| CCNB3 | c.2794G>A | p.A932T | ETLLKKPLALKMSTINEAVLFEDMI[p.A932T]TLNEKPTTGKELSFKEPLAIQESPTY | VLFEDMITL | CLL |
| CCR5 | c.554G>T | p.S185I | SLPGIIFTRSQKEGLHYTCSSHFPY[p.S185I]IQYQFWKNFQTLKIVILGLVLPLLVM | SSHFPYIQY, HPFYIQYQF, IQYQFWKNF, FPYIQYQFW, CSSHFPYIQY, YTCSSHFPYI, SHFPYIQYQF, HFPYIQYQFW, YIQYQFWKNF | KIRC |
| CCZ1 | c.642G>C | p.E214D | IFGGISFFPLDKMTYLKIQSFINRM[p.E214D]ESLNIVKYTAFLYNDLIWSGLEQD | FINRMDESL, RMDESLNIV, DESLNIVKY, RMDESLNIVK, SFINRMDESL, MDESLNIVKY | KIRC |
| CD101 | c.1781G>A | p.R594Q | SDLKVPLTVTWQFQPASSHIFHQLI[p.R594Q]QITHNGTIEWGNFLSRFQKKTKVSQS | HIFHQLIQI, IQITHNGTI, SHIFHQLIQI | CRC |
| CD101 | c.847G>T | p.D283Y | PDETWMFITKKQTDQTTLRIQPAVK[p.D283Y]YFQVNITADSLFAEGKPLELVCLVVS | RIQPAVKYF, KYFQVNITA, AVKYFQVNI, LRIQPAVKY, QPAVKYFQV, IQPAVKYFQV, TLRIQPAVKY, LRIQPAVKYF, VKYFQVNITA | CRC |
| CD109 | c.1409T>A | p.L470Q | AYFLGSKSSMAVHSLFKSPSKTYIQ[p.L470Q]QKTRDENIKVGSPFELVVSGNKRLKE | KTYIQQKTR, PSKTYIQQK, QQKTRDENIK, IQQKTRDENI | CLL |
| CD163L1 | c.2161G>A | p.V721M | SDMELRLVGGSSRCAGKVEVNVQGA[p.V721M]MGILCANGWGMNIAEVVCRQLECGSA | VEVNVQGAM, MGILCANGW, EVNVQGAMGI, KVEVNVQGAM, VQGAMGILCA, AMGILCANGW | GBM |
| CD180 | c.683A>C | p.N228T | SLNFNGNNVKGIELGAFDSTIFQSL[p.N228T]TFGGTPNLSVIFNGLQNSTTQSLWLG | LTFGGTPNL, STIFQSLTF, SLITFGGTPNL, FQSLITFGGTP | CRC |
| CD1B | c.122G>T | p.W41L | GNSEHAFQGPTSFHVIQTSSFTNST[p.W41L]LAQTQGSGWLDDLQIHGWDSDSGTAI | FTNSTLAQT, SSFTNSTLA, TSSFTNSTL, LAQTQGSGW, QTSSFTNSTL, TSSFTNSTLA, TLAQTQGSGW | LUAD |
| CD1C | c.265C>T | p.R89C | TIIFLHNWSKGNFSNEELSDLELLF[p.R89C]CFYLFGLTREIQDHASQDYSKYPFEV | LSDLELLFC, ELLFCFYLF, LFCFYLFGL, CFYLFGLTR, SDLELLFCF, LELLFCFYL, LSDLELLFCF, LLFCFYLFGL, SDLELLFCFY, FCFYLFGLTR, LELLFCFYLF | SKCM |
| CD1D | c.74del|T | p.L25fs | MGCLLFLLLMLALLLQAWGSAEVPQRL[p.L25fs]SPSAASRSRSPIAAGRAPTAWR | RLSPSAASR, ASRSRPSI, RSRSPIAA, AGRAPTAWR, VPQRLSPSA, SPIAAGRAP, AAGRAPTAW, AASRSRPSI, ASRSRPS | GBM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CD1E | c.253T>G | p.F85V | GWGSCRRTAGATTRIPSAL* | PIA,RSRPSPIAAG,AWRGWGSCRR,TAWRGWGSCR,EVPQ RLSPSA,VPQRLSPSAA,RPSPIAAGRA,SPIAAGRAPT,AEVP QRLSPS,IAAGRAPTAW | STAD |
| CD209 | c.847G>A | p.A283T | GDLQTHGWDTVLGTIRFLKPWSHGN[p. F85V]VSKQELKNLQSLFQLYFHSFIQI VQA | KPWSHGNVS,FLKPWSHGNV,KPWSHGNVSK,HGNVSKQE LK | GBM |
| CD4 | c.492del G | p.Q164fs | WEWTFFQGNCYFMSNSQRNWHDSIT [p.A283T]TCKEVGAQLVVIKSAEEQNF LQLQSS | DSITTCKEV | STAD |
| CD55 | c.466G>A | p.E156K | TLESPPGSSPSVQCRSPRGKNIQGG[p. Q164fs]RPSPCLSWSSRIVAPGHALSCR TRRRWSSK* | CLSWSSRIV,RIVAPGHAL,RTRRRWSSK,RGKNIQGGR,SSRI VAPGH,HALSCRTRR,LSWSSRIVA,SSRIVAPGHA,HALSCRT RRR,IQGGRPSPCL,GGRPSPCLSW,SRIVAPCHAL,SPCLSW SSRI | UCEC |
| CD7 | c.521del C | p.P174fs | PGYRREPSLSPKLTCLQNLKWSTAV[p.E 156K]KFCKKKSCPNPGEIRNGQIDVPG GIL | NLKWSTAVK,STAVKFCKK,WSTAVKFCK,TAVKFCKK,LK WSTAVKF,KWSTAVKFCK,WSTAVKFCKK,STAVKFCKKK,NL KWSTAVKF | KIRC |
| CD79B | c.589T>C | p.Y197H | ASALPAPPTGSALPDPQTASALPDP[p.P 174fs]QQPLPSLRPWR* | ALPDPQQPL,DPQQPLPSL,QPLPSLRPW,SALPDPQQPL,Q QPLPSLRPW | DLBCL |
| CD79B | c.589T>G | p.Y197D | LFIIVPIFLLLDKDSKAGMEEDHT[p.Y1 97H]HEGLDIDQTATYEDIVTLRTGEVK WS | EEDHTHEGL,MEEDHTHEGL,HEGLDIDQTA | DLBCL |
| CD93 | c.838del G | p.D280fs | LFIIVPIFLLLDKDSKAGMEEDHT[p.Y1 97D]DEGLDIDQTATYEDIVTLRTGEVK WS | MEEDHTDEGL | STAD |
| CDAN1 | c.1936_1937 insC | p.L646fs | PLCVSPKYGCNFNNGGCHQDCFEGG[p. D280fs]MAPSSAAADQDSGCWMTW* | GMAPSSAAA,HQDCFEGGM,FEGGMAPSS,FEGGMAPSSA | KIRC |
| CDC14A | c.369del C | p.N123fs | GERKQFAVVLLSLRLLAKFLGFVAF[p.L6 46fs]PAIPGA* | FLGFVAPPA,FVAFPAIPG,LGFVAFPAI,FLGFVAFPAI, FVAFPAIPGA,KFLGFVAFPA | STAD |
| | | | AYAVIYLKKTPEEAYRALLSGSNPP[p.N1 23fs]IFHSGMLPLEIALTISPFSTVCRE SERDYNMDFLTLRHLMWMNMNIMSELK MVTSTGLFQENF* | NMDFLTLRH,LLSGSNPPI,GMLPLEIAL,MLPLEIALT,LTI SPFSTV,HLMWMNMNI,NIMSELKMV,IMSELKMVT,STVCRES ER,NMNIMSELK,IFHSGMLPL,DYNMDFLTL,KMVTSTGLF, YNMDFLTLR,EIALTISPF,MNMNIMSEL,PPIFFISGML,LPLEI ALTI,LMWMNMNIM,LSGSNPPIF,LEIALTISP,RESERDYN M,SERDYNMDF,MDFLTLRHL,LRHLMWMNM,MNIMSEL KM,SELKMVTST,LKMVTSTGL,RDYNMDFLT,ALLSGSNPPI, MLPLEIALTI,ALTISPFSTV,NMDFLTLRHL,FLTLRHLMWM, HLMWMNMNIM,WMNMNIMSEL,TISPFSTVCR,MNMNI MSELK,DFLTLRHLMW,RHLMWMNMNI,TLRHLMWMN M,FSTVCRESER,DYNMDFLTLR,EIALTISPFS,NPPIFHSGML, ELKMVTSTGL,LLSGSNPPIF,LEIALTISPF,LKMVTSTGLF, FHSGMLPLEI,SGMLPLEIAL,SERDYNMDFL,RDYNMDFLTL, YNMDFLTLRH,MDFLTLRHLM,NMNIMSELKM,TSTGLFQEN F,LPLEIALTIS | |
| CDC14B | c.1123C>T | p.R375C | GSVIGPQQQFLVMKQTNLWLEGDYF[p. R375C]CQKLKGQENGQHRAAFSKLLS GVDDI | LEGDYFCQKL | CRC |
| CDC25C | c.965del A | p.K322fs | ENLNRPRLKQVEKFKDNTIPDKVKK[p.K 322fs]SIFLAKESSGRAYV* | KVKKSIFLA,IPDKVKKSI,AKESSGRAV,KESSGRAVV,FLAKES SGRA,KVKKSIFLAK,LAKESSGRAY,IFLAKESSGR, IPDKVKKSIF | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CDC27 | c.1379de|T | p.L460fs | ITKLDSSIISEGKISTITPAIQAFN[p.L460fs]HKKQQQKV* | QIQAFNHKK, AFNHKKQQQK | UCS |
| CDC27 | c.1665T>G | p.D555E | EVRRIENYRVEGMEIYSTLWHLQK[p.D555E]EVALSVLSKDLTDMDKNSPEAWCAAG | TLWHLQKEV, LQKEVALSV, EVALSVLSK, WHLQKEVAL, QKEVALSVL, KEVALSVLS, HLQKEVALSV, LQKEVALSVL, TTLWHLQKEV, KEVALSVLSK | CRC |
| CDC27 | c.1712A>T | p.N571I | STTLWHLQKDVALSVLSKDLTDMDK[p.N571I]ISPEAWCAAGNCFSLQREHDIAIKFF | MDKISPEAW, KISPEAWCAA | TGCT |
| CDC27 | c.271de|A | p.I91fs | CTTPQCKYLLAKCCVDLSKLAEGEQ[p.I91fs]SYLVECLISRKAMMILLSLVIQLALLFHCWDMYIARQIGLPKDQNVTKRALV* | AMMILLLSL, MMILLLSLV, LLLSLVIQL, LLSLVIQLA, SLVIQLALI, ALLFHCWDM, CLISRKAMM, LISRKAMMI, LVECLISRK, IARQIGLPK, LVIQLALLF, LFHCWDMYI, MYIARQIGL, ISRKAMMIL, KLAEGEQSY, LLFHCWDMY, YIVECLISR, HCWDMYIAR, SRKAMMILL, RKAMMILLL, MLLLSLVI, LSLVIQLAL, DQNVTKRAL, AEGEQSYLV, GEQSYLVEC, VECLISRKA, WDMYIARQI, KLAEGEQSYL, CLISRKAMMI, KAMMILLLSL, AMMILLLSLV, MMILLLSLVI, ILLLSLVIQL, LLLSLVIQLA, LLSLVIQLAL, LLFHCWDMYI, YIARQIGLPK, YLVECLISRK, SLVIQLALLF, IQLALLFHCW, ISRKAMMILL, ALLFHCWDMY, SKLAEGEQSY, GEQSYLVECL, VECLISRKAM, SRKAMMILLL, LALLFFICWDM, VISSDTVPL, AVISSDTVPL, DSAVISSDTV | BLCA |
| CDC27 | c.724C>T | p.P242S | LESSNSKYSLNTDSSVSYIDSAVIS[p.P242S]SDTVPL6TGTSILSKQVQNKPKTGRS | KQISYSTGV, SYSTGVCSI, KQKQISYST, KQKQISYSTG, KQISYSTGVC, ISYSTGVCSI | CESC, TGCT |
| CDC4 2BPA | c.2023C>A | p.P675T | EQSEHYSKQLENELEGLKQKQISYS[p.P675T]TGVCSIEHQEITKLKTDLEKKSIFYGPCLRNRYGEDVRSALLDPDWVCPP[p. | AIAATVGSV, FIWPSFMVM, MVMTMLRNI, TMLRNIWRA, ATVGSVTAA, TVGSVTAAV, MTMLRNIWR, SSFIWPSFM, SF MVMTMLR, SFIWPSFMV, MLRNIWRAY, LRNIWRAYK, RNI WRAYKR, CPPVVGSAI, WPSFMVMTM, AAVPQESSF, ESSFI WPSF, VMTMLRNIW, QESSFIWPS, VPQESSFIW, DPDWVC PPV, VVGSAIAATV, ATVGSVTAAV, SSFIWPSFMV, FIWPSF MVMT, FMVMTMLRNI, MTMLRNIWRA, SAIAATVGSV, ML RNIWRAYK, PSFMVMTMLR, SFIWPSFMVM, IWPSFMVM TM, MVMTMLRNIW, TMLRNIWRAY, VMTMLRNIWR, WV CPPVVGSA, ESSFIWPSFM, WPSFMVMTML, TAAVPQESSF, IAATVGSVTA, QESSFIWPSF, DPDWVCPPVV, CPPVVGSAIA, VSSNGNAVK, AVSSNGNAVK, AVKDPMEILI | BRCA |
| CDCA 7L | c.1215de|C | p.P405fs | P405fs]VVGSAIAATVGSVTAAVPQESSFIWPSFMVMTMLRNIWRAYKRSW* | | CRC |
| CDH1 | c.727G>A | p.E243K | EPLDRERIATYTLFSHAVSSNGNAV[p.E243K]KDPMEILITVTDQNDNKPEFTQEVFK | | BRCA |
| CDH1 | c.760G>T | p.D254Y | TLFSHAVSSNGNAVEDDPMEILITVT[p.D254Y]YQNDNKPEFTQEVFKGSVMEGALPGT | TVTYQNDNK, MEILIVTY, YQNDNKPEF, ITVTYQNDNK, TY QNDNKPEF | STAD |
| CDH1 | c.1045G>A | p.E349K | DTQEGLIITVKKPLDYESRRLYTLKV[p.E349K]KAENTHVDPRFYYLGPFKDTTIVKIS | RLYTLKVKA, KVKAENTHV, LKVKAENTHV, LKVKAENTH, LKVKAENTHV | CRC |
| CDH1 | c.1414C>T | p.R472C | LDRELSQWHNLTVIAAEINNPKETT[p.R472C]CVAVFVRILDVNDNAPQFAVFYDTFV | TTCVAVFVR, ETTCVAVF, KETTCVAVF, ETTCVAVFVR, TTC VAVFVRI, NPKETTCVAV, KETTCVAVFV | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CDH10 | c.1731C>G | p.S577R | NGFNRHEISTYLLPVVISDNDYPIQ[p.S577R]RSTGTLTIRVCACDSQGNMQSCCSAEA | YPIQRSTGT, IQRSTGTLT, QRSTGTLTI, IQRSTGLTI, YPIQRSTGTL | LUAD |
| CDH10 | c.382C>A | p.R128S | IIDEKTGDIHATRRIDREEKAFYTL[p.R128S]SAQAINRRTLRPVEPESEFVIKIHDI | TLSAQAINR, FYTLSAQAI, EKAFYTLSA, KAFVTLSAQ, YTLSAQAINR, AFYTLSAQAI, KAFYTLSAQA, TLSAQAINRR, SAQAINRRTL, EEKAFYTLSA, REEKAFYTLS | LUAD |
| CDH11 | c.1070A>C | p.K357T | KKPVDFETKRAYSLKVEAANVHIDP[p.K357T]TFISNGPFKDTVTVKISVEDADEPPM | TFISNGPFK, NVHIDPTFI, ANVHIDPTF, PTFISNGPF, PTFISNGPFK, EAANVHIDPT, AANVHIDPTF, DPTFISNGPF | STAD |
| CDH2 | c.2020G>A | p.D674N | SKEDIRDNVIHYDDEGGGEEDTQAF[p.D674N]NIGALRNPKVIEENKIRRDIKPDSLC | TQAFNIGAL, QAFNIGALR, NIGALRNPK, DTQAFNIGA, EEDTQAFNI, TQAFNIGALR, DTQAFNIGAL, GEEDTQAFNI | CRC |
| CDH2 | c.2116C>A | p.P706T | PKVIEENKIRRDIKPDSLCLPRQRP[p.P706T]TMEDNTDIRDFIHQRLQENDVDPTAP | LCLPRQRPTM, RQRPTMEDNT | HNSC |
| CDH18 | c.2161G>T | p.A721S | KLTPRHQTSSTLESIDVQEFIKQRL[p.A721S]SEADLLDPSVPPYDSLQTYAYEGQRSE | FIKQRLSEA, KQRLSEADL, SEADLDPSV | LUAD |
| CDH18 | c.583G>A | p.A195T | EMSDMGTSVLQVTATDADDPTYGNS[p.A195T]TRVVYSILQGQPYFSVDPKTGVIRTA | STRVVYSIL, YGNSTRVVY, NSTRVVYSI, STRVVYSILQ | GBM |
| CDH20 | c.1639G>T | p.D547Y | QDPDRRTMQQNIRYTKLSDPANWLKI[p.D547Y]YPVNGQITTIAVLDRESPNVKNNIYN | KIYPVNGQI, DPANWLKIY, YPVNGQITT, YPVNGQITTI, LKIYPVNGQI | CRC |
| CDH20 | c.1298C>A | p.P433H | IQIISAKDPDVTNNSIRYSIDRSSD[p.P433H]HGRFFYVDITTGALMTARPLDREEFS | SSDHGRFFY, RSSDHGRFF, HGRFFYVDI, RSSDHGRFFY, SSDHGRFFYV, IDRSSDHGRF | LUAD |
| CDH23 | c.401C>T | p.A134V | IDDTTGDIHAIQRLDREERAQYTLR[p.A134V]VQALDRRTGRPMEPESEFIIKIQDIN | QYTLRVQAL, AQYTLRVQA, AQYTLRVQAL, YTLRVQALDR, R AQYTLRVQA, TLRVQALDRR | CRC |
| CDH23 | c.1207G>A | p.V403I | EGLNSMPEVLVGMNSHHFIISPTS[p.V403I]IQGKADIRIRVAIPLDYETVDRYDFD | HFIISPTSI, IQGKADIRI, IISPTSIQGK, HHFIISPTSI | STAD |
| CDH23 | c.3395T>A | p.F1132Y | ASVPEDIPEGHSILQLKATDADEGE[p.F1132Y]YGRVWYRILHGNHGNNFRIHVSNGLL | ATDADEGEY, EYGRVWYRI, YGRVWYRIL, DEGEYGRVW, EY GRVWYRII, KATDADEGEY, EGEYGRVWYR, GEYGRVWYRI, DEGEYGRVWY | KIRC |
| CDH23 | c.531C>A | p.F177L | FIVNATDPDLGAGGSVLYSFQPPSQ[p.F177L]LFAIDSARGIVTVIRELDYETTQAYQ | FQPPSQLFA, SFQPPSQLF, QLFAIDSAR, YSFQPPSQL, SQLFA IDSA, QPPSQLFAI, FQPPSQLFAI, LYSFQPPSQL, YSFQPPSQLF, SFQPPSQLFA, SQLFAIDSAR | CRC |
| CDH6 | c.709C>A | p.Q237K | SETGIKTALLNMDRENREQYQVVI[p.Q237K]KAKDMGGQMGGLSGTTTVNITLTDVN | KAKDMGGQM, REQYQWIKA, YQVVIKAKDM, IKAKDMGG QM | LUAD |
| CDH7 | c.673C>A | p.Q225K | PYFSVEPKTGVIKTALPNMDREAKD[p.Q225K]KYLLVIQAKDMVGQNGGLSGTTSVTV | KYLLVIQAK, EAKDKYLLV, REAKDKYLL, AKDKYLLVI, NMDRE AKDKY, EAKDKYLLVI, REAKDKYLLV | HNSC |
| CDH9 | c.1569C>A | p.F523L | ENAKPGQLIQTVSVMDKDDPPRGHK[p.F523L]LFFEPVPEFTLNPNFTIVDNKDNTAG | LFFEPVPEF, KLFFEPVPEF, RGHKLFFEPV | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CDHR1 | c.652A>G | p.R218G | QAGATLDYERSRTHYITVAKDGGG[p.R218G]GLHGADVVFSATTVTVNVED VQDMA | GLHGADVVF, GGLHGADVVF | MM |
| CDK1B | c.237_239 del\|AGA | p.E79 del\| | SPYRREDSMEDRGEEDDSLAIKPPQ[p.E79de\|]MSRKEKVHRKDEKRKEKCRHH SHSAEG | SLAIKPPQM, AIKPPQMSR, AIKPPQMSRK, LAIKPPQMSR | HNSC |
| CDK1 | c.2638C>A | p.R880S | DFGLARLYSSEESRPYTNKVITLWY[p.R880S]SPPELLLGEERRTPAIDVWSCGCIL G | TLWYSPPEL, LWYSPPELL, WYSPPELLI, ITLWYSPPEL, TLWY SPPELL, LWYSPPELLL | LUAD |
| CDK3 | c.322C>T | p.R108C | GSDGESDQASATSSDEVQSPVRVRM[p.R108C]CNHPPRKISTEDINKRLSLPADI RLP | RMCNHPPRK, RVRMCNHPP, RVRMCNHPPR, RMCNHPPR KI | CRC |
| CDK6 | c.4776C>G | p.H1592Q | LDEEHRRLREASGEWGKGQDPFRDL[p.H1592Q]QSLLMEIQALRLQLERSIETSS TLQS | RDLQSLLMEI, LQSLLMEIQA, DPFRDLQSLL | KIRC |
| CDK5 RAP2 | c.1226_1227 CA>TG | p.P409L | YKFPSLFINQFYPRPGTPAAKMEQV[p.P409L]LAQVKKQRTKDLSRVFHSYSPYD HKIG | KMEQVLAQV, AAKMEQVLA, AKMEQVLAQ, MEQVLAQVK, KMEQVLAQVK, LAQVKKQRTK, QVLAQVKKQR, TPAAKME QVL, AKMEQVLAQV | TGCT |
| CDKAL1 | c.247C>T | p.H83Y | RVAELLLHGAEPNCADPATLTRPV[p.H83Y]YDAAREGFLDTLVVLHRAGARLDV RD | VVDAAREGF, LTRPVYDAA, TLTRPVYDAA, LTRPVYDAAR, D PATLTRPVY | HNSC |
| CDKN2A | c.322G>T | p.D108Y | HDAAREGFLDTLVVLHRAGARLDVR[p.D108Y]YAWGRLPVLDLAEELGHRDVAR YLRAA | RYAWGRLPV, GARLDVRYA, AGARLDVRY, ARLDVRYAW, R AGARLDVRY, RLDVRYAWGR, GARLDVRYAW, VRYAWGRL PV, YAWGRLPVDL | LUSC |
| CDKN2A | c.92T>C | p.V31A | DVDFLEDVPLLEDIPLLED[p.V31A]APLLEDTSRLEDINLMEDMALLEDV D | PLLEDAPLL, VPLLEDAPL, APLLEDTSRL, LEDVPLLEDA, VPLL EDAPLL | KIRP |
| CDR1 | c.179C>G | p.A60G | VSAPDGPSDPSLSVSSEQSGAQQPP[p.A60G]GLQVERIVDKRKNKKGKTEYLVR WKG | AQQPPGLQV, AQQPPGLVQE | TGCT |
| CDYL | c.1918C>A | p.L640I | CHSASNPSPQYSWRINGIPQQHTQV[p.L640I]IFIAKITPNNNGTYACFVSNLATG RN | HTQVIFIAK, IPQQHTQVI, PQQHTQVIF, QQHTQVIFI, TQVIF IAKI, HTQVIFIAKI, IPQQHTQVIFIA | CRC |
| CEACAM5 | c.925G>C | p.A309P | YLNPMAAFAAAQMQQMAALNMNGL A[p.A309P]PAPMTPTSGGSTPPGITAP AVPSIPS | APAPMTPTS, LNMNGLAPA, MNGLAPAPM, ALNMNGLAP A, GLAPAPMTPT, NMNGLAPAPM | LUAD |
| CELF4 | c.1841del\|G | p.G614fs | AVDADSGENARLHYRLVDTASTFLG[p.G614fs]AAALGLRILPPPLTSPSRSTTAP VGSQCVPSWTARRWSTTASGWRRWT TARPP* | FLGAAALGL, STFLGAAAL, STTASGWRR, GLRILPPPL, PSRST TAPV, TARRWSTTA, SGWRRWTTA, GWRRWTTAR, CVPSW TARR, DTASTFLGA, TASTFLGAA, GAAALGLRI, AAALGLRIL, VGSQCVPSW, SQCVPSWTA, RRWSTTASG, RWSTTASGW, RRWTTARPP, VPSWTARRW, ILPPPLTSPS, TFLGAAALGL, R WSTTASGWR, ASGWRRWTTA, SGWRRWTTAR, SQCVPS WTAR, DTASTFLGAA, TASTFLGAAA, TTAPVGSQCV, WTAR RWSTTA, SPSRSTTAPV, ASTFLGAAAL, GAAALGLRIL, RRWS TTASGW | STAD |
| CELSR1 | c.34_35ins CGC | p.16_17 insP | MRSPATGVPLTPPPP[p.16_17insP]P LLLLLLLLPPPLLGDQVGPCRSLGSR | LPTPPPPPL, TPPPPPLL, LPTPPPLL, TPPPPLLL | ACC |
| CELSR2 | c.50T>C | p.L17P | MRSPATGVPLTPPPP[p.L17P]PLLLLL LLLPPPLLGDQVGPCRSLGS | LPTPPPPPL, TPPPPPLL, LPTPPPLL, TPPPPLLL | TGCT |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CEP15 2 | c.61G>A | p.E21K | MSLDFGSVALPVQNEDEEYD[p.E21K]KEDYEREKELQQLLTDLPHDMLDDDL | KEDYEREKEL | CRC |
| CEP19 2 | c.6173C>T | p.S205 8L | TEVYDLPQRPNDVQLFYGSMCKIIL[p.S2058L]IVIGEFRDCISSREFLQPSSKASLE S | SMCKIIILLV, IILLVIGEF, GSMCKIIILLV, SMCKIIILVI, IILLVIGEFR, KIILLVIGEF | BLCA |
| CEP44 | c.758C>T | p.S253 L | VNVNPEITALQTMLAECQENLKKLT[p.S253L]LIEKRLDCLEQKMKGKVMDENTWTN | QENLKKLTL, TLIEKRLDCL, NLKKLITLIEK, CQENLKKLTL, KKLTLIEKRL, QENLKKLTLI | UCEC |
| CERCAM | c.254_260del CGGCTGT | p.A85 fs | RARMALWCATDHNVDNTTEMLQEWL[p.A85fs]GAMTMLLWSGGLRASPGSTQMKRVPSTGPKKGTSF* | MLQEWLGAM, WLGAMTMLL, TMLLWSGGL, LLWSGGLRA, MLLWSGGLR, RVPSTGPKK, RASPGSTQM, STQMKRVPS, MTMLLWSGG, TQMKRVPST, LQEWLGAMT, QEWLGAMTM, LGAMTMLLW, MLQEWLGAMT, MTMLLWSGGL, MLL WSGGLRA, TMLLWSGGLR, RASPGSTQMK, EWLGAMTML L, WLGAMTMLLW, MKRVPSTGPK, EMLQEWLGAM, LQEW LGAMTM, QEWLGAMTML, LRASPGSTQM, TQMKRVPSTG, EMLQEWLGA | KIRC |
| CERS3 | c.285G>T | p.E95D | FVASPLAKSFGIKETVRKVTPNTVL[p.E95D]DNFFKHSTRQPLQTDIYGLAKKCNL T | NTVLDNFFK, TVLDNFFKH, DNFFKHSTR, TPNTVLDNF, VTP NTVLDNF, TPNTVLDNFF | CRC |
| CETN3 | c.189delA | p.K63 fs | TDKDEAIDYHELKVAMRALGFDVKK[p.K63fs]LMY* | GFDVKKLMY, LGFDVKKLM, LGFDVKKLMY, RALGFDVKKL | STAD |
| CFB | c.940_941C G>AT | p.R314 M | INVSVAIITFASEPKVLMSVLNDNS[p.R314M]MDMTEVISSLENANYKDHENGTGTNTY | VLNDNSMDM, NSMDMTEVI, MSVLNDNSM, LMSVLNDNS M, VLNDNSMDMT, MDMTEVISSL | SKCM |
| CFDP1 | c.386_387i nsC | p.P129 fs | ARKKKEDELWASFLNDVGPKSKVPP[p.P129fs]KYTS* | GPKSKVPPK, KSKVPPKYT, KSKVPPKYTS | LUAD |
| CFHR5 | c.1322G>A | p.R441 H | LCKENYLLPEAKEIVCKDGRWQSLP[p.R441H]HCVESTAYCGPPPSINNGDTTSF PLS | SLPHCVEST, RWQSLPHCV, LPHCVESTA, SLPHCVESTA, LPH CVESTAY, GRWQSLPHCV, WQSLPHCVES | CESC |
| CFI | c.111delA | p.K37 fs | CFHLRFCKVTVTSQEDLVEKKCLAK[p.K37fs]NILTSPAIKSSASHGRDALRAPVFVNYRISAQRMALQCVQLTGEASQHTVNKRVWNVFIQGQSF* | RMALQCVQL, TVNKRVWNV, AQRMALQCV, NILTSPAIK, A SHGRDALR, RAPVFVNYR, RISAQRMAL, LRAPVFVNY, VNYR ISAQR, DALRAPVFV, SPAIKSSAS, SASFIGRDAL, APVFVNYRI, NVFIQGQSF, KKCLAKNIL, AKNILTSPA, KNILTSPAI, RDALR APVF, YRISAQRMA, SQHTVNKRV, VNKRVWNVF, RMALQC VQLT, ALRAPVFVNY, FVNYRISAQR, RAPVFVNYRI, TVNKRV WNVF, LAKNILTSPA, KNILTSPAIK, AIKSSASHGR, KSSASHG RDA, HGRDALRAPV, SASHGRDALR, EASQHTVNKR, LTSPAI KSSA, LTGEASQHTV, HTVNKRVWNV, SPAIKSSASH, SSASH GRDAL, AKNILTSPAI, GRDALRAPVF, VNYRISAQRM, YRISA QRMAL, QRMALQCVQL, VQLTGEASQH, SQHTVNKRVW, WNVFIQGQSF, VEKKCLAKNI | STAD |
| CGB8 | c.52A>G | p.T18A | MEMFQGLLLLLLLSMGG[p.T18A]AWASREMLRPRCRPINATLAVEKEGC | AWASREMLR, GGAWASREM, GAWASREML, GAWASREM LR, MGGAWASREM | BLCA |
| CHCH D4 | c.236C>T | p.T79M | PCLGGMASGPCGEQFKSAFSCFHYS[p.T79M]MEEIKGSDCVDQFRAMQECM QKYPDL | AFSCFHYSM, SAFSCFHYS, CFHYSMEEIK, MEEIKGSDCV | HNSC |
| CHD3 | c.1789delC | p.P597 fs | WRWGEPPVAVPAPQQADGNPDVPPP[p.P597fs]VLFKADQSESSLSSG* | NPDVPPPVL, KADQSESSL, VPPPVLFKA, DVPPPVLFKA, FKA DQSESSL, NPDVPPPVLF | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CHD4 | c.2924G>A | p.R975H | LGPHMLRRLKADVFKNMPSKTELIV[p. R975H]HVELSPMQKKYYKILTRNFEAL NAR | HVELSPMQK, IVHVELSPM, TELIVHVEL, HVELSPMQKK, LIV HVELSPM, MPSKTELIVH, ELIVHVELS | CRC, UCEC |
| CHD5 | c.2401G>A | p.A801T | YVVTYTGDKESRSVIRENEFSFEDN[p.A 801T]TIRSGKKVFRMKKEVQIKFHVLLT SY | FSFEDNTIR, NTIRSGKKV, TIRSGKKVFR, EFSFEDNTIR, NTIR SGKKVF, NEFSFEDNTI | CRC |
| CHDH | c.119A>C | p.E40A | ARGALGQQQSLGARALASAGSESRD[p. E40A]AYSYVVVGAGSAGCVLAGRLTED PAE | AGSESRDAY, SESRDAYSY, ESRDAYSYV, RDAYSYVV, GSES RDAYSY, ESRDAYSYVV, DAYSYVVGA, SAGSESRDAY, SESR DAYSYV | ACC |
| CHEK2 | c.1116_1117 CA>TG | p.K373E | LKPENVLLSSQEEDCLIKITDFGHS[p.K3 73E]EILGETSLMRTLCGTPTYLAPEVLVS V | ITDFGHSEI, EILGETSLM, SEILGETSL, TDFGHSEIL, KITDFGHSEI, EILGETSLMR, SEILGETSLM | GBM |
| CHEK2 | c.1117A>G | p.K373E | LKPENVLLSSQEEDCLIKITDFGHS[p.K3 73E]EILGETSLMRTLCGTPTYLAPEVLVS | ITDFGHSEI, EILGETSLM, SEILGETSL, TDFGHSEIL, KITDFGHSEI, EILGETSLMR, SEILGETSLM | KIRC, PRAD, UCS |
| CHIT1 | c.851_852i nsC | p.P284fs | LILGMPTYGRSFTLASSSDTRVGAP[p.P 284fs]SHRVWHSRPLHQGRRDAGLL* | RVWHSRPLH, RVGAPSHRV, HSRPLHQGR, PSHRVWHSR, H RVWHSRPL, VGAPSHRVW, HQGRRDAGL, RVWHSRPLHQ, HSRPLHQGRR, DTRVGAPSHR, RPLHQGRRDA, SHRVWHS RPL, RVGAPSHRVW, HQGRRDAGLL | KIRC |
| CHN1 | c.792G>C | p.K264N | CGLNVHQCSKMVPNDCKPDLKHVK[p. K264N]NVYSCDLTTLVKAHTTKRPM VVDMCI | DLKHVKNW, VKNVYSCDL, NVYSCDLTTL, HVKNVYSCDL | LUAD |
| CHN2 | c.129C>G | p.I43M | AEEYQPPIWKSYLYQLQQEAPRPKR[p. I 43M]MICPREVENRPKYYGREFHGIISR EQ | RPKRMICPR, APRPKRMIC, QEAPRPKRM, KRMICPREV, RM ICPREVE, MICPREVENR, QQEAPRPKRM | LUSC |
| CHRNA3 | c.67_69de|CTG | p.L23del | MGSGPLSLPLAL|SPPRLLLLL[p.L23 de|SLLPVARASRAEHRLFERLFEDY NEIIR | RLLLLLLSL, RLLLLLLSLL | BLCA |
| CHRNA4 | c.1188C>G | p.S396R | LIESMHKMASAPRFWEPEGEPPAT[p. S396R]RGTQSLHPPSPSFCVPLDVPAEP GPS | ATRGTQSLH, PPATRGTQSL | LUAD |
| CHRNA9 | c.1082C>A | p.P361Q | WARVVILKYMSRVLFVYDVGESCLS[p.P 361Q]QHHSRERDHLTKVYSKLPESNLK AAR | ESCLSQHHSR, CLSQHHSRER, SQHHSRERDH, GESCLSQHH S | LUAD |
| CIC | c.1521de|C | p.R507fs | PEGNKGFGPGRKVFSPVIRSSFTHCRP[p.R 507fs]HWTLSPQGPRILL* | TLSPQGPRI, WTLSPQGPR, SFTHCRPH, SSFTHCRPH, RPH WTLSPQ, SPQGPRILL, FTHCRPHWTL, RSSFTHCRPH, HWTL SPQGPR, WTLSPQGPRI, SSFTHCRPHW | STAD |
| CIC | c.3341_3342 insG | p.A1114fs | ITAFYSGSPAPTSSAPLAQPSQAPP[p.A 1114fs]KPGLHCGHQHNPTCSHHSAQ GPASPCHCHPSPD* | AQPSQAPPK, SQAPPKPGL, HQHNPTCSH, SHHSAQGPA, A QGPASPCH, NPTCSHHSA, LAQPSQAPPK, SQAPPKPGLH, H QHNPTCSHH | STAD |
| CIC | c.3341 de|C | p.A1114fs | VITAFYSGSPAPTSSAPLAQPSQAP[p.A 1114fs|QAWSTLWPPAQPHLQPPFCP RARQPLPLPQPRLALSPAPQVP* | ALSPAPQQV, HLQPPFCPR, LWPPAQPHL, AWSTLWPPA, R ARQPLPLP, LPLPPQPRL, LPPQPRLAL, QPRLALSPA, AQPHL QPPF, SQAPQAWST, TLWPPAQPH, QPSQAPQAW, APQA WSTLW, TLWPPAQPHL, SQAPQAWSTL, HLQPPFCPRA, RA RQPLPLPP, CPRARQPLPL, AQPSQAPQAW, QAWSTLWPP A, LPLPPQPRLA, LALSPAPQQV | STAD |
| CIITA | c.2182G>A | p.E728K | AESELAFPSFLLQCPLGALWLALSG[p.E7 28K]KIKDKELPQYLALTPRKKRPYDNW LE | ALWLALSGK, LWLALSGKI, ALWLALSGKI, GALWLALSGK, L WLALSGKIK, KIKDKELPQY | UCEC |

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CILP2 | c.1657G>A | p.V553M | VTFVDPSGEFMDAVRVLPFDPRGAG[p.V553M]MYHEVKAMRKKAPVILHTSQSNTIPL | GMYHEVKAM,MYHEVKAMR,RGAGMYHEVK,MYHEVKAMRK,GMYHEVKAMR,LPFDPRGAGM,AGMYHEVKAM | GBM |
| CIRH1A | c.749G>T | p.S250I | TGTLVKSHLIANADVQSIAVADQED[p.S250I]IFVVGTAEGTVFHFQLVPVTSNSSEK | AVADQEDIFV,IAVADQEDIF,QEDIFVVGTA | HNSC |
| CIZ1 | c.2003T>C | p.V668A | SEPQHQGRLGEIQHMSQACLLSLLP[p.V668A]APRDVLETEDEEPPPRRWCNTCQLYY | SLLPAPRDV,LLSLLPAPR,CLLSLLPAPR,SLLPAPRDVL,LPAPRDVLET | CRC |
| CIZ1 | c.266T>C | p.L89P | QLLQLQOLLQQSPPQAPLPMAVSRG[p.L89P]PPPQQPQQPLLNLQGTNSASLLNGSM | LPMAVSRGPP | GBM |
| CKAP2 | c.2050T>A | p.*684K | GRETDAFVCRPNAALCRVYYEADTT[p.*684K]KEK* | RVYYEADTTK | CLL |
| CKAP5 | c.1727G>C | p.G576A | AGGPPKKGKPAAPGGAGNTGTKNKK[p.G576A]ALETKEIVEPELSIEVCEEKASAVLP | KNKKALETK,KKALETKEI | TGCT |
| CLCN2 | c.1934_1935insCCG | p.645_645R>RR | ILLGSIERSQVVALLGAQLSPARRR[p.645_645R>RR]RQHMQERRATQTSPLSDQEGPPTPEASV | QLSPARRRR,SPARRRRQ,RRRRQHMQER,SPARRRRQHM | KIRC |
| CLCNKA | c.371C>A | p.P124Q | YPVALVSFSSGFSQSITPSSGGSGI[p.P124Q]QELKTMLAGVILEDYILDIKNFGAKVV | SGIQELKTM,QELKTMLAGV,QELKTMLAG | LUAD |
| CLDN23 | c.628G>A | p.V210M | CDERCRRRKGPSAGPRRSSVSTIQ[p.V210M]MEWPEPDLAPAIKYYSDGQHRPPPAQ | RSSVSTIQM,IQMEWPEPD,MEWPEPDLA,IQMEWPEPDL,RRSSVSTIQM,SVSSTIQMEW,MEWPEPDLAP | ACC |
| CLDN7 | c.514T>G | p.S172A | DFYNPLIPTNIKYEFGPAIFIGWAG[p.S172A]AALVIGGALLSCSCPGNESKAGYRV | AIFIGWAGA,FIGWAGAAL,GWAGAALVI,FIGWAGAALV,A IFIGWAGA,IFIGWAGAAL,GWAAGAALVIL,IGWAGAALVI | KIRP |
| CLEC12B | c.650G>T | p.W217L | MSQPLLMFSFFWLGLSWDSSGRSWF[p.W217L]LEDGSVPSPSLFSTKELDQINGSKGC | FLEDGSVPS,DSSGRSWFL,RSWFLEDGSV | LUAD |
| CLEC18A | c.1268G>A | p.R423H | GQPDNHGFGNCVELQASAAFNWNNQ[p.R423H]HCKTRNRYICQFAQEHISRWGPGS* | NQHCKTRNR,AAFNWNNQH,AFNWNNQPICK,NWNNQHCKTR,NQHCKTRNRY | CRC |
| CLEC4A | c.626G>A | p.R209H | YNESSTFWHPREPSDPNERCVVLNF[p.R209H]HKSPKRWGWNDVNCLGPQRSVCEMMK | VLNFHKSPK,RCVVLNFHK,LNFHKSPKR,VVLNFHKSPK,VLNFHKSPKR,LNFHKSPKRW,NERCVVLNPH | PRAD |
| CLEC4C | c.536G>T | p.R179L | QWVDQTPYNENVTFWHSGEPNNLDE[p.R179L]LCAIINFRSSEEWGWNDIHCHVPQKS | NLDELCAII,ELCAIINFR,DELCAIINF,GEPNNLDEL | LUSC |
| CLIC6 | c.892C>G | p.Q298E | EGPAGDSMDAEGPAGRARRVSGEPQ[p.Q298E]ESGDGSLSPQAEAIEVAAGESAGRSP | EPQESGDGSL | ACC |
| CLIP1 | c.3052_3053insA | p.S1018fs | AAKKHEEKKELERKLSDLEKKMET[p.S1018fs]KPQPVSGAESQV* | KMETKPQPV,METKPQPVS,ETKPQPVSGA,KKMETKPQPV | BLCA,KIRP |
| CLK4 | c.203G>T | p.R68L | CKPHHQFKESDCHYLEARSLNERDY[p.R68L]LDRRYVDEYRNDYCEGYVPRHYHRDI | RSLNERDYL,LDRRYVDEY,RDYLDRRYV,YLDRRYVDEY,SLNERDYLDR,NERDYLDRRY | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CLN3 | c.616G>A | p.G206S | ISWWSSGTGGAGLLGALSYLGLTQA[p.G206S]SLSPQQTLLSMLGIPALLLASYFLLL | YIGLTQASL,SLSPQQTLL,ASLSPQQTL,SYLGLTQASL,LSYLG LTQAS,ASLSPQQTLL | LUSC |
| CLSTN1 | c.1844C>T | p.T615M | LEGEDLGELDKAMQHISYLNSRQFP[p.T615M]MPGIRRLKITSTIKCFNEATCISVP | YLNSRQFPM,RQFPMPGIR,QFPMPGIRR,FPMPGIRRL,MP GIRRLKI,RQFPMPGIRR,SYLNSRQFPM,NSRQFPMPGI | STAD |
| CLSTN2 | c.2276C>T | p.P759L | YSIYGVGSMSRYEQVLHHIRYRNWR[p.P759L]LASLEARRFRRIKCSELNGRYTSNE FN | HIRYRNWRL,RYRNWRLAS,RLASLEARR,YRNWRLASL,LAS LEARRF,RYRNWRLASL,HIRYRNWRLA,RLASLEARRF,NWR LASLEAR,LASLEARRFR,HHIRYRNWRL,RNWRLASLEA | HNSC |
| CLUL1 | c.1387G>C | p.G463R | SELANQAPETEIIFNSIQVVPRIHE[p.G463R]RNISKQDETMTDLSILPSSNFTLKI | RIHERNISK,QVVPRIFIER,VPRIHERNI,RNISKQDETM | KIRC |
| CMA1 | c.242T>A | p.I81K | IRRNFVLTAAHCAGRSITVTLGAHN[p.I81K]KTEEEDTWQKLEVIKQFRHPKYNTST | TVTLGAHNK,ITVTLGAHNK,KTEEEDTWQK | CLL |
| CMAS | c.329G>A | p.R110Q | FQSVWVSTDHDEIENVAKQFGAQVH[p.R110Q]QRSSEVSKDSSTSLDAIIEFLNYHNE | HQRSSEVSK,QFGAQVHQR,KQFGAQVHQ,AQVHQRSSEV, KQFGAQVHQR | CRC |
| CMIP | c.688G>A | p.A230T | EIVSKLLSENTNLTTQEHENIIVAI[p.A230T]TPLLENNHPPDLCEFFCKHCRERPR | IIVAITPLL,NIIVAITPL,HENIIVAIT,NIIVAITPLL | CLL |
| CMTM8 | c.77G>C | p.S26T | MEEPQRARSHTVTTASSFAENFST[p.S26T]TSSSFAYDREFLRTLPGFLIVAEIVL | STTSSSFAY,TSSSFAYDR,FSTTSSSFA,AENFSTTSS, NSSFAENFST,FSTTSSSFAY,TSSSFAYDR,ENFSTTSSSF, SSFAENFSTT,AENFSTTSSS | TGCT |
| CNBD1 | c.1187T>C | p.L396P | RSIIGFVKLRSNKVKRSQKLVYMGK[p.L396P]PKEKESFGEISVLLQVPFTCTIITKK | KLVYMGKPK,LVYMGKPEK,MGKPKEKESF | STAD |
| CNGA4 | c.1529A>C | p.K510T | AEIALQEATESRLRGLDQQLDDLQT[p.K510T]TFARLLAELESSALKIAYRIERLEWQ | TFARLLAEL,QLDDLQTTF,LQTTFARLL,QLDDLQTTFA,TTFA RLLAEL,QOLDDLQTTF,LQTTFARLLA | STAD |
| CNKSR2 | c.746C>T | p.P249L | SEGLGMYIKSTYDGLHVITGTTENS[p.P249L]LADRCKKIHAGDEVIQVNHQTVVGWQ | SLADRCKKI,NSLADRCKK | TGCT |
| CNOT3 | c.58G>A | p.E20K | MADKRKLQGEIDRCLKKVS[p.E20K]KGVEQFEDIWQKLHNAANANQKEKYE | CLKKVSKGV,KVSKGVEQF,KKVSKGVEQF | PRAD |
| CNOT6 | c.744del|T | p.S248fs | QEILSCNADIVSLQEVETEQYYSFF[p.S248fs]W* | TEQYYSFFW | STAD |
| CNRIP1 | c.304C>T | p.R102W | EPDGDRMYTGTYDTEGVTPTKSGE[p.R102W]WQPIQITMPFTDIGTFETVWQVKFYN | EWQPIQITM,TKSGEWQPI,GEWQPIQIT,WQPIQITMPF,G EWQPIQITM | CRC |
| CNTFR | c.754G>T | p.D252Y | QTPSTWPDPESSPLKFFLRYRPLIL[p.D252Y]YQWQHVELSDGTAHTITDAYAGKEYI | LILYQWQHV,YRPLLIYQW,LYQWQHVEL,RYRPLLILYQ,LRYR PLILY,YQWQHVELS,ILYQWQHVEL,PLILYQWQHV,FLRYR PLILY,RYRPLLILYQ,YQWQHVELSD | LUAD |
| CNTN5 | c.1136C>T | p.S379F | LEIPNVQLDDAGIYECRAENSRGKN[p.S379F]FFRGQLQVTYPHHVEKLNDTQLDSG | NSRGKNFFR,FFRGQLQVY,AENSRGKNF,GKNFFRGQL,RG KNFFRGQL,KNFFRGQLQV,NFFRGQLQVY,ENSRGKNFFR, RAENSRGKNF,AENSRGKNFF | SKCM |
| CNTN5 | c.533C>A | p.T178N | IDGTFIISNPSEAKDSGHYQCLATN[p.T178N]NVGSILSREATLQFAYLGNFSGRTRS | YQCLATNNV,LATNNVGSI,CLATNNVGSI,HYQCLATNNV,Y QCLATNNVG,LATNNVGSIL | LUSC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CNTN6 | c.2420G>T | p.R807M | NNEGEGSLSTVTIVYSGEDEPQLAP[p.R807M|MGTSLQSFSASEMEVSWNAIA WNRNT | QLQPMGTSL,PMGTSLQSF,APMGTSLQSF,GEDEPQLAPM, PQLAPMGTSL | LUAD |
| CNTNAP1 | c.3086G>T | p.S1029I | EPGTWMRYNLQSALRSAAREFSHML[p.S1029I]IRPVPGYEPGYIPGYDTPGYVP GYHG | FSHMLIRPV,MLIRPVPGY,REFSHMLIR,AAREFSHMLI,HM LIRPVPGY,EFSHMLIRPV,REFSHMLIRP | PRAD |
| CNTNAP2 | c.1185C>A | p.F395L | EPYTVPFFNATSYLEVPGRLNQDL[p.F395L]LSVSFQFRTWNPNGLLVFSHFAD NLG | RLNQDLLSV,LLSVSFQFR,DLLSVSFQF,NQDLLSVSF,LLSVSF QFRT,DLLSVSFQFR,LNQDLLSVSF,QDLLSVSFQF | LUAD |
| CNTNAP4 | c.1307A>C | p.Y436S | LFSELQLISGGILLFLSDGKLKSNL[p.Y436S]SQPGKLPSDITAGVELNDGQWHSV SL | KSNLSQPGK,KLKSNLSQPG,KSNLSQPGKL | KIRC |
| CNTNAP4 | c.34A>T | p.I12F | MLLFYLLVVLS[p.I12F]FDSTKASALTNPNVALFLLADDCDDP | VLSFDSTKA,VVLSFDSTK,FYLLVVLSF,FDSTKASAL,LVVLSF DSTK,LFYLLVVLSF,LSFDSTKASA | CLL |
| CNTRL | c.553C>T | p.P185S | SKIEGIENMCNLQKLNLAGNEIEHI[p.P185S]SVWLGKKLKSLRVLNLKGNKISSLQ D | HISVWLGKK,SVWLGKKLK,EIEHISVWL,NEIEHISVW,ISVW LGKKL,ISVWLGKKLK,NEIEHISVWL | CESC |
| CNTROB | c.2759_2760 insG | p.R920fs | PKTEKPPARKKSGHPAPSSMRSRGG[p.R920fs]SLEMSPPTLSPLCSLIVILINAH* | TLSPLCSLI,SMRSRGGSL,MSPPTLSPL,RSRGGSLEM,SPLCS LIVV,SLEMSPPTL,LEMSPPTLS,TLSPLCSLIV,SLVVILINA, EMSPPTLSPL,SMRSRGGSL,SMRSRGGSLE,RSRGGSLEMS, SPLCSLIVVI,MRSRGGSLEM,GSLEMSPPTL,LEMSPPTLSP IDNNSTASY,RIDNNSTASY,IDNNSTASYL | STAD |
| COBLL1 | c.2196A>C | p.K732N | DPLTVKDPICAHGNDDLLPPVDRID[p.K732N]NNSTASYLKNYPLYRQDYNPKPK PSN | | CRC |
| COG5 | c.1850A>G | p.H617R | TKVVSSQSSFPLAAEQTIISALKA[p.H617R]RALMENAVQPLLTSVGADIEAIITM STVGALNKIGTDGTQVAMVQFTDDP[p.R1082I]ITEFKLNAYKTKETLLDAIKHISY KG | ALKAIRALM,AIRALMENA,IISALKAIR,SALKAIRAL, AIRALMENAV,SALKAIRALM,TIISALKAIR,ISALKAIRAL FTDDPITEF,ITEFKLNAY,MVQFTDDPI,VQFTDDPIT,FTDDP ITEFK,AMVQFTDDPI,ITEFKLNAYK,QFTDDPITEF | TGCT |
| COL14A1 | c.3245G>T | p.R108I | | | CRC |
| COL15A1 | c.2123A>G | p.K708R | ARGPNGSVGEKGDPGNRGLPGPPGK[p.K708R]RGQAGPPGVMGPPGPGPP GPPGPGC | RGQAGPPGVM | TGCT |
| COL18A1 | c.2652de|C | p.G884fs | DRGSRGEKGDPGKDGVGQPGLPGPP[p.G884fs]DPRDLWSTCRSRTDPS* | DLWSTCRSR | KIRP |
| COL19A1 | c.1613C>A | p.P538Q | GPPGLIGSPGLKGQQQSAGSMGPRG[p.P538Q]QPGDVGLPGEHGIPGKQGLKG EKGDP | GPRGQPGDV | LUAD |
| COL4A6 | c.16480A | p.L550I | GPAGAPGLVGPLGPSGPKGKKGEPI[p.L550I]ISTIQGMPGDRGDSGSQGFRGV IGEP | KGKKGEPII,KKGEPIISTI,EPIISTIQGM | CRC |
| COL5A2 | c.1546G>T | p.G516W | QGPIGPPGEEGKRGPRGDPGTVGPP[p.G516W]WPVGERGAPGNRGFPGSDGL PGPKGA | GTVGPPWPV,DPGTVGPPW | LUAD |
| COL5A2 | c.1834G>T | p.G612W | LGPLGAPGEDGRPGPPGSIGIRGQP[p.G612W]WSMGLPGPKGSSGDPGKPGE AGNAGV | WSMGLPGPK,SIGIRGQPW,RGQPWSMGL,QPWSMGLPG, GSIGIRGQPW,IGIRGQPWSM | LUAD |
| COL6A3 | c.7133C>A | p.A2378D | GQKGDPGYPGAPGPKGNRGDSIDQC[p.A2378D]DLIQSIKDKCPCCYGPLECPV FPTEL | DSIDQCDLI | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| COL6A3 | c.8374G>A | p.D2792N | YFFVVLGIGRKVNIKEVYTFASEPN[p.D2792N]NVFFKLVDKSTELNEEPLMRFGRLLP | NVFFKLVDK, FASEPNNVF, ASEPNNVFF, EPNNVFFKL, YTFASEPNNV, ASEPNNVFFK, TFASEPNNVF, FASEPNNVFF, EPNNVFFKLV, SEPNNVFFKL | CRC |
| COL6A5 | c.6671C>T | p.T2224M | QEDFLGGNGFIGQELNSGRESPFVK[p.T2224M]MEDNGSDYLVLYLPSQMFEPQKLMINY | KMEDNGSDY, MEDNGSDYL, KMEDNGSDYL, SGRESPFVK, M, VKMEDNGSDY, MEDNGSDYLV | GBM |
| COL9A1 | c.632C>A | p.P211Q | GVERSSATLFVDCNRIESLPIKPRG[p.P211Q]QIDIDGFAVLGKLADNPQVSVPFELQ | QIDIDGFAV, GQIDIDGFA, LPIKPRGQI, GQIDIDGFAV | LUAD |
| COL9A1 | c.848del C | p.P283fs | RITPSQTTDERGPPGPGQGPGPGP[p.P283fs]LEFQASMASTVTEVLRAPRAPRVLQVNRESQELQASLAHLALMD* | FQASMASTV, SMASTVTEV, ELQASLAHL, LQASLAHLA, VLRAPRAPR, ASLAHLALM, VTEVLRAPR, MASTVTEVL, ESQELQASL, GPLEFQASM, LEFQASMAS, RESQELQAS, QELQASLAH, QASLAHLAL, TEVLRAPRA, ASMASTVTEV, SMASTVTEVL, L QASLAHLAL, FQASMASTVT, VLRAPRAPRV, ELQASLAHLA, MASTVTEVLR, TVTEVLRAPR, EVLRAPRAPR, ESQELQASLA, APPRAPRVLQV, LEFQASMAST, LRAPRAPRVL, LQVNRESQE L, RESQELQASL, SQELQASLAH, QELQASLAHL, QASLAHLALM | STAD |
| COPB1 | c.1273C>T | p.R425C | NVIPVLMEFLSDNNEAAAADVLEFV[p.R425C]CEAIQRFDNLRMLIVEKMLEVFHAIK | EFVCEAIQR, DVLEFVCEA, FVCEAIQRF, EFVCEAIQRF, DVLEFVCEAI, CEAIQRFDNL | CRC |
| COQ2 | c.196G>T | p.V66L | SFALARAAGAPHGGDLQPPACPEPR[p.V66L]WRQLSLSAAAVVDSAPRPLQPYLRLM | RWRQLSLSA, CPEPRWQL, EPRWRQLSL, WRQLSLSAA, R WRQLSLSAA, WRQLSLSAAA, QPPACPEPRW | ACC |
| CORO2A | c.1576T>A | p.*526R | LTQREVQAKQLELEIKNLRMGSEQL[p.*526R]RAETSALLTLRDTTRLHGEV* | QLRAETSAL, TLRDTTRLH, ETSALLTLR, LLTLRDTTR, DTTRLH GEV, LRAETSALL, AETSALLTL, SEQLRAETS, QLRAETSALL, LLTLRDTTRL, NLRMGSEQLR, SEQLRAETSA, EQLRAETSAL, RA ETSALLTL | CRC |
| COX15 | c.256C>A | p.L86I | PSKAABRVVGRWLLVCSGTVAGAVI[p.L86I]IGGVTRLTESGLSMVDWHLIKEMKPP | VIIGGVTRL | CRC |
| COX6A1 | c.23C>T | p.S8L | MAVVGVS[p.S8L]LIVSRLLGRSRPQLGRPMSSGAHGEEG | MAVVGVSLIV, SLVSRLLGR, AVVGVSLVSR, VSLVSRLLGR, LV SRLLGRSR | BLCA |
| CPAMD8 | c.2352de1 C | p.P784fs | TDEAVPAFQPHTGSLVAVAPSRHPP[p.P784fs]EQRREKGLSSPKHGFGIVSTSVTHLVRGHSV* | IVSTSVTHL, STSVTHLVR, REKGLSSPK, VSTSVTHLV, SPKHG FGIV, GLSSPKHGF, IVSTSVTHLV, GIVSTSVTHL, VSTSVTHLV R, VTHLVRGHSV, HGFGIVSTSV, KGLSSPKFGF, FGIVSTSVT H | STAD |
| CPE | c.869C>A | p.P290Q | SAHEYSSSPDDAIFQSLARAYSSFN[p.P290Q]QAMSDPNRPPCRKNDDDSSFVDGTTN | RAYSSFNQA, AYSSFNQAM, RAYSSFNQAM | LUAD |
| CPNE8 | c.381G>T | p.Q127H | SKSPNLSKHDFPLGQVFCTLGEIVGS[p.Q127H]HGSRLLEKPIVGIPGKKCGTILITAE | GSHGSRLEK, EIVGSHGSR, GEIVGSHGS, VGSHGSRLEK, EIV GSHGSRL | LUAD |
| CPS1 | c.2564C>A | p.T855K | TPRLPMNKEWPSNLDLRKELSEPSS[p.T855K]KRIYAIAKAIDDNMSLDEIEKLTYID | SSKRIYAIA, SKRIYAIAK, ELSEPSSKR, SEPSSKRIY, LSEPSSKRIY, SSKRIYAIAK, EPSSKRIYAI, KRIYAIAKAI | LUSC |
| CPSF4 | c.656C>A | p.P219Q | NPPLQRSSSLIQLTSQNSSPNQQRT[p.P219Q]QQVIGVMQSQNSSAGNRGPRPLEQVT | RTQQVIGVM, NQQRTQQVI, SPNQQRTQQV, QQRTQQVIG V, QRTQQVIGVM | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CR1L | c.237del A | p.L79 fs | PIGTYLNYECRPGYSGRPFSIICLK[p.L79 fs]TQSGQVLRTSANVNHVILQIL* | CLKTQSGQV,QVLRTSANV,RTSANVNHV,KTQSGQVLR,TS ANVNHVV,LKTQSGQVL,SANVNHVVI,ANVNHVVIL,,GQVL RTSANV,RTSANVNHVV,TSANVNHVVI,NVNHVVILQI,CLK TQSGQVL,SANVNHVIL | STAD |
| CR2 | c.618del C | p.V206 fs | ESGYLLVGEKIINCLSSGKWSAVPP[p.V 206fs]HVKRHAVNL* | WSAVPPHVK,KWSAVPPHV,HVKRHAVNL,SAVPPHVKR,P PHVKRHAV,GKWSAVPPH,SGKWSAVPPH,KWSAVPPHVK, WSAVPPHVR,VPPHVKRHAV,GKWSAVPPHV | STAD |
| CRB1 | c.1883del T | p.L628 fs | SICAFQNSFLGGLPVGMTSNGVALL[p.L 628fs]TSIICHPHLRL* | SIICHPHLR,SIICHPHLRL,TSIICHPHLR,MTSNGVALLT, LTSIICHPHL | HNSC |
| CRB1 | c.1888T>G | p.F630 V | ICAFQNSFLGGLPVGMTSNGVALLN[p. F630V]VYNMPSTPSFVGCLQDIKIDWN HITL | NGVALLNVY,VALLNVINM,LLNVYNMPST,VYNMPSTPSF, SNGVALLNVY,TSNGVALLNV | STAD |
| CRB2 | c.3329C>T | p.T111 0M | GWEGPRCEAHVDPCHSAPCARGRCH[p. T1110M]MHPDGRFECRCPPGFGGP RCRLPVPS | RGRCHMHPD,CHMHPDGRF,RGRCHMHPDG,APCARGRC HM,RCHMHPDGRF,HMHPDGRFEC | ACC |
| CREBB P | c.4303G>C | p.D143 5H | FGMHVQEYGSDCPPPNTRRVVISYL[p. D1435H]HSIHFFRPRCLRTAVHEILIGY LEY | YLHSIHFPR,HSIHFPRPR,VYISYLHSI,ISYLHSIHF,SYLHS IHFF,RVYISYLHS,YISYLHSIH,RVYISYLHSI,SYLHSIHF FR,YISYLHSIHF,ISYLHSIHFF | BLCA |
| CREBB P | c.4337G>A | p.R144 6H | CPPPNTRRVVISYLDSIHFFRPRCL[p.R1 446H]HTAVVHEILIGYLEVVKKLGYVTG HI | HFFPRRCLH,HTAVVHEIL,RPRCLHTAV,FFRPRCLHT,CLHT AVVHEI,FFRPRCLHTA,RPRCLHTAVV,HTAVVHEILI | DLBCL |
| CREBB P | c.6281C>T | p.P209 4L | DLLRTLKSPSSPQQQQQVLNILKSN[p.P 2094L]LQLMAAFIKQRTAKYVANQPG MQPQP | VLNILKSNL,ILKSNLQLM,NLQLMAAFI,LQLMAAFIK,KSNL QLMAA,SNLQLMAAF,LKSNLQLMA,ILKSNLQLMA,NLQL MAAFIK,KSNLQLMAAF,LKSNLQLMAA | UCEC |
| CREBB P | c.142_143i nsCG | p.M48 fs | PACSCAHVECPPAHTCRCGVPACSH[p. M48fs]TCPCGVPACSHVPMRSARLLT HVSMWSAHLLMCPCGVPTCSHVPM WSATCSHTCPCGVPACSRAHVECPPAH TCRCGVPACSHVPMRSARLLTRAHAEC PPAHTCPCGVPACSHVPTWSARLLTRA HVECPPAHTCQRGVPA* | SMWSAHLLM,HLLMCPCGV,WSARLLTHV,HVSMWSAHL, RLLTHVSMW,LTHVSMWSA,HTCQRGVPA,MWSARLLTH, TWSARLLTR,VPTCSHVPM,VPACSRAHV,VPTWSARLL,AR LLTHVSM,THVSMWSAH,VSMWSAHLL,LMCPCGVPT,SH VPMWSAT,LLTHVSMWSA,SMWSAHLLMC,LLMCPCGVP T,HVSMWSAHLL,GVPACSRAHV,SARLLTHVSM,PTWSAR LLTR,HVPTWSARLL,ARLLTHVSMW,LTHVSMWSAH,THV SMWSAHL,VSMWSAHLLM,VPTCSHVPMW,VPMWSATC SH | BLCA |
| CRIPA K | c.427T>C | p.C143 R | SHVPMRSARLLTRAHAECPPAHTCP[p. C143R]RGVPACSHVPMRSARLLTRAD VECPP | HTCPRGVPA,CPPAHTCPR,RGVPACSHV | ACC |
| CRIPA K | c.520T>C | p.C174 R | SHVPMRSARLLTRADVECPPAHTCP[p. C174R]RGVPACSHVPTWSARLLTRAHV ECSP | HTCPRGVPA,CPPAHTCPR,RGVPACSHV | ACC |
| CRIPA K | c.538_568 del TCA CACCT GCCAA CGTGG AGTGC | p.S180 fs | LTRADVECPPAHTCPCGVPACSHVP[p. S180fs]MWSARLLTRADVECLPAHTCP CGVFACSHVPMRSARLLTRADAECPPA HTCPCGVPACSRADVECPPAHTCPCGV PACSRADVGCPPAHMCRCGVPACSHV PMWSARLLTRADVECPPAHVPIWSARL LTRAIVECPPAHTHADVECPPAHTCPCG VPACSHVPMWSARLLTHVPMWSARLL TRAHVECLPAHTRAHVECPPAHTKPW HGGSVGFLSCRPSQTLLPYILLMVAF* | FLSCRPSQT,TLLPYILLM,LLPYILLMV,CLPAHTCPC,HMCRC GVPA,WSARLLTHV,GSVGFLSCR,VFACSHVPM,RLLTHVP MW,PWHGGSVGF,PYILLMVAF,HTCPCGVFA,SARLLTRAI, LTRAHVECL,RAHVECLPA,MWSARLLTH,RPSQTLLPY,FAC SHVPMR,IWSARLLTR,DVECPPAFV,HVPIWSARL,QTLLPYI LL,VPACSRADV,VPIWSARLL,LPAHTRAHV,AHTCPCGVF,R AIVECPPA,ARLLTHVPM,AHVECLPAH,LSCRPSQTL,SQTLL PYIL,LPYILLMVA,CPPAHVPIW,CPPAHTKPW,LLTRAHVEC L,CLPAHTRAHV,FLSCRPSQTL,TLLPYILLMV,LLPYILLMVA, LLTRADVECL,HVECPPAHTK,GVFACSHVPM,SARLLTRAD | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CRIPAK | c.568A>C | p.I190L | ECPPAHTCPCGVPACSHVPTWSARL[p. I190L]LTRAHVECSPAHTCRCGVPACSH VPM | A, SARLLTRAIV, SARLLTHVPM, HTKPWHGGSV, VFACSHVP MR, PAHVPIWSAR, PIWSARLLTR, HVECLPAHTR, HVPIWS ARLL, WSARLLTRAI, KPWHGGSVGF, RPSQTLLPYI, LPYILLM VAF, SRADVGCPPA, ADVGCPPAHM, AHMCRCGVPA, VECP PAHVPI, AHVPIWSARL, RAIVECPPAH, ARLLTHVPMW, RA HVECLPAH, LSCRPSQTLL, CRPSQTLLPY, SQTLLPYILL, VECL PAHTRA, VECPPAHTA, LPAHTCPCGV, CPPAHTHADV | ACC |
| CRISPLD1 | c.664C>T | p.R222W | PKAVYLVCNYSPKGNWWGHAPYKHG[p. R222W]WPCSACPPSFGGGCRENLC YKEGSDR | TWSARLLTR, VPTWSARLL, PTWSARLLTR, HVPTWSARLL | BRCA |
| CROCC | c.1063G>C | p.A355P | RTSRAVQEAGLGLSTGLRLAESRAE[p.A 355P]PALEKQALLQAQLEEQLRDKVLR EKD | APYKHGWPC, YKHGWPCSA, WPCSACPPS, WPCSACPPSF, YKHGWPCSAC | KIRP |
| CROT | c.1740G>T | p.Q580H | DPLFSKSGGGNFVLSTSLVGYLRV[p.Q 580H]HGVVVPMVHNGYGFFYHIRDDR FVVA | EPALEKQAL, AESRAEPAL, RLAESRAEPA, ESRAEPALEK, AEP ALEKQAL | LUAD |
| CROT | c.96delA | p.L32fs | TEERTPQYQDSLPSLPVPSLEESLK[p.L 32fs]NTLNQSPEHATR* | YLRVHGVVV, GYLRVHGVV, RVHGVVVPM, RVHGVVVPMV, LVGYLRVHGV, GYLRVHGVVV, LRVHGVVVPM | STAD |
| CRTC3 | c.1088C>T | p.S363L | NKTVLSSSLNNHPQTSVPNASALHP[p.S 363L]LLRLFSLSNPSLSTTNLSGPSRRRQ P | LEESLKNTL | LUAD |
| CRYGB | c.427A>G | p.R143G | HLTEIHSLNVLEGSWILYEMPNYRG[p.R 143G]GQYLLRPGEYRRFLDWGAPNAK VGSL | ASALHPLLR, ALHPLLRLF, NASALHPLL, HPLLRLFSL, SALHPL LRLF, NASALHPLLR, VPNASALHPL | TGCT |
| CRYGD | c.476delG | p.G159fs | YEMPNYRGRQYLLRPGDYRRYHDWG[p. G159fs]VQMPKSAL* | NYRGGQYLL, MPNYRGGQY, YEMPNYRGG, EMPNYRGGQ Y, GQYLLRPGEY, NYRGGQYLR, MPNYRGGQYL | STAD |
| CRYM | c.943T>A | p.*315K | FKSLGMAVEDTVAAKLLYDSWSSGK[p. *315K]KNKGT* | RYHDWGVQM, GVQMPKSAL, RRYHDWGVQM, WGVQM PKSAL | CLL |
| CSDE1 | c.658C>T | p.R220C | NVQLETGDKINFVIDNNKHTGAVSA[p. R220C]CNIMLLKKKQARCQGVVCAMK EAFGF | SWSSGKKNK | UCEC |
| CSF2RB | c.892G>A | p.G298S | SFGLFYKPSPDAGEEECSPVLREGL[p.G 298S]SSLHTRHHCQIPVPDPATHGQYI VSV | SACNIMLLK, GAVSACNIM, AVSACNIMLL, VSACNIMLLK, S ACNIMLLKK, HTGAVSACNI | GBM |
| CSF3R | c.1404delC | p.P468fs | SLWVGWEPPNPWPQGVVIEWGLGPP[p. P468fs]ARAIATRPGGWNRMGEPRG FC* | VLREGLSSL, EGLSSLHTR, REGLSSLHT | STAD |
| CSGALNACT2 | c.1086G>T | p.L362F | VSLNEEFNRGRGLNVGARAWDKGEV[p. L362F]FMFFCDVDIYFSAEFLNSCRL NAEPG | ATRPGGWNR, RAIATRPGG, EWGLGPPAR, IEWGLGPPA, A TRPGGWNRM, IATRPGGWNR, RAIATRPGGW, IEWGLGPP AR | ACC, KIRP, TGCT |
| CSHL1 | c.350G>A | p.R117Q | SSNMEETQQKSNLELHISLLLIES[p.R1 17Q]QLEPVRFLRSTFTNNLVYDTSDSD DY | FMFFCDVDI, EVFMFFCDV, RAWDKGEVF, GEVFMFFCD, A WDKGEVFMF, VFMFFCDVDI, RAWDKGEVFM, FMFFCDV DIY, ARAWDKGEVF, GEVFMFFCDV | CESC |
| CSMD2 | c.5564C>A | p.P1855Q | PTCVVPCGGNLTERRGTILSPGFPE[p.P 1855Q]QYLNSLNCVWKIVVPEGAGIQI QVVS | SLLLIESQL, LIESQLEPV, SQLEPVRFL, QLEPVRFLR, LLI ESQLEPV, SQLEPVRFLR, LIESQLEPVR, LSLLLIESQL, IESQLEPVRF | LUAD |

Additional peptides for last row: QYLNSLNCV, FPEQYLNSL, GFPEQYLNSL, QYLNSLNCVW, IL SPGFPEQY, EQYLNSLNCV TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CSMD3 | c.2071C>A | p.Q691K | DPGTPLYGIREGDGFSNRDVLRFEC[p.Q691K]KFGFELIGEKSIVCQENNQWSANIPI | LRFECKFGF,FECKFGFEL,RFECKFGFEL,VLRFECKFGF,RDVLRFECKF,FECKFGFELI | LUSC |
| CSMD3 | c.2854C>T | p.H952Y | AEPGHSIKITFERFQTELNYDVLEV[p.H952Y]YDGPNLLSPLLGSYNGTQVPQFLFS | LNYDVLEVY,EVVDGPNLL,LEVYDGPNL,ELNYDVLEVY,EVYDGPNLLS,LEVYDGPNLL,YDGPNLLSPL | CESC |
| CSMD3 | c.3281C>A | p.T1094K | GDVRGPSGTILSPGYPEFYPNSLNC[p.T1094K]KWTVDVTHGKVQFNFHTPHLEDHHD | NSLNCKWTV,YPNSLNCKW,SLNCKWTVDV,FYPNSLNCKW,KWTVDVTHGK,EFYPNSLNCK | LUSC |
| CSMD3 | c.511G>A | p.E171K | STKSVFSLRLTSDFAVSAHGFKVYY[p.E171K]KELQSSSCGNPGVPPKGVLYGTRFDV | AHGFKVYYK,SAHGFKVYYK,HGFKVYYKEL | GBM |
| CSMD3 | c.522G>T | p.Q174H | SVFSLRLTSDFAVSAHGFKVYYEEL[p.Q174H]HSSSCCNPGVPPKGVLYGTRFDVGDK | YEELHSSSC,HSSSCGNPGV | LUAD |
| CSMD3 | c.7149_7150insT | p.F2383fs | LESVYSTSNQILIKFHSDFTTSGFF[p.F2383fs]CAQLSRLSTKGVPTSTTCAQC* | FTTSGFFCA,AQLSRLSTK,GFFCAQLSR,LSRLSTKGV,QLSRLSTKGV,SGFFCAQLSR,CAQLSRLSTK,TTSGFFCAQL,AQLSRLSTKG | LIHC |
| CSMD3 | c.8179C>A | p.P2727T | LEHGRMRIVNGSHYEYKTKVVFSCD[p.P2727T]TGYHGLGPASIECLPNGTWSWRNERP | VVFSCDTGY,VVFSCDTGYH,KTKVVFSCDT,KVVFSCDTGY,FSCDTGYHGL,DTGYHGLGPA | LUAD |
| CSMD3 | c.8429C>A | p.T2810N | CDLGFMLVGSAVRECLSSGLWSESE[p.T2810N]NRCLAGHCGIPELIVNGQVIGENYGY | SESENRCLA,SENRCLAGH | LUAD |
| CSPG5 | c.355G>A | p.D119N | AVTGTAWLEADSPGLGGVTAEAGSG[p.D119N]NAQALPATLQAPHEVLGQSIMPPAIP | VTAEAGSGNA,AEAGSGNAQA | BLCA |
| CT47B1 | c.702728de|GAAGCTCACAGAGAGGCCACAGAGGA | p.234_243EKLTEEATEE>E | DLAEMAREPAEEAADEKPPEEAAEE[p.234_243EKLTEEATEE>E]PAAEEPTSEEAVAPEEVTKSQPEKMDEEAQDAAGEEEKEQEKEDVENKVKN | EEEAAEEPAA,AEEPAAEEPT | BRCA |
| CTAGE15P | c.1091C>T | p.A364V | IIQISFVDKTKFFITFHIKNIQTQQ[p.A364V]VSLQSENIYFESENQKLQQKLKIMTE | VSLQSENIY,NLQTQQVSL,HIKNLQTQQV,QVSLQSENIY,K NLQTQQVSL,QQVSLQSENI,VSLQSENIYF | KIRP |
| CTCF | c.604_605insAA | p.K202fs | EQGELPQEDPSWQKDPDYQPPAKK[p.K202fs]KQRKPKRANCVIQRRAKM* | RANCVIQRR,KPKRANCVI,KQRKPKRANC,RANCVIQRRA | STAD |
| CTCF | c.604del|A | p.K202fs | EQGELPQEDPSWQKDPDYQPPAKK[p.K202fs]QRKPKRANCVIQRRAKM* | RANCVIQRR,KPKRANCVI,KQRKPKRANC,RANCVIQRRA | STAD |
| CTCFL | c.1267G>A | p.E423K | YECHICHTRFTQSGTMKIHILQKHG[p.E423K]KNVPKYQCPHCATTIARKSDLRVHMR | ILQKHGKNV,KHGKNVPKY,KIHILQKHGK,LQKHGKNVPK,QKHGKNVPKY | CRC |
| CTDNEP1 | c.376G>A | p.E126K | KHPVRFVHKRPHVDFFLEVVSQWY[p.E126K]KLVVFTASMEIYGSAVADKLDNSRSI | KLVVFTASM,VVSQWYKLV,SQWYKLVVF,WYKLVVFTA,EV VSQWYKL,YKLVVFTAS,FLEVVSQWYK,VSQWYKLVVF,EV VSQWYKLV,YKLVVFTASM,LEVVSQWYKL,SQWYKLVVFT | CRC |
| CTNNA3 | c.2567_2568insAA | p.K856fs | IIRIQSPAGPRHPVVWMRMKAPAKK[p.K856fs]NP* | RMKAPAKKNP | STAD |
| CTNNB1 | c.1004A>T | p.K335I | ESKLIILASGGPQALVNIMRTYTYE[p.K335I]ILLWTTSRVLKVLSVCSSNKPAIVEA | IMRTYTYEI,YTYEILLWT,ILLWTTSRV,TYTYEILLW,TYE ILLWTT,RTYTYEIL,EILLWTTSR,MRTYTYEIL,YEILLW | LIHC |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CTNNB1 | c.100G>A | p.G34R | ELDMAMEPDRKAAVSHWQQQSYLDS[p.G34R]RIHSGATTTAPSLSGKNPEEEDVDT | TTS,NIMRTYTYEI,YTYEILLMTT,ILLWTTSRVL,IMRTY TYEIL,RTYTYEILLM,EILLWTTSRV,MRTYTYEILL,YEI LLWTTSR QQSYLDSRI,RIHSGATTT,YLDSRIHSGA,RIHSGATTTA,QQ QSYLDSRI,QQSYLDSRIH | UCEC |
| CTNNB1 | c.101G>T | p.G34V | ELDMAMEPDRKAAVSHWQQQSYLDS[p.G34V]VIHSGATTTAPSLSGKNPEEEDVDT | QQQSYLDSV,YLDSVIHSG,QQQSYLDSVI,WQQQSYLDSV,YL DSVIHSGA,VIHSGATTTA,QQQQSYLDSVI,QQSYLDSVIH | LIHC |
| CTNNB1 | c.107A>C | p.H36P | DMAMEPDRKAAVSHWQQQSYLDSGI[p.H36P]PSGATTTAPSLSGKGNPEEEDVDTSQ | YLDSGIPSG,IPSGATTTA,YLDSGIPSGA | LIHC |
| CTNNB1 | c.109T>G | p.S37A | MAMEPDRKAAVSHWQQQSYLDSGIH[p.S37A]AGATTTAPSLSGKGNPEEEDVDTSQV | YLDSGIHAG,IHAGATTTA,YLDSGIHAGA,GIHAGATTTA,AG ATTTAPSL | UCEC |
| CTNNB1 | c.110C>G | p.S37C | MAMEPDRKAAVSHWQQQSYLDSGIH[p.S37C]CGATTTAPSLSGKGNPEEEDVDTSQV | YLDSGIHCGA,GIHCGATTTA | UCEC |
| CTNNB1 | c.110C>T | p.S37F | MAMEPDRKAAVSHWQQQSYLDSGIH[p.S37F]FGATTTAPSLSGKGNPEEEDVDTSQV | YLDSGIHFG,SYLDSGIHF,IHFGATTTA,YLDSGIHFGA, GIHFGATTTA,QSYLDSGIHF,IHFGATTTAP,FGATTTAPSL | LUAD,UCEC |
| CTNNB1 | c.1161G>A | p.N387K | GMQALGLHLTDPSQRLVQNCLWTLR[p.N387K]KLSDAATKQEGMEGLLGTLVQLLGSD | VQNCLWTLRK | LIHC |
| CTNNB1 | c.121A>G | p.T41A | PDRKAAVSHWQQQSYLDSGIHSGAT[p.T41A]ATAPSLSGKGNPEEEDVDTSQVLYEW | ATAPSLSGK,GATATAPSL,GIHSGATATA,TATAPSLSGK,SG ATATAPSL | PRAD |
| CTNNB1 | c.122C>T | p.T41I | PDRKAAVSHWQQQSYLDSGIHSGAT[p.T41I]ITAPSLSGKGNPEEEDVDTSQVLYEW | ITAPSLSGK,SGIHSGATI,TITAPSLSGK,SGATTTAPSL | UCEC |
| CTNNB1 | c.133T>C | p.S45P | AAVSHWQQQSYLDSGIHSGATTTAP[p.S45P]PLSGKGNPEEEDVDTSQVLYEWEQGF | TTAPPLSGK,GATTTAPPL,TTAPPLSGK,SGATTTAPPL | ACC,LIHC |
| CTNNB1 | c.94G>A | p.D32N | LMELDMAMEPDRKAAVSHWQQQSYL[p.D32N]NSGIHSGATTTAPSLSGKGNPEEEDV | YLNSGIHSG,QQQSYLNSGI,WQQQSYLNS,QQQSYLNSGI, NSGIHSGA,QQQSYLNSGI,WQQQSYLNSG,QQSYLNSGIH | LIHC,UCEC |
| CTNNB1 | c.94G>T | p.D32Y | LMELDMAMEPDRKAAVSHWQQQSYL[p.D32Y]YSGIHSGATTTAPSLSGKGNPEEEDV | YLYSGIHSG,QQSYLYSGIH,HWQQQSYLY,WQQQSYLYS,QQ QSYLYSG,QSYLYSGIH,YLYSGIHSGA,QQQSYLYSGI,SHWQ QSYLY,WQQQSYLYSG,QQSYLYSGIH | UCEC |
| CTNNB1 | c.95A>G | p.D32G | LMELDMAMEPDRKAAVSHWQQQSYL[p.D32G]GSGIHSGATTTAPSLSGKGNPEEEDV | YLGSGIHSG,WQQQSYLGS,QQQSYLGSG,QQSYLGSGI,QS YLGSGIH,YLGSGIHSGA,WQQQSYLGSG,QQQSYLGSGI,Q QSYLGSGIH | CESC,LIHC |
| CTNNB1 | c.95A>T | p.D32V | LMELDMAMEPDRKAAVSHWQQQSYL[p.D32V]VSGIHSGATTTAPSLSGKGNPEEEDV | QQSYLVSGI,YLVSGIHSG,LVSGIHSGA,HWQQQSYLV,WQ QQSYLVS,QQQSYLVSG,QSYLVSGIH,YLVSGIHSGA,QQQS YLVSGI,SHWQQQSYLV,WQQQSYLVSG,QQSYLVSGIH | LIHC |
| CTNNB1 | c.97T>C | p.S33P | MELDMAMEPDRKAAVSHWQQQSYLD[p.S33P]PGIHSGATTTAPSLSGKGNPEEEDV | YLDPGIHSG,WQQQSYLDP,QQSYLDPG,QSYLDPGI,YL DPGIHSGA,WQQQSYLDPG,QQQSYLDPGI,QQSYLDPGIH | LIHC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CTNNB1 | c.98C>A | p.S33Y | MELDMAMEPDRKAAVSHWQQQSYL D[p.S33Y]YGIHSGATTTAPSLSGKGNPE EEDVD | YLDYGIHSG, WQQQSYLDY, YLDYGIHSGA, H WQQQSYLDY, QQQSYLDYGI, QQSYLDYGIH | UCEC |
| CTNNB1 | c.98C>G | p.S33C | MELDMAMEPDRKAAVSHWQQQSYL D[p.S33C]CGIHSGATTTAPSLSGKGNP EEDVD | YLDCGIHSG, WQQQSYLDC, QQQSYLDCGI, YLDCGIHSGA, Q QQSYLDCGI, QQSYLDCGIH | LIHC,UCEC |
| CTNNB1 | c.98C>T | p.S33F | MELDMAMEPDRKAAVSHWQQQSYL D[p.S33F]FGIHSGATTTAPSLSGKGNPE EEDVD | YLDFGIHSG, WQQQSYLDF, QQQSYLDFGI, QSYLDFGIH, YLDF GIHSGA, HWQQQSYLDF, QQQSYLDFGI, QQSYLDFGIH | UCEC |
| CTNND1 | c.1341del A | p.I447 fs | VHLGACGALKNISFGRDQDNKIAIK[p.I 447fs]TVMVCLPLCDCFERLVIWTLLKLL PEPCGIFHPMTQSKWRLWTMHCMP* | KIAIKTVMV, KLLPEPCGI, AIKTVMVCL, LVIWTLLKL, RLVI WTLLK, KTVMVCLPL, IFHPMTQSK, QSKWRLWTM, KWRLWT MHC, EPCGIFHPM, NKIAIKTVM, LPEPCGIFH, RLVIWTLLI, LLPEPCGIF, S KWRLWTMH, WRLWTMHCM, LPEPCGIFH, RLVIWTLKL, L VIWTLLKLL, GIFHPMTQSK, CFERLVIWTL, KLLPEPCGIF, IFHPMTQSKW, KWRLWTMHCM, HPMTQSKWRL, TQSKWRL WTM, IAIKTVMVCL, IKTVMVCLPL, FERLVIWTLL, LPLCDCF ERL, PEPCGIFHPM | STAD |
| CTSC | c.315del T | p.F105 fs | NSGHFTIYNQGFEIVLNDYKWFAF[p.F 105fs]LSIKKRAR* | FLSIKKRAA, KWFAFLSIK, WFAFLSIKK, LSIKKRAAR, FAFL SIKKR, YKWFAFLSI, NDYKWFAFL, KWFAFLSIKK, DYKWF AFLSI, WFAFLSIKKR, FLSIKKRAAR | STAD |
| CTSD | c.267_268i nsC | p.P89 fs | GPIPEVLKNYMDAQYYGEIGIGTPP[p.P 89fs]PVLHSRLRHGLLQPVGPLHPLQTA GHRLLDPPQVQQRQVQHLREEWYLV* | GLLQPVGPL, HLREEWYLV, HSRLRHGLL, RLRHGLLQP, QQR QVQHLR, VQHLREEWY, QPVGPLHPL, IGIGTPPPV, LRHGLL QPV, LQTAGHRLL, VQQRQVQEIL, RQVQHLREE, RLRHGLLQ PV, VLHSRLRHGL, HSRLRHGLLQ, QVQHLREEWY, EIGIGTP PPV, PPPVLHSRL, HPLQTAGHRL, IGIGTPPPVL, LQPVGPL HPL, RQVQHLREEW, VQHLREEWYL, GEIGIGTPPP | STAD |
| CTTNBP2 | c.1259C>T | p.S420 L | TSSTPLPSNAAPPTAQTPGIAPQN[p.S 420L]LQAPPMHSLHSPCANTSLHPGLN PRI | LQAPPMHSL, PQNLQAPPM, NLQAPPMHSL, QTPGIAPQN L, APQNLQAPPM, LQAPPMHSLH | UCEC |
| CTTNBP2 | c.490C>T | p.R164 C | LEMEKLQLQALEQEHKLAARLEEE[p.R 164C]CGKNKQVVLMLVKECKQLSGKVI EEA | CGKNKQVVL, KLAARLEEEC, AARLEEECGK | CRC |
| CUBN | c.1786G>T | p.G596 C | EHLRNGRGFTVRWETQQPECGGILT[p. G596C]CPYGSIKSPGYPGNYPPGRDCV WIVV | ILLTCPYGSI, LTCPYGSIK, CGGILTCPY, ILLTCPYGSIK | LUAD |
| CUBN | c.8448C>G | p.I281 6M | GGGFYATWNTQTLGCCGIFHSDNGT[p. I2816M]MRSPHWPQNFPENSRCSWT AITHKSK | TMRSPHWPQ, IFHSDNGTM, TMRSPHWPQN, IFHSDNGT MR, GIFHSDNGTM, MRSPHWPQNF | KIRP |
| CUL1 | c.1453G>A | p.E485 K | DVFQKFYAKMLAKRLVHQNSASDDA[p. E485K]KASMISKLKQACGFEYTSKLQR MFQD | KASMISKLK, DAKASMISK, AKASMISKL, SASDDAKASM | BLCA |
| CUL7 | c.1113G>C | p.L371 F | QAQPSFRRSRRFPRSEFASGNTYA[p.L 371F]FYVRDTLQPGMRVRMLDDYEEIS AGD | ASGNTYAFY, FASGNTYAF, YAFYVRDTL, FASGNTYAFY, EFA SGNTYAF, TYAFYVRDTL, SGNTYAFYVR | LUAD |
| CUL9 | c.5178T>G | p.D172 6E | SPRCWPVSPLCVLYHPRKCLPTEFC[p.D 1726E]EALDRFSSFYSQSQNHPVLDMG PHRR | CLPTEFCEA, LPTEFCEAL, EALDRFSSF, CEALDRFSS, CLPTEF CEAL, EALDRFSSFY, TEFCEALDRF, CEALDRFSSF | KIRC |
| CUX1 | c.1316_131 7insC | p.A439 fs | LSGSARRKGKDQPESRRPGSLPAPP[p.A 439fs]SFSVAPQPGGAGFQY* | LPAPPSFSV, APQPGGAGF, GSLPAPPSF, QPGGAGFQY, SLP APPSFSV, FSVAPQPGGA, LPAPPSFSVA | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| CWC2 5 | c.1090A>G | p.K364 E | EELERKRQEMMENAKWREEERLNIL[p. K364E]ERHAKDEREQRLEKLDSRDGK FIHR | RLNILERHAK | KIRC |
| CXCL9 | c.366G>C | p.K122 N | KKQKNGKKHQKKKVLLKVRKSQRSRQ[p. K122N]NKT* | KSQRSRQNK | LUAD |
| CXCR4 | c.1033G>C | p.E345 Q | VSRGSSLKILSKGKRGGHSSVSTES[p.E3 45Q]QSSSFHSS* | STESQSSSF, SQSSSFHSS, VSTESQSSSF | LUAD |
| CXXC1 | c.468G>C | p.Q156 H | MLARGSASPHKSSPQPLVATPSQHH[p. Q156H]HQQQQQIKRSARMCGECEAC RRTEDC | HHHQQQQQI | TGCT |
| CXorf 51B | c.127G>A | p.V43I | QTPSTSTKGRKKGKTPQRRSRSGI[p. V43I]IKGLKTTRKAKRPLRGSSSQKAGE TN | RQRRSRSGI, QRRSRSGIK, RSRSGIKGL, RSRSGIKGLK, RQRR SRSGIK, GIKGLKTTRK, RRSRSGIKGL | KIRC |
| CXorf 59 | c.593G>T | p.R198 M | LLHLSGKMPPGINSSQSLPVDNHEK[p. R198M]MVIQLHLQHSSLLDFLNAQGG CISHV | LPVDNHEKM, HEKMVIQLH, HEKMVIQLHL, LPVDNHEKM V | LUAD |
| CYP11 B1 | c.1492C>G | p.R498 G | LVRVFLYSLGRNPALFPRPERYNPQ[p.R 498G]GWLDIRGSGRNFYHVPFGFGMR QCLG | RYNPQGWLDI | LUAD |
| CYP19 A1 | c.1216T>C | p.F406 L | DVIDGYPVKKGTNIILNIGRMHRLE[p.F 406L]LFPKPNEFTLENFAKNVPYRYFQP FG | IGRMHRLEL, MHRLELFPK, ELFPKPNEF, GRMHRLELF, RMH RLELFPK, LFPKPNEFTL, NIGRMHRLEL, IGRMHRLELF, LELFP KPNEF | TGCT |
| CYP19 A1 | c.338G>T | p.S113 I | WISGEETLIISKSSSMFHIMKHNHY[p.S 113I]ISRFGSKLGLQCIGMHEKGIIFNN NP | HIMKHNHYI, YISRFGSKL, HYISRFGSK, ISRFGSKLG, KHNHYI SRF, HYISRFGSKL, IMKHNHYISR, NHYISRFGSK, ISRFGSKLG L, MKHNHYISRF, FHIMKHNHYI | THCA |
| CYP1A 2 | c.1447G>A | p.V483 M | CIGEVLAKWEIPLFLAILLQQLEFS[p.V48 3M]MPPGVKVDLTPIYGLTMKHARCEH VQ | LLQQLEFSM, FSMPPGVKV, MPPGVKVDL, QQLEFSMPP, LE FSMPPGV, ILLQQLEFSM, QLEFSMPPGV, SMPPGVKVDL, L QQLEFSMPP, QQLEFSMPPG | BRCA |
| CYP27 A1 | c.335C>A | p.P112 Q | LYKAKYGPMWMSYLGPQMHVNLASA [p.P112Q]QLLEQVMRQEGKYPVRND MELWKEHR | ASAQLLEQV, HVNLASAQL, VNLASAQLL, SAQLLEQVM, LAS AQLLEQV, HVNLASAQLL, MHVNLASAQL, ASAQLLEQVM | LUAD |
| CYP2B 6 | c.1331C>A | p.A444 E | ALKKTEAFIPFSLGKRICLGEGIAR[p.A44 4E]EELFLFFTTILQNFSMASPVAPEDID | IAREELFLF, AREELFLFF, EELFLFFT, GEGIAREEL, REELFLFFT, GIAREELFLF, IAREELFLFF, EELFLFFTTI, GEGIAREELF, REELFLFFT | LUAD |
| CYP2D 6 | c.1055A>G | p.H352 R | VQRRVQQEIDDVIGQVRRPEMGDQA[p. H352R]RMPYTTAVIHEVQRFGDIVPL GVTHM | MGDQARMPY, RMPYTTAVI, QARMPYTTA, ARMPYTTAV, QARMPYTTAV, EMGDQARMPY, REMGDQARM, ARMPY TTAVI, RMPYTTAVIH | GBM |
| CYP4A 11 | c.553G>T | p.V185 F | GLMADSVRVMLDKWEELLGQDSPLE[p. V185F]FFQHVSLMTLDTIMKCAFSH QGSIQV | LGQDSPLEF, GQDSPLEFF, LEFFQHVSL, EFFQHVSLM, SPLE FFQHV, FFQHVSLMTL, DSPLEFFQFIV, LLGQDSPLEF, LEFFQ HVSLM, LGQDSPLEFF | OV |
| CYP4B 1 | c.1302G>T | p.E434 D | HIYALHRNSAVWPDPEVFDSLRFST[p.E 434D]DNASKRHPFAFMPFSAGPRNCI GQQF | SLRFSTDNQA, RPSTDNASK, TDNASKRHPF | CRC |
| CYP7B 1 | c.995A>C | p.K332 T | YLLRHPEAMAAVRDEIDRLLQSTGQ[p. K332T]TKGSGFPIHLTREQLDSLICLESSI F | QTKGSGFPI, RLLQSTGQTK, GQTKGSGFPI, TKGSGFPIHL | STAD |
| DAB2I P | c.481G>A | p.E161 K | ILGQDYCFEVTTSSGSKCFSCRSAA[p.E1 61K]KRDKWMENLRRAVHPNKDNSRR VEHI | CFSCRSAAK, FSCRSAAKR, RSAAKRDKW, KCFSCRSAAK, SC RSAAKRDK, CFSCRSAAKR, AKRDKWENL | BRCA |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| DACH2 | c.1615C>T | p.R539C | TMQKRLKKEKKTKRKLQEALEFESK[p.R539C]CREQVEQALKQATTSDSGLRMLKDTG | FESKCREQV, EALEFESKCR | CRC |
| DACH2 | c.1616G>T | p.R539L | TMQKRLKKEKKTKRKLQEALEFESK[p.R539L]LREQVEQALKQATTSDSGLRMLKDTG | KLREQVEQA, EALEFESKL, FESKLREQV, KLREQVEQAL, EALE FESKLR, QEALEFESKL | LUAD |
| DBC1 | c.646G>A | p.V216I | AIKVTETRTGPLGCNSYDNLDSVSS[p.V216I]ILLQSTESKLHLQGLQIIFPQYLQEK | NLDSVSSIL, ILLQSTESK, NLDSVSSILL, ILLQSTESKL, SILLQSTESK, YDNLDSVSSI | CRC |
| DBF4B | c.761C>A | p.S254Y | PFLKIEDESRKFRPFHHQFKSFPEI[p.S254Y]YFLGPKDASPFEAPTTLGSMHHTRES | KSFPEIYFL, SPPEIYPLG, QFKSFPEIY, FKSFPEIYF, QFKSFPEIYF, HQFKSFPEIY, FKSFPEIYFL | CRC |
| DCAF12L2 | c.737G>A | p.R246H | RMDPDMPNGSIAWHSEVGLPVYAHI[p.R246H]HPRDVEAIPRASTNPSNRKVRALAFS | PVYAHIHPR, HIHPRDVEA, HIHPRDVEAI, VYAHIHPRDV, LP VYAHIHPR | GBM |
| DCC | c.1337G>A | p.R446H | AIPSSSVLPSAPRDVVPVLVSSRFV[p.R446H]HLSWRPPAEAKGNIQTFTVFFSREGD | LVSSRFVHL, SSRFVHLSW, VLVSSRFVH, VHLSWRPPA, VLVSSRFVHL, FVHLSWRPPA, HLSWRPPAEA, SSRFVHL SWR, VSSRFVHLSW | LUAD |
| DCHS1 | c.703del|C | p.R235fs | LDRENRSHYMLQLEAYDGGSPPRRA[p.R235fs]RPCWT* | SPPRRARPC | STAD |
| DCHS2 | c.6447C>A | p.F2149L | TRENTVEYSIISGNSQNNFHVETK[p.F2149L]LFHSEYPYKQVGYIVLLHSLDREASA | KLFHSEYPY, LFHSEYPY, NFHVETKLF, ETKLFHSEY, KLFHSE YPYK, NNFHVETKLF, VETKLFHSEY, TKLFHSEYPY | CRC |
| DCLK2 | c.1646C>A | p.S549Y | HGLSIVHRDIKPENLLVCEYPDGTK[p.S549Y]YLKLGDFGLATWEGPLYTVCGTPTY | YLKLGDFGL, CEYPDGTKY, TKYLKLGDF, YLKLGDFGLA, KYLK LGDFGL, YPDGTKYLKL, CEYPDGTKYL | CRC |
| DCLRE1B | c.82T>A | p.F28I | GVLIPHTPIAVDFWSLRRAGTARLF[p.F28I]ILSHMHSDHTVGLSSTWARPLYCSPI | RLFILSHMH, RAGTARLFI, ARLFILSHM, ILSHMHSDHT, GTA RLFILSH, RAGTARLFIL, TARLFILSHM, RRAGTARLFI | TGCT |
| DCT | c.1595G>A | p.R532Q | LVVMGTLVALVGLFVLLAFLQYRRL[p.R532Q]QKGYTPLMETHLSSKRYTEEA* | RRLQKG, RLQKGYTPLM, AFLQYRRLQK, LQYRRLQKGY, RRL QKGYTPL, FLQYRRLQK, LQKGYTPLM, QYRRLQKGY, LQY | UCEC |
| DCUN1D4 | c.824T>C | p.L275P | EKDQRSLDINTAKCMLGLLLGKIWP[p.L275P]PFPVPHQFLEQSKYKVINKDQWCNVL | LLLGKIWPP, LLGKIWPPF, KIWPPFVF, PPFVPHQFL, GKIW PPFPV, PPFPVPHQF, LLLGKIWPPF, LGKIWPPFPV, KIWPPF PVFH, GKIWPPPFVF, WPPFPVPHQF | THCA |
| DDC | c.1297del|A | p.I433fs | LVCFRLKGSNKVNEALLQRINSAKK[p.I433fs]STWHFVTSGTSLSCALPSVLARWNLPMCSGPGNTSKSWRPTCCEQRGSRSEASCRNQKLRDISENWNKKQINIILPSWNSAVCGFPCLSPKLSRGL* | SLSCALPSV, VLARWNLPM, ILPSWNSAV, CGFPCLSPK, CAL PSVLAR, CSGPGNTSK, ASCRNQKLK, ALPSVLARW, SWNSA VCGF, SAKKSTWFH, GSRSEASCR, INSAKKSTW, AKKSTWFH V, KKSTWFFIVT, FHVTSGTSL, SGTSLSCAL, LSCALPSVL, LKR DISENW, KQINIILPS, SAVCGFPCL, LPSWNSAVC, CLSPKLLSR VL, VLARWNLPMC, IILPSWNSAV, ILPSWNSAVC, CLSPKLSR GL, RSEASCRNQK, CALPSVLARW, KQINIILPSW, SAKKSTWF HV, SVLARWNLPM, SWRPTCCEQR, STWHFVTSGT, TSLSCA LPSV, NIILPSWNSA, NSAVCGFPCL, LPSVLARWNL, WNKKQ INIIL, RINSAKKSTW, INSAKKSTWF, WFHVTSGTSL, SEASCR NQKL, KLKRDISENW, CGFPCLSPKL, CEQRGSRSEA | STAD |
| DDI1 | c.824G>A | p.R275Q | VNGHPLKAFVDSGAQMTIMSQACAE[p.R275Q]QCNIMRLVDRRWAGVAKGVGTQRIIG | AEQCNIMRL, SQACAEQCNI, AEQCNIMRLV | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| DDX1 | c.1126G>A | p.A376T | PYYGSRLAIPAAQLVVLPYQMLLHA[p.A376T]TTRQAAGIRLQDQVVIIDEAHNLIDT | LLHATTQA,TTRQAAGIR,QMLLHATTR,YQMLLHATT,LH ATTRQAA,MLLHATTQA,LLHATTRQA,TTRQAAGIRL,Y QMLLHATTR,LPYQMLLHAT | TGCT |
| DDX1 | c.622del|A | p.K208fs | AERLEQLESGEEELVLAEYESDEEK[p.K208fs]RWRAEWMRMRMTWRKNT* | MRMRMTWRK,RWRAEWMRM,EWMRMRMTW,RAEW MRMRM,WMRMRMTWR,RMRMTWRKN,EEKRWRAEW, AEWMRMRMT,WMRMRMTWRK,RWRAEWMRM,RM RMTWRKNT,EWMRMRMTWR,RWRAEWMRMR,WRAE WMRMRM,AEWMRMRMTW,DEEKRWRAEW | TGCT |
| DDX11L2 | c.382T>C | p.*128Q | CLFLSLEPPPRDHISHCLLSAQFH[p.*128Q]QK* | LLSAQFHQK,CLLSAQFHQK | UCS |
| DDX1 | c.488del|G | p.G163fs | HPEVARLTPYEVDELRRKKEITVRG[p.G163fs]EMFVLNPCLPSIMLTSHNM* | VLNPCLPSI,SIMLTSHNM,ITVRGEMFV,KEITVRGEM,GEM FVLNPC,EMFVLNPCL,NPCLPSIML,LPSIMLTSH,FVLNPCLP SI,VLNPCLPSIM,EITVRGEMFV,KKEITVRGEM,KEITVRGE MF,GEMFVLNPCL | STAD |
| DDX39B | c.447_448insT | p.F149fs | LAFQISKEYERPSKYMPNVKVAVFF[p.F149fs]WWSVYQEG* | VAVFFWWSV,AVFFWWSVY,FWMSVYQEG,VKVAVFFW W,KVAVFFWWSV,VAVFFWWSVY | KIRC |
| DDX5 | c.986G>T | p.R329L | FNQGFYDCVIATDAEVLGAPVKGKR[p.R329L]LGRGPKGDKASDPEAGVARGIDFHHV | LGRGPKGDK,KGKRLGRGPK,RLGRGPKGDK | LUAD |
| DEFA1 | c.270G>T | p.W90C | DCYCRIPACIAGERRYGTCIYQGRL[p.W90C]CAFCC* | IYQGRLCAF,IYQGRLCAFC,CIYQGRLCAF | LUAD |
| DENND2A | c.1496G>T | p.R499L | GRKKRKIPKLVLRINAIYEVRRGKK[p.R499L]LVKRLSQSMESNSGKVTDENSESD SD | RGKKLVKRL,LVKRLSQSM,YEVRRGKKL,KLVKRLSQSM,EV RRGKKLVK,YEVRRGKKLV | LUAD |
| DENND2A | c.2063G>A | p.R688Q | EVYCIVSRLGCFSLFSRILDEVEKR[p.R688Q]QGISPALVQPLMRSVMEAPF PALGKT | KRQGISPAL,RQGISPALV,EKRQGISPAL,VEKRQGISPA | LUAD |
| DENND4A | c.1070C>A | p.P357H | LYRYSISGPHVLPIEKHISHFMHKV[p.P357H]HFPSPQRPRILVQLSPHDNLI LSQPV | FMHKVHFPS,KVHFPSPQR,HFPSPQRPR,ISHFMHKVF,SH FMHKVHF,KVHFPSPQRP,ISHFMHKVHF,FMHKVHFPSP | CRC |
| DENND4C | c.3242G>A | p.R1081Q | ESEKSSPAVSRSKTFTGRFKQQTPS[p.R1081Q]THKERSTSLSALVRSSPHGSLG SVV | RFKQQTPSQ,KQQTPSQTH,RFKQQTPSQT,KQQTPSQTHK, FKQQTPSQTH | CRC |
| DENND5B | c.3068G>A | p.G1023E | GELGDTGVMQIPKNLLEMTFECQNL[p.G1023E]EKLTTVQIGHDNSGLLAKWLV DCVMV | FECQNLEKL,LEKLTTVQI,CQNLEKLTTV,MTFECQNLEK | HNSC |
| DGCR8 | c.1552G>A | p.E518K | SVQDAPTKKEFVINPNGKSEVCILH[p.E518K]KYMQRVLKVRPVYNFFECENPSE PFG | ILHKYMQRV,KSEVCILHK,CILHKYMQR,KYMQRVLKV,HKY MQRVLK,SEVCILHKY,LHKYMQRVL,KSEVCILHKY,CILHKY MQRV,ILHKYMQRVL,LHKYMQRVLK,KYMQRVLKVR,SEV CILHKYM,HKYMQRVLKV | THCA |
| DGKB | c.38C>T | p.S13L | MTNQEKWAHLSP[p.S13L]LEFSQLQK YAEYSTKKLKDVLEEFHG | EKWAHLSPL,WAHLSPLEF,LEFSQLQKY,HLSPLEFSQL,KW AHLSPLEF,QEKWAHLSPL,LEFSQLQKYA | BRCA |
| DHPS | c.147C>A | p.F49L | LPPESTQVRGYDFNRGVNYRALLEA[p.F49L]LGTTGFQATNFGRAVQQVNAMIE KKL | ALLEALGTT,ALGTTGFQA,NYRALLEAL,LEALGTTGF,EALGT TGFQA,LLEALGTTGF,VNYRALLEAL | CESC |
| DHRS4 | c.653T>C | p.I218T | LGLNKTLAIELAPRNIRVNCLAPGL[p.I218T]TKTSFSRMLWMDKEEESMKETL RIR | CLAPGLTKT,LTKTSFSRM,GLTKTSFSR,APGLTKTSF,TKTSFS RML,GLTKTSFSRM,LTKTSFSRML,LAPGLTKTSF,TKTSFSR MLW | LIHC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| DHTKD1 | c.1229G>A | p.R410Q | DIGKLVGCAIIHVNGDSPEEVVRAT[p.R410Q]QL4FEYQRQFRKDVIIDLLCYRQWGH | TQLAFEYQR,VVRATQLAF,RATQLAFEY,EVVRATQLA,EEVVRATQL,ATQLAFEYQR,VVRATQLAFE,VRATQLAFEY,QLAFEYQRQF,EVVRATQLAF,EEVVRATQLA | CRC |
| DHX9 | c.119T>G | p.V40G | RKMTPSYEIRAVGNKNRQKFMCEVQ[p.V40G]GEGYNYTGMGNSTNKKDAQSNAARDF | GEGYNYTGM,FMCEVQGEGY,CEVQGEGYNY | LUSC |
| DIAPH2 | c.361G>A | p.E121K | ERSLNLSEKEVLDLFEKMMEDMNLN[p.E121K]KEKKAPLRNKDFTTKREMVVQYISAT | MMEDMNLNK,LNKEKKAPL,KMMEDMNLNK,KEKKAPLRNK,NLNKEKKAPL | UCEC |
| DICER1 | c.5113G>A | p.E170 5K | KAYLLQAFTHASYHYNTITDCYQRL[p.E1705K]KFLGDAILDYLITKHLYEDPRQHSPG | RLKFLGDAI,ITDCYQRLK,LKFLGDAIL,ITDCYQRLKF,RLKFLGDAIL,TITDCYQRLK,KFLGDAILDY,YQRLKFLGDA | CLL |
| DIRAS1 | c.235G>T | p.G79C | VCTLQITDTTGSHQFPAMQRLSISK[p.G79C]CHAFILVFSVTSKQSLEELGPIYKLI | SISKCHAFI,RLSISKCHA,ISKCHAFIL,LSISKCHAF,MQRLSISKC,KCHAFILVF,SISKCHAFII,ISKCHAFIIV,LSISKCHAFI,RLSISKCHAF,MQRLSISKCH,SKCHAFILVF | KIRC |
| DIS3 | c.2339G>A | p.R780K | CSGMDNDFHHYGLASPIYTHFTSPI[p.R780K]KRYADVIVHRLLAVAIGADCTYPELT | YTHFTSPIK,HFTSPIKRY,FTSPIKRYA,SPIKRYADV,IKRYADVIV,KRYADVIVH,YTHFTSPIKR,ITYTHFTSPIK,SPIKRYADVI,THFTSPIKRY,IKRYADVIVH | MM |
| DISP1 | c.2194_2195GG>TT | p.G732L | EKVLPCIVIKPRYLWLFWFLALTVG[p.G732L]LAYIVCINPKMKLPSLELSEFQVFRSS | FLALTVGLA,ALTVGLAYI,LTVGLAYIV,WFLALTVGL,LALTVGLAY,FLALTVGLAY,ALTVGLAYIV,LAYIVCINPK,FWFLALTVGL,LALTVGLAYI | SKCM |
| DISP1 | c.2287C>T | p.R763C | INPKMKLPSLELSEFQVFRSSHPFE[p.R763C]YDAEYKKLFMFERVHHGEELHMPIT | RSSHPFECY,HPFECYDAE,CYDAEYKKLF,HPFECYDAEY,FRSSHPFECY | CRC |
| DISP2 | c.3062T>C | p.F1021S | VAGTVLLTVGLLVLLEWQLNTAEAL[p.F1021S]LSLSASVGLSVDFTVNYCISYHLCPHP | NTAEALSLS,EALSLSASV,LNTAEALSL,AEALSLSAS,LSLSASVGL,ALSLSASVGL,SLSASVGLSV,QLNTAEALSL,NTAEALSLSA,WQLNTAEALS,AEALSLSASV | KIRC |
| DKK2 | c.689G>A | p.R230H | KPVLHQGEVCTKQRKKGSHGLEIFQ[p.R230H]HCDCAKGLSCKVWKDATYSSKARLHV | EIFQHCDCA,FQHCDCAKGL,LEIFQHCDCA | CRC |
| DLC1 | c.1049C>T | p.A350V | LATQEPTDNQVRLRKKEIREDRDR[p.A350V]VRLDSMVLLIMKLDQLDQDIENALST | RVRLDSMVL,RDRVRLDSM,VRLDSMVLL,REDRDVRL,RV,RLDSMVLLI,EIREDRDVR,KEIREDRDRV | CRC |
| DLC1 | c.2222G>C | p.S741T | ISALNGNRINVPMVRKRSVSNSTQT[p.S741T]TSSSSQSETSSAVSTPSPVTRTRSLS | RSVSNSTQTT | BLCA,PRAD,TGCT,THCA |
| DLC1 | c.666G>T | p.E222D | ISLSELKDAPKVNAVDTLNVKDIAP[p.E222D]DKQLLNSAVIAQQRRKPDPPKDENER | NVKDIAPDK | CRC |
| DLEU7 | c.248C>T | p.A83V | RARPGPGREERGGVGTRSRRTAAR[p.A83V]VNSPEEEVVRGAEGGAELLPFPRDRG | RSRRTAARV,RTAARVNSP,RSRRTAARVN,RTAARVNSPE | ACC |
| DLG2 | c.1871C>T | p.S624L | KRRVERKERARLKTVKFNAKPGVID[p.S624L]LKGSFNDKRKKSFIFSRKPFFYKNKE | GVIDLKGSF,NAKPGVIDLK,DLKGSFNDKR | UCEC |
| DLGAP3 | c.1130delG | p.G377fs | GLLGPETKAKARTYHYLQVPQDDWG[p.G377fs]VTPPVARMGRSPAAGCGAAATSKPWGMRRAETQTAAPRHLPKQSPDASPPVAPPAWTRPGSTAVSHPGSTPGA | WTRPGSTAV,TAAPRHLPK,ATSKPWGMR,VARMGRSPA,TSKPWGMRR,PVAPPAWTR,QVPQDDWGV,QSPDASPPV,S TPGAPSLA,SPAAGCGAA,KPWGMRRAE,VPSPLDSSA,AR MGRSPAA,RMGRSPAAG,GAAATSKPW,MRRAETQTA,RR | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| DLL3 | | | PSLATAVPSPLDSSAMS* | AETQTAA, TQTAAPRHL, KQSPDASPP, GSTPGAPSL, LATAV PSPL, SPPVAPPAW, LQVPQDDWGV, KQSPDASPPV, SLATA VPSPL, QTAAPRHLPK, ATSKPWGMRR, VARMGRSPAA, TS KPWGMRRA, GMRRAETQTA, RAETQTAAPR, VSHPGSTPG A, DWGVTPPVAR, VTPPVARMGR, DASPPVAPPA, SPAAGC GAAA, KPWGMRRAET, VPSPLDSSAM, WGVTPPVARM, CG AAATSKPW, MRRAETQTAA | BLCA |
| DLL3 | c.952G>C | p.D318 H | PRSFECTCPRGFYGLRCEVSGVTCA[p.D 318H]HGPCFNGGLCVGGADPDSAYIC HCPP | VTCAHGPCF, CEVSGVTCAH, GVTCAHGPCF | BLCA |
| DMBT 1 | c.4562G>T | p.R152 1L | SRASTAGSESTLALRLVNGGDRCRG[p. R1521L]LVEVLYQGSWGTVCDDYWDT NDANVV | GLVEVLYQGS, RCRGLVEVLY | LUAD |
| DMD | c.5316G>C | p.K177 2N | DHCRKLVEPQISELNHRFAAISHRI[p.K1 772N]NTGKASIPLKELEQNSDIQKLLE PL | ISHRINTGK, RINTGKASI, NTGKASIPL, AISHRINTGK, NTGKA SIPLK, HRINTGKASI | BRCA |
| DMD | c.9584G>A | p.R319 5H | NVPLCVDMCLNWLLNVYDTGRTGRI[p. R3195H]HVLSFKTGIISLCKAHLEDKYR YLFK | TGRTGRIHV, HVLSFKTGI, TGRIHVLSF, TGRIHVLSFK, RTGRI HVLSF, RIHVLSFKTG, IFIVLSFKTGI | CRC |
| DMPK | c.131G>A | p.R44H | AGVGPGLPGAGAPARPSPGRPPGAG[p. R44H]HLRTGPGQVRGRLLAVGPKSRV FQSV | HLRTGPGQV, HLRTGPGQVR | CESC |
| DMRT 1 | c.133T>A | p.S45T | PGVPPQGRAGPGKASGALVGAASG[p. S45T]TSAGGSSRGGGSGSGASDLGA GSKKS | ALVGAASGT, GTSAGGSSR | ACC |
| DMRT 2 | c.317C>G | p.T106 S | RGGPQPRPPLAPQASPAGTGPRERC[p. T106S]SPAGGGAEPRKLSRTPKCARCR NHGV | GPRERCSPA, GPRERCSPAG | KIRP |
| DMXL 2 | c.7236C>A | p.D241 2E | GGGVKLVVKPRRQSENISAPPVLSE[p.D 2412E]EIDKHRRRFNMRMLVPGRPVK DATPP | EEIDKHRRRF | MM |
| DNAH 10 | c.5558G>T | p.C185 3F | GAPAGPAGTGKTETTKDLAKALGLL[p. C1853F]FVVTNCGEGMDYRAVGKIFSG LAQCG | KALGLLFVV, LAKALGLLF, AKALGLLLFV, LAKALGLLFV, FVVT NCGEGM, DLAKALGLLF, AKALGLLFVV | THCA |
| DNAH 10 | c.5663G>A | p.R188 8Q | DYRAVGKIFSGLAQCGAWGCFDEFN[p. R1888Q]QIDASVLSVISSAIQTIRNALI HQLT | QIDASVLSV, EFNQIDASV, DEFNQIDAS, NQIDASVLSV, DEF NQIDASV | UCEC |
| DNAH 14 | c.4099C>T | p.R136 7C | QDIGPPAVKMLISAEGEGLVLPKKI[p.R 1367C]CVRSAVEQMLVNVEKSMFDVL KKERY | KKICVRSAV, CVRSAVEQW, CVRSAVEQWL, LVLPKKICVR, L PKKICVRSA | UCEC |
| DNAH 3 | c.10099G> C | p.E336 7Q | LNLRIKYIIDHFTLSIYNNVCRSLF[p.E33 67Q]QKDKLLFSLLLTIGIMKQKKEITEEV KKERY | SLFQKDKLL, NVCRSLFQK, LFQKDKLLF, QKDKLLFSL, FQKDK LLFSL, SLFQKDKLLF | CESC |
| DNAH 5 | c.11465G>T | p.R382 2L | QKLEISAETEVQINSAREEYRPVAT[p.R3 822L]LGSILYFLITEMRLVNEMYQTSLR QF | VATLGSILY, TLGSILYFL, ATLGSILYF, RPVATLGSI, EEYRP VATL, PVATLGSILY, ATLGSILYFL, TLGSILYFLI, RPVATLG SIL, REEYRPVATL, VATLGSILYF | LUAD |
| DNAH 5 | c.2225G>A | p.R742 Q | LFRETECMAQMGLEVSPLATSLFQK[p. R742Q]QDRYKRNFSNMKMMLAEYQR VKSKIP | LFQKQDRYK, SLFQKQDRY, KQDRYKRNF, SLFQKQDRYK, TS LFQKQDRY, LFQKQDRYKR, QKQDRYKRNF | SKCM |

TABLE 8-continued

| gene | cDNA Change | Protein Change | Mutation Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| DNAH5 | c.2945G>A | p.R982H | ELLSHFNHQNMDALLKVTRNTLEAI[p.R982H]HKRIHSSHTINFRDSNSASNMKQNSL | NTLEAIHKR,AIHKRIHSSH,NTLEAIHKRI,HKRIHSSHTI | CRC |
| DNAH5 | c.5389C>G | p.Q1797E | TIELDKPVMAEGNVEVWLNSLLEES[p.Q1797E]ESSLHLVIRQAAANIQETGFQLTEFL | ESESSLHLV,LLEESESSL,ESSLHLVIR,ESESSLHL,SESSLHVI,SLLEESESSL,LEESESSLHL,ESESSLHLV | HNSC |
| DNAH5 | c.671G>A | p.R224Q | FLSSLEGFVNVLSGAQESLKEKVNL[p.R224Q]QKCDILELKTLKEPTDYLTLANNPET | LQKCDILEL,NLQKCDILEL,SLKEKVNLQK,LQKCDILELK | CRC |
| DNAH5 | c.9590G>A | p.R319Q | HVTPKSYLSFIQGYKFIYGEKHVEV[p.R3197Q]QTLANRMNTGLEKLKEASESVAALSK | EKHVEVQTL,HVEVQTLANR,GEKHVEVQTL,VEVQTLANRM | OV |
| DNAH5 | c.9706G>A | p.D323N | KEASESVAALSKELFAKEKELQVAN[p.D3236N]NKADMVLKEVTMKAQAAEKVKAEVQK | ANNKADMVLK,QVANNKADMV,LQVANNKADM,KELQVANNKA | SKCM |
| DNAH5 | c.8882G>A | p.R296Q | LCKGRDIPCSDDCSLMGTLGEAVTI[p.R2961Q]QTWNIAGLPSDSFSIDNGLIIMNARR | IQTWNIAGL,GEAVTIQTW,TIQTWNIAGL,EAVTIQTWNI | UCEC |
| DNAH7 | c.4639G>A | p.D154N | LESIFTGSEDIRAQLPQDSKRFEGI[p.D1547N]NIDFKELAYDAQKIPNVVQTTNKPGL | NIDFKELAY,RFEGINIDF,SKRFEGINI,RFEGINIDFK,INIDFKELAY,KRFEGINIDF | CRC |
| DNAH9 | c.8979C>G | p.S299R | KPPAIVNCTAIHWFHEWPQQALESV[p.S2993R]RLRFLQNTEGIEPTVKQSISKFMAFV | SVRLRFLQN,RLRFLQNTE,QALESVRLR,QQALESVRL,ALESVRLRF,LESVRLRFL,SVRLRFLQNT,RLRFLQNTEG,QALESVRLRF | LUAD |
| DNAH9 | c.691G>T | p.V231L | PNKPELALKPSSPLVTLEFNPKDSH[p.V231L]LLLGGCYNGQIACWDTRKGSLVAELS | NPKDSHLLL,SHLLLGGCY,LEFNPKDSHL | LUAD |
| DNAJC1 | c.578del A | p.K193fs | AVVWSIYLEKQLDELLSRKKREKKK[p.K193fs]RLAARVWMYQNSVLQKKMKDC* | RVWMYQNSV,RLAARVWMY,MYQNSVLQK,VWMYQNSVL,REKKKRLAA,KKRLAARVWM,KRLAARVWMY,WMYQNSVLQ,WMYQNSVLQK,KKRLAARVWM,RVWMYQNSVL,MYQNSVLQKK,KRLAARVWMY,YQNSVLQKKM,KKKRLAARVW,ARVWMYQNSV | STAD |
| DNAJC10 | c.239T>A | p.I80K | FKKLALKLHPDKNPNNPNAHGDFLK[p.I80K]KNRAYEVLKDEDLRKKYDKYGEKGLE | NAHGDFLKK,KNRAYEVLK,LKKNRAYEV,KKNRAYEVL,FLKKNRAYEV,GDFLKKNRAY,LKKNRAYEVL | MM |
| DNAJC12 | c.404G>A | p.R135K | DLMLEESDKTHTTKMENEECNEQRE[p.R135K]KKKEELASTAEKTEQKEPKPLEKSVS | EQREKKKEEL,KKKEELASTA | MM |
| DNAJC13 | c.3742G>A | p.E124 8K | TPRLQSNTRALYQYCPIPIINYPQL[p.E1248K]KNELFCNIYYLKQLCDTLRFPDWPIK | PIINYPQLK,KNELFCNIY,YPQLKNELF,LKNELFCNI,QLKNELFCNI,NYPQLKNELF,KNELFCNIYY,INYPQLKNEL,LKNELFCNIY | UCEC |
| DNAJC24 | c.181G>A | p.E61K | LMYHPDKQSTDVPAGTVEECVQKFI[p.E61K]KIDQAWKILGNEETKREYDLQRCEDD | KFIKIDQAW,FIKIDQAWK,IKIDQAWKI,FIKIDQAWKI,KFIKIDQAWK,QKFIKIDQAW,IKIDQAWKIL | CRC |
| DNASE1L1 | c.634G>A | p.D212N | CASLTKKRLDKLELRTEPGFHHVIA[p.D212N]NGEDTTVRASTHCTYDRVLHGERCR | VIANGEDTTV | CESC |

TABLE 8-continued

| gene | cDNA Change | Protein Change | Mutation Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| DNM2 | c.1134G>C | p.E378D | TLELSGGARINRIFHERFPFELVKM[p.E3 78D]DPFDEKDLRREISYAIKNIHGVRTGL F | LVKMDFDEK, PPFELVKMDF | LIHC |
| DNM2 | c.2371_2 372insC | p.P791 fs | QRRPVSSIHPGRPPAVRGTTPGPP[p. P791fs]PDSCSRGGSSLLLGAPNPIPAW TPERVCQQ* | LLLGAPNPI, CSRGGSSLL, SRGGSSLLL, NPIPAWTPE, IPAWT PERV, SLLLGAPNPI, LLGAPNPIPA, CSRGGSSLLL, NPIPAWT PER, LGAPNPIPAW | STAD |
| DNMB P | c.232A>C | p.T78P | SSFVEIVTIPSLKEGERLFVCICEF[p.T 78P]PSQELDNLPLHRGDLVILDGIPTAGW | FPSQELDNL | KIRC |
| DNMT 1 | c.1294G>A | p.E432K | LTCFSVYCKHGHLCPIDTGLIEKNI[p.E4 32K]KLFFSGSAKPIYDDDPSLEGGVNGK N | GLIEKNIKL, KLFFSGSAK, IEKNIKLFF, IKLFFSGSA, NIKLFFSGS A, GLIEKNIKLF | CRC |
| DNMT 1 | c.151G>A | p.E51K | RRLKDLERDSLTEKECVKEKLNLLH[p.E5 1K]KFLQTEIKNQLCDLETKLRKEELSEE | KLNLLHKFL, KEKLNLLHK, EKLNLLHKF, LLHKFLQTEI, KEKLN LLHKF | UCEC |
| DNMT 1 | c.2984G>A | p.R995Q | PEHYRKYSDYIKGSNLDAPEPYRIG[p.R9 95Q]QIKEIFCPKKSNGRPNETDIKIRVN K | QIKEIFCPK, RIGQIKEIF, GQIKEIFCPK, QIKEIFCPKK, APE PYRIGQI, YRIGQIKEIF | TGCT |
| DNMT 1 | c.4591G>C | p.E1531Q | RHNHWAGLYGRLEWDGFFSTTVTNP[p. E1531Q]QPMGKQGRVLHPEQHRVV | VTNPQPMGK, TTVTNPQPM, QPMGKQGRV, TVTNPQPM GK, QPMGKQGRVL, STTVTNPQPM | CRC |
| DNMT 3A | c.2207G>A | p.R736H | NDLSIVNPARKGLYEGTGRLFPEFY[p.R 736H]HLLHDARPKEGDDRPFFWLFEN VVAM | HLLHDARPK, FYHLLHDAR, FEFYHLLHD, EFYHLLHDAR, PEF YHLLHDA | LAML |
| DNMT 3A | c.2644C>T | p.R882C | DILWCTEMERVFGPVHYTDVSNMS[p. R882C]CLARQRLLGRSWSVPVIRHLFA PLKE | VSNMSCLAR, NMSCLARQR, DVSNMSCLA, YTDVSNMSCL, NMSCLARQRL, CLARQRLLGR, DVSNMSCLAR, SNMSCLAR QR | LAML |
| DNMT 3A | c.2645G>A | p.R882H | DILWCTEMERVFGPVHYTDVSNMS[p. R882H]HLARQRLLGRSWSVPVIRHLF APLKE | YTDVSNMSH, VSNMSHLAR, MSHLARQR, NMSHLARQR, DVSNMSHLA, YTDVSNMSHL, HLARQRLLGR, MSHLARQRL L, DVSNMSHLAR, SNMSHLARQR, NMSHLARQRL | LAML |
| DNMT 3B | c.274C>T | p.R92W | TQDLTGDGDGDGDGDSDTPVMPKLF[p. R92W]WETRTRSESPAVRTRNNNSV SSRERH | VMPKLFWET, KLFWETRTR, MPKLFWETR, TPVMPKLFW, V MPKLFWETR | CRC |
| DOCK 1 | c.2590G>A | p.E864K | SKMFTEFILNVPMGLLTIQKLYCLI[p.E8 64K]KIVHSDLFTQHDCREILLPMMTDQ LK | KLYCLIKIV, IQKLYCLIK, IKIVHSDLF, CLIKIVHSDL, TIQKLY CLIK, LIKIVHSDLF, IQKLYCLIKI | CRC |
| DOCK 10 | c.5489C>T | p.A183 0V | NENILVEQLYMCVEFLMKSERYELI[p.A 1830V]VDVNKPIIAVFEKQRDFKKLSDL YYD | LIVDVNKPI, ELIVDVNKP, WKSERYELIV, SERYELIVDV | CRC |
| DOCK 11 | c.505C>G | p.Q169 E | FEIDEDCEKDEDSSSLCSQKGGVIK[p.Q 169E]EGWLHKANVNSTITVTMKVFKR RYFY | VIKEGWLHKA, GVIKEGWLHK, KEGWLHKANV | TGCT |
| DOCK 3 | c.3547C>T | p.R118 3C | ELFSLLTQLFGPYPSILLEKVEQET[p.R1 183C]CETGISFVTSVTRLMERLLDYRDC MK | TWCETGISF, QETWCETGI, VEQETWCET, CETGISFVT, ETW CETGISF, CETGISFVTS | CRC |
| DOCK 5 | c.529G>A | p.E177K | IDHGNRMLGLDLVRDDNGNILDPD[p. E177K]KTSTIALFKAHEVASKRIEEKIQE EK | KTSTIALFK, ILDPDKTSTI, KTSTIALFKA, DPDKTSTIAL | CRC |
| DOCK 8 | c.3332 del T | p.L111 1fs | TLISMRLEFLRILCSHEHYLNLNLF[p.L1 11fs]L* | HYLNLNLFL | KICH |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| DOCK8 | c.531_532 insG | p.A177 fs | HKTLPKQTFESETLECSEPAAQAGP[p.A177fs]PPLKRAVRRVWERPRHCL* | AQAGPPPLK,RAVRRVWER,GPPPLKRAV,AAQAGPPPL,LK RAVRRVW,AAQAGPPPLK,AVRRVWERPR,RVWERPRHCL | KIRC |
| DOK5 | c.820C>T | p.R274 W | KMSERAASLSTMVPLPRSAYWQHIT[p.R274W]WQHSTGQLYRLQDVSSPLKH RTETF | SAYWQHITW,YWQHITWQH,WQHSTGQLY,WQHITWQH S,RSAYWQHITW,YWQHITWQHS,WQHSTGQLY,WQHIT WQHST,ITWQHSTGQL | CRC |
| DOK7 | c.1382G>A | p.G461 D | GQTSAGCPSGWLGTRRRGLVMEAPQ[p.G461D]DSEATLPGPAPGEPWEAGG PHAGPPP | APQDSEATL,MEAPQDSEA,MEAPQDSEAT | ACC |
| DOPE Y2 | c.3586G>A | p.E119 6K | KAGAKLSLVRVDSDKTQASESFSSD[p.E1196K]KEADLELQALTTSRLLKQORER QEAV | ASESFSSDK,KEADLELQA,QASESFSSDK,KEADLELQAL,SES FSSDKEA | BLCA |
| DOPE Y2 | c.6143A>C | p.Y204 8S | FEQKAMLLKRQAFAVFSGELDQYHL[p.Y2048S]SLPLIQERLTDNLRVGQTSIVA AQMF | SLPLIQERL,QYHLSLPLI,LSLPLIQER,DQYHLSLPL,GELDQYH LS,HLSLPLIQER,GELDQYHLSL,LDQYHLSLPL,DQYHLSLPLI, LSLPLIQERL | KIRC |
| DPCR1 | c.2302_2304de\|TTG | p.L768 de\| | NRERTANENTTPSPAQPTENGDRTP[p.L768de\|]ANEKTTPSLAEPTENGKRTPF ANEKTTS | TENGDRTPA | KIRC |
| DPEP1 | c.31G>T | p.V11L | MWSGWWLWPLL[p.V11L]LAVCTADFF RDEAERIMRDSPVIDGH | WLWPLLAVC,GWWLWPLLA,WWLWPLLAV,LLAVCTADF, SGWWLWPLL,LAVCTADFF,WPLLAVCTA,WLWPLLAVCT, WSGWWLWPLL,GWWLWPLLAV,LAVCTADFFR,LLAVCTA DFF | BRCA |
| DPP10 | c.547G>A | p.V183 I | TASYVIYNIHTREVWELNPPEVEDS[p.V183I]ILQYAAWGVQGQQLIYIFENNIYY QP | EVEDSILQY,ILQYAAWGV,VEDSILQYA,NPPEVEDSI,SILQY AAWGV,EVEDSILQYA,PEVEDSILQY,VEDSILQYAA | GBM |
| DPP6 | c.2271G>T | p.L757 F | TFTCGSALSPITDFKLYASAFSERY[p.L757F]FGLHGLDNRAYEMTKVAHRVSALE EQ | FSERYFGLH,AFSERYFGL,ASAFSERYF,ERYFGLHGL,SAFSE RYFGL,YASAFSERYF,SERYFGLHGL | LUAD |
| DPP8 | c.493G>A | p.G165 R | QATLDYGMYSREEELLRERKRIGTV[p.G165R]RIASYDYHQGSGTFLFQAGSGIY HVK | RKRRIGTVRI,IGTVRIASY,TVRIASYDY,KRIGTVRIA,GTVRIAS YDY,RERKRIGTVR,RIGTVRIASY,TVRIASYDYH,RKRIGTVRI A | CRC |
| DPY19 L1 | c.1134C>A | p.F378 L | ILKYLTSKIFGIADDAHIGNLLTSK[p.F378L]LFSYKDFDTLLYTCAAEFDFMEKETP | LTSKLFSYK,LLTSKLFSY,GNLLTSKLF,SKLFSYKDF,KLFSYK DFDT,LLTSKLFSYK,NLLTSKLFSY,IGNLLTSKLF | CRC |
| DPY19 L1 | c.745G>T | p.V249 L | MLLVTHILRATKLYRGSLIALCISN[p.V249L]LFFMLPWQFAQFVLLTQIASLFAVY V | LIALCISNL,CISNLFFML,IALCISNLF,LFFMLPWQF,ALCISNL FF,LCISNLFFM,SNLFFMLPW,SLIALCISNL,ALCISNLFFM,IA LCISNLFF,NLFFMLPWQF,LIALCISNLF,ISNLFFMLPW | KIRP |
| DPY19 L2 | c.628A>G | p.M21 0V | INAIKRPHLYPEVIIASWYCTFMGI[p.M210V]VNLFGLETKTCWNVTRIEPLNEVQ SC | CTFMGIVNL,CTFMGIVNLF,SWYCTFMGIV | PRAD |
| DQX1 | c.1514G>A | p.R505 H | ASCEFDCVDEMLTLAAMLTAAPGFT[p.R505H]HPPLSAEFEALRRALEHTGDH SSLI | APGFTHPPL,MLTAAPGFTH | GBM |
| DRD5 | c.825C>A | p.S275 R | RIAQVQIRRISSLERAAEHAQSCRS[p.S275R]RAACAPDTSLRASIKKETVKLTLS V | HAQSCRSRA,RSRAACAPD,AQSCRSRAA,RSRAACAPDT,R AACAPDTSL,AQSCRSRAAC | GBM |
| DSG4 | c.383G>T | p.R128 L | NPRTGEINITSVVDREITPLFLIYC[p.R128L]LALNSRGEDLERPLELRVKVMDIND N | FLIYCLALN,IYCLALNSR,TPLFLIYCL,FLIYCLALNS,ITPLFLIYC L,LIYCLALNSR,TPLFLIYCLA | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| DSP | c.478C>G | p.R160G | CDAYQKRLLQLQEQMRALVKAISVP[p. R160G]GVRRASSKGGGGYTCQSGSG WDEFTK | AISVPGVRR,KAISVPGVR,GVRRASSKG,YKAISVPGV,KAISV PGVRR,LYKAISVPGV | HNSC |
| DST | c.13228 G>T | p.A441 0S | TICGKSVERQNKLEEALLFSGQFTD[p.A 4410S]SLQALIDWLYRVEPQLAEDQPV HGDI | FTDSLQALI,SLQALIDWL,FSGQFTDSL,GQFTDSLQA,FTDSL QALID,SLQALIDWLY,GQFTDSLQAL,QFTDSLQALI | LUAD |
| DST | c.5300C>A | p.S176 7Y | ITLTRSLSVQDGLDEMLDWMGNVES[p. S1767Y]YLKEQGQVPLNSTALQDIISKN IMLE | WMGNVESYL,MGNVESYLK,YLKEQGQVPL,WMGNVESYL K,DWMGNVESYL,ESYLKEQGQV,LDWMGNVESY | UCEC |
| DSTN | c.301_302 insT | p.F101 fs | KDCRYALYDASFETKESRKEELMFF[p.F 101fs]FVGTRTSTSEK* | LMFFFVGTR,GIRTSTSEK,ELMFFFVGT,RKEELMFFF,EELM FFFVG,KEELMFFFV,LMFFFVGTRT,ELMFFFVGTR,SRKEEL MFFF,FFFVGTRTST,ELMFFFVGT,KEELMFFFVG | STAD |
| DUOX 2 | c.2640C>A | p.F880 L | SPEDKSRLMFTMYDLDENGFLSKDE[p. F880L]LFTMMRSFIEISNNCLSKAQLAE VVE | FLSKDELFT,GFLSKDELF,LFTMMRSFI,ELFTMMRSF,LSKDE LFTM,SKDELFTMM,DELFTMMRS,FLSKDELFTM,ELFTM MRSFI,NGFLSKDELF,LSKDELFTMM,DELFTMMRSF | CRC |
| DVL2 | c.1801 de|G | p.A601 fs | YGGGSASSQHSEGSRSSGSTRSDGG[p. A601fs]QGARGGEPRSGPPSPSPAVS LSPPAEGAAFGGVGKQVGLAMGALLH PEAQLGVPLISEPTQGSIPMDRPLAWPS PTTP* | ALLHPEAQL,SLSPPAEGA,GAAFGGVGK,GPPSPSPAV,SPP AEGAAF,EPTQGSIPM,IPMDRPLAW,RPLAWPSPT,VGKQV GLAM,KQVGLAMGA,PEAQLGVPL,AQLGVPLIS,GSIPMDR PL,LAWPSPTP,AEGAAFGGV,AMGALLHPEA,LLHPEAQL GV,AVAVSLSPPA,SLSPPAEGAA,KQVGLAMGAL,LISEPTQ GSI,STRSDGGQGA,RSGPPSPSPA,SPSPAVAVSL,HPEAQL GVPL,RPLAWPSPTT,LSPPAEGAAF,GVGKQVGLAM,SEPT QGSIPM,PEAQLGVPLI,AEGAAFGGVG | CRC |
| DVL2 | c.197T>G | p.V66G | GDFKSVLQRPAGAKYFFKSMDQDFG[p. V66G]GVKEEISDDNARLPCFNGRVVS WLVS | SMDQDFGGV,KSMDQDFGGV,SMDQDFGGVK | GBM |
| DYNC 2H1 | c.2649G>T | p.E883 D | KEWIVIGQVDMEALVEKHLFTVHDW[p. E883D]DKNFKALKIKGKEVERLPSAVK VDCL | HLFTVHDMDK,TVHDWDKNFK,HDWDKNFKAL | UCEC |
| DYRK1 B | c.1633 de|C | p.Q545 fs | DVPHKTHQAPASASSLPGTGAQLPP[p. Q545fs]SPDTLWPHHQPHHHPRS* | HHQPHHHPR,LVVPHHQPH,SPDTLVVPH,LPPSPDTLV,QL PPSPDTLV,AQLPPSPDTL,LPPSPDTLVV | STAD |
| DYRK4 | c.1402 de|A | p.K468 fs | TASRRQTFFDSKGFPKNITNNRGKK[p.K 468fs]DTQIPRTSRWC* | TQIPRTSRW,DTQIPRTSR,RGKKDTQIPR | STAD |
| DZIP3 | c.964A>C | p.M32 2L | NLKYPGENDQSFSGKKCLKEGCTGD[p. M322L]LIVRMLQCDVPGIVKILFEWRK DEYI | KEGCTGDLV,CLKEGCTGDL | LUAD |
| E2F7 | c.272T>G | p.I91S | PITPVKFVDRQQAEPWTPTANLKML[p. I91S]SSAASPDIRDREKKKGLFRPIENKD D | NLKMLSSAA,LKMLSSAAS,KMLSSAASP,MLSSAASPDI,LK MLSSAASP | TGCT |
| EAF2 | c.327de|A | p.V109 fs | CILIINHDTGECRLEKLSSNITVKK[p.V10 9fs]QELKEAVKFSIVKNNSNNKCGIQPG LPIL* | ITVKKQELK,IVKNNSNNK,KQELKEAVK,KKQELKEAV,QELK EAVKF,KEAVKFSIV,CGIQPGLPI,SIVKNNSNNK,ELKEAVKF SI,KQELKEAVKF,CGIQPGLPIL | STAD |
| EBAG 9 | c.559G>A | p.E187 K | EEDAAWQAEEVLRQQKLADEREKRAA[p. E187K]KQQRKKMEKEAQRLMKKEQN KIGVKL | RAAKQQRKK,KQQRKKMEK,RAAKQQRKKM | CRC |
| EBF1 | c.1058A>G | p.D353 G | SYKSKQFCKGTPGRFIYTALNEPTI[p.D3 53G]GYGFQRLQKVIPRHPGDPERLPKE VI | ALNEPTIGY,PTIGYGFQR,NEPTIGYGF,IGYGFQRLQK,GYG FQRLQKV,TALNEPTIGY,LNEPTIGYGF | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| EBPL | c.565C>G | p.L189V | YCWLYLPFFNGVWVLIPGLLLWQSW[p.L189V]VELKKMHQKETSSVKKFQ* | GLLLWQSWV, LLMQSWVEL, WQSWVELKK, LLLMQSWVE L, LLMQSWVELK, WQSWVELKM | KICH, KIRP, TGCT |
| EBPL | c.587A>C | p.Q196P | FFNGVWVLIPGLLLWQSWLELKKMH[p.Q196P]PKETSSVKKFQ* | KMHPKETSS, KMHPKETSSV | KICH |
| ECE2 | c.760G>A | p.D254N | DRGVSPCEDFYQFSCCGWIRNPLP[p.D254N]NGRSRWNTFNSLWDQNQAIL KHLLEN | NGRSRWNTF, NPLPNGRSRW | CESC |
| ECI2 | c.164A>G | p.K55R | HMNRTAMRASQKDFENSMNQVKLLK[p.K55R]RDPGNEVKLKLYALYKQATEGP CNMP | LLKRDPGNEV, SMNQVKLLKR | TGCT |
| ECM1 | c.796G>A | p.E266K | EIGYSRCCHCRSHTNRLECAKLVWE[p.E266K]KAMSRFCEAEFSVKTRPHWCCT RQGE | KAMSRFCEA, VWEKAMSRF, LVWEKAMSR, AKLVWEKAM, WEKAMSRFC, KLVWEKAMSR, LVWEKAMSRF, CAKLVWEK AM | BLCA |
| EDA | c.174G>C | p.L58F | RAGEGNSCLLFLGFGLSLALHLLT[p.L58F]FCCYLELRSELRRERGAESRLGGSGT RQGE | HLLTFCCYL, LTFCCYLEL, SLALHLLTF, TFCCYLELR, LHLLTFCC Y, LLTFCCYLEL, SLALHLLTFC, LTFCCYLELR, LSLALHLLTF, AL HLLTFCCY | HNSC |
| EDNRB | c.1349T>G | p.L450R | SRILKLTLYNQNDPNRCELLSFLLV[p.L450R]WDYIGINMASLNSCINPIALYLVSK R | LSFLLVWDY, LLVWDYIGI, SFLLVWDYI, WDYIGINMA, FLLV WDYIGI, LLSFLLVWDY, CELLSFLLVW, LVWDYIGINM | CRC |
| EEA1 | c.1709delA | p.N570fs | EREDLYAKIQAGEGETAVLNQLQEK[p.N570fs]TIHYRSK* | QLQEKTIHY, QLQEKTIHYR, NQLQEKTIHY | STAD |
| EEF1A1 | c.1294_1295AC>TT | p.T432L | GKPMCVESFSDYPPLGRFAVRDMRQ[p.T432L]LVAVGVIKAVDKKAAGAGKVT KSAQKA | QLVAVGVIK, AVRDMRQLV, FAVRDMRQL, RDMRQLVAV, RQLV AVGVI, QLVAVGVIKA, LVAVGVIKAV, AVRDMRQLVA, RQLVAVGVIK, FAVRDMRQLV | LIHC |
| EEF1A2 | c.1253A>C | p.Y418S | SLKSGDAAIVEMVPGKPMCVESFSQ[p.Y418S]SPPLGRFAVRDMRQTVAVGVIK NVEK | ESFSQSPPL, SPPLGRFAV, SQSPPLGRF, SFSQSPPLGR, VESF SQSPPL, FSQSPPLGRF, SQSPPLGRFA | BLCA, TGCT |
| EEF1B2 | c.127A>G | p.S43G | YLADKSYIEGTVPSQADVAVFEAVS[p.S43G]PPPADLCHALRWYNHIKSYEKEK AS | EAVSGPPPA, FEAVSGPPP, FEAVSGPPPA | KIRP, PRAD, SKCM |
| EEF2K | c.2017G>A | p.E673K | TDCDEGGEYDGMQDEPRYMMLAREA[p.E673K]KMLFTGGYGLEKDPQRSGDL YTQAAE | MMLAREAKM, MLAREAKML, YMMLAREAK, AKMLFTGGY, LAREAKMLF, REAKMLFTG, YMMLAREAKM, MMLAREAK ML, KMLFTGGYGL, MLAREAKMLF, RYMMLAREAK, EAKML FTGGY, REAKMLFTGG | BLCA |
| EFCAB4B | c.793G>C | p.E265Q | MEQQIKSEKEQPLLKDTERFQARSQ[p.E265Q]QLEQKLLCKEQELEQLTQKOKR LEGQ | RFQARSQQL, RSQQLEQKL, SQQLEQKLL, QARSQQLEQK, E RFQARSQQL, FQARSQQLEQ, RSQQLEQKLL | LUAD |
| EFCAB6 | c.1136G>A | p.R379K | NWKQFLTSFHEPQGLQVSSKGPLTK[p.R379K]KNSINSRNESHKENIITKLFRHTE DH | SSKGPLTKK, GPLTKKNSI, VSSKGPLTKK, LTKKNSINSR | BLCA, GBM, PRAD |
| EFCAB6 | c.3004G>A | p.E1002K | DQSKTNVISICKMQEVLEECGCSLT[p.E1002K]KGELTHLLNSWGVSRHDNAINY LDFL | SLTKGELTHL | HNSC |
| EGFR | c.1786C>T | p.P596S | CTGRGPDNCIQCAHYIDGPHCVKTC[p.P596S]SAGVMGENNTLVWKYADAGH VCHLCH | CVKTCSAGV, VKTCSAGVM, CVKTCSAGVM | GBM |
| EGFR | c.1787C>T | p.P596L | CTGRGPDNCIQCAHYIDGPHCVKTC[p.P596L]LAGVMGENNTLVWKYADAGH VCHLCH | CVKTCLAGV, GPHCVKTCL, VKTCLAGVM | GBM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| EGFR | c.1793G>C | p.G598A | GRGPDNCIQCAHYIDGPHCVKTCPA[p.G598A]AVMGENNTLVWKYADAGHVCHLCHPN | CVKTCPAAV, VKTCPAAVM, AVMGENNTL, AVMGENNTLV, CVKTCPAAVM, AAVMGENNTL | GBM |
| EGFR | c.1793G>T | p.G598V | GRGPDNCIQCAHYIDGPHCVKTCPA[p.G598V]VVMGENNTLVWKYADAGHVCHLCHPN | CVKTCPAVV, VKTCPAVVM, VVMGENNTLV, CVKTCPAVVM | GBM |
| EGFR | c.185T>G | p.L62R | KLTQLGTFEDHFLSLQRMFNNCEVV[p.L62R]RGNLEITYVQRNYDLSFLKTIQEVAG | MFNNCEVVR, EVVRGNLEI, VRGNLEITY, RMFNNCEVVR, V VRGNLEITY, CEVVRGNLEI | GBM |
| EGFR | c.2125G>A | p.E709K | QERELVEPLTPSGEAPNQALLRILK[p.E709K]KTEFKKIKVLGSGAFGTVYKGLWIPE | RILKKTEFKK, ILKKTEFKK, QALLRILKK, LRILKKTEF, R ILKKTEFKK, NQALLRILKK, LLRILKKTEF | GBM |
| EGFR | c.2156G>C | p.G719A | PSGEAPNQALLRILKETEFKKIKVL[p.G719A]ASGAFGTVYKGLWIPEGEKVKIPV AI | ASGAFGTVY, VLASGAFGT, LASGAFGTV, KIKVLASGA, KVLA SGAFG, IKVLASGAF, KKIKVLASG, VLASGAFGTV, ASGAFGT VVK, KIKVLASGAF, LASGAFGTVY, KKIKVLASGA, TEFKKIKVL A | LUAD |
| EGFR | c.2235_2249de\|GGAAT TAAGAGA GC | p.ELRE A746de\| | GAFGTVYKGLWIPEGEKVKIPVAIK[p.ELREA746de\|]TSPKANKEILDEAYVMAS VDNPHVCRLLGICLTSTVQLIT | AIKTSPKANK, KVKIPVAIKT, KTSPKANKEI | LUAD |
| EGFR | c.2303G>T | p.S768I | AIKELREATSPKANKEILDEAYVMA[p.S768I]IVDNPHVCRLLGICLTSTVQLITQL M | MAIVDNPHV, VMAIVDNPH, DEAYVMAI, IL DEAYVMAI, VMAIVDNPHV, AIVDNPHVCR, YVMAIVDNPH, DEAYVMAIVD | LUAD |
| EGFR | c.2512C>A | p.L838M | YLLNWCVQIAKGMNYLEDRRLVHRD[p.L838M]MAARNVLVKTPQHVKITDFGL AKLLG | RLVHRDMAA, DMAARNVLV, MAARNVLVK, LVHRDMAAR, RDMAARNVL, RLVHRDMAAR, DMAARNVLVK, HRDMAA RNVL, RDMAARNVLV | KIRC |
| EGFR | c.2573T>G | p.L858R | LVHRDLAARNVLVKTPQHVKITDFG[p.L858R]RAKLLGAEEKEYHAEGGKVPIKW MAL | KITDFGRAK, HVKITDFGR, FGRAKLLGA, HVKITDFGRA, RAK LLGAEEK | LUAD |
| EGFR | c.2582T>A | p.L861Q | RDLAARNVLVKTPQHVKITDFGLAK[p.L861Q]QLGAEEKEYHAEGGKVPIKWMA LESI | LAKQLGAEEK, KQLGAEEKEY | LUSC |
| EGFR | c.323G>A | p.R108K | QEVAGYVLIALNTVERIPLENLQII[p.R108K]KGNMYYENSYALAVLSNYDANKTG LK | QIIKGNMYY, LQIIKGNMY, LQIIKGNMYY, KGNMYYENSY | GBM |
| EGFR | c.754C>T | p.R252C | SPSDCCHNQCAAGCTGPRESDCLVC[p.R252C]CKFRDEATCKDTCPPLMLYNPT TYQM | RESDCLVCC | GBM |
| EGFR | c.865G>A | p.A289T | CPPLMLYNPTTYQMDVNPEGKYSFG[p.A289T]TTCVKKCPRNYVVTDHGSCVR | YSFGTTCVK, TTCVKKCPR, GKYSFGTTC, YSFGTTCVKK, KYSF GTTCVK, GTTCVKKCPR, GKYSFGTTCV | GBM |
| EGFR | c.866C>A | p.A289D | CPPLMLYNPTTYQMDVNPEGKYSFG[p.A289D]DTCVKKCPRNYVVTDHGSCVR ACGAD | YSFGDTCVK, DTCVKKCPR, GKYSFGDTC, YSFGDTCVKK, KYS FGDTCVK, GKYSFGDTC | GBM |
| EGFR | c.866C>T | p.A289V | CPPLMLYNPTTYQMDVNPEGKYSFG[p.A289V]VTCVKKCPRNYVVTDHGSCVR ACGAD | YSFGVTCVK, KYSFGVTCV, VTCVKKCPR, GKYSFGVTC, YSFG VTCVKK, KYSFGVTCVK, GVTCVKKCPR, GKYSFGVTCV | GBM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| EGFR | c.910C>T | p.H304Y | VNPEGKYSFGATCVKKCPRNYVVTD[p.H304Y]YGSCVRACGADSYEMEEDGVRKCKKC | VVTDYGSCV, YVVTDYGSCV, WTDYGSCVR, CPRNYVVTDY | GBM |
| EGR1 | c.27G>C | p.Q9H | MAAAKAEM[p.Q9H]HLMSPLQISDPFGSFPHSPTMDNYPK | AAKAEMHLM, AEMHLMSPL, MHLMSPLQI, MAAAKAEMHL, AAAKAEMHLM, KAEMHLMSPL, EMHLMSPLQI, AEMHLMSPLQ | MM |
| EGR1 | c.994del C | p.P332fs | TSYQSQLIKPSRMRKYPNRPSKTPP[p.P332fs]TNALJTLAQWSPVIAASPAPTSSPATSASTQARSPSSAASACATSAAAATTSPPTSAPTQAKSPSPATSVEESLPGAMNARGIPRSTCGRRTRKQTKVLWPLRPPPLSLPTRPRLLPLTRPRLLPLIHPRPPPHTHPLCPPPSPLPAPRPTHPLCTVASPPRRWPPRTPLFPLLSRPRSAASLPQLSPTPSAPPQGFRT* | LTLAQWSPV, TLAQWSPVI, AQWSPVIAA, KQTKVLWPL, VIAASPAPT, AMNARGIPR, RLLPLTRPR, RLLPLIHPR, ATSASTQAR, STCGRRTRK, CTVASPPRR, LWPLRPPPL, STQARSPSS, QARSPSSAA, RSPSSAASA, ASACATSAA, KSPSPATSV, RSTCGRRTR, RTRKQTKVL, QTKVLWPLR, PTRPRLLPL, RPRLLPLTR, LITRPRLLPL, LIHPRPPPH, SLPGAMNAR, ESLPGAMNA, SPVIAASPA, SPAPTSSPA, RPPPLSLPT, LPLTRPRLL, RPRLLPLIH, HPRPPPHTH, RPPPHTHPL, SPLPAPRPT, APRPTHPLC, RPTHPLCTV, SLPTRPRLL, SKTPPTNAL, TQARSPSSA, TQAKSPSPA, VEESLPGAM, LSLPTRPRL, CPPPSPLPA, ALTLAQWSPV, TLAQWSPVIA, VLWPLRPPPL, RLLPLTRPRL, GAMNARGIPR, RSTCGRRTRK, KTPPTNALTL, STQARSPSSA, ASACATSAAA, RGIPRSTCGR, CGRRTRKQTK, RTRKQTKVLW, KQTKVLWPLR, KVLWPLRPPP, LTRPRLLPLI, HTHPLCPPPS, ESLPGAMNAR, WSPVIAASPA, TTSPPTSAPT, RPSKTPPTNA, SPATSSPPAT, APTSSPATSA, SPATSASTQA, SPATSVEESL, LPGAMNARGI, WPLRPPPLSL, LPTRPRLLPL, HPLCPPPSPL, LPAPRPTHPL, APRPTHPLCT, RPTHPLCTVA, LTLAQWSPVI, AQWSPVIAAS, TQARSPSSAA, TQAKSPSPAT, AKSPSPATSV, RKQTKVLWPL, LSLPTRPRLL, EESLPGAMNA | STAD |
| EGR2 | c.1105G>A | p.E369K | SKTPVHERPYPCPAEGCDRRFSRSD[p.E369K]KLTRHIRIHTGHKPFQCRICMRNFSR | RRFSRSDKL | CLL |
| EGR2 | c.1169G>A | p.R390H | SRSDELTRHIRIHTGHKPFQCRICM[p.R390H]HNFSRSDHLTTHIRTHTGEKPFACDY | RICMHNFSR, HNFSRSDHL, FQCRICMHNF, CMHNFSRSDH, MHNFSRSDHL | CRC |
| EGR2 | c.1189C>A | p.H397N | RHIRIHTGHKPFPQCRICMRNFSRSD[p.H397N]NLTTHIRTHTGEKPFACDYCGRKFAR | RNFSRSDNL, RSDNLTTHI, MRNFSRSDNL, FSRSDNLTTH, SRSDNLTTHI | CLL |
| EHD3 | c.130G>A | p.E44K | QTVSEGLKKLYKSKLLPLEEHYRFH[p.E44K]KFHSPALEDADFDNKPMVLLVGQYST | HYRFHKFHS, RFHKFHSPA, FHKFHSPAL, EEHYRFHKF, YRFHKFHSP, RPHKFHSPAL, YRFHKFHSPA, LEEHYRFHKF, EEHYRFHKFH | CRC |
| EHHADH | c.2112G>T | p.Q704H | LQKYYRQNPDIPQLEPSDYLKKLLAS[p.Q704H]HGNPPLKEWQSLAGSPSSKL* | ASHGNPPLK, LASHGNPPL, KLASHGNPPL, LASHGNPPLK | LUAD |
| EIF1AX | c.26G>A | p.G9D | MPKNKGKG[p.G9D]DKNRRGKNENESEKRELVFKEDGQE | KGDKNRRGK | THCA |
| EIF2C1 | c.416G>A | p.R139Q | EVTIPGEGKDRIFKVSIKWLAIVSW[p.R139Q]QMLHEALVSGQIPVPLESVQALDVAM | WLAIVSWQM, WQMLHEALV, AIVSWQMLH, SWQMLHEAL, LAIVSWQML, WLAIVSWQML, IVSWQMLHEA, KWLAIVSWQM, SWQMLHEALV, VSWQMLHEAL, WQMLHEALVS | CRC |
| EIF3J | c.23C>G | p.A8G | MAAAAAA[p.A8G]GGDSDSWDADAFSVEDPVRKVGGGGT | AAAGGDSDSW | TGCT |
| EIF4G3 | c.23G>A | p.R8H | MNSQPQT[p.R8H]HSPFFQRPQIQPPRATIPNSSPSIRP | QTHSPFFQR, SQPQTHSPF, QPQTHSPFF, SQPQTHSPFF, NSQPQTHSPF | CLL |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ELAVL2 | c.789G>T | p.L263F | RLDNLLNMAYGVKRFSPMTIDGMTS[p.L263F]FAGINIPGHPGTGWCIFVVNLAPDAD | MTIDGMTSF, TIDGMTSFA, DGMTSFAGI, MTSFAGINI, MTIDGMTSFA, GMTSFAGINI, PMTIDGMTSF | LUAD |
| ELF3 | c.915del|C | p.F305fs | DILIHPELNEGLMKWENRHEGVFKF[p.F305fs]CAPRLWPNYGAKRKRTAT* | GVFKFCAPR, RLWPNYGAK, VFKFCAPRL, CAPRLWPNY, YG AKRKRTA, FKFCAPRLW, HEGVFKFCA, RLWPNYGAKR, VFK FCAPRLW, FCAPRLWPNY, EGVFKFCAPR, APRLWPNYGA, G VFKFCAPRL | CRC |
| ELF4 | c.1244C>T | p.S415L | KLTKAVSASSVPSNIHLGVAPVGSSG[p.S415L]LALTLQTIPLTTVLTNGPPASTTAPT | GLALTLQTI, GVAPVGSGL, APVGSGLAL, VGSGLALTL, GVAP VGSGLA, LGVAPVGSGL, SGLALTLQTI, LALTLQTIPL | HNSC |
| ELMOD2 | c.422C>T | p.T141M | RKRPYDSDNLQHEELLMKLWNLLMP[p.T141M]MKKLNARISKQWAEIGFQGDDPKTDF | KLWNLLMPM, LWNLLMPMK, MPMKKLNAR, LLMPMKKL NA, KLWNLLMPMK, LWNLLMPMKK, MKKLNARISK, LMP MKKLNAR, MPMKKLNARI, MKLWNLLMPM | CRC |
| EME1 | c.1708G>C | p.D570H | IGPELSRRIYLQMTTLQPHLSLDSA[p.D570H]H* | QPHLSLDSAH | LUSC |
| EMILIN1 | c.79C>G | p.R27G | APRTLWSCYLCCLLITAAGAASYPP[p.R27G]GGFSLYTGSSGALSPGGPQAQIAPRP | SYPPGGFSL, YPPGGFSLY, AASYPPGGF, SYPPGGFSLY, ASYP PGGFSL, GAASYPPGGF | BLCA |
| EML6 | c.2414A>G | p.K805R | FSADGKCLVSVGLDDFHSIVFWDWK[p.K805R]RGEKIATTRGHKDKIFVVKCNPHHVD | SIVFWDWKR, WDMKRGEKI, HSIVFWDWKR, VFWDWKRGEK | TGCT |
| EMR1 | c.1478G>A | p.R493H | EESESTETTGVAFVSFVGMESVLNE[p.R493H]HFFKDHQAPLTTSEIKLKMNSRVVGG | SVLNEHFFK, MESVLNEHF, ESVLNEHFK, HFFKDHQAPL, G MESVLNEHF, MESVLNEHFF, NEHFFKDHQA | LUAD |
| EMR1 | c.1892G>A | p.R631Q | SHVGIIISLVCLVLAIATFLLCRSI[p.R631Q]QNHNTYLHLHLCVCLLLAKTLFLAGI | SIQNHNTYL, RSIQNHNTY, IQNHNTYLH, QNHNTYLHL, RSI QNHNTYL, IQNHNTYLHL, CRSIQNHNTY | UCEC |
| EMR2 | c.224C>T | p.S75L | GFSSFSEIITTPMETCDDINECATL[p.S75L]LKVSCGKFSDCWNTEGSYDCVCSPGY | TLLKVSCGK, DINECATLL, LLKVSCGKF, NECATLLKV, ATLLKV SCGK, DINECATLLK, TLLKVSCGKF | CRC |
| ENAH | c.1541G>T | p.R514L | TPEPTRKPWERTNTMNGSKSPVISR[p.R514L]LDSPRKNQIVFDNRSYDSLHRPKSTP | VISRLDSPR, ISRLDSPRK, SKSPVISRL, VISRLDSPRK, GSKSPVISRL, PVISRLDSPR | LUAD |
| ENAM | c.1118G>A | p.R373H | PFYRNQQVQRGPRWNFFAWERKQVA[p.R373H]HPGNPVYHKAYPPTSRGNYPNYAGNP | QVAHPGNPV, VAHPGNPVY, KQVAHPGNPV, QVAHPGNP VY, FAWERKQVAH | CRC |
| ENOX2 | c.1066C>T | p.R356W | QFEQIVAVYHSASKQKAWDHFTKAQ[p.R356W]KNISVWCKQAEEIRNIHNDELMGIR | AQWKNISVW, KAQWKNISV, HFTKAQWKNI, QWKNISVW CK, KAQWKNISVW, AQWKNISVWC | CRC |
| ENPEP | c.866T>G | p.F289C | EESVDDKWTRTTFEKSVPMSTYLVC[p.F289C]CAVHQFDSVKRISNSGKPLTIYVQPE | STYLVCCAV, MSTYLVCCA, CAVHQFDSV, LVCCAVHQF, YLV CCAVHQF, MSTYLVCCAV, CAVHQFDSVK | KIRC |
| ENPP1 | c.2213G>A | p.G738E | YQDFRIPLSPVHKCSFYKNNTKVSY[p.G738E]EFLSPPQLNKNSSGIYSEALLTTNIV | NTKVSYEFL, YEFLSPPQL, SYEFLSPPQL, EFLSPPQLNK, KNN TKVSYEF, YEFLSPPQLN | LUAD |
| ENTPD2 | c.611del|G | p.G204fs | NFIKYGWVGRWFRPRKGTLGAMDLG[p.G204fs]VPLPRSLLRQPVQLRTEPARSSCISTASTTESTPTAGRGAFPPKCCCSGMWPAPSRPTASTPAGRGAFPPKCCCSGMCTSHHAPWPSGPRTSTAVPLGSSACQGA | TLGAMDLGV, SLLRQPVQL, WLGTLWPSL, TLMPSLPSS, STL WTFCGL, AVTPTSAEI, ASSAMAVTR, TLWTFCGLR, LWTFCG LRW, RSLLRQPVQ, LLRQPVQLR, AMAVTRSSR, RSSRGCWP A, SSRGCWPAP, RGCWPAPSR, AGRGAFPPK, HAPWPSGPR, STTESTPTA, ESTPTASSA, STPTASSAM, EIWFLGSSA, WPAP | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ENTPD7 | c.979G>A | p.E327K | VTPTSAEIWFLGSSASPPAPSPDALSMG SSSPQWLGTLWPSLPSSTLWTFCGLRW GCPWPCSSWRQPQ* | SRPTA,APSRPTAST,RPTASTPAG,FPPKKCCSGM,WPSGPRT ST,APSPDALSM,WPSLPSSTL,LPSSTLWTF,GAMDLGVPL,L GVPLPRSL,ARSSCISTA,MCTSHHAPW,SMGSSSPQW,CGL RWGCPW,TPTSAEIWF,SPQWLGTLW,CPWPCSSW,AEI WFLGSS,GTLGAMDLGV,FLGSSASPPA,SMGSSSPQWL,TL WPSLPSST,AMDLGVPLPR,SAMAVTRSSR,STLWTFCGLR, QWLGTLWPSL,LWPSLPSSTL,SLPSSTLWTF,RSLLRQPVQL, RTEPARSSCI,RSSCISTAST,SSRGCWPAPS,RTSTAVPGSA,S LLRQPVQLR,TASSAMAVTR,HHAPWPSGPR,STPTASSAM A,SAEIWFLGS,SSTLWTFCGL,WTFCGLRWGC,LPRSLLRQ PV,QPVQLRTEPA,TPTASSAMAV,WPAPSRPTAS,WPSGPR TSTA,VPGSACQGAV,SPPAPSPDAL,ASTPAGRGAF,ESTPT ASSAM,LSMGSSSPQW,LGAMDLGVPL,GMCTSHHAPW,C QGAVTPTSA,AEIWFLGSSA,SSSPQWLGTL,TPTSAEIWFL, WPSLPSSTLW,TESTPTASSA,LPSSTLWTFC | CRC |
| ENTPD7 | c.979G>A | p.E327K | HTEHVRVYTTFLGFGGNFARQRY[p. E327K]KDLVLNETLNKNRLLGQKTGLSP DNP | GNFARQRYK,RQRYKDLVL,FARQRYKDL,KDLVLNETL,GGN FARQRYK,RQRYKDLVLN,FARQRYKDLV,YKDLVLNETL | |
| EOMES | c.995de|G | p.G332fs | LNPTAHYNVFVEVVLADPNHWRFQG|p. G332fs]ANG* | HWRFQGANG | STAD |
| EP300 | c.3491G>A | p.C1164Y | YKYCSKLSEVPEQEIDPVMQSLGYC|p.C 1164Y]YGRKLEFSPQTLCCYGKQLCTIP RDA | SLGYCYGRK,YCYGRKLEF,VMQSLGYCY,QSLGYCYGR,LGY CYGRKL,QSLGYCYGRK,GYCYGRKLEF,PVMQSLGYCY,MQ SLGYCYGR | HNSC |
| EP300 | c.4195G>A | p.D1399N | FGMHVQEYGSDCPPPNQRRVVISYL|p. D1399N]NSVHFFRPKCLRTAVVHEILIG YLEY | YLNSVHFFR,NSVHFFRPK,VYISYLNSV,ISYLNSVHF,SYLNSV HFF,RVVISYLNS,YISYLNSVH,RVVISYLNSV,SYLNSVHFFR, YISYLNSVHF,ISYLNSVHFF,LNSVHFFRPK | CESC,HNSC, LUSC |
| EPB41L3 | c.2686G>T | p.A896S | SYSAGDSGDAAAQPAFTGIKGKEGS|p. A896S]SLTEGAKEGGEEVAKAVLEQE ETAA | GSSLTEGAK,IKGKEGSSL,KEGSSLTEGA | LUAD |
| EPG5 | c.1105G>A | p.D369N | KVFSYHRYQRVEMNENALVELKKLF|p. D369N]NAKSEHLHQTLALHSYTSVLSRL QVE | KLFNAKSEH,ELKKLFNAK,VELKKLFNA,KLFNAKSEHL | CRC |
| EPG5 | c.6866G>T | p.R2289L | MALSLLFMEVLMMMNNATIPTAEFL|p. R2289L]LGSIRTWIGQKMHGLVVLPLL TAACQ | LLGSIRTWI,TIPTAEFLL,FLLGSIRTW,FLLGSIRTWI,EFLLGSI RTW,ATIPTAEFLL,AEFLLGSIRT | LUAD |
| EPHA1 | c.332G>T | p.G111V | IYRGEFASRVHVELQFTVRDCKSFP|p.G 111V]VGAGPLGCKETFNLLYMESDQD VGIQ | FPVGAGPLG,TVRDCKSFPV,KSFPVGAGPL,FPVGAGPLGC | LUAD |
| EPHA1 | c.550G>A | p.A184T | LVSGSVKLNVERCSLGRLITRRGLYL|p.A 184T]TFHNPGACVALVSVRVFYQRCPE TLN | YLITFHNPGA,LITRRGLYLT,TRRGLYLIT,LITFHNPGACV,LITRR GLYLTF | GBM |
| EPHA10 | c.2604de|C | p.P868fs | ERPYWDMSGQDVIKAVEDGFRLPPP|p. P868fs]GTVLTFCTD* | RLPPPGTVL,GFRLPPPGTV,LPPPGTVLTF,FRLPPPGTVL | STAD |
| EPHA2 | c.1379de|C | p.P460fs | NQTEPPKVRLEGRSTTSLSVSWSIP|p.P 460fs]RRSRAECGSTRSLTARRETPTAT MCAAPRVSP* | ATMCAAPRV,LSVSWSIPR,SVSWSIPRR,GSTRSLTAR,RSRA ECGST,STRSLTARR,RSLTARRET,TARRETPTA,SWSIPRRSR, TATMCAAPR,EHPTATMCA,IPRRSRAEC,TPTATMCAA,AE CGSTRSL,RRETPTATM,RETPTATMC,SLSVSWSIPR,LSVS WSIPRR,SWSIPRRSRA,RSRAECGSTR,VSWSIPRRSR,PTAT | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| EPHA3 | c.2405C>G | p.T802R | AAYTTRGGKIPIRWTSPEAIAYRKF[p.T802R]RSASDVWSYGIVLWEVMSYGERPYWE | MCAAPR, ETPTATMCAA, TATMCAAPRV, RAECGSTRSL, AR RETPTATM, RETPTATMCA, ARCGSTRSLT RSASDVWSY, KFRSASDVW, IAYRKFRSA, AYRKFRSAS, EAIA YRKFR, RKFRSASDV, AIAYRKFRSA, KFRSASDVWS, IAYRKFR SAS, RKFRSASDVW, FRSASDVWSY | HNSC |
| EPHA6 | c.2854G>C | p.D952H | TTGGKIPIRWTAPEAIAYRKFSSASA[p.D952H]HAWSYGIVMWEVMSYGERPYW EMSNQ | SSASHAWSY, KFSSASHAW, ASHAWSYGI, HAWSYGIVM, Y RKFSSASH, RKFSSASHA, FSSASHAWSY, AYRKFSSASH, ASH AWSYGIV, SASHAWSYGI, RKFSSASHAW, SHAWSYGIVM, HAWSYGIVMW | HNSC |
| EPHB2 | c.1175G>A | p.R392H | SGRGACTRCGDNVQYAPRQLGLTEP[p.R392H]HIYISDLLAHTQYTFEIQAVNGV TDQ | GLTEPHIYI, RQLGLTEPH, LGLTEPHIY, RQLGLTEPHI, QLGLT EPHIY, HIYISDLLAH, TEPHIYISDL | CRC |
| EPHB6 | c.1010G>A | p.R337H | KACQACPRGLYKSSAGNAPCSPCPA[p.R337H]HSHAPNPAAPVCPCLEGFYRAS SDPP | HSHAPNPAA | LUAD |
| EPHB6 | c.160del G | p.G54fs | ALEEVLLDTTGETSEIGWLTYPPGG[p.G54fs]GTR* | LTYPPGGGTR | STAD |
| EPHX1 | c.394del C | p.P132fs | ILNRYPHFKTKIEGLDIHFIHVKPP[p.P132fs]SCPQAIPRSPC* | KPPSCPQAI, HVKPPSCPQA, CPQAIPRSPC | STAD |
| EPHX4 | c.845G>A | p.R282Q | TTEDLEAYIYFSQPGALSGPINHY[p.R282Q]QNIFSCLPLKHHMVTTPTLLMGE ND | HYQNIFSCL, GPINHYQNI, YQNIFSCLP, QNIFSCLPL, YQNIFS CLPL, QNIFSCLPLK, GPINHYQNIF, NHYQNIFSCL | UCEC |
| EPPK1 | c.6044del G | p.G2015fs | FQAMQKQLIEKAEALRLLEVQATG[p.G2015fs]VSSTHSTTTGSHMKQPTDGA VCTRTSMRSFPTRST* | STTTGSHWK, AVCTRTSMR, TSMRSFPTR, CTRTSMRSF, RTS MRSFPT, SMRSFPTRS, LEVQVATGV, VQVATGVSS, HSTTTG SHW, WKQPTDGAV, GAVCTRTSM, LLEVQVATGV, RTSMR SFPTR, HSTTTGSHWK, STHSTTTGSH, CTRTSMRSFP, SMRS FPTRST, VQVATGVSST, VCTRTSMRSF | STAD |
| EPPK1 | c.7132G>C | p.D2378H | HSHRVPVDVAYRRGYFDEEMNRVLA[p.D2378H]HPSDDTKGFFDPNTHENLTY LQLLQR | EEMNRVLAH, HPSDDTKGF, VLAHPSDDTK, HPSDDTKGFF, DEEMNRVLAH | ACC |
| EPRS | c.3451G>T | p.V1151L | MYPAYAKWVQSHRDLPIKLNQWCNV[p.V1151L]LRWEFKHPQPFLRTREFLW QEGHSAF | KLNQWCNVL, CNVLRWEFK, NQWCNVLRW, LNQWCNVLR, WCNVLRWEF, KLNQWCNVLR, QWCNVLRWEF, IKLNQW CNVL | LUAD |
| EPRS | c.4003C>A | p.L1335I | GITNALSEEDKEALIAKCNDYRRRL[p.L1335I]ISVNIRVRADLRDNYSPGWKFNH WEL | RLISVNIRV, RRRLISVNI, DYRRRLISV, RRRLISVNIR, RLISVNI RVR, NDYRRRLISV, YRRRLISVNI | TGCT |
| ERBB2 | c.2264T>C | p.L755S | AFGTVYKGIWIPDGENVKIPVAIKV[p.L755S]SRENTSPKANKEILDEAYVMAGV GSP | VSRENTSPK, IPVAIKVSR, KVSRENTSPK, VSRENTSPKA | BRCA |
| ERBB2 | c.2305G>T | p.D769Y | ENVKIPVAIKVLRENTSPKANKEIL[p.D769Y]YEAYVMAGVGSPYVSRLLGICLTSTV | ILYEAYVMA, YEAYVMAGV, NKEILYEAY, KEILYEAYV, EILYE AYVM, ILYEAYVMAG, ANKEILYEAY, EILYEAYVMA, KEILYEA YVM, SPKANKEILY, YEAYVMAGVG | BRCA |
| ERBB2 | c.2310_2311 insGCATA CGTGATG | p.774_775ins AYVM | AIKVLRENTSPKANKEILDEAYVMA[p.774_775insAYVM]YVMAGVGSPYVSRL LGICLTSTVQLVTQLMPYGCLLD | VMAYVMAG, YVMAYVMAG, DEAYVMAYV, EAYVMAYV, M, LDEAYVMAY, MAYVMAGVG, ILDEAYVMAY, YVMAYV MAGV, EAYVMAYVMA, DEAYVMAYVM | LUAD |
| ERBB2 | c.2326_2327insTCT | p.776G>VC | AIKVLRENTSPKANKEILDEAYVMA[p.776_776G>VC]VCVGSPYVSRLLGICLTS TVQLVTQLMP | AVCVGSPYV, MAVCVGSPY, EAYVMAVCV, YVMAVCVGS, D EAYVMAVC, ILDEAYVMAV, MAVCVGSPYV, VMAVCVGSP Y, DEAYVMAVCV | LUAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ERBB2 | c.2524G>A | p.V842I | LGSQDLLNWCMQIAKGMSYLEDVRL[p.V842I]IHRDLAARNVLVKSPNHVKITDFGLA | RLIHRDLAA, SYLEDVRLI, LIHRDLAAR, RLIHRDLAAR, YLEDVRLIHR, MSYLEDVRLI | CRC |
| ERBB2 | c.2748G>A | p.M916I | LESILRRRFTHQSDVWSYGVTWEL[p.M916I]ITFGAKPYDGIPAREIPDLLEKGERL | YGVTVWELI, VTVWELITF, LITFGAKPY, WELITFGAK, TVWELITFGA, SYGVTVWELI, ELITFGAKPY, GVTVWELITF, WELITFGAKP | HNSC |
| ERBB2 | c.929C>A | p.S310Y | PEGRYTFGASCVTACPYNYLSTDVG[p.S310Y]YCTLVCPLHNQEVTAEDGTQRCEKCS | YLSTDVGYC, STDVGYCTLV, YLSTDVGYCT, YNYLSTDVGY, LSTDVGYCTL, VGYCTLVCPL | LUAD |
| ERBB2 | c.929C>T | p.S310F | PEGRYTFGASCVTACPYNYLSTDVG[p.S310F]FCTLVCPLHNQEVTAEDGTQRCEKCS | STDVGFCTL, YLSTDVGFC, NYLSTDVGF, STDVGFCTLV, YLSTDVGFCT, YNYLSTDVGF, LSTDVGFCTL, VGFCTLVCPL | BLCA, BRCA, CESC, STAD |
| ERBB3 | c.273G>A | p.M91I | VLTGHNADLSFLQWIREVTGYVLVA[p.M91I]INEFSTLPLNLRVVRGTQVYDGKFA | YVLVAINEF, VAINEFSTL, INEFSTLPL, AINEFSTLPL, GYVLVAI NEF, EVTGYVLVAI | BLCA |
| ERBB3 | c.310G>A | p.V104M | WIREVTGYVLVAMNEFSTLPLNLR[p.V104M]MVRGTQVYDGKFAIFVMLNYNTNSSH | RMVRGTQVY, LPLPNLRMV, LRMVRGTQV, TLPLPNLRMV, NLRMVRGTQV, LRMVRGTQVY | CESC, CRC, STAD |
| ERBB3 | c.310G>T | p.V104L | WIREVTGYVLVAMNEFSTLPLNLR[p.V104L]LVRGTQVYDGKFAIFVMLNYNTNSSH | RLVRGTQVY, LPLPNLRLV, TLPLPNLRLV, NLRLVRGTQV, LRLVRGTQVY | BLCA |
| ERBB3 | c.889G>T | p.D297Y | LEPNPHTKYQYGGVCVASCPHNFVV[p.D297Y]YQTSCVRACPPDRMEVDKNGLKMCEP | FVVYQTSCV, VVVYQTSCVR, YQTSCVRAC, ASCPHNFVVY, FVVYQTSCVR | BLCA |
| ERC1 | c.2075A>G | p.K692R | DLSEKEASLLDLKEHASSLASSGLK[p.K692R]RDSRLKTLEIALEQKEECLKMESQL | GLKRDSRLK, SLASSGLKR, SSLASSGLKR, SGLKRDSRLK, LKRDSRLKTL | TGCT |
| ERCC2 | c.41A>G | p.Y14C | MKLNVDGLLVYFP[p.Y14C]CDYIYPEQFSYMRELKRTLDAKGHGV | LVYFPCDYI, VYFPCDYIY, LLVYFPCDY, CDYIYPEQF, FPCDYIYPE, LLVYFPCDYI, LVYFPCDYIY, GLLVYFPCDY | BLCA |
| ERCC2 | c.713A>G | p.N238S | LDPKIADLVSKELARKAVVVFDEAH[p.N238S]SIDNVCIDSMSVNLTRRTLDRCQGNL | VVFDEAHSI, EAHSIDNVCI | BLCA |
| ERCC2 | c.934G>A | p.D312N | RLVEGLREASAARETDAHLANPVLP[p.D312N]NEVLQEAVPGSIRTAEHFLGFLRRLL | NPVLPNEVL, LPNEVLQEA, VLPNEVLQEA, LANPVLPNEV, LPNEVLQEAV | ACC |
| ERCC6 | c.2338G>A | p.V780I | SLPDKNEQVLFCRLTDEQHKVYQNF[p.V780I]IDSKEVYRILNGEMQIFSGLIALRKI | FIDSKEVYR, NFIDSKEVY, YQNFIDSKEV, FIDSKEVYRI, KVYQNFIDSK, NFIDSKEVYR, QNFIDSKEVY | CRC |
| ERCC6 | c.1514G>A | p.R505Q | LVFSQSRQILNIIERLLKNRHFKTL[p.R505Q]QIDGTVTHLLEREKRINLFQQNKDYS | KTLQIDGTV, LQIDGTVTH, LQIDGTVTHL, KNRHFKTLQI | CRC |
| ERCC6L | c.1333C>A | p.L445I | LGDTSILDDLFKSHGNSPTQLPKKV[p.L445I]ISGPMEKAKQRPKDFWDIINEQNDES | KVISGPMEK, VISGPMEKAK, SPTQLPKKVI, LPKKVISGPM | UCEC |
| ERN2 | c.884C>A | p.T295K | TQDLGVPVMGVVTWHQDLGRLQPHL[p.T295K]KLARDTLHFLALRWGHIRLPASGPRD | GLRQLPHLK, KLARDTLFIF, RQLPHLKLA, QLPHLKLAR, HLKLARDTL, KLARDTLHFL, RQLPHLKLAR, LKLARDTLHF | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ERRFI1 | c.1261G>A | p.A421T | LLPERPPYLDKYEKFREAEETNGG[p.A421T[TQIQPLPADCGISSATEKPDSKTKMD | AEETNGGTQI | CRC |
| ESCO1 | c.899G>A | p.R300Q | TLPKSPQPSVPEQSDNELEQAGKSK[p.R300Q]QGSILQLCEEIAGEIESDNVEKKES | KSKQGSILQ, GKSKQGSIL, SKQGSILQL, KSKQGSIIQL | CRC |
| ESF1 | c.295de|A | p.T99fs | LSDSDNLSGEDSKALSQKKIKKKK[p.T99fs]PRLKKKSIQKI* | RLKKKSIQK, KIKKKKPRL, KKKKKPRLKK, KKKKKPRLKKK, KPRLKK KSI, LKKKSIQKI, RLKKKSIQKI, KIKKKKPRLK, KKKKKPRLKKK | STAD |
| ESPN | c.1286_1348de|CACCC CCACCCA CCACCCA GCTTCCCCC CGCCACCC CCGCCCCC AGGCACCC AACTGCCC C | p.PPPP PPSFPP PPPPP GTQLP P430de| | QSYMDMLNPELGLPRGTIGKPTPPP[p.PPPPPSFPPPPPGTQLPP430de|]G YPAPKPPVGPQAADIYMQTKNKLRHVE TEALKKELSSCDGHDGLRRQDSSRKPPA FSKQPSTGDYYRQLGRCPGETLAARPG MAHSE | IGKPTPPPGY, KPTPPPGYPA | PAAD |
| ESPNP | c.1880G>A | p.R627Q | EEEQRWKEEEARLASMPAWRWDLL[p.R627Q]QKKLEEE | AWRWDLLQK, AWRWDLLQKK, WRWDLLQKKL | GBM |
| ESPNP | c.191_198dele|ACGCGCG C | p.H64fs | PLYLACQEGHLEVTQYLVQECGADP[p.H64fs]RPPRHDPTARRGADGPQPGHR VVGELHRREPVGAGQRRRHRHALRGE PRPQQGAQLAAAARGDLG* | GQRRRHHA, RRRHRHALR, RPRRHDPTA, GPQPGHRVV, Q RRRHRHAL, RPQQGAQLA, AAAARGDL, GPQPGHRVVG, GE LHRREPV, GQRRRHHAL, LVQECGADPR, QPGHRVVGEL, E PRPQQGAQL, RPQQGAQLAA, LAAAARGDL, QQGAQLAA AA | PAAD |
| ESPNP | c.888_950dele|ACCCCCA CCAGCTT CCCCCCGC CACCCCG CACCCCAG CACCAAC TGCCCCA CCCCCACC | p.296_317PPP PSFPPP PPPPG TQLPPP PP>P | QSYMDMLNPELGLPWGTIGKPIPPP[p.296_317PPPPSFPPPPPPGTQLPPPP >P|SYPSPKPPVGPQAADIYMQTKNLR HVETEALKKEPSSCDGHDGLRRQDSSR KPRAFSKQPSTGDYYRQLGRCPGETLV ARPGMAHRE | IGKPIPPPSY | PAAD |
| ESRRA | c.655G>A | p.D219N | VNALVSHLLVVEPEKLYAMPDPAGP[p.D219N]NGHLPAVATLCDLFDREIWTIS WAK | GPNGHLPAV, MPDPAGPNGH | HNSC |
| ESYT1 | c.2446C>T | p.R816W | LQVNSLIQTQKSAELAAELAAALLSIYME[p.R816W]WAEDLPLRKGTKHLSPYATLTV GDSS | LLSIYMEWA, ALLSIYMEW, IYMEWAEDL, EWAEDLPLR, ME WAEDLPL, ALLSIYMEWA, YMEWAEDLPL, AALLSIYMEW | BRCA |
| ESYT3 | c.1721C>T | p.S574F | QILPYADLITLEQRFQLDHSGLDSLI[p.S574F]FMRLVLRFLQVEERELGSPYTGPEA L | SLIFMRLVI, FMRLVLRFL, LIFMRLVLR, IFMRLVLRF, DSLIFM RLV, HSGLDSLIF, SGLDSLIFM, GLDSLIFMR, SLIFMRLVLR, I FMRLVLRFL, SGLDSLIFMR, LIFMRLVLRF, HSGLDSLIFM | LUSC |
| ETFDH | c.841A>T | p.I281F | LYKKFDLRANCEPQTYGIGLKELWV[p.I281F]FDEKNWKPGRVDHTVGWPLDR HTYGG | WVFDEKNWK, IGLKELWVF | CLL |
| ETV6 | c.1105C>T | p.R369W | YVYQLLSDSRYENFIRWEDKESKIF[p.R369W]WIVDPNGLARLWGNHKQRTNM TYEKM | WIVDPNGLA, KESKIFWIV, IFWIVDPNGL | CRC |

TABLE 8-continued

| gene | cDNA Change | Protein Change | Mutation_Context_Sequence (SEQ ID NOS 81-3798, respectively in order of appearance) | Peptides (SEQ ID NOS 3799-33502, respectively, in order of appearance) | Exemplary Diseases |
|---|---|---|---|---|---|
| EXOC1 | c.1762C>T | p.R588C | QHNCGTPLPVSSEKDMIRQMMIKIF[p.R588C]CCIEPELNNLIALGDKIDSFNSLYML | MMIKIFCCI,RQMMIKIFC,QMMIKIFCCI,KIFCCIEPEL,RQMMIKIFCC | UCEC |
| EXOSC2 | c.32G>C | p.R11P | MAMEMRLPVA[p.R11P]PKPLSERLGRDTKKHLWPGDTITTD | EMRLPVAPK,APKPLSERL,MEMRLPVA,MEMRLPVAPK,MRLPVAPKPL | KIRP |
| EXOSC8 | c.480del|A | p.L160fs | CDLICLDYDGNILDACTFALLAALK[p.L160fs]MYSCLKLL* | KMYSCLKLL,ALKMYSCLK,ALLAALKMY,FALLAALKM,AALK MYSCL,LKMYSCLKL,LLAALKMYSC,ALKMYSCLKL,AALKM YSCLK,LAALKMYSCL,FALLAALKMY,LKMYSCLKLL | STAD |
| EZH2 | c.1529A>G | p.K510R | VDTPPRKKKRKHRLWAAHCRKIQLK[p.K510R]RDGSSNHVYNYQPCDHPRQPCDSSCP | RDGSSNHVY,LKRDGSSNH,KRDGSSNHVY | TGCT |
| EZH2 | c.1922A>T | p.Y641F | LAPSDVAGWGIFIKDPVQKNEFISE[p.Y641F]FCGEIISQDEADRRGKVYDKYMCSFL | FISEFCGEI,QKNEFISEF,SEFCGEIIS,FISEFCGEII,VQKNEFISEF | DLBCL |
| F10 | c.349G>A | p.E117K | TSPCQNQGKCKDGLGEYTCTCLEGF[p.E117K]KGKNCELFTRKLCSLDNGDCDQFCHE | KGKNCELFT,FKGKNCELF,YTCTCLEGFK,CTCLEGFKGK,GFKGKNCELF,KGKNCELFTR | UCEC |
| F5 | c.1277A>T | p.Q426L | DESFTKHTVNPNMKEDGILGPIIRA[p.Q426L]LVRDTLKIVFKNMASRPYSIYPHGVT | ILGPIIRAL,ALVRDTLKI,LVRDTLKIV,RALVRDTLK,IRALVRDTL,ILGPIIRALV,ALVRDTLKIV,IIRALVRDTL,RALVRDTLKI,LVRDTLKIVF | LIHC |
| F5 | c.3995T>C | p.L1332P | LSQTNLSPALGQOMPISPDLSHTTLS[p.L1332P]PDFSQTNLSPELSQTNLSPALGQMPL | TLSPDFSQT,SPDFSQTNL,SHTTLSPDF,LSHTTLSPDF | CLL |
| F8 | c.6806C>A | p.S2269Y | NPKEWLQVDFQKTMKVTGVTTQGVK[p.S2269Y]YLLTSMYVKEFLLSSSQDGHQWTLFF | YLLTSMYVK,KYLLTSMYV,GVKYLLTSM,GVTTQGVKY,VKYLLTSMY,TTQGVKYLL,KYLLTSMYVK,GVKYLLTSMY,QGVKYLLTSM,VKYLLTSMYV | CRC |
| FAM104B | c.223G>C | p.D75H | SSSRINIPERASGPEGNLNQIVTEP[p.D75H]HANFPQFLHEGLSKPVVINWFMSFG | HANFPQFLH,EPHANFPQF,IVTEPHANF,EPHANFPQFL,QIVTEPHANF,EPHANFPQF | TGCT |
| FAM105A | 0.376C>A | p.H126N | AREWKGETPRNKLMRKAYEELFWRH[p.H126N]NIKCVRQVRRDNYDALRSVLFQIFSQ | ELFWRHNIK,NIKCVRQVR,EELFWRHNI,FWRHNIKCVR,HNIKCVRQVR,NIKCVRQVRR,YEELFWRHNI | KIRC |
| FAM109A | c.466_474del|GGGGT GGC | p.GGG156del | LSRASFDYLRLVVRELEQQLAAVRG[p.GG156de]|MALPQPQPQSLPLPPSLPSALAPVPSLPSAPAPV | QLAAVRGMA,LAAVRGMAL,QQLAAVRGM,QLAAVRGM AL,EQQLAAVRGM,QQLAAVRGMA | ACC |
| FAM111B | c.807del|A | p.S269fs | KIYGKQSMVDEVSGKVLEMDISKKK[p.S269fs]HYNRKISIKKLNRMKVPLMKLITRV* | KLNRMKVPL,PLMKLITRV,RMKVPLMKL,ISKKKHYNR,SKK KHYNRK,KHYNRKISI,HYNRKISIK,YNRKISIKK,KISIKKLNR,SI KKLNRMK,LNRMKVPLM,ISIKKLNRM,MKVPLMKLI,KLNR MKVPLM,RMKVPLMKLI,ISIKKLNRMK,ISKKKHYNRK,KHY NRKISIK,HYNRKISIKK,KISIKKLNRM,SIKKLNRMKV,LNRM KVPLMK,KVPLMKLITR,DISKKKHYNR,KKHYNRKISI,KKLNR MKVPL,VPLMKLITRV | PRAD |
| FAM116A | c.1322del|T | p.L441fs | IKQLQKGVQQKRPSEAQSVILRRYF[p.L441fs]WN* | SVILRRYFW | STAD |
| FAM120B | c.1400C>A | p.P467H | DSEPRQEVPMYTGSEPRQEVPMYTG[p.P467H]HESRQEVPMYTGPESRQEVLIRTDPE | HESRQEVPM,VPMYTGHES,RQEVPMYTGH,HESRQEVPMY | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| FAM126B | c.1145G>A | p.R382H | LSSQPIGTKPSSSSQRGSLRKVATG[p.R382H]HSAKDKETASAIKSSESPRDSVRRK Q | KVATGHSAK, ATGHSAKDK, RKVATGHSA | GBM |
| FAM127C | c.156C>A | p.F52L | IPFPETFDGDTDRLPEFIVQTSSYM[p.F52L]LVDENTFSNDALKVTFLITRLTGPAL | VQTSSYMLV, MLVDENTFS, YMLVDENTF, FIVQTSSYML, IV QTSSYMLV, SYMLVDENTF | LUAD |
| FAM35B | c.1933A>C | p.S645R | KGIDQEGKMVLLSLKLTPSEPCDPL[p.S645R]RSTLREPLDIRSSLKDSHTEEQEEL S | LRSTLREPL, EPCDPLRSTL | STAD |
| FAM35B | c.1942C>A | p.L648M | DQEGKMVLLSLKLTPSEPCDPLSST[p.L648M]MREPLDIRSSLKDSHTEEQEELS VLS | TMREPLDIR, LSSTMREPL, STMREPLDIR, EPCDPLSSTM | LUSC |
| FAM35B | c.2651G>A | p.R884H | GHCLPDGRTENTPGVETKGLNLKIP[p.R884H]HVIALENPRTRSLHRALEETPKG MPK | GLNLKIPHV, HVIALENPR, LKIPHVIAL, GLNLKIPHVI, NLKIPH VIAL, KGLNLKIPHV | CRC |
| FAM35B | c.720G>C | p.W240C | GYCKPTSSEGSFYITSENCMQHAHK[p.W240C]CHRDLCLLLLHAYRGLRLHFLVI MRD | MQHAHKCHR, CMQHAHKCHR | LUAD |
| FAM35B | c.855G>T | p.Q285H | LVIMRDIPELPHTELEALAVEETLS[p.Q285H]HLCSELQMLNNPEKIAEQISKDLA WL | TLSHLCSEL, HLCSELQML, SHLCSELQM, ETLSHLCSEL, LAVE ETLSHL, LSHLCSELQM | LUSC |
| FAM51A1 | c.351del|C | p.P117fs | LEADVNVEGLGTANETGVPIMAHPP[p.P117fs]LSTVTTHWSSGWTLCWALPKR ASNWTSRTSRQWAPPWTSCGS* | IMAHPPLST, MAHPPLSTV, WTLCWALPK, TSRTSRQWA, RT SRQWAPP, TLCWALPKR, SNWTSRTSR, VPIMAHPPL, THW SSGWTL, SGWTLCWAL, TSRQWAPPW, RQWAPPWTS, WS SGWTLCW, IMAHPPLSTV, GWTLCWALPK, WTLCWALPKR, ASNWTSRTSR, HWSSGWTLCW, RTSRQWAPPW, TTHWSS GWTL, WSSGWTLCWA, MAHPPLSTVT, SSGWTLCWAL, W ALPKRASNW, RQWAPPWTSC, PPLSTVTTHW RQRQQQQQR, RRRQQEPSW, RQRQQQQQRR | STAD |
| FAM55A | c.284A>G | p.Q95R | KEHQQQQRQQQQQQQQRQRQQQ QQ[p.Q95R]RRRQQEPSWPALLASMG ESSPAAQAH | | TGCT |
| FAM55B | c.472G>A | p.E158K | VCGGVPEPTGLDAACTKLQSLQRLF[p.E158K]KPTTPAPPLRPPDSLSRAPAEFPS AK | RLFKPTTPA, LQSLQRLFK, KPTTPAPPL, LQRLFKPTT, KLQSL QRLFK, LQRLFKPTTP, RLFKPTTPAP, FKPTTPAPPL | UCEC |
| FAM69B | c.495G>T | p.K165N | NDRPRQPAPGDGSKERMCGEELEDT[p.K165N]NDDPECGVEEEDAGLAGQPP GKLTRS | DTNDDPECGV | CRC |
| FAM70A | c.166G>A | p.E56K | DALQPGSTRVAKGMSQGVGEVTSTS[p.E56K]KYCSCVSSSRKLIHSGIQRIHRDS PQ | STSKYCSCV, GEVTSTSKY, SKYCSCVSS, GVGEVTSTSK, VGEV TSTSKY, TSTSKYCSCV, SKYCSCVSSS | CRC |
| FAM71B | c.1375G>A | p.D459N | SYSPQKKEPSKAETEERVSMVKTRD[p.D459N]NFKIYNEDVSFLSVNQNNYSRN PTQS | MVKTRDNFK, KTRDNFKIY, SMVKTRDNF, SMVKTRDNFK, MVKTRDNFKI, KTRDNFKIYN, VSMVKTRDNF, VKTRDNFKIY | CRC |
| FAM79A | c.2491G>A | p.A831T | QVFDAFTPRLQDSNKKVNQWALESF[p.A831T]TKMIPLLRESLHPMLLSIIITVAD NL | FTKMIPLLR, SFTKMIPLL, ESFTKMIPL, WALESFTKM, NQWA LESFTK, SFTKMIPLLR, ESFTKMIPLL, WALESFTKMI, LESFTK MIPL | BRCA |
| FAM81A | c.326G>A | p.R109H | KAALDKSAPCRRSVDHRKYLQKQLK[p.R109H]HFSQKYSRLPRGLPGRAAEPYL KRGS | KQLKHFSQK, YLQKQLKHF, KHFSQKYSR, QLKFIFSQKY, KYL QKQLKHF, KQLKHFSQKY, RKYLQKQLKH, KHFSQKYSRL | CRC |

TABLE 8-continued

| gene | cDNA Change | Protein Change | Mutation_Context_Sequence (SEQ ID NOS 81-3798, respectively in order of appearance) | Peptides (SEQ ID NOS 3799-33502, respectively, in order of appearance) | Exemplary Diseases |
|---|---|---|---|---|---|
| FAM184B | c.2350C>T | p.R784W | RALGRQASSQCPGDSKDHIIATEE[p.R784W]WGGPGQAGSPPGAAGQGSGEGCGLWE | EEWGGPGQA, EEWGGPGQAG, TEEWGPGQA | ACC |
| FAM186A | c.4667470_2de[TCCCTCCGCAGGCTCAGAATTGGAGATCCCTCTCA | p.IPPQAQELEIPL1556de| | LIPPQAQELGIPLTPQQVQALGIPL[p.IP PQAQELEIPL1556de||TPQQAQALGIP LTPQQAQELGIPLTPQQAQALGIPLTPQ QAQAQGIPLTPQQAQALGISLT | VQALGIPLIT, VQALGIPLTP | KIRC |
| FAM188B2 | c.152G>A | p.C51Y | PRKAKIRHPVASFFHLFFRVSAIIV[p.C51 Y]YLLCELLSSSFITCMVTILLLLSCDF | IIVYLLCEL, YLLCELLSS, QIIVYLLCEL, IIVYLL CELL, YLLCELLSSS | ACC, KIRP, TGCT |
| FAM193A | c.1284_1285insC | p.D428fs | NYRRRCACDDCSLSHILTCGIMDPP[p.D 428fs]RH* | LTCGIMDPPR | STAD |
| FAM193A | c.1284de|C | p.D428fs | NYRRRCACDDCSLSHILTCGIMDPP[p.D 428fs]SLMTSTFTSSHFKWILLTILLRGA RPVCHLQARGPAPALPSQFSSTPGSSSQ TVARHQLFVVMMKMLHHCQPNLLIFI H* | SLMTSTFTS, WILLLTIL, ILLRGARPV, VMMKMLHHC, MLH HCQPNL, GIMDPPSLM, FTSSHFKWI, LLTILLRGA, LQARGPA PA, ALPSQFSST, TVARHQLFV, STFTSSHFK, HQLFWMMK, MTSTFTSSH, GSSSQTVAR, TFTSSHFKW, SHFKWILL, KWIL LLTIL, QTVARHQLF, HCQPNLLIF, CQPNLLIFI, SSHFKWILL, V ARHQLFW, LTILLRGAR, QARGPAPAL, TSTFTSSFIF, LMTST FTSS, FKWILLLTI, RGARPVCHL, SQFSSTPGS, SQTVARHQL, ARHQLFWM, RHQLFWMM, QLFWMMKM, MKMLHHC QP, KMLHHCQPN, TPGSSSQTV, PPSLMTSTF, LLLTILLRGA, TVARHQLFVV, KMLHHCQPNL, MLHHCQPNLL, SLMTSTFT SS, HLQARGPAPA, LQARGPAPAL, QLFVVMMKML, TSTFTS SHFK, TFTSSHFKWI, HFKWILLLTI, KWILLLTILL, SQTVARHQ LF, SSHFKWILLL, GARPVCHLQA, VARHQLFVVM, RHQLFVV MMK, MTSTFTSSHF, WILLLTILLR, LTILLRGAR, FTSSHFKW IL, STPGSSSQTV, QTVARHQLFV, GPAPALPSQF, LMTSTFTS SH, HQLFVVMMKM, CGIMDPPSLM, STFTSSHFKW, FKWIL LLTIL, SQFSSTPGSS, ARHQLFVVMM, MKMLHHCQPN, HHC QPNLLIF, LPSQFSSTPG | STAD |
| FAM194B | c.404_421de e|AGGAGGAAGAGTATCTGG | p.EEEEYL135de| | IEEEEYLGKEGYLEEEEYLGKEEHL[p.EEE EYL135de||GKEGYLEKEDYIEEVDYLGK KAYLEEEEYLGKKSYLEEEKALE | LGKEEHLGK, EEHLGKEGY, HLGKEGYLEK, KEEHLGKEGY, EE HLGKEGYL | KIRC |
| FAM194B | c.415T>C | p.Y139H | EYLGKEGYLEEEEYLGKEEHLEEEE[p.Y1 39H]HLGKEGYLEKEDYIEEVDYLGKKAYL | EEHLGKEGY, HLGKEGYLEK, EEEHLGKEGY, EEHLEEEEHL, EE HLGKEGYL | TGCT |
| FAM210B | c.336G>T | p.L112F | QQLKKIFQEYGTVGVSLHIGISLIS[p.L11 2F]PGIFYMVSSGVDMPAILLKLGFKES | GISLISFGI, LISFGIFYM, ISFGIFYMV, SLISFGIFY, ISLISFGIF, SFGIFYMVV, HIGISLISF, ISLISFGIY, SLISFGIFYM, LISFGI FYMV, ISFGIFYMW, LHIGISLISF, GISLISFGIF | LUAD |
| FAM214B | c.124de|G | p.A42fs | GPSQPPVRQGALQGLLMGYSPAGG[p. A42fs]RHPPGSTRYPSFPLRLVPLSLIG p* | RYPSFPLRL, SFPLRLVPL, STRYPSFPL, RHPPGSTRY, MGYSP AGGR, YPSFPLRIV, SPAGGRHPP, RLVPLSLIG, FPLRLVPLS, S TRYPSFPLR, RYPSFPLRLV, GGRHPPGSTR, LMGYSPAGGR, S PAGGRHPPG, FPLRLVPLSL, MGYSPAGGRH, GRHPPGSTRY, GSTRYPSFPL, TRYPSFPLRL | STAD |
| FAM216A | c.106C>T | p.P36S | RGLGAAEMPGQGPGSDWTERSSSAE[p. P36S]SPAVAGTEGGGGSGAGYSCYQ NSKGS | RSSSAESPAV, AESPAVAGT, RSSSAESPAV | KIRP |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| FAM21B | c.3691C>T | p.P1231S | DMDDIFSSGIQAKTTKPKSRSAQAA[p.P1231S]SEPRFEHKVSNIFDDPLNAFGGQ* | ASEPRFEHK,KSRSAQAAS,SAQAASEPR,AQAASEPRF,SEP RFEHKV,RSAQAASEPR,AASEPRFEHK,KSRSAQAASE,SAQ AASEPRF | TGCT |
| FAM22F | c.2070_2071delTT | p.P690fs | PGGRGPQGALQSPSAQKRGLSPSPS[p.P690fs]CQQVQEATSLWKPIC* | VQEATSLWK,EATSLWKPI,SPSPSCQQV,QQVQEATSL,QV QEATSLWK,CQQVQEATSL,QQVQEATSLW,QEATSLWKPI | KIRC |
| FAM22F | c.2071_2073delTCT | p.S691del | SPGGRGPQGALQSPSAQKRGLSPSP[p.S691del]PASKSKKRPLFGSPSPAEKTHPGPGLR | LSPSPPASK,RGLSPSPPA,GLSPSPPASK | KIRC,PRAD |
| FAM32A | c.26A>G | p.K9R | MEAYEQVQ[p.K9R]RGPLKLKGVAELG VTKRKKKKDKDK | VQRGPLKLK,YEQVQRGPL,QVQRGPLKLK,EQVQRGPLKL | TGCT |
| FAM40B | c.2218C>T | p.R740C | LQTKYLGRQWRKSNMKTMSAIYQKV[p.R740C]CHRMNDDWAYGNDIDARPWDFQAEEC | AIYQKVCHR,IYQKVCHRM,AIYQKVCHRM,CHRMNDDWAY,SAIYQKVCHR | STAD |
| FAM46B | c.1247_1248AC>GT | p.H416R | RPPGTDGWPAITVNYYVTPVQPLLA[p.H416R]RAYPTWLPCN* | LLARAYPTW,LARAYPTWL,RAYPTWLPC,VQPLLARAY,LLA RAYPTWL,PVQPLLARAY | TGCT |
| FAM47A | c.1114G>T | p.G372W | GSSLRSEPSETGVSRLRLAPPKTRR[p.G372W]WSSLHAEPSKTGVSHLSPEPPKTEVS | KTRRWSSLH,WSSLHAEPSK,KTRRWSSLHA,PPKTRRWSSL,RLAPPKTRRW | LUSC |
| FAM47A | c.2069G>T | p.R690L | EDKFFSQEKVWGRKFHTPSNSYTAQ[p.R690L]LVKMKYGAWYLKPKLWKKLRSDEPLI | NSYTAQLVK,YTAQLVKMK,SYTAQLVKM,YTAQLVKMKY,S NSYTAQLVK,LVKMKYGAWY,TPSNSYTAQL,NSYTAQLVK M,QLVKMKYGAW | LUAD |
| FAM47B | c.1701G>T | p.L567F | QRGRIRYGPWYFEPKLGKKLRSDEP[p.L567F]FIDKPVLEKPDEPDILDGLYGPIAF | KLRSDEPFI,KKLRSDEPF,EPFIDPKPV,RSDEPFIDPK,FIDPKP VLEK,EPFIDPKPVL,GKKLRSDEPF,KKLRSDEPFI | LUAD |
| FAM47B | c.489G>T | p.W163C | GKDMPPDLLLQVLKQLDPERKLEDA[p.W163C]CARCEAREKTTEVPTESGKYPCGESC | CARCEAREK,DACARCEAR,LEDACARCEA | LUAD |
| FAM47C | c.1162C>T | p.P388S | VSPLRQLPPEAGVSHLCPEPPKTRV[p.P388S]SPLRPETPKNGVSPLFPEPPKTRISN | KTRVSPLRP,RVSPLRPET,PPKTRVSPL,KTRVSPLRPE,EPPKT RVSPL | KIRC |
| FAM48B1 | c.1495A>G | p.I499V | ISSGNSFPPQQAGSPLKRPFSAAAA[p.I499V]VAAAAAAAAAAAAAAAAPALAA | FSAAAAVAA,SAAAAVAAA,RPFSAAAAV,FSAAAAVAAA,S AAAAVAAAA,RPFSAAAAVA | TGCT |
| FAM48B1 | c.1546P>C | p.A516P | RPFSAAAAIAAAAAAAAAAAAAAA[p.A516P]PAPALAAAAAPALAAAAPALAAA | AAAPAPAPAL,APAPAPPALAA | TGCT |
| FAM50A | c.950A>G | p.H317R | SDATVEKDESHAGKVVLRSVYEKNK[p.H317R]RIFPASRWEPYDPEKKWDKYTIR* | KNKRIFPAS,KRIFPASRW,SWYEKNKRIF,KNKRIFPASR,YEK NKRIFPA,NKRIFPASRW | CLL |
| FAM58BP | c.208G>A | p.A70T | LGMQSIPIATACTIYPKFCETILD[p.A70T]TFDPYLIAMSSIYLAGKVEEQPLWAH | ILDTFDPYL,TILDTFDPY,DTFDPYLIA,ETILDTFDPY,TILDTFD PYL,ILDTFDPYLI,FPCETILDTF,DTFDPYLIAM | BRCA |
| FAM5B | c.1204C>T | p.R402C | AGLKVLFKKTHRILRRLFNLCKRCH[p.R402C]CQPRFRLPKERSLSYWWNRIQSLLYC | CQPRFRLPK,RCHCQPRFR,KRCHCQPRF,RCHCQPRFRL,HC QPRFRLPK,CKRCFICQPRF | CRC |
| FAM5C | c.1274C>G | p.S425W | WLTRIQSFLYCNENGLLGSFSEETH[p.S425W]WCTCPNDQVVCTAFLPCTVGDASACL | GSFSEETHW | TGCT |
| FAM5C | c.1369C>G | p.R457G | QVVCTAFLPCTVGDASACLTCAPDN[p.R457G]GTRCGTCNTGYMLSQGLCKPEVAEST | GTRCGTCNT,GTRCGTCNTG,LTCAPDNGTR | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| FAM70B | c.56C>T | p.S19L | MQPPVPGPLGLLDPAEGL[p.S19L]LRRKKTSLWFVGSLLLVSVLIVTVGL | LLDPAEGLL,LLRRKKTSL,GLLDPAEGLL,GLLRRKKTSL,LLRRKKTSLW,LRRKKTSLWF | STAD |
| FAM70B | c.829C>A | p.P277T | GFRLTPEPVPTCSSYPLPLQPCSRF[p.P277T]TVAPSSALASSEDLQPPSPSSSGSGL | LQPCSRFTV,FTVAPSSAL,TVAPSSALA,CSRFTVAPS,RFTVAPSSA,QPCSRFTVA,FTVAPSSALA,CSRFTVAPSS,LQPCSRFTVA,SRFTVAPSSA,RFTVAPSSAL | LUAD |
| FAM71B | c.1333C>G | p.H445D | PSAEVWNENKERREKKDRHPSRKSS[p.H445D]DHRKAGESHRRAGDKNQKASSHRSA | PSRKSSDHRK | CESC |
| FAM71B | c.1747C>A | p.L583M | VDIVAKMVEKQNIEAKVEKAQGGQE[p.L583M]MEMISGTMTSEKTEMIVFETKSI* | EKAQGGQEM,AQGGQEMEM,QEMEMISGT,MEMISGTMT,QEMEMISGTM,VEKAQGGQEM,KAQGGQEMEM,MEMISGTMTS | LUAD |
| FAM73A | c.68G>T | p.G23V | MSDCCSAPGISWEAGVGRPAVP[p.G23V]VLELQIRRGAMSEETVSESQFSLKTA | RPAVPVLEL,VGRPAVPVL | CESC |
| FAM75A6 | c.161C>T | p.P54L | FLTLVFALGFFFLLLPYLSYFHCDD[p.P54L]LPSPSPGKRKCPVGRRRPRGRMKNH | LSYFHCDDL,YLSYFHCDDL | LUAD |
| FAM75A6 | c.910C>A | p.R304S | ASSRWQETARTSCAFNSSVQQDPLS[p.R304S]SHPPETCQMEAGSLFLLSSDGQNVVG | VQQDPLSSH,SSHPPETCQM | LUAD |
| FAM75D1 | c.3793C>A | p.R1265S | NSQGISSGDMGTSQVVHVHLEDSGI[p.R1265S]SVAQKQEPRVPTCVLQKCQVTNFPPA | HLEDSGISV,SVAQKQEPR,LEDSGISVA,HLEDSGISVA,SVAQKQEPRV | LUAD |
| FAM75D5 | c.665T>C | p.L222P | PPQPVSPLDSKFPIDHSLPQQLPSP[p.L222P]PFPPHIQRAEPSLQPEASLSLNTVF | PQQLPSPPF,LPSPPFPPH,LPQQLPSPF,QQLPSPPFPP | THCA |
| FAM78A | c.575G>T | p.W192L | TWAVPVSESNVAKLTNIYRDQSFTT[p.W192L]LLVATNTSTNDMIILQTLHWRMQLSI | LLVATNTST,YRDQSFTTL,RDQSFTTLL,QSFTTLLVA,IYRDQSFTTL,YRDQSFTTLL,DQSFTTLLVA | KIRC |
| FAM83B | c.617G>A | p.R206Q | DESNFNHFLNMTEKQGCSVQRLRNI[p.R206Q]QVRTVKGQDYLSKTGAKFHGKMEQKF | VQRLRNIQV,RLRNIQVRT,RNIQVRTVK,RLRNIQVRTV,VQRLRNIQVR,QVRTVKGQDY | UCEC |
| FAM86A | c.421G>A | p.A141T | SGGSVVTLSESTAIISYGTTGLVTWD[p.A141T]TALYLAEWAIENPAVFTNRTVLELGS | LVTWDTALY,GLVTWDTAL,VTWDTALYL,VTWDTALYLA,GLVTWDTALY,LVTWDTALYL,DTALYLAEWA,TALYLAEWAI | TGCT |
| FAM86C2P | c.359G>A | p.C120Y | RASCSPLSYAGLGSDGKWNLVMTRN[p.C120Y]YFPTKSTWRWQC* | MTRNYFPTK,NYFPTKSTW,YFPTKSTWR,NLVMTRNYF,WNLVMTRNY,VMTRNYFPTK,YFPTKSTWRW,MTRNYFPTKS,KWNLVMTRNY,NYFPTKSTWR,LVMTRNYFPT,WNLVMTRNYF,RNYFPTKSTW | TGCT |
| FAM8A | c.1148C>T | p.S383L | KVQFERKHSKIHSIRSLASQPTELN[p.S383L]LEVLEQSQQSTSLTFGEGAESPGGQS | QPTELNLEV,SQPTELNLEV,LASQPTELNL,QPTELNLEVL | UCEC |
| FARP1 | c.896G>T | p.R299L | KRFLIKLRPDANSAYQDTLEFLMAS[p.R299L]LDFCKSFWKICVEHHAFFRLFEEPKP | FLMASLDFC,TLEFLMASL,LMASLDFCK,EFLMASLDF,ASLDFCKSF,FLMASLDFCK,SLDFCKSFWK,DTLEFLMASL,MASLDFCKSF,LEFLMASLDF,ASLDFCKSFW,LDFCKSFWKI | LUAD |
| FAS | c.781G>A | p.E261K | IAGVMTLSQVKGFVRKNGVNEAKID[p.E261K]KIKNDNVQDTAEQKVQLLRNWHQLHG | GVNEAKIDK | CESC |
| FASTKD1 | c.9_10insA | p.K3fs | MKK[p.K3fs]NTCFPRVIGYKYASSKSYLSILLESVSISTHQL* | YLSILLESV,IGYKYASSK,KYASSKSYL,SYLSILLES,CFPRVIGYK,ASSKSYLSI,SSKSYLSLI,YKYASSKSY,SVSISTHQL,TCFPRVIG | STAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| FASTKD3 | c.1873C>G | p.Q625E | RFCSNSKHLLGKEAIKQRHLQLLGY[p.Q625E]EVVQIPYHEIGMLKSRRELVEYLQRK | Y,FPRVIGYKY,KKNTCFPRV,SKSYLSILL,LESVSISTFI,ILLESVS IST,VIGYKYASSK,TCFPRVIGYK,CFPRVIGYKY,SYLSILLESV, SSKSYLSILL,NTCFPRVIGY,GYKYASSKSY,ESVSISTHQL,FPR VIGYKYA,YASSKSYLSI,MKKNTCFPRV,KKNTCFPRVI,YKYA SSKSYL,ASSKSYLSIL,LSILLESVSI | BLCA |
| FAT1 | c.13076G>T | p.R4359L | TKVVDLDPCLSKKPLEEKPSQPYSA[p.R4359L]LESLSEVQSLSSPQSESCDDNGYHWD | HLQLLGYEV,LQLLGYEVV,LLGYEVVQI,GYEVVQIPY,YEW QIPYH,HLQLLGYEVV,QLLGYEVVQI,LGYEVVQIPY,EVVQIP YHEI,RHLQLLGYEV SALESLSEV,KPSQPYSAL,QPYSALESL,YSALESLSEV,SQPYS ALESL,LESLSEVQSL | LUAD |
| FAT3 | c.10720C>A | p.H3574N | PTAIPLEIFIVTMEDDFPGGVIGKI[p.H3574N]NATDQDMYDVLTFALKSEQKSLFKVN | KINATDQDM,KINATDQDMY,NATDQDMYDV,GKINATDQDM | LUAD |
| FAT3 | c.12475G>A | p.A4159T | GLRPVVVPNIQAGHSVVGKEELIGI[p.A4159T]TVVLFVIFILVVLFIVFRKKVFRKNY | ELIGITVVL,ITVVLFVIF,TVVLFVIFI,KEELIGITV,LIGITVLF,E LIGITVVLF,LIGITVLFV,IGITVVLFVI,ITVVLFVIFI,TVVLFVIFI L,ELIGITVVLF,KEELIGITVV,GITVVLFVIF,EELIGITVVL | UCEC |
| FAT3 | c.3797G>A | p.R1266H | VVQVLDENDNKPQFPEKVYQIKLPE[p.R1266H]HDRKKRGEPIYRAFAFDREGPNAEI | KVYQIKLPEH,QIKLPEHDRK | LUAD |
| FAT3 | c.5696G>T | p.G1899V | TDVNDNPPVFTQAVFETILLLPTYV[p.G1899V]VVEVLKVSATDPDSEVPPELTYSLME | ILLLPTYVV,LLLPTYVVV,YVVVEVLKV,LPTYVVVEV,TILLLPT YVV,ILLLPTYVVV,LLPTYVVVEV,PTYVVVEVLK,TYVVVEVL KV,LPTYVVVEVL | LUAD |
| FBRSL1 | c.2507C>T | p.A836V | GRSGAPAEREAEPRVKESRSPAKEE[p.A836V]VAKMPARASPPHSKAAPGDVKVKEER | EVAKMPARA,KEEVAKMPA,RSPAKEEVAK,SPAKEEVAKM, EEVAKMPARA | ACC |
| FBXL13 | c.306T>A | p.S102R | RIQQIIYCHKLTIILTKWRNTARHK[p.S102R]RKKKEDELILKHELQLKKWKNRLILK | RNTARHKRK,TARHKRKKK,KWRNTARHKR,RNTARHKRKK, RKKKEDELIL | CLL |
| FBXL14 | c.143T>G | p.V48G | RDKGRAAQVCTAWRDAAYHKSVWRG[p.V48G]GEAKLHLRRANPSLFPSLQARGIRRV | SVWRGGEAK,KSVWRGGEA,KSVWRGGEAK,GEAKLHLRR A | TGCT |
| FBXO18 | c.432G>T | p.M144I | KQPCTNDMAKSNSVGQDSCQDSEGD[p.M144I]IIFPAESSCALPQEGSAGPGSPGSAP | CQDSEGDII,SEGDIIFPA,IIFPAESSCA,CQDSEGDIIF | LUAD |
| FBXO21 | c.432del|T | p.F144fs | KRFFSEHVPCNGFSDIENLEGPEIF[p.F144fs]LRMNWCVS* | IFLRMNWCV,FLRMNWCVS,PEIFLRMNW,EIFLRMNWCV, LEGPEIFLRM,GPEIFLRMNW | STAD |
| FBXO24 | c.1657A>G | p.M553V | HLPASRWGTPEPSLGARAPQDPGG[p.M553V]VAQACEEYLSQIHSCQTLQDRTEKMK | GVAQACEEY,APQDPGGVA,GGVAQACEEY | HNSC |
| FBXO31 | c.1329_1330insG | p.G443fs | TPGEDGGEPGDAVAAAEQPAQCGQG[p.G443fs]AAVRAARGRELQE* | AQCGQGAAV,AVRAARGRE,AVRAARGREL,GQGAAVRAA, VRAARGREL,AVRAARGREL,QPAQCGQGAA | LUAD |
| FBXW7 | c.1268G>T | p.G423V | SDDNTLKVWSAVTGKCLRTLVGHTG[p.G423V]VVWSSQMRDNIIISGSTDRTLKVWNA | TLVGHTGVV,GVVWSSQMR,RTLVGHTGV,LVGHTGVVW, TGVVWSSQM,RTLVGHTGVV,TLVGHTGVVW,HTGVVWSSQM | UCEC |
| FBXW7 | c.1393C>T | p.R465C | DRTLKVWNAETGECIHTLYGHTSTV[p.R465C]CCMHLHEKRVVSGSRDATLRVWDIET | STVCCMHLH,GHTSTVCCM,TLYGHTSTVC,TVCCMHLHEK, HTSTVCCMHL,YGHTSTVCCM | CESC,CRC, STAD,UCEC, UCS |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| FBXW7 | c.1394G>A | p.R465H | DRTLKVNNAETGECIHTLYGHTSTV[p.R465H]HCMHLHEKRVVSGSRDATLRVWDIET | STVHCMHLH, HCMHLHEKR, GHTSTVHCM, TVHCMHLHEK, HTSTVHCMHL, LYGHTSTVH, YGHTSTVHCM | CLL, CRC, UCEC, UCS |
| FBXW7 | c.1436G>A | p.R479Q | IHTLYGHTSTVRCMHLHEKRVVSGSG[p.R479Q]QDATLRVWDIETGQCLHVLMGHVAAV | SQDATLRVW | STAD, UCS |
| FBXW7 | c.1513C>G | p.R505G | DATLRVWDIETGQCLHVLMGHVAAV[p.R505G]GCVQYDGRRVVSGAYDFMVKVWDPET | VAAVGCVQY, HVAAVGCVQY | BLCA, CESC, HNSC, LUSC, UCS |
| FBXW7 | c.1513C>T | p.R505C | DATLRVWDIETGQCLHVLMGHVAAV[p.R505C]CCVQYDGRRVVSGAYDFMVKVWDPET | VAAVCCVQY, VLMGHVAAVC, HVAAVCCVQY, AVCCVQYDGR | CRC, UCEC |
| FBXW7 | c.1637C>T | p.S546L | FMVKVWDPETETCLHTLQGHTNRVY[p.S546L]LLQFDGIHVVSGSLDTSIRVWDVETG | LLQFDGIHV, VYLLQFDGI, TNRVYLLQF, YLLQFDGIH, YLLQFDGIHV, LLQFDGIHVV, RVYLLQFDGI, HTNRVYLLQF, LQGHTNRVYL | BLCA |
| FBXW7 | c.1745C>T | p.S582L | GSLDTSIRVWDVETGNCIHTLTGHQ[p.S582L]LLTSGMELKDNILVSGNADSTVKIWD | QLLTSGMEL, LLTSGMELK, HTLTGHQLL, IHTLTGHQL, GHQLLTSGM, QLLTSGMELK, IHTLTGHQLL, TGHQLLTSGM, HQLLTSGMEL | CRC |
| FBXW7 | c.2065C>T | p.R689W | ESGGSGGVVWRIRASNTKLVCAVGS[p.R689W]WNGTEETKLLVLDFDVDMK* | KLVCAVGSW, GSWNGTEETK, TKLVCAVGSW | CRC, UCEC, UCS |
| FBXW7 | c.41G>A | p.R14Q | MNQELLSVGSKRR[p.R14Q]QTGGSLRGNPSSSQVDEEQMNRVVEE | KRRQTGGSL, RQTGGSLRG, KRRQTGGSLR, SKRRQTGGSL | CRC |
| FBXW9 | c.893_894 insG | p.G298fs | YDKKVTIYDPRDRMETRDALMGWGG[p.G298fs]AFEGL* | GWGGAFEGL, ALMGWGGAF, DALMGWGGA, MGWGG AFEGL | STAD |
| FCAR | c.697G>A | p.V233M | SNALELVVTDSIHQDYTTQNLIRMA[p.V233M]MAGLVLVALLAILVENWHSTALNKE | RMAMAGLVL, MAMAGLVLV, AMAGLVLVA, LIRMAMAGL, TQNLIRMAM, IRMAMAGLV, MAGLVLVAL, NLIRMAMAGL, RMAMAGLVLV, MAMAGLVLVA, AMAGLVLVAL, LIRMAM AGLV, IRMAMAGLVL | HNSC |
| FCGBP | c.12055G>A | p.V4019M | VYYEPEQTVLIDNCRQQCTCHVGKV[p.V4019M]MVCQEHSCKPGQVCQPSGGILSCVTK | VMVCQEHSCK | UCS |
| FCGBP | c.3064G>T | p.A1022S | EALCGLCGNFNGPADDLALRGGGQ[p.A1022S]SANALAFGNSWQEETRPCGATEPGD | ALRGGGQSA, GQSANALAF, LALRGGGQSA, GGQSANALAF | LUAD |
| FCGBP | c.7478C>T | p.A2493V | RPDFMGTCVYVLAQTCCGTRPGLHRF[p.A2493V]VVLQENVAWGNGRVSVTRVITVQVAN | RPGLHRFVV, VVLQENVAW, GTRPGLHRFV, RPGLHRFVVL, FVVLQENVAW | PAAD |
| FCGR2A | c.665T>G | p.V222G | SSKPVTITVQVPSMGSSSPMGIIVA[p.V222G]GVIATAVAAIVAAVVALIYCRKKRIS | IVAGVIATA, PMGIIVAGV, SPMGIIVAG, IIVAGVIATA, IVAG VIATAV, GVIATAVAAI, SPMGIIVAGV | KIRP |
| FCGRT | c.118C>G | p.P40A | LFLLPGSLGAESHLSLLYHLTAVSS[p.P40A]AAPGTPAFWVSGWLGPQQYLSYNSLR | HLTAVSSAA, SSAAPGTPA, SAAPGTPAF, YHLTAVSSA, SSAAPGTPAF, YHLTAVSSAA, SAAPGTPAFW | THCA |
| FCRL2 | c.1513G>T | p.V505L | MQQPESSANIRTLLENKDSQVIYSS[p.V505L]LKKS* | SQVIYSSLK, QVIYSSLKK, SQVIYSSLKK, DSQVIYSSLK, KTAIYSSL | LUAD |
| FEM1A | c.1858C>A | p.L620M | AIMNALIEAGAHMDATNAFKKTAYE[p.L620M]MLDEKLLARGTMQPFNYVTLQCLAAR | TAYEMLDEK, AFKKTAYEM, FKKTAYEML, YEMLDEKLL, KTA YEMLDEK, EMLDEKLLAR, NAFKKTAYEM, YEMLDEKLLA | PRAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| FER | c.1422del A | p.L474fs | SEKPLAEQDWYHGAIPRIEAQELLK[p.L474fs]NKETFWCERVMGNLVNMSFLYILMDRGDILSYNMLITCIDSRALGFQTFLNL* | CIDSRALGF,RVMGNLVNM,ILMDRGDIL,LVNMSFLYI,NM SFLYILM,LITCIDSRA,SYNMLITCI,RALGFQTFL,NLVNMSFL Y,MRGDILSY,SFLYIMDR,MLITCIDSR,ETFWCERVM,DIL SYNMLI,MGNLVNMSF,CERVMGNLV,VNMSFLYIL,RGDIL SYNM,SRALGFQTF,LGFQTFLNL,KETFWCERV,GDILSYNM L,LMDRGDILSY,NLVNMSFLYI,MLITCIDSRA,ALGFQTFLNL, MSFLYILMDR,VMGNLVNMSF,LYILMDRGDI,KNKETFWC ER,GNLVNMSFLY,NMLITCIDSR,DSRALGFQTF,QELLKNKE TF,KETFWCERVM,LVNMSFLYIL,VNMSFLYILM,LSYNMLIT CI,TCIDSRALGF,SRALGFQTFL,GDILSYNMLI | STAD |
| FERD3L | c.275C>A | p.P92H | CEVDQDGEEEEEERGRGVSLLGR[p.P92H]HKRKRVITYAQRQAANIRERKRMFNL | SLLGRHKRK,GVSLLGRHK,VSLLGRHKR,HKRKRVITY,VSLLG RFIKRK,RGVSLLGRH,SLLGRHKRKR,LGRHKRKRVI,RHKRK RVITY | LUAD |
| FEZ2 | c.149C>T | p.P50L | NCNASPEPGAEAEAGGADGFPA[p.P50L]LACSLEEKLSLCFRPSDPGAEPPRTA | ALACSLEEK,GGADGFPAL,ALACSLEEKL,FPALACSLEE | ACC |
| FEZF2 | c.244G>A | p.E82K | GSQGKLLNLCSPLPCMIPLQPLGY[p.E82K]KVPSKTLLSYSELWKSSLRAGGGGG | YKVPSKTLL,MIPLQPLGYK,KVPSKTLLSY,LGYKVPSKTL,IPL QPLGYKV | CESC |
| FGB | c.1015G>C | p.E339Q | NYCGLPGEYWLGNDKISQLTRMGPT[p.E339Q]QLLIEMEDWKGDKVKAHYGGFTVQNE | RMGPTQLLI,LTRMGPTQL,GPTQLLIEM,TRMGPTQLL,QLT RMGPTQL,LTRMGPTQLL,SQLTRMGPTQ | LUAD |
| FGF14 | c.686C>T | p.T229M | KPLEVAMYREPSLHDVGETVPKPGV[p.T229M]PSKSTSASAIMNGGKPVNKSKTT | VMPSKSTSA,MPSKSTSAS,GVMPSKSTSA,VPKPGVMPSK, MPSKSTSASA,GETVPKPGVM | GBM |
| FGF14 | c.707C>T | p.A236V | YREPSLHDVGETVPKPGVTPSKSTS[p.A236V]SAIMNGGKPVNKSKTT* | VTPSKSTSV,VSAIMNGGK,KSTSVSAIM,SKSTSVSAI,GVTPS KSTSV,SVSAIMNGGK,TPSKSTSVSA,SKSTSVSAIM | CRC |
| FGFR3 | c.1138G>A | p.G380R | VVLPAEEELVEADEAGSVYAGILSY[p.G380R]RVGFFLFILVVAAVTLCRLRSPPKKG | YAGILSYRV,ILSYRVGFF,RVGFFLFIL,SVYAGILSYR,GILSYRV GF,LSYRVGFFL,ILSYRVGFFL,RVGFFLFILV,SVYAGILSYR,VY AGILSYRV,LSYRVGFLF,STRVGFFLFI,AGILSYRVGF,GILSY RVGFF,YRVGFLFIL | BLCA |
| FGFR3 | c.1711_1712 insG | p.R571fs | QGGPLYVLVEYAAKGNLREFLRARR[p.R571fs]APCGPGLLLRHLQAARGAAHLQGPGVLCLPGGPGHGVLGLPEVHPQGPGCPQCAGDRGQRDEDRRLRAGPGRAQPRLLQEDDQRPAAREVDGA* | LLLRHLQAA,RARRAPGPG,LLRRHLQAAR,RLRAGPGRA,GP GHGVLGL,FLRARRAPG,LQAARGAAFI,REFLRARRA,ARRA PGPGL,RRAPGPGLL,RAPGPGLLL,RHLQAARGA,AHLQGP GVL,LQGPGVLCL,LQEDDQRPA,LPGGPGHGV,CLPGGPGH GV,GLLLRHLQA,LQAARGAAHL,LLQEDDQRPA,RARRAP GPGL,RLRAGPGRAQ,RAGPGRAQPR,LLLRHLQAAR,LPGG PGHGVL,RPAAREVDGA,FLRARRAPGP,REFLRARRAP,RRA PGPGLLI,RHLQAARGAA,HLQAARGAAH,AAHLQGPGVL, HLQGPGVLCL,LQEDDQRPAA | KIRC |
| FGFR3 | c.2147C>A | p.P716H | GGSPYPGIPVEELFKLLKEGHRMDK[p.P716H]HANCTHDLYMIMRECWHAAPSQRPTF | HANCTHDLY,KHANCTHDLY,RMDKHANCTH,HANCTHDL YM | KIRC |
| FGFR3 | c.2420G>C | p.*807S | SSGDDSVFAHDLLPPAPPSSGGSRT[p.*807S]SRATGPQQCEGSLAAHPAAGAQPLPGMRLSADGETATQSFGLCVCVCVCVCVCAHPRVPVCVRILPPGAEVPVVVSPLLCNGLLTGAAAPRGLCSGGTQCRM* | RILPPGAEV,RLSADGETA,CVCVCAHPR,GSRTSRATG,GSLA AHPAA,CVRILPPGA,LLTGAAAPR,LAAHPAAGA,ETATQSF GL,QSFGLCVCV,EVPWVSPLL,GPQQCEGSL,HPAAGAQPL, SPLLCNGLL,QQCEGSLAA,AGAQPLPGM,AQPLPGMRL,AE VPWVSPL,LPPGAEVPW,VPWVSPLLC,SLAAHPAAGA,TQS FGLCVCV,GLCVCVCV,LLCNGLLTGA,WVSPLLCNGL,ILP | MM |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| FGFR3 | c.742C>T | p.R248C | RGNYTCVVENKFGSIRQTYTLDVLE[p.R248C]CSPHRPILQAGLPANQTAVLGSDVEF | PGAEVPW,ETATQSFGLC,CVCAHPRVPV,QPLPGMRLSA,H PRVPVCVRI,QQCEGSLAAH,ADGETATQSF,GETATQSFGL, AEVPWVSPLL,CEGSLAAFIPA,LPPGAEVPW DVLECSPHR,LECSPHRPI,LECSPHRPIL | BLCA |
| FGFR3 | c.746C>G | p.S249C | GNYTCVVENKFGSIRQTYTLDVLER[p.S249C]CPHRPILQAGLPANQTAVLGSDVEFH | DVLERCPHR,LERCPHRPI,CPHRPILQA,LERCPHRPIL | BLCA,LUSC |
| FGFR1 | c.1435_1436 de|CA | p.H479fs | LGPGPVAGPKLYPKLYTDIHTHTHT[p.H479fs]LSHTLTRGGQGPPAHPLSVLDGT VSAVGTGGPARQADWEDGGRSCRRR QGTHGEEEWPAPQAVCV* | SVLDGTVSA,VLDGTVSAV,HTHTHTLSH,HTLSHTLTR,HTH TLSHTL,RSCRRRQGT,DIHTHTHTL,GPPAHPLSV,PPAHPLS VL,WPAPQAVCV,GQGPPAHPL,EEWPAPQAV,EEEWPAP QA,SVLDGTVSAV,HTHTHTLSHT,HTHTLSHTLT,LTRGGQG PPA,RSCRRRQGTH,GPPAHPLSVL,HPLSVLDGTV,TDIHTH THTL,IHTHTHTLSH,RQGTHGEEEW,EEWPAPQAVC,EEEW PAPQAV,GEEEWPAPQA | BLCA |
| FGFRL1 | c.728G>T | p.R243L | KYTCRVSNRAGAINATYKVDVIQRT[p.R243L]LSKPVLTGTHPVNTTVDFGGTTSF QC | RTLSKPVLT,IQRTLSKPV,VIQRTLSKP,TLSKPVLTGT,RTLS KPVLTG,IQRTLSKPVL,YKVDVIQRTL | LUAD |
| FGFRL1 | c.820G>T | p.V274L | TGTHPVNTTVDFGGTTSFQCKVRSD[p.V274L]LKPVIQWLKRVEYGAEGRHNST IDVG | KVRSDLKPV,QCKVRSDLK,FQCKVRSDL,KVRSDLKPVI,DLK PVIQWLK,CKVRSDLKPV | LUAD |
| FGGY | c.412_413i nsG | p.G138fs | LDHRAVSQVNRINETKHSVLQYVGG[p.G138fs]GDVCGNAGPETSVAERELERD LLG* | SVAERELER,LQYVGGGDV,AERELERDL,VLQYVGGGDV,LQ YVGGGDVC,AERELERDLL | STAD |
| FHDC | c.298de|T | p.F100fs | PGLPPTTHMNGYSHLGKKKRMRSFF[p.F100fs]GKLFRRSKFEAKPTSGPWQPG RNITTKLIQRPLRSSLGSRKTPPSLPFLGE EEL* | RMRSFFGKL,RSFFGKLFR,KRMRSFFGK,SFFGKLFRR,KTPP SLPFL,KKRMRSFFG,FGKLFRRSK,LFRRSKFEA,RSKFEAKPT, TTKLIQRPL,IQRPLRSSL,PLRSSLGSR,GSRKTPPSL,TSGPWQ PGR,NITTKLIQR,GPWQPGRNI,LPFLGEEEL,MRSFFGKLF, GKLFRRSKF,RKTPPSLPF,KLFRRSKFEA,SLPFLGEEEL,RSFF GKLFRR,RMRSFFGKLF,KKRMRSFFGK,LFRRSKFEAK,RSKF EAKPTS,TTKLIQRPLR,IQRPLRSSLG,PLRSSLGSRK,GPWQP GRNIT,LIQRPLRSSL,KRMRSFFGKL,FGKLFRRSKF,SKFEAKP TSG,FEAKPTSGPW,SRKTPPSLPF,RKTPPSLPFL | STAD |
| FHL1 | c.760C>T | p.R254W | SGDVSKIiSLADSFLYGLIQVPNYSL[p.R254W]IEAMVLKKEFLPSCSSLYTDITVL R | YSLWIEAMV,SLWIEAMVL,LWIEAMVLK,WIEAMVLKK,IQ VPNYSLW,NYSLWIEAM,IQVPNYSLWI,SLWIEAMVLK,NYS LWIEAMV,YSLWIEAMVL,VPNYSLWIEA | CRC |
| FKLIP | c.552T>G | p.D184E | AKHCVKCNKAITSGGITYQDQPWHA[p.D184E]ECFVCVTCSKKLAGQRFTAVED QYYC | AECFVCVTC,QPWHAECFV,AECFVCVTCS | CLL |
| FIGNL1 | c.926de|A | p.K309fs | NGPKEDS5LPTFKTAKEQLWDQQK[p.K309fs]STTNLSVHQGLHMV* | SVHQGLHMV,LSVHQGLHM,DQQKSTTNL,QKSTTNLSV,S VHQGLHMVV,QQKSTTNLSV,TTNLSVHQGL,QKSTTNLSV H,NLSVHQGLHM | STAD |
| FILIP1 | c.1565T>A | p.I522K | LKDDLTKLKSFTVMLVDERKNMMEK[p.I522K]KKQERKVDGLNKNFKVEQK VMDVT | MMEKKKQEER | CLL |
| FKBPL | c.481G>C | p.E161Q | GPPEGWTELTMGVGPWREETWGELI[p.E161Q]QKCLESMCQGEEAELQLPGH SGPPVR | ETWGELIQK,LIQKCLESM,ELIQKCLESM | CESC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| FKBPL | c.959G>T | p.R320L | AQAALGNLEKATADLKKVLAIDPKN[p. R320L]LAAQEELGKVVIQGKNQDAGLA QGLR | VLAIDPKNL, KNLAAQEEL, VLAIDPKNLA | LUAD |
| FLG | c.477del|A | p.K159fs | KGNKGRSKSPRETGGKRHESSSEKK[p.K 159fs]KEKDIHLLIEKKNMEKTIIQVKK RKTRLKILD* | KTMIITQVKK, LIEKKNMEK, TIITQVKKR, QVKKRKTRL, KKKEKD IHL, KEKDIHLLI, KKNMEKTII, MEKTIITQV, KKRKTRLKI, NME KTIITQV, LLIEKKNMEK, KTIITQVKKR, TIITQVKKRK, QVKKR KTRLK, ITQVKKRTR, KKKEKDIHLL, TQVKKRKTRL, KKRKTR LKIL | STAD |
| FLG | c.8657G>A | p.R2886H | ASTHADISRHSQAVQGQSEGSRRSR[p. R2886H]HQGSSVSQDSDSEGHSEDSE RWSGSA | GSRRSRHQG, RSRHQGSSV, RSRHQGSSVS, RRSRHQGSSV | GBM |
| FLG | c.9761C>A | p.P3254H | ERWSGSASRNHRGSVQEQSRHGSRH[p. P3254H]HRSHHEDRAGHGHSADRS RQSGTRHA | GSRHHRSHH, QSRHGSRHHR | LUAD |
| FLG2 | c.1716G>T | p.L572F | GSGSSQSSGYGYGSRETSGFGQHG[p. L572F]FGSGQSTGFGQYGSGSGQSSGF GQHG | FGSGQSTGF, GFGSGQSTGF | LUAD |
| FLG2 | c.4634G>T | p.G1545V | HTHGQSGSQHGESESIIHDRHRITH[p.G 1545V]VQTGDTTRHSYSGHEQTTQTG SRTTG | HVQTGDTTR | LUAD |
| FLG2 | c.5703_5704del|CA | p.H1901fs | RRSGHSESSDSEVHSGGSHTHSGHT[p. H1901fs]QPSQVSTWRVRIHSSQETPN YSWTDRRYH* | HSSQETPNY, TWRVRIHSS, RVRIHSSQE, QVSTWRVRI, TQP SQVSTW, SQETPNYSW, HTHSGHTQPS, RVRIHSSQET, IHSS QETPNY, ETPNYSWTDR, HTQPSQVSTW, SQVSTWRVRI, SS QETPNYSW, QPSQVSTWRV | GBM |
| FLI43860 | c.2549_2550insT | p.L850fs | SHTFQLMRALGAGQPTSHLVLTTLL[p.L 850fs]GLSAGATPAHRCQRQQPLPQGE DLPAFAGCHEHAARAAVCPGVQAGRA AV,VQAGRAGGL,RAGGLPQAL,AQRAPQAAG,LQHVTGGT GGLPQALPGPPHPDALCLGAEPAQRAP QAAGPGGGRAQPPKLQHVTGGTEEPA VHHGALA* | LVLTTLLGL, TLLGLSAGA, GLSAGATPA, ALCLGAEPA, AQPP KLQHV, ATPAHRCQR, AARAAVCPG, GGGRAQPPK, EPAVH HGAL, HRCQRQQPL, LSAGATPAH, PQGEDLPAF, HEHAARA E, LPQGEDLPA, HIVLITTLLGL, VLTTLLGLSA, AVCPGVQAGR, AARAAVCPGV, AGRAGGLPQA, RAQPPKLQHV, LSAGATPA HR, FAGCHEHAAR, TTLLGLSAGA, HVTGGTEEPA, LPQGEDL PAF, LPGPPHPDAL, AHRCQRQQPL, GLSAGATPAH, GRAGG LPQAL, LQHVTGGTEE, EEPAVHHGAL, LPAFAGCHEH, LPQA LPGPPH, HEHAARAAVC, AEPAQRAPQA, TEEPAVHHGA | PRAD |
| FLNA | c.3718G>A | p.V1240M | GTHTITYIPLCPGAYTVTIKYGGQP[p.V1 240M]MPNFPSKLQVEPAVDTSGVQCY GPGI | TIKYGGQPM, YGGQPMPNF, KYGGQPMNF, GQPMPNFP SK, QPMNFPSKL, MPNFPSKLQV, VTIKYGGQPM | GBM |
| FLNB | c.1586_1587insG | p.W529fs | LDGVYAFEYYPSTPGRYSIAITWGG[p. W529fs]TPHSKEPL* | ITWGGTPHSK, YSIAITWGGT, IAITWGGTPH | STAD |
| FLNB | c.1586delG | p.W529fs | FLDGVYAFEYYPSTPGRYSIAITWG[p.W 529fs]DTTFQRAPLKFKLALKRVCRKSVL GALGSMVGLSGGQRTSW* | VLGALGSMV, TTFQRAPLK, LALKRVCRK, TFQRAPLKF, FQR APLKFK, RAPLKFKLA, PLKFKLALK, KFKLALKRV, KLALKRVCR, RVCRKSVLG, TWGDTTFQR, MVGLSGGQR, DTTFQRAPL, A PLKFKLAL, AITWGDTTF, SVLGALGSM, KRVCRKSVL, LSGGQ RTSW, SVLGALGSMV, ALKRVCRKSV, KLALKRVCRK, ITWGD TTFQR, TFQRAPLKFK, IAITWGDTTF, TTFQRAPLKF, RVCRKS VLGA, DTTFQRAPLK, RAPLKFKLAL, LKRVCRKSVL, KSVLGAL GSM, FQRAPLKFKL, LKFKLALKRV, GLSGGQRTSW | STAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| FLT3 | c.1800_1801 insTTCAG AGAATATG AATATGAT | p.600_ 601insF REYEYD | LQMVQVTGSSDNEYFYVDFREYEYD[p. 600_601insFREYEYD]FREYEYDLKWEF PRENLEFGKVLGSGAFGKVMNATAYGI SKTGVSI | YEYDFREYE,REYEYDFRE,REYEYDFREY,YEYDFREYEV,DFR EYEYDR,VDFREYEYDF,YDFREYEYDL | LAML |
| FLT3 | c.2503G>C | p.D835 H | RDLAARNVLVTHGKVVKICDFGLAR[p. D835H]HIMSDSNYVVRGNARLPVKW MAPESL | HIMSDSNYV,RHIMSDSNY,CDFGLARHI,HIMSDSNYVV,CD FGLARHIM,ARHIMSDSNY,RHIMSDSNY | LAML |
| FLT3 | c.2503G>T | p.D835 Y | RDLAARNVLVTHGKVVKICDFGLAR[p. D835Y]YIMSDSNYWRGNARLPVKW MAPESL | ICDFGLARY,YIMSDSNYV,RYIMSDSNY,CDFGLARYI,YIMS DSNYVV,KICDFGLARY,RYIMSDSNYV,CDFGLARYIM,ARYI MSDSNY | LAML |
| FLT3 | c.2505T>A | p.D835 E | RDLAARNVLVTHGKVVKICDFGLAR[p. D835E]EIMSDSNYVVRGNARLPVKW MAPESL | EIMSDSNYV,REIMSDSNY,CDFGLAREI,EIMSDSNYVV,CDF GLAREIM,AREIMSDSNY,REIMSDSNY | LAML |
| FMN2 | c.2252C>T | p.S751 F | CLEALRLEEKEVRHHRILEAKSIQT[p.S7 51F]FPTEEGGVLTLPPVDGLPGRPPCPP G | FPTEEGGVL,LEAKSIQTF,QTFPTEEGGV,ILEAKSIQTF,FPTE EGGVLT | BRCA |
| FMN2 | c.2974C>A | p.P992 T | GIPLPPPLPGAGIPPPPLPGAGIP[p.P9 92T]TPPPLPGAGIPPPPLPGAGIPPPP P | AGIPTPPPL | LUAD |
| FMNL1 | c.2779G>C | p.E927 Q | HFLDKAGSVSLLDSVLADVRSLQRGL[p.E 927Q]QLTQREFVRQDDCMVLKEFLRA NSPT | SLQRGLQLT,RSLQRGLQL,QLTQREFVR,LQRGLQLTQ,GLQ LTQREF,LQLTQREFV,GLQLTQREFV,RGLQLTQREF | CESC |
| FMO3 | c.1530C>A | p.F510 L | AILTQWDRSLKPMQTRVVGRLQKPC[p. F510L]LFFHWLKLFAIPILLIAVFLVLT* | CLFFHWLKL,RLQKPCLFF,LFFHWLKLF,LQKPCLFFH,RLQKP CLFFH,LQKPCLFFHW,CLFFHWLKLF,KPCLFFHWLK,GRLQ KPCLFF | CRC |
| FMOD | c.993C>A | p.S331 R | QKIPPVNTNLENLYLQGNRINEFSI[p.S3 31R]RSFCTVVDVVNFSKLQVLRLDGNE IK | FSIRSFCTV,SIRSFCTVV,RSFCTVVDV,INEFSIRSF,FSIRSFCT VV,RSFCTVVDVV,RINEFSIRSF,NEFSIRSFCT | KIRP |
| FN1 | c.868C>T | p.R290 C | RGEWKCERHTSVQTTSSGSGPFTDV[p. R290C]CAAVYQPQPHPQPPYGHCVT DSGVV | FTDVCAAVY,GPFTDVCAAV | UCEC |
| FNBP4 | c.172_177d e|ACCACC | p.TT58 de| | PEPDTEPDSTAAVPSQPAPSAATT[p.T T58de|]AVTAAAASDDSPSEDEQEAVQ EVPRVVQNPP | APSAATTTA,ATTTAVTAAA,APSAATTAV | PRAD |
| FNDC1 | c.1955G>A | p.R652 H | QGTSHRPSLPASLNDNDLVDSDEDE[p. R652H]HAVGSLHPKGAFAQPRPALSPS RQSP | HAVGSLHPK,DEHAVGSLH,DEDEHAVGSL | CRC |
| FNDC1 | c.3535_3537de|GAC | p.D118 Ode| | APGKSEPPSKRPLSSKSQQSVSAED[p.D 1180de|]EEEDAGFFKGGKEDLLSSSVP KWPSSST | AEDEEEDAGF | PAAD |
| FOLH1 | c.1501de|A | p.S501f s | NLTKELKSPDEGFEGKSLYESWTKK[p.S 501fs]VLPQSSVACPG* | KVLPQSSVA,YESWTKKVL,KKVLPQSSV,SLYESWTKKV,LYE SWTKKVL,KKVLPQSSVA | STAD |
| FOLH1 | c.1927G>T | p.A643 S | HPQEMKTYSVSFDSLFSAVKNFTEI[p.A 643S]SSKFSERLQDFDKSNPIVLRMMN DQL | KNFTEISSK,NFTEISSKF,EISSKFSER,ISSKFSERL,EISSKFSERL, KNFTEISKF | LUAD |
| FOXD4L4 | c.1215de|C | p.C405f s | GQFCSNSSSIRRTAPTAALPPRARC[p.C 405fs]GRAPVGLVGAAEVSGSGGGL* | RARCGRAPV,CGRAPVGLV,EVSGSGGGL,APVGLVGAA,RA RCGRAPVG,AEVSGSGGGL | KIRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| FOXK1 | c.1060C>T | p.R354W | SGIYAHITKHYPYRTADKGWQNSI[p.R354W]WHNLSLNRYFIKVPRSQEEPGKGSFW | WQNSIWHNL,NSIWHNLSL,WHNLSLNRY,SIWHNLSLNR,GWQNSIWHNL,IWHNLSLNRY,WHNLSLNRYF | CRC |
| FOXN3 | c.287de\|C | p.P96fs | NLLKSPGESVLRSVSPVQDLDDTP[p.P96fs]HPLPLTLTCPTMPGRTPTANPPTPSAASYLWPSRTLQPSACQ* | TMPGRTPTA,LTCPTMPGR,AASYLWPSR,SYLWPSRTL,DTPHPLPTL,SAASYLWPS,LPTLTCPTM,PPTPSAASY,TPSAASYLW,SAASYLWPSR,ASYLWPSRTL,TLTCPTMPGR,HPLPLTLTCPT,CPTMPGRTPT,WPSRTLQPSA,NPPTPSAASY | CRC,STAD |
| FOXQ1 | c.404C>T | p.S135L | RSKPYTRRPKPPYSYIALIAMAIRD[p.S135L]LAGGRLTLAEINEYLMGKFPFPRGSY | AIRDLAGGR,IAMAIRDLA,ALIAMAIRDL,LIAMAIRDLA,AIRDLAGGRL,MAIRDLAGGR,RDLAGGRLTL | BLCA |
| FOXRED1 | c.407G>T | p.R136L | SVGGICQQFSLPENIQLSLFSASFL[p.R136L]LNINEYLAVVDAPPLDLRFNPSGYLL | SLFSASFLL,FSASFLLNI,FLLNINEYL,LNINEYLAV,SFLLNINEY,LFSASFLLNI,LNINEYLAV,FLLNINEYLA,LNINEYLAV,ASFLLNINEY,LFSASFLLNI,SFLLNI,SFLLNINEYL,LSLFSASFLL,LNINEYLAVV | LUAD |
| FPGS | c.64A>G | p.I22V | MSRARSHLRAALFLAAASARG[p.I22V]VTTQVAARRGLSAWPVPQEPSMEYQD | SARGVTTQV,GVTTQVAAR,VTTQVAARR,LAAASARGV,FL AAASARGV,ASARGVTTQV,SARGVTTQVA | ACC |
| FPGT-TNNI3K | c.1364G>A | p.R455H | NVININHQGRDGHTGLHSACYHGHI[p.R455H]HLVQFLLDNGADMNLVACDPSRSSGE | CYHGHIHLV,HIHLVQFLL,ACYHGHIHL,HGHIHLVQF,GHIH LVQFL,YHGHIHLVQF,HSACYHGHIH,SACYHGHIHL,GHIHL VQFLL | CRC |
| FPR2 | c.161G>A | p.R54Q | PLVVLGVTFVLGVLGNGLVIWVAGF[p.R54Q]QMTRTVTTICYLNLALADFSFTATLP | FQMTRTVTT,QMTRTVTTI,WVAGFQMTR,VIWVAGFQM,AGPQMTRTV,FQMTRTVTTI,IWVAGFQMTR,LVIWVAGFQM | GBM |
| FRAS1 | c.1145G>T | p.C382F | FMSSNASEVKRIPEGEKWEDGPCKV[p.C382F]FECRGAQVTCYEPSCPPCPVGTLALE | WEDGPCKVF,FECRGAQVT,KVFECRGAQV,KWEDGPCKVF | LUAD |
| FRG1 | c.254_256de\|AAG | p.E86de\| | AIEMDKGTYIHALDNGLFTLGAPHK[p.E86de\|]VDEGPSPPEQFTAVKLSDSRIALKSGYG | FTLGAPHKV | PRAD |
| FRG1B | c.101T>C | p.I34T | RIALKSGYGKYLGINSDELVGHSDA[p.I34T]TGPREQWEPVFQNGKMALLASNSCFI | DELVGHSDAT | PRAD |
| FRG1B | c.110G>A | p.R37K | LKSGYGKYLGINSDELVGHSDAIGP[p.R37K]KEQWEPVFQNGKMALLASNSCFIRCN | GPKEQWEPV,DAIGPKEQW,VGHSDAIGPK | UCS |
| FRG1B | c.115C>A | p.Q39K | SGYGKYLGINSDELVGHSDAIGPRE[p.Q39K]KWEPVFQNGKMALLASNSCFIRCNEA | GPREKWEPV,DAIGPREKW,HSDAIGPREK,KWEPVFQNGK,GPREKWEPVF | CLL |
| FRG1B | c.125C>A | p.P42Q | GKYLGINSDELVGHSDAIGPREQWE[p.P42Q]QVFQNGKMALLASNSCFIRCNEAGDI | GPREQWEQV,EQVFQNGKM,GPREQWEQVF,WEQVFQNGKM,QVFQNGKMAL,REQWEQVFQN | PRAD |
| FRG1B | c.145A>G | p.M49V | SDELVGHSDAIGPREQWEPVFQNGK[p.M49V]VALLASNSCFIRCNEAGDIEAKSKTA | FQNGKVALL,FQNGKVALLA,VFQNGKVALL,VALLASNSCF,WEPVFQNGKV | TGCT |
| FRG1B | c.148G>C | p.A50P | DELVGHSDAIGPREQWEPVFQNGKM[p.A50P]PLLASNSCFIRCNEAGDIEAKSKTAG | FQNGKMPLL,VFQNGKMPL,MPLLASNSC,PLLASNSCF,FQ NGKMPLLA,VFQNGKMPLL,MPLLASNSCF | KIRP,PRAD,SKCM |
| FRG1B | c.155T>C | p.L52S | LVGHSDAIGPREQWEPVFQNGKMAL[p.L52S]SASNSCFIRCNEAGDIEAKSKTAGEE | SASNSCFIR,LSASNSCF,ALSASNSCF,FQNGKMALSA,ALSA SNSCFI,KMALSASNSC,LSASNSCFIR,MALSASNSCF | PRAD,UCS |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| FRG1B | c.157G>A | p.A53T | VGHSDAIGPREQWEPVFQNGKMALL[p. A53T]TSNSCFIRCNEAGDIEAKSKTA GEEE | LLTSNSCFI, LTSNSCFIR, ALLTSNSCFI, ALLTSNSCFI, FQNGK MALLT, KMALLTSNSC, LLTSNSCFIR, MALLTSNSCF | GBM, PRAD |
| FRG1B | c.163A>G | p.N55D | HSDAIGPREQWEPVFQNGKMALLAS[p. N55D]DSCFIRCNEAGDIEAKSKTAGEE EMI | LLASDSCFI, LASDSCFIR, ALLASDSCFI, ALLASDSCFI, LLASDS CFIR, MALLASDSCF | PRAD |
| FRG1B | c.175A>G | p.I59V | IGPREQWEPVFQNGKMALLASNSCF[p. I59V]VRCNEAGDIEAKSKTAGEEEMIK SLS | LLASNSCFV, LASNSCFVR, ALLASNSCFV, LLASNSCFVR | PRAD, SKCM |
| FRG1B | c.194G>A | p.G65E | WEPVFQNGKMALLASNSCFIRCNEA[p. G65E]EDIEAKSKTAGEEEMIKSLSHSLP SS | FIRCNEAEDI | UCS |
| FRG1B | c.29T>C | p.I10T | MAVKLSDSR[p.I10T]TALKSGYGKYLGI NSDELVGHSDAIG | LSDSRTALK, KLSDSRTAL, TALKSGYGK, RTALKSGYG, KLSDS RTALK, RTALKSGYGK, AVKLSDSRTA, TALKSGYGKY, VKLSD SRTAL | PRAD, UCS |
| FRG1B | c.31G>A | p.A11T | MAVKLSDSRI[p.A11T]TLKSGYGKYLGI NSDELVGHSDAIG | KLSDSRITL, ITLKSGYGK, LSDSRITLK, TLKSGYGKY, SRITLKSG Y, TLKSGYGKYL, KLSDSRITLK, RITLKSGYGK, ITLKSGYGKY, V KLSDSRITL | PRAD |
| FRG1B | c.39A>T | p.K13N | MAVKLSDSRIAL[p.K13N]NSGYGKYLG INSDELVGHSDAIGPRE | IALNSGYGK, SRIALNSGY, ALNSGYGKY, ALNSGYGKYL, RIAL NSGYGK, IALNSGYGKY, DSRIALNSGY | GBM, PRAD, UCS |
| FRG1B | c.59T>C | p.L20P | MAVKLSDSRIALKSGYGKY[p.L20P]PGI NSDELVGHSDAIGPREQWEPVFQ | YPGINSDEL, KYPGINSDEL, KSGYGKYPGI, YPGINSDELV | KIRP |
| FRG1B | c.95A>T | p.D32V | DSRIALKSGYGKYLGINSDELVGHS[p.D 32V]VAIGPREQWEPVFQNGKMALLAS NSC | ELVGHSVAI, VAIGPREQW, DELVGHSVA, NSDELVGHSV, DE LVGHSVAI | PRAD, UCS |
| FRG2B | c.424G>T | p.D142Y | ECSLSLNKKSRSSTPVHNSEIQETC[p.D1 42Y]YAHHRGRSRACTGRSKRHRSRALG VQ | NSEIQETCY, YAHHRGRSR, CYAHHRGR, SEIQETCYA, IQET CYAHH, ETCYAHHRGR, CYAHHRGRSR, YAHHRGRSRA, SEI QETCYAH | LUAD |
| FRMD4A | c.3014delC | p.P1005fs | CKATSAALPQSQRSSTPSSEIGATP[p.P1 005fs]QAAPTTS* | SEIGATPQA, SEIGATPQAA | STAD |
| FRMPD1 | c.3277G>C | p.E1093Q | APKYTEPLLSPRDEPRSDECGINPG[p.E 1093Q]QKIASIPTKEEPQGQLSLERDRE VTN | NPGQKIAS, GQKIASIP, GQKIASIPTK | LUAD |
| FRS2 | c.140T>C | p.L47S | KVINVDDGNELGSGIMELTDTELI[p.L 47S]SYTRKRDSVKWHYLCLRRYGYDSN LF | LITDTELISY, DTELISYTR, ELISYTRKR, ISYTRKRDSV, SYTRKRD SVK, ELITDTELISY | TGCT |
| FSHB | c.128C>A | p.T43N | CNSCELTNITIAIEKEBCRFCISIN[p.T 43N]NTWCAGYCYTRDLVKDPARPKIQKT QSGARIELQRNPPNADPNMKLFTI[p. | NTWCAGYCY, INNTWCAGY, FCISINNTW, RPCISINNTW, SI NNTWCAGY, NTWCAGYCYT | LUAD |
| FUBP1 | c.1288C>T | p.R430C | R430C]CGTPQQIDYARQLIEEKIGGPV NPLG | CGTPQQIDY, FTICGTPQQI | UCEC |
| FUT6 | c.418_419insA | p.S140fs | NPSAQLPRSPRROGQRMIWFSMESP[p. S140fs]KPLLAAESHGRIIQSHHVLPQ RLRHLHALRLAGAVRPACPPTAQPLG QDRAGGLGSVQLGAKLRQGALLPEPA GPSQGGRVRTLPQAPAPGNFIDGDAVP VQVLSGLRELLLAPRLHHREAVEERPGGL GRARGAGPQQKQLREVPATRRLHPRG RLPEPQGPGPVPAGAGGGPRPLPELLS | VLSGLRELL, FLQGLLETA, GLLETAGGI, NLIFLGPHL, HLSGGL IYI, FSMESPKPL, VLPQRLRFIL, ALRLAGAVV, GLGSVQLGA, P LPELLSLA, LLSLAGDAA, LLQLGTRFL, FLGPHLSGG, IWFSME SPK, RLRHLHALR, ASLLQLGTR, LSGGLIYLR, AWAARNLIF, RI LQSHHVL, VVRPACPPT, KLRQGALLP, RVRTLPQAP, GLRELL APR, RARGAGPQQ, ATRRLHPRG, RLHPRGRLP, GTRFLQGL L, AARNLIFLG, QSHHVLPQR, LLAPRLHHR, QLREVPATR, PA TRRLHPR, GWCGWAAR, ESPKPLLAA, DAAASLLQL, WAA | KIRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| | | | LAGDAAASLLQLGTRFLQGLLETAGGIQ VPDTRHSGLVHLRGWCGAWAARNLIF LGPHLSGGLIYLRTRLPEASPA* | RNLIFL, RPACPPTAQ, VPVQVLSGL, APRLHHREA, HPRGRLP EP, GRPLPELL, RPLPELLSL, VPDTRHSGL, GPHLSGGLI, QRL RHIHAL, GAKLRQGAL, SLLQLGTRF, HLRGWCGAW, SMESP KPLL, MESPKPLLA, LQSHHVLPQ, LRHLHALRL, RHLHALRLA, HLHALRLAG, AKLRQGALL, RQGALLPEP, SQGGRVRTL, KQL REVPAT, REVPATRRL, LSLAGDAAA, LAGDAAASL, LETAGGI QV, TRHSGLVHL, RGWCGAWAA, GAWAARNLI, FSMESPKP LL, LLAAESHGRI, RLAGAVVRPA, GLRELLIAPRL, SLAGDAAAS L, SLLQLGTRFL, FLGPHLSGGL, RLRHLHALRL, HLHALRLAGA, VLSGLRELLA, LLSLAGDAAA, QLGTRFLQGL, LLETAGGIQV, HLRGWCGAWA, WIWFSMESPK, GLGSVQLGAK, HLSGGLI YLR, GAWAARNLIF, AWAARNLIFL, HGRILQSHHV, HVLPQR LRHL, ALRLAGAVVR, VVRPACPPTA, KLRQGALLPE, GGRVR TLPQA, RVRTLPQAPA, RTLPQAPAPG, RARGAGPQQK, ATR RLHPRGR, RLHPRGRLPE, RGWCGAWAAR, ELLAPRLHHR, QLREVPATRR, VPATRRLHPR, EAVEERPGGL, QVPDTRHSG L, LPQRLRHLHA, APGNHDGDAV, APRLHHREAV, GPQQKQ LREV, LPEPQGPGPV, PQRLRHLHQL, GPHLSGGLIY, MESPK PLLAA, LAAESHGRIL, GRILQSHHVL, HALRLAGAVV, RAGGL GSVQL, RQGALLPEPA, VQVLSGLREL, RELLAPRLHH, QQKQ LREVPA, REVPATRRLH, GQGPRPLPEL, GDAAASLLQL, ASLL QLGTRF, LQLGTRFLQG, RFLQGLLETA, IQVPDTRHSG, VHLR GWCGAW, RNLIFLGPFIL, AESHGRILQS, PELLSLAGDA, VPD TRHSGLV | |
| FYB | c.972de|G | p.G324 fs | NQEELASGTPARFPKAPSKLTVGG|p. G324fs|HGAKVRKRKRETRIQPPRNRS HCLPCLPWVHLHQNPTDHQMLT* | LTVGGHGA, GGHGAKVR, HGAKVRKRK, KVRKRKRE, RI QPPRNRS, RNRSHCLPC, TVGGHGAKV, PPRNRSHCL, HQNP TDHQM, IQPPRNRSH, SHCLPCLPW, LPCLPWVHL, LPWVH LHQN, CLPCLPWVHL, KLTVGGHGAK, KVRKRKRETR, RIQPP RNRSH, RNRSHCLPCL, ETRIQPPRNR, LTVGGHGAKV, QPPR NRSHCL, RSHCLPCLPW, LHQNPTDHQM, HQNPTDHQML, LPWVHLHQNP | STAD |
| FZD3 | c.1099G>A | p.D367 N | LTIILLAMNKIEGDNISGVCFVGLY|p.D3 67N|NVDALRYFVLAPLCLYVVGVSLLL A | NVDALRYFV, GLYNVDALR, LYNVDALRY, YNVDALRYF, GVC FVGLYNV, GLYNVDALRY, LYNVDALRYF, YNVDALRYFV | CRC |
| FZD6 | c.1247G>A | p.R416 Q | ISLNHVRQVIQHDGRNQEKLKKFMI|p. R416Q|QIGVFSGLYLVPLVTLLGCYVYE QVN | KLKKFMIQI, IQIGVFSG, KFMIQIGVF, QIGVFSGLY, KKFMI QIGV, FMIQIGVFSG, MIQIGVFSGL, KLKKFMIQIG, IQIGVFS GLY, KKFMIQIGVF | UCEC |
| GABR A3 | c.218G>A | p.R73H | LSPKHAPDIPDDSTDNITIFTRILD|p.R73 H|HLLDGYDNRLRPGLGDAVTEVKTDIY | ILDHLLDGY, IFTRILDHL, HLLDGYDNR, FTRILDHLL, HLLDGY DNRL, TIFTRILDHL, IFTRILDHL, RILDHLLDGY | UCEC |
| GABR A4 | c.1379G>A | p.R460 Q | PFSRANAAETISAARALPSASPTSI|p.R460 Q|QTGYMPRKASVGSASTRHVFGSR LQR | SIQTGYMPR, IQTGYMPRK, SPTSIQTGY, SIQTGYMPRK, TSI QTGYMPR, ASPTSIQTGY, SPTSIQTGYM, IQTGYMPRKA | CRC, UCEC |
| GABR A5 | c.377G>A | p.S126 N | RQSWKDERLRFKGPMQRLPLNNLLA|p. S126N|NKIWTPDTFFHNGKKSIAHNM TTPNK | NKIWTPDTF, ANKIWTPDTF, NKIWTPDTFF | CRC |
| GABR A5 | c.670C>A | p.Q224 K | SEVVYVWTNGSTKSVVVAEDGSRLN|p. Q224K|KYHLMGQTVGTENISTSTGEYT IMTA | KYHLMGQTV, GSRLNKYHL, SRLNKYHLM, GSRLNKYHLM, A EDGSRLNKY, NKYHLMGQTV | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| GABRA6 | c.940G>A | p.V314I | SARHSLPKVSYATAMDWFIAVCFAF[p.V314I]IFSALIEFAAVNYFTNLQTQKAKRKA | FIAVCFAFI, FAFIFSALI, FIFSALIEF, IAVCFAFIF, CFAFIFSAL, FIFSALIEFA, WFIAVCFAFI, CFAFIFSALI, AFIFSALIEF, FIAVCFAFIF, VCFAFIFSAL | GBM |
| GABRB1 | c.1246C>T | p.R416C | KATMYSYDSASIQYRKPLSSREAYG[p.R416C]CALDRHGVPSKGRIRRRASQLKVKIP | SSREAYGCA, EAYGCALDR, SREAYGCAL, SSREAYGCAL | PRAD |
| GABRB3 | c.1498G>A | p.D500N | RSLPHKKTHLRRRSSQLKIKIPDLT[p.D500N]NVNAIDRWSRIVFPFTFSLFNLIVYWL | LTNVNAIDR, IKIPDLTNV, KIKIPDLTNV, KIPDLTNVNA, DLTNVNAIDR, NVNAIDRWSR, IPDLTNVNAI | CRC |
| GABRD | c.1236delG | p.Q412fs | GSYSRVSGVETGETKKEGAARSGGGQG[p.Q412fs]ASVPGSGGPSTQTPLTFTPALCSLRRLRPSMSSTCGRHTPCEHRTQATLACPGARRQLPRNFLGERALGLPSLPRVSKWDDSRPRKTRGSLGLPEL* | FLGERALGL, RLRPSMSST, ATLACPGAR, ALGLPSPLR, RVSKWDDSR, TFTPALCSL, AARSGGQGA, RSGGQGASV, SLRRLRPSM, RQLPRNFLG, RALGLPSPL, KWDDSRPRK, KTRGSLGLP, FTPALCSLR, ALCSLRRLR, TLACPGARR, QTPLTFTPA, TPLTFTPAL, RPRKTRGSL, PSTQTPLTF, CEHRTQATL, TQATLACPG, ARRQLPRNF, RRQLPRNFL, RNFLGERAL, GERALGLPS, RKTRGSLGL, RGSLGLPEL, ALGLPSPLR, ATLACPGAR, RALGLPSPLR, CSLRRLRPSM, SLRRLRPSMS, RLRPSMSSTG, RTQATLACPG, KTRGSLGLPE, TFTPALCSLR, QTPLTFTPAL, LTFTPALCS L, TPALCSLRRL, LPRNFLGERA, RPRKTRGSLG, GSGPSTQTPL, GPSTQTPLTF, TQTPLTFTPA, TQATLACPGA, LACPGARRQL, GARRQLPRNF, RQLPRNFLGE, ERALGLPSPL, TRGSLGLPEL, LPSPLRVSKW, CEHRTQATLA, GERALGLPSP | STAD |
| GABRG1 | c.613G>A | p.E205K | LRLTINAECYLQLHNPMDEHSCPL[p.E205K]KFSSYGYPKNEIEYKWKKPSVEVADP | KFSSYGYPK, PLKFSSYGY, DEHSCPLKF, HSCPLKFSSY, CPLKFSSYGY, MDEHSCPLKF | SKCM |
| GABRR2 | c.1103C>T | p.A368V | VSYVKAVDIYLWVSFVFVFLSVLEY[p.A368V]VAVNYLTTVQERKERKLRKFPCMCG | VFLSVLEYV, FLSVLEYVA, VAVNYLTTV, VLEYVAVNY, LEYVAVNYL, VNYL, FVFLSVLEYV, FLSVLEYVAV, VLEYVAVNYL, YVAVNYLTTV, SVLEYVAVNY, LEYVAVNYLT | PRAD |
| GADL1 | c.1054C>A | p.L352I | VAWNPHKMLMAGIQCCALLVKDKSD[p.L352I]ILKKCYSAKASYLFQQDKFYDVSYDT | KSDILKKCY, ILKKCYSAK, ILKKCYSAKA, LVKDKSDILK, DILKKCYSAK | LUAD |
| GAL3ST3 | c.811G>T | p.A271S | ESLVLLRRLLAWDLDDVLYAKLNAR[p.A271S]SASSRLAAIPAALARAARTWNALDAG | SASSRLAAI, KLNARSASS, RSASSRLAA, NARSASSRL, YAKLNARSA, VLYAKLNARS, KLNARSASSR, NARSASSRLA, RSASSRLAAI, LNARSASSRL, ARSASSRLAA | LUAD |
| GALNT13 | c.1072G>T | p.G358C | LEIVTCSHVGHVFRKATPYTFPGGT[p.G358C]CHVINKNNRLAEVWMDEFKDFFYII | GGTCHVINK, YTFPGGTCH, FPGGTCHVI, YTFPGGTCHV, TFPGGTCHVI | LUSC |
| GALNT14 | c.702T>A | p.D234E | VNRDWLQPLLHRVKEDYTRVVCPVI[p.D234E]EIINLDTFTYIESASELRGGFDWSLH | RVVCPVIEI, IEIINLDTF, CPVIEIINL, EIINLDTFTY, RVVCPVIEII | LUAD |
| GALNTL1 | c.950_951insG | p.W317fs | GIFVIDKSWFNHLGKYDAQMDIWGG[p.W317fs]REF* | AQMDIWGGR, MDIWGGREF, DAQMDIWGGR, QMDIWGGREF | STAD |
| GALNTL2 | c.1183G>A | p.E395K | AMDRHYFQNTGAYDSLMSLRGGENL[p.E395K]KLSFKAWLCGGSVEILPCSRVGHIYQ | SLRGGENLK, GGENLKLSF, NLKLSFKAW, LKLSFKAWL, SLRG GENLKL, MSLRGGENLK, NLKLSFKAWL, RGGENLKLSF, GEN LKLSFKA | UCEC |
| GALNTL5 | c.133G>A | p.A45T | TALLFIYLHHNHVSSWQKKSQEPLS[p.A45T]TWSPGKKVHQQIIYGSEQIPKPHVIV | LSTWSPGKK, KSQEPLSTW, KKSQEPLSTW | LIHC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| GALNTL5 | c.785G>T | p.R262I | LEPLLHAIAKDPKMVVCPLIDVIDD[p.R262I]TLEYKPSPLVRGTFDWNLQFKWDNV | VIDDITLEY,PLIDVIDDI,VIDDITLEYK,DVIDDITLEY,ITLEYKPSPL,CPLIDVIDDI | CRC |
| GALNTL6 | c.1694_1696delAGA | p.K567del | WGYRKDRTLFHPVSNSCMDCNPAEK[p.K567del]IFMARCDPLSETQQWIFEHINMTVLEKF | NPAEKIFMA,CMDCNPAEKI,NPAEKIFMAR,MDCNPAEKIF | BRCA |
| GARS | c.124C>G | p.P42A | LLLLPPRLLARPSLLLRRSLSAASC[p.P42A]APISLPAAASRSSMDGAGAEEVLAPL | RSLSAASCA,LSAASCAPI,APISLPAAA,AASCAPISL,SLSAASCAPI,SAASCAPISL | ACC |
| GART | c.2420delA | p.K807fs | IESMQINGSVLKNGSLTNHFSFEKK[p.K807fs]RPEWLS* | FEKKRPEWL,FSFEKKRPEW | OV |
| GAS2L2 | c.566A>C | p.D189A | AAPTLVQLEEEIEEEVRRELALPPP[p.D189A]APSPPAPPRRQPCHFRNLDQMVQSLV | RELALPPPA,LPPPAPSPPA,RELALPPPAP | TGCT |
| GAS6 | c.449delG | p.G150fs | CDRKGTQACQDLMGNFFCLCKAGWG[p.G150fs]AGSATKMSTNAARRTGAASRSATTSRVASTVPATAASSSPLMAGPAKT* | TTSRVASTV,ATAASSSPL,KMSTNAARR,GWGAGSATK,ATKMSTNAA,ARRTGAASR,RTGAASRSA,ASRSATTSR,RSATTSRVA,STVPATAAS,NAARRTGAA,WGAGSATKM,SRVASTVPA,TAASSSPLM,ATTSRVASTV,RVASTVPATA,ATKMSTNAAR,AASRSATTSR,SSPLMAGPAK,AGWGAGSATK,STNAARRTGA,AARRTGAASR,RTGAASRSAT,ASRSATTSRV,TSRVASTVPA,ATAASSSPLM,SRVASTVPAT | STAD |
| GAS8 | c.937C>A | p.R313S | EEMSEMQKQLANYERDKQILLCTKA[p.R313S]SLKVREKELKDLQMEHEVLEQRFTKV | ILLCTKASL,LLCTKASLK,KASLKVREK,CTKASLKVR,SLKVREKEL,LLCTKASLKV,ILLCTKASLKV,SLKVREKELK,KQILLCTKAS | LUAD |
| GATA3 | c.1002_1003insG | p.N334fs | ARRAGTSCANCQTTTTLWRRNANG[p.N334fs]GPCLQCLWALLQASQY* | CLQCLWALL,WALLQASQY,RNANGGPCL,LWALLQASQY,RRNANGGPCL,LQCLWALLQA | BRCA |
| GATA3 | c.1200_1201insA | p.H400fs | CKKVHDSLEDFPKNSSFNPAALSRH[p.H400fs]NVLPEPHLALQPLQPHADHAHADAPAIQPVLWTTPPLQHGHRHGLEPCSMLTGPPARVPAVPFDLHFCRSSIMKPKRDGYMFLKAESKIMFATLQRSSLWCLCSNH* | VLPEPHLAL,ALQPLQPHA,AIQPVLWTT,MLTGPPARV,FLKAESKIM,IMFATLQRS,YMFLKAESK,KIMFATLQR,SMLTGPPAR,HFCRSSIMK,MFLKAESKI,CSMLTGPPA,RSSIMKPKR,IMKPKRDGY,KAESKIMFA,VPFDLHFCR,AALSRHNVL,EPHLALQPL,GPPARVPAV,KPKRDGYMF,FATLQRSSL,DLHFCRSSI,LHFCRSSIM,ESKIMFATL,LALQPLQPH,LQPHADHAH,HAHADAPAI,LQHGHRHGL,RHGLEPCSM,PARVPAVPF,PAVPFDLHF,LKAESKIMF,ATLQRSSLW,LQRSSLWCL,AESKIMFAT,ADAPAIQPV,APAIQPVLW,SMLTGPPAR V,YMFLKAESKI,LQRSSLWCL,CSMLTGPPAR,LHFCRSSIMK,FCRSSIMKPK,IMKPKRDGYM,YMFLKAESK,SIMKPKRDGY,TTPPLQHGHR,AVPFDLHFCR,HADAPAIQPV,NPAALSRHNV,QPVLWTTPPL,KPKRDGYMFL,DLHFCRSSIM,MFATLQRSSL,FLKAESKIMF,RHNVLPEPHL,HLALQPLQPH,ADAPAIQPVL,HRHGLEPCSM,ARVPAVPFDL,VPAVPFDLHF,FDLHFCRSSI,MKPKRDGYMF,MFLKAESKIM,AESKIMFATL,IMFATLQRSS,FATLQRSSLW,LQRSSLWCLC,PPARVPAVPF,PEPHLALQPL | BRCA |
| GATA3 | c.1222_1223insC | p.S408fs | EDFPKNSSFNPAALSRHMSSLSHIS[p.S408fs]ALQPLQPHADHAHADAPAIQPVLWTTPPLQHGHRHGLEPCSMLTGPPARVPAVPFDLHFCRSSIMKPKRDGYMFLKAESKIMFATLQRSSLWCLCSNH* | ALQPLQPHA,AIQPVLWTT,MLTGPPARV,FLKAESKIM,IMFATLQRS,YMFLKAESK,KIMFATLQR,SMLTGPPAR,HFCRSSIMK,MFLKAESKI,MSSLSHISA,SSLSHISAL,CSMLTGPPA,RSSIMKPKR,MKPKRDGY,KAESKIMFA,VPFDLHFCR,GPPAR,SIMKPKR,MKPKRDGY,KAESKIMFA,VPFDLHFCR,GPPAR,VPAV,KPKRDGYMF,FATLQRSSL,DLHFCRSSI,LHFCRSSIM,ESKIMFATL,SHISALQPL,SALQPLQPH,LQPHADHAH,HAHADAPAI,LQHGHRHGL,RHGLEPCSM,PARVPAVPF,PAVPF | BRCA |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| | | | | DLHF,LKAESKIMF,ATLQRSSLW,LQRSSLWCL,AESKIMFAT, ADAPAIQPV,APAIQPVLW,SMLTGPPAR,YMFLKAESKI,T LQRSSLWCL,HMSSLSHISA,CSMLTGPPAR,LHFCRSSIMK,F CRSSIMKPK,IMKPKRDGYM,GYMFLKAESK,SIMKPKRDGY, TTPPLQHGHR,AVPPDLHFCR,MSSLSHISAL,HADAPAIQPV, QPVLWTTPPL,KPKRDGYMFL,DLHFCRSSIM,MFATLQRSS L,FLKAESKIMF,LSHISALQPL,ADAPAIQPVL,HRHGLEPCSM, ARVPAVPFDL,VPAVPFDLHF,FDLHFCRSSI,MKPKRDGYM F,MFLKAESKIM,AESKIMFATL,IMFATLQRSS,FATLQRSSL W,LQRSSLWCLC,PPARVPAVPF | |
| GATA 3 | c.1223_122 4insT | p.S408f s | EDFPKNSSFNPAALSRHMSSLSHIS[p.S 408fs]ALQPLQPHADHAHADAPAIQPV LWTTPPLQHGHRHGLEPCSMLTGPPA RVPAVPFDLHFCRSSIMKPKRDGYMFL KAESKIMFATLQRSSLWCLCSNH* | ALQPLQPPIA,AIQPVLWTT,MLTGPPARV,FLKAESKIM,IMF ATLQRS,YMFLKAESK,KIMFATLQR,SMLTGPPAR,HFCRSSI MK,MFLKAESKI,MSSLSHISA,SSLSHISAL,CSMLTGPPA,RS SIMKPKR,IMKPKRDGY,KAESKIMFA,VPFDLHFCR,GPPAR VPAV,KPKRDGYMF,FATLQRSSL,DLHFCRSSI,LHFCRSSIM, ESKIMFATL,SHISALQPL,SALQPLQPH,LQPHADHAH,HAH ADAPAI,LQHGHRHGL,RHGLEPCSM,PARVPAVPF,PAVPFDLH F,LKAESKIMF,ATLQRSSLW,LQRSSLWCL,AESKIMFAT, ADAPAIQPV,APAIQPVLW,SMLTGPPARV,YMFLKAESKI,T LQRSSLWCL,HMSSLSHISA,CSMLTGPPAR,LHFCRSSIMK,F CRSSIMKPK,IMKPKRDGYM,GYMFLKAESK,SIMKPKRDGY, TTPPLQHGHR,AVPPDLHFCR,MSSLSHISAL,HADAPAIQPV, QPVLWTTPPL,KPKRDGYMFL,DLHFCRSSIM,MFATLQRSS L,FLKAESKIMF,LSHISALQPL,ADAPAIQPVL,HRHGLEPCSM, ARVPAVPFDL,VPAVPFDLHF,FDLHFCRSSI,MKPKRDGYM F,MFLKAESKIM,AESKIMFATL,IMFATLQRSS,FATLQRSSL W,LQRSSLWCLC,PPARVPAVPF | BRCA |
| GATA 3 | c.1290_129 1insT | p.S430f s | ISPFSHSSHMLTTPTPMHPPSSLSF[p.S4 30fs|WTTPPLQHGHRHGLEPCSMLTG PPARVPAVPFDLHFCRSSIMKPKRDGY MFLKAESKIMFATLQRSSLWCLCSNH* | MLTGPPARV,FLKAESKIM,IMFATLQRS,YMFLKAESK,KIMF ATLQR,SMLTGPPAR,HFCRSSIMK,MFLKAESKI,LSFWTTPP L,CSMLTGPPA,RSSIMKPKR,IMKPKRDGY,KAESKIMFA,VP FDLHFCR,GPPARVPAV,KPKRDGYMF,FATLQRSSL,DLHFC RSSI,LHFCRSSIM,ESKIMFATL,LQHGHRHGL,RHGLEPCSM, PARVPAVPF,PAVPFDLHF,LKAESKIMF,ATLQRSSLW,LQR SSLWCL,AESKIMFAT,HPPSSLSFW,SLSFWTTPPL,SMLTGP PARV,YMFLKAESKI,TLQRSSLWCL,CSMLTGPPAR,MHPPS SLSFW,LHFCRSSIM,FCRSSIMKPK,IMKPKRDGYM,GYMF LKAESK,SIMKPKRDGY,TTPPLQHGHR,AVPPDLHFCR,KPK RDGYMFL,DLHFCRSSIM,MFATLQRSSL,FLKAESKIMF,HR HGLEPCSM,ARVPAVPFDL,VPAVPFDLHF,FDLHFCRSSI,M KPKRDGYMF,MFLKAESKIM,AESKIMFATL,IMFATLQRSS, FATLQRSSLW,LQRSSLWCLC,PPARVPAVPF | BRCA |
| GATA 3 | c.1301_130 2insC | p.H434 fs | FSHSSHMLTTPTPMHPPSSLSFGPH[p. H434fs]PPLQHGHRHGLEPCSMLTGPP ARVPAVPFDLHFCRSSIMKPKRDGYMF LKAESKIMFATLQRSSLWCLCSNH* | MLTGPPARV,FLKAESKIM,IMFATLQRS,YMFLKAESK,KIMF ATLQR,SMLTGPPAR,HFCRSSIMK,MFLKAESKI,CSMLTGP PA,RSSIMKPKR,IMKPKRDGY,KAESKIMFA,VPFDLFIFCR,G PPARVPAV,KPKRDGYMF,FATLQRSSL,DLHFCRSSI,LHFCR SSIM,ESKIMFATL,LSFGPHPPL,LQHGHRHGL,RHGLEPCS M,PARVPAVPF,PAVPFDLFIF,LKAESKIMF,ATLQRSSLW,L QRSSLWCL,AESKIMFAT,SLSFGPHPPL,SMLTGPPARV,YM FLKAESKI,TLQRSSLWCL,CSMLTGPPAR,LHFCRSSIMK,FCR | BRCA |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| GATA 3 | c.1304_130 5insC | p.H435 fs | HSSHMLTPTPMHPPSSLSFGPHHP[p. H435fs]LQHGHRHGLEPCSMLTGPPAR VPAVPFDLHFCRSSIMKPKRDGYMFLK AESKIMFATLQRSSLWCLCSNH* | SSIMKPK,IMKPKRDGYM,GYMFLKAESK,SIMKPKRDGY,A VPPDLHFCR,KPKRDGYMFL,DLHFCRSSIM,MFATLQRSSL, FLKAESKIMF,HRHGLEPCSM,ARVPAVPFDL,VPAVPFDLHF, FDLHFCRSSI,MKPKRDGYMF,MFLKAESKIM,AESKIMFAT L,IMFATLQRSS,FATLQRSSLW,LQRSSLWCLC,PPARVPAVPF MLTGPPARV,FLKAESKIM,IMFATLQRS,YMFLKAESK,KIMF ATLQR,SMLTGPPAR,HFCRSSIMK,MFLKAESKI,CSMLTGP PA,RSSIMKPKR,IMKPKRDGY,KAESKIMFA,VPFDLHFCR,L SFGPFIHPL,GPPARVPAV,KPKRDGYMF,FATLQRSSL,DLHF CRSSI,LHFCRSSIM,ESKIMFATL,LQHGHRHGL,RHGLEPCS M,PARVPAVPF,PAVPPDLHF,LKAESKIMF,ATLQRSSLW,L QRSSLWCL,HPLQHGHRH,AESKIMFAT,SLSFGPHHPL,SML TGPPARV,YMFLKAESKI,LQRSSLWCL,CSMLTGPPAR, LHFCRSSIMK,FCRSSIMKPK,IMKPKRDGYM,GYMFLKAESK,SI MKPKRDGY,AVPPDLHFCR,KPKRDGYMFL,DLHFCRSSIM, MFATLQRSSL,FLKAESKIMF,HRHGLEPCSM,ARVPAVPFDL, VPAVPFDLHF,FDLFIPCRSSI,MKPKRDGYMF,MFLKAESKI M,AESKIMFATL,IMFATLQRSS,FATLQRSSLW,LQRSSLWC LC,PPARVPAVPF | BRCA |
| GATA 3 | c.1329G>T | p.M44 3I | TTPTPMHPPSSLSFGPHHPSSMVTA[p. M443I]IG* | HPSSMVTAI | LUAD |
| GATA 3 | c.983_984 insCTGGAG G | p.L328f s | RRLSAARRAGTSCANCQTTTTLWR[p. L328fs]LEEECQWGPCLQCLWALLQAS QY* | CLQCLWALL,QWGPCLQCL,TTTTTLWRL,WALLQASQY,EE CQWGPCL,QWGPCLQCLW,LWALLQASQY,QTTTTLWRL, CQWGPCLQCL,LQCLWALLQA | BRCA |
| GBP7 | c.1292_129 3insG | p.G431 fs | QAELKRLSELLTESISRGTFFVPGG[p.G4 31fs]AQYLLRSKKED* | FVPGGAQYL,AQYLLRSK,GAQYLLRSK,FFVPGGAQY,VPG GAQYLL,FVPGGAQYLL,GAQYLLRSKK,FFVPGGAQYL,TFFV PGGAQY | STAD |
| GCDH | c.1167deIG | p.L389f s | VSLLKRNNCGKALDIARQARDMLGG[p. L389fs]MGFLTSIT* | MLGGMGFLT,RDMLGGMGF,GGMGFLTSI,RQARDMLGG M,RDMLGGMGFL | STAD |
| GCDH | c.244C>T | p.R82C | EEQLTTDEILIRDTFRTYCQERLMP[p.R8 2C]CILLANRNEVFHREIISEMGELGVLG | RLMPCILLA,MPCILLANR,QERLMPCIL,LMPCILLANR,CQE RLMPCIL,QERLMPCILL | LUAD |
| GDAP 1 | c.919A>G | p.T307 A | RVLKRKTFNKVLGHVNNILISAVLP[p.T3 07A]AAFRVAKKRAPKVLGTTLVVGLLA GV | ILISAVLPA,LISAVLPAA,AVLPAAFRV,VLPAAFRVA,SAVLPA AFR,LPAAFRVAK,ISAVLPAAF,ILISAVLPAAF,VLPAAFRVAK,I SAVLPAAFR,AVLPAAFRVA,SAVLPAAFRV,LISAVLPAAF | BRCA |
| GDF5 | c.315_316i nsA | p.E105f s | GQTGGLTQPKDEPKKLPPRPCGPE[p. E105fs]TQARTPSPNKAGYSPDCDPKRT ASRRQGTPKSRICPQLLPAEEGQGARA PTRAQGAVSPTPHHTPRVHALAVQDA VRC* | RICPQLLPA,ASRRQGTPK,QARTPSPNK,RTASRRQGT,KSRI CPQLL,HTPRVHALA,SPTPHHTPR,HALAVQDAV,APTRAQ GAV,TPRVHALAV,RQGTPKSRI,RAQGAVSPT,AQGAVSPTP,HHTPRVHAL,TPSPNKAGY,AEEGQGARA,LLPAEEGQGA, TQARTPSPNK,TASRRQGTPK,QARTPSPNKA,AGYSPDCDP K,ASRRQGTPKS,KSRICPQLLP,RVHALAVQDA,RTPSPNKA GY,HALAVQDAVR,HTPRVHALAV,TPKSRICPQL,SPTPHHT PRV,SRICPQLLPA,AQGAVSPTPH | TGCT |
| GDPD 5 | c.1779_178 0insC | p.G593 fs | SVCSDNSYDTYANSTATPVPGRGGG[p. G593fs]QPHQDPHRAEWALAEDMSV PPVPDTEAGEPRRAGGSVSELGVLWER APQPPCGLQPLVSRSLS* | GPRGGGQPH,EPRRAGGSV,QPPCGLQPL,HQDPHRAEW, AEWALAEDM,WALAEDMSV,AEDMSVPPV,RAGGSVSEL, WERAPQPPC,LQPLVSRSL,SELGVLWER,DPHRAEWAL,AL AEDMSVPP,GLQPLVSRSL,RAEWALAEDM,RRAGGSVSEL, AEWALAEDMS,SELGVLWERA,QPPCGLQPLV | KIRP |
| GEM | c.803G>T | p.R268 L | RDSKEKNERRLAYQKRKESMPRKAR[p. R268L]LFWGKIVAQNNKNMAFKLKSKS | RLFWGKIVA,SMPRKARLF,RKARLFWGK,KARLFWGKI,LF WGKIVAK,MPRKARLFW,ESMPRKARL,RLFWGKIVAK,SM | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| GEN1 | c.1526C>T | p.S509L | VMSFQSHMTLKPTCEIFHKQNSKLN[p. S509L]LGISPDPTLPQESISASLNSLLLPK N | PRKARLFW,KARLFWGKIV,MPRKARLFWG,KESMPRKARL, RKARLFWGKI HKQNSKLNL,SKLNLGISP,LGISPDPTL,KQNSKLNLGI,FHKQ NSKLNL | UCEC |
| GFM1 | c.49_50ins C | p.A17fs | MRLLGAAVAALGRGRAP[p.A17fs]RL PRLAEEAG* | RLPRLAEEA,ALGRGRAPR,RGRAPRLPR,APRLPRLAE,AALG RGRAPR,RGRAPRLPRL | KICH |
| GFRAL | c.922C>A | p.Q308 K | LGTVLQVQCTCRTITQSEESLCKIF[p.Q3 08K]KHMLHRKSCFNYPTLSNVKGMAL YTR | KIFKHMLHR,IFKHMLHRK,SLCKIFKHM,SLCKIFKHML,KIFK HMLHRK,KHMLHRKSCF | LUAD |
| GGA2 | c.188C>T | p.A63V | MSEQDWSAIQNFCEQVNTDPNGPTH[p. A63V]VPWLLAHKIQSPQEKEALYALT VLEM | HVPWLLAHK,HVPWLLAH,VPWLLAHKI,GPTHVPWLL,N TDPNGPTHV,HVPWLLAHKI,DPNGPTHVPW | UCEC |
| GIGYF 2 | c.680G>A | p.R227 H | PNFEEGGPTSVGRKHEFIRSESENW[p. R227H]HIFREEQNGEDEDGGWRLAGS RRDGE | ESENWHIFR,SESENWHIF,RSESENWHIF | UCEC |
| GIMA P7 | c.827de T | p.V276 fs | LLKLKYDEKIKNIREEAERNIFKDV[p.V27 6fs]LIGFGRCFQKYGIGFCRNVSFILPNL L* | NVSFILPNL,IGFGRCFQK,IFKDVLIGF,CFQKYGIGF,IGFCRN VSF,GFGRCFQKY,VLIGFGRCF,VSFILPNLL,LIGFGRCFQK,K YGIGFCRNV,IGFGRCFQKY,FQKYGIGFCR,NVSFILPNLL,NI FKDVLIGF,AERNIFKDVL,RCFQKYGIGF,GIGFCRNVSF,IGFC RNVSFI,RNVSFILPNL | STAD |
| GIMA P8 | c.1630G>T | p.A544 S | SCCEKGDTFFVLVFQLGRFTEEDKT[p.A 544S]SVAKLEAIFGADFTKYAIMLFTRK ED | KTSVAKLEA,FTEEDKTSV,SVAKLEAIF,KTSVAKLEAI,TSVAK LEIAF,EEDKTSVAKL | KIRP |
| GIPC3 | c.679de G | p.G227 fs | SRSSKCPVEAKVTSGRETLRLRSGG[p.G 227fs]LPQWRKRPVSLRRRHLGRLMTC WKATWAFGTPSWRPPWWRRPRQR APRSLHAV* | RLMTCWKAT,RAPRSLHAV,SLRRRFILGR,TCWKATWAF,T WAFGTPSW,RLRSGGLPQ,QWRKRPVSL,RKRPVSLRR,RRR HLGRLM,LGRLMTCWK,CWKATWAFG,SWRPPWWR,RP RRARAPR,RQRAPRSLH,WAFGTPSWR,RPPWWRPR,MT CWKATWA,LPQWRKRPV,TLRLRSGGL,LRSGGLPQW,LMT CWKATW,RRQRAPRSL,TPSWRPPWW,LMTCWKATWA, GLPQWRKRPV,SLRRRHLGRL,HLGRLMTCWK,RSGGLPQ WRK,VSLRRRHLGR,RLMTCWKATW,MTCWKATWAF,RLR SGGLPQW,QWRKRPVSLR,RKRPVSLRRR,SWRPPWWRRP, WWRRPRRQRA,RQRAPRSLHA,TWAFGTPSWR,TPSWRP PWWR,REPPWWRRPR,ETLRLRSGGL,LPQWRKRPVS,RPV SLRRRHL,LPRRRHLGRL,RPRRRHLGR,RPRRHLGRLM,R HLGRLMTCW,ATWAFGTPSW,FGTPSWRPPW | STAD |
| GIT2 | c.368G>T | p.R123 L | KVHPNKAEFITRAKYQMLAFVHRLPC[p. R123L]LDDDSVTAKDLSKQLHSSVRTG NLET | CLDDDSVTA,LPCLDDDSV,RLPCLDDDS,LAFVHRLPCL | LUAD |
| GJA1 | c.932de C | p.A311 fs | YKLVTGDRNNSSCRNVNKQASEQNW[p. A311fs]VITVQNKIEWGRREAPSLTP MHSLLISPMITRILKN* | SLTPMHSLL,LISPMITRI,KQASEQNWV,LLISPMITR,SPMIT RILK,QASEQNWVI,WVITVQNKI,REAPSLTPM,SEQNWVIT V,WGRREAPSL,MHSLLISPM,IEWGRREAP,KQASEQNWVI, SLTPMHSLLI,LLISPMITRI,LISPMITRIL,SLLISPMITR,ISPMI TRILK,NVVITVQNKI,TVQNKIEWGR,APSLTPMHSL,RREA PSLTPM,REAPSLTPMI,PMHSLLISPM,MHSLLISPMI,IEW GRREAPS | KIRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| GJB3 | c.479G>A | p.R160H | LIFKLIEFLFLYLLHTLWHGFNMP[p.R16 0H]HLVQCANVAPCPNIVDCYIARPTEK K | NMPHLVQCA,HLVQCANVA,MPHLVQCAN,LWHGFNMP HL,MPHLVQCANV | GBM |
| GJB4 | c.64C>A | p.R22S | MNWAFLQGLLSGVNKYSTVLS[p.R22S] SIWLSVVFIFRVLVYVVAAEEVWDDE | VLSSIWLSV,SIWLSVVFI,LSSIWLSVV,KYSTVLSSI,SSIWLSV VF,STVLSSIWL,NKYSTVLSS,YSTVLSSIW,TVLSSIWLSV,VLS SIWLSVV,KYSTVLSSIW,SIWLSVVFIF,SSIWLSVVFI,LSSIWL SVVF,NKYSTVLSSI,YSTVLSSIWL | LUAD |
| GLB1L2 | c.1221C>G | p.I407M | KMPYEPLTPVLYLSLMDALKYLGEP[p.I 407M]MKSEKPINMENLPVNGGNGQS FGYIL | ALKYLGEPM,EPMKSEKPI,MKSEKPINM,ALKYLGEPMK,DA LKYLGEPM | LUAD |
| GLI1 | c.815del|G | p.W272fs | QEQLVHHINSEHIHGERKEFVCHWG[p. W272fs]AAPGS* | KEFVCHWGA,KEFVCHWGAA | STAD |
| GLI3 | c.2993C>T | p.P998L | VHAPRRCSDGGAHGYGRRHLQPHDA[p. p.P998L]LGHGVRRASDPVRTGSEGLAL PRVPR | ALGHGVRRA,DALGHGVRR,RHLQPHDAL,RRHLQPHDAL | ACC |
| GLI3 | c.3098del|C | p.P1033fs | PVRTGSEGLALPRVPRFSSLSSCNP[p.P1 033fs]RRWPRPRRSAVSCFRITRGPRAA SPETSTRPPVLPASPRTSPWSP* | AVSCFRITR,SSLSSCNPR,SLSSCNPRR,SCNPRRWPR,RWPR PRRSA,RRSAVSCFR,RSAVSCFRI,CFRITRGPR,ITRGPRAAS, STRPPVLPA,NPRRWPRPR,WPRPRRSAV,CLRIIFIYK,GP RAASPET,LPASPRTSP,FSSLSSCNPR,SSLSSCNPRR,SSCNP RRWPR,SAVSCFRITR,RWPRPRRSAV,CFRITRGPRA,ITRGP RAASP,RAASPETSTR,STRPPVLPAS,CNPRRWPRPR,SCFRI TRGPR,WPRPRRSAVS,RPRRSAVSCF,SPETSTRPPV,LPASP RTSPW,RWPRPRRSA,RRSAVSCFRI,FRITRGPRAA | STAD |
| GLIPR1L2 | c.276del|A | p.G92fs | IPRGSNLRFMTWDVALSRTARAWGK[p. G92fs]NVCLRIIFIYKMYKWSILNFMVL VKICGSALKMNLLQVLLSEVGMQRRKC TILKMAVALETVLIIFSLFGTTLTKLVVLLL HVQKLDILYMQQFSYATMRQEEH* | HVQKLDILY,SILNFMVLV,ALKMNLLQV,KMNLLQVLL,LLQ VLLSEV,KMAVALETV,LIIFSLFGT,TLTKLMLL,KLVVLLLHV, VLLHVQKL,YMQQFSYAT,VLVKICGSA,CLRIIFIYK,IIFIYKM YK,KMYKWSIL,ILNFMVLVK,SLFGTTLTK,VVLLLHVQK,IL YMAQFSY,QQFSYATMR,IFIYKMYKW,IYKMYKWSI,MYK WSILNF,KWSILNFMV,TVLIIFSLF,IFSLFGTTL,LYMQQFSYA, TARAWGKNV,MQRRKCTIL,QRRKCTILK,RIIFIYKMY,LLSE VGMQR,CTILKMAVA,ETVLIIFSL,LVKICGSAL,YKMYKWSIL, GMQRRKCTI,VQKLDILYM,MQQFSYATM,RAWGKNVCL, KNVCLRIIF,LRIIFIYKM,YKWSILNFM,WSILNFMVL,KICGSA LKM,LKMNLLQVL,LQVLLSEVG,RRKCTILKM,KLMAVALET, MAVALETVL,VALETVLII,ALETVLIIF,LHVQKLDIL,LDILYMQ QF,FIYKMYKWS,YKWSILNFMV,MQQFSYATM,ILNFMVL VKI,NLLQVLLSEV,KMAVALETVL,VLIIFSLFGT,IIFSLFGTTL, SLFGTTLTKL,TLTKLVVLL,ALKMNLLQVL,ILYMQQFSYA,YMQQFSYATM, VLVKICGSAL,ALKMNLLQVL,RIIFIYKMYK,KMYKWSILNF,S ILNFMVLVK,LVKICGSALK,MQRRKCTILK,FSLFGTTLTK,RA WGKNVCLR,LVLLLFIVQK,MQQFSYATMR,AWGKNVCLR I,IYKMYKWSIL,MYKWSILNFM,KWSILNFMVL,VALETVLIIF, ETVLIIFSLF,LYMQQFSYAT,RTARAWGKNV,CLRIIFIYKM,D ILYMQQFSY,CTILKMAVAL,MAVALETVLI,VGMQRRKCTI, GMQRRKCTIL,LQVLLSEVGM,ARAWGKNVCL,GKNVCLRII F,LRIIFIYKMY,IIFIYKMYKW,VKICGSALKM,LKMNLLQVLL, QRRKCTILKM,KLDILYMQQF,LHVQKLDILY,LETVLIIFSL,HV QKLDILYM,KLDILYMQQF,QQFSYATMRQ | STAD |

315
316

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| GLOD4 | c.667_668insC | p.Q223fs | KLELQGVKGGVDHAAAFGRIAFSCP[p.Q223fs]PERVARLRRLDEKGEPEDSDSPGEPGHPRESNSTGGHSGRP* | IAFSCPPER,NSTGGHSGR,HPRESNSTG,RESNSTGGH,CPPERVARL,RIAFSCPPER,VARLRRLDEK,FSCPPERVAR,IAFSCPPERV | LUAD |
| GLRA3 | c.1360C>A | p.L454I | DTISRACFPLAFLIFNIFYWVIYKI[p.L454I]IRHEDIHQQQD* | FYWVIYKII,IFYWVIYKI,IYKIIRHEDI,FYWVIYKIIR | CRC |
| GLRA3 | c.396C>A | p.F132L | AYSEYPDDSLLDLDPSMLDSIWKPDL[p.F132L]LFANEKGANFHEVTTDNKLLRIFKNG | LLFANEKGA,SIWKPDLLF,IWKPDLLFA,DSIWKPDLL,SIWKPDLLFA,LFANEKGANF | CRC |
| GLT8D2 | c.533C>T | p.A178V | IYLDDDVIVQGDIQELYDTTLALGH[p.A178V]VAAFSDDCDLPSAQDINRLVGLQNTY | TLALGHVAA,DTTLALGHV,TTLALGHVA,LALGHVAAF,DTTLALGHVA,TTLALGHVAAF | GBM |
| GLTSCR2 | c.1166A>G | p.Q389R | RHQELFRLRGIKAQVALRLAELARR[p.Q389R]RRRRQARRRAEAADKPRRLGRLKYQAP | RRRRQARR,ELARRRRR,RLAELARRR,LARRRRRQA,RRRRRRQARR,RLAELARRR | ACC |
| GLYR1 | c.1139_1140insG | p.G380fs | CYVDMSTVDADTVTELAQVIVSRGG[p.G380fs]ALSGSPRLRESAAV* | SPRLRESAA,GALSGSPRL,RGGALSGSPR,QVIVSRGGAL,SPRLRESAAV | STAD |
| GNA13 | c.598A>G | p.R200G | KYFLDNLDKLGEPDYIPSQQDILLA[p.R200G]GRPTKGIHEYDFEIKNVPFKMVDVGG | ILLAGRPTK,SQQDILLAG,LLAGRPTKGI | BLCA |
| GNAO1 | c.848C>A | p.P283Q | KWFTDTSIILFLNKKDIFEEKIKKS[p.P283Q]LTICFPEYTGPSAFTEAVAVIQAQY | KIKKSQLTI,QLTICFPEY,KKSQLTICF,KIKKSQLTIC,SQLTICFPEY,IKKSQLTICF,FEEKIKKSQL | LUAD |
| GNAS | c.2530C>T | p.R844C | QYFLDKIDVIKQADYVPSDQDLLRC[p.R844C]CVLTSGIFETKFQVDKVNFHMFDVGG | CCVLTSGIF,RCCVLTSGIF | LIHC |
| GNAS | c.2531G>A | p.R844H | QYFLDKIDVIKQADYVPSDQDLLRC[p.R844H]HVLTSGIFETKFQVDKVNFHMFDVGG | LLRCHVLTS,CHVLTSGIF,RCHVLTSGIF | PAAD |
| GNB1 | c.239T>C | p.I80T | LAKIYAMHWGTDSRLLVSASQDGKL[p.I80T]TIWDSYTTNKVHAIPLRSSWVMTCAY | LTIWDSYTT,SQDGKLTIW,GKLTIWDSY,TIWDSYTTNK,ASQDGKLTIW | CLL |
| GNG12 | c.202delA | p.T68fs | CEEHARSDPLLIGIPTSENPFKDKK[p.T68fs]LASSYSGIEKQLLASSQQRKL* | KLASSYSGI,ASSYSGIEK,LLASSQQRK,KDKKLASS,KKLASSYSG,KQLLASSQQ,IEKQLLASS,LLASSQQRKL,QLLASSQQRK,LASSYSGIEK,SYSGIEKQLL,FKDKKLASSY,KKLASSYSGI,SSYSGIEKQL,SENPFKDKKL | STAD |
| GNPNAT1 | c.162delT | p.F54fs | AISPTHPGCEGLVLRPLCTADLNRGF[p.F54fs]LRYWVS* | RGFLRYWVS,DLNRGFLRY,TADLNRGFLR,CTADLNRGFL,ADLNRGFLRY | STAD |
| GNPTAB | c.3566G>A | p.R1189Q | VKAVLRDFYESMFPIPSQFELPREY[p.R1189Q]QNRFLHMHELQEWRAYRDKLKFWTHC | EYQNRFLHM,LPREYQNRF,REYQNRFLH,YQNRFLHMH,LPREYQNRFL,REYQNRFLHM,SQFELPREYQ | UCEC |
| GOLGA4 | c.4608G>T | p.Q1536H | KKESNLETELKSQTARIMELEDHIT[p.Q1536H]HKTIEIESLNEVLKNYNQQKDIEHKE | MELEDHITH,HKTIEIESL,LEDHITHKTI | CRC |
| GOLGA5 | c.1474C>A | p.L492I | ELEELRHEKEMQREEIQKLMQIHQ[p.L492I]IRSELQDMEAQQVNEAESAREQLQDL | KLMGQIHQI,KLMGQIHQIR,HQIRSELQDM,QKLMQIHQI,GQIHQIRSEL | KIRC |
| GOT2 | c.1063C>T | p.R355W | ILNTPDLRKQWLQEVKVMADRIIGM[p.R355W]WTQLVSNLKKEGSTHNWQHITDQIGM | RIIGMWTQL,IIGMWTQLV,WTQLVSNLK,MWTQLVSNL,MADRIIGMW,RIIGMWTQLV,GMWTQLVSNL,MWTQLVSNLK,WTQLVSNLKK,VMADRIIGMW | PRAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| GP2 | c.122C>T | p.S41L | LALVSCILTQASAVQRGYGNPIEAS[p.S41L]LYGLDLDCGAPGTPEAHVCFDPCQNY | NPIEASLYG, YGNPIEASLY, NPIEASLYGL, IEASLYGLDL | CRC |
| GPAT CH4 | c.629_630i nsA | p.K210fs | FLARLKGQDPGAPQLQSESKPPKKK[p.K210fs]EKEKEAERGGRSYSI* | EAERGGRSY, KEAERGGRSY, AERGGRSYSI | PRAD |
| GPAT CH4 | c.629del A | p.K210fs | AFLARLKGQDPGAPQLQSESKPPKK[p.K210fs]RKRKGGRKRKRKLQHLKGM QMRSTQNMLSRTSEKARRRKGDIKKER SQMKERVQLKGMRRRTLQEQVGLGN* | MQMRSTQNM, QMRSTQNML, MLSRTSEKA, NMLSRTSEK, QMKERVQLK, RSTQNMLS, RVQLKGMR, KRRKGGRK, KGGRKRRKK, RRKKLQHLK, LSRTSEKAR, RTSEKARRR, KARR RKGDI, RRRKGDIKK, KGMRRRTLQ, GMRRRTLQE, HLKGM MQMR, LKGMRRRTL, KKLQHLKGM, QHLKGMMQM, GM MQMRSTQ, SQMKERVQL, KERVQLKGM, RTLQEQVGL, M QMRSTQNML, MMQMRSTQNM, SQMKERVQLK, RTSEKA RRRK, KKRRKGGRK, KRKGGRKRRK, RRKKLQHLK, QMRS TQNMLS, QNMLSRTSEK, LSRTSEKARR, KARRRKGDIK, RSQ MKERVQL, RVQLKGMRRR, MLSRTSEKAR, QLKGMRRRTL, LQHLKGMMQM, RKRRKKLQHL, RKKLQHLKGM, KKLQHLK GMM, MKERVQLKGM, KERSQMKERV | STAD |
| GPC5 | c.1040G>T | p.R347 L | LVNDAVLQAHLNGQKLLEQVNRICG[p.R347L]LPVRTPTQSPRCSFDQSKEKHG MKTT | EQVNRICGL, QVNRICGLPV, VNRICGLPVR, LEQVNRICGL | LUSC |
| GPC6 | c.640G>A | p.A214 T | CVSKYTDQLKPFGDVPRKLKIQVTR[p.A214T]TFIAARTFVQGLTVGREVANRVS KVS | VTRTFIAAR, RTFIAARTF, KIQVTRTFI, QVTRTFIAA, TFIAART FV, LKIQVTRTF, IQVTRTFIA, RTFIAARTFV, KLKIQVTRTF, KI QVTRTFIA, VTRTFIAART, QVTRTFIAAR, LKIQVTRTFI, IQVT RTFIAA, TRTFIAARTF | CRC |
| GPLD 1 | c.2150G>A | p.R717 Q | TRMYALTSDAQPLLLSTFSGDRRFS[p.R717Q]QFGGVLHLSDLDDDGLDEIIMAA PLR | SQFGGVLHL, SGDRRFSQF, RRFSQFGGV, RRFSQFGGVL, FSG DRRFSQF, RRFSQFGGVL, FSQFGGVLHL, SQFGGVLHLS | CRC |
| GPM6 A | c.149C>T | p.A50V | IPYASLIATILLYAGVALFCGCGHE[p.A50V]VLSGTVNILQTYFEMARTAGDTLDV F | VLSGTVNIL, EVLSGTVNI, ALFCGCGFIEV, EVLSGTVNIL, HEV LSGTVNI | KIRC |
| GPNM B | c.522C>G | p.I174 M | GQSHNHVFPDGKPFPHHPGWRRWNF[p.I174M]MYVFHTLGQYFQKLGRCSV RVSVNTA | FMVYFHTLG, RRWNFMVYF, NEMYVFHTL, GWRRWNFMY, RWNFMVYFH, MVYFHTLGQY, GWRRWNFMYV, RWNFM YVFHT, HPGWRRWNFM, WNFMVYFHTL, WRRWNFMVYF, FMVYFHTLGQ | LUAD |
| GPR1 0 | c.910del C | p.C3fs | MECL[p.C3fs]LFPGISAPGCKIAT* | LLFPGISQP, MECLLFPGI, LLFPGISQPG, MECLLFPGIS | TGCT |
| GPR1 10 | c.1327A>G | p.R443 G | TALPLNPSRKFIDWKGIPVNKSQLK[p.R443G]GGYSYQIKMCPQNTSIPIRGRVLI GS | KGGYSYQIK, SQLKGGYSY, LKGGYSYQI, GGYSYQIKM, QLKG GYSYQI, VNKSQLKGGY, KSQLKGGYSY, SQLKGGYSYQ, KGG YSYQIKM | CLL |
| GPR1 12 | c.3848C>A | p.S128 3Y | KDQMTISLGKPTPRTMEVTEMSPSKN[p.S1283Y]YFISYSRGTPSLEMTDTGFPETT KIS | KNYFISYSR, MSPSKNYFI, PSKNYFISY, EMSPSKNYF, TEMSP SKNY, VTEMSPSKNY, EMSPSKNYFI, SPSKNYFISY, TEMSPSK NYF | UCEC |
| GPR1 23 | c.1889T>C | p.L630 P | PRTPHCVGKKVPQPVGAADLAPDTS[p.L630P]PCRKEGSSASRSCRPGPHLTRR EED | DLAPDTSPCR | CLL |
| GPR1 25 | c.338G>A | p.R113 Q | LSNNKISELKNGSFSGLSLLERLDL[p.R113Q]QNNLISSIDPGAFWGLSSLKRLDLT N | LQNNLISSI, LERLDLQNNL | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| GPR137B | c.718G>T | p.G240C | KISKMSLANIYLESKGSSVCQVTAI[p.G240C]CVTVILLYTSRACVNLFILSFSQNKS | QVTAICVTV,ICVTVILLY,TAICVTVIL,CQVTAICVTVIL,CQVTAICVT,CQVTAIC VTV,AICVTVILLY,SVCQVTAICV,QVTAICVTVI,TAICVTVILL | LUAD |
| GPR156 | c.2262C>A | p.F754L | PVPSGCASLSSQHSYFDTESSSSDE[p.F754L]LFCRCHRPYCEICFQSSSDSDSGTS | SSSDELFCR,LFCRCHRPY,TESSSDEL,SSSSDELFCR,ELFCR CHRPY,TESSSDELF | CRC |
| GPR158 | c.1696G>A | p.D566N | LIGWTSSVCQNLEKQISLIGGQKTS[p.D566N]NHLIFNMCLIDRWDYMTAVAEF LFLL | KTSNHLIFN,TSNHLIFNM,GQGKTSNHL,GKTSNHLIF,KTSN HLIFNM,GQGKTSNHLI,QGKTSNHLIF | CRC |
| GPR158 | c.2284C>A | p.P762T | NPHLQKKRCSKKGLGRSIMRRITEI[p.P762T]TETVSRQCSKEDKEGADHGTAKGT AL | RITEITETV,RRITEITETV | LUAD |
| GPR161 | c.1550del G | p.G517 fs | AEAKINLFGEEALPGVLVTARTVPG[p.G517fs]AASGAAEAAELL* | TARTVPGAA,VTARTVPGA,TVPGAASGA,VPGAASGAA,LV TARTVPGA,RTVPGAASGA,VTARTVPGAA,TVPGAASGAA | STAD |
| GPR21 | c.647G>A | p.R216H | FTLFIVMMLYAPAALIVCFTYFNIF[p.R216H]HICQQHTKDISERQARFSSQSGET GE | FTYFNIFHI,TYFNIFHIC,CFTYFNIFHI,IFHICQQHTK,FTYFNI FHIC | CRC |
| GPR6 | c.106_165del e\|GCGGCG GCGGCGGC CACACAG CAGGGGG GCCGGACA CGGCGAA TGGGGACC CCCTGCT | p.AAAA ATAAG GPDTG EWGPP A36del\| | AAMNASAASLNDSQVVVAAEGAAA[p. AAAATAAGGPDTGEWGPPA36de\| LGAGGGANGSLELSSQLSAGPPGLLLP AVNPMDVLLCVSGTVIAGENALVVALI ASTPALRTPMFVLVGSLATADLLAGCGL ILH | VAAEGAAAL,AEGAAALGA,VVAAEGAAAL,AEGAAALGAG | PAAD |
| GPR98 | c.12424C>T | p.R414 2W | RFTIQLISIDEVEISPVKGSASIII[p. R4142W]WGDKRASGEVGIAPSSRHLIGEPSA SIIIW | ASIIIWGDK,SIIIWGDKR,KGSASIIIW,SASIIIWGDK,VKGSA SIIIW | CRC, UCEC |
| GPR98 | c.12919G>T | p.G430 7W | QRVNITIIRSSGDFGHVRLWYKTMS[p. G4307W]WTAEAGLDFVPAAGELLPEA GEMRKS | WTAEAGLDF,KTMSWTAEA,RLWYKTMSW,WYKTMSWT A,MSWTAEAGL,TMSWTAEAGL,WTAEAGLDFV,RLWYKT MSWT,SWTAEAGLDF,VRLWYKTMSW,LWYKTMSWTA,Y KTMSWTAEA | LUAD |
| GPR98 | c.18455A>T | p.Y615 2F | AYRHFWMLVLFVIFNSLQGLYVFMV[p. Y6152F]FFILHNQMCCPMKASYTVEM NGHGPP | YVFMVFFIL,QGLYVFMVF,LYVFMVFFI,VFFILHNQM,GLYV FMVF,GLYVFMVFFI,LQGLYVFMVF,QGLYVFMVFF,LYVF MVFFIL,MVFFILHNQM | CLL |
| GPRA SP1 | c.2117C>T | p.S706 L | KEPCMYPAGGSWKSRPEEEEDIVN[p. S706L]LWFWSRKYTKPEAIIGSWLWAT EESN | IVNLWFWSR,VNLWFWSRK,NLWFWSRKY,EEEDIVNLW,E EDIVNLWF,EEEEDIVNL,IVNLWFWSRK,LWFWSRKYTK,V NLWFWSRKY,DIVNLWFWSR,EEEDIVNLWF,EEDIVNLWF W | HNSC |
| GPRC 5A | c.88G>A | p.V30I | VPDGCRNGLKSKYYRLCDKAEAWGI[p. V30I]ILETVATAGVVTSVAFMLTLPILVC K | IILETVATA,AWGIILETV,EAWGIILET,KAEAWGIIL,AEAWGI ILE,ILETVATAGV,GIILETVATA,EAWGIILETV,AEAWGIILET | CRC |
| GPRIN 1 | c.693_716d e\|GAAGGA GGATCCTG GGTCTTTG AG | p.231_ 239RKE DPGSL R>R | KEDLGSLGKVDPLCSSKTYTVSPRK[p.23 1_239RKEDPGSLR>R]VDPVSSDKVDP VFPRKEEPRYSGKEHPVSSEKVAPTSAE KVDLVLSGKR | TVSPRKVDPV,KTYTVSPRKV | KIRC |
| GPRIN 2 | c.1337G>A | p.R446 H | APASEDSLSVEGRRGPLRAVMQSLR[p. R446H]HPSCCGCSGAAPE* | MQSLRHPSC | ACC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| GPRIN2 | c.298A>C | p.T100P | ARASGPKARPSAGGHWMSSTVGNVS[p.T100P]PMGGSDLCRLRAPSAAAMQRSHSDLV | STVGNVSPM, SSTVGNVSPM | CESC |
| GPRIN2 | c.721G>A | p.V241M | KAAEQLATTTCHALPPAALLCGMRE[p.V241M]MRAGGCCHALPATGILAFPKLVASVS | ALLCGMREM, LLCGMREMR, REMRAGGCC, AALLCGMREM, REMRAGGCCH, MRAGGCCHAL | ACC |
| GPRIN3 | c.1898delG | p.R633fs | PSDPMGDSSPGSGKKTPSRSVKASP[p.R633fs]PGPAASASSSRSKS* | ASASSSRSK, RSVKASPPG, KASPPGPAA, SPPGPAASA, AASASSSRSK, SVKASPPGPA, VKASPPGPAA | HNSC |
| GPT2 | c.29G>C | p.R10P | MQRAAALVR[p.R10P]PGCGPRTPSSWGRSQSSAAAEASAVL | LVRPGCGPR, RPGCGPRTPS, MQRAAALVRP | TGCT |
| GRAMD2 | c.369C>G | p.I123M | DFLLQGRLYISPNWLCFHASLFGKD[p.I123M]MKVVIPVVSVQMIKKHKMARLLPNGL | SLFGKDMKV, ASLFGKDMK, HASLFGKDM, KDMKVVIPV, SLFGKDMKV, HASLFGKDMK, FHASLFGKDM, KDMKVVIPVV, MKVVIPVVSV | CESC |
| GRAP | c.207G>T | p.E69D | GYVPKNFIDIQPPKWFHEGLSRHQA[p.E69D]DNLLMGKEVGFFIIRASQSSPGDFSI | QADNLLMGK, SRHQADNLL, RHQADNLLM, HQADNLLMG, GLSRHQADNL, HQADNLLMGK, SRHQADNLLM | CRC |
| GRB14 | c.898G>A | p.A300T | RHLQFFSEFGNSDIVVSLAGKKKHG[p.A300T]TPTNYGFCFKPNKAGGPRDLKMLCAE | KKHGTPTNY, HGTPTNYGF, TPTNYGFCF, GTPTNYGFCF, KKHGTPTNY, KHGTPTNYGF | BRCA |
| GRB7 | c.716G>T | p.R239L | ISHEDLIQNFLNAGSFPEIQGFLQL[p.R239L]LGSGRKLWKRFFCFLRRSGLYYSTKG | LGSGRKLWK, EIQGFLQLL, LLGSGRKLW, LLGSGRKLWK, LQLLGSGRKL, QLLGSGRKLW, PEIQGFLQLL | LUAD |
| GREB1 | c.1031C>A | p.S344Y | ESPSAPDGGCPQGGGNRAKYESAGM[p.S344Y]YCVPQVGLVGPASVTFPVVASGEPVS | AGMYCVPQV, MYCVPQVGL, AKYESAGMY, YESAGMYCV, GMYCVPQVG, GMYCVPQVGL, KYESAGMYCV, MYCVPQVGLV, RAKYESAGMY, YESAGMYCVP | KIRC |
| GRHL1 | c.1822G>T | p.G608W | LVNMDDNIVKHYSNEDTFQLQIEEA[p.G608W]WGSYKLTLTEI* | AWGSYKLTL, QIEEAWGSY, FQLQIEEAW, ERAWGSYKL, QIEEAWGSYK, TFQLQIEEAW, LQIEEAWGSY, IEEAWGSYKL, EEAWGSYKLT | LUAD |
| GRIA1 | c.652C>T | p.R218C | EGYRMLFQDLEKKERLVVVDCESE[p.R218C]CLNAILGQIIKLEKNGIGYHYILANL | CLNAILGQI, CESECLNAI, CLNQILGQII, CESECLNAIL | CRC |
| GRIA2 | c.2534G>A | p.R845Q | LVGGLGLAMLVALIEFCYKSRAEAK[p.R845Q]QMKVAKNAQNINPSSSQNSQNFATYK | KSRAEAKQM, AEAKQMKVA, KQMKVAKNA, KSRAEAKQM, K, YKSRAEQKQM, KQMKVAKNAQ | CRC |
| GRID1 | c.1864G>A | p.E622K | PRPSASATLHSAIWIVYGAFVQQGG[p.E622K]KSSVNSMAMRIVMGSWWLFTLIVCSS | GAFVQQGGK, KSSVNSMAM, VQQGGKSSV, GGKSSVNSM, FVQQGKSSV, KSSVNSMAMR, GKSSVNSMAM | DLBCL |
| GRID1 | c.2048G>T | p.R683L | VSRMDNPIRTFQDLSKQVEMSYGTV[p.R683L]LDSAVYEYFRAKGTNPLEQDSTFAEL | VLDSAVYEY, VEMSYGTVL, LDSAVYEYF, VLDSAVYEYF, TVLDSAVYEY, MSYGTVLDSA | LUAD |
| GRID2 | c.1947delG | p.T649fs | YTTLATRMMMGAWWLFALIVISSYT[p.T649fs]QTSLLSSLLHALKVPSSLSRTFPSKQKSLMAQS* | SLLSSLLHAL, LLSSLLHAL, TQTSLLSSL, LSSLLHALK, SLSRTFPSK, SSYTQTSLL, SSLSRTFPS, KQKSLMAQS, QTSLLSSLL, HALK, VPSSL, VPSSLSRTF, FPSKQKSLM, ISSYTQTSL, SLLSSLLHAL, VLSSYTQTSL, YTQTSLLSSL, TQTSLLSSLL, LLSSLLHALK, ALKV, PSSLSR, SSLSRTFPSK, KVPSSLSRTF, LSRTFPSKQK, RTFPSKQKSL, FPSKQKSLMA, ISSYTQTSLL, LHALKVPSSL | HNSC |
| GRIK1 | c.1103G>A | p.R368Q | VSSLQCHRHKPWRLGPRFMNLIKEA[p.R368Q]QWDGLTGHITFNKTNGLRKDFDLDII | AQWDGLTGH, KEAQWDGLT, AQMDGLTGHI, LIKEAQWD, GL, FMNLIKEAQM, KEAQWDGLTG | LUAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| GRIN2B | c.1556G>A | p.R519Q | WNGMIGEVVMKRAYMAVGSLTINEE[p.R519Q]QSEVVDFSVPFIETGISVMVSRSNGT | TINEEQSEV, EEQSEVVDF, LTINEEQSEV, TINEEQSEVV, EQS EVVDFSV, NEEQSEVVDF | OV |
| GRK4 | c.64_65insA | p.K22fs | MELENIVANSLLLKARQGGYGKK[p.K22fs]KWS* | RQGGYGKKK | STAD |
| GRM3 | c.2046C>A | p.F682L | SALLTKTNCIARIFDGVKNGAQRPK[p.F682L]LISPSSQVFICLGLLIVQIVMVSVWL | KLISPSSQV, LISPSSQVF, LISPSSQVFI, KLISPSSQVF, AQRPKL ISPS, VKNGAQRPKL | HNSC |
| GRM3 | c.547C>T | p.R183C | ANLLRLFQIPQISYASTSAKLSDKS[p.R183C]CYDYFARTVPPDFYQAKAMAEILR FF | LSDKSCYDY, KSCYDYFAR, AKLSDKSCY, LSDKSCYDYF, KLSD KSCYDY, SAKLSDKSCY | GBM |
| GRM5 | c.2685_2686insC | p.P895fs | SSGETLRYKDRRLAQHKSEIECFTP[p.P895fs]QREYGEWWESNNEQFQWKIRH VGPE* | WWESNNEQF, EIECFTPQR, SEIECFTPQ, REYGEWWES, EQ FQWKIRH, FQWKIRHVG, TPQREYGEW, ESNNEQFQW, EW WESNNEQF, EQFQWKIRHV, IECFTPQREY, WESNNEQFQ W, FQWKIRHVGP, REYGEWWESN, GEWWESNNEQ, TPQR EYGEWW | LUAD |
| GRM6 | c.1089G>T | p.E363D | GFDQYFMTRSLENNRRNIWFAEFWE[p.E363D]DNFNCKLTSSGTQSDDSTRKCT GEER | WEDNFNCKL, EFWEDNFNCK, AEFWEDNFNC | UCEC |
| GRM6 | c.2152_2153insG | p.A718fs | SPTSQLVITFSLTSLQVVGMIAWLG[p.A718fs]GPAPTQRD* | MIAWLGGPA, GMIAWLGGPA | KIRC |
| GRM7 | c.2036G>A | p.R679Q | VCSFRRVFLGLGMCISYAALLTKTN[p.R679Q]QIYRIFEQGKKSVTAPRLISPTSQL A | ALLTKTNQI, LTKTNQIYR, KTNQIYRIF, LLTKTNQIY, QIYRIFE QGK, LTKTNQIYRI, KTNQIYRIFE, ALLTKTNQIY, LLTKTNQIY R, TKTNQIYRIF | CRC |
| GRM8 | c.2554C>T | p.R852C | SVSLGMLYMPKVYIIIFHPEQNVQK[p.R852C]CKRSFKAVVTAATMQSKLIQKGN DRP | VQKCKRSFK, KCKRSFKAV, CKRSFKAVV, NVQKCKRSFK, VQ KCKRSFKA, KCKRSFKAVV | LIHC |
| GTF2E1 | c.575G>T | p.R192L | AMPKKDARTLLARFNEQIEPIYALL[p.R192L]LETEDVNLAYEILEPETEIPALKQ S | ALLLETEDV, IEPIYALLL, LETEDVNLA, LLLETEDVNL, LETEDV NLAY, EPIYALLLET | LUAD |
| GTF3A | c.918G>T | p.K306N | HAGCGKTFAMKQSLTRHAVVHDPDK[p.K306N]NKMKLKVKKSREKRSLASHLS GYIPP | VVFIDDPDKNK, KNKMKLKVK, AVVHDPDKNK, KNKMKLKVK K | CRC |
| GTF3C1 | c.2299delA | p.S767fs | KEGPSCSGGDSQLSASRSESGRMKK[p.S767fs]VIIKWA* | RMKKVIIKW, SGRMKKVII, RMKKVIIKWA, SGRMKKVIIK | STAD |
| GTF3C4 | c.1685delA | p.E562fs | LIDLVRMKILKDKHIPQFLQEALEK[p.E562fs]RLKAVESPIFGVLSPSS* | AVESPIFGV, ALEKRLKAV, RLKAVESPI, SPIFGVLSF, LKAVESP IF, VESPIFGVL, FLQEALEKRL, KAVESPIFGV, RLKAVESPIF, EA LEKRLKAV, KRLKAVESPI, VESPIFGVLS, QEALEKRLKA | STAD |
| GUCY2C | c.1645G>T | p.G549C | NFTEKQKIELNKLLQIDYYNLTKFY[p.G549C]CTVKLDTMIFGVIEYCERGSLREVL N | NLTKFYCTV, LIKFYCTVK, TKFYCTVKL, FYCTVKLDTM, LITKF YCTVKL, YNLTKFYCTV, CTVKLDTMIF | BRCA |
| GUSB | c.1498T>C | p.C500R | PSRPVTFVSNSNYAADKGAPYVDVI[p.C500R]RLNSYYSWYHDYGHLELIQLQLA TQF | RLNSYYSWY, IRLNSYYSW, VIRLNSYYS, DVIRLNSYY, APYVD VIRL, VDVIRLNSY, YVDVIRLNSY, RLNSYYSWYH, DVIRLNSY YS, VDVIRLNSYY, VIRLNSYYSW, IRLNSYYSWY | KIRC |
| GUSB | c.1501T>G | p.L501V | SRPVTFVSNSNVAADKGAPYVDVIC[p.L501V]VNSYYSWYHDYGHLELIQLAT QFE | CVNSYYSWY, DVICVNSYY, VDVICVNSY, VDVICVNSYY, APYV DVICV, VVDVICVNSY, CVNSYYSWYH, DVICVNSYYS, VDVIC VNSYY, CVNSYYSWY | KIRC |
| GXYLT1 | c.667_668insT | p.L223fs | SQRLFLPLILKEVDSLLIYVDTDILFF[p.L223fs]FTTS* | YVDTDILFF, YVDTDILFFT, LVVDTDILFF | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| H1FO | c.642_643i nsA | p.A214 fs | PGAATEKARKQGGAAKDTRAQSGEA[p.A2W 14fs]KEGAPQARQGHAGTFQCWW AQQEGKGQRQQEQPRRC* | APQARQGHA,ARQGHAGTF,GHAGTFQCW,HAGTFQCWW, EAKEGAPQAR,QARQGHAGTF,GEAKEGAPQA,RQGHA GTFQC | BLCA |
| H2AF V | c.374A>G | p.Q125 R | LIKATIAGGGVIPHIHKSLIGKKGQ[p.Q1 25R]RKTA* | SLIGKKGQR,KSLIGKKGQR | TGCT |
| H2AFV 2 | c.432de lG | p.K144f s | GKSETILSPPPEKRGRKATSGKKGG[p.K 144fs]RNPRLPNHGRPKSPNQRTAIKKE LQIPPLKMGQGMDSPFCLLRALFWDRS CP* | GMDSPFCLL,RLPNHGRPK,LLRALFWDR,SPFCLLRAL,MGQ GMDSPF,KKELQIPPL,KSPNQRTAIK,GMDSPFCLLR,KMGQ GMDSPF,SGKKGGRNPR,GGRNPRLPNH,HGRPKSPNQR,R TAIKKELQI,CLLRALFWDR,RPKSPNQRTA,IPPLKMGQGM, SPFCLLRALF,NQRTAIKKEL,IKKELQIPPL,KELQIPPLKM,GQ GMDSPFCL | STAD |
| H3F3C | c.392G>T | p.R131 L | DTNLCAIHAKRVTIMPKDIQLARRI[p.R 131L]LGERA* | LARRILGER,QLARRILGER,KDIQLARRIL | LUAD |
| HAO1 | c.514C>T | p.R172 C | AEKMGYKAIFVTVDTPYLGNRLDDV[p. R172C]CNRFKLPPQLRMKNFETSTLSFS PEE | RLDDVCNRF,RLDDVCNRFK | CRC |
| HAO2 | c.34C>A | p.H12N | MSLVCLTDFQA[p.H12N]NAREQLSKS TRDFIEGGADDSITRDD | CLTDFQANA,FQANAREQL,QANAREQLSK,CLTDFQANAR | LUAD |
| HARS 2 | c.503G>A | p.R168 H | NKVKKMKRYHVGKVWRESPTIVQG[p. R168H]HYREFCQCDFDIAGQFDPMI PDAECL | IVQGHYREF,PTIVQGHYR,SPTIVQGHY,HYREFCQCDF,TIV QGHYREF,RESPTIVQGH | CRC |
| HAUS 6 | c.1588de lA | p.S530f s | ENSPLSDVAKNTESSAFGGSLPAKK[p.S 530fs]VIHFKKSKIIW* | KVIHFKKSK,PAKKVIHFK,AKKVIHFK,LPAKKVIHF,IHFKKS KII,SLPAKKVIHF,PAKKVIHFK,KVIHFKKSKI,IHFKKSKIIW | STAD |
| HBB | c.126C>A | p.F42L | GKVNDEVGGEALGRLLVVYPWTQR[p. F42L]LFESFGDLSTPDAVMGNPKVKA HGKK | VVYPWTQRL,RLFESFGDL,VYPWTQRLF,WTQRLFESF,RLF ESFGDLS,VVYPWTQRLF,PWTQRLFESF,LVVYPWTQRL,YP WTQRLFES | CRC |
| HBB | c.257T>G | p.F86C | VKAHGKKVLGAFSDGLAHLDNLKGT[p. F86C]CATLSELHCDKLHVDPENFRLLG NVL | NLKGTCATL,KGTCATLSEL | KIRC |
| HCN1 | c.1496G>T | p.G499 V | PLFANADPNFVTAMLSKLRFEVFQP[p. G499V]VDYIIREGAVGKKMYFIQHGVA GVIT | VFQPVDYII,EVFQPVDYI,LRFEVFQPVDYI,FEVFQPV,FEVFQPVDY,KLRFE VFQPV,RPEVFQPVDY,VFQPVDYIIR,EVFQPVDYII,FEVFQP VDYI | LUSC |
| HCN1 | c.1976G>T | p.R659 L | QAIAPINYPQMTTLNSTSSTTTPTS[p.R 659L]LMRTQSPPVYTATSLSHSNLHSPS PS | LMRTQSPPV,TTTPTSLMR,STTTPTSLM,SSTTPTSL,SLMR TQSPPV,STTTPTSLMR,LMRTQSPPVY,SSTTPTSLM | LUSC |
| HCN1 | c.2140G>T | p.A714 S | QPSAILSPCSYTTAVCSPPVQSPLA[p.A7 14S]SRTFHYASPTASQLSLMQQQPQQ QVQ | ASRTFHYAS,PLASRTFHY,LASRTFHYA,VQSPLASRT,PLASR TFHYA,ASRTFHYASP,VQSPLASRTF,SPLASRTFHY | LUSC |
| HCN1 | c.692C>A | p.P231 Q | IILDPKVIKMNYLKSWFVVDFISSI[p.P23 1Q]QVDYIFLIVEKGMDSEVYKTARALRI | FISSIQVDY,QVDYIFLIV,IQVDYIFLI,SSIQVDYIF,VVDFISSIQ V,FISSIQVDYI,SIQVDYIFLI,IQVDYIFLIV,SSIQVDYIFL,ISSIQ VDYIF | LUAD |
| HCN1 | c.976C>A | p.P326 T | LIGMLLLCHWDGCLQFLVPLLQDF[p. P326T]TPDCWVSLNEMVNDSWGKQY SYALFK | FTPDCWVSL,FLVPLLQDFT | LUSC |
| HCN4 | c.1574G>A | p.R525 H | IVGATCYAMFIGHATALIQSLDSSR[p.R 525H]HQYQEKYKQVEQYMSFHKLPPD TRQR | SLDSSRHQY,SSRHQYEBK,RHQYQEKYK,IQSLDSSRH,SRH QYQEKY,QSLDSSRHQY,SSRHQYQEKY,HQYQEKYKQV | CRC |
| HCRT R2 | c.26_27ins C | p.S9fs | MSGTKLEDSPP[p.S9fs]LSQLVICFGAE * | DSPPLSQLV,SPPLSQLVI,TKLEDSPPL,LEDSPPLSQL | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| HCRT R2 | c.26del C | p.S9fs | MSGTKLEDS[p.S9fs]LVATGHLLRS* | LVATGHLLR, SPIVATGHL, LEDSPLVAT, GTKLEDSPLV, SPLV ATGHLL | STAD |
| HCRT R2 | c.298G>T | p.D100 Y | VCVAVWKNHHMRTVTNYFIVNLSLA[p. D100Y]YVLVTITCLPATLVVDITETWFF GQS | FIVNLSLAY, IVNLSLAYV, NLSLAYVLV, SLAYVLVTI, YVLVTIT CL, VNLSLAYVL, FIVNLSLAVV, SLAYVLVTIT, YFIVNLSLAY, AY VLVTITCL, IVNLSLAYVL, LSLAYVLVTI | HNSC |
| HDAC 4 | c.2703del C | p.P901f s | PDEVGTGPGVGFNVNMAFTGGLDPP[p. P901fs]WETLSTWRPSERWSCRSPAS LPRMWCWCHQASMPWRATPPLLGAT TSPPDASGT* | GLDPPWETL, RMWCWCHQA, HQASMPWRA, ASLPRMW CW, RWSCRSPAS, RSPASLPRM, PWRATPPLL, LSTWRPSER, RPSERWSCR, MPWRATPPL, WSCRSPASL, WCWCHQASM, WHQASMPW, FTGGLDPPW, PPWETLSTW, SPASLPRM W, RMWCWCHQAS, SMPWRATPPL, RWSCRSPASL, MWC WCHQASM, CWCHQASMPW, SCRSPASLPR, TLSTWRPSER, MPWRATPPLL, SERWSCRSPA, CRSPASLPRM, HQASMPW RAT, WETLSTWRPS, DPPWETLSTW | STAD |
| HDAC 5 | c.3130G>A | p.A104 4T | CVSALLLSVELQPLDEAVLQQKPNIN[p.A 1044T]TVATLEKVIEIQSKHWSCVQKFA AGL | QQKPNINTV, NTVATLEKV, KPNINTVAT, LQQKPNINTV, NI NTVATLEK, NTVATLEKVI, KPNINTVATL, QQKPNINTVA | CRC |
| HDLB P | c.1507C>T | p.R503 C | SNLIRIEGDPQGVQQAKRELLELAS[p.R 503C]CMENERTKDLIIEQRFHRTIIGQK GE | LASCMENER, RELLELASC, LELASCMEN, ELASCMENER, REL LELASCM | TGCT |
| HDLB P | c.2240del G | p.G747 fs | EKQTKSFTVDIRAKPEYHKFLIGKG[p.G7 47fs]AAKFARCATALEHVSSSLRLRTRTR T* | ALEHVSSSL, HVSSSLRLR, SSSLRLRTR, SLRLRTRTR, LIGKGA AKF, AKFARCATA, KFARCATAL, AAKFARCATA, FLIGKGAAKF, KFLIGKGAAK, KGAAKFARCA, AAKFARCATA, SSLRLRTRTR, VSSSLRLRTR, TALEHVSSSL, SLRLRTRTRT, FARCATALEH, HKFLIGKGAA, A KFARCATAL, LEHVSSSLRL | STAD |
| HEAT R7B2 | c.3325G>A | p.E110 9K | TVVVNLLQKPLPFDRDTKTLMKALA[p. E1109K]KKPASSGKLLQALIDKLETELED DIA | KTLMKALAK, TLMKALAKK, WKALAKKPA, KTLMKALAKK, L AKKPASSGK, AKKPASSGKL | BLCA |
| HECA | c.998_999i nsG | p.R333f s | MAGGHVPRNAHFDYSPAGLAVHRGG[p. R333fs]TLRHPRAVPSAAGPLRTPHS HPQA* | AVHRGGTLR, RGTLRHPR, GTLRHPRAV, RTPHSHPQA, HP RAVPSAA, LAVHRGGTL, GLAVHRGGTL, RGGTLRHPRA, LA VHRGGTLR, HPRAVPSAAG, RAVPSAAGPL, LRHPRAVPSA, S AAGPLRTPH | STAD |
| HECT D2 | c.55C>G | p.P19A | MSEAVRVPSPATPLVVAA[p.P19A]AA PEERKGKESEREKLPPIVSAGAGA | ATPLVVAAA, AAAAPEERK, TPLVVAAAA, VAAAAPEERK, AT PLVVAAAA | ACC |
| HECW 1 | c.547G>T | p.A183 S | ICFKYYHGVSGALRATTPSVTVKNS[p.A 183S]SAPIFKSIGADETVQGQGSRRLISF S | KNSSAPIFK, TVKNSSAPI, SSAPIFKSI, VKNSSAPIF, VTVKNSS API, NSSAPIFKSI, TVKNSSAPIF | LUAD |
| HERC 1 | c.6989G>A | p.R233 0H | PVLAVIGGVDAGLRVGGRCVHKQTG[p. R2330H]HHATLLGVVKEGSTSAKVQW DEAEIT | HKQTGHHAT, KQTGHHATL, HKQTGHHATL, KQTGHHATLL | GBM |
| HERC 2 | c.986C>T | p.S329 F | SQMLSAILLLLQLWDSGAQETDNER[p. S329F]FAQGTSAPLLPLLQRFQSIICRKD AP | FAQGTSAPL, AQETDNERF, ERFAQGTSA, RFAQGTSAPL, GA QETDNERF, NERFAQGTSA, FAQGTSAPLL | CESC |
| HES3 | c.286C>A | p.P96T | SCLPGVSQLLRRGDEVGSGLRCPLV[p.P 96T]TESAAGSTMDSAGLGQEAPALFRP CT | TESAAGSTM, CPLVTESAA, VTESAAGSTM | ACC |
| HEXD C | c.1444A>C | p.T482 P | CRSWRLPCSWLSTRMPWRSGWRKTC[p. T482P]PPACSGCKLCCRTSARCLPPR CHPPA | GWRKTCPPA | KIRC,LUSC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| HGF | c.1400C>A | p.S467Y | NPDDAHGPWCYTGNPLIPWDYCPI[p.S467Y]YRCEGDTTPTIVNLDHPVISCAKTKQ | IPWDYCPIY, LIPWDYCPIY, IPWDYCPIYR | CRC |
| HGF | c.2057T>C | p.M686T | AEKIGSSGPCEGDYGGPLVCEQHKMR[p.M686T]TVLGVIVPGRGCAIPNRPGIFVRVAY | KMRTVLGVI, EQHKMRTVL, HKMRTVLGV, CEQHKMRTV, K MRTVLGVIV, VLGVIVPGR, CEQHKMRTVL, HKMRTVLGVI | LUAD |
| HGF | c.686G>C | p.G229A | PQCSEVECMTCNGESYRGLMDHTES[p.G229A]AKICQRWDHQTPHRHKFLPERYPDKG | GLMDHTESA, LMDHTESAK, LMDHTESAKI, GLMDHTESAK, HTESAKICQR, TESAKICQRW | CESC |
| HHIPL1 | c.2075T>C | p.V692A | APRDGEVRLVRPAGLSSGSGRVEVF[p.V692A]AGGRWGTVCDDSWNISGAAVVCRQLG | VEVFAGGRW, EVFAGGRWGT | ACC |
| HIF3A | c.214G>A | p.A72T | VSAHLDKASIMRLTISYLRMHRLCA[p.A72T]TGEWNQVGAGGEPLDACYLKALEGFV | RMHRLCATG, LRMHRLCAT, HRLCATGEW, YLRMHRLCAT, MHRLCATGEW | CESC |
| HIP1 | c.2819G>T | p.R940L | AQLVAASKVKADKDSPNLAQLQQAS[p.R940L]LGVNQATAGVVASTISGKSQIEETDN | QLQQASLGV, LAQLQQASL, LQQASLGVN, AQLQQASLGV, NLAQLQQASL, QQASLGVNQA | LUAD |
| HIPK4 | c.839G>A | p.R280H | PDAANPWQLKSSADYLAETKVRPLE[p.R280H]HRKYMLKSLDQIETVNGGSVASRLTF | KVRPLEHRK, LEHRKYMLK, RPLEHRKYM, HRKYMLKSL, KVR PLEHRKY, ETKVRPLEHR, RPLEHRKYML, EHRKYMLKSL | CRC |
| HIST1 H1B | c.564G>C | p.K188N | AAAGVKKVAKSPKKAKAAAKPKKAT[p.K188N]NSPAKPKAVKPKAAKPKAAKPKAAKP | ATNSPAKPK, KKATNSPAK, KATNSPAKPK, ATNSPAKPKA, K PKKATNSPA | CESC |
| HIST1 H1C | c.194C>T | p.A65V | VSELITKAVAASKERSGVSLAALKK[p.A65V]VLAAAGYDVEKNNSRIKLGLKSLVSK | ALKKVLAAA, VLAAAGYDV, AALKKVLAA, KKVLAAAGY, KVL AAAGYDV, SLAALKKVLA, LAALKKVLAA, LKKVLAAAGY | DLBCL |
| HIST1 H1D | c.243C>G | p.I81M | SGVSLAALKKALMAGVDVEKNNSR[p.I81M]MKLGLKSLVSKGTLVQTKGTGASGSF | RMKLGLKSL, NSRMKLGLK, MKLGLKSLV, RMKLGLKSLV, YD VEKNNSRM, SRMKLGLKSL | BLCA |
| HIST1 H1E | c.398G>C | p.G133A | NKKAASGEAKPKAKKAGAAKAKKPA[p.G133A]AAAKKPKKATGAATPKKSAKKTPKKA | AAAAKKPKK, AAKAKKPAA, AKKPAAAAK, KAKKPAAAAK, A AKAKKPAAA, AKAKKPAAAA | DLBCL |
| HIST1 H1E | c.74G>C | p.R25P | MSETAPAPAAPAAPAPAPAEKTPVKKKA[p.R25P]PKSAGAAKRKASGPPVSELITKAVA | KTPVKKKAPK, KAPKSAGAAK, KKAPKSAGAA | LUAD |
| HIST1 H2AL | c.89G>C | p.R30P | GKQGGKARAKAKTRSSRAGLQPPVG[p.R30P]PVHRLLRKGNYAERVGAGAPVYLAAV | GLQPPVGPV, FPVGPVHRL, LQPPVGPVH, QPPVGPVHRL, F PVGPVHRLL | CESC |
| HIST1 H2BF | c.229G>A | p.E77K | DTGISSKAMGIMNSFVNDIFERIAG[p.E77K]KASRLAHYNKRSTITSREIQTAVRLL | RIAGKASRL, GKASRLAHY, DIFERIAGK, RIAGKASRLA, KASR LAHYNK, AGKASRLAHY, DIFERIAGKA | HNSC |
| HIST1 H2BJ | c.38A>G | p.K13R | MPEPAKSAPAPK[p.K13R]RGSKKAVTKAQKKDGKKRKRSRKESY | RGSKKAVTK, APAPKRGSK, SAPAPKRGSK, APKRGSKKAV | TGCT |
| HIST1 H3B | c.142G>T | p.A48S | TKAARKSAPATGGVKKPHRYRPGTV[p.A48S]SLREIRRYQKSTELLIRKLPFQRLVR | RYRPGTVSL, SLREIRRYQ, VSLREIRRY, TVSLREIRR, HRYRPG TVS, SLREIRRYQK, GTVSLREIRR, RYRPGTVSLR, TVSLREIRR Y, RPGTVSLREI, HRYRPGTVSL | DLBCL |
| HIST1 H3B | c.220G>A | p.E74K | LREIRRYQKSTELLIRKLPFQRLVR[p.E74K]KIAQDFKTDLRFQSSAVMALQRACEA | LVRKIAQDF, FQRLVRKIA, KLPFQRLVRK, LVRKIAQDFK, LPF QRLVRKI, RLVRKIAQDF | LUSC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| HIST1 H3C | c.110A>T | p.K37 M | TGGKAPRKQLATKAARKSAPATGGV[p. K37M]MKPHRYRPGTVALREIRRYQKS TELL | GVMKPHRYR,VMKPHRYRP,KSAPATGGVM,VMKPHRYRP G | HNSC |
| HIST1 H4C | c.203G>C | p.R68P | GVKRISGLIYEETRGVLKVFLENVI[p.R68 P]PDAVTYTEHAKRKTVTAMDVVYALK R | FLENVIPDA,VIPDAVTYT,NVIPDAVTY,LENVIPDAV,FLENV IPDAV,NVIPDAVTY,IPDAVTYTEH,LENVIPDAVT | HNSC |
| HIST2 H2AC | c.89G>C | p.R30P | GKQGGKARAKAKSRSSRAGLQPPVG[p. R30P]PVHRLLRKGNYAERVGAGAPVY MAAV | GLQPPVGPV,FPVGPVHRL,LQPPVGPVH,QPPVGPVHRL,F PVGPVHRL | CESC |
| HIST2 H2BE | c.161G>A | p.G54D | KRKRSRKESYSIYVYKVLKQVHPDT[p.G 54D]DISSKAMGIMNSFVNDIFERIAGE AS | KQVHPDTDI | LUSC |
| HIVEP 3 | c.1601de lC | p.P534f s | LSSHSEKTKPEQSLLSLQHPPSTAP[p.P5 34fs]LCLS* | LQHPPSTAPL,HPPSTAPLCL | STAD |
| HIVEP 3 | c.1660de lC | p.H554 fs | PSTAPPVPLLRSHSMPSAACTISTP[p.H 554fs]TTPSEVATPSMTISPTPKP* | SMTISPTPK,STPTTPSEV,EVATPSMTI,TPSMTISPT,TPSEV ATPS,SEVATPSMT,PSMTISPTPK,TPSEVATPSM,SEVATPS MTI | STAD |
| HLA-A | c.233A>G | p.Q78R | DDTQFVRFDSDAASQRMEPRAPWIE[p. Q78R]REGPEYWDQETRNVKAQSQTD RVDLG | WIEREGPEY,IEREGPEYW,PWIEREGPEY | BLCA, PRAD |
| HLA-C | c.312C>A | p.N104 K | EGPEYWDRNTQIYKAQAQTDRESLR[p. N104K]KLRGYYNQSEAGSHTLQSMYG CDVGP | QTDRESLRK,SLRKLRGYY,KLRGYYNQS,SLRKLRGYYN,KLR GYYNQSE,RESLRKLRGY,ESLRKLRGYY | CESC |
| HLA-DMA | c.250G>A | p.E84K | LSEAYDEDQLFFDFSQNTRVPRLP[p.E 84K]KFADWAQEQGDAPAILFDKEFCE WMI | RLPKFADWA,NTRVPRLPK,RVPRLPKFA,TRVPRLPKF | CRC |
| HLA-DMA | c.706_707i nsG | p.A236 fs | YTAIAYWVPRNALPSDLLENVLCGV[p. A236fs]GLWPGCAGHHRGHCSHHLLP EALLR* | HLLPEALLR,RGHCSHHLL,SHHLLPEAL,LENVLCGVGL,HHR GHCSHHL,CSHHLLPEAL | LUAD |
| HLA-DPB1 | c.340_341i nsA | p.G114 fs | NSQKDILEEKRAVPDRMCRHNYELG[p. G114fs]EAHDPAAPSPA* | ELGEAHDPA,HNYELGEAH,RHNYELGEAH,YELGEAHDPA | CESC |
| HLA-DQB2 | c.740G>A | p.R247 H | AQSKMLSGIGGFVLGLIFLGLGLII[p.R2 47H]HHRGQKGPRGPPPAGNISAMIQS GER | LIIHHRGQK,GLIIHHRGQK | PRAD |
| HLA-DQB2 | c.748G>A | p.G250 S | KMLSGIGGFVLGLIFLGLGLIIRHR[p.G2 50S]SQKGPRGPPPAGNISAMIQSGERA QA | LIIRHRSQK,RHRSQKGPR,GLIIRHRSQK | PRAD |
| HLCS | c.1084G>A | p.E362 K | LPPSSNIVQTPEDFNLLKSSNFRRY[p.E3 62K]KVLREILTTLGLSCDMKQVPALITPL Y | KSSNFRRYK,RYKVLREIL,SSNFRRYKV,NPRRYKVLR,SNFRR YKVL,RRYKVLREI,KVLREILTTL,KSSNFRRYKV,SSNFRRYKVL, SNFRRYKVLR,RYKVLREILT,FRRYKVLREI,RRYKVLREIL | CRC |
| HLX | c.34T>A | p.S12T | MFAAGLAPFVA[p.S12T]TNFSLWSAAY CSSAGPGGCSFPLDPA | ATNFSLWSA,PFYATNFSL,FYATNFSLW,LAPFYATNF,TNFS LWSAA,GLAPFYATNF,PFYATNFSLW,ATNFSLWSAA,TNFS LWSAAY,YATNFSLWSA,APFYATNFSL | HNSC |
| HLX | c.693C>G | p.N231 K | GRPAGVHLSGLQPSAGQFFASLDPI[p. N231K]KEASAILSPLNSNPRNSVQHQF QDTF | KEASAILSP,DPIKEASAI,QFFASLDPIK,KEASAILSPL,DPIKEA SAIL | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| HMCN1 | c.398C>A | p.S133Y | RELYVQGGDCPEMSIGAIKIALEI[p.S133Y]YLPGSFIYVFTDARSKDYRLTHEVLQ | YLPGSFIYV, IYLPGSFIY, AIKIALEIY, EIYLPGSFI, LEIYLPGSF, IK IALEIYL, YLPGSFIYVF, IYLPGSFIYV, AIKIALEIYL, GAIKIALEIY, EIYLPGSFIY, ALEIYLPGSF, LEIYLPGSFI | UCEC |
| HMG20A | c.744G>C | p.E248D | EEFLNHSKAREAELRQLRKSNMEFE[p.E248D]DRNAALQKHVESMRTAVEKLEVDVIQ | MEPEDRNAA, MEPEDRNAAL | CRC |
| HNF1B | c.1250C>T | p.T417M | GHNLLSPDGKMISVSGGGLPVSTL[p.T417M]MNIHSLSHNPQQSQNLIMTPLSGVM | GLPPVSTLM, STLMNIHSL, LMNIHSLSH, MNIHSLSHH, PPVS TLMNI, LMNIHSLSH, LMNIHSLSHH, GGLPPVSTLM, LPPVS TLMNI | GBM |
| HNF1B | c.906C>G | p.N302K | GVSPSKAHGLGSNLVTEVRVYNWFA[p.N302K]KRRKEEAFRQKLAMDAYSSNQTHSLN | RVYNWFAKR, VYNWFAKRR, FAKRREEA, AKRRKEEAF, RV YNWFAKRR, EVRVYNWFAK, WFAKRRKEEA, FAKRRKEEAF | KIRC |
| HOOK1 | c.1083de\|A | p.L361fs | QVKTLQEFTNMMYMHNTVSLEEELKK[p.L361fs]QMQHVHN* | LEEELKKQM, LKKQMQHVH, EELKKQMQHV | STAD |
| HOXA5 | c.31G>T | p.G11C | MSSYFVNSFC[p.G11C]CRYPNGPDYQLHNYGDHSSVSEQFRD | FVNSFCCRY, CRYPNGPDY, YFVNSFCCR, YPNGPDYQ, SYFVNSFCCR | LUAD |
| HOXD10 | c.452A>G | p.Y151C | AEVPSYQRLVPESCPVENPEVPVPG[p.Y151C]CFRLSQTYATGKTQEYNNSPEGSSTV | CFRLSQTYA, EVPVPGCFR, VPVPGCFRL, GCFRLSQTY, EVPV PGCFRL, NPEVPVPGCF | HNSC |
| HOXD8 | c.201G>C | p.Q67H | GRHAAAAALQLYGNSAAGFPHAPP[p.Q67H]HAHAHPHPSPPPSGTGCGGREGRGQE | FPHAPPHAH, AGFPHAPPH, AGFPHAPPHA, FPHAPPHAHA | KIRP |
| HOXD8 | c.364de\|C | p.P122fs | GSPAAAYQAAPPPPHPPPPPPPP[p.P122fs]RAAGLPVTGSPRSFTDTITYRDSRFLRPSKRPSWYNILTVNRPVVILARTQTT* | FTDTITYRD, RSFTDTITY, KRPSWYNIL, ITYRDSRFL, TYRDSR FLR, DSRFLRPSK, SFTDTITYR, DTITYRDSR, WYNILTVNR, NIL TVNRPV, TVNRPVVIL, SPRSFTDTI, RPSKRPSWY, SKRPSWY NI, RSFTDTITYR, ITYRDSRFLR, RDSRFLRPSK, RFLRPSKRPS, VNRPVVILAR, DSRFLRPSKR, SWYNILTVNR, TVNRPVVILA, L PVTGSPRSF, SPRSFTDTIT, RPSWYNILTV, FLRPSKRPSW, SK RPSWYNIL, YNILTVNRPV | STAD |
| HPD | c.852_853de\|AG | p.R284fs | GGAGVQHIALKTEDIITAIRHLRER[p.R284fs]PGVLICSLHVLSLHVLQTTAGEAEDGDQGEGEH* | GVLICSLHV, VLICSLHVL, SLHVLQTTA, VLQTTAGEA, HLRER PGVL, RPGVLICSL, RERRPGVLIC, HLRERPGVLI, RHLRERPGVL, RERRPGVLICS | UCEC |
| HPS3 | c.1403C>T | p.S468L | NHIILLTKAEPEAIPERRQSPKRLL[p.S468L]LRKDTSVKIKIPPVAEAGWNLYIVNT | LLLRKDTSV, LLLRKDTSVK, RQSPKRLLL, RLLLRKDTSV, LLRKD TSVKI, LLLRKDTSVK, RQSPKRLLLR, QSPKRLLLRK, RRSQPKR LLL | CRC |
| HPS3 | c.2436G>C | p.K812N | VACLPDVVLQELFFKLTSQYIWRLS[p.K812N]NRQPPDTTPLRTSEDLINACSHYGLI | QYIWRLSNR, SQYIWRLSN, SQYIWRLSNR, NRQPPDTTPL | HNSC |
| HPSE2 | c.174G>T | p.K58N | LHLSLSSQAGDRRPLPVDRAAGLKE[p.K58N]NTLILLDVSTKNPVRTVNENFLSLQL | GLKENTLIL, LKENTLILL, GLKENTLILL, RAAGLKENTL, KENTLI LLDV | CRC |
| HRAS | c.181C>A | p.Q61K | IEDSYRKQVVIDGETCLLDILDTAG[p.Q61K]KEEYSAMRDQYMRTGEGFLCVFAINN | LDTAGKEEY, AGKEEYSAM, ILDTAGKEEY, DTAGKEEYSA | THCA |
| HRAS | c.182A>G | p.Q61R | IEDSYRKQWIDGETCLLDILDTAG[p.Q61R]REEYSAMRDQYMRTGEGFLCVFAINN | LDTAGREEY, AGREEYSAM, ILDTAGREEY, AGREEYSAMR, D TAGREEYSA | THCA |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| HRAS | c.34G>A | p.G12S | MTEYKLVVVGA[p.G12S]SGVGKSALTIQLIQNHFVDEYDPTIE | LVVVGASGV, KLVVVGASGV, YKLVVVGASG | HNSC |
| HRAS | c.35G>A | p.G12D | MTEYKLVVVGA[p.G12D]DGVGKSALTIQLIQNHFVDEYDPTIE | LVVVGADGV, VVGADGVGK, KLVVVGADGV, VVVGADGVGK | BLCA, HNSC |
| HRAS | c.35G>C | p.G12A | MTEYKLVVVGA[p.G12A]AGVGKSALTIQLIQNHFVDEYDPTIE | LVVVGAAGV, VVGAAGVGK, YKLVVVGAAG, KLVVVGAAGV, VVVGAAGVGK, GAAGVGKSAL | HNSC |
| HRAS | c.38G>T | p.G13V | MTEYKLVVVGAG[p.G13V]VVGKSALTIQLIQNHFVDEYDPTIED | KLVVVGAGV, VVVGAGVGK, KLVVVGAGVV, VVVGAGVVG, K, YKLVVVGAGV | HNSC |
| HRC | c.1317_1318insC | p.P439fs | PHHHHRVPREEDEEVSAELGHQAP[p.P439fs]QPQAKPPR* | HQAPQPQAK, AELGHQAPQ | KIRC |
| HRCT1 | c.275A>C | p.H92P | LGIFHHHRPGHVSHVPNVGLHHHH[p.H92P]PPRHTPHHLHHHHPRHHPR | GLHHHPPR, PPRHTPHHL, VGLHHHPPR, HPPRHTPHHL, HHHPPRHTPH | BLCA |
| HRNR | c.1de|A | p.M1fs | [p.M1fs]CLNSYKASSLSSMFSTNMPPSMGSMIR* | NMPPSMGSM, SYKASSLSS, KASSLSSMF, MPPSMGSMI, LN SYKASSL, YKASSLSSM, LSSMFSTNM, FSTNMPPSM, SMFST NMPP, SLSSMFSTNM, CLNSYKASSL, SMFSTNMPPS, NMP PSMGSMI, SYKASSLSSM, KASSLSSMFS, YKASSLSSMF, MFS TNMPPSM, NMPPSMGSM | OV |
| HRNR | c.7615G>A | p.G2539S | QHGSGSSQSSGYGRQSGSGSQSPGH[p.G2539S]SQRGSSGRQSPSYGRHGSGSGRSSSS | HSQRGSGSR | CESC |
| HRSP12 | c.359G>A | p.R120Q | IYKQYFKSNFPARAAYQVAALPKGS[p.R120Q]QIEIEAVAIQGPLTTASL* | SQIEIEAVA, LPKGSQIEI, AALPKGSQI, SQIEIEAVAI, ALPKGSQIEI | CRC |
| HS3ST1 | c.859G>A | p.E287K | RDRCLHESKGRAHPQVDPKLLNKLH[p.E287K]KYFHEPNKKFFELVGRTFDWH* | KLLNKLHKY, HKYFHEPNK, LLNKLHKYF, KLLNKLHKYF, KYFH EPNKKF, LHKYFHEPNK | CRC |
| HS3ST3A1 | c.1195G>T | p.G399W | EIDREVVRRLREFYRPFNLKFYQMT[p.G399W]WHDFGWDG* | FYQMTWFIDF, NLKFYQMTW, LKFYQMTWFI, YQMTWFIDF G, QMTWHDFGW, FNLKFYQMT, KFYQMTWHDF, YQMT WHDFGW | LUAD |
| HSD17B1 | c.937G>A | p.G313S | VPAKARAGAEAGGGAGPGAEDEAGR[p.G313S]SAVGDPELGDPPAPQ* | AEDEAGRSA, RSAVGDPEL, AEDEAGRSAV, GRSAVGDPEL | ACC |
| HSD17B6 | c.627C>G | p.F209L | EAFSDILRREIQHFGVKISIVEPGY[p.F209L]LRTGMTNMTQSLERMKQSWKEAPKHI | YLRTGMTNM, SIVEPGYLR, YLRTGMTNMT, ISIVEPGYLR, G YLRTGMTNM, VEPGYLRTGM | LUAD |
| HSF4 | c.505C>T | p.R169W | QALRGVQESTEARLRELRQQNEILW[p.R169W]WEVVTLRQSHGQQHRVIGKLIQCLFG | ILWWEVVTL, RQQNEILWW, LWWEVVTLR, NEILWWEVV, WEVVTLRQS, QQNEILWWEV, ILWWEVVTLR, EILWWEVV TL, WEVVTLRQSH, NEILWWEVVT | TGCT |
| HSPA13 | c.253G>T | p.V85L | DENGHISIPSMVSFTDNDVYVGYES[p.V85L]LELADSNPQNTIYDAKRFGIKIFTAE | DVVVGYESL, YVGYESLELA, VVVGYESLEL | LUAD |
| HSPA4L | c.1447C>T | p.R483C | RIGSFFIQNVFPQSDGDSSKVKVKV[p.R483C]CVNIHGIFSVASASVIEKQNLEGDHS | KVKVKVCVN, KVKVCVNIH, VCVNIHGIF, CVNIHGIFSV, SSK VKVKVCV, KVKVKVCVNI, KVKVCVNIHG, VKVCVNIHGI, KV CVNIHGIF | UCEC |
| HSPBAP1 | c.845G>T | p.R282L | HYVESIDPVTVSINSWIELEEDHLA[p.R282L]LVEEAITRMLVCALKTAENPQNTRAW | HLALVEEAI, LEEDHLAIV, ALVEEAITRM, IELEEDHLQL | LUAD |
| HTR2A | c.656C>T | p.S219L | LKIIAWTISVGISMPIPVFGLQDD[p.S219L]LKVFKEGSCLLADDNFVLIGSFVSFF | LQDDLKVFK, GLQDDLKVF, PVFGLQDDLK, GLQDDLKVFK, I PVFGLQDDL, FGLQDDLKVF, LKVFKEGSCL | UCEC |
| HTR3B | c.706C>T | p.R236C | SVSSTYSILQSSAGGFAAIQFNVVM[p.R236C]CRHPLVYVVSLLIPSIFLMLVDLGS | VVMCRHPLV, IQFNVVMCR, VMCRHPLVV, MCRHPLVYV, N VVMCRHPL, VMCRHPLVVV, VMCRHPLVY, QIQFNVVMC | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| HTR5A | c.454C>T | p.R152C | ASIWNVTAIALDRYWSITRHMEYTL[p.R152C]CTRKCVSNVMIALTWALSAVIS LAPL | R,NVVMCRHPLV,AQIQFNVVMC,IQFNVVMCRH,FNVVM CRHPL CTRKCVSNV,HMEYTLCTR,YTLCTRKCV,RHMEYTLCT,HME YTLCTRK,CTRKCVSNVM,MEYTLCTRKC | CRC |
| HTR5A | c.894G>T | p.W298C | DTWREQKEQRAALMVGILIGVFVLC[p.W298C]CIPFFLTELISPLCSCDIPAIWKSI F | VLCCIPFFL,CIPFFLTEL,VFVLCCIPF,FVLCCIPFF,FVLCCIPFF L,CIPFFLTELI,VFVLCCIPFF,GVFVLCCIPF | LUAD |
| HTRA3 | c.1208A>G | p.Q403R | DFPEVSSGIVVQEVAPNSPSCQRGGI[p.Q403R]RDGDIIVKVNGRPLVDSSELQEA VLT | GIRDGDIIVK | GBM |
| HYAL4 | c.664G>A | p.D222N | AFMKETIKLGIKSRPKGLWGYYLYP[p.D222N]NCHNYNVYAPNYSGSCPEDEVL RNNE | YLYPNCHNY,YPNCHNYNV,GLWGYYLYPN,YLYPNCHNYN, YYLYPNCHNY,LYPNCHNYNV,YPNCHNYNV | TGCT |
| HYDIN | c.1352G>A | p.R451Q | NPLEAKLYQQTIYCDILGREIRLPL[p.R451Q]QIKGEGMGPKIHFNFELLDIGKVFT G | EIRLPLQIK,REIRLPLQI,QIKGEGMGPK,LPLQIKGEGM | CRC |
| HYDIN | c.2816G>A | p.R939Q | PELNLGAHFSLDTHYFHFKLLINKGR[p.R939Q]QIQQLFWMNDSFRPQAKLSKKG RVKK | RQIQQLFWM,KLINKGRQI,KGRQIQQLF,KGRQIQQLFW,F KLINKGRQI,NKGRQIQQLF,RQIQQLFWMN | CRC |
| HYDIN | c.3559C>T | p.R1187C | VHYPNLSFETKELDFGCILNDTELI[p.R1187C]YVTITNCSPLVVKFRWFFLVNDE EN | LNDTELICY,TELICYVTI,ILNDTELICY,DTELICYVTI,TELI CYVTIT | CRC |
| HYOU1 | c.472C>T | p.R158C | TVHFQISSQLQFSPEEVLGMVLNYS[p.R158C]CSLAEDFAEQPIKDAVITVPVFFN QA | MVLNYSCSL,VLNYSCSLA,YSCSLAEDF,GMVLNYSCSL,MVL NYSCSLA,NYSCSLAEDF | CRC |
| IARS2 | c.2494C>T | p.R832C | YCEKENDPKRRSCQTALVEILDVIV[p.R832C]CSFAPILPHLAEEVFQHIPYIKEPKS | VIVCSFAPI,CSFAPILPH,ILDVIVCSF,ILDVIVCSFA,VIVCSFA PIL,DVIVCSFAPI,EIlDVIVCSF,CSFAPILPHL | SKCM |
| IBA57 | c.390C>A | p.S130R | RTLYDVILYGLQEHSEVSGFLLECD[p.S130R]RSVQGALQKHLALYRIRRKVTVEP HP | FLLECDRSV,RSVQGALQK,LECDRSVQGA | ACC |
| IBTK | c.3638de1A | p.K1213fs | PVNAWASSLHSVSSKSFRDFLLEEK[p.K1213fs]SLLLAIVQAIMSKKFLLKELKILR HQKLSDALPMVPQDQKATIFQIYHF* | FLLEEKSLL,LLEEKSLLL,SLLLAIVQA,LLLAIVQAI,AIMSKKFLL, FLLKELKIL,KLSDALPMV,LLAIVQAIM,AIVQAIMSK,IVQAI MSKK,IMSKKFLLK,KFLLKELKI,ATIFQIYHF,ELKILRHQK,LLK ELKILR,VPQDQKATI,VQAIMSKKF,SKKFLLKEL,LKILRHQKL, RHQKLSDAL,QKLSDALPM,QKATIFQIY,EEKSLLLAI,LEEKS LLLA,FLLEEKSLLL,SLLLAIVQAI,LLLAIVQAIM,LLEEKSLLLA, AIVQAIMSKK,AIMSKKFLLK,LAIVQAIMSK,IVQAIMSKKF,K ATIFQIYHF,KSLLLAIVQA,MSKKFLLKEL,DQKATIFQIY,VPQ DQKATIF,ELKILRHQKL,HQKLSDALPM,RDFLLEEKSL,LEEK SLLLAI,VQAIMSKKFL,KKFLLKELKI,LRHQKLSDAL,EEKSLLL AIV,LPMVPQDQKA | STAD |
| IDE | c.110de1A | p.K37fs | ALPSTPRSVLGARLPPPERLCGFQK[p.K37fs]RLTAK* | GFQKRLTQK,CGFQKRLTQK | STAD |
| IDH1 | c.394C>G | p.R132G | VFREAIICKNIPRLVSGWVKPIIIG[p.R132G]GHAYGDQYRATDFWPGPGKVEIT YT | PIIIGGFIAY,GGHAYGDQY,KPIIIGGHAY,IGGHAYGDQY | GBM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| IDH1 | c.394C>T | p.R132C | VFREAIICKNIPRLVSGWVKPIIIG[p.R13 2C]CHAYGDYRATDFVVPGPGKVEITY T | PIIIGCHAY, GCHAYGDQY, KPIIIGCHAY, IGCHAYGDQY | LAML,LIHC, MM,SKCM |
| IDH1 | c.395G>A | p.R132H | VFREAIICKNIPRLVSGWVKPIIIG[p.R13 2H]HHAYGDYRATDFVVPGPGKVEIT YT | PIIIGHHAY, GHHAYGDQY, KPIIIGHHAY, IGHHAYGDQY | GBM,LAML, PRAD |
| IDH2 | c.419G>A | p.R140Q | TITPDEARVEEFKLKMWKSPNGTI[p.R 140Q]QNILGGTVFREPIICKNIPRLVPG WT | IQNILGGTV, QNILGGTVF, SPNGTIQNI, TIQNILGGTV, SPNG TIQNIL, IQNILGGTV | LAML |
| IDH2 | c.515G>A | p.R172K | VFREPIICKNIPRLVPGWTKPITIG[p.R17 2K]KHAHGDYKATDFVADRAGTFKM VFT | WTKPITIGK, KHAHGDQYK, GKHAHGDQY, IGKHAHGDQY | LAML |
| IDUA | c.1120A>C | p.T374P | DNAFLSYHPHPPAQR TLTARFQVNN[p. T374P]PRPPHVQLLRKPVLTAMGLLAL LDEE | NPRPPHVQL, FQVNNPRPP, TARFQVNNPR, QVNNPRPPH V, NPRPPHVQLL, FQVNNPRPPH | ACC |
| IDUA | c.99T>G | p.H33Q | AALLALLASLLAAPPVAPAEAPHLV[p. H 33Q]QVDAARALWPLRRFWRSTGFCPP LPH | HLVQVDAAR, VQVDAARAL, AEAPHLVQV, HLVQVDAARA, APHLVQVDAA, VQVDAARALW | KIRP |
| IER5 | c.580C>G | p.R194G | SRAARRPCGCPLGGEDPPGTPAATP[p. R194G]GAACCCAPQPAEDEPPAPPAV CPRKR | TPAATPGAA, TPAATPGAAC | KIRP |
| IFNA10 | c.236T>C | p.V79A | KDRHDFPRIPQEEFDGNPQFQKAQAIS[p. V79A]ALHEMIQQTFNLFSTEDSSAAW EQSL | ALHEMIQQT, AISALHEMI, KAQAISALH, QAISALHEM, QKA QAISAL, FQKAQAISAL, QAISALHEMI, AQAISALHEM, ALHE MIQQTF | GBM, LUSC |
| IFNA10 | c.238C>T | p.L80F | DRHDFPRIPQEEFDGNQFQKAQAISV[p. L80F]FHEMIQQTFNLFSTEDSSAAWEQ SLL | KAQAISVFH, QAISVFHEM, QKAQAISVF, AQAISVFHEM, VF HEMIQQTF, QAISVFHEMI, FQKAQAISVF | GBM |
| IFT140 | c.1990G>A | p.E664K | VDEGLKNYVPVNHFWDQSEPRLFVC[p. E664K]KAVQETPRSQPQSANGQPQD GRAGPA | QSEPRLFVCK, EPRLFVCKAV, SEPRLFVCKA | HNSC |
| IFT172 | c.2509G>A | p.A837T | YERAGDLFEKIHNPQKALECYRKGN[p. A837T]TFMKAVELARLAFPVEVKLEE AWGD | CYRKGNTFM, KGNTFMKAV, NTFMKAVEL, CYRKGNTFMK, TFMKAVELAR, NTFMKAVELA, LECYRKGNTF, RKGNTFMK AV | STAD |
| IFT172 | c.2831C>T | p.A944V | AQHYASLQEYEIAEELYTKGDRTKD[p.A 944V]VIDMYTQAGRWEQAHKLAMKC MRPED | RTKDVIDMY, DVIDMYTQA, RTKDVIDMYT | CRC |
| IGF2BP2 | c.556A>T | p.T186S | SSPSPPQRAQRGDHSSREQHAPGG[p. T186S]SSQARQIDFPLRILVPTQFVGAII GK | SSQARQIDF, GSSQARQIDF | CLL |
| IGF2R | c.3942_3943insG | p.T1314fs | HKVAGLLTQKLTYENGLLKMNFTGG[p. T1314fs]GHLP* | KMNFTGGGH, MNFTGGGHL, KMNFTGGGHL, LKMNFTGG GH | STAD |
| IGHMBP2 | c.1843C>A | p.R615S | FLAEDRRINVAVTRARRHVAVICDS[p.R 615S]STVNNHAFLKTLVEYFTQHGEVR TAF | AVICDSSTV, STVNNHAFL, SSTVNNHAF, STVNNHAFLK, DSS TVNNHAF | LUAD |
| IGJ | c.230G>A | p.R77Q | KCARITSRIIRSSEDPNEDIVERNI[p.R77 Q]QIIVPLNNRENISDPTSPLRTRFVYH | QIIVPLNNR, DIVERNIQI, VERNIQIIV, RNIQIIVPL | CRC |
| IK | c.268_269dele|GA | p.E90fs | DPAARRKKKSYYAKLRQQEIERER[p.E 90fs]ASREVPGSCQGTERMSEQRL* | EIERERASR, REVPGSCQG, TERMSEQRL, RQQEIERERA, IER ERASREV, REVPGSCQGT | UCEC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| IKZF3 | c.485T>G | p.L162R | KRSHTGERPFQCNQCGASFTQKGNL[p. L162R]RRHIKLHTGEKPFKCHL CNYAC QRRD | KGNLRRHIK, SFTQKGNLR, FTQKGNLRR, ASFTQKGNLR, KG NLRRHIKL, SFTQKGNLRR, NLRRHIKLHT, TQKGNLRRHI | CLL |
| IL17B | c.100C>T | p.R34W | FLLTISIFLGLGQPRSPKSKRKGQG[p.R3 4W]WPGPLAPGPHQVPLDLVSRMKPY ARM | GQGWPGPLA, RKGQGWPGPL, WPGPLAPGPH | BRCA |
| IL17RA | c.2409_241 0insC | p.Q803fs | PYEEEQRQSVQSDQGYISRSSPQPP[p. Q803fs]RGTHGNGGRGRGAGPREA GPATLSRGPGEPEEPPAAAAFPPAAEEL GLGHDGVRVRGAQCMRAAPQGPPRS | GLGHDGVRV, RAAPQGPPR, RGRGAGPR, RVRGAQCMR, GPREAGPAT, VRVRGAQCM, EEPPAAAAF, REAGPATLS, ISR SSPQPPR, GVRVRGAQCM, RVRGAQCMRA, GPREAGPATL, APQGPPRSQL, AAFPPAAEEL, EELGLGHDGV | CRC |
| IL17RA | c.1091_109 2insG | p.L364fs | KEASSTPSWGIVLAPLSLAFLVLGG[p.L3 64fs]NMDAQTVQTQNWKSRWSDCA MASSSRLSILSQVK* | RLSILSQVK, QTVQTQNWK, KSRWSDCAM, MASSSRLSI, AQ TVQTQNW, CAMASSSRL, ASSSRLSIL, SRLSILSQV, FLVLGG NMDA, AMASSSRLSI, KSRWSDCAMA, SSRLSILSQV, TVQT QNWKSR, MASSSRLSIL, LAFLVLGGNM, VQTQNWKSRW, WKSRWSDCAM, DAQTVQTQNW | CLL |
| IL1R2 | c.149T>G | p.F50C | DDWGLDTMRAIQVFEDEPARIKCPL[p. F50C]CEHFLKFNYSTAHSAGLTLTIWYW TRQ | RIKCPLCEH, IKCPLCEHF, CEHFLKFNY, RIKCPLCEHF, CPLCE HFLKF, CEHFLKFNYS | KIRC |
| IL1RAPL2 | c.1940C>T | p.T647M | KHEIPATTLPVPSLGNHHTYCNLPL[p.T 647M]MLLNGQLPLNNTLKDTQEFHRN SSLL | MLLNGQLPL, YCNLPLML, HTYCNLPLM, LMLLNGQLPL, H TYCNLPLML, TYCNLPLML, LPLMLLNGQL, HHTYCNLPLM | CRC |
| IL2 | c.308G>T | p.R103M | CLEEELKPLEEVLNLAQSKNFHLRP[p.R1 03M]MDLISNINVIVLELKGSETTMCEY A | RPMDLISNI, NFHLRPMDL, SKNFHLRPM, QSKNFHLRPM, K NFHLRPMDL, MDLISNINVI | LUAD |
| IL25 | c.502_503d el|TG | p.C168fs | HGEKGTHKGYCLERRLYRVSLACVC[p.C 168fs]AAPCDGLAGPAGGWSLFGKPG ARCTTTCHEGPGCPDAWPL* | AGGWSLFGK, SLFGKPGAR, GPAGGWSLF, HEGPGCPDA, SL ACVCAAPC, RVSLACVCAA, WSLFGKPGAR, GPGCPDAWPL, LAGPAGGWSL, HEGPGCPDAW | KIRP |
| IL3 | c.268G>A | p.A90T | DILMENNLRRPNLEAFNRAVKSLQN[p. A90T]TSAIESILKNLLPCLPLATAAPTRH P | TSAIESILK, KSLQNTSAI, NTSAIESIL, LQNTSAIESI, NTSAI ESILK, AVKSLQNTSA, VKSLQNTSAI | CRC |
| IL32 | c.643C>A | p.P215T | LWKQFQSFCCSLSELFMSSFQSYGA[p. P215T]TRGDKEELTPQKCCSEPQSSK* | SYGATRGDK, SFQSYGATR, SSFQSYGAT, FQSYGATRG, SSF QSYGATR, QSYGATRGDK | LUAD |
| IL32 | c.653_654i nsG | p.D218fs | QFQSFCCSLSELFMSSFQSYGAPRG[p.D 218fs]EQGGADTPEVL* | APRGEQGGA | SKCM |
| IL5RA | c.139C>A | p.L47I | LLPDEKISLLPPVNFTIKVTGLAQV[p.L47 I]ILQWKPNPDQEQRNVNLEYQVKINA P | GLAQVILQW, GLAQVILQWK, IKVTGLAQVI, TGLAQVILQW | CRC |
| IL6ST | c.647C>A | p.P216H | FVNIEVWVEAENALGKVTSDHINFD[p. P216H]HVYVKPNPPHNLSVINSEELSS ILK | TSDHINFDH, HINFDHVYK, DHINFDHVY, TSDHINFDHV, HI NFDHVYKV, SDHINFDHVY | MM |
| IL7R | c.161C>T | p.S54L | DLEDAELDDYSFSCYSQLEVNGSQH[p.S 54L]LLTCAFEDPDVNITNLEFEICGALVE NGSQHLL | EVNGSQHLL, SQHLLTCAF, LEVNGSQHL, GSQHLLTCAF, LEV NGSQHLL | LUSC |
| ILF3 | c.1450G>A | p.E484K | VKVLQDMGLPTGAEGRDSSKGEDSA[p. E484K]KETEAKPAVVAPAPVVEAVSTP SAAF | SSKGEDSAK, KETEAKPAV, KETEAKPAVV, GEDSAKETEA | BLCA |
| INADL | c.4018C>G | p.P1340A | KLVFIRNEDAVNQMAVTPFPVPSSS[p. P1340A]ASSIEDQSGTEPISSEEDGSVE VGIK | FPVPSSSAS, VPSSSASSI, TPFPVPSSSA, FPVPVPSSSASS | LUSC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| INF2 | c.1581del C | p.S527fs | PLLPGMGWGPPPPPPLLPCTCSPP[p. S527fs]WREAWRRSSWPRWTMAWA QHGSPAIGG* | SWPRWTMAW, AWRRSSWPR, RSSWPRWTM, SSWPRWT MA, WPRWTMAWA, WAQHGSPAI, REAWRRSSW, WRRSS WPRW, AWAQHGSPA, AQHGSPAIG, LPCTCSPPW, AWRRS SWPRW, SSWPRWTMAW, RSSWPRWTMA, MAWAQHGS PA, CSSPWREAWR, EAWRRSSWPR, WTMAWAQHGS, WP RWTMAWAQ, LLPCTCSPPW, WREAWRRSSW, RRSSWPR WTM, AWAQHGSPAI | STAD |
| ING1 | c.658G>T | p.A220 S | DECYERFSRETDGAQKRRMLHCVQR[p. A220S]SLIRSQELGDEKIQIVSQMVELV ENR | MLHCVQRSL, RSLIRSQEL, RMLHCVQRS, RMLHCVQRSL, M LHCVQRSLI, RSLIRSQELG | LUAD |
| INMT | c.167G>T | p.G56V | PSPEAEMLKFNLECLHKTFGPGGLQ[p. G56V]VDTLIDIGSGPTIYQVLAACDSFQ DI | LQVDTLIDI, GLQVDTLIDI, KTFGPGGLQV | LUAD |
| INMT | c.635C>T | p.S212 F | LKPGGHLIVTTVTLRLPSYMVGKREF[p.S 212F]FCVALEKEEVQAVLDAGFDIEQL LH | EFFCVALEK, YMVGKREFF, GKREFFCVA, KREFFCVAL, REFF CVAL, MVGKREFFC, MVGKREFFCV, SYMVGKREFF, GKR EFFCVAL, REFFCVALEK | SKCM |
| INPP5 D | c.1568G>A | p.R523 Q | SFMFNGTSLGFVNSHLTSGSEKKLR[p.R 523Q]QNQNYMNILRFLALGDKKLSPF NITH | RQNQNYMNI, KLRQNQNYM, KKLRQNQNY, KLRQNQNYM N, RQNQNYMNIL, KKLRQNQNYM | CRC |
| INPP5 K | c.787C>T | p.R263 C | EGRLLFPPTYKFDRNSNDYDTSEKK[p.R 263C]CKPAWTDRILWRLKRQPCAGPD TPIP | KCKPAWTDR, SEKKCKPAW | CRC |
| INPPL 1 | c.1478C>T | p.T493 M | VFGTQENSVGDREWLDLLRGGLKEL[p. T493M]MDLDYRPIAMQSLWNIKVAVL VKPEH | LMDLDYRPI, LKELMLDLY, ELMDLDYRPI, GLKELMLDLY, LL RGGLKELM, MDLDYRPIAM | HNSC |
| INPPL 1 | c.2921del C | p.A974 fs | APREEPLTPRLKPEGAPEPEGVAAP[p.A 974fs]HPRTASITLPTTSLKGSRTSCCPRS HPRLPGPLSHLHPPRTKWPLQCLLHSLGT TGTLVWERGVLQMRSLEAHCPLQTFHL HHCRTQPSSCPPAWILYQGQWSGAVV GLRPVAHHLPRPIQGLHCPQQAPHQPAL SWGKWPVGMTGPARCCRWPRR* | RLPGPLSHL, SLGTTGTLV, YQGQWSGAV, ALSWGKWPV, VL QMRSLEA, GLRPVAHHL, HLPRPIQGL, ITLPTTSLK, LSHLPPR TK, TTGTLVWER, QTFHLHHCR, HQPALSWGK, MTGPARCC R, AWILYQGQW, SWGKWPVGM, RTASITLPT, GSRTSCCPR, RTSCCPRSH, RSHPRLPGP, RTKWPLQCL, RSLEAHCPL, RPVA HHLPR, PARCCRWPR, SCPPAWILY, EGVAAPHPR, SCCPRS HPR, WSGAVVGLR, APHPRTASI, HPRTASITL, HPRLPGPLS, L PPRTKWPL, CPQAPHQPA, APHQPALSW, WPVGMTGPA, L QMRSLEAH, EAHCPLQTF, SHLPPRTKW, TKWPLQCLL, LLHS LGTTG, HSLGTTGTL, LGTTGTLVW, RGVLQMRSL, TQPSSCCP PA, SSCPPAWIL, ILYQGQWSG, GQWSGAVVG, VAHHLPRPI, GLHCPQAPH, PQAPHQPAL, EPEGVAAPH, CPLQTFHLH, Q PSSCPPAW, QPALSWGKW, LEAHCPLQT, SSCPPAWILY, HL PPRTKWPL, ILYQGQWSGA, YQGQWSGAVV, GQWSGAVV GL, LLHSLGTTGT, SITLPTTSLK, TSCCPRSHPR, GTTGTLVWE R, RTASITLPTT, KGSRTSCCPR, RSHPRLPGPL, RTKWPLQCLL, RTQPSSCPPA, PARCCRWPRR, LQTFHLHHCR, QWSGAVV GLR, HSLGTTGTLV, APHPRTASIT, CPRSHPRLPG, HPRLPGP LSH, WPLQCLLHSL, CPQAPHQPAL, LEAHCPLQTF, LVWERG VLQM, ASITLPTTSL, LSHLPPRTKW, LHSLGTTGTL, SLGTTGT LVW, LQMRSLEAHC, MRSLEAHCPL, QPSSCPPAW, HQPA LSWGKW, LSWGKWPVGM, WERGVLQMRS, QPSSCPPAWI | STAD |
| INPPL 1 | c.3460del C | p.P115 4fs | SEVDVAPAGPARSALLPGPLLELQPP[p.P 1154fs]GDCPRTMAGPSASLHPASGRA | TMAGPSASL, SLHPASGRA, ASLHPASGR, RASRKTWQR, RT MAGPSAS, ASRKTWQRR, KTWQRRLRA, WQRRLRACR, RL | STAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| INTS12 | c.1A>G | p.M1V | SRKTWQRRLRACRAGGPAGWARQA* | RACRAGG, RACRAGGPA, HPASGRASR, CPRTMAGPS, GPSASLHPA, SGRASRKTW, RTMAGPSASL, RASRKTWQRR, ASRKTWQRRL, KTWQRRLRAC, RLRACRAGGP, ELQPPGDCPR, SASLHPASGR, TWQRRLRACR, CPRTMAGPSA, WQRRLRACRA, TMAGPSASLH, ASGRASRKTW | MM |
| INTS4 | c.1378T>G | p.M1V | [p.M1V]VAATVNLELDPIFLKALGFLHSKSKD | VAATVNLEL | TGCT |
| INTS4 | c.1378T>G | p.S460A | MRKISNNITLREDQLDTVLAVLEDS[p.S460A]ARDIREALHELLCCTNVSTKEGIHLA | VLAVLEDSA, SARDIREAL, SARDIREALH, DSARDIREAL | UCEC |
| INTS7 | c.2818C>T | p.R940C | GIVWKTGPRTTIFVKSLEDPYSQQI[p.R940C]CLQQQAQQPLQQQQQRNAYTRF* | DPYSQQICL, QQICLQQQQA | UCEC |
| INTS7 | c.317G>T | p.R106I | LCVLKVTQQSEKHLEKILNVDEFVK[p.R106I]IIFSVIHSNDPVARAITLRMLGSLAS | FVKIIFSVI, EFVKIIFSV, DEFVKIIFS, ILNVDEFVKI, EFVKIIFSVI, DEFVKIIFSV | CESC |
| INVS | c.2396G>A | p.R799K | WKPSRRHDTEPKAKCAPQKRRTQEL[p.R799K]KGGRCSPAGSSRPGSARGEAVHAGQN | PQKRRTQELK, ELKGGRCSPA | STAD |
| INVS | c.2444del G | p.R815fs | KRRTQELRGGRCSPAGSSRPGSARG[p.R815fs]RRSMLGRILPTIVHQETK* | SMLGRILPT, MLGRILPTI, SARGRRSML, RGRRSMLGR, RSMLGRILP, GSARGRRSM, RRSMLGRIL, SMLGRILPTI, MLGRILPTIV, ILPTIVHQET, SSRPGSARGR, SARGRRSMLG, RGRRSMLGRI, RSMLGRILPT | STAD |
| IPO11 | c.2532del T | p.S844fs | ERYPVVMSTYLGVMGRVLLQNTSFF[p.S844fs]LHYLMRWPINLIRRWTSFWEI* | LLQNTSFFL, YLMRWPINL, LMRWPINLI, TSFFLHYLM, SFFLHYLMR, FFLHYLMRW, RRWTSFWEI, LQNTSFFLH, QNTSFFLHY, NTSFFLHYL, LHYLMRWPI, NLIRRWTSF, LIRRWTSFW, WPINLIRRW, NTSFFLHYLM, VLLQNTSFFL, FLHYLMRWPI, YLMRWPINLI, TSFFLHYLMR, SFFLHYLMRW, HYLMRWPINL, RWPINLIRRW, LMRWPINLIR, LQNTSFFLHY, INLIRRWTSF, NLIRRWTSFW, IRRWTSFWEI | CRC |
| IRAK3 | c.800G>A | p.R267Q | PYMRNGTLFDRLQCVGDTAPLPWHI[p.R267Q]QIGILIGISKAIHYLHNVQPCSVICG | IQIGILIGI, APLPWHIQI, WHIQIGILI, LPWHIQIGI, QIGILIGIS K, TAPLPWHIQI, LPWHIQIGIL | CRC |
| IREB2 | c.1256G>A | p.R419Q | HLEHTGFSKAKLESMETYLKAVKLF[p.R419Q]QNDQNSSGEPEYSQVIQINLNSIVPS | FQNDQNSSG | MM |
| IRF4 | c.368A>G | p.K123R | RCALNKSNDFEELVERSQLDISDPY[p.K123R]RVYRIVPEGAKKGAKQLTLEDPQMSM | ISDPYRVYR, RVYRIVPEG, DISDPYRVY, DPYRVYRIV, QLDISDPYRV, RVYRIVPEGA, SQLDISDPYR, DISDPYRVYR, LDISDPYRVY | STAD |
| IRS4 | c.1771_1772insG | p.G591fs | GHGSGGGQGPGDGHGSGGGKNSGG G[p.G591fs]QRLRKWERIRW* | GQRLRKWER, RLRKWERIR, RLRKWERIRW, GKNSGGGQRL | PAAD |
| IRS4 | c.63_65del GGC | p.21_22AA>A | MASCSFTRDQATRRLRGAAAAAAA[p.21_22AA>A]LAAVVTTPLLSSGTPTALIGTGSSCPGA | RGAAAAAAAL | ACC |
| IRX3 | c.1265T>C | p.L422P | LVSAPLGKFPAWTNRPFPGPPPGPR[p.L422P]PHPLSLLGSAPPHLLGLPGAAGHPAA | PPGPRPHPL, GPRPHPLSL, GPRPHPLSLL | |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| IRX6 | c.1274C>T | p.A425V | CDESSCCIPKAFGNPKFALQGLPLNC[p.A425V]VPCPRRSEPVVQCQYPSGAEAG* | PLNCVPCPR, ALQGLPLNCV, VPCPRRSEPV | STAD |
| ISX | c.256C>T | p.R86C | AASGSGLEKPPKDQPQEGRKSKRRV[p.R86C]CTTFTTEQLHELEKLFHFTHYPDVHI | KSKRRVCTT, CTTFTTEQL, SKRRVCTTF, RRVCTTFTT, KSKRRVCTTF | SKCM |
| ISX | c.5G>T | p.C2F | M[p.C2F]FAEVGPALCRGMERNSLGCCEAPKKL | MFAEVGPAL | LUSC |
| ITGA10 | c.2006G>A | p.R669Q | PIVHLTPSLEVTPQAISWQRDCRR[p.R669Q]QGQEAVCLTAALCFQVTSRTPGRWDH | CRRQGQEAV, RQGQEAVCL, RRQGQEAVCL, ROGQEAVCLT | HNSC |
| ITGA4 | c.2018C>T | p.T673M | YLAVGSMKTLMLNVSLFNAGDDAYE[p.T673M]MTLHVKLPVGLYFIKILELEEKQINC | MTLHVKLPV, DAYEMTLHV, YEMTLHVKL, NAGDDAYEM, A YEMTLHVKL, DAYEMTLHVK, EMTLHVKLPV, FNAGDDAYE M, YEMTLHVKLP | CRC |
| ITGA4 | c.2700C>A | p.F900L | GIVRFLSKTDKRLLYCIKADPHCLN[p.F900L]LLCNFGKMESGKEASVHIQLEGRPSI | HCLNLLCNF, CLNLLCNFGK, IKADPHCLNL | CRC |
| ITGA5 | c.143C>A | p.A48D | PPLLPLLLLLLPPPPRVGGFNLDAE[p.A48D]DPAVLSGPPGSFFGFSVEFYRPGTDG | NLDAEDPAV | KICH |
| ITGA8 | c.1846G>T | p.G616C | TEFRDKLSPINISLNYSLDESTFKE[p.G616C]CLEVKPILNYYRENIVSEQAHILVDC | STFKECLEV, TFKECLEVK, KECLEVKPI, DESTFKECL, CLEVKPI LNY, STFKECLEVK, ESTFKECLEV, KECLEVKPIL | LUAD |
| ITGAX | c.2054G>A | p.R685H | KRSKNLLGSRDLQSSVTLDLALDPG[p.R685H]HLSPRATFQETKNRSLSRVRVLGLKA | GHLSPRATF | LUSC |
| ITGAX | c.848G>A | p.R283H | TDGKKEGDSLDYKDVIPMADAAGII[p.R283H]HYAIGVGLAFQNRNSWKELNDIASKP | GIIHYAIGV, DAAGIIHYA, ADAAGIIHY, IHYAIGVGL, MADAA GIIHY, IIHYAIGVGL, HYAIGVGLAF, DAAGIIHYAI, IHYAIGVG LA | LUAD |
| ITGB1 | c.1132C>A | p.L378I | PKSAVGTLSANSNVIQLIIDAYNSI[p.L378I]ISSEVILENGKLSEGVTISYKSYCKN | LIIDAYNSI, QLIIDAYNS, AYNSISSEVI, DAYNSISSEV | STAD |
| ITGB1 | c.472G>A | p.D158N | LKFKRAEDYPIDLYYIMDLSYSMKD[p.D158N]NLENVKSLGTDLMNEMRRITSDFRIG | SMKDNLENV, LSYSMKDNL, YSMKDNLENV, SMKDNLENVK | HNSC |
| ITGB8 | c.21_22insT | p.A7fs | MCGSALAFF[p.A7fs]YRCICLPAKRPARSRLVPLGSLGVFTCSWTGPR* | CGSALAFFY, ALAFFYRCI, LVPLGSLGV, GSALAFFYR, FTCSWT GPR, FYRCICLPA, RSRLVPLGS, CLPAKRPAR, RPARSRLVP, VPLGSLGVF, PARSRLVPL, AKRPARSRL, SRLVPLGSL, SLGVF TCSW, RLVPLGSLGV, FYRCICLPA, CGSALAFFY, FYRCICLP AK, RSRLVPLGSL, MCGSALAFFY, VFTCSWTGPR, RPARSRL VPL, LAFFYRCICL, GSLGVFTCSW, SALAFFYRCI | STAD |
| ITIH1 | c.760G>T | p.G254W | KGHVLFRPTVSQQQSCPTCSTSLLN[p.G254W]WHFKVTYDVSRDKICDLLVANNHFAH | SLLNWHFKV, TSLLNWHFK, STSLLNWHF, LNWHFKVTY, ST SLLNWHFK, CSTSLLNWHF, LLNWHFKVTY, TSLLNWHFKV | LUAD |
| ITIH2 | c.2524C>G | p.L842V | TLDKEMSFSVLLHRVWKKHPVNVDF[p.L842V]VGIYIPPTNKFSPKAHGLIGQFMQEP | VNVDFVGIY, NVDFVGIYI, HPVNVDFVG, VGIYIPPTNK, PVN VDFVGIY, HPVNVDFVGI | LUAD |
| ITK | c.586G>A | p.E196K | PEETVVIALYDYQTNDPQELALRRN[p.E196K]KEYCLLDSSEIHWWRVQDRNGHEGYV | LALRRNKEY, RRNKEYCLL, KEYCLLDSS, ALRRNKEYCL, ELAL RRNKEY | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ITK | c.86G>T | p.R29L | FILLEQLIKKSQQKRRTSPSNFKV[p.R29L]LFFVLTKASLAYFEDRHGKKRTLKGS | SNFKVLFFV, VLFFVLTKA, KVLFFVLTK, NFKVLFFVLT, SPSNFK VLF, KVLFFVLTKA, TSPSNFKVLF, RTSPSNFKVL, SPSNFKVLF F, SNFKVLFFVL, LFFVLTKASL | LUAD |
| ITM2C | c.499G>A | p.E167K | ADIIHDFQRGLTAYHDISLDKCYVI[p.E167K]KLNTTIVLPRNFWELLMNVKRGT YL | YVIKLNTTI, VIKLNTTIV, SLDKCYVIK, IKLNTTIVL, SLDKCYVIK L, YVIKLNTTIV, SLDKCYVIK, CYVIKLNTTI | UCEC |
| ITPR1 | c.4707G>T | p.M15 69I | CGLERDKFDNKTVTFEEHIKEEHNM[p.M1569I]CHYLCFIVLVKVKDSTEYTGPE SYVA | NMCHYLCFI, HNMCHYLCF, KEEHNMCHY, CHYLCFIVL, EEH NMCHYL, NMCHYLCFIV, HNMCHYLCFI, IKEEHNMCHY, KE EHNMCHYL, MCHYLCFIVL | TGCT |
| ITPR2 | c.1073C>A | p.P358Q | RDGVPPTSKKKRQAGEKIMYTLVSV[p.P358Q]QHGNDIASLFELDATTLQRADC LVPR | IMYTLVSVQ, VQHGNDIAS, IMYTLVSVQH, VQHGNDIASL, QHGNDIASLF | LUAD |
| IWS1 | c.2404de\|A | p.S802fs | FQATSKKGISRLDKQMRKFTDIRKK[p.S802fs]ADLHTQ* | RKFTDIRKKA | STAD |
| JAG1 | c.1384G>A | p.A462T | DCLPGWMGQNCDININDCLGQCQND[p.A462T]TSCRDLVNGYRCICPPGYAG DHCERD | TSCRDLVNGY, CQNDTSCRDL | CRC |
| JAK1 | c.928G>A | p.V310I | IFETSMLLISSENEMMWFHSNDGGN[p.V310I]ILYYEVMVTGNLGIQWRHKPNV VSVE | SNDGGNILY, NILYYEVMV, ILYYEVMVT, HSNDGGNIL, GNIL YYEVM, HSNDGGNILY, SNDGGNILYY, FHSNDGGNIL | CRC |
| JAKMIP2 | c.848G>T | p.R283I | MSSPKREIPGRAGDGSEHCSSPDLR[p.R283I]INQKRIAELNATIRKLEDRNTLLG DE | INQKRIAEL, RINQKRIAEL, SSPDLRINQK | UCEC |
| JARID2 | c.1180_1181insG | p.G394fs | VNHTISGKTESSNAKTRKQVLSLGG[p.G394fs]GVQVHWARRQWPQGQWQVE PKVMH* | GQWQVEPKV, QWPQGQWQV, GVQVHWARR, RQWPQGQWQ, WQVEPKVMH, VLSLGGGVQV, RQWPQGQWQV, KQVLSLGGGV, LSLGGGVQVH, SLGGGVQVHW, VQVHWAR RQW, ARRQWPQGQW, GQWQVEPKVM | STAD |
| JARID2 | c.1266de\|G | p.V422fs | TGPAVNGLKVSGRLNPKSCTKEVGG[p.V422fs]GSCGRACSCGRGCGTPRGDW KRHTRRRSRSRPPRR* | CGRACSCGR, KRHTRRRSR, HTRRRSRSR, RRSRSRPPR, RSRS RPPRR, EVGGGSCGR, KRHTRRRSRP, HTRRRSRSRP, RRRSRSRPPR | STAD |
| JHDM1D | c.289de\|A | p.R97fs | HHAVFDIDLYHCPNCAVLHGSSLMKK[p.R97fs]GGTGTDMTTQKLMMVPNQCK LELELSLRNYALESSQVPMK* | MMVPNQCKL, MTTQKLMMV, LMMVPNQCK, VPNQCKLE L, ELSLRNYAL, KKGGTGTDM, TDMTTQKLM, NQCKLELEL, C KLELELSL, ALESSQVPM, LELSLRNYA, GTDMTTQKLM, LM MVPNQCKL, SLMKKGGTGT, KLMMVPNQCK, ALESSQVPM K, GTGTDMTTQK, YALESSQVPM, MKKGGTGTDM, TDMTT QKLMM, LELELSLRNY, LELSLRNYAL, RNYALESSQV | STAD |
| JHDM1D | c.938G>A | p.R313H | TSVWYHVLWGEKIFYLIKPTDENLA[p.R313H]HYESWSSSVTQSEVFFGDKVDKC YKC | PTDENLQHY, AHYESWSSS, DENLQHYES, KPTDENLAHY, AH YESWSSSV, DENLAHYESW | GBM |
| JMJD1C | c.3592C>A | p.R1198S | SHSVTTFRNDCRSPTHLTVSSTNTL[p.R1198S]SSMPALHRAPVFHPPIHHSLERK EGS | LSSMPALHR, SSMPALHRA, NTLSSMPAL, SSTNTLSSM, TLS SMPALHR, STNTLSSMPA, VSSTNTLSSM | LUAD |
| JMJD4 | c.32C>T | p.A11V | MRAGPEPQAL[p.A11V]VGQKRGALRL LVPRLVLTVSAPAEVR | LVGQKRGAL, LVGQKRGALR | ACC |
| JMY | c.2429_2464de\|CACCA CCACCTCCC CCACCTCCT | p.PPPPP PPPPPP PP811de\| | LNNNLEPCSVTINPLPSLPPTPPP[p.PPPPPPPPPPP811de\|]LPVAKDSGPETLE KDLPRKEGNEKRIPKSASAPSAHLFDSS QLVSARKKLRKTAEGLQRRR | SPLPPTPPPL, LPPTPPLPV | PAAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| JPH1 | CCCCCTCCC CCAC c.1183G>A | p.A395 T | ARTKVEIANSRTAHARAKADAADQA[p. A395T]TLAARQECDIARAVARELSPDFY QPG | DAADQATLA, TLAARQECDI, DAADQATLAA, KADAADQAT L | GBM |
| JPH3 | c.1299G>C | p.Q433 H | EARIARITAKEFSPSFQHRENGLEY[p.Q4 33H]HRPKRQTSCDDIEVLSTGTPLQQE SP | NGLEYHRPKR, YHRPKRQTSC | CESC |
| JSRP1 | c.275T>C | p.V92A | EKEPAARGTPGTGKERLKAGASPRS[p. V92A]APARKKAQTAPPLQPPPPPALS EEL | KAGASPRSA, SPRSAPARK, RSAPARKKA, ASPRSAPARK/GA SPRSAPAR, APARKKAQTA, LKAGASPRSA | KIRP |
| JUP | c.1880C>T | p.S627 L | RVAAGVLCELAQDKEAADAIDAEGA[p. S627L]LAPLMELLHSRNEGTATYAAAV LFRI | ALAPLMELL, AEGALAPLM, GALAPLMEL, DAIDAEGAL, DAI DAEGALA, DAEGALAPL | CESC |
| KAL1 | c.907G>A | p.V303I | SKHFRSSKDPSAPPAPANLRLANST[p.V 303I]INSDGSVTVTIVWDLPEEPDIPVH HY | STINSDGSV, NLRLANSTI, TINSDGSVTV, NSTINSDGSV, ANL RLANSTI | CRC |
| KANK 3 | c.1076G>A | p.R359 H | VEADAMVTEALLGLPAAAERELELL[p. R359H]HASLEHQRGVSELLRGRLRELEE ARE | AERELELH, RELELLHAS, LLHASLEHQR, AERELELLHA, RELE LLHASL, LELLHASLEH | ACC |
| KANK 4 | c.757T>C | p.S253 P | VQEGAEPPEGVVKVPNHLPLPGPPF[p. S253P]PFQNVLVVLEDKEDEHNAREAE VLFT | PLPGPPPF, PFQNVLVVL, FPFQNVLVV, GPPFPFQNV, LPLP GPPPF, GPPFPFQNVL, FPFQNVLVVL, PFPFQNVLV | KIRC |
| KANSL 3 | c.1127G>A | p.G376 E | IGWNTGALVACHVSVMEYVTAVVCL[p. G376E]EPLLTVDGPRGDVDDPLLDM KTPVL | AVVCLEFPL, CLEFPLLTV, VTAVVCLEF, LEFPLLTVD, YVTAVV CLEF, TAVVCLEFPL | TGCT |
| KBTB D13 | c.242C>T | p.A81V | GGFRATLQVLRGDRPALAAEDELLQ[p. A81V]VVECAAFLQAPALARFLEHNLTS DNC | QVVECAAFL, LQVVECAAF, AEDELLQVV, LLQVVECAAF, LQ VVECAAFL, DELLQVVECA | ACC |
| KBTB D6 | c.1325_132 6insG | p.G442 fs | LADRLLCREGMDVAYLNGYIYILGG[p.G 442fs]ARPYYWS* | YILGGARPY, IIGGARPYY, YIYILGGAR, ILGGARPYYW, IYILG GARPY, YILGGARPYY, GYIYILGGAR | STAD |
| KBTB D8 | c.1645G>A | p.V549I | YLKLVLFQNKLHLFVRATQVTVEEH[p.V 549I]IFRTSRKNSLYQYDDIADQWMKV YET | VTVEEHIFR, TQVTVEEHI, IFRTSRKNSL, QVTVEEHIFR, TQVT VEEHIF | CRC |
| KCNA 1 | c.1126G>T | p.G376 C | EAESHFSSIPDAFWWAVVSMTTVGY[p. G376C]CDMYPVTIGGKIVGSLCAIAGV LTIA | TTVGYCDMY, VGYCDMYPV, MTTVGYCDMY, TVGYCDMY PV, GYCDMYPVTI, SMTVGYCDM | LUAD |
| KCNA 3 | c.1244C>T | p.A415 V | TLKASMRELGLLIFFLFIGVILFSS[p.A41 5V]VYFAEADDPTSGFSSIPDAFWWA VV | ILFSSVVYF, GVILFSSVV, VILFSSVVY, SSVVYFAEA, FIGVILFS SV, ILFSSVVYFA, FSSVVYFAEA, VILFSSVVYF, GVILFSSVVY | CRC |
| KCNB 2 | c.692G>A | p.R231 H | STIALSLNTLPELQETDEFGQLNDN[p.R 231H]HQLAHVEAVCIAWFTMEYLLRFL SSP | HQLAHVEAV, QLNDNHQLA, GQLNDNHQL, GQLNDNHQL A, HQLAHVEAVC, DEFGQLNDNH | BRCA |
| KCNC 1 | c.1363delA | p.K455f s | VPVIVNNFGMVYSLAMAKQKLPKKK[p. K455fs]RSIFRGHRSWDLPIIVNLS* | KQKLPKKKR, RSWDLPIIV, LPKKKRSIF, SIFRGFIRSW, GHRS WDLPI, WDLPIIVNL, IFRGHRSWDL, KKRSIFRGHR, RGHRS WDLPI, LPKKKRSIFR, RSIFRGHRSW, GHRSWDLPII | STAD |
| KCND 3 | c.1313C>T | p.S438 L | NQRADKRRAQKKARLARIRVAKTGS[p.S4 38L]LNAYLHSKRNGLLNERALELTGTP EEE | SLNAYLHSK, KTGSLNAYL, LNAYLHSKR, IRVAKTGSL, AKTGS LNAY, GSLNAYLHSK, KTGSLNAYLH, SLNAYLHSKR, RIRVAK TGSL, RVAKTGSLNA, VAKTGSLNAY, AKTGSLNAYL | CRC, UCEC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| KCNH2 | c.446G>C | p.G149A | MFILNFEVVMEKDMVGSPAHDTNHR[p.G149A]APPTSWLAPGRAKTFRLKLP ALLALT | RAPPTSWLA,NHRAPPTSW,HRAPPTSWL | STAD |
| KCNH8 | c.1365G>A | p.M455I | SSLTSVGFGNVSANTDAEKIFSICT[p.M455I]ILIGALMHALVFGNVTAIIQRMYS EK | KIFSICTIL,ILIGALMHA,SICTILIGA,IFSICTILI,CTILIGALM, IFSICTI,KIFSICTILI,FSICTILIGA,ILIGALMHAL,SICTILI-GAL,AEKIFSICTI,EKIFSICTIL | LUAD |
| KCNJ10 | c.305del|C | p.P102fs | GTWFLFGVVWLVAVAHGDLLELDP[p.P102fs]RPTTPVWYRCTHSLEPSSSPL NPKPPLAMASATSVRNVHWPLCFLLPS WCSPPSWKSSSQVPSWRRLPGPRSGL RPFVSASMQLWPPTMASPAS* | LAMASATSV,SMQLWPPTM,MQLWPPTMA,SLEPSSSPL, NVHWPLCFL,RLPGPRSGL,AMASATSVR,SSSQVPSWR,SS QVPSWRR,VWYRCTHSL,RNVHWPLCF,VHWPLCFLL,SVR NVHWPL,SWCSPPSWK,SWRRLPGPR,SGLRPFVSA,PTTPP VWYR,DRPPTTPPV,SPLNPKPPL,KPPLAMASA,VPSWRRLP G,GPRSGLRPF,WPPTMASPA,FLLPSWCSP,KSSSQVPSW,S QVPSWRRI,LRPFVSASM,FVSASMQLW,ASMQLWPPT,W PLCFLLPS,LPSWCSPPS,LELDPRPTT,FLLPSWCSPP,SMQL WPPTMA,PLAMASATSV,LLPSWCSPPS,GLRPFVSASM,LA MASATSVR,PSWCSPPSWK,KSSSQVPSWR,SSSQVPSWRR, PFVSASMALW,HSLEPSSSPL,SVRNVHWPLC,SWKSSSQV PS,SWRRLPGPRS,RSGLRPFVSA,ASMQLWPPTM,RPTTPP VWYR,MASATSVRNV,TSVRNVHWPL,NVHWPLCFLL,GPR SGLRPFV,RPFVSASMQL,SATSVRNVHW,VRNVHWPLCF,R NVHWPLCFL,WKSSSQVPSW,SQVPSWRRLP,RRLPGPRSG L,MQLWPPTMAS,WPLCFLLPSW,LPSWCSPPSW,DPRPTT PPVW | STAD |
| KCNJ3 | c.1290G>T | p.L430F | KITGRED[p.L430F]FGDLPMKLQRISSVPGNSEEKLVSK T | YSFGDLPMK,AYSFGDLPM,SFGDLPMKL,TTSEKAYSF,KAY SFGDLPM,AYSFGDLPMK,YSFGDLPMKL,STTSEKAYSF,SEK AYSFGDL | LUAD |
| KCNK17 | c.61A>G | p.S21G | MYRPRARAAPEGRVRGCAVP[p.S21G]GTVLLLLAYLAYLALGTGVFWTLEGR | GTVLLLLAY,RVRGCAVPG,CAVPGTVLL,VPGTVLLLL,RVRG CAVPGT,PGTVLLLLAY,RGCAVPGTVL,CAVPGTVLLL,VPGT VLLLLA | ACC |
| KCNK18 | c.68G>T | p.G23V | MEVSGHPQARRCCPEALGKLFP[p.G23V]VLCFLCFLVTYALVGAVVFSAIEDGQ | ALGKLFPVL,KLFPVLCFL,VLCFLCFLV,EALGKLFPV,GKLFPV LCF,FPVLCFLCF,KLFPVLCFLC,LFPVLCFLCF,FPVLCFLCFL,L GKLFPVLCF,GKLFPVLCFL,PEALGKLFPV | LUAD |
| KCNK2 | c.17C>G | p.S6W | MLPSA[p.S6W]WRERPGYRAGVAAPD LLDPKSAAQNS | AWRERPGYR,SAWRERPGY,MLPSAWRER,SAWRERPGYR, AWRERPGYRA,PSAWRERPGY | BLCA |
| KCNK2 | c.497G>T | p.R166L | HWDLGSSFFFAGTVITTIGFGNISP[p.R166L]LTEGGKIFCIIYALLGIPLFGFLLAG | IGFGNISPL,SPLTEGGKIF | LUAD |
| KCNMB2 | c.453T>G | p.N151K | KLLLYHTEETIKINQKCSYIPKCGK[p.N151K]KFEESMSLVNVVMENFRKYQHFSC YS | CGKKFEESM,KKFEESMSL,CSYIPKCGKK,SYIPKCGKKF,KKF EESMSLV | STAD |
| KCNS2 | c.631G>A | p.D211N | SRVFSILSILVVMGSIITMCLNSLP[p.D211N]NFQIPDSQGNPGEDPRFEIVEHFGI A | MCLNSLPNF,CLNSLPNFQI,TMCLNSLPNF | UCEC |
| KCTD20 | c.942del|A | p.L314fs | KLYRFFKYIENRDVAKTVLKERGLK[p.L314fs]TFALELKVTLPVKKLREGLAAGLK SSIIMVNAPSSRCHGKRKKGRVAMWIS SVFEANPSRIW* | KTFALELKV,RVAMWISSV,GLKTFALEL,KLREGLAAG,KVTL PVKKK,IMYNAPSSR,SVFEANPSR,VAMWISSVF,ELKVTLPV K,KSSIIMYNA,SSRCHGKRK,KRKKGRVAM,KGRVAMWIS, GLKSSIIMY,LKERGLKTF,FALELKVTL,LELKVTLPV,KKLREGL AA,LAAGLKSS,AGLKSSIIM,RKKGRVAMW,MWISSVFEA,F | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| KCTD21 | c.17C>T | p.T6M | MSDPI[p.T6M]MLNVGGKLYTTSLATLTSFPDSMLGA | EANPSRIW, KERGLKTFA, ALELKVTLPV, KLREGLAAGL, GLA AGLKSSI, AWWISSVFEA, IMYNAPSSRC, SVFEANPSRI, GLKT FALELK, IMYNAPSSR, TFALELKVTL, RVAMWISSVF, VFEAN PSRIW, RGLKTFALEL, SSRCHGKRKK, KGRVAMWISS, AGLK SSIIMY, VTLPVKKKLR, VLKERGLKTF, KERGLKTFAL, LAAGLK SSII, AAGLKSSIIM, GKRKKGRVAM, RKKGRVAMWI, GRVA MWISSV, REGLAAGLKS MSDPIMLNV, MLNVGGKLY, IMLNVGGKL, IMLNVGGKLY | STAD |
| KDELC1 | c.1339C>A | p.L447I | LKWAKDHDEEAKKIAKAGQEFARNNI[p.L447I]IMGDDIFCYYFKLFQEYANLQVSEPQ | IMGDDIFCY, GQEFARNNI, QEFARNNIM, IMGDDIFCYY, NI MGDDIFCY, GQEFARNNIM, RNNIMGDDIF | CRC |
| KDM1B | c.1083C>A | p.F361L | HLSNLEYACGSNLHQVSARSWDHNE[p.F361L]LFAQFAGDHTLLTPGYSVIIEKLAEG | RSWDHNELF, ARSWDHNEL, DHNELFAQF, NELFAQFAG, S ARSWDHNEL, RSWDHNELFA, ARSWDHNELF, WDHNELFA QF | UCEC |
| KDM3B | c.3946del C | p.P1316fs | SLRDLLHSGPGKLPQTPLDTGIPFP[p.P1316fs]RSSLHPQQE* | FPPRSSLHPQ, IPPPRSSIH, TGIPFPRSSL | STAD |
| KDM5A | c.1267C>T | p.P423S | VSSIEEDVIVEYGADISSKDFGSGF[p.P423S]SVKDGRRKILPEEEEYALSGWNLNNM | SVKDGRRKI, DFGSGFSV, KDFGSGFSV, SSKDFGSGFS, KDF GSGFSVK, SVKDGRRKIL | TGCT |
| KEAP1 | c.1408C>T | p.R470C | PERDEWHLVAPMLTRRIGVGVAVLN[p.R470C]CLLYAVGGFDGTNRLNSAECYYPERN | VAVLNCLLY, AVLNCLLYA, VLNCLLYAV, CLLYAVGGF, GVAV LNCLLY, AVLNCLLYAV | LUSC |
| KEAP1 | c.1438G>T | p.G480W | PMLTRRIGVGVAVLNRLLYAVGGFD[p.G480W]WTNRLNSAECYYPERNEWRMITAMNT | LYAVGGFDW, AVGGFDWTNR, LLYAVGGFDW, FDWTNRL NSA | LUSC |
| KEAP1 | c.1807G>T | p.G603W | LDSVECYDPDTDTWSEVTRMTSGRS[p.G603W]WVGVAVTMEPCRKQIDQQNCTC* | RMTSGRSWV, SWVGVAVTM, SGRSWVGVA, TRMTSGRS W, GRSWVGVAV, RSWVGVAVT, MTSGRSWVGV, SGRSWV GVAV, RSWVGVAVTM, VTRMTSGRSW, RMTSGRSWVG | LUAD |
| KEAP1 | c.431C>T | p.S144F | GMEVVSIEGIHPKVMERLIEFAYTA[p.S144F]FISMGEKCVLHVMNGAVMYQIDSVVR | FISMGEKCV, TAFISMGEK, FAYTAFISM, YTAFISMGE, LIEFA YTAF, IEFAYTAFI, RLIEFAYTAF, LIEFAYTAFI, FISMGEKCVL, Y TAFISMGEK, IEFAYTAFIS, EFAYTAFISM | LUAD |
| KEAP1 | c.463G>T | p.V155F | PKVMERLIEFAYTASISMGEKCVLH[p.V155F]FMNGAVMYQIDSVVRACSDFLVQQLD | VLHFMNGAV, FMNGAVMYQ, HFMNGAVMY, CVLHFMN GA, MGEKCVLHF, GEKCVLHFM, LHFMNGAVM, CVLHFMN GAV, FMNGAVMYQI, SMGEKCVLHF, LHFMNGAVMY, VLH FMNGAVM | LUSC |
| KEAP1 | c.779G>T | p.R260L | DDLNVRCESEVFHACINWVKYDCEQ[p.R260L]LRFYVQALLRAVRCHSLTPNFLQMQL | QLRFYVQAL, KYDCEQLRF, LRFYVQALL, QLRFYVQALL, KYD CEQLRFY, WVKYDCEQLR, EQLRFYVQAL, VKYDCEQLRF, CE QLRFYVQA | LUAD |
| KEL | c.1231G>A | p.V411M | RKLSQKLRELTEQPPMPARPWWKC[p.V411M]MEETGTFFEPTLAALFVREAFGPSTR | CMEETGTFF, KCMEETGTF, MKCMEETGTF, KCMEETGTFF | GBM |
| KHDRBS2 | c.608C>T | p.S203L | LNGSEDSGRGRGIRGRGAI[p.S203L]LRGRGGAIPPPPPGRGVLTPRGSTV | RIAPTAPLR, APLRGRGGA, PLRGRGGAI, IRIAPTAPL, GIRIAP TAPL, APLRGRGGAI | LUAD |
| KIAA0020 | c.188A>G | p.K63R | RKVAKEGGPKVTSRNFEKSITKLGK[p.K63R]RGVKQFKNKQQGDKSPKNKFQPANKF | KSITKLGKR, ITKLGKRGV, RGVKQFKNK, LGKRGVKQF, ITKLG KRGVK, LGKRGVKQFK, KLGKRGVKQF | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| KIAA0 182 | c.359_360i nsC | p.T120f s | STPKRVPMGPIIVPPGGHSVPSTPP[p.T 120fs]RGDHRSNQNREWCLEE* | HSVPSTPPR,RSNQNREWCL | STAD |
| KIAA0 195 | c.2706de|C | p.I902f s | GLETGWNCHISLTPNGDMPGSEIPP[p.I 902fs]PAPATQAPCMMT* | APATQAPCM,SEIPPPAPA,APATQAPCMM,SEIPPPAPAT, MPGSEIPPPA | STAD |
| KIAA0 240 | c.2683de|A | p.K895f s | PMNHDQPHLVPNHIWSAEGNISKK[p. K895fs]QNALAEH* | ISKKQNALA,NISKKQNAL,KKQNALAEH | STAD |
| KIAA0 528 | c.542G>A | p.R181 Q | YRAVIIHGFVEELVVNEDPEYQWID[p.R 181Q]QIRTPRASNEARQRLISLMSGEL QRK | EYQWIDQIR,WIDQIRTPR,PEYQWIDQI,QWIDQIRTPR,YQ WIDQIRTP,DPEYQWIDQI | CRC |
| KIAA0 556 | c.3244C>T | p.R108 2W | SHSITIDFTHPCHVALIRIWNYNKS[p.R1 082W]IHSFRGVKDITMLLDTQCIFEG EIA | WIHSFRGVK,YNKSWIHSF,KSWIHSFRG,NKSWIHSFR,RIW NYNKSW,WNYNKSWI,NYNKSWIHS,RIWNYNKSWI,KS WIHSFRGV,SWIHSFRGVK,YNKSWIHSFR,IRIWNYNKSW | CRC |
| KIAA0 556 | c.988C>A | p.L330I | FPDQERMCSRPGSRRERPLSATRKT[p.L 330I]ICEAEYPEEDASAVLQAIQVENAA LQ | ATRKTICEA,RKTICEAEY,RPLSATRKTI,TRKTICEAEY | UCEC |
| KIAA0 586 | c.4775de|C | p.A159 2fs | PRWESSATLRFTDAPCQDVSDAAVS[p. A1592fs]DLEDCSQSLSLSTMQEDMES SGADTF* | DVSDAAVSDL,SDLEDCSQSL | STAD |
| KIAA0 907 | c.1337A>C | p.Q446 P | GQSPMGGPFIPAAPVKTALPAGPQP[p. Q446P]PPQPQPPLPSQPQAQKRFTE ELPDE | QPPPQPQPPL | BLCA |
| KIAA0 907 | c.1546_154 7de|AG | p.R516f s | TGFSSQNEIEGAGSKPASSSGKERE[p.R 516fs]GQAVDASTSLSSDWNKNRVR* | TSLSSDWNK,LSSDWNKNR,QAVDASTSL,STSLSSDWNK, SLSSDWNKNR,KEREGQAVDA,REGQAVDAST,GQAVDAST SL,DASTSLSSDW | GBM |
| KIAA1 109 | c.14039T>C | p.L468 0P | SMSLHGNHMTLLACFHGPNFRSKSWA[p. L4680P]PFHLEEPNIAFWTEAQKIWE DGSSDH | RSKSWAPPH,KSWAPFHLE,FRSKSWAPF,SKSWAPPHL,NF RSKSWAPF,RSKSWAPFHL,APFHLEEPNI | CLL |
| KIAA1 109 | c.14810C>A | p.S493 7Y | ITYTTVDWRDFMCNTWHLEPTLRLI[p. S4937Y]YWTGRKIDPVGVDYILQKLGF HHART | RLIYWTGRK,LEPTLRLIY,LIYWTGRKI,EPTLRLIYW,HLEPTL RLIY,RLIYWTGRKI,TLRLIYWTGR | CRC |
| KIAA1 109 | c.4763de|A | p.E158 8fs | ANSLLDRGMQLSGSTNTPYTPLEK[p.E 1588fs]NSLITQMMKH* | NSLITQMMK,EKNSLITQM,KNSLITQMM,TPLEKNSLI,KNS LITQMMK,LEKNSLITQM,EKNSLITQMM | STAD |
| KIAA1 147 | c.446C>T | p.A149 V | YFRKGPPFGLACFANMPVESELERG[p. A149V]VRMKSVGILSPSYTLLYRYMHFL ENQ | GVRMKSVGI,SELERGVRM,VRMKSVGIL,VESELERGV,GVR MKSVGIL,LERGVRMKSV | UCEC |
| KIAA1 211 | c.3608C>A | p.P120 3Q | SVTVELSDSAPPAPLVKEVTKRFST[p.P1 203Q]QDAAPVSTEPAWLALAKRKAKA WSDC | FSTQDAAPV,KRFSTQDAA,VTKRFSTQDA | LUAD |
| KIAA1 211 | c.924de|T | p.R308f s | ERAPREEQQRSLEAPGWEDAERRER[p. R308fs]RSASAWRRRRSEGVCRPRPKR RRGGGWRRTPGWRSGGGRRRRKEDA RRSSKGRRRRRLRDGKSWNSRRRRCRG RPRRWRRLGRAGGARRRRIWGKRRRR ARRTWRTGGGSVSF* | RSASAWRRR,SASAWRRRR,KRRRGGGWR,GWRRTPGWR, GWRSGGGRR,RSGGGRRRR,SGGGRRRRK,RSSKGRRRR,S SKGRRRRR,KGRRRRRLR,RRRRLRDGK,KSWNSRRRR,RRR CRGRPR,RGRPRRWR,RWRRLGRAG,LGRAGGARR,RAG GARRRR,GARRRRIWG,ARRRRIWGK,RRRRIWGKR,RIWG KRRRR,RRRARRTWR,RARRTWRTG,DGKSWNSRR,RPRR WRRLG,RERRSASAW,RLRDGKSW,RRRAARTW,WRTG GGSSV,TGGGSSVSF,AERRERRSA,RTGGGSSVSF,RERRSAS AWR,RSASAWRRRR,AWRRRSEGV,KRRRGGGWRR,RSG GGRRRRK,RSSKGRRRR,SSKGRRRRL,KGRRRRRLRD,RR RRRLRDGK,RLRDGKSWNS,KSWNSRRRRC,NSRRRRCRGR, | CESC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| KIAA1211 | c.926_927insG | p.E309fs | RAPREEQQRSLEAPGWEDAERREREE[p.E309fs]GARAPGGGGGAKASAGPGPSGGEAAAGGGRQAGGAEAAGGGGRKMRGGAQKAGGGGG* | RRRRCRGRPR,RRRCRGRPRR,RCRGRPRRW,RGRPRRWRRL,RPRRWRRLGR,RWRRLGRAGG,LGRAGGARRR,RAGGARRRI,GARRRIWGK,RIWGKRRRA,RRPRARRTWR,RARRTWRTGG,TWRTGGGSV,DARRSSKGRR,DGKSWNSRR,R,SWNSRRRCR,RPRPKRRRG,RPKRRRGGGW,ERRERRSASA,RRERRSASAW,RRRLRDGKSW | CESC |
| KIAA1429 | c.413C>T | p.S138F | LRGWYNCLTLAIYGSVDRVISHDRD[p.S138F]FPPPPPPPPQPQPSLKRNPKHAD | RKMRGGAQK,KMRGGAQKA,REREGARAP,RQAGGAEAA,ABRREREGA,RAPGGGGGAK,KMRGGAQKAG,REREGARAPG,RQAGGAEAAG,RKMRGGAQKA | HNSC |
| KIAA1429 | c.4576G>A | p.D1526N | VLSAPESLQNLFNNRTAYVLADVMD[p.D1526N]NQLKSMWFTPFQAEEIDTDLDLVKVD | RVISHDRDF | HNSC |
| KIAA1549 | c.3816G>T | p.L1272F | DGERLSAVKSSDLINKMDLQRAAIIF[p.L1272F]FGYRIQGVIAQPVDRVKRPSPESQSN | VMDNQLKSM,MDNQLKSMW,VLADVMDNQL,DVMDNQLKSM,VMDNQLKSMW,MDNQLKSMWF | LUAD |
| KIAA1751 | c.189G>C | p.L63F | LQEAEDDVDPGHSSSVKELDTDADK[p.L63F]FKKKTAEDRTQAFHLRQNLSALDKMH | RAAIIFGYR,LQRAAIIFG,QRAAIIFGY,AAIIFGYRI,FGYRIQGVI,IIFGYRIQGV,RAAIIFGYRI,FGYRIQGVI,LQRAAIIFGY,MDLQRAAIIF | LUSC |
| KIAA1751 | c.291G>C | p.K97N | TQAFHLRQNLSALDKMHEEQELFTE[p.K97N]NMRGELRACRQRRDLIDKQQEAVAAE | KFKKKTAEDR,KELDTDADKF | KIRC |
| KIAA1755 | c.324A>C | p.Q108H | CLRDEVVHLAPLNPLLLRQGDFYLL[p.Q108H]HVEPQEEQSVCIMIKCLSLDLCTVDK | EQELFTENM,EEQELFTEN,FTENMRGELR,NMRGELRACR,EEQELFTENM,TENMRGELRA | LUAD |
| KIAA1804 | c.1420G>A | p.V474M | AALQQKSQEELLKRREQQLAEREID[p.V474M]MLERELNILIFQLNQEKPKVKKRKGK | RQGDFYLHV,LLRQGDFYLH,RQGDFYLHVE | CRC |
| KIAA1804 | c.1429C>T | p.R477W | QQKSQEELLKRREQQLAEREIDVLE[p.R477W]WELNILIFQLNQEKPKVKKRKGKFKR | MLERELNIL,REIDMLERE,QLAEREIDML,MLERELNILI,QQLAEREIDM,REIDMLEREL,IDMLERELNI | CRC |
| KIAA1967 | c.1243delC | p.P415fs | TGIDLSGCTKWWRFAEFQYLQPGPP[p.P415fs]GGFRQWWCTCRMSGPSCLLWRSGRPCASRKLQRQLPQPRRHKGKRSLLNRHLMPWSKQQTLLDGTQKLQRPPHSRKRTLISQRPLHPP* | EWELNILIF,EIDVLEWEL,DVLEWELNI,LEWELNILI,WELNILIF,VLEWELNILI,ABREIDVLEW,REIDVLEWEL,LEWELNILIF,WELNILIFQL | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| KIAA2022 | c.1034G>T | p.C345F | NVRDKTLLMQEDAQFNFFPSVFTT[p.C345F]FPKRESKSGALKQSSDFSQFKVPDVS | SVFTTPKR,TTFPKRESK,PSVFTTPK,FPPSVFTTF,FTTFPK RESK,NFFPSVFTF,FPSVFTTFPK | LUSC |
| KIAA2026 | c.1720C>T | p.R574C | PAKMILDNHDISVEMGVKSNYEIRI[p.R574C]CRPCEIKKTDCCKENLEKPRSPGEVT | RICRPCEIK,ICRPCEIKK,SNVEIRICR,YEIRICRPC,RICRPCEIK, KSNYEIRICR,EIRICRPCEI | UCEC |
| KIAA2026 | c.2069deA | p.K690fs | LEQSLQSHKKLKLTKMRAKKKKKKK[p.K690fs]RN* | RAKKKKKKR | STAD |
| KIDINS220 | c.2552A>G | p.N851S | SNINGHDYMRNIVHLPVFLNSRGLS[p.N851S]SARKFLVTSATNGDVPCSDTTGIQED | FLNSRGLSS,GLSSARKFL,SARKFLVTS,NSRGLSSAR,LSSARKFLV, RGLSSARKF,FLNSRGLSSA,GLSSARKFLV,NSRGLSSARK,RGLSSARKFL,SARKFLVTSA,SRGLSSARKF | TGCT |
| KIF13A | c.3345deA | p.K1115fs | LNCVREBWSDALIKRREYLDEQIKK[p.K1115fs]SAIKQRKQRTMWSGKPSLWSSG* | TMWSGKPSL,KQRTMWSGK,MWSGKPSLW,KQRKQRTM W,RTMWSGKPS,SAIKQRKQR,IKQRKQRTM,YLDEQIKKSA, TMWSGKPSLW,KSAIKQRKQR,AIKQRKQRTM,KQRKQRT MWS,RKQRTMWSGK,KQRTMWSGKP,RTMWSGKPSL,QI KKSAIKQR,IKQRKQRTMW | STAD |
| KIF14 | c.1793G>A | p.R598Q | VFTLVMTQTKTEFVEGEEHDHRITS[p.R598Q]QINLIDLAGSERCSTAHTNGDRLKEG | RITSQINLI,SQINLIDLA,HRITSQINL,HRITSQINLI,SQINLIDL AG | CRC |
| KIF15 | c.754G>C | p.E252Q | TSMNRESSRSHAVFTITIESMEKSN[p.E252Q]QIVNIRTSLLNLVDLAGSERQKDTHA | SMEKSNQIV,KSNQIVNIR,ESMEKSNQI,QIVNIRTSLL,ESM EKSNQIV,IESMEKSNQI,MEKSNQIVNI,NQIVNIRTSL | LUAD |
| KIF16B | c.434G>A | p.R145Q | GLIPRICEGLFSRINETTRWDEASF[p.R145Q]QTEVSYLEIYNERVRDLLRRKSSKTF | SFQTEVSYL,ASFQTEVSY,DEASFQTEV,QTEVSYLEIY,FQTE VSYLEI,EASFQTEVSY,ASFQTEVSYL,DEASFQTEVS | CRC |
| KIF18A | c.49C>T | p.R17C | MSVTEEDLCHHMKVVV[p.R17C]CVRPENTKEKAAGFHKVVHVVDKHLI | HMKVVVCVR,VVCVRPENTK,CVRPENTKEK,HHMKVVVCV R | CRC |
| KIF1B | c.3958C>T | p.R1320W | TVTIIHEKGSELHWKDVRELVVGRI[p.R1320W]WNKPEVDEAAVDAILSLNIISAKYLK | LVVGRIWNK,RELVVGRIW | BRCA |
| KIF20B | c.160G>A | p.E54K | NFDGIKLDLSHEFSLVAPNTEANSF[p.E54K]SKDYLQVCLRIRPFTQSEKELESEG | KSKDYLQVC,FKSKDYLQV,NTEANSFKSK,SFKSKDYLQV,KS KDYLQVCL,EANSFKSDY | UCEC |
| KIF20B | c.2971G>A | p.E991K | NEIETATRSITNNVSQIKLMHTKID[p.E991K]KLRTLDSVSQISNIDLLNLRDLSNGS | LMHTKIDKL,KLMHTKIDK,KLRTLDSVS,TKIDKLRTL,KLMHT KIDKL,HTKIDKLRTL,LMHTKIDKLR | CRC |
| KIF23 | c.1048G>A | p.E350K | KEQITISQLSLVDLAGSERTNRTRA[p.E350K]KGNRLREAGNINQSLMTLRTCMDVLR | RTNRTRAKG,RTRAKGNRL,RTRAKGNLR,RAKGNRLREA | BLCA |
| KIF25 | c.449G>A | p.R150Q | SPGEGGLLPRCLDMIFNSIGSFQAK[p.R150Q]QYVFKSNDRNSMDIQCEVDALLERQK | FQAKQYVFK,SFQAKQYVF,IGSFQAKQY,SFQAKQYVF,KQ YVFKSNDR,SIGSFQAKQY,GSFQAKQYVF | UCEC |
| KIF25 | c.7T>A | p.W3R | MT[p.W3R]RTSGQLQREKQARPGSGAVLAFPDDK | MIRTSGQLQ,RTSGQLQREK,MTRTSGQLQR | PRAD |
| KIF26B | c.3194deC | p.S1065fs | SLQSSRESLNSCGFVEGKPRPMGSP[p.S1065fs]GWASPACPRPRSTSHPALLPRDAKSTPRRGSCRLPPHCLPRARIPAWRLGSPCCSPRCVRPLE* | RLPPHCLPR,TSHPALLPR,RSTSHPALL,RGSCRLPPH,RARIP AWRL,STPRRGSCR,KPRPMGSPG,RPMGSPGWA,CPRPRS TSH,RPRSTSHPA,HPALLPRDA,TPRRGSCRL,LPRARIPAW,I PAWRLGSP,SPRCVRPRL,LPPHCLPRA,RLPHCLPRA,STSH PALLPR,RPRSTSHPAL,KSTPRRGSCR,RARIPAWLG,WAS PACPRPR,LPRARIPAWR,RLGSPCCSPR,KPRPMGSPGW,R | STAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| KIF26B | c.3337G>A | p.V1113M | RCKVYTQKGVLPSPAPLPPSSKDSG[p.V1113M]MASRESLLQPEVRTPPVGMSPQVLKK | PMGSPGWAS, SPACPRPRST, IPAWRLGSPC, MGSPGWASPA | BRCA |
| KIF26B | c.3341C>T | p.A1114V | CKVYTQKGVLPSPAPLPPSSKDSGV[p.A1114V]VSRESLLQPEVRTPPVGMSPQVLKKS | GMASRESLL, SGMASRESL, SSKDSGMASR, LPPSSKDSGM, SGMASRESLL | CRC |
| KIF26B | c.6097G>A | p.A2033T | SKEAMCFNAKLKILEHRQQRIAEVR[p.A2033T]TKYEWLMKELEATKQYLMLDPNKWLS | SSKDSGVVSR | LIHC |
| KIF26B | c.6097G>A | p.A2033T | | RTKYEWLMK, RIAEVRTKY, EVRTKYEWL, AEVRTKYEW, QQRIAEVRTK, RTKYEWLMKE, RQQRIAEVRT, QRIAEVRTKY, AEVRTKYEWL, TKYEWLMKEL, IAEVRTKYEW | |
| KIF27 | c.2775G>T | p.K925N | LDACNLKRRKGSFGSIDHLQKLDEQ[p.K925N]JNKWLDEEVEKVLNQRQELEELEADLK | KLDEQNKWL, EQNKWLDEEV, LQKLLDEQNKW | UCEC |
| KIF9 | c.1438G>A | p.G480R | ISAIQKAGLVDVDGHLVGEPEGQNF[p.G480R]RLGVAPFSTKPGKKAKSKKTFKEPLS | NFRLGVAPF, GQNFRLGVA, RLGVAPFSTK, QNFRLGVAPF, GEPEGQNFRL | LUAD |
| KIF9 | c.1781G>A | p.R594Q | IRPDTPPSKPVAFEEFKNEQGSEIN[p.R594Q]QIFKENKSILNERRKRASETTQHINA | GSEINQIFK, QGSEINQIF, EQGSEINQIF, NQIFKENKSI, NEQGSEINQI | UCEC |
| KIRREL | c.1003delC | p.P335fs | VDPKPTTTDIGSDVTLTCVWVGNPP[p.P335fs]SLLSPGPKRTQIWS* | VWVGNPPSL, SPGPKRTQI, CVWVGNPPSL, SPGPKRTQIW | STAD |
| KIRREL | c.1810G>T | p.G604C | VDLKQDLRCDTIDTREEYEMKDPTN[p.G604C]CYYNVRAHEDRPSSRAVLYADYRAPG | EMKDPTNCY, PTNCYYNVR, MKDPTNCYY, YEMKDPTNC, DPTNCYYN, EMKDPTNCY, YEMKDPTNCY | LUAD |
| KIRREL2 | c.1947delC | p.V649fs | PPSPLGPPGTPTFYDFNPHLGMVPP[p.V649fs]ADFTEPGQAISPHPTLELSPATSNPHPLGPQIWPPGLPSHMLPSPHLATRVSRLTCDIFPMEESWDLQLAIMDCSDF* | HMLPSPHLA, RLTCDIFPM, HLATRVSRL, ATRVSRLTC, LPSPHLATR, ESWDLQLAI, HPTLELSPA, NPHPLGPQI, SPHLATRVS, FPMEESWDL, LAIMDCSDF, LGMVPPADF, GQAISPHPT, QAISPHPTL, SHMLPSPHL, VSRLTCDIF, MEESWDLQL, EPGQAISPH, EESWDLQLA, DIFPMEESW, AISPHPTLEL, HLATRVSRLT, IFPMEESWDL, MLPSPHLATR, ESWDLQLAIM, NPHLGMVPPA, SPATSNPHPL, WPPGLPPSHM, LPSPHLATR, QLAIMDCSDF, HLGMVPPADF, ADFTEPGQAI, GQAISPHPTL, HMLPSPFILAT, RVSRLTCDIF, SRLTCDIFPM, EESWDLQLAI, HPTLELSPAT, NPHPLGPQIW, FPMEESWDLQ, MEESWDLQLA | STAD |
| KIT | c.1669T>G | p.W557G | VAGMMCIIVMLITYKLQKPMYEVQ[p.W557G]GKVVEEINGNNYVIIDPTQLPYDHKW | PMYEVQGKV, VQGKVVEEI, EVQGKVVEEI, KPMYEVQGKV | TGCT |
| KIT | c.2446G>C | p.D816H | RDLAARNILLTHGRITKICDFGLAR[p.D816H]HIKNDSNYVVKGNARLPVKWMAPESI | HIKNDSNYV, RHIKNDSNY, CDFGLARHI, HIKNDSNYVV, ARHIKNDSNY, RHIKNDSNYV | TGCT |
| KIT | c.2446G>T | p.D816Y | RDLAARNILLTHGRITKICDFGLAR[p.D816Y]YIKNDSNYVVKGNARLPVKWMAPESI | ICDFGLARY, YIKNDSNYVV, RYIKNDSNY, DFGLARYIK, CDFGLARYI, YIKNDSNYV, KICDFGLARY, RYIKNDSNYV, ARYIKNDSNY | TGCT |
| KIT | c.2447A>T | p.D816V | RDLAARNILLTHGRITKICDFGLAR[p.D816V]VIKNDSNYVVKGNARLPVKWMAPESI | VIKNDSNYVV, RVIKNDSNY, CDFGLARVI, RVIKNDSNYV, VIKNDSNYV, ARVIKNDSNY | LAML, TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| KIT | c.2464A>T | p.N822Y | NILLTHGRITKICDFGLARDIKNDS[p.N822Y]YVVVKGNARLPVKWMAPESIFNCVYT | KNDSYYVVK,SYYVVKGNA,RDIKNDSYY,YVVVKGNAR,DIKNDSYYV,IKNDSYYVV,YVVVKGNARL,LARDIKNDSY,SYYVVKGNAR,DIKNDSYYVI,DSYYVVKGNA | TGCT |
| KIT | c.2466T>G | p.N822K | NILLTHGRITKICDFGLARDIKNDS[p.N822K]YVVVKGNARLPVKWMAPESIFNCVYT | KNDSKYYVK,RDIKNDSKY,IKNDSKYVV,KYVVKGNARL,LARDIKNDSK | TGCT |
| KLC2 | c.1703de|C | p.T568fs | SFGKLRDALRSSEMLVKKLQGGTP[p.T568fs]RSPLTPG* | TPRSPLTPG,LQGGTPRSPL | STAD |
| KLF3 | c.312de|A | p.I1104fs | SLKFPSSHRRASPGLSMPSSSSPPIK[p.I1104fs]NTHPLLQACSPSACRCPCHQ* | LLQACSPSA,QACSPSACR,PPIKNTHPL,SPSACRCPC,LQACSPSAC,SPPIKNTHPL | STAD |
| KLF3 | c.671_672insC | p.S224fs | GIEPQRTDYYPEEMSPPLMNSVSPP[p.S224fs]ASIVARESPFGHRAAWEETFTCGIPGYSKEAEDTQM* | LMNSVSPPA,SVSPPASIV,TFTCGIPGY,NSVSPPASI,FTCGIPGYS,SPFGHRAAW,SIVARESPP,RESPFGHRA,HRAAWEETF,SKEAEDTQM,WEETFTCGI,PLMNSVSPPA,FTCGIPGYSK,VARESPFGHR,EITFTCGIPGY,NSVSPPASIV,ASIVARESPF,LMNSVSPPAS,MNSVSPPASI,RESPFGHRAA,GHRAAWEETF,YSKEAEDTQM | STAD |
| KLF4 | c.1300A>C | p.K434Q | GRRSWPRKRTATHTCDYAGCGKTYT[p.K434Q]QSSHLKAHLRTHTGEKPYHCDWDGCG | KTYTQSSHL,TQSSHLKAH,KTYTQSSHLK,QSSHLKAHLR,GKTYTQSSHL,TQSSHLKAHL | BRCA |
| KLF5 | c.1255G>C | p.E419Q | LRTHTGEKPYKCTWEGCDWRFARSD[p.E419Q]QLTRHYRKHTGAKPFQCCGVCNRSFSR | RSDQLTRHY,FARSDQLTR,DQLTRHYRK,WRFARSDQL,RSDQLTRHY,ARSDQLTRHY | LUAD,LUSC |
| KLF5 | c.353C>T | p.S118L | EKYLTPQLPPVPIIPEHKKYRRDSA[p.S118L]LVVDQFFTDTEGLPYSINMNVFLPDI | KYRRDSALV,SALVVDQFF,KKYRRDSAL,YRRDSALVV,KYRRDSALV,SALVVDQFF,KKYRRDSAL,KKYRRDSALV,RDSALVVDQF | BLCA |
| KLHDC2 | c.962G>C | p.W321S | DAWTYCISKNEWIQFNHPYTEKPRL[p.W321S]SHTACASDEGEVIVFGGCANNLLVHH | KPRLSHTAC,KPRLSHTACA,TEKPRLSHTA | TGCT |
| KLHDC7A | c.1903G>A | p.E635K | DRWDFAPPLPSDTFALAHTATVRAK[p.E635K]KIFVTGGSLRFLLFRFSAQEQRWWAG | HTATVRAKK,TVRAKKIFV,RAKKIFVTG,KIFVTGGSL,KIFVTGGSLR,TVRAKKIFVT,RAKKIFVTGG,HTATVRAKKI,KKIFVTGGSL | SKCM |
| KLHL13 | c.637G>A | p.E213K | FLISGVTLDNCVEVGRIANTYNLTE[p.E213K]MDKYVNSFVLKNFPALLSTGEFLKLP | NLTEMDKYV,EMDKYVNSF,ANTYNLTEM,TEMDKYVNS,MDKYVNSFV,NTYNLTEMDK,TEMDKYVNSF,IANTYNLTEM,MDKYVNSFVL | UCEC |
| KLHL14 | c.693de|C | p.P231fs | KYLVEDVLLLNFEEMRALLDSLPPP[p.P231fs]WSRSWRSSRCPCCGWSTTARPACSMRLTS* | WSRSWRSSR,SWRSSRCPC,TARPACSMR,DSLPPWSR,TTARPACSM,RPACSMRLT,LLDSLPPPW,LPPPWSRSW,TTARPACSMR,RSWRSSRCPC,SWRSSRCPCC,SSRCPCCGWS,STTARPACSM,TARPACSMRL,RPACSMRLTS,ALLDSLPPPW,SLPPPWSRSW,RSSRCPCCGW | STAD |
| KLHL15 | c.554A>G | p.D185G | DNFVPLMSRPDFLSYLSFEKLMSYL[p.D185G]CNDHLSRFPEIELYEAVQSWLRHDRR | MSYLGNDHL,LMSYLGNDH,LGNDHLSRF,FEKLMSYLG,LMSYLGNDHL,YLGNDHLSRF,SYLGNDHLSR | BLCA |
| KLHL28 | c.97G>A | p.E33K | YMLANLTHLHSEQLLQGLNLLRQHH[p.E33K]KLCDIILRVGDVKIHAHKVVLASVSP | KLCDIILRV,LNLLRQHHK,NLLRQHHKL,RQHHKLCDI,GLNLLRQHHK,RQHHKLCDII | UCEC |
| KLHL5 | c.976C>T | p.R326C | QLSQVVEACCKFLMKQLHPSNCLGI[p.R326C]CSFADAQGCTDLHKVAHNYTMEHFME | SNCLGICSF | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| KLK2 | c.169C>A | p.P57T | EKHSQPMQVAVVSHGWAHCGGVLVH[p.P57T|TQWVLTAAHCLKKNSQVWL GRHNLFE | VLVHTQWVL, GVLVHTQWV, HTQWVLTAA, TQWVLTAAH, VHTQWVLTAA | CRC |
| KLK2 | c.481G>A | p.E161K | VKVLGLPTQEPALGTTCYASGWGSI[p.E161K]KPEEFLRPRSLQCVSLHLLSNDMCAR | YASGWGSIK, SIKPEEFLR, GSIKPEEFLR, GWGSIKPEEF | CESC |
| KLK6 | c.359G>A | p.R120H | QSSVVRAVIHPDYDAASHDQDIMLL[p.R120H]HLARPAKLSELIQPLPLERDCSANTT | MLLHLARPA, LLHLARPAK, DIMLLHLAR, IMLLHLARPA, LLH LARPAK, MLLHLARPAK, HDQDIMLLHL | GBM |
| KPNA4 | c.86G>A | p.R29Q | NEKLDNQRLKNFKNKGRDLETMRRQ[p.R29Q]QNEVVVELRKNKRDEHLLKRRN VPHE | QQNEVVVEL, TMRRQQNEV, RRQQNEVVV, RQQNEVVVE, TMRRQQNEVV, ETMRRQQNEV, MRRQQNEVVV, RQQNE VVVEL | CRC |
| KPRP | c.1659_1660insC | p.E553fs | YCGPSSYNQGQESGAGCGPGDVFPE[p.E553fs]PEGSGWPWRPRQCLCWSER GSKECLFLKER* | GSKECLFLK, WPWRPRQCL, RPRQCLCWS, SERGSKECL, FPE PEGSGW, EPEGSGWPW, CLCWSERGSK, RGSKECLFLK, EGS GWPWRPR, SERGSKECLF | HNSC |
| KRAS | c.176C>G | p.A59G | PTIEDSYRKQVVIDGETCLLDILDT[p.A59G]GQEEYSAMRDQYMRTGEGFLCVFAI | LDTGGQEEY, GGQEEYSAM, ILDTGGQEEY | MM |
| KRAS | c.180_181TC>AA | p.Q61K | IEDSYRKQVVIDGETCLLDILDTAG[p.Q61K]KEEYSAMRDQYMRTGEGFLCVFAINNT | LDTAGKEEY, AGKEEYSAM, LDTAGKEEY, DTAGKEEYSA | CRC, THCA |
| KRAS | c.182A>G | p.Q61R | IEDSYRKQVVIDGETCLLDILDTAG[p.Q61R]REEYSAMRDQYMRTGEGFLCVFAINN | LDTAGREEY, AGREEYSAM, ILDTAGREEY, AGREEYSAMR, D TAGREEYSA | MM, TGCT |
| KRAS | c.182A>T | p.Q61L | IEDSYRKQVVIDGETCLLDILDTAG[p.Q61L]LEEYSAMRDQYMRTGEGFLCVFAIN | LDTAGLEEY, AGLEEYSAM, ILDTAGLEEY, LLDILDTAGL, DTA GLEEYSA | CRC, LUAD, TGCT |
| KRAS | c.183A>C | p.Q61H | IEDSYRKQVVIDGETCLLDILDTAG[p.Q61H]HEEYSAMRDQYMRTGEGFLCVFAINN | LDTAGHEEY, AGHEEYSAM, ILDTAGHEEY, DTAGHEEYSA | LUAD, PAAD, STAD |
| KRAS | c.183A>T | p.Q61H | IEDSYRKQVVIDGETCLLDILDTAG[p.Q61H]HEEYSAMRDQYMRTGEGFLCVFAINN | LDTAGHEEY, AGHEEYSAM, ILDTAGHEEY, DTAGHEEYSA | MM, TGCT |
| KRAS | c.34G>A | p.G12S | MTEYKLVVVGA[p.G12S]SGVGKSALTIQLIQNHFVDEYDPTIE | LVVVGASGV, KLVVVGASGV, YKLVVVGASG | CRC, STAD |
| KRAS | c.34G>C | p.G12R | MTEYKLVVVGA[p.G12R]RGVGKSALTIQLIQNHFVDEYDPTIE | ARGVGKSAL, KLVVVGARGV, VVVGARGVGK, EYKLVVVGA R, GARGVGKSAL, RGVGKSALTI | MM, PAAD, TGCT |
| KRAS | c.34G>T | p.G12C | MTEYKLVVVGA[p.G12C]CGVGKSALTIQLIQNHFVDEYDPTIE | LVVVGACGV, VVVGACGVGK, KLVVVGACGV, VVVGACGVGK | CRC, LUAD |
| KRAS | c.35G>A | p.G12D | MTEYKLVVVGA[p.G12D]DGVGKSALTIQLIQNHFVDEYDPTIE | LVVVGADGV, VVVGADGVGK, KLVVVGADGV, VVVGADGVGK | CESC, CRC, GBM, KIRP, LAML, LUAD, MM, PAAD, STAD, UCEC, UCS |
| KRAS | c.35G>C | p.G12A | MTEYKLVVVGA[p.G12A]AGVGKSALTIQLIQNHFVDEYDPTIE | LVVVGAAGV, VVVGAAGVGK, YKLVVVGAA, KLVVVGAAGV, VVVGAAGVGK, KLVVVGAAG, GAAGVGKSAL | CRC, LUAD, MM, TGCT, UCEC |
| KRAS | c.35G>T | p.G12V | MTEYKLVVVGA[p.G12V]VGVGKSALTIQLIQNHFVDEYDPTIE | LVVVGAVGV, VVVGAVGVGK, YKLVVVGAV, KLVVVGAVGV, VVVGAVGVGK, GAVGVGKSAL | BRCA, CESC, CRC, LUAD, |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| KRAS | c.37G>T | p.G13C | MTEYKLVVVGAG[p.G13C]CVGKSALTI QLIQNHFVDEYDPTIED | VVGAGCVGK, KLVVVGAGCV, VVVGAGCVGK | OV,PAAD,TGCT, UCEC,UCS LUAD |
| KRAS | c.38G>A | p.G13D | MTEYKLVVVGAG[p.G13D]DVGKSALT IQLIQNHFVDEYDPTIED | VVGAGDVGK, KLVVVGAGDV, VVVGAGDVGK | CESC,CLL, CRC,DLBCL, LUAD,MM, STAD,UCEC |
| KRAS | c.436G>A | p.A146 T | PSRTVDTKQAQDLARSYGIPFIETS[p.A1 46T]TKTRQRVEDAFYTLVREIRQYRLKK L | ETSTKTRQR, GIPFIETSTK, ETSTKTRQRV | CRC,MM,TGCT |
| KRBA 1 | c.2515A>G | p.R839 G | DRLATALAGLAQEVATMRTQVNRLG[p. R839G]GRPQGPGPMGQASWMWTL PRGPRWAH | RTQVNRLGG, TQVNRLGGR, RTQVNRLGGR | TGCT |
| KRT2 | c.896T>G | p.L299 W | KRTAAENDFVTLKKDVDNAYMIKVE[p. L299W]MQSKVDLLNQEIEFLKVLYDAE ISQI | YMIKVEWQS, MIKVEWQSK, IKVEWQSKV, VEWQSKVDL, N AYMIKVEW, MIKVEWQSKV, YMIKVEWQSK, VEWQSKVDL L | KIRC |
| KRT4 | c.462_463i nsC | p.F154f s | RGNKSISMSVAGSRQGACFGGAGGF[p. F154fs]RHWLWWWIWGLLQW* | WLWWWIWGL, GGFRHWWLM, GFRHWWLWW, FRHW WLWW, RHWWLWWWI, HWWLWWWIW, LWWWIW GLL, WWIWGLLQW, CFGGAGGFR, GGAGGFRHW, WLWW WIWGLL, AGGFRHWWLW, GFRHWWLWWW, RHWWLW WWIW, WWLMWWIWGL, WWWIWGLLQW, FGGAGGFR HW | KIRC |
| KRT6B | c.590T>C | p.L197 P | NKFASFIDKVRFLEQQNKVLDTKWT[p. L197P]PLQEQGTKTVRQNLEPLFEQYIN NLR | VLDTKWTPL, KVLDTKWTPL | CRC |
| KRT8 | c.175T>G | p.S59A | TQKSYKVSTSGPRAFSRSYTSGPG[p.S 59A]ARISSSSFSRVGSSNFRGGLGGGY GG | RSYTSGPGA, GARISSSSF, SYTSGPGAR, YTSGPGARI, RSYTS GPGAR, SYTSGPGAR, GARISSSSFS | ACC,KIRP, LIHC |
| KRTAP 1-1 | c.346A>G | p.I116V | CGTGCGIGGGIGYGQEGSSGAVSTR[p.I 116V]VRWCRPDCRVEGTCLPPCCVS CTPP | VSTRVRWCR, STRVRWCRP, RVRWCRPDC, GAVSTRVRW, AVSTRVRWCR, STRVRWCRPD, RVRWCRPDCR, SGAVSTR VRW | TGCT |
| KRTAP 27-1 | c.372G>T | p.M12 4I | ACQSESSSAGLACVSQPCQSESTQQ[p. M124I]IGFVAQSCQPASLKGNSCPPKT SKSK | CQSESTQQI, ESTQQIGFV, SESTQQIGF, QSESTQQIGF, QQI GFVAQSC, SESTQQIGFV | LUAD |
| KRTAP 4-11 | c.144C>G | p.S48R | TCCRPSCCETTCCRTTYCRPSCCVS[p.S4 8R]RCCRPQCCQSVCCQPTCCRPRCCIS S | VSRCCRPQC | GBM,PRAD |
| KRTAP 4-5 | c.220A>T | p.S74C | VCYQPTCCHPSCCISSCCRPYCCES[p.S7 4C]CCRPCCCQTTCCRTTCCRTTCCCP S | CESCCCRPC | KIRP |
| KRTAP 4-5 | c.272G>T | p.C91F | CRPYCCESSCCRPCCQTTCCRTT[p.C 91F]FRTTCCPSCCVSSCCRPQCCQSV CC | TCCRTTCFR, TTCCRTTCFR | LUAD |
| KRTAP 4-8 | c.188C>G | p.T63S | TCYRPSYSVSCCCRPSCCVSSCCRPQCCQSVCCQP[p.T 63S]SCCCRPSCCVSSCCKPQCCQSVCCQ PT | SVCCQPSCCR | TGCT |
| KRTAP 4-9 | c.53A>T | p.D18V | MVSSCCGSVCSDQGCGQ[p.D18V]VLC QETCCRPSCCETTCCRTTCCRPS | CSDQGCGQV, SDQGCGQVL, QVLCQETCCR | PRAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| KRTAP 5-1 | c.578C>A | p.S193Y | GSCGGSKGGCGSCGGCKGGCGSCGG[p.S193Y]YKGGCGSCGGCGSCGCGVPV CCCSCS | GGCGSCGGY, KGGCGSCGGY | LUAD |
| KSR2 | c.1664C>T | p.T555M | FNLPASHYYKKQQFIFPDVVPVPE[p.T555M]MPTRAPQVILHPVTSNPILEGNP LLQ | MPTRAPQVI, FPDVVPVPEM, MPTRAPQVIL, PEMPTRAPQ V | HNSC |
| L1CAM | c.1894C>A | p.R632S | LVVGSPGVPRLVLSDLHLLTQSQV[p.R632S]SVSWSPAEDHNAPIEKYDIEFEDK EM | LLTQSQVSV, QVSVSWSPA, TQSQVSVSW, SQVSVSWSP, HL LTQSQVSV, SQVSVSWSPA, LTQSQVSVSW | LUAD |
| L1CAM | c.557C>T | p.T186M | PPSAEPLRIYWMNSKILHIKQDERV[p.T186M]MMGQNGNLYFANVLTSDNHS DYICHA | MMGQNGNLY, VMMGQNGNL, HIKQDERVM, IKQDERVM M, VMMGQNGNLY, MMGQNGNLYF, RVMMGQNGNL, LH IKQDERVM | CRC |
| L2HGDH | c.1321_1323del | p.P441del | VEDFVFDAGVGDIGNRILHVRNAPS[p.P441del]|AATSSIAISGMIADEVQQRFEL * | HVRNAPSAA, SAATSSIAI, APSAATSSI, LHVRNAPSA, IL HVRNAPSA, HVRNAPSAAT, NAPSAATSSI, APSAATSSIA, LHVRN APSAA | TGCT |
| L3MBTL4 | c.485G>T | p.W162L | HPVGWCEKTKHELHIPKGYRKDKFV[p.W162L]LMDYLKACKLQNAPKKLFRNR SPNGP | VLMDYLKAC, LMDYLKACK, KFVLMDYIK, KDKFVLMDY, YR KDKFVLM, LMDYLKACKL, VLMDYLKACK, KGYRKDKFVL, RK DKFVLMDY | LUAD |
| LACTB | c.13A>C | p.M5L | MYRL[p.M5L]LSAVTARAAAPGGLASS CGRRGVHQR | LLSAVTARA, RLLSAVTAR, YRLLSAVTA, RLLSAVTARA, LLSA VTARAA, MYRLLSAVTA, LSAVTARAAA | ACC |
| LALBA | c.121G>A | p.A41T | AILAKQFTKCELSQLLKDIDGYGGI[p.A41T]TLPELICTMFHTSGYDTQAIVENNES CGRRGVHQR | TLPELICTM, IDGYGGITL, GYGGITLPEL, TLPELICTMF, ITLPE LICTM | CRC |
| LAMA1 | c.3088G>T | p.D1030Y | NTCDPETGECVCPPHTGGVKCEECE[p.D1030Y]YGHWGYDAEVGCQACNCSL VGSTHHR | GVKCEECEY, CEYGHWGYDA, EECEYGHWGY | LUAD |
| LAMA4 | c.1673C>T | p.A558V | SLSTSADSLTTPRLTLSELDDIIKN[p.A558V]VSGIYAEIDGAKSELQVKLSNLSNLS | ELDDIIKNV, NVSGIYAEI, IIKNVSGIY, DIIKNVSGI, IKNVSGIY A, IIKNVSGIYA, DIIKNVSGIY, KNVSGIYAEI, SELDDIIKNV | CRC |
| LAMA4 | c.1915G>A | p.E639K | NGLVQKALDASNVYENIVNVVSEAN[p.E639K]KTAEFALNTTDRIYDAVSGIDTQ IIY | VNVVSEANK, YVVSEANKTA, EANKTAEFA, SEANKTAEF, IVNY VSEANK, EANKTAEFAL, VSEANKTAEF, SEANKTAEFA | BLCA |
| LAMA4 | c.3879G>A | p.M1293I | PNGLLFYYASGSDVFSISLDNGTVI[p.M1293I]IDVKGIKVQSVDKQYNDGLSHFV ISS | SLDNGTVII, VIIDVKGIK, TVIIDVKGI, VIIDVKGIKV, TVIIDVK GIK, ISLDNGTVII | LUSC |
| LAMA5 | c.6668T>G | p.L2223R | SSMAWARLHRLNASIADLQSQLRSP[p.L2223R]RGPRHETAQQLEVLEQQSTSL GQDAR | QLRSPRGPR, LQSQLRSPR, SPRGPRHET, SQLRSPRGPR, QL RSPRGPRH, DLQSQLRSPR, SPRGPRHETA | KIRP |
| LAMB4 | c.1762G>T | p.G588W | GLAPLGSETFGQSPAVHVVLGEPVP[p.G588W]WNPVTWTGPGFARVLPGAGL RFAVNN | GEPVPWNPV, VVLGEPVPW, HVVLGEPVPW, EPVPWNPVT W | LUAD |
| LAMB4 | c.3715G>T | p.G1239W | EADFKDLRGNVSEIERILKHPVFPS[p.G1239W]WKFLKVKDYHDSVRRQIMQLN EQLKA | VFPSWKFLK, KHPVFPSWK, FPSWKFLKV, HPVFPSWKF, LKH PVFPSW, WKFLKVKDY, PVFPSWKFLK, KHPVFPSWKF, VFPS WKFLKV, SWKFLKVKDY, HPVFPSWKFL, ILKHPVFPSW | LUAD |
| LAMC3 | c.521_522CC>AG | p.P174Q | KRSRADGPWEPYQFYSASCQKTYGR[p.P174Q]QEGQYLRPGEDERVAFCTSEFS DISPL | TYGRQEGQY, YGRQEGQYL, KTYGRQEGQY, TYGRQEGQYL, RQEGQYLRPG | TGCT |
| LARP1 | c.668_669insC | p.A223fs | PRHIPANRGELKGSESATYVPVAPP[p.A223fs]HPSLATRDQTGACLARPG* | APPHPSLAT, SLATRDQTGA, ATYVPVAPPH, ATRDQTGACL, VPVAPPHPSL | STAD |
| LARP4B | c.487del|A | p.T163fs | PENSETGGNESQPDSQEDPREVLKK[p.T163fs]HWNSAYLGRTLLVTCILYHRWI | CILYHRWIV, VLKKHWNSA, YLGRTLLVT, ILYHRWIVT, VTSM CQSQR, AYLGRTLLV, RTLLVTCIL, LYHRWIVTS, SAYLGRTLL, | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| LARS | c.554_555insC | p.P185fs | VTSMCQSQRWLTSTTSRSSALMWT* | RWLTSTTSR, STTSRSSAL, TTSRSSALM, LKKHWNSAY, TLLIV TCILY, HWNSAYLGR, LVTCILYHR, YHRWIVTSM, KKHWNSA YL, NSAYLGRTL, SMCQSQRWL, CQSQRWLTS, SQRWLTSTT, TSRSSQLMW, TSMCQSQRW, SAYLGRTLLV, RTLLVTCILY, L YHRWIVTSM, STTSRSSALM, VLKKHWNSA, LLVTCILYHR, I VTSMCQSQR, EVLKKHWNSA, NSAYLGRTLL, LKKHWNSAY L, WNSAYLGRTL, CQSQRWLTST, SQRWLTSTS, REVLKKH WNS, TTSRSSALMW | KIRC |
| LAT2 | | p.P185fs | MKSLGLSDEEIVKFSEAEHWLDYFP[p.P 185fs]ATGYSGFKKQNGFEGRLASFLHHH * | ATGYSGFKK, RLASFLHHH, GFEGRLASF, FPATGYSGF, LDYF PATGY, FEGRLASFL, WLDYFPATGY, YFPATGYSGF, NGFEG RLASF, AEHWLDYFPA, FKKNGFEGRL | GBM |
| LBX1 | c.53T>G | p.L18W | MSSGTELLWPGAALLVL[p.L18W]WG VAASLCVRCSRPGAKRSEKIYQQR | AALLVLWGV, VLMWGVAASL, LVLWGVAA, GAALLVLWGV, ALLVLWGVAA, LVLWGVAASL, WPGAALLVLW | GBM |
| LCP1 | c.526C>T | p.R176W | SPADRDQIAQQLGLTNAQVITWFQN[p. R176W]WRAKLKRDLEEMKADVESAK KLGPSG | VITWFQNWR, QVITWFQNW, WFQNWRAKL, TWFQNWR AK, ITWFQNWRA, ITWFQNWRAK, QVITWFQNWR, TWFQ NWRAKL, WFQNWRAKLK, NWRAKLKRDL, AQVITWFQNW | CRC |
| LHCGR | c.1334_1335insC | p.P445fs | SDALVIFQLYEKIKVPVDWNRVNKP[p.P 445fs]AIPQTGRQYEEA* | RVNKPAIPQT | KIRC |
| LILRA1 | c.47T>A | p.L16Q | MKQRFSALQLLKLLL[p.L16Q]QLQPPL PRALREALCPEPCNCVPDGA | QLLKLLLQL, LLLQLQPPL, QLQPPLPRA, KLLLQLQPPL, QLQP PLPRAL, LQLLKLLLQL, LQLQPPLPRA | TGCT |
| LILRB1 | c.1228C>T | p.H410Y | SPVTSAHSGTYRCYGSLSSNPYLLS[p.H4 10Y]YPSDSLELMVSGAAETLSPPQNKS DS | SSNPYLLSY, LLSYPSDSL, SYPSDSLEL, YPSDSLELM, NPYLLSY PS, LSSNPYLLSY, YLLSYPSDSL, SYPSDSLELM, LSYPSDSLEL, Y PSDSLELMV | BLCA |
| LILRB5 | c.1417_1419delCTC | p.L479del | GLGRHLGVVIGILVAVILLLLLLLL[p.L479 de|]FLILRHRRQGKHWTSTQRKADFQH PAGA | ILLLLLLLF | BLCA |
| LIM2 | c.1792T>C | p.S598P | TKDRQAEEDRQMDTERVLSPGPQA[p. S598P]PPPPPRSLPLTLPRCRLLHLKPP RM* | APPPPPRSL, PPPPPRSLPL | PRAD |
| LIMK2 | c.448T>A | p.S150T | IMAFAHQPTFSRISRPFSAGIMFFS[p.S1 50T]TTLFVVLALAIVTGVTVSFLGRRFG D | GIMFFSTTL, MFFSTTLFV, FFSTTLFVV, IMFFSTTLF, FSTTLFV VL, STTLFVVLA, TTLFVVLAL, IMFFSTTLFV, MFFSTTLFVV, GI MFFSTTLF, FFSTTLFVVL, FSAGIMFFST, FSTTLFVVLA, STTLF VVLAL, TTLFVVLALA, AGIMFFSTTL | LUAD |
| LIN9 | c.608G>A | p.R203H | TTVQVKEVNRMHISPNNRNAIHPGD[p. R203H]HILEINGTPVRTLRVEEVEDAIS QTS | NAIHPGDHI, HPGDHILEI, AIHPGDHIL, HILEINGTPV | GBM |
| LIN9 | c.547C>T | p.R183W | FCVCLKESFPNLKTRKLTRVEWGKI[p.R 183W]WRLMGKPRRCSSAFFEERSAL KQKR | RVEWGKIWR, IWRLMGKPR, VEWGKIWRL, WGKIWRLMG K, KIWRLMGKPR, IWRLMGKPRR, VEWGKIWRLM | UCEC |
| LINGO2 | c.691G>A | p.E231K | QKRQKIRLLQQRKVADVSQFKDLPD[p. E231K]KIPLPLVIGTKVTARLRGVHDGL FTG | SQFKDLPDK, LPDKIPLPL, KDLPDKIPL, VSQFKDLPDK, SQFK DLPDKI, FKDLPDKIPL, LPDKIPLPLV | CESC |
| LIPJ | c.1228C>A | p.P410T | PDTIRERSFKDFHSTALSFYFTCKK[p.P4 10T]TKIREKKLQHLLVDEGQTVQLECSA D | KTKIREKKL, FTCKKTKIR, FYFTCKKTKI, SFYFTCKKTK, TCKKT KIREK, YFTCKKTKIR | HNSC |
| LIPJ | c.707C>A | p.P236Q | GSKLCPLQIFDKICLNLFMMFGYD[p.P 236Q]QKNLNMSRLDVYFSHNPAGTSV QNML | FMMFGYDQK, DQKNLNMSR, MMFGYDQKN, MMFGYDQ KNL, LFMMFGYDQK, FGYDQKNLNM | LUAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| LLGL2 | c.2864_2865insG | p.P955fs | PRCLVDSAETKNHRPGNGAGPKKAP[p.P955fs]EPSQELRDSE* | KKAPEPSQEL | BLCA |
| LMLN | c.595G>T | p.G199C | PVIVPEHLQQCRVYRGGKWPHGAV[p.G199C]CVPDQEGISDADFVLYVGALATERCS | GKWPHGAVC, GKWPHGAVCV | LUSC |
| LMX1B | c.844_846del|CAG | p.Q285del| | RHQQQQEQQNSQRLGQGEPGPGQL[p.Q285de|]QEVLSSRMEGMMASYTPLAPPQQQIVAM | LQEVLSSRM, GLQEVLSSRM | THCA |
| LOC100132247 | c.1594A>C | p.T532P | ADDNLKTPSERQLTALPPSADDNIK[p.T532P]PPAERLRGPLPPSADDNLKTPSERQL | DNIKPPAER, NIKPPAERLR, PPAERLRGPL | LIHC |
| LOC151174 | c.268C>T | p.P90S | AEGIAMLLGTAGPSRLPAAPDASQA[p.P90S]SLRSPWALSVAAALCSPVSCHPCGRH | SLRSPWALS, APDASQASL, SQASLRSPW, ASLRSPWAL, SLRSPWALSV, SQASLRSPWA, ASQASLRSPW | CESC |
| LOC401296 | c.430C>A | p.L144M | CVLAPGSGSRPTPHIYYSVPAARTC[p.L144M]MGAPGSLSPCHLCVHICAHTYSGTPV | AARTCMGAPG, RTCMGAPGSL, VPAARTCMGA, YSVPAAR TCM | TGCT |
| LOC554223 | c.438_458del|GCGGGCGCCGTGGATGGAGCA | p.RAPWMEQ147del| | LSVGDVDDTQCVRLDSDATSPRMEP[p.RAPWMEQ147de|]EGPEYWEEETGTAKAKAQFYRVNLRTLSGYYNQSEA* | RMEPEGPEY, RMEPEGPEYW | PRAD |
| LOC649330 | c.278G>A | p.G93E | AGEDGRMIASQVVDINLAAEPKVNR[p.G93E]ENAGVKRSAAEMYGSSFDLDYGFQRD | KVNRENAGV, VNRENAGVK, KVNRENAGVK, RENAGVKRSA | SKCM |
| LPHN2 | c.2716T>A | p.F906I | EFIFLIGIDKTKYAIACPIFAGLLH[p.F906I]IFFLAAFAWMCLEGVQLYLMLVEVFE | GLLHIFFLA,LLHIFFLAA,HIFFLAAFA,IFAGLLHIF,IFFLAAFAW,LHIFFLAAF,FAGLLHIFF,GLLHIFFLAA,IFAGLLHIFF,IFFLAAFAWM,CPIFAGLLHI,LLHIFFLAAF,PIFAGLLHIF,HIFFLAAFAW | TGCT |
| LPHN3 | c.2220G>T | p.E740D | FPENMGHGSTIQLSANTLKQNGRNG[p.E740D]DIRVAFVLYNNLGPYLSTENASMKLG | DIRVAFVLY,KQNGRNGDI,RNGDIRVAF,GDIRVAFVL,GRNGDIRVAF,GDIRVAFVLY | LUAD |
| LPHN3 | c.2477G>A | p.R826H | VFTVKHIKQSENFNPNCSFWSYSK[p.R826H]HTMTGYWSTQGCRLLTTNKTHTTCSC | YSKHTMTGY,CSFWSYSKH,HTMTGYWST,FWSYSKHTM,SKHTMTGYW,SFWSYSKHTM,SYSKHTMTGY,WSYSKHTMTG,YSKHTMTGYW | PRAD |
| LPHN3 | c.3548G>A | p.R1183Q | SGSRTPCRYSTCGSQSRIRRMWNDTV[p.R1183Q]QKQSESSFITGDINSSASLNREGLLN | RMWNDTVQK,VQKQSESSF,TVQKQSESSF,RMWNDTVQ,KQ,VQKQSESSFI | CRC |
| LPIN1 | c.2921C>T | p.S974L | SDTFSNFTFWREPLPPFENQDIHSA[p.S974L]LA* | FENQDIHSAL | BLCA |
| LPPR2 | c.556G>T | p.A186S | TDQGACAGSPSLVAAARRAFPCKDA[p.A186S]SLCAYAVTYTAMVTLVFRVKGSRLV | SLCAYAVTY,DASLCAYAV,CKDASLCAY,SLCAYAVTYT,RAFPCKDASL,ASLCAYAVTY,FPCKDASLCA,KDASLCAYAV | ACC |
| LPPR4 | c.1579C>A | p.R527S | LKIQPGAVPGCNNSMPGGPRVSIQS[p.R527S]SPGSSQLVHIPEETQENISTSPKSSS | RVSIQSSPG,IQSSPGSSQ,QSSPGSSQLV,IQSSPGSSQL,SPGSSQLVHI | LUAD |
| LRBA | c.6307G>A | p.E2103K | VSLSTPAQLVAPSVVKGTLSVTSS[p.E2103K]KLYFEVDEEDPNFKKIDPKILAYTEG | LSVTSSKLY,TLSVTSSKL,GTLSVTSSK,TSSKLYFEV,SVTSSKLYF,VTSSKLYFEV,KGTLSVTSSK,TLSVTSSKLY,LSVTSSKLYF | UCEC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| LRCH2 | c.2150A>G | p.D717G | SIHVSPAVPKLSMAKCRRNVENFL[p.D717G]GACKKLGVSQERLCLPHHILEERGLV | FLGACKKLGV | KIRC |
| LRFN5 | c.396C>A | p.N132K | NSNRLTKITNDMFSGLSNLHHLILN[p.N132K]KNQLTLISSTAFDDVFALELDLSYN | ILNKNQLTL, NLHHLILNK, ILNKNQLTLI, SNLHHLILNK, LILNKNQLTL | LUAD |
| LRIG1 | c.70C>G | p.L24V | MARPVRGGLGAPRRSPCLLLLWL[p.L24V]VLLRLEPVTAAAGPRAPCAAACTCAG | LLLLWLVLL, LLMLVLLRL, LVLLRLEPV, LLLWLVLLR, LLLWLV LLRL, WLVLLRLEPV, SPCLLLLWLV | ACC |
| LRIG1 | c.76C>G | p.L26V | MARPVRGGLGAPRRSPCLLLLWLL[p.L26V]VRLEPVTAAAGPRAPCAAACTCAGDS | LLLLWLLLV, LLMLLLVRL, LLLVRLEPV, VRLEPVTAA, CLLLLW LLLV, LLLWLLLVRL, WLLLVRLEPV | ACC |
| LRP1 | c.3172C>A | p.P1058T | TCDGDNDCGDYSDETHANCTNQATR[p.P1058T]TPGGCHTDEFQCRLDGLCIPLRWRCD | ATRTPGGCH, ATRTPGGCHT, TPGGCHTDEF | KIRP, PRAD |
| LRP1 | c.4462_4463insG | p.G1488fs | GSGHMEVLRGHEFLSHPFAVTLYGG[p.G1488fs]GGLLD* | TLYGGGGLL | STAD |
| LRP1 | c.4462delG | p.G1488fs | GSGHMEVLRGHEFLSHPFAVTLYGG[p.G1488fs]RSTGLTGEQTHWLRPTSGPATMSPWYRGPTPSPLTCRCTTPPASPWLPIPVRPMGARAPAPTCVSSTTTGPCPAPAPTS* | WLRPTSGPA, PVRPMGARA, FAVTLYGGR, PATMSPWYR, TTPPASPWL, TTGPCPAPA, RPTSGPATM, PPASPWLPI, RPM GARAPA, YRGPTPSPL, CTTPPASPW, WLPIPVRPM, GPATM SPWY, TLYGGRSTGL, GLTGEQTHWL, TMSPWYRGPT, WYR GPTPSPL, HWLRPTSGPA, GARAPAPTCV, SGPATMSPWY, P FAVTLYGGR, LTGEQTHWLR, CTTPPASPWL, TTTGPCPAPA, SPWYRGPTPS, TPPASPWLPI, LPIPVRPMGA, IPVRPMGAR A, RPMGARAPAP, APAPTCVSST, WLRPTSGPAT, LRPTSGP ATM, TSGPATMSPW, RCTTPPASPW, GEQTHWLRPT | STAD |
| LRP10 | c.15_17delCCT | p.L11del | MLLATLLLL[p.L11del]GGALAHPDRIIFPNHACEDPPAVLLEVQ | TLLLLLGGA | PRAD |
| LRP11 | c.275C>G | p.P92R | QQERPQEELELELRAGGGPQEDCPG[p.P92R]RGSGGYSAMPDAIIRTKDSLAAGASF | RGSGGYSAM, CPGRGSGGY, GRGSGGYSAM | ACC |
| LRP12 | c.928G>T | p.G310C | CTWLIDTGDHRKVILRFTDFKLDGT[p.G310C]CYGDYVKIYDGLEENPHKLLRVLTAF | GTCYGDYVK, KLDGTCYGDY, TDFKLDGTCY, TCYGDYVKIY | TGCT |
| LRP1B | c.10687G>T | p.G3563C | FDCADGSDERNCETSCSKDQFRCSN[p.G3563C]CQCIPAKWKCDGHEDCKYGEDEKSCE | CSNCQCIPAK | LUAD |
| LRP1B | c.4174C>T | p.L1392F | SLRTTLIAGAMEHPRAIALDPRYGI[p.L1392F]FFWTDWDANFPRIESASMSGAGRKTI | RYGIFFWTD, ALDPRYGIF, YGIFFWTDW, DPRYGIFFW, GIFF WTDWDA, IALDPRYGIF, RYGIFFWTDW, FFWTDWDANF, A LDPRYGIFF | UCS |
| LRP2 | c.12117G>C | p.M4039I | FGTCPCPHCRNTKGSYECVCADGFTS[p.M4039I]ISDRPGKRCAAEGSSPLLLLPDNVRI | TSISDRPGK, DGFTSISDR, SISDRPGKR, FTSISDRPGK, TSISDRPGKR | LUAD |
| LRP2 | c.1547C>T | p.A516V | IDMVNLDGSYRVTLITENLGHPRGI[p.A516V]VVDPTVGYLFFSDWESLSGEPKLERA | IVVDPTVGY, LGHPRGIVV, VVDPTVGYLF, IVVDPTVGYL, GI VVDPTVGY, HPRGIWVDPT | LUSC |
| LRP2 | c.2210C>T | p.S737L | IFSSQVAIRGIPFTLSTQEDVMVPV[p.S737L]LGNPSFFVGIDFDAQDSTIFFSDMSK | VLGNPSFFV, VPVLGNPSF, QEDVMVPVL, VPVLGNPSFF, M VPVLGNPSF, TQEDVMVPVL | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| LRP2 | c.7295G>T | p.R2432I | NHSPPFQTINVERTVMSLDYDSVSD[p.R2432I]IYFTQNLASGVGQISYATLSSGIHT | SVSDIIYFT, IIYFTQNLA, DIIYFTANL, LDYDSVSDI, YDSVSDII, DSVSDIIYFT, DIIYFTQNLA, LDYDSVSDII, YDSVSDIIYF, SDIYFTQNL | UCEC |
| LRP2 | c.9127C>T | p.R3043C | CGDYSDERGCLYQTCQQNQFTCQNG[p.R3043C]CCISKTFVCDEDNDCGDGSDELMHLC | CQNGCCISK | CRC |
| LRP5 | c.4825T>C | p.S1609P | LSAEDSCPPSPATERSYFHLFPPPP[p.S1609P]PPCTDSS* | HLFPPPPPPC | PRAD |
| LRP6 | c.2024G>A | p.R675Q | NNNNVAIPLTGVKEASALDFDVTDN[p.R675Q]QIYWTDISLKTISRAFMNGSALEHVV | FDVTDNQIY, QIYWTDISL, NQIYWTDISL, QIYWTDISLK | CRC |
| LRRC16A | c.679G>A | p.D227N | LDHRDLIPIIAALEYNQWFTKLSSK[p.D227N]NLKLSTDVCEQILRVVSRSNRLEELV | KLSSKNLKL, FTKLSSKNLK, TKLSSKNLKL | BLCA |
| LRRC16B | c.2359C>T | p.R787W | AVDKELQVILESMVSLLTQELCPVAM[p.R787W]WVAEGHNKMLSNVAERVTVPRNFIRG | ELCPVAMVV, WVAEGHNKM, QELCPVAMW, AMWVAEGHNK, MWVAEGHNKM, ELCPVAMWVA, WVAEGHNKML, QELCPVAMWV | PRAD |
| LRRC18 | c.652C>T | p.R218W | RRLENLYVVEEKDLCAACLRKCQNA[p.R218W]WDNLNRIKNMATTTPRKTIFPNLISP | NAWDNLNRI, CLRKCQNAW, RKCQNAWDNL | CRC |
| LRRC31 | c.68A>C | p.K23T | RKKTSSEGETKPQTSTVNKFLR[p.K23T]ASNAESRKEDNDLKTSDSQPSDWIQK | FLRASNAES, RASNAESRK, STVNKFLRA, FLRASNAESR | CRC |
| LRRC37A2 | c.305C>G | p.T102S | ELEQPHTQQGPEKLAGNAIYTKPSF[p.T102S]SQEHKAAVSVLTPFSKGAPSTSSPAK | FSQEHKAAV, SQEHKAAVSV | PRAD |
| LRRC37A3 | c.1217C>A | p.A406D | ETPGQPPEHHEVTVSPPGHHQTHHL[p.A406D]DSPSVSVKPPDVQLTIAAEPSAEVGT | HLDSPSVSV, HLDSPSVSVK, QTHHLDSPSV, HQTHHLDSPS | CESC |
| LRRC4 | c.1674del | p.D558fs | KEPAKEWKVLKKKEPPKELRQDPP[p.D558fs]SSRCWAGAW* | SSRCWAGAW, ELRQDPPSSR, RQDPPSSRCW | STAD |
| LRRC7 | c.4166G>A | p.R1389H | VPPDTITKKAGSHIQTLMGSQSLQH[p.R1389H]HSREQQPYEGNINKVTIQQFQSPLPI | HSREQQPYE, SQSLQHHSR, HHSREQQPY, LMGSQSLQHH, QHHSREQQPY | CRC |
| LRRCC1 | c.17C>T | p.A6V | MEAAA[p.A6V]VVVAAEAEVENEDGDSSCGDVCFMDK | VVVAAEAEV, EAAAVVVAA, MEAAAVVVA, AVVVAAEAEV, MEAAAVVVAA | TGCT |
| LRRIQ1 | c.2375G>T | p.W792L | RKRPVKCPANMTPALDKLEILRCGP[p.W792L]LDTLQQVTTVTFQDLPGCVLSTLAEC | LEILRCGPL, GPLDTLQQV, ILRCGPLDTL | LUAD |
| LRRIQ3 | c.732_733insA | p.K244fs | LIVQRWIRGFLVRKNLSPVFFHKKK[p.K244fs]TAGKNY* | KKKTAGKNY, FFHKKKTAGK, HKKKTAGKNY | PRAD |
| LRRT M4 | c.728C>A | p.S243Y | SKINFAHFPRLFNLRSIYLQWNRIR[p.S243Y]YISQGLTWTWSSLHNLDLSGNDIQGI | LQWNRIRYI, RIRYISQGL, YISQGLTWT, RYISQGLTW, YLQWNRIRY, LQWNRIRYI, IYLQWNRIRY, YISQGLTWTW, RIRYISQGLT, LQWNRIRYIS, NRIRYISQGL, IRYISQGLTW | LUAD |
| LRTM2 | c.416C>T | p.S139L | DLTNLTELQLRNNSIRTLDRDLLRH[p.S139L]LPLLRHLDLSINGLAQLPPGLFDGLL | LLRHLPLLR, LPLLRHLDL, DLLRHLPLL, RDLLRHLPLL, RHLPLLRHL, DLLRHLPLLR, LPLLRHLDLS, INGLAQLPPG, RDLLRHLPL, LRHLPLLRHL | BLCA |
| LRTM2 | c.526C>G | p.L176V | GLAQLPPGLFDGLLALRSLSRSNR[p.L176V]VQNLDRLTFEPLANLQLLQVGDNPWE | SLSLRSNRV, VQNLDRLTF, LRSNRVQNL, SLRSNRVQNL, RS NRVQNLDR, RVQNLDRLTF, RSLSLRSNRV | CESC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| LSG1 | c.1550G>T | p.R517L | ITPREDEDPHRPPTSEELLTAYGYM[p.R517L]LGFMTAHGQPDQPRSARYILKDYVSG | LLTAYGYML,TAYGYML,AYGYMLGFM,GYMLGFMTA,YMLGFMTAH,LTAYGYMLGF,YMLGFMTAHG,TAYGYMLGFM,YGYMLGFMTA | LUSC |
| LTA4H | c.319T>C | p.F107L | YKGSPMEISLPIALSKNQEIVIEIS[p.F107L]LETSPKSSALQWLTPEQTSGKEHPYL | EISLETSPK,QEIVIEISL,LETSPKSSA,NQEIVIEISL,LETSPKSSAL | KIRC |
| LTB4R | c.217T>C | p.F73L | QKRSVTALMVLNLALADLAVLLTAP[p.F73L]LFLHFLAQGTWSFGLAGRCLCHYVCG | VLLTAPLFL,LTAPLFLFL,TAPLFLHFL,LAVLLTAPL,TAPLFLHFL,AVLLTAPLF,LTAPLFLHFL,DLAVLLTAPL,LLTAPLFLHF,TAPLFLHFLA,LAVLLTAPLF | TGCT |
| LUC7L3 | c.442T>A | p.S148T | GKNEEKIQVLTDKIDVLLQQIEELG[p.S148T]TEGKVEEAQGMMKLVEQLKEERELLR | IEELGTEGKV | TGCT |
| LUM | c.929G>T | p.R310L | QLEKFDIKSFCKILGPLSYSKIKHL[p.R310L]LLDGNRISETSLPPDMYECLRVANEV | SYSKIKHLL,YSKIKHLLL,SYSKIKHLLL,LSYSKIKHLL | LUSC |
| LUM | c.988C>T | p.R330C | KIKHLRLDGNRISETSLPPDMYECL[p.R330C]CVANEVTLN* | DMYECLCVA,YECLCVANEV | GBM |
| LY9 | c.205A>C | p.I69L | RASGKDSAPTVVSGILGGSVTLPLN[p.I69L]LSVDTEIENVIWIGPKNALAFARPKE | VTLPLNLSV,SVTLPLNLSV | BRCA |
| LYPD4 | c.191C>A | p.T64K | AVAFHNWKWLLMRNMVCKLQEGCEE[p.T64K]KLVFIETGTARGVVGFKGCSSSSSYP | EEKLVFIET,KLQEGCEEKL,KLVFIETGTA,QEGCEEKLVF,CEEKLVFIET | TGCT |
| LYST | c.2130G>T | p.Q710H | DLLWKWDALKAYQNFVEEDRLHSI[p.Q710H]HIANHICNLIQKGNIVVQWKLYNYIF | HIANHICNL,HSIFHIANHI,EEDRLHSIH,HIANHICNL,RLHSIHIANH,FEEDRLHSIH,IHIANHICNL,EEDRLHSIHI | KIRC |
| LZTS1 | c.1294_1341de\|AGGACCCAGGACCGCCCTGCGCACCAAGGGCTGGAGCTG | p.RTQDLEGALRTKGLEL432de\| | AKASEILGLKAQLKDTRGKLEGLEL[p.RTQDLEGALRTKGLEL432de\|]EVCENELQRKKNEAELLREKVNLLEQELQELRAQAALARDMGPPTFPEDVPALQRELRLRAELREERQGHDQ | KLEGLELEV,GKLEGLELEV | PAAD |
| LZTS2 | c.298de\|C | p.P100fs | VPPRKAVPVTSFTYINEDFRTESPP[p.P100fs]AQAVMLRMPESSGHTMPTSAAHHQSSLSLESWRRTWRS* | SSLSLESWR,HTMPTSAAH,SWRRTWRRS,ESWRRTWRR,ESSGHTMPT,SPPAQAVML,MPESSGHTM,AAHHQSSSL,TESPPAQAV,HHQSSLSL,SSSLSLESWR,SLESWRRTW,RMPESSGHTM,SSSLSLESWR,SSLSLESWR,MLRMPESSGH,HTMPTSAAHH,SLESWRRTWR,SAAHHQSSSL,TESPPAQAVM,AHQSSSLSL,HQSSLSLES,QSSSLSLESW,LSLESWRRTW,MPTSAAHHQS | CRC |
| MAEL | c.1033C>T | p.R345C | EAHVPLQDYEASNSVTPKMVLDAG[p.R345C]CYQKLRVGSSGFSHFNSSNEEQRSNT | VLDAGCYQK,MVLDAGCY,DAGCYQKLR,VLDAGCYQKL,VVLDAGCYQK,KMVLDAGCY | CRC |
| MAF | c.158de\|G | p.G53fs | MKFEVKKEPVETDRIISQCGRLIAG[p.G53fs]ARCPPP* | CGRLIAGAR,SQCGRLIAGA,RLIAGARCPP | CLL |
| MAGEC1 | c.1826T>A | p.L609H | PQGEDSLSPHYFPQSPPQGEDSMSP[p.L609H]HYFPQSPLQGEEFQSSLQSPVSICSS | GEDSMSPHY,SMSPHYFPQ,SMSPHYFPQS,QGEDSMSPHY,SPHYFPQSPL,GEDSMSPHYF | CLL |
| MAGEC1 | c.714_716de\|CCC | p.P239de\| | FQSSPERTQSTFEGFAQSPLQIPVS[p.P239de\|]SSSSTLLSLFQSFERTQSTFEGFAQSS | IPVSSSSST,VSSSSSTLL,IPVSSSSSTL | KIRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MAGEE1 | c.1138G>A | p.V380M | SVLPIPGEGLSTVSPPTASDGSDTS[p.V380M]MPPTPGEGASTLVQPTAPDGPGSSVL | ASDGSDTSM, SMPPTPGEGA, TASDGSDTSM | CRC |
| MAGEE2 | c.133del|C | p.Q45fs | GDGRGRBIQATNASGSPTSMLVVDAP[p.Q45fs]SALRRQSTLSVSTLPRPFRTRMTWRS* | MLVVDAPSA, LVVDAPSAL, TLSVSTLPR, VVDAPSALR, VSTLPRPFR, TLPRPFRTR, PFRTRMTWR, SALRRQSTL, LPRPFRTRM, RPFRTRMTW, LRRQSTLSV, RQSTLSVST, QSTLSVSTL, SVSTLPRPF, SMLVVDAPSA, MLVVDAPSAL, ALRRQSTLSV, RQSTLSVSTL, STLSVSTLPR, LVVDAPSALR, VVDAPSALRR, SVSTLPRPFR, STLPRPFRT, RPFRTRMTWR, APSALRRQST, LPRPFRTRMT, LSVSTLPRPF, RRQSTLSVST | STAD |
| MAGI1 | c.3467G>T | p.G1156V | KGFGFSLRGGREYNMDLYVLRLAED[p.G1156V]VPAERCGKMRIGDEILEINGETTKNM | YVLRLAEDV, VPAERCGKM, RLAEDVPAER | LUAD |
| MAGI1 | c.3592C>T | p.R1198C | INGETTKNMKHSRAIELIKNGGRRV[p.R1198C]CLFLKRGDGSVPEYDPSSDRHGPATG | GGRRVCLFL, GRRVCLFLK, GGRRVCLFLK, IKNGGRRVCL, KNGGRRVCLF | CRC |
| MAGI2 | c.1348C>A | p.L450M | LSTTLKKSNMGFGFTIIGGDEPDEF[p.L450M]MQVKSVIPDGPAAQDGKMETGDVIVY | EFMQVKSVI, MQVKSVIPD, DEFMQVKSV, MQVKSVIPDG, DEFMQVKSVI | UCEC |
| MAGI2 | c.3130C>A | p.P1044T | PSSEKQSPMAQQSPLAQQSPLAQPS[p.P1044T]TATPNSPIAQPAPPQPLQLQGHENSY | STATPNSPI, STATPNSPIA, SPLAQPSTAT, QQSPLAQPST | LUAD |
| MAML2 | c.1771C>A | p.Q591K | QANQOMPSVLPSQNKPSLLHYTQQQ[p.Q591K]KQQQQQQQQQQQQQQQQQQQQQQQQ | LLHYTQQQK, SLLHYTQQQI | KIRP |
| MAMLD1 | c.1715A>T | p.Q572L | YLQQPTPTQASSATASSTATATLQL[p.Q572L]LQQQQQQQQPDHSSFLLQQMMQQPQ | STATATLQLL | TGCT, UCS |
| MAMSTR | c.484_485insC | p.P162fs | QPHPRMKPSPLTPCPPGVPSPSPPP[p.P162fs]TQVGTSDP* | SPSPPPTQV | STAD |
| MAN1C1 | c.1291_1292insG | p.G431fs | MEAKNMYYEALEAIETYLLNVSPGG[p.G431fs]ADLHCRVARGDSGPDGAPGLFLRGHDRPWRRGCQGRKEGPLPRARSPDHQDVSRVIRPLRHQTWA* | LLNVSPGGA, RGHDRPWRR, VSRVIRPLR, DGAPGLFLR, DVSRVIRPL, GPDGAPGL, LFLRGHDRPW, QGRKEGPLPR, RARSPDHDRPW, YLLNVSPGGA, LFLRGHDRPW, FLRGHQDV, VSRVIRPLRH, FLRGHDRPWR, DVSRVIRPLR, VIRPLRHQTWLTPPAVPPV, SLTPPAVPPV | STAD |
| MAP1A | c.6187del|C | p.P2063fs | GPTVPPRPEPGPSMEPSLTPPAVPP[p.P2063fs]VLLS* | LTPPAVPPV, SLTPPAVPPV | STAD |
| MAP1B | c.6138G>T | p.E2046D | EGYSYETSTKTTRTPDTSTYCYETA[p.E2046D]DKIIRTPQASTYSYETSDLCYTAEKK | ETADKITRT, STYCYETADK, TYCYETADKI | CRC |
| MAP1S | c.1232C>G | p.S411C | EKMGVGRLDMVLHPPSAGAERTLA[p.S411C]CVCALLVWHPAGPGEKVVRVLFPGCT | RTLACVCAL, LACVCALL, AERTLACVC, RTLACVCALL, TLACVCALLV, LACVCALLVW, AERTLACVCA | ACC |
| MAP2 | c.1590G>T | p.K530N | QAVTDSAMTSKTLEKAMTEPSALIE[p.K530N]NSSIQELFEMRVDDKDKIEGVGAATS | SALIENSSI, IENSSIQEL, IENSSIQELF | CRC |
| MAP2 | c.4414_4415insA | p.K1472fs | EPSTVSRDEVRRKAVYKKAELAKK[p.K1472fs]NRSSGPLSLQEIHFKTCYQIY* | SLQEIHFKT, LSLQEIHFK, KNRSSGPLS, HFKTCYQIY, KKNRSSGPL, NRSSGPLSL, QEIHFKTCY, IHFKTCYQI, KNRSSGPLSL, IHFKTCYQIY, EIHFKTCYQI, AKKNRSSGPL, LQEIHFKTCY | STAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MAP2K1 | c.171G>C | p.K57N | ALQKKLEELELDEQQRKRLEAFLTQ[p.K57N]NQKVGELKDDDFEKISELGAGNGGVV | TQNQKVGEL, TQNQKVGELK, EAFLTQNQKV | CLL |
| MAP2K1 | c.171G>T | p.K57N | ALQKKLEELELDEQQRKRLEAFLTQ[p.K57N]NQKVGELKDDDFEKISELGAGNGGVV | TQNQKVGEL, TQNQKVGELK, EAFLTQNQKV | LUAD |
| MAP2K4 | c.370C>T | p.P124S | IHLEIKPAIRNQIIRELQVLHECNS[p.P124S]SYIVGFYGAFYSDGEISICMEHMDGG | NSSYIVGFY, SYIVGFYGA, VLHECNSSY, HECNSSYIV, CNSSYIVGF, CNSSYIVGFY, VLHECNSSYI, SYIVGFYGAF, SSYIVGFYGA, QVLHECNSSY | SKCM |
| MAP2K4 | c.551C>T | p.S184L | PYIVQPYGALFREGDCWICMELMST[p.S184L]LFDKFYKYVYSVLDDVIPEEILGKIT | MSTLFDKFY, STLFDKFYK, TLFDKFYKY, ELMSTLFDK, LMSTLFDKF, ICMELMSTL, CMELMSTLF, LMSTLFDKFY, STLFDKFYKY, LFDKFYKYV, TLFDKFYKYV, WICMELMSTL, MSTLFDKFYK, ICMELMSTLF, ELMSTLFDKF | BRCA |
| MAP2K4 | c.752G>T | p.S251I | IHRDIKPSNILLDRSGNIKLCDFGI[p.S251I]TGQLVDSIAKTRDAGCRPYMAPERID | IIGQLVDSI, IKLCDFGII, GIIGQLVDSI | BRCA |
| MAP2K4 | c.783_784dele\|AA | p.T261fs | DRSGNIKLCDFGISGQLVDSIAKTR[p.T261fs]CWL* | SIAKTRCWL | BRCA |
| MAP2K4 | c.860G>A | p.R287H | RDAGCRPYMAPERIDPSASRQGYDV[p.R287H]HSDVWSLGITLYELATGRPYPKWNS | DVHSDVWSL, RQGYDVHSDV, QGYDVHSDVW, YDVHSDVWSL | CRC |
| MAP2K5 | c.1334A>G | p.Q445R | VQFNDGNAAVVSMWVCRALEERRSQ[p.Q445R]RGPP* | RALEERRSQR | KIRC |
| MAP3K1 | c.2281_2284de\|ATAG | p.I761fs | LNCILGNQTESNNWQELLGRLCLID[p.I761fs]CCWNFLLNFLILILSVLMFHKLSLLKSGIRSCCPS* | LIDCCWNFL, FLLNFILIL, FILILSVLM, VLMFHKLSL, LMFHKLSLL, KLSLLKSGI, ILSVLMFHK, MFHKLSLLK, CLIDCCWNF, CW NFLLNFI, NFLLNFIL, ILILSVLMF, CCWNFLLNF, WNFLLNFIL, LSVLMFHKL, CLIDCCWNFL, LIDCCWNFLL, FLLNFILILS, LLN FILILSV, ILSVLMFHKL, VLMFHKLSLL, LILSVLMFHK, LMFHK LSLLK, CWNFLLNFIL, NFLLNFLIL, NFILILSVLM, SVLMFFIKL SL, LNFILILSVL, FILILSVLMF, HKLSLLKSGI | BRCA |
| MAP3K1 | c.4036_4038de\|GTT | p.V1346de\| | LFIEWMAGGSVAHLLSKYGAFKESV[p.V1346de\|]INYTEQLLRGLSYLHENQIIHRDVKGAN | SVINYTEQL, AFKESVINY, SVINYTEQLL, KYGAFKESVI, GAFKESVINY, ESVINYTEQL | BRCA |
| MAP3K1 | c.4150_4151insT | p.L1384fs | LHENQIIHRDVKGANLLIDSTGQRL[p.L1384fs]KNCRFWSCSQVGIKRNWCRRVSGTTTGDNCIYGT* | WSCSQVGIK, RLKNCRFWS, GIKRNWCR, VGIKRNWCR, GQRLKNCRF, CRFWSCSQV, SQVGIKRNW, LIDSTGQRLK, RFWSCSQVGI, RLKNCRFWSC, GIKRNWCRRV, GTTTGDNCIY, STGQRLKNCR, QVGIKRNWCR, GQRLKNCRFW | BRCA |
| MAP3K1 | c.953_954insA | p.L318fs | DGFSPYSPEETNRRVNKVMRARLYL[p.L318fs]TAADRA* | VMRARLYLT, RLYLTAADR, RARLYLTAA, MRARLYLTA, VMR ARLYLTA, RLYLTAADRA, KVMRARLYLT, RARLYLTAAD, MR ARLYLTAA | BRCA |
| MAP3K1 | c.971C>T | p.P324L | YSPEETNRRVNKVMRARLYLYLLQQIG[p.P324L]LNSFLIGGDSPDNKYRVFIGPQNCSC | QQIGLNSFL, LYLLQQIGL, LQQIGLNSF, RLYLLQQIGL, QQIGL NSFLI, LIQQIGLNSF, LQQIGLNSFL | GBM |
| MAP3K12 | c.1345_1347de\|AGG | p.R449de\| | KLHFEKIKSEGTCLHRLEEELVMR[p.R449de\|]EELRHALDIREHYERKLERANNLYMELN | LVMRREELR, ELVMRREEL, ELVMRREELR, MRREELRHAL, E ELVMRREEL | STAD |
| MAP3K4 | c.824G>A | p.R275Q | ENTSGFWLNRSNELIWLELQAWHAG[p.R275Q]QTINDQDFFLYTARQAIPDIIN EILT | LQAWHAGQT, QAWHAGQTI, GQTINDQDF, LQAWHAGQ T, QTINDQDFFL, GQTINDQDFF, LELQAWHAGQ | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MAP3K7 | c.1570G>C | p.E524Q | AYLTLDHQLQPLAPCPNSKESMAVF[p.E524Q]QQHCKMAQEYMKVQTEIALLLQRKQE | MAVFQQHCK, AVFQQHCKM, SMAVFQQHCK, QQHCKMA QEY, MAVFQQHCKM, KESMAVFQQH | HNSC |
| MAP4K2 | c.1021C>G | p.R341G | SRGQHGPAERTPSEIQFHQVKFGAP[p.R341G]GRKETDPLNEPWEEEWTLLGKEELSG | QVKFGAPGR, HQVKFGAPG, QVKFGAPGRK, HQVKFGAPGR, APGRKETDPL | TGCT |
| MAP4K3 | c.1970del C | p.P657fs | LFDYARQMQKLPVAIPAHKLPDRIL[p.P657fs]QGNFLYQQKSLKPNGARSVVL* | RILQGNFLY, FLYQQKSLK, KSLKPNGAR, KPNGARSVV, YQQKSLKPN, SLKPNGARSV, NFLYQQKSLK, KPNGARSVVL, GNFLYQQKSL, YQQKSLKPNG, LPDRILQGNF | HNSC |
| MAP7D1 | c.239_240insC | p.A80fs | ATSSKQLPLEPESPSGQVGPPAPP[p.A80fs]AGRVPFL* | RPAPPAGRV, APPAGRVPF, PPAGRVPFL, RPAPPAGRVP, APPAGRVPFL | STAD |
| MAP7D2 | c.1459C>T | p.R487C | ERLEKEEQDRLEREELKRKAEEERL[p.R487C]CLEEEARKQEEERKRQEEEKKKQEGE | RKAEEERLCL, EERLCLEEEA | CRC |
| MAP7D3 | c.922del C | p.Q308fs | PQTKVEESPLEKVETPPKASVDAPP[p.Q308fs]R* | KASVDAPPR | STAD |
| MAP9 | c.1455G>T | p.K485N | QKKAAKREEALASFRAWKAMKEKEA[p.K485N]NKIAAKKRLEEKNKKKTEEENAARKG | AMKEKEANK, KEANKIAAK, KEKEANKIA, AMKEKEANKI, KA MKEKEANK, EANKIAAKKR, KEKEANKIAA | HNSC |
| MAPK1 | c.964G>A | p.E322K | NPHKRIEVEQALAHPYLEQYYDPSD[p.E322K]KPIAEAPFKFDMELDDLPKEKLKELI | YYDPSDKPI, KPIAEAAPPK, QYYDPSDKPI, SDKPIAEAPF, KPIA EAPFKF | CESC, HNSC |
| MAPK13 | c.943G>A | p.E315K | ELDVDKRLITAAQALTHPFFEPFRDP[p.E315K]KEETEAQQPFDDSLEHEKLTVDEWKQ | KEETEAQQPF | BRCA |
| MAPK15 | c.1533del G | p.Q511fs | PPRLPPEARPGRRMFSTSALQGAQG[p.Q511fs]VPGLCLEATPKPTGLSATRHWATCPCWRGTMCEPPYSLHLALCSCPSPFPRPLSSLHPLALPALPGLPKFQGACPGLLGGADEGPAPAPLTSSNKVMSAPN | TMCEPPYSL, PLSSLLHPL, LLHPLALPA, GLSATRHWA, SLHLA LCSC, ALPALPGPL, GLCLEATPK, CSCPSPFPR, KFQGACPGL, RGTMCEPPY, HWATCPCWR, EPPYSLHLA, TPKPTGLSA, PP YSLHLAL, CPSPFPRPL, SPFPRPLSS, FPRPLSSLL, APLTSSNKV, SSLLHPLAL, ALCSCPSPF, LQGAQGVPG, AQGVPGLCL, RH WATCPCW, LKFQGACPG, FQGACPGLL, DEGPAPAPL, CEPP YSLHL, GTMCEPPYSL, SLLHPLALPA, LLHPLALPAL, GLSATRHWAT, ALPALPGPLK, PPPRPLSSLL, KFQGACPGLL, ATRHW ATCPC, TSALQGAQGV, TPKPTGLSAT, EPPYSLHLAL, SPFPR PLSSL, FPRPLSSLLH, RPLSSLLHPL, LPALPGPLKF, APLTSSNK VM, LALCSCPSPF, LQGAQGVPGL, LEATPKPTGL, WRGTMC EPPY, LSSLLHPLAL, LALPALPGPL, LKFQGACPGL, CEPPYSLH LA | STAD |
| MAPK4 | c.298G>A | p.V100M | DNIVKYEVLGPKGTDLQGELFKFS[p.V100M]MAYIVQEYMETDLARLLEQGTLAEEH | LFKFSMAYI, ELFKFSMAY, SMAYIVQEY, MAYIVQEYM, FKFS MAYIV, GELFKFSMA, FSMAYIVQEY, ELFKFSMAYI, SMAYIV QEYM, LQGELFKFSM, GELFKFSMAY, FKFSMAYIVQ | BRCA |
| MAPK7 | c.1502C>A | p.A501D | KAALKAALLKSLRSRLRDGPSAPLE[p.A501D]DPEPRKPVTAQERQREREEKRRRQE | LEDPEPRKPV | KIRP, TGCT |
| MAPK8IP1 | c.651_652insCC | p.L217fs | SSSPLKTGEQTPPHEHICLSDELPP[p.L217fs]PRAAPPPPQIEAPPPTALAAAAQPPRWHLRVVPLLPRLGVGATRIETESTTRPMCD* | RVVPLLPRL, LLPRLGVGA, RLGVGATRI, RWHLRVVPL, RAAP PPPQI, AQPPRWHLR, LAAAAQPPR, EAPPPTALA, APPPTAL AA, PPRWHLRVV, VPLLPRLGV, LPRLGVGAT, IEAPPPTAL, A AQPPRWHL, WHLRVVPLL, DELPPPRAA, ETESTTRPM, QPP RWHLRV, ALAAAAQPPR, HLRVVPLLPR, AAQPPRWHLR, R WHLRVVPLL, CLSDELPPPR, EAPPPTALAA, APPPTALAAA, I | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MAPK APK2 | c.640_641i nsC | p.T214f s | ENLLYTSKRPNAILKLTDFGFAKET[p.T2 14fs]HQPQLFDHSLLYTVLCGSRSAGSR EV* | EAPPPTALA,LAAAAQPPRW,AAAQPPRWHL,LRVVPLLPRL, IETESTTRPM,DELPPPRAAP,QPPRWHLRVV QLFDHSLLY,LLYTVLCGS,QPQLFDHSL,AKETHQPQL,KETH QPQLF,FDHSLLYTV,QLFDHSLLYT,GSRSAGSREV,PQLFDH SLLY,LLYTVLCGSR,TYVLCGSRSA,QPQLFDHSLL,FAKETHQ PQL,AKETHQPQLF,HQPQLFDHSL,FDHSLLYTVL | KIRC |
| 11-Mar | c.578G>T | p.R193 L | PICKICFQGAEQGELLNPCRCDGSV[p.R 193L]LYTHQLCLLKWISERGSWTCELCC YR | VLYTHQLCL,LYTHQLCLL,GSVLYTHQL,VLYTHQLCLL,NPCR CDGSVL | LUAD |
| 5-Mar | c.508C>T | p.R170 C | GLPTIPVMLLIGKMIRWEDYVLRLW[p. R170C]CKYSNKLQILNSIFPGIGCPVPRI PA | RLWCKYSNK,LWCKYSNKL,YVLRLWCKY,DVYLRLWCIK,CK YSNKLQI,RLWCKYSNKL,CKYSNKLQIL | BRCA |
| MARC KS | c.454de|A | p.K152f s | ASSTSSPKAEDGATPSPSNETPKKK[p.K 152fs]RSAPPSRSLSS* | KKRSAFPSR,RSAFPSRSL,SAFPSRSLS,TPKKKRSAF,KKKRSA FPSR,RSAFPSRSLS,KRSAFPSRSL,SAFPSRSLSS | KIRC |
| MARS 2 | c.1442G>A | p.R481 Q | LPKQVADHVDNFRIYKALEAVSSCV[p.R 481Q]QQTNGFVQRHAPWKLNWESP VDAPWL | SCVQQTNGF,VQQTNGFVQ,SSCVQQTNGF,QQTNGFVQR H | HNSC |
| MAS1 L | c.970A>G | p.R324 G | ISLFLIINSSANPIYFFVGSLRKK[p.R324 G]GLKESLRVILQRALADKPEVGRNKKA | GLKESLRVI,GSLRKKGLK,RKKGLKESL,GLKESLRVIL,VGSLR KKGLK | PRAD,THCA |
| MAT2 A | c.497A>G | p.E166 G | YATDETEECMPLTIVLAHKLNAKLA[p.E 166G]GLRRNGTLPWLRPDSKTQVTVQ YMQD | KLNAKLAGL,KLNAKLAGLR,LAGLRRNGTL,GLRRNGTLPW, HKLNAKLAGL | TGCT |
| MAX | c.106A>T | p.R36 W | SDEEQPRFQSAADKRAHHNALERK[p. R36W]MDHIKDSFHSLRDSVPSLQGEK ASRA | RWDHIKDSF,KRWDHIKDSF | MM |
| MAX | c.83A>G | p.H28R | DNDDIEVESDEEQPRFQSAADKRAH[p. H28R]RNALERKKRRDHIKDSFHSLRDSV PSL | RAHRNALER,SAADKRAHR,AHRNALERK,DKRAHRNAL,RA HRNALERK,QSAADKRAHR | UCEC |
| MB21 D2 | c.931C>G | p.Q311 E | EWRLSFARSEVQLKKCISSSLMQAY[p.Q3 11E]EACKAIIIKLLSRPKAISPYHLRS MM | SLMQAYEAC,MQAYEACKA,LMQAYEACK,QAYEACKAI, YEACKAIII,LMQAYEACKA,MQAYEACKAI,SLMQAYEACK,EA CKAIIIKL,QAYEACKAII | HNSC,LUSC |
| MBD6 | c.2194de|C | p.P732f s | SVTTATTDPGASSLGKAPSNSGRPP[p.P 732fs]NSLALCWVPACWTCLH* | SLALCWVPA,SGRPPNSLA,VPACWVTCL,PPNSLALCW,SLA LCWVPAC,ALCWVPACWV,SGRPPNSLAL,NSLALCWVPA, WVPACWVTCL,RPPNSLALCW,LALCWVPACW | STAD |
| MBD6 | c.2338_233 9insG | p.G780 fs | LPSLLQPPGPLLSGQLGLQLLPGGG[p.G 780fs]SSSTPLRGF* | SSSTPLRGF,LLPGGGSSST,LQLLPGGGSS,GSSSTPLRGF | STAD |
| MBOA T2 | c.128G>A | p.R43Q | AVQLPIDQVNFVVCQLFALLAAIWF[p. R43Q]QTYLHSSKTSSFIRHVVATLLGLYL A | LAAIWFQTY,LLAAIWFQT,AIWFQTYLFI,AAIWFQTYL,FQT YLHSSK,LLAAIWFQTY,ALLAAIWFQT,WFQTYLHSSK,LAAI WFQTYL,FQTYLHSSKT | CRC,UCEC |
| MBOA T7 | c.1270C>T | p.R424 W | HWFLKMRAYDYMCMGFVLLSLADTL[p. R424W]WYWASIYFCIHFLALAALGL GLALGG | LSLADTLWY,SLADTLWYW,TLMYWASIY,TLMYWASIYL,W YWASIYFC,DTLMYWASI,LLSLADTLW,LLSLADTLWY,SLAD TLMYWA,LSLADTLWYW,TLMYWASIYF,WYWASIYFCI,DT LWYWASIY,VLLSLADTLW,ADTLWYWASI | HNSC |
| MC5R | c.325G>A | p.A109 T | LVSMSSAWETITIYLLNNKHLVIAD[p.A 109T]TFVRHIDNVFDSMICISVVASMC SLL | HLVIADTFV,LVIADTFVR,KHLVIADTF,TFVRHIDNV,VIADT FVRHI,TFVRHIDNVF,HLVIADTFVR,DTFVRHIDNV,NKHLVI ADTF | UCEC |
| MCF2 L2 | c.2777G>A | p.R926 Q | KTMKLMTLSIRQLGRGSHRKFEIAS[p.R 926Q]QNGLEKYILQAASKEIRDCWFSEI SK | ASQNGLEKY,IASQNGLEK,FEIASQNGL,SQNGLEKYI,IASQ NGLEKY,RKFEIASQNG,SQNGLEKYIL | CRC |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MCHR1 | c.917C>T | p.S306F | QFFLAFALPFVVITAAYVRILQRMT[p.S306F]FSVAPASQRSIRLRTKRVTRTAIAIC | ILQRMTFSV,RMTFSVAPA,RILQRMTFS,LQRMTFSVA,MTFSVAPAS,VRILQRMTF,RILQRMTFSV,ILQRMTFSVA,TFSVAPASQR,YVRILQRMTF,LQRMTFSVAP,QRMTFSVAPA,RMTFSVAPAS | LUSC |
| MCOLN3 | c.421G>A | p.V141I | VYTQSDVYDQLIFAVNQYLQLYNVS[p.V141I]IGNHAYENKGTKQSAMAICQHFYKRG | YLQLYNVSI,NVSIGNHAY,LQLYNVSIG,SIGNHAYENK,QYLQLYNVSI,YNVSIGNHAY | GBM |
| MECOM | c.2744G>A | p.R915Q | SELLQSVPSMFNFRAPPNALPENLL[p.R915Q]QKGKERYTCRYCGKIFPRSANLTRHL | LLQKGKERY,NALPENLLQK | PRAD |
| MECOM | c.2905C>T | p.R969C | TGEQPYRCKYCDRSFSISSNLQRHV[p.R969C]CNIHNKEKPFKCHLCDRCFGQQTNLD | NLQRHVCNI,RHVCNIHNK,LQRHVCNIH,HVCNIHNKEK,CNIHNKEKPF | CRC |
| MED1 | c.107T>G | p.L36R | HRPLKRPRLGPPDVYPQDPKQKEDE[p.L36R]RTALNVKQGFNNQPAVSGDEHGSAKN | QKEDERTAL,KQKEDERTAL,RTALNVKQGF,KEDERTALNV | CLL |
| MED1 | c.130G>A | p.G44S | LGPPDVYPQDPKQKEDELTALNVKQ[p.G44S]SFNNQPAVSGDEHGSAKNVSFNPAKI | KQSFNNQPA,TALNVKQSF,QSFNNQPAV,KQSFNNQPAV,LTALNVKQSF,VKQSFNNQPA | CLL |
| MED1 | c.3670C>T | p.L1224F | IRSSCDRHLLAASQNRIVDGAVFAV[p.L1224F]FKAVFVLGDAELKGSGFTVTGGTEEL | AVFAVFKAV,FAVFKAVFV,AVFKAVFVL,VFAVFKAVF,VDGAVFAVF,AVFAVF,FAVFKAVFVL,AVFAVFKAVF,IVDGAVFAVF | PRAD |
| MED1 | c.3875G>A | p.C1292Y | LCTDKELILDVLSNMQAQKLLQLI[p.C1292Y]YYPHGIKECTEGDNLQRQHIKRILQN | QLIYYPHGI,LIYYPHGIK,AQKLLQLI,AQKLLQLIYY,QKLLQLIYY,QAQKLL QLIY,LQLIYYPHGI,QLIYYPHGIK,AQKLLQLIYY | TGCT |
| MED1 | c.6211C>T | p.P2071S | QDPMRPRQPQVRQQQRLLQMQQPQQ[p.P2071S]SQPQQPPQPQQSSQSQSQTLGLQAMQ | LQMQQPQQS,MQQPQQSQP,LQMQQPQQSQ,MQQPQ QSQPQ | KIRC |
| MED1 | c.6331_6333delCAG | p.Q2115del | LGLQAMQPQQPLFPRQGLQQTQQQQ[p.Q2115del|TTAALVRQLQKQLSSNQPQGVTPYGHPS | QQTQQQQTA,TQQQQTAAL,TQQQQTAALV,LQQTQQQ QTA,QQTQQQQTAA | PRAD |
| MED1 | c.104G>T | p.S35I | WRSTAFRQKLVSQIEDAMRKAGVAH[p.S35I]IKSSKDMESHVFLKAKTRDEYLSLVA | GVAHIKSSK,MRKAGVAHI,AHIKSSKDM,AMRKAGVAHI,MRKAGVAHIK,AGVAHIKSSK | THCA |
| MED16 | c.1347C>G | p.H449Q | TAGPAVHLKAMQLSWTSLALVGIDS[p.H449Q]QGKLSVLRLSPSMGHPLEVGALRHL | DSQGKLSVLR,IDSQGKLSVL,SQGKLSVLRL | KIRP |
| MEF2A | c.295C>T | p.P99S | EPHESRTNSDIVEALNKKEHRGCDS[p.P99S]SDPDTSYVLTPHTEEKYKKINEEFDN | SSDPDTSYV,DSSDPDTSY,DSSDPDTSYV,CDSSDPDTSY | KIRP |
| MEF2A | c.380G>A | p.R127Q | DTSYVLTPHTEEKYKKINEEFDNM[p.R127Q]QNHKIAPGLPPQNFSMSVTVPVTSPN | NMMQNHKIA,MMQNHKIAP,MQNHKIAPG,MQNHKIAPGL,MMQNHKIAPG,EEFDNMMQNH | TGCT |
| MEFV | c.1130G>A | p.R377H | CPRCQDSHERKSPGSLSPQPLPQCK[p.R377H]HHLKQVQLLFCEDHDEPICLICSLSQ | KHHLKQVQL,HHLKQVQLL,HHLKQVQLLF,QPLPQCKHHL,CKHHLKQVQL,KHHLKQVQLL | BRCA |
| MEGF10 | c.3158C>T | p.S1053L | NPYATIKDPPVLIPKSSECGYVEMK[p.S1053L]LPARRDSPYAEINNSTSANRNVYEVE | YVEMKLPAR,LPARRDSPY,KLPARRDSPY,YVEMKLPARR,LPARRDSPYA,SECGYVEMKL | UCEC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MEGF6 | c.1178A>G | p.Y393C | RTCIDVDDCADSPCCQQVCTNNPGG[p.Y393C]CECGCYAGYRLSADGCGCEDVDECAS | CECGCYAGY, NPGGCECGCY | THCA |
| MEGF6 | c.1746_1747insC | p.A582fs | DTFGKNCSFSCSCQNGGTCDSVTGA[p.A582fs]LPLPPGCQWN* | LPLPPGCQW, CDSVTGALPL | KIRC |
| MET | c.3280C>T | p.H1094Y | VVIGPSSLIVHFNEVIGRGHFGCVY[p.H1094Y]YGTLLDNDGKKIHCAVKSLNRITDIG | RGHFGCVYY, HFGCVYYGTL | KIRP |
| MET | c.3749T>C | p.M1250T | LARDMYDKEYYSVHNKTGAKLPVKW[p.M1250T]TALESLQTQKFTTKSDVWSFGVLLWE | KLPVKWTAL, VKWTALESL, TALESLQTQK, AKLPVKWTAL, LPVKWTALES | KIRP |
| METTL15 | c.157C>G | p.Q53E | VWPNRIHTTAEKYREYEAREQTDQT[p.Q53E]EAQELHRSQDRDFETMAKLHIPVMVD | REQTDQTEA | BRCA |
| METTL16 | c.599G>A | p.R200Q | EIIYDRCMCNPPFFANQLEAKGVNS[p.R200Q]QNPRRPPPSSVNTGGITEIMAEGGEL | SQNPRRPPP, SQNPRRPPPS | CRC |
| METTL21A | c.521G>A | p.R174Q | EETFTDLLQTLEHLCSNHSVILLAC[p.R174Q]QIRYERDNNFLAMLERQFTVRKV | ILLACQIRY, LACQIRYER, VILLACQIRY, SVILLACQIR, LLACQIRYER | CRC |
| METTL6 | c.168C>A | p.F56L | DFKQQKLEQEAQKNWDLFYKRNSTN[p.F56L]LFKDRHWTREFEELRSCREFEDQKL | FYKRNSTNL, KRNSTNLF, YKRNSTNLFK, LFYKRNSTNL, FYKRNSTNLF, YKRNSTNLFK, LFKDRHWTTR | CRC |
| METTL9 | c.170A>T | p.Y57F | LYVNMTSGPGGPAAAAGGRKENHQW[p.Y57F]FVCNREKLCESLQAVFVQSYLDQGTQ | QWFVCNREK, NHQWFVCNR, GRKENHQWF, KENHQWFV C, HQWFVCNREK, ENHQWFVCNR | CLL |
| MEX3C | c.1600C>A | p.R534S | IWTPFBPVNPLSGFGSDPSGNMKTQ[p.R534S]SRGSQPSTPRLSPTFPESIEHPLARR | TQSRGSQPS, KTQSRGSQPS, TQSRGSQPST | TGCT |
| MEX3C | c.537_545del e|CGCGGCGGC | p.179_182AAAA>A | IPGGSLGSVLLPAARPDAREAAAAA[p.179_182AAAA>A]GVLYGGDDAQGMMAAMLSHAYGPGGCGAAAAALN | EAAAAAGVL, REAAAAAGV, EAAAAAGVLY, REAAAAAGVL | ACC |
| MFF | c.19_20AG>TT | p.S7F | MSKGTS[p.S7F]FDTSLGRVSRAAPPSPTAAEMAEISRI | TSFDTSLGR, KGTSFDTSL, GTSFDTSLGR, TSFDTSLGRV, SKGTSFDTSL | TGCT |
| MFF | c.484C>T | p.R162C | TTPQNEIRAVGRLKRERSMSENAV[p.R162C]CQNGQLVRNDSLWHRSDSAPRNKISR | RSMSENAVC, SENAVCQNG, NAVCQNGQLV | CRC |
| MFGE8 | c.508G>A | p.D170N | GASRLASHEYLKAFKVAYSLNGHEF[p.D170N]NFIHDVNKHKEFVGNWNKNAVHVNL | SLNGFIEFNF, HEFNFIHDV, SLNGHEFNFI, YSLNGHEFNF, EFNFIHDVNK, HEFNFIHDVN | UCEC |
| MFSD5 | c.839G>A | p.R280Q | FEAWYIHEHVERHDFPAEWIPATFA[p.R280Q]QAAFWNHVLAVVAGVAAEAVASWIGL | WIPATFAQA, AQAAFWNHV, QAAFWNHVL, IPATFAQAA, ATFAQAAFW, FAQAAFWNHV, AQAAFWNHVL, WIPATFAQAA, QAAFWNHVLA, IPATFAQAAF, AEWIPATFAQ | CRC |
| MGA | c.7304G>A | p.R2435Q | WSDKLQKEAEAFAYYRRTHTANERR[p.R2435Q]QRGEMRDLFEKLKITLGLLHSSKVSK | HTANERRQR, NERRQRGEM, RQRGEMRDL, RQRGEMRDLF | OV |
| MGAT4B | c.1330A>C | p.T444P | STSLKTYQHFTLEKAYLREDFWAF[p.T444P]PPAAGDFIRFRFFQPLRLERFFFRSG | FFWAFPPAA, AFPPAAGDF, DFFWAFPPA, FPPAAGDFI, AFPPAAGDFI, WAFPPAAGDF, PPAAGDFIRF, REDFFWAFPP, EDFFWAFPPA | GBM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MGAT 4C | c.1034C>T | p.T345 M | LAQKNVIRFKPSLFQHMGYYSSYKG[p.T 345M]MENKLKDDFEEESPDIPDPP ASLY | SSYKGMENK,SYKGMENKL,GYYSSYKGM,YSSYKGMENK,S YKGMENKLK,MGYYSSYKGM,SSYKGMENKL,MENKLKDD DF | PRAD |
| MGST 2 | c.304de|A | p.K102f s | FATCLGLVIYGRHLYFWGYSEAAK[p.K 102fs]NGSPVSD* | EAAKNGSPV,SEAAKNGSPV | STAD |
| MGST 3 | c.429_430i nsT | p.G143 fs | SIALLGLVGTTVCSARQHLGWVKSG[p. G143fs]FGQWTQMLPLKNYRGLKTLIH FK* | GQWTQMLPL,GLKTLIHFK,QMLPLKNYR,GFGQWTQML, RGLKTLIHF,QWTQMLPLK,PLKNYRGLK,TQMLPLKNY, LPLKNYRGL,HLGWVKSGF,WVKSGFGQW,SGFGQWTQM, KNYRGLKTL,WTQMLPLKN,MLPLKNYRGL,GQWTQMLPLK, RGLKTLIHFK,TQMLPLKNY,GWVKSGFGQW,QHLGWVKS GF,KSGFGQWTQM,SGFGQWTQML,FGQWTQMLPL,LKN YRGLKTL,KNYRGLKTLI,YRGLKTLIHF | KIRC |
| MICA | c.952de|G | p.G318 fs | HPVPSGK[VLVLQSHWQTFHVSAVAA[p. G318fs]LLLFLLLLFSMSVVVRRKHQLQR VQSS* | VSAVAALLF,AVAALLFLL,LLLLFSMSV,LLLFSMSVV,LLFSMS WV,HVSAVAALL,SMSVVVRRK,FSMSVVVRR,ALLFLLLLF, LFLLLLFSM,VVRRKHQLQ,LFSMSVVVR,SAVAALLFL,VVVR RKHQL,FHVSAVAAL,VAALLFLLL,HQLQRVQSS,SAVAALLF LL,AVAALLFLLL,LLFLLLLFSM,FLLLLFSMSV,LLLLFLLLLF,V VRRKHQLQR,HVSAVAALLF,LFSMSVVVR,SVVVRRKHQL, FHVSAVAALL | CESC |
| MIER2 | c.391C>T | p.L131 F | ESEGGDVAPNLPDMTLDKEQIAKDL[p. L131F]FSGEEEETQSSADDLTPSVTSH EAS | KEQIAKDLF | TGCT |
| MKI67 | c.3241C>A | p.R108 1S | REPAGDGKSIRTFKESPKQILDPAA[p.R 1081S]SVTGMKKWPRTPKEEAQSLEDL AGFK | AASVTGMKK,DPAASVTGM,SVTGMKKWPR,AASVTGMK KW | LUAD |
| MKI67 | c.4991_499 2insCA | p.T166 4fs | VGVKEELLAVGKLTQTSGETTHTHT[p.T 1664fs]KSQQEMVRA* | HTKSQQEMV,HTHTKSQQEM,HTKSQQEMVR | STAD |
| MKI67 | c.4992_499 3insCA | p.T166 4fs | VGVKEELLAVGKLTQTSGETTHTHT[p.T 1664fs]QSQQEMVRA* | HTQSQQEMV,THTQSQQEM,HTHTQSQQEM,HTQSQQE MVR | UCEC |
| MKI67 | c.6637C>G | p.H221 3D | AQPLEDIAGLKELFQTPICTDKPTT[p.H 2213D]DEKTKIACRSPQPDPVGTPTIF KPQ | CTDKPTTDEK | CLL |
| MKL1 | c.920de|C | p.P307f s | HHNYQAILPAPPKSAGEALGSSGTP[p.P 307fs]QYAASPLPIAAPARAPLGPVGW HVRTAPH* | PLGPVGWHV,QYAASPLPI,GWHVRTAPH,LGSSGTPQY,YA ASPLPIA,IAAPARAPL,TPQYAASPL,SPLPIAAPA,LPIAAPAR A,ALGSSGTPQY,YAASPLPIA,APARAPLGPV,PQYAASPLP I,ARAPLGPVGW,APLGPVGWHV | STAD |
| MKLN 1 | c.1455C>A | p.F485 L | CMLFHSKNRCLYVFGGQRSKTYLND[p. F485L]LFSYDVDSDHVDIISDGTKKDSG MVP | YLNDLFSYD,TYLNDLFSY,RSKTYLNDL,KTYLNDLFS,SKTYLN DLF,KTYLNDLFSY,YLNDLFSYDV,RSKTYLNDLF | UCEC |
| MKRN 3 | c.1343C>A | p.P448 H | PEGWGDEPPGPGGGSFSAYWHQLVE[p. P448H]HVRMGEGNMLYKSIKKELVV LRLASL | YWHQLVEH,HVRMGEGNM,HQLVEHVRM,AYWHQLVE HV,HVRMGEGNML,YWHQLVEHVR,SAYWHQLVEH,WH QLVEHVRM | LUAD |
| MKRN 3 | c.809G>T | p.G270 V | YYASRGVCFRGESCMYLHGDI[p.G270V]VLQTLHPMDAAQREHMRACI EAHEK | CVLQTLHPM,CDMCVLQTL,MCVLQTLHPM | LUSC |
| MLL2 | c.1939_194 0insC | p.P647f s | ASRLSPPPEDSPMSPPPEESPMSPP[p.P 647fs]T* | EESPMSPPT | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|------|-------------|----------------|---|---|---|
| MLL2 | c.1940del|C | p.P647fs | EASRLSPPPEDSPMSPPPEESPMSP[p.P647fs]HLRYRAYPPCLWCHACLHRLRN LPCPHRLRSLPRPLHLRLHASPHHLRTPP HPHHLRTHLLPHHRRTRSCPCRWRSHP CCHYLRSNSAPGPRGRTCHPGLRSRT CPPGLRSHTYLRRLRSHTCPPSLRSHAY ALCLRSHTCPPRLRDHICPLSLRNCTCPP RLRSRTCLLCLRSHACPPNLRNHTCPPSL RSHACPPGLRNRICPLSLRSHPCPLGLKS PLRSQANALHLRSCPCSLPLGNHPYLPC LESQPCLSLGNHLCPLCPRSCRCPHLGS HPCRLS* | RLHASPHHL,SLRSHAYAL,RLRDHICPL,SLGNHLCPL,RLRSR TCLL,GLRNRICPL,SLRSHPCPL,HLRSCPCSL,HLGSHPCRL,H LRTHLLPH,GLRSHTYLR,RTHLLPHHR,SQANALHLR,RYRAY PPCL,HLRYRAYPP,RLRNLPCPH,RLRSLPRPL,RSLPRPLHL,H LRLHASPH,HLRTPPHPH,RTPPHPHL,RTRSCPCRW,RWR SHPCCH,RSHPCCHYL,HYLRSRNSA,RSRNSAPGP,RGRTCH PGL,RSRTCPPGL,RSHTYLRRL,HTYLRRLRS,RLRSHTCPP,RS HTCPPSL,RSHAYALCL,RSHTCPPRL,RSRTCLLCL,RSHACPP NL,RNHTCPPSL,RSHACPPGL,RNRICPLSL,RSHPCPLGL,RS QANALHL,RSCPCSLPL,SPMSPHLRY,SLPLGNHPY,ESPMSP HLR,PMSPHLRYR,NLPCPHRLR,SLPRPLHLR,LLPHHRRTR,S HAYALCLR,DHICPLSLR,MSPHLRYRA,SPHLRYRAY,LPRPL HLRL,RPLHLRLHA,SPHHLRTPP,HPHHLRTHL,LPHHRRTRS, APGPRGRTC,CPLGLKSPL,LPLGNHPYL,CPRSCRCPH,CPHL GSHPC,YLRSRNSAP,NLRNHTCPP,WRSHPCCHY,RDHICPL SL,LESQPCLSL,EESPMSPHL,PPSLRSHAY,CPPRLRDHI,CPP GLRNRI,ESPMSPHLRY,CSLPLGNHPY,SLPLGNHPYL,SLPRP LHLRL,GLKSPLRSQA,YLPCLESQPC,RLRNLPCPHR,RLRSLP RPLH,RLHASPHHLR,GLRSHTYLRR,RSHAYALCLR,CLRSHT CPPR,SLRNCTCPPR,RSRTCLLCLR,RSHPCPLGLK,RSLPRPL HLR,RTHLLPHHRR,RSHPCCHYLR,RTCHPGLRSR,RSHTCPP SLR,RSHTCPPRLR,CTCPPRLRSR,RSHACPPNLR,RSHACPP GLR,RSAQANALHLR,RYRAYPPCLW,LWCHACLHRL,HLRYR AYPPC,RNLPCPHRLR,HLRLHASPHH,HLRTPPHPHH,RTPP HPHHLR,HLRTHLLPHH,HLLPHHRRTR,RTRSCPCWRR,RSC PCRWRSH,RWRSHPCCHY,RSRNSAPGPR,RGRTCHPGLR, GLRSRTCPPG,RSRTCPPGLR,RSHTYLRRLR,HTYLRRLRSH,R LRSHTCPPS,SLRSHAYALC,RLRDHICPLS,RLRSRTCLLC,RN HTCPPSLR,SLRSHACPPG,GLRNRICPLS,RNRICPLSLR,SLRS HPCPLG,KSPLRSQANA,MSPHLRYRAY,SPMSPHLRYR,CL WCHACLHR,CPHRLRSLPR,HPCCHYLRSR,HACPPGLRNR,L PCPHRLRSL,RPLHLRLHAS,SPHHLRTPPH,HPHHLRTHLL,L PHHRRTRSC,PPRLRSRTCL,SPLRSQANAL,CPRSCRCPHL,Y LRSRNSAPG,YLRRLRSHTC,HAYALCLRSH,LRYRAYPPCL,R AYPPCLWCH,HRLRSLPRPL,LRSLPRPLHL,LHLRLHASPH,LR LHASPHHL,LRTPPHPHL,HHLRTHLLPH,WRSHPCCHYL,C HYLRSRNSA,LRSHTYLRRL,LRSHTCPPSL,LRSHAYALCL,LRS HTCPPRL,LRNCTCPPRL,LRSHACPPNL,LRNHTCPPSL,LRSH ACPPGL,LRNRICPLSL,LSLRSHPCPL,LRSQANALHL,SQANA LHLRS,LHLRSCPCSL,LRSCPCSLPL,LSLGNHLCPL,CPPGLRS HTY,CPPSLRSHAY | STAD |
| MLL2 | c.1966del|C | p.L656fs | EDSPMSPPPEESPMSPPPEVSRLSP[p.L656fs]CLWCHACLHRLRNLPCPHRLRSL PRPLHLRLHASPHHLRTPPHPHHLRTHL LPHHRRTRSCPCRWRSHPCCHYLRSRN SAPGPRGRTCHPGLRSRTCPPGLRSHTY LRRLRSHTCPPSLRSHAYALCLRSHTCPP RLRDHICPLSLRNCTCPPRLRSRTCLLCL RSHACPPNLRNHTCPPSLRSHACPPGLR | RLHASPHHL,SLRSHAYAL,RLRDHICPL,SLGNHLCPL,RLRSR TCLL,GLRNRICPL,SLRSHPCPL,HLRSCPCSL,HLGSHPCRL,H LRTHLLPH,GLRSHTYLR,RTHLLPHHR,SQANALHLR,RLRNL PCPH,RLRSLPRPL,RSLPRPLHL,HLRLHASPH,HLRTPPHPH, RTPPHPHL,RTRSCPCRW,RWRSHPCCH,RSHPCCHYL,HY LRSRNSA,RSRNSAPGP,RGRTCHPGL,RSRTCPPGL,RSHTYL RRL,HTYLRRLRS,RLRSHTCPP,RSHTCPPSL,RSHAYALCL,RS HTCPPRL,RSRTCLLCL,RSHACPPNL,RNHTCPPSL,RSHACP | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| | | | NRICPLSLRSHPCPLGLKSPLRSQANALH LRSCPCSLPLGNHPYLPCLESQPCLSLGN HLCPLCPRSCRCPHLGSHPCRLS* | PGL, RNRICPLSL, RSHPCPLGL, RSQANALHL, RSCPCSLPL, SL PLGNHPY, NLPCPHRLR, SLPRPLHLR, LLPHHRRTR, SHAYAL CLR, DHICPLSLR, EVSRI, PCL, LPRPLHLRL, RPLHLRLHA, SPH HLRTPP, HPHHLRTHL, LPHHRRTRS, APGPRGRTC, CPLGLKS PL, LPLGNHPY, CPRSCRCPH, CPHLGSHPC, YLRSRNSAP, NL RNHTCPP, VSRLSPCLW, WRSHPCCHY, RDHICPLSL, LESQP CLSL, PPSLRSHAY, CPPRLRDHI, CPPGLRNRI, CSLPLGNHPY, RLSPCLWCHA, SLPLGNHPYL, SLPRPLHLRL, GLKSPLRSQA, Y LPCLESQPC, RLRNLPCPHR, RLRSLPRPLH, RLHASPHHLR, GL RSHTYLRR, RSHAYALCLR, CLRSHTCPPR, SLRNCTCPPR, RSR TCLLCLR, RSHPCPLGLK, RSLPRPLHLR, RTHLLPHHRR, RSHP CCHYLR, RTCHPGLRSR, RSHTCPPSLR, RSHTCPPRLR, CTCP PRLRSR, RSHACPPNLR, RSHACPPGLR, RSQANALHLR, LWC HACLHRL, RNLPCPHRLR, HLRLHASPHH, HLRTPPHPHH, RT PPHPHHLR, HLRTHLLPHH, HLLPHHRTR, RTRSCPCRWR, R SCPCRWRSH, RWRSHPCCHY, RSRNSAPGPR, RGRTCHPGL R, GLRSRTCPPG, RSRTCPPGLR, RSHTYLRRLR, HTYLRRLRSH, RLRSHTCPPS, SLRSHAYALC, RLRDHICPLS, RLRSRTCLLC, R NHTCPPSLR, SLRSHACPPG, GLRNRICPLS, RNRICPLSLR, SL RSHPCPLG, KSPLRSQANA, CLWCHACLHR, CPHRLRSLPR, H PCCHYLRSR, HACPPGLRNR, LPCPHRLRSL, RPLHLRLHAS, S PHHLRTPPH, HPHHLRTHLL, LPHHRRTRSC, PPRLRSRTCL, S PLRSQANAL, CPRSCRCPHL, YLRSRNSAPG, YLRRLRSHTC, H AYALCLRSH, HRLRSLPRPL, LRSLPRPLHL, LHLRLHASPH, LRL HASPHHL, LRTPPHPHHL, HHLRTHLLPH, WRSHPCCHYL, CH YLRSRNSA, LRSHTYLRRL, LRSHTCPPSL, LRSHAYALCL, LRSH TCPPRL, LRNCTCPPRL, LRSHACPPNL, LRNHTCPPSL, LRSHA CPPGL, LRNRICPLSL, LSLRSHPCPL, LRSQANALHL, SQANAL HLRS, LHLRSCPCSL, LRSCPCSLPL, LSLGNHLCPL, CPPGLRSH TY, CPPSLRSHAY | |
| MLL2 | c.7061delC | p.P235 4fs | APLTPRASQVEPQSPGLGLRPQEPP[p.P 2354fs]LPRLWHLLLQVTQTSFALAPTL THMLSPH* | RLWHLLLQV, ALAPTLTHM, LQVTQTSFA, VTQTSFALA, QVT QTSFAL, QTSFALAPT, LPRLWHLLL, LLQVTQTSF, GLRPQEP PL, TQTSFALAP, TSFALAPTL, FALAPTLTH, RLWHLLLQVT, LAPTLTHML, LLQVTQTSFA, LQVTQTSFAL, LLLQVTQTSF, Q VTQTSFALA, QTSFALAPTL, RPQEPPLPRL, FALAPTLTHM, TQTSFALAPT | STAD |
| MLL3 | c.1066C>A | p.Q356 K | IDQAPERSKEDANCAVCDSPGDLLD[p. Q356K]KFFCTTCGQHYHGMCLDIAVT PLKRA | LLDKFFCTT, SPGDLLDKF, SPGDLLDKFF | LUAD |
| MLL3 | c.1179C>A | p.N393 K | GMCLDIAVTPLKRAGWQCPECKVCQ[p. N393K]KCKQSGEDSKMLVCDTCDKGY HTFCL | KCKQSGEDSK | LUAD |
| MLL3 | c.13488del T | p.F449 6fs | TSGCHRPRCTNIYHFTCAIKAQCMF[p.F 4496fs]LRTKLCFAPCTNQREFMSKN* | FLRTKLCFA, AIKAQCMFL, AQACMFLRTK, MFLRTKLCF, RTKL CFAPC, CFAPCTNQR, AIKAQCMFLR, KAQCMFLRTK, CTNQ REFMSK, CMFLRTKLCF, RTKLCFAPCT, FLRTKLCFAP, AQCM FLRTKL, FAPCTNQREF | STAD |
| MLL5 | c.197A>G | p.Y66C | YPHQLYTSSSHHSHSYIGLPYADHN[p.Y 66C]CGARPPTPPASPPPSVLISKNEVG I | LPYADHNCGA | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MLXIPL | c.2368A>C | p.S790R | NWKFWFSILIRPLFESFNGMVSTA[p.S790R]RVHTLRQTSLAWLDQYCSLPALRPTV | STARVHTLR, RVHTLRQTS, GMVSTARVH, VSTARVHTL, STARVHTL, VSTARVHTLR, RVHTLRQTSL, SFNGMVSTAR | KIRC |
| MMAA | c.976C>T | p.R326C | RIQAEYVSALKLLRRSQVWKPKVI[p.R326C]CISARSGEGISEMDKMKDFQDLMLA | CISARSGEGI | CRC |
| MMP3 | c.190del|A | p.I64fs | ENYYDLKKDVKQFVRRKDSGPVVKK[p.I64fs]SEKCRSSLDWR* | KSEKCRSSL, KCRSSLDWR, KKSEKCRSSL, SEKCRSSLDW | STAD |
| MMRN1 | c.2751C>A | p.F917L | QALQLQVLNSRFKALEAKSIHLSIN[p.F917L]LFSLNKTLHEVLTMCHNASTSVSELN | HLSINLFSL, NLFSLNKTL, SINLFSLNK, KSIHLSINLF, KSIHLSINL, LSINLFSLNK, KSIFHLSINLF, AKSIHLSINL, IHLSINLFSL | UCEC |
| MMRN1 | c.3037G>T | p.A1013S | RSLPGSLANVKSQKQVKSLPKKIN[p.A1013S]SLKKPTVNLTTVLIGRTQRNTDNIIY | SLPKKINSL, SLKKPTVNL, KSLPKKINS, LPKKINSLK, SLPKKINS LK, KSLPKKINSL, KINSLKKPTV | LUAD |
| MMS19 | c.3013G>A | p.D1005N | ALTRLPTPVLLPYKPQVIRALAKPL[p.D1005N]NDKKRLVRKEPAVSARGEWFLLGSPGS | ALAKPLNDK, LAKPLNDKK, RALAKPLNDK, ALAKPLNDKK | TGCT |
| MN1 | c.1415C>T | p.S472L | APPYMNVAKRPRFDFPGSAGVDRCA[p.S472L]LWNGSMHNGALDNHLSPSAYPGLPGE | RCALWNGSM | BLCA |
| MOCOS | c.2545T>C | p.S849P | NQHVFQKLSESRETKVNFGMYLMHA[p.S849P]PLDLSSPCFLSVGSQVLPVLKENVEG | GMYLMHAPL, YLMHAPLDL, FGMYLMHAPL, YLMHAPLDLS, MYLMHAPLDL, APDLSSPCF, LMHAPLDLSS | KIRC |
| MOCS2 | c.65del|C | p.P22fs | MSSLEISSSCFSLETKLPLSP[p.P22fs]H* | LETKLPLSPH | STAD |
| MOGAT2 | c.197_198insG | p.Q66fs | TRFWLLTVLYAAWYLDRDKPRQGGI[p.Q66fs]PAHPGHQVLDYMEVHEGLFPHLAGQDC* | HQVLDYMEV, GLFPHLAGQ, DYMEVHEGL, KPRQGGPAH, GPAHPGHQV, RQGGPAHPG, DYMEVHEGLF, HPGHQVLDY, EVHEGLFPH, HEGLFPHLA, DYMEVHEGLF, EVHEGLFPHL, GPAHPGHQVL, RQGGPAHPGH, AHPGHQVLDY, HQVLDYM EVH, LDYMEVHEGL, MEVHEGLFPH, HPGHQVLDYM | LUAD |
| MORC1 | c.337G>T | p.D113Y | KRLSTLKFIGQYGNGLKSGSMRIGK[p.D113Y]YFILFTKKEETMTCVFFSQTFCEEES | SMRIGKYFI, RIGKYFILF, KYFILFTKK, SGSMRIGKY, MRIGKYF IL, GSMRIGKYF, IGKYFILFTK, MRIGKYFILF, GSMRIGKYFI, S MRIGKYFIL, KSGSMRIGKY, SGSMRIGKYF | CRC |
| MORC2 | c.2219G>A | p.R740H | SDSAGEDSADLKRAQKDKGLHVEV[p.R740H]HVNREWYTGRVTAVEVGKHVVRWKVK | VEVHVNREW, HVNREWYTGR, VEVHVNREWY | CRC |
| MPDZ | c.2410C>A | p.L804I | VRIGVAKPLPLSPEEGVSAKEDSF[p.L804I]IYPPHSCEEAGLADKPLFRADLALVG | SAKEDSFIY, KEDSFIYPP, VSAKEDSFIY, YVSAKEDSFI | CRC |
| MPDZ | c.4745del|A | p.K1582fs | KLTIHAENPDSQAVPSAAGAASGEK[p.K1582fs]RTAPSL* | GEKRTAPSL | STAD |
| MPRIP | c.1052del|C | p.A351fs | SSDTRQGRSEKRAFPPKRDFTNEAP[p.A351fs]QLLSQTPRLPPCLHTEEPSHWTGGPRSPP* | FTNEAPQLL, QLLSQTPRL, SQTPRLPPC, RDFTNEAPQL, SQT PRLPPCL, CLHTEEPSHW, NEAPQLLSQT | STAD |
| MR1 | c.137C>T | p.S46L | DSRTHSLRYFRLGVSDPIHGVPEFI[p.S46L]LVGYVDSHPITTYDSVTRQKEPRAPW | VPEFILVGY, GVPEFILVGY, VPEFILVGYV | CRC |
| MRPL47 | c.700C>A | p.L234I | LRLEREKRARIKARKENLERKKAKI[p.L234I]ILKKFPHLAEFAQKSSLV* | ILKKFPHLA, RKKAKIILK, IILKKFPHL, KAKIILKKF, RKKAKIILKK, KIILKKFPHL, LERKKAKIIL, KKAKIILKKF | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MRPS25 | c.355_357de|GAG | p.E119del | SNKEIMEHIRKILGKNEETLREEE|p.E119de|]KKQLSHPANFGPRKYCLRECICEVEGQV | REEEEKKQL | TGCT |
| MS4A4A | c.295G>A | p.V99M | ALMSLSMGITMMCMASNTYGSNPISM|V99M]MYIGYTIWGSVMFIISGSLSIAAGIR | ISMYIGYTI, TYGSNPISM, SMYIGYTIW, MYIGYTIWG, YGSNPISMY, NPISMYIGY, ISMYIGYTIW, MYIGYTIWGS, TYGSNPISMY, NTYGSNPISM | BRCA |
| MS4A8B | c.8C>T | p.S3L | MN[p.S3L]LMTSAVPVANSVLVVAPHNGYPVTPG | NLMTSAVPV, LMTSAVPVA, NLMTSAVPVA, MNLMTSAVPV | CRC, UCEC |
| MSH4 | c.1392G>T | p.K464N | KNCNTPLLRAYYGSLEDKRFGIILE|p.K464N]NIKTVINDDARYMKGCLNMRTQKCYA | IILENIKTV, RFGIILENI, GIILENIKTV, RFGIILENIK, KRFGIILENI | CRC |
| MSH4 | c.2188G>A | p.E730K | YVPAEYSSFRIAKQIFTRISTDDDI[p.E730K]KTNSSTFMKEMKEIAYILHNANDKSL | KTNSSTFMK, KTNSSTFM | UCEC |
| MSH6 | c.1727A>C | p.D576A | GHTRAYGCVFDTSLGKFFIGQFSD[p.D576A]ARHCSRFRTLVAHYPPVQVLFEKGNL | FSDARHCSR, DARHCSRFR, GQFSDARHC, SDARHCSRF, FSDARHCSRF, KFFIGQFSDA, FFIGQFSDAR, QFSDARHCSR, GQFSDARHCS, ARHCSRFRTL | TGCT |
| MSH6 | c.3254_3255insC | p.T1085fs | LANYSRGGDGPMCRPVILLPEDTPP[p.T1085fs]LLRA* | LLPEDTPPL, LPEDTPPLL, ILLPEDTPPL, LLPEDTPPLL | CRC, STAD |
| MSH6 | c.3284G>A | p.R1095H | GDGPMCRPVILLPEDTPPFLELKGS[p.R1095H]HHPCITKTFFGDDFIPNDILIGCEEE | GSHHPCITK, KGSHHPCITK, ELKGSHHPCI, SHHPCITKF, LELKGSHHPC | CRC |
| MSLNL | c.202A>C | p.T68P | MTSARRRTDVGPRVAFTYPCTQLSP[p.T68P]PRAHRHLPVHTVTYPCTQLSPTRAHS | QLSPPRAHR, SPPRAHRHL, TQLSPPRAH, PPRAHRHLPV | PRAD |
| MST1 | c.1304de|A | p.N435fs | AETPHKPQFTFTSEPHAQLEENFCR[p.N435fs][TQMGIAMGPGATRWTQGPHSTTVPCDAALMTSRHQSWTPQTRCSLRSVARGWIGWISGVPSCAWLGAIRATHPGQSACGIGRASISAGGL* | GWIGWISGV, WISGVPSCA, RTQMGIAMG, QTRCSLRSV, RCSLRSVAR, AIRATHPGQ, HQSWTPQTR, HPGQSACGI, EENFCRTQM, CRTQMGIAM, SLRSVARGW, ISGVPSCAW, RATHPQQSA, SLRSVARGWI, SVARGWIGWI, QTRCSLRSVA, RGWIGWISGV, AIRATHPGQS, WTPQTRCSLR, VPSCAWLGAI, FCRTQMGIAM, LEENFCRTQM, CSLRSVARGW, RSVARGWIGW, WISGVPSCAW | KIRP |
| MTG1 | c.1390A>G | p.M464V | FNGLLGPVQVTALYVTRLDNVTVAH[p.M464V]VGTMDGRILQVELVRSLNLLYVSNF | VTVAHVGTM, RLDNVTVAHV | KIRC |
| MTG1 | c.315de|A | p.L105fs | LNKMDLADLTEQQKIMQHLEGEGLK[p.L105fs]MSFLPTV* | HLEGEGLKM, LKMSFLPTV, GEGLKMSFL, GLKMSFLPTV, LEGEGLKMSF | STAD |
| MTG1 | c.981de|C | p.H327fs | DFLQTFRRGLLGSVMLDLDVLRGH[p.H327fs]RLRLCPELVRVGRAGGMWPPRPPDLGG* | RLCPELVRV, RLRLCPELV, RAGGMWPPR, MWPPRPPDL, VLRGHPRLR, RGHPRLRLC, LVRVGRAGG, HPRLRLCPE, RVGRAGGMW, GMWPPRPPDL, RLRLCPELVR, VLRGHPRLRL, LVRVGRAGGM, DLDVLRGHP, DVLRGHPLR, HPRLRLCPEL | STAD |
| MTIF2 | c.326de|A | p.N109fs | STKSKKVVEVWIGMTIEELARAMEK[p.N109fs]TQIMYMKLY* | AMEKTQIMY, KTQIMYMKL, RAMEKTQIM, TQIMYMKLY, MEKTQIMYM, KTQIMYMKLY, RAMEKTQIMY, MEKTQIMY, MK, ARAMEKTQIM, AMEKTQIMYM | STAD |
| MTMR9 | c.577de|A | p.K193fs | DEALRKVATFRHGGRFPVLSYHKK[p.K193fs]MGW* | SYHKKMGW, VLSYYHKKM, LSYYHKKMGW | KICH |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MTOR | c.4379T>C | p.L146 0P | YAMKHFGELEIQATWEKLHEWEDA[p. L1460P]PVAYDKKMDTNKDDPELML GRMRCLE | APVAYDKKM,HEWEDAPVA,KLHEWEDAPV,HEWEDAPV AY | KIRC |
| MTOR | c.4448G>T | p.C148 3F | DALVAYDKKMDTNKDDPELMLGRMR[p. C1483F]FLEALGEWGLHQQCCEK WTLVNDET | LMLGRMRFL,RFLEALGEW,LGRMRFLEA,RMRFLEALG,EL MLGRMRF,GRMRFLEAL,MLGRMRFLEA,RMRFLEALGE LMLGRMRFL,LGRMRFLEAL,MRFLEALGEW | KIRC |
| MTOR | c.6644C>A | p.S221 5Y | EDLRQDERVMQLFGLVNTLLANDPT[p. S2215Y]YLRKNLSIQRYAVIPLSTNSGLI GWV | LLANDPTYL,LANDPTYLR,TYLRKNLSI,TLLANDPTY,TLLAN DPTYL,LLANDPTYLR,LANDPTYLRK,NTLLANDPTY,YLRKNL SIQR | UCEC |
| MTUS 2 | c.3013C>T | p.R100 5W | YPKQRTAAARNGFPPKPDPQAREAE[p. R1005W]WQLVLRLKERCEQQTRQLGV AQGELK | EAEWQLVLR,REAEWQLVL,AEWQLVLRL,DPQAREAEW,A EWQLVLRLK | STAD |
| MUC1 6 | c.15355C>T | p.P511 9S | LPNFSSTSDKILATSKDSKDTKEIF[p.P51 19S]SSINTEETNVKANNSGHESHSPAL AD | DTKEIFSSI,KEIFSSINT,KDTKEIFSSI | SKCM |
| MUC1 6 | c.18466G>A | p.A615 6T | PDISPEASSSHSNSPPLTISTHKTI[p.A61 56T]TTQTGPSGVTSLGQLTLDTSTIATS A | TTQTGPSGV,ITTQTGPSGV | STAD |
| MUC1 6 | c.25817G>A | p.R860 6H | ESISSSPHPVTALLTLGPVKITDML[p.R8 606H]HTSSEPETSSPPNLSSTSAEILATS E | MLHTSSEPET | CRC |
| MUC1 6 | c.31355_31 356insC | p.P104 52fs | GIMEHITKIPNEAAHRGTIRPVKGP[p.P 10452fs]SDIHFACQS* | RPVKGPSDI,VKGPSDIHF | KICH |
| MUC1 6 | c.33014C>T | p.T110 05I | VLPEVPGMVTSLVASSRAVTSTTLP[p.T H005I]ILTLSPGPETTPSMATSHGAE ASST | AVTSTTLPI,LPILTLSPG,RAVTSTTLPI | CLL |
| MUC1 6 | c.33778C>G | p.P112 60A | IDSWVAHPGTEASSVVPTLTVSTGE[p.P 11260A]AFTNISLVTHPAESSSTLPRTTS RFS | STGEAFTNI,EAFTNISLV,LTVSTGEAF,GEAFTNISL,TLTVST GEAF,GEAFTNISLV | KIRC |
| MUC1 6 | c.34782C>A | p.N115 94K | YEPETTATWLTHPAETSTTVSGTIP[p.N 11594K]KFSHRGSDTAPSMVTSPGVDT RSGVP | TTVSGTIPK,GTIPKFSHR,STTVSGTIPK,TTVSGTIPKF | LUSC |
| MUC1 6 | c.38321G>A | p.R127 74H | SGCRLTLLRSEKDGAATGVDAICTH[p.R 12774H]HLDPKSPGVDREQLYWELSQL TNGIK | HLDPKSPGV,AICTHHLDPK | HNSC |
| MUC1 7 | c.13244G>A | p.R441 5H | LVYGLVGAGVVLMLIIVALLMLVF[p.R44 15H]HSKREVKRQKYRLSQLYKWQEE DSGP | LLMLVFHSK,VFHSKREVK,LMLVFHSKR,MLVFHSKREV, ALLMLVFHSK,LVFHSKREVK,HSKREVKRQK,LLMLVFHSKR,VF HSKREVKR | BRCA |
| MUC1 7 | c.229G>A | p.V77 M | CQQLSQHVRTGSAANTATGTTSTNV[p. V77M]MEPRMYLSCCSTNPEMTSIESSV TSDT | NVMEPRMYL,TSTNVMEPR,MEPRMYLSC,STNVMEPRMY, TTSTNVMEPR,NVMEPRMYLS,ATGTTSTNVM | GBM |
| MUC1 7 | c.3680_368 1insC | p.R122 7fs | PTAEVTSMPTSTPGERSTPLTSMPV[p. R1227fs]STHASGQF* | TSMPVSTHA,VSTHASGQF,MPVSTHASG,LTSMPVSTHA, MPVSTHASGQ | KIRC |
| MUC1 7 | c.3683de lA | p.H122 8fs | TAEVTSMPTSTPGERSTPLTSMPVR[p. H1228fs]PRQWPVLRLAPFQHLPLTPA HL* | FQHLPLTPA,HLPLTPAHL,LTSMPVPR,PVRPRQWPV,RPR QWPVLR,RQWPVLRLA,WPVLRLAPF,LRLAPFQHL,LAPFQ HLPL,RLAPFQHLPL,VLRLAPFQHL,QWPVLRLAPF,PVRPR QWPVL,MPVRPRQWPV,RPRQWPVLRL,FQHLPLTPAH,TS MPVRPRQW,RQWPVLRLAP | KIRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MUC17 | c.6836C>A | p.T2279N | STEATSSPTTAEGTSIPTSTLSEGT[p.T2279N]NPLTSIPVSHTLVANSEVSTLSTTPV | TLSEGTNPL, TLSEGTNPLT, GTNPLTSIPV, STLSEGTNPL, SEG TNPLTSI, NPLTSIPVSH | TGCT |
| MUC2 | c.4703C>T | p.T1568M | TTTVTPTPTGTQTPTTPITTT[p.T1568M]MVTPTPTPTGTPTSTPITTTTTVT | TTPITTTM, TPITTTMV, TTTTMVTPT, TTMVTPTPT, MVTPTPT, TTTPITTTTM, TTPITTTTMV, TMVTPTPTPT, TPITTTTMVT | TGCT |
| MUC2 | c.4739C>A | p.T1580N | TQTPTTTPITTTTTVTPTPTPTGTQ[p.T1580N]NPTSTPITTTTVTPTPTPTGTQTPT | TQNPTSTPI, TQNPTSTPIT | TGCT |
| MUC2 | c.4745C>G | p.T1582R | TPTTTPITTTTTVTPTPTPTGTQTP[p.T1582R]RSTPITTTTTVTPTPTPTGTQTPTTT | TQTPRSTPI, GTQTPRSTPI, TPRSTPITTT | KIRP |
| MUC2 | c.4790C>T | p.T1597I | TPTPTGTATPTSTPITTTTTVTPTP[p.T1597I]IPTGTQTPTTTPITTTTTVTPTPTPT | TTTVTPTPI, TTTTVTPTPI, TTVTPTPTPT, | TGCT |
| MUC2 | c.5111C>T | p.T1704I | TTTTVTPTPTGTQTPTSTPITT[p.T1704I]ITTVTPTPTGTQTPTPTSTTTTT | TTITTVTPT, TPITTITTV, STPITTITTV, TPITTTTTVT, TPTSTPITTI | TGCT |
| MUC2 | c.5117C>T | p.T1706M | TTTVTPTPTGTQTPTSTPITTN[p.T1706M]MVTPTPTGTQTPTPTSTTT | TPITTTMV, TTTTMVTPT, TTMVTPTPT, MVTPTPTPT, STPI TTTTMV, TSTPITTTTM, TMVTPTPTPT, TPITTTMVT | TGCT |
| MUC2 | c.5143G>A | p.G1715S | PTGTQTPTSTPITTTTVTPTPTPT[p.G1715S]STQTPTPTPISTTTTVTPTPTPTGT Q | STQTPTPTPI | TGCT |
| MUC2 | c.5165C>T | p.T1722I | TSTPITTTTVTPTPTGTQTPTP[p.T1722I]IPISTTTTVTPTPTGTQTPTTTPI | IPISTTTTV, TQTPTPIPI, TPIPISTTT, TPIPISTTT, IPISTTTTVT | KIRP |
| MUC5B | c.2041A>G | p.S681G | YMGIFLVIETHGMAVSMDRKTSVFI[p.S681G]GLHQDYKGRVCGLCGNFDDNAI NDFA | KTSVFIGLH, FIGLHQDYK, VFIGLHQDY, RKTSVFIGL, GLHQD YKGRV, VFIGLHQDYK, SVFIGLHQDY | ACC |
| MUC5B | c.2045A>G | p.D682G | MGIFLVIETHGMAVSMDRKTSVFIR[p.D682G]RHQDYKGRVCGLCGNFDDNAINDFAT | FIRRHQDYK, KTSVFIRRH, VFIRRHQDY, VFIRRHQDYK, SVFI RRHQDY | ACC, KIRP |
| MUC6 | c.4707_4708insA | p.P1569fs | ITPNPTSTRTRPTPVAHTNSATSSRP[p.P1569fs]TTTLHHTLPTYREQSLLFHRSHD GNILQDHHYLSNPITPSDHTSHSRSTFL HLFGDSKYSHSHHPYPCTDGHFCLHPL NANRHDSSTDNAQGHRVHPHSANND ADHQRDQPSPELIKHSQNLYIPTFTHFL HTPC* | CTDGHFCLH, YLSNPITPS, YIPTFTHFL, FLHLFGDSK, CLHPLN ANR, TYREQSLLF, SRSTFLHLF, KYSHSHHPY, SQNLYIPTF, LYIPTFTHF, SSRPTTTLH, TSHSRSTFL, HSRSTFLHL, RSTFLH LFG, RVHPHSANN, TLHHTLPTY, LHLFGDSKY, LIKHSQNLY, FTHF LHTPC, LPTYREQSL, HPHSANNDA, ELIKHSQNL, HTSHSRST F, TSSRPTTTL, HRSHDGNIL, GNILQDHHY, HHYLSNPIT, SKY SHSHHP, AQGHRVHPH, IKHSQNLYI, HPYPCTDGH, IPTFTH FLH, TTLHHTLPTY, STDNAQGHRV, LIKHSQNLYI, TLHHTLPT YR, TSHSRSTFLH, TFLHLFGDSK, PTYREQSLLF, HSRSTFLHLF, HSQNLYIPTF, NLYIPTFTHF, LYIPTFTHFL, ATSSRPTTTL, SSR PTTTLHH, HTSHSRSTFL, RVHPHSANND, HQRDQSPEL, FL HLFGDSKY, SKYSHSHHPY, ELIKHSQNLY, RPTTTLHHTL, LPT YREQSLL, HPYPCTDGHF, EQSLLFHRSH, FHRSHDGNIL, SHS RSTFLHL, HLFGDSKYSH, YSHSHHPYC, KHSQNLYIPT, SQN LYIPTFT, YPCTDGHFCL, REQSLLFHRS, QDHHYLSNPI, IPTFT HFLHT | KIRC |
| MUC6 | c.5930C>A | p.P1977H | AHTTSASSRLPTPFTTHSPPTGSS[p.P1977H]HFSSTGPMTATSFQTTTYPTPS HPQ | SHFSSTGPM, SSHFSSTGPM, HSPPTGSSHF, SHFSSTGPMT | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MUC6 | c.6000C>G | p.H200 0Q | SSPFSSTGPMTATSFQTTTYPTPS[p.H2000Q]QPQTTLPTHVPPFSTSLVTPSTHTVI | TPSQPQTTL, SQPQTTLPT, SQPQTTLPTH, QPQTTLPTHV | TGCT |
| MUC6 | c.6387_6389del CTC | p.2129_2130S S>S | SPITTQLPHLSSATTPVSTTNQLSS[p.2129_2130SS>S]FSPSPSAPSTVSSYVPSSHSSPQTSSPS | STTNQLSSF, NQLSSFSPS, VSTTNQLSSF, NQLSSFSPSP | STAD |
| MUC7 | c.1007C>T | p.S336 L | PNSSPTTLAPDTSETSAAPTHQTTT[p.S336L]LVTTQTTTTKQPTSAPGQNKISRFLL | APTHQTTTL, HQTTTLVT, LVTTQTTTTK, APTHQTTTLV, HQTTTLVTTQ | UCEC |
| MVK | c.412del C | p.P138f s | YLSICRKQRALPSLDIVVWSELPPG[p.P138fs]RAWAPAPPTRCVWQPS* | RAWAPAPPT, APAPPTRCV, SELPPGRAW, RAWAPAPPTR, VVWSELPPGR, WAPAPPTRCV, LPPGRAWAPA, APAPPTRCVW, SELPPGRAWA | STAD |
| MXRA5 | c.970G>T | p.D324 Y | EEDGGSQLILEKFQLPQWSISLNMT[p.D324Y]YEHGNMVNLVCDIKKPMDVYKIHLNQ | WSISLNMTY, MTYEHGNMV, NMTYEHGNM, YEHGNMVNL, NMTYEHGNMV, TYEHGNMVNL, QWSISLNMTY, LNMTYEHGNM, YEHGNMVNLV | LUAD |
| MYB | c.1443del A | p.R481f s | ESSLDPPKVLPPARHSTIPLVILRK[p.R481fs]NGARPAP* | VILRKNGAR, ILRKNGARPA, LVILRKNGAR | STAD |
| MYBPC2 | c.1937G>A | p.R646 H | TNPVGEDVASIFLQWDVPDPPEAV[p.R646H]HITSVGEDWAILVWEPPMYDGGKPVT | PEAVHITSV, VPDPPEAVHI | UCEC |
| MYD8 | c.719T>C | p.M24 0T | TCVWSIASELIEKRLARRPRGGCRR[p.M240T]TVVVVSDDYLQSKECDFQTKFALSLS | TVVVVSDDY, RPRGGCRRT, RTVVVVSDDY, TVVVVSDDYL, RPRGGCRRTV | CLL |
| MYD8 | c.752G>A | p.S251 N | EKRLARRPRGGCRRMVVVVSDDYLQ[p.S251N]NKECDFQTKFALSLSPGAHQKRLIPI | YLQNKECDF, VVSDDYLQNK, NKECDFQTKF | DLBCL |
| MYD8 | c.818T>C | p.L273 P | YLQSKECDFQTKFALSLSPGAHQKR[p.L273P]PIPIKYKAMKKEFPSILRFITVCDYT | HQKRPIPIK, RPIPIKYKA, QKRPIPIKY, AHQKRPIPIK, QKRPIPIKY, HQKRPIPIKY, SPGAHQKRPI, RPIPIKYKAM | CLL, DLBCL |
| MYEF2 | c.967A>G | p.K323 E | LFDRPMHVKMDDKSVPHEEYRSHDG[p.K323E]ETPQLPRGLGGIGMGLGPGGQPISAS | ETPQLPRGL, RSHDGETPQL, GETPQLPRGL | TGCT |
| MYEOV | c.807del G | p.L269f s | CSTWGLPLRVAGSWLTVVTVEALGG[p.L269fs]GAWELGGLARWGPLCTHPQCQVLLLSSTTSSSSSSSSLVEDVLCAKWFICPASFNPQNDSMR* | ALGGGAWEL, SLVEDVLCA, GLARWGPLC, LVEDVLCAK, KWFICPASF, SSSSSSSLV, CAKWFICPA, DVLCAKWFI, HPQCQVLLL, VEALGGGAW, WELGGLARW, CQVLLLSSS, SFNPQNDSM, SLVEDVLCAK, SSSSSSSSLV, SFNPQNDSMR, VTVEALGGGA, EALGGGAWEL, LARWGPLCTH, CQVLLLSSST, AKWFICPASF, ASFNPQNDSM, WELGGLARWG | STAD |
| MYEOV | c.905T>A | p.L302 H | RRTGQVGPTMHPPPVSGASPLLLHH[p.L302H]HLLLLLILTC* | LLLHHLLLL, LLHHHLLLL, SPLLLHHHL, LHHHLLLLL, LLLHHHL, LLL, LLHHHLLLL, SPLLLHHHL, LHHHLLLLLI, HHHLLLLLII | TGCT |
| MYH10 | c.3271_3272insC | p.L109 1fs | MISDLEERLKKEEKTRQELEKAKRK[p.L1091fs]PRRGDDRPAGPDRRAAGAD* | KAKRKPRRG, RPAGPDRRA, KPRRGDDRPA, RPAGPDRRAA | LUAD |
| MYH1 | c.2977G>A | p.E993 K | EEEAARQKLQLEKVTAEAKIKKLED[p.E993K]KILVMDDQNNKLSKERKLLEERISDL | KLEDKILVM, KKLEDKILVM | HNSC |
| MYH1 | c.3787_3789del AAG | p.K126 3del | KENADLAGELRVLGQAKQEVEHKKK[p.K1263del]LEAQVQELQSKCSDGERARAELNDKVHK | VEHKKKLEA, KQEVEHKKKL | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MYH3 | c.931G>A | p.D311N | HIFYQIMSNKKPELIDLLLLISTNPF[p.D311N]NPFPFVSQGEVTVASIDDSEELLATDN | LISTNPFNF,STNPFNPF,TNPFNFPFV,NPFNFPFVS,STNPF NFPFV,LLISTNPFNF,ISTNPFNFPF | CRC |
| MYH4 | c.2369C>T | p.T790M | TKVFFKAGLLGTLEEMRDEKLAQLI[p.T790M]MRTQAICRGFLMRVEFRKQME RRESI | KLAQLIMRT,QLIMRTQAI,IMRTQAICR,AQLIMRTQA,DEK LAQLIM,LIMRTQAICR,IMRTQAICRG,RDEKLAQLIM,AQLI MRTQAI,MRTQAICRGF | LUAD |
| MYH6 | c.2540C>T | p.T847M | AFMGVKNWPWMKLYFKIKPLLKSAE[p.T847M]MEKEMATMKEEFGRIKETLEK SEARR | LLKSAEMEK,KPLLKSAEM,KSAEMEKEM,AEMEKEMAT,E MEKEMATM,IKPLLKSAEM,LKSAEMEKEM,AEMEKEMAT M | BRCA |
| MYH7 | c.4459G>A | p.A1487T | ESQSELESSQKEARSLSTELFKLKN[p.A1487T]TYEESLEHLETFKRENKNLQEEISD L | TYEESLEHL,ELFKLKNTY,LKNTYEESL,KLKNTYEESL,NTYEES LEHL,TELFKLKNTY | KIRP |
| MYH7 | c.5065C>T | p.R1689C | NDDLKENIAIVERRNNLLQAELEEL[p.R1689C]CAVVEQTERSRKLAEQELIETSE RVQ | AELEELCAV,EELCAVVEQ,AELEELCAVV,EELCAVVEQT | CRC |
| MYH8 | c.2354C>T | p.A785V | KFGHTKVFFKAGLLGLLEEMRDEKL[p.A785V]VQIITRTQAVCRGFLMRVEYQK MLQR | KLVQIITRT,VQIITRTQA,DEKLVQIIT,VQIITRTQAV,EMRDE KLVQI | TGCT |
| MYH8 | c.3016C>A | p.H1006N | LTEEMAGLDETIAKLSKEKKALQET[p.H1006N]NQQTLDDLQAEEDKVNILTKAK TKLE | LQETNQQTL,ALQETNQQTL | LUAD |
| MYH8 | c.3143G>A | p.R1048Q | LTKAKTKLEQQVDDLEGSLEQEKKL[p.R1048Q]QMDLERAKRKLEGDLKLAQES TMDME | KLQMDLERA,LEQEKKLQM,LQMDLERAK,QEKKLQMDL,K LQMDLERAK | CRC |
| MYH8 | c.3349C>T | p.R1117C | NLISKIEDEQAVEIQLQKKIKELQA[p.R1117C]CIEELGEEIEAERASRAKAEKQRS DL | KIKELQACI,KKIKELQAC,KKIKELQACI,KELQACIEEL | LUAD |
| MYO18A | c.627del|C | p.P209fs | PRPGHRSRAPELVTKFPVDLRLPP[p.P209fs]WCPCPHLPSGSWSCNDGPLETL ASPCGAQPCWIGAPRARPVGVWSTLL SLVQAPRTWPWGWCQEIDWWRLMG TMWRASPGMRLWR* | GVWSTLLSL,RLMGTMWRA,TMWRASPGM,VWSTLLSLV, VQAPRTWPW,WWRLMGTMW,RARPVGVWS,GTMWRA SPG,MWRASPGMR,QPCWIGAPR,CWIGAPRAR,LLSLVQA PR,ETLASPCGA,CPHLPSGSW,APRARPVGV,RPVGVWSTL, SLVQAPRTW,QEIDWWRLM,WRASPGMRL,RASPGMRL W,LPPWCPCPH,SPCGAQPCW,WPWGWCQEI,GVWSTLL SLV,WIGAPRARPV,TMWRASPGMR,TLLSLVQAPR,RASPG MRLWR,TWPWGWCQEI,DWWRLMGTMW,MWRASPG MRL,RARPVGVWST,GTMWRASPGM,WWRLMGTMWR, FPVDLRLPPW,APRARPVGVW,RPVGVWSTLL,GSWSCND GPL,VGVWSTLLSL,LSLVQAPRTW,LVQAPRTWPW,CQEID WWRLM,IDWWRLMGTM,WRASPGMRLW,LETLASPCGA, LPPWCPCPHL | STAD |
| MYO1D | c.326C>T | p.T109M | AAYKAMKRRSKDTCIVISGESGAGK[p.T109M]MEASKYIMQYIAAITNPSQRAEV ERV | GAGKMEASK,AGKMEASKY,GKMEASKYI,KMEASKYIM,SG AGKMEASK,GAGKMEASKY,MEASKYIMQY,GKMEASKYI M,GESGAGKMEA | GBM |
| MYO1D | c.736G>A | p.E246K | LQKSLSSYNYIHVGAQLKSSINDAA[p.E246K]KFRVVADAMKVIGFKPEEIQTVY KIL | KSSINDAAK,SINDAAKFR,KFRVVADAM,DAAKFRVVA,SSI NDAAKF,SINDAAKFRV,SSINDAAKFR,AAKFRVVADA,KFR VVADAMK,KSSINDAAKF,AKFRVVADAM | CRC |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MYO3A | c.1573A>C | p.N525H | AVVGAQISEYLLEKSRVIHQAIGEK[p.N525H]HFHIFYYIYAGLAEKKKLAHYKLPEN | AIGEKHFHI,IGEKHFHIF,KHFHIFYYI,HFHIFYYIY,HQAIGEK HF,GEKHFHIFY,EKHFHIFYY,HFHIFYYIA,IGEKHFHIFY,GE KHFHIFYY,KHFHIFYYI,QAIGEKHFHI,IHQAIGEKHF,AIGEK HFHIF | CRC |
| MYO3A | c.1574A>G | p.N525S | AVVGAQISEYLLEKSRVIHQAIGEK[p.N525S]FHIFYYIYAGLAEKKKLAHYKLPEN | AIGEKSFHI,KSFHIFYYI,GEKSFHIFY,SFHIFYYIY,HQAIGEKS F,IGEKSFHIF,EKSFHIFYY,KSFHIFYYI,SFHIFYYIA,IGEKSF HIFY,GEKSFHIFY,QAIGEKSFHI,IHQAIGEKSF,HQAIGEKSF H,AIGEKSFHIF | KIRC,OV |
| MYO5A | c.1214C>T | p.A405V | KLVTTSETYVKTMSLQQVINARNAL[p.A405V]VKHIYAQLFGWIVEHINKALHTSLKQ | VINARNALV,LVKHIYAQL,RNALVKHIY,VKHIYAQLF,ALVKH IYAQL,QVINARNALV,VINARNALVK,RNALVKHIYA,LVKHI YAQLF,ARNALVKHIY | BRCA |
| MYO5B | c.2123G>T | p.R708L | VLETIRISAAGYPSRWAYHDFNRY[p.R708L]LVLVKKRELANTDKKAICRSVLEN LI | FFNRYLVLV,DFNRYLVL,FNRYLVLVK,HDFNRYLIV,AYHD FFNRYL,HDFNRYLVL | LUAD |
| MYO5B | c.2742_2743insA | p.Q914fs | EQIQKEYDALVKSSEELLSALQKKK[p.Q914fs]TAGRGSRKAEAYSRRNGKGKKK T* | KTAGRGSRK,LQKKKTAGR,GSRKAEAYS,EAYSRRNGK,YSR RNGKGK,RGSRKAEAY,KTAGRGSRKA,GSRKAEAYSR,AYSR RNGKGK,YSRRNGKGKK | GBM |
| MYO6 | c.3538G>A | p.D1180N | IPARQREIEMNRQQRFFRIPFIRPA[p.D1180N]NQYKDPQSKKKGWWYAHFDG PWIARQ | FIRPANQYK,IPFIRPANQY | CRC |
| MYO7B | c.6119C>A | p.P2040H | KQTSEPSYPDVLIIAINRHGVLLIH[p.P2040H]HKTKDLLTTYPFTKISSWSSGSTYF H | VLLIHHKTK,LLIHHKTKDL,GVLLIHHKTK,RHGVLLIHHK,HKT KDLLTTY | LUAD |
| MYO9A | c.500G>A | p.R167Q | QPQQKDFDDLCSLPDLNEKTLLENL[p.R167Q]QNRFKHEKIYTYVGSILIVINPFKF L | LQNRFKHEK,TLLENLQNR,LLENLQNRF,KTLLENLQNR,TLL ENLQNRF,LQNRFKHEKI | CRC |
| MYO9A | c.6536G>A | p.R2179Q | FLRAMGLQERKETIRGVYSVIDQLS[p.R2179Q]QTHLNTLERLIFHLVRIALQEDT NRM | SVIDQLSQT,QTHLNTLER,LSQTHLNTL,QLSQTHLNTL | CRC |
| MYO9B | c.281G>T | p.R94L | KESGGEWVLDANDSPVHRVLLWPR[p.R94L]LAQDEHPQEDGYYFLLQERNAD GTIK | RVLLWPRLA,HRVLLWPRL | LUAD |
| MYOD | c.1478C>T | p.T493M | AGSLPDTFNDASPSFGLHPSPVHVC[p.T493M]MEEESLMSSLNGGSVPSELDGLD SEKD | HPSPVHVCM,MEEESLMSSL,CMEEESLMSSL,VHVCMEESLM | HNSC |
| MYOD | c.678del|C | p.G226fs | ENDRNDSASQPSHQSDAGKQGLGPP[p.G226fs]APP* | GKQGLGPPA | STAD |
| MYOC | c.910_912del|CAG | p.Q310del | AYARLLQQQQLFLQLQILSQQQQQQ[p.Q310del|]HRFSYLGMHQAQLKEPNEQ MVRNPNSSS | SQQQQQQHRF | PRAD |
| MYOF | c.495_496insG | p.G165fs | PGMGGDGEEDEGDEDRLDNAVRGPG[p.G165fs]AQGASWDGVGSSACSEAH QSKEQPADAVK* | GPGAQGASW,SACSEAHQSK,AVRGPGAQGA | LUAD |
| MYOM1 | c.188G>A | p.R63Q | VYTQGSTAYSSRSSAAHRRESEAFR[p.R63Q]QASASSSQQQASQHALSSEVSRK AAS | AFRQASASS,RESEAFRQA,SEAFRQASA,RQASASSSQ,AFR QASASSS,RESEAFRQAS,RQASASSSQQ,SEAFRQASAS | HNSC |
| MYOM2 | c.2962G>A | p.D988N | DHSKYLYLKNPDKEDLGTYSVSVSDT[p.D988N]NGVSSSFVLDPEELERLMALSNEI KN | VSVSDTNG,DTNGVSSSF,NGVSSSFVL,SVSVSDTNG,DT NGVSSSFV,SDTNGVSSSF | CESC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| MYOZ2 | c.751G>A | p.E251K | LSGRRSFNRTPKGWISENIPIVITT[p.E251K]KPTDTTVPESEDL* | TTKPTDDTTV | CRC |
| MYT1 | c.676G>A | p.E226K | AAEGAASEEGEKGLFIQPEDAEEVV[p.E226K]KVTTERSQDLCPQSLEDAASEESSKQ | EVVKVTTER, AEEVVKVTT | CRC |
| MYT1L | c.1052C>A | p.P351Q | SLECLRNQCFDLARKLSETNPQERN[p.P351Q]QQQNMNIRQHVRPEDFPGRTPDRNY | QERNQQQNM, QQQNMNIRQH | LUAD |
| N4BP2L2 | c.1516C>T | p.R506C | STKNKRKRKRIFNLVPNFDLLGQS[p.R506C]CIGVKEREKCDLLTKNHGLKITLGEE | LLGQSCIGV, FDLLGQSCI, LLGQSCIGVK | UCEC |
| NAA1 | c.551C>A | p.T184K | RRQMDLKKGGTVVLGSRENQETQGS[p.T184K]KLSDSEEACQQKNPATEESGSDSKEP | NQETQGSKL | LUAD |
| NAA16 | c.1542del T | p.H514fs | CISAYQRLGRYGDALKKCHEVERHF[p.H514fs]LR* | HEVERHFLR | STAD |
| NAA25 | c.2420C>A | p.S807Y | DIYELDTSGLEDTMEIQERIENSFK[p.S807Y]YLLDQLKDVFSKCKGDLLEVKDGNLK | YLLDQLKDV, RIENSFKYL, IENSFKYLL, KYLLDQLKDV, YLLDQLKDVF, SFKYLLDQLK, QERIENSFKY, NSFKYLLDQL | CRC |
| NAB1 | c.216G>C | p.L72F | EEFLEIMALVGMASKPLHVRRLQKA[p.L72F]FRDWVTNPGLFNQPLTSLPVSSIPIY | RLQKAFRDW, HVRRLQKAF, LQKAFRDWV, RLQKAFRDWV, HVRRLQKAFR, LHVRRLQKAF, RRLQKAFRDW, LQKAFRDWVT | LUAD |
| NANOS3 | c.548C>T | p.S183L | KTQDTGHRRGGGGAGPRGAGKSEP[p.S183L]LPSCSPSMST* | RGAGKSEPL, EPLPSCSPSM, FRGAGKSEPL | HNSC |
| NAP1L3 | c.1058C>G | p.P353R | MIQKYDEPILKFLSDVSLKFSKPGQ[p.P353R]RVSYTFEFHFLPNPYFRNEVLVKTYI | RVSYTFEFH, PGQRVSYTF, QRVSYTFEF, SKPGQRVSY, RVSYTFEFHF, SLKFSKPGQR, FSKKPGQRVSY, KPGQRVSYTF, GQRVSYTFEF, LKFSKPGQRV | TGCT |
| NAP1L4 | c.854_855CC>AA | p.P285Q | VTVKTIKKQHKGRGTVRTITKQV[p.P285Q]ONESFFNFNPLKASGDGESLDEDSEF | VQNESFFNF, KQVQNESFF, TKQVQNESF, QVQNESFFNF, V QNESFFNFF, ITKQVQNESF, TKQVQNESFF | SKCM |
| NAPSA | c.362G>A | p.R121Q | DTGSSNLWVPSRRCHFFSVPCWLHH[p.R121Q]QFDPKASSSFQANGTKFAIQYGTGRV | WLHHQFDPK, VPCWLHHQF, HQFDPKASS, WLHHQFDPKA, CWLHHQFDPK, SVPCWLHHQF, QFDPKASSSF, HQFDPKASSS | UCEC |
| NARS | c.719C>G | p.P240R | AFLTVSGQLHLEVMSGAFTQVFTFG[p.P240R]RTFRAENSQSRRHLAEFYMIEAEISF | FTFGRTFRA, FTQVFTFGR, VFTFGRTFR, QVFTFGRTF, QVFTFGRTFR, AFTQVFTFGR, TQVFTFGRTF | BRCA |
| NAT10 | c.1178T>C | p.I393T | IQYIHPADAVKLGQAELVVIDEAAA[p.I393T]TPLPLVKSLLGPYLVFMASTINGYEG | AAATPLPIV, AATPLPLVK, LGQAELVVID, EAAATPL, IDEAAAA TPL, DEAAATPLP, VIDEAAATPL, AAATPLPLVK, EAAATPLPL V, TPLPLVKSLL, DEAAATPLPL | TGCT |
| NBPF1 | c.2428G>A | p.E810K | SSSHVEWEDAVHIIPENESDDEEEE[p.E810K]KKGPVSPRNLQESEEEEVQESWDEG | KKGPVSPRNL | MM |
| NBPF14 | c.73C>T | p.R25C | MVVSAGPWSSEKAEMNILEINEKL[p.R25C]CPQLAENKQQFGNLKERCFVTQLAGF | KLCPQLAENK | PAAD |
| NBPF16 | c.1347del T | p.D449fs | RELLDEKEPEVLQDSLLDRCYSTPSD[p.D449fs]ILNCLT* | RCYSTPSDI, TPSDILNCL, STPSDILNCL, RCYSTPSDIL | PAAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| NBPF3 | c.1472A>T | p.D491V | QEEEDQGPPCPRLSRELPEVVEPE[p.D491V]VLQDSLDRWYSTPFSYPELPDSCQPY | LPEVVEPEV, ELPEVVEPEV | KIRC |
| NCAM2 | c.2092G>T | p.G698C | GYSEPTVYEFSMPPKPNIIKDTLFN[p.G698C]CLGLGAVIGLGVAALLLIVVTDVSC | DTLFNCLGL, TLFNCLGLGA, IIKDTLFNCL, KDTLFNCLGL | LUAD |
| NCAPD2 | c.659G>T | p.R220L | VSLVTGCCYRLLENPTINHQKNRPT[p.R220L]LEAITHLLGVALTRYNHMLSATVKII | TLEAITHLL, KNRPTLEAI, LEAITHLLG, HQKNRPTLEA, RPTLEAITHL, INHQKNRPTL, QKNRPTLEAI, LEAITHLLGV | LUAD |
| NCAPD3 | c.2725delC | p.Q909fs | ASSADADHSPSSQGSSEAPASQPPP[p.Q909fs]RSEVLSCPL* | QPPPRSEVL, RSEVLSCPL, EAPASQPPPR, SQPPPRSEVL | STAD |
| NCAPH | c.1398delA | p.T466fs | HWRFRPPRRKQDAPSQSENKKKSTKK[p.T466fs]ILKLTLKMILTLMYILEKQRLLLF* | KMILTLMYI, MILTLMYIL, YILEKQRLL, ILKLTLKMI, TLKMILTLM, LTLMYILEK, MYILEKQRL, KKSTKKILK, KILKLTLKM, LKMIL TLMY, LMYILEKQR, LKLTLKMIL, LTLKMILTL, LEKQRLLLF, KL TLKMILTL, KMILTLMYIL, YILEKQRLLL, ILTLMYILEK, MYILEK QRLL, ILEKQRLLLF, KKKSTKKILK, STKKILKLTL, TLKMILTLMY, TLMYILEKQR, ILKLTLKMIL, KKSTKKILKL, KKILKLTLKM, LTL KMILTLM, LKMILTLMYI, LMYILEKQRL | STAD |
| NCOA3 | c.3759_3760del|GC | p.Q1253fs | RSRELLSHHFRQQRVAMMQQQQQQ[p.Q1253fs]TAAAAAAAAATATATATAATAANPGLQPTS* | QTAAAAAAA, MQQQQQQTA, QQQQQQTAA, QQQQQTA, AQ, QQQQQTAAAA, QQQQTAAAAA, QQTAAAAAA, MMMQQ QQQQT, MMQQQQQQTA, ATATATATAA, ATATATAATA, QTAAAAAAAA, TAATAANPGL, MQQQQQQTAA, QQQQQ QTAAA, QQQQQTAAAA, QQQQTAAAAA, QQQTAAAAAA, QQQTAAAAAAA | PAAD |
| NCOA4 | c.1685G>A | p.R562Q | ADWVLPGKKMGNLSQLSSGEDKWLL[p.R562Q]QKKAQEVLLNSPLQEEHNFPPDHYGL | LLQKKAQEV, LQKKAQEVL, WLLQKKAQEV, LLQKKAQEVL, L QKKAQEVLL | CRC |
| NCOA7 | c.1107G>T | p.E369D | DSRPIVPLEKSTGHTPTKPSGGSVS[p.E369D]DKLKKLDSSRETSHGSPTVTKLSKEP | SSVSDKLKK, GSSVSDKLKK | UCEC |
| NCOR1 | c.4682G>A | p.R1561Q | PGVDPWSHSPFDPHHRGSTAGEVY[p.R1561Q]QSHLPTHLDPAMPFHRALDPAAAAYL | YQSHLPTHL, EVYQSFILPT, VYQSHLPTHL, EVYQSHLPTF, GE VYQSHLPT | HNSC |
| NCR1 | c.772C>T | p.R258W | TYLLTTETGLQKDHALWDHTAQNLL[p.R258W]WMGLAFLVLVALVWFLVEDWLSRKRT | LLWMGLAFL, WMGLAFLVL, AQNLLWMGL, LWMGLAFLV, HTAQNLLWM, NLLWMGLAF, NLLWMGLAFL, LLWMGLAF LV, WMGLAFLVLV, AQNLLWMGLA, LWMGLAFLVL, QNLL WMGLAF | UCEC |
| NDST3 | c.1279G>A | p.V427I | LNKKFALEHGIPTDMGYAVAPHHSG[p.V427I]IYPVHVQLYEAAWKKVWNIKITSTEEY | GIYPVHVQL, AVAPHHSGI, IYPVHVQLY, VAPHHSGIY, GIYP VHVQLY, AVAPHHSGIY, YAVAPHHSGI, APHHSGIYPV, SGIY PVHVQL | LUAD |
| NEDD4L | c.570_572del|TCC | p.P194del | DMEHGWEVVDSNDSASQHQEELPPP[p.P194del]|LPPGWEEKVDNLGRTYYVNHNNRTTQWH | HQEELPPPL, LPPLPPGW | CLL |
| NEDD9 | c.2392G>A | p.A798T | RNKVMNSSNQLCEQLKTIVMATKMA[p.A798T]TLHYPSTTALQEMVHQVTDLSRNAQL | VMATKMATL, TLHYPSTTA, ATKMATLHY, KMATLHYPS, M ATKMATLHY, IVMATKMATL, KMATLHYPST, TLHYPSTTAL, ATKMATLHYP, ATLHYPSTTA, VMATKMATLH, TKMATLHY PS | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| NEDD9 | c.946G>A | p.A316T | ARRHQSLSPNHPPQLGQSVGSQND[p.A316T]TYDVPRGVQFLEPPAETSEKANPQER | SVGSQNDTY,DTYDVPRGV,TYDVPRGVQF,QSVGSQNDTY | CRC |
| NEFH | c.1933G>A | p.E645K | SPVKEEAKSPAEVKSPEKAKSPTKE[p.E645K]KAKSPEKAKSPEKERAKSPEKAKSPV | KAKSPTKEK,KSPTKEKAK,KEKAKSPEK,KAKSPTKEKA,KEKAKSPEKA | KIRP |
| NEFH | c.1993_1994insAGGAAG | p.665_666insEE | PTKEEAKSPEKAKSPEKEEAKSPEK[p.665_666insEE]EEAKSPVKAEAKSPEKAKSPVKAEAKSPEKA | EEAKSPVKA,KEEAKSPVKA | ACC, KIRP |
| NEFH | c.2009T>A | p.V670E | EAKSPEKAKSPEKEEAKSPEKAKSP[p.V670E]EKAEAKSPEKAKSPVKAEAKSPEKAK | KSPEKAEAK,KAKSPEKAEA | TGCT |
| NEFM | c.638C>T | p.A213V | RPEEEARLRDTEAAIRALRKDIEE[p.A213V]VSLVKVELDKKVQSLQDEVAPLRSNH | ALRKDIEV,EVSLVKVEL,RKDIEEVSL,IEEVSLVKV,VSLVKVELDK,EEVSLVKVEL | STAD |
| NEK1 | c.1822C>T | p.R608C | EVYLARLRQIRLQNFNERQQIKAKL[p.R608C]CGEKKEANHSEGQEGSEEADMRRKKI | KAKLCGEKK,QIKAKLCGEK | CRC |
| NEK11 | C.1121G>A | p.R374Q | KLQAADEKARKLKKIVEEKYEENSK[p.R374Q]QMQELRSRNFQQLSVDVLHEKTHLKG | NSKQMELR,QMQELRSRNF,EKYEENSKQM,KQMQELRSRN | UCEC |
| NEK2 | c.715C>A | p.R239S | PPFTAFSQKELAGKIREGKFRRIPY[p.R239S]SYSDELNEIITRMLNLKDYHRPSVE | KFRRIPYSY,SYSDELNEI,IPYSYSDEL,SYSDELNEII,KFRRIPYS YS,GKFRRIPYSY,YSYSDELNEI | LUAD |
| NEK8 | c.2070del | p.V690fs | VTSVSCCHGNTLLAVRSVTDEPVPP[p.V690fs]EAPGFTSGPP* | EPVPPEAPGF | STAD |
| NELL2 | c.509G>A | p.G170D | QTHLNSGVILSIHHLDHRYLELESS[p.G170D]DHRNEVRLHYRSGSHRPHTEVFPYIL | ESSDHRNEV,ESSDHRNEVR,LESSDHRNEV | TGCT |
| NES | c.1831G>C | p.V611L | LKSLEKENKELLKDVEVVRPLEKEA[p.V611L]LGQLKPTGKEDTQTLQSLQKENQELM | LEKEALQGL,ALGQLKPTGK,KEALGQLKPT | KIRC |
| NF1 | c.2027_2028insC | p.T676fs | PGASLRKGKGNSSMDSAAGCSGTPP[p.T676fs]DLPTSPDqTRSGPVHVSVEP* | QTRSGPVHV,RSGPVHVSV,SPDQTRSGPV | STAD |
| NF1 | c.4974_4977delTCTC | p.F1658fs | AKPYEIVVDLTHTGPSNRFKTDFLS[p.F1658fs]GLLFFLALLTTTSPQSISITVTPGSGSTPSIMSGC* | KTDFLSGLL,FLSGLLFFL,GLLFFLALL,FLALLTTTS,DFLSGLLFF,RFKTDFLSG,TTSPQSISI,STPSIMSGC,SPQSISITV,FKTDFLSGL,TDFLSGLLF,SGLLFFLAL,GSGSTPSIM,KTDFLSGLLF,FLSGLLFFLA,LLFFLALLTT,FLALLTTTSP,LLTTTSPQSI,DFLSGLLFFL,RFKTDFLSGL,TTTSPQSISI,TSPQSISITV,TPGSGSTPSI,FKTDFLSGLL,TDFLSGLLFF,LSGLLFFLAL | GBM |
| NFASC | c.766G>A | p.V256I | QFEEDQFQPGVWHDHSKYPGSVNSA[p.V256I]ILRLSPYVNYQFRVIAINEVGSSHPS | AILRLSPYV,GSVNSAILR,SAILRLSPY,YPGSVNSAI,NSAILRLSPY,SAILRLSPYV,KYPGSVNSAI,ILRLSPYVNY,YPGSVNSAIL | CRC |
| NFAT5 | c.2716C>G | p.Q906E | QQQQQQQVMESSAAMVMEMQQSIC[p.Q906E]EAAAIQSELFPSTASANGNLQQSPV | EMQQSICEA,SICEAAAQI,MQQSICEAA,CEAAAQIQS,QSICEAAAQI,EAAAQI,EAAAIQSEL,MEMQQSICEA,MQQSICEAAA | KIRC |
| NFE2L2 | c.100C>G | p.R34G | PGLPSQQDMDLIDILWRQDIDLGVS[p.R34G]GEVFDFSQRRKEYELEKQKKLEKERQ | IDLGVSGEVF,LGVSGEVFDF | BLCA |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| NFE2L2 | c.101G>A | p.R34Q | PGLPSQQDMDLIDILWRQDIDLGVS[p. R34Q]QEVFDFSQRRKEYELEKQKKLEK ERQ | IDLGVSQEVF,LGVSQEVFDF | LUSC |
| NFE2L2 | c.235G>A | p.E79K | LEKERQEQLQKEQEKAFFAQLQLDE[p. E79K]KTGEFLPIQPAQHIQSETSGSANY SQ | QLDEKTGEFL,LQLDEKTGEF,DEKTGEFLPI | BLCA,HNSC |
| NFE2L2 | c.235G>C | p.E79Q | LEKERQEQLQKEQEKAFFAQLQLDE[p. E79Q]QTGEFLPIQPAQHIQSETSGSAN YSQ | AQLQLDEQT,QLDEQTGEF,EQTGEFLPI,QLDEQTGEFL,LQL DEQTGEF,DEQTGEFLPI | HNSC,LUSC |
| NFE2L2 | c.241G>A | p.G81S | KERQEQLQKEQEKAFFAQLQLDEET[p. G81S]SEFLPIQPAQHIQSETSGSANYSQ VA | QLDEETSEF,EETSEFLPI,SEFLPIQPA,QLDEETSEFL,LQLDEE TSEF,DEETSEFLPI,SEFLPIQPAQ | LUSC |
| NFE2L2 | c.85G>C | p.D29H | LELPPPGLPSQQDMDLIDILWRQDI[p. D29H]HLGVSREVFDFSQRRKEYELEKQ KKL | ILWRQDIHL,HLGVSREVF,DIHLGVSREV,IHLGVSREVF | CESC,HNSC,LUSC |
| NFE2L2 | c.88C>T | p.L30F | ELPPPGLPSQQDMDLIDILWRQDID[p. L30F]FGVSREVFDFSQRRKEYELEKQKK KKL | ILWRQDIDF,IDPGVSREV,IDFGVSREVF,FGVSREVFDF | LUSC |
| NFE2L2 | c.92G>C | p.G31A | LPPPGLPSQQDMDLIDILWRQDIDL[p. G31A]AVSREVFDFSQRRKEYELEKQKK LEK | DLAVSREVF,WRQDIDLAV,AVSREVFDF,ILWRQDIDLA,IDL AVSREVF,LAVSREVDF | LUSC |
| NFIA | c.882G>C | p.L294F | SVTELVRVSQTPIAAGTGPNFSLSD[p. L294F]FESSSYYSMSPGAMRRSLPSTSST SS | LSDFESSSY,SDFESSSYY,FESSSYYSM,GPNFSLSDF,LSDFES SSY,SLSDFESSSY,FESSSYYSMS | LUAD |
| NHEJ1 | c.326G>A | p.R109Q | LKDAAHPSEATFSCDCVADALILRV[p. R109Q]QSELSGLPFYWNFHCMLASPSLV SQH | RVQSELSGL,QSELSGLPF,QSELSGLPFY,ALILRVQSEL,VQSE LSGLPF,LRVQSELSGL | UCEC |
| NHLRC1 | c.612del T | p.F204fs | DVTITNDCHVVTDAGDRSIKVFDF[p. F204fs]LARSSLSLEANSPYLGVWRPPLR MGLW* | LSLEANSPY,FLARSSLSL,SLEANSPYL,YLGVWRPPL,RSIKVF DFL,SIKVFDFLA,LGVWRPPLR,EANSPYLGV,FDFLARSSL,A NSPYLGVW,SIKVFDFLAR,DFLARSSLSL,PYLGVWRPPL,RSI KVFDFLA,LARSSLSLEA,VWRPPLRMGL,SLSLEANSPY,YLG VWRPPLR,LSLEANSPYL,LEANSPYLGV,LGVWRPPLRM,EA NSPYLGVW | STAD |
| NHP2L1 | c.250C>T | p.R84C | DAEPLEIILHLPLLCEDKNVPYVFV[p.R8 4C]CSKQALGRACGVSRPVIACSVTIKEG | YVFVCSKQAL,NVPYVFVCSK,FVCSKQALGR | GBM |
| NHS | c.4681G>A | p.D156IN | ATEILKSPILPKPPGELTAESPQST[p.D15 6IN]NDAHQSQGAEALSPLSPCSPRV NAE | AESPQSTNDA | TGCT |
| NID2 | c.3103del C | p.R1035fs | EPTQRPPTICERWRENLLEHYGGTP[p.R 1035fs]GMTSTCPSAMTWATSSPCSAT ERATSAGVWTKMAERCRAPAPSQAPP LRVYPPSLHPWSGPRPGQM* | GMTSTCPSA,ATSAGVWTK,SLHPWSGPR,GVWTKMAER, VYPPSLHPW,RVYPPSLHP,MTSTCPSAM,SQAPPLRVY,WT KMAERCR,MTWATSSPC,TSAGVWTKM,HPWSGPRPG,PL RVYPPSL,LEHYGGTPG,EHYGGTPGM,STCPSAMTW,AMT WATSSP,TERATSAGV,CPSAMTWAT,AERCRAPAP,KMAE RCRAPA,GMTSTCPSAM,AMTWATSSPC,TSSPCSATER,RA TSAGVWTK,RVYPPSLHPW,WTKMAERCRA,RCRAPAPSQ A,MTSTCPSAMT,MTWATSSPCS,TSAGVWTKMA,APAPS QAPPL,APSQAPPLRV,LEHYGGTPGM,TERATSAGVW,ATS AGVWTKM,SQAPPLRVYP,CPSAMTWATS,AERCRAPAPS,TSTCPSAMTW | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| NINL | c.4096C>T | p.R1366C | VRALQATEEKQRGAEKQSRLLEEKV[p.R1366C]CALNKLVSRIAPAALSV* | LLEEKVCAL, KVCALNKLV, CALNKLVSR, RLLEEKVCAL | CRC |
| NKD1 | c.856_857insC | p.P286fs | AGIENYTSQFGPGSPSVAQKSELPP[p.P286fs]PHLQSHSISLP* | HLQSHSISL, AQKSELPPP, LQSHSISLP, AQKSELPPPH, QKSEL PPPHL | STAD |
| NKD2 | c.1315_1317del|CAC| | p.H447del | GYAVPVIQRHEHHHHEHHHHHH[p.H447del]FHPS* | EHHHHHHHF | TGCT |
| NLK | c.570del|T | p.C190fs | KKMPNVFQNLVSCKRVFRELKMLCF[p.C190fs]LSMIMYSLPLTYSNLHTLTILKKY MLSQN* | IMYSLPYY, YSNLHTLTI, KMLCFLSMI, FLSMIMYSL, SMIMY SLPL, MIMYSLPLT, LTYSNLHTL, SLPLTYSNL, NLHTLTILK, HT LTILKKY, LTILKKYML, MLCFLSMIM, RELKMLCFL, LKMLCFL SM, LCFLSMIM, SNLHTLTIL, LPLTYSNLH, MIMYSLPLTY, K MLCFLSMIM, SMIMYSLPLT, IMYSLPLTY, FLSMIMYSLP, M LCFLSMIMY, NLHTLTILK, SNLHTLTIL, CFLSMIMYSL, YSL PLTYSNL, TYSNLFITLI, ELKMLCFLSM, LSMIMYSLPL, LKML CFLSMI, SNLHTLTI, LHTLTILIK, RELKMLCFLS, LPLTYSN LHT | STAD |
| NLRC4 | c.1225G>A | p.E409K | SDFIRSLDHCGDLALEGVFSHKFDF[p.E409K]KLQDVSSVNEDVLLTTGLLCKYTA QR | VFSHKFDFK, FSHKFDFKL, FKLQDVSSV, GVFSHKFDFK, VFS HKFDFKL, HKFDFKLQDV | CRC |
| NLRC4 | c.1777G>A | p.D593N | KSALSQEFEAFFQGKSLYINSGNIP[p.D593N]NYLFDFFEHLPNCASALDFIKLDFY G | NIPNYLFDF, INSGNIPNY, IPNYLFDFF, SGNIPNYLF, NSGNIP NYLF, GNIPNYLFDF, NIPNYLFDFF, NYLFDFFEHL, YINSGNIP NY | CRC |
| NLRC4 | c.862C>T | p.R288W | ALIKENHRFKNMVIVTTTECLRHI[p.R288W]FQGALTAEVGDMTEDSAQALI REVL | ECLRHIWQF, RHIWQFGAL, WQFGALTAE, WQFGALTAEV, CLRHIWQFGA, TECLRHIWQF, LRHIWQFGAL, RHIWQFGA LT, HIWQFGALTA | BRCA |
| NLRP3 | c.469C>T | p.R157C | MKKDYRKKYRKYVRSRFQCIEDRNA[p.R157C]CLGESVSLNKRYTRLRLIKEHRS QQE | RNACLGESV, CLGESVSLNK | LUAD |
| NLRP4 | c.685G>A | p.V229I | LISREWPDPAAPITEIVSQPERLLF[p.V229I]IIDSFEELQGGLNEPDSDLCGDLME K | SQPERLLFI, FIIDSFEEL, RLLFIIDSF, QPERLLFII, SQPERLL- FII,L FIIDSFEEL | CRC |
| NLRP5 | c.1175G>A | p.R392H | LGSVLNNDTKLLCKDWAEKQPPFTLI[p.R392H]HSLLRKVLLPESFLIVTVRDVGTEK L | LIHSLLRKV, TLIHSLLRK, FTLIHSLLR, PFTLIHSLL, HSLLRKVLL, PPFTLIHSL, KQPPFTLIH, TLIHSLLRKV, FTLIHSLLRK, QPPFTLI HSL, LIHSLLRKVL | CRC |
| NLRP5 | c.2209C>T | p.R737W | LPINQNLDLIASSFCLQHCPYLRKI[p.R737W]WVDVKGIFPRDESAEACPVVPL WMRD | YLRKIWVDV, IWVDVKGIF, CPYLRKIWV, YLRKIWVDVK, PYL RKIWVDV, WVDVKGIFPR, RKIWDVKGI, KIWVDVKGIF | GBM |
| NLRP6 | c.1832A>G | p.E611G | CPGVAPEVTEGAKGLEDTEEPEEEE[p.E611G]GGEBPNYPLELLYCLYETQEDAFV RQ | EEGGEEPNY, EEEGGEEPNY | THCA |
| NME9 | c.223G>A | p.E75K | QKMRIEVGLDLLHFALAEADRLDVL[p.E75K]KKYRGKCEPTFLFYAGGELVAVVR GA | KKYRGKCEPT | CRC |
| NMU | c.53C>A | p.A18E | MLRTESCRPRSPAGQVA[p.A18E]EASP LLLLLLLLLAMCAGACRGAPILP | QVAEASPLL, EASPLLLLL, GQVAEASPL, AEASPLLLL, QVAEA SPLLL, EASPLLLLLL, GQVAEASPLL, AEASPLLLLL | ACC |
| NMU | c.56C>A | p.A19E | MLRTESCRPRSPAGQVAA[p.A19E]ESP LLLLLLLAMCAGACRGAPILPQ | QVAAESPLL, GQVAEASPL, VAAESPLLL, AESPLLLLL, QVAAE SPLLL, GQVAAESPLL, VAAESPLLLL, AESPLLLLLL | ACC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| NNMT | c.697G>A | p.E233K | EQKFSSLPLGREAVEAAVKEAGYTI[p.E233K]KWFEVISQSYSSTMANNEGLFSLVAR | YTIKWFEVI, GYTIKWFEV, KEAGYTIKW, AVKEAGYTI, GYTI KWFEVI, KWFEVISQSY, KEAGYTIKWF | UCEC |
| NOL9 | c.172T>G | p.S58A | PRRRLGSLRWCGRRRLRWRLLQAQA[p.S58A]AGVDWREGARQVSRAAAARPNTATP | WRLLQAQAA, RWRLLQAQAA | ACC |
| NOLC1 | c.1283C>T | p.T428M | VTTKSPAVKPAAAPKQPVGGGQKLL[p.T428M]MRKADSSSSEEESSSEEKTKKMVA | LMRKADSSS, LMRKADSSSS | CRC |
| NOM1 | c.70C>G | p.R24G | MAASRSAGEAGPGGSQGRVVRMK[p.R24G]GRGRGPRRGPAGGGEKALKRLKLAV | RMKGRGGRG, KGRGGRGPR, QGRVVRMKGR, VVRMKGR GGR, KGRGGRGPRR | ACC |
| NOS1AP | c.901_903del\|CAG | p.Q306del | LGTETPLSTHHQMQLLQQLLQQQQ[p.Q306del\|]TQVAVAQVHLLKDQLAAEAAARLEAQAR | LQQQQQTQV, LLQQQQQTQV, LQQQQQTQVA | BLCA |
| NOS1AP | c.7541_7542del\|CT | p.P2514fs | SYSSPVDNTPSHQLQVPEHPFLTPS[p.P2514fs]RVP* | HPPLITPSRV | CLL |
| NOTCH1 | c.17_18del\|CC | p.P6fs | MPALR[p.P6fs]RSAVGAAGALAVLRGPRACIAVSRWL* | ALRRSAVGA, AAGALAVLR, RSAVGAAGA, VLRGPRACI, ALA VLRGPR, MPALRRSAV, ALRRSAVGAA, AVGAAGAL, GAAGA LAVL, RACIAVSRW, ALRRSAVGAA, AVGAAGALAV, ALAVLR GPRA, RSAVGAAGAL, GALAVLRGPR, VLRGPRACIA, RACIA VSRWL, MPALRRSAVG, VGAAGALAVL | BLCA |
| NOTCH2 | c.57C>G | p.C19W | MPALRPALLWALLALWLC[p.C19W]WAAPAHALQCRDGYEPCVNEGMCVTY | LLALWLCWA, CWAAPAHAL, ALLALWLCW, WLCWAAPAH, ALLALWLCWA, LLALWLCWAA, ALWLCWAAPA, WLCWAA PAHA, WALLALWLCW, LCWAAPAHAL | ACC |
| NOTCH2 | c.6314G>T | p.R2105L | LSPVICGPNRSFPLSLKHTPMGKKSR[p.R2105L]LPSAKSTMPTSLPNLAKERAKDAKGSR | KSRLPSAKS, TPMGKKSRL, RLPSAKSTM, MGKKSRLPSA, KS RLPSAKST, LPSAKSTMPT, SRLPSAKSTM | LUAD |
| NOTCH2 | c.6892C>T | p.R2298W | APAEGTHPGIAPQSRPPEGKHITTP[p.R2298W]WEPLPPIVTFQLIPKGSTAQPAGAPQ | HITTPWEPL, TPWEPLPPI, WEPLPPIVT, TTPWEPLPPI, KHIT TPWEPL, WEPLPPIVTF, TPWEPLPPIV | CESC |
| NOX3 | c.1210_1211del\|TG | p.C404fs | SLPRLAVDGPFGTALTDVFHYPVCV[p.C404fs]RCRGDRSHSLRCSSEIYMVQMQ* | RSHSLRCSS, SLRCSSEIY, VFHYPVCVR, HSLRCSSEI, LRCSSEI YM, SLRCSSEIYM, CVRCRGDRSH, RSHSLRCSS, HSLRCSSEI Y, DVFHYPVCVR, RCRGDRSHSL, CSSEIYMVQM | PRAD |
| NOX5 | c.1401del\|T | p.P467fs | AVCIMEVNLLPSKVTHLLIKRPPFF[p.P467fs][TIDLVTTCI* | FTIDLVTTC, RPPFFTIDL, IKRPPFFTI, PPFFTIDLV, LLIKRPPFF T, FTIDLVTTCI, LIKRPPFFTI | STAD |
| NOXA1 | c.18C>G | p.D6E | MASLG[p.D6E]ELVRAWHLGAQAVDRGDWARALHLFS | SLGELVRAW, GELVRAWHL, ELVRAWHLGA, ASLGELVRAW, GELVRAWHLG | ACC |
| NOXO1 | c.8_9insG | p.G3fs | MAGP[p.G3fs]PIPSFSARGSPGADQEAPNVCLLCALVRRQRHLRAQELGRIQAAQEDPQGDLPGGGGPAAEI* | FSARGSPGA, LVRRQRHLR, RQRHLRAQE, HLRAQELGR, CLL CALVRR, NVCLLCALV, LPGGGGPAA, ALVRRQRHL, QRHLR AQEL, MAGPPIPSF, QEAPNVCLL, AQELGRIQA, QELGRIQA A, HLRAQELGRI, SFSARGSPGA, LVRRQRHLRA, RQRHLRAQ EL, RAQELGRIQA, NVCLLCALVR, LLCALVRRQR, ALVRRQRFI LR, APNVCLLCAL, CALVRRQRHL, AQELGRIQAA | KIRC |
| NPAS2 | c.602A>G | p.Q201R | DSITPLLGHLPSDVMDQNLLNFLPE[p.Q201R]REHSEVYKILSSHMLVTDSPSPEYLK | NLLNFLPER, PEREHSEVY, REHSEVYKI, LPEREHSEV, FLPERE FISEV, LPEREHSEVY, REHSEVYKIL | OV |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| NPC1 | c.1351G>A | p.E451K | GADVPFGPPLDIQILHQVLDLQIAI[p.E451K]KNITASYDNETVTLQDICLAPLSPYN | AIKNITASY, LQIAIKNIT, QVLDLQIAIK, IAIKNITASY, LQIAIKNITA | CRC |
| NPIP | c.812C>T | p.A271V | QPPPPTQQHSIIDNSLSLKTPSELS[p.A271V]VHSPSTLSSTLSG* | LKTPSELSV, SELSVHSPS, LSVHSPSTL, SLKTPSELSV, LKTPSE LSVH, SELSVHSPST | PRAD |
| NPM1 | c.859_860insTCTG | p.L287fs | KVEAKFINYVKNCFRMTDQEAIQDL[p.L287fs]CLAVEEVSLRK* | AIQDLCLAV, AVEEVSLRK, EAIQDLCLA, QEAIQDLCL, LAVEE VSLRK, EAIQDLCLAV, QEAIQDLCLA | LAML |
| NPM1 | c.861_862insCTGC | p.L287fs | KVEAKFINYVKNCFRMTDQEAIQDL[p.L287fs]LLAVEEVSLRK* | AIQDLLLAV, LLAVEEVSL, LAVEEVSLRK, EAIQDLLLA, QEAIQ DLLL, LLLAVEEVSL, LAVEEVSLRK, EAIQDLLLAV, QEAIQDLL LA | LAML |
| NPM1 | c.863_864insTCTG | p.W288fs | KVEAKFINYVKNCFRMTDQEAIQDL[p.W288fs]CLAVEEVSLRK* | AIQDLCLAV, AVEEVSLRK, EAIQDLCLA, QEAIQDLCL, LAVEE VSLRK, EAIQDLCLAV, QEAIQDLCLA | LAML |
| NPR3 | c.412T>C | p.Y138H | LFSLVDRVAAARGAKPDLILGPVCE[p.Y138H]HAAAPVARLASHWDLPMLSAGALAAG | ILGPVCEHA, HAAAPVARL, CEHAAAPVA, GPVCEHAAA, ILG PVCEHA, HAAAPVARLA | STAD |
| NPSR1 | c.704G>A | p.R235Q | YMTIVAFLVYFIPLTIISIMYGIVI[p.R235Q]QTIWIKSKTYETVISNCSDGKLCSSY | IMYGIVIQT, IVIQTIWIK, MYGIVIQTI, QTIWIKSKT, YGIVIQTI W, IMYGIVIQTI, SIMYGIVIQT, VIQTIWIKSK, GIVIQTIWIK, M YGIVIQTIW, QTIWIKSKTY | CRC |
| NPTX1 | c.787G>A | p.A263T | YMYAKVKKSLPEMYAFTVCMWLKSS[p.A263T]TTPGVGTPFSYAVPGQANELVLIEWG | LKSSTTPGV, WLKSSTTPGV, STTPGVGTPF | GBM |
| NPY1R | c.1111G>A | p.A371T | DYETIAMSTMHTDVSKTSLKQASPV[p.A371T]TFKKINNNDDNEKI* | KQASPVTFK, QASPVTFKK, LKQASPVTF, KQASPVTFKK, SLK QASPVTF | UCEC |
| NR2C1 | c.809G>T | p.S270I | HPSGVKTESAVLMTSDKAESCQGDL[p.S270I]ITLANVTSLANLGKTKDLSQNSNEM | AESCQGDLI, ITLANVVTSL, GDLITLANVV, AESCQGDLIT | KIRC |
| NR4A2 | c.941G>T | p.R314L | RTVQKNAKYVCLANKNCPVDKRRRN[p.R314L]LCQYCRFQKCLAVGMVKEVRTDSLK | RNLCQYCRF, KRRRNLCQY, NLCQYCRFQK, CPVDKRRRNL, R RNLCQYCRF | LUAD |
| NR5A2 | c.238G>A | p.E80K | SHGEQGQMPENMQVSQFKMVNYSYD[p.E80K]KDLEELCPVCGDKVSGYHYGLLTCES | KMVNYSYDK, KDLEELCPV, YSYDKDLEEL | CESC |
| NRAP | c.979G>A | p.E327K | YEEHRGKGSFPAMITPAYQNAKKAH[p.E327K]KLASDIKYRQDFNMKGAAHYHSLPA | YQNAKKAHK, KAHKLASDI, KLASDIKYR, HKLASDIKY, YQNA KKAHKL, KAHKLASDIK, AYQNAKKAHK, KKAHKLASDI, AHKL ASDIKY | CRC |
| NRAS | c.181C>A | p.Q61K | IEDSYRKQWIDGETCLLDILDTAG[p.Q61K]KEEYSAMRDQYMRTGEGFLCVFAINN | LDTAGKEEY, AGKEEYSAM, ILDTAGKEEY, DTAGKEEYSA | CRC, LAML, MM, SKCM, THCA |
| NRAS | c.182A>G | p.Q61R | IEDSYRKQVVIDGETCLLDILDTAG[p.Q61R]REEYSAMRDQYMRTGEGFLCVFAINN | LDTAGREEY, AGREEYSAM, ILDTAGREEY, AGREEYSAMR, D TAGREEYSA | CLL, MM, OV, SKCM, TGCT, THCA, UCEC |
| NRAS | c.182A>T | p.Q61L | IEDSYRKQVVIDGETCLLDILDTAG[p.Q61L]LEEYSAMRDQYMRTGEGFLCVFAINN | LDTAGLEEY, AGLEEYSAM, ILDTAGLEEY, LLDILDTAGL, DTA GLEEYSA | CRC, LUAD, MM, SKCM |
| NRAS | c.183A>C | p.Q61H | IEDSYRKQVVIDGETCLLDILDTAG[p.Q61H]HEEYSAMRDQYMRTGEGFLCVFAINN | LDTAGHEEY, AGHEEYSAM, ILDTAGHEEY, DTAGHEEYSA | MM |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| NRAS | c.183A>T | p.Q61H | IEDSYRKQVVIDGETCLLDILDTAG[p.Q61H]HEEYSAMRDQYMRTGEGFLCVFAINN | LDTAGHEEY, AGHEEYSAM, ILDTAGHEEY, DTAGHEEYSA | LAML |
| NRAS | c.34G>T | p.G12C | MTEYKLVVVGA[p.G12C]CGVGKSALTIQLIQNHFVDEYDPTIE | LVVVGACGV, VVVGACGVG, KLVVVGACGV, VVVGACGVGK | CRC |
| NRAS | c.35G>A | p.G12D | MTEYKLVVVGA[p.G12D]DGVGKSALTIQLIQNHFVDEYDPTIE | LVVVGADGV, VVVGADGVG, KLVVVGADGV, VVVGADGVGK | CRC, LAML, MM |
| NRAS | c.37G>C | p.G13R | MTEYKLVVVGAG[p.G13R]RVGKSALTIQLIQNHFVDEYDPTIED | VVVGAGRVG, RVGKSALTI, KLVVVGAGR, AGRVGKSAL, KLVVVGAGRV, VVVGAGRVGK, GRVGKSALTI | CRC, MM |
| NRAS | c.38G>A | p.G13D | MTEYKLVVVGAG[p.G13D]DVGKSALTIQLIQNHFVDEYDPTIED | VVVGAGDVGK, KLVVVGAGDV, VVVGAGDVGK | LAML |
| NRG1 | C.1441G>T | p.V481L | VSSMTVSMPSMAVSPFMEEERPLLL[p.V481L]LTPPRLREKKFDHHPQQFSSFHHNPA | LLLLTPPRL, LTPPRLREK, LLLTPPRL, EEERPLLLL, EERPLLLLT, LLTPPRLREK, MEEERPLLLL | LUAD |
| NRG2 | c.737C>T | p.T246M | LKKEVGKILCTDCATRPKLKKMKSQ[p.T246M]MGQVGEKQSLKCEAAAGNPQPSYRWF | KMKSQMGQV, SQMGQVGEK, KLKKMKSQM, MKSQMGQVG, KSQMGQVGEK, KLKKMKSQMG, KMKSQMGQVG, KKMKSQMGQV | CRC |
| NRG4 | c.63_64insG | p.G21fs | ANRSRRALWSQSQVVLPEWGA[p.G21fs]VM* | VLPEWGAVV, LPEWGAVVM, VVLPEWGAVV, VLPEWGAVV, VM, QVVLPEWGAV | CLL |
| NRXN3 | C.307C>T | p.R103C | FETPEAYISLPKWNTKRMGSISFDF[p.R103C]CTTEPNGLILFTHGKPQERKDARSQK | CTTEPNGLI | LUAD |
| NRXN3 | c.68C>A | p.P23H | MLGSDDFFYVGGSPSTADLPGS[p.P23H]HVSNNFMGCLKEVVYKNNDIRLELSR | GSHVSNNFM, STADLPGSH, STADLPGSHV, HVSNNFMGCL, LPGSHVSNNF | LUAD |
| NSMCE1 | c.730G>A | p.D244N | YFQSNAEPRCPHCNDYWPHEIPKVF[p.D244N]NPEKERESGVLKSNKKSLRSRQ | KVFNPEKER, HEIPKVFNP, HEIPKVFNPE | UCEC |
| NSMCE2 | c.91_92insA | p.Q31fs | SNSGSTGFISFSGVESALSSLKNFQ[p.Q31fs]SLYQLWYGHSF* | FQSLYQLWY, YQLWYGHSF, SLKNFQSLY, SSLKNFQSL, NFQSLYQLW, KNFQSLYQL, SLYQLWYGFI, SSLKNFQSLY, KNFQSLYQLW, LYQLWYGHSF, NFQSLYQLWY, LSSLKNFQSL, LKNFQSLYQL | KIRC |
| NT5C3 | c.7G>C | p.A3P | MR[p.A3P]PPSMDRAAVARVGAVASASVCALVAG | RPPSMDRAA, PPSMDRAAV, RPPSMDRAAV | TGCT |
| NT5M | c.616del C | p.P206fs | AEPTPSWEHVLFTACHNQHLQLQPP[p.P206fs]AAGCTRGRTTGRPFWTASGPAELDCASGSSVGL* | LQLQPPAAG, NQHLQLQPPA | STAD |
| NTM | c.997G>T | p.G333C | IMLFEVKTTALTPWKGPGAVSEVSN[p.G333C]CTSRRAGCVWLLPLLVLHLLLKF* | EVSNCTSRR | LUAD |
| NTN4 | C.175G>A | p.E59K | CNPRMGNLALGRKLWADTTCGQNAT[p.E59K]KLYCFYSENTDLTCRQPKCDKCNAAY | TTCGQNATK, ATKLYCFYS, CGQNATKLY, NATKLYCFY, KLYCFYSENT, QNATKLYCFY, DTTCGANATK, GQNATKLYCF | CRC |
| NUAK1 | c.517G>T | p.G173C | RRLSERETRHFFRQIVSAVHYCHKN[p.G173C]CVVHRDLKLENILLDDNCNIKIADFG | AVHYCHKNCV, KNCVVHRDLK, VHYCHKNCVV, HKNCVVHRDL | LUAD |
| NUB1 | c.1118G>A | p.R373Q | RLVHIKGNCGKEKVLFLRLYLLQGI[p.R373Q]QNYHSGNDVEAYEYLNKARQLFKELY | YLLQGIQNY, IQNYHSGNDV | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| NUDT 15 | c.248C>A | p.S83Y | ECAQRETWEEAALHLKNVHFASVVN[p. S83Y]YFIEKENYHVTILMKGEVDVTH DSE | FASVVNYFI,SVVNYFIEK,HFASVVNYF,VHFASVVNY,ASVV NVYFIEK,VHFASVVNYF,HFASVVNYFI,YFIEKENYHY,NVHFA SVVNY,VNYFIEKENY | CRC |
| NUDT 21 | c.39_40ins G | p.W13fs | MSVVPPNRSQTGW[p.W13fs]APGG HSVRQQVHPADEAPHPGAHHQPVPSYQ LYFWYKRAPLREGQLCCSQISAHEGRI* | QLYFWYKRA,SYQLYFWYK,YQLYFWYKR,YFWYKRAPL,RSQTGWAPG, SVRQQVHPA,FWYKRAPLR,AAHHQPVSY,PSYQLYFWY,HPGAHHQPV, QPVPSYQLY,HQPVPSYQL,DEAPHPGAH,VPSYQLYFW,YQLYFWYKRA, PSYQLYFWYK,SYQLYFWYKR,LYFWYKRAPL,GAHHQPVPSY,HQPVPSY QLY,YFWYKRAPLR,VPSYQLYFWY,RQQVHPADEA,HHQPVP SYQL,QPVPSYQLYF,REGQLCCSQI,GQLCCSQISA,SQISAHEGRI, DEAPHPGAHH | KIRC |
| NUF2 | c.1019C>T | p.S340 L | KESLNLEDQIESDESELKKLKTEEN[p.S3 40L]LFKRLMIVKKEKLATAQFKINKKHE D | NLFKRLMIV,KTEENLFKR,LFKRLMIVK,KKLKTEENL,KLKTEE NLF,EENLFKRLM,TEENLFKRL,KLKTEENLFK,NLFKRLMIVK, LFKRLMIVKK,KKLKTEENLF,TEENLFKRLM,EENLFKRLMI | CRC |
| NUFIP 2 | c.670del A | p.R224fs | TNGYMGKGADNDGSGSESGYTTPKK[p. R224fs]GKLGAIVPRVVKTLI* | KLGAIVPRV,GAIVPRVVK,VPRWKTLI,KKGKLGAIV,KLGAI VPRVV,AIVPRVVKTL,SGYTTPKKGK,KGKLGAIVPR,LGAIVP RVVK,TPKKGKLGAI | STAD |
| NUFIP 2 | c.86_88del AGC | p.Q29del | KPGQPQHHHSHHHPHHHPQQQQ Q[p.Q29del]PHHHHHYFYNHSHNHH HHHHHQQPHQY | HPQQQQQPH | GBM |
| NUP2 10 | c.403del C | p.L135fs | DAIVDLIHDIQIVSTTRELYLEDSP[p.L13 5fs]WS* | ELYLEDSPW,RELYLEDSPW | STAD |
| NUP8 8 | c.905C>T | p.A302 V | FLTYISLLHSPGNIGKLLGPLPMHP[p.A3 02V]VAEDNYGYDACAVLCLPCVPNILVI A | PVAEDNYGY,LLGPLPMHPV,PMHPVAEDNY,HPVAEDNY GY | CRC |
| NUP9 3 | c.40G>A | p.E14K | MDTEGFGELLQQA[p.E14K]KQLAAET EGISELPHVERNLQEIQQA | LQQAKQLAA,KQLAAETEG,KQLAAETEGI,LLQQAKQLAA,G ELLQQAKQL | BRCA |
| NYAP 1 | c.1438C>T | p.P480 S | DKAVSTMVYSAVKVTTHSVLPAGP[p. P480S]SLGAGEPKTEKEISVLHGMLCTS SRP | SVLPAGPSL,LPAGPSLGA,VLPAGPSLGA,HSVLPAGPSL | TGCT |
| NYAP 2 | c.1310C>T | p.P437 L | SSPPPPSTLYRTQSPHGYPKSHSTS[p.P4 37L]LSPVSMGRSLTPLSLKRPPPYDAVH S | SLSPVSMGR,KSHSTSLSP,YPKSHSTSL,SHSTSLSPV,STSLSP VSM,TSLSPVSMGR,KSHSTSLSPV,HSTSLSPVSM | LUAD |
| NYAP 2 | c.590G>A | p.R197 Q | RTEASAKPRPHSDEYSKKIPPPKPK[p.R1 97Q]QNPNTQLSTSFDETYIKKHGPRRT SL | KQNPNTQLS,KPKQNPNTQL,KQNPNTQLST | CESC |
| NYNRI N | c.339del C | p.G113fs | AFLGAQGLFLDCLCWSTLAYLVPG[p. G113fs]LAP* | LAYLVPGPL,TLAYLVPGPL | STAD |
| OBSC N | c.13546C>T | p.R451 6W | LLLRSAQPHHAGEVTFACRDAVASA[p. R4516W]WLTVLGLPDPPEDAEVVARS SHTVTL | AVASAWLTV,VASAWLTVL,SAWLTVLGL,AVASAWLTVL,D AVASAWLTV,ACRDAVASAW,ASAWLTVLGL | ACC |
| OBSC N | c.2721_272 2TG>CA | p.A908 T | VSEPKVVFAKEQLARRKLQAEAGAS[p.A90 8T]TTLSCEVAQAQTEVTWYKDGK KLSSSS | LQAEAGAST,AEAGASTTL,LQAEAGASTT, QAEAGASTTL,AEAGASTTLS | TGCT |
| OBSC N | c.2989_299 0insG | p.G997fs | LDVKEPKVVFAKDQVAHSEVQAEAG[p.G9 97fs]GQCHAELRGPGPGDGGDVVQRWEEA ELQLESACRGQGLQTEAGGAA VQAEAGGQCH,AELRGGPGP,AELQLESAC,GLLPPAHHRA, VQAEAGGQCH,QRWEEAELQL,LESACRGQGL,LQTEAGGAAG, GRQDRCRGLQL,LQLRGQGPEG,EEAELQLESA | LLPPAHHRA,AEAGGQCHA,VQRWEEAEL,LQTEAGGAA, EEAELQLES,AELRGGPGP,AELQLESAC,GLLPPAHHRA, VQAEAGGQCH,QRWEEAELQL,LESACRGQGL,LQTEAGGAAG, RQDRCRGLQL,LQLRGQGPEG,EEAELQLESA | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| OBSL1 | c.4924G>A | p.E164 2K | RCAARLIVREVPVTIVRGPHDLEVT[p.E1642K]KGDTATFECELSQALADVTWEKDGNA | VTKGDTATF, LEVTKGDTA, EVTKGDTATF | CESC |
| ODF2L | c.1221del A | p.K407fs | TTLAALKDEVVSVENELSELQEVEK[p.K407fs]NRKPLLKCIKLRYKSCKKQLK* | KLRYKSCKK, RYKSCKKQL, LLKCIKLRY, ELQEVEKNR, KPLLKC IKL, CIKLRYKS, VEKNRKPLL, LLKCIKLRYK, VEKNRKPLLK, K NRKPLLKCI, CIKLRYKSCK, RYKSCKKQLK, QEVEKNRKPL, LRY KSCKKQL | KICH |
| ODF2L | c.880G>A | p.E294 K | DQEAKLSETISASNAWKSHYEKIVI[p.E294K]KKTELEVQIETMKKQIINLLEDLKKM | KKTELEVQI, YEKIVIKKT, IVIKKTELEV, KSHYEKIVIK | MM |
| ODF4 | c.181C>T | p.R61C | TGELGQDGRLLSSTLSLSSNRSLGQ[p.R61C]CQNSPLPFQWRITHSFRWMAQVLASE | QCQNSPLPF, SLGQCQNSPL, GQCQNSPLPF, CQNSPLPFQW | GBM |
| ODZ1 | c.1097G>T | p.R366 M | HLFGLITWQLQPVEGELYANGVSKGN[p.R366M]MGTESMDTTYSPIGGKVSDKSEKKVF | KGNMGTESM, MGTESMDTTY, YANGVSKGNM, SKGNMGTESM | HNSC |
| ODZ1 | c.7666C>T | p.R255 6W | KGIKFAIKDGIVTADIIGVANEDSR[p.R2556W]WLAAILNNAHYLENLHFTIEGRDTHY | WLAAILNNA, NEDSRWLAA, RWLAAILNNA, WLAAILNNAH, NEDSRWLAAI | CRC |
| ODZ2 | c.1882_188 3ins6 | p.W62 8fs | KAACPVLCSGNGQYSKGTCQCYSGW[p.W628fs]ERCRVRRAHESVHRSFLRGPRLLH* | SFLRGPRLL, RVRRAHESV, SVHRSFLRG, RSFLRGPRL, CYSG WERCR, SGWERCRVR, ESVHRSFLR, AHESVHRSF, HESVHR SFL, WERCRVRRA, RVRRAHESVH, RAHESVHRSF, VHRSFLR GPR, RSFLRGPRLL, SGWERCRVRR, WERCRVRRAH | KIRC |
| ODZ3 | c.653C>A | p.P218 Q | SAQHHPSITSLNRNSLTNRRNQSPA[p.P218Q]QPAALPAELQTTPESVLQDSWVLGS | QPAALPAEL, NQSPAQPAA, SPAQPAALPA, RRNQSPAQPA, NQSPAQPAAL, AQPAALPAEL | LUAD |
| OGDH | c.233del T | p.I78fs | NYVEEMYCAWLENPKSVHKSWDIFF[p.I78fs]ATRMPEPHRALPTRVPFP* | RMPEPHRAL, RALPTRVPF, ATRMPEPHR, SWDIFFATR, WD IFFATRM, FATRMPEPH, KSWDIFFATR, ATRMPEPHRA, RAL PTRVPFP, FATRMPEPFIR, MPEPHRALPT, TRMPEPHRAL, H RALPTRVPF, EPHRALPTRV | GBM |
| OGDH | c.2844_284 5insC | p.Y948f s | VAITRIEQLSPPFPFDLLLKEVQKYP[p.Y948fs]QC* | KEVQKYPQC | STAD |
| OGDH L | c.1279G>A | p.A427 T | TKAEQFYRGDAQGKKVMSILVHGDA[p.A427T]TFAGQGVVYETFHLSDLPSYTTNGTV | LVHGDATFA, ATFAGQGVV, TFAGQGVVY, DATFAGQGV, IL VHGDATF, ATFAGQGVVY, ILVHGDATFA, SILVHGDATF | CRC |
| OGDH L | c.169C>T | p.R57C | RLLPSRLGVQAARLLAAHDVPVFGW[p.R57C]CSRSSGPPATFPSSKGGGGSSYMEEM | CSRSSGPPA, VPVFGWCSR, CSRSSGPPAT, DVPVFGWCSR | UCEC |
| OGFO D1 | c.1430_1431 insGTTTTT TT | p.G477 fs | SKAEFALDLILYCGCEGWEPEYGG[p.G477fs]FFLLLTLPKVKMSC* | FLLLTLPKV, FFLLLTLPK, LTLPKVKMK, EYGGFFFLL, YGGFFFL LL, GFFFLLLTL, LPKVKMKSC, WEPEYGGFF, PEYGGFFFL, EPE YGGFFF, FFFLLLTLPK, GWEPEYGGFF, EYGGFFFLLL, WEPEY GGFFF, GGFFFLLLTL, LLLTLPKVKM, PEYGGFFFLL, EPEYGGF FFL | PAAD |
| OGFR | c.1670G>C | p.S557 T | DEPAESPSETPGPRAGPAGDEPAE[p.S557T]TPSETPGPRPAGPAGDEPAESPSETP | ETPSETPGPR | ACC |
| OIT3 | c.1522C>A | p.R508 S | FVGKDHKEVFLHCRVLVCGVLDERS[p.R508S]SCAQGCHRRMRRGAGGEDSAGLQGQT | VLDERSSCA, RSSCAQGCHR | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| OLFM4 | c.396G>T | p.K132N | HVLSQKFEKELSKVREYVQLISVYE[P.K132N]KLLNLTVRIDIMEKDTISYTELDFE | QLISVYENK,VYENKLLNL,YENKLLNLIT,QLISVYENKL,SVYEN KLLNL,VQLISVYENK,YENKLLNLTV | CRC |
| OMA1 | c.1334G>A | p.R445Q | MEFVDSLHGQPKMPEWLSTHPSHGNI[R445Q]QVEYLDRLIPQALKIREMCNCPPLSN | NQVEYLDRL,PSHGNQVEY,STHPSHGNQV,HPSHGNQVEY, NQVEYLDRLI | UCEC |
| ONECUT1 | c.1270T>A | p.L424M | TLHAIFKENKRPSKELQITISQQLGM[L424M]MELSTVSNFFMNARRSLDKWQDEGS | QLGMELSTV,ITISQQLGM,MELSTVSNF,ISQQLGMEL,QQL GMELST,QQLGMELSTV,GMELSTVSNF,MELSTVSNFF,SQ QLGMELST | KIRC |
| OOEP | c.301C>T | p.R101C | TSQALLTVDIVDSGNLVEITVFGRP[p.R101C]CVQNRVKSMLLCLAWFHREHRARAEK | ITVFGRPCV,CVQNRVKSM,EITVFGRPCV,VEITVFGRPC | LUAD |
| OPLAH | c.2699C>A | p.A900D | QQEGAVPLSFKLVQGGVFQEEAVTE[p.A900D]DLRAPGKVPNCSGTRNLHDNLSDLRA | QEEAVTEDL,VTEDLRAPGK,FQEEAVTEDL,EEAVTEDLRA | TGCT |
| OPN1LW | c.848C>A | p.P283H | STQKAEKEVTRMVVMLFAYCVCWG[p.P283H]HYTFPACFAAANPGYAFHPLMAALPA | CVCWGHYTF,VCWGHYTFF,AYCVCWGHY,GHYTFFACF,Y CVCWGHYTF,CVCWGHYTFF,FAYCVCWGHY,WGHYTFFACF | LUAD |
| OPN1MW | c.853G>A | p.A285T | QKAEKEVTRMVWMLAFCFCWGPY[p.A285T]TFFACFAAANPGYPFHPLMAALPAFF | CFCWGPYTF,FCWGPYTFF,FCWGPYTFFA,FCFCWGPYTF, CFCWGPYTFF | HNSC |
| OPRD1 | c.80G>T | p.C27F | EPAPSAGAELQPPLFANASDAYPSA[p.C27F]FPSAGANASGPPGARSASSLALAIAI | ASDAYPSAF,AYPSAFPSA,FPSAGANAS,YPSAFPSAG,DAYP SAFPSA,YPSAFPSAGA,NASDAYPSAF,SAFPSAGANA,FPSA GANASG | ACC |
| OPRM1 | c.1058G>A | p.R353H | KICVFIFAFIMPVLLITVCYGLMIL[p.R353H]HLKSVRMLSGSKEKDRNLRRITRMVL | LMILHLKSV,YGLMILHLK,CYGLMILHL,HLKSVRMLS,MILHL KSVR,ILHLKSVRM,LHLKSVRML,GLMILHLKSV,ILHLKSVR ML,HLKSVRMLSG,LMILHLKSVR,MILHLKSVRM | CRC |
| OPRM1 | c.1384C>T | p.R462C | NFKRCFREFCIPTSSNIEQQNSTRI[p.R462C]CQNTRDHPSTANTVDRTNHQLENLEA | STRICQNTR,NSTRICQNTR | UCEC |
| OPTN | c.70del C | p.P24fs | MSHQPLSCLITEKEDSPSESTGNGPP[p.P24fs]TWPTQWTRLPRRSCCCSR* | TQTWTRLPR,QTWTRLPRR,TWPTQTWTR,WPTQTWTRL, PPTWPTQTW,TWPTQTWTRL,RLPRRSCCCSR,PTWPTQTW TR,PTQTWTRLPR,TQTWTRLPRR,SESTGNGPPT,ESTGNG PPTW | STAD |
| OR10A3 | c.217T>G | p.F73V | IISLNQSLHVPMYLFLLNLSVVEVS[p.F73V]VSAVITPEMLVVLSTEKTMISPVGCF | NLSVVEVSV,SVVEVSVA,VEVSVSAVI,VSAVITPEM,SVVE VSVSAV,SVSAVSAVIT,VEVSVSAVIT | KIRC |
| OR10A3 | c.278C>A | p.S93Y | VVEVSPSAVITPEMLVVLSTEKTMI[p.S93Y]YFVGCFAQMYFILLFGGTECFLLGAM | LSTEKTMIY,VLSTEKTMIY,MIYFVGCFA,YFVGCFAQM,KTMI YFVGC,TMIYFVGCF,TEKTMIYFV,TMIYFVGCFA,KTMIYFV GCF,IYFVGCFAQM,VLSTEKTMIY,YFVGCFAQMY,STEKTM IYFV,LSTEKTMIYF | CRC |
| OR10H4 | c.597G>T | p.M199I | VIHHFPCHVLSLLKLACENKTSSVI[p.M199I]IGVMLVCVTALIGCLFLIILSYVFIV DRYVALCNPLRYMVIMNKRLRIQLV | KTSSVIIGV,SVIIGVMLV,IIGVMLVCV,TSSVIIGVM,VIIGVM LVCV,KTSSVIIGVM,SVVIIGVMLV,CENKTSSVII | LUAD |
| OR10J1 | c.470T>A | p.L157Q | DRYVALCNPLRYMVIMNKRLRIQLV[p.L157Q]QGACSIGLIVAITQVTSVRLPFCAR | QLVQGACSI,RLRIQLVQG,VQGACSIGL,RLRIQLVQGA,IQL VQGACSI,VQGACSIGLI | LUAD |
| OR10J1 | c.731G>A | p.R244Q | VPMGLVFISYVLIISTILKIASVEG[p.R244Q]QKKAFATCASHLTVVIVHYSCASIAY | KIASVEGQK,KIASVEGQKK,ASVEGQKKAF | TGCT |
| OR10X1 | c.892C>A | p.L298I | IVYLKPEASGDDTLIAVPYTVITPF[p.L298I]ISPIIFSLRNKDMKNAFRRMGNTVA | VITPFISPI,FISPIIFSL,ISPIIFSLR,PYTVITPFI,ITPFIS PII,TPFISPIIF,TVITPFISPI,VITPFISPII,FISPIIFSLR, ITPFISPIIF,PPISPIIFSL,VPYTVTPFI | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| OR10 Z1 | c.615G>C | p.L205 F | DTPPVLSLACGDTGPSELRIFILSL[p.L20 5F]FVLLVSFFFITISYAYILAAILRIPS | RIFILSLFV, FIILSLFVLL, IiLSLFVLLV, LRIFILSLF, IFILSLFVL, SLFVLLVSF, LFVLLVSFF, FVLLVSFFF, RIFILSLFVL, FILSLFV-LLV, FVLLVSFFFI, IFILSLFVLL, LSLFVLLVSF, SLFVLLVSFF, LFVLL VSFFF, ELRIFILSLF | LUAD |
| OR11 H12 | c.461A>C | p.H154 P | LLTVMAFDQYLAICRPLLYPNIMTGP[p. 154P]PLCAKLVILCWVCGFLWFLIPIVLI S | IMTGPLCAK, MTGPLCAKL, YPNIMTGPL, GPLCAKLVI, IMTG PLCAKL, LLYPNIMTGP, NIMTGPLCAK, LYPNIMTGPL, MTG PLCAKLV, GPLCAKLVIL, YPNIMTGPLC | GBM |
| OR13 C2 | c.25C>G | p.L9V | MEWENHTI[p.L9V]VEFFLKGLSGHPR LELLFVLIFIM | TIVVEFFLK, HTIVVEFFL, MEWENHTIV, IVVEFFLKGL, HTIVV EFFLK, MEWENHTIVV, WENHTIWEF | CESC |
| OR13 G1 | c.773G>A | p.R258 H | KAFSTCSSHLTVVTLYYSPVIYTYI[p.R25 8H]HPASSYTFERDKVVAALYTLVTPTLN S | VIYTYIHPA, YIHPASSYT, IHPASSYTF, TYIHPASSY, YTYIHPAS S, SPVIYTYIH, YTYIHPASSY, YIHPASSYTF, HPASSYTFER | BRCA |
| OR14 A16 | c.478G>T | p.G160 C | DRSTCVQRATVSWLYGGLIAVMHTA[p. G160C]CTFSLSYCGSNMVHQFFCDIP QLLAI | TACTFSLSY, HTACTFSLS, AVMHTACTF, MHTACTFSL, HTAC TFSLSY, VMHTACTFSL, GLIAVMHTAC, IAVMHTACTF | LUAD |
| OR1M 1 | c.205G>A | p.V69I | LILALISIDSHLHTPMYFFLANLSL[p.V69I] IDFCLATNTIPKMLVSLQTGSKAISY | NLSLIDFCL, SLIDFCLAT, FFLANLSLI, LANLSLIDF, NLSLIDFCL A, FLANLSLIDF, YFFLANLSLI, IDFCLATNTI | PRAD |
| OR2A 25 | c.240G>A | p.M80I | HTPMYFFLSHLAVVDIACACSTVPQ[p. M80I]ILVNLLHPAKPISFAGCMTQMFL FLS | ILVNLLHPA, CSTVPQIIV, TVPQILVNL, VPQILVNLL, ILVNLL HPAK, STVPQILVNL, TVPQILVNLL | LUAD |
| OR2A 25 | c.313A>T | p.S105 C | MLVNLLHPAKPISFAGCMTQMFLFL[p. S105C]CFAHTECLLLVVMSYDRYVAICH PLR | QMFLFLCFA, FLFLCFAHT, FLCFAHTEC, TQMFLFLCF, LCFAH TECL, MTQMFLFLCF, TQMFLFLCFA, FLCFAHTECL, CFAHTE CLLL, QMFLFLCFAH | CLL |
| OR2A 5 | c.212C>T | p.S71L | GLIWLDSRLHTPMYFFLSHLAIIDI[p.S7 1L]LYASNNVPKMLTNLGLNKRKTISFVP | HLAIIDILY, AIIDILYAS, LYASNNVPK, DILYASNNV, ILYASNN VP, HLAIIDILYA, ILYASNNVPK, LYASNNVPKM, SHLAIIDILY, LSHLAIIDIL, IDILYASNNV | SKCM |
| OR2A G2 | c.745G>T | p.G249 W | TVLRMPSNEGRKKALVTCSSHLIVV[p.G 249W]WMFYGAATFMYVLPSSFHSPK QDNII | IVVWMFYGA, WMFYGAATF, HLIVVWMFY, SHLIVVWMF, SSHLIVVWM, CSSHLIVVW, LIVVWMFYGA, WMFYGAATF M, SSHLIVVWMF, VWMFYGAATF, SHLIWWMFY, IWWM FYGAA | LUAD |
| OR2A K2 | c.111G>C | p.W37 C | LVSAMKTGNQSFGTDFLLVGLFQYG[p. W37C]CINSLLFVVIATLFVVALTGNIMLI H | FQYGCINSL, CINSLLFVV, QYGCINSLL, YGCINSLLF, FQYGCI NSLL, CINSLLFVVI, QYGCINSLLF | LUAD |
| OR2A K2 | c.133G>A | p.V45I | NQSFGTDFLLVGLFQYGWINSLLFV[p.V 45I]IIATLFVALTGNIMLIHLIRLNTRL | WINSLLFVI, SLLFVIIAT, LLFVIIATL, VIIATLFTV, IIATLFTVA, L FVIIATLF, WINSLLFVI, SLLFVIIATL, FVIIATLFTV, VIIATLFTV A, IIATLFTVAL, GWINSLLFVI, LLFVIIATLF | BRCA |
| OR2B 11 | c.29G>T | p.G10V | MKSDNHSFL[p.G10V]VDSPKAFILLGV SDRPWLELPLFVL | KSDNHSFLV, FLVDSPKAF, HSFLVDSPK, FLVDSPKAFI, SFLV DSPKAF, MKSDNHSFLV | LUSC |
| OR2H 1 | c.859G>A | p.V287I | NPYAQGRGKFFGLFYAVGTPSLNPL[p. V287I]IYTLRNKEIKRALRLLGKERDSR ES | IYTLRNKEI | GBM |
| OR2H 2 | c.615G>C | p.L205 F | PALIRLSCEDTSYNEIQVAVASVFI[p.L20 5F]FVVPLSLILVSYGAITWAVLRINSAK | AVASVFIPV, SVFIFVVPL, FIFVVPLSL, FVVPLSLIL, VAVASVFI F, IFVVPLSLI, VASVFIFVV, VAVASVFIFV, AVASVFIFVV, FIFV VPLSLI, FVVPLSLILV, VFIFVVPLSL, IFVVPLSLIL, QVAVASVFI F, ASVFIFVVPL | LUAD |
| OR2J2 | c.700G>T | p.G234 W | LIPLILILTTYGAIARAVLSMQSTT[p.G23 4W]WLQKVFRTCGAHLMVSLFFIPV MCM | MQSTTWLQK, TTWLQKVFR, QSTTWLQKV, VLSMQSTTW, LSMQSTTWL, STTWLQKVF, VLSMQSTTWL, MQSTTWLQK V, SMQSTTWLQ, STTWLQKVFR, AVLSMQSTTW, QSTTW LQKVF | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| OR2L13 | c.318G>T | p.M106I | AYNFLSGQKGISFLGCGVQSFFFLT[p.M106I]IACSEGLLLTSMAYDRYLAICHSLY | VQSFFFLTI,QSFFFLTIA,LTIACSEGL,IACSEGLLL,FLTIACSEG L,GVQSFFFLTI,LTIACSEGLL,VQSFFLTIA | LUAD |
| OR2L13 | c.724A>G | p.T242A | CGRVLFAVYHMHSKEGRKKAFTTIS[p.T242A]AHLTVVIFYYAPFVYTLRPRNLR SP | TISAHLTVV,KAFTTISAH,AHLTVVIFY,FTTISAHLT,TTISAHL TV,SAHLTVVIF,KKAFTTISA,ISAFILTVVI,FTTISAHLTV,TTIS AFILTVV,TISAFILTVVI,ISAFILTVVIF,RKKAFTTISA,KAFTTIS AHL,SAHLTVVIFY,AHLTVVIFYY,KAFTTISAH | LUAD |
| OR2L3 | c.199C>A | p.L67I | LSMILIFLDTHLHTPMYFLLSQLS[p.L67I]IIDLNYISTIVPKMASDFLSGNKSIS | QLSIIDLNY,FLLSQLSII,LLSQLSIIDL,QLSIIDLNYI, YFLLSQLSII,SQLSIIDLNY | LUAD |
| OR2L3 | c.3G>T | p.M1I | [p.M1I]IENYNQTSTDFILLGFFPPSRIGL FL | IENYNQTST | LUAD |
| OR2L3 | c.881A>G | p.K294R | EDKVLAVFYTTLTPMLNPIIYSLRN[p.K294R]REVMGALTRVSQRICSGKM* | IIYSLRNREV,RNREVMGALT,REVMGALTRV | TGCT |
| OR2L8 | c.361C>T | p.R121C | CGIQSFFLALGGAEAILLASMAYD[p.R121C]CYIAICFPLHYLIRMSKRVCVLMIT G | ASMAYDCYI,SMAYDCYIA,MAYDCYIAI,CYIAICFPL,SMAY DCYIAI,AYDCYIAICF,CYIAICFPLH | LUAD |
| OR2L8 | c.513G>T | p.R171S | GSWIIGSINACAHTVVLHIPYCRS[p.R171S]SAINHFFCDVPAMVTLACMDTWV YEG | RSSAINHFF,IPYCRSSAI,CRSSAINHF,HIPYCRSSAI,SAINHF FCDV,RSSAINHFFC,YCRSSAINHF,LHIPYCRSSA,CRSSAINH FF | LUAD |
| OR2L8 | c.603_604del|TG | p.S201fs | FCDVPAMVTLACMDTWVYEGTVFLS[p.S201fs]HHLSRVSLHWYFMFLWPGSL CCLPHEICRREEESLFDLQHPPHCSNFLL CTFCLHLSTSKIPAISNRGQGSGCLLHHP HPNAQPHHL* | FLSHHLSRV,SLHWYFMFL,FMFLWPGSL,FMFLWPGSLC,SLC CLPHEI,LLCTFCLHL,SLFDLQHPP,CLHLSTSKI,HLSTSKIPA,L LHHPHPNA,SRVSLHWYF,VSLHWYFMF,WYFMFLWPG,C SNFLLCTF,NFLLCTFCL,VFLSHHLSR,RVSLHWYFM,LSRVSL HWY,HPPHCSNFL,HPHNAQPHL,HPNAQPHHL,YEGTVFL SH,SHHLSRVSL,HLSRVSLHW,CRREEESLF,REEESLFDL,LQ HPPHCSN,RGQGSGCLL,GQGSGCLLH,EESLFDLQH,LHWY FMFLW,HLSRVSLHWY,VSLHWYFMFL,FMFLWPGSLC,FL WPGSLCCL,FLLCTFCLHL,HLSTSKIPAI,CLLHHPHNA,FLSH HLSRVS,TVFLSHHLSR,TFCLHLSTSK,VFLSHHLSRV,RVSLH WYFMF,SLHWYFMFLW,YFMFLWPGSL,TSKIPAISNR,HPP HCSNFLL,LSRVSLHWYF,LQHPPHCSNF,SLFDLQHPPH,YE GTVFLSHH,LSHHLSRVSL,HHLSRVSLHW,SRVSLHWYFM,I CRREEESLF,HCSNFLLCTF,LHLSTSKIPA,GQGSGCLLHH,WP GSLCCLPH | KIRP |
| OR2M2 | c.284delC | p.A95fs | DLMLICTTVPKMAFNVLSGKSISM[p.A95fs]VVVSHKFSSIYHCLALNVFWLLW LMTAILLFATL* | VSHKFSSIY,LALNVFFWL,ALNVFWLL,NVFFWLLWL,WLL WLMTAI,LLWLMTAIL,LMTAILLFA,VVSHKFSSI,ISMVVVS HK,SMVVVSHKF,KFSSIYHCL,IYHCLALNV,CLALNVFFW,VF FWLLWLM,LWLMTAILL,WLMTAILLF,GSKSISMVV,FSSIY HCLA,MTAILLFAT,TAILLFATL,SSIYHCLAL,SKSISMVVV,HK FSSIYHC,YHCLALNVF,HCLALNVFF,SIYHCLALNV,CLALNV FFWL,LALNVFFWLL,WLMTAILLFA,LMTAILLFAT,MTAILLFATL,VVS HKFSSI,SISMVVVSHK,VSHKFSSIYH,ISMVVVSHKF,IYHCLA LNVF,YHCLALNVFF,FWLLWLMTAI,LWLMTAILLF,GSKSIS MVVV,KFSSIYHCLA,VVSHKFSSIY,KSISMVVVSH,HKFSSIY HCL,FSSIYHCLAL | HNSC |
| OR2M2 | c.531C>A | p.F177L | GSTDGIIDAVATFSFCGSREIAH[p.F177L]LFCEFPSLLILSCNDTSIFEEVIFIC AHLFCEFPSL | HLFCEFPSL,GSREIAHLF,EIAHLFCEF,REIAHLFCE,HLFCEFP SLL,REIAHLFCEF,LFCEFPSLLI,GSREIAHLF,CGSREIAHLF, AHLFCEFPSL | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| OR2M2 | c.967T>C | p.F323L | TRAFMKILGKSESELPHKLYVLL[p.F323L]LAKFFFLISIFFYDVKILALIMYIA | LLLAKFFFL,LLAKFFFLI,LLAKFFFLIS,KLYVLLLAK,LVVLLLAKF,VLLLAKFFF,VLLLAKFFFL,LLLAKFFFLI,LLAKFFFLIS,KLYVLLLAKF,LYVLLLAKF,YVLLLAKFFF,LAKFFFLISI,LPHKLYVLLL | LUAD |
| OR2M3 | c.704G>A | p.R235H | PVAIIIASYARVILAVIHMGSGEGR[p.R235H]HKAFTTCSSHLLWGMYYGAALF MYI | SGEGRHKAF,HMGSGEGRHK,GSGEGRHKAF,HKAFTTCSS H,GEGRHKAFTT | CRC |
| OR2M3 | c.819G>T | p.M273I | VGMYYGAALFMYIRPTSDRSPTQDK[p.M273I][IVSVFYTILTPMLNPLIYSLRNKE VT | KIVSVFYTI,TQDKIVSVF,TQDKIVSVFY,KIVSVFYTIL,SPTQD KIVSV | HNSC |
| OR2M5 | c.613G>T | p.V205L | DFPSLLILSCNDTSIFEKVLFICCI[p.V205L][LMVFPVAIIIASYARVILAVIHMGS | FICCILMIV,CILMIVFPV,ILMIVFPVA,LMIVFPVAI,LFICCILM I,KVLFICCIL,VLFICCILM,VLFICCILMI,ILMIVFPVAI,LMIVFP VAII,KVLFICCILM,FICCILMIVF | LUAD |
| OR2M12 | c.551G>A | p.R184H | VATLSFPYCGAHEIDHFFCEAPVLV[p.R184H]HLACADTSVFENAMYICCVLMLL VPF | HLACADTSV,EAPVLVHLA,CEAPVLVHL,HLACADTSVF,CEA PVLVHLA | GBM |
| OR2M12 | c.772A>T | p.M258L | KKAFATCSSHVAVVGLFYGAGIFTY[p.M258L]LRPKSHRSTNHDKVVSAFYTM FTPLL | YGAGIFTYL,GIFTYLRPK,GAGIFTYLR,TYLRPKSHR,YLRPKS HRS,AGIFTYLRPK,FTYLRPKSHR,FYGAGIFTYL,YGAGIFTYL R,YLRPKSHRST | LUAD |
| OR2T2 | c.37T>G | p.F13V | MGMEGLLQNSTN[p.F13V]VVLTGLIT HPAFPGLLFAIVFSIFVV | GLLQNSTNVV,LLQNSTNVV,STNVVLTGL,LQNSTNVVL,GLL QNSTNVV,LLQNSTNVVL,NSTNVVLTGL,STNVVLTGLI,LQ NSTNVVLT | LUSC |
| OR2T27 | c.31G>T | p.D11Y | MEQSNYSVSYA[p.D11Y]YFILLGLFSNA RFPWLLFALILIVFL | QSNYSVYAY,SVVAYFIL,YAYFILLGL,SNYSVYAYF,NYSVYA YFI,YSVYAYFIL,VYAYFILLG,AYFILLGLF,YSVYAYFIL,NYSV YAYFIL,VYAYFILLGL,YAYFILLGLF,EQSNYSVYAY,QSNYSVY AYF,SNYSVYAYFI | LUAD |
| OR2T33 | c.358C>A | p.R120S | CGVQIFLPLPTLGGGECFLLAAMAYD[p.R120S]SYAAVCHPLRYPTLMSWQLCLR MTMS | AMAYDSYAA,MAYDSYAAV,AAMAYDSYA,SYAAVCHPL,L AAMAYDSY,FLLAAMAYDS,AMAYDSYAAV,AAMAYDSYA A,LLAAMAYDSY,SYAAVCHPLR,LAAMAYDSTA,DSYAAVC HPL,MAYDSYAAVC | HNSC |
| OR2T33 | c.494C>A | p.P165Q | LRMTMSCWLLGAADGLLQAWTLSF[p.P165Q]QYCCGAHEIDHFFCETPVLVRLA CADT | FQYCCGAHEI,TLSFQYCGA,AVVTLSFQY,LSFQYCCGAH,SFQY CGAHEI,QAVVTLSFQY,FQYCCGAHEID | LUAD |
| OR2T34 | c.737G>T | p.C246F | SSYTLILHLIHRMNSAAGRRKALAT[p.C246F]FSSHMIIVLLLFGASFYTYMLRSSY H | ALATFSSHM,KALATFSSH,ATFSSHMII,GRRKALATF,RKAL ATFSS,FSSHMIIVL,LATFSSHMI,ALATFSSHMI,ATFSSHMII V,FSSHMIIVLL,TFSSHMIIVL,KALATFSSHM,AGRRKALATF, RKALATFSSH,LATFSSHMII | LUAD |
| OR2T4 | c.408_409CG>TC | p.V137L | KMLLDQVMGVNKISAPECGMQMFFY[p.V137L][LTLAGSEFFLLATMAYDRYVAI CHPLR | GMQMFFYLT,MQMFFYLTL,CGMQMFFYL,GMQMFFYLT L,MQMFFYLTLA,FYLTLAGSEF | LIHC |
| OR2T6 | c.637G>T | p.V213L | ACGDKITYETVMYVCCVAMLLIPFS[p.V213L][LVTASYTRILITVHQMTSAEGRK KAF | AMLLIPFSL,MLLIPFSLV,LLIPFSLVT,LIPFSLVTA,LVTASYTRI, SLVTASYTR,PFSLVTASY,IPFSLVTAS,AMLLIPFSLV,LLIPFSL VTA,SLVTASYTRI,FSLVTASYTR,IPFSLVTASY,VAMLLIPFSL | LUAD |
| OR4C12 | c.744C>A | p.F248L | LKNNSLEGRCKALSTCISHIIVVVL[p.F248L]LFVPCIFVYLRSVTTLPIDKAVAVFY | IIVVVLLFV,LLFVPCIFV,HIIVVVLLF,VLLFVPCIF,LFVPCIFVY, HIIVVVLLFV,LLFVPCIFVY,IIVVVLLFVP,SHIIVVVLLF,VVLLF VPCIF,LFVPCIFVYL,ISHIIVVVLL | UCEC |
| OR4C12 | c.837G>T | p.M279I | FVYLRSVTTLPIDKAVAVFYTMWVP[p.M279I][ILNPVVYTLRNAEVKSAIRKLWR KKV | MVVPILNPV,ILNPVVTL,VFYTMVVPI,FYTMVVPIL,VPILN PVVY,AVFYTMVVPI,TMVVPILNPV,MVVPILNPVV,ILNPV VTLR,VFYTMVVPIL,VVPILNPVVY | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| OR4C12 | c.925G>T | p.D309Y | VYTLRNAEVKSAIRKLMRKKVTSDN[p.D309Y]Y | RKKVTSDNY,WRKKVTSDNY | LUAD |
| OR4C16 | c.188A>T | p.Y63F | LGNLLIISVKTSQALKNPMFFLF[p.Y63F]LSLSDTCLSTSITPRMIVDALLKKT | PMFFLFFL,FLSLSDTCL,FFFLFFLSL,NPMFFLFF,FLFFLSLS DT,FLSLSDTCLS,KNPMFFLFF,MFFFLFLSL,NPMFFFLFFL | CLL |
| OR4C16 | c.403A>C | p.S135R | IFILILTAVDRYVDICKPLHVMTII[p.S135R]RQWVCGVLMAVAWVGSCVHSLVQIFL | YMTIIRQWV,IIRQWVCGV,HYMTIIRQW,RQWVCGVLM,T IIRQWVCGV,RQWVCGVLMA,HVMTIIRQWV,LHYMTIIRQ W,IRQWVCGVLM | STAD |
| OR4C16 | c.484C>A | p.L162M | WVCGVLMAVAWVGSCVHSLVQIFLA[p.L162M]MSLPFCGPNVINHCFCDLQP LLKQAC | SLVQIFLAM,VQIFLAMSL,FLAMSLPFC,IFLAMSLPF,MSLPF CGPNV,FLAMSLPFCG,QIFLAMSLPF,HSLVQIFLAM,VQIFL AMSLP | LUAD |
| OR4C3 | c.389_390insT | p.H130fs | IADSLYEGRTISYECCMAQLFGAHF[p.H130fs]FGRC* | AQLFGAHFF,LFGAHFFGR,QLFGAHFFGR,MAQLFGAHFF | LUAD |
| OR4E2 | c.677G>A | p.R226Q | TNSGTISLSCFLAVVTSYMVLVSL[p.R226Q]QKHSAEGRQKALSTCSAHFMVA LFF | MVILVSLQK,ILVSLQKFISA,YMVILVSLQK | SKCM |
| OR4K2 | c.761G>T | p.C254F | SSRGSSKALSTCTAHFIVVFLFFGP[p.C254F]FIFIYMWPLSSFLTDKILSVFYTIFT | FLFFGPFIF,FIFIYMWPL,VFLFFGPFI,LFFGPFIFI,FFGPFIFIY,VVFLFFGPF,GPFIFIYMW,VVFLFFGPFI,FLFFGPFIFI,IVVFLF FGPF,VFLFFGPFIF,FFGPFIFIYM,FGPFIFIYMW,PFIFIYMW PL,LFFGPFIFIY | LUSC |
| OR4K5 | c.529del T | p.F177fs | VHTLSQLSFTVNLPFCGPNWDSFF[p.F177fs]VIFLESPNLPAWTLTSLKY* | NVVDSFFVI,FLESPNLPA,PAWTLTSLK,AWTLTSLKY,SPNLP AWTL,LPAWTLTSL,VVDSFFVIF,LESPNLPAW,VVDSFFVIFL, FVIFLESPNL,NLPAWTLTSL,PAWTLTSLKY,ESPNLPAWTL, NVVDSFFVIF,FLESPNLPAW,LESPNLPAWT | STAD |
| OR4M1 | c.122G>A | p.G41E | GLSQTREVQLVLFVIFLSFYLFILP[p.G41E]ENILLICTIRLDPHLTSPMYFLLANL | YLFLFILPEN,FILPENILI,ILPENILLI,YLFILPENIL,FILPEN ILLI,FYLFILPENI,LFILPENILI,ENILLICTIR | SKCM |
| OR4M2 | c.355G>T | p.A119S | FDGCIAQLFFLHFAGASEMFLTVMI[p.A119S]SFDLYTAICRPLFIYATIMNQRLC CIL | LTVMSFDLY,LLTVMSFDL,VMSFDLYTA,MSFDLYTAI,MFLL TVMSF,TVMSFDLYT,LLTVMSFDLY,FLLTVMSFDL,TVMSF DLYTA,VMSFDLYTAI,EMFLLTVMS,MSFDLYTAIC,SEMFL LTVMS | LUAD |
| OR4M2 | c.481G>T | p.A161S | MNQRLCCILVALSWRGGFIHSIIQV[p.A161S]LIVRLPFCGPNELDSYFCDITQVV R | SIIQVSLIV,IQVSLIVRL,SLIVRLPFC,VSLIVRLPF,HSIIQVSLI,I HSIIQVSL,FIHSIIQVSL,SIIQVSLIVR,HSIIQVSLIV,QVSLIVRL PF | LUAD |
| OR4M2 | c.803C>T | p.S268F | YSHITIVVLMFGPSIYIYARPFDSF[p.S268F]FLDKVVSVFNTLIFPLRNPIIYTLRN | FFLDKVVSV,FLDKVVSVF,YARPFDSFF,IYARPFDSFF,FFLDK VVSVF,YARPFDSFFL,RPFDSFFLDK | SKCM |
| OR4N2 | c.122G>A | p.G41E | GLTQSQDIQLLVFVLVLIFYFIILP[p.G41E]ENFLIIFTIKSDPGLTAPLYFFLGNL | FILPENFLI,IILPENFLII,LLPENFLII,YFIILPENF,ENFLIIFTI, LPENFLIIF,FIILPENFLI,FYFIILPENF,YFIIL PENFL,ILPENFLIIF,PENFLIIFTI | SKCM |
| OR4N2 | c.448_449insT | p.L150fs | ICRPLHYPTVMNPRTCYAMMLALWL[p.L150fs]WGFCPLHYPGGPHPPLAFLM PKPAGQLL* | MLALWLWGF,AMMLALWLW,LWLWGFCPL,LWGFCPLH Y,YPGGPHPPL,GPHPPLAFL,WPKPAGQLL,LHYPGGPHP,L AFLWPKPA,MMLALWLWGF,MLALWLWGFC,ALWLWGF CPL,FLWPKPAGQL,YAMMLALWLW,HYPGGPHPPL,LWP KPAGQLL,WLWGFCPLHY,WPKPAGQLLL,LHYPGGPHPP, GPHPPLAFLW | BLCA,KIRC |
| OR4N4 | c.448_449insT | p.L150fs | ICRPLHCSTVMNPRACYAMMLALWL[p.L150fs]WGFCPLHYPGGPHPPLAFLM PKPAGQLL* | MLALWLWGF,AMMLALWLW,LWLWGFCPL,LWGFCPLH Y,YPGGPHPPL,GPHPPLAFL,WPKPAGQLL,LHYPGGPHP,L AFLWPKPA,MMLALWLWGF,MLALWLWGFC,ALWLWGF CPL,FLWPKPAGQL,YAMMLALWLW,HYPGGPHPPL,LWP KPAGQLL,WLWGFCPLHY,WPKPAGQLLL,LHYPGGPHPP, GPHPPLAFLW | CLL |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| OR51A7 | c.371T>G | p.L124R | AQEFFIHGFTVMESSVLLIMSLDRF[p.L124R]RAIHNPLRYSSILTSNRVAKMGLILA | IMSLDRFRA,LIMSLDRFR,RFRAIHNPL,MSLDRFRAI,RAIHNPLRY,IMSLDRFRAI,LIMSLDRFRA,MSLDRFRAIH,RFRAIHNPLR,FRAIHNPLRY,LLIMSLDRFR | STAD |
| OR51B2 | c.488C>T | p.S163L | RVIALGVGVFLRGFVSILPVIILRF[p.S163L]LFSYCKSHVITRAFCLHQEIMRLACA | RLFLFSYCK,PVILRLFLF,ILRLFLFSY,LPVILRLFL,FLFSYCKSH,FLFSYCKSHV,ILPVILRLF,VILRLFLFSY,LPVILRLFLF | SKCM |
| OR51B5 | c.197_213del e\|CCACAGACCTGGGGCTG | p.A66fs | GTLLLLIKEDHNLHEPMYFFLAMLA[p.A66fs]GPDHNAHGAGSPLAGSQGDWKCGLLFPGLLYTLTFLSRVWHSACHGL* | MLAGPDHNA,LLFPGLLYT,GLLYTLTFL,LLYTLTFLS,YTLTFLSRV,FLSRVWHSA,GLLFPGLLY,LFPGLLYTL,VWHSACHGL,LYTLTFLSR,NAHGAGSPL,SQGDWKCGL,GDWKCGLLF,FPGLLYTLT,AMLAGPDHNA,GLLFPGLLYT,LLFPGLLYTL,FLSRVWHSAC,RVWHSACHGL,LLYTLTFLSR,LYTLTFLSRV,YTLTFLSRVW,LSRVWHSACH,CGLLFPGLLY,HNAHGAGSPL,FPGLLYTLTF,MLAGPDHNAH,SQGDWKCGLL,WKCGLLFPGL,SPLAGSQGDW | KIRC |
| OR51F2 | c.200G>C | p.R67P | SIPFCLLYVAVSGNSMILFVVLCE[p.R67P]PSLHKPMYYFLSMLSATDLSLSLCTL | VLCEPSLHK,PSLHKPMYY,CEPSLFHPM,VVLCEPSLHK,LCEPSLHKPM,EPSLHKPMYY | LUSC |
| OR51S1 | c.476G>A | p.R159Q | ICRPLHYPALLTNGVISKISLAISF[p.R159Q]QCLGLHLPLPFLLAYMPYCLPQVLTH | SLAISFQCL,SFQCLGLHL,ISFQCLGLH,FQCLGLHLPL,ISLAISFQCL,LAISFQCLGL,ISFQCLGLHL | LUSC |
| OR51V1 | c.892C>A | p.P298T | FGKHLSPVAHVLIGNIYILFPPLMN[p.P298T]TIIYSVKTQQIHTRMRLFSLKRY | ILFPPLMNT,LMNTIIYSV,LFPPLMNTI,MNTIIYSVK,NTIIYSVKT,PPLMNTIIY,FPPLMNTII,ILFPPLMNTI,PLMNTIIYSV,LMNTIIYSVK,LFPPLMNTII,FPPLMNTIIY | LUAD |
| OR52M1 | c.397C>T | p.R133C | FVHALTAMESGVLLAMACDRAAAIG[p.R133C]CPLHYPVLVTKACVGYAALALALKAV | RAAAIGCPL,AAIGCPLHY,CPLHYPVLV,AIGCPLHYPV,RAAAIGCPLH,AAAIGCPLHY,IGCPLHYPVL | CRC |
| OR5AK2 | c.267G>T | p.K89N | QHLAFVDICYTSAITPKMLQSFTEE[p.K89N]NNLMLFQGCVIQFLVYATFATSDCYL | FTEENLML,TEENNLMLF,FTEENNLMLF,LQSFTEENNL,QSFTEENNLM | UCEC |
| OR5AS1 | c.117G>T | p.M39I | FVGFTDYLPLRVTLFLVFLVYTLT[p.M39I]IVGNILLIILVNINSSLQIPMYFLS | FLLVYTLTI,LLVYTLTIV,VFLLVYTLTI,YTLTIVGNI,LLVYTLTIV,TIVGNILLI,LTIVGNILL,LLVYTLTIV,VFLLVYTLTI,YTLTIVGNI,YTLTIVGNIL,LTIVGNILLI | LUAD |
| OR5AU1 | c.935G>A | p.R312H | KAFSTCASHLTAICLFFGTTLFMYL[p.R312H]HPRSSYSLTQDRTVAVIYTVVIPVLN | FMYLHPRSS,YLHPRSSYS,TLFMYLHPR,GTTLFMYLH,MYLHPRSSY,HPRSSYSLT,LHPRSSYSL,YLHPRSSYSL,FMYLHPRSSY,TTLFMYLHPR | CRC |
| OR5B12 | c.865A>T | p.S289C | HFMGTDKMASVFYAIVIPMLNPLVY[p.S289C]CLRNKEVKSAFKKTVGKAKASIGFIF | MLNPLVYCL,LVYCLRNKEV,MLNPLVYCLR,CLRNKEVKSA | LUAD |
| OR5B17 | c.488G>A | p.R163H | VCACLAIGCVVIGFLNASIQIGDTF[p.R163H]HLSFCMSNVIHHFFCDKPAVITLTCS | IQIGDTFHL,HLSFCMSNV,DTFHLSFCM,IGDTFHLSF,HLSFCMSNVI,DTFHLSFCMS,QIGDTPHLSF | CRC |
| OR5B17 | c.798G>T | p.M266I | SHLIAIFLFYITVIMIRPSSSHS[p.M266I]IDTDKIASVFYTMIIPMLSPIVYTLR | SSHSIDTDK,SIDTDKIASV,YIRPSSSHSI,SSSHSIDTDK,RPSSSHSIDT,IDTDKIASVF | LUAD |
| OR5D13 | c.706C>T | p.R236C | SSLIIILTSYMLIFFTIMKMRSASG[p.R236C]CQKTFSTCASHLTAITIFHGTILFLY | KMRSASGCQ,SASGCQKTF,CQKTFSTCA,KMRSASGCQK,RSASGCQKTF,CQKTFSTCAS | GBM |
| OR5D14 | c.736C>A | p.H246N | VFIFVTVLKIRSVSGRHKAFSTWAS[p.H246N]NLTSITIFHGTILFLYCVPNSKNSRQ | TWASNLTSI,KAFSTWASN,ASNLTSITI,SNLTSITIF,STWASNLTSI,KAFSTWASNL,WASNLTSITI,ASNLTSITIF | LUAD |
| OR5D16 | c.790C>A | p.P264T | VFSTCASHLTAITIFHGTILFLYCV[p.P264T]TNSKNSRHTVKVASVFYTVVIPLLNP | FLYCVTNSK,CVTNSKNSR,LFLYCVTNSK | LUAD |
| OR5D18 | c.812C>A | p.T271K | LTAITIFHGTILFLYCVPNSKNSRH[p.T271K]KVKVASVFYTVVIPMLNPLIYSLRNK | KVKVASVFY,RHKVKVASV,HKVKVASVF,NSKNSRHVK,KVKVASVFYT,RHKVKVASVF,HKVKVASVFY | LUSC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| OR5F1 | c.131G>T | p.G44V | DTLELQIILFLFFLVIYTLTVLGNL[p.G44V]VMILLIRIDSQLHTPMYFFLANLSFV | VLGNLVMIL,TLTVLGNLIV,TVLGNLVMI,LTVLGNLVM,YTLT VLGNLV,VLGNLVMILL,NLVMILLIRI,TLTVLGNLVM | LUAD |
| OR5J2 | c.106G>T | p.A36S | EFILLGLTDHAELKAVLFVVFLVIY[p.A36]S|STLLRNLGMILLIQITSKLHTPMYF | VVFLVIYSI,FLVIYSITL,LVIYSITLL,VIYSITLLR,YSITLLRNL, FV VFLIVIYSI,FLVIYSITLL,LVIYSITLL,VFLIVIYSITL,IYSITILL-RNL | LUAD |
| OR5L1 | c.824C>A | p.T275N | VFHGTVLSIYCRPSSGNSGDADKVA[p.T275N]NVFYTVVIPMLNSVIYSLRNKDVKEA | KVANVFYTV,ANVFYTVVI,DADKVANVF,DADKVANVFY,K VANVFYTVV,NVFYTVVIPM,GDADKVANVF,VANVFYTVVI | LUAD |
| OR5M3 | c.265de|A | p.T89fs | LSFVDVNFSSNVTPKMLENLLSDKK[p.T89fs]QLLMLVV* | LSDKKQLLM,LLSDKKQLL,KKQLLMLW,LSDKKQLLML,LLS DKKQLLM | STAD |
| OR5P2 | c.299C>T | p.A100V | PNMLVNFLVERNTVSYLGCAIQLGS[p.A100V]VAFFATVECVLLAAMAYDRFVAICSP | QLGSVAFFA,GSVAFFATV,IQLGSVAFF,AIQLGSVAF,CAIQL GSVA,IQLGSVAFFA,VAFFATVECV,CAIQLGSVAF,AIQLGS VAFF | GBM |
| OR6C65 | c.460_461insT | p.I154fs | TTIMSNKVCNWLVISSWLAGFLIIF[p.I154fs]SPRDYGPPTGFL* | DYGPPTGFL,GFLIIFSPR,LIIFSPRDY,SPRDYGPPT,RDYGPP TGF,WLAGFLIIFS,AGFLIIFSPR,FLIIFSPRDY,RDYGPPTGFL | LUAD |
| OR6C75 | c.280G>T | p.G94W | ISFTSVCIPRFLVTVVTGNRTISYN[p.G94W]WCVAQLFFFIFLGVTEFYLLAAMSYD | RTISYNWCV,SYNWCVAQL,YNWCVAQLF,NWCVAQLFF,S YNWCVAQLF,NWCVAQLFFF,RTISYNWCVA,ISYNWCVAQL | LUAD |
| OR6K2 | c.236C>A | p.P79Q | HLHTPMYTFISALSPLEIWYTTATI[p.P79Q]QKMLSSLLSERSISFNGCLLQMYFFH | TIQKMLSSL,IQKMLSSLL,YTTATIQKM,TTATIQKML,ATIQK MLSSL,TIQKMLSSLL,IWYTTATIQK,WYTTATIQKM,YTTATI QKML,IQKMLSSLLS | LUAD |
| OR6K6 | c.931T>C | p.F311L | YLRFSATYSVFWDTAIAVTFVILAP[p.F311L]LFNPIIYSLKNDMKEAIGRLFHYQK | VTFVILAPL,ILAPLFNPI,TFVILAPLF,APLFNPIIY,VILAPLFNPI, ILAPLFNPII,AVTFVILAPL,LFNPIIYSLK,VTFVILAPLF,LAPLF NPIIY | TGCT,THCA |
| OR6N2 | c.877C>T | p.R293C | LTLDRTLAIVVSVLTPMVNPIIYSL[p.R293C]CNKEIIKAIKRTIFQKGDKASLAHL | SLCNKEIIK,PIIYSLCNK,IYSLCNKEI,YSLCNKEII,IYSLCNKEI, YSLCNKEIIK,IYSLCNKEII,CNKEIIKQIK,MVNPIIYSLC | GBM |
| OR6V1 | c.744de|C | p.I248fs | VLRIPSASSCQKAFSTCGSHLTLVF[p.I248fs]MATVVPSFCMSGLAKLTLCKSGRSWPW* | LTLVFMATV,TLVFMATVV,FMATVVPSF,FCMSGLAKL,GL AKLTLCK,SFCMSGLAK,GSHLTLVFM,VPSFCMSGL,MSGLA KLTL,TLCKSGRSW,CKSGRSWPW,HLTLVFMATV,LTLVFM ATW,FMATVVPSFC,VVPSFCMSGL,CMSGLAKLTL,PSFC MSGLAK,SGLAKLTLCK,VFMATVVPSF,MATVVPSFCM,LTL CKSGRSW | HNSC |
| OR7C1 | c.311de|T | p.F104fs | PKMLNLILTQNKFITYAGCLSQIFF[p.F104fs]SLHLDAWTIYS* | CLSQIFFSL,SQIFFSLHL,SLHLDAWTI,FFSLHLDAW,LHLDA WTIY,FSLHLDAWTI,IFFSLHLDAW,SLHLDAWTIY,LSQIFFS LHL | KIRC |
| OR7C1 | c.535de|T | p.C179fs | MGSLLETLTVLRLSFCTEMEIPHFF[p.C179fs]VIYLKS* | MEIPHFFVI,EMEIPHFFV,IPHFFVYL,MEIPHFFVIY,IPHFFV IYLK,TEMEIPHFFV,EMEIPHFFVI,EIPHFFVYL | STAD |
| OR7E24 | c.21_22insT | p.L7fs | MSYFPILFFFF[p.L7fs]PQKVSELHRATESHRCLRIPPPGTLRGSRTAAGPRWAVPVHVPGHGAGEPAHHPGCQL* | ILFFFFPQK,LFFFFPQKA,ATESHRCLR,GSRTAAGPR,RTAAG PRWA,TAAGPRWAV,TLRGSRTAA,RATESHRCL,LRIPPPGT L,FPQKVSELH,ILFFFFPQKV,RTAAGPRWAV,PLLFFFFPQK, FFFFPQKVSEL,RATESHRCLR,CLRIPPPGTL,GTLRGSRTAA,R GSRTAAGPR,ELHRATESHR,GPRWAVPVHV,EPAHHPGCQ L,SELHRATESH,HRATESHRCL,GSRTAAGPRW,FPILFFFFP Q | PRAD |
| OR8D2 | c.917G>T | p.R306M | IIPMLNPLIYSLRNKDVKNALKKMT[p.R306M]MGRQSS | ALKKMTMGR,KNALKKMTM,KKMTMGRQS,KMTMGRQSS,NALKKMTMGR,VKNALKKMTM,KKMTMGRQSS | LUAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| OR8H2 | c.498G>T | p.L166F | CLALITGPYVIGFIDSFVNVSMSR[p.L166F]FHFYDSNVIHHFFCDTSPILALSCTD | VSMSRFHPY,VVSMSRFHF,MSRFHFYDS,RFHFYDSNV,VN VVSMSRF,FHFYDSNVI,VVSMSRFHFY,RFHFYDSNVI,MSR FHFYDSN,FVNVSMSRF,NVVSMSRFHF,SRFHFYDSNV,F HFYDSNVIH | LUSC |
| OR8J3 | c.479C>T | p.S160L | VVSRRLCLLLVSLTYLYGFSTAIVV[p.S160L]LPCIFSVSYCSSNIINHFYCDIAPLL | VVLPCIFSV,TAIVVLPCI,LPCIFSVSY,AIVVLPCIF,IVVLPCIFS V,VLPCIFSVSY,STAIVVLPCI,YGFSTAIVVL,TAIVVLPCIF | LUSC |
| OR8K3 | c.705G>T | p.K235N | SLLIVLLSYLLILVAILRMNSAGRQ[p.K235N]NAFSTCGAHLTVIVFYGTLLFMYV Q | NSAGRQNAF,NAFSTCGAH,RQNAFSTCG,RMNSAGRQNA, RQNAFSTCGA,MNSAGRQNAF,NAFSTCGAHL | LUSC |
| OR8S1 | c.296C>T | p.A99V | SSVIVPKMLENLLSQRKTISVEGCL[p.A9 9V]VQVFFVFVTAGTEACLLSGMAYDR HA | LVQVFFVFV,TISVEGCLV,CLVQVFFVF,VEGCLVQVF,VQVF FVFVT,CLVQVFFVFV,VQVFFVFVTA,KTISVEGCLV,GCLVQ VFFVF,EGCLVQFFV,SVEGCLVQVF,VEGCLVQVFF | CRC |
| OR9A2 | c.865C>T | p.R289W | VEYNKIVSLLVSVLTPFLNPFIFTL[p.R28 9W]WNDKVKEALRDGMKRCCQLLKD* | FIFTLWNDK,FLTWNDKVK,LNPFIFTLW,FIFTLWNDKV,TL WNDKVKEA,FLNPFIFTLW | LUAD |
| OR9G9 | c.506G>T | p.R169L | VAVSYCGGFINSSIITKKTFSFNFC[p.R16 9L]LENIIDDFFCDLLPLVELACGEKGGY | KTFSFNFCL,SFNFCLENI,FNFCLENII,LENIIDDFF,FSFNFCLE NI,SFNFCLENII,KTFSFNFCLE,KKTFSFNFCL | LUAD |
| OSBP | c.2163G>C | p.Q721H | FSELALTLNAWESGTAPTDSRLRPD[p. Q721H]HRLMENGRMDEANAEKQRLE EKQRLS | RLRPDHRLM,DSRLRPDHR,RLRPDHRLME,SRLRPDHRLM | CESC |
| OSBP2 | c.1881_1882insC | p.H627fs | ETFELDRLDDMGLRSLCEQVSHHPP[p. H627fs]LSCALRVLQAWLEPLAGDHHL QQVPGKIHLHHAARCHPLR IPGQWESL RVEEEHLNCSQHHRGQALDRPVRGHR DCEP* | VLQAWLEPL,ALRVLQAWL,KIHLHHAAR,HAARCHPLR,AA RCHPLRI,HLNCSQHHR,SQHHRGQAL,HHAARCHPL,EQVS HHPPL,CALRVLQAW,LQAWLEPLA,LQQVPGKIH,QQVPG KIHL,GKIHLHHAA,GQWESLRVE,EPLAGDHHL,HPLRIPGQ W,RVLQAWLEPL,VLQAWLEPLA,KIHLHHAARC,HHAARC HPLR,CEQVSHHPPL,SHHPPLSCAL,LQAWLEPLAG,LQQVP GKIHL,QQVPGKIHLH,LHHAARCHPL,LRIPGQWESL,WESL RVEEEH,LEPLAGDHHL,HPPLSCALRV,IPGQWESLRV | STAD |
| OSBPL6 | c.1730G>A | p.R577Q | SEDNTSVADNISRQILNGELTGGAF[p.R 577Q]QNGRRACLPAPCPDTSNINLWN ILRN | FQNGRRACL,LTGGAFQNGR | UCEC |
| OSTN | c.344G>A | p.R115Q | PLDRLSAGSVDHKGKQRKVVDHPKR[p. R115Q]QFGIPMDRIGRNRLSNSRG | RQFGIPMDR,PKRQFGIPM,RQFGIPMDRI,HPKRQFGIPM, KVVDHPKRQF | CRC |
| OTOF | c.1163C>T | p.T388M | DDISSGLKGYVKCDVAWGKGDNIK[p. T388M]MPHKANETDEDDIEGNLLLPE GVPPE | KGDNIKMPHK | BRCA |
| OTOF | c.3910G>A | p.E1304K | KLETMVKLDATSEAVVKDVAEEEK[p. E1304K]KKKKKKKGTAEEPEEEEPDES MLDWW | KVDAEEEKK | STAD |
| OTOL1 | c.1291G>A | p.V431I | VAQNKFQFKSRETLYGQEIDQASLL[p.V 431I]IILKLSAGDQVWLEVSKDWNGVY VSA | QASLLIIIK,DQASLLIII,QEIDQASLLI,DQASLLIIL | CRC |
| OTOP1 | c.310_318delCTGCTGTGG | p.LLW104del | AWAVHAAGVSKSDLLCFLTALMLLQ[p. LLW104de|]MLWVGRSSAHRRLFRLK DTHAGAGWLRGSITLF | MLLQMLWVY,LQMLWYVGR,LMLLQMLWY,LTALMLLQ M,ALMLLQMLW,FLTALMLLQM,LMLLQMLWYV,ALMLL QMLWY,LLQMLWYVGR,TALMLLQMLW | ACC |
| OTUD3 | c.830G>T | p.R277I | VQNLEAENYNIESAIIAVLRMNQGK[p. R277I]INNAEENLEPSGRVLKQCGPLW EEGG | RMNQGKINNA,GKINNAEENL | CRC |
| OTUD4 | c.2726C>T | p.T909I | ALASIPPVAEGKAHPPTQILNRERE[p.T9 09I]IVPVELEPKRTIQSLKEKTEKVKDPK | ILNREREIV,RREREIVPVE,LNREREIVPV,TQILNREREI,REREI VPVEL,REIVPVELEP | BLCA,PRAD, THCA |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| OTUD4 | c.458_460del\|CTG | p.A153 del\| | VADEDNSEISDSEDDSCKSKTAAAA[p.A153del\|]DVNGFKPLSGNEQLKNNGNSTSLPLSRK | KSKTAAAAD, KSKTAAAADV, TAAAADVNGF | PRAD |
| OTX2 | c.130de\|C | p.R44fs | TSGMDLLHPSVGYPGPWASCPAATP[p.R44fs\|GNSAGRGRRSLGRS* | RGRRSLGRS, SAGRGRRSL, AGRGRRSLGR, CPAATPGNSA, N SAGRGRRSL | STAD |
| OXR1 | c.364G>A | p.E122K | GTIEYTVESRDSLNSIALKFDTTPN[p.E122K]KLVQLNKLFSRAVVTGQVLIVPDPEY | KLVQLNKLF, ALKFDTTPNK, DTTPNKLVQL, LKFDTTPNKL, N KLVQLNKLF | UCEC |
| P2RX1 | c.58de\|C | p.R20fs | MARRFQEELAAFLFEYDTP[p.R20fs\|AWCWCVIRRWALSSD* | FLFEYDTPA, DTPAWCWCVI, TPAWCWCVI, WCVIRRWAL, F LFEYDTPAW, AWCWCVIRRW, CWCVIRRWAL, TPAWCWC VIR, DTPAWCWCVI, FEYDTPAWCW | STAD |
| P2RX7 | c.425C>A | p.P142Q | RLCPEYPTRRTLCSSDRGCKKGWMD[p.P142Q]QQSKGIQTGRCVVYEGNQKTCEVSAW | WMDQQSKGI, KGWMDQQSK | LUAD |
| PABPC1 | c.1223A>T | p.Y408F | MQRMASVRAVNPVINPYQPAPPSGF[p.Y408F]FFMAAIPQTONRAAYYPPSQIAQLRP | YQPAPPSGF, QPAPPSGFY, PYQPAPPSGF, YQPAPPSGFF, Q PAPPSGFFM, APPSGFFMAA, PPSGFFMAAI | KIRC |
| PABPC1 | c.280C>T | p.R94C | LDTMNFDVIKGKPVRIMWSQRDPSL[p.R94C]CKSGVGNIFIKNLDKSIDNKALYDTF | SQRDPSLCKXK, CSGVGNIF, SLCKSGVGN, WSQRDPSLCK, LC KSGVGNIF | DLBCL |
| PABPC1 | c.467_468i nsG | p.E156fs | DENGSKGYGFVHFETQEAAERAIEK[p.E156fs]NEWNAPK* | AERAIEKNEW | KIRC |
| PABPC1 | c.541G>A | p.A181T | EKMNGMLLNDRKVFVGRFKSRKERE[p.A181T]TELGARAKEFTNVYIKNFGEDMDDER | SRKERETEL, KERETELGA, RETELGARA, KSRKERETEL, TELG ARAKEF | KIRC |
| PABPC1 | c.761_762i nsT | p.K254fs | KSKGFGFVSFERHEDAQKAVDEMNG[p.K254fs]NGAQWKTNLCWSSSEKGGTADGT* | NLCWSSSEK, KTNLCWSSS, AQWKTNLCW, DEMNGNGAQ, TNLCWSSSEK, AQWKTNLCWS, DEMNGNGAQW | CLL |
| PABPC1 | c.999de\|A | p.K333fs | LRKEFSPFGTITSAKVMMEGGRSKG[p.K333fs\|]VLYLYVSPPQKKPLKQLQK* | VLYVSPPQK, RSKGLVLYV, GRSKGLVLY, MMEGGRSKGL, LV LYVSPPQK, VLYVSPPQKK, RSKGLVLYVS, VSPPQKKPLK, GG RSKGLVLY | KIRC |
| PABPC3 | c.975_979d e\|TATGA | p.V325 fs | LDDGIDDERLRKAFSPFGTITSAKV[p.V325fs\|GRWSQQRVWFCMFLLPRRSH* | RVWFCMFLL, KVGRWSQQR, RWSQQRVWF, QQRVWFC MF, TITSAKVGR, WFCMFLLPR, GRWSQQRVW, SQQRVWF CM, GTITSAKVGR, VWFCMFLLPR, SQQRVWFCMF, KVGR WSQQRV, QQRVWFCMFL, WFCMFLLPRR, VGRWSQQRV W, GRWSQQRVWF, WSQQRVWFCM, CMFLLPRRSH | TGCT |
| PABPC3 | c.997de\|A | p.K333fs | LRKAFSPFGTITSAKVMMEGGRSKG[p.K333fs\|]LVLYVSPPQKKPLKQLQK* | VLYVSPPQK, RSKGLVLYV, GRSKGLVLY, MMEGGRSKGL, LV LYVSPPQK, VLYVSPPQKK, RSKGLVLYVS, VSPPQKKPLK, GG RSKGLVLY | BLCA |
| PACSIN1 | c.1075G>A | p.E359K | AVESTSQAGDRGSVSSYSDRGQPYAT[p.E359K]KWSDDESGNPFGGSETNGGANPFEDD | RGQPYATKW | HNSC |
| PACSIN2 | c.993G>C | p.Q331H | ADLNRTLSRREKKKATDGVTLTGIN[p.Q331H]HTGDQSLPSKPSSTLNVPSNPAQSAQ | INHTGDQSL, HTGDQSLPSK | BRCA |
| PADI2 | c.340A>C | p.T114P | SSDKVTVNYDEEGSIPIDQAGLFL[p.T114P]PAIEISLDVDADRDGVVEKNNPKKAS | GLFLPAIEI, FLPAIEISL, DQAGLFLPA, LFLPAIEISL, DQAGLFL PAI, LPAIEISLDV, IDQAGLFLPA | MM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PAFAH1B1 | c.904del|A | p.K302fs | VECISWAPESSYSSISEATGSETKK|p.K302fs]VVNLGHSCCLDPETRLLRCGMSVLACAL* | RLLRCGMSV, GMSVLACAL, LLRCGMSVL, SETKKVVNL, RLL RCGMSVL, LLRCGMSVLA, CGMSVLACAL | STAD |
| PALB2 | c.839del|A | p.N280fs | DSGSSQHLEHIPPKGSSELTTHDLK|p.N280fs]TLDLLHL* | LKTLDLLHL, SELTTHDLKT | STAD |
| PALLD | c.2986G>A | p.A996T | DSAHKMLVRENGVHSLLIEPVTSRD|p.A996T]TGIYTCIATNRAGQNSFSLELVVAAK | VTSRDTGIY, RDTGIYTCI, PVTSRDTGIY | KIRC |
| PALM2-AKAP2 | c.3213_3214insGAAGCT | p.1075_1076insEA | KAVSKTSRDGAEQQGPEATVEEAEA|p.1075_1076insEA]EAAAFGSEKPQSMFEPPQVSSPVQEKRDVLP | EAEAEAAAF, VEEAEAEAA, AEAEAAAFG, EEAEAEAAAF, AE AEAAAFGS, VEEAEAEAAA | KIRC |
| PALM2-AKAP2 | c.3354_3355insC | p.G1118fs | VQEKRDVLPKILPAEDRALRERGPP|p.G1118fs]PATASCAAQWPD* | RERGPPPAT, ALRERGPPPA, RERGPPPATA | KIRC |
| PALM2-AKAP2 | c.895G>A | p.A299T | KLEMVHKSRKDHSSGNPGQQQAQAPS|p.A299T]TAGPEANLDQPVTMIFMGYQNIEDEE | STAGPEANL, APSTAGPEA, GQQAQAPST, QQAQAPSTA, G QQAQAPSTA, QQAQAPSTAG | BRCA |
| PAMR1 | c.302del|G | p.G101fs | CDSCLIHPGCTIFENCKSCRNGSWG|p.G101fs]VPWMTSM* | WGVPWMTSM, RNGSWGVPW, KSCRNGSWGV, CRNGSW GVPW, RNGSWGVPWM, SWGVPWMTSM | STAD |
| PANK1 | c.1199del|A | p.K400fs | DSVGFNGKPECYFENPTNPELCQK|p.K400fs]SRTALITHTLCCWLTWAQVSAF* | TLCCWLTWA, WLTWAQVSA, RTALITHTL, HTLCCWLTW, C QKSRTALI, KSRTALITH, LTWAQVSAF, LCQKSRTAL, LITHTLC CWL, KSRTALITHT, HTLCCWLTWA, ELCQKSRTAL, WLTWA QVSAF, SRTALITHTL, ALITHTLCCW | STAD |
| PANK2 | c.1251del|T | p.T417fs | VSILAVYSKDNYKRVTGTSLGGGTF|p.T417fs]LVSAVFLLAVPLLKKLLKWHLVEIAPKWIN* | SLGGGTFLV, FLVSAVFLL, AVFLLAVPL, LLKWHLVEI, LVSAVF LLA, FLLAVPLLK, LLAVPLLKK, TFLVSAVFL, VFLLAVPLL, GTFL VSAVF, VSAVFLLAV, LKWHLVEIA, HLVEIAPKW, FLVSAVFLL, A, LVSAVFLLAV, AVFLLAVPLL, LLAVPLLKKL, KLLKWHLVEI, L LKKLLKWHL, LLKWHLVEIA, HLVEIAPKWI, FLLAVPLLKK, VF LLAVPLLK, AVPLLKKLLK, TFLVSAVFLL, GTFLVSAVFL, KWHL VEIAPK, TSLGGGTFLV, SAVFLLAVPL, GGTFLVSAVF, VPLLK KLLKW | PRAD |
| PANK2 | c.377G>C | p.G126A | AAEEARRNPTLGGLLGRQRLLLRMG|p.G126A]AGRLGAPMERHGRASATSVSSAGEQA | LLRMGAGRL, RMGAGRLGA, LLLRMGAGR, GAGRLGAPM, RQRLLLRMGA, RLLLRMGAGR, AGRLGAPMER, MGAGRLG APM, LRMGAGRLGA | ACC |
| PANK3 | c.779G>T | p.R260I | LEMASKGDSTQADKLVRDIYGGDYE|p.R260I]IFGLPGWAVASSPGNMIYKEKRESVS | IYGGDYEIF, IFGLPGWAV, DIYGGDYEI, EIFGLPGWA, YEIFG LPGW, EIFGLPGWAV, DIYGGDYEIF, RDIYGGDYEI, YEIFGLP GWA | CRC |
| PANK3 | c.319C>T | p.H107Y | QLAAEYGLLGEKELSQENQLVETGG|p.H107Y]YVGLPSVSYASSGASVSLQIVAEMAT | QLVETGGYV, NQLVETGGY, YVGLPSVSY, VETGGVVGL, YVG LPSVSYA, GYVGLPSVSY | CESC |
| PAPD4 | c.675_676insT | p.C225fs | SLNGFGTRSSDGDLCLWKEEPCFF|p.C225fs]SGKSED* | KEEPCFFSG | STAD |
| PAPPA2 | c.2749C>A | p.P917T | QYVHTASSRRVCDSSGYWTPEEAVG|p.P917T]TPDVDQPCEPSLQAWSPEVHLYHMNM | EEAVGTPDV | LUAD |
| PAPPA2 | c.5049del|C | p.I1683fs | NSVEYKCEQGYGIGAVCSPLCVIPP|p.I1683fs]VTP* | SPLCVIPPV, CSPLCVIPPV | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PAPPA2 | c.5117C>A | p.P1706H | CVIPPSDPVMLPENITADTLEHWME[p. P1706H]HVKVQSIVCTGRRQWHPDV LVHCIQ | TLEHWMEHV,MEHVKVQSI,WMEHVKVQSI,TLEHWMEH VK,DTLEHWMEHV,MEHVKVQSIV,LEHWMEHKV | LUAD |
| PARD6A | c.252_253insC | p.G84fs | TDAHGDLLPLTNDDSLHRALASGPP[p. G84fs]ATAPTGAFAGRS* | ALASGPPAT,RALASGPPA,ALASGPPATA,RALASGPPAT,H RALASGPPA | KIRC |
| PARG | c.1750G>A | p.A584T | KYNVAYSKKWDFTALIDFWDKVLEE[p. A584T]TEAQHLYQSILPDMVKIALCLPN ICT | EETEAQHLY,LEETEAQHL,TEAQHLYQS,LEETEAQHLY,TEA QHLYQSI | KIRP,PRAD |
| PARP1 | c.1381delA | p.K461fs | PSLKTVKVVIFQPELLNIFYDSMKK[p.K 461fs]ETSLHH* | SMKKETSLH,DSMKKETSL,MKKETSLHH,SMKKETSLHH | STAD |
| PARP4 | c.2541delA | p.K847fs | SSLDSGFSLHIGLSAAYLPRMWVE[p.K 847fs]NIQKKKARLACLSFNPISMSTSLT* | RMWVENIQK,IQKKKARLA,KARLACLSF,LPRMWVENI,NPI SMSTSL,NIQKKKARL,KKKARLACL,LACLSFNPI,CLSFNPIS M,YLPRMWVENI,RLACLSFNPI,RMWVENIQKK,KARLACL SFN,KKARLACLSF,ACLSFNPISM | STAD |
| PASD1 | c.685_687del\|GCT | p.A236 del\| | SSQGQRGHTSMKAVVVEPAAAAAAA[p. A236de\|]ISDDQIDIAEVEQYGPQEN VHMFVDSDS | EPAAAAAAI | GBM |
| PASK | c.185C>T | p.T62I | PSRSFSSAHRHLSRRNGLSRLCQSR[p.T 62I]IALSEDRWSSYCLSSLAAQNICTSKL YSHPQYTAYNEAWRFSNPALLMPPV[p. P395fs]VRPCRCCRCL* | RLCQSRIAL,LSRLCQSRI,GLSRLCQSRI,LSRLCQSRIA,SRLCQ SRIAL | KIRC |
| PAX2 | c.1183delC | p.P395fs | | PVRPCRCCR,MPPPVRPCR,RPCRCCRCL,LLMPPPVRPC,L MPPPVRPCR,NPALLMPPPV | STAD |
| PAX3 | c.1271C>T | p.T424M | HGGVPHQPQTDYALSPLTGGLEPTT[p. T424M]MVSASCSQRLDHMKSLDSLPT SQSYC | MVSASCSQR,LEPTTMVSA,MVSASCSQRL,TMVSASCSQR | CRC |
| PAX3 | c.590C>T | p.S197L | LERKEAEESEKKAKHSIDGILSERA[p.S1 97L]LLAPQSDEGSDIDSEPDLPLRKQRR S | SERRALAPQS | BLCA |
| PAX6 | c.1124delC | p.P375fs | QTSSYSCMLPTSPSVNGRSYDTYTP[p.P 375fs]HICRHT* | RSYDTYTPH,SYDTYTPHI,DTYTPHICR,RSYDTYTPHI | STAD |
| PBLD | c.164C>A | p.P55Q | LDEDMHQKIAREMNLSETAFIRKLH[p. P55Q]QTDNFAQSSCFGLRWFTPASEV PLCG | KLHQTDNFA,RKLHQTDNF,IRKLHQTDNF,HQTDNFAQSS | LUAD |
| PBX2 | c.208G>A | p.E70K | PGGRKQDIGDILQQIMTITDQSLD[p. E70K]KAQAKKHALNCHRMKPALFSVL CEIK | TITDQSLDK,QSLDKAQAK,SLDKAQAKK,KAQAKKHAL,MTI TDQSLDK,QSLDKAQAKK | BLCA |
| PBX2 | c.785A>T | p.Y262F | LRSRFLDARRKRRNFSKQATEVLNE[p.Y 262F]FFYSHLSNPYPSEEAKEELAKKCGI T | QATEVLNEF,TEVLNEFFY,NEFFYSHLS,ATEVLNEFFY,VLNE FFYSHL,KQATEVLNEF,FFYSHLSNPY,NEFFYSHLSN | KIRP,LUSC,TGCT |
| PBXIP1 | c.2186_2188delACC | p.H729del | KKDKHSQSPRAAGPREGHSHSHHHH[p. H729de\|]RG* | HSHSHHHHR | BLCA |
| PCBP1 | c.305T>A | p.L102Q | DKLEEDINSSMTNSTAASRPPVTLR[p.L 102Q]QVVPATQCGSLIGKGGCKIKEIRE ST | RPPVTLRQV,RQVVPATQC,RPPVTLRQVV,RQVVPATQCG | CRC |
| PCCA | c.689G>A | p.R230H | AVRIAREIGYPVMIKASAGGGKGM[p. R230H]HIAWDDEETRDGFRLSSQEAAS SFGD | HIAWDDEETR | STAD |
| PCDH10 | c.1429G>A | p.V477M | QVSDVNDNAPRFSQPVYDVYVTENN[p. V477M]MPGAYIYAVSATDRDEGANA QLAYSI | NMPGAYIYA,TENNMPGAY,NNMPGAYIY,MPGAYIYAV,V TENNMPGAY,YVTENNMPGA,NMPGAYIYAV,YDVYVTEN NM,MPGAYIYAVS,TENNMPGAYI | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PCDH 10 | c.1759C>A | p.R587 S | ILIVDQNDNAPAIVAPLPGRNGTPA[p.R 587S]SEVLPRSAEPGYLLTRVAAVDAD DGE | GTPASEVLPR, RNGTPASEVL | LUAD |
| PCDH 10 | c.2956G>T | p.V986 L | SDGRQAADYRSNLHVPGMDSVPDTE[p. V986L]LFETPEAQPGAERSFSTGKEK ALHS | TELFETPEA, GMDSVPDTEL, MDSVPDTELF | LUAD |
| PCDH 10 | c.354_355i nsC | p.N118 fs | EVFLENPLELFQVEIEVLDINDNPP[p.N1 18fs]LFPGARPDGGNL* | VLDINDNPPL, LDINDNPPLF | STAD |
| PCDH 10 | c.673_674i nsC | p.P225f s | TAVDGGGGGVGEGGGGGGAGLPP [p.P225fs]PAAAHRHGPTHHPSAGLQ* | AAHRHGPTH, GPTHHPSAGL, RHGPTHHPSA | STAD |
| PCDH 11X | c.1457C>T | p.T486 M | DNAPVFTQSFVTVSIPENNSPGIQL[p.T 486M]MKVSAMDADSGPNAKINYLLG PDAPP | IQLMKVSAM, QLMKVSAMDA | GBM |
| PCDH 11X | c.3029G>T | p.R101 0I | SSDPYSVSDCGYPVTTFEVPVSVHT[p.R 1010I]IPPMKEVVRSCTPMKESTTMEI WIHP | SVHTIPPMK, EVPVSVHTI, HTIPPMKEV, VSVHTIPPM, VSVH TIPPMK, TIPPMKEVVR, HTIPPMKEVV, FEVPVSVHTI | LUAD |
| PCDH 15 | c.4655G>T | p.R155 2I | DDLSAHNPLYKENISQVSTNSDISQ[p.R 1552I]ITDFVDPFSPKIQAKSKSLRGPRE KI | DISQITDFV, QITDFVDPF, SDISQITDF, SQITDFVDPF | CRC |
| PCDH 15 | c.5138G>T | p.C171 3F | VELKSEPNVISSPAECSLELSPSRP[p.C17 13F]FVLHSSLSRRETPICMLPIETERNIF | ELSPSRPFV, FVLHSSLSR, RPFVLHSSL, LELSPSRPF, FVLHSSL SRR, SLELSPSRPF, LELSPSRPFV | KIRC |
| PCDH 19 | c.1588G>A | p.E530 K | YVSINPNSGDIYALRSFNHEQTKAF[p.E 530K]KFKVLAKDGGLPSLQSNATVRVII LD | QTKAFKFKV, KAFKFKVLA, APKFKVLAK, TKAFKFKVL, HEQT KAFKF, KAFKFKVLAK, QTKAFKFKVL | UCEC |
| PCDH 19 | c.856C>T | p.R286 C | NASDPDEGTNGQVVYSFYGYVNDRT[p. R286C]CELFQIDPHSGLVTVTGALDYE EGHV | YVNDRTCEL, YVNDRTCELF | BRCA |
| PCDH AC2 | c.1555G>A | p.A519 T | LVERRVGERALSNYVSVHAESGKVY[p. A519T]TLQPLDHEELELLQFQVSARDA GVPP | AESGKVYTL, GKVYTLQPL, TLQPLDHEEL, KVYTLQPLDH, SG KVYTLQPL, HAESGKVYTL | CRC |
| PCDH AC2 | c.2207C>T | p.A736 V | ALSTVSFIFLLTIIILSIIKCYRYT[p.A736V] VYGTACCGGFCGVRERSPAELYKQAN | IIKCYRYTV, YTVYGTACC, IKCYRYTVY, YRYTVYGTA, SIIKCYR YTV, VYGTACCGGF, IIKCYRYTVY, CYRYTVYGTA, YRYTVYGT AC | CRC |
| PCDH AC2 | c.2225C>T | p.A742 V | TALRCSAAPTEGACGPVKPTLVCSS[p.A 742V]VVGSWSYSQQRRQRVCSGEGLP KADL | SSVVGSWSY, KPTLVCSSV, CSSVVGSWSY, KPTLVCSSVV, LV CSSVVGSW | LUAD |
| PCDH AC2 | c.414G>T | p.K138 N | PLQVFHVDVEVKDINDNPPVPPATQ[p. K138N]NNLFIAESRPLDSRFPLEGASDA DIG | VFPATQNNL, NNLFIAESR, FPATQNNLF, VPPATQNNLF, FP ATQNNLFI | UCEC |
| PCDH AC2 | c.467C>T | p.A156 V | RFSRQEQRLFILESRMPDSRFPLEG[p.A 156V]VSDLLDIGANAQLRYRLNPNEYFD LDV | DSRFPLEGV, FPLEGVSDL | CRC |
| PCDH AC2 | c.568G>A | p.E190 K | NALLSYKLSSSEFFFLDIQANDELS[p.E19 0K]KSLSLVLGKSLDREETAEVNLLVAT | ELSKSLSLIV, KSLSLVLGK, LSKSLSLVL, DELSKSLSL, DELSKSLS LV | CRC |
| PCDH AC2 | c.796G>A | p.A266 T | AFERTIYKVRLLENAPNGTLVVTVN[p.A 266T]TTDLDEGVNKDIAYSFNTDMSAD ILS | NTTDLDEGV, TTDLDEGVNK | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PCDHAC2 | c.811G>A | p.E271K | SYKVVLSENVQNDTRVIQLNASDPD[p.E271K]KGLNGEISYGIKMLPVSEKCMFSIN | QLNASDPDK, KGLNGEISY | CRC |
| PCDHB1 | c.1704C>G | p.N568K | SSQVTVRVVLDDNDNRPMILYPLQ[p.N568K]KGTLPCNDLVPRSAEAGYLVTKVVAV | ILYPLQKGT, PMILYPLQK, ILYPLQKGTL, RPMILYPLQK, YPLQKGTLPC | LUSC |
| PCDHB12 | c.865C>T | p.R289C | VSAWDLDSGTNSELSYTFSHASEDI[p.R289C]CKTFEINQKSGDITLTAPLDFEAIES | ASEDICKTF, FSHASEDICK, HASEDICKTF, SEDICKTFEI | UCEC |
| PCDHB13 | c.662C>T | p.P221L | VLDKALDREEEAELRLTLTALDGGS[p.P221L]LPRSGTAQVIEVLDVNDNAPEFEQP | LPRSGTAQV, SLPRSGTAQV, TALDGGSLPR, LPRSGTAQVY | GBM |
| PCDHB4 | c.763_764CC>TT | p.P255F | LIMDINDNAPEFVHTPYGVQVLENS[p.P255F]FLDSPIVRVLARDIDAGNPGSVSYGLF | FLDSPIVRV, SFLDSPIVR, NSFLDSPIV, GVQVLENSF, VQVLENSFL, FLDSPIVRVL, NSFLDSPIVR, YGVQVLENSF, LENSFLDSPI | TGCT |
| PCDHB5 | c.151G>T | p.D51Y | AGSEAVRYSIPEETESGYSVANLAK[p.D51Y]YLGLGVGELATRGARMHYKGNKELLQ | YSVANLAKY, YLGLGVGEL, AKYLGLGVG, NLAKYLGLGV, YLGLGVGELA, KYLGLGVGEL, GYSVANLAKY, YSVANLAKYL | CRC |
| PCDHB5 | c.1945C>T | p.P649S | RTARLLSERDAAKHRLVLVKDNGE[p.P649S]SPRSATATLHVLLVDGFSQPYLPLPE | SPRSATATL, GESPRSATA, LVKDNGESPR, ESPRSATATL, GESPRSATAT | LUAD |
| PCDHB8 | c.703G>A | p.D235N | RLTLTALDGGSPPRSGTAQVIEVV[p.D235N]NVNDNAPEFEQPFYRVQISEDSPISF | QVYIEVNV, EVVNVNDNA, NVNDNAPEF, AQVYIEVNV, V NVNDNAPEF, IEVVNVNDNA | CRC |
| PCDHGC5 | c.1796G>T | p.G599V | GVELAPRSAERGYLVTKVVAVDRDS[p.G599V]VQNAWLSYRLLKASEPGLFSVGLHTG | SVQNAWLSY, VQNAWLSYR, VVAVDRDSV, VQNAWLSYRL, SVQNAWLSY, DSVQNAWLSY, VDRDSVQNAW | KIRC |
| PCDHGC5 | c.1984G>A | p.V662M | ALKQSLVVAVQDHGQPPLSATVTLT[p.V662M]MAVADSIPEVLADIGSLEPSDGPYNY | LSATVTLTM, ATVTLTMAV, LTMAVADSI, TVTLTMAVA, MAVADSIPEV, TLTMAVADSI, SATVTLTMAV, PLSATVTLTM | CRC |
| PCDHGC5 | c.1990G>A | p.D664N | RLLVAVRDGGQPPLSATATLHLVFA[p.D664N]NSLQEVLPDITDRPDPSDLQAELQFY | VFANSLQEV, LHLVFANSL, FANSLQEVL, LVFANSLQEV, TLH LVFANSL, VFANSLQEVL | BRCA |
| PCDHGC5 | c.2051C>A | p.P684H | TVTVAVADRIPDILADLGSIKTPID[p.P684H]HEDLDLTLYLVVAVAVSCVPLAFVI | HEDLDLTLY, IDHEDLDLTL, TPIDHEDLDL, HEDLDLTLYL | LUAD |
| PCDHGC5 | c.208G>A | p.A70T | SVVGNLAKDLGLSVLDVSARKLRVS[p.A70T]TEKLHFSVDAESGDLLVKNRIDREQI | SARKLRVST, RKLRVSTEK, KLRVSTEKL, STEKLHFSV, RVSTEKLHF, KLRVSTEKLH, VSTEKLHFSV, RKLRVSTEKL, LRVSTEKLHF, TEKLHFSVDA | UCEC |
| PCDHGC5 | c.36G>T | p.K12N | MAALQKLPHCR[p.K12N]NLVLLCFLLATLMEARAGQIRYSVRE | KLPHCRNLV, NLVLLCFLL, LPHCRNLVL, QKLPHCRNL, KLPH CRNLVL, LPHCRNLVLL, LQKLPHCRNL, HCRNLVLLCF | LUAD |
| PCDHGC5 | c.866C>T | p.S289L | LTATDPDEGINGKLTYSFRNEEEKI[p.S289L]LETFQLDSNLGEISTLQSLDYEESRF | EEEKILETF, NEEEKILETF, LETFQLDSNL | CRC |
| PCDHGC5 | c.877C>T | p.R293C | DPDEGANGEVTYSFHNVDHRVAQIF[p.R293C]CLDSYTGEISNKEPLDFEEYKMYSME | CLDSYTGEI, AQIFCLDSY, HRVAQIFCL, VAQIFCLDSY, AQIFCLDSYT | SKCM |
| PCGF3 | c.189delC | p.H63fs | SCLVKYLEENNTCPTCRIVIHQSHP[p.H63fs]CSTSVMTEPCKILFTNWYQASKKRK* | ILFTNWYQA, FTNWYQASK, TSVMTEPCK, HQSHPCSTS, QS HPCSTSV, SHPCSTSVM, VMTEPCKIL, MTEPCKILF, CKILFTN WY, KILFTNWYQA, HQSHPCSTSV, ILFTNWYQAS, FTNWYQ | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PCLO | c.11836C>A | p.P3946T | PYQTQPTFQAVATMSFTPQVQPTPT[p.P3946T]TQPSYQLPSQMMVIQQKPRQTTLYLE | ASKK,STSVMTEPCK,VMTEPCKILF,LFTNWYQASK,QSHPCSTSVM,EPCKILFTNW PTPTTQPSY,TPTTQPSYQL,QPTPTTQPSY | LUAD |
| PCLO | c.12397C>T | p.R4133C | VKAEEDPMEDPYELKLLKHQIKQEFI[p.R4133C]CRGTESLDHLAGLSHYYHADTSYRHF | HQIKQEFCR,QEFCRGTES,QEFCRGTESL | SKCM |
| PCMTD1 | c.812G>T | p.R271M | LARIYIRRTLRNFINDEMQAKGIPQ[p.R271M]MAPPKRKRKRVKQRINTYVFVGNQLI | MQAKGIPQM,GIPQMAPPK,MAPPKRKRK,QMAPPKRKR,MQAKGIPQMA,KGIPQMAPPK,QMAPPKRKRK,MAPPKRKRKR,EMQAKGIPQM | LUAD |
| PCMTD1 | c.842T>C | p.V281A | RNFINDEMQAKGIPQRAPPKRKRKR[p.V281A]AKQRINTYVFVGNQLIPQLDSEEDE | RAKQRINTY,RAKQRINTYV,KRAKQRINTY,AKQRINTYVF | TGCT |
| PCNXL2 | c.404G>A | p.R135Q | GEHITNHRNPSNNRQIHNGKKEEAS[p.R135Q]QNLSTPPLRCSSRQSITSHHSGPL | SQNLSTPPL,KKEEASQNL,SQNLSTPPLR,GKKEEASQNL,ASQNLSTPPL,KEEASQNLST | CRC |
| PCOLCE2 | c.1043C>T | p.A348V | ITTITRDGSLHATVSIINIYKEGNL[p.A348V]VIQQAGKNMSARLTVVCKQCPLLRG | NIYKEGNLV,IYKEGNLVI,LVIQQAGKNM,KEGNLVIQQA | CRC |
| PCOLCE2 | c.260G>A | p.R87H | KITVPEGKVVLNFRFIDLESDNLC[p.R87H]HYDFVDYNGHANGQRIGRFCGTFRP | LESDNLCHY,CHYDFVDV,SDNLCHYDF,ESDNLCHYDF,NLCHYDFVDV,LCHYDFVDY | CRC |
| PCP4L1 | c.191A>G | p.K64R | DLTAPETEKAALAIQGKFRRFQKRK[p.K64R]RDPSS* | KFRRFQKRKR | TGCT |
| PDE4B | c.1250C>T | p.S417L | MMTLEDHYHSDVAYHNSLHAADVAQ[p.S417L]LTHVLLSTPALDAVFTDLEILAAIFA | HAADVAQLT,DVAQLTHVL,LHAADVAQL,AQLTHVLLS,SLHAADVAQL,DVAQLTHVLI,LTHVLLSTPA,HAADVAQLTH,ADVAQLTHVL,AQLTHVLLST | CRC |
| PDGFRA | c.685G>A | p.E229K | NVYALKATSELDLEMEALKTVYKSG[p.E229K]KTIVVTCAVFNNEVVDLQWTYPGEVK | KTIVVTCAV,TVYKSGKTI,YKSGKTIVV,ALKTVYKSGK,KTIVVTCAVF,KTVYKSGKTI,TVYKSGKTIV,YKSGKTIVVT | GBM |
| PDGFRB | c.1949C>T | p.S650L | SQATMKVAVKMLKSTARSSEKQALM[p.S650L]LELKIMSHLGPHLNVVNLLGACTKGG | KQALMLELK,EKQALMLEL,ALMLELKIM,LELKIMSHL,MLELKIMSHL,RSSEKQALMI,SEKQALMLEL,KQALMLELKI,LMLELKIMSH | GBM |
| PDIA6 | c.168T>G | p.N56K | PCSPTSPAHSLSRKSPIMYPSTTMA[p.N56K]KAPGLVSCTFLAVNGLYSSSDDVIE | TMAKAPGLV,MYPSTTMAK,TTMAKAPGL,YPSTTMAKA,TTMAKAPGLV,IMYPSTTMAK,MYPSTTMAKA,KAPGLVSCTF | TGCT |
| PDILT | c.1498G>A | p.E500K | LYKGEHTLKGFSDFLESHIKTKIED[p.E500K]DELLSVEQNEVIEEEVLAEEKEVPM | HIKTKIEDK,IEDKDELLSV | CESC |
| PDPR | c.2377G>T | p.G793W | TMFILDDHDSDLDLMPWWGEPIYRN[p.G793W]WQYVGKTTSSAYSYSLERHVCLGFVH | EPIYRNWQY,WQYVGKTTS,WWGEPIYRNW,IYRNWQYVGK,EPIYRNWQYV,WQYVGKTTSS | LUAD |
| PDS5A | c.3927G>C | p.L1309F | KNDDLNKPINKGRKRAAVGQESPGG[p.L1309F]FEAGNAKAPKLQDLAKKAAPAERQID | QESPGGFEA,GQESPGGFEA | TGCT |
| PDYN | c.571G>T | p.G191W | EDPKEQVKRYCGFLRKYPKRSSEVA[p.G191W]WEGDGDSMGHEDLYKRYGGFLRR.IRP | YPKRSSEVAW,VAWEGDGDSM | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PDZD2 | c.1693C>A | p.R565S | RKHSLPQLLDSSASQEYHIVKKST[p.R565]SLSLSTTQVESPWRLIRPSVISIIGLY | IVKKSTSSL,TSSLSTQV,KKSTSSLST,HIVKKSTSSL,STSSLST TQV,IVKKSTSSLS,KKSTSSLSTT | LUAD |
| PDZD2 | c.302_303insG | p.R101fs | DTETVGLSFGNIPVFGDYGEKRGG[p.R101fs]QEEENPGSCAGCGLHLGDRAEEEQPSREEWEGPTAG* | REEWEGPTA,EEQPSREEW,EEWEGPTAG,EENPPGSCA | STAD |
| PELI2 | c.589del|G | p.G197fs | AKWKNPDGHMDGLTTNGVLVMHPRG[p.G197fs]ASPRSPSPGSGARSLSVEMCTPCEKPGRPSNEESWWKVRPTSCRTAPSLTCVGPLSSGEQMGFFILQLRST* | RTAPSLTCV,QMGFFILQL,VLVMHPRGA,MGFFILQLR,GAR SLSVEM,KVRPTSCRT,SPGSGARSL,RPTSCRTAP,VMHPRG ASP,SSGEQOMGF,GEQOMGFFI,EQQMGFFIL,RPSNEES WW,QOMGFFILQL,VMHPRGASPR,SVEMCTPCEK,QMGF FILQLR,RSPSPGSGAR,KVRPTSCRA,WWKVRPTSCR,HPR GASPRSP,RPTSCRTAPS,APSLTCVGPL,GPLSSGEQQM,SG ARSLSVEM,LSSGEQOMGF,GEQOMGFFIL,EESWWKVRPT | STAD |
| PEX1 | c.1108del|A | p.I1370fs | QSKTKQNVLSPEKEKQMSEPLDQKK[p.I1370fs]LGQIIMKKMRRPVCYK* | KLGQIIMKK,KMRRPVCYK,IMKKMRRPV,QIIMKKMRR,M KKMRRPVC,QKKLGQIIM,KKMRRPVCY,IIMKKMRRPV,KK MRRPVCYK,IMKKMRRPVC,DQKKLGQIIM,KLGQIIMKKM, MKKMRRPVCY | BLCA,PRAD |
| PFKM | c.352C>A | p.R118S | TSGGDAQGMNAAVRAVVRVGIFTGA[p.R118S]SVFFVHEGYQGLVDGGDHIK EATWES | FTGASVFFV,SVFFVHEGY,IFTGASVFF,GIFTGASVF,VGIFT GASV,RVGIFTGASV,ASVFFVHEGY,IFTGASVFFV,VGIFTGA SVF,GIFTGASVFF | LUAD |
| PFKP | c.1779del|G | p.M593fs | SGTKRRVFIIETMGGYCGYLANMGG[p.M593fs]SRPELMPHTFSKSPSTSGICSP TWST* | ELMPHTFSK,GSRPELMPH,HTPSKSPST,YLANMGGSR,STS GICSPT,RPELMPHTF,NMGGSRPEL,SKSPSTSGI,TSGICSPT W,MPHTFSKSPS,ANMGGSRPEL,NMGGSRPELM,SRPEL MPHTF,FSKSPSTSGI,STSGICSPTW | STAD |
| PGAM1 | c.719G>A | p.R240H | PIVYELDKNLPIKPMQFLGDEETV[p.R240H]HKAMEAVAAQGKAKK* | TVHKAMEAV,ETVHKAMEA,HKAMEAVAA,DEETVHKAM, ETVHKAMEAV,EETVHKAMEA | CRC |
| PGAP1 | c.1694T>G | p.F565C | QAPSSTEISLKLHIAQPENNTHVAL[p.F565C]CKMYTSSDCRYEVTVKTSFSQILG QV | THVALCKMY,NTHVALCKMY | OV |
| PGM5 | c.1277_1278insC | p.G426fs | VWLSIIAARKQSVEEIVRDHWAKFG[p.G426fs]PPLLLQV* | HWAKFGPPL,AKFGPPLLL,HWAKFGPPLL,KFGPPLLLQV | KIRC |
| PGM5 | c.292A>G | p.I98V | RTAIEIVVQMAAANGIGRLIIGQNG[p.I98V]VLSTPAVSCIIRKIKAAGGIILTASH | RLIIGQNGV,VLSTPAVSCI,RLIIGQNGVL,GQNGVLSTPA | STAD |
| PGPEP1L | c.490_491insA | p.R164fs | KGCAALIHVPPLSRGLPASLLGRAL[p.R164fs]KSHHPGNAGRGGKAQAQSPVRR KLNHGPSSQRELTGGLLL* | SQRELTGGL,ASLLGRALK,RALKSHHPG,KSHHPGNAG,KAQ AQSPVR,QAQSPVRRK,GKAQAQSPV,AQSPVRRKL,RKLNH GPSS,RELTGGLLL,ALKSHHPGNA,KLNHGPSSQR,KSHHPG NAGR,KAQAQSPVRR,AQAQSPVRRK,SQRELTGGLL | KIRC |
| PHACTR1 | c.752_753insG | p.V251fs | LPCLPVKLSPPLPPKKVMICMPVGG[p.V251fs]ARPLTGVLHSPEEWPAGCGPAP PHCPALPDPAPAAVRQPRPAPPLHHRL PPHAPLGLQNDRRAQQNAGHDHAEA GKL* | ALPDPAPAA,AVRQPRPAP,RQPRPAPPL,MICMPVGGA,M PVGGARPL,GARPLTGVL,GPAPPHCPA,LPDDAPAAV,LPPH APLGL,HRLPPHAPL,AQQNAGHDH,WPAGCGPAP,VMIC MPVGGA,VLHSPEEWPA,ALPDDAPAAV,RLPPHAPLGL,C MPVGGARPL,MICMPVGGAR,GARPLTGVLH,AVRQPRPA PP,AGHDHAEAGK,MPVGGARPLT,GPAPPHCPAL,CPALPD PAPA,RPAPPLHHRL,HRLPPHAPL,EEWPAGCGPA,VRQP RPAPPL,RQPRPAPPLH,AQQNAGHDHA,WPAGCGPAPP | LAML |
| PHACTR1 | c.753del|G | p.V251fs | LPCLPVKLSPPLPPKKVMICMPVGG[p.V251fs]QTSHWCPTQPRVASRVWPST TTLSCPPRSSTSCSTAATASTSPPPPAPS PCTPRAAE* | RVWPSTTL,TTTLSCPPR,RVASRVWPS,ASRVWPSTT,RSS TSCSTA,HWCPTQPRR,TQPRRVASR,CPTQPRRVA,QPRRV ASRV,WPSTTTLSC,GQTSHWCPT,SRVWPSTTT,MPVGGQ TSH,TSHWCPTQPR,STTTLSCPPR,RVASRVWPST,ASRVW PSTTT,RSSTSCSTAA,STSCSTAATA,PTQPRRVASR,CPTQP | STAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PHACTR2 | c.711_712insA | p.S237fs | APVPPPKPASRNTTREAAGSSHSKK[p.S237fs]NNWL* | RRVAS, QPRRVASRVW, APSPCTPRAA, MPVGGQTSHW, SR VWPSTTTL, SSHSKKNNWL | STAD |
| PHACTR4 | c.1061del|C | p.S354fs | DEREKSTCMGSELLPMISPRSPSP[p.S354fs]HCLLIYLQSLHAPLHSLLRLFKLCQKLSFHHP* | CLLIYLQSL, YLQSLHAPL, SLHAPLHSL, RLFKLCQKL, LIYLQSL HA, RSPSPHCLL, LHSLLRLFK, HAPLHSLLR, SPSPHCLLI, SPHC LLIYL, APLHSLLRL, LQSLHAPLH, LHAPLHSLL, FKLCQKLSF, LL IYLQSLHA, SLHAPLHSL, PLHSLLRLFK, LIRLFKLCQK, RSPSP HCLLI, IYLQSLHAPL, LFKLCQKLSF, SPSPHCLLY, SPRSPSPH CL, APLHSLLRLF, YLQSLHAPLH, QSLHAPLHSL | STAD |
| PHC3 | c.104_106del|CCA | p.T35del | STAMDTEPNPGTSVSVSTTTSSTTTT[p.T35del]ITTSSSRMQQPQISVYSGSDRHAVQVIQ | TTSSTTTTI, TTTSSTTTI | GBM |
| PHGDH | c.517_518GG>TT | p.G173L | LGILGLGRIGREVATRMQSFGMKTIL[p.G173L]LYDPIISPEVASFGVQQLPLEEIWPL | KTILYDPII, SFGMKTILY, QSFGMKTIL, MKTILYDPI, GMKTILY DPI, QSFGMKTILY, LYDPIISPEV, MQSFGMKTIL, MKTILYDPII | SKCM |
| PHIP | c.5043C>G | p.I1681M | KKRGRKPKKLQYAKPEDLEQNNVHP[p.I1681M]MRDEVLPSSTCNFLSETNNVKEDLLQ | EQNNVHPMR, NVHPMRDEV, LEQNNVHPM, HPMRDEVLPS | LUSC |
| PHOSPHO1 | c.95_97del|CCT | p.S32del | PWPANQPLPGGLLPRPLSLAPSSSSS[p.S32del]CCSSPPCSQDGRMAAQGAPRFLLTFDFDE | SLAPSSSSC, SLAPSSSSCC | PRAD |
| PI15 | c.64G>T | p.V22F | MIAISAVSSALLFSLLCEAST[p.V22F]FVLLNSTDSSPPTNNFTDIEAALKAQ | LLCEASTFV, SLLCEASTF, CEASTFVLL, SLLCEASTFV, LLCEAS TFVL, FSLLCEASTF | LUAD |
| PIAS2 | c.1556C>T | p.S519L | SETQSSPTKGVLMYQPSSVRVPSVT[p.S519L]LVDPAAIPPSLTDYSVPFHHTPISSM | SVRVPSVTL, SVRVPSVTLV, SSVRVPSVTL | CRC |
| PIAS3 | c.1378G>A | p.D460N | GGDPSENKKVEVIDLTIESSSDEE[p.D460N]NLPPTKKHCSVTSAAIPALPGSKGVL | IESSSDEENL | CESC |
| PIAS3 | c.348del|C | p.H116fs | LAPIPPTLLAPGTLLGPKREVDMHP[p.H116fs]LCPSLCTLMSP* | KREVDMHPL, REVDMHPLC, DMHPLCPSL, HPLCPSLCTL, V DMHPLCPSL, REVDMHPLCP | STAD |
| PIGM | c.674G>T | p.R225L | NDKSLRQFRYTFQACLYELLKRLCN[p.R225L]LAVLLFVAVAGLTFFALSFGFYYEYG | RLCNLAVLL, NLAVLLFVA, LLKRLCNLA, LAVLLFVAV, ELLKRL CNL, LKRLCNLAV, KRLCNLAVL, LCNLAVLLF, NLAVLLFVAV, L LKRLCNLAV, RLCNLAVLLF, YELLKRLCNL, LKRLCNLAVL, KRL CNLAVLL | LUAD |
| PIGO | c.2361del|C | p.P787fs | VTVLVKAGAGAPRTRTVLTPFSGPP[p.P787fs]LLLKLTWIMWSLKSTDTCRRSSGAG* | KLTWIMWSL, WIMWSLKST, LTWIMWSLK, SLKSTDTCR, TP FSGPPLL, LLKLTWIMW, VLTPFSGPPL, KLTWIMWSL, SLKS TDTCRR, LKLTWIMWSL | STAD |
| PIGR | c.548T>G | p.V183G | NAQKRKSLYKQIGLYPLVIDSSGY[p.V183G]GNPNYTGRIRLDIQGTGQLLFSVVIN | SSGYGNPNY, DSSGYGNPNY | TGCT |
| PIGT | c.1037del|C | p.A346fs | TAMINNSRNLNIQLKWKRPPENEAP[p.A346fs]QCPSCMPSGT* | NEAPQCPSCM | STAD |
| PIK3C2B | c.4419C>G | p.F1473L | EELNGYIWHLIHAPPEVAECDLVYT[p.F1473L]LFHPLPRDEKAMGTSPAPKSSDGTWA | LVYTLFHPL, YTLFFIPLPR, AECDLVYTL, DLVYTLFFIPL, LFHPL PRDEK, VYTLFHPLPR, AECDLVYTLF | KIRC |
| PIK3C2B | c.859del|C | p.R287fs | PLDFSKDTSGKPVARSKTMPQVPP[p.R287fs]APMPPAMATERMRLARTAG | TMPPQVPPA, LLHFATCWI, AMSGVLSPL, RLARTAGFL, FLQ PRWAPG, LLPMAMSCL, EMRLLHFA, WISFDLALT, VLSPLA | GBM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| | | | FLQPRWAPGPTLLPMAMSCLRSQRE MRRLLHFATCWISFDLALTSKTTSSLAM SGVLSPLAQSTSGMRST* | QST, AMATERMR, AMSCLRSQK, RTAGFLQPR, RWAPGPT LL, REMRRLLHF, HFATCWISF, CWISFDLAL, RMRRLARTA, R SQKREMR, TSKTTSSLA, LPMAMSCLR, MSCLRSQKR, LTSK TISSL, TSSLAMSGV, PPQVPPAPM, VPPAPMPPA, PPAPMP PAM, APMPPAMAT, QPRWAPGPT, APGPTLLPM, GPTLLP MAM, MATERMRRL, CLRSQKREM, RRLARTAGF, PRWAPG PTL, SQKREMRRL, QKREMRLL, RLLHFATCW, SKTTSSLAM, SSLQMSGVL, LAMSGVISP, TLLPMAMSCL, RLLHFATCWI, L AMSGVLSPL, AMSGVLSPLA, KTMPPQVPPA, AMATERMR RL, ALTSKTTSSL, TTSSLAMSGV, MAMSCLRSQK, ISFDLALTS K, ATERMRRLAR, RMRRLARTAG, CLRSQKREMR, RSQKRE MRRL, SQKREMRLL, TSKTTSSLAM, RTAGFLQPRW, LLPM AMSCLR, AMSCLRSQKR, QVPPAPMPPA, FATCWISFDL, LT SKTTSSLA, MPPQVPPAPM, VPPAPMPPAM, MPPAMATER M, QPRWAPGPTL, SPLAQSTSGM, MRRLARTAGF, EMRRLL HFAT, RRLARTAGFL, WAPGPTLLPM, KREMRRLLFIF, REMR RLLHFA, RRLLHFATCW, LHFATCWISF, AQSTSGMRST, LPM AMSCLRS | |
| PIK3C A | c.1035T>A | p.N345 K | GETSTKSLWVINSALRIKILCATYV[p. N3 45K]KVNIRDIDKIYVRTGIYHGGEPLCD N | ILCATYKV, KILCATYVK, KVNIRDIDK, ATYVKVNIR, KILCATY VKV, TYVKVNIRDI, CATYVKVNIR | BRCA, CRC, STAD, UCEC |
| PIK3C A | c.1049A>G | p.D350 G | KSLWVINSALRIKILCATYVNVNIR[p. D3 50G]GIDKIYVRTGIYHGGEPLCDNVNT QR | YVNVNIRGI, NVNIRGIDK, NIRGIDKIY, TVNVNIRGI, VNIRG IDKIY | CRC |
| PIK3C A | c.113G>A | p.R38H | IHLMPPRILVECLLPNGMIVTLECL[p. R3 8H]HEATLITIKHELFKEARKYPLHQLLQ | VTLECLHEA, LECLHEATL, CLHEATLITI, HEATLITIKH, LECLH EATLI | UCEC |
| PIK3C A | c.115G>A | p.E39K | HLMPPRILVECLLPNGMIVTLECLR[p. E 39K]KATLITIKHELFKEARKYPLHQLLQD | IVTLECLRK, LRKATLITI, LECLRKATL, CLRKATLITI, MIVTLECL RK, RKATLITIKH, LECLRKATLI | UCEC |
| PIK3C A | c.1258T>C | p.C420 R | DLPRAARLCLSICSVKGRKGAKEEH[p. C 420R]RPLAWGNINLFDYTDTLVSGKM ALNL | KEEEHRPLAW, GAKEEHRPLA, RPLAWGNINL, AKEEHRPLA W | BRCA, UCEC |
| PIK3C A | c.1338_136 4de\|GCCAG TACCTCAT GGATTAGA AGATTT | p.PVPH GLEDL4 47de\| | LAWGNINLFDYTDTLVSGKMALNLW[p. PVPHGLEDL447de\|\|LNPIGVTGSNPN KETPCLELEFDWFSSVVKFPDMSVIEEH ANWSVSREAGFS | ALNLWLNPI, NLWLNPIGV, GKMALNLWL, MALNLWLNPI | BRCA |
| PIK3C A | c.1357G>A | p.E453 K | NLFDYTDTLVSGKMALNLWVPHGL[p. E453K]KDLLNPIGVTGSNPNKETPCLEL EFD | GLKDLLNPI, LWPVPHGLK, VPHGLKDLL, NLWPVPHGLK, W PVPHGLKDL, HGLKDLLNPI | BRCA |
| PIK3C A | c.1364_136 5insG | p.L455fs | DYTDTLVSGKMALNLWPVPHGLEDL[p. L455fs]AEPYWCYWIKSK* | GLEDLAEPY, DLAEPYWCY, AEPYWCYWI, LAEPYWCYW, H GLEDLAEPY | BRCA |
| PIK3C A | c.1624G>A | p.E542 K | LARDNELRENDKEQLKAISTRDPLS[p. E 542K]KITEQEKDFLWSHRHYCVTIPEILP K | ISTRDPLSK, STRDPLSKI, LSKITEQEK, AISTRDPLSK, SKITEQE KDF | BLCA, BRCA, CESC, CRC, HNSC, LUAD, LUSC, STAD, UCEC |
| PIK3C A | c.1633G>A | p.E545 K | DNELRENDKEQLKAISTRDPLSEIT[p. E5 45K]KQEKDFLWSHRHYCVTIPEILPKLL L | SEITKQEKDF, KQEKDFLWSH | BLCA, BRCA, CESC, CRC, GBM, HNSC, KIRC, |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PIK3CA | c.1634A>C | p.E545A | DNELRENDKEQLKAISTRDPLSEIT[p.E545A]AQEKDFLWSHRHYCVTIPEILPKLLL | TAQEKDFLW, SEITAQEKDF, AQEKDFLWSH, ITAQEKDFLW | LUAD, LUSC, STAD, TGCT, UCEC, UCS |
| PIK3CA | c.1634A>G | p.E545G | DNELRENDKEQLKAISTRDPLSEIT[p.E545G]QEKDFLWSHRHYCVTIPEILPKLLL | SEITGQEKDF, GQEKDFLWSH | BRCA, CRC |
| PIK3CA | c.1636C>A | p.Q546K | NELRENDKEQLKAISTRDPLSEITE[p.Q546K]EKDFLWSHRHYCVTIPEILPKLLLS | KEKDFLWSH, TEKEKDFLW, SEITEKEKDF | CRC |
| PIK3CA | c.1637A>C | p.Q546P | NELRENDKEQLKAISTRDPLSEITE[p.Q546P]EKDFLWSHRHYCVTIPEILPKLLLS | EITEPEKDFL, SEITEPEKDF, EPEKDFLWSH | BRCA, CRC, UCEC |
| PIK3CA | c.1637A>G | p.Q546R | NELRENDKEQLKAISTRDPLSEITE[p.Q546R]EKDFLWSHRHYCVTIPEILPKLLLS | REKDFLWSH, TEREKDFLW, SEITEREKDF | UCEC |
| PIK3CA | c.1A>G | p.M1V | [p.M1V]VPPRPSSGELWGIHLMPPRIIVECLL | VPPRPSSGEL | BRCA, UCEC |
| PIK3CA | c.2176G>A | p.E726K | HLNRQVEAMEKLINLITDILKQEKKD[p.E726K]KTQKVQMKFLVEQMRRPDFMDALQGF | KTQKVQMKF, KDKTQKVQMK, KTQKVQMKFL, KKDKTQKV QM | GBM |
| PIK3CA | c.263G>A | p.R88Q | QDESSYIFVSVTQEAEREEFFDETR[p.R88Q]LCDLRLFQPPLKVIEPVGNREEKIL ALQGF | RQLCDLRLF, ETRQLCDLR, EEFFDETRQL | BRCA, CESC, LUSC |
| PIK3CA | c.278G>A | p.R93Q | YIFVSVTQEAEREEFFDETRRLCDL[p.R93Q]QLFQPFLKVIEPVGNREEKILNREIG | QLFQPFLKV, LQLFQPFLK, RRLCDLQLF, CDLQLFQPF, LQLF QPPLKV, QLFQPFLKVI, DLQLFQPFLK, TRRLCDLQLF, LCDLQ LFQPF, CDLQLFQPFL | BRCA, CRC, GBM, STAD, UCEC |
| PIK3CA | c.3012G>A | p.M1041I | RFQEMCYKAYLAIRQHANLFINLFS[p.M1041I]IMLGSGMPELQSFDDIAYIRKT LALD | NLFINLFSI, FINLFSIML, LFINLFSIM, FSIMLGSGM, IMLGSG MPEL, NLFINLFSIM, LFINLFSIML, LFSIMLGSGM | UCEC |
| PIK3CA | c.3127A>G | p.M1043V | DIAYIRKTLALDKTEQEALEYFMKQ[p.M1043V]VNDAHHGGWTTKMDWIFHTI KQHALN | ALEYFMKQV, FMKQVNDAH, MKQVNDAH, EALEYFMKQ V, FMKQVNDAHH | BRCA |
| PIK3CA | c.3129G>A | p.M1043I | DIAYIRKTLALDKTEQEALEYFMKQ[p.M1043I]INDAHHGGWTTKMDWIFHTI QHALN | FMKQINDAH, KQINDAHHG, EALEYFMKQI, FMKQINDAHH, KQINDAHHGG | GBM, HNSC, UCEC |
| PIK3CA | c.3130A>T | p.N1044Y | IAYIRKTLALDKTEQEALEYFMKQM[p.N1044Y]YDAHHGGWTTKMDWIFHTIK QHALN* | MYDAHHGGW, FMKQMYDAH, LEYFMKQMY, MKQMYDA HH, KQMYDAHHG, ALEYFMKQMY, FMKQMYDAHH, QMY DAHHGGW, KQMYDAHHGG | BRCA, UCEC |
| PIK3CA | c.3132T>A | p.N1044K | IAYIRKTLALDKTEQEALEYFMKQM[p.N1044K]KDAHHGGWTTKMDWIFHTIK QHALN* | FMKQMKDAH, FMKQMKDAHH, MKDAHHGGW, ALEYFMK QMK, FMKQMKDAH, KQMKDAHHGG, QMKDAHHGGW | BRCA |
| PIK3CA | c.3140A>G | p.H1047R | IRKTLALDKTEQEALEYFMKQMNDA[p.H1047R]RHGGWTTKMDWIFHTIKQH ALN* | FMKQMNDAR, KQMNDARHG, RHGGWTTKM, YFMKQM NDAR, FMKQMNDARH, KQMNDARHG, QMNDARHGG W, ARHGGWTTKM | KIRC |
| PIK3CA | c.3140A>G | p.H1047R | | | BRCA, CRC, GBM, HNSC, LIHC, LUSC, STAD, UCEC, UCS |
| PIK3CA | c.3140A>T | p.H1047L | IRKTLALDKTEQEALEYFMKQMNDA[p.H1047L]LHGGWTTKMDWIFHTIKQH ALN* | FMKQMNDAL, ALHGGWTTK, KQMNDALHG, LHGGWTTK M, QLHGGWTTKM, YFMKQMNDAL, DALHGGWTTK, FMK QMNDALH, KQMNDALHGG, QMNDALHGGW | BRCA, HNSC, UCEC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PIK3CA | c.317G>T | p.G106V | EFFDETRRLCDLRLFQPFLKVIEPV[p.G106V]VNREEKILNREIGFAIGMPVCEFDMV | FLKVIEPVV, KVIEPVVNR | UCS |
| PIK3CA | c.323G>A | p.R108H | FDETRRLCDLRLFQPFLKVIEPVGN[p.R108H]EEKILNREIGFAIGMPVCEFDMVKD | HEEKILNREI | UCEC |
| PIK3CA | c.325_327del GAA | p.E110del | ETRRLCDLRLFQPFLKVIEPVGNRE[p.E110del]KILNREIGFAIGMPVCEFDMVKDPEVQD | REKILNREI | BRCA, UCEC |
| PIK3CA | c.331A>G | p.K111E | TRRLCDLRLFQPFLKVIEPVGNREE[p.K111E]ILNREIGFAIGMPVCEFDMVKDPEV | REEEILNREI, EEILNREIGF | UCEC |
| PIK3CA | c.331_333del AAG | p.K111del | TRRLCDLRLFQPFLKVIEPVGNREE[p.K111del]ILNREIGFAIGMPVCEFDMVKDPEVQDF | REEILNREI, EEILNREIGF | BRCA |
| PIK3CD | c.1141T>C | p.C381R | CFALYAVIEKAKKARSTKKKSKKAD[p.C381R]RPIAWANLMLFDYKDQLKTGERCLYM | KSKKADRPI, RPIAWANLM, KKADRPIAW, KSKKADRPIA, RPIAWANLML, KKSKKADRPI, SKKADRPIAW, ADRPIAWANL | TGCT |
| PIK3G | c.493G>A | p.V165I | RHPPSEESQAFQRQLTALIGYDVTD[p.V165I]ISNVHDDELEFTRRGLVTPRMAEVAS | LIGYDVTDI, ALIGYDVTDI | LUAD |
| PIK3R1 | c.1126G>A | p.G376R | ADGTFLVRDASTKMHGDYTLTLRKG[p.G376R]RNNKLIKIFHRDGKYGFSDPLTFSSV | TLRKGRNNK, KGRNNKLIK, YTLTLRKGR, RNNKLIKIF, LTLRK GRNNK, TLRKGRNNKL, KGRNNKLIKI, GRNNKLIKIF | GBM |
| PIK3R1 | c.1137A>T | p.K379N | TFLVRDASTKMHGDYTLTLRKGGNN[p.K379N]NLIKIFHRDGKYGFSDPLTFSSVVEL | KGGNNNLIK, NNLIKIFHR, RKGGNNNLI, GNNNLIKIF, TLRKG GNNNL, NNNLIKIFHR, GGNNNLIKIF | GBM |
| PIK3R1 | c.1697_1708del TTAAACCAGACC | p.KPDL567del | RRRLEEDLKKQAAEYREIDKRMNSI[p.KPDL567del][IQLRKTRDQYLMWLTQKGVRQKKLNEWLGNENTEDQY | RMNSIIQLR, MNSIIQLRK, SIIQLRKTR, KRMNSIIQL, RMNSIIQLRK, NSIIQLRKTR | BRCA |
| PIK3R5 | c.1112T>G | p.L371R | LLSTSSLASHDSTLSLASSQASGPA[p.L371R]RSRHLLTSFVSGLSDGMDSGYVEDSE | SSQASGPAR, RSRHLLTSF, GPARSRHLL, ASSQASGPAR, RSR HLLTSFV, ARSRHLLTSF | KIRC |
| PILRA | c.872_873insC | p.S291fs | VYASLALSSSTSPRAPPSHRPLKSP[p.S291fs]PERDPVLCLKGLTNGQPSQD* | SPPERDPVL | LUAD |
| PIM1 | c.490C>T | p.L164F | LQEELARSFFWQVLEAVRHCNCGV[p.L164F]FHRDIKDENILIDLNRGELKLIDFGS | RHCHNCGVF, HCHNCGVFHR, VRHCHNCGVF | DLBCL |
| PIM1 | c.550C>T | p.L184F | HNCGVLHRDIKDENILIDLNRGELK[p.L184F]FIDFGSGALLKDTVTFDFDGTRVYSP | FIDFGSGAL, RGELKFIDF, FIDFGSGALL, IDLNRGELKF, LKFID FGSGA, KFIDFGSGAL, GELKFIDFGS | DLBCL |
| PIP4K2A | c.656G>A | p.R219K | IVTRNVFSHRLSVYRKYDLKGSTVA[p.R219K]KEASDKEKAKELPTLKDNDFINEGQK | TVAKEASDK, KEASDKEKA, STVAKEASDK, VAKEASDKEK | KIRP |
| PIP4K2C | c.611G>A | p.R204H | NTLLPQFLGMYRVSVDNEDSYMLVM[p.R204H]HNMFSHRLPVHRKYDLKGSLVSREAS | VMHNMFSHR, LVMHNMFSH, SYMLVMHN, YMLVMHN MF, MHNMFSHRL, VMHNMFSHRL, LVMHNMFSHR, SYML VMHNMF, DSYMLVMHNM, HNMFSHRLPV, MLVMHNMFSH | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PITPN M1 | c.884del|C | p.P295fs | PPGKPSTEARSAASNTGTPDGPEAP|p. P295fs|QAQMPPPMPALGSSGPHPPV PPTHPNMEGLCLPRACLSGACRTLPETL RTAPRKSSLMPTKASRTVRRSSPRR* | AQMPPPMPA,QMPPPMPAL,CLSGACRTL,TLPETLRTA,RT VRRSSPR,ETLRTAPRK,RTAPRKSSL,RKSSLMPTK,KSSLMPT KA,SLMPTKASR,ASRTVRRSS,TVRRSSPRR,NMEGLCLPR,G PEAPQAQM,HPNMEGLCL,LPRACLSGA,MPTKASRTV,PQ AQMPPPM,MEGLCLPRA,AQMPPPMPAL,CLPRACLSGA,S LMPTKASRT,LMPTKASRTV,RTVRRSSPRR,SSLMPTKASR, RTLPETLRTA,RTAPRKSSLM,PTKASRTVRR,APQAQMPPP M,MPALGSSGPH,LPRACLSGAC,APRKSSLMPT,LRTAPRKS SL,RKSSLMPTKA | STAD |
| PIWIL 1 | c.2095G>A | p.V699 M | GLKVCLQAALRAWNSCNEYMPSRII|p. V699M|MYRDGVGDGQLKTLVNYEVP QFLDCL | RIIMYRDGV,EYMPSRIIM,YMPSRIIMY,MPSRIIMYR,YMPS RIIMYR,NEYMPSRIIM | HNSC |
| PKD1 | c.2813C>T | p.T938 M | VENSASRANLSLRVTAEEPICGLRA|p.T 938M|MPSPEARVLQGVLVRYSPVVEA GSDM | AMPSPEARV,RAMPSPEAR,RAMPSPEAR,EPICGLRAM,MPSPEARVL,GL RAMPSPEA,RAMPSPEARV,AMPSPEARVL,EEPICGLRAM | TGCT |
| PKD2 | c.1457A>T | p.Y486 F | KLIRYVTTFDFFLAACEIIFCFFIF|p.Y486 F|FYVVEEILEIRIHKLHYFRSFWNCLD | FCFFIFFYV,IIFCFFIFF,CFFIFFYVV,IFFYVVEEI,FFYVVEEIL, IF CFFIFFY,FCFFIFFYVV,FIFFYVVEI,IIFCFFIFFY,IF- CFFIFFYV, IFFYVVEEIL,FYVVEEILEI,EIIFCFFIFF | CLL |
| PKHD 1L1 | c.5568C>A | p.F185 6L | PPVASLSPTSGSIGGGTTLVITGNG|p.F1 856L|LYPGNTTVTIGDEPCQIISINPNEV Y | LVITGNGLY,GLYPGNTTV,TLVITGNGL,GLYPGNTTVT,LYP GNTTVTI,TLVITGNGLY,TTLVITGNGL | CRC |
| PKN2 | c.226del|A | p.K76fs | KREIRKELKIKEGAENLRKVTTDKK|p.K7 6fs|VWLM* | TTDKKVWLM,RKVTTDKKVW | STAD |
| PLA2G 15 | c.689del|G | p.W23 0fs | FLQRQPQAWKDKYIRAFVSLGAPWG|p. W230fs|AWPRPCASWLQETTTGSQSS GP* | WLQETTTGS,AWPRPCASW,GAPWGAWPR,WPRPCASW L,SLGAPWGAW,FVSLGAPWGA,LGAPWGAWPR,VSLGAP WGAW,GAWPRPCASW | STAD |
| PLA2G 1B | c.157_158i nsTG | p.L53fs | KMIKCVIPGSDPFLEYNNYGCYCGL|p.L 53fs|WGAOAPPWMNWTSAARHMTT AMTRPRSWTAVNFCWTWTRTPTPIHTR ALARQSPVAAKTKSVRPSFATATATLPS AFQKLHITRHTRTWTPRSIVRVEYHLSK ASPLSASSHTVLSNKAPC* | ALARQSPVA,SVRPSFATA,TLPSAFQKL,PLSASSHTV,ATLPS AFQK,SSHTVLSNK,MTTAMTRPR,AVNFCWTTR,NYGCYC GLW,LWGAQAPPW,SWTAVNFCW,SFATATATL,AARHM TTAM,RHMTTAMTR,MTRPRSWTA,RSWTAVNFC,TTRTP TPIH,RTPTPIHTR,HTRALARQS,RALARQSPV,LARQSPVAA, KTKSVRPSF,KLHITRHTR,ITRHTRTWT,HTRTWTPRS,RTW TPRSIV,RSIVRVEYH,RVEYHLSKA,LSKASPLSA,WMNWTSA AR,AFQKLHITR,TWTPRSIVR,WTSAARHMT,WTAVNFCW T,WTTRTPTPI,WTPRSIVRV,RPRSWTAVN,TPIHTRALA,RP SFATATA,YHLSKASPL,ATATLPSAF,AQAPPWMNW,TAMT RPRSW,RQSPVAAKT,FQKLHITRH,HITRHTRTW,SKASPLS AS,LSASSHTVL,VEYHLSKAS,AMTRPRSWTA,MTRPRSWT AV,ALARQSPVAA,ATATATLPSA,HLSKASPLSA,RTWTPRSI VR,IVRVEYFILSK,ASSFITVLSNK,TAVNFCWTTR,TATLPSAF QK,SAFQKLHITR,RSWTAVNFCW,CWTRTPTPI,AARHMT TAMT,TRRTPTPIHT,RTPTPIHTRA,HTRALARQSP,RALARQ SPVA,LARQSPVAAK,RQSPVAAKTK,KTKSVRPSFA,KSVRPS FATA,SVRPSFATAT,KLHITRHTRT,ITRHTRTWTP,HTRTWT PRSI,RSIVRVEYHL,SSHTVLSNKA,PWMNWTSAAR,HMTI AMTRPR,TPIHTRALAR,TSAARHMTTA,WTAVNFCWTT,A PPWMNWTSA,SAARHMTTAM,RPRSWTAVNF,TPTPIHTR | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PLA2G3 | c.602G>A | p.R201Q | GPDLCCREHDRCPQNISPLQYNYGI[p.R201Q]QNYRFFITISFICDCDTRFQQCLQNQHD | AL,SPVAAKTKSV,RPSFATATAT,LPSAFQKLHI,SPLSASSHTV,MNWTSAARHM,TATATLPSAF,GLMGAQAPPW,WMNWTSAARH,AKTKSVRPSF,PSFATATATL,FQKLHITRHT,LHITRHTRTW,KASPLSASSH,TPRSIVRVEY IQNYRFHTI,NYGIQNYRF,QYNYGIQNY,YNYGIQNYR,LQYNYGIQN,YNYGIQNYRF,LQYNYGIQNY,QYNYGIQNYR,IQNYRFHTIS,QNYRFHTISH | UCEC |
| PLAG1 | c.551del|A | p.K184fs | FESTGVLLEHLKSHAGKSSGGVKEK[p.K184fs]STSANIVIAGSTPERMSGDTWWCTLEERTSSVSIVHRDLGERIT* | RMSGDTWWC,TLEERTSSV,VIAGSTPER,RTSSVSIVH,TSSVSIVHR,GVKEKSTSA,KSTSANIVI,TWWCTLEER,RMSGDTWWCT,CTLEERTSSV,IVIAGSTPER,RTSSVSIVHR,KSTSANIVIA,DTWWCTLEER,SIVHRDLGER,KEKSTSANIV,MSGDTWWCTL,LEERTSSVSI,EERTSSVSIV,TPERMSGDTW | STAD |
| PLAGL2 | c.30del|C | p.P10fs | MTTFFTSVPP[p.P10fs]GFKMQSRRRKWAGN* | FTSVPPGFK,FFTSVPPGF,TSVPPGFKM,KMQSRRRKW,FFTSVPPGFK,TFFTSVPPGF,GFKMQSRRRK,KMQSRRRKWA,FTSVPPGFKM,FKMQSRRRKW | STAD |
| PLAU | c.602_603insG | p.R201fs | IIGGEFTTIENQPWFAAIYRRHRGG[p.R201fs]LCFILRVWRQPHQPLLGDQRHTLLH* | LLGDQRHTL,VWRQPHQPL,HLRVWRQPH,GLCHLRVWR,RHRGGLCHL,WRQPHQPLL,LLGDQRHTLL,VWRPHQPLL,AIYRRHRGGL,RHRGGLCHLR,HLRVWRQPHQ,RVWRQPHQPL,RRHRGGLCHL,RGGLCHLRVVV | STAD |
| PLCD3 | c.1495del|G | p.E499fs | KGRVLVKGKKLPAARSEDGRALSDR[p.E499fs]RRRRRMTRRKKRRWRLQRRGGWPSRSPRSCRPWLCTATPPA* | WLCTATPPA,RALSDRRRR,RRRRRMTR,RRRRRMTRR,RRRMTRRK,RRRMTRKKR,RMTRKKKR,KKRRWRLQR,KRRWRLQRR,RWRLQRRGG,GGWPSRSPR,WPSRSPRSC,SPRSCRPWL,RRKKRRWRL,LQRRGGWPS,RSPRSCRPW,RALSDRRRRR,ALSDRRRRRR,RRRRRRMTRR,RRRRRMTRRK,RRRRMTRRKK,MTRRKKRWR,RKKRRWRLQR,KKRRWRLQRR,RWRLQRRGGW,LQRRGGWPSR,RGGWPSRSPR,RSPRSCRPWL,RSCRPWLCTA,RPWLCTATPP,TRRKKRRWRL,RMTRRKKRRW,SRSPRSCRPW | CLL |
| PLCE1 | c.1315G>T | p.G439C | NTVGSLLHFLTKLPASETAHGRISV[p.G439C]CPCLKQCVRDTVCEYRATLQRTSISQ | RISVCPCLK,GRISVCPCL,HGRISVCPCL | LUSC |
| PLCE1 | c.1690G>T | p.G564C | LMEQEQTIYRRVLPVDYLCFLTRDL[p.G564C]CTPECQSSLLPCLKASISASILTTQNG | CTPECQSSL | LUAD |
| PLCL1 | c.1692G>T | p.M564I | VKGKKLPSDPDVLEGEVTDEDEEAE[p.M564I]ISRRMSVDYINGEQKQIRLCRELSDLV | ISRRMSVDY,AEISRRMSV,EEAEISRRM,EISRRMSVDY,DEEAEISRRM | LUAD |
| PLEC | c.4157G>A | p.R1386Q | QDARRRQEQIQAMPLADSQAVREQL[p.R1386Q]QQEQALLEEIERHGEKVEECQRFAKQ | EQLQQEQAL,REQLQQEQA,REQLQQEQAL,EQLQQEQALL,QQEQALLEEI | ACC |
| PLEKHA6 | c.329G>T | p.R110L | VDRCLFYYKDEKEESILGSIPLLSF[p.R110L]LVAAVQPSDNISRKHTFKAEHAGVRT | SIPLLSFLV,LLSFLVAAV,FLVAAVQPS,IPLLSFLVA,GSIPLLSFL,GSIPLLSFLV,PLLSFLVAAV,IPLLSFLVAA | LUAD |
| PLEKHA6 | c.982del|G | p.V328fs | TNPDKIAQRKSSMNQLQQWVNLRRG[p.V328fs]YPRLKTFGVPLGSILCLAGSLSTMAPTPPSTPMIISTTRQECGRRASVPCRPMIGSARPGPWRTSAMPSAMGVALPTSCESGRSPPATGGRMPPSGSQAPPG | RLKTFGVPL,CLAGSLSTM,SAMPSAMGV,IMMSWMPPL,MMSWMPPLA,WMPPLAPCA,FTPLSAHPV,PLSAHPVPV,VLSGCHLAV,NLRRGYPRL,TMAPTPPST,AMPSAMGVA,RMPPSGSQA,HLAVRTSML,RGYPRLKTF,RAPTAVPAF,LRRGYPRLK,STMAPTPPS,RASVPCRPM,SARPGPWRT,RTSAMP | CRC,STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PLEKHB1 | | | SQSIMMSWMPPLAPCAACPCSPAPTLCPAHPARAPTAVPAFTPLSAHPVPVLSGCHLAVRTSMLTLLPM* | SAM, AVRTSMLTL, QWNLRRGY, VNLRRGYPR, TPMIISTT R, STTRQECGR, TLCPAHPAR, CAACPCSPA, TAVPAFTPL, YP RLKTFGV, APTPPSTPM, RPGPWRTSA, MPSAMGVAL, SPPA TGGRM, APPGSQSIM, MPPLAPCAA, CPCSPAPTL, SPAPTLC PA, HPARAPTAV, VPAFTPLSA, VPVLSGCHL, SQSIMMSWM, TS MLTLLPM, FGVPLGSIL, RQECGRRAS, IGSARPGPW, WRTSQMPSA, SAMGVALPT, CESGRSPPA, SQAPPGSQS, GSQSIMMSW, MSWMPPLAP, ARAPTAVPA, LSAHPVPVL, CHLAVRTSM, VRTSMLTLL, VPLGSILCL, QECGRRASV, TPPSTPMI, RTSMLTLLPM, CLAGSLSTMA, AMPSAM GVAL, SIMMSWMPPL, IMMSWMPPLA, WMPPLAPCAA, KTFGVPLGSI, SQAPPGSQSI, TLCPAHPARA, HLAVRTSMLT, AVRTSMLTLL, NLRRGY PRLK, WVNLRRGYPR, STPMIISTTR, RGYPRLKTFG, RLKTFGVPLG, ST MAPTPPST, CGRRASVPCR, RASVPCRPMI, SARPGPWRTS, PWRTSAMP SA, RTSAMPSAMG, SWMPPLAPCA, QOWNLRRGY, PTLCPAHPAR, VLS GCHLAVR, MAPTPPSTPM, TSAMPSAMGV, YPRLKTFGVP, APTPPST PMI, RPMIGSARPG, RPGPWRTSAM, APPGSQSIMM, APTLCPAHPA, CPAHPARAPT, TPLSAHPVPV, RRGYPRLKTF, LCLAGSLSTM, RQECGRRASV, RRASVPCRPM, MIGSARPGPW, WRTSAMP SAM, SAMPSAMGVA, RMPPSGSQAP, MMSWMPPLAP, A RAPTAVPAF, GCHLAVRTSM, CHLAVRTSML, LAVRTSMLTL, MPSAMGVALP, MPPLAPCAAC, SPAPTLCPAH, VPAFTPLSA H, HPVPVLSGCH, CESGRSPPAT, VPLGSILCLA, VPVLSGCHL A | |
| | c.436T>C | p.S146P | TALLEANSTPAPAGATVPPRSRRVC[p.S146P]PKVRCVTRSWSPCKVERRIWVRVYSP | RSRRVCPKV, RVCPKVRCV, CPKVRCVT, RSRRVCPKVR | CLL |
| | c.1150G>A | p.E384K | AIIFLQNSFCSLNTHRTPRTAQEVA[p.E384K]KLIDQHETMMKLVLEDPLIVSLRLEG | KLIDQHETM, RTAQEVAKL, KLIDQHETMM, AKLIDQHETM | CRC |
| PLEKHM1 | c.2684C>T | p.A895V | RIIHMWDLTKRPICRQALKFLTQIR[p.A895V]VQPLINLQMVNASLYEHVERMHLIGR | TQIRVQPLI, LTQIRVQPL, LKFLTQIRV, IRVQPLINL, VQPLINL QM, FLTQIRVQPL, ALKFLTQIRV, QIRVQPLINL, RVQPLINLQ M | TGCT |
| PLEKHM2 | c.1376C>T | p.S459L | DQSFRTGSPGDAPERPPLCDFSEGL[p.S459L]LAPMDFYRFTVESPSTVTSGGGFIHDP | LLAPMDFYR, LAPMDFYRF, GLLAPMDFY, FSEGLLAPM, LLA PMDFYRF, GLLAPMDFYR, SEGLLAPMDF, DFSEGLLAPM | BLCA |
| PLEKHO1 | c.761del|C | p.T254fs | QPSADRASSLSRPWEKTDKGATYTP[p.T254fs]RHPRS* | ATYTPRHPR, ATYTPRHPRS, GATYTPRHPR | STAD |
| PLEKHO2 | c.1051G>C | p.E351Q | GEMQASGPPAPGTVQVSVNGMDDSP[p.E351Q]QPAKPSQAEGTPGTPPKDATTSTALP | GMDDSPQPA, GMDDSPQPAK, SPQPAKPSQA | CESC |
| PLIN5 | c.916C>T | p.R306W | LETLVLSRSLITQELQGTVEALESSV[p.R306W]WGLPAGAQEKVAEVRRSVDALQTAFA | ALESSVWGL, ESSVWGLPA, SVWGLPAGA, VEALESSVW, EA LESSVWGL, SSVWGLPAGA, LESSVWGLPA | ACC |
| PLK1 | c.698A>G | p.D233G | KKTLCGTPNYIAPEVLSKKGHSFEV[p.D233G]GVWSIGCIMYTLLVGKPPFETSCLKE | SFEVGVWSI, KGHSFEVGV, GVWSIGCIM, FEVGVWSIG, GV WSIGCIMY, HSFEVGVWSI, EVGVWSIGCI, KGHSFEVGVW, VGVWSIGCIM, FEVGVWSIGC | CRC |
| PLOD3 | c.888_889insC | p.P296fs | GWTPEGGCGFCNQDRRTLPGGQPPP[p.P296fs]PGVSGRVCGTAYSVSAPLPAAATPGLSPRQGHPFPAQQRGLP* | RVCGTAYSV, SVSAPLPAA, SGRVCGTAY, AATPGLSPR, TAYS VSAPL, YSVSAPLPA, APLPAAAT, LPAAAATPG, LSPRQGHP F, RQGHPFPAQ, VSGRVCGTAY, GTAYSVSAPL, SVSAPLPAA | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PLOD3 | c.889de|C | p.R297fs | GWTPEGGCGFCNQDRRTLPGGQPPP|p.R297fs]GCFWPCLWNSLLRFCPASCSGCYSWTIPPTGSPFSCTTTRSSMNPTSLTPGRSSRTTSQL* | A,AAATPGLSPR,YSVSAPLPAA,LPAAAATPGL,SPRQGHPFPA,HPFPAQORGL,GLSPQGHPF,GRVCGTAYSV,FWPCLWNSL,CLWNSLLRF,NSLLRFCPA,TRRSSMNPT,RSSMNPTSL,RSSRTTSQL,SPFSCTTTR,SLTPGRSSR,TIPPTGSPF,CPASCSGCY,ASCSGCYSW,SCTTTRSSM,SMNPTSLTP,WPCLWNSLL,CFWPCLWNSL,FWPCLWNSLL,WTIPPTGSPF,TTRSSMNPTS,RSSMNPTSLT,TSLTPGRSSR,MNPTSLTPGR,FSCTTTRSSM,TRSSMNPTSL,SMNPTSLTPG,GRSSRTTSQL | CRC,STAD |
| PLSCR3 | c.229G>A | p.E77K | FPSPGPVALGSAAPFLPLPGVPSGL|p.E77K]KFLVQIDQILIHQKAERVETPLGWET | KFLVQIDQI,VPSGLKFLV,GVPSGLKFLV,KFLVQIDQIL,LPGVPSGLKF,LKFLVQIDQI | CRC |
| PLXNA1 | c.3046de|C | p.P1016fs | LTPPGQSPGSAPIIININRAQLTNP|p.P1016fs]R* | INRAQLTNPR | STAD |
| PLXNA1 | c.3883G>A | p.E1295K | ALECKEAFAELQTDIHELTNDLDGA|p.E1295K]SIPFLDYRTYAMRVLFPGIEDHPVLK | ASIPFLDYR,GASIPFLDY,DLDGASIPF,GASIPFLDY,SIPFLDYRTY,LTNDLDGASI,NDLDGASIPF | UCEC |
| PLXNA2 | c.1392_1393insCC | p.P464fs | YNGYSVVFVGTKSGKLKKIRADGPP|p.P464fs]PMVGSSTRWSLCSRTEAPSSGTWPSPLISATCTSCLRDRSPGSPWSHVSSIRLVGSA* | STRWSLCSR,KIRADGPPP,SATCTSCLR,WPSPLISAT,SPWSHVSSI,IRADGPPPM,PMVGSSTRW,VGSSTRWSL,TEAPSSGTW,ISATCTSCL,RDRSPGSPW,WSHVSSIRL,SPGSPWSHV,LISATCTSCL,SSTRWSLCSR,ISATCTSCLR,KIRADGPPPM,STRWSLCSRT,RWSLCSRTEA,MVGSSTRWSL,RTEAPSSGTW,WPSPLISATC,PPMVGSSTRW | STAD |
| PLXNA3 | c.172C>T | p.P58S | LTHLAVHRVTGEVFVGAVNRVFKLA|p.P58S]SNLTELRAHVTGPVEDNARCYPPPSM | KLASNLTEL,RVFKLASNL,LASNLTELR,KLASNLTELR,RVFKLASNLT,FKLASNLTEL | HNSC |
| PLXNC1 | c.1385C>T | p.S462L | IYIYLTAGKEVRRIRVANCNKHKSC|p.S462L]LECLTATDPHCGWCHSLQRCTFQGDC | NKHKSCLECL | CRC |
| PLXNC1 | c.2455C>T | p.R819C | NINVSEYCVATYCGFLAPSLKSSKV|p.R819C]CTNVTVKLRVQDTYLDCGTLQYREDP | KVCTNVTVK,CTNVTVKLR,KSSKVCTNV,SKVCTNVTV,SSKVCTNVTV | CRC |
| PLXND1 | c.1100G>T | p.R367L | GLQCAGGAGRGDLYSRLVSVPPARE|p.R367L]LLFAVFERPQGSPAARAAPAALCAFR | VFPARELLF,SVPPARELL,ELLFAVFER,ARELLFAVF,FPARELLFA,RELLFAVFE,SVPPARELLF,FPARELLFAV,PARELLFAVF | TGCT |
| PMEPA1 | c.624de|C | p.P208fs | RAPPNRTIFDSDLMDSARLGGPCPP|p.P208fs]AVTRASAPRATAAGAWRGRPPTARSSATTRGPPSSTSRAVGRPCWRGPGSTTHTSRP* | RLGGPCPPA,AVTRASAPR,ATAAAGAWR,SSTSRAVGR,AVGRPPCWR,VTRASAPRA,RASAPRATA,AWRGRPPT,RGRPPTAR,TARSSATTR,AAGAWRGRR,SAPRATAAA,APRATAAAG,RPPTARSSA,RPPCWRGPG,RATAAGAW,RAVGRPPCW,RLGGPCPPAV,VTRASAPRAT,RASAPRATAA,ASAPRATAAA,RATAAAGAWR,AWRGRPPTA,RGRPPTARS,TSRAVGRPPC,CPPAVTRASA,APRATAAAGA,RPPTARSSAT,GPPSSTSRAV,ARLGGPCPPA | STAD |
| PMS2 | c.1952A>G | p.K651R | AKRIKQLHHEAQQSEGEQNYRKFRA|p.K651R]RICPGENQAAEDELRKEISKTMFAEM | NYRKFRARI,KFRARICPG,RARICPGEN,QNYRKFRAR,KFRARICPGE,RARICPGENQ,EQNYRKFRAR,RKFRARICPG | TGCT |
| PNKP | c.520G>T | p.G174W | NLEKLLVFTAAGVKPQGKVAGFDLD|p.G174W]WTLITTRSGKVFPTGPSDWRILYPEI | AGFDLDWTL,WTLITTRSGK,DLDWTLITTR,GKVAGFDLDW | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PNLIP | c.110C>T | p.T37M | GAVAGKEVCYERLGCFSDDSPWSGI[p. T37M]MERPLHILPWSPKDVNTRFLLYT NEN | GIMERPLHI, SPWSGIMER, IMERPLHIL, GIMERPLHIL, DSP WSGIMER, MERPLHILPW | MM |
| PNPLA 4 | c.668T>C | p.L223 P | LDLYVNIAKQDIMLSLANLVRLNQA[p.L 223P]PFPPSKRKMESLYQCGFDDTVKF LLK | NQAPFPPSK, LVRLNQAPF, LNQAPFPPSK, NQAPFPPSKR, A PFPPSKRKM, NLVRLNQAPF, RLNQAPFPPS | TGCT |
| PNPLA 7 | c.3597del C | p.P119 9fs | LAYVCCVRQLEVVKSSDYCEYLRPP[p.P 1199fs]STATAPWTSASSTRSAKWATST GARCLTSGAAAACWRRCSATSRGRARS PRVRSSPVPTPPSRTLPKLCLALSPPSPP WWMTNLTTRRSTRRSCWTSPGMHTQ TSRAPQPSRAQTWRTSPHCGIDTPVWL SQNCLRAPLTRTGRGLC* | YLRPPSTAT, CLTSGAAAA, TLPKLCLAL, GMHTQTSRA, WLS QNCLRA, SQNCLRAPL, SASSTRSAK, STRSAKWAT, KWATST GAR, GARCLTSGA, AACWRRCSA, RGRARSPRV, RARSPRVR S, RVRSSPVPT, RTLPKLCLA, TTRRSTRRS, STRRSCWTS, RSC WTSPGM, TSRAPQPSR, LTRTGRGLC, SATSRGRAR, WWMT NLTTR, WMTNLTTRR, NLTTRRSTR, LTTRRSTRR, VWLSQNC LR, RAPLTRTGR, TATAPWTSA, ATAPWTSAS, APWTSASST, SPRVRSSPV, VPTPPSRTL, SPPWWMTNL, AQPSRAQT, RS AKWATST, AKWATSTGA, ALSPPSPPW, AQTWRTSPH, PPS TATAPW, CEYLRPPST, YLRPPSTATA, TSASSTRSAK, RTLPKL CLAL, STATAPWTSA, STRSAKWATS, SAKWATSTGA, GARC LTSGAA, AAACWRRCSA, CWRRCSATSR, TSRGRARSPR, RG RARSPRVR, RARSPRVRSS, RSPRVRSSPV, RVRSSPVPTP, RS SPVPTPPS, TTRRSTRRSC, STRRSCWTSP, TSRAPQPSRA, RA QTWRTSPH, TWRTSPHCGI, CSATSRGRAR, WWMTNLTTR R, TNLTTRRSTR, NLTTRRSTRR, QTSRAPQPSR, PVWLSQNC LR, WTSASSTRSA, RPPSTATAPW, TPPSRTLPKL, APQPSRA QTW, SPHCGIDTPV, TPVWLSQNCL, APLTRTGRGL, CEYLRP PSTA, SASSTRSAKW, WATSTGARCL, LALSPPSPPW, ALSPP SPPWW, RRSCWTSPGM, AQTWRTSPHC, LSQNCLRAPL, S QNCLRAPLT, LTSGAAAACW | STAD |
| PNRC 1 | c.217C>T | p.R73C | PRALPPTLFLPHFLGGDGPCLTPQP[p.R 73C]CAPAALPNRSLAVAGGTPRAAPKK RR | LTPQPCAPA, TPQPCAPAA, CLTPQPCAPA, TPQPCAPAAL | CESC |
| PODN | c.903del C | p.I301f s | RHVPKHLPPALYKLHLKNNKLEKIP[p.I3 01fs]RGPSAS* | LEKIPRGPSA | STAD |
| PODN L1 | c.449C>T | p.A150 V | QLQHLCVAHNKLSVAPQFLPRSLRV[p. A150V]VDLAANQVMEIFPLTFGEKPAL RSVY | FLPRSLRVV, RSLRVVDLA, VDLAANQVM, RVVDLAANQV, R SLRVVDLAA, LPRSLRVVDL | GBM |
| PODX L | c.486_487i nsC | p.S162f s | TATAKPNTTSSQNGAEDTTNSGGKS[p. S162fs]QPQCDHRPHIH* | QPQCDHRPHI, SQPQCDHRPH | GBM |
| POGZ | c.223G>T | p.G75 W | SAPVPIAAHASVAGHLSTSTTVSSS[p.G 75W]WAQNSDSTKKTLVTLIANNNAG NPLV | TSTTVSSSW, STSTTVSSSW | LUAD |
| POLA 1 | c.1809G>T | p.E603 D | PFQSHFCVVSKPKDCIFPYAFKEVI[p.E6 03D]DKKNVKVEVAATERTLLGFFLAKV HK | YAFKEVIDK, AFKEVIDKK, YAFKEVIDKK, EVIDKKNVKV | CRC |
| POLE | c.1231G>T | p.V411 L | EIGFQKDSQGEYKAPQCIHMDCLRW[p. V411L]LKRDSYLPVGSHNLKAAAKAKL GYDP | HMDCLRWLK, RWLKRDSYL, IHMDCLRWL, LRWLKRDSY, L KRDSYLPV, WLKRDSYLPV, IHMDCLRWLK, CLRWLKRDSY, HMDCLRWLKR, LRWLKRDSYL | CRC, UCEC |
| POLE | c.1376C>T | p.S459 F | YDPVELDPEDMCRMATEQPQTLATY[p. S459F]FVSDAVATYYLYMKYVHPPIFAL CTI | FVSDAVATY, ATYFVSDAV, QPQTLATYF, FVSDAVATYY, TLA TYFVSDA, ATYFVSDAVA, YFVSDAVATY, LATYFVSDAV, EQP QTLATYF, QPQTLATYFV | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| POLE | c.1718G>T | p.R573L | ESGVFRSDIPCRFRMNPAAFDFLLQ[p.R573L]LVEKTLRHALEEEKVPVEQVTNFEE | FLLQLVEKT,DFLLQLVEK,AAPDFLLQL,AAFDFLLQLV,FLLQL VEKTL,QLVEKTLRHA,LQLVEKTLRH | LUAD |
| POLE | c.857C>G | p.P286R | DDLVERPDPVVLAFDIETTKLPLKF[p.P286R]RDAETDQIMMISYMIDGQGYLITNRE | TTKLPLKFR,RDAETDQIM,KFRDAETDQI,ETTKLPLKFR,RD AETDQIMM | UCEC |
| POLM | c.290de|C | p.P97fs | EETSAEEAVSWQERRMAAAPPGCTP[p.P97fs]QLCWT* | APPGCTPQL | STAD |
| POLQ | c.2579G>A | p.R860Q | NAVPFKSARKAVDEEEEAVEERRNM[p.R860Q]QTIWVTGRKGLTEREAAALIVEARM | QTIWVTGRK,MQTIWVTGR,RNMQTIWVT,MQTIWVTGR K,NMQTIWVTGR,RNMQTIWVTG,EERRNMQTIW | CRC |
| POLR1C | c.994A>C | p.K332Q | IFSVESTGVLPPDVLVSEAIKVLMG[p.K332Q]QCRRFLDELDAVQMD* | KVLMGQCRR,VLMGQCRRF,LMGQCRRFL,VLMGQCRRFL, AIKVLMGQCR,KVLMGQCRRF,GQCRRFLDEL | KIRC |
| POLR3B | c.1114C>T | p.L372F | GDNKVDDRDYYGNKRLELAGQLLSL[p.L372F]FFEDLFKKFNSEMKKIADQVIPKQRA | LLSLFFEDL,SLFFEDLFK,LFFEDLFKK,LSLFFEDLF,FFEDLFKK F,LAGQLLSLF,AGQLLSLFF,QLLSLFFED,LSLFFEDLFK,SLFF EDLFKK,LFFEDLFKKF,ELAGQLLSLF,LAGQLLSLFF,LLSLFFE DLF | BLCA |
| POM121L12 | c.691C>A | p.P231T | GRRNLQPRPSAFKPLSKNGAVASFV[p.P231T]TRPGPLKPSLGPWSLSFCDDAWPSVL | FVTRPGPLK,GAVASFVTR,SFVTRPGPL,SFVTRPGPLK,ASF VTRPGPL,NGAVASFVTR | LUAD |
| POM121L12 | c.725C>A | p.P242H | FKPLSKNGAVASFVPRPGPLKPSLG[p.P242H]HWSLSFCDDAWPSVLVQPAPSAIWDF | SLGHWSLSF,KPSLGHWSL,PSLGHWSLSF,LKPSLGHWSL,G PLKPSLGHW | LUAD |
| PON1 | c.917G>A | p.R306Q | WVGCHPNGMKIFFYDSENPPASEVL[p.R306Q]QIQNILTEEPKVTQVYAENGTVLQGS | SEVLQIQNI,LQIQNILTE,PPASEVLQI,SEVLQIQNIL,NPPASE VLQI | UCEC |
| POP1 | c.2248de|A | p.K750fs | VASSPNGKESDLRRSEVPCAPMPKK[p.K750fs]LISHLMKWAHP* | LISHLMKWA,KLISHLMKW,KKLISHLMK,APMPKKLIS,MPK KLISHL,ISHLMKWAH,KLISHLMKWA,APMPKKLISH,MPKK LISHLM,KKLISHLMKW | STAD |
| POSTN | c.1522C>T | p.R508C | GAIHIFREIIKPAEKSLHEKLKQDKL[p.R508C]CFSTFLSLLEAADLKELLTQPGDWTL | KQDKCFSTF,CFSTFLSLL,KCFSTFLSL,KQDKCFSTFL,LKQDK CFSTF,KCFSTFLSLL | CRC |
| POTEC | c.1519A>G | p.K507E | EEQNTGISQDEILTNKQKQIEVAEK[p.K507E]EMNSELSLSHKKEEDLLRENSMLQEE | AEKEMNSEL,KEMNSELSL,KEMNSELSLS,AEKEMNSELS | GBM, PRAD |
| POTE | c.496G>A | p.V166M | DKLHRAAWWGKVPRKDLIVMLRDTD[p.V166M]MNKKDKQKRTALHLASANGNSEVVKL | MLRDTDMNKK | GBM |
| POTEE | c.862G>A | p.V288M | ADIESKNKHGLTPLLGVHEQKQQVP[p.V288M]MKFLIKKKANLNALDRYGRTALILAV | QVMKFLIKK,VMKFLIKKK,KQQVMKFLI,QQVMKFLIK,VHE QKQQVM,EQKQQVMKF,QVMKFLIKKK,KQQVMKFLIK,Q QVMKFLIKK,GVHEQKQQVM,HEQKQQVMKF | LUAD |
| POTEE | c.908G>T | p.R303I | LGVHEQKQQVKFLIKKKANLNALD[p.R303I]IYGRTALILAVCCGSASIVSLLLEQN | IYGRTALIL,DIYGRTALI,KANLNALDI,ANLNALDIY,LDIYGRT AL,ALDIYGRTAL,IYGRTALILA,KANLNALDIY,NLNALDIYGR, KKANLNALDI | UCEC |
| POTEF | c.2022G>T | p.K674N | STLREEIAMLRELDTMKHQSLRE[p.K674N]NKYLEDIESVKKRNDNLLKALQLNEL | SQLRENKYL,RENKYLEDI,KHQSQLRENK,HQSQLRENKY,N KYLEDIESV | UCEC |
| POTEF | c.334A>G | p.S112G | DDSAMKTLRNKMGKWCCHCFPCCRG[p.S112G]GSKSKVGAWGDYDDSAFMEPRYHVRG | CCRGGSKSK | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| POTEG | c.151G>A | p.D51N | KWCRHCFPWCRGSGKSNVGTSGDHD[p. D51N]NSAMKTLRSKMGKMCRHCFP WCRGSS | DNSAMKTLR, NSAMKTLRSK | SKCM |
| POTEG | c.407G>A | p.R136H | GSGKSKVGPWGDYDDSAFMEPRYHV[p. R136H]HREDLDKLHRAAWWGKVPR KDLIVML | HVHREDLDK, FMEPRYHVH, FMEPRYHVHR | GBM |
| POU2F2 | c.715A>G | p.T239A | RIKLGFTQGDVGLAMGKLYGNDFSQ[p. T239A]ATISRFEALNLSFKNMCKLKPLL FKW | ATISRFEAL, DFSQATISR, FSQATISRF, KLYGNDFSQA, SQATI SRFFA, DFSQATISRF, YGNDFSQATI | DLBCL |
| POU2F2 | c.715A>T | p.T239S | RIKLGFTQGDVGLAMGKLYGNDFSQ[p. T239S]STISRFEALNLSFKNMCKLKPLLE KW | STISRFEAL, FSQSTISRF, DFSQSTISR, DFSQSTISRF, YGNDFS QSTI, SQSTISRFEA | DLBCL |
| POU3F3 | c.961G>T | p.D321Y | GGGGGAGPGLNSHDPHSDEDTPTSD[p.D 321Y]YLEQFAKQFKQRRIKLGFTQA DVGLA | YLEQFAKQF, DEDTPTSDY, TSDYLEQFAK, DYLEQFAKQF, TP TSDYLEQF | LUAD |
| PPARGC1B | c.403del|C | p.P135fs | APPALDGGDALSCTSASPAPSSAPP[p. P135fs]ALPRRSPRPQPLRWTSSHCCRSS SWPHPTQHQALTPRRKGPPGARQASD LKVNGLVLRRTAPKTRRLP* | KVNGLVLRR, LVLRRTAPK, SSAPPALPR, RSPRPQPLR, SSHC CRSSS, HQALTPRRK, GARQASDLK, RTAPKTRRL, PALPRRSP R, TQHQALTPR, APSSAPPAL, RPQPLRWTS, WPHPTQHQA, RRSPRPQPL, SHCCRSSSW, SPRPQPLRW, ASDLKVNGLV, GL VLRRTAPK, SSAPPALPRR, VLRRTAPKTR, RTAPKTRRLP, DLK VNGLVLR, SPAPSSAPPA, SPRPQPLRWT, RPQPLRWTSS, W PHPTQHQAL, TPRRKGPPGA, SSHCCRSSSW, SDLKVNGLVL KSSHSHTRK, SSHSHTRKK, HSHTRKKHK, HTRKKHKKK, KSSHSHTRKK, HSHTRKKHKK, DSKSHSHTR | STAD |
| PPIL4 | c.1146T>A | p.S382R | PKQDTKYDLIIDEQAEDSKSSHSHT[p. S382R]RKKHKKKTHHCSEEKEDEDYMPIK NT | KSSHSHTRK, SSHSHTRKK, HSHTRKKHK, HTRKKHKKK, KSSHSHTRKK, HSHTRKKHKK, DSKSHSHTR | CLL |
| PPL | c.1362del|C | p.P454fs | GESWELMDSAGNKLIAPAVCFVIPP[p. P454fs]QTLRPWLWLTAWAASTGACG RRQLGANARCSSGMRC* | TLRPWLWLT, WLWLTAWAA, WLTAWAAST, FVIPPQTLR, C FVIPPQTL, PQTLRPWLW, NARCSSGMR, TAWAASTGA, RP WLWLTAW, RQLGANARC, ANARCSSGM, IPPQTLRPW, TLR PWLWLTA, LTAWAASTGA, CGRRQLGANA, CFVIPPQTLR, WAASTGACGR, IPPQTLRPWL, RPWLWLTAWA, RQLGANA RCS, GANARCSSGM | STAD |
| PPL | c.976C>T | p.H326Y | DWKEYLNLLICEESHLKYMEDYHQF[p.H3 26Y]YEDVKDAQELLRKVDSDLNQKY GPDF | YMEDYHQFY, KYMEDYHQFY, HQFYEDVKDA, YEDVKDAQ EL | BLCA |
| PPM1E | c.931C>T | p.R311W | IHLHVNLVRQEMFPHDPAEALCRAF[p. R311W]WVTDERFVQKAARESLRCGTT GVVTF | RAFWVTDER, AFWVTDERF, EALCRAFWV, AEALCRAFW, WVTDERFVQK, RAFWVTDERF, AEALCRAFWV | KIRC |
| PPM1H | c.678del|C | p.P226fs | NSRTLTRAASLRGGVGAPGSPSTPP[p. P226fs]HASLPRRRFPMSAWSSERLKVH SRKWTYR* | SLPRRRFPM, SAWSSERLK, ASLPRRRFP, RLKVHSRKW, KVH SRKWTY, PMSAWSSER, MSAWSSERL, FPMSAWSSE, LPRR RFPMS, HASLPRRRF, RRRFPMSAW, MSAWSSERLK, KVHS RKWTYR, STPPHASLPR, ASLPRRRFPM, SERLKVHSRK, RLKV HSRKWT, FPMSAWSSER, SPSTPPHASL, LPRRRFPMSA, RRF PMSAWSS, LKVHSRKWTY | STAD |
| PPP1R12C | c.1116del|C | p.P372fs | LSSREKISLQDLSKERRPGAGGPP[p.P 372fs]SRTRMRGKKVPPNHPLQNPEPS MASPPRRTPALRVPCSLKRPPSPGALAS* | ALRVPCSLK, PSRTRMRGK, RTRMRGKKV, RMRGKKVPP, RG KKVPPNH, ASPPRRTPA, SLKRPPSPG, SPPRRTPAL, RPPSPG ALA, KKVPPNHPL, LQNPEPSMA, SLKRPPSPGA, PSRTRMR GKK, RTRMRGKKVP, RMRGKKVPPN, MASPPRRTPA, ALRV PCSLKR, RPGGAGGPPS, HPLQNPEPSM, TPALRVPCSL, LKR PPSPGAL, GKKVPPNHPL, LQNPEPSMAS | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PPP2R1A | c.536C>G | p.P179R | CYPRVSSAVKAELRQYFRNLCSDDT[p.P1 79R]RMVRRAAASKLGEFAKVLELDNVKSE | TRMVRRAAA, RMVRRAAAS, NLCSDDTRMV, RMVRRAAAS K, RNLCSDDTRM | UCEC, UCS |
| PPP2R1A | c.547C>T | p.R183W | VSSAVKAELRQYFRNLCSDDTPMVR[p. R183W]WAAASKLGEFAKVLELDNVKSE IIPM | MVRWAAASK, DTPMVRWAA, TPMVRWAAA, VRWAAASK L, CSDDTPMVRW, MVRWAAASKL, DTPMVRWAAA, TPMV RWAAAS, WAAASKLGEF | CRC, UCS |
| PPP2R1A | c.656C>T | p.S219L | KVLELDNVKSEIIPMSNLASDEQD[p.S 219L]LVRLLAVEACVNIAQLLPQEDLEA LV | DEQDLVRLL, NLASDEQDLV, DEQDLVRLLA | UCS |
| PPP2R1A | c.767C>T | p.S256F | IAQLLPQEDLEALVMPTLRQAAEDK[p.S 256F]FWRVRYMVADKFTELQKAVGPE ITKT | KFWRVRYMV, FWRVRYRYMVA, QAAEDKFWR, RQAAEDKF W, DKFWRVRYM, KFWRVRYMVA, QAAEDKFWRV, TLRQA AEDKF, AEDKFWRVRY | UCEC |
| PPP2R2B | c.977C>T | p.P326L | SKGTIRLCDMRASALCDRHTKFFEE[p.P 326L]LEDPSNRSFFSEIISSISDVKFSHSG | RHTKFFEEL, LEDPSNRSF, ELEDPSNRSF, LEDPSNRSFF | CRC |
| PPP2R 3B | c.1165de[A | p.T389fs | RKVQKEGKISYADFVWFLISEEDKK[p.T 389fs]HRPASSTGSAAWTWTGTAPCW CSSSSTSTRSSAEGWTAWPSRPCPSRT ASARCWTWSSRGLKGRSRCRT* | WTWSSRGLK, CSSSSSTSR, STGSAAWTW, SSTSTRSSA, RTA SARCWT, SARCWTWSS, EGWTAWPSR, WTWTGTAPC, WT AWPSRPC, RPASSTGSA, RPCPSRTAS, SSAEGWTAW, KKHR PASST, ASSTGSAAW, RSSAEGWTA, AEGWTAWPS, TASAR CWTW, RTASARCWTW, SSSTSTRSSA, SARCWTWSSR, CW TWSSRGLK, SSRGLKGRSR, RGLKGRSRCR, TWSSRGLKGR, S AAWTWTGTA, RPASSTGSAA, RPCPSRTASA, SSTGSAAWT W, RSSAEGWTAW, RCWTWSSRGL, SEEDKKHRPA | STAD |
| PPP2R 3B | c.930C>A | p.F310 L | ELRRSSFLQNVALLEEEADINQLTE[p. 310L]LFSYEHFYVIYCKFWELDTDHDLLID | LTELFSYEH, NQLTELFSY, ELFSYEHFV, ADINQLTEL, TELFSYE HF, ELFSYEHFVI, LFSYEHFVYI, INQLTELFSY, ADINQLTELF, L TELFSYEHF, TELFSYEHFY | UCEC |
| PPP2R 5C | c.776C>A | p.S259 Y | GFALPLKEEHKIFLLKVLLPLHKVK[p.S 259Y]YLSVYHPQLAYCVVQFLEKDSTLTEP | YLSVYHPQL, KYLSVYHPQ, KVKYLSVYH, LPLHKVKYL, LHKVK YLSV, HKVKYLSVY, YLSVYHPQLA, LLPLHKVKYL, KYLSVYHP QL, KVKYLSVYHP, VLLPLHKVY, LHKVKYLSVY, HKVKYLSVY H | CRC |
| PPP4R 1 | c.1791G>C | p.L597 F | DSVPLLISDAVENMDSTLHYIHSDSD[p.L 597F]FSNNSSFSPDEERRTKVQDVVPQ ALL | HYIHSDSDF, SDFSNNSSF, LHYIHSDSDF | CESC |
| PPP6C | c.901C>T | p.R301 C | LVHEGYKFMFDEKLVTVWSAPNYCY[p. R301C]CCGNIASIMVFKDVNTREPKLF RAVP | CYCCGNIASI, YCCGNIASIM | SKCM |
| PPT2 | c.794G>T | p.R265 L | WQSSFPGFYDANETVLEMEEQLVYL[p. R265L]LDSFGLKTLLARGAIVRCPMAGI SHT | VLLDSFGLK, VILLDSFGL, QLVYLLDSF, MEEQLVILL, LVYLLLD SFGL, YLLDSFGLKT, LLDSFGLKTL, EQLVLLLDSF | LUAD |
| PRAM 1 | c.802G>A | p.A268 T | QPEFSEAAQTPLWKPQSSEPKRDSS[p. A268T]TFPKKASQPPLSDFPKPPQPEL GDL | RDSSTFPKK, EPKRDSSTF, SEPKRDSSTF | UCEC |
| PRAM EF11 | c.251G>C | p.C84S | KLQVLDLQDVCENFWMVWSEAMAH G[p.C84S]SFLNAKRNKTPVQDCPRMR ERQPLTV | MAHGSFLNA, SFLNAKRNK, HGSFLNAKR, EAMAHGSFL, SE AMAHGSF, AMAHGSFLNA, MAHGSFLNAK, GSFLNAKRNK, WSEAMAHGSF, SEAMAHGSFL | SKCM |
| PRAM EF11 | c.311G>A | p.R104 Q | AMAHGCFLNAKRNKTPVQDCPRMRE[p. R104Q]QQPLTVFVELMLKNRTLDEY LTCLLL | RMREQQPLT, EQQPLTVFV, REQQPLTVF, RMREQQPLTV, C PRMREQQPL, MREQQPLTVF, REQQPLTVFV | CLL |
| PRAM EF4 | c.743G>A | p.R248 H | LTQFTPYLGHMRNLQKLILSHMDVS[p. R248H]HYVSPEQKEIVTQFTTQFLKLR CLQ | LSHMDVSHY, SHMDVSHYV, VSHYVSPEQK, ILSHMDVSHY, LSHMDVSHYV | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PRAMEF8 | c.1342A>G | p.I1448V | ALCWGRFAELGAELMKTPRDLRQPK[p.I448V]VIVFCTVPCPRCGIRASYDLEPSHCL | LRQPKVIVF, TPRDLRQPKV, DLRQPKVIVF, QPKVIVFCTV | TGCT |
| PRAMEF8 | c.956G>A | p.R319H | LEMVVMTDCLLSESDLKHLSWCPSI[p.R319H]HQLKELDLRGVTLTHFSPEPLTGLLE | SWCPSIHQL, HLSWCPSIH, SWCPSIHQLK, CPSIHQLKEL, LSWCPSIHQL | PRAD |
| PRB1 | c.820del|C | p.R274fs | KPQGPPPGKPQGPPAQGGSKSQSA[p.R274fs]DLLQESHKDHPNKKATILKVPHLQQEAIPSSLRHLLLDSPRDHHALLKGADLPDLPSDSLPSHLGFNDRK* | HPNKKATIL, VPHLQQEAI, IPSSLRHLL, SPRDHHALL, LPDLPSDSL, DSLPSHLGF, SKSQSADLL, LQQEAIPSS, QQEAIPSSL, LPSDSLPSH, LQQEAIPSSL, AIPSSLRHLL, LLKGADLPDL, SADLLQESHK, SPRDHHALLK, EAIPSSLRHL, IPSSLRHLLL, LPSDSLPSHL, KKATILKVPH, LKVPHLQQEA, SDSLPSHLGF | HNSC |
| PRDM1 | c.1763C>G | p.S588C | PYPLKKQNGKIKYECNVCAKTFGQL[p.S588C]CNLKVHLRVHSGERPFKCQTCNKGFT | KTFGQLCNL, GQLCNLKVH, KTFGQLCNLK, QLCNLKVHLR, AKTFGQLCNL, GQLCNLKVHL | MM |
| PRDM16 | c.3107C>T | p.P1036L | HLCNRCFGQQTNLDRHLKKHEHENA[p.P1036L]LVSQHPGVLTNHLGTSASSPTSESDN | ALVSQHPGV, KKHEHENAL, HEHENALVS, HENALVSQH, ALVSQHPGVL, LKKHEHENAL, KKHEHENALV | LUAD |
| PRDM16 | c.811G>C | p.E271Q | RRHKKYTCGSVGAALYEGLAEELKP[p.E271Q]QLGGGSGQAHECKDCERMPNKYSL | AEELKPQGL | BLCA |
| PRDM4 | c.2404T>A | p.*802K | DSVGTEDCRINSAVYSADESLSAHK[p.*802K]KKEKKQAILDENANGKIHITSYLL* | KIHITSYLL, SAHKKKEKK, NGKIHITSY, GKIHITSYL, ILDENANGKI, SLSAHKKKEK, AILDENANGK, ANGKIHITSY, NGKIHITSYL, GKIHITSYLL | CLL |
| PRDM7 | c.1159A>C | p.M387L | GQELGIRSSIEPAESLGQAVNCWSG[p.M387L]LGMSMARNWASSGAASGRKSSWQGEN | SGLGMSMAR, QAVNCWSGL, VNCWSGLGM, CWSGLGMSM, LGMSMARNW, GQAVNCWSGL, AVNCWSGLGM, NCWSGLGMSN | PRAD |
| PRELP | c.601G>T | p.D201Y | LRLSQNHISRIPPGFVSKLENLLL[p.D201Y]YLQHNRLSDGVFKPDTPHGLKNLMQL | KLENLLLY, LLYLQHNR, LLLYLQHNRL, LENLLLYL, KLENLLLYL, LYL, LLLYLQHNRL, SKLENLLLY, LLLYLQHNR | LUAD |
| PREP | c.1407C>A | p.F469L | SKDGTKIPMFIVHKKGIKLDGSHPA[p.F469L]LLYGYGGFNISITPNYSVSRLIFVRH | KLDGSHPAL, SHPALLYGY, ALLYGYGGF, KLDGSHPALL, LLYGYGGFNI, GSHPALLYGY, LDGSHPALLY, IKLDGSHPAL | CESC |
| PREX1 | c.2191G>A | p.V731I | AKEIIKIPDQPDTLCFQIRGAAPPY[p.V731I]YAVRGSEAMAAGLCAGQCILKVNG | AAPPYIYAV, RGAAPPYIY, GAAPPYIYAV, QIRGAAPPYI, RGAAPPYIYA, IRGAAPPYIY | CRC |
| PREX1 | c.3736G>A | p.E1246K | CLEHLFNQVDSINALLKGPVMSRAF[p.E1246K]KETKHFPMNHSLQEFKQKEECTIRGR | MSRAFKETK, FKETKHFPM, RAFKETKHF, VMSRAFKETK, KGPVMSRAFK, MSRAFKETKH, AFKETKHFPM, SRAFKETKHF | UCEC |
| PREX2 | c.1088G>A | p.R363Q | WFVCMAKTPEEKHEWFEAILKERER[p.R363Q]QKGLKLGMEQDTWVMISEQGEKLYKM | ILKERERQK, RQKGLKLGM, KERERQKGL, RERQKGLKL, AILKERERQK, KERERQKGLK | BRCA |
| PREX2 | c.1686_1687insT | p.R562fs | CDNGFMHHVLEKSEFKDEPLLRFF[p.R562fs]FG* | EPLLRFFF, DEPLLRFFF | STAD |
| PRG4 | c.2023A>C | p.N675H | PTTPEEPTPTTPEEPAPTTPKAAAP[p.N675H]HTPKEPAPTTPKEPAPTTPKEPAPTT | KAAAPHTPK, APHTPKEPA | CLL |
| PRIC285 | c.3865G>C | p.E1289Q | LFWVQIVLWRQGFYYPLGIVREVLP[p.E1289Q]QASTWEQGLRILGLEYSLRVPPSDQA | IVREVLPQA, REVLPQAST, EVLPQASTW, GIVREVLPQA, QASTWEQGLR, REVLPQASTW | BLCA |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PRKA A2 | c.1220G>A | p.R407 Q | CPLDALNTTKPKSLAVKKAKWHLGI[p.R407Q]QSQSKPYDIMAEVYRAMKQLDF EWKV | GIQSQSKPY, KAKWHLGIQS, LGIQSQSKPY, IQSQSKPYDI | CRC |
| PRKA B1 | c.311C>A | p.P104 H | PTVFRWTGGGKEVYLSGSFNNWSKL[p.P104H]HLTRSHNNFVAILDLPEGEHQY KPFV | NWSKLHLTR, HLTRSHNNF, FNNWSKLHL, SKLHLTRSH, HLT RSHNNFV, SFNNWSKLHL, NNWSKLHLTR, LHLTRSHNNF | CLL |
| PRKA R2B | c.926C>T | p.S309 L | ERLKVVDIGTKVYNDGEQIIAQGD[p.S309L]LADSFFIVESGEVKITMKRGKSE VE | DLADSFFIV, AQGDLADSF, GDLADSFFI, AQGDLADSFF, IAQ GDLADSF, GEQIIAQGDL, GDLADSFFIV | CRC |
| PRKC D | c.1294del G | p.G432fs | FLTHLICTFQTKDHLFFVMEFLNGG[p.G432fs]T* | FVMEFLNGGT | GBM |
| PRKCE | c.470_471 insG | p.Q157fs | SSGEAPKDNEERVFRERMRPKRQG[p.Q157fs]GRQAQGPSGQRPQVHGHLSS AAHLLLPLQRLHLGCHRKAGIPVSSLHL RGPQAVPRAHNHKVCWVKEAGDPRP GGLPAVQRQHAPQVRYPQLQGPYLLR SLWVPALGTLAAGFAV* | HLSSAAHLL, YLLRSLWVP, GTLAAGFAV, QVHGHLSSA, SLHL RGPQA, LLRSLWVPA, RLHLGCHRK, AVPRAHNHK, PYLLRSL WV, LWVPALGTL, RPRKRQGGR, HNHKVCWVK, VQRQHAP QV, RQHAPQVRY, RSLWVPALG, RYPQLQGPY, WVKEAGDP R, QLQGPYLLR, SAAHLLLPL, GPSGQRPQV, RPQVHGHLS, V PRAHNHKV, DPRPGGLPA, APQVRYPQL, YPQLQGPYL, VPA LGTLAA, ALGTLAAGF, RKRQGGRQA, GQRPQVHGH, HGHL SSAAH, GHLSSAAHL, LSSAAHLL, LQRLHLGCH, CHRKAGIP V, KAGIPVSSL, LHLRGPQAV, RAHNHKVCW, PQLQGPYLL, G PYLLRSLW, LRSLWVPAL, HLSSAAHLLL, LLLPLQRLHL, SLHL RGPQAV, YLLRSLWVPA, LLRSLWVPAL, SLWVPALGTL, ALG TLAAGFA, AAHLLLPLQR, RYPQLQGPYL, RMRPRKRQGG, L QRLHLGCHR, RLHLGCHRKA, SSLHLRGPQA, HLRGPQAVPR, QAVPRAHNHK, RAHNHKVCWV, VQRQHAPQVR, VRYPQL QGPY, SSAAHLLLPL, RPQVHGHLSS, VPRAHNHKVC, DPRPG GLPAV, YPQLQGPYLL, GPYLLRSLWV, HLGCHRKAGI, GQRP QVHGHL, HGHLSSAAHL, GHLSSAAHLL, RKAGIPVSSL, AGIP VSSLHL, RQHAPQVRYP, LQGPYLLRSL, VPALGTLAAG | KIRC |
| PRKC G | c.1033C>T | p.R345 C | SSSPIPSPSPSPTDPKRCFFGASPG[p.R345C]CLHISDFSFLMVLGKGSFGKVMLA ER | CLHISDFSF, CLHISDFSFL, SPGCLHISDF, GCLHISDFSF | STAD |
| PRKCI | c.1438C>T | p.R480 C | IVGSSDNPDQNTEDYLFQVILEKQI[p.R480C]CIPRSLSVKAASVLKSFLNKDPKER L | KQICIPRSL, CIPRSLSVK, KQICIPRSLS, LEKQICIPRS | CRC |
| PRKC Q | c.971C>T | p.A324 V | GMNVHHRCQTKVANLCGINQKLMAE[p.A324V]VLAMIESTQQARCLRDTEQIF REGPV | KLMAEVLAM, LMAEVLAMI, NQKLMAEVL, AEVLAMIES, GI NQKLMAEV, KLMAEVLAMI, QKLMAEVLAM, AEVLAMIEST | UCEC |
| PRKD C | c.10702C>G | p.Q356 8E | DTSTGHKNKEFVARIKSKLDQGGVI[p.Q3568E]EDFINALDQLSNPELLFKDWSN DVRA | GVIEDFINA, GVIEDFINAL | CESC |
| PRKR A | c.366G>T | p.K122 N | NILKANASICFAVPDPLMPDPSKQP[p.K122N]NNQLNPIGSLQELAIHHGWRLPE YTL | QPNNQLNPI, KQPNNQLNPI | CRC |
| PRMT 8 | c.84del C | p.S28fs | SSRCLLLRRKMAENAAESTEVNSPP[p.S28fs]PSPSPSSLLSPCNASIMCPLNPAA QDGARCPSC* | LLSPCNASI, SIMCPLNPA, IMCPLNPAA, SPPSPSSLL, LSPCN ASIM, SLLSPCNASI, SIMCPLNPAA, LLSPCNLNPAA SSL | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PRMT8 | c.91T>C | p.S31P | SSRCLLLRRKMAENAAESTEVNSPP[p.S31P]PQPPQPVVPAKPVQCVHHVSTQPSCP | SPPPQPPQPV | BLCA |
| PRODH | c.1579C>G | p.L527V | TVRFALRRMEELGLHPADHRVYFGQ[p.L527V]VLGMCDQISFPLGQAGYPVYKVPYG | VYFGQVLGM,RVYFGQVLG,HRVYFGQVL,RVYFGQVLGM,VLGMCDQISF,QGVLGMCDQI | TGCT |
| PROKR2 | c.889G>A | p.V297I | KTVLVLMCILTAYVLCWAPFYGFTI[p.V297I]IRDFFPTVFVKEKHYLTAFVVVECIA | IIRDFFPTV,GFTIIRDFF,TIIRDFFPT,APPYGFTII,YGFTIIRDF,I RDFFPTVF,TIIRDFFPTV,FYGFTIIRDF,YGFTIIRDFF,APFYGF TIIR,FTIIRDFFPT,IIRDFFPTVF | GBM |
| PROX1 | c.1774del|T | p.F592fs | SPYSGSAMQEGLSPNHLKKAKLMFF[p.F592fs]IPVIPAPIC* | KLMFFIPVI,FIPVIPAPI,KAKLMFFIP,MFFIPVIPA,KKAKLMF FI,AKLMFFIPV,LMFFIPVIPA,FFIPVIPAPI,KAKLMFFIPV,AK LMFFIPVI | STAD |
| PROX1 | c.674T>A | p.V225D | PRESTRENKRKQKLPQQQQQSFQQL[p.V225D]DSARKEQKREERRQLKQQLEDMQKQL | SFQQLDSAR,QSFQQLDSAR | KIRC |
| PRPF31 | c.865C>T | p.R289W | STSVLPHTGYIYHSDIVQSLPPDLR[p.R289W]WKAARLVAAKCTLAARVDSFHESTEG | RWKAARLVA,DLRWKAARL,WKAARLVAA,LRWKAARLV,L PPDLRWKA,SLPPDLRWKA,QSLPPDLRWK,RWKAARLVAA, DLRWKAARLV,VQSLPPDLRW,LRWKAARLVA,LPPDLRW KAA | TGCT |
| PRPF6 | c.2288G>T | p.R763L | KCPHSTPLWLLLSRLEEKIGQLTRA[p.R763L]LAILEKSRLKNPKNPGLWLESVRLEY | QLTRALAIL,KIGQLTRAL,GQLTRALAI,ALAILEKSRL,LTRALA ILEK,KIGQLTRALA,RALAILEKSR,EKIGQLTRAL,GQLTRALAI L | LUAD |
| PRRC2C | c.5647C>A | p.P1883T | SASIPILASALASTSAPTPAPAASS[p.P1883T]TAAPVITAPTIPASAPTASVPLAPAS | AASSTAAPV,STAAPVITA,TPAPAAST,TPAPAASSTA,ASST AAPVI,TAAPVITAPT,TPAPAASSTA,APAASSTAAP,AASSTA APVI | KIRC |
| PRRX1 | c.587C>T | p.A196V | DVTAVEQPIVPRPAPRPTDYLSWGT[p.A196V]VSPYSAMATYSATCANNSPAQGINMA | LSWGTVSPY,YLSWGTVSP,TVSPYSAMA,GTVSPYSAM,TD YLSWGTV,PTDYLSWGTV,YLSWGTVSPY,VSPYSAMATY,W GTVSPYSAM | BRCA |
| PRSS1 | c.319G>A | p.D107N | EGNEQFINAAKIIRHPOYDRKTLNN[p.D107N]NIMLIKLSSRAVINARVSTISLPTAP | TLNNNIMLI,KTLNNNIML,RKTLNNNIM,KTLNNNIMLI,TLN NNIMLIK,NIMLIKLSSR,RKTLNNNIML | HNSC |
| PRSS36 | c.2038del|C | p.L680fs | LPQGHQVSRLVLISIRLPQHLGLRPP[p.L680fs]WPSWS* | GLRPPWPSW,QHLGLRPPW,PQHLGLRPPW,LGLRPPWPS W | STAD |
| PRSS57 | c.115G>C | p.E39Q | TVATAMLPVKPPAGSWGAQIIGGH[p.E39Q]QVTPHSRPYMASVRPGGQHHCGGFLL | AQIIGGHQV,QVTPHSRPY,HQVTPHSRPY,AQIIGGHQVT | LUSC |
| PSD2 | c.766del|G | p.G256fs | NVLSRLSLMAMPNGFHEDGPQGPGG[p.G256fs]MRMMMRTRTSC* | GGMRMMMRR,GMRMMMRRT,RMMMRTRT,MMMR RTRTS,MMRRTRTSC,GPGGMRMMM,PQGPGGMRM,M MMRTRTSC,GMRMMMRRTR,RMMMRTRTS,GPQGP GGMRM,PQGPGGMRMM | STAD |
| PSD3 | c.1687A>C | p.T563P | PEIAFWGSNAGVKTTRLEAHSEMGS[p.T563P]PEILEKETPENLSNGTSSNVEAAKRL | MGSPEILEK,SEMGSPEIL,EMGSPEILEK,AHSEMGSPEI | KIRC |
| PSG8 | c.1189C>T | p.R397C | FQLSGQKLFIPQITTKHSGLYACSV[p.R397C]CNSATGKESSKSMTVKVSGKRIPVSL | SVCNSATGK,GLYACSVCNS,CSVCNSATGK | CRC |
| PSG8 | c.958C>T | p.R320C | LILPSVTRNETGPYQCEIRDQYGGI[p.R320C]CSYPVTLNVLYGPDLPRIYPSFTYR | DQYGGICSY,CSYPVTLNV,QYGGICSYPV,RDQYGGICSY,GG ICSYPVTL,CSYPVTLNVL | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PSG9 | c.1210G>A | p.E404K | LFIPQITRNHSGLYACSVHNSATGK[p.E404K]KISKSMTVKVSGPCHGDLTESQS* | KISKSMTVK,SATGKKISK,KKISKSMTV,KISKSMTVKV,SVHN SATGKK | SKCM |
| PSMD11 | c.14C>T | p.A5V | MAAA[p.A5V]VVEFQRAQSLLSTDRE ASIDILHSI | MAAAVVEF,AAAVVEFQR | TGCT |
| PSMD12 | c.602G>A | p.R201Q | SMEKKERVEFIIEQMRLCLAVKDYI[p.R201Q]QTQIISKKINTKFQEENTEKLKLK Y | YIQTQISK,IQTQIISKK,KDYIQTQII,AVKDYIQTQI,YIQTQIIS KK,IQTQISKKI | CRC |
| PSME3 | c.691C>T | p.R231W | IAKYPHVEDYRRTVTEIDEKEYISL[p.R231W]WLIISELRNQYVTLHDMILKNIEKIK | SLWLIISEL,KEYISLWLI,EYISLWLII,DEKEYISLW,SLWLIISEL R,KEYISLWLII,ISLWLIISEL,DEKEYISLWL | CESC |
| PSME4 | c.1483A>G | p.N495D | GGRWFPEGPTHMLPLMRALPGPD[p.N495D]DDFSKCMITFQFIATFSTIVPL VDCS | GVDPDDFSK,LPGVDPDDF,DDFSKCMTF,DPDDFSKCMI | TGCT |
| PSPH | c.433G>A | p.V145I | IRELVSRLQERNVQVFLISGGFRSI[p.V145I]IEHVASKLNIPATNVFANRLKFYFN G | SIIEHVASK,ISGGFRSII,SIEHVASKL,LISGGFRSII,RSIIEHVA SK,GFRSIIEHVA,IEHVASKLNI | GBM |
| PTCH1 | c.2066C>A | p.P689H | LRTEYDPHTHVYYTAEPRSEISVQ[p.P689H]HVTVTQDTLSCQSPESTSSTRDLLS Q | EISVQHVTV,SEISVQHVT,SEISVQHVTV,VQHVTVTQDT | KIRC |
| PTCH1 | c.3921del|C | p.P1307fs | RQQPHLDSGSLLPPGRGQQPRRDPP[p.P1307fs]EKACGHPPTDRAETLLKFLL KGILALAIGPAGALAGPVLTTLGTQRPLP WAAPCPATASPSPL* | FLLKGILAL,LLKGILALA,ILALAIGPA,ALAIGPAGA,LLKFLLKG I,AIGPAGALA,ALAGPVLTT,ETLLKFLLK,KFLLKGILA,TQRPL PWAA,WAAPCPATA,LAIGPAGAL,RPLPWAAPC,LPWAAP CPA,LKFLLKGIL,LKGILALAI,AGALAGPVL,LAGPVLTTL,LGT QRPLPW,AETLLKFLL,ILLKFLLKGI,FLLKGILALA,LLKGILALA I,ALAIGPAGAL,ALAGPVLTTL,KFLLKGILAL,HPPTDRAETL, GPAGALAGPV,CPATASPSPL,LLKFLLKGIL,TDRAETLLKF,LK FLLKGILA,TQRPLPWAAP,LPWAAPCPAT | STAD |
| PTCHD3 | c.1764del|T | p.F588fs | KKFCCFPFGSVPDEHGTDIHPISLF[p.F588fs]LETILAPFSQGVSPSIL* | SLFLETIIA,FLETILAPF,ILAPFSQGV,DIHPISLFL,ISLFLETIL,F SQGVSPSI,SQGVSPSIL,HPISLFLET,LETILAPFS,TILAPFSQG V,LFLETILAPF,HPISLFLETI,FSQGVSPSIL | STAD |
| PTEN | c.388C>G | p.R130G | CEDLDQWLSEDDNHVAAIHCKAGKG[p.R130G]GTGVMICAYLLHRGKFLKAQE ALDFY | GTGVMICAY,GGTGVMICAY,KAGKGGTGVM | UCEC |
| PTEN | c.389G>A | p.R130Q | CEDLDQWLSEDDNHVAAIHCKAGKG[p.R130Q]QTGVMICAYLLHRGKFLKAQE ALDFY | QTGVMICAY,GKGQTGVMI,GQTGVMICAY,KAGKGQTGV M | CESC,CRC,UCEC |
| PTEN | c.389G>C | p.R130P | CEDLDQWLSEDDNHVAAIHCKAGKG[p.R130P]PTGVMICAYLLHRGKFLKAQEA LDFY | PTGVMICAY,GKGPTGVMI,GPTGVMICAY,KAGKGPTGVM | UCEC |
| PTEN | c.389G>T | p.R130L | CEDLDQWLSEDDNHVAAIHCKAGKG[p.R130L]LTGVMICAYLLHRGKFLKAQEA LDFY | LTGVMICAY,GLTGVMICA,KAGKGLTGV,GKGLTGVMI,GL TGVMICAY,KAGKGLTGVM | UCEC |
| PTEN | c.407G>A | p.C136Y | WLSEDDNHVAAIHCKAGKGRTGVMI[p.C136Y]YAYLLHRGKFLKAQEALDFYGE VRTR | GVMIYAYLL,VMIYAYLLH,RTGVMIYAY,KGRTGVMIY,VMI YAYLLHR,GVMIYAYLLH,KGRTGVMIYA,RTGVMIYAYL,GK GRTGVMIY,GRTGVMIYAY | GBM |
| PTEN | c.509G>A | p.S170N | FLKAQEALDFYGEVRTRDKKGVTIP[p.S170N]NQRRYVYYSYLLKNHLDYRPVA LLF | VTIPNQRRY,NQRRYVYY,IPNQRRYVY,GVTIPNQRRY,TIP NQRRYVY,VTIPNQRRYV,IPNQRRYVY | GBM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PTEN | c.518G>A | p.R173H | AQEALDFYGEVRTRDKKGVTIPSQR[p.R173H]HVYYYYSYLLKNHLDYRPVALLFHKM | TIPSQRHYV,HVYYYYSYL,SQRHYVYYY,RHVYYYSY,VTIPS QRHY,IPSQRHYVY,PSQRHYVY,PSQRHYVYY,VTIPSQRH YV,RHVYYYSYL,SQRHYVYYS,GVTIPSQRH Y,TIPSQRHYV,QRHYVYYSY,IPSQRHYVY | GBM |
| PTEN | c.701G>T | p.R234L | GTCNPQFVVCQLKVKIYSSNSGPTR[p.R234L]LEDKFMYFEFPQPLPVCGDIKVEF FH | RLEDKFMYF,YSSNSGPTRL,TRLEDKFMYF,LEDKFMYFEF | LUAD |
| PTEN | c.795de1A | p.L265fs | EFPQPLPVCGDIKVEFFHKQNKMLK[p.L265fs]RTKCFTFG* | KMLKRTKCF,MLKRTKCFT,LKRTKCFTF,MLKRTKCFTF,KQN KMLKRTK,KMLKRTKCFT,NKMLKRTKCF | STAD |
| PTEN | c.830C>T | p.T277I | DIKVEFFHKQNKMLKKDKMFHFWVN[p.T277I]IFFIPGPEETSEKVENGSLCDQE IDS | KMFHFWVNI,MFHFWVNIF,FHFWVNIFF,HFWVNIFFI,K MFHFWVNIF,MFHFWVNIFF,FHFWVNIFFI | GBM |
| PTGR1 | c.119A>C | p.E40A | GYPTNSDFELKTAELPPLKNGEVLL[p.E40A]AALFLTVDPYMRVAAKRLKEGDTM MG | VLLAALFLT,LLAALFLTV,EVLLAALFL,GEVLLAALF,VLLAALF LTV,AALFLTVDPY,LKNGEVLLAA,GEVLLAALFL | TGCT |
| PTH2 | c.64C>G | p.L22V | METRQVSRSPRVRLLLLLLLL[p.L22V]VVPWGVRTASGVALPPVGVLSLRPP | LLLLLLVVV,LLLVVPWGV,LVVVPWGVR,LLLLVVVPW,RLLL LLLLLV,LLLLLLLVVV,LLLLVVPWGV,LLLVVPWGVR,LLLLLV VVPW | PRAD |
| PTPDC1 | c.1288C>T | p.R430W | AVAADFDNRGMIFSNEQQFDPLWKR[p.R430W]MNVECLQPLTHLKRRLSYSD SDLKRA | WKRWNVECL,WNVECLQPL,LWKRWNVECL,RWNVECLQ PL,QQFDPLWKRM | CRC |
| PTPN1 | c.1508G>T | p.G503V | IIREKGVDCDIDVPKTIQMVRSQRS[p.G503V]VMVQTEAQYRFIYMAVQHYIETL QRR | QMVRSQRSV,MVRSQRSVM,RSVMVQTEA,VMVQTEAQY, SQRSVMVQT,IQMVRSQRSV,SVMVQTEAQY,MVRSQRS VMV,QMVRSQRSVM | LUAD |
| PTPN1 | c.226G>A | p.E76K | VTHIKIQNTGDYDYDLYGGEKPATLA[p.E76K]KLVQYYMEHHGQLKEKNGDVIEL KYP | KLVQYYMEH,ATLAKLVQY,LAKLVQYYM,TLAKLVQYY,EKF ATLAKL,TLAKLVQYYM,ATLAKLVQY,FATLAKLVQY,GEKF ATLAKL,KLVQYYMEHH | MM |
| PTPN2 | c.2294G>A | p.R765Q | PPTFSDKREQISENPTEATDIGFGN[p.R765Q]QCGKPKGPRDPPSEWT* | IGFGNQCGK | CRC |
| PTPN3 | c.2660C>T | p.S887L | SYQHKFQLQMRARQSNQDAQDIERA[p.S887L]LFRSLNLQAESVRGFNMGRAI STGSL | RALFRSLNL,LFRSLNLQA,AQDIERALF,IERALFRSL,ALFRSL NLQA | CRC |
| PTPN13 | c.6199G>A | p.E2067K | YIQEDDIYDDSQEAEVIQSLLDVVD[p.E2067K]KEAQNLLNENNAAGYSCCPGT LKMNG | QSLLDVVDK,SLLDVVDKEA | LUAD |
| PTPN14 | c.2147_2149delAGG | p.E716del | QYHHKKTFSDATMLIHSSESEEEEE[p.E716del]APESVPQIPMLREKMEYSAQL QAALARI | SESEEEEEA | GBM |
| PTPN4 | c.856G>A | p.E286K | THNKSTILVELINKEETALFHTDDI[p.E286K]KNAKYISRLFATRHKFYKQNKICTEQ | ALFHTDDIK,HTDDIKNAK,KNAKYISRL,HTDDIKNAKY,TALF HTDDIK,DIKNAKYISR,IKNAKYISRL,KNAKYISRLF | MM |
| PTPN18 | c.1113_1118de1GACGG | p.TG378del | TYAVVQKRGAPAGAGSGTQTGTGT[p.TG378de1]ARSAEEAPLYSKVTPRAQ RPGAHAEDARGTL | QTGTGTGAR | UCS |
| PTPN4 | c.957de1T | p.N319fs | NLWKACVEHHTFFRLLDRPLPPQKNF[p.N319fs]LHIILH* | QKNFLHIIL,RPLPPQKNFL,LPPQKNFLHI | STAD |
| PTPRB | c.2178A>T | p.Q726H | SLTPGRLYTVTITTRSGKYENHSFS[p.Q726H]ERTVPDKVQGVSVSNSARSDYL RVS | HSFSHERTV,ENHSFSHER,FSHERTVPDK,GKYENHSFSH | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| PTPRB | c.4678G>A | p.D156 0N | ENPNSNSKSFNIKLGAEMESLGGKC[p. D1560N]NPTQQKFCDGPLKPHTAYRIS IRAFT | KCNPTQQKF, GGKCNPTQQK, GKCNPTQQKF | SKCM |
| PTPRC | c.2685A>C | p.Q895 H | GLEAENKVDVYGYVVKLRRQRCLMV[p. Q895H]HVEAQYILIHQALVEYNQFGET EVNL | RQRCLMVHV, LMVHVEAQY, MVHVEAQYI, VHVEAQYIL, L MVHVEAQY, RQRCLMVHE, CLMVHVEAQY, MVHVEAQ YIL | STAD |
| PTPRF | c.3521G>A | p.R117 4Q | PRWSTPEELELDELLEAIEQGEEQ[p.R 1174Q]QRRRRQAERLKPYVAAQLDVL PETFT | EQQRRRQA, QQRRRRQAER | PRAD |
| PTPRJ | c.1000G>T | p.G334 W | HDESLVGPVDPSSGQQSRDTEVLLV[p. G334W]WLEPGTRYNATVYSQAANGT EGQPQA | LVWLEPGT, RDTEVLLVW, VWLEPGTRY, VLLVWLEPGT, WLEPGTRYNA, LVWLEPGTRY, RDTEVLLVWL | LUAD |
| PTPRT | c.2783G>T | p.R928 L | SWDTAKEDENRNKNRYGNIISYDHS[p. R928L]LVRLLVLDGDPHSDYINANYIDG YHR | IISYDHSLV, NIISYDHSL, ISYDHSLVR, SYDHSLVRLL, HSLVRLL VL, YDHSLVRLL, NIISYDHSLV, IISYDHSLVR, SYDHSLVRLL, IS YDHSLVRL, YDHSLVRLLV | LUAD |
| PTPRT | c.3224de|C | p.P107 5fs | WPDHGVPCYATGLLGFVRQVKFLNP[p. P1075fs]RKLGP* | RQVKFLNPR, QVKFLNPRK, VKFLNPRKL, RQVKFLNPRK | STAD |
| PTPR U | c.1675C>T | p.P559 S | VNVPGPRRTISKLRNETYHVFSNLH[p. P559S]SGTTYLFSVRARTGKFGQAALT EIT | NLHSGTTYL, LHSGTTYLF, SNLHSGTTY, FSNLHSGTTY, NLHS GTTYLF, SGTTYLFSVR, HVFSNLHSGT, HSGTTYLFSV, SNLHS GTTYL | LUAD |
| PTPR U | c.4300G>A | p.D143 4N | FFAAKTLRNYKPNMVETMDQYHFCY[p. D1434N]NVALEYLEGLESR* | CYNVALEYL, FCYNVALEY, DQYHFCYNV, YHFCYNVAL, QYH FCYNVAL, HFCYNVALEY, NVALEYLEGL, DQYHFCYNVA, MD QYHFCYNV | CRC |
| PUF60 | c.1187C>T | p.S396 L | VMAAQAPGVITGVTPARPPIPVTIP[p.S 396L]LVGVVNPILASPPTLGLLEPKKEKE E | VTIPLVGV, PLVGVVNPI, PPIPVTIPL, RPPIPVTIPL, IPLVGV VNPI, PPIPVTIPLV, IPVTIPLVGV | BLCA |
| PVRL4 | c.1072G>A | p.A358 T | LDPQEDSGKQVDLVSASVVVGVIA[p. A358T]TLLFCLLVVVVVMSRYHRRKA QQMT | VIATLLFCL, ATLLFCLLV, TLLFCLLVV, VVVGVIATL, VGVIATL LF, GVIATLLFCL, VIATLLFCLL, ATLLFCLLVV, TLLFCLLVVV, V VVGVIATLL, VVGVIATLLF | UCEC |
| PWW P2B | c.251de|C | p.S84fs | PVNDSHGRAPEEGDAEVMQLGSSSP[p. S84fs]LLPAGFSPPRPPAPSHPRPSCRR CPPEACPRTLPTSKAPPSLTRCGSGTRTS CGCPSRRPGPSSARGGVCPATATRGAS SSAPSACGRARCSVRSARAR* | MQLGSSSPL, QLGSSSPLL, RTSCGCPSR, GVCPATATR, SSAP SACGR, GFSPPRPPA, LTRCGSGTR, SARGGVCPA, ATRGASS SA, CGRARCSVR, RARCSVRSA, TSCGCPSRR, APSHPRPSC, H PRPSCRRC, RPSCRRCPP, GPSSARGGV, CPATATRGA, LPAG FSPPR, VMQLGSSSPL, MQLGSSSPLL, TSKAPPSLTR, RTSCG CPSRR, SSSAPSACGR, AGFSPPRPPA, RTLPTSKAPP, GTRTS CGCPS, PSRRPGPSSA, RGASSSAPSA, RARCSVRSAR, SSSPLL PAGF, LLPAGFSPPR, RPSCRRCPPE, CPRTLPTSKA, LPTSKAP PSL, CPATATRGAS | STAD |
| PXDN L | c.3935C>T | p.T131 2M | IPKVDLRVWQDCCADCRSRGQFRAV[p. T1312M]MQESQKKRSAQYSYPVDKD MELSHLR | RAVMQESQK, AVMQESQKK, SRGQFRAVM, RSRGQFRAV M, RAVMQESQKK, GQFRAVMQES | CRC |
| PXDN L | c.4366C>A | p.P145 6T | CPPAPCPSPELVKGTCCPVCRDRGM[p. P1456T]TSDSPEK* | GMTSDSPEK, MTSDSPEKR, RGMTSDSPEK | LUAD |
| PYGO 2 | c.448de|C | p.Q150 fs | GPQPLRRQPPPFPPNPMGPAFNMPP[p. Q150fs]RVLATHPQAT* | NMPPRVLAT, VLATHPQAT, RVLATHPQA, MPPRVLATH, AF NMPPRVLA, RVLATHPQAT, MGPAFNMPPR, GPAFNMPPR V | STAD |
| PYHIN 1 | c.443G>C | p.G148 A | NRLTAKGAEETLGPQKRKKPSEEET[p. G148A]ATKRSKMSKEQTRPSCSAGASTS TAM | ATKRSKMSK, TATKRSKMSK | LUSC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| QRSL1 | c.677C>T | p.S226L | AHCGLVGFKPSYGLVSRHGLIPLVN[p.S226L]LMDVPGILTRCVDDAAIVLGALAGPD | GLIPLVNLM,NLMDVPGIL,IPLVNLMDV,NLMDVPGILT,LV NLMDVPGI | CRC |
| QSOX1 | c.1202G>T | p.R401L | DDRKEGAVLAKKVNWIGCQGSEPHF[p.R401L]LGFPCSLWVLFHFLTVQAARQ NVDHS | HFLGFPCSL,CQGSEPHFL,GSEPHFLGF,EPHFLGPC,FLGFP CSLWV,HFLGFPCSLW,QGSEPHFLGF,LGFPCSLWVL,SEPH FLGFPC | LUAD |
| QSOX2 | c.2048G>T | p.R683L | SLDMSLCVVLTVASSLFLMVMYFFF[p.R683L]LVRSRRWKVKHHHPAV* | LMVMYFFFL,MVMYFFLV,VMYFFFLVR,FLVRSRRWK,FFL VRSRRW,LVRSRRWKV,YFFFLVRSR,FFFLVRSRR,FLMVMY FFFL,LMVMYFFFLV,FLVRSRRWKV,MVMYFFFLVR,FFFLV RSRRW,MYFFFLVRS,FFLVRSRRWK,LVRSRRWKVK,YFFF LVRSRR | LUAD |
| R3HDM2 | c.1763G>A | p.S588N | MPNQQQAAYQGMIGVQQPQNQCLL S[p.S588N]NQRSSMGGQMGQLVVQY TPLPSYQVP | LLSNQRSSM,NQRSSMGGQM,GLLSNQRSSM | CLL |
| R3HDM2 | c.1774A>G | p.S592G | QQAAYQGMIGVQQPQNQGLLSSQRS[p.S592G]GMGGQMQGLVVQYTPLPSY QVPVGSD | GMGGQMQGL,LLSSQRSGM,QRSGMGGQM,GMGGQM QGLV,SQRSGMGGQM,GLLSSQRSGM | CLL |
| R3HDM2 | c.616C>T | p.R206W | EFINDNNQFKKFPQQMTSYHRMLLH[p.R206W]WVAAYFGMDHNVDQTGKA VIINKTSN | RMLLHWVAA,MLLHWVAAY,SYHRMLLHW,HWVAAYFG M,LLHWVAAYF,HRMLLHWVA,MLLHWVAAYF,RMLLHW VAAY,SYHRMLLHWV,YHRMLLHWVA,TSYHRMLLHW,HR MLLHWVAA,LHWVAAYFGM | CLL |
| RAB11 FIP4 | c.1787C>T | p.S596L | SLYEAKNLFAAQTKAQSLAAEIDTA[p.S596L]LRDELMEALKEQEEINFRLRQYM DKI | ALRDELMEA,LAAEIDTAL,SLAAEIDTAL,ALRDELMEAL,LAA EIDTALR | BLCA |
| RAB11 FIP5 | c.509G>A | p.R170H | WYKLHSKPGKKEKERGEIEVTIQFT[p.R170H]HNNLSASMFDLSMDKPRSPFS KIRD | IEVTIQFTH,IQFTHNNLS,THNNLSASM,HNNLSASMF,IQFT HNNLSA,FTHNNLSASM,VTIQFTHNNL,THNNLSASMF | GBM |
| RAB13 | c.500G>T | p.R167L | EHGIRFPETSAKSSMNVDEAFSSLA[p.R167L]LDILLKSGGRRSGNGNKPPSTDLK TC | SLALDILLK,DEAFSSLAL,FSSLALDIL,SSLALDILLK,EAFSSLAL DI,VDEAFSSLAL | LUAD |
| RAB7L1 | c.235C>T | p.R79W | YEIVRLQLWDIAGQERFTSMTRLYY[p.R79W]WDASACVIMFDVTNATTFSNSQ RWKQ | RLYYWDASA,TSMTRLYYW,YYWDASACV,MTRLYYWDA, WDASACVIM,SMTRLYYWDA,RLYYWDASAC,FTSMTRLYY W,LYYWDASACV,YYWDASACVI,MTRLYYWDAS,YWDAS ACVIM,WDASACVIMF | CRC |
| RAB8A | c.58G>T | p.G20W | MAKTYDYLFKLLLIGDSGV[p.G20W]W KTCVLFRFSEDAFNSTFISTIGIDF | LLIGDSGVWK,GVWKTCVLF,VWKTCVLFR,LLIGDSGVW,W KTCVLFRF,GVWKTCVLFR,SGVWKTCVLF,VWKTCVLFRF,L LLIGDSGVW | LUAD |
| RABGAP1 | c.2782_2783insA | p.K928fs | LEEESAQLKEMCRRELDKAESEIKK[p.K928fs]KQFYHW* | SEIKKKQFY,IKKKQFYHW,AESEIKKQF | STAD |
| RABGAP1 | c.2782delA | p.K928fs | LEEESAQLKEMCRRELDKAESEIKK[p.K928fs]TVLSLVTISRFVLS* | SLVTISRFV,KTVLSLVTI,VLSLVTISR,EIKKTVLSL,LSLVTISRF, KKTVLSLVT,AESEIKKTV,SLVTISRFVL,TVLSLVTISR,EIKKTV LSLV,VLSLVTISRF,AESEIKKTVL,SEIKKTVLSL,KKTVLSLVTI RLQSDIQYI,LQSDIQYIT,SDIQYITRF,QSDIQYITRF | STAD |
| RABGEF1 | c.619A>G | p.N207D | PASADDFLPTLIYIVLKGNPPRLQS[p.N207D]IQYITRFCNPSRLMTGEDGYYFT NL | RTVFDNYSA,YIRTVFDNY,NAFPGEYIR,FPGEYIRTV,FPGEYI RTVF | TGCT |
| RAC1 | c.101C>G | p.P34R | VGDGAVGKTCLLISYTTNAFPGEYI[p.P34R]RTVFDNYSANVMDGKPVNLGLM DTA | | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| RAC1 | c.476C>T | p.A159V | LTPITYPQGLAMAKEIGAVKYLECS[p.A159V]VLTQRGLKTVFDEAIRAVLCPPPVKK | AVKYLECSV, SVLTQRGLK, KYLECSVLT, VKYLECSVL, VLTQRGLKTV, CSVLTQRGLK, AVKYLECSVL | HNSC |
| RAC1 | c.85C>T | p.P29S | IKCVVVGDGAVGKTCLLISYTTNAF[p.P29S]SGEYIPTVFDNYSANVMDGKPVNLG | TTNAFSGEY, FSGEYIPTV, SGEYIPTVF, YTTNAFSGEY, TTNAFSGEYI, FSGEYIPTVF | SKCM |
| RAD50 | c.205G>T | p.D69Y | TIIECLKYICTGDFPPGTKGNTFVH[p.D69Y]YPKVAQETDVRAQIRLQFRDVNGELIRDFTNIYWSQNRPDVKKQLQNDKK[p.T316fs]L* | GNTFVHYPK, NTFVHYPKV, TFVHYPKVA, KGNTFVHYPK, G TKGNTFVHY, NTFVHYPKVA, YPKVAQETDV KQKLQNDKKL | LUAD |
| RAD51AP2 | c.946del|A | p.T316fs | RDFTNIYWSQNRPDVKKQLQNDKK[p.T316fs]L* | | STAD |
| RAD51C | c.499G>A | p.D167N | VQIPECFGGVAGEAAVFIDTEGSFMV[p.D167N]NRVVDLATACIQHLQLIAEKHKGEEH | FMVNRVVDL, MVNRVVDLA, EGSFMVNRV, FMVNRVVDL A, SFMVNRVVDL, DTEGSFMVNR, TEGSFMVNRV | BLCA |
| RAD51C | c.670T>C | p.Y224H | FTLDNILSHIYYFRCRDYTELLAQV[p.Y224H]HLLPDFLSEHSKVRLVIVDGIAFPFR | ELLAQVHLL, AQVHLLPDF, TELLAQVHL, AQVHLLPDFL, LAQ VHLLPDF, HLLPDFLSEH, TELLAQVHLL | BLCA |
| RAF1 | c.770C>T | p.S257L | YSTPHAFTENTSSPSSEGSLSQRQR[p.S257L]LTSTPNVHMVSTTLPVDSRMIEDAIR | RQRLTSTPN, LTSTPNVHM, SQRQRLTST, RLTSTPNVH, LIST PNVHM, RQRLTSTPNV, RLTSTPNVHM, SQRQRLTSTP | CRC |
| RALGAPA1 | c.1192C>T | p.R398C | LTEREPSSSSLCSIDEEHLTDIEIV[p.R398C]CRVFSSKRSNVNFVTEIFRQAFLLPI | IVCRVFSSK, LTDIEIVCRV, EIVCRVFSSK, IVCRVFSSKR, HLTDI EIVCR, TDIEIVCRVF, IEIVCRVFSS | CRC |
| RALGAPB | c.1136del|C | p.T379fs | RSDSAPPTPVNRLSMPQSAAVSTTP[p.T379fs]HITGGTGLL* | TTPHITGGT, SAAVSTTPH, AAVSTTPHI, TPHITGGTGL, SAAV STTPHI | STAD |
| RALGPS1 | c.1142G>A | p.R381Q | SKSATFPSEKARHLLDDSVLESRSP[p.R381Q]QRGLALTSSSAVTNGLSLGSSESSEF | RSPQRGLAL, SVLESRSPQR, LESRSPQRGL, SRSPQRGLAL | BLCA |
| RANBP17 | c.2700G>T | p.M900I | HSDLLQYRKLSQSYYPLLECLTQDH[p.M900I]SFIINLEPPVLMVLTSISEGLITTL | LTQDHISFI, CLTQDHISF, TQDHISFII, CLTQDHISFI, LLECLTQ DHI, LTQDHISFII, QDFIISFIINL | TGCT |
| RANBP2 | c.3691C>T | p.R1231C | VESKEWKERGIGNVKILRHKTSGKI[p.R1231C]CLLMRREQVLKICANHYISPDMKLTP | KTSGKICLL, CLMRREQV, SGKICLLMR, HKTSGKICL, TSGKIC LLMR, KTSGKICLLM, SGKICLLMR, CLLMRREQVL, RHKTSG KICL, HKTSGKICLL | CRC |
| RANBP3 | c.1157T>G | p.L386W | EATPEKESLAESAAAYTKATARKCL[p.L386W]WEKVEVITGEEAESNVLQMQCKLFVF | CLWEKVEVI, TARKCLWEK, KATARKCLW, ATARKCLWEK | KIRC |
| RANBP6 | c.2743C>T | p.R915W | QWGLCIFDDIIEHCSPTSFKYVEYF[p.R915W]WPMLLNMRDNNPEVRQAAAYGLGVM | YVEYFWPM, SPKYVEYFW, KVVEYFWPM, EYFWWPMLL, FWWPMLLNM, FKYVEYFWW, VEYFWWPML, YVEYFWW PML, SPKYVEYFWW, KVVEYFWPM, VEYFWWPMLL, YF WWPMLLNM, FWWPMLLNMR, TSFKYVEYFW | CESC |
| RANBP6 | c.2950A>C | p.I984L | LVKVIKCANSKTKNVIATENCISA[p.I984L]LGKILKFKPNCVNVDEVLPHWLSWLP | ISALGKILK, ALGKILKFK, SALGKILKF, TENCISALG, CISALGKIL K, SALGKILKFK, IATENCISAL, ISALGKILKF | LUSC |
| RAPGEFL1 | c.1067G>T | p.R356L | LPGKFKNLFRKFPENLTDPCRNHKSY[p.R356L]LEVISKMKPPVIPFVPLLIKDLTFLHP | KSYLEVISK, SYLEVISKM, RNHKSYLEV, KSYLEVISKM, SYLEVI SKMK, RNHKSYLEV | LUAD |
| RARS2 | c.16C>T | p.R6C | MACGF[p.R6C]CRAIACQLSRVLNLPPENLITSISAV | MACGFCRAI | BLCA |
| RASAL3 | c.245G>A | p.R82H | VSTQPAPRSIFRRVLSAPPKKESRTS[p.R82H]HLRLSKALWGRHKNPPEPDPEPEQE | RTSHLRLSK, TSHLRLSKA, SHLRLSKAL, HLRLSKALW, RTSHL RLSKA, HLRLSKALWG, KESRTSHLRL, SHLRLSKALW | GBM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| RASGEF1C | c.562G>A | p.A188T | LAALRQQSPEGLVGADKPISYRTKPP[p.A188T]TSIHRELLGVCSDPYTLAQQLTHVEL | SYRTKPPTS,RTKPPTSIH,YRTKPPTSI,SYRTKPPTSI,RTKPPTSIHR,TSIHRELLGV,KPPTSIHREL | KIRC |
| RASIP1 | c.1801C>T | p.R601C | ATLLALCVQHSARELELGHLPRLLG[p.R601C]CLARLIKEAVWEKIKEIGDRQPENHP | RLLGCLARL,HLPRLLGCL,LLGCLARLI,CLARLIKEA,LPRLLGCLA,RLLGCLARLI,CLARLIKEAV,HLPRLLGCLA,LLGCLARLIK | ACC |
| RB1 | c.948_951del|TCTT | p.N316fs | FKNFIPFMNSLGLVTSNGLPEVENL[p.N316fs]NDTKKFILKIKI* | KKFILKIKI,DTKKFILKIK,VENLNDTKKF | GBM |
| RBBP4 | c.988G>A | p.E330K | NLKLKLHSFESHKDEIFQVQWSPHN[p.E330K]KTILASSGTDRRLNVWDLSKIGEQS | QVQWSPHNK,SPHNKTILA,VQWSPHNKT,FQVQWSPHNK,SPHNKTILAS,VQWSPHNKTI | LAML |
| RBBP7 | c.820G>A | p.E274K | QKLIMWDTRSNTTSKPSHLVDAHTA[p.E274K]KVNCLSFNPYSEFILATGSADKTVAL | LVDAHTAKV,HLVDAHTAK,HTAKVNCLS,TAKVNCLSF,HLVDAHTAKV,KVNCLSFNPY,HTAKVNCLSF | CRC |
| RBBP7 | c.937G>A | p.E313K | LATGSADKTVALWDLRNLKLKLHTF[p.E313K]KSHKDEIFQVHWSPHNETILASSGTD | KLHTFKSHK,KLKLHTFKS,LKLHTFKSH,FKSHKDEIF,NLKLKLHTFK,KLKLHTFKSH,KSHKDEIFQV,HTFKSHKDEI | CRC |
| RBFOX2 | c.1018G>A | p.A340T | NTYIPLISLPLVPGFPYPTAATTAA[p.A340T]TFRGAHLRGRGRTVGAVRAVPPTAI | ATPRGAHLR,AATTAATFR,TTAATFRGA,TAATTAATF,TAATTAATFR,TFRGAHLRGR,AATFRGAHLR,YPTAATTAAT,PTAATTAATF | CRC |
| RBL2 | c.379G>A | p.E127K | VSKGTVEGNYVSLTRILKCSEQSLI[p.E127K]KFFNMKKWEDMANLPPHFRERTERL | SLIKFFNKM,QSLIKFFNK,LIKFFNKMK,KFFNKMKKW,CSEQSLIKF,SEQSLIKFF,SLIKFFNKMK,LIKFFNKMKK,EQSLIKFFNK,KCSEQSLIKF,IKFFNKMKKW | UCEC |
| RBM14 | c.856_876del|GCTGCTGCTGCAGCAGCAGCC | p.AAAAAAA286del | LTSTSLDPYDRHLLPTSGAAATAAA[p.AAAAAAA286del]|VTAASTSYYGRDRSPLRRATAPVPTVGEGYGYGHESELSQASAAAR | GAAATAAAV,ATAAAVTAA,TAAAVTAAS,SGAAATAAAV,TAAAVTRAST | PAAD |
| RBM19 | c.1168G>T | p.G390W | FREKNVPTTKGAPKNTTKSWQGRIL[p.G390W]WENEEEEDLAESGRLFVRNLPYTSTE | KSWQGRILW,WENEEEEDL,TKSWQGRILW | LUAD |
| RBM26 | c.1930C>G | p.P644A | TTSPKPLVQQPILPVVKQSVKERLG[p.P644A]|AVPSSTIEPAEAQSASSDLPQNVTKL | SVKERLGAV,KERLGAVPS,LGAVPSSTI,RLGAVPSSTI,KERLGAVPSS | BLCA |
| RBM39 | c.1058C>T | p.T353I | ERTDASSASSFLDSDELERTGIDLG[p.T353I]TGRLQLMARLAEGTGLQIPPAAQQA | LGITGRLQL,ITGRLQLMAR,LERTGIDLGI,LGITGRLQLM | UCEC |
| RBM47 | c.1485_1505del|GGCCGCAGCCGCCCAGCGCGCAGCCGC | p.495_502AAAAAAAA>A | HTVEHMISPIAVQPDPASAAAAAAA[p.495_502AAAAAAAA>A]|VIPTVSTPPFQGRPITPVYTVAPNVQRIPTAGIYGASYVPPAAPA | ASAAAAAAAV,SAAAAAAAVI | PAAD |
| RBM6 | c.2024T>G | p.V675G | RQDGESKTIMLKRIYRSTPPEVIVE[p.V675G]GLEPYVRLTTANVRIIKNRTGPMGHTSYGARDGPHGDYRGGEGPGHDFRGGI | VIVEGLEPY,VIVEGLEPYV,EVIVEGLEPY | MM |
| RBM6 | c.287_288insG | p.R96fs | R96fs|RFFVF* | FRGGRFFVF,HDFRGGRFF,DFRGGRFFVF,HDFRGGRFFV | STAD |
| RCL1 | c.335C>A | p.P112Q | HDCSVLRGIGYYLESLLCLAPFMKH[p.P112Q]|QLKIVLRGVTNDQVDPSVDVLKATAL | FMKHQLKIV,QLKIVLRGV,PFMKHQLKI,APPMKHQLK,MKHQLKIVL,CLAPFMKHQL,HQLKIVLRGV,FMKHQLKIVL,LAPFMKHQLK,APFMKHQLKI | LUAD |
| RDH8 | c.593C>T | p.A198V | LLQFNIFISLVEPGPVVTEFEGKLL[p.A198V]|VQVSMAEFPGTDPETLHYFRDLYLPA | KLLVQVSMA,LVQVSMAEF,TEFEGKLLV,GKLLVQVSM,FEGKLLVQV,VTEFEGKLLV,LLVQVSMAEF,VQVSMAEFPG,TEFEGKLLVQ,FEGKLLVQVS | GBM |
| REG1B | c.170G>T | p.W57L | PRISCPEGTNAYRSYCYYFNEDPET[p.W57L]|LVDADLYCQNMNSGNLVSVLTQAEGA | ETIVDADLIY,YFNEDPETL,YYFNEDPETL | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|------|-------------|----------------|-----|-----|-----|
| REG1B | c.201G>T | p.M67I | AYRSYCYFNEDPETWVDADLYCQN[p. M67I]INSGNLVSVLTQABGAFVASLIKESS | CQNINSGNL,NINSGNLVSV,CQNINSGNLV,INSGNLVSVL | LUSC |
| REG3A | c.449C>T | p.S150L | SDVMNYFAWERNPSTISSPGHCASL[p. S150L]LRSTAFLRWKDYNCNVRLPYVCKFTD | SLLRSTAFL,LLRSTAFLR,SPGHCASLL,ASLLRSTAF,LRSTAFLRW, SLLRSTAFLR,ASLLRSTAFL,CASLLRSTAF,LLRSTAFLRW | LUAD |
| REG4 | c.329G>T | p.G110V | GYQRSQPIWIGLFIDPQKRQQWQWID[p. G110V]VAMYLYRSWSGKSMGGNKHCAEMSSN | WIDVAMYLY,QWIDVAMYL,WQWIDVAMY,RQQWQWID V,QQWQWIDVA,QWQWIDVAM,VAMYLYRSW,WQWID VAMYL,WIDVAMYLYR,QWQWIDVAMY,QWIDVAMYLY,QQW QWIDVAM,RQQWQWIDVA | LUAD |
| REN | c.45_47 del|GCT | p.15_16 LL>L | MDGWRRMPRWGLLLL[p.15_16|LL>L] WGSCTFGLPTDTTTFKRIFLKRMPSIRE | MPRWGLLLLW | GBM |
| RERE | c.528G>C | p.K176N | PACSLPVASQPPQHLSEAGRGPVGS[p. K176N]NRDHLLMNVKWYYRQSEVPDSVYQHL | GSNRDHLLM,AGRGPVGSNR,GPVGSNRDHL | BLCA |
| REV3L | c.88G>T | p.A30S | RIVTADYYMASPLQGLDTCQSPLTQ[p. A30S]SPVKKVPVVRVFGATPAGQKTCLHIH | SPVKKPVV,CQSPLTQSP,CQSPLTQSPV,TQSPVKKVPV | TGCT |
| RFC3 | c.245T>A | p.I82N | RELYGVGVEKLRIEHQTITTPSKKK[p.I82 N]NEISTIASNYHLEVNPSDAGNSDRVV | TPSKKKNEI,KKKNEISTI,KKNEISTIA,NEISTIASNY, SKKKNEISTI | TGCT |
| RFC3 | c.888G>T | p.K296N | LLEVRGRLYELLTHCIPPEIIMKAC[p.K29 6N]NEESRSCDIF* | IMKACNEESR,NEESRSCDIF | TGCT |
| RGMB | c.187A>C | p.S63R | AWTGMGLRAAPSSAAAAAEVEQRR[p.S63R] RPGLCPPPLELLLLLLFSLGLLHAGD | RPGLCPPPL,VEQRRRPGL,RRPGLCPPPL | ACC |
| RGS6 | c.1097G>T | p.W366L | LKDQVGRDQFLRFLESEFSSENLRF[p. W366L]LLAVQDLKKQPLQDVA | FLLAVQDLK,LLAVQDLKK,RFLLAVQDL,FSSENLRFL,SENLR FLLA,FLLAVQDLKK,RFLLAVQDLKK,FSSENLRFLL,SENLRFLL AV,LRFLLAVQDL | LUSC |
| RGS7 | c.130C>T | p.R44C | PNMLVYRKMEDVIARMQDEKNGIPI[p. R44C]CTVKSFLSKIPSVFSGSDIVQWLIKN | CTVKSFLSK,IPICTVKSF,KNGIPICTVK,CTVKSFLSKI,IPICT-VKSFL | SKCM |
| RGS9BP | c.286G>T | p.A96S | ERAEFERLWVAFSGCLDLLEADMRR[p. A96S]SLELGAAFPLHAPRRPLVRTGVAGAS | RSLELGAAF,LEADMRRSL,ADMRRSLEL,SLELGAAFPL,RRSLELGAAF | ACC |
| RGSL1 | c.664G>A | p.V222I | HTKMTMAKEERACHGLMQEYETRLYS[p.V 222I]CYTHIGGLPLNMSIKKCHHFQKRYS | RLYSICYTH,EYETRLYSI,LYSICYTHI,ETRLYSIC,YETRLYSICY, RLYSICYTFHI,SICYTHIGGL,QEYETRLYSI,YETRLYSICY | BRCA |
| RHBDD3 | c.101_102 insG | p.G34fs | SPALPLASSVLMLLMSTLWLVGAGP[p. G34fs]RPGPGPGAVAGPLAGAPAADP CPGPHGAPARPAPEPAAPAHCGLAAGV PPGHAEIPACLSPARPGFWAAGSAAGR PWAVQCSRQLWIHACPPGHAGWGGTPP* | AVAGPLAGA,GLAAGVPPG,EIPACLSPA,SAAGRPWAV,CS RQLWIHA,WAAGSAAGR,RPWAVQCSR,GPRPGPGPG,RP GPGPGAV,GPGAVAGPL,GPLAGAPAA,GPHGPARPA,APA HCGLAA,SPARPGFWA,CLSPARPGF,AEIPACLSP,GFWAA GSAA,AGSAAGRPW,WAVQCSRQL,VQCSRQLWI,RQLWIHACP,WIH ACPPGHA,TLWLVGAGPR,GPRPGPGPGA,RPGPGPGAVA,GPARPAPE PA,RPAPEPAAPA,SPARPGFWAA,RPGFWAAGS A,AEIPACLSPA,ACLSPARPGF,AAGSAAGRPW,WAVQCSRQLW, RQLWIHACPP,HACPPGHAGW | KICH |
| RHEB | c.103T>A | p.Y35N | AILGYRSVGKSSLTIQFVEGQFVDS[p.Y3 5N]NDPTIENTFTKLITVNGQEYHLQLVD | FVDSNDPTI,GQFVDSNDPT,SNDPTIENTF | KIRC |
| RHOA | c.118G>C | p.E40Q | ACGKTCLLIVFSKDQFPEVVPTVF[p.E4 0Q]QNVADIEVDGKQVELALWDTAGQED | VFQNYVADI,VVVPTVFQNY,VPTVFQNYV,F QNYVADIEV,VVVPTVFQNY,TVFQNVADI,VPTVFQNYVA | HNSC |
| RHOA | c.125A>G | p.Y42C | GKTCLLIVFSKDQFPEVYPTVFEN[p.Y4 2C]CVADIEVDGKQVELALWDTAGQEDYD | VPTVFENCV,VVVPTVFENC,TVFENCVADI,CVADIEVDGK, VVVPTVFENC,FENCVADIEV | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| RHOBTB1 | c.1391C>T | p.T464M | VLEMFDLRMMVENIMNKEAFMNQEI[p.T464M]MKAFHVRKANRIKECLSKGTFSDVTF | FMNQEIMKA,IMKAFHVRK,AFMNQEIMK,EIMKAFHVR, MNQEIMKAF,MKAFHVRKA,EAFMNQEIM,QEIMKQFHV, FMNQEIMKAF,IMKAFHVRKA,EAFMNQEIMK,EIMKAFHVRK, KEAFMNQEIM | CRC |
| RHPN2 | c.217G>A | p.V73M | LKAVRMRTGAENLLKVATNSKVREQ[p.V73M]MRLELSFVNSDLQMLKEELEGLNISV | QMRLELSFV,KVREQMRLE,NSKVREQMR,EQMRLELSF,SK VREQMRL,VREQMRLEL,REQMRLELS,EQMRLELSFV,KVR EQMRLEL,REQMRLELSF | TGCT |
| RILPL1 | c.1074C>A | p.S358R | RIPQPPIAHPRTSPQPESGIKRLF[p.S358R]RFFSRDKKRLANTQRNVHIQ ESFGQW | SGIKRLRFF,GIKRLRFFR,KRLFRFFSR,LFRFFSRDK,ESGIKRLF R,RFFSRDKKR,RLFRFFSRDK,SGIKRLFRFF,GIKRLFRFFS,IK RLFRFFSR,LRFFFSRDKK | KICH |
| RIMBP2 | c.2489G>A | p.R830H | FPRGSAGPQRSRPVTVPSIDDYGRD[p.R830H]HLSPDFYEESETDPGAEELPARIFVA | RDHLSPDFY,YGRDHLSPDF | GBM |
| RIMBP3 | c.1187_1189 de|CGG | p.A396de| | HELIKLNWLLAKALWVLARRCYTLQ[p.A396 de|]ENKQLRRAGCPYQADEKVKRLKVKRAEL YADGLKVCEVADATAGSTLLEFSQL[p.Q115 4R]RVPLTWQKVSVRTMSLCGESLDSVPA | RCYTLQENK,TLQENKQLR,QENKQLRRA,YTLQENKQLR | KIRC |
| RIMBP3 | c.3461A>G | p.Q1154R | | LLEFSQLRV,TLLEFSQLR,SQLRVPLTW,LEFSQLRVP,TLLEFSQLRV, QLRVPLTWQK,STLLEFSQLR,PSQLRVPLTW,LEFSQLRVPL | TGCT |
| RIMS2 | c.1203de|A | p.V401fs | LGLKVVGGKWTESGRLCAFITKVKK[p.V 401fs]EV* | FITKVKKEV | STAD |
| RIMS2 | c.164G>T | p.R55L | EREEYSQYATSDTAMPRSPSDYADR[p.R55L]LSQHEPQFYEDSDHLSYRDSNRRSHR | LSQHEPQFY,SPSDYADRL,RLSQHEPQF,RLSQHEPQFY | LUAD |
| RIMS2 | c.1796G>A | p.R599Q | KRRTKVKKTLEPKWNQTFIYSPVH[p.R 599Q]QREFRERMLEITLMDQARVREEESEF | FIYSPVHQR,HQREFRERM,IYSPVHQREF,TFIYSPVHQR,YS PVHQREF,HQREFRERML | CRC |
| RIN3 | c.1345C>G | p.L449V | DTPRESTEQGQDTEVKASDPHSMPE[p.L44 9V]VPRTAKQPPVPPPRKKRISRQLASTL | SMPEVPRTA,SMPEVPRTAK,HSMPEVPRTA,VPRTAKQPPV | KIRC |
| RIN3 | c.2123C>T | p.S708L | LYKCVLKPLKEAINSCLHQIHSKDG[p.S 708L]LLQQLKENQLVILATTTDLGVTTSV | HQIHSKDGL,SKDGLLQQL,HQIHSKDGLL | CRC |
| RING1 | c.511de|G | p.G171fs | QAMHRAQRVRRPIPGSDQTTTMSGG[p.G171fs]KESPGREKGMEKM* | QTTTMSGGK,GGKESPGREK,KESPGREKGM | STAD |
| RINL | c.1205C>T | p.P402L | RRQTALRAGAGPPGAQGPGPEGQS[p.P402L]LAPALRSRIHERLAHLHAACAPRRKV | SLAPALRSR,GPGPEGQSL,PEGQSLAPA,SLAPALRSRI,EGQ SLAPALR,PEGQSLAPL | ACC |
| RINT1 | c.321de|A | p.L107fs | SKMQLEEQVLTISSEIPKRIRSALK[p.L10 7fs]MQKNQSNFLISFWSRKLISSAPLTAIC* | MQKNQSNFL,KLISSAPLT,FLISFWSRK,KMQKNQSNF,RIRS ALKMQ,ISFWSRKLI,WSRKLISSA,NFLISFWSR,NQSNFLISF, KRIRSALKM,QKNQSNFLI,RKLISSAPL,ISSAPLTAI,KMQKN QSNFL,FLISFWSRKL,KLISSAPLTA,LISSAPLTAI,MQKNQSNFLI, RIRSALKMQK,SNFLISFWSR,KNQSNFLISF,NFLISFWSRK,SRKLI SSAPL,LKMQKNQSNF,NQSNFLISFW | STAD |
| RIT1 | c.270G>T | p.M90I | DDEPANLDILDTAGQAEFTAMRDQY[p.M90I]IRAGEGFIIYIRAGEGFIIYSITDRRSFHEVREFK | FTAMRDQYI,AMRDQYIRA,YIRAGEGFI,QYIRAGEGF,TAM RDQYIR,IRAGEGFII,YIRAGEGFII,QYIRAGEGFI,AMRDQYI RAG,FTAMRDQYIR,DQYIRAGEGF | LUAD |
| RIT2 | c.254G>T | p.R85L | QVRIDNEPAYLDILDTAGQAEFTAM[p.R85L]LEQYMRGGEGFIICYSVTDRQSFQEA | GQAEFTAML,TAMLEQYMR,FTAMLEQYM,AEFTAMLEQ,FTAM LEQYMR,AEFTAMLEQY | LUAD |
| RLBP1 | c.215C>T | p.A72V | KAKDELNEREETREEAVRELQEMVQ[p.A72V]VQAASGEELAVAVAERVQEKDSGFFL | RELQEMVQV,QEMVQVQAA,VQAASGEEL,LQEMVQVQAA,VQAA SGEELA,QEMVQVQAAS | CRC |
| RLBP1 | c.841G>A | p.D281N | PFLKSKLLERVFHGDDLSGFYQEI[p.D2 81N]NENILPSDFGGTLPKYDGKAVAEQLF | FYQEINENI,YQEINENIL,NENILPSDF,GFYQEINENI,FYQEI NENIL,QEINENILPS | CRC |
| RLIM | c.1502C>T | p.S501L | SPSSSSGGEESETSSDLFEGSNEGS[p.S 01L]LSSGSSGARREGRHRAPVTFDESGSL | SLSSGSSGA,FEGSNEGSL | KIRC |
| RLN2 | c.412A>T | p.S138C | QQHVPVLKDSLLFEEFKKLIRNRQ[p.S 138C]CEAADSSPSELKYLGLDTHSRKKRQL | LIRNRQCEA,RQCEAADSS,CEAADSSPS,KLIRNRQCEA,LIRN RQCEAA,RQCEAADSSP | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| RNAS ET2 | c.380C>T | p.A127V | HSFPNRSRFWKHEWEKHGTCAAQVD[p. A127V]VLNSQKKYFGRSLELYRELDLNSVLL | QVDVLNSQK,VLNSQKKYF,AQVDVLNSQK,QVDVLNSQKK | CRC |
| RNF11 | c.2313de|C | p.R771fs | HEVMQRMEVQPRRMMQHPTRAHERP[p. R771fs]HPIHIGCTQTMVMGIIFM CLRLCPHILDRLQRGLPGNWELKLE* | TMVMGIIFM,VMGIIFMCL,HIGCQTMV,RLCPHILDR,QT MVMGIIF,RGLPGNWEL,RAHERPHPI,MGIIFMCLR,CTQT MVMGI,MVMGIIFMC,CRLCPHIL,HERPHPIHI,IHIGCTQT M,IGCTQTMVM,FMCLRLCPH,LQRGLPGNW,LPGNWELK, MVMGIIFMCL,FMCLRLCPH,RLCPHILDR,VMGIIFMCLR, RGLPGNWELK,RAHERPHPIH,QTMVMGIIFM,RPHPIHI GCT,HIGCTQTMVM,TQTMVMGIIF,RLQRGLPGNW | STAD |
| RNF11 3B | c.515C>T | p.A172V | YRGIHSYLRYLKPKDTSMGNSSSGM[p.A172 V]VRKGPIRAPGHLRATVRMDYQPDICK | NSSSGMVRK,SMGNSSSGMV | CRC |
| RNF14 9 | c.25A>G | p.S9G | MAWRRREA[p.S9G]GVGARGVLALAL LALALCVPGARGRA | AWRRREAGV,MAWRRREAG,RRREAGVGAR,MAWRRRE AGV,REAGVGARGV | ACC |
| RNF15 0 | c.623C>T | p.S208L | LERNITVTMYITIGTRNLQKYVSRT[p.S2 08L]LVVFVSISFIVLMIISLAWLVFYIQ | RTLVFVSI,KYVSRTLVV,YVSRTLVVF,VSRTLVVFV,LQKYVS RTL,LVVFVSISF,QKYVSRTLV,YVSRTLVVF,NLQKYVSRTL, LQKYVSRTLV,LVVFVSISFI,KYVSRTLVVF,RTLVVFVSIS,TLV VFVSISF,QKVVSRTLVV | CRC |
| RNF150 | c.707G>A | p.R236Q | FVSISFIVLMIISLAWLVFYYIQRF[p.R23 6Q]QYANARDRNQRRLGDAAKKAISKLQI | FYYIQRFQY,YYIQRFQYA,IQRFQYANA,YIQRFQYANA,FYYI QRFQYA,YYIQRFQYAN,IQRFQYANAR,VFYYIQRFQY,FQY ANARDRN | CRC |
| RNF15 2 | c.283C>T | p.P95S | PDDPEVLAVIAIPHTSEHTPVFIKL[p.P9 5S]SSNGCYMLPLPISKERALLPGDMGCR | KLSSNGCYM,IKLSSNGCY,LSSNGCYML,KLSSNGCYML,FIK LSSNGCY,IKLSSNGCYM,SSNGCYMLPL | SKCM |
| RNF17 | c.1052C>G | p.S351C | KKYNNKKELSCYDTYPPLEKKKVDM[p.S 351C]CVLTSEAPPPLQPETNDVHLEAKNF | KKKVDMCVL | KIRC |
| RNF22 | c.397G>A | p.A133T | PLAASSPAWRPPPGQARPPGSPGQS[p. A133T]TQLPLDLLPSLPRESQIFVISRHGMP | SPGQSTQLPL,GQSTQLPLDL,TQLPLDLLPS | ACC |
| RNF39 | c.787G>T | p.G263C | HRRLLISADRRSVQLAPPGTPAPPD[p.G 263C]CPKRFPDLPAVLGAQGFGAGRHCWEV | GTPAPPDCPK | ACC |
| RNF43 | c.1976de|G | p.G659fs | PSTSSLFNLQKSSLSARFIPQRKRRG[p.G 659fs]VPPSPPLALGPRRMQLCTQLARFF PITPPVWHILGPQRHTP* | RMQLCTQLA,TQLARFFPI,RFFPITPPV,FFPITPPVW,ITPPV WHIL,RGVPPSPPL,MQLCTQLAR,HPQRKRRGV,VPPSPPL AL,RKRRGVPPS,LALGPRMQL,QLCTQLARF,FPITPPVWFI, RMQLCTQLAR,MQLCTQLARF,CTQLARFFPI,RFFPITPPVW, RGVPPSPPLA,FPITPPVWHI,SPPLALGPRM,GPRMQLCTQ L,RRGVPPSPPL,QLCTQLARFF,TQLARFFPIT,ARFFPITPPV SPRRAPPPL,RRAPPPLPV | STAD |
| RNF43 | c.348_349 insC | p.P116fs | NASDDDNLEPGFISIVKLESPRRAP[p.P116fs] PPLPVTG* | | STAD |
| RNMT | c.647C>T | p.S216L | PPAWPDYDVWIlMTVVGTIFVIILA[p.S 216L]LVLRIRCRPRFISRPDPLQQRTAWAIS | IILALVLRI,IFVIILAIV,VIIILAVLR,TIFVIILAL,FVIILA LVL,TIFVIILAV,VIILALVLRI,IFVIILALVL,LVLRIRCRPR, FVIILALVLR,IILALVLIR,LALVLRIRCR,GTIFVIILAL | CRC |
| RNMT | c.1174de|A | p.K392fs | PEFLVVFPLLNEMAKKYNMKLVYKK[p. K392fs]HFWNSTKKRLRTMKIKCS* | VYKKHFWNS,KKHFWNST,KHFWNSTK,STKKRLRTM,K KRLRTMKI,RLRTMKIKC,HFWNSTKKR,MKLVYKKHF,YKKH FWNST,STKKRLRTMK,KKHFWNSTKK,KKRLRTMKIK,RLRT MKIKCS,FWNSTKKRLR,NMKLVYKKHF,MKLVYKKHFW | STAD |
| RNPC3 | c.347de|A | p.E116fs | LVVEFAKEQDRVHSPCPTSGSEKKK[p.E 116fs]GLMTLSKMIKKKKNLVI* | GLMTLSKMI,LMTLSKMIK,MTLSKMIKK,TLSKMIKKK,LSK MIKKKK,MIKKKKNLV,KGLMTLSKM,IKKKKNLVI,KMIKKKK NLV,GLMTLSKMIK,LMTLSKMIKK,MTLSKMIKKK,TLSKMI KKKK,KKKGLMTLSK,MIKKKKKNL,SKMIKKKKNL,SEKKKG LMTL,KKGLMTLSKM | CESC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ROBO2 | c.3052G>A | p.D1018N | SQITQATPYATTQILHSNSIHELAV[p.D1 018N]NLPDPQWKSSIQQKTDLMGFGYSLPD | SIHELAVNL,HELAVNLPD,AVNLPDPQWK,NSIHELAVNL,L AVNLPDPQW,HELAVNLPDP | UCEC |
| ROBO2 | c.3238_323 9insC | p.P1080fs | KNKNSSKPQKNNGSTWANVPLPPPP[p. P1080fs]SPAPSWHGAGTLCSGTTRKWL* | TLCSGTTRK,GTLCSGTTR,SPAPSWHGA,APSWHGAGT,GT LCSGTTRK,VPLPPPSPA,SPAPSWHGAG,APSWHGAGTL | STAD |
| ROBO2 | c.3877de|A | p.K1293fs | PTSPFSTDSNTSAALSQSQRPRPTK[p.K 1293fs]NTREGGWTNNQHCLIEGKE* | WTNNQHCLI,REGGWTNNQH | STAD |
| ROCK1 | c.1552A>T | p.T518S | HRINEYQRKAEQENEKRRNVENEVS[p. T518S]SLKDQLEDLKKVSQNSQLANEKLSQL | EVSSLKDQL,NVENEVSSLK,RNVENEVSSL,NEVSSLKDQL | PRAD |
| ROR2 | c.2014G>A | p.D672N | KLLGNSLLPIRWMAPEAIMYGKFSI[p.D6 72N]NSDIWSYGVVLWEVFSYGLQPYCGYS | NSDIWSYGV,KFSINSDIW,SINSDIWSY,IMYGKFSIN,GKFSI NSDI,FSINSDIWSY,NSDIWSYGVV,IMYGKFSINS,INSDIWS YGV,GKFSINSDIW | CRC |
| RORB | c.280G>T | p.G94W | NRNRCQHCRLQKCLALGMSRDAVKF[p. G94W]WRMSKKQRDSLYAEVQKHQQRLQEQR | AVKFWRMSK,MSRDAVKFW,AVKFWRMSKK,MSRDAVKF WR,DAVKFWRMSK,GMSRDAVKFW | LUAD |
| ROS1 | c.734G>T | p.R245I | FPGGPPILGYNLRLISKNQKLDAGTQ[p.R 245I]ITSFQFYSTLPNTIYRFSIAAVNEVG | GTQITSFQF,TQITSFQFY,QKLDAGTQI,GTQITSFQFY,ITS FQFYSTL,NQKLDAGTQI,LDAGTQITSF,AGTQITSFQF | UCEC |
| RP1 | c.5312C>T | p.S1771L | WLLKENHLLRMSSENPGMCGNADTT[p. S1771L]LVDTLLDDNNSSEVPYSHFGNLAPGPT | DTTLVDTLL,GMCGNADTTL | LUSC |
| RPA1 | c.92G>A | p.R31H | SEGAIAAIMQKGDTNIKPILQVINI[p.R3 1H]PITTGNSPPRYRLLMSDGLNTLSSF | LQVINIHPL,ILQVINIHPIL,LQVINIHPIT | HNSC |
| RPL10L | c.560A>C | p.K187T | RQKIHISKKWGFTKFNADEFEDMVA[p. K187T]TKCLIPDGCGVKVPSHGPLDKWRVL | DEFEDMVAT,DEFEDMVATK,FEDMVATKCL | LUAD |
| RPL13 | c.319G>C | p.G107R | QTMRGMPPHKTKPGQAALDCLKVFD[p.G107R] RIPPPYDKKKRMVVPAALKVVRLKPA | VFDRIPPPY,RIPPPYDKK,KVFDRIPPP,KVFDRIPPPY, RIPPPYDKKK | UCS |
| RPL19 | c.451C>T | p.R151C | KVKGNVFKNKRILMEHIHKLKADKA[p. R151C]CKKLLADQAEAARRSKTKEARKRREER | KLKADKACK,KLKADKACKK | TGCT |
| RPL22 | c.44de|A | p.K15fs | MAPVKLVVKGGKK[p.K15fs]RSKF* | VVKGGKKRSK,VKGGKKRSKF | UCEC |
| RPL5 | c.172_173 de|AG | p.R58fs | KRLVIQDKNKYNTPKYRMIVRTVNR[p. R58fs]YHLSDCLCPYRGGYDSLRSVCTR TAKIWCEGWPDKLCCSILYWPAAGPQASQ* | HLSDCLCPY,RSVCTRTAK,MIVRVTNRY,IVRVTNRYH,RVTN RYHLS,RTAKIWCEG,CLCPYRGGY,DSLRSVCTR,VRVTNRY HL,KLCCSILYW,CSILYWPAA,DKLCCSILY,WPAAGPQAS,W PDKLCCSI,SLRSVCTRTA,RMIVRVTNRY,IVRVTNRYHL,RSVCTRTAKI,Y HLSDCLCPY,CPYRGGYDSL,WPDKLCCSIL,RTAKIWCEGW | TGCT |
| RPL6 | c.578T>G | p.F193C | LASGLLLVTGPLVLNRVPLRRTHQK[p.F 193C]CVIATSTKIDISNVKIPKHLTDAYFK | CVIATSTKI,RTHQKCVIA,KCVIATSTK,HQKCVIATS, RTHQKCVIAT,HQKCVIATST | CRC |
| RPRD2 | c.289C>A | p.R97S | PHRLNLPYLANDVIQNCKRKNAIIF[p.R9 7S]SESFADVLPEAAALVKDPSVKSVER | AIIFSESFA,NAIIFSESF,FSESFADVL,IIFSESFADV, IFSESFADVL,NAIIFSESFA,KNAIIFSESF | LUAD |
| RPS2 | c.598A>G | p.R200G | GKPHTVPCKVTGRCGSVLVRLIPAP[p.R 200G]GGTGIVSAPVPKKLLMMAGIDDCYTS | RLIPAPGGT,LVRLIPAPG,IPAPGGTGI,LIPAPGGTGI, IPAPGGTGIV | CLL |
| RPS6KA5 | c.496G>A | p.E166K | THLSQRERFTEHEVQIYVGEIVLAL[p. E166K]KHLHKLGIIYRDIKLENILLDSNGHV | VLALKHLHK,LALKHLHKL,VLALKHLHKL,VIALKHLHKL,ALKH LHKLGI,IVLALKHLHK,YVGEIVLALK,KHLHKLGIIY, GEIVLALKHL,LKHLHKLGII | CRC |
| RPS6KA6 | c.1181C>A | p.S394Y | ATSIAEEYKITPITSANVLPIVQIN[p. S394Y]ENAAQFGEVYELKEDIGVGSYSVCKR | ENAAQFGEV,QINENAAQF,VQINENAAQ,VQINENAAQF,EN AAQFGEVY,NENAAQFGEV,LPIVQINENA | UCEC |
| RPS6KA6 | c.327de|A | p.K109fs | KKASLKVRDRVRTKMERDILVEVNH[p. K109fs]HLLSNCTMPFRLKGNCT* | ILVEVNHHL,LLSNCTMPF,LSNCTMPFR,HHLLSNCTM,ILVEV NHHLL,LLSNCTMPFR,SNCTMPFRLK,HLLSNCTMPF, NHHLLSNCTM | STAD |
| RPSA | c.331C>G | p.Q111E | AVLKFAAATGATPIAGRFTPGTFTN[p.Q 111E]IQAAFWEPRLLVVTDPRADHQPLTE | FTNEIQAAF,TPGTFTNEI,FTPGTFTNEI,TFTNEIQAAF,EIQ AAFWEPR,NEIQAAFWEP,FTNEIQAAFW | GBM |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| RPTN | c.1090G>A | p.G364S | QSSHYGQMDRKGQCYHDQTNRQGQ[p.G364S]SSHYSQPNRQGQSSHYGQPDTQDQSS | SSHYSQPNR,TNRQGQSSHY,QQSSHYSQPN | CLL |
| RPTN | c.1614G>A | p.M538I | QTDRQGQSFHYGQPDRQGQSSHYSQ[p.M538I]IDRQGQSSHYGQTDRQGQSSHYGQTD | GQSHYSQI,SSHYSQIDR,SQIDRQGQSS,IDRQGQSSHY | TGCT |
| RPTN | c.886G>A | p.G296S | CGQSERLGQELGCGQQTDRQGQSSHY[p.G296S]SQTDRQDQSYFIYGQTDRQGQSSHYSQ | SQTDRQDQSY | PRAD |
| RRAD | c.833C>A | p.A278E | LRRDSKEANARRQAGTRRRESLGKK[p.A278E]EKRFLGRIVARNSRKMAFRAKSKSCH | KEKRFLGRI,KEKRFLGRIV | KIRC,TGCT |
| RREB1 | c.2348G>T | p.G783V | CGEDLKHYRALRIHMRTHCGRLGG[p.G783V]VHKGRKPFECKECSAAFAAKRNCIHH | GVHKGRKPF,CGRGLGGVHK | ACC |
| RRN3 | c.25C>T | p.R9C | MAAPLLHTR[p.R9C]CLPGDAAASSSAVK | MAAPLLHTC,LLHTCLPGDA,MAAPLLHTCL,HTCLPGDAAA | KIRP |
| RRN3 | c.31C>T | p.P11S | MAAPLLHTRL[p.P11S]SGDAAASSSAV KKLGASRTGISNM | HTRLSGDAA,LLHTRLSGDA,HTRLSGDAAA | KIRP |
| RRP15 | c.642G>T | p.L214F | KEAGSSMRKRAKLISTVSKKDFISV[p.L214F]FRGMDGSTNETASSRKKPKAQTEVK | SKKDFISVF,VSKKDFISVF,KDFISVFRGM | LUSC |
| RRS1 | c.135de|C | p.N45fs | QRITVHKELELQFDLGNLLASDRNP[p.N45fs]RPGCGAPDPRRRPSYRPWRGTTR NCSSTSCGSCPRSAWKR* | GSCPRSAWK,STSCGSCPR,RRRPSYRPW,SYRPWRGTT,LLA SDRNPR,APDPRRRPS,CGSCPRSAW,SSTSCGSCPR,CGSCP RSAWK,GSCPRSAWKR,RRRPSYRPWR,SYRPWRGTTR,NL LASDRNPR,APDPRRRPSY,RPSYRPWRGT,RPWRGTTRNC | STAD |
| RSBN1 | c.1714G>A | p.E572K | SPFKRRRSMNEIKNLQYLPRTSEPR[p.E572K] KVLFEDRTRAFIADHVGQGFDWQSTAA | RTSEPRKVL,RTSEPRKVLF,LPRTSEPRKV | UCEC |
| RSF1 | c.1158de|A | p.K386fs | HEITEKSTEETEKLKNDQQAKIPLK[p.K386fs]NEKLN* | QAKIPLKNEK,AKIPLKNEKL | STAD |
| RSPO2 | c.82C>T | p.R28C | FRLFSFALIILNCMDYSHCQGNRWR[p.R28C]CSKRASYVSNPICKGCLSCSKDNGCS | QGNRWRCSK,RWRCSKRAS,RCSKRASYV,WRCSKRASY,CQG NRWRCSK,RWRCSKRASY,QGNRWRCSKR | CRC |
| RTN1 | c.308C>G | p.S103W | ASTGVAGVSSAMDHTFSTTSKDGEG[p.S103W]WCYTSLSIDICYPPQEDSTYFTGILQ | EGWCYTSLI,GEGWCYTSL,TSKDGEGWCY,GEG WCYTSLI | LUAD |
| RTN2 | c.938de|C | p.P313fs | KTVPILELSPPLWTAIGWVQRGPTP[p.P313fs]LLLSSGFY* | VQRGPTPLL,PLLLSSGFY,WVQRGPTPL,TPLLLSSGF,VQRG PTPLLL,GWVQRGPTPL,TPLLLSSGFY | STAD |
| RUNX1 | c.286_287 insG | p.D96fs | LCSVLPTHWRCNKTLPIAFKVVALG[p.D96fs]GCSRWHSGHCDGW* | VVALGGCSR,VALGGCSRW,KVVALGGCSR,RWHSGHCDGW | BRCA |
| RUNX1 | c.403A>G | p.R135G | DENYSAELRNATAAMKNQVARFNDL[p.R135G]GFVGRSGRGKSFTLTITVFTNPPQVA | LGFVGRSGR,VARFNDLGF,VARFNDLG FV,RFNDLGFVGR,DLGFVGRSGR,QVARFNDLGF | LAML |
| RUNX1 | c.424_425 insA | p.R142fs | LRNATAAMKNQVARFNDLRFVCRSG[p.R142fs]KREKLHSDHHCLHKPTASRH LPQSHQNHSGWAPRTSKTSAETR* | KLHSDHHCL,CLHKPTASR,HSDHHCLHK,SGWAPRTSK,VG RSGKREK,ASRHLPQSH,RTSKTSAET,RFVGRSGKR,QNHS GWAPR,APRTSKTSA,QSHQNHSGW,HQNHSGWAP,HSGW APRTSK,RTSKTSAETR,KLHSDHHCLH,HQNHSGWAPR, HCLHKPTASR,LHKPTASRHL | BRCA |
| RUNX2 | c.1010G>T | p.R337M | SPSIHSTTPLSSTRGTGLPAITDVP[p.R337M]MRISDDDTATSDFCLMPSTLSKKSQA | AITDVPMRI,LPAITDVPM,GLPAITDVPM | LUAD |
| RUNX2 | c.1397C>A | p.P466H | STPYLYGTSSGSYQFPMVPGGDRS[p.P466H]HSRMLPPCTTTSNGSTLLNPNLPNQN | RSHSRMLPP,HSRMLPPCT,RSHSRMLPPC,HSRMLPPCTT | KIRC |
| RUNX2 | c.211C>G | p.Q71E | VAAQQQQQQQQQQQQQQQQQQQ QQQ[p.Q71E]ERAAAAAAAAAAA AAAVPRLRPP | QQQQEEAAA,QQQEEAAAA,QQEEAAAAA,QQQQEEAAA A,QQQQEEAAAAA,QQEEAAAAAA,QEEAAAAAAA | KIRP,TGCT |
| RUSC2 | c.1456de|C | p.P486fs | SSTQAAAAVGPTVLEGQVYTNTSPP[p.P486fs]TSALDVSAPAAMIAACSAALL SAWARMNVC* | AMIAACSAA,MIAACSAAL,AALLSAWAR,ALLSAWARW,N TSPPTSAL,SALDVSAPA,DVSAPAAMI,SAPAAMIAA,IAACS AALL,SAALLSAWA,LSAWARMNV,APAAMIAAC,LDVSAP | STAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| RUVBL1 | c.1291G>A | p.E431K | SVQLLTPANLLAKINGKDSIEKEHV[p.E4 31K]KEISELFYDAKSSAKILADQQDKYMK | AAM,CSAALLSAW,AMIAACSAAL,MIAACSAALL,LLSAWA RWNV,SAALLSAWAR,YTNTSPPTSA,TSALDVSAPA,DVSAP AAMIA,CSAALLSAWA,ALDVSAPAAM,AAMIAACSAA,ACS AALLSAW,AALLSAWARW | CRC |
| RUVBL1 | c.349C>T | p.R117C | PFCPMVGSEVYSTEIKKTEVLMENF[p.R 117C]CRAIGLRIKETKEVYEGEVTELTPCE | HVKEISELF,VKEISELFY,IEKEHVKEI,HVKEISELFY, KEHVKEISEL,KEISELFYDA VLMENFCRA,EVLMENFCR,NFCRAIGLR,LMENFCRAI,VL MENFCRAI,NFCRAIGLRI,FCRAIGLRIK,ENFCRAIGLR,EVL MENFCRA,MENFCRAIGL | CRC |
| RWDD2B | c.761G>A | p.R254H | VEGPQSACEEFWSRLRKLNWKRILI[p.R 254H]HHREDIPFDGTNDETERQRKPSIFEE | ILIHHREDI,IIHHREDIPF,KLNWKRILIH,RILIHHREDEI,NWKRI LIHHR,LIHHREDIPF | CRC |
| RXFP1 | c.668C>A | p.S223Y | HRLEWLIIEDNHLSRISPPTFYGLN[p.S2 23Y]YLILLVLMNNVLTRLPDKPLCQHMPR | GLNYLILLV,TFYGLNYLI,FYGLNYLIL,YGLNYLILL,NYLILLVL M,LNYLILLVL,YGLNYLILLV,GLNYLILLVL,TFYGLNYLIL,FYG LNYLILL,LNYLILLVLM,SPPTFYGLNY | UCEC |
| RXRA | c.1280C>A | p.S427Y | AYCKHYPEQPGRFAKLLLRLPALR[p.S 427Y]YIGLKCLEHLFFFKLIGDTPIDTFLM | LLRLPALRY,LPALRYIGL,LRYIGLKCL,RLPALRYIGL,LLRLPAL RYI,ALRYIGLKCL,YIGLKCLEHL,LLLRLPALRY | BLCA |
| RXRA | c.1280C>T | p.S427F | AYCKHYPEQPGRFAKLLLRLPALR[p.S 427F]FIGLKCLEHLFFFKLIGDTPIDTFLM | LPALRFIGL,LLRLPALRF,LRFIGLKCL,RLPALRFIGL,FIG LKCLEHL,LLRLPALRFI,LLLRLPALRF | BLCA |
| RYR1 | c.2002G>T | p.D668Y | IRPNIFVGRAEGTTQYSKWYFEVMV[p. D668Y]YEVTPFLTAQATHLRVGNALTEGYTP | MVYEVTPFL,KWYFEVMVY,VMVYEVTPF,YEVTPFLTA, FEVMVYEVT,WYPEVMVEV,VMVYEVTPFL,MVYEVTPFLT,EV MVYEVTPF,SKWYFEVMVY,YEVTPFLTAQ,FEVMVYEVTP | TGCT |
| RYR1 | c.7726G>A | p.A2576T | NRYLCLAVLPLLITKCAPLFAGTEHR[p.A2 576T]TIMVDSMLHTVYRLSRGRSLTKAQRD | RTIMVDSML,HRTIMVDSM,RTIMVDSMLH,LFAGTEHRTI, FAGTEHRTIM | UCEC |
| RYR2 | c.13002G>T | p.M4334I | ICSLLLGGSLVEGAKKIKVAELLAN[p. M4334I]IPDPTQDEVRGDGEEGERKPLEAALP | KVAELLANI,LLANIPDPT,IPDPTQDEV,NIPDPTQDEV,IKVA ELLANI,AELLANIPDP | LUAD |
| RYR2 | c.2131G>A | p.E711K | VTAEATHLRVGWASTEGYSPYPGGG[p. E711K]KEWGGNGVGDDLFSYGF DGLHLWSGC | KEWGGNGVG,SPYPGGGKEW | LUSC |
| RYR2 | c.6069A>C | p.L2023F | DFHEDLMTHCGIELDEDGSLLDGNSD[p. L2023F]FTIRGRLLSLVEKVTYLKKKQAEKPV | GSLDGNSDF,SLLDGNSDFTI,FTIRGRLLSL | TGCT |
| RYR2 | c.7239G>C | p.K2413N | IMTFYSALIDLLGRCAPEMHLIHAG[p.K 2413N]NGEAIRIRSILRSLIPLGDLVGVISI | LIHAGNGEA,IHAGNGEAI,HLIHAGNGEA,LIHAGNGEAI | LUAD |
| RYR3 | c.5008C>A | p.P1670T | DESKRHGLPGVGLRTCLKPGFRFST[p.P 1670T]TCFVVTGEDHQKQSPEIPLESLRTKA | RFSTTCFVV,GFRFSTTCF,FRFSTTCFV,GFRFSTTCFV,PGFRF STTCF,FRFSTTCFVV | LUAD |
| RYR3 | c.8114G>A | p.R2705Q | LAVGWTTVERTKEGEALVQQRENEKL[p. R2705Q]QSVSQANQGNSYSPAPLDLSNVVLSR | RENEKLQSV,RENEKLQSVS,NEKLQSVSQA | CRC |
| SACS | c.8717G>A | p.R2906Q | FHVNGHFALDSARRNLMRDDNGVGV[p. R2906Q]QSDWNNSLMTALLIAPAVELLIQLKK | QSDWNNSLM,VQSDWNNSL,VQSDWNNSLM | UCEC |
| SAFB | c.2393del|G | p.W798fs | REGQHYPERHGGSPERHGRDSRDGWG[p. W798fs]AMALTRG* | DSRDGWGAM,RDGWGAMAL,DGWGAMALTR,RDSRDG WGAM,SRDGWGAMAL | STAD |
| SAFB | c.2396G>T | p.G799V | EREGQHYPERHGGPERHGRDSRDGW[p. G799V]VGYGSDKRMSEGRGLPPPGRRDWG | DSRDGWVGY,VGYGSDKRM,RDSRDGWVGY | TGCT |
| SAGE1 | c.685C>T | p.R229C | HNVCEQKMENVQPAPDNVLLTLRPR[p. R229C]CINMTDTGISPMSTRDPYATITYNVP | TLRPRCINM,RPRCINMTDT,RCINMTDTGI | CRC |
| SAGE1 | c.894C>A | p.H298Q | STGLINVAGAGTPAISTNGLYSTV[p. H298Q]QNVCEEKMENDQPQPNNVLSTVQPVI | LYSTVPQNV,GLYSTVPQNV | LUAD |
| SALL3 | c.1777C>G | p.L593V | PGLNHYESGVSATAESPQSLLGGPP[p.L 593V]VTKAEPVSLPCTNARAGDAPVGAQAS | SLLGGPPVT,LLGGPPVTK,SLLGGPPVTKA,SLLGGPPVTK | ACC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SALL4 | c.2983de|G | p.V995fs | NQYTSMLNGGLAVKTNEISVIQSGG[p.V995fs]FLPSRFPWGPPPL* | FLPSRFPWG,GFLPSRFPW,RFPWGPPPL,ISVIQSGGF,IQSG GFLPS,SGGFLPSRF,SRFPWGPPP,FLPSRFPWGP,QSGGFL PSRF,GGFLPSRFPW,SRFPWGPPPL | STAD |
| SALL4 | c.560G>T | p.R187L | PPTPQDISYILAKGKVANTNVTLQAL[p.R187L]LGTKVAVNQRSADALPAPVPGANSIP | ALLGTKVAV,LQALLGTKV,TLQALLGTK,TLQALLGTKV,VTL QALLGTK,NTNVTLQALL,LQALLGTKVA | LUAD |
| SAMD3 | c.618G>T | p.Q206H | DMTKYLEGSLYPSTQQYNDVVNALI[p.Q206H]HAHPFLDEDGCGFFLWKRALKDRPKY | ALLHAHPFL,NALLHAHPF,VNALLHAHPF | LUSC |
| SAMD4B | c.1429C>T | p.R477W | APAPTDGSEPAPAPVADGDIPSQFT[p.R477W]WMGKVCTQLLVSRPDEENITSYLQL | SQFTWVMGK,DIPSQFTWV,IPSQFTWVM,GDIPSQFTW,S QFTWVMGKV,WVMGKVCTQL,PSQFTWVMGK,DIPSQFT WVM | UCS |
| SBF1 | c.3228de|C | p.P1076fs | SRNLVQNAKKTIGRQHVTRKKYNPP[p.P1076fs]AGSTGASRPLRTRTRTRSQCRRSW SPAR* | STGASRPLR,ASRPLRTRR,RTRRTRSQC,RTRSQCRRS,RSQC RRSWS,VTRKKYNPPA,ASRPLRTRRT,RTRRTRSACR,RTRS QCRRSW,RSQCRRSWSP,QCRRSWSPAR,RPLRTRRTRS,KK YNPPAGST,SQCRRSWSPA | STAD |
| SBNO1 | c.3415_341 6insA | p.N1139fs | EVHQQNALFQYFADTLTAVVQNAKK[p.N1139fs]KWKI* | AVVQNAKKK,VQNAKKKWK,VVQNAKKKWK | STAD |
| SBSPON | c.397G>T | p.G133W | GGAPCPPLEERAGCLEYSTPQGQDC[p.G133W]MHTYVPAFITTSAFNKERTRQATSPH | GQDCWHTYV,CWHTYVPAF,QGQDCWHTY,CWHTYVPAF I,PQGQDCWHTY,YSTPQGQDCW | LUAD |
| SCAF11 | c.624_625 insC | p.P208fs | PPPAPSSASSSPSPSPSPSSSPPPP[p.P208fs]TPTAPCTPSPTCPPIRYL* | SPSPPPTPT,TPSPTCPPI,SPTCPPIRY,CTPSPTCPPI,SPSPPP TPTA,SPTCPPIRYL | KIRC |
| SCAF8 | c.2776_277 7de|GA | p.E926fs | SSPGEKSRSQSRERESDRDGQRRER[p.E926fs]KENQKVV* | RERKENQKV,RERKENQKVV | GBM,KIRP |
| SCAF8 | c.2218G>T | p.G740C | LVQPSLSMTPETVKDVGFGSLVIPG[p.G740C]CSVASNLATSALPAGNVFNAPTKQAE | SLVIPGCSV,LVIPGCSVA,SLVIPGCSVA,IPGCSVASNL | LUAD |
| SCAPER | c.1097G>A | p.R366Q | AEKTQFTVSTLDDVKNSGSIRDNYV[p.R366Q]QTSEISAVHIDTECVSVMLQAGTPPL | VQTSEISAV,YVQTSEISAV,QTSEISAVHI,RDNYVQTSEI,VQ TSEISAVH | UCEC |
| SCARF1 | c.1841G>A | p.R614Q | SVSFARGTKFAPQSRRSSGELSSPL[p.R614Q]QKPKRLSRGAQSGPEGREAEESTGPE | LSSPLQKPK,LQKPKRLSR,SPLQKPKRL | STAD |
| SCFD2 | c.1633C>T | p.R545W | TDWDSSINLITFHKSKIAVDELFTSL[p.R545W]WDIAGARSLLKQFKSVYVPGNHT HQA | ELFTSLWDI,SLWDIAGAR,TSLWDIAGA,WDIAGARSL,FTSL WDIAGA,ELFTSLWDIA,TSLWDIAGAR,WDIAGARSLL,DEL FTSLWDI | CRC |
| SCLT1 | c.327de|A | p.K109fs | MKLQLENVIKENERLHSELKDAVEK[p.K109fs]NWRPFPWAQR* | KNWRPFPWA,AVEKNWRPF,EKNWRPFPW,NWRPFPWA QR,VEKNWRPFPW,DAVEKNWRPF | STAD |
| SCML4 | c.581G>A | p.R194Q | GKQHLRSLPVVNSIGVVLRFLAKLC[p.R194Q]QSLLCDDLFSHQPFPRGCSASEKVQE | FLAKLCQSL,FLAKLCQSLL,RPLAKLCQSL,CQSLLCDDLF | CRC |
| SCML4 | c.783G>T | p.L261F | YLVNPVGMNRYSVDTSASTFNHRGS[p.L261F]FHPSSSLYCKRQNSGDSHLGGPAAT | STFNHRGSF,SFHPSSSLY,GSFHPSSSL,STFNHRGSFH,GSFH PSSSLY,RGSFHPSSSL,ASTFNHRGSF | LUAD |
| SCN10A | c.3425G>A | p.R1142H | EGCIRHCPCCKLDTTKSPWDVGWQV[p.R1142H]HKTCYRIVEHSWPESFIIFMILLSSG | WQVHKTCYR,WQVHKTCYRI,VGWQVHKTCY,SPWDVGW QVH | MM |
| SCN10A | c.4709C>T | p.T1570M | IVVLSIASLIFSAILKSLQSYFSP[p.T157 0M]MLFRVIRLARIGRILRLIRAAKGIRT | SLQSYFSPM,LQSYFSPML,YFSPMLFRV,MLFRVIRLA,SYFSP MLFR,QSYFSPMLF,SPMLFRVIR,SLQSYFSPML, QSYFSPMLFR,MLFRVIRLAR,LQSYFSPMLF,SYFSPMLFRV, YFSPMLFRVI,KSLQSYFSPM,FSPMLFRVIR,SPMLFRVIRL | CRC |
| SCN2A | c.107G>A | p.R36K | PDSFRFTRESLAAIEQRIAEEKAK[p.R3 6K]KPKQERKDEDDENGPKPNSDLEAGKS | RIAEEKAKK,KAKKPKQER,KAKKPKQERK | BRCA |
| SCN2A | c.464C>A | p.T155K | LFNMLIMCTLLTNCVFMTMSNPPDW[p.T155K]KKNVEYTFGIYTFESLIKILARGFC | TMSNPPDWK,MSNPPDWKK,WKKNVEYTF,MTMSNPPD WK,TMSNPPDWKK,DWKKNVEYTF | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SCN7A | c.4073G>A | p.R1358H | MTVGSYLVPPSLVQLILLSRIIHML[p. R1358H]HLGKGPKVFHNLMLPLMLSLPAL LNI | IIHMLHLGK,MLHLGKGPK,LSRIIHMLH,SRIIHMLHL,HLGK GPKVF,MLHLGKGPKV,RIIHMLHLGK,HMLHLGKPK,LSRII HMLHL,LHLGKGPKVF | GBM |
| SCNN1G | c.1691G>A | p.R564H | MSCSVVCVIEIIEVFFIDFFSIIAR[p.R564 H]HQWQKAKEWWAWKQAPPCPEAP RSPQ | IIARHQWQK,IARHQWQKA,DFFSIIARH,FSIIARHQW,HQ WQKAKEW,IIARHQWQKA,SIIARHQWQK,FFSIIARHQW,I ARHQWQKAK,HQWQKAKEWW | GBM |
| SCRIB | c.995G>T | p.G332V | SLGKLTKLTNLNVDRNHLEALPPEI[p.G 332V]VGCVALSVLSLRDNRLAVLPPELAHT | IVGCVALSV,ALPPEIVGC,LEALPPEIV,PEIVG CV,ALPPEIVGCV,ALPPEIVGC,EIVGCVALSV,LPPEIVGCVA | TGCT |
| SCRT1 | c.397T>G | p.S133A | VSEGYAADAFFITDGRSRRKASNAG[p.S 133A]AAAAPSTASAAAPDGDAGGGGGAGGR | RRKASNAGA,KASNAGAAA,RKASNAGAA,KAS NAGAAAA,RKASNAGAA,AAAAPSTASA | ACC |
| SCUBE2 | c.1024G>A | p.V342M | DGKTCKDIDECQTRNGGCDHFCKNI[p. V342M]MGSFDCGCKKGFKLLTDEKSCQDVDE | FCKNIMGSF,CDHFCKNIM,IMGSFDCGCK,HPFCKNIMGSF | CRC |
| SDAD1 | c.824de1A | p.K275fs | YATGKKSSKNKKLEKAMKVLKKQK[p. K275fs]RRKNQRCLTFQPT* | KVLKKQKRR,VLKKQKRK,KQKRRKNQR,RKNQRCLTF,QR CLTFQPF,KVLKKQKRRK,AMKVLKKQKR,NQRCLTFQPF,RR KNQRCLTF | STAD |
| SDHAP1 | c.196C>T | p.H66Y | DYKVRIDEYDHSKPIQGQQKPFEE[p.H 66Y]YWRKHTLSYVDVSTGKVTVEYRPIID | YWRKHTLSY,QQKKPFEEY,EEYWRKHTL,EYWRKHTLSY,Y WRKHTLSYV,GQQKKPFEEY,QQKKPFEEYW,FEEYWRKHTL | CESC |
| SDHAP2 | c.110_111 insTT | p.S37fs | VGRPPVPLHMVSTASGQTRCWTWLS[p. S37fs]LVRHVP* | CWTWLSLVR,TRCWTWLSL,WTWLSLVRHV,QTRCWTWLSL | CESC |
| SDHAP3 | c.91C>T | p.R31C | LCPACTPVGRPPVPLHMVSTASGQT[p. R31C]CCWTWLSGQACALSIAESCRPGDKVP | SGQTCCWTW,GQTCCWTWL,TASGQTCCW | GBM,PRAD |
| SDHAP3 | c.196G>A | p.A66T | AACASVHGANRLGANSLLDLVVFGQ[p. A66T]TCALSIEESCRPGDKVPPIKPNAGEE | VVFGQTCAL,FQGTCALSI,VFGQTCALSI,LVVFGQTCAL | GBM |
| SDK1 | c.1524_1525 insC | p.K508fs | RPVDTTVTDGMTAILRCEVSGAKP[p. K508fs]RHHLEKRKPHSGQWLCPDS* | EVSGAPKPR,KRKPHSGQW,RKPHSGQWL,APKPRHHLEK, KPPRHHLEKRK,KRKPHSGQWL | KIRC |
| SDK1 | c.3542C>T | p.T1181M | PSPYSPSSRVIQTLQAPPDVAPTSV[p. T1181M]MVRTASETSLRLRWVPLPDSQYNGNP | DVAPTSVMV,MVRTASETSL,DVAPTSVMVR,APTSVMRTA | CRC |
| SDK1 | c.6437A>G | p.Y2146C | ADASESEATDSDYEDALPKHSFVNH[p. Y2146C]CMSDPTTYNSWKRRAQGRAP APHRYE | HCMSDPTTY,KHSFVNHCM,NHCMSDPTY, FVNHCMSDPT,VNHCMSDPTY | TGCT |
| SEC24D | c.150_151 insC | p.A50fs | YGHYGDPSHTASPTGMMKPAGPLGA[p. A50fs]HRH* | MKPAGPLGAH | LUAD |
| SEC31B | c.2713C>T | p.P905S | GVRPASSQPQLLGGQRVQVPNPVGF[p. P905S]SGTWPLPGSPLPMACPGIMRP GSTSL | VGFSGTWPL,NPVGFSGTW | TGCT |
| SEC61A2 | c.377G>T | p.G126V | EVGDTPKDRALFNGAQKLFGMIITI[p.G 126V]VQAIVYVMTGMYGDPAEMGAG ICLLI | ITIVQAIVY,MIITIVQAI,TIVQAIVYV,GMIITIVQA,IITIVQAIV, IVQAIVYVM,KLFGMIITIV,GMIITIVQAI,MIITIVQAIV,ITIV QAIVYVL,IITIVQAIVY,TIVQAIVYVM | LUAD |
| SECISBP2 | c.1824C>G | p.D608E | GMDELISTPSVEDKSEEPPGTELQR[p.D 608E]ETEASHLAPNHTTPKIHSRRFRD YC | LQRETEASH,RETEASHLA,TELQRETEA,LQRETEASFIL,RETE ASHLAP | KIRC |
| SELP | c.1285C>T | p.R429W | RAFQYDTNCSFRCAEGFMLRGADIV[p. R429W]WCDNLGQWTAPAPVCQALQ CQDLPVP | VWCDNLGQW,MLRGADIVW,FMLRGADIVW,IVWCDNL GQW | UCEC |
| SELP | c.889G>A | p.A297T | NMTCLHSAKFQHQSSCSFSCEEGF[p. A297T]TLVGPEVVQCTASGVWTAPAP VCKAV | FTLVGPEVV,FSCEEGFTL,FSCEEGFTLV,EGFTLVGPEV | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SEMA3A | c.241G>A | p.D81N | SYHTFLLDEERSRLYVGAKDHIFSF[p.D8 1N]NLVNIKDFQKIVWPVSTRRDECK WA | FSFNLVNIK, IFSFNLVNI, KDHIFSFNL, HIFSFNLVNI, NLVNIK DFQK, SFNLVNIKDF, KDHIFSFNLV | CRC |
| SEMA4D | c.755G>A | p.R252Q | EDDRVFFFTEVSVEYEFVFRVLIP[p.R2 52Q]QIARVCKGDQGGLRTLQKKWTSF LKA | VLIPQIARV, RVLIPQIAR, FVFRVLIPQI, RVLIPQIARV, VFRVLI PQIA | CRC |
| SEMG2 | c.874C>T | p.R292C | QHQTKNLSQDQEHGRKAHKISYPSS[p. R292C]CTEERQLHHGEKSVQKDVSKGS ISIQ | CTEERQLHH, HKISYPSSC | GBM |
| SENP7 | c.2018C>A | p.S673Y | ELELSYPLSWVQAFPLFQNLSSKES[p.S6 73Y]YFIHYYCVSTCSFPAGVAVAEEMKL K | SYFIHYYCV, SSKESYFIH, KESYFIHYY, ESYFIHYYC, QNLSSKES Y, NLSSKESYF, SKESYFIHY, NLSSKESYFI, SSKESYFIHY, FQNL SSKESY, SKESYFIHYY, ESYFIHYYCV, QNLSS KESYF, KESYFIHYYC | UCEC |
| SEPHS1 | c.1112G>A | p.R371Q | GEGHQAWIIGIVEKGNRTARIIDKP[p.R 371Q]QIIEVAPQVATQNVNPTPGATS* | QIIEVAPQV, RIIDKPQII, IIDKPQIIEV | CRC |
| SEPHS1 | c.37G>A | p.E13K | MSTRESFNPESY[p.E13K]KLDKSFRLTR FTELKGTGCKVPQDVL | ESFNPESYK, SFNPESYKL, SYKLDKSFR, ESYKLDKSF, YKLDKS FRL, KLDKSFRLTR, SYKLDKSFRL, ESYKLDKSFR, ESFNPESYKL | UCEC |
| SERPIN A12 | c.631C>G | p.R211G | HGKINNLIENIDPGTVMLLANYIFF[p.R2 11G]GARWKHEFDPNVTKEEDFFLEKN SSV | LLANYIFFG, YIFFGARWK, NYIFFGARW, FGARWKHEF, ANYI FFGAR, LANYIFFGA, MLLANYIFFG, LLANYIFFGA, LANYIFFG AR, FFGARWKHEF, ANYIFFGARW | BLCA |
| SERPIN A12 | c.757G>T | p.D253Y | FFLEKNSSVKVPMMFRSGIYQVGYD[p. D253Y]YKLSCTILEIPYQKNITAIFILPDEG | YQVGYDKL, GIYQVGYD, YDYKLSCTI, GIYQVGYDYK, IYQ VGVGYKL, SGIYQVGYDY, YDYKLSCTIL, YKLSCTILEI | LUAD |
| SERPINA3 | c.474G>C | p.K158N | LQLSMGNAMFVKEQLSLLDRFTEDA[p. K158N]NRLYGSEAFATDFQDSAAAKKL INDY | FTEDANRLY, NRLYGSEAF, RFTEDANRLY, ANRLYGSEAF | CESC |
| SERPINA4 | c.292C>T | p.R98C | HQQILETGEGSPSLKIAPANADFAF[p.R 98C]CFYYLIASETPGKNIFFSPLSISAAY | NADFAFCFY, FAFCFYYLI, DFAFCFYYL, ADFAFCFYY, ANADF AFCF, NADFAFCFYY, FAFCFYYLIA, DFAFCFYYLI, ANADFAFC FY, ADFAFCFYYL | CESC |
| SERPINA9 | c.1242G>T | p.M414I | TTKFIVRSKDGPSYFTVSFNRTFLM[p.M 414I]IITNKATDGILFLGKVENPTKS* | FLMIITNKA, TFLMIITNK, SFNRTFLMI, FNRTFLMII, FLMIITN KAT, RTFLMIITNK, VSFNRTFLMI, SFNRTFLMII | LUAD |
| SERPIN B12 | c.503del A | p.Q168fs | PICQEYILDGVIQFYHTTIESVDFQK[p.Q 168fs]TLKNPDKRLTSGLNVNPKVKSRNS SARTLMLRLCWYw* | NSSARTLLM, SVDFQKTLK, KTLKNPDKR, TSGLNVNPK, SAR TLLMLR, LMLRLCWYN, KVKSRNSSA, KSRNSSART, RNSSA RTLL, LLMLRLCWY, NVNPKVKSR, KRLTSGLNV, SRNSSARTL, SSARTLLML, IESVDFQKT, LTSGLNVNPK, SSARTLMLR, RT LLMLRLCW, LLMLRLCWYW, FQKTLKNPDK, SGLNVNPKVK, KVKSRNSSAR, KSRNSSARTL, RNSSARTLLM, SARTLLMLRL, TLLMLRLCWY, NPDKRLTSGL, IESVDFQKTL, SRNSSARTLL | STAD |
| SERPINB3 | c.626C>G | p.S209C | GQWENKFPKKENTKEEKFWPNKNTYK[p. S209C]CVQMMRQYNSFNFALLEDV QAKVLEI | KCVQMMRQY, TYKCVQMMR, NTYKCVQMM, NTYKCVQMMR, WPNKNTYKCV, NKNTYKCVQM, YKCVQMMRQY | KIRC |
| SERPINC1 | c.134G>T | p.R45L | SLLLIGFWDCVTCHGSPVDICTAKP[p.R 45L]LDIPMNPMCIYRSPEKKATEDEGS EQ | TAKPLDIPM, VDICTAKPL, CTAKPLDIPM, KPLDIPMNPM | LUAD |
| SERPINI1 | c.243del A | p.L81fs | GMMELGAQGSTQKEIRHSMGYDSLK[p. L81fs]MVKNFLS* | SLKMVKNFL, SMGYDSLKM, SMGYDSLKMV, MGYDSLKMV K, SLKMVKNFLS, HSMGYDSLKM | STAD |
| SESTD1 | c.918T>G | p.I306M | VMQVVNWLEGPGSEQLRAQWGIGDS[p.I3 06M]MRASQALQQKHEEIESQHS EWFAVTV | SMRASQALA, DSMRASQAL, AQWGIGDSM, SMRASQALQ Q, RAQWGIGDSM | KIRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SETDB2 | c.2145de1A | p.R715fs | YGYEAGTVPEKEIFCQCGVNKCRKK[p.R715fs]YYKVTNACL* | KYYKVTNA,KCRKKYYK,GVNKCRKKY,YKVTNACL,KYYK VTNAC,YYKVTNACL,VNKCRKKYK,KCRKKYY KYY,GVNKCRKKY,KKYYKVTNA | STAD |
| SEZ6L | c.620C>T | p.S207L | VPLWLDRKESAVPTTPAPLQISPFT[p.S207L]LQPYVAHTLPQRPEPGEPDM AQEA | TLQPYVAHT,LQPYVAHTL,ISPFTLQPY,LQISPFTLQ,SPFTLQ PYV,TLQPYVAHTL,QISPFTLQPY,ISPFTLQPYV,APLQISPFT L,LQISPFTLQP,SPFTLQPYVA | CRC |
| SEZ6L2 | c.221G>C | p.R74P | EALAELLHGALLRRGPEMGYLPGSD[p.R74P]PDPTLATPPAGQTLAVPSLPRAT EPG | YLPGSDPDT,LPGSDPDTL | ACC |
| SF1 | c.763C>T | p.R255W | IETPEDQNDLRKMQLRELARLNGTL[p.R255W]WEDDNRILRPWQSETRSITN TTVCT | TLWEDDNRI,LARLNGTLW,TLWEDDNRIL | CESC |
| SF3B1 | c.1868A>G | p.Y623C | SNLAKAAGLATMISTMRPDIDNMDE[p.Y623C]CVRNTTARAFAVVASALGIPSL LPFL | CVRNTTARA,CVRNTTARAF | CLL |
| SF3B1 | c.1876A>T | p.N626Y | AKAAGLATMISTMRPDIDNMDEYVR[p.N626Y]YTTARAFAVVASALGIPSLLPFL KAV | NMDEYVRYT,YTTARAFAV,YVRYTTARA,RYTTARAFA,EYV RYTTAR,VRYTTARAF,DEYVRYTTA,NMDEYVRYTT,YTTAR AFAVV,RYTTARAFAV,YVRYTTARAF,IDNMDEYVRY,DEYV RYTTAR | CLL |
| SF3B1 | c.1996A>G | p.K666E | IPSLLPPLKAVCKSKKSWQARHTGI[p.K666E]EIVQQIAILMGCAILPHLRSLVEIIE | QARHTGIEI,EIVQQIAIL,IEIVQQIAI,WQARHTGIEI,EIVQQI AILM,IEIVQQIAIL | CLL |
| SF3B1 | c.2098A>G | p.K700E | MGCAILPHLRSLVEIIEFIGLVDEQQ[p.K700E]EVRTISALAIAALAEAATPYGIESFD | GLVDEQQEV,EVRTISALA,QEVRTISAL,DEQQEVRTI,EVRTI SALAI,QQEVRTISAL,DEQQEVRTIS,QEVRTISALA | BRCA,CLL |
| SF3B1 | c.2704G>A | p.E902K | GNLGAADIDHKLEEQLIDGILYAFQ[p.E902K]KQTTEDSVMLNGFGTVVNALGK RVKP | ILYAFQKQT,KQTTEDSVM,ILYAFQKQTT, FQKQTTEDSV,QKQTTEDSVM,KQTTEDSVML | BLCA |
| SF3B1 | c.2870G>A | p.R957Q | ICGTVLMRLNNKSAKVRQQADLIS[p.R957Q]QTAVVMKTCQEEKLMGFFIGGV VLYEYL | DLISQTAVV,ISQTAVVMK,LISQTAVVM,ADLISQTAV,LLISQ TAVVMK,QAADLISQTA,DLISQTAVVM,RQQAADLISQ | UCEC |
| SFI1 | c.2462G>A | p.R821Q | THHLQCVRKRLLHRQSTQLIAQRLS[p.R821Q]QTCFRQWRQQLAARRQEQRA TVRALW | LLAQRLSQT,SQTCFRQWR,AQRLSQTCF,LSQTCFRQW,LL AQRLSQTC,AQRLSQTCFR,LSQTCFRQWR,LAQRLSQTCF,R LSQTCFRQW | HNSC |
| SFPQ | c.1832G>A | p.R611Q | EEQMRRQREESYSRMGYMDPRERDM[p.R611Q]QMGGGGAMNMGDPYGS GGQKFPPLGG | MQMGGGGAM,DMQMGGGGAM,QMGGGGAMNM,M QMGGGGAMN | CRC |
| SFRP4 | c.695G>A | p.R232Q | QRSGCNEVTTVVDVKEIFKSSSPIP[p.R232Q]QTQVPLITNSSCQCPHILPHQDVLIM | IPQTQVPL,SSSPIPQTQV,SPIPQTQVPL | UCEC |
| SFSWAP | c.1850C>A | p.S617Y | PLEKNRVKLDDDSDDDEESKEGQES[p.S617Y]YSSAANTNPAVAPPCVVVEKK PQLT | ESKEGQESY,GQESYSSAA,YSSAANTNPA,KEGQESYSSA,EE SKEGQESY,QESYSSAANT | CRC |
| SGCG | c.659C>T | p.A220V | ESPTRSLSMDAPRGVHIQAHAGKIE[p.A220V]VLSQMDILFHSSDGMLVLDAET VCLP | EVLSQMDIL,VLSQMDILF,GKIEVLSQM,IEVLSQMDI,IQAH AGKIEV,QAHAGKIEVL,IEVLSQMDIL,EVLSQMDILF | CRC |
| SGCZ | c.123T>G | p.I41M | REQYILATQQNNLPRTENAQLYPVG[p.I41M]MYGWRKRCLYFFVLLLLVTMIVN LAM | LYPVGMYGW,MYGWRKRCL,AQLYPVGMY,GMYGWRKR CL,MYGWRKRCLY,NAQLYPVGMY,QLYPVGMYGW | CRC |
| SGIP1 | c.1505G>T | p.R502L | GVGDVSRPFSPPIHSSSPPPIAPLA[p.R502L]LAESTSSISSTNSLSAATTPTVENEQ | ALAESTSSI,ALAESTSSIS,SPPPIAPLAL,LALAESTSSI | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SGK1 | c.1100_1102 del AGA | p.K367del | AKDDFMEIKSHVFFSLINWDLLINK[p.K367del]ITPPFNPVSGPNDLRHFDPEFTEEPVP | LINKITPPF,DLINKITPPF | UCEC |
| SGK3 | c.183del A | p.L61fs | SEWFVFRRYAEFDKLYNTLKKQFPPA[p.L61fs]WP* | TLKKQFPAW | STAD |
| SGOL2 | c.1220del A | p.E407fs | KKSNKKTNEHGMKTFRKVKDSSSEK[p.E407fs]REKDQRDSLKIVQMSILGKRLKTGQKDLMSWMAKGVQKIPVLFSIMNSWLR* | LMSWMAKGV,WMAKGVQKI,SLKIVQMSI,IVQMSILGK,MSIIGKRLK,SWMAKGVQK,FSIMNSWLR,GVQKIPVLF,KDLMSWMAK,GQKDLMSWM,REKDQRDSL,RDSLKIVQM,LKIVQMSIL,KGVQKIPVL,QKIPVLFSI,KIPVLFSIM,VLFSIMNSW,DLMSWMAKGV,VLFSIMNSWL,SLKIVQMSIL,KIVQMSILGK,QMSILGKRLK,MSWMAKGVQK,SWMAKGVQKI,KGVQKIPVLF,KVKDSSSEKR,REKDQRDSLK,LGKRLKTGQK,RLKTGQKDLM,MAKGVQKIPV,IVQMSILGKR,LFSIMNSWLR,VQMSILGKRL,KRLKTGQKDL,GQKDLMSWMA,AKGVQKIPVL,VQKIPVLFSI,QKIPVLFSIM | STAD |
| SGSM1 | c.2452G>A | p.E818K | VLDAQRNTPTVLRPRDGSVDDRQSS[p.E818K]KATTSQDERAPREELAVQDSLESDLLA | SVDDRQSSK,RQSSKATTS,GSVDDRQSSK,RQSSKATTSQ | CESC |
| SGSM1 | c.3351C>A | p.F1117L | IALALVEVYRDIILENNMDFTDIIK[p.F1117L]LFNEMAERHNTKQVLKLARDLIVYKVQ | FTDIIKLFN,KLFNEMAER,DFTDIIKLF,DIIKLFNEM,MDFTDIIKL,NMDFTDIIKL,DIIKLFNEMA,MDFTDIIKLF | CRC |
| SH3KBP1 | c.1688_1689 insC | p.P563fs | ISQVSDNKASLPPKPGTMAAGGGGP[p.P563fs]SPSVLSGALPPVILFGNSWTQSQLPVSVRHGR,KTKDGACGQQPGGRGGAKDTGPRAEEHHRDHEGPAETRD* | VLSGALPPV,TQSQLPVSV,GALPPVILF,PVSVRHGRK,SVRHGRKTK,LPVSVRHGR,SPSVLSGAL,SWTQSQLPV,SQLPVSVRH,SVLSGALPPV,VLSGALPPVI,ILFGNSWTQS,WTQSQLPVSV,VSV,VSVRHGRKTK,QLPVSVRHGR,NSWTQSQLPV,SGALPPVILF,FGNSWTQSQL,SQLPVSVRHG,PPVILFGNSW | KIRC |
| SH3KBP1 | c.1720del C | p.L574fs | LPPKPGTMAAGGGGPAPLSSAAPSP[p.L574fs]CHPLWEQLDTEPTPRLCSARKENQRWSLRPAARRPWRS* | RWSLRPAAR,RPAARRPWR,CSARKENQR,WSLRPAARR,RKENQRWSL,NQRWSLRPA,QRWSLRPAA,WEQLDTEPT,APSPCHPLW,RWSLRPAARR,SLRPAARRPW,EQLDTEPTPR,SAAPSPCHPL,RPAARRPWRS,NQRWSLRPAA | STAD |
| SH3PXD2A | c.2276C>T | p.S759L | SSDLITLPATTPPCPTKKEWEGPAT[p.S759L]LYMTCSAYQKVQDSEISFPAGVEVQV | TLYMTCSAY,ATLYMTCSA,KEWEGPATL,WEGPATLYM,ATLYMTCSAY,LYMTCSAYQK,KEWEGPATLY,KKEWEGPATL,WEGPATLYMT | LUAD |
| SH3RF2 | c.952C>T | p.R318C | RKVPGGQFSITTALNTLNRMVHSPSG[p.R318C]CHMVEISTPVLISSSNPSVITQPMEK | HSPSGCHMV,VHSPSGCHM,MVHSPSGCHM,SPSGCHMVEI,RMVHSPSGCH,CHMVEISTPV | GBM |
| SH3TC2 | c.265C>T | p.R89C | RCVNGPLQEAARRLWALENEDQEV[p.R89C]CMLFKDLSARLVSIQSQRAQFLITFK | NEDQEVCML,CMLFKDLSAR,LENEDQEVCM,NEDQEVCMLF,QEVCMLFKDL | CRC |
| SHB | c.1378G>A | p.A460T | RNSQTSKHDYSLSLRSNQGFMHMKL[p.A460T]TKTKEKYVLGQNSPPFDSVPEVIHYY | FMHMKLTKT,GFMHMKLTK,KLTKTKEKY,KLTKTKEKYV,FMHMKLTKT,QGFMHMKLTK,HMKLTKTKE,LTKTKEKYV,MKLTKTKEKY | GBM |
| SHROOM4 | c.3468_3470 del AGA | p.1156_1157EE>E | EEEEEEEEEEEEEEEEEEEEAEEEEE[p.1156_1157EE>E]LPPQYFSSETSGSCALNPEEVLEQPQPL | ERAEEEEEL | PAAD |
| SI | c.3649G>T | p.V1217F | LDFYMFLGPTPEVATKQYHEVIGHP[p.V1217F]FMPAYWALGFQLCRYGYANTSEVREL | FMPAYWALG,PFMPAYWAL,IGHPFMPAY,HPFMPAYWA,YHEVIGHPF,HEVIGHPFM,FMPAYWALGF,QYHEVIGHPF,VIGHPFMPAY,EVIGHPFMPA,HPFMPAYWAL,YHEVIGHPFM,IGHPFMPAYW | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SI | c.5042T>A | p.I1681K | WFDYHTGKDIGVRGQFQTFNASYDT[p. I1681K]KNLHVRGGHILPCQEPAQNTF YSRQK | TFNASYDTK, QTFNASYDTK, ASYDTKNLHV | TGCT |
| SIGLEC1 | c.954del|C | p.P318fs | QAAWSDAGVTCQAENGVGSLVSPP[p. P318fs]SASTSSWLRSR* | SASTSSWLR, STSSWLRSR, PPSASTSSW, ASTSS WLRSR, SPPSASTSSW | STAD |
| SIGLEC10 | c.749C>T | p.T250M | SAQRTVRLRVAYAPRDLVISISRDN[p.T 250M]MPALEPQGNVPYLEAQKGQ FLRLL | ISRDNMPAL, MPALEPQPQ, SISRDNMPAL, LVISISRDNM, ISISRDNMPA, MPALEPQPG | GBM |
| SIGLEC11 | c.1088C>T | p.S363F | NRLGSQQQALLDLSVQYPPENLRVMV[p. S363F]FQANRTVLENLGNGTSLPVLEG QSLR | MVFQANRTV, RVMVFQANR, VMVFQANRTV, RVMVFQANRT, MVFQANRTVL, FQANRTVLEN | CRC |
| SIK1 | c.2032del|C | p.Q678fs | EVLEQQRLLQLQHHPAAAPGCSQAP[p. Q678fs]SRPLPRL* | QAPSRPLPR, APSRPLPRL, CSQAPSRPL, SQAPSRPLP, SQAP SRPLPR | STAD |
| SIM1 | c.637G>A | p.V213M | YLKIRQYSLDMSPFDGCYQNVGLVA[p. V213M]MGHSLPPSAVTEIKLHSNMFM FRASL | YQNVGLVAM, GLVAMGHSL, MGHSLPPSA, VAMGHSLPP, AMGHSLPPSA, CYQNVGLVAM, YQNVGLVAMG, MGHSLP PSAV | CESC |
| SIPA1 | c.3188G>A | p.R106 3Q | SETYRMPVMEYKMNEGVSYEFKFPF[p. R1063Q]QNNNKWQRNASKGPHSPQ VPSQVQSP | KPPFQNNNK, FQNNNKWQR, FPFQNNNKW, YEFKFPFQN, KPPFQNNNKW, YEFKFPFQNN | CRC |
| SIPA1 | c.3680C>A | p.S122 7Y | PSWQRSEDSIADQMAYSYRGPQDFN[p. S1227Y]YFVLEQHEYTEPTCHLPAVSK VLPAF | RGPQDFNYF, YFVLEQHEY, YRGPQDFNY, YRGPQDFNYF, SY RGPQDFNY, NYFVLEQHEY, GPQDFNYFVL | CRC |
| SIPA1 L3 | c.2330G>C | p.G777A | RVHNPCTDNVCYSMAVTRSKDAPPF[p. G777A]APPIPSGTTFRKSDVFRDFLLAK VIN | RSKDAPPFA, DAPPFAPPI, RSKDAPPFAP, APPIPSGTTF, KDA PPFAPPI | KIRC |
| SIRPA | c.387_389 del|CGA | p.D131 del | IRIGNITPADAGTYYCVKFRKGSPD[p.D 131del]VEFKSGAGTELSVRAKPSAPVV SGPAAR | KGSPDVEFK, KFRKGSPDV, RKGSPDVEF, VKFRKGSPDV, FR KGSPDVEF | KIRC |
| SIRPA | c.697G>A | p.V233I | SIHSTAKVLTREDVHSQVICEVAH[p.V 233I]ITLQGDPLRGTANLSETIRVPPTLEV | QVICEVAHI, VICEVAHITL, SQVICEVAHI | PRAD |
| SIX1 | c.571G>A | p.E191K | TQVSNWFKNRRQRDRAAEAKERENT[p. E191K]KNNNSSSNKQNQLSPLEGGK | KNNNSSSNK | UCEC |
| SIX3 | c.79A>C | p.I27L | VFRSPLDLYSSHFLLPNFADSHHRS[p.I2 7L]LLLASSGGGNGAGGGGAGGSGG PLMSSS | FADSHHRSL, FADSHHRSLL | CLL |
| SKI | c.185C>G | p.A62G | APSARWAQEAYKKESAKEAGAAAVP[p. A62G]GPVPAATEPPVLHLPAIQPPPP VLP | GAAAVPGPV, KEAGAAAVPG | KIRP |
| SKOR1 | c.2648A>G | p.Y883C | EEMVQQLQIVRDTLCNELDQERKAR[p. Y883C]CAIQQKLKEAHDALHHFSCKML TPRH | KARCAIQQK, RCAIQQKLK, QERKARCAI, KARCAIQQKL | LUAD |
| SLAMF1 | c.829del|A | p.S277fs | LIMVVILQLRRRGKTNHYQTTVEKK[p.S 277fs]ALRSMPKSRNQVLFRRNLTPSQL RTLAPPYMLLPQSLSQSLSRKQIPSQSM LV* | TLAPPYMLL, SMPKSRNQV, KQIPSQSML, QIPSQSMLV, KSR NQVLFR, SLSQSLSRK, QSLSQSLSR, RTLAPPYML, PYMLLPQ SL, KKALRSMPK, ALRSMPKSR, RSMPKSRNQ, RNLTPSQLR, QLRTLAPPY, TIVEKKALR, MPKSRNQVL, TPSQLRTLA, LPQS LSQSL, VEKKALRSM, NQVLFRRNL, RRNLTPSQL, SQLRTLAP P, LRTLAPPYM, SQSLSRKQI, RKQIPSQSM, LLPQSLSQSL, KQ IPSQSMLV, SMPKSRNQVL, KSRNQVLFRR, QSLSQSLSRK, R | BLCA |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SLC10A4 | c.843C>G | p.F281L | YKYSRVADYIVKVSLMWSLLVTLVVL[p.F281L]LIMTGTMLGPELLASIPAAVYVIAIF | TLAPPYMLL,KALRSMPKSR,RSMPKSRNQV,QLRTLAPPYM,SQLRTLAPPY,QTTVEKKALR,MPKSRNQVLF,PPYMLLPQS L,YQTTVEKKAL,FRRNLTPSQL,YMLLPQSLSQ,SRKQIPSQS M,RKQIPSQSML | CESC |
| SLC10A6 | c.326de|G | p.G109fs | YLLAISFSLKPVQAIAVLIMGCCPG[p.G109fs]APSLTFSPSGLMEIWISASV* | LLVTLVVLL,LLIMTGTML,VLLIMTGTM,SLLVTLVVLL,LLV TLVVLLI LIMGCCPGA,GLMEIWISA,SLITFSPSGL,FSPSGLMEI,LITFSP SGLM,MEIWISASV,CPGAPSLTF,APSLTFSPS,SPSGLMEIW, VLIMGCCPGA,GLMEIWISAS,LMEIWISASV,SLITFSPSGLM, TFSPSGLMEI,MGCCPGAPSL,SPSGLMEIWI | STAD |
| SLC10A7 | c.782C>T | p.S261L | LILFIIFSIQL[p.S261L]SFMLLTFIFSTRNN[p.S261L]LGFTPADTVAIIFCSTHKSLTLGIPM | FIFSTRNNL,STRNNLGFT,RNNLGFTPA,FSTRNNLGF,NLGF TPADTV,TFIFSTRNNL,IFSTRNNLGF | UCEC |
| SLC12A1 | c.875C>T | p.S292L | ANAVAVAMYVGFAETVDLLKESD[p.S292L]LMMVDPTNDIRIIGSITVVILLGI SV | LLKESDLMM,LLKESDLMMV,LMMVDPTNDI | CRC |
| SLC12A2 | c.2483G>A | p.R828Q | ALLHLVHDFTKNVGLMICGHVHMGP[p.R828Q]QRQAMKEMSIDQAKYQRWLIKNKMKA | MGPQRQAMK,HMGPQRQAM,PQRQAMKEM,HMGPQR QAMK,HVHMGPQRQA,GPQRQAMKEM,VHMGPQRQA M | UCEC |
| SLC12A7 | c.2056de|C | p.H686fs | WDGIRGLSLNAARYALLRVEHGPP[p.H686fs]TPRTGGPRCW* | LRVEHGPT,RVEHGPPTPR | STAD |
| SLC13A2 | c.1478_1479insG | p.L493fs | IVLLGGGYALAKGSERSGLSEWLG[p.L493fs]KQADPTAECASSSHCHHPLPPG GHLHRVH* | SGLSEWLGK,SSHCHHPLP,HPLPPGGHL,KQADPTAEC,SSS HCHHPL,SEWLGKQAD,GLSEWLGKQA,RSGLSEWLGK,KQ ADPTAECA,ASSSHCHHPL,SEWLGKQADP,LPPGGHLHRV | KIRC |
| SLC13A5 | c.818A>C | p.Q273P | VNFASWFAFAFPNMLVMLLFAWLWL[p.Q273P]PFVYMRFNFKKSWGCGLESK KNEKAA | LLFAWLWLP,FAWLWLPFVY,WLPFVYMRF,LWLPFVYM,LFAWLWLPF, AWLWLPFVY,LFAWLWLPF,LFAWLWLPFV,AWLWLPFV YM,LWLPFVYMRF,PFVYMRFNFK,WLWLPFVYMR,LPFVY MRFNF | GBM |
| SLC16A14 | c.1484G>A | p.R495Q | YDFSFYICGLLYMIGILFLLIQPCI[p.R495Q]QIIEQSRRKYMDGAHV* | LLIQPCIQI,CIQIIEQSR,FLLIQPCIQI,LLIQPCIQII, QIIEQSRRKY,CIQIIEQSRR | UCEC |
| SLC16A6 | c.293_294 insG | p.G98fs | LTFSAPLATVLSNRFGHRLVVMLGG[p.G98fs]ATCQHRDGGRLLLTRGFSYVRR HRHHLWSGILL* | LLTRGFSYV,RLVVMLGGA,LTRGFSYVR,YVRRHRHHL,RHR HHLWSG,LLLTRGFSY,GFSYVRRHR,CQHRDGGRL,GRLLLT RGF,RGFSYVRRH,RHHLWSGIL,HHLWSGILL,LLLTRGFSYV, RLLLTRGFSY,SYVRRHRHHL,LTRGFSYVRR,RGFSYVRRHR, RHRHHLWSGI,MLGGATCQHR,ATCQHRDGGR,LLTRGFSY VR,VMLGGATCQH,CQHRDGGRLL,FSVVRRHRHH,YVRRH RHHLW,HRHHLWSGIL,RHHLWSGILL | STAD |
| SLC16A9 | c.1407_1424de|CTGCGTCCTGCTGGGAGG | p.CVLL GG470 de| | LGPPIVGWFYDWTQTYDIAFYFSGF[p.CVLLGG470de|]FILLLAALPSWDTCNK QLPKPAPTTFLYKVASNV* | AFYFSGFFI,FYFSGFFIL,YFSGFFILL,YPSGFFILL,IAFYFSGFF,IAFYFSG FFI,AFYFSGFFIL,FYFSGFFILL,YPSGFFFLLL,DIAFYFSGFF | KIRC |
| SLC17A9 | c.970G>A | p.V324I | HLINQGYRAITVRKLMQGMGLGLSS[p.V324I]IFALCLGHTSSFCESVVFASASIGLQ | GMGLGLSSI,GLSSIFALC,SIFALCLGH,MGLGLSSIF,LGLSSIF AL,LSSIFALCL,GLGLSSIFAL,GLSSIFALCL,GMGLGLSSIF,QG MGLGLSSI | GBM |
| SLC1A2 | c.1044_1045 insT | p.F348fs | LIIFIGGIFLPLIYVVTRKNPFSFF[p.F348fs]CWHFPSLDHCPGHRFQCWNFACHL SLPGRKSGD* | KNPFSFFCW,PFSFFCWHF,SFFCWHFPS,FFCWHFPSL,LDH CPGHRF,GHRFQCWN,FPSLDHCPG,CPGHRFQCW,WNFACHLSL,NPFS FFCWH,FPSLDHCPG,CPGHRFQCWN,SFFCWHFPSL,FQCW NFACHL,CWNFACHLSL,FACHLSLPGR,FSFFCWHFPS,RKN PFSFFCWH,NPFSFFCWHF,SLDHCPGHRF,FPSLDHCPGH | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SLC20A1 | c.984_985delAG | p.P328fs | PLQAVVEERTVSFKLGDLEEAPERE[p.P328fs]ASQRGLERGNQHR* | LEEAPEREA,RGLERGNQHR | UCEC |
| SLC22A15 | c.602C>T | p.S201L | NGGMSLVAFVLLNECVGTAYWALAG[p.S201L]LIGGLFFAVGIAQYALLGYFIRSWRT | ALAGLIGGL,GLIGGLFPA,LIGGLFFAV,TAYWALAGL,AYWALAGLI,LAGLIGGLF,AGLIGGLFF,GLIGGLFFAV,GTAYWALAGL,ALAGLIGGLF,TAYWALAGI,LAGLIGGLFF | CRC |
| SLC22A9 | c.1220G>A | p.R407Q | LQTLFGAVILLANCVAPWALKYMNR[p.R407Q]QASQMLLMFLLAICLLAIIFVPQEMQ | YMNRQASQM,ALKYMNRQA,KYMNRQASQ,RQASQMLL,M,MNRQASQML,QASQMLLMF,LKYMNRQAS,YMNRQASQML,KYMNRQASQM,RQASQMLLMF,MNRQASQMLL,L,KYMNRQASQ,NRQASQMLLM | GBM |
| SLC24A2 | c.401C>T | p.A134V | SENSTDHAQGDYPKDIFSLEERRKG[p.A134V]VIILHVIGMIYMFIALAIVCDEFFVP | RKGVIILHV,VIILHVIGMI,SLEERRKGVI,RKGVIILHVI,EERRKGVIIL | CRC |
| SLC24A5 | c.103C>A | p.R35S | ARRALLLGILWATAHLPLSGTSLPQ[p.R35S]SLPRATGNSTQCVISPSSEFPEGFFT | SLPQSLPRA,TSLPQSLPR,LPQSLPRAT,GTSLPQSLPR | LUAD |
| SLC25A17 | c.84del|T | p.F28fs | LSYESLVHAVAGAVGSVTAMTVFFP[p.F28fs]WIQLDFDFRLMRKENPKLHTWCSWRSLKKKDSWHHIEGGFQ* | AMTVFFPWI,IQLDFDFRL,RLMRKENPK,KLHTWCSWR,CSWRSLKKK,TWCSWRSLK,TAMTVFFPW,FFPWIQLDF,PWIQLDFDF,SWHHIEGGF,LMRKENPKL,HTWCSWRSL,WIQLDFDFR,DFDFRLMRK,TVFFPWIQL,KENPKLHTW,RSLKKKDSW,KKKDSWHHI,RLMRKENPKL,HTWCSWRSLK,TWCSWRSLKK,VTAMTVFFPW,TAMTVFFPWI,VFFPWIQLDF,LMRKENPKLH,MTVFFPWIQL,IQLDFDFRLM,RKENPKLHTW,L,HTWCSWRSL,LKKKDSWHHI,FPWIQLDFDF,NPKLHTWCSW | STAD |
| SLC25A32 | c.247C>G | p.Q83E | LRPKYNGILHCLTTIWKLDGLRGLY[p.Q83E]EGVTPNIWGAGLSWGLYFFYNAIKS | GLYEGVTPN,GLRGLYEGV,LYEGVTPNI,YEGVTPNIW,GLYEGVTPN,LYEGVTPNIW | BRCA |
| SLC25A40 | c.287G>A | p.R96Q | EGGNKLWYKKPGNFQGTLDAFFKII[p.R96Q]QNEGIKSLWSGLPPTLVMAVPATVIY | IQNEGIKSL,KIIQNEGIK,FKIIQNEGI,IQNEGIKSLW | CRC |
| SLC25A45 | c.316G>T | p.G106C | LLVLTATSHQERRAQPPSYMHIFLA[p.G106C]CTGGFLQAYCLAPPDLIKVRLQNQT | FLACCTGGF,YMHIFLACC,SYMHIFLAC,YMHIFLACCT,FLACCTGGFL,SYMHIFLACC,IFLACCTGGF,CCTGGFLQAY | BRCA |
| SLC25A48 | c.199G>A | p.A67T | TLSCIRVVYRRESMFGFFKGMSFPL[p.A67T]TSIAVYNSVVFGVFSNTQRFLSQHRC | GMSFPLTSI,TSIAVYNSV,MSFPLTSIA,FPLTSIAVY,MSFPLTSIAV,GMSFPLTSIA,LTSIAVYNSV,KGMSFPLTSI,SFPLTSIAVY,SIAVYNSVV | DLBCL |
| SLC25A48 | c.301C>A | p.R101S | VFGVFSNTQRFLSQHRCGEPEASPP[p.R101S]STLSDLLLASMVAGVVSVGLGGPVDL | SPPSTLSDL,EPEASPPSTL | LUAD |
| SLC25A5 | c.235A>T | p.I79F | IIDCVVRIPKEQGVLSFWRGNLANV[p.I79F]FRYFPTQALNFAFKDKYKQIFLGGVD | NLANVFRYF,RGNLANVFR,VFRYFPTQA,GNLANVFR,WRGNLANVF,FRYFPTQAL,NVFRYFPTQA,FWRGNLANVF,VFRYFPTQAI,RGNLANVFRY,GNLANVFRYF | CESC |
| SLC25A5 | c.352G>A | p.A118T | DKYKQIFLGGVDKRTQFWLYFAGNL[p.A118T]TSGGAAGATSLCFVYPLDFARTRLAA | WLYFAGNLT,LTSGGAAGA,NLTSGGAAGA,WLYFAGNLTS | KIRC |
| SLC26A3 | c.262G>A | p.V88I | WLPAYRLKEWLLSDIVSGISTGIVA[p.V88I]ILQGLAFALLVDIPPVYGLYASFFPA | GISTGIVAI,GIVAILQGL,AILQGLAFA,ILQGLAFAL,VAILQGL,AF,ISTGIVAIL,AILQGLAFAL,ILQGLAFALL,GISTGIVAIL,GIVAILQGLA,IVAILQGLAF,SGISTGIVAI | GBM |
| SLC26A7 | c.1886del|T | p.I629fs | LAHCTASLIKAMTYYGNLDSEKPIF[p.I629fs]LNRYLLQ* | KPIFLNRYL,NLDSEKPIFL,SEKPIFLNRY,DSEKPIFLNR,KPIFLNRYLL | STAD |
| SLC27A3 | c.1927del|C | p.P643fs | VNVYGVTVPGHEGRAGMAALVLRP[p.P643fs]TLWTLCSSTPTCLRTCHLM | WQMRASTPA,ALVLRPPTL,CSSTPTCLR,LTHCTFWTR,GSRSLWPPQ,PQRPSNSRK,QMRASTPAP,RASTPAPCL,NSRKF | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SLC2A6 | c.689C>A | p.A230D | PGPDSSGSRSLWPPQRPSNSRKFGWQ MRASTPAPCLTHCTFWTRL* | GWQM, LVLRPPTLW, RKFGWQMRA, APCLTHCTF, VLRPPT LWTL, TLCSSTPTCL, GSRSLWPPQR, RSLWPPQRPS, NSRKF GWQMR, QMRASTPAPC, LTHCTFWTRL, CLTHCTFWTR, TP TCLRTCHL, GPDSSGSRSL, AALVLRPPTL, ALVLRPPTLW, PQ RPSNSRKF, SNSRKFGWQM, RKFGWQMRAS, WQMRASTP AP, MRASTPAPCL, RPSNSRKFGW, APCLTHCTFW | PRAD |
| SLC2A7 | c.193G>A | p.A65T | LIMILLLSFMPNSPRFLLSRGRDEE[p.A2 30D]DLRALAWLRGTDVDVHWEFEQI QDNV | DLRALAWLR, EEDLRALAW, DEEDLRALAW, EEDLRALAWL | CRC |
| SLC2A7 | c.804C>A | p.H268Q | YNLSVNTPHKVFKSFYNETYFERH[p.A 65T]TTFMDGKLMLLLWSCTVSMPPLG GLL | TYFERHTTF, ETYFERHTT, HTTFMDGKL, YFERHTTFM, TTF MDGKLM, TYFERHTTFM, ETYFERHTTF | CRC |
| SLC2A7 | c.804C>A | p.H268Q | LRGHTMEAELEDMRAEARAEREAEG[p. H268Q]QLSVLHLCALRSLRWQLLSIIV LMAG | RAEGQLSVL, AERAEGQLS, AEGQLSVLH, QLSVLHLCAL, AER AEGQLSV, AEGQLSVLHL, GQLSVLHLCA | TGCT |
| SLC30 A9 | c.581G>A | p.R194H | LRSDVEAKSLEVWGSPEALAREKKL[p.R 194H]HKEAEIEYRERLFRNQKILREYRD FL | LAREKKLHK, LHKEAEIEY, REKKLHKEA, ALAREKKLHK, KLHK EAEIEY | CRC |
| SLC32 A1 | c.1480G>A | p.V494I | CFLLPSLFHLRLLWRKLLWHQVFFDI[p.V 494I][IAIFVIGGICSVSGFVHSLEGLIEEAY | VFFDIAIFV, LWHQVFFDI, FFDIAIFVI, IAIFVIGGI, QVFFDI AIF, HQVFFDIAI, LLWHQVFFDI, QVFFDIAIFV, VFFDIAIFVI, DIAIFVIGGI, HQVFFDIAIF, WHQVFFDIAI | STAD |
| SLC33 A1 | c.1625C>T | p.S542L | CVFIGFGWWFPLGPKFPKKL[QDEGSSL[p. S542L]LWKCKRNN* | KLIQDEGSSL, LQDEGSSLW, KKLQDEGSSL, KLIQDEGSSLW | CRC |
| SLC35 D3 | c.1250G>C | p.*417S | VWRLVRGTRYMKKDYLIENEELPSP[p. *417S]SEGGACTYLCAYTYFIC* | PSEGGACTY, CTYLCAYTY, YLCAYTYFI, TYLCAYTYFL, GACTYL CAY, SEGGACTYL, YLCAYTYFIC, CTYLCAYTYF, TYLCAYTYFI, GGACTYLCAY, ACTYLCAYTY, SPSEGGACTY | HNSC |
| SLC35 F2 | c.838G>A | p.A280T | CNKAFVFLLSWIVLRDRFMGVRIVA[p. A280T][TILAIAGIVMMTYADGFHSHSVI GIA | FMGVRIVAT, RIVATILAI, IVATILAIA, ATILAIAGI, GVRIVATIL, TILAIAGIV, MGVRIVATI, FMGVRIVATI, RIVATILAIA, ATILAI AGIV, RFMGVRIVAT, GVRIVATILA, MGVRIVATIL, VRIVATIL AI, TILAIAGIVM | CRC |
| SLC35 G2 | c.184del A | p.K62fs | INEGYGNFMEENPKKGLLSEMKKKG[p. K62fs]ELSLEPWIPYLHQOKT* | LSLEPWIPY, SLEPWIPYL, SEMKKKGEL, MKKKGELSL, GELSL EPWI, IPYLHQQKT, LSLEPWIPYL, EMKKKGELSL, ELSLEPWI PY, KKGELSLEPW | CESC |
| SLC37 A1 | c.1582G>A | p.V528I | ACALLFLIRLIHKELSCPGSATGDQ[p.V5 28I][IPFKEQ* | ATGDQIPFK, SATGDQIPF, SATGDQIPFK, GSATGDQIPF, CP GSATGDQI | TGCT |
| SLC38 A1 | c.298G>A | p.G100R | MSVFNLSNAIMGSGILGLAFALANT[p. G100R]RILLFLVLLTSVTLLSIYSINLLLIC | ALANTRILL, RILLFLVLL, LAFALANTR, NTRILLFLV, LANTRILL F, FALANTRIL, TRILLFLVL, ALANTRILLF, NTRILLFLVL, GLAPA LANTR, LAFALANTRI, FALANTRILL | TGCT |
| SLC38 A10 | c.3213_321 5del CAT | p.1071_107 2II>I | SDLRRRRRDLGPHAEGQLAPRDGVI[p. 1071_1072II>I]GLNPLPDVQNDLRG ALDAQLRQAAGGA | APRDGVIGL, RDGVIGLNPL | PAAD |
| SLC39 A12 | c.1883G>C | p.C628S | ILMNFISSLTAFMGLYIGLSVSADP[p.C6 28S]SVQDWIFTVTAGMFLYLSLVEMLP EM | SVQDWIFTV, DPSVQDWIF, GLSVSADPSV | LUAD |
| SLC39 A6 | c.158G>T | p.R53L | AFPQTEKISPNWESGINVDLAIST[p.R 53L]LQYHLQQLFYRYGENNSLSVEGFR KL | TLQYHLQQL, AISTLQYHL, LQYHLQQLF, DLAISTLQY, LQYHL QQLFY, TLQYHLQQLF, INVDLAISTL, VDLAISTLQY, LAISTLQ YHL, STLQYHLQQL | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SLC39 A7 | c.1144C>T | p.R382C | LHEVPHEVGDPAILVQSGCSKKQAM[p. R382C]CLQLLTAVGALAGTACALLTEG GAVG | KQAMCLQLL, AMCLQLLTA, KKQAMCLQL, AMCLQLLTAV, S KQAMCLQL, KKQAMCLQLL, KQAMCLQLLT | CRC |
| SLC39 A7 | c.1367_136 8insG | p.L456fs | SVLPELLREASPLQSLLEVLGLLGG[p.L4 56fs]SYHDGADCPP* | VLGLLGGSY, LLGGSYHDGA, EVLGLLGGSY, LEVLGLLGGS | CLL |
| SLC43A1 | c.398C>T | p.P133L | LVGSACFTASCTLMALASRDVEALS[p.P 133L]LLIFLALSLNGFGGICLTFTSLTLPN | ALSLLIFLA, LLIFLALSL, EALSLLIFL, RDVEALSLL, VEALSLL LIF, LSLLIFLAL, ALSLLIFLAL, SLLIFLALSL, ASRDVEALSL, EALSLLIFLA, RDVEALSLLI, VEALSLLIFL | CRC |
| SLC43A3 | c.647G>A | p.R216H | LLYEKGISLRASFIFISVCSTWHVA[p.R21 6H]HTFLLMPRGHIPYPLPPNYSYGLCP G | STWHVAHTF, TWHVAHTFL, HVAHTFLM, WHVAHTFLL, S TWHVAHTFL, VAHTFLLMPR, CSTWHVAHTF, TWHVAHTFL L, WHVAHTFLLM | CRC |
| SLC44A5 | c.208G>T | p.V70F | KPADTPSEEEDFGDPRTYDPDFKGP[p. V70F]FANRSCTDVLCCMIFLLCIIGYIVL G | FANRSCTDV, DFKGPFANR, TYDPDFKGPF, FANRSCTDVL | KIRC |
| SLC44A5 | c.554G>A | p.R185H | CPEKFLTYVEMQLLYTKDKSYWEDY[p. R185H]HQFCKTTAKPVKSLTQLLLDDD CPTA | HQFCKTTAK, SYWEDYHQF, YHQFCKTTA, KSYWEDYH QF, SYWEDYHQFC, HQFCKTTAKP, WEDYHQFCKT | CRC |
| SLC4A3 | c.3183de|G | p.L1061fs | SQKARRLLKGSGFHLDLLLIGSLGG[p.L1 061fs]SVGCLGCPGSRLPRSAPSPMSM R* | LLIGSLGGS, LIGSLGGSV, SLLGGSVGCL, RSAPSPMSM, SAPS PMSMR, LPRSAPSPM, LLIGSLGGSV, RLPRSAPSPM, RSAPSPMS MR, GSRLPRSAPS | STAD |
| SLC4A5 | c.1597A>G | p.I533V | WFPSDFYDGFHIQSIAILFIYLGC[p.I53 3V]VTNAITPFGGLLGDATDNYQGVMES FL | ILFIYLGCV, YLGCVTNAI, GCVTNAITF, AILFIYLGCV, FIYLGCV TNA, YLGCVTNAIT, ILFIYLGCVT, IYLGCVTNAI, LGCVTNAITF | LUAD |
| SLC4A8 | c.687C>G | p.N229K | LNDSMRVKVREALLKKHHHQNEKKR[p. N229K]KNLIPIVRSFAEVGKKQSDPHL MDKH | KKRKNLIPI, KRKNLIPIV, KKRKNLIPIV, EKKRKNLIPI, HQNEK KRKNL, KNLIPIVRSF | KIRC |
| SLC52A1 | c.1108_111 0de|GGC | p.G370de| | LSLLGMLFGAYIMALAILSPCPPLV[p.G 370de|]TTAGVLVLVLSWVLCLCVFSYV KVAASS | VTTAGVLV, LVTTAGVL, LVTTAGVLIV, VTTAGVLVV, C PPLVTTAGV | KIRC |
| SLC52A2 | c.1197_1198 insG | p.G399fs | LSWVLCLGVFSYVKVAASSLLHGGG[p. G399fs]PAGIAGSRRGHPGGLSARRCC YVPPDQHLSRVPQQKGLCRPL* | SLLHGGGPA, LSARRCCYV, HLSRVPQQK, CVVPPDQHL, GSR RGHPGG, RGHPGGLSA, GLSARRCCY, QQKGLCRPL, LLHGG GPAGI, GLSARRCCYV, GSRRGHPGGL, RGHPGGLSAR, SARR CCYVPP, VPPDQHLSRV | KIRC |
| SLC5A1 | c.157G>T | p.G53W | DISIVIYFVVVMAVGLWAMFSTNR[p. G53W]WTVGGFFLAGRSMVWWPIGA SLFASN | WTVGGFFLA, WAMFSTNRW, MFSTNRWTV, RWTVGGFFL, AMFSTNRWT, TNRWTVGGF, NRWTVGGFF, AMPSTNRW TV, LWAMFSTNRW, RWTVGGFFLA, STNRWTVGGF, TNR WTVGGFF | LUAD |
| SLC5A7 | c.1006G>T | p.G336C | KTTEEADMILPIVLQCLPVVISFF[p.G3 36C]CLGAVSAAVMSSADSSILSASSMF AR | YISFFCLGA, CLGAVSAAV, ISFFCLGAV, VVISFFCL, YISFFCL GAV, FCLGAVSAAV, VYISFFCLGA, CLGAVSAAVM, CPVYISF FCL | HNSC |
| SLC5A7 | c.1325G>T | p.G442V | IFPQLLCVLFVKGTNTYGAVAGYVS[p.G 442V]VLFLRITGGEPYLYLQPLIFYPGYY P | AVAGYVSVL, YVSVLFLRI, VAGYVSVLF, GYVSVLFLR, AGVVS VLFL, AGVVSVLFLR, AVAGYVSVLF, GYVSVLFLRI, YGAVAGY VSV, GAVAGYVSVL | LUAD |
| SLC6A10P | c.264A>C | p.K88N | WSFFTPLVCMGLFIFNVVYYKPLVV[p.K 88N]NNTNVYPWWGEAMGWAFVLSS MLCMP | YYKPLVVNN, YYKPLVVNNT, KPLVYNNTNV | GBM, KIRC |
| SLC6A11 | c.896G>T | p.W299L | TLPGASEGIKFYLYPDLSRLSDPQV[p.W 299L]LVDAGTQIFFSYAICLGCLT ALGSYN | RLSDPQVLV, VLVDAGTQI, SRLSDPQVL, LVDAGTQIF, LVDA GTQIFF, VLVDAGTQIF, LSRLSDPQVL | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SLC6A14 | c.255_256 insG | p.A85fs | FPYLTYSNGGAFLIPYAIMLALAGF[p. A85fs]FTFVLSGVFTGTIC* | LALAGFTFV,ALAGFTFVL,VLSGVFTGT,MLALAGFTF,FTFVL SGVF,AIMLALAGF,MLALAGFTFV,FVLSGVFTGT,VLSGVFT GT,AIMLALAGE,ALAGFTFVLS,AGFTFVLSGV,YAIMLALA GFT,IMLALAGFTF,GFTFVLSGVF,FTFVLSGVF,LALAGFTFVL AVPSEATKK,ATKKDQNLK,ATKKDQNLKR | KIRC |
| SLC6A9 | c.281G>A | p.R94K | LLPQLMAQHSLAMAQNGAVPSEATK[p. R94K]KDQNLKRGNWGNQIEFVLTSV GYAVG | | CLL |
| SLC6A9 | c.727C>T | p.R243W | AYCNNPWNTHDCAGVLDASNLTNGS[p. R243W]WPAALPSNLSHLLNHSLQRT SPSEEY | NLTNGSWPA,WPAALPSNL,ASNLTNGSW,NLTNGSWPAA, SWPAALPSNL,LTNGSWPAAL,DASNLTNGSW | BLCA |
| SLC7A10 | c.471de|C | p.P157fs | TSLAVISMTFSNYVLQPVFPNCIPP[p. P157fs]PQPPGCCPWPA* | FPNCIPPPQ | STAD |
| SLC7A2 | c.964C>T | p.R322W | TLAGAATCFYAFVGPDCIATTGEEV[p. R322W]WNPQKAIPIGIVTSLLVCFMAYF GVS | EVVNPQKAI,EEVWNPQKA,IATTGEEVW,EEVWNPQKAI, GEEVWNPQKA | UCEC |
| SLC8A1 | c.1292G>A | p.R431H | VSKIFFEQGTYQCLENCGTVALTII[p. R431H]HRGGDLTNTVFVDFRTEDGTANA GSD | GTVALTIIH,TVALTIIH,GTVALTIIHR | CRC |
| SLC8A1 | c.1297G>T | p.G433C | KIFFEQGTYQCLENCGTVALTIIRR[p.G4 33C]CGDLTNTVFVDFRTEDGTANAGS DYE | CGDLTNTVF,RCGDLTNTVF | LUAD |
| SLC9A2 | c.2237de|C | p.T746fs | SPQSYKMEWKNEVDVDSGRDMPSTP[p. T746fs]QHPTAEKRAPRRQAYYSSPF SLKTSLAQRGKTV* | SLAQRGKTV,KTSLAQRGK,RQAYYSSPF,AYYSSPFSL,RAPR RQAYY,YYSSPFSLK,SLKTSLAQR,KRAPRRQAY,PTAEKRAP R,MPSTPQHPT,SFSLKTSL,AYYSSPFSLK,STPQHPTAEK,FS LKTSLAQR,RQAYYSSPFS,QAYYSSPFSL,KRAPRRQAYY,PT AEKRAPRR,MPSTPQHPTA,SPFSLKTSLA,RRQAYYSSPF,AE KRAPRRQA | STAD |
| SLC9A4 | c.1892G>A | p.R631H | RTLSYNKYNLKPQTSEKQAKEILIR[p.R6 31H]HQNTLRESMRKGHSLPWGKPAG TKNI | ILIRHQNTL,LIRHQNTLR,HQNTLRESM,KEILIRHQN,ILIRH QNTLR,HQNTLRESMR,EILIRHQNTL,KQAKEILIRH,RHQNT LRESM,KEILIRHQNT | GBM |
| SLC9A5 | c.1341G>C | p.L447F | TKVPAKDYFVATTIWVFFTVIVQG[p.L4 47F]FTIKPLVKWLKVKRSEHHKPTLNQE L | VIVQGFTIK,FFTVIVQGF,FTIKPLVKW,GFTIKPLVK,FTVIVQGFT, TVIVQGFTI,VQGFTIKPL,FTIKPLVKWL,TVIVQGFTIK,QGFTIK PLVK,VFFTVIVQGF,GFTIKPLVKW,FTVIVQGFTI | BLCA |
| SLC9B1 | c.1338_1339 de|GT | p.V446fs | FAGPSFKEKIPIALAWMPKATVQAV[p. V446fs]RSSGSRNSKSLRTPLGTICEGCD DSSIFSHLDHSSKWSSTYGHSGA* | HSSKWSSTY,SLRTPLGTI,RSSGSRNSK,FSHLDHSSK,GSRNSKS LR,SSKWSSTYG,NSKSLRTPL,SHLDHSSKW,SKWSSTYG H,AVRSSGSRNS,KSLRTPLGTI,IFSHLDHSSK,SSKWSSTYGH, MPKATVQAVR,RNSKSLRTPL,CEGCDDSSIF,FSHLDHSSKW | KIRC |
| SLCO2A1 | c.1437G>C | p.M479I | IFHPVCGDNGIEYLSPCHAGCSNIN[p.M 479I]ISSATSKQLIYLNCSCVTGGSASAKT | ISSATSKQL,NININSATSK,ISSATSKQLI | CESC |
| SLIT1 | c.4379G>T | p.R1460L | SGTKGAHCVCDPGFSGELCEQESEC[p. R1460L]LGDPVRDFHQVQRGYAICQTT RPLSW | ESECLGDPV,CLGDPVRDF,QESECLGDPV | LUAD |
| SLITRK1 | c.134de|A | p.K45fs | TGDVCKEKICSCNEIEGDLHVDCEK[p.K 45fs]RASQCVSVSLPRLPSFTIYFCMAIP SLDFSLMSSLTFIMRLVCTWKTMACMK SFRGLFWGCSW* | FTIYFCMAI,SLMSSLTFI,LMSSLTFIM,SLTFIMRLV,IMRLVC TWK,TMACMKSFR,QVCSVSLPR,MSSLTFIMR,VSLPRLPSF, RLPSFTIYF,YFCMAIPSL,CMAIPSLDF,FSLMSSLTF,FIMRLV CTW,KITMACMKSF,CMKSFRGLF,RGLFWGCSW,TWKTM ACMK,KSFRGLFWG,LPRLPSFTI,IPSLDFSLM,RLVCTWKT M,KRASQVCSV,ASQVCSVSL,SQVCSVSLP,LDFSLMSSL,CT WKTMACM,MKSFRGLFW,CEKRASQVC,LPSFTIYFC,SLPR | STAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SLITRK1 | c.155G>A | p.R52H | KICSCNEIEGDLHVDCEKKGFTSLQ[p.R52H]HFTAPTSQFYHLFLHGNSLTRLFPNE | LPSFTI,RLPSFTIYFC,SLDFSLMSSL,FSLMSSLTFL,SLMSSLTFI M,RLVCTWKTMA,LMSSLTFIMR,FIMRLVCTWK,CTWKTM ACMK,KTMACMKSFR,SQVCSVSLPR,SFTIYFCMAI,IYFCM AIPSL,FCMAIPSLDF,DFSLMSSLTF,TFIMRLVCTW,CMKSF RGLFW,SSLTFIMRLV,MAIPSLDFSL,MSSLTFIMRL,RASQV CSVSL,LPRLPSFTIY,LPSFTIYFCM,MACMKSFRGL,SVSLPRL PSF,MRLVCTWKTM,WKTMACMKSF,ACMKSFRGLF,FRGL FWGCSW,CEKRASQVCS SLQHFTAPT,KGFTSLQHF,HFTAPTSQF,FTSLQHFTA, LQHFTAPTS,HFTAPTSQFY,KKGFTSLQHF,LQHFTA PTSQ,QHFTAPTSQF | CRC |
| SLITRK3 | c.641G>T | p.R214L | PTNLFKAVSLTHLDLRGNRLKVLFY[p.R214L]LGMLDHIGRSLMELQLEENPWN CTCE | FYLGMLDHI,RLKVLFYLG,KVLFYLGML,LKVLFYLG M,LFYLGMLDHI,RLKVLFYLGM,YLGMLDHIGR, LKVLFYLGML | LUSC |
| SLITRK3 | c.893C>T | p.S298L | REIRKTELCPLLSDSEVEASLGIPH[p.S298L]LSSSKENAWPTKPSSMLSSVH FTASS | GIPHLSSSK,LSSSKENAW,LGIPHLSSSK,VEASLGIPHL,HLSS SKENAW | CRC |
| SLITRK5 | c.1403G>T | p.R468M | NRISMIQDRAFGDLTNLRRLYLNGN[p.R468M]MIERLSPELFYGLQSLQYLFLQY NLI | RLYLNGNMI,YLNGNMIER,RRLYLNGNM,YLNGNMIERL,N MIERLSPEL,LYLNGNMIER,LRRLYLNGNM,RRLYLNGNMI, MIERLSPELF | LUAD |
| SLITRK5 | c.203G>T | p.R68L | YYGEICDNACPCEEKDGILTVSCEN[p.R68L]LGIISLSEISPPRFPIYHLLLSGNLL | ILTVSCENL,TVSCENLGI,CENLGIISL,NLGIISLSEI,LTVSCENL GI,CENLGIISLS | LUAD |
| SLITRK6 | c.2223C>A | p.N741K | HLQRSLLEQENHSPLTGSNMKYKT T[p.N741K]KQSTEFLSFQDASSLYRNILEKE REL | KQSTEFLSF,SNMKYKTTK,KYKTTKQST,TTKQSTEFL,KTTKQ STEF,GSNMKYKTTK,KTTKQSTEFL,MKYKTTKQST,YKTTKQ STEF,TKQSTEFLSF | LUAD |
| SMAD2 | c.962G>A | p.R321Q | SLTVDGFTDPSNSERFCLGLLSNVN[p.R321Q]QNATVEMTRRHIGRGVRLYYIG GEVF | LLSNVNQMA,VNQNATVEM,GLLSNVNQNA,NVNQNATVEM | CRC |
| SMAD4 | c.1082G>A | p.R361H | GETFKVPSSCPIVTVDGYVDPSGGD[p.R361H]HFCLGQLSNVHRTEAIERARLHIG KG | YVDPSGGDHF,DPSGGDHFCL | CRC |
| SMAP1 | c.506del A | p.E169fs | QPLVSSPSLQAAVDKNKLEKEKEKK[p.E169fs]RKKREKRSQKSRQNHLQLKSCR RKISNWSLKKVPALKLRSPLWIF* | ALKKLRSPL,KISNWSLKK,SLKKVPALK,KLRSPLWIF,KKRKRK REK,RKREKRSQK,RSQKSRQNH,SQKSRQNHL,KSRQNHLQ L,RRKISNWSL,RKISNWSLK,KVPALKKLR,HLQLKSCRR,WSL KKVPAL,RQNHLQLKS,KKVPALKKL,LKKLRSPLW,KKLRSPL WI,KISNWSLKKV,KSRQNHLQLK,SLKKVPALKK,WSLKKVP ALK,KRKREKRSQK,RSQKSRQNFIL,HLQLKSCRRK,RRKISN WSLK,CRRKISNWSL,NWSLKKVPAL,QKSRQNHLQL,RQNH LQLKSC,LQLKSCRRKI,ALKKLRSPLW,KKLRSPLWIF | UCS |
| SMARCA4 | c.1142G>A | p.R381Q | QKPRGLDPVEILQEREYRLQARIAH[p.R381Q]QIQELENLPGSLAGDLRTKATIEL KA | LQARIAHQI,RIAHQIQEL,HQIQELENL,RLQARIAHQI, ARIAHQIQEL | CRC |
| SMARCA4 | c.2738C>T | p.P913L | NHHCKLTQVLNTHYVAPRLLLTGT[p.P913L]LLQNKLPELWALLNFLLPTIFKSC ST | RLLLTGTLL,LLQNKLPEL,LTGTLLQNK,RRLLLTGTL, TLLQNKLPEL,LLTGTLLQNK,RRLLLTGTLL | HNSC |
| SMARCA5 | c.468_471 de lAGAA | p.T156fs | KQNLLSVGDYRHRRTEQEEDEELLT[p.T156fs]APKQPMFALDLKTLHRM* | APKQPMFAL,LLTAPKQPM,LTAPKQPMF,KQPMFALDL,LD LKTLHRM,KQPMFALDLK,LTAPKQPMFA,FALDLKTLHR,TA PKQPMFAL,LLTAPKQPMF,PMFALDLKTL,QEEDEELLTA | TGCT |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SMC3 | c.2908G>C | p.E970Q | ELGSLPQEAFEKYQTLSLKQLFRKL[p.E970Q]QQCNTELKKYSHVNKKALDQFVN FSE | KLQQCNTEL, KLQQCNTELK, QQCNTELKKY, RKLQQCNTEL | TGCT |
| SMCR8 | c.523G>A | p.E175K | VRPFCMAYISADQHKIMQQFQELSA[p.E175K]KFSRASECLKTGNRKAFAGELEK KLK | ELSAKFSRA, QQFQELSAK, QFQELSAKF, AKFSRASEC, AKFSRASEC, MQQ FQELSAK, KFSRASECLK, QQFQELSAKF, AKFSRASECL, QELS AKFSRA | UCEC |
| SMG1 | c.8087C>A | p.P2696H | LICNTTVERCQELYRKYEMQYAPQP[p.P2696H]HPTVCQFITATEMTLQRYAAD INSRL | YAPQPHPTV, APQPHPTVC, QPHPTVCQF, MQYAPQPHP, Q YAPQPHPTV, YEMQYAPQPH, MQYAPQPHPT, HPTVCQFIT A, QPHPTVCQFI | TGCT |
| SMG7 | c.2536_2537 insA | p.E846fs | TQDPIKLFEPSLQPPVMQQQPLEKK[p.E846fs]NEAFSHGAI* | NEAFSHGAI, QPLEKNEAF, KKNEAFSHGA | PRAD |
| SNAPC1 | c.633de|T | p.D211fs | QNMKHVISVDKSKPDKALSLIKDDF[p.D211fs]LTILRT* | LIKDDFLTI, IKDDFLTIL, SLIKDDFLTI, ALSLIKDDFL, LIKDDFLTIL | STAD |
| SNAPC2 | c.875del|C | p.T292fs | IPAGGSLGPAAEGDGAGSKAPEETP[p.T292fs]QPPRRPSTAN* | TPQPPRRPS, TPQPPRPST | STAD |
| SND1 | c.112C>G | p.Q38E | GPAVPTVQRGIIKMVLSGCAIIVRG[p.Q38E]EPRGGPPPERQINLSNIRAGNLAR RA | AIIVRGEPR, CAIIVRGEPR | CESC |
| SND1 | c.2163de|C | p.H721fs | VQDVETGTQLEKLMENMRNDIASHP[p.H721fs]L* | RNDIASHPL, MRNDIASHPL | STAD |
| SOAT1 | c.190de|T | p.F64fs | GRIDIKQLIAKKIKLTAEAEELKPF[p.F64fs]L* | AEAEELKPFL | STAD |
| SOLH | c.2141G>A | p.R714H | GFLMGASCGGGNMKVDDSAYESLGL[p.R714H]HPRHAYSILDVRDVQGTRLLRLRNPW AQMLASGTMDAQMLASSTQDSAMLG | GLHPRHAYS, LGLHPRHAY, HPRHAYSIL, SAYESLGLH, YESL GLHPR, GLHPRHAYSI, SLGLHPRHAY, YESLGLHPRH | LIHC |
| SON | c.2723C>T | p.S908L | [p.S908L]LKSPDPYRLAQDPYRLAQDP YRLGHD | GLKSPDPYR, LGLKSPDPY, TQDSAMLGL, LKSPDPYRL, GLKS PDPYRL, TQDSAMLGLK, MLGLKSPDPY, STQDSAMLGL | LUSC |
| SON | c.4075_4098de|GTCCTGGAGTCTTCGGCTGTGACC | p.VLES SAVT13 59de| | LAESILEPPAMAAPESSAMAVLESS[p.VLESSAVT1359de|]TVTVLESSTVTVLEP SVVTVPEPPVVAEPDYVTIPVPVVSALE PSVPVL | AMAVLESST, MAVLESSTV, AMAVLESSTV, AVLESSTVTV | KIRC |
| SORBS1 | c.1710C>A | p.F570L | VLTNEKMSRDISPEEIDLKNEPWYK[p.F570L]LFSELEFGKPPPKIWDYTPGDCSIL | KNEPWYKLF, PWYKLFSEL, LKNEPWYKL, YKLFSELEF, KLFSE LEFGK, WYKLFSELEF, EPWYKLFSEL, LKNEPWYKLF | CRC |
| SORBS1 | c.3466G>A | p.V1156M | AERGAGERGPCGPKISKKSCLKPSD[p.V1156M]MVRCLSTEQRLSDLNTPEESRP GKPL | CLKPSDMVR, KPSDMVRCL, MVRCLSTEQR, KKSCLKPSDM | CRC |
| SORBS2 | c.2596C>T | p.P866S | VFEALDSALKICDQIKAEKKRGSL[p.P866S]SDNSIIHRLISELLPDVPERNSSLRA | RGSLSDNSI, LSDNSILHRL, SLSDNSILHR, RGSLSDNSIL | PAAD |
| SORBS2 | c.3472 de|G | p.E1158fs | DRIHSLSSNKPQRPVFTHENIQGGG[p.E1158fs]NRFRLCITILPGMKMSWSSEKV MSLMSWKSVMTAGLWGPQEEPNSLV LSPETTSRGCELRSLLI* | SSEKVMSLM, KMSWSSEKV, SLMSWKSVM, LMSWKSVMT, KVMSLMSWK, CITILPGMK, RFRLCITIL, ILPGMKMSW, MS LMSWKSV, MSWKSVMTA, TTSRGCELR, MTAGLWGPQ, ET TSRGCEL, GPQEEPNSL, MSWSSEKVM, NRFRLCITI, ITILPG MKM, WSSEKVMSL, EKVMSLMSW, WKSVMTAGL, KSVMT AGLM, QEEPNSLVL, SEKVMSLMS, VMSLMSWKSV, SLMS WKSVMT, LMSWKSVMTA, RLCITILPGM, GMKMSWSSEK, LVLSPETTSR, RFRLCITILP, MSLMSWKSVM, SWKSVMTAGL, | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SORCS2 | c.958C>T | p.R320W | FWSVSGVDADPDLVHVEAQDLGGDF[p.R320W]MYVTCAIHNCSEKMLTAPFAGPIDHG | NIQGGNRFR, ETTSRGCELR, WSSEKVMSLM, KMSWSSE KVM, IQGGNRFRL, NRFRLCITIL, MKMSWSSEKV, SEKVM SLMSW, MSWKSVMTAG, WKSVMTAGLW | CRC |
| SORL1 | c.614G>T | p.R205L | ADAYAQYLWITFDFCNTLQGFSIPF[p.R205L]LAADLLLHSKASNLLLGFDRSHPNKQ | DLGGDFWV, DFWYVTCAI, GDFWYVTCA, AQDLGGDFWY, GDFWYVTCAI, EAQDLGGDFW | LUAD |
| SOS1 | c.697A>T | p.N233Y | FMAEIRQYIRELNLIIKVFREPFVS[p.N233Y]YSKLFSANDVENIFSRIVDIHELSVK | LQGFSIPFL, PFLAADLLI, IPFLAADLL, TLQGFSIPFL, FLAADLL LHS, LAADLLLHSK, FSIPFLAADL, IPFLAADLLL | LUAD,UCEC |
| SOWAHA | c.371G>C | p.R124P | AAQPSKPTSTVLPRSASAPGAPPLV[p.R124P]PVPRPVEPPGDLGLPTEPQDTPGGPA | PFVSYSKLF, VFREPFVSY, VSYSKLFSA, EPFVSYSKL, REPFVSY SK, FVSYSKLFSA, KVFREPFVSY, VFREPFVSYS, REPFVSYSKL, EPFVSYSKLF | LUAD,UCEC |
| SOX17 | c.1208G>T | p.S403I | PYQGHDSGVNLPDSHGAISSVVSDA[p.S403I]ISAVYYCNYPDV* | APGAPPLVPV | ACC |
| SOX6 | c.2155C>T | p.R719W | HLEKPYNYKYKPRPKRTCIVDGKKL[p.R719W]IGEYKQLMRSRRQEMRQFFTVGQQP | VSDAISAVY, ISAVYYCNY, VVSDAISAV, ISSVVSDAI, SDAISA VYY, VVSDAISAVY, VSDAISAVYY, SVVSDAISAV, AISSVVSD AI, AISAVYYCNY | UCEC |
| SOX7 | c.925del|C | p.L309fs | RRIPHLPGHPYSPEYAPSPLHCSHP[p.L309fs]WAPWLASPPASP* | LWIGEYKQL, GKKLWIGEY, KLWIGEYKQL, LWIGEYKQLM, WIGEYKQLMR | CRC |
| SOX9 | c.223G>A | p.E75K | ENTFPKGEPDLKKESEEDKPFVCIR[p.E75K]KAVSQVLKGYDWTLVPMPVRVNGSSK | SHPWAPWPL, SPLHCSHPW, HPWAPWPLA, HCSHPWAP W, WPLASPPAS, CSHPWAPWPL, APWPLASPPA, LHCSHP WAPW, HPWAPWPLAS | STAD |
| SP4 | c.17_19 del|AGG | p.E11del | MSDQKEEEE[p.E11de]|AAAAAAAA TEGGKTSEPENNNKKPKTSG | CIRKAVSQV, RKAVSQVLK, FPVCIRKAV, IRKAVSQVL, CIRKA VSQVL, IRKAVSQVLK, KAVSQVLKGY, FPVCIRKAVS | LUAD |
| SP4 | c.19G>A | p.E7K | MSDQKK[p.E7K]KEEEEAAAAAAMATEGGKTSEPENNN | KEEEEAAAA, KEEEEAAAAA | LUSC |
| SPAG16 | c.1315G>T | p.V439L | GDTTVKLWDLCKGDCILTFEGHSRA[p.V439L]LWSCTWHSCGNFVASSSLLDKTSKIWD | KEEEEAAAA, KEEEEAAAAA | TGCT |
| SPAG16 | c.1462C>T | p.P488S | WDVNSERCRCTLYGHTDSVNSIEFF[p.P488S]SFSNTLLTSSADKTLSIWDARTGICEGQESTGQYVIDEEPTWDIMVRQSYP | ALWSCTWHS, HSRALWSCT, FEGHSRALW, SRALWSCTW, R ALWSCTWH, ALWSCTWHSC, LITPEGHSRAL, TPEGHSRALW, HSRALWSCTW | LUAD |
| SPAG17 | c.3790 de|C | p.Q1264fs | LVYTFGETVALGASGIVIWGTLSIM[p.Q1264fs]RG* | EFFSFSNTL, NSIEFFSFS, VNSIEFFSF, IEFFSFSNT, FSFSNTLLT, SVNSIEFFSF, EFFSFSNTL, IEFFSFSNTL, FSFSNTLLTS IMVRQSYPR, MVRQSYPRG, DIMVRQSYPR | SKCM |
| SPAM1 | c.1037G>A | p.R346Q | QVRAYIRHLNRIVTIIQKWWRSFLG[p.R346Q]QSMKSCLLLDNYMETILNPYIINVTL | IMQSMKSCLL, MQSMKSCLL, TLSIMQSM, GTLSIMQSM, Q SMKSCLLL, IMQSMKSCLL, SIMQSMKSCL, MQSMKSCLL, G TLSIMQSMK, WGTLSIMQSM | STAD |
| SPATA17 | c.215G>A | p.R72K | NDFKPQCKRTNLVANDGKNSCPVSS[p.R72K]KKQYQLTVQVAYYTMMMNLYNAMAVR | FLGKKQYQL, KWWRSFLGK, WWRSFLGKK, RSFLGKKQY, G KKQYQLTV, FLGKKQYQLT, SFLGKKQYQL, KWWRSFLGKK, WRSFLGKKQY, KKQYQLTVQV | GBM |
| SPATA22 | c.449C>T | p.S150L | KVCTKTMPIGPDVSLENLAAETCFF[p.S150L]VAQQQKQLRIPEPPNLSRNKETELLR | VSSVAQQQK, SVAQQQKQLR, GKNSCPVSSV | CESC |
| SPATA5L1 | c.2055 de|T | p.C685fs | KVCTKTMPIGPDVSLENLAAETCFF[p.C685fs]|LELILETSAQKLL|CWLCKKMD* | LAAETCFFL, LILETSAQK, KLLCWLCKK, ETCFFLELI, AETCFFL EL, LETSAQKLL, LELILETSA, NLAAETCFFL, FLELILETSA, LILET | CRC |
| | | | | | STAD |

TABLE 8-continued

| gene | cDNA Change | Protein Change | Mutation Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SPATA9 | c.566G>T | p.C189F | AVLKKVKNIFQEEESIRQNREESEN[p.C189F]FRKAFSEPVLSEPMFAEGEIKAKPYR | SAQKL, KLLCWLCKKM, AQKLLCWLCK, ETCFFLELIL, AETCFFLELI FRKAFSEPV, EESENFRKA, NFRKAFSEPV, RQNREESENF, EE SENFRKAF, FRKAFSEPVL, REESENFRKA | KIRC |
| SPEG | c.2831C>T | p.A944V | EAEGGLCRLRILAAERGDAGFYTCK[p.A944V]VVNEYGARQCEARLEVRAHPESRSLA | YTCKVVNEY, DAGFYTCKV, FYTCKVVNEY | CRC |
| SPEG | c.2975_2976insG | p.A992fs | AVLAPLQDVDVGAGEMALFECLVAG[p.A992fs]AH* | FECLVAGAH, ALFECLVAGA | KIRC |
| SPEN | c.2407_2408de|GA | p.E803fs | RLERYTKNEKTDKERTFDPERVERE[p.E803fs]TLNTEGKSGKGQN* | TLNTEGKSGK | GBM |
| SPESP1 | c.363C>G | p.F121L | EETTFPTGGFTPEIGKKKHTESTPL[p.F121L]LWSIKPNNVSIVLHAEEPYIENEEPE | KKHTESTPL, KHTESTPLW, TESTPLWSI, KKKHTESTPL, KKHT ESTPLW | BLCA |
| SPG20 | c.696de|T | p.F232fs | QPPPLETLGLDADELLIPNGVQIF[p.F232fs]L* | IPNGVQIFL, LIPNGVQIFL | STAD |
| SPIN2B | c.448A>G | p.M150V | ANTIIGKAVEHMFEGEHGSKDEWRG[p.M150V]VVLAQAPIMKAWFYITYEKDPVLYMY | KDEWRGVVL, VVLAQAPIM, DEWRGVVLA, VVLAQAPIMK, SKDEWRGVVL, RGVVLAQAPI, DEWRGVVLAQ | TGCT |
| SPIN4 | c.512A>G | p.Y171C | PVMDTWFYITYEKDPVLYMYTLLDD[p.Y171C]CKDGDLRIIPDSNYYFPTAEQEPGEV | YMYTLLDDC, YMYTLLDDCK | LUAD |
| SPINT1 | c.947C>T | p.A316V | LREEECILACRGVQQGPLRGSSGAQ[p.A316V]VTFPQGPSMERRHPVCSGTCQPTQFR | VTFPQGPSM, GSSGAQVTF, RGSSGAQVTF, AQVTFPQGPS | GBM |
| SPOP | c.148G>A | p.E50K | TQIKVVKFSYMWTINNFSFCREEMG[p.E50K]KVIKSSTFSSGANDKLKWCLRVNPKG | KVIKSSTFS, GKVIKSSTF, FSFCREEMGK, MGKVIKSSTF | UCEC |
| SPOP | c.304T>G | p.F102V | DEESKDYLSLYLLLVSCPKSEVRAK[p.F102V]VKFSILNAKGEETKAMESQRAYRFVQ | KSEVRAKVK, RAKVKFSIL, KVKFSILNA, SEVR AKVKF, KVKFSILNAK, RAKVKFSILN, EVRAKVKFSI, KSE VRAKVKF, VRAKVKFSIL, AKVKFSILNA, CPKSEVRAKV | PRAD |
| SPOP | c.305T>G | p.F102C | DEESKDYLSLYLLLVSCPKSEVRAK[p.F102C]CKFSILNAKGEETKAMESQRAYRFVQ | KSEVRAKCK, RAKCKFSIL, KCKFSILNA, SEVRAKCKF, RAKCKFSILN, KCKFSILNAK, EVRAKCKFSI, KSEVRAKCKF, VRAKCKFSIL | PRAD |
| SPOP | c.391T>G | p.W131G | ILNAKGEETKAMESQRAYRFVQGKD[p.W131G]GGFKKFIRRDFLLDEANGLLPDDKLT | QGKDGGFKK, GGFKKFIRR, GKDGGFKKF, RFVQGKDGGF | PRAD |
| SPOP | c.397T>A | p.F133I | NAKGEETKAMESQRAYRFVQGKDWG[p.F133I]IKKFIRRDFLLDEANGLLPDDKLTLF | FVQGKDWGI, DWGIKKFIR, WGIKKFIRR, GKDWGIKKF, RFV QGKDWGI, DWGIKKFIRR | PRAD |
| SPOP | c.397T>G | p.F133V | NAKGEETKAMESQRAYRFVQGKDWG[p.F133V]VKKFIRRDFLLDEANGLLPDDKLTLF | FVQGKDWGV, DWGVKKFIR, GKDWGVKKF, DWGVKKFIRR | PRAD |
| SPOP | c.398T>G | p.F133C | NAKGEETKAMESQRAYRFVQGKDWG[p.F133C]CKKFIRRDFLLDEANGLLPDDKLTLF | DWGCKKFIR, GKDWGCKKF, DWGCKKFIRR | PRAD |
| SPOP | c.399C>G | p.F133L | NAKGEETKAMESQRAYRFVQGKDWG[p.F133L]LKKFIRRDFLLDEANGLLPDDKLTLF | FVQGKDWGL, DWGLKKFIR, GKDWGLKKF, LKKFIRRDF, FV QGKDWGLK, RFVQGKDWGL, DWGLKKFIRR | PRAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SPTA1 | c.5195A>C | p.K1732T | EKLKEAVALFQFFQDLDDESWIEE[p.K1732T]TLIRVSSQDYGRDLQGVQNLLK KHKR | WIEETLIRV,EESWIEETL,SWIEETLIRV,TLIRVSSQDY,ESWIE ETLIR,DEESWIEETL,EESWIEETLI | STAD |
| SPTA1 | c.6032C>T | p.A2011V | PEITDLKDKLISAQHNQSKAIEERY[p.A2 011V]VALLKRWEQLLEASAVHRQKLLE KQL | RYVALLKRW,AIEERYVAL,KAIEERYVA,IEERYVALL,AIEERY VALL,KAIEERYVAL | GBM |
| SPTA1 | c.6727G>T | p.D2243Y | DLGDNLEDALILDIKYSTIGLAQQW[p.D 2243Y]YQLYQLGLRMQHNLEQQIQAK DIKGV | LAQQWYQLY,GLAQQWYQL,QOWYQLYQL,WYQLYQLGL, AQQWYQLYQ,STIGLAQQWY,AQQWYALYQL,QWYQLYQ LGL,GLAQQWYQLY,WYQLYQLGLR,YQLYQLGLRM | LUAD |
| SPTA1 | c.7099G>T | p.G2367C | FLIDKESENIKSSDEIENAFQALAE[p.G2 367C]CKSYITKEDMKQALTPEQVSFCA THM | ALAECKSYI,QALAECKSY,ALAECKSYIT,NAFQALAECK,FQA LAECKSY,CKSYITKEDM | LUAD |
| SPTB | c.256C>T | p.R86C | KWVNSHLARVSCRITDLYKDLRDGR[p. R86C]LLIKLLEVLSGEMLPKPTGKMRI HC | RLLIKLLEVL,LLIKLLEVL,RDGRLLIKL,RLLIKLLEVL,DLRDGRLL IK | CRC |
| SPTB | c.5591C>T | p.T1864I | APERELHLLGVGVQQFQDVATRLQT[p. T1864I]VAGEKAEAIQNKEQEVSAAW QALLD | ATRLQTVVA,VATRLQTVY,DVATRLQTV,RLQTVYAGEK,VY AGEKAEAI,ATRLQTVYAG,TVYAGEKAEA,DVATRLQTVY,L QTVYAGEKA | KIRC |
| SPTBN4 | c.5978C>T | p.A1993V | ADKPRDVSSVEVLMNVHQGLKTELE[p. A1993V]VRVPELTTCQELGRSLLLNKSA MADE | ELEVRVPEL,TELEVRVPE,GLKTELEVRV,HQGLKTELEV,TEL EVRVPEL,LEVRVPELTT | CRC |
| SPTLC3 | c.290G>A | p.R97K | IGTLFGVLRDFLRNWGIEKCNAAVE[p.R 97K]KKEQKDFVPLYQDFENFYTRNLYM RI | KKEQKDFVPL | SKCM |
| SPTY2D1 | c.1454del|C | p.P485fs | GSSRGPGRPVSSPHELRRPVSGLGP[p.P 485fs]RGGLSVALGDP* | GPRGGLSVA,GLGPRGGLSV,GPRGGLSVAL | STAD |
| SRCAP | c.5625_562 6insC | p.Q1875fs | RSGPPSPPSTATSFGGPRPRRQPPP[p. Q1875fs]TTSFPFLSGLPGGKAEAAAV* | GLPGGKAEA,RQPPPTSF,TSFPFLSGL,RPRRQPPT,PPFLS GLPG,FLSGLPGGA,GLPGGKAEAA,TTSFPFLSGL,RPRRQP PPTT,QPPPTTSPPF,RRQPPPTTSF,PPFLSGLPGG | KIRP |
| SRCAP | c.5626_562 7insC | p.P1876fs | RSGPPSPPSTATSFGGPRPRRQPPP[p.P 1876fs]TTSFPFLSGLPGGKAEA AAV* | GLPGGKAEA,RQPPPTSF,TSFPFLSGL,RPRRQPPT,PPFLS GLPG,FLSGLPGGA,GLPGGKAEAA,TTSFPFLSGL,RPRRQP PPPT,QPPPTTSPPF,RRQPPPTTSF,PPFLSGLPGG | STAD |
| SRCIN1 | c.2595del|C | p.P865fs | LSQSPKKVTAETDFNKSVDFEMPPP[p. P865fs]APR* | FEMPPPAPR,VDFEMPPPA,DFEMPPPAPR | STAD |
| SREBF2 | c.2289del|C | p.H763fs | LSRAQSLCGPEHSAVPDSLRWLCHP[p. H763fs]WARSFSWSGAGL* | RWLCHPWAR,RSFSWSGAG,HPWARSFSW,SLRWLCHPW,LCH PWARSF,SLRWLCHPWA,CHPWARSFSW,RW LCHPWARS,WARSFSWSGA,RSFSWSGAGL,HPWARSFSWS, WLCHPWARSF,DSLRWLCHPW | STAD |
| SRGAP1 | c.182C>T | p.T61M | EQQTEMRVQLIQDLQDFFRKKAEIE[p. T61M]MEYSRNLEKLAERFMAKTRSTK DHQQ | MEYSRNLEK,KKAEIEMEY,IEMEYSRNL,RKKAEIEMEY,MEY SRNLEKL | MM |
| SRPRB | c.40G>A | p.G14S | MASADSRRVADGG[p.G14S]SAGGTF QPYLDTLRQELQQTDPTLLS | SAGGTFQPY,GSAGGTFQPY,ADGGSAGGTF | BLCA |
| SRRM2 | c.6769G>T | p.A2257S | IPAASAAMNLASARTPAIPTAVNL[p. A2257S]SDSRTPAAAAMNLASPRTAV APSAV | NLSDSRTPA,NLSDSRTPAA | TGCT |
| SRSF11 | c.51_52ins G | p.G17fs | MSNTTVVPSTAGPGPSGG[p.G17fs]A RWRWWWRRRRRHRGNPGD* | RWRRWWWRR,RWWWRRRRR,GARWRRWWWR,RWR RWWWRRR,RWWWRRRRRH,WWWRRRRRHR | PRAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SSPO | c.12593del C | p.S4198fs | PRGQQSRFRSSTSGSWAPECREEQS[p. S4198fs]RASPALSPRAHPCACRALAPA PWGTAGCRGSASGAPAPRRV* | ALAPAPWGT, ALSPRAHPC, RASPALSPR, SASGAPAPR, QSR ASPALS, RAHPCACRA, RGSASGAPA, SPALSPRAH, SPRAHP CAC, APAPWGTAG, EQSRASPAL, CRALAPAPW, EEQSRASP A, ALAPAPWGTA, ALSPRAHPCA, GSASGAPAPR, RASPALSPRA, RAHPCACRAL, REEQSRASPA, EEQSRAS PAL, ACRALAPAPW | PRAD |
| ST18 | c.2334C>A | p.H778Q | KTLKSLMAANSQELKCPTPGCDGSG[p. H778Q]QVTGNYASHRSLSGCPRARKG GVKMT | GSQVTGNY, GQVTGNYAS, QVTGNYASHR, GQVTGNYAS H | LUAD |
| ST6GA LNAC1 | c.1061G>A | p.S354N | ELNYSLVQKVVTRFPPVPQQQLLLA[p. S354N]NLPAGSLRCITCAVVGNGGILNN SHM | LLANLPAGS, QQQLLLANL, LANLPAGSL, LLANLPAGSL, NLPAGSLRCI, LANLPAGSLR, QQLLLANLPA | TGCT |
| STAB1 | c.3358_335 9insC | p.P1120fs | ASVDVADLLATNGVLHILSQVLLPP[p.P 1120fs]PRGCARWAGVAAAAGLGACL QPLPGIAAAPWVGAPD* | GLGACLQPL, RGCARWAGV, CARWAGVAA, RWAGVAAAA, IAAAPWVGA, QPLPGIAAA, ARWAGVAAA, LQPLPGIAA, LPGIAAAPW, GIAAAPWVGA, RGCARWAGVA, CAR WAGVAAA, LLPPPRGCAR, ARWAGVAAAA, AAAAGLGACL, AGLGACLQPL, LQPLPGIAAA, LPPPRGCARW, LPGIAAAPWV | STAD |
| STAC3 | c.349G>T | p.G117W | FKDHFFKKPKFCDVCARMIVLNNKF[p. G117W]WLRCKNCKTNIHEHCQSVTE MQRCFG | VLNNKFWLR, WLRCKNCKT, IVLNNKFWLR, RMIVLNNKFW, KFWLRCKNCK, MIVLNNKFWL | LUAD |
| STAM | c.427T>C | p.Y143H | TDELKNDLLLKKVNVEYQEYLQSKNK[p.Y 143H]HKAEILKKLEHQRLIEAERKRIAQ MR | KHKAEILKK, YLQSKNKHKA, KNKHKAEILK, SKNKHKAEIL | TGCT |
| STARD8 | c.1985G>C | p.G662A | RRNKTPDYRGQHVFGVPPLIHVQRT[p. G662A]AQPLPQSIQQAMRYLRSQCLD QVGIF | HVQRTAQPL, RTAQPLPQSI, IHVQRTAQPL | TGCT |
| STAT2 | c.1466_146 7insC | p.P489fs | AWASVLWFNLLSPNLQNQQFFSNPP[p. P489fs]NGPLELAGPCSQLAVLLLCWP RPQLRPAEHAEKQAVRAEL* | LLCWPRPQL, AVILLLCWPR, FSNPPNGPL, ELAGPCSQL, NPP NGPLEL, WPRPQLRPA, RPQLRPAEH, QQFFSNPPN, AEHAE KQAV, LLLCWPRPQL, QLRPAEHAEK, SQLAVLLLCW, LAVLL LCWPR, LLCWPRPQLR, ELAGPCSQLA, WPRPQLRPAE, RPQ LRPAEHA, RPAEHAEKQA, QQFFSNPPNG, FFSNPPNGPL, LE LAGPCSQL, AEKQAVRAEL | STAD |
| STAT3 | c.1982A>T | p.D661V | SVEPYTKQQLNNMSPAEIIMGYKIM[p. D661V]VATNILVSPLIVYLYPDIPKEEAFG KY | IIMGYKIMV, IMGYKIMVA, IMVATNILV, KIMVATNIL, YKIM VATNI, IIMGYKIMVA, KIMVATNILV, IMGYKIMVAT, GYKIM VATNI, EIIMGYKIMV, YKIMVATNIL, IMVATNILVS, VATNILVSPL | HNSC |
| STAT5B | c.1101_110 2insC | p.P367fs | KTQTKFAATVRLLVGGKLNVHMNPP[p. P367fs]PGEGHHHQ* | HMNPPPGEGH | STAD |
| STAT6 | c.1061_106 2insC | p.P354fs | QVLKTQTKFQAGVRFLLGLRFLGAP[p.P 354fs]SQASAGQGRHGDREAGAGAEC ASGSWGWSRKHWRNHQQHCALGEQ HSWELLLCPVQEPASQEDQAV* | LLCPVQEPA, ASGSWGWSR, SGSWGWSRK, SWGWSRKH W, RFLGAPSQA, WSRKHWRNH, WGWSRKHWR, REAGAG AEC, RNHQQHCAL, CALGEQHSW, GEQHSWELL, EQHSWE LLL, WELLLCPVQ, FLGAPSQASA, ALGEQHSWEL, HSWELLLCPV, LLLCPVQEPA, CASGSWGWSR, ASGSWGWSRK, HWR NHQQHCA, SWGWSRKHW, LRFLGAPSQA, SQASAGQGRL H, REAGAGAECA, AGABCASGSW, WRNHQQHCAL, WRNHQQHCA, WRNHQQHCAL, QQHCALGE QH, GEQHSWELL | KIRC |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| STAT6 | c.1402G>C | p.D468H | LGPGKLPIQLQALSLPLVIVHGNQ[p.D468H]HNNAKATILWDNAFSEMDRVPFVVAE | HGNQHNNAK, NQHNNAKAT, NQHNNAKATI | DLBCL |
| STK11 | c.837del|C | p.G279fs | EGDNIYKLFENIGKGSYAIPGDCGP[p.G279fs]RSLTC* | YAIPGDCGPR, IPGDCGPRSL | LUSC |
| STK11IP | c.464C>A | p.A155E | PLHCLHGLRGIYSQLETLICSRSLQ[p.A155E]ELEELLSACGDFCSALPWLALLSAN | SLQELELL, QELEELLSA, LICSRSLQEL, RSLQELEELL, LQELEE LLSA, QELEELLSAC | KIRC |
| STK19 | c.265G>A | p.D89N | RGARPGGDAGTPGETVRHCSAPE[p.D89N]NPIFRFSSLHSYPPPGTIKSRDMSWK | SAPENPIFR, NPIFRFSSL, CSAPENPIF, CSAPENPIFR, SAPEN PIFRF, RHCSAPENPI, HCSAPENPIF, NPIFRFSSLH | SKCM |
| STK19 | c.52_53ins G | p.R18fs | MQKWFSAPDDAIIQRQW R[p.R18fs]GKPLPGRGRCELHEGG* | IIQRQWRGK, LPCRGRCEL, QROWRGKPL, RQWRGKPLP, AI IQRQWRGK, QWRGKPLPGR, RGKPLPGRGR, IQRQWRGKP L, RQWRGKPLPG | PRAD |
| STOML3 | c.256G>T | p.D86Y | VVFRLGRIQADKAKGPGLILVLPCI[p.D86Y]VFVKVDLRTVTCNIPPQEILTRDSV | ILVLPCIYV, VLPCIYVFV, YVFVKVDLR, LVLPCIYVF, IYVFVKV DL, LILVLPCIY, LILVLPCIYV, LVLPCIYVFV, VLPCIYVFVK, ILVL PCIYVF, GLILVLPCIY, IYVFVKVDLR, LPCIYVFVKV | LUAD |
| STON1-GTF2A 1L | c.1352A>G | p.N451S | KVTKEGKFVESAVITQIYCLCFVNG[p.N451S]LECFLTLNDLELPKRDESYYEKDS E | CLCFVNGSL, FVNGSLECF, GSLECFLTL, FVNGSLECFL, CFVN GSLECF | TGCT |
| STRA6 | c.203A>G | p.Q68R | QPAGNQTSPGATEDYSYGSWYIDEP[p.Q68R]RGGEELQPEGEVPSCHTSIPPGLYHA | GSWYIDEPR | BRCA |
| STRADA | c.997del|C | p.R333fs | EELTMSPSRSVANSGLSDSLLTTSTP[p.R333fs]GPPTVTRPPTPTTEPSPPTSTTLWSSAFSATRMPGPVPAPS* | TLWSSAFSA, WSSAFSATR, VTRPPTPTT, ATRMPGPVP, TTL WSSAFS, STTLWSSAF, SSAFSATRM, TRMPGPVPA, MPGPV PAPS, SPPTSTTLW, TLWSSAFSAT, FSATRMPGPV, TTLWSS AFSA, AtRMPGPVPA, STPGPPTVTR, LWSSAFSATR, TTSTP GPPTV, EPSPPTSTTL, TSTTLWSSAF, WSSAFSATRM | STAD |
| STRN3 | c.654G>T | p.K218N | LDVRSRQRVRSLLGLSNSEPNGSVET[p.K218N]NNLEQILNGGESPKQKGQEIKRSSGD | ETNNLEQIL, VETNNLEQI, VETNNLEQIL | UCEC |
| STT3B | c.1747G>T | p.D583Y | TSNAYSSPSVVLASYNHDGTRNILD[p.D583Y]YFREAYFWLRQNTDEHARVMSWWDYG | ILDYFREAY, NILDYFREA, DYFREAYFW, YFREAYF WL, GTRNILDYF, LDYFREAYF, GTRNILDYFR, DYFREAYFWL, YFREAYFWLR, NILDYFREAY, ILDYFREAYF | CRC |
| STX2 | c.320G>T | p.R107L | KKTANKIRAKLKAIEQSFDQDESGN[p.R107L]LTSVDLRIRRTQHSVLSRKFVEAM AE | DESGNLTSV, LTSVDLRIRR | LUAD |
| STX2 | c.756del|A | p.K252fs | MINNIERNVMNATDYVEHAKEETKK[p.K252fs]LSNIRARQEGKSG* | NIRARQEGK, ETKKLSNIR | STAD |
| STXBP6 | c.274G>A | p.D92N | QFEGSTSFVRRSQWMLEQLRQVNGI[p.D92N]NPNGDSAEFDLLFENAFDQMVASTAS | RQVNGINPN, NPNGDSAEF, RQVNGINPNG | UCEC |
| SULT1C4 | c.254G>A | p.R85Q | WTQEIVELIQNEGDVEKSKRAPTHQ[p.R85Q]QFPPLEMKIPSLGSSLEQAHAMPSPR | QQFPPLEMK, QPPFLEMKI, APTHQQPPF, HQQFPFLEM, KR APTHQQF, HQQFPFLEMK, RAPTHQQF PF, KSKRAPTHQQ, APTHQQPPFL, SKRAPTHQQF, THQQPPFL EM, QQFPPLEMKI | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SULT1E1 | c.230G>A | p.R77Q | WVSEIVMIYKEGDVEKCKEDVIFN[p.R77Q]QIPFLECRKENLMNGVKQLDEMNSPR | VIFNQIPFL,DVIFNQIPF,KEDVIFNQI,DVIFNQIPFL | UCEC |
| SUMF2 | c.329G>A | p.G110E | IFPVTNKDFRDFVREKKYRTEAEMF[p.G110E]EWSFVFEDFVSDELRNKATQPMKSVL | EMFEWSFVF,EWSFVFEDF,AEMFEWSFV,FEWSFVFED,EAEMFEWSF,TEAEMFEWS,AEMFEWSFVF,EAEMFEWSFV,TEAEMFEWSF,FEWSFVFEDF | LUAD |
| SUN3 | c.1016C>A | p.P339Q | TFELQHAVSEYLLCVKLNIFSNWGH[p.P339Q]QKYTCLYRFRVHGTPGKHI* | FSNWGHQKY,IFSNWGHQK,HQKYTCLYR,GHQKYTCLY,W GHQKYTCLQKYTCLYRF,NIFSNWGHQ,HQKYTCLYRF,IFSNWG HQKY,WGHQKYTCLY | LUAD |
| SUN3 | c.370C>A | p.L124I | LRMPKEQLELLKKESQNLENNFRQI[p.L124I]IFLIEQIDVLKALLRDMKDGMDNNHN | QIIFLIEQI,NFRQIIFLI,LENNFRQI,RQIIFLIEQ,RQIIFLIEQI,IFLIEQIDVL,LENNFRQIIF | UCEC |
| SUN3 | c.382G>A | p.E128K | KEQLELLKKESQNLENNFRQILFLI[p.E128K]KQIDVLKALLRDMKDGMDNNHNWNTH | FLIKQIDVL,KQIDVLKAL,LIKQIDVLK,LLFLIKQIDV,KQIDVLKALL,RQIIFLIKQI,FLIKQIDVLK,NFRQILFLIK,IKQIDVLKAL | CRC |
| SUPT6H | c.2869G>A | p.A957T | SSDEDILCLKFHPLQEHVVKEELLN[p.A957T]TLYCEFINRVNEVGVDVNRAIAHPYS | TLYCEFINR,LLNTLYCEF,VKEELLNTL,KEELLNTLY,LLNTLYC EFI,TLYCEFINRV,NTLYCEFIN,ELLNTLYCEF,VKEELLNTLY | CRC |
| SUSD1 | c.1027C>T | p.R343C | SRRINPKISVVISIKGQRLDPMESV[p.R343C]CEETVNLTTDSRTPEVCLALYPGTNY | MESVCEETV,CEETVNLTT | UCEC |
| SUSD5 | c.1538C>T | p.T513M | YELTSSTLEILTVNTVKQTPNHIPS[p.T513M]MIMATTQPPVETTVPEIQDSPFYLLS | TPNHIPSMI,SMIMATTQP,MIMATTQPF,IPSMIMATT,MI MATTQPPV,KQTPNHIPSM,QTPNHIPSMI,TPNHIPSMIM,SMIMATTQPP | GBM |
| SV2A | c.412del|G | p.E138fs | MADGAPLAGVRGGLSDGEGPPGGRG[p.E138fs]RHNDGKNEKNWPNSMKPSYGSVATAASSGHCILCLVWR* | SMKPSYGSV,KPSYGSVAT,WPNSMKPSY,NEKNWPNSM,MKPSYGSVA,AASSGHCIL,SMKPSYGSVA,GGRGRHNDGK,NWPNSMKPSY,NSMKPSYGSV,KPSYGSVATA,KNEKNWPNSM,MKPSYGSVAT,TAASSGHCIL,SGHCILCLVW | STAD |
| SV2C | c.179C>A | p.P60Q | DRAQDEYTQRSYSRFQDEEDDDYY[p.P60Q]QAGETYNGFANDDEGSSEATEGHDED | YYQAGETYNG,DDYYQAGETY | LUAD |
| SVIL | c.278T>C | p.M93T | EKQTRSKYCTETSGVHGDSPYGSGT[p.M93T]TDTHSLESKAERIARYKAERRRQLAE | TTDTHSLESK | KIRC |
| SVIL | c.5586del|G | p.G1862fs | ERGAQVQVLQCKEPPCFLQCFQGG[p.G1862fs]WMCTRGGGKRKKMCKVSGGCTACVERCPWKGICWKWPVTVAA* | KGICWKWPV,PWKGICWKW,CTRGGGKRK,RGGGKRKKK,CWKWPVTVA,FQGGWWCTR,LQCFQGGWW,CKVSGGCTA,WKWPVTVAA,VERCPWKGI,KVSGGCTACV,GICWKWP VTV,TACVERCPWK,CFLQCFQGGW,GWWCTRGGGK,CTRGGGKRKK,GGKRKKKMCK,CWKWPVTVAA,CFQGGWWC TR,CPWKGICWKW | STAD |
| SYCP2 | c.1422A>T | p.K474N | KPSKYIKNSDKGNRNNSQLEKTTPS[p.K474N]NRKMSEASMIVSGADRYTMRSPVLFS | KTTPSNRKM,NRKMSEASM,TPSNRKMSEA,SQLEKTTPSN,SNRKMSEASM | HNSC |
| SYMPK | c.1007C>G | p.A336G | HPASLEFQAQITTLLVDLGTPQAEI[p.A336G]GRNMPSSKDTRKRPRDDSDSTLKKMK | IGRNMPSSK,PQAEIGRNM,AEIGRNMPS,TPQAEIGRNM,AEIGRNMPSS | TGCT |
| SYN2 | c.99_101del AGC | p.A34del | LSDSSFIANLPNGYMTDLQRPEPQQ[p.A34del]PTPPPGPGAASAAAPPTASPGPERTPP | LQRPEPQQPT | BLCA,KIRP,PRAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| SYNDIG1 | c.403G>T | p.D135Y | CCETTFIEDRSPTKDSLEYPDGKFI[p.D135Y]YLSADDIKIHTLSVDEEEEFQELE | YLSADDIKI,FIYLSADDI,YPDGKFIYL,FIYLSADDIK,EYPDG KFIYL,KFIYLSADDI,IYLSADDIKI,LEYPDGKFIY | LUAD |
| SYNE2 | c.9309G>T | p.K3103N | ESRRLNAQILSQRIEKAKCLCDEII[p.K3103N]NKLLNENKTFDDSFKEKEILQIKLNAE | CLCDEIINK,IINKLNENK,NKLNENKTF,CLCDEINKL | CRC |
| SYNGR4 | c.506G>A | p.R169Q | QAAIAFTFFSIILVWIFOAYLARQDL[p.R169Q]QNDAPVPYKRFLDEGMVLTTLPLPS | LQNDAPVPY,FQDLQNDAPV,LQNDAPVPYK,DLQNDAPVPY | CRC |
| SYNJ1 | c.2041A>T | p.I681F | KTISRDNKYVLLASEQLVGVCLFVF[p.I681F]FRPQHAPFIRDVAVDTVKTGMGGATG | FVFFRPQHA,GVCLFVFFR,VGVCLFVFF,FFRPQHAPF,VFFR PQHAPF,FFRPQHAPFI,VGVCLFVFFR | CLL |
| SYNJ2 | c.2495A>C | p.K832T | WRKKHPPDKTAGELNLLLDSDLLDVDT[p.K832T]TVRHTWSPGALQYYGRAELQASDHRP | TVRHTWSPG,TVRHTWSPGA | KIRC |
| SYNJ2 | c.3331_3332insC | p.P1111fs | HRSPSRSLSVPNRPRPPQPPQRPPP[p.P1111fs]SNRPNGEKVGFRCVHLLRHPWTVFNFADGKTSTRSTSATSQGSDWNK* | HLLRHPWTV,TVFNFADGK,TSQGSDWNK,RFNGEKVGF,RH PWTVFNF,KVGFRCVHL,GFRCVHLLR,KTSTRSTSA,STRST SATS,LLRHPWTVF,CVHLLRHPW,HPWTVFNFA,GEKVGFR CV,VGFRCVHLLR,WTVFNFADGK,ATSQGSDWNK,HLLRH PWTVF,LRHPWTVFNF,KVGFRCVHLL,GFRCVHLLRH, KTSTRSTSAT,STRSTSATSQ,RFNGEKVGFR,NFADGKT STR,PQRPPPSNRF,NRFNGEKVGF,RCVHLLRHPW TIQTKPEEK,IQTKPEEKM,RNRPETIQTK,IQTKPEKMF | STAD |
| SYNM | c.1547G>A | p.R516Q | RTVILGKKTEVKATRQERNRPETI[p.R516Q]QTKPEEKMFDSKEKASEERNLRWEEL | GQPQIHVYF,MARRGQPQI,RGGPQIHVY,QPQIHVFR,AQ GDPESRL,SMARRGQPQI,RGGPQIHVYF,MARRGQPIH,R RGQPQIHVY | UCEC |
| SYNPO | c.1856_1857insC | p.G619fs | SSHLKGQAVPASKTGILEESMARRG[p.G619fs]QPQIHVYPRGEAQGDPESRLAGSGTDSG* | | KIRC |
| SYT4 | c.1de|A | p.M1fs | [p.M1fs]MLRSPPAGKNLMKSPQWWGSSVHLAWSSQSLSLHGSAVRENHPSLTRLLHTSLCMCLRELIFTLKT* | HLAWSSQSL,SLSLHGSAV,CLRELIFTL,LLHTSLCMC,SLCMC LREL,WLRSPPAGK,HTSLCMCLR,QWWGSSVHL,AVRENH PSL,LTRLLHTSL,LSLHGSAVR,SPPAGKNLM,SPQWWGSSV, RLLHTSLCM,KNLMKSPQW,PQWWGSSVH,WGSSVHLA W,AWSSQSLSL,CMCLRELIF,RELIFTLKT,SLTRLLHTSL,LLHT SLCMCL,SLCMCLRELI,CLRELIFTLK,WWGSSVHLAW,KSPQ WWGSSV,AVRENHPSLT,SLSLHGSAVR,HPSLTRLLHT,LA WSSQSLSL,SQSLSLHGSA,GKNLMKSPQW,PQWWGSSVHL,VHLAWSSQ SL,SQSLSLHGSA,SAVRENHPSL,RENHPSLTRL,TRLLHTSLC M,LCMCLRELIF,SPQWWGSSVH | STAD |
| SYT7 | c.1046C>T | p.T349M | TMKRNLNPIFNESFAFDIPTEKLRE[p.T349M]MTIIITVMDKDLSRNDVIGKIYLSW | KLREMTIII,IPTEKLREM,REMTIIITV,EMTIIITVM,MTIIITV MDK,KLREMTIIIT,REMTIIITVM | CRC |
| SYT8 | c.1117C>T | p.R373W | GARASGQPLQHWADMLAHARRPIAQ[p.R373W]WHPLRPAREVDRMLALQPRLRLRLPL | QWHPLRPAR,PIAQWHPLR,RPIAQWHPL,HARRPIAQW,A QWHPLRPA,HARRPIAQWH,RPIAQWHPLR,AHARRPIAQ W,RRPIAQWHPL | ACC |
| SYTL2 | c.1320C>G | p.I440M | FPINGLHSHSEVLTARPQSMENSPT[p.I440M]MNEPKDKSSELTRLESVLPRSPADEL | QSMENSPTM,PQSMENSPTM | BLCA |
| TAB3 | c.632G>C | p.R211T | HIPRYSTNPITVTVSQNLPSGQTVP[p.R211T]TALQILPQIPSNLYGSPGSIYIRQTS | QTVPTALQI,LPSGQTVPT,TALQILPQI,GQTVPTALQI,LPSG QTVPTA | BLCA |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TADA2B | c.199G>A | p.E67K | IGHHRYHGYQLVDGGRFTLWGPEAp.E67K]KGGWTSREEQLLLDAIEQFGFGNWED | FTLWGPEAK,EAKGGWTSR,RFTLWGPEAK | CESC |
| TAF1 | c.2527C>T | p.R843W | SKDRPRRIRMEDIKKAFPSHSESSI[p.R843W]WKRLKLCADFKRTGMDSNWWVLKSDF | IWKRLKLCA,HSESSIWKR,SESSIWKRL,FPSHSESSIW,WKRLKLCADF | UCEC |
| TAF1A | c.514_515CG>AT | p.R172M | HGMLKDAKRNLSEAETWRHGENTSS[p.R172M]MEILINLIQAYKGLLQYYTWSEKKMEL | SSMEILINL,SMEILINLI,NTSSMEILI,RHGENTSSM,GENTSSMEI,MEILINLIQ,SSMEILINLI,WRHGENTSSM,GENTSSMEIL,MEILINLIQA | SKCM |
| TAF1B | c.874C>T | p.R292C | GIESWPDYEDIYKKTVEVGTFLDLP[p.R292C]CFPDITEDCYLHPNILCMKYLMEVNL | GTFLDLPCF,LDLPCFPDI,FLDLPCFPDI,VGTFLDLPCF | BLCA |
| TAF1L | c.2553de|A | p.K851fs | QVFIYRLFWKSKDRPRRIMEDIKK[p.K851fs]PFLPIQKAASGRG* | DIKKPFLPI,RMEDIKKPF,MEDIKKPFL,KPFLPIQKAA,IRMEDIKKPF,RMEDIKKPFL | STAD |
| TAF5 | c.388T>G | p.S130A | RQSKLREAEEALRREAGLLEEAVAG[p.S130A]AGAPGEVDSAGAEVTSALLSRVTASA | LLEEAVAGA,EEAVAGAGA,GLLEEAVAGA,LEEAVAGAGA | ACC |
| TANK | c.1139C>T | p.S380L | LDSPGKAIRGPQQPIWKPFPNQDSD[p.S380L]LVVLSGTDSELHIPRVCEFCQAVFPP | NQDSDLVVL,FPNQDSDLV,KPFPNQDSDL,FPNQDSDLVV | CRC |
| TAOK2 | c.2696_2697insG | p.Q899fs | QRVEEELLALQTGRSERIRSLLERQ[p.Q899fs]GP* | RIRSLLERQG | KIRC |
| TARBP1 | c.2344C>G | p.L782V | VLTELINLHLKVGWKRGNPIWRVIS[p.L782V]VLKNASIQHLQEMDSGQEPTVGSAIQ | RVISVLKNA,IWRVISVLK,NPIWRVISV,VLKNASIQHL,PIWRVISVLK,NPIWRVISVL | LUSC |
| TARS2 | c.595G>A | p.E199K | RGSELPVLERICQELTAAARPFRRL[p.E199K]KASRDQLRQLFKDNPFKLHLIEEKVT | AARPFRRLK,RLKASRDQL,RPFRRLKAS,AAARPFRRLK,AARPFRRLKA,RPFRRLKASR,RLKASRDQLR,RRLKASRDQL | LUAD |
| TARSL2 | c.1097G>A | p.G366D | KGPHVRHTGKIKTIKIFKNSSTYWE[p.G366D]DNPEMETLQRIYGISFPDNKMM | TYWEDNPEM,STYWEDNPEM,WEDNPEMETL | GBM |
| TAS1R2 | c.808C>T | p.R270C | PNQNMTSEERQRLVTIVDKLQQSTA[p.R270C]CVVVVFSPDLTLYHFFNEVLRQNFTG | KLQQSTACV,LQQSTACVV,STACVVVV,QSTACVVVV,QQSTACVVV,KLQQSTACVV,QQSTACVVVV,STACVVVVFS,LQQSTACVVV,QSTACVVVVF | CRC |
| TAS1R3 | c.1573G>A | p.E525K | SRQCQEGQVRRVKGPHSCCYDCVDC[p.E525K]KAGSYRQNPDDIACTFCGQDEWSPER | CVDCKAGSY,CVDCKAGSYR | BLCA |
| TAS2R1 | c.549C>A | p.F183L | KFFSQNATIQKEDTLAIQIFSFVAE[p.F183L]LSVPLLIFLFAVLLLIFSLGRHTRQM | QIFSFVAEL,FVAELSVPL,FSFVAELSVP,LL,IFSFVAELSV,SF,VAELSVPL,LSVPLLIFLF,ELSVPLLIFL,FSFVAELSVP,AELSVPLLIF | CRC |
| TAS2R16 | c.531G>T | p.Q177H | IQLLTMEHLPRNSTVDKLENFHQY[p.Q177H]HFQAHTVALVIPFILFLASTIFLMAS | QYHFQAHTV,HFQAHTVAL,LENFHQYHF,FHQYHFQAH,HQYHFQAHT,YHFQAFITVA,HQYHFQAHTV,KLENFHQYHF,YHFQAHTVAL | LUAD |
| TAS2R16 | c.691G>A | p.V231I | QIQHHSTGHCNPSMKARFTALRSLA[p.V231I]ILFIVFTSYFLTLITIIGTLFDKRC | RSLAILFIV,FTALRSLAI,ILFIVFTSY,SLAILFIV,ALRSLAILF,ALRSLAIL,ALRSLAILFI,FTALRSLAIL,SLAILFIVFT,RFTALRSLAI,TALRSLAILF,RSLAILFIVF,ILFIVFTSYF,AILFIVFTSY,T MM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TAS2R30 | c.707_708 insT | p.L236fs | HGKGSQDPSTKVHIKALQTVTSFLL[p.L 236fs]VMCHLLSVHDHISL* | FLLVMCHLL,LVMCHLLSV,HLLSVHDHI,SFLLVMCHL,QTVT SFLLV,TVTSFLLVM,VMCHLLSVH,LSVHDHISL,LIVMCHLL SV,LLSVHDHISL,SFLLVMCHLL,QTVTSFLLVM,LVMCHLLS VH,LQTVTSFLLV,TSFLLVMCHL | KICH |
| TAS2R38 | c.932T>C | p.I311T | MAACPSGHAAILISGNAKLRRAVMT[p. I311T]TLLWAQSSLKVRADHKADSRTL C* | AVMTTLLWA,TLLWAQSSL,RAVMTTLLW,KLRRAVMTT,L RRAVMTTLL,RRAVMTTLL,KLRRAVMTTL,TLLWAQSSLK,RR AVMTTLLW,RAVMTTLLWA,TLLLWAQSSL,LRRAVMTTLL | KIRC |
| TAS2R41 | c.763G>A | p.A255T | TRALKSLISFLLIYALSFLSLLIIDA[p.A 255T]TKFISMQNDFYWPWQIAVVLCISVHP | FLSLIIDAT,LIIDATKFI,LSLIIDATKF,SLIIDATKF,IDATKFISM,S LIIDATKFI,LSLIIDATKF,IIDATKFISM,TKFISMQNDF | GBM |
| TAS2R8 | c.294G>C | p.W98C | PDVYTKNKQQIVIFFTWTFANYLNM[p. W98C]CITTCLNVFYFLKIASSSHPLFLW LK | YLNMCITTC,FANYLNMCI,LNMCITTCL,CITTCLNVF,YLN MCITTCL,NMCITTCLNV,TFANYLNMCI,CITTCLNVFY, MCITTCLNVF | TGCT |
| TAS2R9 | c.487G>C | p.E163Q | FLISLIISVPKNDDMWYHLFKVSHE[p.E1 63Q]QNITWKFKVSKIPGTFKQLTLNLG VM | HEQNITWKF,FKVSHEQNI,VSHEQNITW,VSHEQNITWK,K VSHEQNITW,SHEQNITWKF | BLCA |
| TAT | c.1100G>A | p.R367H | TLSFLKSNADLCYGALAAIPGLRPV[p.R 367H]HPSGAMYLMVGIEMEHFPEFEND VEF | GLRPVHPSG,PVHPSGAMY,RPVHPSGAM,HPSGAMYLM, GLRPVHPSGA,RPVHPSGAMY,HPSGAMYLMV,AAIPGLRP VH,LRPVHPSGAM | GBM |
| TBC1D1 | c.212C>T | p.S71F | EVRRLSRQSTRKEPVTKQVRLCVSP[p.S 71F]FGLRCEPEPGRSQQWDPLIYSSIFEC | RLCVSPFGL,QVRLCVSPF,RLCVSPFGLR,KQVRLCVSPF,QV RLCVSPFG,VRLCVSPFGL | BLCA |
| TBC1D1 | c.830A>G | p.H277R | DGGLRSSGFFSSFEESDIENHLISG[p.H2 77R]RNIVQPTDIEENRTMLFTIGQSEVYL | HLISGRNIV,DIENHLISGR | KIRC |
| TBC1D12 | c.1823T>A | p.F608Y | PDVGYVQGMSFIAAVLILNLEEADA[p.F 608Y]YIAFANLLNKPCQLAFFRVDHSM MLK | NLEEADAYI,AYIAFANLL,EADAYIAFA,DAYIAFANL,EEADA YIAF,LNLEEADAY,LEEADAYIA,YIAFANLLNK,IINLEEADAY, DAYIAFANLL,LEEADAYIAF,EEADAYIAFA,ADAYIAFANL | KIRC |
| TBC1D2B | c.2759G>A | p.R920Q | ILDARKLISISFGDLNPFPLRQIRN[p.R92 0Q]QRAYHLEKVRLELTELEAIREDFLRE | QIRNQRAYH,NQRAYHLEK,RQIRNQRAY,IRNQRAYHL,RQI RNQRAYH,QIRNQRAYH,RNQRAYHLEK,LRQIRNQRAY, NQRAYHLEKV | BLCA,KIRP, PRAD |
| TBC1 D9 | c.3697C>A | p.P123 3T | DWAITFEQFLASLLTEPALVKYFDK[p.P 1233T]TVCMMARITSAKNIRMMGKPL TSASD | ALVKYFDKT,KTVCMMARI,KYFDKTVCM,YFDKTVCMM,AL VKYFDKTV,KYFDKTVCMM,VKYFDKTVCM | PRAD |
| TBCD | c.1426C>T | p.R476C | DEKRGACSVGTNVRDAACYVCWAFA[p. R476C]CAYEPQELKPFVTAISSALVIA AVFD | YVCWAFACA,CAYEPQELK,VCWAFACAY,YVCWAFACAY,F ACAYEPQEL | LUSC |
| TBL1X R1 | c.377de lA | p.N126fs | DKLAQQOAAAAAAAAAAAASQQCSAK[p. N126fs]MEKTQQMGRRMEHIL* | QMGRRMEHI,KTQQMGRRM,MGRRMEHIL,ASQQGSAK M,AKMEKTQQM,QQMGRRMEH,QQMGRRMEHI,SQQG SAKMEK,AASQQGSAKM,QQMGRRMEH | STAD |
| TBX3 | c.559C>T | p.H187Y | RYKFHNSRWMVAGKADPEMPKRMYI[p. H187Y]YPDSPATGEQWMSKVVTFH KLKLTNN | YIYPDSPAT,EMPKRMYIY,MYIYPDSPA,RMYIYPDSP,RMYI YPDSPA,PEMPKRMYIY | BRCA |
| TBX4 | c.1109de lC | p.S370fs | LDLPCKRSYLEAPSSVGEDHYFRSP[p.S 370fs]LPTTSKC* | RSPLPTTSK,GEDHYFRSPL | STAD |
| TCEB3 C | c.922G>A | p.E308K | DLLSAFEAMTSQANPEALSAPALQE[p. E308K]KAAFPGRRVNAKMPVYSGSRP ACQLQ | LSAPALQEK,KAAFPGRRV,LQEKAAFPG,ALSAPALQEK,AP ALQEKAAF | SKCM |
| TCF7 | c.419A>C | p.H140P | GMYKEFVYSAFNLLMHYPPPSGAGQ[p. H140P]PPQPQPPLHKANQPPHGVPQ LSLYEH | QPPQPQPPL,GQPPQPQPPL | KIRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TCHP | c.515del A | p.E172fs | KLREMELDLHQKHVVNSWEMQKEEK[p. E172fs]NSKKPPQSKRTNGMKMNM KGPEGRR* | MQKEEKNSK,NSKKPPQSK,QSKRTNGMK,RTNGMKMNM, KMNMKGPEG,MNMKGPEGR,NMKGPEGRR,SKRTNGM KM,RTNGMKMNMK,MQKEEKNSKK,KNSKKPPQSK,KMN MKGPEGR,NSKKPPQSKR,MNMKGPEGRR,KRTNGMKMN M,MKMNMKGPEG | STAD |
| TCOF1 | c.4084_4086 del AAG | p.K1366del | GWESRKRKLSGDQPAARTPRSKKKK[p. K1366del]LGAGEGEASVSPEKTSTTS KGKAKRDK | RSKKKKLGA,TPRSKKKKL,RSKKKKLGAG | PRAD |
| TCOF1 | c.791A>G | p.K264R | APAPGKVGDVTPQVKGGALPPAKRA[p. K264R]RKPEEESESSEEGSESEEEAPAG TRS | ALPPAKRARK | LUAD |
| TCTE1 | c.380G>T | p.S127I | PEHQQKVLNHLSPDLPLAVTANLID[p.S 127I]IENYWLRCCMHRWPVCHVAHH GGSWK | NLIDIENYWL,IENYWLRCCM,TANLIDIENY | LUAD |
| TCTEX 1D2 | c.221C>T | p.S74L | HAVLKEELANAEYSPEMPQLTKHL[p.S 74L]LENIKDKLKEMGFPDRYKMVQVVI GE | MPQLTKHLL,QLTKHLLENI,LTKHLLENIK | CESC |
| TDO2 | c.591G>C | p.Q197H | RVPYNRRHYRDNFKGEENELLLKSE[p. Q197H]HEKTLLELVEAWLERTPGLEPH GFNF | LLLKSEHEK,LKSEHEKTL,NELLLKSEH,HEKTLLELIV,LKSE HEKTLL,SEHEKTLLEL | LUAD |
| TDRD 10 | c.828G>T | p.W276C | CLAEYHLGDYGHAWNRCWVLDRVDT[p. W276C]CAVVMFIDFGQLATIPVQSL RSLDSD | DTCAVVMFI,RVDTCAVVM,CAVVMFIDF,VLDRVDTCAV,R VDTCAVVMF | KIRC |
| TDRD 10 | c.965C>T | p.S322L | SLDSDDFWTIPPLTQPFMLEKDILS[p.S 22L]LYEVVHRILKGKITGALNSAVTAPA S | MLEKDILSL,SLYEVVHRI,LYEVVHRIL,LEKDILSLY,DILSLYEV V,KDILSLYEV,MLEKDILSLY,FMLEKDILSL,SLYEVVHRIL, ILSLYEVVHR,KDILSLYEVV | CRC |
| TEAD2 | c.894_895 insC | p.P298fs | DVRQIYDKFPEKKGGLRELYDRGP[p.P 298fs]PCLLPGQVLGGPELGPKW* | GQVLGGPEL,VLGGPELGPK,RELYDRGPPP | STAD |
| TECTB | c.85C>A | p.L29I | KAFVLLAIFAEASAKSCAPNKADVI[p.L2 9I]IVFCYPKTIITKIPECPYGWEVHQLA | VIIVFCYPK,APNKADVII,NKADVIIVF,IVFCYPKTI,KADVIIVF CY,DVIIVFCYPK,APNKADVIIV,IVFCYPKTII | CRC |
| TEDD M1 | c.498G>A | p.M166I | LLVLITAELWAPNMCHLQLMETFLIL[p. M166I]IMGSWLMQAGFIIYRPVSGYP WQDDD | LMETFLILI,ILIMGSWLM,IMGSWLMQA,METFLILIM,FLILI MGSW,QLMETFLILI,FLILIMGSWL,LIMGSWLMQA,TFLILI MGSW,ETFLILIMGS,LMETFLILIM,LILIMGSWLM | CESC |
| TEKT5 | c.1202G>A | p.R401H | LLERSIMAKEGPLKVAQTRLECRTR[p.R 401H]HPNMELCRDIPQLKLVNEVFTID DTL | RTRHPNMEL,RTRHPNMELC,LECRTRHPNM,HPNMELCR DI | CRC |
| TET1 | c.4415C>G | p.T1472S | AAVREIMENRYGQKGNAIRIEIVVY[p.T 1472S]SGKEGKSSHGCPIAKWVLRRSS DEEK | VVYSGKEGK,RIEIVVYSGK,IVVYSGKEGK | TGCT |
| TEX15 | c.4954G>C | p.E1652Q | ASSLQILQEETKVCLNILPLFVEAF[p.E16 52Q]QRKQECSVEQILISRELLVDQNLW NN | FQRKQECSV | CESC |
| TFE3 | c.1444_144 5insG | p.G482fs | SLKPEQLDIEEEGRPGAATFHVGG[p. G482fs]TCPECSPSAAPCTALRCPSGPA LSQRPPGGPGRPLPPGAGGHSDGGGG GGGGRTVGGCPVPTAGCLRSPALFSVP CCLQGGQPPQQLQHGRGVLIRPHPSP GTFPPRKGGPVRMRPRLFPHPPMRLPC PGILGEEM* | ALFSVPCCL,ALRCPSGPA,RMRPRLFPH,RLFPHPPMR,SAA PCTALR,LFPHPPMRL,LIRPHPSPG,PPGGPGRPL,CPVPTAG CL,SPALFSVPC,RPHPSPGTF,FPPRKGGPV,GPVRMRPRL,R PRLFPHP,LRCPSGPAL,SQRPPGGPG,GCLRSPALF,LRSPA LFSV,QQLQHGRGV,LQHGRGVLI,MRLPCPGIL,HPSPGTFP P,CLRSPALFSV,RLFPHPPMRL,ALRCPSGPAL,SQRPPGGPG R,KGGPVRMRPR,RMRPRLFPH,RPRLFPHPM,HPSPGTF | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TFG | c.1145C>T | p.A382V | YQPRPGFTSLPGSTMTPPPSGPNPY[p.A382V]VRNRPPFGQGYTQPGPGYR* | PPR, SPSAAPCTAL, RPPGGPGRPL, PPRKGGPVRM, GPVRM RPRLF, FPHPPMRLPC, AGCLRSPALF, LQGQOPPQQL, GQQ PPQQLQH, QQLQHGRGVL, IRPHPSPGTF, CPGILGEEEM PYVRNRPPF, YVRNRPPFG, NPYVRNRPPF | CLL |
| TFPI2 | c.616C>T | p.R206C | RTCDAFTYTGCGNDNNFVSREDCK[p.R206C]CACAKALKKKKKMPKLRFASRIR KIR | CACAKALKK, KCACAKALK, CKCACAKAL, REDCKCACA, CAC AKALKKK, KCACAKALKK | GBM |
| TFPI2 | c.664C>T | p.R222C | NFVSREDCKRACAKALKKKKKMPKL[p.R222C]CFASRIRKIRKKQF* | LCFASRIRK, CFASRIRKI, MPKLCFASR, KLCFASRIR, KKKMPK LCF, KKMPKLCFA, KLCFASRIRK, KKKMPKLCFA, KMPKLCFA SR, CFASRIRKIR, MPKLCFASRI, KKKMPKLCF, KMPKLCFAS | BLCA |
| TFPT | c.755C>G | p.S252C | EALDSSWVSRGPDKLLPYPTLASPA[p.S252C]CD* | YPTLASPAC | BRCA |
| TGFBR1 | c.722C>T | p.S241L | FGEVWRGKWRGEEVAVKIFSSREER[p.S241L]LWFREAEIYQTVMLRHENILGFI AAD | RLWFREAEI, LWFREAEIY, SSREERLWF, EERLWFREA, FSSR EERLW, SSREERLWFR, IFSSREERLW, KIFSSREERL, RLWFRE AEIY, FSSREERLWF, REERLWFREA | CRC |
| TGM6 | c.1073delC | p.T358fs | WNESWFARQDLGPSYNGWQVLDATP[p.T358fs]RRRVKVCSGAAQPQSPPSA RVMCTWLTMAPSCLRRSTPTTSPGCGT RMRAGSVYTQTRRRLGDASAPRRWAV TPAWTSLTSTSIRKGPGKRGRCTARR* | RVMCTWLTM, VMCTWLTMA, WLTMAPSCL, LTMAPSCLR, TMAPSCLRR, SVYTQTRRR, SLTSTSIRK, RLGDASAPR, TSLTS TSIRK, TSIRKGPGK, RVKVCSGAA, SARVMCTWL, GTRMRAGSV, RMRAGSVYT, QTRRRLGDA, ASAPRRWAV, SIRKGPGKR, QVLDATPRR, TTSPGCGTR, WTSLTSTSI, APSCLRRST, AVTP AWTSL, TPRRRVKVC, AQPQSPPSA, TRMRAGSVY, RRWAV TPAW, TPAWTSLTS, RVMCTWLTMA, LTMAPSCLRR, TSLTS TSIRK, STSIRKGPGK, TWLTMAPSCL, RVKVCSGAAQ, SARV MCTWLT, GTRMRAGSVY, RMRAGSVYTQ, RAGSVYTQTR, SVYTQT RRRL, QVLDATPRRR, WLTMAPSCLR, WTSLTSTSIR, TSIRKGPGKR, DASAPRRWAV, WAVTPAWTSL, RLGDASAPRR, QPQSPPSARV, APR RWAVTPA, TPAWTSLTST, RRVKVCSGAA, PQSPPSARVM, ARVMCTWLTM, AWTSLTSTSI, PPSARVMCTW | STAD |
| THADA | c.5822C>T | p.S1941L | RLLAFLEGKEGEDTLVLSVWDSYAE[p.S1941L]LRQLTLPRTEAAC* | SVWDSYAEL, ELRQLTLPR, YAELRQLTL, SVWDSYAELR, SYA ELRQLTL, LSVWDSYAEL | UCEC |
| THAP5 | c.860C>A | p.S287Y | EELNTNKESVIAIFVPAENSKPSVN[p.S287Y]YFISAQKETTEMEDTDIEDSLYKDVD | VNYFISAQK, NSKPSVNYF, SVNYFISAQK, NSKPSVNYFI, KPS VNYFISA, AENSKPSVNY | CRC |
| THEM4 | c.50T>G | p.L17R | MLRSCAARLRTLGALC[p.L17R]RPPVG RRLPGSEPRPELRSFSSEEVI | ALCRPPVGR, TLGALCRPPV, RLRTLGALCR, RPPVGRRLPG | ACC |
| THRAP3 | c.1652A>G | p.K551R | YKAVQEKSSSPPPRKTSESRDKLGA[p.K551R]RGDFPTGKSSFSITREAQVNVRM DSF | ESRDKLGAR, GARGDFPTGK | KIRC |
| THSD7B | c.268C>T | p.R90C | VCDWHSDLFQWEVSDWHHCVLVPYA[p.R90C]CGEVKPRTAECVTAQHGLQH RMVRCI | LVPYACGEV, VLVPYACGEV | GBM |
| THSD7B | c.269G>A | p.R90H | VCDWHSDLFQWEVSDWHHCVLVPYA[p.R90H]HGEVKPRTAECVTAQHGLQH RMVRCI | LVPYAHGEV, YAHGEVKPR, VLVPYAHGEV | CRC |
| THSD7B | c.376G>A | p.E126K | VTAQHGLQHRMVRCIQKLNRTVVAN[p.E126K]KICEHFALQPPTEQACLIPCPR DCVV | LNRTVVANK, VANKICEHF, NKICEHFAL, KLNRTVVANK, VV ANKICEHF | SKCM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TIAM1 | c.739_740 GG>AT | p.G247 M | QLSTCQRANSLGDLYAQKNSGVTAN[p. G247M]MGPGSKFAGYCRNLVSDIPNL ANHKMP | TANMGPGSK,KNSGVTANM,ANMGPGSKF,VTANMGPGS K,MGPGSKFAGY,QKNSGVTANM,TANMGPGSKF | TGCT |
| TIFAB | c.129C>A | p.D43E | GPSAFANVPPRLQHDTSPLLLGRGQ[p. D43E]EAHLQLQLPRLSRRHLSLEPYLEK GS | LLLGRGQEA,RGQEAHLQL,QEAHLQLQL,LLGRGQEAHL,E AHLQLQLPR,GQEAHLQLQL | LUAD |
| TIGD4 | c.935C>T | p.S312F | VESFPAHPEVNLKSIELAFFPSCL[p.S3 12F]FSKCIAMKQGVIKSLKIKYRHCLIKK | CLFSKCIAM,LFSKCIAMK,LAFFPSCLF,FPSCLFSKC,AFFPSC LFSK,CLFSKCIAMK,ElAFFPSCLF,SCLFSKCIAM,FPSCLFSKC I | LUAD |
| TIMD4 | c.455_457 de\|CAA | p.T152de\| | VRLNLQRASTTTHRTATTTTRRTTT[p.T 152de\|]SPTTTRQMTTTPAALPTTVVTT PDLTTG | RTTTSPTTTR,TTRRTTTSPT | PRAD |
| TIMM 44 | c.249de\|A | p.K83fs | GFLSGLLDNVKQELAKNKEMKESIK[p.K 83fs]NSVTRPEG* | ESIKNSVTR,KESIKNSV,EMKESIKNSV,KEMKESIKNS | STAD |
| TIMP3 | c.596_597 insC | p.A199fs | YQSKHYACIRQKGGYCSWYRGWA PP[p.A199fs]G* | SWYRGWAPPG | STAD |
| TINAG | c.1207G>A | p.E403K | MQVREDFFHYKTGIYRHVTSTNKES[p. E403K]KKYRKLQTHAVKLTGWGTLRG AQGQK | VTSTNKESK,STNKESKKY,KKYRKLQTH,VTSTNKESKK,STN KESKKYR,HVTSTNKESK,KKYRKLQTHA | MM |
| TLL1 | c.158C>A | p.P53Q | CAGLDYDYTFDGNEEDKTETIDYKD[p.P 53Q]QCKAAVFWGDIALDDEDLNIFQID RT | KDQCKAAVF,YKDQCKAAVF | LUAD |
| TLL1 | c.458C>T | p.T153M | VKGKVPLQFSGQNEKNRVPRAATSR[p. T153M]MERIWPGGVIPYVIGGNFTGS QRAMF | RAATSRMER,VPRAATSRM,MERIWPGGV,RMERIWPGGV, RVPRAATSRM,RAATSRMER,MERIWPGGVI | CRC |
| TLL2 | c.2615C>T | p.S872L | LGRFCGSKKPDPTVASGSSMFLRFY[p.S 872L]LDASVQRKGFQAVHSTECCGRLK AEV | FLRFYLDAS,SSMFLRFYL,FYLDASVQR,LRFYLDASV,SMFLR FYLDA,FLRFYLDASV,RFYLDASVQR | CRC |
| TLN2 | c.623C>T | p.S208L | REQGVDENETLLLRRKFFYSDQNVD[p. S208L]LRDPVQLNLLYVQARDDILNGS HPVS | FFYSDQNVDL | UCEC |
| TLR2 | c.980A>T | p.D327V | RVIDPGKVETLTIRRLHIPRFYLFY[p.D32 7V]VLSTLYISLTERVKRITVENSKVFLVP | YLFYVLSTL,YVLSTLYSL,VLsTLYSLT,FYLFYVLST,LFYVLSTLY, IPRFYLFYV,HIPRFYLFYV,YLFYVLSTLY,FYLFYVLSTL,FYVLS TLYSL,RFYLFYVLST,IPRFYLFYVL | CLL |
| TLR4 | c.1492T>G | p.L498V | LEVLKMAGNSPQENFLPDIFTELRN[p.L 498V]VTFLDLSQCQLEQLSPTAFNSLSS LQ | DIFTELRNV,FTELRNVTF,TELRNVTFL,LRNVTFLDL,IFTELR NVTF,ELRNVTFLDL | STAD |
| TM6S F1 | c.44C>G | p.S15W | MSASAATGVFVLSL[p.S15W]WAIPVT YVFNHLAAQHDSWTIVGVAA | VLSLWAIPV,VFVLSLWAI,WAIPVTYV,SLWAIPVTY,GVFV LSLWAI,FVLSLWAIPV,VLSLWAIPVT,SLWAIPVTYV,LWAIP VTYVF,LSLWAIPVTY | BLCA |
| TM9S F2 | c.272G>A | p.R91H | RLDSVESVLPYEYTAFDFCQASEGK[p.R 91H]HPSENLGQVLFGERIEPSYKFTFN K | HPSENLGQV,HPSENLGQVL,SEGKHPSENL | CRC |
| TMC5 | c.826C>T | p.R276C | DYGSSETPKMTRGVLSRTSSIQPSF[p.R 276C]CHRSDDPVGSLWGENDYPEGIE MASM | SIQPSFCHR,SSIQPSFCHR,RTSSIQPSFC | SKCM |
| TMCC 3 | c.329G>A | p.R110H | EQTSRDGNVAEYLKLVNNADKQQAG[p. R110H]HIKQVFEKKNQKSAHSIAQLQ KKLEQ | QQAGHIKQV,HIKQVFEKK,QAGHIKQVF,AGHIKQVFEK,Q QAGHIKQVF,KQQAGHIKQV | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TMCO2 | c.43_44del|TC | p.S15fs | MSTSSSSWDNLLESLS[p.S15fs]QHS MELDTSKFFGRD* | SLSQHSML,HSMELDTSK,MELDTSKFF,LESLSQHSM,SQH SMELDT,SMELDTSKF,ELDTSKFFGR,ESLSQHSMEL,HSME LDTSKF,LLESLSQHSM,SQHSMELDTS,SMELDTSKFF,MEL DTSKFFG | BLCA |
| TMEM102 | c.328G>C | p.A110P | AELLLRGGIREGSLDLGHAPLGPY[p.A1 10P]PRGPHYDAGFTLLVPMFSLDGTEL QL | HAPLGPYPR,YPRGPHYDA,GPYPRGPHY,LGPYPRGPHY,YP RGPHYDAG | KIRC |
| TMEM121 | c.879_881 de|GCC | p.P299del | FPPPALSLELQPPPQRNSVPPPPL[p.P 299del]LHGPPGRPHMSSPTRDPLDT* | NSVPPPPPL,RNSVPPPPL | PRAD |
| TMEM131 | c.3955G>C | p.E1319Q | AHSPLEQHPQPLPPPVPQPQEPQP[p.E1319Q]QRLSPAPLAHPSHPERASSAR HSSED | PQRLSPAPL,QPQEPQPQRL,EPQPQRLSPA,QPQRLSPAPL | CESC |
| TMEM132A | c.1441C>T | p.R481C | EACDAVFVAGKESRGARGVRVDFWW[p. R481C]CRLRASLRLITVWAPLLPLRIEL TDTT | RVDFWWCRLR,FWWCRLRASL,GVRVDFWWCR, WWCRLRASLR,WCRLRASLRL,VRVDFWWCRL | CRC |
| TMEM132D | c.1732C>T | p.R578W | GDSEEEEDDERRGRGCTLQYQHAMV[p. R578W]WVLTQFVAEAAGPGGHLA HLLGSDWQ | YQHAMVVL,MVWVLTQFV,AMVWVLTQF,LQYQHAMV W,QYQHAMVW,LQYQHAMVV,YQHAMVVLT,AM VVVLTQFV,MVWVLTQFVA,WVLTQFVAEA,QYQHAMV WVL,HAMVWVLTQF,TLQYQHAMVW | CRC |
| TMEM132D | c.618del|C | p.P206fs | SCRLQGDLGLCVAELELLSSWFSPP[p.P 206fs]RWLPGGGSPWTSRRGPPWSST TPCTQGVREGTASGKTRGEAMGSGQA TVTSMSPGPPCRGSGASSFIRHTGNPP* | AMGSGQATV,STTPCTQGV,LSSWFSPPR,SMSPGPPCR,GS GASSFIR,SWFSPPRWL,TSRRGPPWS,GVREGTASG,KTRGE AMGS,RGSGASSFI,SGKTRGEAM,SSWFSPPRW,WLPGGG SPW,WTSRRGPPW,SGQATVTSM,CRGSGASSF,GEAMGS GQA,WLPGGGSPWT,LLSSWFSPPR,GVREGTASGK,TSMS PGPPCR,RWLPGGGSPW,KTRGEAMGSG,RGSGASSFIR,ST TPCTQGVR,SSTTPCTQGV,EAMGSGQATV,SPWTSRRGPP, LSSWFSPPRW,SWFSPPRWL,ASGKTRGEAM,GEAMGSG QAT,GSGQATVTSM | STAD |
| TMEM147 | c.275C>T | p.A92V | FIGEFMKASVDVADLIGLNLVMSRN[p. A92V]VGKGEYKIMVAALGWATAELIM SRCI | LVMSRNVGK,SRNVGKGEY,GLNLVMSRNV,MSRNVGKGE Y | GBM |
| TMEM156 | c.241C>T | p.R81C | SFVTFLQPVRETQIIMRIFLNPSNF[p.R8 1C]CNFTRTCQDITGEFKMCSSCLVCES K | PSNFCNFTR,FLNPSNFCNF,NPSNFCNFTR | GBM |
| TMEM161B | c.425T>C | p.L142P | VYLVTEVYYNFMKPTQEMNISLVWC[p. L142P]PLVLSFAIKVLFSLTTHYFKVEDG GE | ISLVWCPLV,SLVWCPLVL,VWCPLVLSF,NISLVWCPL,CPLIV LSFAI,NISLVWCPLV,ISLVWCPLVL,LVWCPLVLSF,MNISLV WCPL | KIRC |
| TMEM161B | c.944G>A | p.R315Q | KDYIMNPPLGKESIPLMTEATFDTL[p.R 315Q]QLWLILLLCALRLAMMRSHLQAY LNL | TLQLWLIIL,LQLWLIILL,EATFDTLQL,ATFDTLQLW,TLQLW LIIIL,QLWLIILLCA,ATFDTLQLWI,TFDTLQLWLI,TEATFDTL QL,EATFDTLQW | UCEC |
| TMEM19 | c.993del|T | p.G331fs | LDNNAVNLFSSVLIALLLPTAAWGF[p.G 331fs]GPGGELYFISTG* | GFGPGGELY,WGFGPGGEL,GELYFISTG,GFGPGGELYF,W GFGPGGELY | BLCA |
| TMEM230 | c.419A>G | p.D140G | LFLIGAFLIIIGSLLLSGYISKGGA[p.D140 G]GRAVPVLIGILVFLPGFYHLRIAYY | ISKGGAGRA,AGRAVPVLI,YISKGGAGR,SKGGAGRAV,YISK GGAGRA,AGRAVPLII | KIRC |
| TMEM247 | c.382C>G | p.Q128E | EMELEKVRMEFELTRLKYLHEKNQR[p. Q128E]ERQHEVVMEQLQRERQHEVV MEQLQQ | NQRERQHEV,YLHEKNQRER,NQRERQHEVV | ACC |
| TMEM41A | c.467del|T | p.F156fs | VVSYFPDKVALLQRKVEENRNSLFF[p.F 156fs]SYCF* | NSLFFSYCF,NRNSLFFSY,RNSLFFSYCF,ENRNSLFFSY | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TME M41B | c.690del|T | p.F230fs | RITPFLPNWFINITSPVINVPLKVF|p. F230fs|LLVLF* | NVPLKVFLL,LKVFLLVLF,VPLKVFLLV,NVPLKVFLLV,VPLKV FLLVL | STAD |
| TME M47 | c.259G>A | p.G87S | ASLDIWHCESTLSSDWQIATLALLL|p.G 87S|SGAAILIIAFLVGLISICVGSRRRFY | TLALLLSGA,ALLLSGAAI,LLLSGAAII,LLLSGAAIL,ALLLSGAAI I,LLLSGAAIIL,TLALLLSGAA,SGAAIILIAF,LALLL SGAAI | KIRC |
| TME M55A | c.566G>A | p.R189Q | MELRFNTLAKCPHCKKISSVGSALP|p.R 189Q|QRRCCAYITIGMICIFIGVGLTVG TP | SVGSALPQR,LPQRRCCAY,SSVGSALPQR,ALPQRRCCAY,L PQRRCCAYI | CRC |
| TME M60 | c.231del|A | p.K77fs | LIVKMAGRCKSGFDPRHGSHNIKKK|p. K77fs]PGTSLQCYIN* | IKKKKPGTSL,NIKKKKPGTSL,KKPGTSLQCY | KIRP |
| TME M71 | c.188G>A | p.R63Q | DSLDGYHSFECGSIDPLTGSHYTCR|p.R 63Q|QSPRLLTNGYYIWTEDSFLCDKDG NI | HYTCRQSPR,RQSPRLLTN,SHYTCRQSPR,QSPRLLTNGY,R QSPRLLTNG | BRCA |
| TME M74 | c.374G>A | p.R125Q | CNCCSQELETSFTYVDKNINLEQRN|p.R 125Q|QSSPSAKGHNHPGELGWENPN EWSQE | RNQSSPSAK,EQRNQSSPSA | CRC |
| TME M79 | c.481_482 insC | p.P161fs | ERQPQEDLIVRCEAGEGECRTFMPP|p. P161fs|PGHPPRPH* | RTFMPPPGH,MPPPGHPPR,RTFMPPPGHP,FMPPPGHPP R,GECRTFMPPP | STAD |
| TMPR SS11A | c.863C>T | p.S288L | IHEKYRSAAREYDIAVVQVSSRVTF|p.S2 88L|LDDIRQICLPEASASFQPNLTVHITG | QVSSRVTFL,FLDDIRQICL,VQVSSRVTFL,SSRVTFLDDI | CRC |
| TMPR SS11E | c.775G>T | p.G259C | FTTYKNPARWTASFGVTIKPSKMKR|p. G259C|CLRRIIVHEKYKHPSHDYDISLAE LS | KMKRCLRRI,PSKMKRCLR,KPSKMKRCL,MKRCLRRII,CLRRI IVHEK,KMKRCLRRI,SKMKRCLRRI,MKRCLRRIIV | LUAD |
| TMPR SS11F | c.821G>A | p.R274Q | CFWKNKDPTQWIATFGATITPPAVK|p. R274Q|QNVRKIILHENYHRETNENDIAL VQL | KQNVRKIIL,TPPAVKQNV,KQNVRKIILH,ITPPAVKQNV,VK QNVRKIIL | LUSC |
| TMPR SS3 | c.47G>A | p.R16Q | MGENDPPAVEAPFSF|p.R16Q|QSLFG LDDLKISPVAPDADAVAAQIL | FSFQSLFGL,EAPFSFQSL,APFSFQSLF,VEAPFSFQS,QSLFGL DDLK,VEAPFSFQSL,FQSLFGLDDL | UCEC |
| TMPR SS6 | c.904G>A | p.V302I | ITSVYGCSRQPEVVEVLASGAIMAV|p.V 302I|IWKKGLHSYYDPFVLSVQPVVFQ ACE | AIMAVIWKK,GAIMAVIWK,IWKKGLHSY,SGAIMAVIW,IM AVIWKKGL,SGAIMAVIWK,GAIMAVIWKK,VIWKKGLHSY,I WKKGLHSYY,LASGAIMAVI,ASGAIMAVIW | GBM |
| TMTC 2 | c.1226C>G | p.T409R | RTQLPSTENIVVLSLSLLIIPFVPA|p. T409R|RNLFFYVGFVIAERVLYIPSM GFCLL | LIIPFVPAR,PFVPARNLF,FVPARNLFF,RNLFFYVGF,PARNL FFYV,VPARNLFFY,IPFVPARNL,FVPARNLFFY,PFVPARNLF F,RNLFFYVGFV,LIIPFVPA,VPARNLFFYV,IPFVPARNL,A RNLFFYVGF | HNSC |
| TMTC 4 | c.1831C>T | p.R611C | EAAEQSYRTAIKHRRKYPDCYNLG|p.R 611C|CLYADLNRHVDALNAWRNATVL KPEH | CYNLGCLY,CLYADLNRHV | STAD |
| TMX3 | c.451C>T | p.R151C | AHRVSGALIRPLPSQQMFEHMQKRH|p. R151C|CVFFVYVGGESPLKEKYIDAASE LIV | HMQKRHCVF,MQKRHCVFF,KRHCVFFVY,EHMQKRHCV, MQKRHCVFFV,HMQKRHCVFF,KRHCVFFVYV,QKRHCVFF VY,EHMQKRHCVF,FEHMQKRHCV | LUAD |
| TNF | c.139C>T | p.L47F | GGPQGSRRCLFLSLFSFLIVAGATT|p.L4 7F|FFCLLHFGVIGPQREEFPRDLSLISP | ATTFFCLLH,IVAGATTF,TTFFCLLHF,LIVAGATTF,TFFCLLH FGV,FLIVAGATTF,ATTFFCLLHF,FFCLLHFGVI, LIVAGATTFF | DLBCL |
| TNFSF 9 | c.694G>A | p.A232T | SAGQRLGVHLHTEARARHAWQLTQG|p. A232T|TTVLGLFRVTPEIPAGLPSPRS E* | WQLTQGTTV,QLTQGTTVL,GTTVLGLFR,TTVLG LFRV,TQGTTVLGL,TQGTTVLGLF,WQLTQGTTVL | GBM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TNIP2 | c.217C>G | p.R73G | LRARLAALEGDAAPSLVDALLEQVA[p.R 73G]GFREQLRRQEGGAARAQMRQEIE RLT | ALLEQVAGF,QVAGFREQL,ALLEQVAGFR,QVAGFREQLR,E QVAGFREQL,DALLEQVAGF | ACC |
| TNIP2 | c.415G>A | p.A139T | QPQHEREKEVLLRRSMAEGERARA[p. A139T]TSDVLCRSLANETHQLRRTLTAT AHM | RARATSDVL,AEGERARAT,RARATSDVLC,GERARATSDV | CRC |
| TNK2 | c.1894_189 5insC | p.P632fs | PTRALPRPLHPTPVVDWDARPLPPP[p. P632fs]ARL* | RPLPPPARL,DARPLPPPAR | STAD |
| TNKS2 | c.1856_185 7insA | p.T619fs | HEAAAKGKYEICKLLLQHGADPTKK[p.T 619fs]KQGWKYSFGSC* | PTKKKQGWK,KKQGWKYSF,PTKKKQGWKY,KKKQGWKYS | CESC,CLL |
| TNR | c.2074C>A | p.L692I | SAVMNSQQSVPATMNARTELDSPRD[p. L692I]IMVTASSETSISLIWTKASGPI DHYR | IMVTASSET,SPRDIMVTA,TELDSPRDI,DSPRDIMVTA,SPR DIMVTAS,TELDSPRDIM,IMVTASSETS | LUAD |
| TNS1 | c.547C>T | p.P183S | GQPSQRRYVHYPSGLLSGSIKMNNK[p. P183S]SLFLHHVIMHGIPNFESKGGCRP FLR | KMNNKSLFL,KSLFLHHVI,SIKMNNKSL,SLFLHHVIM,IKMN NKSLF,KMNNKSLFLH,SIKMNNKSLF,KSLFLHHVIM,IKMN NKSLFL,NKSLFLHHVI,SLFLHHVIMH | TGCT |
| TNXB | c.2116_211 7de\|GT | p.V706fs | EEPPASACPGGCGPRELCRAGQCVC[p. V706fs]RGLLPRP* | RAGQCVCRGL | ACC |
| TOP2 A | c.2207G>T | p.R736L | NERSIPSMVDGLKPGQRKVLFTCFK[p.R 736L]LNDKREVKVAQLAGSVAEMSSY HHGE | KVLFTCFKL,KLNDKREVK,FTCFKLNDK,KLNDKREVKV,FTCF KLNDKR,RKVLFTCFKL | LUAD |
| TOP2 A | c.3595A>G | p.K1199E | FIEELEAVEAKEKQDEQVGLPGKGG[p.K 1199E]EAKGKKTQMAEVLPSPRGQRVI PRIT | KGGEAKGKK,GEAKGKKTQM | THCA |
| TOP2 B | c.1967G>A | p.R656H | IKYYKGLGTSTAKEAKEYFADMERH[p. R656H]HILFRYAGPEDDAAITLAFSK KKIDD | DMERHHILF,MERHHILFR,RHHILFRYA,ADMERHHIL,FAD MERHHI,YFADMERHHI,MERHHILFRY,DMERHHILFR,FA DMERHHI,ADMERHHILF | CRC |
| TOPB P1 | c.4141de\|A | p.I1381fs | ILDVLTGINVQQRRLALAAMEWRKK[p. I1381fs]SSKDKNLALLREHLVGGRLFY MWISLEKQASNAFFSQEEQRCYLVLYL YLKRPHIFFLT* | FSQEEQRCY,LVGGRLFYM,RLFYMWISL,YLVLYLYL,YLYLK RPHI,NLALLREHL,HLVGGRLFY,LVILYLYLK,FYMWISLEK,VI LYLYLKR,VGGRLFYMW,CYLVLYLYL,YLKRPHIF,YLKRPHIF F,KSSKDKNLA,SSKDKNLAL,GGRLFYMWI,AFFSQEEQR,A MRWRKKKS,EQRCYLVIL,LKRPHIFFL,LEKQASNAF,REHLV GGRL,EKQASNAFF,KQASNQFFS,SQEEQRCYL,RCYLVILYL, EEQRCYLVI,QEEQRCYLV,NLALLREHLV,HLVGGRLFYM,Y MWISLEKQA,YLKRPHIFFL,AMRWRKKSSK,LFYMWISLEK, YLVILYLYLK,LVGGRLFYMW,CYLVILYLYL,LYLYLKRPH,YLY LKRPHIF,LYLKRPHIFF,RWRKKSSKDK,SSKDKNLALL,EQRC YLVILY,RCYLVILYLY,LLREHLVGGR,NAFFSQEEQR,LVILYLY LKR,SLEKQASNAF,LEKQASNAFF,KSSKDKNLAL,KNLALLRE HL,REFILVGGRLF,GRLFYMVVISL,KQASNAFFSQ,ILYLYLKR PH,EEQRCYLVIL,QEEQRCYLVI | STAD |
| TOR1 AIP2 | c.436G>A | p.G146R | PSDKVGRADAHLGSSSVALPKEASD[p. G146R]RTGASQEPPTTDSQEAQSPGH SSAGQ | KEASDRTGA | TGCT |
| TOR3 A | c.37T>C | p.F13L | MLRGPWRQLWLF[p.F13L]LLLLLPGAP EPRGASRPWEGTDEPGS | RQLWLFLLL,QLWLFLLLL,FLLLLLPGA,PWRQLWLFL,LWLF LLLLL,RQLWLFLLLL,QLWLFLLLLL,PWRQLWLFLL,GPWRQ LWLFL | ACC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TOX | c.1061C>T | p.S354L | RASLVSKSYSEPVDVKTSQPPQLIN[p.S354L]LKPSVFHGPSQAHSALYLSSHYHQQP | QLINLKPSV, LINLKPSVF, SQPPQLINL, SQPPQLINLK, QLINLKPSVF | CRC |
| TP53 | c.1010G>T | p.R337L | TSSSPQPKKKPLDGEYFTLQIRGRE[p.R337L]LFEMPRELNEFALELKDAQAGKEPGGS | ELFEMFREL, LQIRGRELF, RGRELFEMF, TLQIRGREL, IRGRELFEM, RGRELFEMFR, TLQIRGRELF, IRGRELFEMF, RELFEMFREL | LUAD, LUSC |
| TP53 | c.173del C | p.P58fs | SPLPSQAMDDLMLSPDDIEQWFTED[p.P58fs]QVQMKLPECQRLLPPWPLHQQLLHRRPLHQPPPGPCHLLSLPRKPTRAATVSVWASCILGQPSL* | KLPECQRLL, SLPRKPTRA, RLLPPWPLH, LSLPRKPTR, PTRAATVSV, RAATVSVWA, QMKLPECQR, TVSVWASCI, LPRKPTRAA, QQLLHRRPL, MKLPECQRL, QRLLPPWPL, TRAATVSVW, VSVWASCIL, WPLHQQLLH, TEDQVQMKL, SLPRKPTRAA, C QRLLPPWPL, LLSLPRKPTR, ATVSVWASCI, TVSVWASCIL, L PPWPLHQQL, LPRKPTRAAT, KPTRAATVSV, HQQLLHRRPL, QWFTEDQVQM, MKLPECQRLL, QQLLHRRPLH, HQPPPGP CHL, ASCILGQPSL, IEQWFTEDQV | HNSC |
| TP53 | c.216del C | p.P72fs | DDIEQWFTEDPGPDEAPRMPEAAPP[p.P72fs]WPLHQQLLHRRPLHQPPPGPCHLLSLPRKPTRAATVSVWASCILGQPSL* | SLPRKPTRA, RMPEAAPPW, LSLPRKPTR, PTRAATVSV, RAA TVSVWA, TVSVWASCI, LPRKPTRAA, QQLLHRRPL, TRAATV SVW, VSVWASCIL, WPLHQQLLH, PEAAPPWPL, SLPRKPTR AA, LLSLPRKPTR, ATVSVWASCI, TVSVWASCIL, MPEAAPP WPL, APPWPLHQQL, LPRKPTRAAT, KPTRAATVSV, HQQL HRRPL, QQLLHRRPLH, HQPPPGPCHL, ASCILGQPSL | LUAD |
| TP53 | c.313G>T | p.G105C | PTPAAPAPAPSWPLSSSVPSQKTYQ[p.G105C]CSYGFRLGFLHSGTAKSVTCTYSPAL | YQCSYGFRL, KTYQCSYGF, CSYGFRLGF, SQKTYQCSY, TYQCSYGFR, KTYQCSYGFR, TYQCSYGFRL, PSQKTY QCSY, QKTYQCSYGF, YQCSYGFRLG, CSYGFRLGFL | LUAD |
| TP53 | c.323del G | p.G108fs | AAPAPAPSWPLSSSVPSQKTYQGSY[p.G108fs]VSVWASCILGQPSL* | YVSVWASCI, TYQGSYVSV, YQGSYVSVW, SYVSVWASC, KT YQGSYVS, VSVWASCIL, KTYQGSYVSV, YQGSYVSVWA, SQ KTYQGSYV, YVSVWASCIL, TYQGSYVSVW, SYVSVWASCI, A SCILGQPSL | BRCA |
| TP53 | c.328del C | p.R110fs | PAPAPSWPLSSSVPSQKTYQGSYGF[p.R110fs]VWASCILGQPSL* | TYQGSYGFV, YQGSYGFVW, SYGFVWASC, YGFVWASCI, KTYQGSY GFV, YQGSYGFVWA, TYQGSYGFVW, SYGFVWASCI, YGFVWASCIL, ASCILGQPSL | BRCA |
| TP53 | c.329G>T | p.R110L | PAPAPSWPLSSSVPSQKTYQGSYGF[p.R110L]LLGFLHSGTAKSVTCTYSPALNKMFC | YQGSYGFLL, FLLGFLHSG, TYQGSYGFL, SYGFLLGFL, GSYGFLLGF, FLLGFLHSGT, KTYQGSYGFL, LLGFLHSGTA, TYQGSYGFLL, YQGSYGFLLG, QGSYGFLLGF | HNSC, LUAD |
| TP53 | c.396G>C | p.K132N | YGFRLGFLHSGTAKSVTCTYSPALN[p.K132N]NMFCQLAKTCPVQLMVDSTPPPGTRV | ALNNMFCQL, NMFCQLAKT, TYSPALNNM, YSPALNNMF, A LNNMFCQLA, TYSPALNNMF, CTYSPALNNM | BLCA, BRCA |
| TP53 | c.396G>T | p.K132N | YGFRLGFLHSGTAKSVTCTYSPALN[p.K132N]NMFCQLAKTCPVQLMVDSTPPPGTRV | ALNNMFCQL, NMFCQLAKT, TYSPALNNM, YSPALNNMF, A LNNMFCQLAT, XSPALNNMF, CTYSPALNNM | OV |
| TP53 | c.421T>G | p.C141G | SGTAKSVTCTYSPALNKMFCQLAKT[p.C141G]GPVQLMVDSTPPPGTRVRAMAIYKQS | CQLAKTGPV, KTGPVQLMV, AKTGPVQLW, QLAKTGPVQL, KMFCQLAKTG, LAKTGPVQLW | PRAD |
| TP53 | c.422G>A | p.C141Y | SGTAKSVTCTYSPALNKMFCQLAKT[p.C141Y]YPVQLMVDSTPPPGTRVRAMAIYKQS | CQLAKTYPV, KTYPVQLWV, MFCQLAKTY, LAKTYPVQL, AKT YPVQLW, QLAKTYPVQL, KMFCQLAKTY, LAKTYPVQLW, YP VQLMVDST | BRCA |
| TP53 | c.427G>A | p.V143M | TAKSVTCTYSPALNKMFCQLAKTCP[p.V143M]MQLMVDSTPPPGTRVRAMAIYKQSQH | KTCPMQLMV, CQLAKTCPM, AKTCPMQLMV, MQLMVDST P, QLAKTCPMQL, FCQLAKTCPM, LAKTCPMQLW, MQLWV DSTPP, CPMQLMVDST | HNSC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TP53 | c.451C>A | p.P151T | YSPALNKMFCQLAKTCPVQLWDST[p.P151T]TPPGTRVRAMAIYKQSQHMTEVVRRC | STPPGTR,VQLWDSTT,STPPGTRVR,TPPGTRVRAM,VQLWDSTTP | HNSC |
| TP53 | c.455de|C | p.P152fs | SPALNKMFCQLAKTCPVQLWDSTP[p.P152fs]RPAPASAPWPSTSSHST* | QLWDSTPR,TPRPAPASA,RPAPASAPW,APWPSTSSH,W PSTSSHST,STRPAPASA,TPRPAPASAP,APASAPWPST | STAD |
| TP53 | c.461G>T | p.G154V | ALNKMFCQLAKTCPVQLWDSTPPP[p.G154V]VTRVRAMAIYKQSQHMTEVV RRCPHH | WDSTPPPV,VTRVRAMAI,DSTPPPVTR,STPPPVTRV,PPV TRVRAM,VTRVRAMAIY,DSTPPPVTRV,LWDSTPPPV | LUAD |
| TP53 | c.464C>A | p.T155N | LNKMFCQLAKTCPVQLWDSTPPPG[p.T155N]NRVRAMAIYKQSQHMTEVVR RCPHHE | STPPPGNRV,PPGNRVRAM,GNRVRAMAI,NRVRAMAIY,G NRVRAMAIY,DSTPPPGNRV | GBM |
| TP53 | c.469G>T | p.V157F | KMFCQLAKTCPVQLWDSTPPPGTR[p.V157F]FRAMAIYKQSQHMTEVVRRCP HHERC | RFRAMAIYK,GTRFRAMAI,TRFRAMAIY,PPGTRFRAM,TRF RAMAIYK,GTRFRAMAIY,RFRAMAIYKQ,STPPPGTRFR | HNSQ,LIHC, LUAD,LUSC,OV |
| TP53 | c.473G>A | p.R158H | MFCQLAKTCPVQLWDSTPPPGTRV[p.R158H]HAMAIYKQSQHMTEVVRRCP HHERCS | RVHAMAIYK,GTRVHAMAI,PPGTRVHAM,TRVHAMAIY,G TRVHAMAIY | GBM,LIHC |
| TP53 | c.473G>T | p.R158L | MFCQLAKTCPVQLWDSTPPPGTRV[p.R158L]LAMAIYKQSQHMTEVVRRCPH HERCS | RVLAMAIYK,GTRVLAMAI,TPPPGTRVL,PPGTRVLAM,TRV LAMAIY,GTRVLAMAIY | LUAD,LUSC |
| TP53 | c.475G>C | p.A159P | FCQLAKTCPVQLWDSTPPPGTRVR[p.A159P]PMAIYKQSQHMTEVVRRCPHH ERCSD | RVRPMAIYK,GTRVRPMAI,PPGTRVRPM,TRVRPMAIY,GT RVRPMAIY,RVRPMAIYKQ | LUAD |
| TP53 | c.476C>T | p.A159V | FCQLAKTCPVQLWDSTPPPGTRVR[p.A159V]VMAIYKQSQHMTEVVRRCPH HERCSD | RVRVMAIYK,GTRVRVMAI,RVMAIYKQS,TRVRVMAIY,GT RVRVMAIY,RVRVMAIYKQ,VMAIYKQSQH | BLCA,OV |
| TP53 | c.488A>G | p.Y163C | AKTCPVQLWDSTPPPGTRVRAMAI[p.Y163C]CKQSQHMTEVVRRCPHHERCS DSDGL | RVRAMAICK,AICKQSQHM,GTRVRAMAIC,RVRAMAICKQ, MAICKQSQHM | BRCA,HNSQ, LUAD,LUSC,OV |
| TP53 | c.517G>A | p.V173M | DSTPPPGTRVRAMAIYKQSQHMTEV[p.V173M]MRRCPHHERCSDSDGLAPPQ HLIRVE | MRRCPHHER,QSQHMTEVM,VMRRCPHHER,KQSQHMT EVM | BRCA,HNSC |
| TP53 | c.517G>T | p.V173L | DSTPPPGTRVRAMAIYKQSQHMTEV[p.V173L]LRRCPHHERCSDSDGLAPPQH LIRVE | VLRRCPHHER,QSQHMTEVLR,KQSQHMTEVL | BRCA,HNSC |
| TP53 | c.523C>G | p.R175G | TPPPGTRVRAMAIYKQSQHMTEVVR[p.R175G]GCPHHERCSDSDGLAPPQHLI RVEGN | TEVVRGCPH,VVRGCPHHER | LUSC |
| TP53 | c.523C>T | p.R175C | TPPPGTRVRAMAIYKQSQHMTEVVR[p.R175C]CCPHHERCSDSDGLAPPQHLIR VEGN | TEVVRCCPH,VVRCCPHHER | CRC |
| TP53 | c.524G>A | p.R175H | TPPPGTRVRAMAIYKQSQHMTEVVR[p.R175H]HCPHHERCSDSDGLAPPQHLI RVEGN | TEVVRHCPH,VVRHCPHHER,SQHMTEVVRH | BLCA,BRCA, CLL,CRC, GBM,HNSC, LUAD,OV, PAAD,PRAD, STAD,UCS |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TP53 | c.527G>A | p.C176Y | PPPGTRVRAMAIYKQSQHMTEVVRR[p.C176Y]YPHHERCSDSDGLAPPQHLIRVEGNL | HMTEVVRRY,TEVVRRYPH,VVRRYPHHER,QHMTEVVRRY | OV |
| TP53 | c.527G>T | p.C176F | PPPGTRVRAMAIYKQSQHMTEVVRR[p.C176F]FPHHERCSDSDGLAPPQHLIRVEGNL | HMTEVVRRF,TEVVRRFPH,VVRRFPHHER,QHMTEVVRRF | BRCA,LUAD,STAD |
| TP53 | c.535C>T | p.H179Y | GTRVRAMAIYKQSQHMTEVVRRCPH[p.H179Y]YERCSDSDGLAPPQHLIRVEGNLRVE | VVRRCPHYE,EVVRRCPHY,VVRRCPHY,TEVVRRCPHY,YERCSDSDGL | HNSC |
| TP53 | c.536A>G | p.H179R | GTRVRAMAIYKQSQHMTEVVRRCPH[p.H179R]RERCSDSDGLAPPQHLIRVEGNLRVE | EVVRRCPHR,VVRRCPHRER,RERCSDSDGL | BRCA,GBM,HNSC,OV,UCS |
| TP53 | c.536A>T | p.H179L | GTRVRAMAIYKQSQHMTEVVRRCPH[p.H179L]LERCSDSDGLAPPQHLIRVEGNLRVE | EVVRRCPHL,VVRRCPHLER,TEVVRRCPHL,LERCSDSDGL | LUSC |
| TP53 | c.572_574 del CTC | p.P191del | SQHMTEVVRRCPHHERCSDSDGLAP[p.P191del]QHLIRVEGNLRVEYLDDRNTFRHSVVVP | GLAPQHLIR,GLAPQHLIRV | OV |
| TP53 | c.577C>T | p.H193Y | HMTEVVRRCPHHERCSDSDGLAPPQ[p.H193Y]YLIRVEGNLRVEYLDDRNTFRHSVVV | GLAPPQYLI,YLIRVEGNL,DSDGLAPPQY,GLAPPQYLIR,QYLIRVEGNL,YLIRVEGNLR | BRCA |
| TP53 | c.578A>G | p.H193R | HMTEVVRRCPHHERCSDSDGLAPPQ[p.H193R]RLIRVEGNLRVEYLDDRNTFRHSVVV | GLAPPQRLI,RLIRVEGNL,RLIRVEGNLR | BRCA,LIHC,OV,UCS |
| TP53 | c.578A>T | p.H193L | HMTEVVRRCPHHERCSDSDGLAPPQ[p.H193L]LLIRVEGNLRVEYLDDRNTFRHSVVV | GLAPPQLLI,LLIRVEGNL,GLAPPQLLIR,LLIRVEGNLR | BRCA,HNSC,LUSC |
| TP53 | c.581T>G | p.L194R | MTEVVRRCPHHERCSDSDGLAPPQH[p.L194R]RIRVEGNLRVEYLDDRNTFRHSVVVP | GLAPPQHRI,RIRVEGNLR,APPQHRIRV,RIRVEGNLRV | BRCA,OV |
| TP53 | c.584T>C | p.I195T | TEVVRRCPHHERCSDSDGLAPPQHL[p.I195T]TRVEGNLRVEYLDDRNTFRHSVVVPY | GLAPPQHLT,LTRVEGNLR,GLAPPQHLTR,LTRVEGNLRV,HLTRVEGNLR | BRCA,OV |
| TP53 | c.587G>C | p.R196P | EVVRRCPHHERCSDSDGLAPPQHLI[p.R196P]PVEGNLRVEYLDDRNTFRHSVVVPYE | HLIPVEGNL,APPQHLIPV,IPVEGNLRV,HLIPVEGNLR,LAPPQHLIPV | HNSC |
| TP53 | c.596G>T | p.G199V | RRCPHHERCSDSDGLAPPQHLIRVE[p.G199V]VNLRVEYLDDRNTFRHSVVVPYEPPE | HLIRVEVNL,LIRVEVNLR,EVNLRVEYL,VEVNLRVEY,LIRVEVNLRV,RVEVNLRVEY,HLIRVEVNLR,VEVNLRVEYL | BRCA |
| TP53 | c.614A>G | p.Y205C | ERCSDSDGLAPPQHLIRVEGNLRVE[p.Y205C]CLDDRNTFRHSVVVPYEPPEVGSDCT | CLDDRNTFR,ECLDDRNTFR,VECLDDRNTF,VEGNLRVECL | OV |
| TP53 | c.626_627 del GA | p.R209fs | DSDGLAPPQHLIRVEGNLRVEYLDD[p.R209fs]KHFST* | YLDDKHFST,VEYLDDKHF,RVEYLDDKHF | BRCA |
| TP53 | c.641A>G | p.H214R | APPQHLIRVEGNLRVEYLDDRNTFR[p.H214R]RSVVVPYEPPEVGSDCTTIHYNYMCN | NTFRRSVVV,FRRSVVVPY,TFRRSVVVPY,YLDDRNTFRR | LUSC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TP53 | c.644G>T | p.S215I | PPQHLIRVEGNLRVEYLDDRNTFRH[p.S215I]IVVVPYEPPEVGSDCTTIHYNYMCNS | NTFRHIVVV, RNTFRHIVV, FRHIVVVPY, FRHIVVVPY | LUAD |
| TP53 | c.645T>G | p.S215R | PPQHLIRVEGNLRVEYLDDRNTFRH[p.S215R]RVVVPYEPPEVGSDCTTIHYNYMCNS | NTFRHRVVV, RHRVVVPYE, FRHRVVVPY, TFRHRVVVPY | OV |
| TP53 | c.646G>A | p.V216M | PQHLIRVEGNLRVEYLDDRNTFRHS[p.V216M]MVVPYEPPEVGSDCTTIHYNYMCNSS | NTFRHSMVV, DRNTFRHSM, FRHSMVVPY, MVVPYEPPEV, TFRHSMVVPY | BRCA, GBM, OV |
| TP53 | c.659A>C | p.Y220S | IRVEGNLRVEYLDDRNTFRHSVVVP[p.Y220S]SEPPEVGSDCTTIHYNYMCNSSCMGG | VVPSEPPEV, VVVPSEPPEV | BRCA |
| TP53 | c.659A>G | p.Y220C | IRVEGNLRVEYLDDRNTFRHSVVVP[p.Y220C]CEPPEVGSDCTTIHYNYMCNSSCMGG | VVPCEPPEV, VVVPCEPPEV | BRCA, GBM, HNSC, LUSC, OV, UCEC |
| TP53 | c.701A>G | p.Y234C | RNTFRHSVVVPYEPPEVGSDCTTIH[p.Y234C]CNYMCNSSCMGGMNRRPILTIITLED | CTTIHCNYM, TTIHCNYMC, CNYMCNSSCM | BRCA, GBM, LUSC, OV |
| TP53 | c.706T>G | p.Y236D | TFRHSVVVPYEPPEVGSDCTTIHYN[p.Y236D]DMCNSSCMGGMNRRPILTIITLEDSS | NDMCNSSCM | HNSC |
| TP53 | c.707A>G | p.Y236C | TFRHSVVVPYEPPEVGSDCTTIHYN[p.Y236C]CMCNSSCMGGMNRRPILTIITLEDSS | YNMCMCNSSCM | HNSC, OV |
| TP53 | c.711G>A | p.M237I | FRHSVVVPYEPPEVGSDCTTIHYNY[p.M237I]ICNSSCMGGMNRRPILTIITLEDSSG | CTTIHYNYI, YNYICNSSCM | HNSC |
| TP53 | c.711G>C | p.M237I | FRHSVVVPYEPPEVGSDCTTIHYNY[p.M237I]ICNSSCMGGMNRRPILTIITLEDSSG | CTTIHYNYI, YNYICNSSCM | LUAD |
| TP53 | c.713G>A | p.C238Y | RHSVVVPYEPPEVGSDCTTIHYNYM[p.C238Y]YNSSCMGGMNRRPILTIITLEDSSGN | TTIHYNYMY, YMYNSSCMG, YNYMYNSSC, CTTIHYNYMY, Y MYNSSCMGG, YNYMYNSSCM, IHYNYMYNSS, MYNSSCMGGM | BRCA, GBM |
| TP53 | c.713G>T | p.C238F | RHSVVVPYEPPEVGSDCTTIHYNYM[p.C238F]FNSSCMGGMNRRPILTIITLEDSSGN | YMFNSSCMG, TTIHYNYMF, NYMFNSSCM, YNYMFNSSC, Y MFNSSCMGG, CTTIFIYNYMF, YNYMFNSSCM, IHYNYMFNSS, MFNSSCMGGM | BRCA, GBM, HNSC |
| TP53 | c.722C>A | p.S241Y | VVVPYEPPEVGSDCTTIHYNYMCNS[p.S241Y]YCMGGMNRRPILTIITLEDSSGNLLG | NYMCNSYCM, HYNYMCNSY, SYCMGGMNR, NSYCMGGM NR, IHYNYMCNSY, SYCMGGMNRR, YNYMCNSYCM, MCN SYCMGGM | UCS |
| TP53 | c.722C>T | p.S241F | VVVPYEPPEVGSDCTTIHYNYMCNS[p.S241F]FCMGGMNRRPILTIITLEDSSGNLLG | HYNYMCNSF, NYMCNSFCM, SFCMGGMNR, YMCNSFCM G, NSFCMGGMNR, IHYNYMCNSF, SFCMGGMNRR, YNYM CNSFCM | OV |
| TP53 | c.723del C | p.S241fs | VVVPYEPPEVGSDCTTIHYNYMCNSS[p.S241fs]AWAA* | YMCNSSAWA, NVMCNSSAW, YNYMCNSSA, YMCNSSAW AA, HYNYMCNSSA, YNYMCNSSAW | BRCA |
| TP53 | c.725G>T | p.C242F | VVPYEPPEVGSDCTTIHYNYMCNSS[p.C242F]FMGGMNRRPILTIITLEDSSGNLLGR | SSFMGGMNR, YNYMCNSSF, NYMCNSSFM, SFMGGMNR R, YMCNSSFMG, FMGGMNRRPI, SSFMGGMNRR, HYNYM CNSSF, NSSFMGGMNR, YNYMCNSSFM, YMCNSSFMGG, MCNSSFMGGM | CLL, HNSC, LUSC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TP53 | c.730G>T | p.G244C | PYEPPEVGSDCTTIHYNYMCNSSCM[p.G244C]CGMNRPILTIITLEDSSGNLLGRNS | YMCNSSCMC, SSCMCGMNR, CGMNRRPIL, SSCMCGMNR, R, NSSCMCGMNR, MCNSSCMCGM, CMCGMNRRPI | OV |
| TP53 | c.731G>A | p.G244D | PYEPPEVGSDCTTIHYNYMCNSSCM[p.G244D]DGMNRPILTIITLEDSSGNLLGRNS | SSCMDGMNR, DGMNRRPIL, NSSCMDGMNR, CMDGIVINRRPI | CRC |
| TP53 | c.733G>A | p.G245S | YEPPEVGSDCTTIHYNYMCNSSCMG[p.G245S]SMNRRPILTIITLEDSSGNLLGRNSF | SSCMGSMNR, GSMNRRPIL, MGSMNRRPI, CNSSCMGSM, SMNRRPILTI, SSCMGSMNR, NSSCMGSMNR, MGSMNR RPIL, MCNSSCMGSM, CMGSMNRRPI | CRC, GBM, HNSC, OV, PRAD |
| TP53 | c.734G>A | p.G245D | YEPPEVGSDCTTIHYNYMCNSSCMG[p.G245D]DMNRRPILTIITLEDSSGNLLGRNSF | SSCMGDMNR, NSSCMGDMNR, CMGDMNRRPI | OV |
| TP53 | c.734G>T | p.G245V | YEPPEVGSDCTTIHYNYMCNSSCMG[p.G245V]VMNRRPILTIITLEDSSGNLLGRNSF | SSCMGVMNR, GVMNRRPIL, SCMGVMNRR, MGVMNRRP I, CNSSCMGVM, YMCNSSCMGV, VMNRRPILTI, SSCMGVM NRR, NSSCMGVMNR, MGVMNRRPIL, MCNSSCMGVM, C MGVMNRRPI | HNSC, LUSC, OV |
| TP53 | c.742C>T | p.R248W | PEVGSDCTTIHYNYMCNSSCMGGMN[p.R248W]WRPILTIITLEDSSGNLLGRNSFEVR | NWRPILTII, SSCMGGMNW, MGGMNWRPI, MNWRPILTI, CMGGMNWRPI, GMNWRPILTI, SSCMGGMNWR, MNWR PILTII, NSSCMGGMNW | BLCA, BRCA, CLL, CRC, GBM, HNSC, OV, PAAD, UCEC |
| TP53 | c.743G>A | p.R248Q | PEVGSDCTTIHYNYMCNSSCMGGMN[p.R248Q]QRPILTIITLEDSSGNLLGRNSFEVR | MNQRPILTII, NQRPILTII, CMGGMNQRPI, GMNQRPILTI, SS CMGGMNQR, NQRPILTIIT | BLCA, BRCA, CLL, GBM, HNSC, OV, PRAD, STAD, UCEC, UCS |
| TP53 | c.743G>C | p.R248P | PEVGSDCTTIHYNYMCNSSCMGGMN[p.R248P]PRPILTIITLEDSSGNLLGRNSFEVR | SCMGGMNPR, NPRPILTII, GMNPRPILTI, CMGGMNPRPI, S SCMGGMNPR, NPRPILTIIT | LUAD |
| TP53 | c.745A>G | p.R249G | EVGSDCTTIHYNYMCNSSCMGGMNR[p.R249G]GPILTIITLEDSSGNLLGRNSFEVRV | GPILTMTL, MNRGPILTI, GMNRGPILTI, CMGGMNRGPI, MN RGPILTII | LUAD |
| TP53 | c.746G>T | p.R249M | EVGSDCTTIHYNYMCNSSCMGGMNR[p.R249M]MPILTIITLEDSSGNLLGRNSFEVRV | MNRMPILTI, MPILTIITL, MGGMNRMPI, SCMGGMNRM, N RMPILTII, CMGGMNRMPI, GMNRMPILTI, RMPILTIITL, M NRMPILTII, SSCMGGMNRM, MPILTIITLE | LUAD |
| TP53 | c.747G>T | p.R249S | EVGSDCTTIHYNYMCNSSCMGGMNR[p.R249S]SPILTIITLEDSSGNLLGRNSFEVRV | MNRSPILTI, SPILTIITL, MGGMNRSPI, GMNRSPILTI, CMGG MNRSPI, RSPILTIITL, MNRSPILTII | HNSC, LIHC, LUAD |
| TP53 | c.749C>T | p.P250L | VGSDCTTIHYNYMCNSSCMGGMNRR[p.P250L]LILTIITLEDSSGNLLGRNSFEVRVC | RLILTIITL, GMNRRLILT, MNRRLILTI, GGMNRRLIL, GMNRR LILTI, MNRRLILTII, RRLILTIITL | OV |
| TP53 | c.763A>T | p.I255F | TTIHYNYMCNSSCMGGMNRRPILTI[p.I255F]FTLEDSSGNLLGRNSFEVRVCACPGR | RPILTIFTL, NRRPILTIF, FTLEDSSGNL, MNRRPILTIF, RRPILTI FTL | LUAD |
| TP53 | c.775G>T | p.D259Y | YNYMCNSSCMGGMNRRPILTIITLE[p.D259Y]YSSGNLLGRNSFEVRVCACPGRDRRT | ILTIITLEY, LEYSSGNLL, PILTIITLEY, EYSSGNLLGR, LEYSSGNLLG | OV |
| TP53 | c.785G>T | p.G262V | MCNSSCMGGMNRRPILTIITLEDSS[p.G262V]VNLLGRNSFEVRVCACPGRDRRTEEE | IITLEDSSV, DSSVNLLGR, LEDSSVNLL, VNLLGRNSF, MTLEDSSV, TLEDSSVNLL, SVNLLGRNSF | HNSC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TP53 | c.796G>A | p.G266R | SCMGGMNRRPILTIITLEDSSGNLL[p.G266R]RRNSFEVRVCACPGRDRRTEEENLRK | LLRRNSFEV,DSSGNLLRR,GNLLRRNSF,NLLRRNSFEV,LLRR NSFEVR,SGNLLRRNSF | OV |
| TP53 | c.797G>A | p.G266E | SCMGGMNRRPILTIITLEDSSGNLL[p.G266E]ERNSFEVRVCACPGRDRRTEEENLRK | LLERNSFEV,DSSGNLLER,GNLLERNSF,NLLERNSFEV,SGNL LERNSF,LERNSFEVRV | BRCA,HNSC |
| TP53 | c.797G>T | p.G266V | SCMGGMNRRPILTIITLEDSSGNLL[p.G266V]VRNSFEVRVCACPGRDRRTEEENLRK | LLVRNSFEV,LVRNSFEVR,GNLLVRNSF,NLLVRNSFEV,LVR NSFEVRV,SGNLLVRNSF,LEDSSGNLLV | OV |
| TP53 | c.800G>C | p.R267P | CMGGMNRRPILTIITLEDSSGNLLG[p.R267P]PNSFEVRVCACPGRDRRTEEENLRKK | LLGPNSFEV,GNLLGPNSF,NLLGPNSFEV,SGNLLGPNSF | LUSC |
| TP53 | c.811G>A | p.E271K | MNRRPILTIITLEDSSGNLLGRNSF[p.E271K]KVRVCACPGRDRRTEEENLRKKGEPH | LLGRNSFKV,NLLGRNSFK,LGRNSFKVR,KVRVCACPG,NSFK VRVCA,SFKVRVCAC,NLLGRNSFKV,GNLLGRNSFK,KVRVC ACPGR | BLCA,LUSC |
| TP53 | c.814G>A | p.V272M | NRRPILTIITLEDSSGNLLGRNSFE[p.V272M]MRVCACPGRDRRTEEENLRKKGEPHH | LLGRNSFEM,LGRNSFEMR,NSFEMRVCA,FEMRVCACPG,NL LGRNSFEM,EMRVCACPGR,FEMRVCACPG | BRCA,OV |
| TP53 | c.817C>T | p.R273C | RRPILTIITLEDSSGNLLGRNSFEV[p.R273C]CVCACPGRDRRTEEENLRKKGEPHHE | NSFEVCVCA,EVCVCACPGR,FEVCVCACPG | BLCA,BRCA, CRC,HNSC,OV, STAD,UCEC |
| TP53 | c.818G>A | p.R273H | RRPILTIITLEDSSGNLLGRNSFEV[p.R273H]HVCACPGRDRRTEEENLRKKGEPHHE | NSFEVHVCA,LGRNSFEVH,EVHVCACPGR,HVCACPGRDR, FEVHVCACPG | BRCA,CLL, CRC,GBM, HNSC,LUAD, OV,STAD, UCEC,UCS |
| TP53 | c.818G>T | p.R273L | RRPILTIITLEDSSGNLLGRNSFEV[p.R273L]LVCACPGRDRRTEEENLRKKGEPHH E | NSFEVLVCA,LGRNSFEVL,LLGRNSFEVL,EVLVCACPGR,FE VLVCACPG | LUAD,LUSC,OV |
| TP53 | c.820G>T | p.V274F | RPILTIITLEDSSGNLLGRNSFEVR[p.V274F]FCACPGRDRRTEEENLRKKGEPHHE L | NSFEVRFCA,GRNSFEVRF,EVRFCACPGR,LGRNSFEVRF,FE VRFCACPG | LUAD |
| TP53 | c.824G>A | p.C275Y | PILTIITLEDSSGNLLGRNSFEVRV[p.C275Y]YACPGRDRRTEEENLRKKGEPHHEL | RNSFEVRVY,YACPGRDRR,NSFEVRVYA,RVYACPGRDR,EV RVYACPGR,GRNSFEVRVY,FEVRVYACPG | OV |
| TP53 | c.824G>T | p.C275F | PILTIITLEDSSGNLLGRNSFEVRV[p.C275F]FACPGRDRRTEEENLRKKGEPHHEL P | FACPGRDRR,NSFEVRVFA,RNSFEVRVF,FEVRVFACP,RVF ACPGRDR,EVRVFACPGR,VFACPGRDRR,GRNSFEVRVF,FE VRVFACPG | HNSC,LUAD |
| TP53 | c.830G>T | p.C277F | LTIITLEDSSGNLLGRNSFEVRVCA[p.C277F]FPGRDRRTEEENLRKKGEPHHELP PG | CAPPGRDRR,SFEVRVCAF,EVRVCAPPGR,NSFEVRVCAF,F EVRVCAPPG | LUAD |
| TP53 | c.832C>T | p.P278S | TIITLEDSSGNLLGRNSFEVRVCAC[p.P278S]SGRDRRTEEENLRKKGEPHHELPP GS | CACSGRDRR,FEVRVCACS,EVRVCACSGR,FEVR VCACSG | HNSC |
| TP53 | c.841G>A | p.D281N | TLEDSSGNLLGRNSFEVRVCACPGR[p.D281N]NRRTEEENLRKKGEPHHELPPG STKR | CACPGRNRR,RVCACPGRNR | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TP53 | c.844C>T | p.R282W | LEDSSGNLLGRNSFEVRVCACPGRD[p.R282W]WRTEEENLRKKGEPHHELPPG STKRA | CACPGRDWR,RDWRTEEENL | BRCA,CRC,GBM, HNSC,OV,STAD |
| TP53 | c.853G>A | p.E285K | SSGNLLGRNSFEVRVCACPGRDRRT[p.E285K]KEENLRKKGEPHHELPPGSTKR ALPN | RTKEENLRK,RTKEENLRKK | BLCA,CESC, HNSC,LUAD |
| TP53 | c.856G>A | p.E286K | SGNLLGRNSFEVRVCACPGRDRRTE[p.E286K]KENLRKKGEPHHELPPGSTKRAL PNN | RTEKENLRK,RTEKENLRKK | BRCA,STAD |
| TP53 | c.945_946 de\|TC | p.S315fs | KGEPHHELPPGSTKRALPNNTSSSP[p.S315fs]AKEETTGWRIFHPSDPWA* | KEETTGWRI,RIFHPSDPW,EETTGWRIF,RIFHPSDPWA,LP NNTSSSPA,KEETTGWRIF,WRIFHPSDPW,EETTGWRIFH,S PAKEETTGW | OV |
| TP53R K | c.520de\|C | p.L174fs | VLARMHDEDLIHGDLTTSNMLLKPP[p.L174fs]WNS* | SNMLLKPPW | STAD |
| TPO | c.1193G>C | p.S398T | AACAPEPGIPGETRGPCFLAGDGRA[p.S398T]TEVPSLTALHTLWLREHNRLAA ALKA | FLAGDGRAT,GRATEVPSL,TEVPSLTAL,TEVPSLTALH | ACC |
| TPO | c.1672G>A | p.E558K | GGLDPLIRGLLARPAKLQVQDQLMN[p.E558K]KELTERLFVLSNSSTLDLASINLQ RG | QVQDQLMNK,KELTERLFV,LMNKELTERL,QLMNKELTER, VQDQLMNKEL,MNKELTERLF,KELTERLFVL | LUAD |
| TPO | c.2476G>A | p.A826T | ADGAHPPCHASARCRNTKGGFQCLC[p.A826T]TDPYELGDDGRTCVDSGRLPR VTWIS | CLCTDPYEL,FQCLCTDPY,GFQCLCTDPY | CRC |
| TPPP | c.89G>A | p.R30K | AKPAKAANRTPPKSPGDPSKDRAAK[p.R30K]KLSLESEGAGEGAAASPELSALEE AF | KLSLESEGA,PSKDRAAKK,DRAAKKLSL | KIRP |
| TPR | c.6464C>T | p.S2155L | EDRTVPSTPTLVVPHRTDGFAEAIH[p.S2155L]LPQVAGVPRFRFGPPEDMPQT SSSHS | AEAIHLPQV,FAEAIHLPQV,AIHLPQVAGV,HLPQVAGVP R,LPQVAGVPRF,AEAIHLPQVA | CRC |
| TPRX1 | c.598T>C | p.S200P | NPGPIPGPNPGPIPGPISGPIPGPI[p.S200P]PVPIPGPIPGPISGPNPGPIPG | GPIPGPIPV,IPGPIPVPI,IPVPIPGPI | TGCT |
| TPTE | c.1268C>T | p.S423L | AQVKHLYNWNLPPRRLFIKHFIIYL[p.S423L]LIPRYVRDLKIQIEMEKKVFSTISL | FIKHFIIYL,IIYLIPRYV,FIIYLIPRY,HFIIYLIPR,IYLIPRYV R,IKHFIIYLI,FIKHFIIYLI,FIIYLIPRYV,YLIPRYVRDL,IIYL IPRYVR,LIPRYVRDLK,LFIKHFIIYL,KHFIIYLIPR,HFIIYLIPRY VEILFGEKI,GEKITSSDVV,VEILFGEKIT | CRC,UCEC |
| TPTE2 | c.1623G>A | p.M541I | DNLHKQKARRIYPSDFAVEILFGEK[p.M541I]ITSSDVVAGSD* | KHQNHYRVY,QNHYRVINL,KKHQNHYRV,FLDKKHQNHY, HQNHYRVYNL,KKHQNHYRVI | LUSC |
| TPTE2 | c.773G>A | p.R258Q | FPSSGRQSFYRNPIEEVVRFLDKKH[p.R258Q]QNHYRVYNLCSERAYDPKHFHN RVSR | | CRC |
| TRAF3 | c.26C>T | p.S9F | MESSKKMD[p.S9F]FPGALQTNPPLKL HTDRSAGTPVFVP | MESSKKMDF,KKMDFPGAL,SSKKMDFPGA,SKKMDFPGAL | CESC |
| TRAF7 | c.32G>A | p.R11H | MSSGKSARYN[p.R11H]HFSGGPSNLP TPDVTTGTRMETTFGP | KSARYNHFS,SARYNHFSG,GKSARYNHF,KSARYNH FSG,SARYNHFSGG,SGKSARYNHF,NHFSGGPSNL | DLBCL |
| TRAK1 | c.1879G>A | p.D627N | DPRPGVVTKGFRTLDVDLDEVYCLN[p.D627N]NFEEDTGDHISLPRLATSTPV QHPE | DEVYCLNNF | CRC |
| TRAM 1 | c.121G>C | p.E41Q | HEFVLQNHADIVSCVAMVFLLGLMF[p.E41Q]ITAKASIIFVTLQVNVTLPATEE QA | FLLGLMFQI,LMFQITAKA,FQITAKASI,GLMFQITAK,FLLGL MFQIT,GLMFQITAKA,FQITAKASII,LGLMFQITAK,VFLLGL MFQI,MFQITAKASI,LMFQITAKAS,QITAKASIIF | BLCA |

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TRAM1L1 | c.1033de|A | p.R345fs | LQRWVEDSNIQASCMKKKRSRSSKK[p. R345fs]EQKTEWEWKLQIE* | SKKEQKTEW,TEMEWKLQI,KEQKTEWEW,RSRSSKKEQK | STAD |
| TRANK1 | c.2536G>A | p.E846K | YNISRRLSKLRVLPWSIHELYGDEI[p.E8 46K]KDFTQAELALLMKCINDPNSMFLT GD | LYGDEIKDF,IKDFTQAEL,DEIKDFTQA,EIKDFTQAEL,KDFT QAELAL,DEIKDFTQAE | UCEC |
| TRAPPC10 | c.399_400 insA | p.K133fs | WQNVLKAHSSVDWLIVIVENDAKKK[p. K133fs]KQNQHPSPNLYCGQNKK* | NLYCGQNKK,NQHPSPNLY,KQNQHPSPN,KQNQHPSPNL, QNQHPSPNLY | GBM |
| TRAPPC11 | c.1703G>A | p.R568Q | MNESPDPEPDCDILAVKTAQKLWAD[p. R568Q]QISLAGSNIFTIGVQDFVPFVQ CKAK | KLWADQISL,AQKLWADQI,KLWADQISLA,QISLAGSNIF,Q KLWADQISL,DQISLAGSNI | CRC |
| TRDN | c.2190A>C | p.*730Y | PFTPADRPGESSGQANSPGQKQQGQ[p. *730Y]YTHMYDPYKCFKILKM* | YTHMYDPYK,MYDPYKCFK,QQGQYTHMY,KQQGQYTHM, HMYDPYKCF,QKQQGQYTH,GQYTHMYDP,YKCFKILKM, DPYKCFKIL,HMYDPYKCFK,MYDPYKCFKI,KQQGQYTHMY, GQYTHMYDPY,QQKQQGQYTH,QKQQGQYTHM,THMY DPYKCF,SPGQKQQGQY | KIRC |
| TRIM23 | c.1187G>A | p.R396Q | QQQFTEVADHIQLDASIPVTFTKDN[p. R396Q]QVHIGPKMEIRVVTLGLDGAG KTTIL | FTKDNQVHI,NQVHIGPKM,KDNQVHIGPK | CRC |
| TRIM23 | c.866G>A | p.R289Q | IVEDGIGMAHTEHVPGTAENARSCI[p. R289Q]QAYFYDLHETLCRQEEMALSVV DAHV | RSCIQAYFY,CIQAYFYDL,NARSCIQAY,ARSCIQAYF, IQAYFYDLH,ARSCIQAYFY,ENARSCIQAY,NARSCIQAYF, AENARSCIQA | CRC |
| TRIM4 | c.1193G>T | p.R398L | NVFTSGKHYWEVESRDSLEVAVGVC[p. R398L]LEDVMGITDRSKMSPDVGIWAI YWSA | LEVAVGVCL | LUAD |
| TRIM42 | c.379C>A | p.Q127K | TFHKGRLRSIHTSSKTALRTGSSDT[p.Q1 27K]KVDEVKSIPANSHLVNHLNCPMCS RL | ALRTGSSDTK | LUAD |
| TRIM48 | c.278C>A | p.A93D | CFECIKTIQQRNLKTNIRLKKMASL[p.A9 3D]DRKASLWLFLSSEEQMCGIHRETKK M | RLKKMASLD,KMASLDRKA,RLKKMASLDR,MASLDRKASL, KKMASLDRKA,ASLDRKASLW,LDRKASLWLF | LUAD |
| TRIM61 | c.294G>C | p.K98N | SLTEIAKQLQIRSKKKRRQEEKHVC[p.K9 8N]NKHNQVLTFFCQKDLELLCPRCSLS T | NKHNQVLTF,RQEEKHVCNK,CNKHNQVLTF,KHNQVLTF F | CESC |
| TRIM7 | c.994C>A | p.L332I | MKNKVWNVSLKTFVLKGMLKKFKED[p. L332I]IRGELEKEEKVELTLDPDTANPRL IL | MLKKFKEDI,KFKEDIRGEL,MLKKFKEDIR | LUSC |
| TRIM9 | c.1009C>A | p.R337S | FEACLVAQCDALIDALNRRKAQLLA[p.R 337S]SVNKEHEFIKLKVVRDQISHCTVK LRQ | AQLLASVNK,SVNKEHEHK,RKAQLLASV,KAQLLASVN K,ASVNKEHEHK,RRKAQLLASV | LUAD |
| TRIML1 | c.1197C>A | p.H399Q | DLFSLIGLKIGDDYSLMVSSPLKGQ[p.H 399Q]QVREPVCKVGVFLDYESGHIAFY NGT | LKGQQVREPV | LUAD |
| TRIO | c.1981C>T | p.R661W | QTGECDPEEIYQAAHQLEDRIQDFV[p. R661W]WRVEQRKILLDMSVSFHTHVK ELWTW | RIQDFVWRV,FVWRVEQRK,DFVWRVEQR,WRVEQRKIL, DFVWRVEQRK,WRVEQRKILL | CRC |
| TRIOBP | c.3899A>G | p.H1300R | DLPPPRRLAQRQPGPQAQCSSGGRT[p. H1300R]RSPGRAEVERLFGQERRKSEA AGAFQ | GGRTRSPGR,RTRSPGRAE,GGRTRSPGRA,RTRSPGRAEV | ACC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TRIP11 | c.1622de|A | p.K541fs | DQLSKQQNEGDSIISKLKQDLNDEK[p.K541fs]REFINLKMIKWTLLKS* | KMIKWTLLK,EFINLKMIK,NLKMIKWTL,LKMIKWTLL,KREFINLKM,REFINLKMI,DEKREFINL,NLKMIKWTLL,EKREFINLKM,KMIKWTLLKS | STAD |
| TRIP12 | c.5324T>C | p.L1775P | KLMAKAIMDFRLVDLPLGLPFYKWM[p.L1775P]PRQETSLTSHDLFDIDPVVARSVYHL | WMPRQETSL,KWMPRQETS,LPFYKWMPR,MPRQETSLT,YKWMPRQET,KWMPRQETSL,GLPFYKWMPR,MPRQETSLTS,YKWMPRQETS | MM |
| TRMT61A | c.731G>T | p.S244I | ALAARGFSELSTLEVLPQVYNVRTV[p.S244I]ILPPPDLGTGTDGPAGSDTSPFRSGT | VYNVRTVI,QVYNVRTVI,PQVYNVRTVI,QVYNVRTVIL | TGCT |
| TRPA1 | c.162G>T | p.K54N | TEDFKESLKVVPEGSAYGLQNFNKQ[p.K54N]NKLKRCDDMDTFFLHYAAAEGQIELM | NFNKQNKLKR,LQNFNKQNKL | CRC |
| TRPA1 | c.2017de|A | p.T673fs | DKSCRDYYIEYNFKYLQCPLEFTKK[p.T673fs]HLHRMLYMNRLQPSTQWYKITA* | YMNRLQPST,RLQPSTQWY,LQPSTQWYK,LHRMLYMNR,STQWYKITA,KKHLHRMLY,EFTKKHLHR,FTKKHLHRM,LEFTKKHLH,KHLHRMLYM,HRMLYMNRL,QPSTQWYKI,MLYMNRLQPS,HLHRMLYMNR,RLQPSTQWYK,LQPSTQWYKI,KKHLHRMLY,FTKKHLHRML,TKKHLHRMLY,RMLYMNRLQP,YMNRLQPSTQ,MNRLQPSTQW,CPLEFTKKHL | STAD |
| TRPC5 | c.1469C>T | p.S490L | PREEWEMWHPTLIAEALFAISNILS[p.S490L]LLRLILSLFTANSHLGPLQISLGRML | FAISNILSL,AISNILSLL,ISNILSLLR,SLLRLISLF,LSLLRLISL,FAISNILSLL,ILSLLRLISL,LLRLISLFTA,AISNILSLLR,LFAISNILSL,LSLLRLISLF,ISNILSLLRL | CRC, UCEC |
| TRPM3 | c.1285C>T | p.R429W | TRTQAQHLFIILMECMKKKELITVF[p.R429W]WMGSEGHQDIDLAILTALLKGANASA | KELITVFWM,WMGSEGHQDI,KKKELITVFW,KKELITVFWM,KELITVFWMG | UCEC |
| TRPM3 | c.892G>T | p.G298W | QTMSNPMSKLTVLNSMHSHFILADN[p.G298W]WTTGKYGAEVKLRRQLEKHISLQKIN | FILADNWTT,LADNWTTGK,ADNWTTGKY,SHFILADNW,LADNWTTGKY,ILADNWTTGK,WTTGKYGAEV,HSHFILADNW | LUAD |
| TRPM6 | c.2984G>A | p.R995H | IAKMTANMFYIVIIMAIVLLSFGVA[p.R995H]HKAILSPKEPPSWSLARDIVFEPYWM | LLSFGVAHK,SFGVAHKAI,AHKAILSPK,LSFGVAHKA,VLLSFGVAH,LLSFGVAHKA,VLLSFGVAHK,V AHKAILSPK,LSFGVAHKAI | CRC |
| TRPM7 | c.2528G>A | p.R843Q | VRILDSNEGKNEMEIQMKSKKLPIT[p.R843Q]QKFYAFYHAPIVKFWFNTLAYLGFLM | ITQKFYAFY,KSKKLPITQ,KLPITQKFY,KKLPITQKF,TQKFYAF YH,QKFYAFYHA,LPITQKFYA,KLPITQKFYA,KSKKLPITQK,IT QKFYAFYH,TQKFYAFYHA,KKLPITQKFY,PITQKFYAFY,LPIT QKFYAF,SKKLPITQKF,QKFYAFYHAP | CRC |
| TRPM7 | c.5584C>T | p.R1862C | PQDEPSDLNLQPGNSTKESESTNSV[p.R1862C]CLML* | SESTNSVCL,KESESTNSVC,SESTNSVCLM | CRC |
| TRPM8 | c.2295_2296insC | p.H765fs | VFYIAFILLFAVLLMDFHSVPHPP[p.H765fs]RAGPVLAGLCPLL* | VLAGLCPLL,HSVPHPPRA,HPPRAGPVL,RAGPVLAGL,DFH SVPHPPR,VPHPPRAGPV,GPVLAGLCPL | STAD |
| TRPS1 | c.3373C>T | p.R1125W | IEKYQYPLFGLPFVHNDFQSEADWL[p.R1125W]WFWSKYKLSVPGNPHYLSHVPGLPNP | WLWFWSKYK,FQSEADWLW,SEADWLWFW,LWFWSKYK L,WLWFWSKYKL,EADWLWFWSK,DFQSEADWLW,FQSE ADWLWF,WFWSKYKLSV,DWLWFWSKYK,ADWLWFWSK Y,SEADWLWFWS | CRC |
| TRPV2 | c.1865_1867de|TGC | p.L627 de| | KFTIGMGELAFQEQLHFRGMVLLLL[p.L627de|]AVVLLTYILLLNMLIALMSETVNSVATD | MVLLLLAYV,VLLLLAYVL,RGMVLLLLA,GMVLLLLAY,GMVL LLLAYV,MVLLLLAYVL,VLLLLAYVLL,RGMVLLLLAY | CLL |
| TRPV3 | c.653C>A | p.A218E | FAEENDILGRFINAEYTEEAYEGQT[p.A218E]ELNIAIERRQGDIAALLIAAGADVNA | GQTELNIAI,ELNIAIERR,EAYEGQTEL,YEGQTELNI,AYEGQ TELNI,QTELNIAIER,EEAYEGQTEL,YEGQTELNIA | KIRP |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TRPV5 | c.1475G>A | p.R492H | YFTRGFQMLGPFTIMIQKMIFGDLM[p.R492H]HFCWLMAVVILGFASAFYIIFQTEDP | LMHFCWLMA,MHFCWLMAV,KMIFGDLMH, F,DLMHFCWLM,GDLMHFCWL,MIFGDLMHF,LMHFCW LMAV,KMIFGDLMHF,IFGDLMHFCW,HFCWLMAVVI,MH FCWLMAVV,GDLMHFCWLM | CRC |
| TRRAP | c.10543C>T | p.R3515W | THYYIKIARFMPRVEIVQKHNTAAR[p.R3515W]WLYIRGHNGKIYPYLVMNDACLTESR | TAARWLYIR,AARWLYIRG,HNTAARWLY,NTAARWLYI,QK HNTAARW,KHNTAARWL,WLYIRGHNGK,NTAARWLYIR, AARWLYIRGH,RWLYIRGHNG,KHNTAARWLY,VQKHNTA ARW,QKHNTAARWL | CRC |
| TRRAP | c.2917G>T | p.A973S | DCLKSANTEPYYRRQ[p.A973S]WEVIKCFLV[p.A973S]SMMSLEDNKHALYQLLAHPNFTEKTI | SMMSLEDNK,CFLVSMMSL,VIKCFLVSM,IKCFLVSMM,VS MMSLEDNK,EVIKCFLVSM,KCFLVSMMSL,SMMSLEDNKH, WEVIKCFLVS | KICH |
| TSC1 | c.1132G>T | p.G378C | CGMTTPPTSPGNVPPDLSHPYISKVF[p.G378C]CTTAGGKGTPLGTPATSPPPAPLCHS | KVFCTTAGG,YSKVFCTTA,SKVFCTTAG,KVFCTTAGGK, HPYSKVFCTT | LUAD |
| TSC22D2 | c.1255G>A | p.A419T | AQPSSTGAAASPATAATLPVGTGQN[p.A419T]TSSVGAQLMGASSQPSEAMAPRTGPA | NTSSVGAQL,GQNTSSVGA,NTSSVGAQLM | ACC |
| TSG101 | c.794A>G | p.K265R | WRMKEEMDRAQAELNALKRTEEDLK[p.K265R]RGHQKLEEMVTRLDQEVAEVDKNIEL | DLKRGHQKL,RGHQKLEEM | THCA |
| TSG101 | c.826C>A | p.R276S | AELNALKRTEEDLKKGHQKLEEMVT[p.R276S]SLDQEVAEVDKNIELLKKKDEELSSA | KLEEMVTSL,SLDQEVAEV,MVTSLDQEV,EMVTSLDQEV,TS LDQEVAEV,QKLEEMVTSL | LUAD |
| TSHZ1 | c.1503G>C | p.K501N | EDSLEKFEPSTLYPYLREEDLDDSP[p.K501N]NGGLDILKSLENTVSTAISKAQNGAP | SPNGGLDIL | LUAD |
| TSHZ1 | c.2642G>T | p.R881M | QAQFASSLRETTEGKYIMSDLGPQE[p.R881M]MVHISKFTGLSMTTISHWLANVKYQL | MSDLGPQEM,QEMVHISKF,MSDLGPQEMV,IMSDLGPQE M,MVHISKFTGL,PQEMVHISKF,QEMVHISKFT | CRC |
| TSHZ2 | c.664G>A | p.A222T | LYRQSSKMCGTVFTGASRFRCRQCS[p.A222T]TAYDTLVELTVHMNETGHYQDDNRKK | RFRCRQCST,RCRQCSTAY,CSTAYDTLV,TAYDTLVEL,RQCS TAYDT,STAYDTLVEL,RFRCRQCSTA,FRCRQCSTAY,RQCST AYDTL | GBM |
| TSHZ3 | c.2030G>T | p.G677V | EPIKMEASSDGGFRSQENSPSPPRD[p.G677V]VCKDGSPLAEPVENGKELVKPLASSL | RDVCKDGSPL | LUAD |
| TSKS | c.1537G>A | p.E513K | CPSCQRLHKKILELERQALAKHVRA[p.E513K]KALSSTLRLAQDEALRAKNLLLTDKM | ALAKHVRAK,LAKHVRAKA,HVRAKALSS,RAKALSSTL,KALS STLRL,AKHVRAKAL,ALAKHVRAKA,QALAKHVRAK, HVRAKALSST,RAKALSSTLR,KALSSTLRLA,LAKHVRAKAL, VRAKALSSTL,AKALSSTLRL | BLCA |
| TSPAN4 | c.274C>G | p.L92V | IGFVGCLGAIKENKCLLLTFFLLL[p.L92V]VFLLEATIAILFFAYTDKIDRYAQQ | LTFFLLLIV,FLLLLVFL,LLLLVVFLL,LLVVFLLEA,FFLLLVVF, LLTFFLLLIV,LTFFLLLIVV,FLLLLVVFLL,LLLVVFLLEA,TFFLLL LVVF,FFLLLVVFL | PRAD,CT |
| TSSK1B | c.901G>A | p.E301K | ARGSPSVAINKEGESSRGTEPLWTP[p.E301K]KPGSDKKSATKLEPEGEAQPQAQPET | GTEPLWTPK,RGTEPLWTPK | UCEC |
| TTBK2 | c.249T>G | p.C83W | KQVLKMEVAVLKKLQGKDHVCRFIG[p.C83W]WGRNDRFNYVVMQLQGRNLADLRRSQ | WGRNDRFNY,VCRFIGWGR,FIGWGRNDR,IGWGRNDRF, HVCRFIGWGR,GWGRNDRFNY,RFIGWGRNDR,FIGWGR NDRF | KIRP |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TTC21A | c.809C>A | p.S270Y | ESNIDACQILTVHELAREGNMTTVSl[p.S270Y]YLKTQKATNHVRNLIKALETREPENP | NMTTVSYLK,TVSYLKTQK,EGNMTTVSY,GNMTTVSYL,RLSKGH,RLSKGH, GN MTTVSYLK,TTVSYLKTQK,REGNMTTVSY | CRC |
| TTF1 | c.1007 de|A | p.K336fs | RPAVGLHGETAGIPAPAYKNKSKKK[p.K336fs]RKKSPITRNLRQWPCLRASRVHTLKDHRWAVRLGLWKAVQLLKGSRNPTVQRRSLRKGSLRLSKGHECLVMIFQCPVRTLRAHSLIQ* | TLKDHRWAV,GLWKAVQLL,LVMIFQCPV,SLRKGSLRL,RLSKGH ECL,RASRVHTLK,TVQRRSLRK,WAVRLGLWK,LWKAV QLLK,RSLRKGSLR,RWAVRLGLW,IFQCPVRTL,RTLRAHSLI, KNKSKKKRK,KKRKSPITR,KSPITRNLR,RNLRQWPCL,CLRAS RVHT,RVHTLKDHR,HTLKDHRWA,AVRLGLWKA,GSRNPT VQR,NLRQWPCLR,QWPCLRASR,PTVQRRSLR,VMIFQCP VR,FQCPVRTLR,WPCLRASRV,NPTVQRRSL,SKKKRKSPI,LRA SRVHTL,RKSPITRNL,RQWPCLRAS,HRWAVRLGL,SKGH ECLVM,GHECLVMIF,VRTLRAHSL,CPVRTLRAH,KDHRWA VRL,RLSKGHECLV,CLVMIFQCPV,MIFQCPVRTL,CLRASRV HTL,LLKGSRNPTV,GLWKAVQLLK,RWAVRLGLWK,LVMIF QCPVR,KSKKKRKSPI,KKKRKSPITR,KRKSPITRNL,ITRNLRQ WPC,RNLRQWPCLR,RQWPCLRASR,HTLKDHRWAV, TLKDHRWAVR,AVRLGLWKAV,GSRNPTVQRR,RSLRKGSLRL, SLRKGSLRLS,RTLRAHSLIQ,IFQCPVRTLR,LSKGHECLVM, RVHTLKDHRW,HRWAVRLGLW,LRLSKGHECL,KG HECLVMIF,FQCPVRTLRA,SPITRNLRQW | STAD |
| TTF1 | c.1589A>G | p.Q530R | IKDRATSTIKRMYRDDLERFKEFKA[p.Q530R]RGVAIKFGKFSVKENKQLEKNVEDFL | RGVAIKFGK,RFKEFKARG,KARGVAIKF,EFKARGVAI,KEFKA RGVA,RPKEFKARGV,EFKARGVAIK,KARGVAIKFG,KEFKAR GVAI,FKARGVAIKF,RGVAIKFGKF | TGCT |
| TTF2 | c.2281C>A | p.R761S | LDEAHNVKNPRVQTSIAVCKLQACA[p.R761S]SWAVTGTPIQNNLLDMYSLLKFLRCS | KLQACASWA,LQACASWAV,CKLQACASW,SWAVTGTPI,KLQA CASWAV,LQACASWAVT,ASWAVTGTPI | LUAD |
| TTI1 | c.2120G>A | p.R707H | CGYDSLQHLINQNSDYLVNGISLNL[p.R707H]HHLALHPHTPKVLEVMLRNSDANLLP | SLNLHHLAL,GISLNLHHL,LHHLALHPH,GISLNLHHLA,ISLNL HHLAL | STAD |
| TTLL11 | c.367_368 insAGG CCA | p.122_123insKA | SELAARWEAEAVAAAKAAAAKAEAEA[p.122_123insKA]KATAETVAEQVRVDAGAAGEPECKAGEEQPK | AAKAEAEAK,EAKATAETV,ARAEAKATA,AKATAETVA,AEA KATAET,AAAKAEAEAK,AEAKATAETV | ACC |
| TTLL7 | c.2252G>A | p.R751H | LIKLDSVKQRKVLDIVKTSIRTVLP[p.R751H]IHWKVPDVEEVNLYRIFNRVFNRLLW | TVLPHIWKV,SIRTVLPHI,RTVLPHIWK,TSIRTVLPH,KTISIRT VLPH,RTVLPHIWKV,TSIRTVLPHI,SIRTVLPHIW,LPHIWKV PDV | UCEC |
| TUBA1C | c.436C>T | p.L146F | EDGVVGLNYSCGNLGRRVNGELQLG[p.L146F]FLAIIN* | LQLGFLAII,ELQLGFLAI,VNGELQLGF,GELQLGFLA,RVNGE LQLGF,GELQLGFLAI | ACC, GCT |
| TUBA3C | c.526_527 insC | p.Q176fs | SLLMERLSVDYGKKSKLEFAIYPAP[p.Q176fs]PGLHGRGGAlQLHPDHPDPGTF* | AIYPAPPGL,GLHGRGGAL,HGRGGALQL,LQLHPDHPH,FAI YPAPPGL,AIYPAPPGLH,LEFAIYPAPP,LHGRGGALQL | LUAD |
| TUBA3D | c.728G>A | p.R243Q | DIERPTYTNLNRLIGQIVSSITASL[p.R243Q]QFDGALNVDLTEFQTNLVPYPRIHFP | LQFDGALNV,SSITASLQF,ASLQFDGAL,SLQFDGALNV,ITA SLQFDGA,VSSITASLQF,LQFDGALNVD | CRC |
| TUBB P5 | c.304G>A | p.V102M | TYHGDSHLQLERINVHHHEASGGRY[p.V102M]MPRAVLVDLEPGTMDSVRSGPFGQVL | ASGGRYMPR,RYMPRAVLV,GGRYMPRAV,MPRAVLVDL, HEASGGRYM,GRYMPRAVL,YMPRAVLVDL,EASGGRYMP R,HHEASGGRYM | GBM |
| TUBB P5 | c.356G>A | p.R119H | HEASGGRYVPRAVLVDLEPGTMDSV[p.R119H]HSGPFGQVLRPDNFIFGELRARTGVR | MDSVHSGPF,HSGPFGQVL,SVHSGPFGQV,HSGPFGQVLR, TMDSVHSGPF,VHSGPFGQVL | UCS |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| TUBD1 | c.599C>T | p.A200V | YGTGEVIVQNYNSILTLSHLYRSSD[p.A200V]VLLLHENDAIHKICAKLMNIKQISFS KSQQRKVRQMIEQLQNSKAVIQSKD[p.A340T]TTIQELKEKIAYLEAENLEMHDR MEH | HLYRSSDVL,RSSDVLLLH,LYRSSDVLL,YRSSDVLLL,HLYRSS DVLL,VLLLHENDAI,LYRSSDVLL,SHLYRSSDVL | BRCA |
| TUFT1 | c.1018G>A | p.A340T | | TTIQELKEK,SKDTTIQEL,AVIQSKDTTI | CRC |
| TUFT1 | c.303G>C | p.L101F | HSAGHSLASELVESHDGHEEIIKVY[p.L101F]FKGRSGDKMIHEKNINQLKSEVQY IQ | IIKVYFKGR,KVYFKGRSG,YFKGRSGDK,FKGRSGDKM,HEEIIKVYF, VYFKGRSGDK,EIIKVYFKGR | CESC |
| TWIST NB | c.918T>A | p.H306Q | KKKHQEVQDQDPVFQGSDSSGYQSD[p.H306Q]QKKKKKKKRKHSEEAEFTPLK CSPKR | SSGYQSDQK | CLL |
| TXND C15 | c.1028G>A | p.R343Q | LIKSVDWLLVFSLFFLLISFIMYATI[p.R343Q]QTESIRWLIPGQEQEHVE* | FIMYATIQT,IQTESIRWL,QTESIRWLI,YATIQTESI,IMYATIQ TE,IQTESIRWLI,IMYATIQTES,MYATIQTESI | CRC |
| TXNL1 | c.700C>T | p.R234C | AERSEPTQALELTEDDIKEDGIVPL[p.R234C]CYVKFQNVNSVTIFVQSNQGEEET TR | GIVPLCYVK,IVPLCYVKF,DGIVPLCYV,KEDGIVPLCY,GIVPL CYVKF | UCEC |
| TYRP1 | c.1054_1057delACAA | p.T352fs | PEPQDVAQCLEVGLPDTPPFYSNST[p.T352fs]VSETQWKVTVTPRESMTLLFEVF TIWLIYS* | TVSETQWKV,ESMTLLFEV,TLLFEVFTI,STVSETQWK,SMTL LFEVF,EVFTIWLIY,QWKVTVTPR,MTLLFEVFT,TPRESMTLL, SETQWKVTV,TQWKVTVTP,LLFEVFTIW,FEVFTIWLI,MTL LFEVFTL,LLFEVFTIWL,STVSETQWKV,TQWKVTVTPR,ESM TLLFEVF,TLLFEVFTIW,LFEVFTIWLI,KVTVTPRESM,EVFTI WLIYS,TPRESMTLLF,RESMTLLFEV,FEVFTIWLIY,SETQWK VTVT,TPPFYSNSTV | GBM |
| U2AF1 | c.101C>A | p.S34Y | FGTEKDKVNCSFYFKIGACRHGDRC[p.S34Y]YRLHNKPTFSQTIALLNIYRNPQNS | YRLHNKPTF,CYRLHNKPTF,GDRCYRLHNK,GACRHGDRCY | LAML |
| U2AF1 | c.101C>T | p.S34F | FGTEKDKVNCSFYFKIGACRHGDRC[p.S34F]FRLHNKPTFSQTIALLNIYRNPQNS | FRLHNKPTF,CFRLHNKPTF,ACRHGDRCFR,GDRCFRLHNK, GACRHGDRCF | CESC, LAML, LUAD, UCS |
| UBC | c.2051del G | p.G684fs | EDGRTLSDYNIQKESTLHLVLRLRG[p.G684fs]VSKFPPLLRFQQISLHFPFNKVVAF | SLHFPFNKV,HVLRLRGV,LLRFQQISL,VLRLRGVSK,GVSKF PLLR,ISLHFPFNK,RFQQISLHF,QQISLHFPF,RLRGVSKFP,R GVSKFPLL,FPLLRFQQI,FPFNKVVAF,LRLRGVSKF,LRGVSK FPL,VSKFPLLRF,LHFPFNKVV,RLRLRGVSK,KFPPLLRFQQI,FQQISLHFPF,HF PFNKVVAF,RGVSKFPLLR,ISLHFPFNKV,VLRLRGVSKF,GVS KFPLLRF,LRFQQISLHF,LHFPFNKVVA,FPLLRFQQIS | STAD |
| UBC | c.572T>C | p.I191T | TLEVEPSDTIENVKAKIQDKEGIPP[p.I191T]TSRGSSLQASSWKMAVLFLTTTSRR S | TSRGSSLQA,PPTSRGSSL,IPPTSRGSSL,IQDKEGIPPT | PRAD |
| UBE2J2 | c.577G>T | p.G193W | KQKQKAQDELSSRPQTLPLPDVVPD[p.G193W]METHLVQNGIQLLNGHAPGA VPNLAG | VPDWETHLV,VVPDWETHL,DVVPDWETHL,WETH LVQNGI,LPLPDVVPDW | LUAD |
| UBE2M | c.392G>A | p.G131D | LEGNVCLNILREDWKPVLTINSIIY[p.G131D]DLQYLFLEPNPEDPLNKEAAEVLQ NN | NSIIYDLQY,SIIYDLQYLF,TINSIIYDL,IIYDLQYLF,IYDLQYL- FL,I IYDLQYLFL,SIIYDLQYLF,INSIIYDLQY,LTINSIIYDL,NSIIYDL QYL | TGCT |
| UBE2 NL | c.257G>T | p.R86I | EEYPMAAPKVRFMTKIYHPNVDKLE[p.R86I]IISLDILKDKWSPALQIRTVLLSIQA | EIISLDIIK,HPNVDKLEI,LEIISLDIL,HPNVDKLEII | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| UBE2O | c.3354_3355insG | p.R1118fs | YENSRCVNEMALIRVVQSMTQLVRR[p.R1118fs]APRGL* | SMTQLVRRA, TQLVRRAPR, LVRRAPRGL, MTQLVRRAPR | KIRC |
| UBIAD1 | c.289G>A | p.A97T | AYRSHGVLDPRLLVGCAVAVLAVHG[p.A97T]TGNLVNTYDFSKGIDHKKSDDRTLV | GTNLVNTY, AVHGTGNLV, TGNLVNTY, GTGNLVNTYY, V LAVHGTGNL, HGTGNLVNTY, LAVHGTGNLV | CRC |
| UBOX5 | c.1250C>T | p.S417L | LPTTSEHTAKKMKATNEPSLTHMDC[p.S417L]LTGPLSHEQKLSQSLEIALASTLGSM | HMDCLTGPL, LTGPLSHEQK, THMDCLTGPL | BLCA |
| UBQLN2 | c.1568de|C | p.A523fs | PIGPIVPFTPIGPIGPIGPTGPAAP[p.A523fs]LAPPALIVAPRGLLCPALIHLVKPRVLHQNLDPTSSSFSKWCRPWLEQMLHSCRIQKSDFSNNWNSSTQWGS* | GLLCPALHL, LLCPALHLV, ALHLVKPRV, ALVAPRGLL, VLHQNLDPT, MLHSCRIQK, SSSFSKWCR, SFSKWCRPW, APRGLLCPA, KPRVLHQNL, EQMLHSCRI, NLDPTSSSF, WCRPWLEQM, QKSDFSNNW, NWWNSSTQW, APLAPPALV, GLLCPALHLV, LLCPALHLVK, QMLHSCRIQK, TSSSFSKWCR, SFSKWCRPW L, KWCRPWLEQM, LAPPALVAPR, GPAAPLAPPA, APLAPPA LVA, APRGLLCPAL, IQKSDFSNNW, RGLLCPALHL, HQNLDP TSSS, QNLDPTSSSF, SSFSKWCRPW, LEQMLHSCRI, HSCRIQ KSDF, SNNWNSSTQW, DPTSSSFSKW | STAD |
| UBR1 | c.4939G>T | p.G1647W | KHPVLCLFCGAILCSQNICCQEIVN[p.G1647W]WEEVGACIFHALHCGAGVCIFLKIRE | WEEVGACIF, QEIVNWEEV, WEEVGACIFH | LUAD |
| UBR4 | c.8406de|C | p.P2802fs | TAENVNGNPSPLEALLAGAEGFPP[p.P2802fs]CWTSHLMQMTRPWLN* | LMQMTRPWL, TSHLMQMTR, CWTSHLMQM, FPPCWTSH L, HLMQMTRPW, AEGFPPCWT, HLMQMTRPWL, WTSHL MQMTR, GFPPCWTSHL, FPPCWTSHLM, SHLMQMTRPW, AEGFPPCWTS | STAD |
| UBR5 | c.6360de|A | p.K2120fs | EVLPTKMSYAANLKNVMNMQNRQKK[p.K2120fs]KGKNSPCCQKKLRVQNQGHLLMILLHN* | KNSPCCQKK, KLRVQNQGH, RVQNQGHLL, VQNQGHLLM, LRVQNQGHL, NQGHLLMIL, MQNRQKKGK, KGKNSPCCQ K, KLRVQNQGHL, RVQNQGHLLM, LRVQNQGHLL, VQNQG HLLMI, NQGHLLMILL | KICH |
| UBR5 | c.7551G>T | p.R2517S | LDDTDDGDDNAPLFYQPGKRGFYTP[p.R2517S]SPGKNTEARLNCFPRNIGRILGLCLLQ | GFYTPSPGK, RGFYTPSPG, RGFYTPSPGK, SPGKNTEARL | TGCT |
| UBXN7 | c.827C>T | p.A276V | LDQVTGFLGEHGQLDGLSSSPPKKC[p.A276V]VRSESLIDASEDSQLEAAIRASLQET | KKCVRSESL | CLL |
| UGP2 | c.784G>C | p.D262H | ASFYNSGLLDTPIGEGKEYIFVSNI[p.D262H]HNLGATVDLYILNHLMNPPNGKRCEF | NIHNLGATV, IFVSNIHNL, IFVSNIHNLA, HNLGATVDLY, KEYIFVSNIH | BLCA |
| UGT1A1 | c.10A>G | p.T4A | MAR[p.T4A]AGWTSPIPLCVSLLLTCGFAEAGKLL | ARAGWTSPI, AGWTSPIPL, MARAGWTSPI, RAGWTSPIPL | KIRP |
| UGT2A1 | c.290de|A | p.N97fs | EIYRVPFGKERIEGVIKDFVLTWLE[p.N97fs]IDHLLQPFGDSIRRWPK* | LLQPFGDSI, DFVLTWLEI, TWLEIDHLL, LEIDHLLQP, VLTWL EIDHL, HLLQPFGDSI, LEIDHLLQPF, KDFVLTWLEI, QPFGDSI RRW | CRC |
| UGT2B11 | c.1340G>T | p.R447I | STDLLNALKTVINDPLYKENIMKLS[p.R447I]IQHDQPVKPLDRAVFWIEFVMPHKG | KENIMKLSI, IMKLSIIQH, YKENIMKLSI, KENIMKLSII | TGCT |
| UGT2B28 | c.866C>A | p.P289H | FQFPHPFLPNIDFVGGLHCKPAKPL[p.P289H]HKEMEEFVQSSGENGVVVFSLGSVIS | HCKPAKPLHK, KPAKPLHKEM | GBM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| UGT2B7 | c.642G>A | p.M214I | FPPSYVPVVMSELTDQMTFMERVKN[p.M214I][IIYVLYFDFWFEIFDMKKWDQFYSEV | RVKNIIYVL,TFMERVKNI,KNIIYVLYF,IIYVLYFDF,VKNIIYVL Y,MERVKNIIY,FMERVKNII,FMERVKNII,RVKNIIYVLY,TF MERVKNI,NIIYVLYFD,IIYVLYFDW,MTFMERVKNI,MERV KNIIYV,VKNIIYVLYF | LUAD |
| UGT8 | c.304G>A | p.E102K | FNSTTSDAFLQSKMRNIFSGRLTAI[p.E102K]KLFDILDHYTKNCDLMVGNHALIQGL | KLFDILDHY,FSGRLTAIK,SGRLTAIKL,TAIKLFDIL,GRLTAIKL F,RLTAIKLFDI,KLFDILDHYT,IFSGRLTAIK,SGRLTAIKLF,IKLF DILDHY | CRC, UCEC |
| UHRF1BP1 | c.3990de|C | p.I1330fs | EIPVVVPMQIELLNSSITLKDDIPP[p.I1330fs]SIQHLQAPSPSLWPWNMLC* | HLQAPSPSL,SLWPWNMLC,IQHLQAPSP,LQAPSPSLW,AP SPSLWPW,SPSLWPWNM,TLKDDIPPSI,SPSLWPWNML,IQHLQAPS PS,QHLQAPSPSL,HLQAPSPSLW,IPPSIQHLQA | STAD |
| UMODL1 | c.1677G>A | p.M559I | CQCRTTRDATPSRAGRACEGDLVSP[p.M559I]IGGGLSAATGVTVPGLGTCTAALGLE | LVSPIGGGL,SPIGGGLSA,CEGDLVSPI,SPIGGGLSAA | TGCT |
| UNC93A | c.1334_1335TC>CG | p.V445A | LTMVAYGLVECVESKNPIRPHAPGQ[p.V445A]ANQAEDEEIQTKM* | RPHAPGQAN | TGCT |
| UNC93B1 | c.1492G>A | p.V498M | YHWWQAVAIFTVYLGSSLHMKAKLA[p.V498M]MLLVTLVAAAVSYLRMEQKLRRGVAP | KLAMLLVTL,LAMLLVTLV,AMLLVTLVA,MLLVTLVAA,HMK AKLAML,KAKLAMLL,LHMKAKLAM,MKAKLAMLL,AKLA MLLVT,KLAMLLVTLV,AMLLVTLVAA,MLLVTLVAAA,HMK AKLAMLL,KAKLAMLLVT,SLHMKAKLAM,LHMKAKLAML, MKAKLAMLLV,AKLAMLLVTL,LAMLLVTLVA | CESC |
| UPK2 | c.145de|C | p.P49fs | DFNISSLSGLLSPALTESLLVALPP[p.P49fs]VTSQEAMPH* | SLLVALPPV,ALPPVTSQEA,ESLLVALPPV,LPPVTSQEAM | STAD |
| UPK3A | c.816_817insC | p.G272fs | QITQEAVPKSLGASESSYTSVNRGP[p.G272fs]ATGQG* | YTSVNRGPA | KIRC |
| UQCRFS1 | c.16T>G | p.S6A | MLSVA[p.S6A]ARSGPFAPVLSATSRGVAGALRPLVQ | SVAARSGPF,ARSGPFAPV,SVAARSGPFA, AARSGPFAPV,LSVAARSGPF,ARSGPFAPVL | ACC |
| UQCRFS1 | c.247A>G | p.I83V | QAVRRPLVASVGLNVPASVCYSHTD[p.I83V]VKVPDFSEYRRLEVLDSTKSSRESSE | VKVPDFSEY,SVCYSHTDVK,DVKVPDFSEY,SHTDVKVPDF | KIRC |
| URGCP | c.1916_1917insG | p.G639fs | HFLREMGQFYEAESCLVEAGRLPAG[p.G639fs]PEAFCPLPRLGLGAAADRAAS GANRWEHAEHARPLGHRAPEGAARPT GETVKAGGSVNRGARHGQVHTPQH HVWAAVCHREELRSSRGLHAAHHSG* | HVWAAVCHR,RLPAGPEAF,HARPLGHRA,AARPTGETV,RS SRGLHAA,SSRGLHAAH,AVCHREELR,EAFCPLPRL,ETVKA GGS,QVHTPQHHV,HTPQHHVWA,LPRLGLGAA,RPLGHR APE,APEGAARPT,TPQHHVWAA,RAASGANRW,AEHARPL GH,RGARHGQVH,GQVHTPQHH,EELRSSRGL,GQVHTPQ HHV,AGRLPAGPEA,AARPTGETVK,TVKAGGSVNR,RSSRG LHAAH,SSRGLHAAHH,HTPQHHVWAA,LPRLGLGAAA,RP LGHRAPEG,TPQHHVWAAV,ELRSSRGLHA,GRLPAG PEAF,WEHAEHARPL,QVHTPQHHVW,WAAVCHREEL,REELRSS RGL,LRSSRGLHAA,PEAFCPLPRL,GETVKAGGSV,CPLPRLGLGA | KICH |
| URI1 | c.39_40insC | p.S13fs | MEAPTVETPDDPSPP[p.S13fs]FGPGPCPGSVARPGCGAAARGAGKGGH* | GAAARGAGK,VARPGCGAA,CGAAARGAGK,SVARPGCGAA RPGCGAAA,CGAAARGAGK,SVARPGCGAA | HNSC |
| USF1 | c.155G>A | p.R52Q | DPTSVAIASIQSAATFPDPNVKYVF[p.R52Q]QTENGGQVMYRVIQVSEGQLDGQTEG | FQTENGGQV,QTENGGQVM,VARPGCGAA,SVARPGCGAA FQTENGGQV,QTENGGQVMY,FQTENGGQVM | UCEC |
| USH2A | c.11156G>A | p.R3719H | NSTTVELYWSLLPEKPNGLVSQYQLS[p.R3719H]HNGNLLFLGGSEEQNFTDKNLEPNSR | YQLSHNGNL,QLSHNGNLL,LSHNGNLLF,SQYQLSHNG,SH NGNLLFL,YQLSHNGNLL,QYQLSHNGNL,QLSHNGNLLF,SQ YQLSHNGN,LSHNGNLLFL | GBM |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| USH2A | c.7107C>A | p.F2369L | KAHVRWEAPFRPNGLLTHSVLFTGI[p.F2369L]LYVDPVGNNYTLLNVTKVMYSG EETN | VLFTGILYV, SVLFTGILY, TGILYVDPV, HSVLFTGIL, HSVLFTGILY, SVLFTGILY, FTGILYVDPV, LYVDPVGNNY | CRC |
| USP11 | c.856G>A | p.A286T | VLDAALETGQLIIMETRKKDGTWPS[p.A286T]TQLHVMNNNMSEEDEDFKGQ PGICGL | GTWPSTQLH, TWPSTQLHV, WPSTQLHVM, TWPSTQLHV M, TQLHVMNNNM | CRC |
| USP15 | c.2344de|A | p.K782fs | KKRYFDENAAEDFEKHESVEYKPPK[p.K782fs]NPL* | VEYKPPKNPL | STAD |
| USP16 | c.1364G>A | p.R455Q | DIPSGTSKHLQKKAKKQAKKQAKNQ[p.R455Q]QRQQKIQGKVLHLNDICTIDHP EDSE | QAKNQQRQQK, QQRQQKIQGK, AKNQQRQQKI | UCEC |
| USP25 | c.2618G>A | p.R873H | FKAIKLEYARLVKLAQEDTPPETDY[p.R873H]HLHHVVVYFIQNQAPKKIIEKTLLE Q | ETDYHLHHV, HLHHVVVYF, YHLHHVVVY, TDYHLHHVV, ET DYHLHHVV, HLHHVVVYFI, YHLHHVVVYF, DTPPETDYH L, TDYHLHHVV | UCEC |
| USP25 | c.3356G>A | p.R1119Q | EPPKLPSYSTHELCERFARIMLSLS[p.R1119Q]QTPADGR* | MLSLSQTPA, RIMLSLSQT, IMLSLSQTP, IMLSLSQTPA | CRC |
| USP26 | c.2582G>A | p.R861Q | TLKSGHYICDAYDFEKQIWFTYDDM[p.R861Q]QVLGIQEAQMQEDRRCTGYIF FYMHN | FTYDDMQVL, MQVLGIQEA, TYDDMQVLGI, MQVLGIQEAQ | CRC |
| USP29 | c.243C>A | p.F81L | NIRSVLRHCKKRQSHLRLTLKNNV[p.F81L]LLFIDKLSYRDAKQLNMFLDIIHQN K | LLFIDKLSY, TLKNNVLLF, RLTLKNNVL, LKNNVLLFI, TLLKNNV LLFI, LLFIDKLSYR, LTLKNNVLLF, KNNVLLFIDK, VLLFIDKLSY, LRLTLKNNVL, RLTLKNNVL | CRC |
| USP31 | c.1171G>A | p.D391N | LTEMYDGFHRSFCDTDDLETVHES[p.D391N]NCIFAFETPEIFRPEGIlSQRGIH LN | ETVHESNCI, TVHESNCIF, HESNCIFAF, TVHESNCIFA, ESNCI FAFET, VHESNCIFAF | CRC |
| USP33 | c.107G>A | p.R36Q | LTLKVLPHFESLGKQEKIPNKMSAF[p.R36Q]QNHCPHLDSVGEITKEDLIQKSLG TC | KMSAFQNHC, SAFQNHCPH, MSAFQNHCPH, SAFQNHCP HL | UCEC |
| USP4 | c.775C>G | p.L259V | STAPSRNFTTSPKSSASPYSSVSAS[p.L259V]VIANGDSTSTCGMHSSGVSRGGS GFS | YSSVSASVI, PYSSVSASVI, SPYSVSVASV, YSSVSASVIA | CESC |
| USP40 | c.2552C>T | p.S851L | DSYTLKEAELKMGSSLGLCLGKAPS[p.S851L]LSQLFLFFAMGSDVQPGTEMEIV VEE | KAPSLSQLF, PSLSQLFLF, SLSQLFLFF, APSLSQLFLF, GKAPSLS QL, SLSQLFLFFA, PSLSQLFLFF, KAPSLSQLFL, LGKAPSLSQL, GKAPSLSQLF, APSLSQLFLF, LSQLFLFFAM | CRC |
| USP42 | c.2336G>C | p.R779P | SPAAESLEEPDAAAGLSSTKKAPP[p.R779P]PDPGTPATKEGAWEAMAVAPEE | STKKAPPP, STKKAPPPPD | ACC |
| USP46 | c.410A>G | p.Q137R | LFDNYMQQDAHEFLNVILLNTIADIL[p.Q137R]REEKKQEKQNGKLKNGNMNE PAENNK | TIADILREEK, ILREEKKQEK, LLNTIADILR | TGCT |
| UTP14A | c.442G>A | p.V148I | EEIERIHREVAFNKTAQVLSKWDPV[p.V148I]ILKNRQAEQLVFPLEKEEPAIAPIE H | VLSKWDPVI, VLSKWDPVIL, ILKNRQAEQL, LSKWDPVILK | CRC |
| UTP3 | c.226_228 de|GAG | p.E81de| | SRAALAKGWNEVQSGDEEDGEEEE[p.E81de|]VLALDMDDEDDEDGGNAGEE EEEENADD | GEEEEEVLAL | PRAD |
| UTS2R | c.866C>A | p.A289E | VLLFWACFLPFWLWQLLAQYHQAPL[p.A289E]EPRTARIVNYLTTCLTYGNSCA NPFL | LEPRTARIV, APLEPRTARI, AQYHQAPLEP, HQAPLEPRTA, E PRTARIVNY | KIRP |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| UXS1 | c.298G>C | p.V100L | QKYPPVKFLSEKDRKRILITGGAGF[p.V100L]LGSHLTDKLMMDGHEVTVVDNFFTGR | LIITGGAGFL, ILITGGAGFL, FLGSHLTDKL | OV |
| VARS | c.151_152C>AG | p.P51S | EAGEGPGWGGAHPRICLQPPPTSRT[p.P51S]SFPPPRLPALEQPGGLWVVGATAVAQ | TSRTSFPPP, RTSFPPPRL, SRTSFPPPR, SFPPPRLPAL, TSFPPPRLPA, QPPPTSRTSF | ACC |
| VASH1 | c.7de|G | p.G3fs | MPGG[p.G3fs]RRWLGVAAAVPLQRPLRPPPLGSGVWRPAKEPQPREMRSQKRKGKRTCETEASPSLSTGVGYLWMRPPGKGCGNTWPRSTPMERRWRNGSVGPQTCPRSPYRVCLRSSRLHLSLSAWKLCSATSESCSTITQGHSSLKLRRADL* | SLSTGVGYL, HLsLSAWKL, LSAWKLCSA, ATSESCSTI, YLWMRPPGK, ITQGHSSLK, VAAAVPLQR, GGSGVWRPAK, SVGPQTCPR, QTCPRSPYR, RWLGVAAAV, GGRRWLGVA, AVPLQRPLR, RSQKRKGK, RWRNGSVGP, RSPYRVCLR, RVCLRSSRL, CLRSSRLHL, RSSRLHLSL, TGVGYLWMR, NTWPRSTPM, RPLRPPPL, CPRSPYRVC, ERRWRNGSV, SLKLRRADL, RLHLSLSAW, GRRWLGVAA, RRWLGVAAA, LGVAAAVPL, AAVPLQRPL, LQRPLRPPP, AKEPQPREM, CETEASPSL, LSTGVGYLW, RSTPMERRW, RWRNGSVG, PQTCPRSPY, SRLHL SLSA, TQGHSSLKL, TEASPSLST, WLGVAAAVPL, SLSAWKLC SA, RLHLSLSAWK, TITQGHSSLK, GVAAAVPLQR, STGVGYL WMR, GSVGPQTCPR, GGRRWLGVAA, LGSGVWRPAK, EM RSQKRKGK, KGKRTCETEA, GYLWMRPPGK, RSTPMERRW R, RWRNGSVGPQ, RVCLRSSRLH, CLRSSRLHLS, RSSRLHLSL S, SSRLHLSLSA, TWPRSTPMER, EASPSLSTGV, QTCP RSPYRV, STITQGHSSL, MPGGRRWLGV, RPPPLGSGV, CPR SPYRVCL, MERRWRNGSV, SPSLSTGVGY, RRWLGVAAAV, AAAVP LQRPL, LQRPLRPPP, SLSTGVGYLW, LSTGVGYLWM, GNT WPRSTPM, GPQTCPRSPY, YRVCLRSSRL, LRSSRLHLSL, SRL HLSLSAW, LHLSLSAWKL, SATSESCSTI | STAD |
| VAV3 | c.2053G>A | p.E685K | CVPKPVDYSCQPWYAGAMERLQAET[p.E685K]KLINRVNSTYLVRHRTKESGEYAISI | RLQAETKLI, KLINRVNST, AETKLINRV, KLINRVNSTY, AMER LQAETK, MERLQAETKL | CRC |
| VCAN | c.3374G>A | p.R1125H | HSVSYPPGAVTEHKVKTDEVVTLTP[p.R1125H]HIGPKVSLSPGPEQKYETEGSSTTGF | TLTPHIGPK, EVVTLTPHI, LTPHIGPKV, DEVVTLTPH, T LTPHIGPKV, VTLTPHIGPK, TPHIGPKVSL, DEVVTLTPHI | CRC |
| VCAN | c.3923C>G | p.S1308C | SSPPATQPTRPPTVEDKEAFGPQAL[p.S1308C]CTPQPPASTKFHPDINVYIIEVRENK | ALCTPQPPA, CTPQPPASTK, KEAFGPQALC | CESC |
| VEZF1 | c.1063_1064insACA | p.355_356insN | ETSNQKQQQQQQQQQQQQQQQQH[p.355_356insN]NVTSWPGKQVETLRLWEEAVKARKKEAA | HNVTSWPGK, QQQQHNVTS, QQQQHNVTS W, NVTSWPGKQV, QQQQQQQHNV, QQQQQHNVT, QQQQH NVTSW, QQHNVTSWPG | STAD |
| VHL | c.115G>A | p.G39S | GAEEAGVEEYGPEEDGGEESGAEES[p.G39S]SPEESGPEELGAEEEMEAGRPRPVLR | SPEESGPEEL | KIRC |
| VHL | c.134C>T | p.P45L | VEEYGPEEDGGEESGAEESGPEESG[p.P45L]LEELGAEEEMEAGRPRPVLRSVNSRE | PEESGLEEL, LEELGAEEEM, EESGPEESGL | KIRC |
| VHL | c.194C>T | p.S65L | PEESGPEELGAEEEMEAGRPRPVLR[p.S65L]LVNSREPSQVIFCNRSPRWLPVWLN | RPRPVLRLV, PVLRLVNSR, LVNSREPSQV, AGRPRPVLRL, RPRPVLRLVN | KIRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| VHL | c.221T>A | p.V74D | GAEEMEAGRPRPVLRSVNSREPSQ[p.V74D]DIFCNRSPRVLPVWLNFDGEPQPYP | PSQDIFCNR,DIFCNRSPR,SREPSQDIF,DIFCNRSPRV,NSREPSQDIF | KIRC |
| VHL | c.232A>G | p.N78D | EMEAGRPRPVLRSVNSREPSQVIFC[p.N78D]DRSPRVVLPVWLNFDGEPQPYPTLPP | VIFCDRSPR,VIFCDRSPRV,QVIFCDRSPR | KIRC |
| VHL | c.236G>C | p.R79P | MEAGRPRPVLRSVNSREPSQVIFCN[p.R79P]PSPRVVLPVWLNFDGEPQPYPTLPPG | VIFCNPSPR,SQVIFCNPS,VIFCNPSPRV,QVIFCNPSPR,NPSPRVVLPV,SQVIFCNPSP,FCNPSPRVVL | KIRC |
| VHL | c.245G>C | p.R82P | GRPRPVLRSVNSREPSQVIFCNRSP[p.R82P]PVVLPVWLNFDGEPQPYPTLPPGTGR | RSPPVVLPV,SPPVVLPVW,VIFCNRSPPV,RSPPVVLPVW | KIRC |
| VHL | c.263G>T | p.W88L | LRSVNSREPSQVIFCNRSPRVVLPV[p.W88L]LLNFDGEPQPYPTLPPGTGRRIHSYR | VVLPVLLNF,SPRVVLPVL,RVVLPVLLNF,SPRVVLPVLL,RSPRVVLPVL | KIRC |
| VHL | c.266T>A | p.L89H | RSVNSREPSQVIFCNRSPRVVLPVW[p.L89H]HNFDGEPQPYPTLPPGTGRRIHSYRG | VVLPVWHNF,RVVLPVWHNF,HNFDGEPQPY | KIRC |
| VHL | c.266T>C | p.L89P | RSVNSREPSQVIFCNRSPRVVLPVW[p.L89P]PNFDGEPQPYPTLPPGTGRRIHSYRG | VVLPVWPNF,WPNFDGEPQ,RVVLPVWPNF | KIRC |
| VHL | c.320G>C | p.R107P | RVVLPVWLNFDGEPQPYPTLPPGTG[p.R107P]PRIHSYRGHLWLFRDAGTHDGLLVNQ | GTGPRIHSY,TLPPGTGPR,TGPRIHSYR,LPPGTGPRI,TLPPGTGPRI,GTGPRIHSYR | KIRC |
| VHL | c.332G>A | p.S111N | PVWLNFDGEPQPYPTLPPGTGRRIH[p.S111N]NYRGHLWLFRDAGTHDGLLVNQTELF | NYRGHLWLF,TGRRIHNYR,RIHNYRGHL,GTGRRIHNY,IHNYRGHLW,HNYRGHLWL,GTGRRIHNYR,HNYRGHLWLF,RIHNYRGHL,HNYRGHLWL | KIRC |
| VHL | c.333C>A | p.S111R | PVWLNFDGEPQPYPTLPPGTGRRIH[p.S111R]RYRGHLWLFRDAGTHDGLLVNQTELF | RYRGHLWLF,TGRRIHRYR,RIHRYRGHL,GTGRRIHRY,IHRYRGHLW,HRYRGHLWL,GTGRRIHRYR,HRYRGHLWLF,RIHRYRGHL,IHRYRGHLWL | KIRC |
| VHL | c.343C>A | p.H115N | NFDGEPQPYPTLPPGTGRRIHSYRG[p.H115N]NLWLFRDAGTHDGLLVNQTELFVPSL | SYRGNLWLF,RIHSYRGNL,HSYRGNLWL,IHSYRGNLW,HSYRGNLWLF,RIHSYRGNLW,SYRGNLWLFR,RIHSYRGNL,IHSYRGNLWL | KIRC |
| VHL | c.347delT | p.L116fs | DGEPQPYPTLPPGTGRRIHSYRGHL[p.L116fs]GSSEMQGHTMGFWLTKLNYLCHLSMLTDSLFLPISHCQCIL* | LTDSLFLPI,TMGFWLTKL,YLCHLSMLT,SMLTDSLFL,HLSMLTDSL,SLFLPISHC,FLPISHCQC,HTMGFWLTK,FWLTKLNYL,NYLCHLSML,RGHLGSSEM,GFWLTKLNY,EMQGHTMGF,LSMLTDSLF,LNYLCHLSM,SSEMQGHTM,SEMQGHTMG,MQGHTMGFW,TKLNYLCHL,LPISHCQCI,KLNYLCHLSM,MLTDSLFLPI,FLPISHCQCI,HTMGFWLTKL,GFWLTKLNYL,RIHSY RGHLG,LTKLNYLCHL,MGFWLTKLNY,LPISHCQCIL,SEMQGHTMGF,HLSMLTDSLF,HSYRGHLGSS,YRGHLGSSEM,GSSEMQGHTM,MQGHTMGFWL,LNYLCHLSML,CHLSMLTDSL,LSMLTDSLFL | KIRC |
| VHL | c.361G>T | p.D121Y | QPYPTLPPGTGRRIHSYRGHLWLFR[p.D121Y]YAGTHDGLLVNQTELFVPSLNVDGQP | RYAGTHDGL,RGHLWLFRY,WLFRYAGTH,RYAGTHDGLL,RGHLWLFRYA,YRGHLWLFRY,FRYAGTHDGL | KIRC |
| VHL | c.367delG | p.G123fs | PTLPPGTGRRIHSYRGHLWLFRDAG[p.G123fs]HTMGFWLTKLNYLCHLSMLTDSLFLPISHCQCIL* | LTDSLFLPI,TMGFWLTKL,YLCHLSMLT,SMLTDSLFL,WLFRDAGHT,HLSMLTDSL,SLFLPISHC,FLPISHCQC,HTMGFWLTK,FWLTKLNYL,NYLCHLSML,GFWLTKLNY,LSMLTDSLF,LFRDAGHTM,LNYLCHLSM,RDAGHTMGF,TKLNYLCHL,LPIS | KIRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| VHL | c.383T>A | p.L128H | PGTGRRIHSYRGHLWLFRDAGTHDG[p.L128H]HLVNQTELFVPSLNVDGQPIFANITL | HCQCI, WLFRDAGHTM, KLNYLCHLSM, MLTDSLFLPI, FLPIS HCQCI, HTMGFWLTKL, GFWLITKLNYL, LTKLNYLCHL, MGF WLTKLNY, LPISHCQCI1, HLSMLTDSLF, FRDAGHTMGF, RD AGHTMGFW, LNYLCHLSML, CHLSMLTDSL, LSMLTDSLFL HLVNQTELF, GHLVNQTEL, HLVNQTELFV, GHLVNQTELF | KIRC |
| VHL | c.405A>T | p.L135F | HSYRGHLWLFRDAGTHDGLLVNQTE[p.L135F]FFVPSLNVDGQPIFANITLPVYTLKE | LIVNQTEFFV, EFFVPSLNV, GLLIVNQTEFF, LLVNQTEFF, NQTE FFVPS, LLVNQTEFFV, NQTEFFVPSL, GLLVNQTEFF, TEFFVP SLNV | KIRC |
| VHL | c.452T>C | p.I151T | DGLLVNQTELFVPSLNVDGQPIFAN[p.I151T]TTLPVYTLKERCLQVVRSLVKPEN YR | FANTTLPVY, TTLPVYTLK, IFANTTLPV, NTTLPVYTL, QPIFAN M, PIFANTTLPV, NTTLPVYTLK, IFANTTLPVY, GQPIFANTT L | KIRC |
| VHL | c.458T>C | p.L153P | LLVNQTELFVPSLNVDGQPIFANIT[p.L153P]PVYTLKERCLQVVRSLVKPENYRR L | IFANITPPV, ITPPVYTLK, FANITPPVY, NLIPPVYTL, PIFANITP PV, NITPPVYTLK, IFANITPPVY, ANITPVYTL | KIRC |
| VHL | c.472C>G | p.L158V | TELFVPSLNVDGQPIFANITLPVYT[p.L158V]VKERCLQVVRSLVKPENYRRLDIVR S | NITLPVYTV, ITLPVYTVK, TVKERCLQV, YTVKERCLQV, NITLP VYTVK, TVKERCLQVV | KIRC |
| VHL | c.473T>C | p.L158P | TELFVPSLNVDGQPIFANITLPVYT[p.L158P]KERCLQVVRSLVKPENYRRLDIVR S | ITLPVYTPK, TPKERCLQV, NITLPVYTPK, YTPKERCLQV, TPKE RCLQVV | KIRC |
| VHL | c.492del G | p.Q164fs | LNVDGQPIFANITLPVYTLKERCLQ[p.Q164fs]LSGA* | TLKERCLQL, KERCLQLSGA | KIRC |
| VHL | c.506T>C | p.L169P | GQPIFANITLPVYTLKERCLQWRS[p.L169P]PVKPENYRRLDIVRSLYEDLEDHPN V | CLQVVRSPV, LQVVRSPVK, RSPVKPENY, PVKPENYRR, CLQ VVRSPVK, VRSPVKPENY | KIRC |
| VHL | c.551T>C | p.L184P | KERCLQVVRSLVKPENYRRLDIVRS[p.L184P]PYEDLEDHPNVQKDLERLTQERIA HQ | RLLDIVRSPY, SPYEDLEDH, RRLDIVRSPY | KIRC |
| VHL | c.563T>C | p.L188P | LQVVRSLVKPENYRRLLDIVRSLYED[p.L188P]PEDHPNVQKDLERLTQERIAHQR MGD | YEDPEDHPNV | KIRC |
| VLDLR | c.692G>A | p.R231H | IPISWCDDDADCSDQSDESLEQCG[p.R231H]HQPVIHTKCPASEIQCGSGECIH KKW | LEQCGHQPV, EQCGHQPVI, SLEQCGHQPV, CGHQPVIHTK, LEQCGHQPVI | BRCA |
| VMP1 | c.1105G>C | p.E369Q | AQRQKLHHKSEMGTPQGENWLSWM F[p.E369Q]QKLVVVMVCYFILSIINSMA QSYAKR | WLSWMFQKL, WMFQKLVVV, FQKLVVVMV, NWLSWMF QK, SWMFQKLVV, MFQKLVVVM, WLSWMFQKLV, WMFQ KLVVVM, NWLSWMFQKL, SWMFQKLVVV, MFQKLVVVM V, ENWLSWMFQK, LSWMFQKLVV, QKLVVVMVCY | LUAD |
| VPRBP | c.2405G>A | p.R802Q | ARLQKADVVAQSRISFPEKELLLLI[p.R802Q]QNHLLISKGLGETATVLTKEADLPM TA | LLLLIQNHL, LLLIQNHLI, LIQNHLISK, KELLLLIQN, LLLLIQNHL L, IQNHLISKGL, LLIQNHLISK | UCEC |
| VPRB P | c.2817de A | p.K939fs | CNGRKIRVLRQKSDHGAYSQSPAIK[p.K939fs]NSWTDIFLPHLRWTV* | WTDIFLPHL, FLPHLRWTV, AIKNSWTDI, SWTDIFLPH, IKNS WTDIF, WTDIFLPHLR, SWTDIFLPHL, IFLPHLRWTV, AIKNS WTDIF, SQSPAIKNSW, IKNSWTDIFL | STAD |
| VPS 13A | c.8647de T | p.F2883fs | ILGLDVLGNPFGLIREFSEGVEAFF[p.F2883fs]MNLTREPSRVLKSLMKEWH* | NLTREPSRV, LTREPSRVL, EAFFMNLTR, MNLTREPSR, EPSR VLKSL, SEGVEAFFM, FMNLTREPS, VLKSLMKEW, VEAFFM NLT, FSEGVEAFFM, LTREPSRVLK, RVLKSLMKEW, PSRVLKS | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| VPS13B | c.2075G>A | p.R692Q | IMGEKNSSNFMNTTNFQSLRPLPSI[p.R692Q]QILVDKINLEHSVPMYAEQLVHVVSS | LWK,FMNLTREPSR,EGVEAFFMNL,REPSRVLKSL,EPSRVLKSLW RPLPSIQIL,SLRPLPSIQI,RPLPSIQILV,IQILVDKINL | UCEC |
| VPS13B | c.7723G>T | p.G2575W | AQADCKLLECRNVTMQSVVKPFSIF[p.G2575W]WQMAVSSDVVEKLLDCTVIVDSVFVN | FSIFWQMAV,WQMAVSSDV,KPFSIFWQM,WQMAVSSD VV,FSIFWQMAVS,VKPFSIFWQM,KPFSIFWQMA | LUAD |
| VPS13C | c.4075G>T | p.D1359Y | SWYHKVPVVEIKGHLDSMNVSLNQE[p.D1359Y]YLNLLFRILTENLCEGTEDLDKVKPR | SLNQEYLNL,YLNLLFRIL,EYLNLLFRI,MNVSLNQEY,NVSLNQEYL,NQEYLNLLF,SLNQEYLNLL,YLNLLFRILT,EYLNLLFRIL,SMNVSLNQEY,MNVSLNQEYL,LNQEYLNLLF,QEYLNLLFRI | CRC |
| VWA2 | c.950G>A | p.G317D | RTTCPGPCDSQPCQNGGTCVPEGLD[p.G317D]DYQCLCPLAFGGEANCALKLSLECRV | DDYQCLCPL,DYQCLCPLAF | TGCT |
| VWA3A | c.2863G>A | p.V955I | LEKVLRRYVQRLQWLLSGSRRLFGT[p.V955I]ILESKVCILLDTSGSMGPYLQQVKTE | RLFGTILES,ILESKVCIL,GSRRLFGTI,SRRLFGTIL,ILESKVCILL,RLFGTILESK,GSRRLFGTIL | BRCA |
| VWA3B | c.1670G>T | p.R557L | QFIQEQLKYKSKFNFVKFDGQQAVAW[p.R557L]LEQLAEVNEDNLEQAQSWIRDIKIGS | QAVAWLEQL,VAWLEQLAEV,CQAVAWLEQL | LUAD |
| VWA7 | c.2375T>G | p.V792G | FSLTSNLSRAHLELNESAWGRLWLE[p.V792G]GPDSAAPDSVVMVTVTAGREANPVP | RLWLEGPDSA | TGCT |
| VWF | c.5160A>T | p.K1720N | LLDGSSSFPASYFDEMKSFAKAFIS[p.K1720N]MANIGPRLTQVSVLQYGSITTIDVPW | FAKAFISNA,ISNANIGPR,KAFISNANI,KSFAKAFISN,SFAKAFISNA,FISNANIGPR,AKAFISNANI,ISNANIGPRL | BRCA |
| WAPAL | c.1564delA | p.R522fs | GFDDLSESEDEDDCQVERKTSKK[p.R522fs]ELKQLHHPPCSLPQKAMIPRTVSLVLTMQRTCLVCLKV* | MIIPRTVSL,IIPRTVSLV,LTMQRTCLV,QLHHPPCSL,SLPQKAMI,MQRTCLVCL,VSLVLTMQR,KAMIIPRTV,RTVSLVLTM,IPRTVSLVL,KQLHHPPCSL,AMIIPRTVSL,MIIPRTVSLV,VLTMQRTCLV,MQRTCLVCLK,TVSLVLTMQR,VERKTSKKEL, TMQRTCLVCL,KELKQLHHPP | STAD |
| WASF3 | c.913_914insC | p.P305fs | EHEYRPPSASARHMALNRPQQPPPP[p.P305fs]ASPSGPRGVPGLCTDGSSRLRDAPSADN* | SSRLRDAPS,RPQQPPPPA,GLCTDGSSRL,SSRLRDAPSA,RPQQPPPPAS,SPSGPRGVPG | STAD |
| WASH3P | c.523G>A | p.G175S | APREVDPSGGRATLLESIRQAGGI[p.G175S]SKAKLRSMKERKLEKKQQKEQQVRA | RQAGGISKA,ISKAKLRSM,SIRQAGGISK,RQAGGISKAK,ISKAKLRSMK | GBM,KIRC,PRAD,SKCM |
| WASH3P | c.559C>G | p.L187V | ATLLESIRQAGGIGKAKLRSMKERK[p.L187V]VEKKQQKEQEQVRATSQGGHLMSDLF | SMKERKVEK,RSMKERKVEK,SMKERKVEKK,KLRSMKERKV | PRAD,TGCT |
| WBP1 | c.412_413insC | p.P138fs | LRFLSTFKPPAYEDVVHRPGTPPPP[p.P138fs]LYCGPRPPLDCFQ* | LYCGPRPPL,RPGTPPPPL,GPRPPLDCF | STAD |
| WBSCR17 | c.682C>T | p.R228C | LEEYVHKRYPGLVKVVRNQKREGLI[p.R228C]CARIEGWKVATGQVTGFFDAHVEFTA | REGLICARI,LICARIEGWK | CRC |
| WDFY3 | c.5525delT | p.L1842fs | FIFGVPASSGTWSSIHNVCTEAVFY[p.L1842fs]YYWECSAAC* | CTEAVFYYW,YYWECSAAC,EAVFYYWEC,FYYWECSAA,AVFYYWECSA,HNVCTEAVFY,TEAVFYYWEC | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| WDR17 | c.832C>T | p.P278S | SESLSCITTFNLPSAAASVQCLAWV[p.P278S]SSAPGMFITGDSQVGVLRIWNVSRTT | AWVSSAPGM,WVSSAPGMF,WVSSAPGMFI,AWVSSAPG MF,LAWVSSAPGM,VQCLAWVSSA | CESC |
| WDR3 | c.2521G>A | p.E841K | KSSELEESLLVLPFSVVPDILKLFN[p.E841K]FIQLGSDVELICRCLFFLLRIHFGQ | KLFNKFIQL,LKLFNKFIQL | CRC |
| WDR34 | c.178T>G | p.W60G | PGPLQDETLGVASVPSQWRAVQGIR[p.W60G]GETKSCQTASIATASASAQARNHVDA | GETKSCQTA,AVQGIRGETK | ACC |
| WDR5 | c.642del C | p.N214fs | DGLCRIWDTASGQCLKTLIDDDNPP[p.N214fs]CLL* | TLIDDDNPPC | STAD |
| WDR59 | c.2509C>A | p.R837S | EHLSSPWGESSPEELRFGSLTYSDP[p.R837S]SERERDQHDKNKRLLDPANTQQFDDF | LTYSDPSER | LUAD |
| WDR59 | c.479del A | p.N160fs | IKDTRKPTVALSAVAGASQVKWNK[p.N160fs]MLTALPPAMTAMCGYGIRGNPVQQWNI* | KMLTALPPA,MLTALPPAM,ALPPAMTAM,KWNKKMLTA, PAMTAMCGY,TAMCGYGIR,MTAMCGYGI,WNKKMLTAL, SQVKWNKKM,KKMLTALPP,KMLTALPPAM,AMTAMCGY GI,MLTALPPAMT,ALPPAMTAMC,MTAMCGYGIR,KWNK KMLTAL,LTALPPAMTA,TALPPAMTAM,SQVKWNKKML,V KWNKKMLTA,KKMLTALPPA,PPAMTAMCGY | STAD |
| WDR60 | c.1235del A | p.Q412fs | DGDDDESSNEPESREKLEELPLAQK[p.Q412fs]RKYKKFKELLMQRMKGLASYL* | LLMQKMKGL,KMKGLASYL,KYKKFKELL,LAQKRKYKK,KFK ELLMQK,QKMKGLASY,RKYKKFKEL,MQKMKGLAS,AQKR KYKKF,YKKFKELLM,FKELLMQKM,LPLAQKRKY,LLMQKM KGLA,KYKKFKELLM,AQKRKYKKFK,KFKELLMQKM,MQK MKGLASY,LAQKRKYKKF,RKYKKFKELL,QKMKGLASYL | STAD |
| WDR7 | c.784del G | p.G262fs | RVFDAGDYSLLCSGPSENGQTWTGG[p.G262fs]TLSHQIKSSFGQKMGKVIFTNYLPVAFQLVIHSAVMWGRQLKI* | FTNYLPVAF,VIFTNYLPV,YLPVAFQLV,FQLVIHSAV,VMWG RQLKI,QIKSSFGQK,SSFGQKMGK,AVMWGRQLK,NYLPVA FQL,MGKVIFTNY,LPVAFQLVI,LSHQIKSSF,QLVIHSAVM,G QTWTGGTL,HQIKSSFGQ,IKSSFGQKM,GQKMGKVIF,GKV IFTNYL,LVIHSAVMW,SAVMWGRQL,KVIFTNYLPV,VIFTN YLPVA,YLPVAFQLVI,HQIKSSFGQK,KSSFGQKMGK,KMGK VIFTNY,VIHSAVMWGR,SAVMWGRQLK,IFTNYLPVAF,NY LPVAFQLV,MGKVIFTNYL,AVMWGRQLKI,WTGGTLS HQI,SSFGQKMGKV,TLSHQIKSSF,FQLVIHSAVM,FGQKM GKVIF,VAFQLVIFSA,HSAVMWGRQL,LPVAFQLVIH | STAD |
| WDR73 | c.944_961 de ATGGAACACGGAGCCAAG | p.DGTRSQ315 de | CLAISGFPDGTVQVYDATSWDGTRSQ[p.DGTRSQ315de ]VEPLFTHRGHIFLDGNGMDPAPLVTTHTWHPCRPRTLLSATND | TSWDGTRSQV | KIRC |
| WDR75 | c.860C>A | p.P287Q | SLLSGGRESVLVEWRDATEKNKEFL[p.P287Q]QRLGATIEHISVSPAGDLFCTSHSDN | FLQRLGATI,KEFLQRLGA,EFLQRLGATI,KEFLQRLGAT, LQRLGATIEH | LUAD |
| WDR78 | c.330T>A | p.N110K | NQSRMAVSKTVLIPPELKTVEKPNP[p.N110K]KIKTTQVFDINGTDVTPRPLYHPDPL | KTVEKPNPK,KIKTTQVFD,NPKIKTTQV,PKIKTTQVF,KIKTT QVFDI,NPKIKTTQVF | CLL |
| WDR88 | c.298G>T | p.G100W | KHQVPEKLIWGDQDPLSKIPFKILS[p.G100W]WHEHAVSTCHFCVDDTKLLSGSYDCT | KILSWHEHA,ILSWHEHAV,KIPFKILSW,FKILSWHEH,KILS WHEHAV,SKIPFKILSW,FKILSWHEHA | LUAD |
| WDTC1 | c.861_862 insG | p.M287fs | RLRVLVATYVTFSPNGTELLVNMGG[p.M287fs]GTGLFV* | NMGGGTGLF,VNMGGGTGL,NMGGGTGLFV,VNMGGGT GLF | STAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| WHSC1L1 | c.1254_1255insA | p.K418fs | YIDKQPEEALSQAKKSVASKTEVKK[p.K418fs]NPTTKICAEYSARTDQCRGGGLLTLKY* | PTTKICAEY, KICAEYSAR, RGGGLLTLK, GGGLLTLKY, CRGGG LLTL, TTKICAEYSA, RGGGLLTLKY, EYSARTDQCR, NPTTKICA EY, AEYSARTDQC | STAD |
| WNK4 | c.1816del|G | p.G606fs | CETDGYLSSSGFLDASDPALQPPGG[p.G606fs|CHPAWLSPISACPRLLPYPFHV LALEVTFPPGTAMPQMQLQALAMWE KGWDK* | RLLPYPFHV, LLPYPFHVL, AMPQMQLQA, AMWEKGWDK, S ACPRLLPY, LQALAMWEK, PYPFHVLAL, HVLALEVTF, MQLQ ALAMW, EVTFPPGTA, SPISACPRL, CPRLLPYPF, MPQMQL QAL, VTFPPGTAM, QMQLQALAM, HPAWLSPIS, LPYPFHVL A, LEVTFPPGT, ISACPRLLPY, RLLPYPFHVL, LLPYPFHVLA, A MPQMQLQAL, QLQALAMWEK, LAMWEKGWDK, WLSPIS ACPR, YPFHVLALEV, EVTFPPGTAM, HPAWLSPISA, SPISAC PRLL, LPYPFHVLAL, FPPGTAMPQM, MPQMQLQALA, LQP PGGCHPA, FHVLALEVTF, LEVTFPPGTA, PQMQLQALAM, Q MQLQALAMW, QPPGGCHPAW, QALAMWEKGW | STAD |
| WNT1 | c.500del|G | p.W167fs | SEGSISCTCDYRRRGPGGPDWHWG[p.W167fs]AAATTLTSAASSAGSSWTPG RRGGTCASS* | TLTSAASSA, GPDWHWGAA, WHWGAAATT, HWGAAATT L, AASSAGSSW, SAGSSWTPGR, TTLTSAASSA, GPD WHWGAAA, SAASSAGSSW, WHWGAAATTL, AAATTLTSAA | STAD |
| WNT11 | c.1031G>A | p.C344Y | NPYTDRVERCHCKYHWCCYVTCRR[p.C344Y]YERTVERYVCK* | CCYVTCRRY, RYERTVERY, YVTCRRYER, YERTVERYVC RYV, RRYERTVERY, CYVTCRRYER, YERTVERYVCK | OV |
| WNT16 | c.494del|G | p.W165fs | GNMTECSCDTTLQNGSSASEGWHWG[p.W165fs]AAPMMSSMACGSAESS* | MMSSMACGS, SMACGSAES, MSSMACGSA, APMMSSMA C, GAAPMMSSM, SEGWHWGAA, GWHWGAAPM, MHW GAAPMM, WGAAPMMSSM, GNHWGAAPMM, SMACGSAESS | STAD |
| WNT5B | c.979A>G | p.K327E | RLCNKTSEGMDGCELMCCGRGYNQF[p.K327E]ESVQVERCHCKFHWCCFVRC KKCTEI | RGYNQFES, QFESVQVER, NQFESVQVE, NQFESVQVER | TGCT |
| WT1 | c.1142_1143insCGGTC | p.S381fs | HTHGVFRGIQDVRRVPGVAPTLVRS[p.S381fs|GRHLRPVRNAPSCVLTQAAIRD ILSCPTYRCTAGSTLVRNHTSVTSRTVNE GFLVQTSSKDTKGDIQV* | TLVRNHTSV, CTAGSTLVR, LVRSGRHLR, RSGRHLRPV, SGRH LRPVR, LVRNHTSVT, RNHTSVTSR, HTSVTSRTV, GFLVQTS SK, RDILSCPTY, CVLTQAAIR, DILSCPTYR, RPVRNAPSC, TLVRSGRH L, VRNAPSCVL, TQAAIRDIL, YRCTAGSTL, TSRTVNEGF, LVQTSS KDTK, TYRCTAGSTL, RSGRHLRPVR, HLRPVRNAPS, STLVR NHTSV, TSRTVNEGFL, TLVRSGRHLR, RPVRNAPSCV, APSCV LTQAA, IRDILSCPTY, VTSRTVNEGF | LAML |
| WWP2 | c.1373G>C | p.G458A | EDPRTQCMIQEPALPGWEMKYTSE[p.G458A]AVRYFVDHNTRTTTFKDPRPG FESGT | EMKYTSEAV, KYTSEAVRY, YTSEAVRYF, TSEAVRYFV, WEMKYTSEA, YTSEAVRYFV, KYTSEAVRYF, MKYTSEAVRY, EMKY TSEAVR, WEMKYTSEAV, SEAVRYFVDH | KIRC |
| XAB2 | c.2344G>A | p.E782K | SDLAPGQSGMDDMKLLEQRAEQLAA[p.E782K]KAERDQPLRAQSKILFVRSDA SREEL | EQLAAKAER, AKAERDQPL, EQRAEQLAAK | BLCA |
| XDH | c.1228C>T | p.P410S | MDHTFPGVYRKTLLSPEEILLSIEI[p.P410S]SYSREGEYFSAFKQASREDDIAKVT | ISYSREGEY, LSIEISYSR, SYSREGEYF, LLSIEISY, IEISYSREG, IS YSREGEYF, LLSIEISYSR, EILLSIEIS | TGCT |
| XIRP2 | c.7315G>A | p.D2439N | GKTGVLPPPTLPKPKLPKHIKDNKN[p.D2439N]NFSPKVELATSLSDMECKITTSK DQK | KDNKNNFSPK, KHIKDNKNNF | SKCM |
| XIRP2 | c.9023T>A | p.V3008E | IPGWLISEDKREYAVHIAMENNLEK[p.V3008E]EKEEITHIKTQAEDMLVSYENIIQ TA | KEKEEITHI | CLL |
| XKR6 | c.803G>A | p.R268Q | SVIHLLQMGQVWRYIRTMYLGIQSQ[p.R268Q]QRKEHQRRFYWAMMYEYAD VNMLRLL | MYLGIQSQQR, QQRKEHQRRF | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| XPO1 | c.1711G>A | p.E571K | QYPRFLRAHWKFLKTWNKLFEFMH[p.E571K]KTHDGVQDMACDTFIKIAQKCRRHFV | KLFEFMHKT, FMHKTHDGV, KTHDGVQDM, KLFEFMKTH, VNKLFEFMHK, KTHDGVQDMA, EFMHKTHDGV, FMHKTHDGVQ, HKTHDGVQDM | BRCA, CLL |
| XPOT | c.1621C>T | p.R541W | EPQHIPCVLMAFLDHRGLRHSSAKV[p.R541W]WSRTAYLFSRFVKSLNKQMNPFIEDI | KVWSRTAYL, HSSAKVWSR, VWSRTAYLF, SAKVWSRTA, W SRTAYLFS, AKVWSRTAY, LRHSSAKVW, KVWSRTAYLF, SAKVWS RTAY, WSRTAYLFSR, GLRHSSAKVW, AKVWSRTAYL | CRC |
| XYLB | c.260C>T | p.S87F | TSPVLMWVQALDIILEKMKASGFDF[p.S87F]FQVLALSGAGQQHGSIYWKAGAQQAL | FQVLALSGA, MKASGFDFF, SGFDFFQVL, FDFFQVLAL, KAS GFDFFQV, KMKASGFDFF, FQVLALSGAG | BLCA |
| XYLT2 | c.1578del|C | p.Y526fs | RKFESTVNQEVLEILDFHLYGSYPP[p.Y526fs]ARQPSRPTGRTPTTRLMAPVGSVMSCSLLTQPSPASACTMPPLLHPQWAPHSAGLSPGACRPACTCISMTTISRATW* | HLYGSYPPA, RLMAPVGSV, SLLTQPSPA, LMAPVGSVM, CIS MTTISR, RTPTTRLMA, TRLMAPVG, ASACTMPPL, ISMTTI SRA, LYGSYPPAR, PTTRLMAPV, HSAGLSPGA, RPTGRTPTT, HPQWAPHSA, SPGACRPAC, RPACTCISM, LLHPQWAPH, G SVMSCSLL, MTTISRATW, MPPLLHPQW, RLMAPVGSVM, L LTQPSPASA, GLSPGACRPA, HLYGSYPPAR, TMPPLLHPQW, TGRTPTTRLM, ASACTMPPLL, SYPPARQPSR, TCISMTTISR, TPTTRLMAPV, QPSPASACTM, HPQWAPHSAG, APHSAGLS PG, RPACTCISMT, FHLYGSYPPA, PQWAPHSAGL, SMTTISR ATW, MPPLLHPQWA | STAD |
| YBX1 | c.749C>T | p.P250L | GAGEQGRPVRQNMYRGVRPRFRRGP[p.P250L]LRQRQPREDGNEEDKENQGDETQGGQ | RPFRRGPLRQ, RPRFRRGPL, RPRFRRGPLR, RPRRGPLRQR | KIRP |
| YBX2 | c.677del|C | p.P226fs | SAGTGPGSKGERAEDSGQRPRRWCP[p.P226fs]HPSSTDGGLCEAPGLPTSSSL* | RWMCPHPSST, HPSSTDGGL, CEAPGLPTS, GQRPRRWCPH, R PRRWCPHPS, APGLPTSSSL, RRWCPHPSST, CEAPGLPTSS | STAD |
| YIF1A | c.391del|C | p.R131fs | LGLLVFPYTHQNWEVQYSRDAPLPP[p.R131fs]GKTSTPLTSISPRWPSLLTCSWLGWHWAFRKGSPRRCWACVQAQRWGW* | KTSTPLTSI, SISPRWPSL, LGWHWAFRK, WLGWHWAFR, IS PRWPSLL, SWLGWHWAF, AFRKGSPRR, KGSPRRCWA, TPL TSISPR, WAFRKGSPR, CWACVQAQR, PPGKTSTPL, SPRWP SLLT, SPRRCWACV, LLTCSWLGW, RKGSPRRCW, VQAQRW CGW, WPSLLTCSW, WACVQAQRW, SISPRWPSLL, WLGW HWAFRK, STPLTSISPR, SWLGWHWAFR, RWPSLLTCSW, SL LTCSWLGW, CSWLGWHWAF, CWACVQAQRW, TSISPRW PSL, HWAFRKGSPR, WAFRKGSPRR, APLPGKTST, LPPGKT STPL, SPRWPSLLTC, WPSLLTCSWL, GKTSTPLTSI, TPLTSISP RW | STAD |
| YLPM1 | c.3533del|A | p.E1178fs | RGLGRSDFGRDRGPRPEPGDGGEK[p.E1178fs]CIHITGMSLLGLHGTMEKSEGMKSFH* | LGLHGTMEK, TMEKSEGMK, CIHITGMSLL, IHITGMSLL, SLLG LHGTM, EKSEGMKSF, CIHITGMSLLL, HITGMSLLGL, GMSLL GLHGT, LLGLHGTMEK, GTMEKSEGMK, MEKSEGMKSF, MS LLGLHGTM, GEKCIHITGM, KCIHITGMSL | STAD |
| YTHDC2 | c.1900G>A | p.E634K | IMHLLYNICHSCDAGAVLIFLPGYD[p.E634K]IVGLRDRILFDDKRFADSTHRYQVF | FLPGYDKIV, LIFLPGYDK, IFLPGYDKI, VLIFLPGYDK, LPGYDKI VGL | CRC |
| YTHDC2 | c.553G>A | p.E185K | NREMSKTSGRLNNGIPQIPVKRGES[p.E185K]KFDSFRQSLPVFEKQEEIVKIIKENK | RGESKFDSF, IPVKRGESKF, KRGESKFDSF, SKFDSFRQSL | UCEC |
| ZAR1 | c.126G>C | p.Q42H | CPPCSYRYPYPAATKGKGAAGGSWQ[p.Q42H]HRGRGCLPASSPCSAGAASLSFPGCG | WQHRGRGCL, WQHRGRGCLP | ACC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZBBX | c.1787G>T | p.R596I | TKSSLLQEIACRSKPITKQYQGLEI[p.R596I]LFFIFDTNERLNLLPSHRLECNNSST | YQGLEIFFI, KQYQGLEIF, QYQGLEIFF, QGLEIFIFF, TKQ YQGLEI, LEIFFIFDT, KQYQGLEIFF, QYQGLEIFFI, YQGL EIFFIF, ITKQYQGLEI, IFFIFDTNER, TKQYQGLEIF | CRC |
| ZBBX | c.453_455 delAGA | p.E151del | KPKINGKVCGQCENKAALLVCLECG[p.E151del]DYCSGCFAKVHQKGALKLHRT TLLQAKS | LVCLECGDY, LLVCLECGDY | STAD |
| ZBED4 | c.1154C>T | p.S385L | PSLLPPEGELSVSSSPVKPVRESP[p.S385L]LASSSPDRLTEDLQSHLNPGDGLMED | RESPLASSS, RESPLASSSP | CESC |
| ZBTB20 | c.2075delC | p.P692fs | CKKKFSHKTLLERHVALHSASNGTP[p.P692fs]LQAHPQVPALAPQAWWPARR GPLTSAPSAQQSLITKSSSSTTT* | APQAWWPAR, HSASNGTPL, LAPQAHPQV, TPLQAHPQV, WPARRGPLT, WPARRGPL, LQAHPQVPA, QAHPQVPAL, VPALAPQAW, LQAHPQVPAL, ALAPQAWWPA, AWWPAR RGPL, LAPQAWWPAR, APQAWWPARR, WPARRGPLTS, LH SASNGTPL, TSAPSAQQSL, AQQSLITKSSS, VPALAPQAWW | STAD |
| ZBTB24 | c.1819C>A | p.L607I | QNMTADQAANLTLLTQQPEQLQNLI[p.L607I]ISAQQEQTEHIQSLNMIESQMG PSQT | QLQNLIISA, LQNLIISAQ, EQLQNLIISA, QPEQLQNLII | CRC |
| ZBTB40 | c.786_787insA | p.L262fs | QLNFLLENEGVFSDALMVTQDVLKK[p.L262fs]TRNVFRN* | VLKKTRNVF, VLKKTRNVFR, VTQDVLKKTR | STAD |
| ZBTB7C | c.1025_1026 insG | p.G342fs | ELPPPPPPFPNDFFKDMFPDLPGG[p.G342fs]ASGTHQGGERLRCLSQLPECH PPGRPLPTLAPGRRAQAEAQGLSAVPH LPQSHGGREAAAAHEDPYRGEAIHVH HLRGPLHQAGQAENPHAEAHRGAALP VHPLQRQVRAQLRPQEPHAHPHGRAA LPVRVLLQELHAL* | VLLQELHAL, HLRGPLHQA, RLRCLSQLP, HVHHLRGPL, QLR PQEPHA, HAHPHGRAA, HGRAALPVR, AALPVRVLL, RVLLQ ELHA, AAAAHEDPY, EAIHVHHLR, HPPGRPLPT, RPLPTLAPG, HAEAHRGAA, HPLQRQVRA, AEAQGLSAV, AQGLSAVPFI, SHH LPECHPP, RAQAEAQGL, RAQAEAQGL, AEAQGLSAV, AQGLSAVPFI, SHH GGREAA, GEAIHVHHL, AENPHAEAH, AEAHRGAAL, AHRG AALPV, GAALPVHPL, RQVRAQLRP, AQLRPQEPH, FPDLPG GAS, DPYRGEAIH, DMPPDLPGGA, TLAPGRRAQA, AQAEA QGLSA, GQAENPHAEA, AAAAHEDPYR, AALPVHPLQR, RLR CLSQLPE, HVHHLRGPLH, LQRQVRAQLR, HAHPHGRAAL, H GRAALPVRV, RAALPVRVLL, RVLLQE LHAL, HLPQSHHGGR, EAHRGAALPV, HPPGRPLPTL, APG RRAQAEA, HAEAHRGAAL, LPVHPLQRQV, RPQEPHAHPH, HPHGRAALPV, LPVRVLLQEL, EAAAAHEDPY, HQGGERLRCL, GERLRCLSQL, SQLPECHPPG, RRAQAEAQGL, AQGLSAVPHL, HEDPYRGEAI, IHVHHLRGPL, HQAGQAENPH, AHRGAAL PVH, RGAALPVHPL, RQVRAQLRPQ, AQLRPQEPHA, GRAALPVRVL, FPDLPGGASG, AEAQGLSAVP, DPYRGEAIHV TMMTRRTLL, SLTPSRLAV, CLTPRTSAA, KMMMMRRTK, M MMMMRRTKR, MMMRRTKRR, MTRRTLLTK, GTGGRRMTR, TTTKMMMMR, TTKMMMMR, SAATKALPR, RMTRRTMT T, MTRRTMTTT, TRRTMTTTK, RTMTTTKMM, MMRRTKRR R, RTKRRRRKR, RRRMTMMTR, MTMMTRRTL, RTSAATKAL, MTTTKMMMM, QTISQRRPI, RRKRRRMTM, TLLTKKTCL, I QTPPGTSL, RRTMTTTKM, TMTTTKMMM, RKRRRMTMM, TKALPRQTI, SQRRPIQTP, SRLAVLAIW, TMMTRRTLLT, CLT PRTSAAT, SLTPSRLAVL, MTRRTMTTTK, KMMMMRRTKR, MMMMRRTKRR, MMMMRRTKR, MMMRRTKR, MMMRRTLLTK, MTRRT LLTKK, MTTKMMMMR, TTTKMMMMR, LTPRTSAATK, T SAATKALPR, RTMTTTKMMM, MMRRTKRRR, MRRTKRRR | STAD |
| ZBTB7C | c.460delG | p.D154fs | ILNAARMLEIQCIVNVCLEIMEPGG[p.D154fs]TGGRRMTRRTMTTTKMMMM RRTKRRRKRRRMTMMTRRTLLTKKTC LTPRTSAATKALPRQTISQRRPIQTPPGT SLTPSRLAVLAIWG* | | STAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZBTB7C | c.469de|G | p.E157fs | AARMLEIQCIVNVCLEIMEPGDGG[p. E157fs]RRMTRRTMTTTKMMMRRT KRRRRKRRRMTMMTRRTLLTKKTCLTP RTSAATKALPRQTISQRRPIQTPPGTSLT PSRLAVLAIWG* | RRK,RTKRRRKRR,RRRKRRRMTM,KRRRMTMMTR,RRR MTMMTRR,RMTMMTRRTL,MTMMTRRTLL,RTLLTKKTCL, LTKKTCLTPR,KTCLTPRTSA,ATKALPRQTI,RQTISQRRPI,TP RTSAATKA,TPSRLAVLAI,RRKRRRMTM,RMTRRTMTTT, TRRTMTTTKM,RTMTTTKMM,TMTTTKMMMM,SQRRP IQTPP,IQTPPGTSLT TMMTRRTLL,SLTPSRLAV,CLTPRTSAA,KMMMMRRTK,M MMMRRTKR,MMMRRTKRR,MTRRTLLTK,TTTKMMMM R,TKMMMMRR,SAATKALPR,RMTRRTMTT,MTRRTMTTT,TR RTMTTTK,RTMTTTKMM,MMRRTKRRR,RTKRRRRKR,RRR MTMMTTR,MTMMTRRTL,RTSAATKAL,MTTTKMMMM,QTISQRR PI,RRKRRRMTM,TLLLTKKTCL,IQTPPGTSL,RRTMTTTKM, TMTTTKMMM,RKRRRMTMM,TKALPRQTI,SQRRPIQTP, SRLAVLAIW,TMMTRRTLLT,CLTPRTSAAT,SLTPSRLAVL, MTRRTMTTTK,KMMMMRRTKR,MMMMRRTKRR, MMMRRTKRRR,MMTRRTLLTK,MTRRTLLLTK,MTTTKMMMM R,TTTKMMMMR,MMRRTKRRRR,MRRRTKRRRK,RTKRRR RKRR,RRKRRRRMTM,KRRRMTMMTR,RRRMTMMTR,R MTMMTRRTL,MTMMTRRTLL,RTLLTKKTCL,LTKKTCLTPR, KTCLTPRTSA,ATKALPRQTI,RQTISQRRPI,TPRTSAATKA, TPSRLAVLAI,RRKRRRMTMM,RMTRRTMTTT,TRRTMTTTK M,RTMTTTKMM,TMTTTKMMMM,SQRRPIQTPP,IQTP PGTSLT | STAD |
| ZC3H12D | c.1213C>T | p.P405S | SAGGRVPGPLSLPSPESQFSPGDLL[p.P 405S]SPPGLQLQPRGEHRPRDLHGDLL SPR | LPSPPGLQL,SQFSPGDLPS | ACC |
| ZC3H13 | c.3018de|A | p.K1006fs | NIETTSEDGQVFSPKKGQKKKSIEK[p.K1 006fs]NVKNPKVILIFLMKKQPSKVRRK EAHGLPL* | LMKKQPSKV,KVILIFLMK,VILIFLMKK,FLMKKQPSK,KNPK VILIF,KQPSKVRRK,KVRRKEAHG,RKEAHGLPL,FLMKKQPS KV,KVILIFLMCK,SIEKNVKNPK,IFLMKKQPSK,LMKKQPSKV R,KVRRKEAHGL,QPSKVRRKEA,VKNPKVILI F,NPKVILIFLM,IEKNVKNPKV | STAD |
| ZC3H18 | c.2102_2103 insC | p.T701fs | PVPEPTKPGDPREARRKERPARTPP[p.T 701fs]QEADAKRQRQWQW* | AKRQRQWQW,RTPPQEADAK,RPARTPPQEA | STAD |
| ZC3H18 | c.2473de|C | p.P825fs | PKSAKPPAGGKSSQQPSTPQQAPPG[p. P825fs]SPSRAHLWPTRRSS* | RAHLWPTRR,QQAPPGSPS,PSRAHLWPTR,RAHLWPTRRS, SPSRAHLWPT | STAD |
| ZC3H4 | c.2392G>A | p.E798K | IQQKQQEEEERARRLAESSKQDREN[p. E798K]KEGDTGNWYSSDEDEGGSSVT SILKT | SSKQDRENK,KEGDTGNWY | BLCA |
| ZC3H7A | c.1724G>C | p.C575S | NGKINLTVFKLLQEHLGEFIFLCEK[p.C5 75S]SFDHKPRMISKRNKDNSTACSHPV TK | KSFDHKPRM,FIFLCEKSF,EFIFLCEKSF,KSFDHKPRMI,GEFI FLCEKS | TGCT |
| ZCCHC6 | c.2811A>T | p.K937N | GKHVERALLVELNKISLKEENVCEE[p.K9 37N]NNSPVDQSDFFYEFSKLIFTKGKSP T | NVCEENNSPV | KIRC |
| ZCRB1 | c.228A>T | p.L76F | KGVAFILFLDKDSAQNCTRAINNKQ[p.L 76F]FFGRVIKASIAIDNGRAAEFIRRRNY | KQFFGRVIK,RAINNKQFF,INNKQFFGR,NKQFFGRVI,AINNKQ FFGR,FFGRVIKASI,RAINNKQFFG,KQFFGRVIKA,CTRAI NNKQF | CLL |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZCWPW2 | c.430G>A | p.D144N | DRFKGKVTYDPDGNVEEYHIEFLG[p.D144N]NPHSRSWIKATFVGHYSITLKPEK CK | EFLGNPHSR,LGNPHSRSW,IEFLGNPHS,YHIEFLGNPH,FLG NPHSRSW | CRC |
| ZDHHC11 | c.750C>G | p.H250Q | PVQVQTLIVLIVIGMLVLLLDFLGLV[p.H250Q]QLGQLLIFHIYLKAKKMTTFEYLIN N | GLVQLGQLL,VQLGQLLIF,LDFLGLVQL,LLDFLGLVQL, FLGLVQLGQL,QLGQLLIFHI,GLVQLGQLLI,LVQLGQLLIF | TGCT |
| ZDHHC4 | c.899G>A | p.R300H | LFVLYLAATNQTTNEWYRGDWAWCQ[p.R300H]HCPLVAWPPSAEPQVHRNIH SHGLRS | WAWCQHCPL,CQHCPLVAW,WAWCQHCPLV | GBM |
| ZDHHC5 | c.1947_1949 de|AGA | p.E651de| | PTAPYLGRSMSYSSSQAPGVSETE[p.E651de|]VALQPLLTPKDEVQLKTTYSKS NGQPKS | ETEVALQPL,TEVALQPLL,AQPGVSETEV,ETEVALQPLL,SET EVALQPL,TEVALQPLLT | STAD |
| ZDHHC7 | c.948de|C | p.P316fs | LKSEKPTWERRLRWEGMKSVFGGPP[p.P316fs]HSSG* | KSVFGGPPH,MKSVFGGPPH | STAD |
| ZEB2 | c.3280G>A | p.E1094K | SYSQHMNHRYSYCKREABERFAAER[p.E1094K]KAREKGHLEPTELLMNRAYLQ SITPQ | KAREKGHLE,KAREKGHLEP | CESC |
| ZEB2 | c.467G>A | p.R156H | NNGTVKNANCTSDFEEYFAKRKLEE[p.R156H]HDGHAVSIEEYLQRSDTAIIYPE APE | LEEHDGHAV,EEHDGHAVS,KLEEHDGHAV,EEHDGHAVSI | CRC |
| ZFAND2B | c.446T>C | p.I149T | IKHRHPLDHDCSGEGHPTSRAGLAA[p.I149T]TSRAQAVASTSTVPSPSQTMPSC TSP | TSRAGLAAT,RAGLAATSR,ATSRAQAVA,GLAATS RAQA,TSRAQAVAST,LAATSRAQAV | KIRC |
| ZFC3H1 | c.1155de|A | p.K385fs | KKLGEDEEELSELQLRLLALQSASK[p.K385fs]NGMKNSR* | QSASKNGNK,LQSASKNGNK | STAD |
| ZFHX3 | c.2287de|G | p.E763fs | KGNLSIHMQSDKHLNNMQNLQNGG[p.E763fs]SRSSATLPGRRRRRWLRRRR QPISVAPAGPPRRPNQKPNPDGGARCV IMRPTWPGTSAFT* | RQPISVAPA,RSSATLPGR,SSATLPGRR,SVAPAGPPR,ATLP GRRRR,RRRRRWLRR,RRRRQPISV,IMRPTWPGT,TLPGRR RRR,WLRRRRQPI,RPNQKPNP,RPTWPGTSA,LQNGGGSRS, RRRQPISVA,RCVIMRPTW,PTWPGTSAF,QPISVAPAG, RSSATLPGRR,ISVAPAGPPR,SVAPAGPPRR,RWLRRRRQPI, GSRSSATLPG,ATLPGRRRRR,RRRRRWLRRR,RRRRQPISVA, AGPPRRPNQK,IMRPTWPGTS,LPGRRRRRWL,RPNQKPN PPG,RPTWPGTSAF,WLRRRRQPIS,LRRRRQPISV,LQNGG GSRSS,RRQPISVAPA | STAD |
| ZFHX3 | c.2330_2332 de|TGG | p.V777de| | NNMQNLQNGGEQVFSHTAGAAAAA[p.V777de|]AAAAAANISSSCGAPSPT KPKTKPTWR | HTAGAAAAA | PAAD |
| ZFHX3 | c.5677_5678 de|AG | p.R1893fs | LQPSQHPEKKNKLVIKEKEKESQRE[p.R1893fs]GQRRGGRGQHRSEGNTARCL EGQREERVGTRGWF* | TARCLEGQR,SEGNTARCL,EERVGTRGW,NTARCLEGQR,G QRRGGRGQH,GQHRSEGNTA,REERVGTRGW,EERVGTRG WF | STAD,UCEC |
| ZFHX4 | c.1224_1225 insG | p.L408fs | ASTSSSAEQPLGITQMPKAEVNLGG[p.L408fs]AV* | AEVNLGGAV | STAD |
| ZFHX4 | c.2433G>T | p.L811F | MTSEKHMHNMMLLQQNMKQIQHNL H[p.L811F]FGLAPAEAELYQYYLAQNIG LTGMKL | IQHNLHFGL,NLHFGLAPA,KQIQHNLHF,MKQIQHNLHF,K QIQHNLHFG,IQHNLHFGLA,LHFGLAPAEA | LUAD |
| ZFHX4 | c.4988C>A | p.T1663N | IAANVNSPGQGMLDSMSLAAVNSKD[p.T1663N]NHLDAKELNKKQTPDLISAQ PAHHPP | NSKDNHLDAK | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZFHX4 | c.7533C>A | p.H2511Q | LPPQLLQYQCDQCTVAFPTLELWQE[p. H2511Q]QQHMHFLAAQNQPLHSPPLE RPMDMP | QQHMHFLAA, ELWQEQQHM, WQEQQHMHF, QEQQHM HFL, LWQEQQHMHF, LELWQEQQHM, WQEQQHMHFL, E QQHMHFLAA, QQHMHFLAAQ, QEQQMHFLA | LUAD |
| ZFP14 | c.1156C>T | p.R386C | SIHTGEKPYECKECGKTFRLRQQLV[p. 386C]CHQRIHTREKPYECMECWKTFSS YSQ | RLRQQLVCH, QQLVCHQRI, RQQLVCHQRI, LVCHQRIHTR, QQLVCHQRIH | CRC |
| ZFP14 | c.50A>T | p.Q17L | MAHGSVTFRDVAIDFS[p.Q17L]LEEW EFLDPAQRDLYRDVMWENYSNF | DFSLEEWEF, RDVAIDFSL, VAIDFSLEEW, IDFSLEEWEF, LEE WEFLDPA | LUAD |
| ZFP2 | c.449G>T | p.R150I | TGEKPYKCNVCGKHFIERSSLTVHQ[p.R 150I]IIHTGEKPYKCNECGKAFSQSMNL TV | RSSLTVHQI, SSLTVHQII, RSSLTVHQII | CRC |
| ZFP3 | c.818G>T | p.R273I | TGEKPYECNECGKTFRVSSQLIQHQ[p.R 273I]IIHTEERYHECNECGKAFKHSSGLI R | QIHTEERY, HQIIHTEER, IQHQIIHTE, HQIIHTEERY | CRC |
| ZFP36L2 | c.718G>A | p.D240N | IHNADERRPAPSGGASGDLRAFGTR[p. D240N]NALHLGFPREPRPKLHHSLSFS GFPS | RAFGTRNAL, GTRNALHLG, NALHLGFPR, TRNALHLGF, RAF GTRNALH, GTRNALHLGF, RNALHLGFPR, LRAFGTRNAL | LUSC |
| ZFP42 | c.679G>A | p.V227I | RAALRKHLLIHGPRDHVCAECCKAF[p. V227I]IESSKLKRHFLVHTGEKPRCTFE GC | AFIESSKLK, KAFIESSKL, KAFIESSKLK, CGKAFIESSK, AFIESSK LKR, GKAFIESKL, IESSKLKRHF, AECGKAFIES | GBM |
| ZFP42 | c.791C>T | p.T264M | HTGEKPPRCTFEGCGKRFSLDFNLR[p.T 264M]MHVRIHTGEKRFVCPFQGCNRR FIQS | RMHVRIHTG, DFNLRMHVR, FSLDFNLRM, SLDFNLRMHV, RFSLDFNLRM, RMHVRIHTGE, NLRMHVRIHT | GBM |
| ZFP90 | c.1772_177 3insA | p.R591fs | IQHERTHTGEKPYECNECGRAFRKK[p.R 591fs]NQPA* | AFRKKNQPA, RAFRKKNQPA | PRAD |
| ZFPM1 | c.1330_133 1delGA | p.E444fs | GLAPTPSGLDRKALAEATNGEARA[p. E444fs]ASGPEWRQQRAPGGPQQHQ GGGGAGGGGPHPGHPPRAWAPGV ADAVAAQPRPGQGQGRAVQPHAGLQ PGARRAGPGRGPVPSAVRVRARRGAP RLGDPGQDVRAGAQPAAAGRGRGRR RRADRALPRGPQGRYVLRVRDHLQQR QQLLRAQAPLLFRPPCARGRACRAQAQ GAPRGPRAPRPARRTRRAALVPGPRS ARGGGWGRGHARGRRGRPGPGQP EPG* | QLLRAQAPL, RLGDPGQDV, LLRAQAPLL, ALVPGPRSA, RAQ APLLFR, LLFRPPCAR, RAQAQGAPR, RAALVPGPR, RAWAP GPVA, QGRAVQPHA, GARRAGPGR, RAGPGPGPV, SAVRV RARR, AVRVRARRG, RVRARRGAP, RARRGAPRL, RAGAQP AAA, AGRGRGRR, RGRGRRRRA, RGRRRRADR, RALPRGP QG, QGRYVLRVR, RVRDHLQQR, CARGRACRA, RGRACRAQ A, RTRRAALVP, SARGGWGR, RGHARGRRG, RGRRGRPG Q, SGPEWRQQR, HAGLQPGAR, LVPGPRSAR, HPGPRRAW A, GPRRAWAPG, APGPVADAV, RPGQQGRA, RAVQPHA GL, VPSAVRVRA, RRRRADRAL, RPPCARGRA, APRPGPRAP, RPARRTRRA, ARRTRRAAL, RPGQRGQPE, HLQQRQQLL, AR AASGPEW, RRAWAPGPV, GQGRAVPQH, RQQLLRAQA, LR AQAPLLF, GPVADAVAA, LPRGPQGRY, QLLRAQAPLL, RVR ARRGAPR, RSARGGWGR, RYVLRVRDHL, AVRVRARRGA, RARRGAPRLG, AGRGRGRRR, RGRRRRADRA, RRRADRAL PR, RALPRGPQGR, RVRDHLQQRQ, LLRAQAPLLF, LFRPPCA RGR, RGRACRAQAQ, RAPRPARRTR, RTRRAALVPG, RGHA RGRRGR, RGRRGRPGQP, ALPRGPQGRY, HAGLQPGARR, H LQQRQQLLR, WAPGPVADAV, GPHPGPRAW, RPGQGQG RAV, LPRGPQGRYV, RPPCARGRAC, RPGPRAPRPA, RPARR TRRAA, PARRTRRAAL, GPRSARGGGW, QQLLRAQAPL, RQ QRAPGGPQ, RRAWAPGPVA, GQGRAVQPHA, RRAGPGRG PV, VRARRGAPRL, RDHLQQRQQL, LQQRQQLLRA, RQQLL RAQAP, AQAPLLFRPP, AQAQGAPRPG | ACC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|------|-------------|----------------|-------------------------------------------------------------------------------------|-----------------------------------------------------------------------|--------------------|
| ZFPM1 | c.1335del|T | p.P445fs | APTPSPGLDRKALAEATNGEARAEP[p.P445fs]WPRMEAAASPRRPPGASRWR RWRSRRRPPSWAPESLGPRPRGRRR RAAPPRPGSRPSCPAPRRAPARCPASW AWPGPCSFRSTCSGPTRRPPPRRSWPR CPSWCTAGCSRARARAPAARRPGSSPGP PRALRASSARSPSATSTTTTCTSASTVQ AAVRPRTRLPRAGPRRPARPARPPAS PPNPTRARPRAPERARRGLGARPRPR TARAAGAARARARVAPWTTRRTTPA ARCARPATSASAATRPTPCTSGTTAPRA TTRRRADRPRPRDPLGRPRPPLPPRL CARADAASSTSCTRPAPRPRPATPPR PSRRGPEAEAEAAPASPLRARPAPRPTA PST* | RMEAAASPR, RVAPWTRR, STCSGPTRR, RALRASSAR, TV QAAVRPR, ATSASAATR, CTSGTTAPR, TTAPRATTR, TSCTRP APR, WAWGPCSF, RSWPRCPSW, ASRWRRWS, RWR WRSRR, RWRSRRRPP, RSRRRPPSW, RPRRGRRRR, RGRRR RAAP, RERRAAPPR, RSTCSGPTR, PTRRPPPRR, RARARAPA A, RARAPAARR, ALRASSARS, RASSARSPS, ASSARSPSA, AV RPRTRLP, RPRTRLPRA, RTRLPRAGP, RLPRAGPRR, RAGPRR PPA, PARPARPPA, PTRRARPRA, RARPRAPER, RARRGLGAR, GARPRPRTA, RPRPRTARA, RTARAAGAA, TARAAGAAR, A AGAARAAR, RARAARARV, AARARVAPW, RARVAPWTT, TT RRTTPAA, RTTPAARCA, AARCARPAT, ATRPTPCTS, ATTRR RADR, RPRPPLPPR, CTRPAPRPP, RPAPRPPR, PLRARPAPR, RARPAPRPT, EARAEPWPR, GASRWRRWR, ESLGPRPPR, S WCTAGCSR, CTAGCSRAR, QAAVRPRTR, TTPAARCAR, EAA PASPLR, TTCTSASTV, CTSASTVQA, SASTVQAAV, WTTRRT TPA, EPWPRMEAA, WPRMEAAAS, SPRRPPGAS, CPAPRRA PA, APARCPASW, APAARRPGS, RPARPPASP, APERARRGL, RPRTARAAG, RAAGAARAA, APWTTRRTT, RPATSASAA, RP TPCTSGT, RPRRPPPLP, RPRPPRRPA, RPATPPRPS, RPSRRG PEA, RPAPRPTAP, APRPTAPST, ARAEPWPRM, RRAPARCP A, ARCPASWAW, AAVRPRTRL, AEAAPASPL, CPASWAWPG, AEAEAAPAS, AEPWPRMEA, LPPRLCARA, STVQAAVRPR, R TARAAGAAR, RTTPAARCAR, GTTAPRATTR, TTAPRATTRR, STSCTRPAPR, SWAWPGPCSF, RMEAAASPRR, AASPRRP GA, ASRWRRWRSR, RWRRWRSRRR, RWR.SRRRPPS, RSRR RPPSWA, RGRRRRAAPP, RAAPPRPGSR, GSRPSCPAPR, SFR STCSGPT, RSTCSGPTRR, SGPTRRPPPR, RSWPRCPSWC, CS RARARAP, RARAPAARR, RARAPAARRP, AARRPGSSPG, RALRASSARS, RASSARSPSA, AVRPRTRLPR, RTRLPRAGPR, RAGPRRPPAR, RARPRAPERA, RPRAPERAR, RARRGLGAR P, RGLGARPRPR, GARPRPRTAR, TARAAGAARA, RAAGAAR AAR, AARAARARVA, AARARVAPWT, RARVAPWTTR, TTRR TTPAAR, AARCARPATS, CARPATSASA, ATRPTPCTSG, RATT RRRADR, TTRRRADRPR, RRRADRPRPR, RPRPRDPLGR, RPR DPLGRPR, LGRPRPRPPL, RPRPPLPPRL, CTRPAPRPPR, RAR PAPRPTA, SWAPESLGPR, CPAPRRAPAR, WAWPGPCSFR, R PPPRRSWPR, TAGCSRARAR, SASTVQAAVR, DAASSTSCTR, SPLRARPAPR, CTAGCSRARA, TTTCTSASTV, CTSASTVQAA, TSASTVQAAV, WTTRRTTPAA, CTSGTTAPRA, EAEAAPASP L, EAAPASPLRA, WPRMEAAASP, RPPSWAPESL, RPRRGRR RRA, RPGSRPSCPA, RPSCPAPRRA, APARCPASWA, WPRCP SWCTA, APAARRPGSS, PPRALRASSA, RPRTRLPRAG, LPRA GPRRPP, GPRRPPARPA, RPARPPASPP, RPRPRTARAA, RPR TARAAGA, APWTTRRTTP, TPAARCARPA, RPATSASAAT, R PTPCTSGT, APRATTRRRA, RPRPRPPLPP, RPPLPPRLCA, A PRPPRRPAT, RPAPRPTAPS, WRSRRRPPSW, RAPARCPAS W, RRSWPRCPSW, ARAAGAARAA, RAARARVAPW, EPWP RMEAA, AEPWPRMEAA, AEAEAAPASP, PEAEAEAAPA | ACC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZFR2 | c.319T>A | p.Y107N | TTMATYQDSYGQSAAARSYEDRP[p.Y107N]NFQSAALQSGRMTAADSGQPGTQEAC | RSYEDRPNF, RPNFQSAAL, ARSYEDRPNF, YEDRPNFQSA | KIRC |
| ZFYVE1 | c.797G>A | p.R266Q | GATVNLSQRTRLLLKVLAISDLVIY[p.R266Q]QTHADRLHNDLFKFLGDASFAYLKHF | IYQTHADRL, VIYQTHADR, YQTHADRLH, AISDLVIYQT, LVIYQTHADR, VIYQTHADRL | UCEC |
| ZFYVE9 | c.3441G>C | p.M1147I | VVQGLVVDMEVRKTSIKIPSNRYNE[p.M1147I]IMKAMNKSNEHVLAGGACFNEKADSH | SNRYNEIMK, IPSNRYNEI, RYNEIMKAM, IPSNRYNEIM, NRYNEIMKAM | CESC |
| ZHX3 | c.747C>A | p.N249K | EVREGDHSFINGAVPVSQASASSAK[p.N249K]KPHAANGPLIGTVPVLPAGIAQFLSL | QASASSAKK, ASSAKKPHA, KPHAANGPL, SQASASSAKK, KPHAANGPLI, KKPHAANGPL | STAD |
| ZIC1 | c.335C>A | p.A112E | GSYSSAAFNSTRDFLFRNRGFGDAA[p.A112E]EAASAQHSLFAASAGGFGGPHGHTDA | EAASAQHSL, AEAASAQHS, EAASAQHSLF, RGFGDAAEAA, AEAASAQHSL | LUAD |
| ZIC4 | c.914C>T | p.S305L | GEKPFRCEFEGCERRFANSSDRKKH[p.S305L]LHVHTSDKPYTCKVRGCDKCYTHPSS | HLHVHTSDK, KKHLHVHTS, KHLHVHTSDK, LHVHTSDKPY | CRC |
| ZIM3 | c.1054G>A | p.D352N | RIHTGEKPYKCSICEKAFSQKSNVI[p.D352N]NHEKIHTGKRAYECDLCGNTFIQKKN | KSNVINHEK, SQKSNVINH, KSNVINHEKI, INHEKIHTGK | CRC |
| ZIM3 | c.1150de|A | p.I384fs | GKRAYECDLCGNTFIQKKNLIQHKK[p.I384fs]SILGKSPMNVTDVEKPSFRSQTFIAIRKLIAERGPIDVVNVEKPSSGN* | ILGKSPMNV, FIAIRKLIA, KLIAERGPI, SQTFIAIRK, RSQTFIAIR, TFIAIRKLI, QHKKSILGK, KSILGKSPM, SFRSQTFIA, AIRKLIAER, KPSFRSQTF, NLIQHKKSI, LIQHKKSIL, FRSQTFIAI, AERGPIDVV, SILGKSPMNV, LIAERGPIDV, IQHKKSILGK, RSQTFIAIRK, SFRSQTFIAI, IAIRKLIAER, QTFIAIRKLI, KPSFRSQTFI, NLIQHKKSIL, KKSILGKSPM, SQTFIAIRKL, RKLIAERGPI, NVTDVEKPSF | STAD |
| ZKSCAN1 | c.1621_1622de|AG | p.R541fs | KCTKCGKAFTRSSTLTLHHRIHARE[p.R541fs]SL* | HRIHARESL, HHRIHARESL | UCEC |
| ZKSCAN3 | c.598_599A>GC | p.K200A | VGSQPLQDRVLQVPVLAHGGCCRED[p.K200A]AVVASRLTPESQGLLKVEDVALTLTPE | REDAVVASRL | TGCT |
| ZKSCAN4 | c.956G>A | p.R319Q | IPTHAERAGEQEGRLQRKQKNAIGSR[p.R319Q]QHYCHECGKSFAQSSGLTKHRIHTG | NAIGSRQHY, RQHYCHECG, RQHYCHECGK, KNAIGSRQHY | CRC |
| ZKSCAN5 | c.39de|C | p.D13fs | MIMTESREVIDLDP[p.D13fs]QLRLPRS*RKTFS | QLRLPRSRK, EVIDLDPQL, RLPRSRKTF, EVIDLDPQLR, DLDPQLRLPR, REVIDLDPQL, LRLPRSRKTF | STAD |
| ZMIZ1 | c.3144de|C | p.D1048fs | MPEPSLDLLPELTNPDELLSYLDPP[p.D1048fs]TCRAIVTMTSCLYLRTTEGHPVGAIPPHSASYPTYPTHFSTWEPVPSDRPAPEPRAVGRGALPRCSPLRTEG* | IVTMTSCLY, YLDPPTCRA, AIVTMTSCL, TMTSCLYLR, AVGRGALPR, SYPTYPTHF, TYPTHFSTW, VTMTSCLYL, AIPPHSASY, SYPTYPTCR, SASYPTYPT, RPAPEPRAV, EPRAVGRGA, GALPRCSPL, RAIVTMTSC, ASYPTYPTH, THFSTWEPV, HPVGAIPPH, YPTYPTHFS, EPVPSDRPA, TEGHPVGAI, YLDPPTCRAI, YLRTTEGHPV, VTMTSCLYLR, LSYLDPPTCR, AIVTMTSCLY, STWEPVPSDR, RAVGRGALPR, ASYPTYPTHF, PTYPTHFSTW, RAIVTMTSCL, RTTEGHPVGA, RGALPRCSPL, GALPRCSPLR, GAIPPHSASY, HSASYPTYPT, YPTYPTHFST, RPAPEPRAVG, EPRAVGRGAL, PPHSASYPTY, WEPVPSDRPA | PRAD |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZMIZ2 | c.457_501 del GT GGCTG CTGCGGCA GCCACTGC CACCGCCA CAGCCACA GCCACC | p.VAAA AATAT ATATA T153de | LGLPSHAARPSTDFTQAAAAAVAAL PVAAAATATATATAT153de LQEKQS QELSQYGAMGAGQSFNSQFLQHGGP RGPSVPAGMNPTGIGGVMGPSGLSPL AMNPTRAAGMTPL | AAAAAVAAL, AAVAALQEK, AAVAALQEK, AAAAAVAAL | PAAD |
| ZMYM4 | c.1033de A | p.K345fs | SSGMNKMLPSVPATAVRVSCSGCKK p. K345fs SSRRGKLLIRGKLLSYSAPHCA SLDIQFHLPAHRLLSPRKLVQVAQKTF* | LLIRGKLL, YSAPHCASL, KSSRRGKLL, SSRRGKLLI, RGKLLIR GK, RGKGLLSYS, AHRLLSPRK, RLLSPRKLV, IRGKGLLSY, CSG CKKSSR, IQFHLPAHR, PAHRLLSPR, APHCASLDI, LPAHRLLSP, SP RKLVQVA, LVQVAQKTF, GLLSYSAPH, HCASLDIQF, ASL DIQFHL, LDIQFHLPA, FHLPAHRL, SLDIQFHLPA, IQFHLPAHRL, LLSPRKLVQV, LLSYSAPHCA, SYSAPHCASL, GCKKSSRR GK, KSSRRGKLLI, SSRRGKLLIR, RGKGLLSYSA, PAHRLLSPRK, LIRGKGLLSY, DIQFHLPAHR, LPAHRLLSPR, KLVQV AQKTF, KKSSRRGKLL, LDIQFHLPAH | STAD |
| ZMYM4 | c.1100C>T | p.T367I | SGCKKILQKGQTAYQRKGSTQLFCS p.T 367I ILCLTGYTVPPARPPPLTKKTCSS C | CSILCLTGY, QLFCSILCL, ILCLTGYTV, GSTQLFCSI, TQLFCSIL CL, QLFCSILCLT, SILCLTGYTV, KGSTQLFCSI, GSTQLFCSIL, FCSILCLTGY | TGCT |
| ZMYM4 | c.4337G>A | p.R1446Q | TYLRFPPLQKQESEPDKLTVGKRK p.R 1446Q QNEDDEVPVGVEMAENTDNP LRCPVR | KQNEDDEVPV | CRC |
| ZNF11 | c.554G>T | p.R185I | TGEKPYKCKECGKAFNQTSHLIRHK p.R 185I IIHTEEKPYKCEECGKAFNQSSTLI T | QTSHLIRHKI | CRC |
| ZNF124 | c.1015de A | p.T339fs | GEKPYECQKCGKAFSRASTLMKHKK p. T339fs LILEKSPINVKKCKGFNHYSFCQ KHEQSHT* | KLILEKSPI, ILEKSPINV, KHKKLILEK, KGFNHYSFC, FNHYSFC QK, KKCKGFNHY, LWKHKKLIL, CKGFNHYSF, LILEKSPINV, IL EKSPINVK, GFNHYSFCQK, KSPINVKKCK, TLWKHKKLIL, KKL ILEKSPI, VKKCKGFNHY, KCKGFNHYSF | STAD |
| ZNF154 | c.1223C>A | p.T408N | RPYECSECGKSFTQNSGLIKHRRVH p.T 408N NGEKPYECTECGKSFSHNSSLIKH QR | HRRVHNGEK, KHRRVHNGEK, RRVHNGEKPY | LUAD |
| ZNF16 | c.1354C>T | p.R452W | HTGEKPYKCSDCGKAFSQSSSLIQH p.R 452W WRIHTGEKPHVCNVCGKAFSYS SVLR | QSSSLIQHW, QSSSLIQHWR, SQSSSLIQHW | CESC |
| ZNF167 | c.2048G>T | p.R683I | TGEKPYECNECCKVFSYSSSLMVHQ p. R683I ITHTGEKPYKCNDCGKAFSDSSQ LIV | LMVHQITHT, SLMVHQITH, SLMVHQITHT, YSSSLMVHQI | CRC |
| ZNF174 | c.1057C>A | p.P353T | CDDCGKSFTWNSELKRHKRVHTGER p. P353T TYTCGECGNCFGRQSTLKLHQR IHTG | RVHTGERTY, RVHTGERTYT, KRVHTGERTY | TGCT |
| ZNF180 | c.1202G>T | p.R401I | TGEKPYECSECGKSFSRSSHLVSHQ p.R 401I THTGEKPYRCNQCGKSFSQSYVL VV | HLVSHQITH, HLVSHQITHT, ITHTGEKPYR, RSSHLVSHQI | CRC |
| ZNF180 | c.1706G>T | p.R569I | TGEKPYECSECGKSFNRSSHLVMHQ p. R569I IIHTGEKPYECNQCGKSFSQSYVL VV | SHLVMHQII, RSSHLVMHQI, SSHLVMHQII | UCEC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZNF180 | c.1874G>T | p.R625I | TGEKPYECSQCGKSFRQSSCLTQHQ[p.R625I]ITHTGEKPFECNQCGKTFSLSARLIV | ITHTGEKPF,TQHQITHTG,QITHTGEKPF | UCEC |
| ZNF19 | c.1046G>T | p.R349I | TGEKPYSCKVCGQAFNFHTKLTRHQ[p.R349I]IIHSEEKPFDCVDCGKAFSAQEQLKR | HTKLTRHQI,HQIIHSEEK,TKLTRHQII,IIHSEEKPF,HTKLTRHQII,RHQIIHSEEK,QIIHSEEKPF | CRC |
| ZNF195 | c.176G>A | p.R59Q | LENYRNLFSVGLTVCKPGLITCLEQ[p.R59Q]QKEPWNVKRQEAADGHPEMGFHHATQ | QQKEPWNVK,QQKEPWNVKR,LEQQKEPWNV | UCEC |
| ZNF205 | c.1150C>T | p.R384C | TGEKPYTCPACRKSFSHHSTLIQHQ[p.R384C]CIHTGEKPYVCDRCAKRFTRRSDLVT | HQCIHTGEK,IQHQCIHTG,CIHTGEKPYV,QCIHTGEKPY | CRC |
| ZNF223 | c.67G>T | p.G23W | MTMSKEAVTFKDVAVVFTEEEL[p.G23W]WLLDLAQRKLYRDVMLENFRNLLSVG | FTEEELWLL,EELWLLDLA,EEELWLLDL,VVFTEEELW,WLLDLAQRKL,VFTEEELWLL,ELWLLDLAQR,TEEELWLLDL,EELWLLDLAQ,EEELWLLDLA | LUAD |
| ZNF23 | c.366del T | p.F122fs | NIKKEKSNTIDGTVKDETSPVEECF[p.F122fs]LVKVQTHISVIPSLESSPLGVQDWGNPSALIQNS* | FLVKVQTHI,KVQTHISVI,SLESSPLGV,IPSLESSPL,VKVQTHISV,THISVIPSL,KVQTHISVI,VQDWGNPSA,QDWGNPSAL,VEECFLVKV,SPVEECFLV,VQDWGNPSAL,VIPSLESSPL,CFLVKVQTHI,LVKVQTHISV,QTHISVIPSL,ETSPVEECFL,TSPVEECFLV,VKVQTHISVI,QLMGEPGLA,AQQLMGEPG,QQLMGEPGL,LMGEPGLAP,AQQLMGEPGL | STAD |
| ZNF236 | c.4229C>T | p.T1410M | NITLQIDPSILQQTLQQGNLLAQQL[p.T1410M]MGEPGLAPQNSSLQTSDSTVPASVVI | | STAD |
| ZNF236 | c.4439C>T | p.S1480L | GPLSEQDSVLTTNSSGTQDLTQVMT[p.S1480L]LQGLVSPSGGPHEITLTINNSSLSOV | TQVMTLQGL,QVMTLQGLV,TQVMTLQGLV,MTLQGLVSP,S,TQDLTQVMTL | CRC |
| ZNF248 | c.1703G>T | p.R568I | TGEKPYECNACGKTFSQRSVLTKHQ[p.R568I]IIHTRVKALSTS* | HQIIHTRVK,SVLTKHQII,IIHTRVKAL,RSVLTKHQI,LTKHQIIHTR,KHQIIHTRVK,RSVLTKHQII,HQIIHTRVKA | CRC |
| ZNF254 | c.537G>T | p.K179N | FQCDKYLKVFYKFLNSNRPKIRHTE[p.K179N]NKSFKCKKRVKLFCMLSHKTQHKSIY | KIRHTENKS,RHTENKSFK,IRHTENKSF,HTENKSFKCK,RPKIRHTENK,KIRHTENKSF | UCEC |
| ZNF257 | c.1175G>T | p.R392I | TKEKPYKCEECGKAFNRSSHLTKHK[p.R392I]IIHTREKAYKCDEYCKAFNWSSALIT | IIHTREKAY,IIHTREKAYK,KIIHTREKAY,RSSHLTKHKI | UCEC |
| ZNF259 | c.521G>T | p.R174I | LITRAISGLEQDQPARRANKDATAE[p.R174I]IIDEFIVKLKELKQVASPFTLIIDDP | IIDEFIVKL,ATAEIIDEF,AEIIDEFIV,ATAEIIDEFI,IIDEFIVKLK,EIIDEFIVKL,RANKDATAEI | CRC |
| ZNF263 | c.1529G>T | p.R510I | TGEKPYKCPECGEIFAHSSNLLRHQ[p.R510I]IIHTGERPYKCPECGKSFSRSSHLVI | SNLLRHQII | UCEC |
| ZNF266 | c.1031G>A | p.R344Q | TAKDPFECKICGKSFRNSSCLSDHF[p.R344Q]IHTGIKPYKCKDCGKAFTQNSDLTK | HFQIHTGIK,FQIHTGIKP,CLSDHFQIHT,QIHTGIKPYK,FQIHTGIKPY | CRC |
| ZNF266 | c.1535G>A | p.R512Q | TGEKPYKCKQCGKSFSYSNSFQLHE[p.R512Q]QTHTGEKPYECKECGKAFSSSSSFRN | FQLHEQTHT,EQTHTGEKPY,FQLHEQTHTG | CRC |
| ZNF268 | c.2700_2702del CTT | p.F901del | NSQLIVHQRTHSGEKPYGCNECGKT[p.F901del]SQKSILSAHQRTHTGEKPCKCTECGKAF | KTSQKSILS,KTSQKSILSA | BRCA |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZNF273 | c.957T>A | p.N319K | DCGKVFSVFSVLTKHKIIHTGTKPY[p.N319K]KCEECGKGFSIFSTLTKHKIIHTGEK | IIHTGTKPYK | KIRC |
| ZNF280B | c.1087G>A | p.E363K | SWENHTCQHCHRQFPTPFQLQCHI[p.E363K]KNVHTAQEPSTVCKICELSFETDQVL | QLQCHIKNV, LQCHIKNVH, CHIKNVHTA, FQLQCHIKNV | CRC |
| ZNF280B | c.1198G>A | p.E400K | CKICELSFETDQVLLQHMKDHHKPG[p.E400K]KMPYVCQVCHYRSSVFADVETHFRTC | HHKPGKMPY, GKMPYVCQV, HMKDHHKPGK, MKDHHKP GKM, GKMPYVCQVC | GBM |
| ZNF283 | c.1175G>A | p.R392Q | KIHTGKKPYECKICGKAFCWGYQLT[p.R392Q]QHQIFHTGEKPYECKECGKAFNCGSS | GYQLTQHQI, YQLTQHQIF, TQHQIFHTG, GYQLTQHQIF, W GYQLTQHQI, YQLTQHQIFH | CRC |
| ZNF32 | c.185C>T | p.S62L | EATGSSSWDIQNSFRREKLEQKSPD[p.S62L]LKTLQEDSPGVRQRVYECQECGKSFR | KLEQKSPDLK | CRC |
| ZNF322 | c.318G>T | p.K106N | VQSSDLTSHQRIHNYEKPYKCSKCE[p.K106N]NSFWHHLVLSGHQRTHAGKKFYTCDI | ENSFWHHLV, NSFWHHLVL, KCSKCENSF, CENSFWHHL, YK CSKCENSF, CENSFWHHLV | LUAD |
| ZNF333 | c.1661G>A | p.R554Q | TGEKLYECATCGQVLSRLSTLKSHM[p.R554Q]QTHTGEKPYVCQECGRAFSEPSSLRK | HMQTHTGEK, KSHMQTHTG, SHMQTHTGEK, MQTHTGEK PY, QTHTGEKPYV | UCEC |
| ZNF334 | c.1278de|A | p.K426fs | ECKECGKTFFCQSALTAHQRIHTGE[p.K426fs]NPMNVVNVRKPSFVNLPSMCIEEVIQERSPMNAVNVENFYVRNQPSLHIR* | AVNVENFYV, FVNLPSMCI, FVYRNQPSL, RIHTGENPM, HTG ENPMNV, EVIQERSPM, NAVNVENFY, VVNVRKPSF, VRKPS FVNL, PSFVNLPSM, QERSPMNAV, MNAVNVENF, VRNQPS LHI, LPSMCIEEV, NLPSMCIEEV, VVNVRKPSFV, AVNVENFY VR, SFVNLPSMCI, NVRKPSFVNL, YVRNQPSLHI, MNQVNVE NFY, HTGENPMNVV, NAVNVENFYV, KPSFVNLPSM, NFYV RNQPSL, QRIHTGENPM, GENPMNVVNV, NVNVRKPSF, E EVIQERSPM, IQERSPMNAV, PMNAVNVENF, LPSMCIEEVI | STAD |
| ZNF354B | c.1205G>T | p.R402I | TGEKPFKCSECGRAFSQSASLIQHE[p.R402I]IIHTGEKPYRCNECGKGFTSISRLNR | SASLIQHEI, IQHEIIHTG, SLIQHEIIHT, QSASLIQHEI | UCEC |
| ZNF354B | c.1825G>A | p.D609N | GKLFSQRSSLTNHYKIHIEEDSLKA[p.D609N]NLHV* | EEDSLKANL, IEEDSLKANL | UCEC |
| ZNF358 | c.389de|C | p.T130fs | DPNSDTLSPGDPKVDPISSGLTATP[p.T130fs]RSWPPAPRCSPPPPARPGPSPARIAGEPSAAAPG* | RIAGEPSAA, SSGLTATPR, ATPRSWPPA, RPGPSPARI, GLTA TPRSW, ARIAGEPSA, RIAGEPSAAA, ISSGLTATPR, PARPGP SPAR, TPRSWPPAPR, APRCSPPPPA, RPGPSPARIA, SGLTAT PRSW, ARIAGEPSAA | STAD |
| ZNF382 | c.558T>A | p.H186Q | FGDSTGWEKSLLNTKHEKIHPAVNL[p.H186Q]QKQTERVLSGKQELIQHQKVQAPEQP | NLQKQTERV, LQKQTERVL, KIHPAVNLQK | CLL |
| ZNF385D | c.677C>G | p.T226S | KRLLYCSLCKVAVNSASQLEAHNSG[p.T226S]SKHKTMLEARNGSGTIKAPPRAGVKG | SKHKTMLEA, GSKHKTMLEA, SQLEAHNSGS, LEAHNSGSKH | LUAD |
| ZNF43 | c.752de|A | p.N251fs | GEKPYTCEECGKVFNWSSRLTTHKK[p.N251fs]IILDTNSTNVKNVAKLLTSPQSLLPIR* | ILDTNSTNV, KLLTSPQSL, LLTSPQSLL, IILDTNSTNV, KLLTSP QSLL, ILDTNSTNVK, SRLTTHKKI, DTNSTNVKNV, LTSPQSL LPI, RLTTHKKIIL, AKLLTSPQSL | STAD |
| ZNF43 | c.838C>T | p.R280C | YKLYKCEECGKAFNKSSILTTHKII[p.R280C]CTGEKFYKCKECAKAFNQSSNLTEHK | IICTGEKFY, KIICTGEKF, IICTGEKFYK, CTGEKFYKCK, THKIICT GEK, KIICTGEKFY, HKIICTGEKF | UCEC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZNF434 | c.916C>T | p.R306C | QNSQIYRAMAEGLWEQFLRTPEQC[p.R306C]CTKFKSLQLSYRKVRRGRVPEPCIFY | RTPEQCCTK,CTKFKSLQL,TPEQCCTKF,RTPEQCCTKF | CRC |
| ZNF439 | c.785G>T | p.R262I | TGEKPYECKQCCGKSFSYASATHRIHE[p.R262I]ITHIGEKPYECQECGKAFHSPRSCHR | ITHIGEKPY,HRIHEITHI,YSATHRIHEI | CRC |
| ZNF442 | c.926G>A | p.R309Q | ERTHTGEKPYKCKRCGRAFSVSSSL[p.R309Q]QIHERTHTGEKPYECKQCGKAFHHLG | SSSLQIHER,FSVSSSLQI,VSSSLQIHER,RAFSVSSSLQ,FSVSSSLQIH | UCEC |
| ZNF443 | c.902G>T | p.R301I | TGEKPYKCKQCSKAPDSSSCLIHE[p.R301I]THTGEKPYTCKQCGKAFSVSGSLQR | CLIHEITHT,SSSCLIHEI,DSSSCLIHEI,EITHTGEKPY | CRC |
| ZNF445 | c.2044C>A | p.L682M | ECREGFRQSPDCSQPQGAPAVEKTF[p.L682M]MCQQCGKTFTRKKTLVDHQRIHTGEK | TFMCQQCGK,KTFMCQQCG,APAVEKTFM,MCQQCGKTF,KTFMCQQCGK,FMCQQCGKTF | CRC |
| ZNF454 | c.1127G>T | p.R376I | TGEKPFECNECCGKAFRVNSSLTEHQ[p.R376I]IIHTGEKPYKCNECGKAFRDNSSFAR | SSLTEHQII,TEHQIIHTG,SLTEHQIIHT | UCEC |
| ZNF454 | c.569G>T | p.S190I | SDQSQGFQPSKNAFECSECGKVFSK[p.S190I]ISTLNKHQKIHNEKNANQKIHIKEKR | KVFSKISTL,FSKISTLNK,ISTLNKHQK,VFSKISTLNK,KISTLNKHQK,GKVFSKISTL,SECGKVFSKI | LUAD |
| ZNF462 | c.1948T>A | p.S650T | FCDNLPKFEGQPSSLPLENETDSHP[p.S650T]TSSNTVKKSQTSILGLSSKNNFVAKA | PTSSNTVKK,DSHPTSSNTV,LENETDSHPT | KIRC |
| ZNF470 | c.1922G>T | p.R641I | TGEKPYECNVCGKAFSHRKSLTLHQ[p.R641I]IIHTGEKPYECKECSKAFSQVAHLTL | KSLTLHQII,RKSLTLHQI,KSLTLHQIIH,RKSLTLHQII | CRC |
| ZNF471 | c.845G>T | p.R282I | TGEKLFECKECRKAFKQSEHLIQHQ[p.R282I]IIHTGEKPYKCKECRKAFRQPAHLAQ | SEHLIQHQI,SEHLIQHQII | CRC |
| ZNF48 | c.704G>A | p.R235H | HQRTHTGEKPYKCGICGKGFGDSSA[p.R235H]HIKHARTHRGEQPPRPVVPRRQPSRA | SSAHIKHQR,HIKHQRTHR,KGFGDSSAH,AHIKHQRTH,DSSAHIKHQR,KGFGDSSAHI | LUSC |
| ZNF48 | c.739del|C | p.P247fs | ICGKGFGDSSARIKHQRTHRGEQPP[p.P247fs]DQWCPDGSHLGQPRQLPRDRRPRTSHISALIAARGLCSAAS* | RTSHISALI,HISALIAAR,RPRTSHISA,AARGLCSAA,LPRDRR,PRT,SHISALIAA,LIAARGLCSA,RQLPRDRRPR,RTSHISALIA,TSHISALIA,AARGLCSAAA,HLGQPRQLPR,SHISALIAAR,LPRDRRPRTS,RPRTSHISAL,DQWCPDGSHL,IAARGLCSAA | STAD |
| ZNF484 | c.412C>T | p.R138C | SILEELWKDDEHTRKCGENQNKPLS[p.R138C]CVVFINKKTLANDSIFEYKDIGEIVH | NQNKPLSCV,LSCVVFINK,NKPLSCVVF,KPLSCVVFI,NQNKPLSCVV,PLSCVV,PLSCVVFINK,LSCVVFINKK,QNKPLSCVVF | CRC |
| ZNF485 | c.1121G>T | p.R374I | SGNKPYQCRDCGKAFTKSSLTGHQ[p.R374I]IIHTGEKPYHCKKCGKAFRHSSGLVE | KSSTLTGHQI | UCEC |
| ZNF488 | c.617G>A | p.R206Q | PAGESADALGELSGLLNTTDLACWG[p.R206Q]QLSTPKLLVGDLWNLQALPQNAPLCS | QLSTPKLLV,GQLSTPKLL,CWGQLSTPKLL,GQLSTPKLLV | UCEC |
| ZNF491 | c.1028G>A | p.R343Q | ERTHTGEKPFDGCKQCGKAFRSAKYI[p.R343Q]QIHGRTHTGEKPYECKQCGKAFHCVS | SAKYIQIHG,RSAKYIQI,FRSAKYIQI,IQIHGRTHT,APRSAKYIQI,SAKYIQIHGR,IQIHGRTHTG | CRC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZNF492 | c.1175C>A | p.P392H | CEVCSKAFSRFSHLTTHKRIHTGEK[p.P392H]HYKCEECGKAFNLSSQLTTHKIIHTG | RIHTGEKHY, RIHTGEKHYK, KRIHTGEKHY | LUAD |
| ZNF514 | c.242T>G | p.V81G | PGEEGTTNSFLKARPRDLMTFEDVA[p.V81G]GEFSQWEWGQLNPAQKDLYREVMLEN | MTFEDVAGE, MTFEDVAGEF, VAGEFSQWEW | KIRP |
| ZNF519 | c.1291C>T | p.H431Y | CKECGKAFNRASHLTQHQRIHTGEK[p.H431Y]YFKCKECGKAFNRGSHLTRHQRIHTG | YFKCKECGK, QRIHTGEKY, RIHTGEKYF, RIHTGEKYFK, HTGEKYFKCK, KYFKCKECGK, HQRIHTGEKY, QRIHTGEKYF | KIRC |
| ZNF521 | c.1918G>T | p.G640C | TSLKMMQAVGGAPARPTGEYICNQC[p.G640C]CAKYTSLDSFQTHLKTHLDTVLPKLT | ICNQCCAKY, GEYICNQCC, YICNQCCAKY, CAKYTSLDSF, NQCCAKYTSL, GEYICNQCCA | LUAD |
| ZNF521 | c.809C>A | p.P270H | TQKCSQCEEGFDFPEDLQKHIAECH[p.P270H]HECSPNEDRAALQCVYCHELFVEETS | LQKHIAECHH | LUAD |
| ZNF528 | c.836G>A | p.R279Q | SNLSQHQRIHTGEKPYKCHECDKVF[p.R279Q]QSSSKLLAQHQRIHTGEKPYKCHECDK | KVFQSSSKL, FQSSSKLAQ, KVFQSSSKLA, FQSSSKLAQH, HECDKVFQSS | CRC |
| ZNF534 | c.1749T>A | p.N583K | TGEKPYSCNECGKVFSRNSHLARHR[p.N583K]KIHTGEKPHSCNECGKVFSRNSHLAR | RKIHTGEKPH | GBM |
| ZNF536 | c.1987G>T | p.G663W | RVFRTYHQVVVHSRVHKRDRKGEED[p.G663W]WLHVGLDERRGSGSDQESQSVSRSTT | EEDWLHVGL, DWLHVGLDER, GEEDWLHVGL | LUAD |
| ZNF536 | c.556G>T | p.G186C | PYCDHRAAQKGNLKIHLRTHKLGNL[p.G186C]CKGRGRVREENRLLHELERAILRDK | RTHKLGNLC, RTHKLGNLCK, NLCKGRGRVR | LUAD |
| ZNF559 | c.850G>A | p.E284K | PSSSHLRECVRIYGGERPYTHKEYV[p.E284K]KTFSHSTALFVHMQTQDGEKPYECKA | KTFSHSTAL, THKEYVKTFSH, KEYVKTFSH, VKTFSHSTA, Y VKTFSHSTA, KTFSHSTALF, YTHKEYVKTF, RPYTHKE YVK, VKTFSHSTAL, KEYVKTFSHS | UCEC |
| ZNF563 | c.622del|T | p.W208fs | NLRRHMVVQGGNRPYKCKLCGKAFF[p.W208fs]GPVYYVCMKELTLERNRMNVSSVLKPPLFTVPIEDMRECTLGRNRMNVSSVLKPCLIPVPI* | AFFGPVYYV, VLKPFLFTV, KAFFGPVYY, CMKELTLER, FFGPV YYVC, VYYVCMKEL, SSVLKPFLF, CGKAFFGPV, GKAFFGPVY, FTVPIEDMR, KPPLFTVPI, NVSSVLKPF, KAFFGPVYYV, SVLK PFLFTV, FLFTVPIEDM, FFGPVYYVCM, YYVCMKELTL, VSSV LKPFLF, CGKAFFGPVY, GKAFFGPVYY, NVSSVLKPFL, MNVS SVLKPF, KELTLERNRM, LKPFLFTVPI | GBM |
| ZNF563 | c.78G>T | p.K26N | MDAVAFEDVAVNFTQEEWALLGPSCTI[p.K26N]NNLYRYVMQETIRNLDCIRMIWEEQN | PSQNNLYRY, LLGPSQNNL, SQNNLYRYV, LGPSQNN LY, QNNLYRYVM, ALLGPSQNNL, LLGPSQNNLY, SQNN LYRYVM, GPSQNNLYRY | CRC |
| ZNF573 | c.1049G>T | p.R350I | TGKKPYECKECGKGYTTASFLLHQ[p.R350I]IIHKGGKPYECKECKKTFLYRNLTR | FLLHQIIHK, SYFLLHQII, HQIIHKGGK, IIHKGGKPY, ASYFLLH QI, QIIHKGGKPY, TASYFLLHQI, ASYFLLHQII | CRC |
| ZNF578 | c.931G>A | p.G311S | PYKCNECGKSFSYKSSLTCHRRCHT[p.G311S]SEKPYKCNECGKSFSYKSSLTCHRC | CHRRCHTSEK | CLL |
| ZNF583 | c.1031G>T | p.R344I | TGERPFECIECGKAFSNGSFLAQHQ[p.R344I]IIHTGEKPYVCNVCGKAFSHRGYLIV | SFLAQHQII, GSFLAQHQI, FLAQHQIIH, FLAQHQIIHT, GSFL AQHQII | CRC |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZNF585A | c.1473G>T | p.E491D | YMCNKCGKAFTNRSNLITHQKTHTG[p. E491D]DKSYICSKCCGKAFTQRSDLITHQ RIH | HQKTHTGDK, KTHTGDKSY, KTHTGDKSYI, QKTHTGDKSY | CRC |
| ZNF585A | c.1912G>A | p.E638K | KSFTSKSQLLVHQPVHTGEKPYVCA[p.E 638K]KCGKAFSGRSNLSKHQKTHTGEK PYI | VCAKCGKAF, KPYVCAKCGK, YVCAKCGKAF, G EKPYVCAKC | CRC |
| ZNF592 | c.1498C>A | p.P500T | PGSQTGKKQQSTALQASTLAPANLL[p. P500T]TKAVHLANLNLVPHSVAASVTA KSSV | LLTKAVHLA, NLLTKAVHL, TKAVHLANL, NLLTKAVHLA, TLA PANLLTK, LTKAVHLANL, APANLLTKAV | TGCT |
| ZNF592 | c.970A>C | p.K324Q | VTKEDQPGHTKDLSGPTKESSKGSP[p.K 324Q]QMPKSPKSPRSPLEATRKSIKPSD SP | SSKGSPQMPK, QMPKSPKSPR, KESSKGSPQM | TGCT |
| ZNF594 | c.860G>T | p.R287I | TGEKPYECYDCGQMFSQSSHLVPHQ[p. R287I]IIHTGEKPLKCNECEKAFRQHSH LTE | HLVPHQIIH, IIHTGEKPLK, SSHLVPHQII | UCEC |
| ZNF598 | c.74A>G | p.E25G | MAAAGGAEGRRADMEAEAAAAPER[p. E25G]GGGSCVLCCGDLEATALGRCDH PVCY | AEAAAAPERG | ACC, KIRP |
| ZNF608 | c.1393del G | p.A465fs | SAAAAPGSEASFTESRGLQNKNRGG[p. A465fs]PMGKGGGAASMPADEGHPQI VLLRISKPALPPPTKGKTSLQWSWT* | QIVLLRISK, KNRGGPMGK, LLRISKPAL, KPALPPPTK, GPMG KGGGA, PPTKGKTSL, GKKGGAASM, TKGKTSLQW, GKTSL QWSW, DEGHPQIVL, MPADEGHPQ, HPQIVLLRI, VLLRISKP AL, ISKPALPPPT, EGHPQIVLLR, MPADEGHPQI, GPMG KGGGAA, MGKGGGAASM, LQNKNRGGPM, KGKTS LQWSW, DEGHPQIVLL | STAD |
| ZNF611 | c.1169G>T | p.R390I | TGEKPYKCEECDKVFSRKSTIETHK[p.R 390I]IIHTGEKPYRCKVCDTAFTWHSQLA R | RKSTIETHKI | UCEC |
| ZNF625 | c.704G>A | p.R235Q | TGEKPYECSECGKAFHSSTCLHAHK[p.R 235Q]KTHTGEKPYECKQCGKAFVSFNS VRY | STCLHAHKK, SSTCLHAHKK, AHKKTHTGEK | CRC |
| ZNF626 | c.1418A>G | p.K473R | TGEKPYKCEECGKAFKCSSNLTTHK[p.K 473R]RIHTGERPYKCEECGKAFNQSSIL TT | CSSNLTTHKR | LUSC |
| ZNF638 | c.1198G>A | p.D400N | SQADIPIRSPPGIVKASWLPKFSHA[p.D 400N]NAQKMKRLPTPSMMNDYYAAS PRIFP | KPFSHANAQK, HANAQKMKR, FSHANAQKM, WLPKFSHAN A, FSHANAQKMK, KFSHANAQKM | LIHC |
| ZNF644 | c.61G>T | p.G21W | MRSFLQQDVNKTKSRLNVLN[p.G21 W]WLANNMDDLKINTDITGAKEELLDD N | RLNVLNWLA, WLANNMDDL, VLNWLANNM, KSRLNVLN W, SRLNVLNWL, WLANNMDDLK, KSRLNVLNWL, NVLNWL ANNM, TKSRLNVLNW | LUAD |
| ZNF645 | c.460C>T | p.R154C | SLQAHIKRRHKRARKQVTSASLEKV[p.R 154C]CPHIAPPQTEISDIPKRLQDRDHL SY | SLEKVCPHI, LEKVCPHIA | UCEC |
| ZNF649 | c.593G>T | p.R198I | NIEKAHECTDCGKAFLKKSQLTEHK[p.R 198I]IIHTGKKPHVCSLCGKAFYKKYRLT E | SQLTEHKII, IIHTGKKPHV, KKSQLTEHKI, SQLTEHKIIH | UCEC |
| ZNF652 | c.981G>T | p.K327N | VSCNKSFKKLWSLHEHIKIVHGYAE[p.K 327N]NKFSCEICEKKFYTMAHVRKHM VAHT | IVHGYAENK, AENKFSCEI, KIVHGYAENK, IVHGYAENKF, AENKFSCEIC | CRC |

TABLE 8-continued

| gene | cDNA Change | Protein Change | Mutation_Context Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZNF674 | c.1214G>T | p.R405I | TKENIYECSKCGKSFRGKSHLSVHQ[p.R405I]IHTGEKPYECSICGKTFSGKSHLSV | SHLSVHQI,KSHLSVHQI,KSHLSVHQII,GKSHLSVHQI | UCEC |
| ZNF675 | c.659G>T | p.R220I | TKVNFCKCEECEKAVNQSSKLTKHK[p.R220I]IYTCEKLYKCQECDRTFNQFSNLTE | KLTKHKIY,IIYTCEKLY,SSKLTKHKI,IIYTCEKLYK,SSKLTKHKII,KHKIIYTCEK,KIIYTCEKLY,SKLTKHKIIY,HKIIYTCEKL | UCEC |
| ZNF676 | c.127C>A | p.P43T | PDLIIFLEQGKEPWNMKRHEMVEEP[p.P43T]TVICSHFSQEFWPEQIEDSFQKMIL | HEMVEEPTV,EPTVICSHF,HEMVEEPTVI,EPTVICSHFE | LUSC |
| ZNF677 | c.1352G>T | p.R451I | PGEKPHKCNVCGRAFIQSSSLVEHQ[p.R451I]IHTGEKPYKCNKCDKAFIKRSHLWG | SSLVEHQII,VEHQIIHTG,SLVEHQIIHT | CRC |
| ZNF677 | c.392G>C | p.R131T | FDSLWDYDVKNYKGMPLTCNKNLTH[p.R131T]TKDQQHNKSSIHFSLKQSVSIRDSAH | HTKDQQHNK,CNKNLTHTK | CESC |
| ZNF680 | c.1501C>T | p.R501W | TLANHKRIHAREKPYKCEECGKAFN[p.R501W]WSSHLTRHKKIHTGEKLYKPEKCDNN | FNWSSHLTR,WSSHLTRHKK,AFNWSSHLTR,FNWSSHLTRH | TGCT |
| ZNF687 | c.2573T>G | p.F858C | DTVFTHKPLLSSHFDQHLLPQRVSV[p.F858C]CKCPSCPLLFAQKRTMLEHLKNTHQS | LLPQRVSVC,CKCPSCPLLF | KIRC |
| ZNF699 | c.122G>T | p.R41I | QDSVVFEDVAVDFTQEEWALLDLAQ[p.R41I]INLYRDVMLENFQNLASLGYPLHTPH | LLDLAQINL,DLAQINLYR,LDLAQINLY,AQINLYRDV,QINLYRDVM,WALLDLAQI,LLDLAQINLY,ALLDLAQINL,AQINLYRDVM | CRC |
| ZNF7 | c.1010G>T | p.R337I | TGEKPYRCEECGKAFGQSSSLIHHQ[p.R337I]IIHTGERPYGCRECGKAFSQQSQLVR | SSSLIHHQI,SSLIHHQII,SLIHHQIIHT,QSSSLIHHQI | CRC |
| ZNF70 | c.731G>T | p.R244I | TGKRPYECRECGKDFSRSSSLRKHE[p.R244I]IIHTGERPYQCKECGKSFNQSSGLSQ | SLRKHEIIH,RSSSLRKHEI,EIIHTGERPY | CRC |
| ZNF700 | c.1946C>G | p.S649C | NLRKHGRTHTGEKPYECKQCGKAFR[p.S649C]CASNLQMHERTHTGEKPYECKECEKA | KAFRCASNL,FRCASNLQM,CASNLQMHER,AFRCASNLQM,GKAFRCASNL | CLL |
| ZNF700 | c.1954A>C | p.N652H | KHGRTHTGEKPYECKQCGKAFRSAS[p.N652H]HLQMHERTHTGEKPYECKECEKAFCK | ASHLQMHER,AFRSASHLQ,RSASHLQMH,FRSASHLQM,SASHLQMHER,AFRSASHLQM | CLL |
| ZNF700 | c.1961A>G | p.Q654R | GRTHTGEKPYECKQCGKAFRSASNL[p.Q654R]RMHERTHTGEKPYECKECEKAFCKFS | ASNLRMHER,AFRSASNLR,FRSASNLRM,KAFRSASNLR,SASNLRMHER,AFRSASNLRM | CLL |
| ZNF705A | c.892G>A | p.D298N | GNKIIHTGEKPHACLLCGKAFSLSS[p.D298N]NLR* | AFSLSSNLR,KAFSLSSNLR | CLL |
| ZNF706 | c.23T>A | p.I8N | MARGQQK[p.I8N]NQSQQKNAKKQAGQKKKQGHDQKAAA | QQKNQSQQK,KNQSQQKNAK | BLCA |
| ZNF709 | c.1403G>T | p.R468I | TGEKPYECKQCGKAFSCSSSFRMHE[p.R468I]IIHTGEKPYECKQCGKAFSFSSSFRM | RMHEIIHTG,SFRMHEIIH,SSFRMHEII,SFRMHEIIHT,CSSSFRMHEI,SSFRMHEIIH | UCEC |
| ZNF71 | c.1231G>T | p.V411L | ICKKHFTGRSSLIVHQIVHTGEKPY[p.V411L]LCGECGKAFSQSAYLIEHQRIHTGEK | YLCGECGKA,LCGECGKAF,YLCGECGKAF,GEKPYLCGEC | LUAD |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZNF711 | c.2211del A | p.L737fs | SVHTKDQPLKCKCRKRGFRQQNELKP.L737fs]NI* | RQQNELKNI | STAD |
| ZNF716 | c.788A>T | p.H263L | EKPYRCECGKAFSWSASLTKHKRI[p.H263L]LTGEKPYTCEERGKVFSRSTLTNYKR | LTKHKRILT, SLTKHKRIL, KHKRILTGEK | LUAD |
| ZNF717 | c.1781A>T | p.N594I | GKSFHCKSFLTIHQRTHAGKKPYEC[p.N594I]IECEKTFINKLNLGIHKRTHTGERPY | YECIECEKTF | MM |
| ZNF717 | c.2530T>A | p.C844S | CRKTFSQKSKLFVHHRTHTGEKPFR[p.C844S]SNECRKTFSQKSGLSIHQRTHTGEKP | RSNECRKTF, KPFRSNECRK, RSNECRKTFS, FRSNECRKTF | MM |
| ZNF717 | c.945G>C | p.W315C | KPSISKSDLMLQCKMPTEEKPYACN[p.W315C]CCEKLFSYKSSLLIHQRIHTGEKPYG | KPYACNCCEK, YACNCCEKLF | MM |
| ZNF750 | c.287_288del CT | p.S96fs | LDPKQTNQPDATAKPASSKSVANGL[p.S96fs]CLRLEASAQLCQGRHQGKPGAASPGNPQVPGTEASPPQGITLQEPSSGSRPRCPACSGRRSSAFCICSSRRAQTQGARQRRGARDTGFTQPHCQGRVFPHQVGLPHSWLPLESRLTFPSTRVST* | RVFPHQVGL, GLPHSWLPL, RLTFPSTRV, SVANGLCLR, SAFCICSSR, HSWLPLESR, SWLPLESRL, GSRPRCPAC, SGRRSSAFC, GARQRRGAR, AFCICSSRR, QTQGARQRR, FTQPHCQGR, PRCPACSG, QPHCQGRVF, FPHQVGLPH, LPLESRLTF, CSGRRSSAF, KSVANGLCL, LRLEASAQL, HQGKPGAAS, RRGARDTGF, HQVGLPHSW, TEASPPQGI, LESRLTFPS, SVANGLCLRL, GLCLRLEASA, CLRLEASAQL, FTQPHCQGRV, KSVANGLCLR, SSAFCICSSR, SAFCICSSRR, MLPLESRLTF, SSGSRPRCPA, GSRPRCPACS, RPRCPACSGR, SGRRSSAFCI, SRRAQTQGA, RAQTQGARQR, RVFPHQVGLP, EASAQLCQGR, TLQEPSSGS R, ESRLTFPSTR, EASPPQGITL, SKSVANGLCL, HQGKPGAAS P, ACSGRRSSAF, RQRGARDTG, QRRGARDTGF, TQPHCQ GRVF, GRVFPHQVGL, HQVGLPHSWL, VGLPHSWLPL, HSW LPLESRL, LESRLTFPST | HNSC |
| ZNF765 | c.761C>T | p.S254L | LLRKHQLIHLGEKQYKCDICGKVFN[p.S254L]LKRYVARHRCHTGEKPYKCNECGKT | KVFNLKRYV, FNLKRYVAR, GKVFNLKRY, KVFNLKRYVA, CG KVFNLKRY, DICGKVFNLK, VFNLKRYVAR, NLKRYVARHR | UCEC |
| ZNF774 | c.1268G>A | p.R423Q | TGERPYKCGECGKSFNQSSHFITHQ[p.R423Q]IHLGDRPYRCPECGKTFNQRSHFLT | FITHQQIHL, QIHLGDRPY, SHFITHQQI, SSHFITHQQI, QQIH LGDRPY, QIHLGDRPYR, SHFITHQQIH | CRC |
| ZNF780A | c.1397G>A | p.R466Q | SNEKPVCRECEMAFRYHCQLIEHS[p.R466Q]QIHTGDKPFECQDCGKAFNRGSSLVQ | HSQIHTGDK, QIHTGDKPF, CQLIEHSQI, QLIEHSQIH, QLIEH SQIHT, SQIHTGDKPF, CQLIEHSQIH | UCEC |
| ZNF782 | c.1450G>T | p.G484W | FNYKSLLIVHQRTHTGEKPFECNEC[p.G484W]WKSFSHMSGLRNHRRTHTGERPYKCD | NECWKSFSH, KPFECNECW, CWKSFSHMSG, FECNECWKSF, NECWKSFSHM, WKSFSHMSGL | LUAD |
| ZNF782 | c.434G>T | p.C145F | KPHNRDINIFRARMMPCKCDIAGSA[p.C145F]FQGLSLMAPHCQYSKEKAHERNVCDK | SAFQGLSLM, KCDIAGSAF, IAGSAFQGL, GSAFQGLSL, FQG LSLMAP, DIAGSAFQGL, CKCDIAGSAF, AGSAFQGLSL, GSAF QGLSLM, SAFQGLSLMA, FQGLSLMAPH | TGCT |
| ZNF782 | c.740A>C | p.K247T | KAFLEKAALVTSNSTHPKGKSYNFN[p.K247T]TFGENKYDKSTFIIPQNMNPEKSHYE | KGKSYNFNT, KSYNFNTFG, GKSYNFNTF, FNTFGENKY, NTF GENKYDK, KGKSYNFNTF | CRC |
| ZNF799 | c.121T>G | p.W41G | IRVDAGHKPHEYQEYGEKRNTRKQF[p.W41G]KTFSYCHSFQTHKISHTGHKPYDCK | KQFGKTFSY, RNTRKQFGK, TRKQFGKTF, KRNTRKQFGK, RK QFGKTFSY, KQFGKTFSYC, GKTFSYCHSF | BLCA |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZNF799 | c.127A>G | p.T43A | VDAGHKPHEYQEYGEKRNTRKQFWK[p.T43A]APSYCHSFQTHKISHTGHKPYDCKEC | KQFWKAFSY,KAFSYCHSF,NTRKQFWKA,TRKQFWKAF,KAFSYCHSFQ,RKQFWKAFSY,NTRKQFWKAF,WKAFSYCHSF,KQFWKAFSYC | BLCA |
| ZNF799 | c.1357T>C | p.C453R | KAYRISSSLRRHETTHTGEKPYKCK[p.C453R]RGKAFIDFYSFQNHKTTHAGEKPYEC | KPYKCKRGK,KCKRGKAFI,RGKAFIDFY,YCCKRGKAF,KRGKAFIDF,RGKAFIDFYS,KRGKAFIDFY,KPYYCKRGKA,CKRGKAFIDF | TGCT |
| ZNF804B | c.1930_1931 CC>AG | p.P644S | NDIDEDLSFPSYISRFKKHKLIPCS[p.P644S]SHLEFEDERQFNCKSSPCTVGGHSDHG | KLIPCSSHL,IPCSSHLEF,HKLIPCSSH,LIPCSSHLEF,HKLIPCSS,HL | TGCT |
| ZNF814 | c.959_960 GG>AA | p.G320E | KHECGECGKSFSKYVSFSNHQRVHT[p.G320E]EKRPYECGECGKSFSKYASFSNHQRVH | HQRVHTEKR,RVHTEKRPY,RVHTEKRPYE,QRVHTEKRPY | KIRP |
| ZNF814 | c.968C>A | p.P323H | CGECGKSFSKVVSFSNHQRVHTGKR[p.P323H]HYECGECGKSFSKYASFSNHQRVHTE | RVHTGKRHY,RVHTGKRHYE,HQRVHTGKRH,QRVHTGKRHY | KIRP |
| ZNF814 | c.970T>C | p.Y324H | GECGKSFSKVVSFSNHQRVHTGKRP[p.Y324H]HECGECGKSFSKYASFSNHQRVHTEK | RVHTGKRPH,RVHTGKRPHE | TGCT |
| ZNF823 | c.1640G>T | p.R547I | SGEKPYECKECGKAFSMLTCLLRHE[p.R547I]IIHTGEKPYECLQCGKAFTRSRFLRG | WLTCLLRHEI | UCEC |
| ZNF831 | c.146_147 insC | p.A49fs | PGGQASPHLTLGTLGPVLLPPEQGLAPP[p.A49fs]HCVPEGPAHPTVPHGASRGPPAPRPASDGQPRWGQRALHTQPCAAA* | ALHTQPCAA,HGASRGPPA,ASRGPPAPR,RALHTQPCA,DGQPRWGQR,QPRWGQRAL,ALHTQPCAA,RALHTQPCAA,VPEGPAHPTV,GQPRWGQRAL,GQRALHTQPC,RPASDGQPRW | STAD |
| ZNF831 | c.1849C>A | p.Q617K | AREAMAGKGRAGGRKCGQRRLKMFS[p.Q617K]KEKWQVYGDETFKRIYQKMKASPHGG | RLKMFSKEK,MFSKEKWQV,QRRLKMFSK,FSKEKWQVY,LKMFSKEKW,KMFSKEKWQV,GQRRLKMFSK,RRLKMFSKEK,MFSKEKWQVY,RLKMFSKEKW | LUAD |
| ZNF831 | c.2847G>T | p.E949D | QAPRVLSALADNAFSPKYLLRLPQA[p.E949D]DTPLPLPIPWGPRHSQDSLCSSGWPE | RLPQADTPL,PQADTPLPL,LPQADTPLPL,LRLPQADTPL | CRC |
| ZNF831 | c.4178G>A | p.R1393Q | EGDCRQTLGTLSLGTSSRIVREMDK[p.R1393Q]QTVKDISPSAGEHGDCTTHSTAATSG | REMDKQTVK,QTVKDISPSA | SKCM |
| ZNF836 | c.1712T>A | p.I571N | RIHTGEQPYKCNVCGKVFNYSGNLS[p.I571N]NHKRIHTGEKPFQCNECGTVFRNYSC | YSGNLSNHK,FNYSGNLSNH | CLL |
| ZNF836 | c.1822A>C | p.K608Q | QCNECGTVFRNYSCLARHLRIHTGQ[p.K608Q]QPYKCNVCGKVFNDSGNLSNHKRIHT | RIHTGQQPY,GQQPYKCNV,RIHTGQQPYK,LRIHTGQQPY | CLL |
| ZNF836 | c.1889G>T | p.R630I | TGQKPYKCNVCGKVFNDSGNLSNH[p.R630I]IIHTGEKPFQCNECGKVFSYYSCLAR | KIIHTGEKPF | UCEC |
| ZNF836 | c.2561G>T | p.R854I | TGDKPYKCNECGKAFIERSKLVYH[p.R854I]INHTGEKPYKCIECGKAFGRFSCLNK | KLVYHQINH,HQINHTGEK,RSKLVYHQI,INHTGEKPY,KLVYHQINHT,RSKLVYHQIN,INHTGEKPYK,QINHTGEKPY | UCEC |
| ZNF841 | c.2270G>T | p.R757I | TGEMPYKCIECGKVFNSTTTLARH[p.R757I]IIHTGEKPYKCNECGKVFRYRSGLAR | TTTLARHRI | UCEC |

TABLE 8-continued

| gene | cDNA Change | Protein Change | Mutation_Context_Sequence (SEQ ID NOS 81-3798, respectively, in order of appearance) | Peptides (SEQ ID NOS 3799-33502, respectively, in order of appearance) | Exemplary Diseases |
|---|---|---|---|---|---|
| ZNF845 | c.1269G>A | p.M423I | LTRHRRLHTGEKPYKCNDCGKTFSQ[p.M423I]ISSLVYHRRLHTGEKPYKCEECDEAF | FSQISSLVY,KTFSQISSL,QISSLVHR,ISSLVYHR,TFSQISSLV,SQISSLVYH,KTFSQISSLV,SQISSLVHR,QISSLVYHRR,TFSQISSLVY,GKTFSQISSL | CLL |
| ZNF845 | c.2774G>A | p.R925H | AHLACHHRIHTGEKPYKCNECGKTF[p.R925H]HHNSVLVIHKTIHTGEKPYKCNECGK | KTFHHNSVL,GKTFHHNSV,FHHNSVLVI,KTFHHNSVLV,TFHHNSVLVI,CGKTFHHNSV,HHNSVLVIHK,GKTFHHNSVL,FHHNSVLVIH | PRAD |
| ZNF880 | c.1217A>G | p.Q406R | ECKECGK[VFRHKFCLTNHHRMHTGE[p.Q406R]RPYKCNECGKAFRDCSGLTAHLLIHT | HHRMHTGER,HRMHTGERPY | KIRC |
| ZP3 | c.1085_1086insG | p.V362fs | VMSQWSRSASRNRRHVTEEADVTVG[p.V362fs]ATDLPGQEG* | EEADVTVGA,EEADVTVGAT,TEEADVTVGA | KIRC |
| ZPBP | c.460C>T | p.R154C | NFEESMSGIYTCFLEYKPTVEEIVK[p.R154C]CLQLKYAIYAYREPHYYQFTARYHA | IVKCLQLKY,CLQLKYAIY,EEIVKCLQL,CLQLKYAIYA,IVKCLQLKYA,KCLQLKYAIY,VEEIVKCLQL | GBM |
| ZSCAN18 | c.674_675insC | p.P225fs | SSILSDGVYERHMDPLLLPGELASP[p.P225fs]QPGPWSWGDPGTF* | WSWGDPGTF,LASPQPGPW,SPQPGPWSW,GELASPQPG | STAD |
| ZSWIM2 | c.641C>A | p.S214Y | TSMLKCPLCRKEFAPLKLILEEFKN[p.S214Y]YSKLVAAAEKERLDKHLGIPCNNCKQ | KNYSKLVAA,LILEEFKNY,FKNYSKLVA,EEFKNYSKL,ILEEFKNYSK,YSKLVAAAEK,KNYSKLVAAA,KLILEEFKNY,FKNYSKLVAA,LEEFKNYSKL,EEFKNYSKLV | LUAD |
| ZSWIM4 | c.1219G>A | p.E407K | GPSLQPTMAPAPELLQKGSTCITNT[p.E407K]KGWVGHPLDPIGCLCRALLEACRLEE | GSTCITNTK,TKGWVGHPL,KGSTCITNT,NTKGWVGHPL | CESC |
| ZSWIM6 | c.1829delA | p.Q610fs | LAIAIVNTLRRQQQKQLEMFRTQKK[p.Q610fs]SYPIKT* | RTQKKSYPI,TQKKSYPIK,MFRTQKKSY,RTQKKSYPIK,EMFRTQKKSY,FRTQKKSYPI | KICH |
| ZZEF1 | c.89T>C | p.V30A | PSHSSEDEAAAAGEGWGPHQDWAA[p.V30A]ASGTTPGPGVAAPALPPAAALLEPAR | GPHQDWAAA,WAAASGTTPG | ACC |
| ZZZ3 | c.14G>A | p.R5Q | MAAS[p.R5Q]QSTRVTRSTVGLNGLDESFCGRTLRN | MAASQSTRV,ASQSTRVTR,SQSTRVTRST | HNSC |
| ZZZ3 | c.485G>A | p.R162Q | IKSDKESVEQRSTWDNDADFQGTK[p.R162Q]QACRCLILDDCEKREIKVNVSEEGP | KQACRCLIL,GTKQACRCLI,DFQGTKQACR,TKQACRCLIL | LUSC |

Example 5

Recurrent Mutations for Cancer Subtype Specific Immunogenic Compositions.

The Cancer Genome Atlas (TCGA) contains comprehensive large-scale genome sequencing data from tumor samples to catalogue genetic mutations responsible for cancer. Tumor-specific neoantigenic peptides for use in an immunogenic composition can be selected based on a number of criteria. The first criteria is based on gene expression. The fraction of patients (per tumor type) who express the gene at >10 transcripts per million was determined. Estimates assume a random assortment of HLA type vs. mutation status of each gene vs. gene expression (per tumor type). National yearly incidence was used to quantify the population that could be treated with each peptide. Peptides were ranked by expected population. The results of the analysis is shown in Table 9.

TABLE 9

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| RBM14 p.AAAAAAA286del (uc009yrj.2) | VTAASTSYY | 19282 | Pancreatic Cancer | HLA.A01.01<br>HLA.A03.01<br>HLA.A11.01<br>HLA.A26.01<br>HLA.A26.02<br>HLA.A26.03<br>HLA.A29.02<br>HLA.A68.01<br>HLA.A80.01<br>HLA.B15.01<br>HLA.B15.03<br>HLA.B15.17<br>HLA.B58.01 |
| HRAS p.G12D (uc001pv.2)<br>KRAS p.G12D (uc001rgp.1)<br>NRAS p.G12D (uc009wgu.2) | KLVVVGADGV | 16466 | Colorectal Cancer<br>Pancreatic Cancer<br>Uterine Corpus Endometrial Carcinoma | HLA.A02.01<br>HLA.A02.03<br>HLA.A02.06 |
| NRAS p.G12V (uc009wgu.2)<br>KRAS p.G12V (uc001rgp.1) | KLVVVC-3AVGV | 13995 | Colorectal Cancer<br>Lung Adenocarcinorna<br>Pancreatic Cancer<br>Uterine Corpus Endometrial Carcinoma | HLA.A02.01<br>HLA.A02.03<br>HLA.A02.06 |
| NRAS p.G12V (uc009wgu.2)<br>KRAS p.G12V (uc001rgp.1) | VVGAVGVGK | 11278 | Colorectal Cancer<br>Lung Pancreatic Cancer Adenocarcinorna<br>Uterine Corpus Endometrial Carcinoma | HLA.A03.01<br>HLA.A11.01 |
| KRAS p.G12C (uc001rgp.1)<br>NRAS p.G12C (uc009wgu.2)<br>HRAS p.G12C (uc001pv.2) | KLVVVGACGV | 7538 | Colorectal Cancer<br>Lung Adenocarcinoma | HLA.A02.01<br>HLA.A02.03<br>HLA.A02.06 |
| KRAS p.G12C (uc001rgp.1)<br>NRAS p.G12C (uc009wgu.2)<br>HRAS p.G12C (uc001pv.2) | VVGACGVGK | 5751 | Colorectal Cancer<br>Lung Adenocarcinoma | HLA.A03.01<br>HLA.A11.01 |
| NRAS p.G12V (uc009wgu.2)<br>KRAS p.G12V (uc001rgp.1) | VVVGAVGVGK | 5535 | Colorectal Cancer<br>Lung Adenocarcinoma<br>Pancreatic Cancer | HLA.A11.01<br>HLA.A68.01 |
| TP53 p.R248W (uc002gim.2) | GMNWRPILTI | 5006 | Breast Cancer<br>Colorectal Cancer<br>Pancreatic Cancer | HLA.A02.01<br>HLA.A02.03 |
| PIK3CA p.E542K (uc003fjk.2) | AISTRDPLSK | 4852 | Bladder Cancer<br>Breast Cancer | HLA.A03.01<br>HLA.A11.01 |
| FRG1B p.l10T (uc010ztl.1) | KLSDSRTAL | 4782 | Prostate Cancer | HLA.A02.01<br>HLA.A02.02<br>HLA.A02.03<br>HLA.B07.02<br>HLA.B15.03 |

TABLE 9 -continued

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| GATA3 p.H435fs (uc001ijz.2) | KIfV1FATLQR | 4535 | Breast Cancer | HLA.A03.01<br>HLA.A11.01<br>HLA.A30.01<br>HLA.A31.01<br>HLA.A68.01 |
| HRAS p.G12D (uc001lpv.2)<br>KRAS p.G12D (uc001rgp.1)<br>NRAS p.G12D (uc009wgu.2) | VVGADGVGK | 4530 | Colorectal Cancer<br>Pancreatic ancer | HLA.A11.01 |
| NRAS p.Q61R (uc009wgu.2)<br>KRAS p.Q61R (uc001rgp.1)<br>HRAS p.Q61R (uc001lpv.2) | ILDTAGREEY | 4433 | Melanoma<br>Thyroid Cancer | HLA.A01.01 |
| NRAS p.Q61K (uc009wgu.2)<br>HRAS p.Q61K (uc001lpv.2)<br>KRAS p.Q61K (uc001rgp.1) | ILDTAGKEEY | 4203 | Colorectal Cancer<br>Melanoma | HLA.A01.01 |
| GATA3 p.H435fs (uc001ijz.2) | MLTGPPARV | 4113 | Breast Cancer | HLA.A02.01<br>HLA.A02.02<br>HLA.A02.03<br>HLA.A02.06<br>HLA.A68.02<br>HLA.A69.01 |
| RBM47 p.495_502AAAAAAAA>A (uc003gvc.2) | AAAAVIPTV | 4035 | Pancreatic Cancer | HLA.A02.01<br>HLA.A02.02<br>HLA.A02.03<br>HLA.A02.06<br>HLA.A68.02<br>HLA.A69.01<br>HLA.B15.17 |
| RBM47 p.495_502AAAAAAAA>A (uc003gvc.2) | AAAAAVIPTV | 3864 | Pancreatic Cancer | HLA.A02.01<br>HLA.A02.03<br>HLA.A02.06<br>HLA.A68.02 |
| GATA3 p.H435fs (uc001ijz,2) | YMFLKAESK | 3832 | Breast Cancer | HLA.A03.01<br>HLA.A11.01<br>HLA.A68.01 |
| GATA3 p.H435fs (uc001ijz.2) | SMLTGPPARV | 3718 | Breast Cancer | HLA.A02.01<br>HLA.A02.03<br>HLA.A02.06 |
| GATA3 p.H435fs (uc001ijz.2) | YIVIFLKAESKI | 3718 | Breast Cancer | HLA.A02.01<br>HLA.A02.03<br>HLA.A02.06 |
| GATA3 p.H435fs (uc001ijz.2) | TLQRSSLWCL | 3621 | Breast Cancer | HLA.A02.01<br>HLA.A02.03 |
| AP3S1 p.K41fs (uc003krl.2) | LVSEMKMIN | 3603 | Pancreatic Cancer | HLA.A02.01<br>HLA.A02.02<br>HLA.A02.03<br>HLA.A02.06<br>HLA.A68.02<br>HLA.A69.01 |
| PIK3CA p.H1047R (uc003fjk.2) | FMKQMNDAR | 3582 | Breast Cancer | HLA.A31.01<br>HLA.A33.01<br>HLA.A68.01 |
| KRAS p.Q61L (uc001rgp.1)<br>NRAS p.Q61L (uc009wgu.2)<br>HRAS p.Q61L (uc001lpv.2) | LLDILDTAGL | 3563 | Colorectal Cancer<br>Lung Adenocarcinoma<br>Melanoma | HLA.A02.01<br>HLA.A02.03<br>HLA.A02.06 |
| GATA3 p.H435fs (uc001ijz.2) | FATLQRSSL | 3551 | Breast Cancer | HLA.B07.02<br>HLA.B08.01<br>HLA.B39.01 |

TABLE 9 -continued

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| AP3S1 p.K41fs (uc003krl.2) | HINSEMKMFV | 3524 | Pancreatic Cancer | HLA.A02.01<br>HLA.A02.03<br>HLA.A02.06<br>HLA.A68.02 |
| FRG1B p.L52S (uc010ztl.1) | ALSASNSCH | 3502 | Prostate Cancer | HLA.A02.01<br>HLA.A02.03<br>HLA.A02.06 |
| FRG1B p.L52S (uc010ztl.1) | FQNGKMALSA | 3502 | Prostate Cancer | HLA.A02.01<br>HLA.A02.03<br>HLA.A02.06 |
| RBM14 p.AAAAAAA286del (uc009yrj.2) | AVTAASTSY | 3477 | Pancreatic Cancer | HLA.A26.02<br>HLA.A29.02<br>HLA.615.01<br>HLA.B15.03<br>HLA.B15.17 |
| KRAS p.G12R (ruc001rgp.1)<br>NRAS p.G12R (uc009wgu.2) | VVGARGVGK | 3176 | Pancreatic Cancer | HLA.A03.01<br>HLA.A11.01 |
| PIK3CA p.E545K (uc003fjk.2) | SEITKQEKDF | 3090 | Breast Cancer | HLA.B44.02 |
| FRG1B p.A53T (uc010ztl.1) | LLTSNSCFI | 3016 | Prostate Cancer | HLA.A02.01<br>HLA.A02.02<br>HLA.A02.03<br>HLA.A02.06 |
| FRG1B p.A53T (uc010ztl.1) | ALLTSNSCH | 2959 | Prostate Cancer | HLA.A02.01<br>HLA.A02.03<br>HLA.A02.06 |
| FRG1B p.I10T (uc010ztl.1) | RTALKSGYGK | 2787 | Prostate Cancer | HLA.A03.01<br>HLA.A11.01<br>HLA.A68.01 |
| FRG1B p.A50P (uc010ztl.1) | FQNGKMPLL | 2781 | Prostate Cancer<br>Melanoma | HLA.A02.01<br>HLA.A02.02<br>HLA.A02.03<br>HLA.A02.06<br>HLA.B15.03<br>HLA.B39.01 |
| PIK3CA p.H1047L (uc003fik.2) | FMKQMNDAL | 2610 | Breast Cancer | HLA.A02.01<br>HLA.A02.02<br>HLA.A02.03<br>HLA.A02.06<br>HLA.B08.01<br>HLA.B15.01<br>HLA.B15.03 |
| KRAS p.Q61L (uc001rgp.1)<br>NRAS p.Q61L (uc009wgu.2)<br>HRAS p.Q61L (uc0011pv.2) | ILDTAGLEEY | 2555 | Colorectal Cancer<br>Lung Adenocarcinoma<br>Melanoma | HLA.A01.01 |
| FRG1B p.A113 (uc010ztl.1) | ITLKSGYGIK | 2523 | Prostate Cancer<br>Melanoma | HLA.A03.01<br>HLA.A11.01<br>HLA.A30.01<br>HLA.A31.01<br>HLA.A68.01 |
| ANAPC1 p.T537A (uc002thi.2) | VSAPKPLSK | 2521 | Pancreatic Cancer<br>Prostate Cancer | HLA.A03.01<br>HLA.A11.01<br>HLA.A30.01 |
| GATA3 p.H435fs (uc001ijz.2) | FLKAESKIIVI | 2496 | Breast Cancer | HLA.A02.03<br>HLA.B08.01<br>HLA.B15.01<br>HLA.B15.03 |

TABLE 9 -continued

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| FRG1B p.A50P (uc010ztl.1) | FQNGKMPLLA | 2486 | Prostate Cancer Melanoma | HLA.A02.01 HLA.A02.03 HLA.A02.06 |
| PIK3CA p.H1047R (uc003fik.2) | YFIVIKQMNDAR | 2478 | Breast Cancer | HLA.A33.01 HLA.A68.01 |
| GATA3 p.S408fs (uc001ijz.2) | AIQPVLWTT | 2371 | Breast Cancer | HLA.A02.01 HLA.A02.02 HLA.A02.06 |
| RBM1.4 p.AAAAAAA286del (uc009yrj.2) | AVTAASTSYY | 2363 | Pancreatic Cancer | HLA.A11.01 |
| FRG1B p.I10T (uc010ztl.1) | KLSDSRTALK | 2356 | Prostate Cancer | HLA.A03.01 HLA.A11.01 |
| FRG1B p.A11T (uc010ztl.1) | KLSDSRITL | 2328 | Prostate Cancer Melanoma | HLA.A02.01 HLA.A02.02 HLA.A02.03 HLA.A02.06 HLA.B15.03 |
| ANAPC1 p.T537A uc002thi.2) | GVSAPKPLSK | 2260 | Pancreatic Cancer Prostate Cancer | HLA.A03.01 HLA.A11.01 |
| TP53 p.Y220C (uc002gim.2) | VVVPCEPPEV | 2200 | Breast Cancer | HLA.A02.01 HLA.A02.06 |
| TP53 p.R248W (uc002gim.2) | SSCMGGMNWR | 2135 | Colorectal Cancer | HLA.A11.01 HLA.A68.01 |
| KRAS p.G12R (uc001rgp.1) NRAS p.G12R (uc009wgu.2) | GARGVGKSAL | 2075 | Pancreatic Cancer | HLA.B07.02 |
| RAC1 p.P29S (uc003spx.2) | TTNAFSGEY | 2042 | Melanoma | HLA.A01.01 HLA.A11.01 HLA.A25.01 HLA.A26.01 HLA.A26.02 HLA.A26.03 HLA.A29.02 HLA.A68.01 HLA.A80.01 HLA.B15.01 HLA.B15.03 HLA.B15.17 |
| GATA3 p.H435fs (uc001ijz.2) | GPPARVPAV | 2039 | Breast Cancer | HLA.B07.02 |
| GATA3 p.H435fs (uc001ijz.2) | KPKRDGYMF | 2039 | Breast Cancer | HLA.B07.02 |
| GATA3 p.H435fs (uc001ijz.2) | KPKRDGYMEL | 2039 | Breast Cancer | HLA.B07.02 |
| KRAS p.G12A (uc001rgp.1) HRAS p.G12A (uc001lpv.2) NRAS p.G12A (uc009wgu.2) | KLVVVGAAGV | 2034 | Colorectal Cancer Lung Adenocarcinoma | HLA.A02.01 HLA.A02.03 HLA.A02.06 |
| SPOP p.F133L (uc002ipg.2) | FVQGKDWGL | 2002 | Prostate Cancer | HLA.A02.01 HLA.A02.02 HLA.A02.03 HLA.A02.06 HLA.A68.02 HLA.A69.01 |
| GATA3 p.H435fs (uc001ijz.2) | CSMLTGPPAR | 1995 | Breast Cancer | HLA.A11.01 HLA.A33.01 HLA.A68.01 |
| WASH3P p.G175S (uc002cdi.2) WASH2P p.G175S (uc002tkh.2) | SIRAAGGISK | 1978 | Prostate Cancer Melanoma | HLA.A03.01 HLA.A11.01 |
| ARFGAP3 p.N299fs (uc003bdd.2) | EIAEVLFHI | 1959 | Prostate Cancer | HLA.A02.01 HLA.A02.02 |

TABLE 9 -continued

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| | | | | HLA.A02.03 |
| | | | | HLA.A02.06 |
| | | | | HLA.A26.02 |
| | | | | HLA.A26.03 |
| | | | | HLA.A68.02 |
| | | | | HLA.A69.01 |
| GATA3 p.S408fs (uc001ijz.2) | ALQPLQPHA | 1906 | Breast Cancer | HLA.A02.01 |
| | | | | HLA.A02.02 |
| | | | | HLA.A02.03 |
| ARFGAP3 p.N299fs (uc003bdd.2) | SAWDLEIAEV | 1892 | Prostate Cancer | HLA.A02.01 |
| | | | | HLA.A02.06 |
| | | | | HLA.A68.02 |
| FRG1B p.I59V (uc010ztl.1) | LLASNSCFV | 1824 | Prostate Cancer | HLA.A02.01 |
| FRG1 p.I157V (uc003izs.2) | | | Melanoma | HLA.A02.02 |
| | | | | HLA.A02.03 |
| | | | | HLA.A02.06 |
| | | | | HLA.A68.02 |
| | | | | HLA.A69.01 |
| ARFGAP3 p.N299fs (uc003bdd.2) | KMLTQTDSA | 1818 | Prostate Cancer | HLA.A02.01 |
| | | | | HLA.A02.02 |
| | | | | HLA.A02.03 |
| | | | | HLA.A02.06 |
| PTH2 p.L22del (uc002pnn.1) | LLLLLLLLV | 1807 | Prostate Cancer | HLA.A02.01 |
| CTSA p.L37del (uc002xqh.2) | | | | HLA.A02.02 |
| AGPAT2 p.17_18insL (uc004cii.1) | | | | HLA.A02.03 |
| | | | | HLA.A02.06 |
| TP53 p.R2480 (uc002gim.2) | SSCMGGMNQR | 1795 | Bladder Cancer | HLA.A11.01 |
| | | | | HLA.A68.01 |
| KRAS p.G12(2 (uc001rgp.1) | VVVGACGVGK | 1785 | Colorectal Cancer | HLA.A11.01 |
| NRAS p.G12C (uc009wgu.2) | | | Lung | |
| HRAS p.G12C (uc001lpv.2) | | | Adenocarcinorna | |
| PiK3CA p.N345K (uc003fjk.2) | KILCATYVK | 1776 | Breast Cancer | HLA.A03.01 |
| | | | | HLA.A11.01 |
| | | | | HLA.A30.01 |
| | | | | HLA.A31.01 |
| FRG1B p.A11T (uc010ztl.1) | KLSDSRITLK | 1749 | Prostate Cancer | HLA.A03.01 |
| | | | | HLA.A11.01 |
| FRG1B p.A11T (uc010ztl.1) | RITLKSGYGK | 1749 | Prostate Cancer | HLA.A03.01 |
| | | | | HLA.A11.01 |
| GATA3 p.H435fs (uca11ijz.2) | AVPFDLHFCR | 1749 | Breast Cancer | HLA.A11.01 |
| | | | | HLA.A68.01 |
| PIK3CA p.E542K (uc003fjk.2) | ISTRDPLSK | 1746 | Breast Cancer | HLA.A11.01 |
| TP53 p.G245S (uc002gim.2) | SSCMGSMNR | 1732 | Colorectal Cancer | HLA.A11.01 |
| | | | | HLA.A31.01 |
| | | | | HLA.A68.01 |
| GATA3 p.H435fs (uca11ijz.2) | AESKIMFATL | 1731 | Breast Cancer | HLA.B40.01 |
| | | | | HLA.B44.02 |
| AKT1 p.E17K (uc001ypk.2) | WLHKRGKYIK | 1717 | Breast Cancer | HLA.A03.01 |
| AKT2 p.E17K (uc002onf.2) | | | | |
| PIK3CA p.N345K (uc003fjk.2) | ILCATYVKV | 1715 | Breast Cancer | HLA.A02.01 |
| | | | | HLA.A02.02 |
| | | | | HLA.A02.03 |
| | | | | HLA.A02.06 |
| FRG1B p.I59V (uc010ztl.1) | ALLASNSCFV | 1698 | Prostate Cancer | HLA.A02.01 |
| FRG1 p.I157V (uc003izs.2) | | | Melanoma | HLA.A02.03 |
| | | | | HLA.A02.06 |

TABLE 9 -continued

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| FRG1B p.L52S (uc010ztl.1) | SASNSCFIR | 1685 | Prostate Cancer | HLA.A11.01<br>HLA.A31.01<br>HLA.A33.01<br>HLA.A68.01 |
| PIK3CA p.N345K (uc003fjk.2) | KILCATYVKV | 1679 | Breast Cancer | HLA.A02.01<br>HLA.A02.03<br>HLA.A02.06 |
| AP3S1 p.K41fs (uc003krl.2) | ETFHLVSEM | 1635 | Pancreatic Cancer | HLA.A25.01<br>HLA.A26.01<br>HLA.A26.02<br>HLA.A26.03<br>HLA.A68.01<br>HLA.A68.02<br>HLA.A69.01<br>HLA.B15.17 |
| PIK3CA p.N345K (uc003fik.2) | KVNIRDIDK | 1620 | Breast Cancer | HLA.A03.01<br>HLA.A11.01<br>HLA.A30.01 |
| KRAS p.G12A (uc00irgp.1)<br>HRAS p.G12A (uc001lpv.2)<br>NRAS p.G12A (uc009wgu.2) | VVGAAGVGK | 1613 | Colorectal Cancer<br>Lung Adenocarcinoma | HLA.A03.01<br>HLA.A11.01 |
| CDC27 p.D555E (uc002ile.3) | TLWHLOKEV | 1577 | Colorectal Cancer | HLA.A02.01<br>HLA.A02.02<br>HLA.A02.03<br>HLA.A02.06 |
| GATA3 p.H435fs (uc00lijz.2) | ESKIMFATL | 1573 | Breast Cancer | HLA.A68.02<br>HLA.B08.01 |
| TP53 p.P75fs (uc002gim.2) | KPTRAATVSV | 1536 | Colorectal Cancer | HLA.B07.02 |
| CTNNB1 p.T41A (uc010hla.1) | ATAPSLSGK | 1536 | Prostate Cancer | HLA.A03.01<br>HLA.A11.01<br>HLA.A30.01<br>HLA.A31.01<br>HLA.A68.01 |
| CDC27 p.D555E (uc002ile.3) | HLQKEVALSV | 1530 | Colorectal Cancer | HLA.A02.01<br>HLA.A02.03<br>HLA.A02.06 |
| PIK3CA p.H1047L (uc003fik.2) | ALHGGWTTK | 1513 | Breast Cancer | HLA.A03.01<br>HLA.A11.01<br>HLA.A30.01 |
| UBC p.R73L (uc002gyy.3) | RLRGGMOIFV | 1474 | Prostate Cancer | HLA.A02.01<br>HLA.A02.03<br>HLA.A02.06 |
| PEX1 p.I370fs (uc003uly.2) | KMRRPVCYK | 1456 | Prostate Cancer | HLA.A03.01<br>HLA.A11.01<br>HLA.A30.01 |
| TP53 p.C238Y (uc002gim.2) | TTIHYNYMY | 1454 | Colorectal Cancer | HLA.A31.01<br>HLA.A01.01<br>HLA.A11.01<br>HLA.A25.01<br>HLA.A26.01<br>HLA.A26.02<br>HLA.A26.03<br>HLA.A29.02<br>HLA.A68.01<br>HLA.A80.01<br>HLA.B15.17 |
| ANAPC1 p.T537A (uc002thi.2) | APKPLSKLL | 1449 | Pancreatic Cancer | HLA.B07.02<br>HLA.A11.01<br>HLA.A31.01 |

TABLE 9 -continued

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| FRG1B p.A53T (uc010ztl.1) | LTSNSCFIR | 1447 | Prostate Cancer | HLA.A33.01<br>HLA.A68.01 |
| RNF43 p.G659fs (uc002iwf.2) | TQLARFFPI | 1442 | Colorectal Cancer<br>Prostate Cancer | HLA.A02.01<br>HLA.A02.02<br>HLA.A02.03<br>HLA.A02.06<br>HLA.A23.01<br>HLA.A30.01<br>HLA.A31.01<br>HLA.A69.01<br>HLA.B08.01<br>HLA.B08.03<br>HLA.B15.03<br>HLA.B38.01<br>HLA.B39.01<br>HLA.B40.01<br>HLA.B40.02 |
| AP3S1 p.K41fs (uc003krl.2) | EIFFILVSEMK | 1440 | Pancreatic Cancer | HLA.A11.01<br>HLA.A68.01 |
| PIK3CA p.H1047R (uc003fjk.2) | ARHGGWTTK | 1426 | Breast Cancer | HLA.B27.05 |
| PIK3CA p.H1047R (uc003fjk.2) | ARHGGWTTKM | 1426 | Breast Cancer | HLA.B27.05 |
| GATA3 p.S408fs (uc001ijz.2) | QPVLWITPPL | 1421 | Breast Cancer | HLA.B07.02 |
| FRG1B p.A50P (uc010ztl.1) | MPLLASNSCF | 1374 | Prostate Cancer | HLA.B07.02 |
| WASH3P p.G175S (uc002cdi.2)<br>WASH2P p.G175S (uc002tkh.2) | ISKAKLRSM | 1337 | Prostate Cancer<br>Melanoma | HLA.A30.01<br>HLA.B08.01<br>HLA.B15.17 |
| HRAS p.G13R (uc001lpv.2)<br>NRAS p.G13R (uc009wgu.2) | VVGAGRVGK | 1324 | Colorectal Cancer | HLA.A03.01<br>HLA.A11.01<br>HLA.A30.01 |
| ACADS p.R330H (uc001tza.3) | RLLTWHAAM | 1321 | Prostate Cancer | HLA.A02.01<br>HLA.A02.02<br>HLA.A02.03<br>HLA.A02.06<br>HLA.B08.01<br>HLA.B15.01<br>HLA.B15.03<br>HLA.B15.17 |
| HRAS p.G12D (uc001lpv.2)<br>KRAS p.G12D (uc001rgp.1)<br>NRAS p.G12D (uc009wgu.2) | LVVVGADGV | 1284 | Pancreatic Cancer | HLA.A02.06<br>HLA.A68.02<br>HLA.A69.01 |
| KRAS p.G12S (uc001rgp.1)<br>HRAS p.G12S (uc001lpv.2)<br>NRAS p.G12S (uc009wgu.2) | KLVVVGASGV | 1278 | Colorectal Cancer | HLA.A02.01<br>HLA.A02.03<br>HLA.A02.06 |
| TP53 p.A159V (uc002gim.2) | RVRVMAIYK | 1271 | Bladder Cancer | HLA.A03.01<br>HLA.A11.01<br>HLA.A30.01<br>HLA.A31.01 |
| HLA-A p.Q78R (uc003nol.2) | IEREGPEYW | 1271 | Prostate Cancer | HLA.B44.02<br>HLA.B44.03 |
| GATA3 p.H435fs (uc001ijz.2) | LQRSSLWCL | 1248 | Breast Cancer | HLA.A02.06<br>HLA.B15.01<br>HLA.B15.03 |
| ZMIZ2 p.VAAAAATATATATAT153del (uc003tlr.2) | ALQEKQSCIEL | 1226 | Pancreatic Cancer | HLA.A02.01<br>HLA.A02.03 |
| GIGYF2 p.Q1005del (uc002vtj.3) | KLSGWGNVSK | 1204 | Pancreatic Cancer | HLA.A03.01<br>HLA.A11.01 |

TABLE 9 -continued

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| FRG1B p.L52S (uc010ztl.1) | LSASNSCFIR | 1190 | Prostate Cancer | HLA.A11.01<br>HLA.A68.01 |
| AKT1 p.E17K (uc001ypk.2)<br>AKT2 p.E17K (uc002onf.2) | WLHKRGKYI | 1172 | Breast Cancer | HLA.A02.03<br>HLA.B08.01 |
| PEX1 p.I370fs (uc003uly.2) | KLGQIIMKK | 1165 | Prostate Cancer | HLA.A03.01<br>HLA.A11.01 |
| RAC1 p.P29S (uc003spx.2) | FSGEYIPTV | 1152 | Melanoma | HLA.A02.01<br>HLA.A02.02<br>HLA.A02.03<br>HLA.A02.06<br>HLA.A68.02<br>HLA.A69.01 |
| GATA3 p.H435fs (uc001ijz.2) | IMKPKRDGY | 1151 | Breast Cancer | HLA.B15.01<br>HLA.B15.03 |
| AEBP1 p.K1133del (uc003tkb.2) | EEEIATGQAF | 1143 | Pancreatic Cancer | HLA.B44.02<br>HLA.A03.01 |
| FBXW7 p.R465H (uc003ims.2) | TVHCMHLHEK | 1142 | Colorectal Cancer | HLA.A11.01<br>HLA.A68.01 |
| TSPAN4 p.L92V (uc001lsd.1) | LTFFLLLLV | 1140 | Prostate Cancer | HLA.A02.01<br>HLA.A02.02<br>HLA.A02.03<br>HLA.A02.06<br>HLA.A68.02<br>HLA.A69.01<br>HLA.B15.17 |
| TP53 p.R158L (uc002gim.2) | RVLAMAIYK | 1136 | Lung Squamous Cell Carcinoma | HLA.A03.01<br>HLA.A11.01<br>HLA.A30.01<br>HLA.A31.01<br>HLA.A68.01 |
| NRAS p.G12V (uc009wgu.2)<br>KRAS p.G12V (uc001rgp.1) | LVVVGAVGV | 1130 | Pancreatic Cancer | HLA.A02.03<br>HLA.A02.06<br>HLA.A68.02<br>HLA.A69.01 |
| GATA3 p.S408fs (uc001ijz.2) | HMSSLSHISA | 1127 | Breast Cancer | HLA.A02.01<br>HLA.A02.03<br>HLA.A02.06 |
| CTNNB1 p.S37F (uc010hia.1) | YLDSGIHFG | 1121 | Uterine Corpus Endometrial Carcinoma | HLA.A02.01<br>HLA.A02.02<br>HLA.A02.06 |
| CTNNB1 p.S37F (uc010hia.1) | YLDSGIHFGA | 1120 | Uterine Corpus Endometrial Carcinoma | HLA.A02.01<br>HLA.A02.03<br>HLA.A02.06 |
| CTNNB1 p.S37C (uc010hia.1) | YLDSGIHCGA | 1111 | Uterine Corpus Endometrial Carcinoma | HLA.A02.01<br>HLA.A02.03<br>HLA.A02.06 |
| SF3B1 p.K700E (uc002uue.2) | GLVDEQQEV | 1099 | Breast Cancer | HLA.A02.01<br>HLA.A02.02<br>HLA.A02.03<br>HLA.A02.06 |
| KRAS p.G12R (uc001rgp.1)<br>NRAS p.G12R (uc009wgu.2) | VVVGARGVGK | 1082 | Pancreatic Cancer | HLA.A11.01 |
| EGFR p.L858R (uc003tqk.2) | KITDFGRAK | 1054 | Lung Adenocarcinoma | HLA.A03.01<br>HLA.A11.01<br>HLA.A30.01 |

TABLE 9 -continued

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| TP53 p.E271K (uc002gim.2) | NLLGRNSFK | 1046 | Bladder Cancer | HLA.A03.01<br>HLA.A11.01<br>HLA.A68.01 |
| TSPAN4 p192V (uc001lsd.1) | FLLLLVVFL | 1044 | Prostate Cancer | HLA.A02.01<br>HLA.A02.02<br>HLA.A02.03<br>HLA.A02.06 |
| TSPAN4 p.L92V (uc001lsd.1) | LLVVELLEA | 1044 | Prostate Cancer | HLA.A02.01<br>HLA.A02.02<br>HLA.A02.03<br>HLA.A02.06 |
| TSPAN4 p.L92V (uc001lsd.1) | LLLLVVFLL | 1030 | Prostate Cancer | HLA.A02.01<br>HLA.A02.02<br>HLA.A02.06 |
| TSPAN4 p.L92V (uc001lsd.1) | FLLLLVVFLL | 1027 | Prostate Cancer | HLA.A02.01<br>HLA.A02.03<br>HLA.A02.06 |
| TSPAN4 p.L92V (uc001lsd.1) | LLLVVFLLEA | 1027 | Prostate Cancer | HLA.A02.01<br>HLA.A02.03<br>HLA.A02.06 |
| TSPAN4 p.L92V (uc001lsd.1) | LLTFFLLLLV | 1027 | Prostate Cancer | HLA.A02.01<br>HLA.A02.03<br>HLA.A02.06 |
| ARFGAP3 p.N299fs (uc003bdd.2) | LEIAEVLFHI | 1024 | Prostate Cancer | HLA.B40.01<br>HLA.B44.02 |
| FRG1B p.I10T (uc010ztl.1) | TALKSGYGK | 1020 | Prostate Cancer | HLA.A11.01<br>HLA.A68.01 |
| RBM14 p.AAAAAAA286del (uc009yrj.2) | ATAAAVTAA | 1020 | Pancreatic Cancer | HLA.A02.02<br>HLA.A02.03<br>HLA.A02.06<br>HLA.A68.02<br>HLA.A69.01 |
| KRAS p.G12S (uc001rgp.1)<br>HRAS p.G12S (uc001lpv.2)<br>NRAS p.G12S (uc009wgu.2) | VVGASGVG K | 1019 | Colorectal Cancer | HLA.A03.01<br>HLA.A11.01 |
| UBC p.L149R (uc002gyy.3) | STLHLVLRR | 1014 | Prostate Cancer | HLA.A11.01<br>HLA.A31.01<br>HLA.A33.01<br>HLA.A68.01 |
| PIK3CA p.N345K (uc003fjk.2) | ATYV KV N IR | 1007 | Breast Cancer | HLA.A11.01<br>HLA.A31.01<br>HLA.A33.01<br>HLA.A68.01 |
| ERBB3 p.V104M (uc001sjh.2) | RMVRETOVY | 990 | Colorectal Cancer | HLA.A03.01<br>HLA.A29.02<br>HLA.A80.01<br>HLA.B15.01<br>HLA.B15.03<br>HLA.B15.17 |
| GATA3 p.H435fs (uc001ijz.2) | AESKIMFAT | 984 | Breast Cancer | HLA.B40.01<br>HLA.B40.02<br>HLA.B45.01 |
| FRG1B p.L52S (uc01ztl.1) | ALSASNSCF | 982 | Prostate Cancer | HLA.B15.01<br>HLA.B15.03 |
| TP53 p.E271K (uc002gim.2) | LLGRNSFKV | 978 | Bladder Cancer | HLA.A02.01<br>HLA.A02.02<br>HLA.A02.03<br>HLA.A02.06 |

TABLE 9 -continued

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| TP53 p.E271K (uc002gim.2) | NLLGRNSFKV | 969 | Bladder Cancer | HLA.A02.01<br>HLA.A02.03<br>HLA.A02.06 |
| FRG1B p.A11T (uc010ztl.1) | TLKSGYGKY | 969 | Prostate Cancer | HLA.A26.02<br>HLA.A29.02<br>HLA.B15.01<br>HLA.B15.03 |
| NFE2L2 p.E79Q (uc002ulh.3) | QLDEQTGEFL | 966 | Lung Squamous Cell Carcinoma | HLA.A02.01<br>HLA.A02.06 |
| TP53 p.K132N (uc002gim.2) | ALNNMFCQL | 955 | Bladder Cancer | HLA.A02.01<br>HLA.A02.02<br>HLA.A02.03<br>HLA.A02.06<br>HLA.B15.01<br>HLA.B15.03 |
| MAP2K1 p.P124S (uc010bhq.2) | NSSYIVGFY | 943 | Melanoma | HLA.A01.01<br>HLA.A26.01<br>HLA.A26.02<br>HLA.A29.02<br>HLA.A68.01<br>HLA.A80.01<br>HLA.B15.03<br>HLA.B15.17 |
| TSPAN9 p.S50L (uc001qlp.2) | ATESPSFPL | 937 | Melanoma | HLA.A02.01<br>HLA.A02.02<br>HLA.A02.03<br>HLA.A02.06<br>HLA.A11.01<br>HLA.A30.01<br>HLA.A31.01<br>HLA.A68.02<br>HLA.A69.01<br>HLA.B15.03<br>HLA.B15.17<br>HLA.B58.01 |
| SF361 p.K700E (uc002uue.2) | QEVRTISAL | 936 | Breast Cancer | HLA.B15.03<br>HLA.B39.01<br>HLA.B40.01<br>HLA.B40.02<br>HLA.B44.02<br>HLA.B44.03 |
| ZNF91 p.R333H (uc002nre.2) | FSHSSTLAK | 907 | Prostate Cancer | HLA.A03.01<br>HLA.A11.01<br>HLA.A30.01<br>HLA.A68.01 |
| FNBP4 p.TT58del (uc009ylv.2) | APSAATTTA | 905 | Prostate Cancer | HLA.B07.02 |
| FNBP4 p.TT58del (uc009ylv.2) | APSAATTTVA | 905 | Prostate Cancer | HLA.B07.02 |
| RAC1 p.P29S (uc003spx.2) | YTTNAFSGEY | 901 | Melanoma | HLA.A01.01<br>HLA.A68.01 |
| ACADS p.R330H (uc001tza.3) | LTWHAAMLK | 896 | Prostate Cancer | HLA.A03.01<br>HLA.A11.01<br>HLA.A30.01<br>HLA.A31.01<br>HLA.A68.01 |
| TP53 p.C242F (uc002gim.2) | SSFMGGMNR | 889 | Lung Squamous Cell Carcinoma | HLA.A03.01<br>HLA.A11.01<br>HLA.A31.01<br>HLA.A33.01<br>HLA.A68.01 |

TABLE 9 -continued

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| CNPY3 p.17_18LL>L (uc003ota.3) | LLLLPAPEL | 878 | Prostate Cancer | HLA.A02.01<br>HLA.A02.02<br>HLA.A02.06 |
| CNPY3 p.17_18LL>L (uc003ota.3) | LLLLLLLLPA | 876 | Prostate Cancer | HLA.A02.01<br>HLA.A02.03<br>HLA.A02.06 |
| CNPY3 p.17_18ll>L (uc003ota.3) | LLLLLLLPA | 876 | Prostate Cancer | HLA.A02.01<br>HLA.A02.03<br>HLA.A02.06 |
| CNPY3 p.17_18LL>L (uc003ota.3) | LLLLLPAPEL | 876 | Prostate Cancer | HLA.A02.01<br>HLA.A02.03<br>HLA.A02.06 |
| ZMIZ2 p.VAAAAATATATATAT153del (uc003tlr.2) | AAAAAVAAL | 855 | Pancreatic Cancer | HLA.A02.02<br>HLA.A02.03<br>HLA.A02.06<br>HLA.A68.02<br>HLA.B07.02<br>HLA.B15.03<br>HLA.B15.17 |
| PODXL p.28_30PSP>P (uc003vqw.3) | SPSPSQNAT | 852 | Prostate Cancer | HLA.B07.02 |
| PODXL p.2830PSP>P (uc003vqw.3) | SPSQNATQTT | 852 | Prostate Cancer | HLA.B07.02 |
| AP3S1 p.K41fs (uc003krl.2) | HLVSEMKMF | 849 | Pancreatic Cancer | HLA.A26.02<br>HLA.B15.01<br>HLA.B15.03 |
| STK19 p.D89N (uc003nyv.2) | NPIFRFSSL | 849 | Melanoma | HLA.A26.02<br>HLA.B07.02<br>HLA.B08.01<br>HLA.B39.01 |
| NUF2 p.S340L (uc001gcq.1) | NLFKRLMIV | 845 | Colorectal Cancer | HLA.A02.01<br>HLA.A02.02<br>HLA.A02.03<br>HLA.A02.06<br>HLA.B08.01 |
| FRG1B p.A53T (uc010ztl.1) | ALLTSNSCF | 833 | Prostate Cancer | HLA.B15.01<br>HLA.B15.03 |
| UBC p.L149R (uc002gyy.3) | LVLRRRGGM | 829 | Prostate Cancer | HLA.B08.01 |
| TP53 p.A159P (uc002gim.2) | RVRPMAIYK | 820 | Lung Adenocarcinoma | HLA.A03.01<br>HLA.A11.01<br>HLA.A30.01<br>HLA.A31.01<br>HLA.A68.01 |
| FRG1B p.K13N (uc010ztl.1) | IALNSGYGK | 791 | Prostate Cancer | HLA.A03.01<br>HLA.A11.01<br>HLA.A30.01<br>HLA.A31.01<br>HLA.A68.01 |
| GATA3 p.H435fs (uc001ijz.2) | VPFDLHFCR | 791 | Breast Cancer | HLA.A33.01<br>HLA.A68.01 |
| UBC p.L149R (uc002gyy.3) | STI.HLVL.RRR | 789 | Prostate Cancer | HLA.A11.01<br>HLA.A33.01<br>HLA.A68.01 |
| ACADS p.R330H (uc001tza.3) | LLTWHAAML | 789 | Prostate Cancer | HLA.A02.01<br>HLA.A02.02<br>HLA.A02.03<br>HLA.A02.06 |

TABLE 9 -continued

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| GATA3 p.H435fs (uc001ijz.2) | ATLQRSSLW | 782 | Breast Cancer | HLA.B15.17<br>HLA.B57.01<br>HLA.B58.01 |
| MAP2K1 p.P124S (uc010bhq.2) | VLHECNSSYI | 779 | Melanoma | HLA.A02.01<br>HLA.A02.03<br>HLA.A02.06 |
| ACADS p.R330H (uc001tza.3) | RLLTVVHAAML | 773 | Prostate Cancer | HLA.A02.01<br>HLA.A02.03<br>HLA.A02.06 |
| RXRA p.S427F (uc004cfb.2)<br>RXRG p.S428F (uc001gda.2) | RLPALRFIGL | 771 | Bladder Cancer | HLA.A02.01<br>HLA.A02.03<br>HLA.A02.06 |
| ERBB3 p.V104M (uc001sjh.2) | LPLPNLRMV | 765 | Colorectal Cancer | HLA.B07.02 |
| TSPAN9 p.S50L (uc001qlp.2) | LLSAANLVI | 759 | Melanoma | HLA.A02.01<br>HLA.A02.02<br>HLA.A02.03<br>HLA.B15.01<br>HLA.B15.03<br>HLA.B15.17 |
| CTNNB1 p.S33F (uc010hia.1) | YLDI-GIHSGA | 755 | Uterine Corpus Endometrial Carcinoma | HLA.A02.01<br>HLA.A02.03<br>HLA.A02.06 |
| CTNNB1 p.S33F (uc010hia.1) | YLDFGIHSG | 754 | Uterine Corpus Endometrial Carcinoma | HLA.A02.01<br>HLA.A02.02<br>HLA.A02.06 |
| PTEN p.R130G (uc001kfb.2) | GTGVMICAY | 751 | Uterine Corpus Endometrial Carcinoma | HLA.A29.02<br>HLA.B15.01<br>HLA.B15.17 |
| RXRA p.S427F (uc004cfb.2)<br>RXRG p.S428F (uc001gda.2) | LPALRFIGL | 748 | Bladder Cancer | HLA.B07.02<br>HLA.B08.01 |
| NOTCH2 p.P6fs (uc001eik.2) | WIPALRRSAV | 747 | Bladder Cancer | HLA.B07.02<br>HLA.B08.01 |
| JMY p.PPPPPPPPPPPP811del (uc003kfx.3) | LPPTPPPLPV | 733 | Pancreatic Cancer | HLA.B07.02 |
| JMY p.PPPPPPPPPPPP811del (uc003kfx.3) | SPLPPTPPPL | 733 | Pancreatic Cancer | HLA.B07.02 |
| ACADS p.R330H (uc001tza.3) | LLTWHAAMLK | 729 | Prostate Cancer | HLA.A03.01<br>HLA.A11.01<br>HLA.A68.01 |
| GATA3 p.H435fs (uc001ijz.2) | RSSIMKPKR | 703 | Breast Cancer | HLA.A30.01<br>HLA.A31.01 |
| OGEOD1 p.G477fs (uc002ejb.2) | FL.LLTLPKV | 702 | Pancreatic Cancer | HLA.A02.01<br>HLA.A02.02<br>HLA.A02.03<br>HLA.A02.06 |
| HERC2P3 p.A803V (uc001ytg.2) | RVRDIVI KO. M | 699 | Pancreatic Cancer | HLA.A30.01<br>HLA.B07.02<br>HLA.B15.17 |
| C1QB p.GPKGPMGPKGGPGAPGAP90del (uc001bgd.2) | ESGDYKATQK | 697 | Pancreatic Cancer | HLA.A68.01 |
| SLC38A10 p.1071_1072II>I (uc002jzz.1) | GLNPLPDVQV | 689 | Pancreatic Cancer | HLA.A02.01<br>HLA.A02.03 |
| UBB p.I188fs (uc002gpx.2)<br>UBC p.I191T (uc002gyy.3) | IPPTSRGSSL | 686 | Prostate Cancer | HLA.B07.02 |

TABLE 9 -continued

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| UBB p.I188fs (uc002gpx.2) UBC p.I191T (uc002gyy.3) | PPTSRGSSL | 686 | Prostate Cancer | HLA.B07.02 |
| CTNNB1 p.D32N (uc010hia.1) | YLNSG1HSGA | 672 | Uterine Corpus Endornetrial Carcinoma | HLA.A02.01 HLA.A02.03 HLA.A02.06 |
| FRG1B p.K13N (uc010ztl.1) | ALNSGYGKYL | 670 | Prostate Cancer | HLA.A02.01 HLA.A02.03 |
| NBPF14 p.R25C (uc001eqf.2) | KLCPQLAENK | 667 | Pancreatic Cancer | HLA.A03.01 HLA.A11.01 |
| IARS2 p.R832C (uc001hmc.2) | VIVCSFAPI | 662 | Melanoma | HLA.A02.01 HLA.A02.02 HLA.A02.03 HLA.A02.06 HLA.A68.02 HLA.A69.01 HLA.B15.03 |
| P1K3CA p.H1047R (uc003fjk.2) | KONINDARHG | 661 | Breast Cancer | HLA.B15.03 |
| CTNNB1 p.D32N (uc010hia.1) | YLNSGIHSG | 658 | Uterine Corpus Endometrial Carcinoma | HLA.A027.01 HLA.A02.02 HLA.A02.03 |
| SIK3 p.950_951QQ>Q (uc001ppy.2) | QEYQELFRHM | 653 | Pancreatic Cancer | HLA.B40.01 HLA.B44.02 |
| IARS2 p.R832C (uc001hmc.2) | ILDVIVCSFA | 651 | Melanoma | HLA.A02.01 HLA.A02.03 HLA.A02.06 |
| AP3S1 p.K41fs (uc003krl.2) | RETFHLVSEM | 650 | Pancreatic Cancer | HLA.B40.01 |
| PPP2R1A p.P179R (uc002pyp.2) | RMVRRAAASK | 649 | Uterine Corpus Endometrial Carcinoma | HLA.A03.01 HLA.A11.01 |
| ZMIZ2 p.VAAAAATATATATAT153del (uc003tlr.2) | AAAAAVAAL | 641 | Pancreatic Cancer | HLA.B07.02 |
| HSD17B7P2 p.N175S (uc010qex.1) | SARKSNFSL | 637 | Prostate Cancer | HLA.A30.01 HLA.B07.02 HLA.B08.01 HLA.B15.17 |
| ARL16 p.G6R (uc002kbf.2) | RVAGRRALSR | 632 | Melanoma | HLA.A03.01 HLA.A11.01 HLA.A33.01 HLA.A68.01 |
| GATA3 p.S408fs (uc001ijz.2) | TIPPLOHGHR | 623 | Breast Cancer | HLA.A33.01 HLA.A68.01 |
| AP3S1 p.K4ifs (uc003krl.2) | FHLVSEMKM | 619 | Pancreatic Cancer | HLA.B38.01 HLA.B39.01 |
| PLEKHA6 p.V328fs (uc001hau.2) | SIMIVISWMPPL | 613 | Colorectal Cancer | HLA.A02.01 HLA.A02.03 HLA.A02.06 HLA.A68.02 HLA.B07.02 |
| LZTS1 p.RTQDLEGALRTKGLEL432del (uc003wzr.2) | KLEGLELEV | 609 | Pancreatic Cancer | HLA.A02.01 HLA.A02.02 HLA.A02.03 HLA.A02.06 |

TABLE 9 -continued

| Mutation | Mutant Sequence (SEQ ID NOS 33503-33732 respectively, in order of appearance) | Estimated Yearly Population | Relevant Tumor Types (>500 patients per year) | Presenting HLAs (predicted <500 nm) |
|---|---|---|---|---|
| HSD17B7P2 p.N175S (uc010qex.1) | WTSSRSARK | 607 | Prostate Cancer | HLA.A03.01<br>HLA.A11.01<br>HLA.A30.01<br>HLA.A68.01 |
| RBM14 p.AAAAAAA286del (uc009yrj.2) | GAAATAAAV | 606 | Pancreatic Cancer | HLA.A02.03<br>HLA.A68.02 |
| TP53 p.R249M (uc002gim.2) | MPILTIITL | 606 | Lung Adenocarcinorna | HLA.A69.01<br>HLA.B07.02<br>HLA.B08.01<br>HLA.B15.03<br>HLA.B39.01<br>HLA.B53.01 |
| IRF2BPL p.114_115QQ>Q (uc001xsy.2) | QLNHVDGSSK | 605 | Prostate Cancer | HLA.A03.01<br>HLA.A11.01 |
| POLI p.D17del (uc002lfj.3) | EEDAEAWAM | 599 | Prostate Cancer | HLA.B40.01<br>HLA.B44.02<br>HLA.B44.03 |
| ZNF780A p.Q600H (uc010xvh.1) | HMHURHO,K | 594 | Prostate Cancer | HLA.A03.01<br>HLA.A11.01<br>HLA.A30.01<br>HLA.A31.01<br>HLA.A33.01<br>HLA.A58.01 |
| FRG1B p.I10T (uc010ztI.1) | LSDSRTALK | 589 | Prostate Cancer | HLA.A11.01 |
| PARG p.A584T (uc001jih.2) | EETEAQHLY | 585 | Prostate Cancer | HLA.B44.02<br>HLA.B44.03 |
| GATA3 p.S408fs (uc001ijz.2) | SSLSHISAL | 573 | Breast Cancer | HLA.A02.06<br>HLA.B08.01<br>HLA.B15.03<br>HLA.B15.17<br>HLA.B39.01 |
| EGFR p.L858R (uc003tkq.2) | FGRAKLLGA | 564 | Lung Adenocarcinorna | HLA.B08.01 |
| TP53 p.R249M (uc002gim.2) | RMPILTIITL | 563 | Lung Adenocarcinorna | HLA.A02.01<br>HLA.A02.03<br>HLA.A02.06 |
| PARG p.A584T (uc001jih.2) | TEAQHLYQSI | 557 | Prostate Cancer | HLA.B40.01<br>HLA.B44.02 |
| CDC27 p.D555E (uc002ile.3) | EVALSVLSK | 557 | Colorectal Cancer | HLA.A11.01<br>HLA.A68.01 |
| GATA3 p.H435fs (uc001ijz.2) | MFLKAESKI | 554 | Breast Cancer | HLA.A23.01 |
| FRG1B p.K13N (uc010zt1.1) | RIALNSGYGK | 546 | Prostate Cancer | HLA.A03.01<br>HLA.A11.01 |
| CTNNB1 p.G34R (uc010hia.1) | YLDSRIHSGA | 530 | Uterine Corpus Endornetrial Carcinoma | HLA.A02.01<br>HLA.A02.03<br>HLA.A02.06 |
| FRG1B p.L525 (uc010zt1.1) | LSASNSCH | 528 | Prostate Cancer | HLA.A68.02<br>HLA.B15.17<br>HLA.B58.01 |
| AXIN2 p.W663fs (uc002jfi,2) | TPAPPPVPT | 520 | Colorectal Cancer | HLA.B07.02 |
| AXIN2 p.W663fs (uc002jfi.2) | VPTCSPRTL | 520 | Colorectal Cancer | HLA.B07.02 |
| FCGBP p.A2493V (uc002omp.3) | RPGLHRFVV | 504 | Pancreatic Cancer | HLA.B07.02<br>HLA.B08.01 |

Example 6

Therapeutic Targeting of Recurrent Mutations Expressed in Genes Containing Extracellular Domains.

Tumor-specific mutations present in greater than 1% of a population of cancer patients may be targeted with a drug or therapy that recognizes the tumor-specific neoepitope resulting from the mutation. The mutation is preferably within an extracellular domain. The drug or therapy is an antibody, antibody fragment, antibody drug conjugate, aptamer, CAR, or T cell receptor. The antibody or fragment thereof may be humanized, fully humanized, or chimeric. The antibody fragment may be a nanobody, Fab, Fab', (Fab')2, Fv, ScFv, diabody, triabody, tetrabody, Bis-scFv, minibody, Fab2, or Fab3 fragment.

A recurrent mutation that may be targeted is FGFR3:p.S249C. Fibroblast growth factor receptor 3 (FGFR3) is a protein that in humans is encoded by the FGFR3 gene. FGFR3 has also been designated as CD333 (cluster of differentiation 333). The full-length protein includes an extracellular region, composed of three immunoglobulin-like domains, a single hydrophobic membrane-spanning segment and a cytoplasmic tyrosine kinase domain. The mutation occurs in the extracellular domain of the protein. The mutation is present in 6.92% of bladder cancer (BLCA) patients analyzed and 1.12% of lung squamous cell carcinoma (LUSC) patients analyzed.

Another recurrent mutation that may be targeted is ERBB3:p.V104M. Receptor tyrosine-protein kinase erbB-3, also known as HER3 (human epidermal growth factor receptor 3), is a membrane bound protein that in humans is encoded by the ERBB3 gene. ErbB3 is a member of the epidermal growth factor receptor (EGFR/ERBB) family of receptor tyrosine kinases. The mutation is present in 1.72% of colorectal cancer (CRC), 2.86% of colon adenocarcinoma (COAD), 2.42% of stomach adenocarcinoma (STAD), and 2.06% of cervical squamous cell carcinoma and endocervical adenocarcinoma (CESC) patients analyzed.

Another recurrent mutation that may be targeted is EGFR:p.L858R. The epidermal growth factor receptor (EGFR; ErbB-1; HER1 in humans) is the cell-surface receptor for members of the epidermal growth factor family (EGF-family) of extracellular protein ligands. The mutation is present in 3.24% of lung adenocarcinoma (LUAD) patients analyzed.

Another recurrent mutation that may be targeted is MUC4:p.H4205Q. Mucin 4 (MUC 4) is a mucin protein that in humans is encoded by the MUC4 gene. This gene encodes an integral membrane glycoprotein found on the cell surface, although secreted isoforms may exist. The mutation is present in 2.3% of prostate adenocarcinoma (PRAD), 2.31% of bladder urothelial carcinoma (BLCA), and 7.14% of uterine carcinosarcoma (UCS) patients analyzed.

Another recurrent mutation that may be targeted is PDGFRA:p.R483fs. Platelet-derived growth factor receptor, alpha polypeptide is a protein that in humans is encoded by the PDGFRA gene. This gene encodes a cell surface tyrosine kinase receptor for members of the platelet-derived growth factor family. The mutation is present in 1.92% of prostate adenocarcinoma (PRAD) patients analyzed.

Another recurrent mutation that may be targeted is TMEM52 23_26LLPL>L. Transmembrane protein 52 is encoded by the TMEM52 gene. The mutation is present in 1.53% of prostate adenocarcinoma (PRAD) patients analyzed.

Another recurrent mutation that may be targeted is PODXL 28_30PSP>P. Podocalyxin-like protein 1 is a protein that in humans is encoded by the PODXL gene. The mutation is present in 1.53% of prostate adenocarcinoma (PRAD), 15.56% of adrenocortical carcinoma (ACC), and 3.57% of uterine carcinosarcoma (UCS) patients analyzed.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10835585B2). An electronic copy of the "Sequence Listing" will also be available from the USPTO upon request and payment of the fee set forth in 37 CFR 1.19(b)(3).

What is claimed is:

1. A method of treating cancer in a subject in need thereof comprising administering to the subject a pharmaceutical composition comprising:
   (i) a polypeptide comprising at least one amino acid sequence comprising at least 8 contiguous amino acids of: PPLQHGHRHGLEPCSMLTGPPARVPAVPFDLHFCRSSIMKPKRDGYMFLKAES KIMFATLQRSSLWCLCSNH (residues 26-97 of SEQ ID NO: 1297); or
   (ii) a nucleic acid encoding the polypeptide; and
   a pharmaceutically acceptable carrier.

2. The method of claim 1, wherein the at least 8 contiguous amino acids binds to an HLA protein in the subject.

3. The method of claim 1, wherein the polypeptide comprises at least two distinct amino acid sequences.

4. The method of claim 3, wherein the polypeptide comprises at most 20 distinct amino acid sequences.

5. The method of claim 1, wherein the polypeptide is from 8 to 50 amino acids in length.

6. The method of claim 1, wherein the at least 8 contiguous amino acids binds to a protein expressed by an HLA-A, HLA-B or HLA-C allele of the subject with a KD of less than 500 nM.

7. The method of claim 1, wherein the pharmaceutical composition is an immunogenic composition or a vaccine composition.

8. The method of claim 7, wherein the pharmaceutical composition further comprises an immunomodulator or adjuvant.

9. The method of claim 8, wherein the immunomodulator or adjuvant is poly(I:C).

10. The method of claim 1, further comprising administering an additional cancer therapy to the subject.

11. The method of claim 10, wherein the additional therapy is a checkpoint inhibitor; or wherein the additional therapy is surgery, chemotherapy, a targeted therapy, or a combination thereof.

12. The method of claim 1, wherein the cancer is breast cancer.

13. The method of claim 1, wherein the subject has a GATA3 frameshift mutation.

14. The method of claim 13, wherein the GATA3 frameshift mutation is a GATA3:p.H434 frameshift mutation.

15. The method of claim 12, wherein the breast cancer is non-metastatic breast cancer.

16. The method of claim 12, wherein the breast cancer is metastatic breast cancer.

17. The method of claim 12, wherein the breast cancer is HER-2-positive breast cancer.

18. The method of claim 12, wherein the breast cancer is a stage I breast cancer, stage II breast cancer, stage IIA breast cancer or operable stage IIC breast cancer.

19. The method of claim 1, wherein the polypeptide comprises an amino acid sequence ESKIMFATL (SEQ ID NOs: 13457, 13526, 13595, 13661, 13717, 13772, 33585).

20. The method of claim 1, wherein the polypeptide comprises an amino acid sequence FATLQRSSL (SEQ ID NOs: 13454, 13523, 13592, 13658, 13714, 13769, 33527).

21. The method of claim 1, wherein the polypeptide comprises an amino acid sequence FLKAESKIM (SEQ ID NOs: 13438, 13507, 13576, 13643, 13700, 13754, 33542).

22. The method of claim 1, wherein the polypeptide comprises an amino acid sequence FLKAESKIMF (SEQ ID NOs: 13488, 13559, 13628, 13687, 13741, 13796).

23. The method of claim 1, wherein the polypeptide comprises an amino acid sequence GPPARVPAV (SEQ ID NOs: 13452, 13521, 13590, 13656, 13712, 13767, 33554).

24. The method of claim 1, wherein the polypeptide comprises an amino acid sequence IMKPKRDGYM (SEQ ID NOs: 13477, 13548, 13617, 13679, 13734, 13789).

25. The method of claim 1, wherein the polypeptide comprises an amino acid sequence KIMFATLQR (SEQ ID NOs: 13441, 13510, 13579, 13646, 13703, 13757, 33513).

26. The method of claim 1, wherein the polypeptide comprises an amino acid sequence KPKRDGYMF (SEQ ID NOs: 13453, 13522, 13591, 13657, 13713, 13768, 33555).

27. The method of claim 1, wherein the polypeptide comprises an amino acid sequence KPKRDGYMFL (SEQ ID NOs: 13485, 13556, 13625, 13684, 13738, 13793, 33556).

28. The method of claim 1, wherein the polypeptide comprises an amino acid sequence LHFCRSSIM (SEQ ID NOs: 13456, 13525, 13594, 13660, 13716, 13771).

29. The method of claim 1, wherein the polypeptide comprises an amino acid sequence MFATLQRSSL (SEQ ID NOs: 13487, 13558, 13627, 13686, 13740, 13795).

30. The method of claim 1, wherein the polypeptide comprises an amino acid sequence MFLKAESKI (SEQ ID NOs: 13444, 13513, 13582, 13649, 13706, 13760, 33726).

31. The method of claim 1, wherein the polypeptide comprises an amino acid sequence MLTGPPARV (SEQ ID NOs: 13437, 13506, 13575, 13642, 13699, 13753, 33517).

32. The method of claim 1, wherein the polypeptide comprises an amino acid sequence SMLTGPPARV (SEQ ID NOs: 13471, 13541, 13610, 13672, 13728, 13783, 33521).

33. The method of claim 1, wherein the polypeptide comprises an amino acid sequence TLQRSSLWCL (SEQ ID NOs: 13473, 13543, 13612, 13674, 13730, 13785, 33523).

34. The method of claim 1, wherein the polypeptide comprises an amino acid sequence YMFLKAESK (SEQ ID NOs: 13440, 13509, 13578, 13645, 13702, 13756, 33520).

35. The method of claim 1, wherein the polypeptide comprises an amino acid sequence YMFLKAESKI (SEQ ID NOs: 13472, 13542, 13611, 13673, 13729, 13784, 33522).

* * * * *